(12) United States Patent
Janardhan et al.

(10) Patent No.: US 10,751,159 B2
(45) Date of Patent: *Aug. 25, 2020

(54) SYSTEMS FOR ASPIRATING THROMBUS DURING NEUROSURGICAL PROCEDURES

(71) Applicant: Insera Therapeutics, Inc., Sacramento, CA (US)

(72) Inventors: Vallabh Janardhan, Dallas, TX (US); Vikram Janardhan, Sacramento, CA (US)

(73) Assignee: Insera Therapeutics, Inc., Sacramento, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/241,639

(22) Filed: Jan. 7, 2019

(65) Prior Publication Data

US 2019/0133747 A1 May 9, 2019

Related U.S. Application Data

(63) Continuation of application No. 16/103,410, filed on Aug. 14, 2018, now Pat. No. 10,390,926, which is a
(Continued)

(51) Int. Cl.
*A61M 1/00* (2006.01)
*A61F 2/01* (2006.01)
(Continued)

(52) U.S. Cl.
CPC .......... *A61F 2/01* (2013.01); *A61B 17/0057* (2013.01); *A61B 17/12109* (2013.01);
(Continued)

(58) Field of Classification Search
CPC ...... A61F 2/01; A61F 2/013; A61F 2002/016; A61F 2002/018; A61F 2210/0014;
(Continued)

(56) References Cited

U.S. PATENT DOCUMENTS

| 3,378,282 A | 4/1968 | Demler, Sr. |
| 3,381,114 A | 4/1968 | Nakanuma |

(Continued)

FOREIGN PATENT DOCUMENTS

| CN | 101808690 | 8/2010 |
| EP | 0 521 595 | 1/1993 |

(Continued)

OTHER PUBLICATIONS

US 6,348,062 B1, 02/2002, Hopkins et al. (withdrawn)
(Continued)

*Primary Examiner* — Andrew J Mensh
(74) *Attorney, Agent, or Firm* — Knobbe, Martens, Olson, & Bear LLP

(57) ABSTRACT

An aspiration system includes a pump and a control system in communication with the pump. The control system includes a microcontroller, an antenna configured to receive a signal, and a pump control board in communication with the microcontroller. The antenna is in communication with the microcontroller. Upon receiving the signal, the pump control board operates the pump to create negative pressure according to the signal.

17 Claims, 254 Drawing Sheets

Related U.S. Application Data continuation of application No. PCT/US2017/017824, filed on Feb. 14, 2017, application No. 16/241,639, which is a continuation-in-part of application No. 15/903,587, filed on Feb. 23, 2018, which is a continuation of application No. 15/085,083, filed on Mar. 30, 2016, now Pat. No. 9,901,435, which is a continuation of application No. 14/848,079, filed on Sep. 8, 2015, now Pat. No. 9,314,324, which is a continuation of application No. PCT/US2014/022843, filed on Mar. 10, 2014, which is a continuation-in-part of application No. 13/953,540, filed on Jul. 29, 2013, now Pat. No. 8,715,314, application No. 16/241,639, which is a continuation-in-part of application No. 15/829,416, filed on Dec. 1, 2017, which is a continuation of application No. 14/926,980, filed on Oct. 29, 2015, now Pat. No. 9,833,251, which is a continuation of application No. 14/012,913, filed on Aug. 28, 2013, now Pat. No. 9,179,995, which is a continuation of application No. 13/953,540, filed on Jul. 29, 2013, now Pat. No. 8,715,314.

(60) Provisional application No. 62/295,662, filed on Feb. 16, 2016.

(51) Int. Cl.
*A61B 17/12* (2006.01)
*A61B 17/221* (2006.01)
*A61F 2/90* (2013.01)
*A61F 2/07* (2013.01)
*A61F 2/856* (2013.01)
*A61F 2/82* (2013.01)
*A61B 17/00* (2006.01)
*B23K 26/142* (2014.01)
*B23K 26/146* (2014.01)
*A61B 90/00* (2016.01)
*A61B 17/22* (2006.01)
*A61B 17/3205* (2006.01)
*A61B 17/3207* (2006.01)
*A61M 25/00* (2006.01)
*A61M 25/10* (2013.01)
*A61M 29/00* (2006.01)
*B23K 26/08* (2014.01)
*B23K 26/14* (2014.01)
*B23K 26/20* (2014.01)
*B23K 26/38* (2014.01)
*B26F 3/00* (2006.01)
*D04C 1/06* (2006.01)
*D04C 3/48* (2006.01)
*A61F 2/06* (2013.01)

(52) U.S. Cl.
CPC .. *A61B 17/12113* (2013.01); *A61B 17/12122* (2013.01); *A61B 17/12163* (2013.01); *A61B 17/12172* (2013.01); *A61B 17/22* (2013.01); *A61B 17/221* (2013.01); *A61B 17/22031* (2013.01); *A61B 17/22032* (2013.01); *A61B 17/3207* (2013.01); *A61B 17/32056* (2013.01); *A61B 90/39* (2016.02); *A61F 2/013* (2013.01); *A61F 2/07* (2013.01); *A61F 2/82* (2013.01); *A61F 2/856* (2013.01); *A61F 2/90* (2013.01); *A61M 1/008* (2013.01); *A61M 1/0023* (2013.01); *A61M 1/0031* (2013.01); *A61M 1/0033* (2014.02); *A61M 1/0037* (2013.01); *A61M 25/0023* (2013.01); *A61M 25/10* (2013.01); *A61M 29/00* (2013.01); *B23K 26/083* (2013.01); *B23K 26/14* (2013.01); *B23K 26/142* (2015.10); *B23K 26/146* (2015.10); *B23K 26/1435* (2013.01); *B23K 26/20* (2013.01); *B23K 26/38* (2013.01); *B26F 3/004* (2013.01); *D04C 1/06* (2013.01); *D04C 3/48* (2013.01); *A61B 17/12177* (2013.01); *A61B 2017/00154* (2013.01); *A61B 2017/00159* (2013.01); *A61B 2017/00185* (2013.01); *A61B 2017/00199* (2013.01); *A61B 2017/00309* (2013.01); *A61B 2017/00526* (2013.01); *A61B 2017/00575* (2013.01); *A61B 2017/00592* (2013.01); *A61B 2017/00606* (2013.01); *A61B 2017/00641* (2013.01); *A61B 2017/00867* (2013.01); *A61B 2017/1205* (2013.01); *A61B 2017/12054* (2013.01); *A61B 2017/22001* (2013.01); *A61B 2017/22002* (2013.01); *A61B 2017/22034* (2013.01); *A61B 2017/22035* (2013.01); *A61B 2017/22067* (2013.01); *A61B 2017/22079* (2013.01); *A61B 2090/061* (2016.02); *A61B 2090/3966* (2016.02); *A61B 2217/005* (2013.01); *A61F 2002/016* (2013.01); *A61F 2002/018* (2013.01); *A61F 2002/061* (2013.01); *A61F 2002/068* (2013.01); *A61F 2002/823* (2013.01); *A61F 2210/0014* (2013.01); *A61F 2230/001* (2013.01); *A61F 2230/0015* (2013.01); *A61F 2230/0019* (2013.01); *A61F 2230/0069* (2013.01); *A61F 2230/0071* (2013.01); *A61F 2240/001* (2013.01); *A61F 2250/0017* (2013.01); *A61F 2250/0023* (2013.01); *A61F 2250/0032* (2013.01); *A61F 2250/0039* (2013.01); *A61F 2250/0097* (2013.01); *A61F 2250/0098* (2013.01); *A61M 2025/0042* (2013.01); *A61M 2202/06* (2013.01); *A61M 2205/3561* (2013.01); *A61M 2205/50* (2013.01); *A61M 2207/10* (2013.01); *A61M 2210/12* (2013.01); *D10B 2403/0333* (2013.01); *D10B 2509/06* (2013.01); *Y10T 29/49913* (2015.01); *Y10T 29/49995* (2015.01); *Y10T 82/2521* (2015.01); *Y10T 137/8376* (2015.04); *Y10T 137/85954* (2015.04); *Y10T 156/10* (2015.01)

(58) Field of Classification Search
CPC .. B23K 26/142; B23K 26/146; B23K 26/083; B23K 26/14; B23K 26/1435; B23K 26/20; B23K 26/38; A61B 90/39; A61B 17/12109; A61B 17/12113; A61B 17/12122; A61B 17/12172; A61B 17/22; A61B 17/22031; A61B 17/22032; A61B 17/221; A61B 17/32056; A61B 17/3207; A61B 2090/3966; A61B 2017/00526; A61B 2017/00592; A61B 2017/00606; A61B 2017/00641; A61B 2017/22001; A61B 2017/22002; A61B 2017/22034; A61B 2017/22035; A61B 2017/22067; A61M 1/0031; A61M 1/008; A61M 25/0023; A61M 25/10; A61M 29/00; A61M 2025/0042; A61M 2202/06; A61M 2207/10; A61M 2210/12; B26F 3/004; D04C 1/06; D04C 3/48; Y10T 82/2521; Y10T 156/10; Y10T 29/49913; Y10T 29/49995; Y10T 137/8376; Y10T 137/85954; D10B 2509/06
USPC ..................................................... 604/540
See application file for complete search history.

(56) References Cited

U.S. PATENT DOCUMENTS

| | | | |
|---|---|---|---|
| 3,596,545 A | 8/1971 | Eisenhardt | |
| 3,790,744 A | 2/1974 | Bowen | |
| 4,030,503 A | 6/1977 | Clark, III | |
| 4,334,535 A | 6/1982 | Wilson et al. | |
| 4,560,378 A | 12/1985 | Weiland | |
| 4,585,436 A | 4/1986 | Davis et al. | |
| 4,778,559 A | 10/1988 | McNeilly | |
| 4,930,997 A | 6/1990 | Bennett | |
| 4,964,320 A | 10/1990 | Lee, Jr. | |
| 4,984,581 A | 1/1991 | Stice | |
| 4,989,606 A | 2/1991 | Gehrich et al. | |
| 5,073,694 A | 12/1991 | Tessier et al. | |
| 5,108,419 A | 4/1992 | Reger et al. | |
| 5,160,342 A | 11/1992 | Reger et al. | |
| 5,171,383 A | 12/1992 | Sagae et al. | |
| D333,664 S | 3/1993 | Carroll | |
| 5,195,408 A | 3/1993 | Niehaus | |
| 5,211,183 A | 5/1993 | Wilson | |
| 5,234,451 A | 8/1993 | Osypka | |
| 5,265,622 A | 11/1993 | Barbere | |
| 5,324,276 A | 6/1994 | Rosenberg | |
| 5,370,609 A | 12/1994 | Drasler et al. | |
| 5,378,234 A | 1/1995 | Hammerslag et al. | |
| 5,383,387 A | 1/1995 | Chesterfield et al. | |
| 5,398,568 A | 3/1995 | Worrell et al. | |
| 5,419,774 A * | 5/1995 | Willard | A61B 17/3207 604/22 |
| 5,423,849 A | 6/1995 | Engelson et al. | |
| 5,449,372 A | 9/1995 | Schmaltz et al. | |
| 5,484,409 A | 1/1996 | Atkinson et al. | |
| 5,522,822 A | 6/1996 | Phelps et al. | |
| 5,537,696 A | 7/1996 | Chartier | |
| 5,562,641 A | 10/1996 | Flomenblit et al. | |
| 5,573,520 A | 11/1996 | Schwartz | |
| 5,578,074 A | 11/1996 | Mirigian | |
| 5,622,867 A | 4/1997 | Livesey et al. | |
| 5,624,508 A | 4/1997 | Flomenblit et al. | |
| 5,645,558 A | 7/1997 | Horton | |
| 5,649,949 A | 7/1997 | Wallace et al. | |
| 5,690,120 A | 11/1997 | Jacobsen | |
| 5,695,506 A | 12/1997 | Pike et al. | |
| 5,695,507 A | 12/1997 | Auth et al. | |
| 5,697,899 A | 12/1997 | Hillman et al. | |
| 5,725,552 A | 3/1998 | Kotula et al. | |
| 5,725,570 A | 3/1998 | Heath | |
| 5,725,572 A | 3/1998 | Lam et al. | |
| 5,733,400 A | 3/1998 | Gore et al. | |
| 5,741,429 A | 4/1998 | Donadio, III et al. | |
| 5,766,219 A | 6/1998 | Horton | |
| 5,772,674 A | 6/1998 | Nakhjavan | |
| 5,776,162 A | 7/1998 | Kleshinski | |
| 5,780,807 A | 7/1998 | Saunders | |
| 5,788,558 A | 8/1998 | Klein | |
| 5,792,156 A | 8/1998 | Perouse | |
| 5,827,229 A | 10/1998 | Auth et al. | |
| 5,827,304 A | 10/1998 | Hart | |
| 5,836,066 A | 11/1998 | Ingram | |
| 5,843,051 A | 12/1998 | Adams et al. | |
| 5,843,117 A | 12/1998 | Alt et al. | |
| 5,846,261 A | 12/1998 | Kotula et al. | |
| 5,849,037 A | 12/1998 | Frid | |
| 5,865,816 A | 2/1999 | Quinn | |
| 5,868,708 A | 2/1999 | Hart et al. | |
| 5,876,568 A | 3/1999 | Kindersley | |
| 5,879,499 A | 3/1999 | Corvi | |
| 5,882,444 A | 3/1999 | Flomenblit et al. | |
| 5,895,398 A | 4/1999 | Wensel et al. | |
| 5,895,407 A | 4/1999 | Jayaraman | |
| 5,897,567 A | 4/1999 | Ressemann et al. | |
| 5,911,731 A | 6/1999 | Pham et al. | |
| 5,919,614 A | 7/1999 | Livesey et al. | |
| 5,925,063 A | 7/1999 | Khosravi | |
| 5,928,260 A | 7/1999 | Chin et al. | |
| D413,123 S | 8/1999 | Leonhard et al. | |
| 5,935,145 A | 8/1999 | Villar et al. | |
| 5,941,869 A | 8/1999 | Patterson et al. | |
| 5,944,701 A | 8/1999 | Dubrul | |
| 5,951,599 A | 9/1999 | McCrory | |
| 5,972,019 A | 10/1999 | Engelson et al. | |
| 5,994,667 A | 11/1999 | Merdan et al. | |
| 5,996,929 A | 12/1999 | Mazodier et al. | |
| 6,019,778 A | 2/2000 | Wilson et al. | |
| 6,022,747 A | 2/2000 | Gherson et al. | |
| 6,027,863 A | 2/2000 | Donadio, III | |
| 6,030,406 A | 2/2000 | Davis et al. | |
| 6,030,586 A | 2/2000 | Kuan | |
| 6,062,215 A | 5/2000 | Leininger et al. | |
| 6,066,149 A | 5/2000 | Samson et al. | |
| 6,071,267 A | 6/2000 | Zamierowski | |
| 6,080,170 A | 6/2000 | Nash et al. | |
| 6,090,118 A | 7/2000 | McGuckin, Jr. | |
| 6,093,199 A | 7/2000 | Brown et al. | |
| 6,102,890 A | 8/2000 | Stivland et al. | |
| 6,102,933 A | 8/2000 | Lee et al. | |
| 6,107,004 A | 8/2000 | Donadio, III | |
| 6,114,653 A | 9/2000 | Gustafson | |
| 6,115,860 A | 9/2000 | Vralik | |
| 6,142,987 A | 11/2000 | Tsugita | |
| 6,145,143 A | 11/2000 | Hicks et al. | |
| 6,146,370 A | 11/2000 | Barbut | |
| 6,146,396 A | 11/2000 | Konya et al. | |
| 6,149,682 A | 11/2000 | Frid | |
| 6,163,908 A | 12/2000 | Vralik | |
| 6,165,199 A | 12/2000 | Barbut | |
| 6,165,292 A | 12/2000 | Abrams et al. | |
| 6,168,579 B1 | 1/2001 | Tsugita | |
| 6,168,622 B1 | 1/2001 | Mazzocchi | |
| 6,174,330 B1 | 1/2001 | Stinson | |
| 6,183,488 B1 | 2/2001 | Ross et al. | |
| 6,203,561 B1 | 3/2001 | Ramee et al. | |
| 6,221,006 B1 | 4/2001 | Dubrul et al. | |
| 6,221,091 B1 | 4/2001 | Dubrul et al. | |
| 6,221,669 B1 | 4/2001 | Livesey et al. | |
| 6,227,436 B1 | 5/2001 | Nishikawa et al. | |
| 6,237,460 B1 | 5/2001 | Frid | |
| 6,241,691 B1 | 6/2001 | Ferrera et al. | |
| D445,804 S | 7/2001 | Tsai | |
| 6,254,633 B1 | 7/2001 | Pinchuk et al. | |
| 6,258,115 B1 | 7/2001 | Dubrul | |
| 6,262,390 B1 | 7/2001 | Goland | |
| 6,281,262 B1 | 8/2001 | Shikinami | |
| 6,290,721 B1 | 9/2001 | Heath | |
| 6,306,163 B1 | 10/2001 | Fitz | |
| 6,344,048 B1 | 2/2002 | Chin et al. | |
| 6,346,117 B1 | 2/2002 | Greenhalgh | |
| 6,348,063 B1 | 2/2002 | Yassour et al. | |
| 6,350,271 B1 | 2/2002 | Kurz et al. | |
| 6,353,950 B1 | 3/2002 | Bartlett et al. | |
| 6,358,260 B1 | 3/2002 | Ross et al. | |
| 6,369,355 B1 | 4/2002 | Saunders | |
| 6,375,668 B1 | 4/2002 | Gifford et al. | |
| 6,383,204 B1 | 5/2002 | Ferrera | |
| 6,383,205 B1 | 5/2002 | Samson et al. | |
| 6,387,065 B1 | 5/2002 | Tumey | |
| 6,391,044 B1 | 5/2002 | Yadav et al. | |
| 6,395,014 B1 | 5/2002 | Macoviak et al. | |
| 6,402,771 B1 | 6/2002 | Palmer et al. | |
| 6,425,905 B1 | 7/2002 | Guimaraes et al. | |
| 6,428,558 B1 | 8/2002 | Jones et al. | |
| 6,447,531 B1 | 9/2002 | Amplatz | |
| 6,461,370 B1 | 10/2002 | Gray et al. | |
| 6,468,237 B1 | 10/2002 | Lina | |
| 6,482,217 B1 | 11/2002 | Pintor et al. | |
| 6,506,204 B2 | 1/2003 | Mazzocchi | |
| 6,511,492 B1 | 1/2003 | Rosenbluth et al. | |
| 6,511,504 B1 | 1/2003 | Lau et al. | |
| 6,514,273 B1 | 2/2003 | Voss et al. | |
| 6,517,513 B1 | 2/2003 | Covington et al. | |
| 6,517,888 B1 | 2/2003 | Weber | |
| 6,521,865 B1 | 2/2003 | Jones et al. | |
| 6,530,935 B2 | 3/2003 | Wensel et al. | |
| 6,530,939 B1 | 3/2003 | Hopkins et al. | |
| 6,540,722 B1 | 4/2003 | Boyle et al. | |
| 6,544,276 B1 | 4/2003 | Gholam-Azizi | |

(56) References Cited

U.S. PATENT DOCUMENTS

| | | |
|---|---|---|
| 6,544,279 B1 | 4/2003 | Hopkins et al. |
| 6,547,756 B1 * | 4/2003 | Greter .................... A61M 1/06 |
| | | 604/346 |
| 6,554,848 B2 | 4/2003 | Boylan et al. |
| 6,563,080 B2 | 5/2003 | Shapovalov et al. |
| 6,569,183 B1 | 5/2003 | Kim et al. |
| 6,585,755 B2 | 7/2003 | Jackson et al. |
| 6,589,263 B1 | 7/2003 | Hopkins et al. |
| 6,589,265 B1 | 7/2003 | Palmer et al. |
| 6,602,261 B2 | 8/2003 | Greene, Jr. et al. |
| 6,602,264 B1 | 8/2003 | McGuckin, Jr. |
| 6,602,265 B2 | 8/2003 | Dubrul et al. |
| 6,605,074 B2 | 8/2003 | Zadno-Azizi et al. |
| 6,605,111 B2 | 8/2003 | Bose et al. |
| 6,610,077 B1 | 8/2003 | Hancock et al. |
| 6,612,012 B2 | 9/2003 | Mitelberg et al. |
| 6,616,676 B2 | 9/2003 | Bashiri et al. |
| 6,626,861 B1 | 9/2003 | Hart et al. |
| 6,626,936 B2 | 9/2003 | Stinson |
| 6,632,241 B1 | 10/2003 | Hancock et al. |
| 6,635,070 B2 | 10/2003 | Leeflang et al. |
| 6,652,576 B1 | 11/2003 | Stalker |
| 6,656,218 B1 | 12/2003 | Denardo et al. |
| 6,663,644 B1 | 12/2003 | Ross et al. |
| 6,666,882 B1 | 12/2003 | Bose et al. |
| 6,669,721 B1 | 12/2003 | Bose et al. |
| 6,673,028 B1 | 1/2004 | Argenta et al. |
| 6,673,089 B1 | 1/2004 | Yassour et al. |
| 6,679,893 B1 | 1/2004 | Tran |
| 6,682,546 B2 | 1/2004 | Amplatz |
| 6,689,986 B2 | 2/2004 | Patel et al. |
| 6,692,504 B2 | 2/2004 | Kurz et al. |
| 6,695,813 B1 | 2/2004 | Boyle et al. |
| 6,696,666 B2 | 2/2004 | Merdan et al. |
| 6,696,667 B1 | 2/2004 | Flanagan |
| 6,706,054 B2 | 3/2004 | Wessman et al. |
| 6,710,285 B2 | 3/2004 | Brown et al. |
| 6,712,835 B2 | 3/2004 | Mazzocchi et al. |
| 6,719,934 B2 | 4/2004 | Stinson |
| 6,740,112 B2 | 5/2004 | Yodfat et al. |
| 6,749,560 B1 | 6/2004 | Konstorum et al. |
| 6,749,619 B2 | 6/2004 | Ouriel et al. |
| 6,773,448 B2 | 8/2004 | Kusleika et al. |
| 6,777,647 B1 | 8/2004 | Messal et al. |
| 6,818,063 B1 | 11/2004 | Kerrigan |
| 6,827,701 B2 | 12/2004 | MacMahon et al. |
| 6,837,901 B2 | 1/2005 | Rabkin et al. |
| 6,840,950 B2 | 1/2005 | Stanford et al. |
| 6,843,798 B2 | 1/2005 | Kusleika et al. |
| 6,844,603 B2 | 1/2005 | Georgakos et al. |
| 6,849,081 B2 | 2/2005 | Sepetka et al. |
| 6,855,153 B2 | 2/2005 | Saadat |
| 6,855,154 B2 | 2/2005 | Abdel-Gawwad |
| 6,855,909 B2 | 2/2005 | Patel et al. |
| 6,860,893 B2 | 3/2005 | Wallace et al. |
| 6,861,615 B2 | 3/2005 | Wojcik et al. |
| 6,862,794 B2 | 3/2005 | Hopkins |
| 6,866,680 B2 | 3/2005 | Yassour et al. |
| 6,867,389 B2 | 3/2005 | Shapovalov et al. |
| 6,878,163 B2 | 4/2005 | Denardo et al. |
| 6,904,631 B2 | 6/2005 | Vralik et al. |
| 6,913,618 B2 | 7/2005 | Denardo et al. |
| 6,920,677 B2 | 7/2005 | Dolan et al. |
| 6,927,359 B2 | 8/2005 | Kleine et al. |
| 6,932,828 B2 | 8/2005 | Bonnette et al. |
| 6,949,103 B2 | 9/2005 | Mazzocchi et al. |
| 6,953,472 B2 | 10/2005 | Palmer et al. |
| 6,964,670 B1 | 11/2005 | Shah et al. |
| 6,977,355 B2 | 12/2005 | Duley et al. |
| 6,989,019 B2 | 1/2006 | Mazzocchi et al. |
| 7,004,915 B2 | 2/2006 | Boynton et al. |
| 7,004,954 B1 | 2/2006 | Voss et al. |
| 7,018,401 B1 | 3/2006 | Hyodoh et al. |
| 7,029,494 B2 | 4/2006 | Soun et al. |
| 7,033,375 B2 | 4/2006 | Mazzocchi et al. |
| D520,023 S | 5/2006 | Goto et al. |
| 7,037,316 B2 | 5/2006 | McGuckin, Jr. et al. |
| 7,038,334 B2 | 5/2006 | Botos et al. |
| 7,048,752 B2 | 5/2006 | Mazzocchi et al. |
| 7,083,640 B2 | 8/2006 | Lombardi et al. |
| 7,090,688 B2 | 8/2006 | Nishtala et al. |
| 7,093,416 B2 | 8/2006 | Johnson et al. |
| 7,093,527 B2 | 8/2006 | Rapaport et al. |
| 7,105,003 B2 | 9/2006 | Hiltebrandt |
| 7,108,683 B2 | 9/2006 | Zamierowski |
| 7,118,539 B2 | 10/2006 | Vrba et al. |
| 7,125,414 B2 | 10/2006 | Blackledge et al. |
| 7,128,073 B1 | 10/2006 | van der Burg et al. |
| 7,128,752 B2 | 10/2006 | Bales |
| 7,131,986 B2 | 11/2006 | Sirhan et al. |
| 7,135,039 B2 | 11/2006 | De Scheerder et al. |
| 7,144,390 B1 | 12/2006 | Hannigan et al. |
| 7,152,605 B2 | 12/2006 | Khairkhahan et al. |
| 7,172,614 B2 | 2/2007 | Boyle et al. |
| 7,179,273 B1 | 2/2007 | Palmer et al. |
| 7,198,046 B1 | 4/2007 | Argenta et al. |
| 7,211,109 B2 | 5/2007 | Thompson |
| 7,216,651 B2 | 5/2007 | Argenta et al. |
| 7,220,269 B1 | 5/2007 | Ansel et al. |
| 7,220,271 B2 | 5/2007 | Clubb et al. |
| 7,252,680 B2 | 8/2007 | Freitag |
| 7,276,052 B2 | 10/2007 | Kobayashi et al. |
| 7,300,429 B2 | 11/2007 | Fitzgerald et al. |
| 7,306,618 B2 | 12/2007 | Demond et al. |
| 7,306,624 B2 | 12/2007 | Yodfat et al. |
| 7,311,700 B2 | 12/2007 | Guimaraes et al. |
| 7,323,001 B2 | 1/2008 | Clubb et al. |
| 7,344,546 B2 | 3/2008 | Wulfman et al. |
| 7,367,985 B2 | 5/2008 | Mazzocchi et al. |
| 7,367,986 B2 | 5/2008 | Mazzocchi et al. |
| 7,371,250 B2 | 5/2008 | Mazzocchi et al. |
| 7,374,564 B2 | 5/2008 | Brown |
| 7,381,198 B2 | 6/2008 | Noriega et al. |
| D573,609 S | 7/2008 | Bilger |
| 7,404,820 B2 | 7/2008 | Mazzocchi et al. |
| 7,410,491 B2 | 8/2008 | Hopkins et al. |
| 7,410,492 B2 | 8/2008 | Mazzocchi et al. |
| 7,410,602 B2 | 8/2008 | Davey et al. |
| 7,442,200 B2 | 10/2008 | Mazzocchi et al. |
| 7,462,192 B2 | 12/2008 | Norton et al. |
| 7,476,034 B2 | 1/2009 | Shedlov et al. |
| 7,514,075 B2 | 4/2009 | Hedrick et al. |
| 7,537,600 B2 | 5/2009 | Eskuri |
| 7,556,635 B2 | 7/2009 | Mazzocchi et al. |
| 7,556,636 B2 | 7/2009 | Mazzocchi et al. |
| 7,566,338 B2 | 7/2009 | Mazzocchi et al. |
| 7,572,273 B2 | 8/2009 | Mazzocchi et al. |
| 7,572,290 B2 | 8/2009 | Yodfat et al. |
| 7,582,101 B2 | 9/2009 | Jones et al. |
| 7,588,597 B2 | 9/2009 | Frid |
| D604,746 S | 11/2009 | Nishido et al. |
| 7,618,434 B2 | 11/2009 | Santra et al. |
| 7,621,870 B2 | 11/2009 | Berrada et al. |
| 7,622,070 B2 | 11/2009 | Atladottir et al. |
| 7,645,261 B2 | 1/2010 | Hinchliffe |
| 7,645,291 B2 | 1/2010 | Ross et al. |
| 7,651,514 B2 | 1/2010 | Salahieh et al. |
| 7,658,746 B2 | 2/2010 | Ross et al. |
| 7,666,161 B2 | 2/2010 | Nash et al. |
| 7,669,799 B2 | 3/2010 | Elzey et al. |
| 7,670,355 B2 | 3/2010 | Mazzocchi et al. |
| 7,670,356 B2 | 3/2010 | Mazzocchi et al. |
| 7,678,130 B2 | 3/2010 | Mazzocchi et al. |
| 7,686,815 B2 | 3/2010 | Mazzocchi et al. |
| 7,717,853 B2 | 5/2010 | Nita |
| 7,717,935 B2 | 5/2010 | Tsugita et al. |
| 7,735,493 B2 | 6/2010 | van der Burg et al. |
| 7,763,011 B2 | 7/2010 | Ortiz et al. |
| 7,780,646 B2 | 8/2010 | Farnholtz |
| 7,786,406 B2 | 8/2010 | Flanagan |
| 7,798,992 B2 | 9/2010 | Ortiz |
| 7,828,790 B2 | 11/2010 | Griffin |
| 7,828,815 B2 | 11/2010 | Mazzocchi et al. |
| 7,828,816 B2 | 11/2010 | Mazzocchi et al. |

(56) References Cited

U.S. PATENT DOCUMENTS

| | | |
|---|---|---|
| 7,837,726 B2 | 11/2010 | Von Oepen et al. |
| 7,846,175 B2 | 12/2010 | Bonnette et al. |
| 7,857,844 B2 | 12/2010 | Norton et al. |
| 7,862,577 B2 | 1/2011 | Gray et al. |
| 7,875,050 B2 | 1/2011 | Samson et al. |
| 7,879,062 B2 | 2/2011 | Galdonik et al. |
| 7,892,188 B2 | 2/2011 | Walker et al. |
| 7,909,801 B2 | 3/2011 | Hinchliffe |
| 7,914,549 B2 | 3/2011 | Morsi |
| 7,918,822 B2 | 4/2011 | Kumar et al. |
| 7,922,732 B2 | 4/2011 | Mazzocchi et al. |
| 7,931,651 B2 | 4/2011 | Webb et al. |
| 7,931,659 B2 | 4/2011 | Bose et al. |
| 7,931,664 B2 | 4/2011 | Gray et al. |
| 7,932,479 B2 | 4/2011 | Bialas et al. |
| 7,942,925 B2 | 5/2011 | Yodfat et al. |
| 7,955,345 B2 | 6/2011 | Kucharczyk et al. |
| 7,955,449 B2 | 6/2011 | Prokoshkin et al. |
| 7,971,333 B2 | 7/2011 | Gale et al. |
| 7,989,042 B2 | 8/2011 | Obara et al. |
| 7,993,302 B2 | 8/2011 | Hebert et al. |
| 7,993,363 B2 | 8/2011 | Demond et al. |
| 7,993,364 B2 | 8/2011 | Morsi |
| 7,996,993 B2 | 8/2011 | Gray et al. |
| 7,998,163 B2 | 8/2011 | Salahieh et al. |
| 8,003,157 B2 | 8/2011 | Andreacchi et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,044,322 B2 | 10/2011 | Merdan |
| 8,052,640 B2 | 11/2011 | Fiorella et al. |
| 8,057,497 B1 | 11/2011 | Raju et al. |
| 8,070,735 B2 | 12/2011 | Koch et al. |
| 8,070,764 B2 | 12/2011 | Ross et al. |
| 8,070,769 B2 | 12/2011 | Broome |
| 8,070,791 B2 | 12/2011 | Ferrera et al. |
| 8,088,140 B2 | 1/2012 | Ferrera et al. |
| 8,092,483 B2 | 1/2012 | Gladonik et al. |
| 8,092,486 B2 | 1/2012 | Berrada et al. |
| 8,092,508 B2 | 1/2012 | Leynov et al. |
| 8,105,580 B2 | 1/2012 | Fraser et al. |
| 8,142,456 B2 | 3/2012 | Rosqueta et al. |
| 8,147,534 B2 | 4/2012 | Berez et al. |
| 8,152,833 B2 | 4/2012 | Zaver et al. |
| 8,157,833 B2 | 4/2012 | Au et al. |
| 8,163,276 B2 | 4/2012 | Hedrick et al. |
| 8,192,484 B2 | 6/2012 | Frid |
| 8,197,493 B2 | 6/2012 | Ferrera et al. |
| 8,217,303 B2 | 7/2012 | Baxter et al. |
| 8,231,651 B2 | 7/2012 | Tsugita |
| 8,235,047 B2 | 8/2012 | Swann et al. |
| 8,235,955 B2 | 8/2012 | Blott et al. |
| 8,236,042 B2 | 8/2012 | Berez et al. |
| 8,252,010 B1 | 8/2012 | Raju et al. |
| 8,252,016 B2 | 8/2012 | Anwar |
| 8,257,421 B2 | 9/2012 | Berez et al. |
| 8,261,648 B1 | 9/2012 | Marchand et al. |
| 8,267,960 B2 | 9/2012 | Argenta et al. |
| 8,267,985 B2 | 9/2012 | Garcia et al. |
| 8,267,986 B2 | 9/2012 | Berez et al. |
| 8,273,101 B2 | 9/2012 | Garcia et al. |
| 8,278,593 B2 | 10/2012 | Bialas et al. |
| 8,292,914 B2 | 10/2012 | Morsi |
| 8,308,712 B2 | 11/2012 | Provost et al. |
| RE43,882 E | 12/2012 | Hopkins et al. |
| 8,333,796 B2 | 12/2012 | Tompkins et al. |
| 8,333,897 B2 | 12/2012 | Bialas et al. |
| 8,361,095 B2 | 1/2013 | Osborne |
| 8,361,138 B2 | 1/2013 | Adams |
| 8,366,620 B2 | 2/2013 | Nita |
| 8,366,735 B2 | 2/2013 | Bose et al. |
| 8,377,016 B2 | 2/2013 | Argenta et al. |
| 8,394,119 B2 | 3/2013 | Zaver et al. |
| 8,398,670 B2 | 3/2013 | Amplatz et al. |
| 8,398,701 B2 | 3/2013 | Berez et al. |
| 8,409,114 B2 | 4/2013 | Parins |
| 8,409,267 B2 | 4/2013 | Berez et al. |
| 8,409,269 B2 | 4/2013 | Berez et al. |
| 8,409,270 B2 | 4/2013 | Clerc et al. |
| 8,419,658 B2 | 4/2013 | Eskuri |
| 8,419,787 B2 | 4/2013 | Yodfat et al. |
| 8,425,549 B2 | 4/2013 | Lenker et al. |
| 8,435,218 B2 | 5/2013 | Hinchliffe |
| 8,444,668 B2 | 5/2013 | Jones et al. |
| 8,454,603 B2 | 6/2013 | Webb et al. |
| 8,460,312 B2 | 6/2013 | Bose et al. |
| 8,465,467 B2 | 6/2013 | Gao |
| 8,468,678 B2 | 6/2013 | Salahieh et al. |
| 8,475,487 B2 | 7/2013 | Bonnette et al. |
| 8,486,104 B2 | 7/2013 | Samson et al. |
| 8,486,105 B2 | 7/2013 | Demond et al. |
| 8,500,788 B2 | 8/2013 | Berez et al. |
| 8,529,614 B2 | 9/2013 | Berez et al. |
| 8,585,713 B2 | 11/2013 | Ferrera et al. |
| 8,591,453 B2 | 11/2013 | Stubkjaer et al. |
| 8,597,320 B2 | 12/2013 | Sepetka et al. |
| 8,603,132 B2 | 12/2013 | Anwar |
| 8,617,201 B2 | 12/2013 | Hopkins et al. |
| 8,617,234 B2 | 12/2013 | Garcia et al. |
| 8,623,067 B2 | 1/2014 | Berez et al. |
| 8,623,071 B2 | 1/2014 | Lundkvist et al. |
| 8,628,564 B2 | 1/2014 | Berez et al. |
| 8,632,498 B2 | 1/2014 | Rimsa et al. |
| 8,663,273 B2 | 3/2014 | Khairkhahan et al. |
| 8,671,815 B2 | 3/2014 | Hancock et al. |
| 8,679,150 B1 | 3/2014 | Janardhan et al. |
| 8,690,907 B1 | 4/2014 | Janardhan et al. |
| 8,696,621 B2 | 4/2014 | Gunday et al. |
| 8,715,314 B1 | 5/2014 | Janardhan et al. |
| 8,715,315 B1 | 5/2014 | Janardhan et al. |
| 8,715,316 B1 | 5/2014 | Janardhan et al. |
| 8,715,317 B1 | 5/2014 | Janardhan et al. |
| 8,715,338 B2 | 5/2014 | Frid |
| 8,721,676 B1 | 5/2014 | Janardhan et al. |
| 8,721,677 B1 | 5/2014 | Janardhan et al. |
| 8,728,116 B1 | 5/2014 | Janardhan et al. |
| 8,728,117 B1 | 5/2014 | Janardhan et al. |
| 8,733,618 B1 | 5/2014 | Janardhan et al. |
| 8,735,777 B1 | 5/2014 | Janardhan et al. |
| 8,747,432 B1 | 6/2014 | Janardhan et al. |
| 8,753,371 B1 | 6/2014 | Janardhan et al. |
| 8,758,315 B2 | 6/2014 | Chen et al. |
| 8,758,424 B2 | 6/2014 | Sacher et al. |
| D710,003 S | 7/2014 | Rimsa et al. |
| 8,764,787 B2 | 7/2014 | Ren |
| 8,764,794 B2 | 7/2014 | Argenta et al. |
| 8,771,299 B2 | 7/2014 | Diamant et al. |
| 8,783,151 B1 | 7/2014 | Janardhan et al. |
| 8,784,434 B2 | 7/2014 | Rosenbluth et al. |
| 8,784,446 B1 | 7/2014 | Janardhan et al. |
| 8,789,452 B1 | 7/2014 | Janardhan et al. |
| 8,790,299 B2 | 7/2014 | Gunday et al. |
| 8,790,365 B1 | 7/2014 | Janardhan et al. |
| 8,795,244 B2 | 8/2014 | Randolph et al. |
| 8,795,305 B2 | 8/2014 | Martin et al. |
| 8,795,330 B1 | 8/2014 | Janardhan et al. |
| 8,801,748 B2 | 8/2014 | Martin |
| 8,803,030 B1 | 8/2014 | Janardhan et al. |
| 8,813,625 B1 | 8/2014 | Janardhan et al. |
| 8,816,247 B1 | 8/2014 | Janardhan et al. |
| D712,933 S | 9/2014 | DeOreo et al. |
| 8,828,045 B1 | 9/2014 | Janardhan et al. |
| 8,834,520 B2 | 9/2014 | Argenta et al. |
| 8,845,678 B1 | 9/2014 | Janardhan et al. |
| 8,845,679 B1 | 9/2014 | Janardhan et al. |
| 8,852,227 B1 | 10/2014 | Janardhan et al. |
| 8,859,934 B1 | 10/2014 | Janardhan et al. |
| 8,863,631 B1 | 10/2014 | Janardhan et al. |
| 8,866,049 B1 | 10/2014 | Janardhan et al. |
| 8,869,670 B1 | 10/2014 | Janardhan et al. |
| 8,870,901 B1 | 10/2014 | Janardhan et al. |
| 8,870,910 B1 | 10/2014 | Janardhan et al. |
| 8,872,068 B1 | 10/2014 | Janardhan et al. |
| 8,874,434 B2 | 10/2014 | Collobert et al. |

(56) References Cited

U.S. PATENT DOCUMENTS

| | | |
|---|---|---|
| 8,882,797 B2 | 11/2014 | Janardhan et al. |
| 8,895,891 B2 | 11/2014 | Janardhan et al. |
| 8,904,914 B2 | 12/2014 | Janardhan et al. |
| 8,906,057 B2 | 12/2014 | Connor et al. |
| 8,910,555 B2 | 12/2014 | Janardhan et al. |
| 8,911,487 B2 | 12/2014 | Bennett et al. |
| 8,920,402 B2 | 12/2014 | Nash et al. |
| 8,932,320 B1 | 1/2015 | Janardhan et al. |
| 8,932,321 B1 | 1/2015 | Janardhan et al. |
| 8,968,330 B2 | 3/2015 | Rosenbluth et al. |
| 8,974,512 B2 | 3/2015 | Aboytes et al. |
| 8,992,553 B2 | 3/2015 | Diamant et al. |
| 8,998,947 B2 | 4/2015 | Aboytes et al. |
| 9,023,273 B2 | 5/2015 | Kibalo |
| 9,034,007 B2 | 5/2015 | Janardhan |
| 9,050,136 B2 | 6/2015 | Webb et al. |
| D737,431 S | 8/2015 | Rimsa et al. |
| 9,095,326 B2 | 8/2015 | Ritchie et al. |
| 9,119,656 B2 | 9/2015 | Bose et al. |
| 9,125,731 B2 | 9/2015 | Ross et al. |
| 9,132,000 B2 | 9/2015 | Vantassel et al. |
| 9,179,931 B2 | 11/2015 | Janardhan et al. |
| 9,179,995 B2 | 11/2015 | Janardhan et al. |
| 9,186,151 B2 | 11/2015 | Tompkins et al. |
| 9,198,687 B2 | 12/2015 | Fulkerson et al. |
| 9,211,132 B2 | 12/2015 | Bowman |
| 9,211,396 B2 | 12/2015 | Aboytes |
| 9,220,522 B2 | 12/2015 | Fulkerson et al. |
| 9,289,193 B2 | 3/2016 | Argenta et al. |
| 9,314,324 B2 | 4/2016 | Janardhan et al. |
| 9,314,568 B2 | 4/2016 | Gurtner et al. |
| 9,333,024 B2 | 5/2016 | Woloszko et al. |
| 9,370,611 B2 | 6/2016 | Ross et al. |
| 9,375,513 B2 | 6/2016 | Sun et al. |
| 9,445,831 B2 | 9/2016 | Mark |
| 9,446,189 B2 | 9/2016 | Rimsa et al. |
| 9,526,865 B2 | 12/2016 | Quick |
| 9,532,792 B2 | 1/2017 | Galdonik et al. |
| 9,532,863 B2 | 1/2017 | Hayzlett |
| 9,549,805 B2 | 1/2017 | Hayzlett et al. |
| 9,554,805 B2 | 1/2017 | Tompkins et al. |
| 9,561,129 B2 | 2/2017 | Ross et al. |
| 9,566,089 B2 | 2/2017 | Webb et al. |
| 9,592,068 B2 | 3/2017 | Janardhan et al. |
| 9,594,004 B2 | 3/2017 | Fry et al. |
| 9,615,832 B2 | 4/2017 | Bose et al. |
| 9,615,951 B2 | 4/2017 | Bennett et al. |
| D785,679 S | 5/2017 | Hartung |
| D786,939 S | 5/2017 | Nelson et al. |
| 9,655,633 B2 | 5/2017 | Leynov et al. |
| 9,662,129 B2 | 5/2017 | Galdonik et al. |
| 9,675,358 B2 | 6/2017 | Wagner et al. |
| D795,420 S | 8/2017 | Rimsa et al. |
| 9,737,455 B2 | 8/2017 | Argenta et al. |
| 9,750,524 B2 | 9/2017 | Janardhan et al. |
| 9,775,621 B2 | 10/2017 | Tompkins et al. |
| 9,833,251 B2 | 12/2017 | Janardhan et al. |
| D810,145 S | 2/2018 | Sinico |
| 9,883,854 B2 | 2/2018 | Mak |
| 9,883,877 B2 | 2/2018 | Look |
| 9,901,435 B2 | 2/2018 | Janardhan et al. |
| 9,913,705 B2 | 3/2018 | Hayzlett et al. |
| 9,913,936 B2 | 3/2018 | Look et al. |
| 9,915,674 B2 | 3/2018 | Zordan |
| 9,943,321 B2 | 4/2018 | Nita |
| 9,999,710 B2 | 6/2018 | Ross et al. |
| D822,718 S | 7/2018 | Hartung |
| 10,022,214 B2 | 7/2018 | Hayzlett |
| D826,282 S | 8/2018 | Mead et al. |
| D826,283 S | 8/2018 | Mead et al. |
| 10,058,339 B2 | 8/2018 | Galdonik et al. |
| 10,076,318 B2 | 9/2018 | Argenta et al. |
| D838,746 S | 1/2019 | Gan |
| D838,747 S | 1/2019 | Gan |
| 10,251,739 B2 | 4/2019 | Janardhan et al. |
| D847,864 S | 5/2019 | Janardhan et al. |
| D847,865 S | 5/2019 | Janardhan et al. |
| D847,866 S | 5/2019 | Janardhan et al. |
| D850,490 S | 6/2019 | Janardhan et al. |
| 10,335,260 B2 | 7/2019 | Janardhan et al. |
| 10,342,655 B2 | 7/2019 | Janardhan et al. |
| 10,390,926 B2 | 8/2019 | Janardhan et al. |
| 10,463,468 B2 | 11/2019 | Janardhan et al. |
| 2001/0031980 A1 | 10/2001 | Wensel et al. |
| 2002/0010487 A1 | 1/2002 | Evans et al. |
| 2002/0013548 A1 | 1/2002 | Hinchliffe |
| 2002/0026211 A1 | 2/2002 | Khosravi et al. |
| 2002/0045916 A1 | 4/2002 | Gray et al. |
| 2002/0052638 A1 | 5/2002 | Zadno-Azizi |
| 2002/0082558 A1 | 6/2002 | Samson et al. |
| 2002/0091355 A1 | 7/2002 | Hayden |
| 2002/0099408 A1 | 7/2002 | Marks et al. |
| 2002/0099436 A1 | 7/2002 | Thornton et al. |
| 2002/0111648 A1 | 8/2002 | Kusleika et al. |
| 2002/0133111 A1 | 9/2002 | Shadduck |
| 2002/0143349 A1 | 10/2002 | Gifford, III et al. |
| 2002/0161395 A1 | 10/2002 | Douk et al. |
| 2002/0169473 A1 | 11/2002 | Sepetka et al. |
| 2002/0188314 A1 | 12/2002 | Anderson et al. |
| 2002/0193866 A1 | 12/2002 | Saunders |
| 2002/0194670 A1 | 12/2002 | Hashemi |
| 2002/0198550 A1 | 12/2002 | Nash et al. |
| 2002/0198589 A1 | 12/2002 | Leong |
| 2003/0004537 A1 | 1/2003 | Boyle et al. |
| 2003/0023262 A1 | 1/2003 | Welch |
| 2003/0065356 A1 | 4/2003 | Tsugita et al. |
| 2003/0069549 A1 | 4/2003 | MacMahon et al. |
| 2003/0078519 A1 | 4/2003 | Salahieh et al. |
| 2003/0097094 A1 | 5/2003 | Ouriel et al. |
| 2003/0097710 A1 | 5/2003 | Adrian |
| 2003/0100945 A1 | 5/2003 | Yodfat et al. |
| 2003/0114919 A1 | 6/2003 | McQuiston et al. |
| 2003/0135265 A1 | 7/2003 | Stinson |
| 2003/0139255 A1 | 7/2003 | Lina |
| 2003/0176884 A1 | 9/2003 | Berrada et al. |
| 2003/0195553 A1 | 10/2003 | Wallace et al. |
| 2003/0225448 A1 | 12/2003 | Gerberding |
| 2003/0226833 A1 | 12/2003 | Shapovalov et al. |
| 2004/0004061 A1 | 1/2004 | Merdan |
| 2004/0004063 A1 | 1/2004 | Merdan |
| 2004/0024416 A1 | 2/2004 | Yodfat et al. |
| 2004/0039435 A1 | 2/2004 | Hancock et al. |
| 2004/0044391 A1 | 3/2004 | Porter |
| 2004/0073293 A1 | 4/2004 | Thompson |
| 2004/0073300 A1 | 4/2004 | Chouinard et al. |
| 2004/0088037 A1 | 5/2004 | Nachreiner et al. |
| 2004/0089643 A1 | 5/2004 | Jones et al. |
| 2004/0093015 A1 | 5/2004 | Ogle |
| 2004/0098023 A1 | 5/2004 | Lee et al. |
| 2004/0098033 A1 | 5/2004 | Leeflang et al. |
| 2004/0118902 A1 | 6/2004 | Adams |
| 2004/0148007 A1 | 7/2004 | Jackson et al. |
| 2004/0167613 A1 | 8/2004 | Yodfat et al. |
| 2004/0168298 A1 | 9/2004 | Dolan et al. |
| 2004/0182451 A1 | 9/2004 | Poirier |
| 2004/0193140 A1 | 9/2004 | Griffin et al. |
| 2004/0204737 A1 | 10/2004 | Boismier et al. |
| 2004/0220610 A1 | 11/2004 | Kreidler et al. |
| 2004/0225186 A1 | 11/2004 | Horne, Jr. et al. |
| 2004/0236412 A1 | 11/2004 | Brar et al. |
| 2005/0015110 A1 | 1/2005 | Fogarty et al. |
| 2005/0021075 A1 | 1/2005 | Bonnette et al. |
| 2005/0035101 A1 | 2/2005 | Jones et al. |
| 2005/0050624 A1 | 3/2005 | Pangramuyen |
| 2005/0085769 A1 | 4/2005 | MacMahon et al. |
| 2005/0085846 A1 | 4/2005 | Carrison et al. |
| 2005/0120471 A1 | 6/2005 | Lim |
| 2005/0124969 A1 | 6/2005 | Fitzgerald et al. |
| 2005/0131522 A1 | 6/2005 | Stinson et al. |
| 2005/0133486 A1 | 6/2005 | Baker et al. |
| 2005/0149108 A1 | 7/2005 | Cox |
| 2005/0192548 A1 | 9/2005 | Dolliver et al. |
| 2005/0192624 A1 | 9/2005 | Mazzocchi et al. |
| 2005/0203553 A1 | 9/2005 | Maschke |

(56) References Cited

U.S. PATENT DOCUMENTS

| | | |
|---|---|---|
| 2005/0228417 A1 | 10/2005 | Teitelbaum et al. |
| 2005/0234474 A1 | 10/2005 | DeMello et al. |
| 2005/0236911 A1 | 10/2005 | Botos et al. |
| 2005/0251200 A1 | 11/2005 | Porter |
| 2005/0256563 A1 | 11/2005 | Clerc et al. |
| 2005/0267510 A1 | 12/2005 | Razack |
| 2005/0277975 A1 | 12/2005 | Saadat et al. |
| 2005/0283166 A1 | 12/2005 | Greenhalgh |
| 2005/0283186 A1 | 12/2005 | Berrada et al. |
| 2006/0004346 A1 | 1/2006 | Begg |
| 2006/0009799 A1 | 1/2006 | Kleshinski et al. |
| 2006/0020286 A1 | 1/2006 | Niermann |
| 2006/0030878 A1 | 2/2006 | Anderson et al. |
| 2006/0047286 A1 | 3/2006 | West |
| 2006/0058837 A1 | 3/2006 | Bose et al. |
| 2006/0070516 A1 | 4/2006 | McCullagh et al. |
| 2006/0100687 A1 | 5/2006 | Fahey et al. |
| 2006/0116712 A1 | 6/2006 | Sepetka et al. |
| 2006/0116713 A1 | 6/2006 | Sepetka et al. |
| 2006/0122687 A1 | 6/2006 | Bassler et al. |
| 2006/0136043 A1 | 6/2006 | Cully et al. |
| 2006/0155305 A1 | 7/2006 | Freudenthal et al. |
| 2006/0161198 A1 | 7/2006 | Sakai et al. |
| 2006/0161253 A1 | 7/2006 | Lesh |
| 2006/0206143 A1 | 9/2006 | West |
| 2006/0206196 A1 | 9/2006 | Porter |
| 2006/0206200 A1 | 9/2006 | Garcia et al. |
| 2006/0229638 A1 | 10/2006 | Abrams et al. |
| 2006/0229645 A1 | 10/2006 | Bonnette et al. |
| 2006/0241739 A1 | 10/2006 | Besselink et al. |
| 2006/0264904 A1 | 11/2006 | Kerby et al. |
| 2006/0276887 A1 | 12/2006 | Brady et al. |
| 2006/0282111 A1 | 12/2006 | Morsi |
| 2007/0016233 A1 | 1/2007 | Ferrara et al. |
| 2007/0027522 A1 | 2/2007 | Chang et al. |
| 2007/0034615 A1 | 2/2007 | Kleine |
| 2007/0038100 A1 | 2/2007 | Nita |
| 2007/0045255 A1 | 3/2007 | Kleine et al. |
| 2007/0060880 A1 | 3/2007 | Gregorich et al. |
| 2007/0060942 A2 | 3/2007 | Zadno-Azizi |
| 2007/0088383 A1 | 4/2007 | Pal et al. |
| 2007/0112381 A1 | 5/2007 | Figulla et al. |
| 2007/0118165 A1 | 5/2007 | DeMello et al. |
| 2007/0129652 A1 | 6/2007 | Nita |
| 2007/0135832 A1 | 6/2007 | Wholey et al. |
| 2007/0135833 A1 | 6/2007 | Talpade et al. |
| 2007/0142903 A1 | 6/2007 | Dave |
| 2007/0168019 A1 | 7/2007 | Amplatz et al. |
| 2007/0173921 A1 | 7/2007 | Wholey et al. |
| 2007/0185500 A1 | 8/2007 | Martin et al. |
| 2007/0185501 A1 | 8/2007 | Martin et al. |
| 2007/0197103 A1 | 8/2007 | Martin et al. |
| 2007/0198029 A1 | 8/2007 | Martin et al. |
| 2007/0198030 A1 | 8/2007 | Martin et al. |
| 2007/0225749 A1 | 9/2007 | Martin et al. |
| 2007/0228023 A1 | 10/2007 | Kleine et al. |
| 2007/0233174 A1 | 10/2007 | Hocking et al. |
| 2007/0239261 A1 | 10/2007 | Bose et al. |
| 2007/0265656 A1 | 11/2007 | Amplatz et al. |
| 2007/0288054 A1 | 12/2007 | Tanaka et al. |
| 2008/0015478 A1 | 1/2008 | Bose |
| 2008/0027356 A1 | 1/2008 | Chen et al. |
| 2008/0033475 A1 | 2/2008 | Meng |
| 2008/0045881 A1 | 2/2008 | Teitelbaum et al. |
| 2008/0051708 A1 | 2/2008 | Kumar et al. |
| 2008/0065008 A1 | 3/2008 | Barbut et al. |
| 2008/0077119 A1 | 3/2008 | Snyder et al. |
| 2008/0097374 A1 | 4/2008 | Korleski et al. |
| 2008/0097393 A1 | 4/2008 | Chen |
| 2008/0097395 A1 | 4/2008 | Adams et al. |
| 2008/0097398 A1 | 4/2008 | Mitelberg et al. |
| 2008/0097401 A1 | 4/2008 | Trapp et al. |
| 2008/0107641 A1 | 5/2008 | Kuebler |
| 2008/0109063 A1 | 5/2008 | Hancock et al. |
| 2008/0147110 A1 | 6/2008 | Wijeratne |
| 2008/0177224 A1 | 7/2008 | Kelly et al. |
| 2008/0195230 A1 | 8/2008 | Quijano et al. |
| 2008/0221601 A1 | 9/2008 | Huynh et al. |
| 2008/0228209 A1 | 9/2008 | DeMello et al. |
| 2008/0234722 A1 | 9/2008 | Bonnette et al. |
| 2008/0262487 A1 | 10/2008 | Wensel et al. |
| 2008/0269774 A1 | 10/2008 | Garcia et al. |
| 2008/0275464 A1 | 11/2008 | Abrams et al. |
| 2008/0275488 A1 | 11/2008 | Fleming |
| 2008/0294181 A1 | 11/2008 | Wensel et al. |
| 2008/0296274 A1 | 12/2008 | Bialas et al. |
| 2008/0300673 A1 | 12/2008 | Clerc et al. |
| 2008/0306499 A1 | 12/2008 | Katoh et al. |
| 2008/0312681 A1 | 12/2008 | Ansel et al. |
| 2008/0319355 A1 | 12/2008 | Nita |
| 2009/0024085 A1 | 1/2009 | To et al. |
| 2009/0025820 A1 | 1/2009 | Adams |
| 2009/0030400 A1 | 1/2009 | Bose et al. |
| 2009/0036833 A1 | 2/2009 | Parins |
| 2009/0043283 A1 | 2/2009 | Turnland et al. |
| 2009/0062841 A1 | 3/2009 | Amplatz et al. |
| 2009/0076540 A1 | 3/2009 | Marks et al. |
| 2009/0082800 A1 | 3/2009 | Janardhan |
| 2009/0099647 A1 | 4/2009 | Glimsdale et al. |
| 2009/0105737 A1 | 4/2009 | Fulkerson et al. |
| 2009/0105748 A1 | 4/2009 | Fogarty et al. |
| 2009/0105753 A1 | 4/2009 | Greenhalgh et al. |
| 2009/0112251 A1 | 4/2009 | Qian et al. |
| 2009/0114626 A1 | 5/2009 | Oberg |
| 2009/0125097 A1 | 5/2009 | Bruszewski et al. |
| 2009/0157048 A1 | 6/2009 | Sutermeister et al. |
| 2009/0172935 A1 | 7/2009 | Anderson et al. |
| 2009/0188269 A1 | 7/2009 | Attarwala et al. |
| 2009/0198269 A1 | 8/2009 | Hannes et al. |
| 2009/0208385 A1 | 8/2009 | Howorth et al. |
| 2009/0209855 A1 | 8/2009 | Drilling et al. |
| 2009/0216326 A1 | 8/2009 | Hirpara et al. |
| 2009/0221995 A1 | 9/2009 | Harlan |
| 2009/0248071 A1 | 10/2009 | Saint et al. |
| 2009/0264985 A1 | 10/2009 | Bruszewski |
| 2009/0275974 A1 | 11/2009 | Marchand et al. |
| 2009/0287120 A1 | 11/2009 | Ferren et al. |
| 2009/0297582 A1 | 12/2009 | Meyer et al. |
| 2009/0306702 A1 | 12/2009 | Miloslayski et al. |
| 2009/0306762 A1 | 12/2009 | McCullagh et al. |
| 2009/0312834 A1 | 12/2009 | Wood et al. |
| 2009/0318892 A1 | 12/2009 | Aboytes et al. |
| 2009/0318948 A1 | 12/2009 | Linder et al. |
| 2010/0010622 A1 | 1/2010 | Lowe et al. |
| 2010/0023034 A1 | 1/2010 | Linder et al. |
| 2010/0023038 A1 | 1/2010 | Santra et al. |
| 2010/0023105 A1 | 1/2010 | Levy et al. |
| 2010/0030256 A1 | 2/2010 | Dubrul et al. |
| 2010/0049240 A1 | 2/2010 | Papp |
| 2010/0069882 A1 | 3/2010 | Jennings et al. |
| 2010/0069948 A1 | 3/2010 | Veznedaroglu et al. |
| 2010/0087850 A1 | 4/2010 | Razack |
| 2010/0102046 A1 | 4/2010 | Huang et al. |
| 2010/0114017 A1 | 5/2010 | Lenker et al. |
| 2010/0131000 A1 | 5/2010 | DeMello et al. |
| 2010/0137892 A1 | 6/2010 | Krolik et al. |
| 2010/0137899 A1 | 6/2010 | Razack |
| 2010/0152834 A1 | 6/2010 | Hannes et al. |
| 2010/0191178 A1* | 7/2010 | Ross ................. A61F 9/00736 604/22 |
| 2010/0191319 A1 | 7/2010 | Lilburn et al. |
| 2010/0193485 A1 | 8/2010 | Anukhin et al. |
| 2010/0204672 A1 | 8/2010 | Lockhart et al. |
| 2010/0217276 A1 | 8/2010 | Garrison et al. |
| 2010/0217303 A1 | 8/2010 | Goodwin |
| 2010/0230391 A1 | 9/2010 | Baxter et al. |
| 2010/0262221 A1 | 10/2010 | Schafer et al. |
| 2010/0268264 A1 | 10/2010 | Bonnette et al. |
| 2010/0280434 A1 | 11/2010 | Raney et al. |
| 2010/0280592 A1 | 11/2010 | Shin et al. |
| 2010/0318097 A1 | 12/2010 | Ferrera et al. |
| 2011/0036820 A1 | 2/2011 | Merdan |
| 2011/0046719 A1 | 2/2011 | Frid |
| 2011/0056350 A1 | 3/2011 | Gale et al. |

(56) References Cited

U.S. PATENT DOCUMENTS

| | | |
|---|---|---|
| 2011/0060359 A1 | 3/2011 | Hannes et al. |
| 2011/0060400 A1 | 3/2011 | Oepen et al. |
| 2011/0077620 A1 | 3/2011 | deBeer |
| 2011/0082491 A1 | 4/2011 | Sepetka et al. |
| 2011/0082493 A1 | 4/2011 | Samson et al. |
| 2011/0087147 A1 | 4/2011 | Garrison et al. |
| 2011/0094708 A1 | 4/2011 | Cardone |
| 2011/0125132 A1 | 5/2011 | Krolik et al. |
| 2011/0125181 A1 | 5/2011 | Brady et al. |
| 2011/0152993 A1 | 6/2011 | Marchand et al. |
| 2011/0160621 A1 | 6/2011 | Nita |
| 2011/0160757 A1 | 6/2011 | Ferrera et al. |
| 2011/0160760 A1 | 6/2011 | Ferrera et al. |
| 2011/0160761 A1 | 6/2011 | Ferrera et al. |
| 2011/0184454 A1 | 7/2011 | Barry et al. |
| 2011/0190797 A1 | 8/2011 | Fulkerson et al. |
| 2011/0190868 A1 | 8/2011 | Ducke et al. |
| 2011/0203446 A1 | 8/2011 | Dow et al. |
| 2011/0208227 A1 | 8/2011 | Becking |
| 2011/0210108 A1 | 9/2011 | Bialas et al. |
| 2011/0213403 A1 | 9/2011 | Aboytes |
| 2011/0213407 A1 | 9/2011 | Morsi |
| 2011/0238041 A1 | 9/2011 | Lim et al. |
| 2011/0264133 A1 | 10/2011 | Hanlon et al. |
| 2011/0265943 A1 | 11/2011 | Rosqueta et al. |
| 2011/0283871 A1 | 11/2011 | Adams |
| 2011/0295359 A1 | 12/2011 | Clerc et al. |
| 2011/0307072 A1 | 12/2011 | Anderson et al. |
| 2011/0313328 A1 | 12/2011 | Nita |
| 2011/0319917 A1 | 12/2011 | Ferrera et al. |
| 2011/0319927 A1 | 12/2011 | Nita |
| 2012/0016406 A1 | 1/2012 | Ferrera et al. |
| 2012/0022579 A1 | 1/2012 | Fulton |
| 2012/0029616 A1 | 2/2012 | Guerriero et al. |
| 2012/0041460 A1 | 2/2012 | Ferrera et al. |
| 2012/0055614 A1 | 3/2012 | Hancock et al. |
| 2012/0057813 A1 | 3/2012 | Von Oepen |
| 2012/0059285 A1 | 3/2012 | Soltani et al. |
| 2012/0065660 A1 | 3/2012 | Ferrera et al. |
| 2012/0078140 A1 | 3/2012 | Nita |
| 2012/0078285 A1 | 3/2012 | Griffin |
| 2012/0083824 A1 | 4/2012 | Berrada et al. |
| 2012/0116443 A1 | 5/2012 | Ferrera et al. |
| 2012/0150147 A1 | 6/2012 | Leynov et al. |
| 2012/0158124 A1 | 6/2012 | Zaver et al. |
| 2012/0164157 A1 | 6/2012 | Kuebler |
| 2012/0179192 A1 | 7/2012 | Fogarty et al. |
| 2012/0197283 A1 | 8/2012 | Marchand et al. |
| 2012/0197285 A1 | 8/2012 | Martin et al. |
| 2012/0209312 A1 | 8/2012 | Aggerholm et al. |
| 2012/0231414 A1 | 9/2012 | Johnson |
| 2012/0232655 A1 | 9/2012 | Lorrison et al. |
| 2012/0239066 A1 | 9/2012 | Levine et al. |
| 2012/0239074 A1 | 9/2012 | Aboytes et al. |
| 2012/0245517 A1 | 9/2012 | Tegels |
| 2012/0259404 A1 | 10/2012 | Tieu et al. |
| 2012/0265238 A1 | 10/2012 | Hopkins et al. |
| 2012/0271337 A1 | 10/2012 | Figulla et al. |
| 2012/0271403 A1 | 10/2012 | Gries |
| 2012/0273467 A1 | 11/2012 | Baxter et al. |
| 2012/0277850 A1 | 11/2012 | Bertini |
| 2012/0283768 A1 | 11/2012 | Cox et al. |
| 2012/0290067 A1 | 11/2012 | Cam et al. |
| 2012/0310367 A1 | 12/2012 | Connor |
| 2012/0316598 A1 | 12/2012 | Becking et al. |
| 2012/0323267 A1 | 12/2012 | Ren |
| 2012/0330196 A1 | 12/2012 | Nita |
| 2012/0330347 A1 | 12/2012 | Becking et al. |
| 2012/0330350 A1 | 12/2012 | Jones et al. |
| 2013/0030460 A1 | 1/2013 | Marks et al. |
| 2013/0060323 A1 | 3/2013 | McHugo |
| 2013/0066357 A1 | 3/2013 | Aboytes et al. |
| 2013/0085515 A1 | 4/2013 | To et al. |
| 2013/0090682 A1 | 4/2013 | Bachman et al. |
| 2013/0092298 A1 | 4/2013 | Bregulla et al. |
| 2013/0096587 A1 | 4/2013 | Smith et al. |
| 2013/0116284 A1 | 5/2013 | Salzman |
| 2013/0121970 A1 | 5/2013 | Owens et al. |
| 2013/0138136 A1 | 5/2013 | Beckham et al. |
| 2013/0167960 A1 | 7/2013 | Pethe et al. |
| 2013/0201316 A1 | 8/2013 | Binder et al. |
| 2013/0220610 A1 | 8/2013 | Mosing et al. |
| 2013/0240096 A1 | 9/2013 | Browne et al. |
| 2013/0261656 A1 | 10/2013 | Lorenzo |
| 2013/0289589 A1 | 10/2013 | Krolik et al. |
| 2013/0327469 A1 | 12/2013 | Pingleton et al. |
| 2014/0005712 A1 | 1/2014 | Martin |
| 2014/0046359 A1 | 2/2014 | Bowman et al. |
| 2014/0074144 A1 | 3/2014 | Shrivastava et al. |
| 2014/0081315 A1 | 3/2014 | McIntosh et al. |
| 2014/0121758 A1 | 5/2014 | Ferrera et al. |
| 2014/0128905 A1 | 5/2014 | Molaei |
| 2014/0128907 A1 | 5/2014 | Hui et al. |
| 2014/0180377 A1 | 6/2014 | Bose et al. |
| 2014/0188208 A1 | 7/2014 | Hancock et al. |
| 2014/0194871 A1 | 7/2014 | Sanai |
| 2014/0200608 A1 | 7/2014 | Brady et al. |
| 2014/0214067 A1 | 7/2014 | Sachar et al. |
| 2014/0243882 A1 | 8/2014 | Ma |
| 2014/0249569 A1 | 9/2014 | Kusleika |
| 2014/0276403 A1 | 9/2014 | Follmer et al. |
| 2014/0276897 A1 | 9/2014 | Rockley et al. |
| 2014/0276922 A1 | 9/2014 | McLain et al. |
| 2014/0277013 A1 | 9/2014 | Sepetka et al. |
| 2014/0277082 A1 | 9/2014 | Janardhan et al. |
| 2014/0324091 A1 | 10/2014 | Rosenbluth et al. |
| 2014/0330302 A1 | 11/2014 | Tekulve et al. |
| 2014/0371839 A1 | 12/2014 | Henkes et al. |
| 2015/0005801 A1 | 1/2015 | Marquis et al. |
| 2015/0018928 A1 | 1/2015 | Sachar et al. |
| 2015/0028005 A1 | 1/2015 | Janardhan et al. |
| 2015/0032121 A1 | 1/2015 | Janardhan et al. |
| 2015/0032146 A1 | 1/2015 | Janardhan et al. |
| 2015/0032147 A1 | 1/2015 | Janardhan et al. |
| 2015/0080941 A1 | 3/2015 | Janardhan et al. |
| 2015/0133829 A1 | 5/2015 | DeBusk et al. |
| 2015/0196304 A1 | 7/2015 | Rabkin et al. |
| 2015/0196744 A1 | 7/2015 | Aboytes |
| 2015/0202338 A1 | 7/2015 | Kibalo |
| 2015/0209050 A1 | 7/2015 | Aboytes et al. |
| 2015/0209058 A1 | 7/2015 | Ferrera et al. |
| 2015/0216650 A1 | 8/2015 | Shaltis |
| 2015/0223829 A1 | 8/2015 | Aboytes |
| 2015/0238303 A1 | 8/2015 | Janardhan |
| 2015/0250497 A1 | 9/2015 | Marks et al. |
| 2015/0265299 A1 | 9/2015 | Cooper et al. |
| 2015/0272590 A1 | 10/2015 | Aboytes et al. |
| 2015/0297240 A1 | 10/2015 | Divino et al. |
| 2015/0305756 A1 | 10/2015 | Rosenbluth et al. |
| 2015/0314111 A1 | 11/2015 | Solar et al. |
| 2015/0320911 A1 | 11/2015 | Sun et al. |
| 2015/0342613 A1 | 12/2015 | Aboytes et al. |
| 2015/0352325 A1 | 12/2015 | Quick |
| 2015/0359666 A1 | 12/2015 | Zacharias |
| 2015/0360001 A1 | 12/2015 | Quick |
| 2015/0374391 A1 | 12/2015 | Quick et al. |
| 2015/0374393 A1 | 12/2015 | Brady et al. |
| 2016/0058614 A1 | 3/2016 | Ross et al. |
| 2016/0128869 A1 | 5/2016 | Zacharias |
| 2016/0166265 A1 | 6/2016 | Nita |
| 2016/0166352 A1 | 6/2016 | Rimsa et al. |
| 2016/0193429 A1 | 7/2016 | Gurtner et al. |
| 2016/0244722 A1 | 8/2016 | Wang et al. |
| 2016/0271295 A1 | 9/2016 | Sun et al. |
| 2017/0021072 A1 | 1/2017 | Forsell |
| 2017/0105743 A1 | 4/2017 | Vale et al. |
| 2017/0112562 A1 | 4/2017 | Woloszko et al. |
| 2017/0112981 A1 | 4/2017 | Friedman et al. |
| 2017/0147765 A1 | 5/2017 | Mehta |
| 2017/0151032 A1 | 6/2017 | Loisel |
| 2017/0172581 A1 | 6/2017 | Bose et al. |
| 2017/0173227 A1 | 6/2017 | Jessop et al. |
| 2017/0181761 A1 | 6/2017 | Janardhan et al. |
| 2017/0212014 A1 | 7/2017 | Fry et al. |

(56) References Cited

U.S. PATENT DOCUMENTS

| | | |
|---|---|---|
| 2017/0215902 A1 | 8/2017 | Leynov et al. |
| 2017/0296422 A1 | 10/2017 | Park et al. |
| 2017/0340797 A1 | 11/2017 | Raman et al. |
| 2017/0360450 A1 | 12/2017 | Tompkins et al. |
| 2017/0360469 A1 | 12/2017 | Janardhan et al. |
| 2017/0367857 A1 | 12/2017 | Bennett et al. |
| 2018/0000510 A1 | 1/2018 | Nash et al. |
| 2018/0057787 A1 | 3/2018 | Friedman et al. |
| 2018/0085136 A1 | 3/2018 | Janardhan et al. |
| 2018/0153675 A1 | 6/2018 | Hayzlett et al. |
| 2018/0153760 A1 | 6/2018 | Rosen et al. |
| 2018/0185130 A1 | 7/2018 | Janardhan et al. |
| 2018/0197633 A1 | 7/2018 | Mehta |
| 2018/0228502 A1 | 8/2018 | Shaffer et al. |
| 2018/0242989 A1 | 8/2018 | Nita |
| 2018/0263642 A1 | 9/2018 | Nita |
| 2018/0263646 A1 | 9/2018 | Loisel |
| 2018/0296317 A1 | 10/2018 | Hayzlett et al. |
| 2018/0303498 A1 | 10/2018 | Galdonik et al. |
| 2018/0338770 A1 | 11/2018 | Mogi et al. |
| 2018/0339130 A1 | 11/2018 | Ogle |
| 2018/0353194 A1 | 12/2018 | Shaffer et al. |
| 2018/0353644 A1 | 12/2018 | Sun et al. |
| 2018/0368965 A1 | 12/2018 | Janardhan et al. |
| 2019/0008626 A1 | 1/2019 | Janardhan et al. |
| 2019/0008627 A1 | 1/2019 | Janardhan et al. |
| 2019/0133744 A1 | 5/2019 | Janardhan et al. |
| 2019/0133745 A1 | 5/2019 | Janardhan et al. |
| 2019/0142567 A1 | 5/2019 | Janardhan et al. |
| 2019/0142568 A1 | 5/2019 | Janardhan et al. |
| 2019/0239910 A1 | 8/2019 | Brady et al. |

FOREIGN PATENT DOCUMENTS

| | | |
|---|---|---|
| EP | 0 777 504 | 10/1998 |
| EP | 0 853 950 | 10/2002 |
| EP | 1 210 032 | 12/2003 |
| EP | 1 059 890 | 12/2004 |
| EP | 1 028 671 | 1/2005 |
| EP | 1 026 997 | 10/2005 |
| EP | 1 156 757 | 12/2005 |
| EP | 1 117 344 | 6/2006 |
| EP | 1 676 545 | 7/2006 |
| EP | 1 214 016 | 6/2007 |
| EP | 1 389 959 | 11/2007 |
| EP | 1 028 670 | 1/2008 |
| EP | 1 459 703 | 1/2008 |
| EP | 1 402 848 | 10/2008 |
| EP | 1 482 859 | 10/2008 |
| EP | 1 715 795 | 12/2008 |
| EP | 1 479 357 | 5/2009 |
| EP | 1 494 619 | 8/2009 |
| EP | 1 589 900 | 9/2009 |
| EP | 1 681 034 | 1/2010 |
| EP | 1 487 526 | 9/2010 |
| EP | 1 377 224 | 5/2011 |
| EP | 2 113 224 | 6/2011 |
| EP | 1 583 485 | 9/2011 |
| EP | 2 301 450 | 11/2011 |
| EP | 1 539 030 | 1/2012 |
| EP | 2 217 315 | 5/2012 |
| EP | 0 851 777 | 12/2012 |
| EP | 2 057 967 | 1/2013 |
| EP | 1 904 217 | 3/2013 |
| EP | 1 706 063 | 10/2013 |
| EP | 2 517 658 | 12/2013 |
| EP | 0 998 228 | 6/2014 |
| EP | 1 981 413 | 11/2014 |
| EP | 2 482 913 | 11/2014 |
| EP | 2 700 368 | 2/2015 |
| EP | 1 483 009 | 10/2015 |
| EP | 2 474 277 | 10/2015 |
| EP | 1 006 890 | 9/2016 |
| GB | 667071 | 2/1952 |
| JP | H10-511586 | 11/1998 |
| JP | 2004-089457 | 3/2004 |
| JP | 2009-528907 | 8/2009 |
| WO | WO 2001/060442 | 8/2001 |
| WO | WO 2004/093738 | 11/2004 |
| WO | WO 2007/011353 | 1/2007 |
| WO | WO 2010/014447 | 2/2010 |
| WO | WO 2011/119872 | 9/2011 |
| WO | WO 2012/011097 | 1/2012 |
| WO | WO 2012/057881 | 5/2012 |
| WO | WO 2012/110619 | 8/2012 |
| WO | WO 2012/120490 | 9/2012 |
| WO | WO 2014/127738 | 8/2014 |
| WO | WO 2014/141226 | 9/2014 |
| WO | WO 2014/150288 | 9/2014 |
| WO | WO 2014/151209 | 9/2014 |
| WO | WO 2014/154137 | 10/2014 |
| WO | WO 2015/138649 | 9/2015 |
| WO | WO 2015/157330 | 10/2015 |
| WO | WO 2016/018448 | 2/2016 |
| WO | WO 2017/142874 | 8/2017 |

OTHER PUBLICATIONS

6th Annual MedTech Investing Conference, "Venture Capital and Private Equity Investing in Medical Devices and Healthcare Technologies," May 16-17, 2007.
Abbott Laboratories, "Xact Carotid Stent System, RX Acculink Carotid Stent System, 2006 Clinical Update for Physicians", 2007.
Adams et al., "Guidelines for the Early Management of Patients with Ischemic Stroke: A Scientific Statement from the Stroke Council of the American Stroke Association," Stroke, 2003, vol. 34, pp. 1056-1083.
Adams et al., "Guidelines for the Early Management of Patients with Ischemic Stroke—2005 Guidelines Update—A Scientific Statement from the Stroke Council of the American Stroke Association," Stroke, 2005, vol. 36, pp. 916-923.
Alligator Retrieval Device Product Brochure, 2009.
Bose et al., "A Novel, Self-Expanding, Nitinol Stent in Medically Refractory Intracranial Atherosclerotic Stenoses, The Wingspan Study," http://stroke.ahajournals.org/, American Heart Association, Inc., 2007, pp. 1531-1537.
Boston Scientific, "Excelsior 1018 Microcatheter, for Peak Performance in GDC Delivery," 2000.
Boston Scientific, "Excelsior 1018 Microcatheter, Neurovascular Access," 2004.
Boston Scientific, "Excelsior SL-10 Microcatheter, Neurovascular Access," 2004.
Boston Scientific, "Excelsior SL-10 Microcatheter, The 10 Microcatheter with a 14 Lumen," 2002.
Boston Scientific, "FilterWire EX, Embolic Protection System, Instruction for Use," Apr. 2004.
Boston Scientific, "Neuroform$^2$ Microdelivery Stent System, Technical Bulletin No. 1—Parent Vessel Protection," 2004.
Boston Scientific, "Neuroform$^2$ Microdelivery Stent System, Neurovascular Reconstruction," 2004.
Boston Scientific, "Neuroform$^3$ Microdelivery Stent System, Confidence Begins with Control," 2005.
Boston Scientific, "Pre-Shaped Microcatheters, Product Selection Guide," 2004.
Boston Scientific, "Renegade 18 Microcatheter, Neurovascular Access," 2004.
Boston Scientific, "Synchro Guidewires, Neurovascular Access," 2004.
Boston Scientific, "Tracker Excel-14 Microcatheter, Engineered for GDC Coil Delivery," 1998.
Boston Scientific, "Tracker Excel-14 Microcatheter, Neurovascular Access," 2004.
Boston Scientific, "Transend Guidewires, Neurovascular Access," 2003.
Braley et al., "Advancements in Braided Materials Technology," 46th Int'l Sample Symposium, May 2001, pp. 2445-2454.
Chestnut Medical Technologies, Inc., "Instructions for Use (IFU), Alligator Retrieval Device (ARD)," 2005.

(56) References Cited

OTHER PUBLICATIONS

Concentric Medical, "Instructions for Use, Concentric Micro Catheters", 2003.
Concentric Medical, "Instructions for Use, Merci Retriever X51X6," 2004.
Cordis Corporation, "Cordis CarotidSystem, Cordis Precise Nitinol Self-Expanding Stent and Cordis Angioguard Emboli Capture Guidewire System," 2004.
Cordis Corporation, "Cordis CarotidSystem, Technical Specification and Product Codes," 2006.
Cordis Corporation, "Cordis CarotidSystem RX, Technical Specifications and Product Codes," 2007.
Cordis Endovascular, "Diagnosing Carotid Artery Disease: The Leading Cause of Stroke," Sample News Article #1: "Diagnosis," 2008 or earlier.
Embo Shield, "Xact, Customized for Carotid Arteries, The Barewaire Revolution is Here," 2005.
Ev3, "ev3 Carotid Innovations, Redefining Confidence, See what you've been missing . . . ", ev3 The Endovascular Company, 2008 or earlier.
Furlan et al., "Intra-arterial Prourokinase for Acute Ischemic Stroke, The PROCT II Study: A Randomized Controlled Trial," JAMA, Dec. 1, 1999, vol. 282, Issue 21, pp. 2003-2011.
Henkes et al., "A New Device for Endovascular Coil Retrieval from Intracranial Vessels: Alligator Retrieval Device", AJRN Am J. Neuroradiol, Feb. 2006, vol. 27, pp. 327-329.
Micro Therapeutics, Inc., "Mirage .008", Hydrophilic Guidewire, 2000.
Micrus Endovascular, "WATUSI guidewire, Let's Dance," 2006.
Neale, "Medtronic's Riptide System Cleared for Thrombus Aspiration in Acute Stroke", tctMD / the heart beat, Jan. 16, 2018.
Penumbra System, Science of Aspiration the Penumbra System Approach, 2016.
Powerex, "Medical Dry Rotary Vane Vacuum", Retrieved from the internet Mar. 27, 2017, <URL: http://www/powerexinc.com/article/image_182000000000197>.
Rymer et al., "Organizing regional networks to increase acute stroke intervention", Neurological Research, 2005, vol. 27, Issue 1, pp. S9-S16.
Sarti et al., "International Trends in Mortality From Stroke, 1968 to 1994", http://stroke.ahajournals.org/, American Heart Association, Inc., Apr. 20, 2000, pp. 1588-1601.
Simon et al., "Exploring the efficacy of cyclic vs static aspiration in a cerebral thrombectomy model: an initial proof of concepts study", *J NeuroIntervent Surg.*, 2014, vol. 6, pp. 677-683.
University of Minnesota, "Design of Medical Devices Conference," Apr. 17-19, 2007.
Yadav, "Carotid stenting in high-risk patients: Design and rationale of the SAPPHIRE trial", Cleveland Clinic Journal of Medicine, Jan. 2004, vol. 71, Issue 1, pp. S45-S46.
Yadav et al., "Protected Carotid-Artery Stenting versus Endarterectomy in High-Risk Patients," The New England Journal of Medicine, Oct. 7, 2004, vol. 351, Issue 15, pp. 1493-1501 & 1565-1567.
U.S. Appl. No. 60/980,736, filed Oct. 17, 2007.
U.S. Appl. No. 61/044,392, filed Apr. 11, 2008.
U.S. Appl. No. 61/015,154, filed Dec. 19, 2007.
U.S. Appl. No. 60/989,422, filed Nov. 20, 2007.
U.S. Appl. No. 61/019,506, filed Jan. 7, 2008.
U.S. Appl. No. 60/987,384, filed Nov. 12, 2007.
U.S. Appl. No. 61/129,823, filed Jul. 22, 2008.
U.S. Appl. No. 61/202,612, filed Mar. 18, 2009.
Dictionary.com definition for "bonding" as accessed Nov. 21, 2019; https://www.dictionary.com/browse/bonding.

* cited by examiner

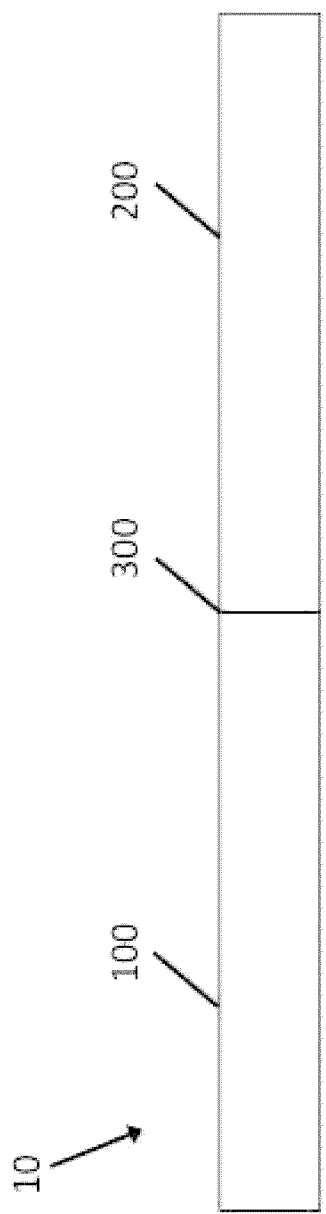

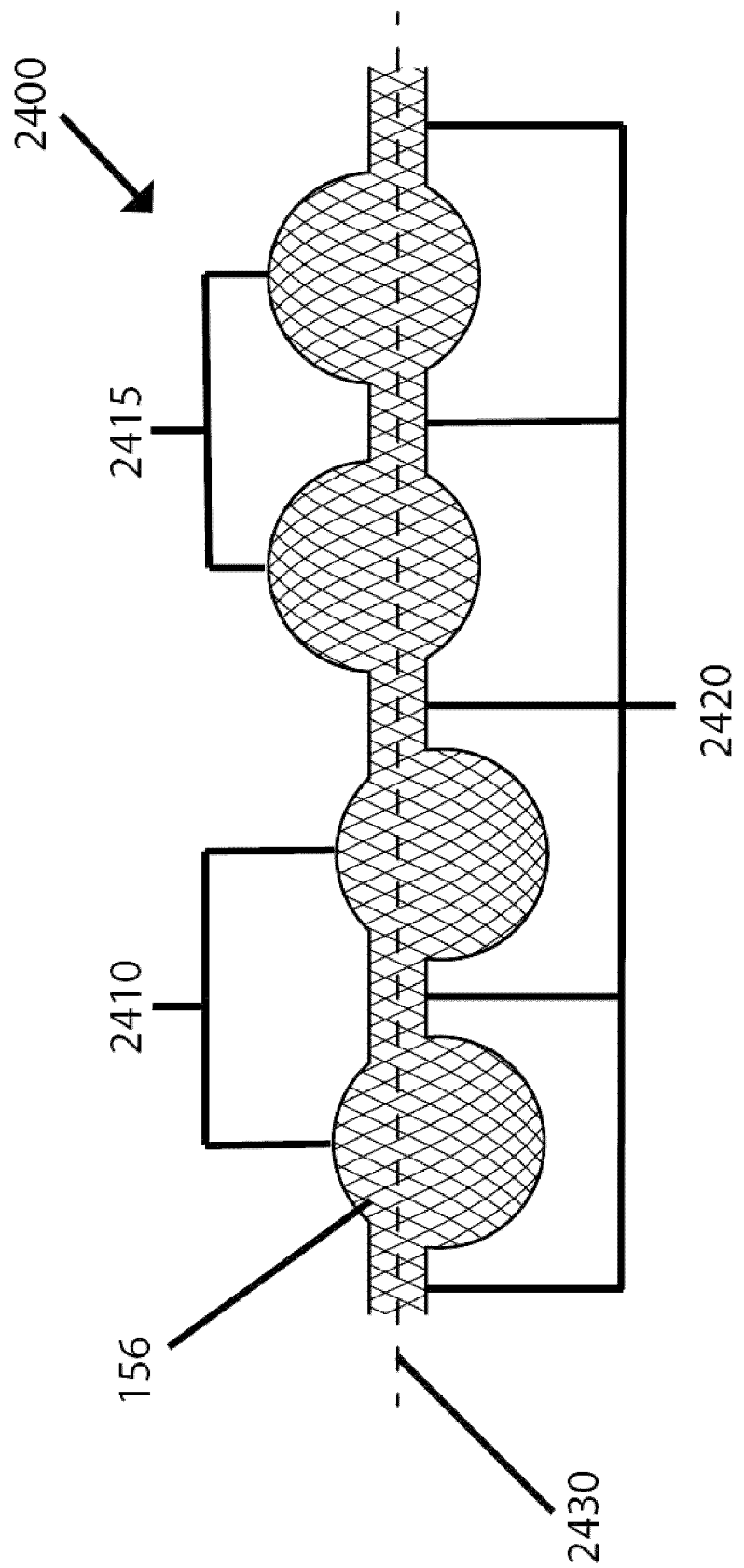

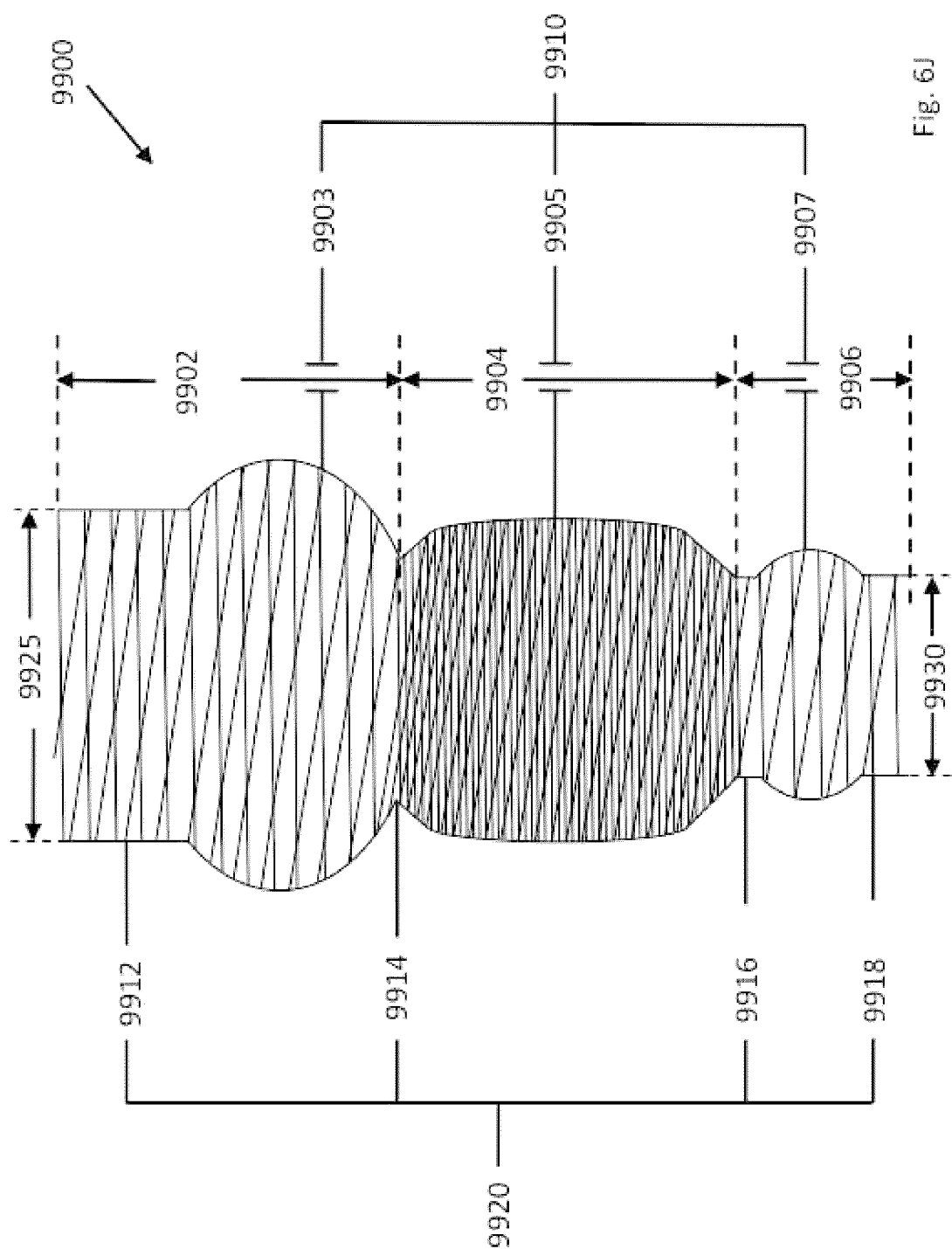

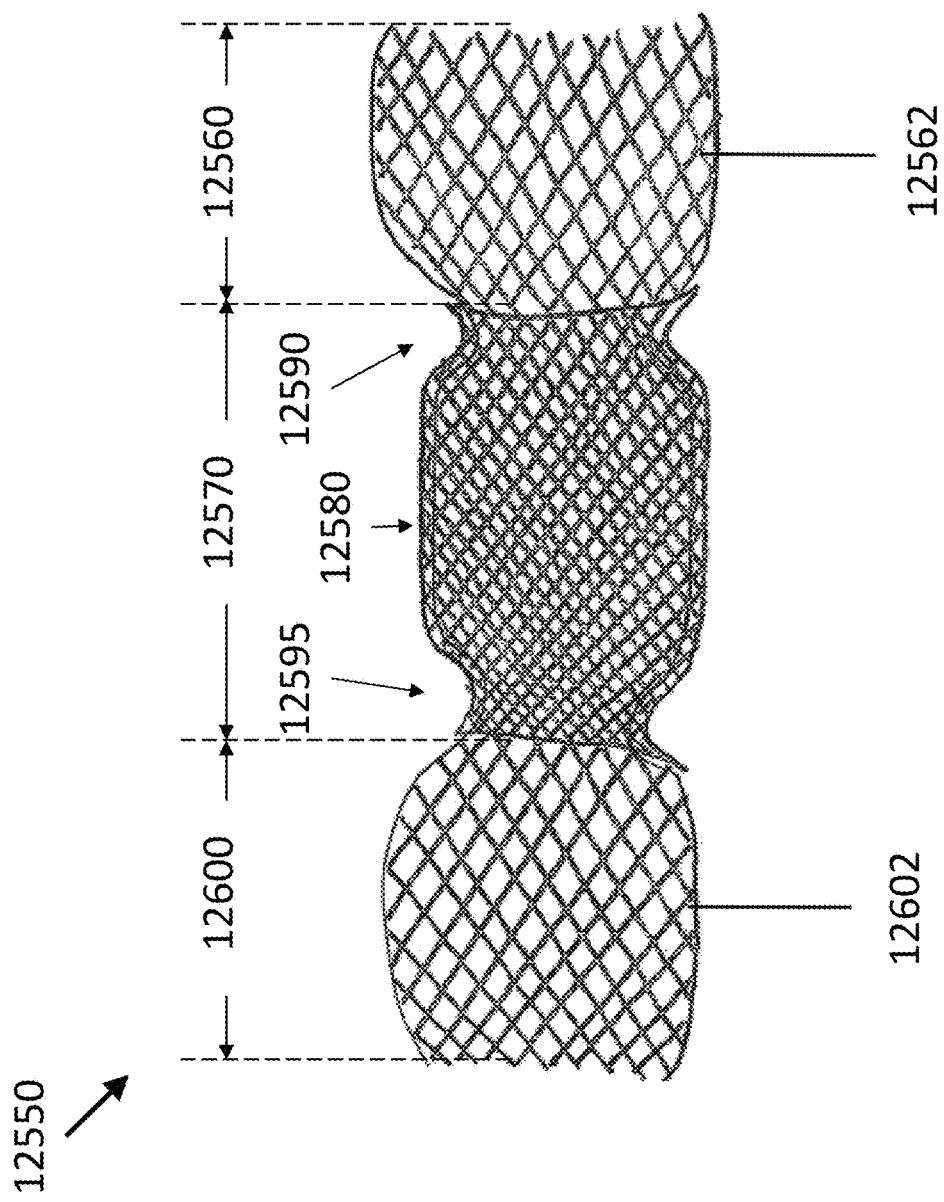
Fig. 6K-1iii

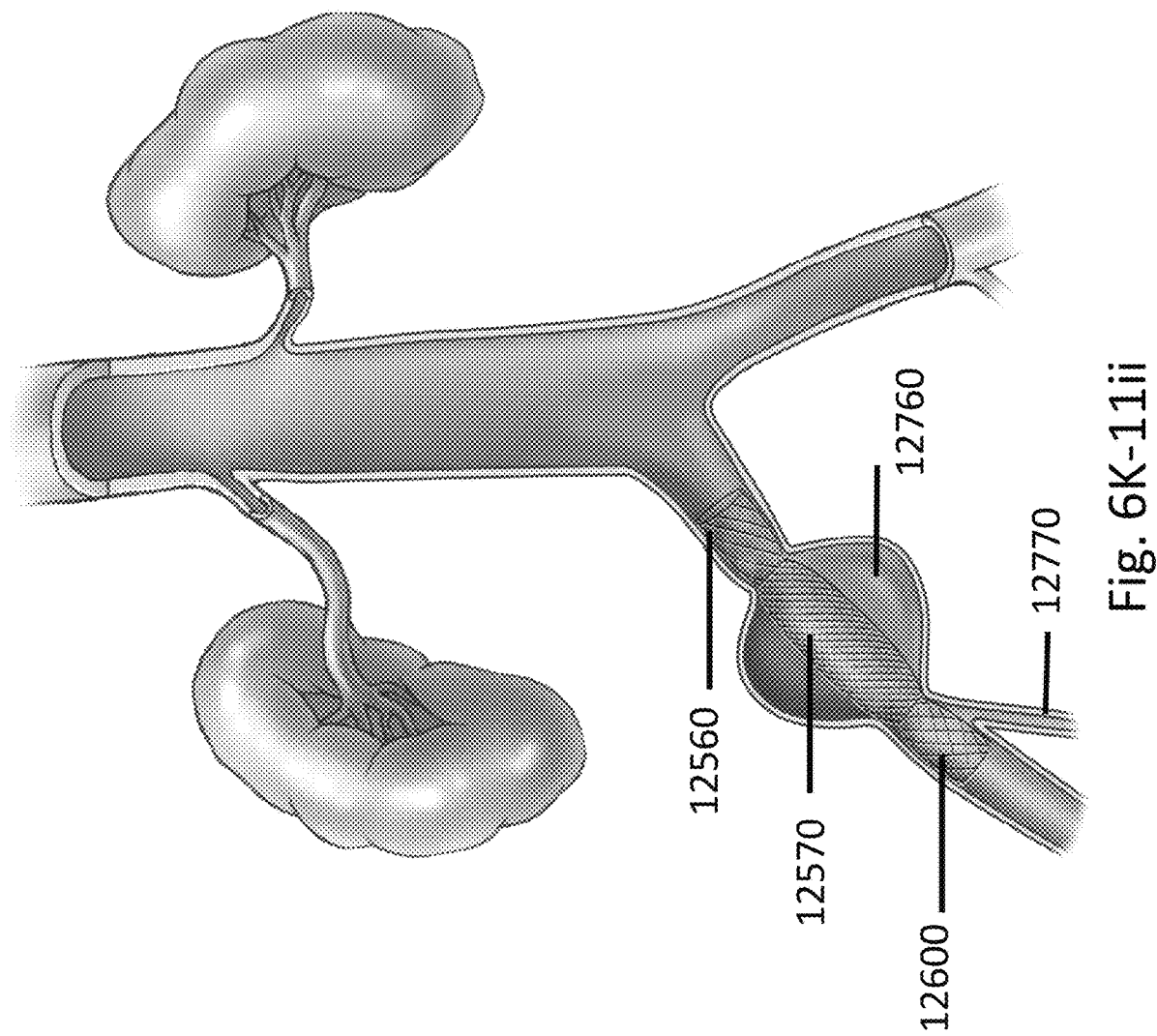

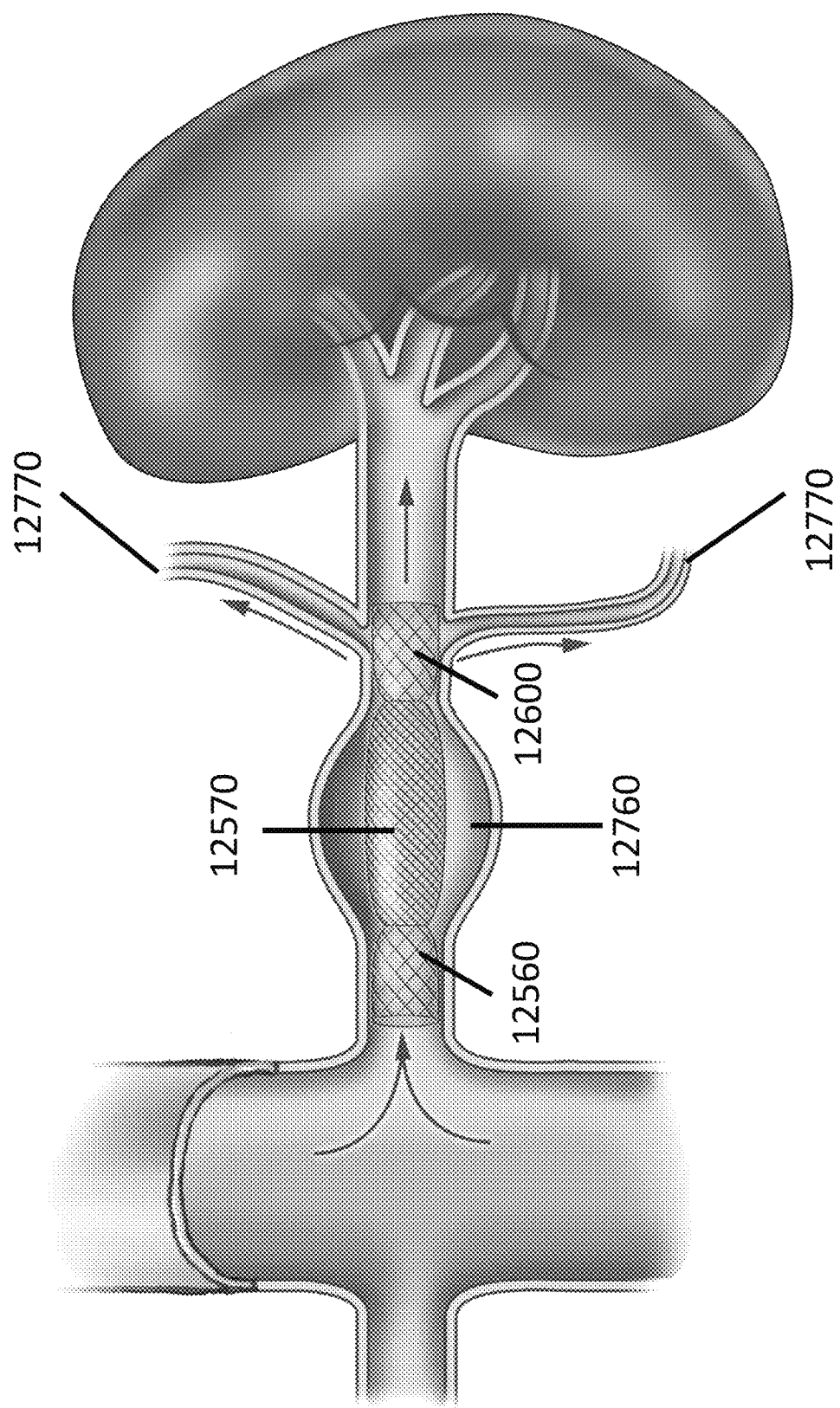
Fig. 6K-11iii

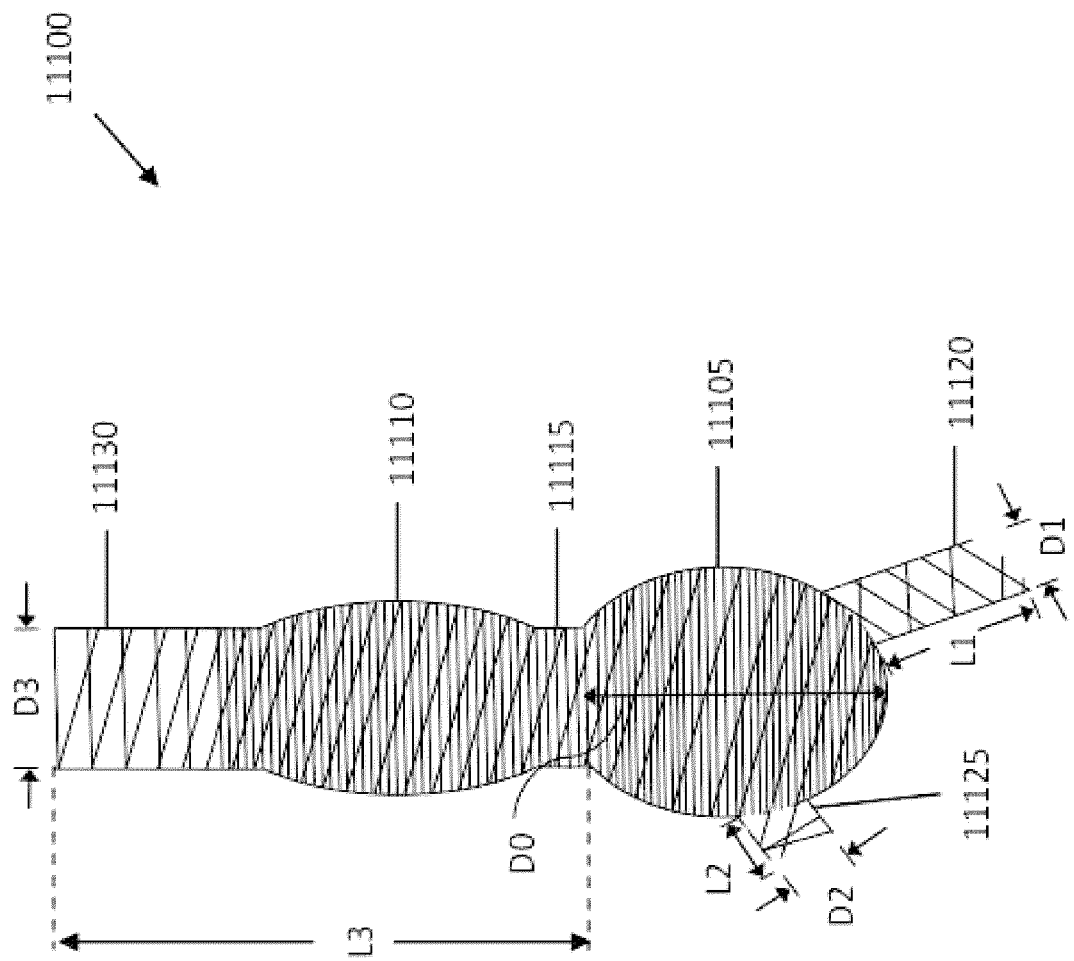

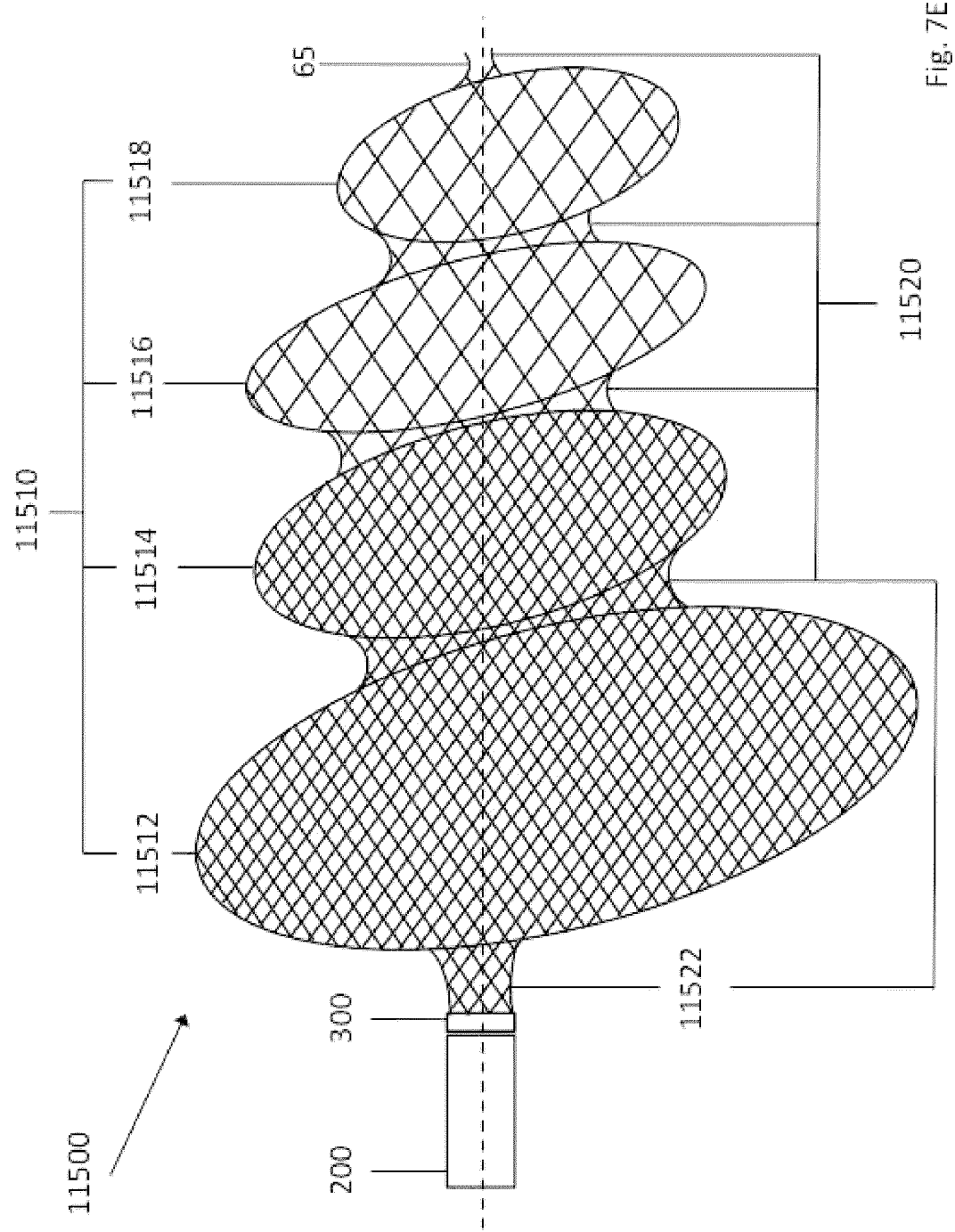

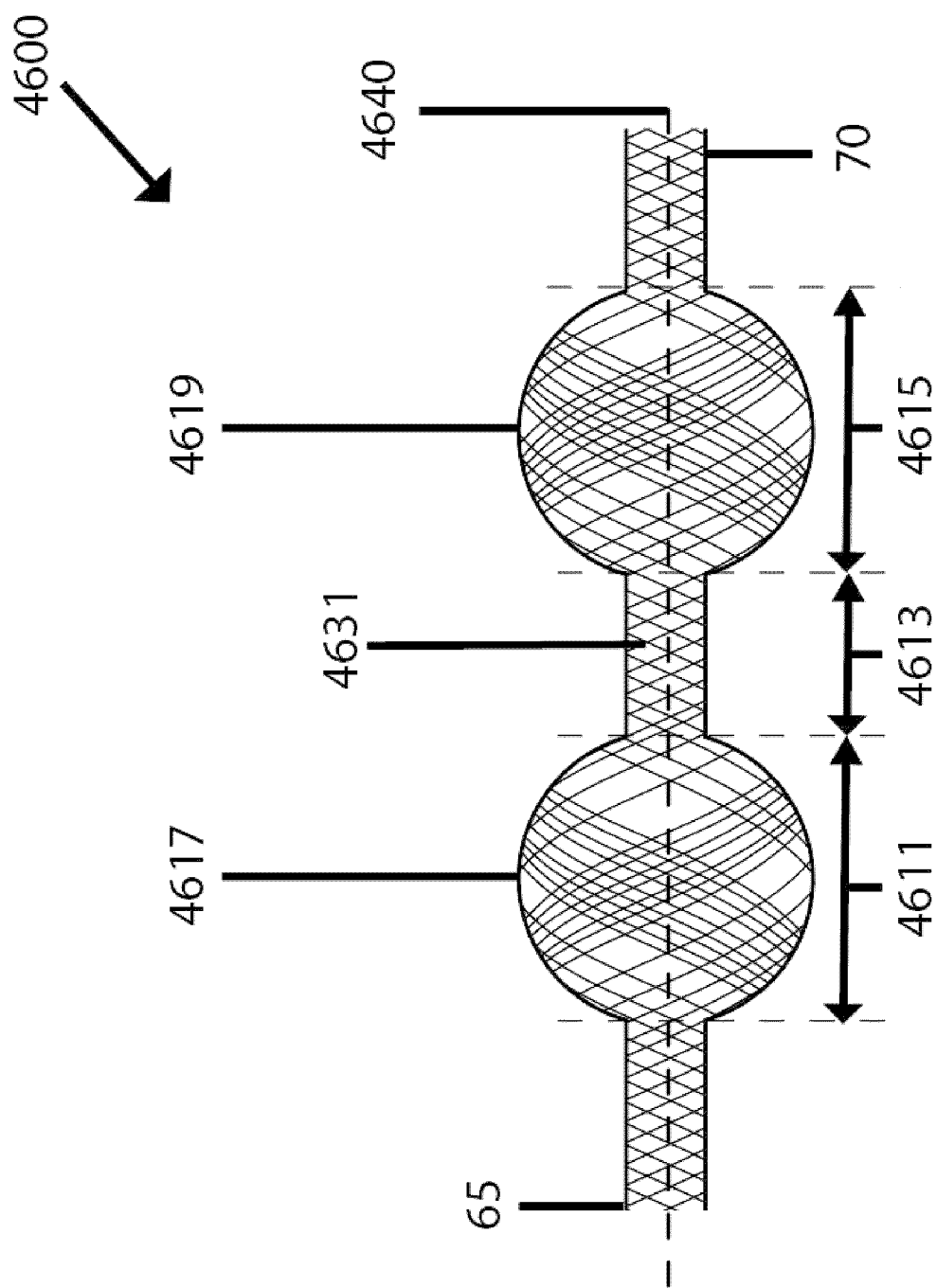

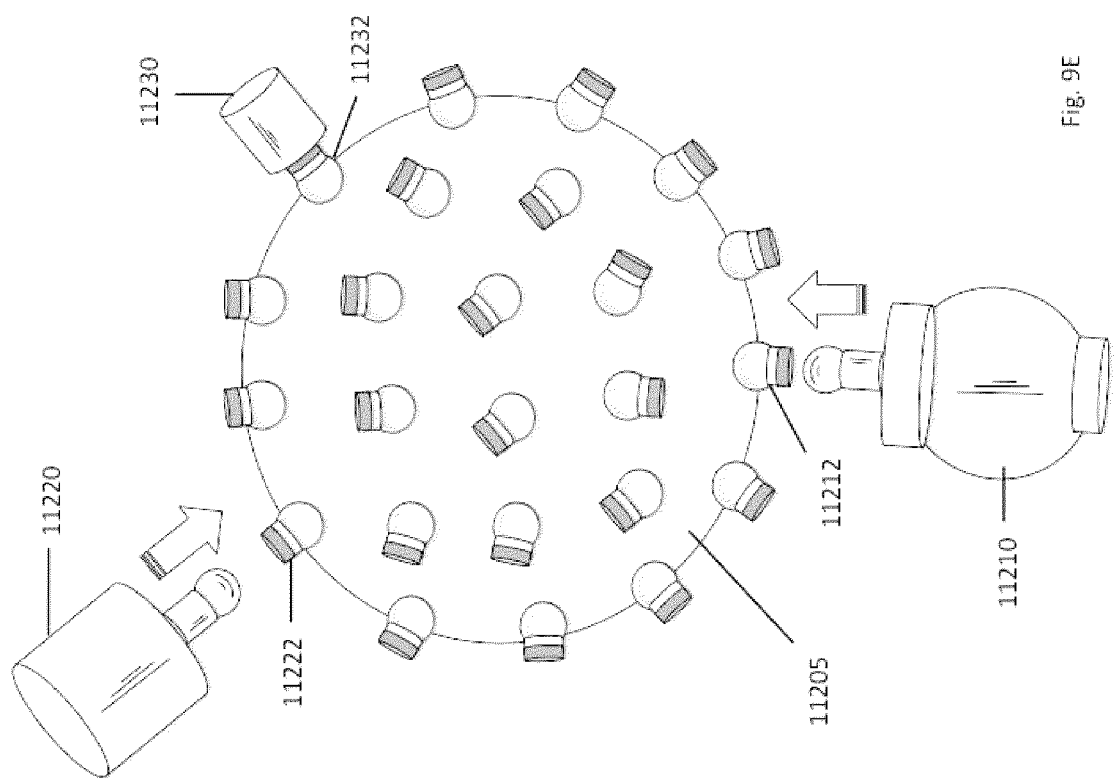

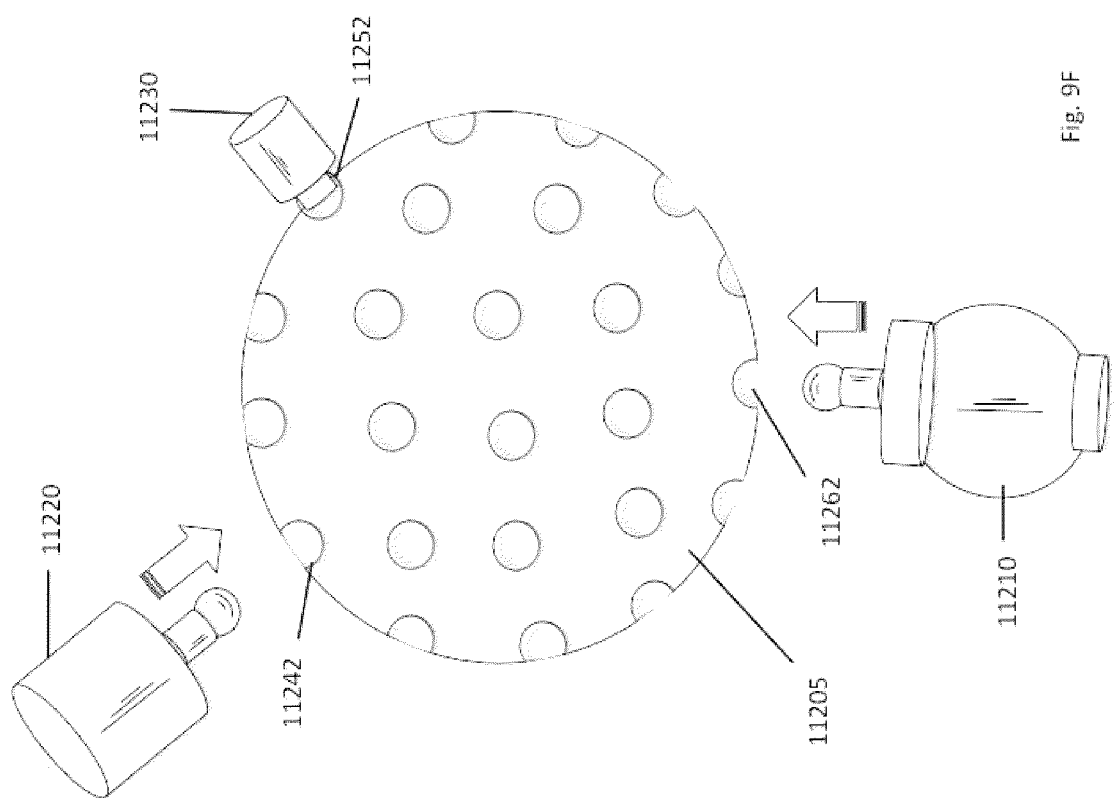

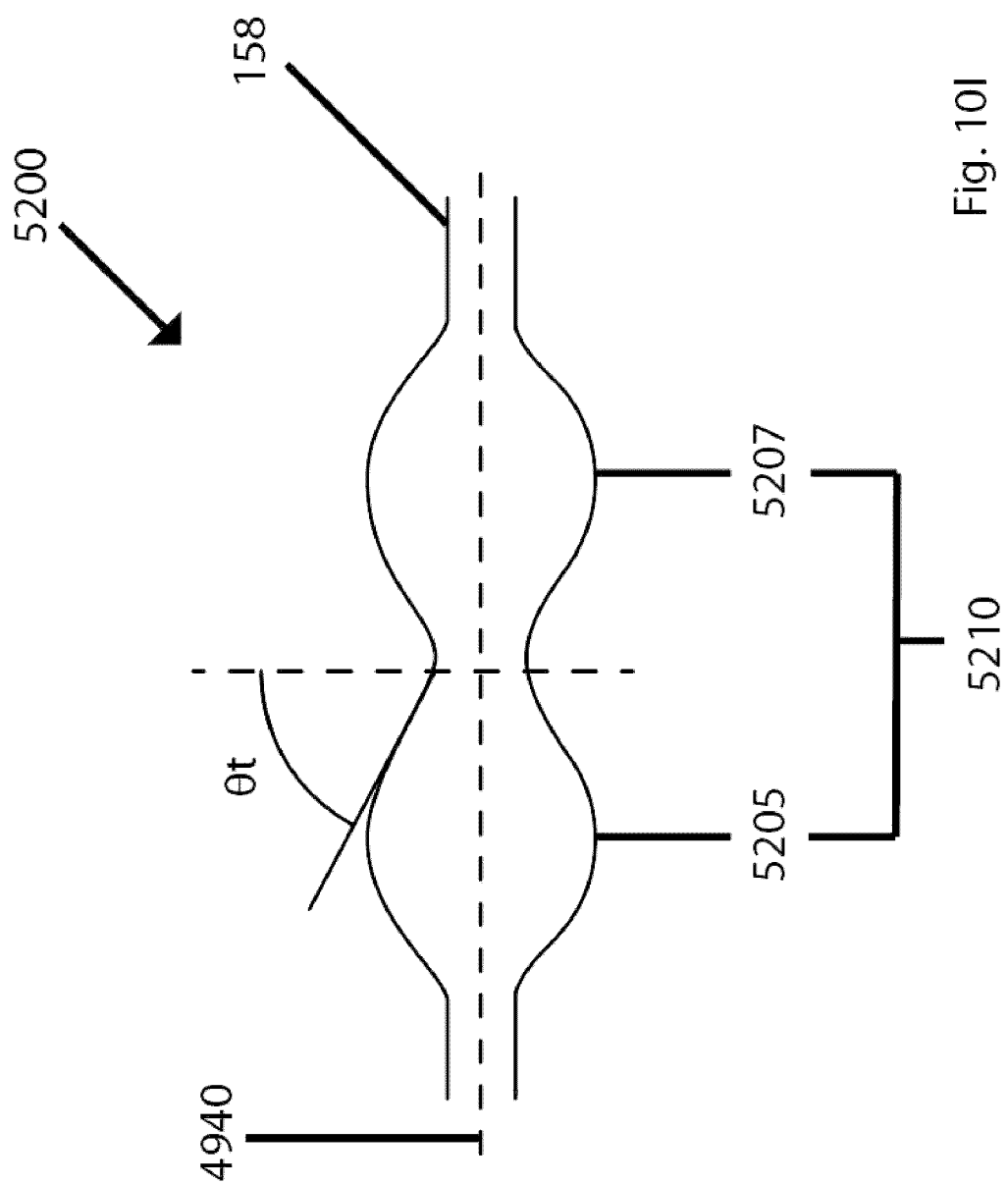

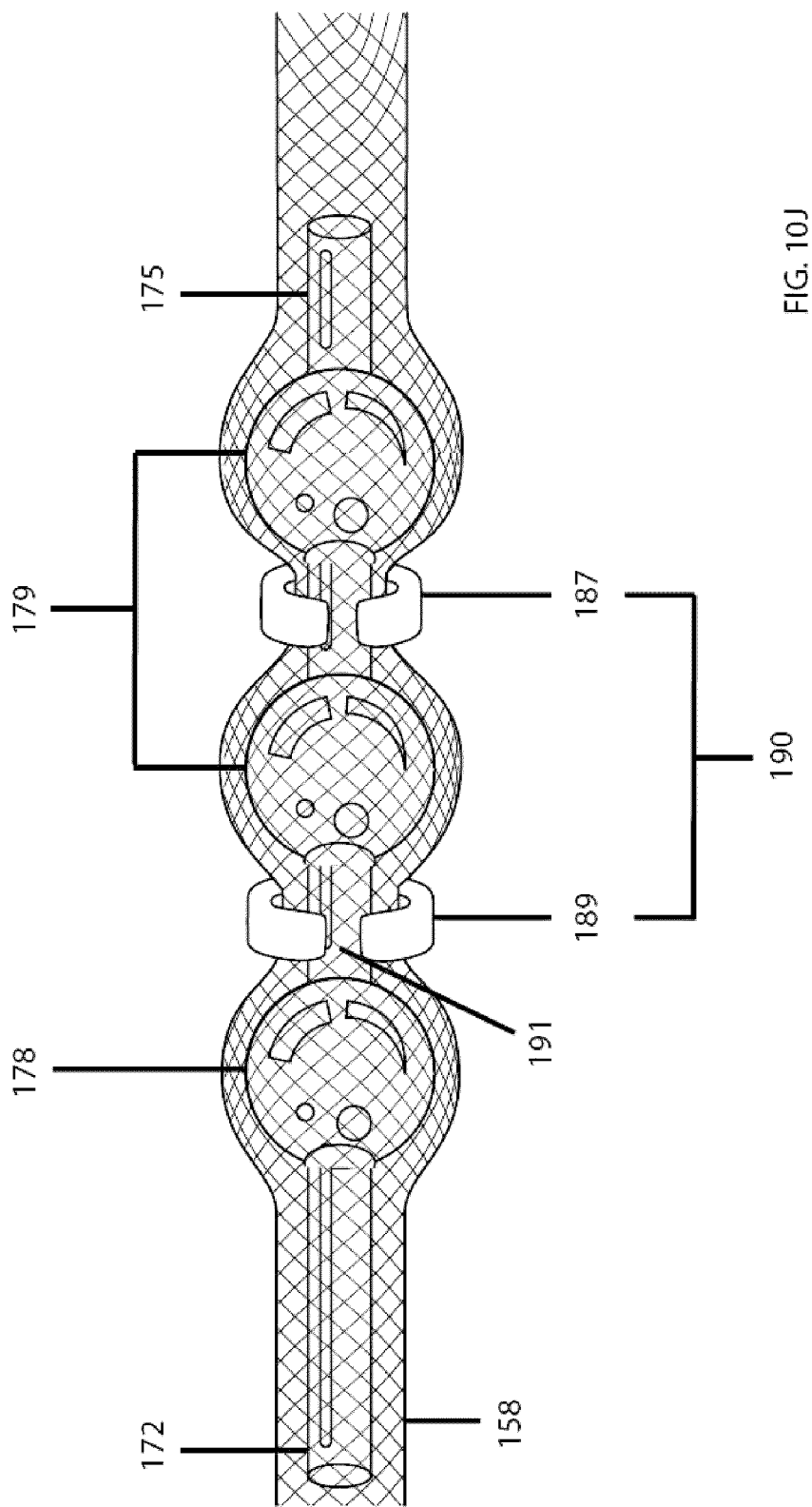

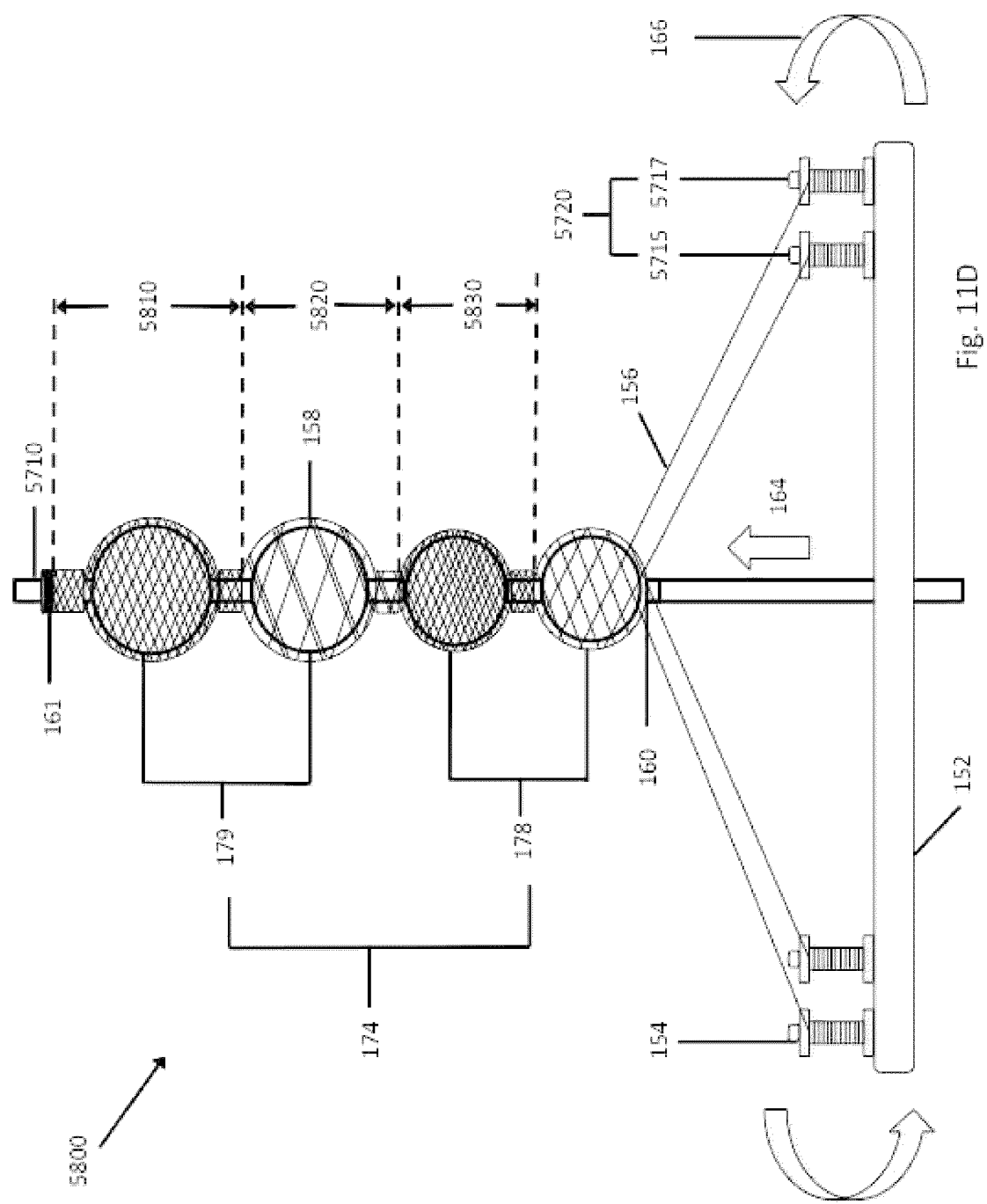

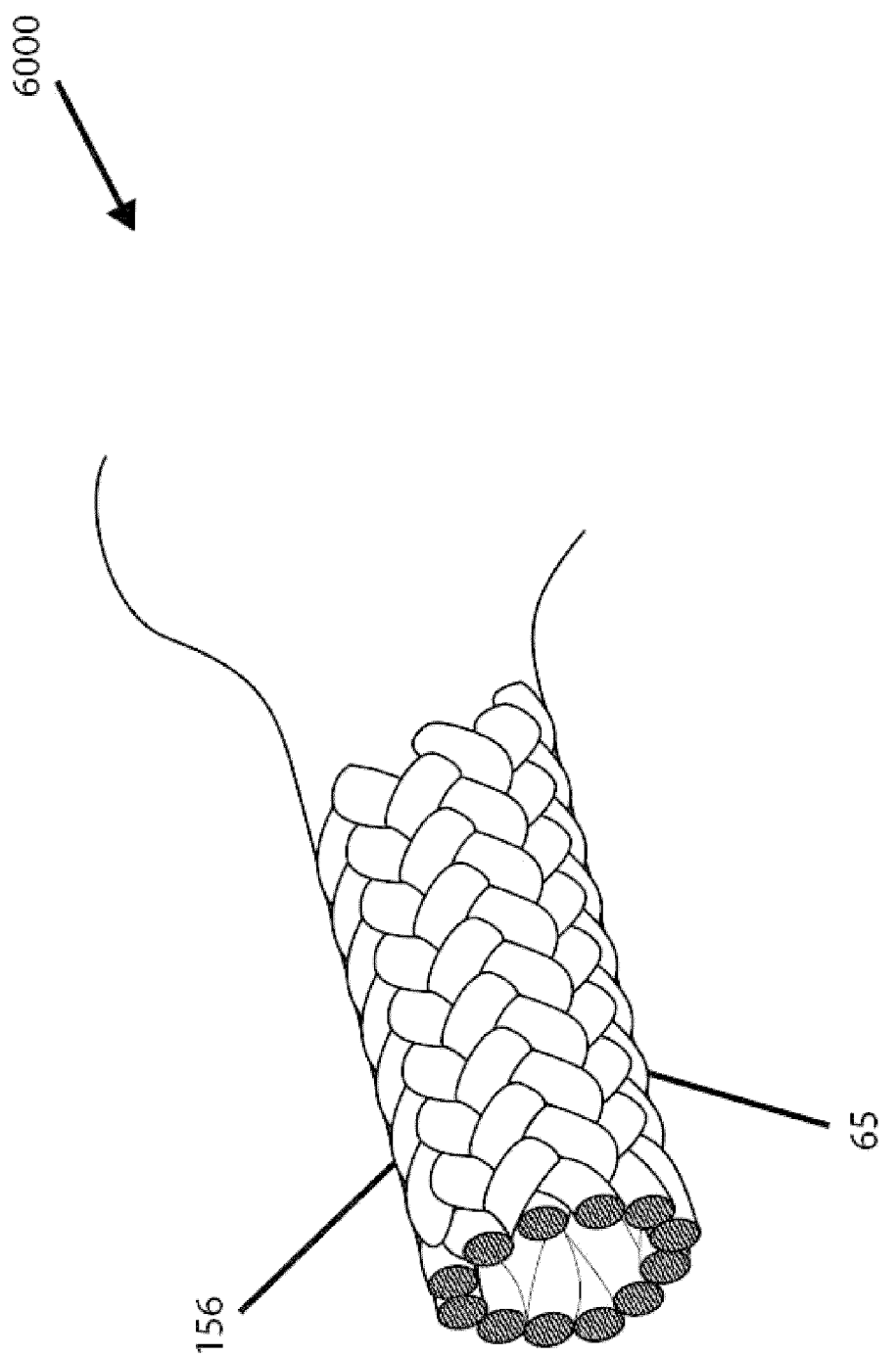

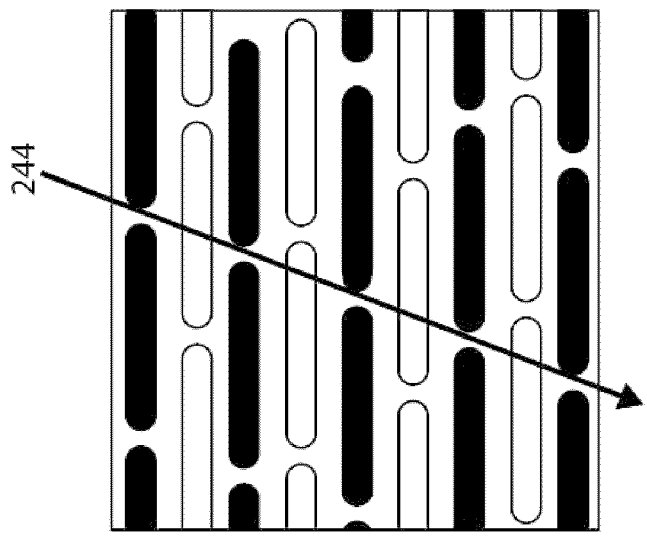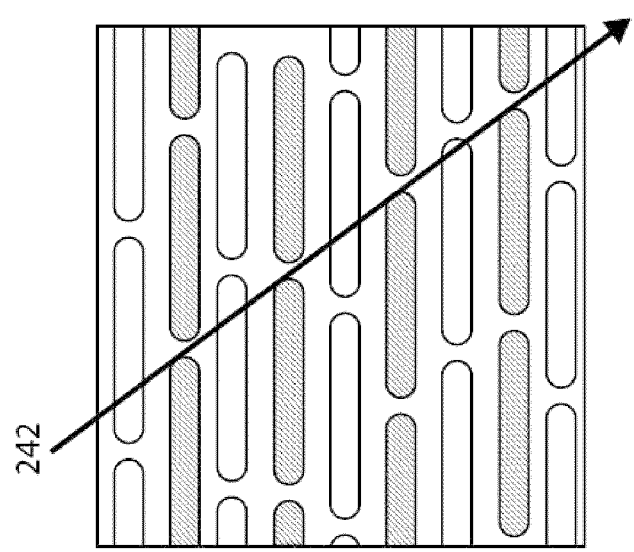
Fig. 16D

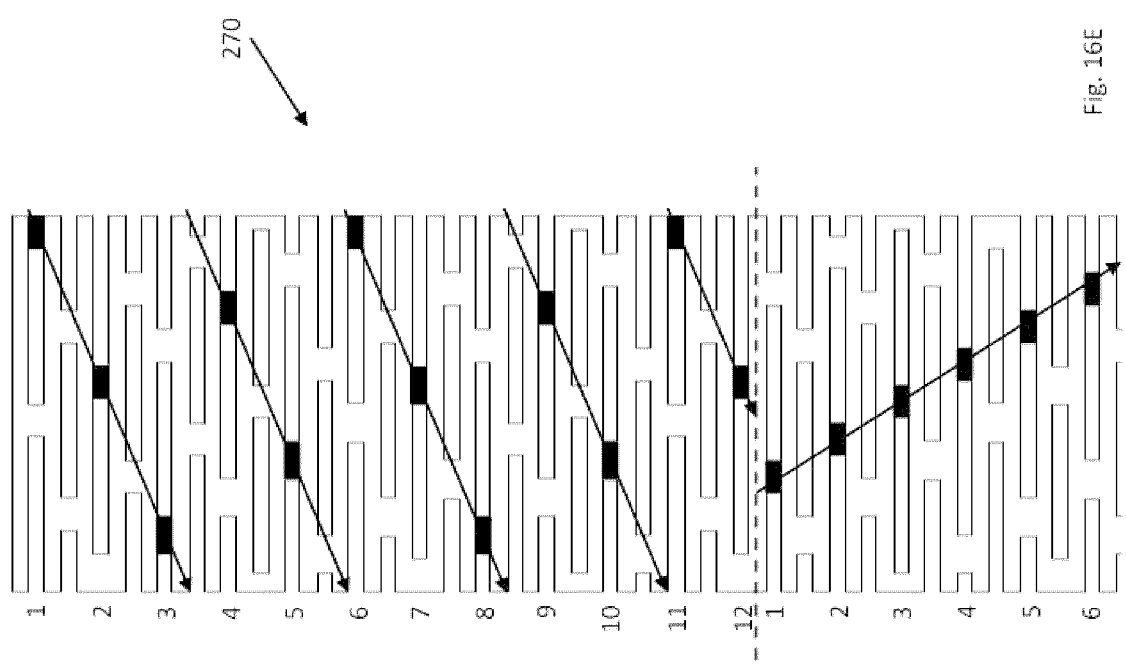

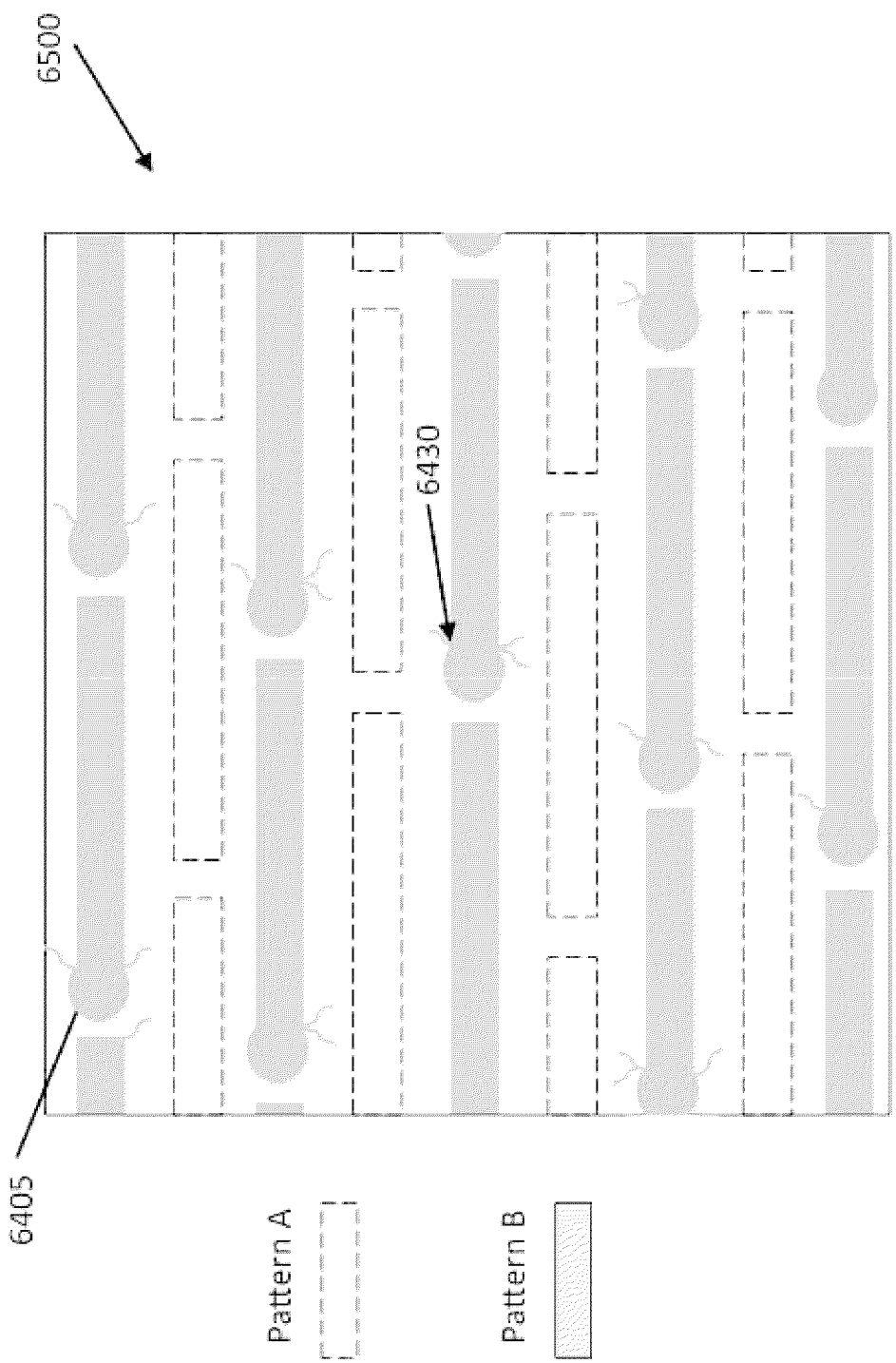

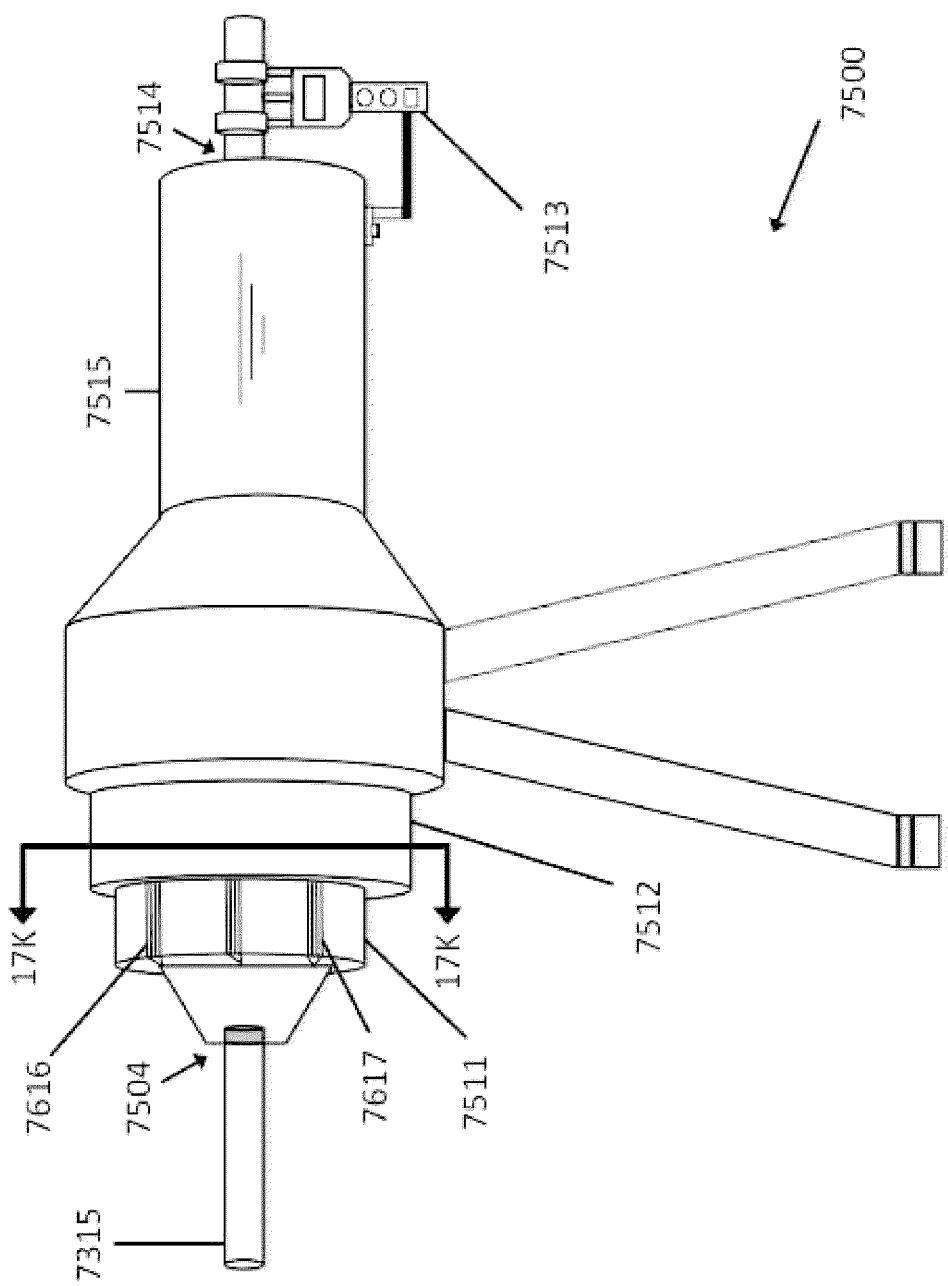

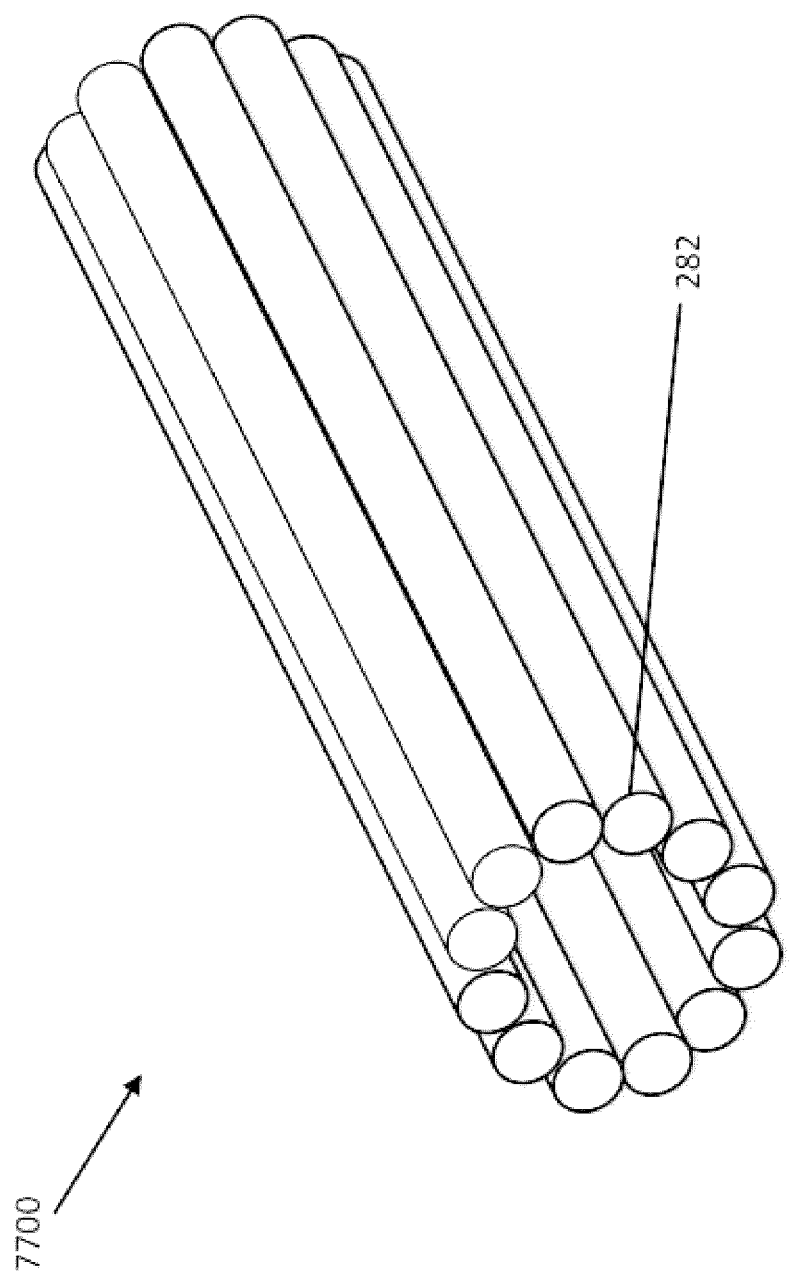

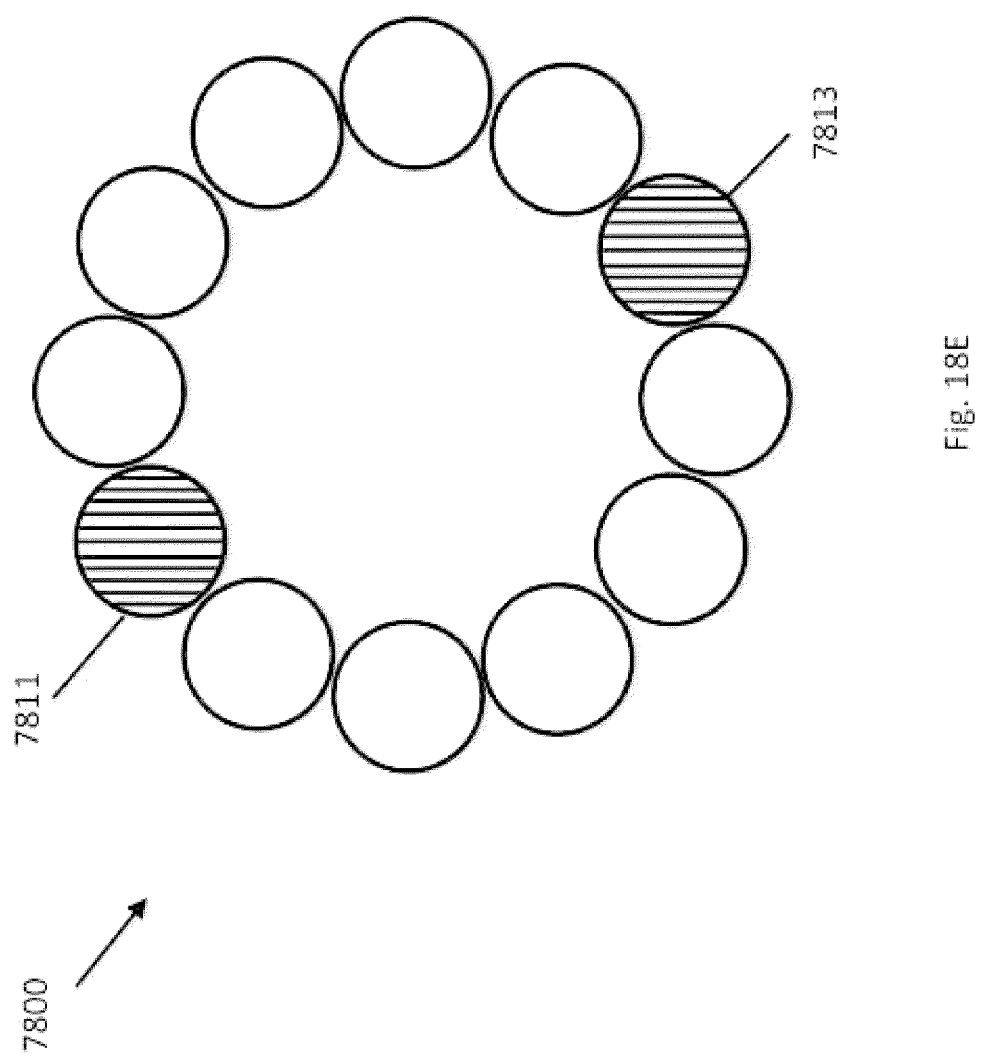

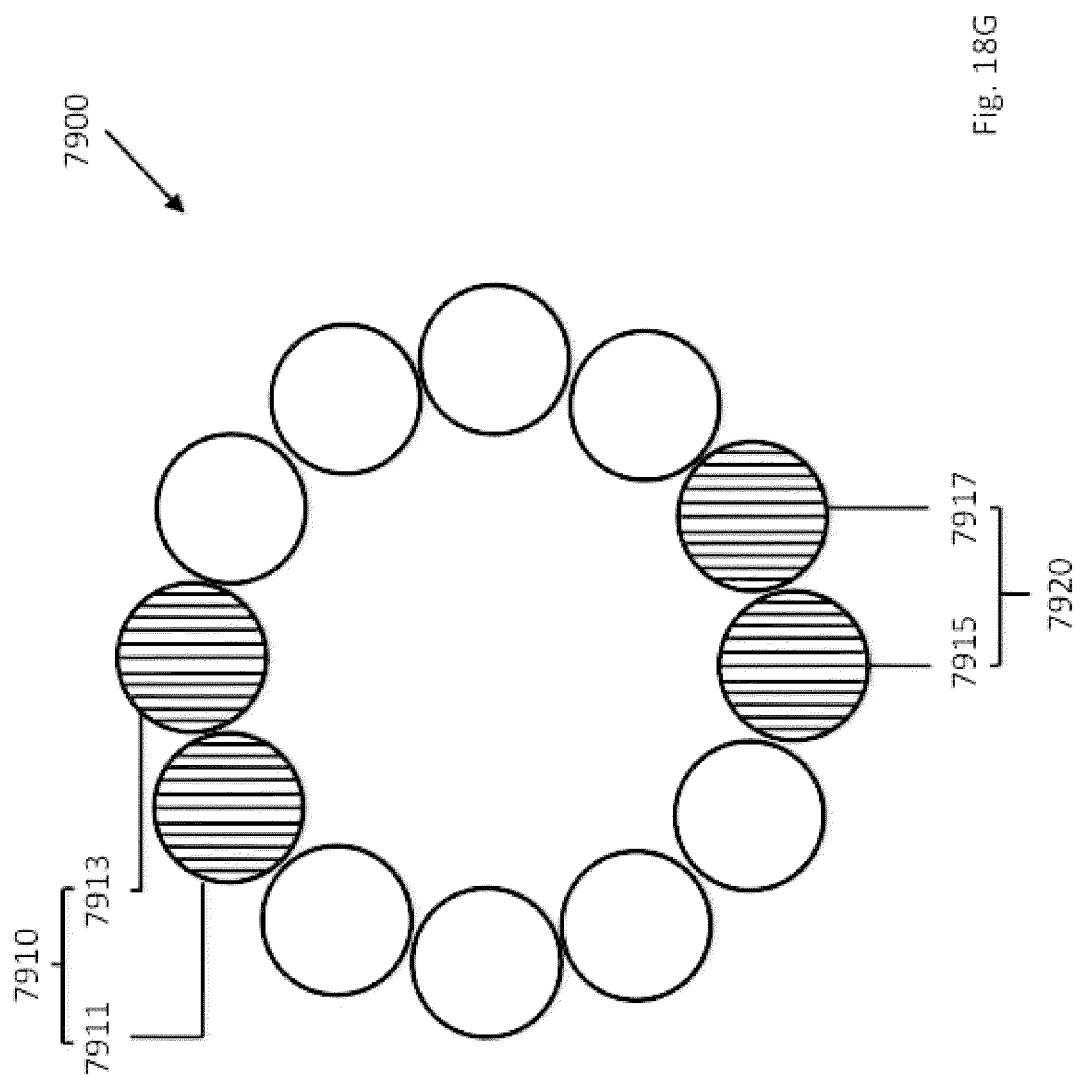

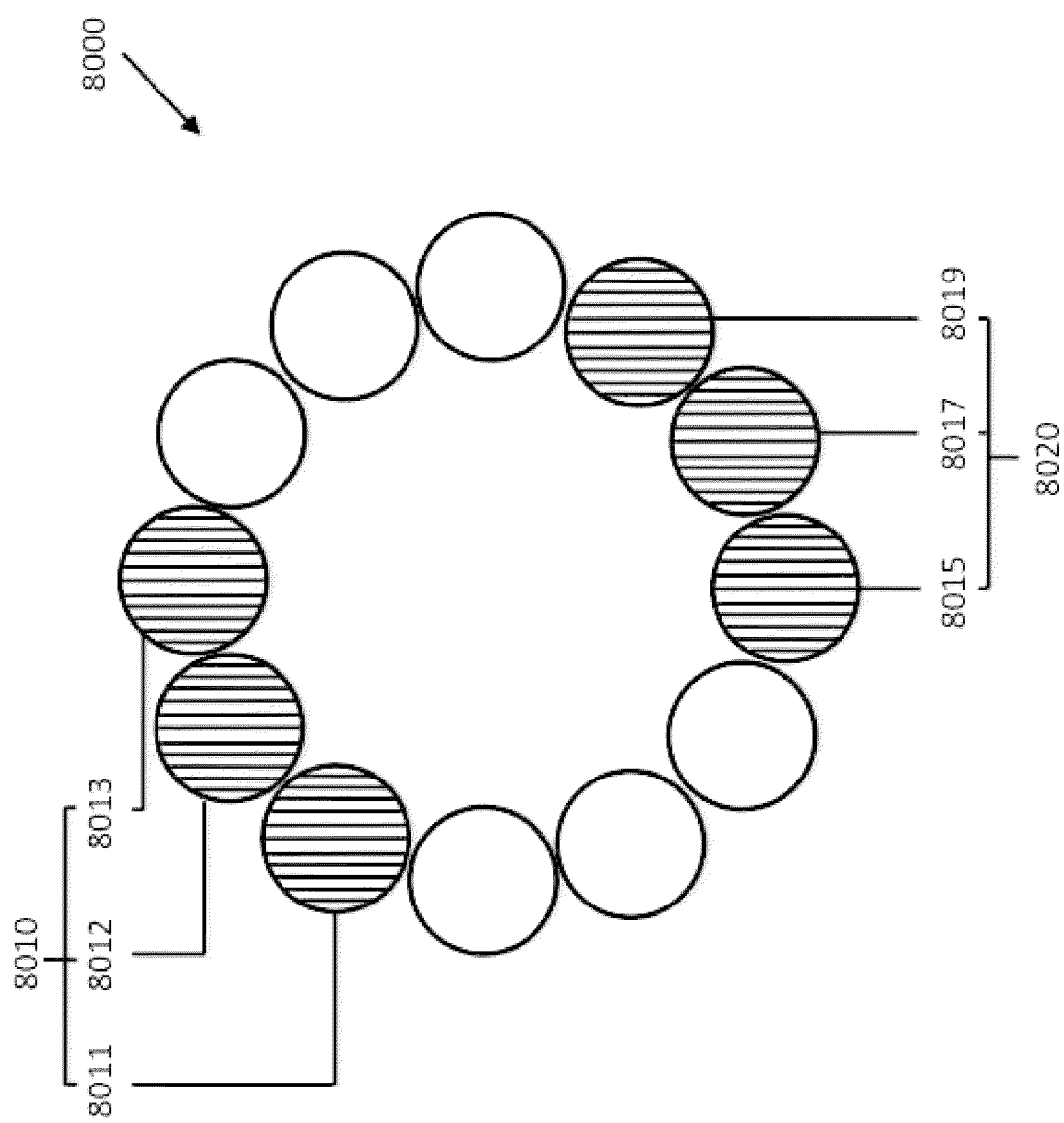

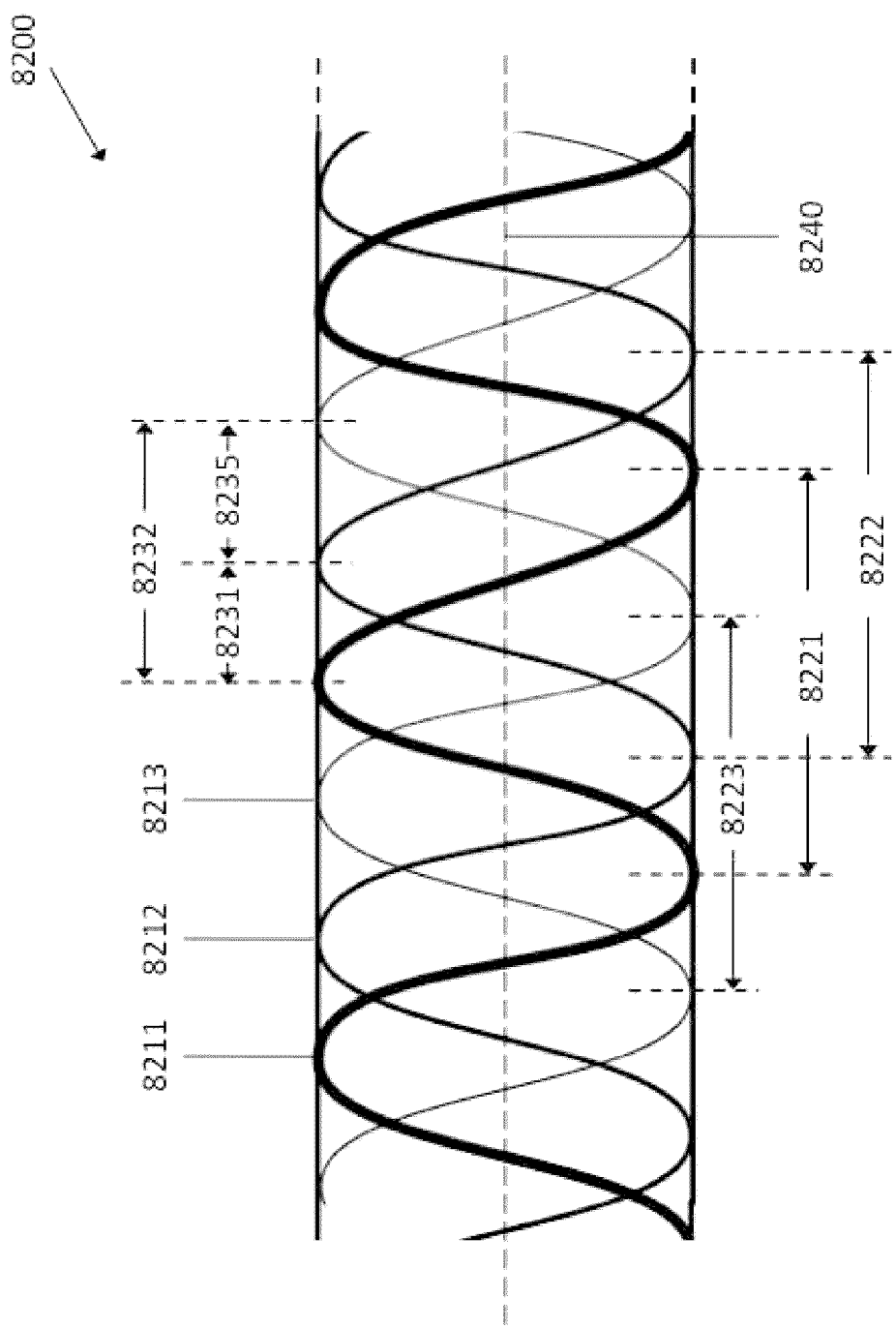

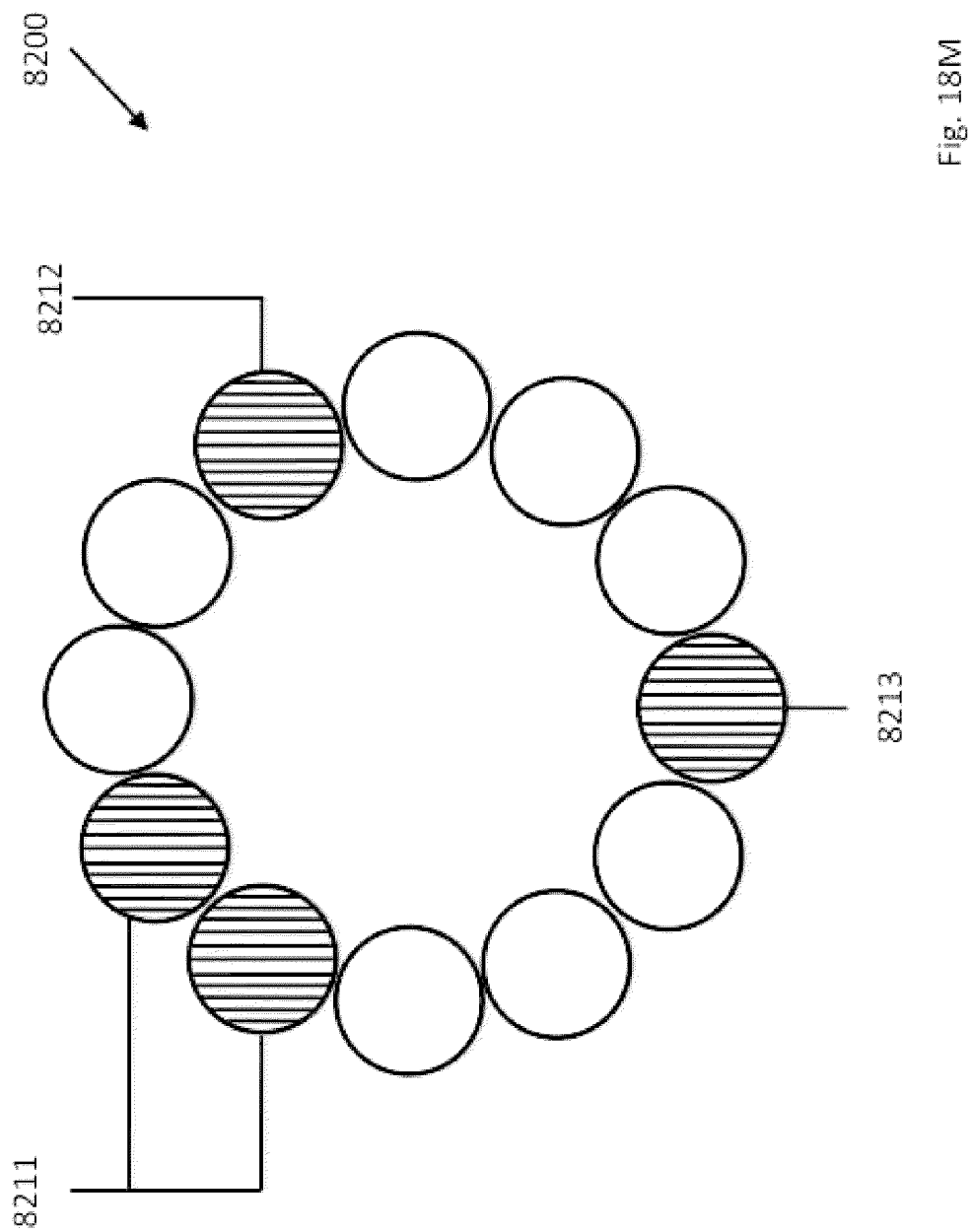

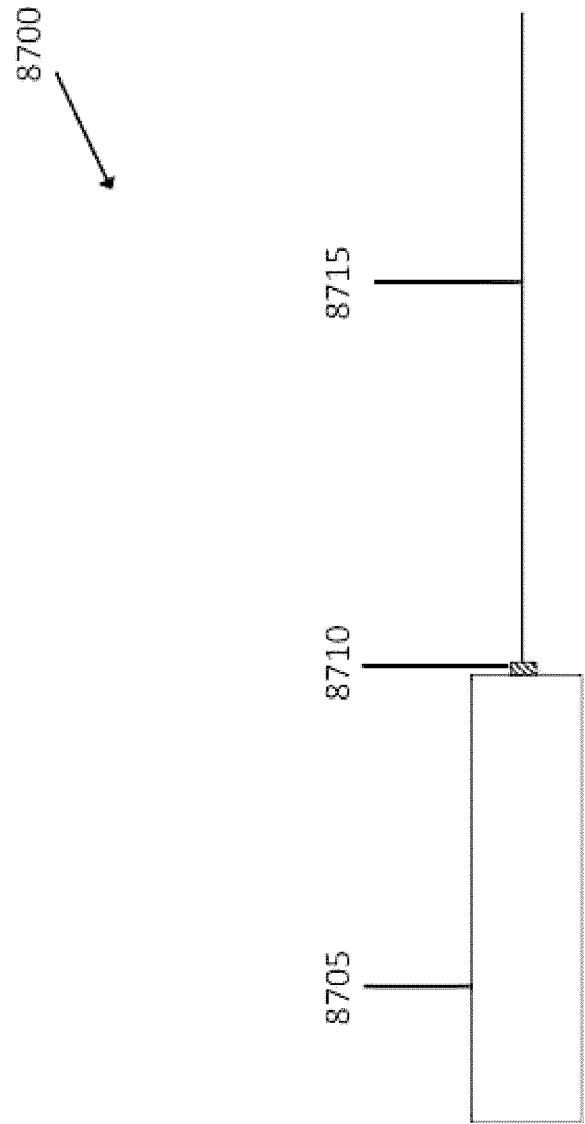

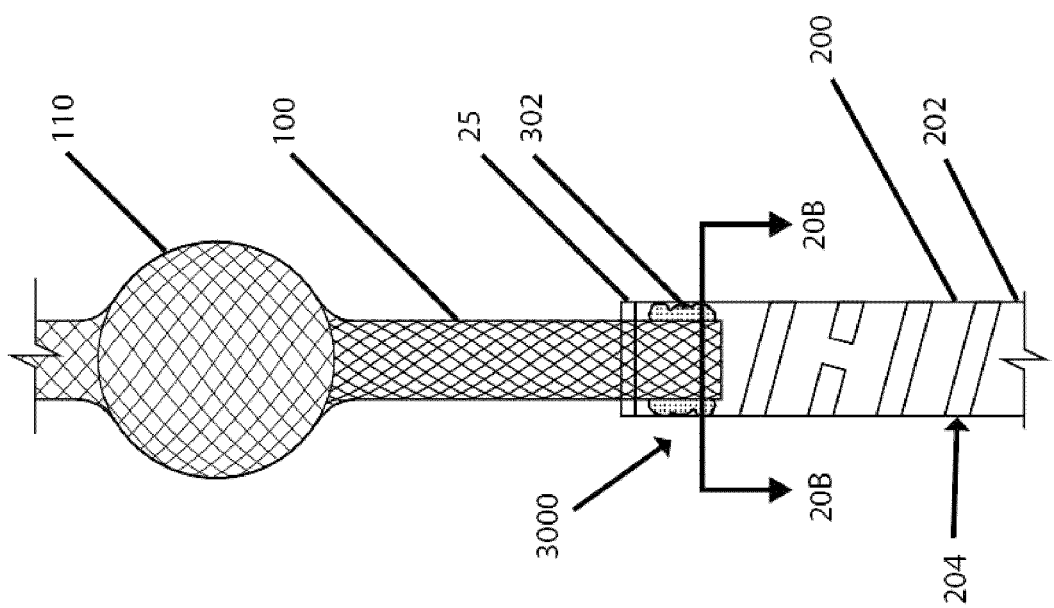

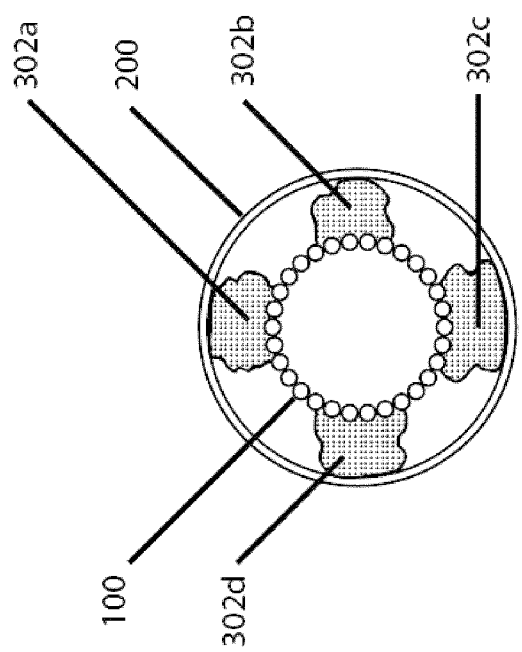

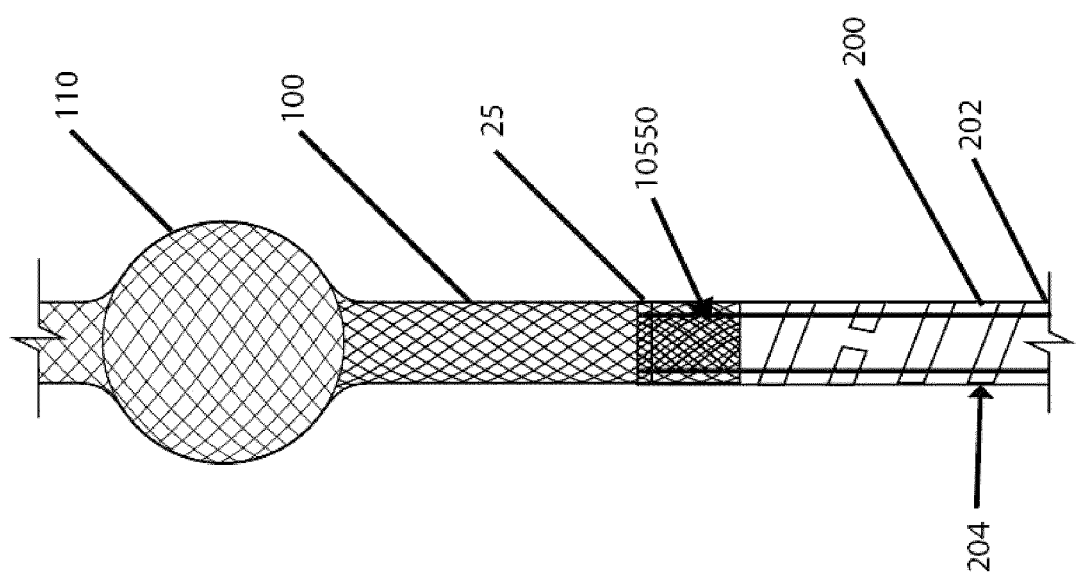

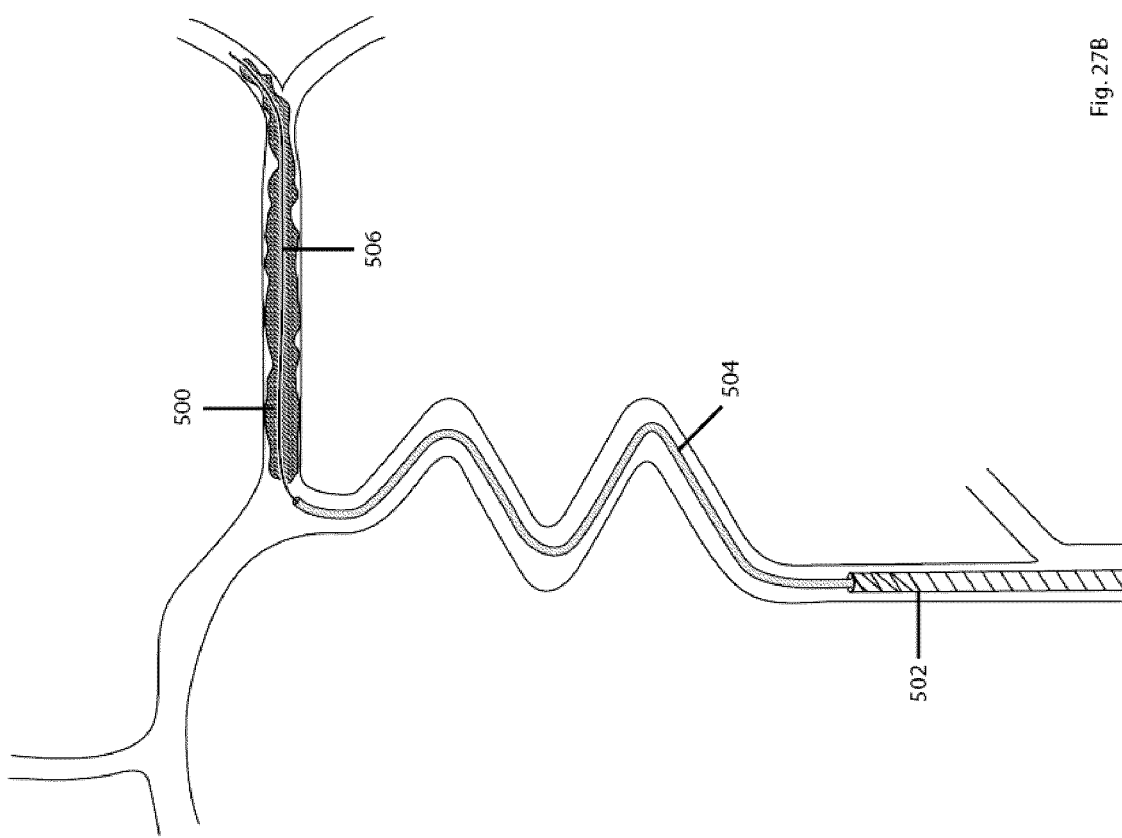

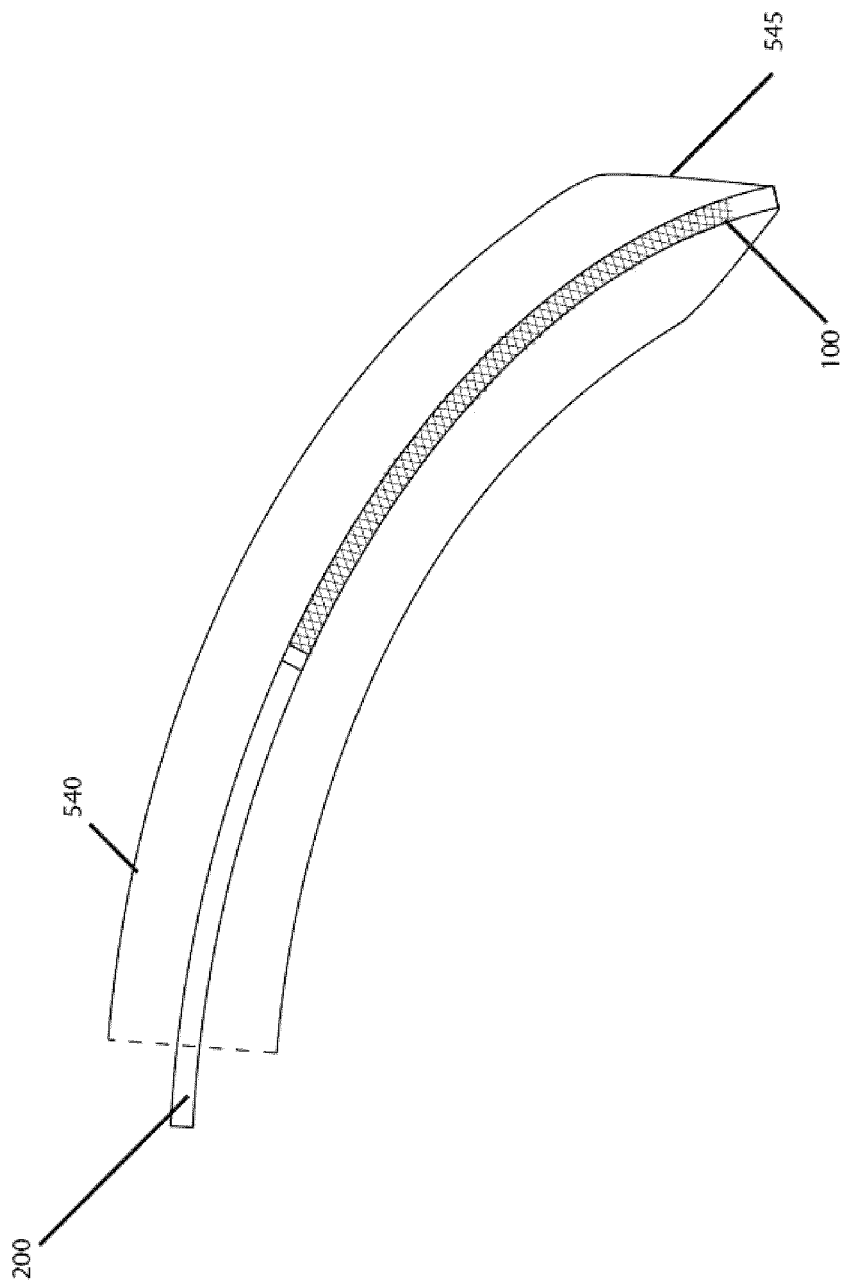

| No. | Crescendo Suction Pattern | Graphical Representation |
|---|---|---|
| 11800 | S. S. S. S. M. M. M. M. L. L. L. L. | |
| 11805 | S M L. S M L. S M L. | |
| 11810 | S. M. L. S. M. L. | |
| 11815 | S. L. S. L. S. L. | |
| 11820 | S. L. M. L. S. L. M. L. | |

Fig. 271-2

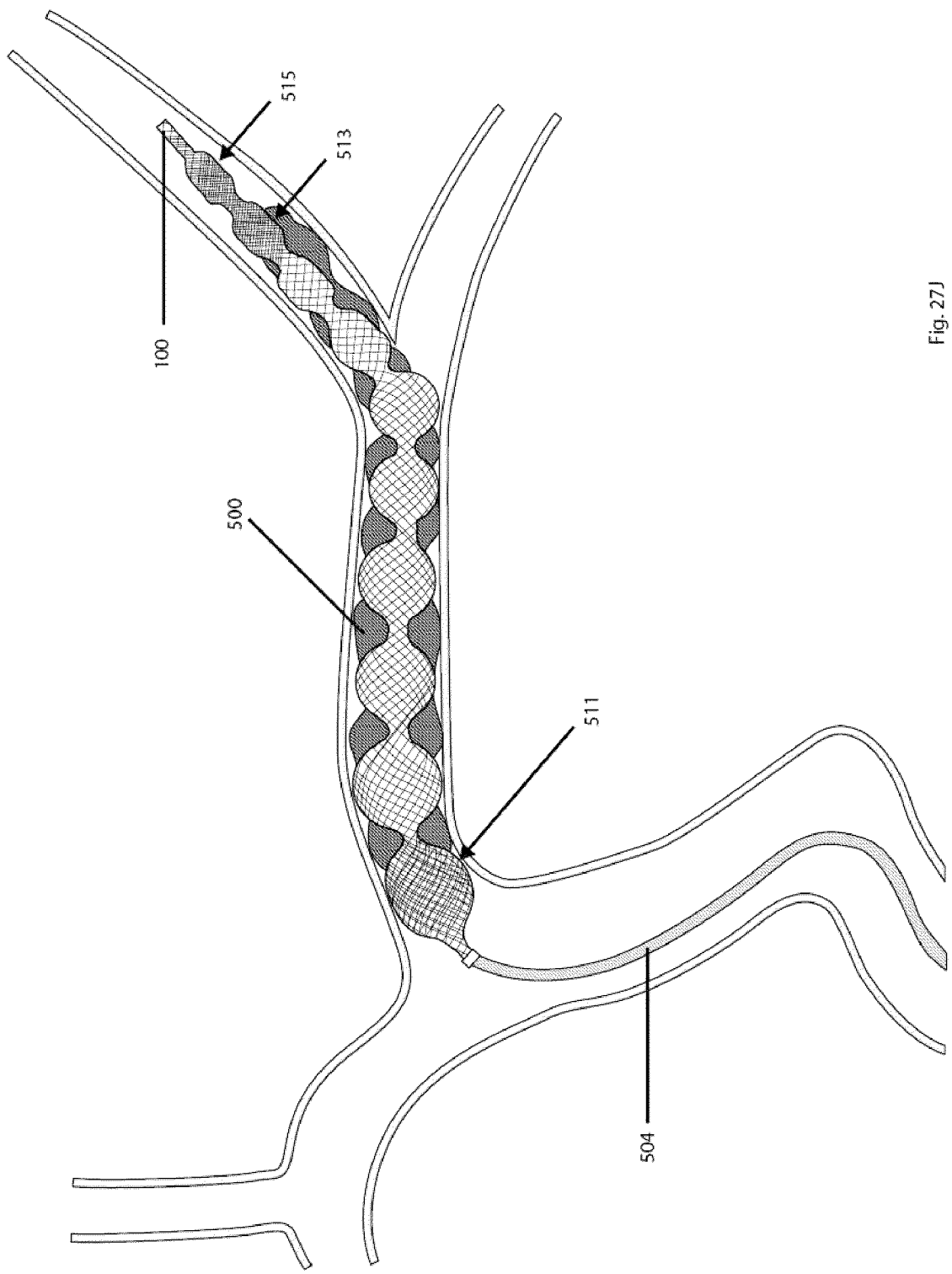

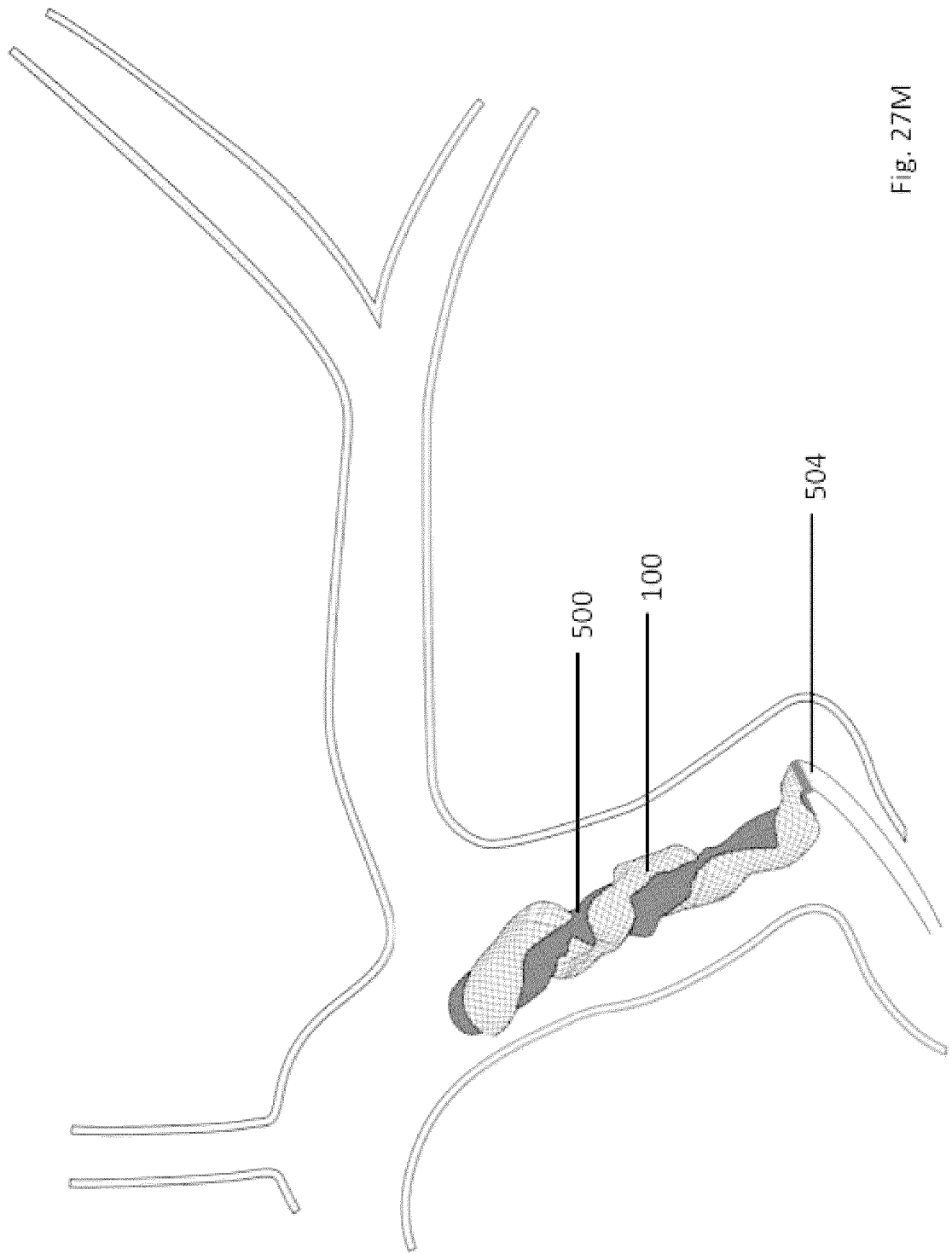

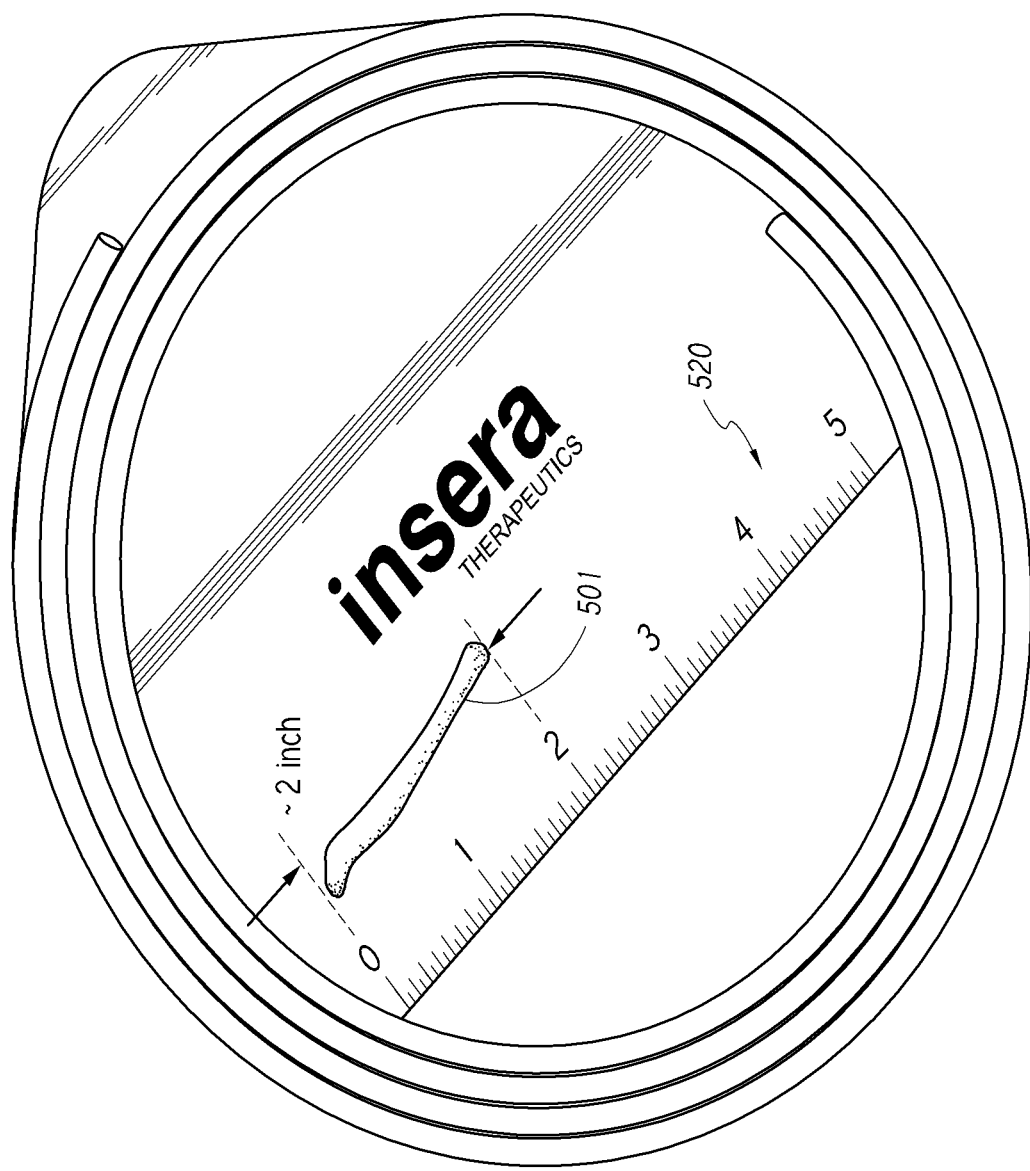

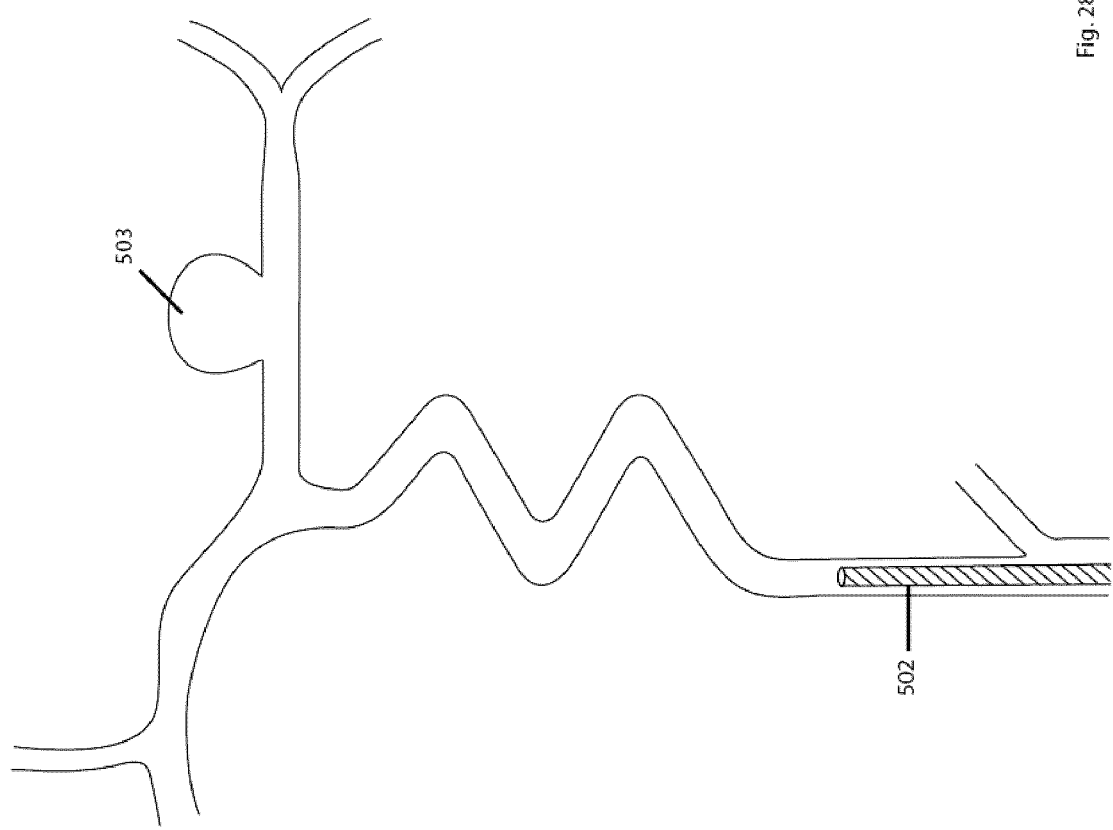

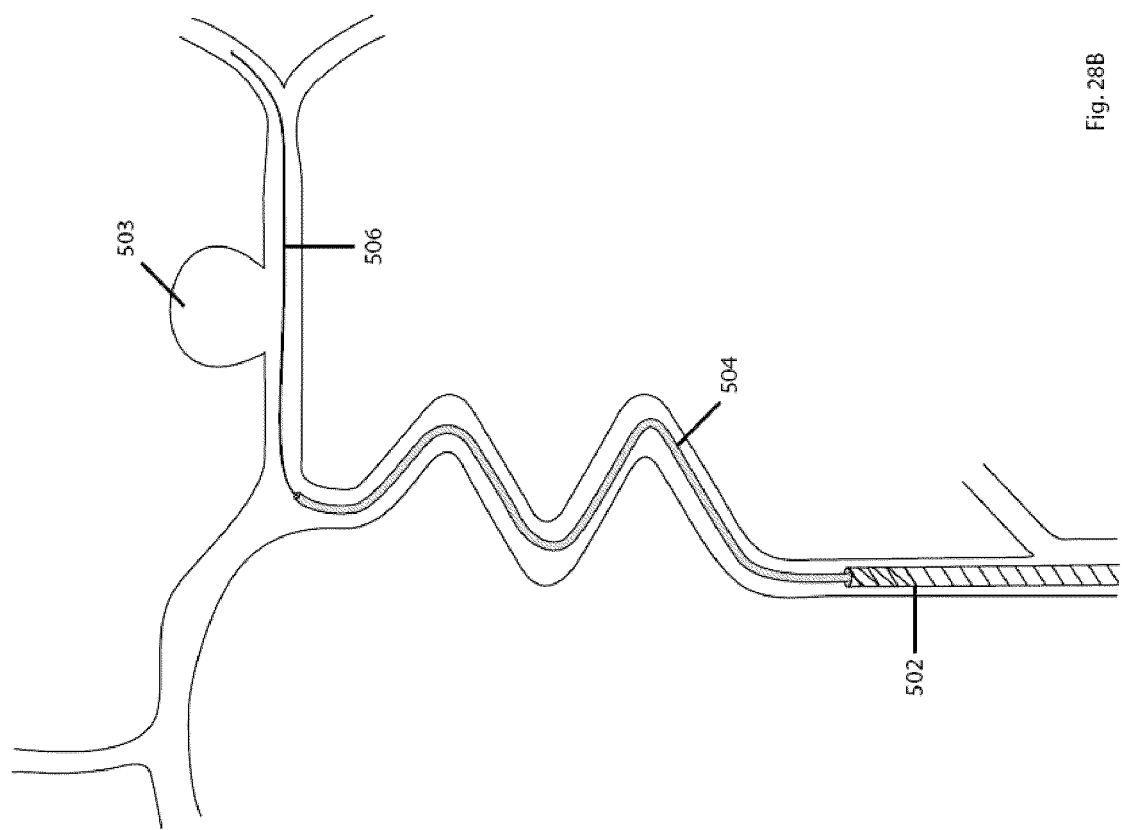

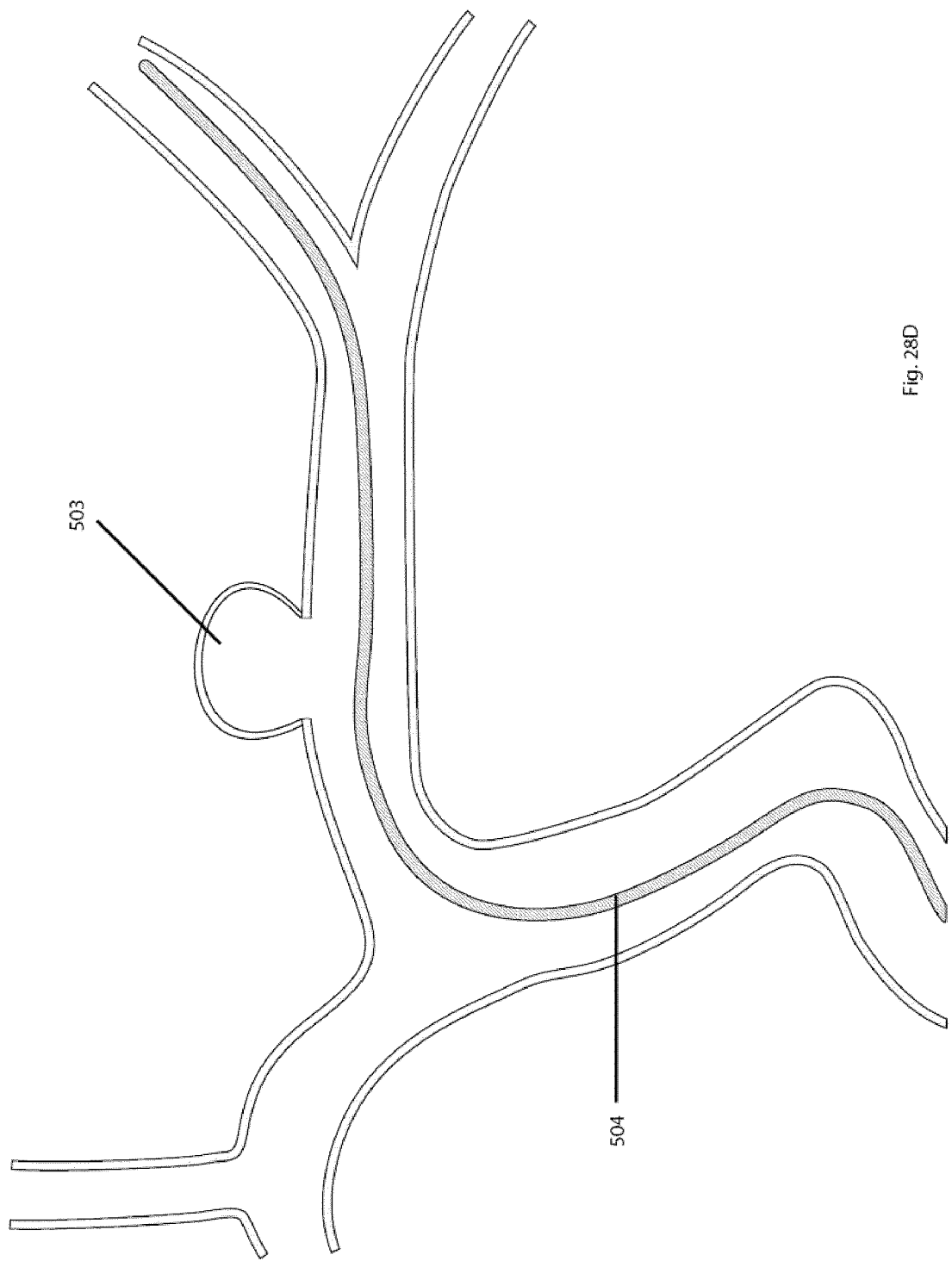

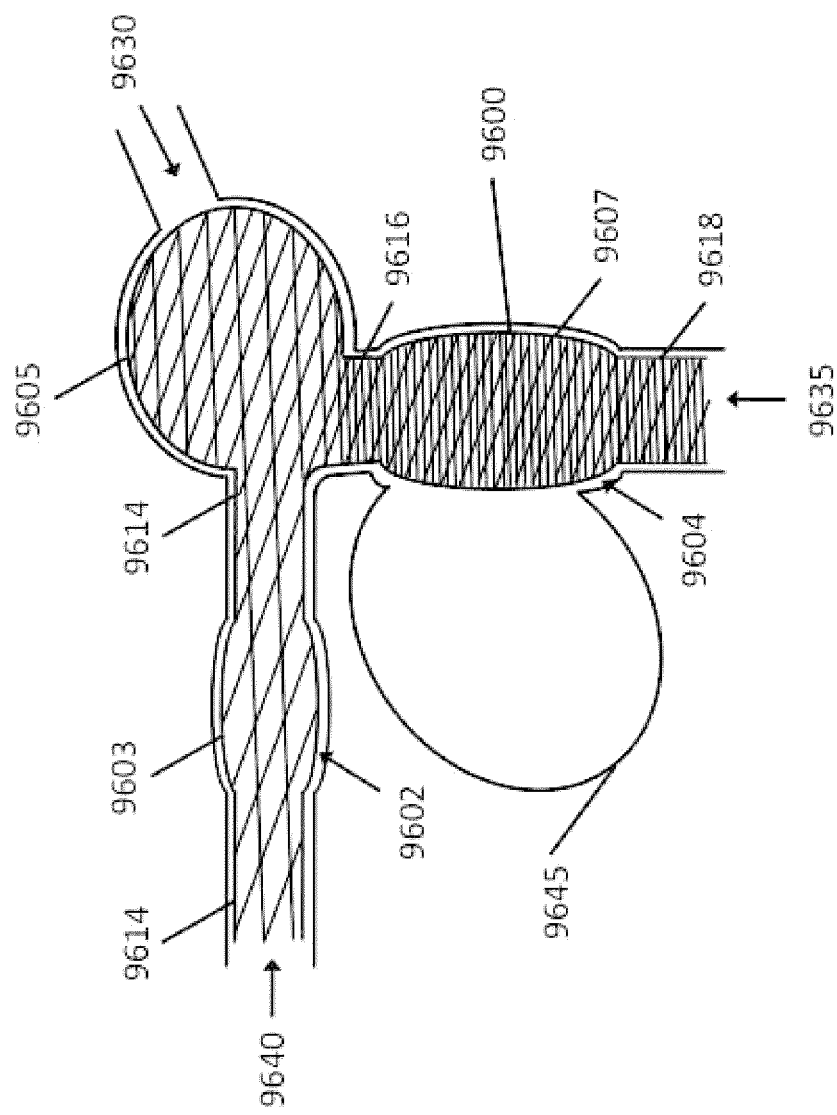

SYSTEMS FOR ASPIRATING THROMBUS DURING NEUROSURGICAL PROCEDURES

INCORPORATION BY REFERENCE

The present application is a continuation of U.S. patent application Ser. No. 16/103,410, filed on Aug. 14, 2018 and issued as U.S. Pat. No. 10,390,926, which is a continuation of PCT Application No. PCT/US2017/017824, filed on Feb. 14, 2017, which claims priority benefit of U.S. Provisional Patent App. No. 62/295,662, filed on Feb. 16, 2016, and any and all applications related thereto by way of priority thereto or therefrom are hereby incorporated by reference in their entirety; this application is also a continuation-in-part of U.S. patent application Ser. No. 15/903,587, filed on Feb. 23, 2018, which is a continuation of U.S. patent application Ser. No. 15/085,083, filed on Mar. 30, 2016 and issued as U.S. Pat. No. 9,901,435, which is a continuation of U.S. patent application Ser. No. 14/848,079, filed on Sep. 8, 2015 and issued as U.S. Pat. No. 9,314,324, which is a continuation of PCT App. No. PCT/US2014/022843, filed Mar. 10, 2014, which is a continuation-in-part of U.S. patent application Ser. No. 13/953,540, filed Jul. 29, 2013 and issued as U.S. Pat. No. 8,715,314; and this application is also a continuation-in-part of U.S. patent application Ser. No. 15/829,416, filed on Dec. 1, 2017, which is a continuation of U.S. patent application Ser. No. 14/926,980, filed on Oct. 29, 2015 and issued as U.S. Pat. No. 9,833,251, which is a continuation of U.S. patent application Ser. No. 14/012,913, filed on Aug. 28, 2013 and issued as U.S. Pat. No. 9,179,995, which is a continuation of U.S. patent application Ser. No. 13/953,540, filed Jul. 29, 2013 and issued as U.S. Pat. No. 8,715,314.

BACKGROUND

Field

The present disclosure generally relates to devices, systems, methods for making, and methods for use in vascular procedures such as thrombectomy and/or flow diversion. Several embodiments relate to thrombectomy systems and methods for providing approaches for the treatment of stroke, peripheral vascular disease, coronary artery disease, saphenous vein graft disease, clogged hemodialysis grafts, cerebral venous sinus thrombosis, and deep venous thrombosis. Several embodiments relate to flow diversion and flow disruption systems and methods for providing approaches for the treatment of brain arterial aneurysms, aortic aneurysms, cardiac wall aneurysms, atrial septal defects and aneurysms including patent foramen ovale, ventricular septal defects and aneurysms, coronary arterial aneurysms, peripheral arterial aneurysms, renal arterial aneurysms, and vascular malformations including arterio-venous malformations and arterio-venous fistulae of the brain, spine, coronary and peripheral vasculature.

Description of the Related Art

Stroke is the leading cause of long term disability in the United States and the second leading cause of death worldwide with over 4.4 million deaths in a year (1999). There are over 795,000 new strokes every year in the United States. Around 85% of all strokes are acute ischemic strokes caused from a blockage in a blood vessel or a blood clot occluding a blood vessel. In 1996, the FDA approved a thrombolytic drug to dissolve blood clots called recombinant tissue plasminogen activator (r-tpa). Despite practice guidelines from multiple national organizations stating that intravenous r-tpa is the standard of care for patients with acute ischemic stroke within 3 hours from symptom onset, only 3-4% of patients with acute ischemic stroke received this drug in the United States. Unlike intravenous r-tpa, catheter-based therapies for mechanical thrombectomy can be used for up to 8 hours or beyond from acute ischemic stroke symptom onset and could benefit more people. With advances in regional stroke networks, an increasing number of stroke patients are able to obtain access to intra-arterial thrombolysis and therapies.

SUMMARY

Certain embodiments described herein disclose devices and methods for removing debris and/or fluids from a body, including, but not limited to, arterial and/or venous clots including ischemic strokes and cerebral venous sinus thrombosis, brain abscesses, brain tumors (e.g., soft tumors, fibrous tumors, and hard tumors), brain bleeds (e.g., intracerebral hemorrhage, intra-ventricular hemorrhage, subdural hematomas, epidural hematomas, other hemorrhages), and clots in dialysis AV grafts or fistulas. Several embodiments provide devices comprising a programmable or pre-programmed vacuum pump, for example customized or customizable for the procedure, debris, fluid, anatomy, etc.

In some embodiments, an aspiration system comprises, or alternatively consists essentially of, a pump and a control system in communication with the pump. The control system comprises a microcontroller, an antenna configured to receive a signal, and a pump control board in communication with the microcontroller. The antenna is in communication with the microcontroller. Upon receiving the signal, the pump control board operates the pump to create negative pressure according to the signal.

The negative pressure may comprise a variable suction pattern according to the signal. The variable suction pattern may comprise a first suction level and a second suction level greater than the first suction level. The variable suction pattern may comprise a third suction level greater than the second suction level. The variable suction pattern may comprise a plurality of suction levels. The variable suction pattern may comprise immediate transition between the plurality of suction levels. The variable suction pattern may comprise no suction between the plurality of suction levels. The system may further comprise a control device configured to send the signal to the antenna. The variable suction pattern may be selectable by a user of the control device. The variable suction pattern may be selectable based on a type of procedure. The variable suction pattern may be selectable based on a type of clot. The control device may be configurable to customize the variable suction pattern. The control device may comprise a computer. The control device may comprise a smart phone. The control device may comprise a tablet computer. The signal may comprise a wireless signal.

The system may further comprise a cannula. The cannula may comprise an aspiration lumen. The cannula may comprise a blunt tip. The cannula may comprise a tapered tip. The cannula may be in electrical communication with a switch. The switch may comprise a foot pedal. The system may further comprise a handle coupled to the cannula. The cannula may comprise an aspiration lumen. The handle may comprise a vacuum port in communication with the aspiration lumen and the pump. The vacuum port may be configured to be covered by a hand of a user to complete a fluid circuit. The vacuum port may be configured to be covered by at least one of a spring-loaded mechanical linkage and porous membrane to complete a fluid circuit.

The pump may comprise a rotary vane pump. The pump may comprise an oil-less dry running low-vibration rotary vane pump. The pump may have a maximum flow rate between 0.25 L/min and 283 L/min. The pump may have a high negative vacuum suction pressure between 0 mm Hg and −698.4 mm Hg. The pump may comprise a linear pump. The pump may have a maximum flow rate between 0.9 L/min and 375 L/min. The pump may have a high negative vacuum suction pressure between 0 mm Hg and −338 mm Hg. The pump may comprise a diaphragm pump. The pump may have a maximum flow rate between 0.38 L/min and 91 L/min. The pump may have a high negative vacuum suction pressure between 0 mm Hg and −742 mm Hg. The pump may comprise a peristaltic pump. The pump may have a maximum flow rate between 0.0001 L/min and 3 L/min. The pump may have a high negative vacuum suction pressure between 0 mm Hg and −760 mm Hg. The pump may comprise a piston pump. The pump may have a maximum flow rate between 2.5 L/min and 200 L/min. The pump may have a high negative vacuum suction pressure between 0 mm Hg and −742 mm Hg. The pump may have a maximum flow rate between 0.25 L/min and 300 L/min. The pump may have a high negative vacuum suction pressure between 0 mm Hg and −700 mm Hg. The pump may be reversible.

In some embodiments, a method of treating an intracerebral hemorrhage uses the system. The method comprises inserting an end of the cannula into the skull, receiving the signal, and aspirating blood using the negative pressure through the cannula. The method may further comprise selecting a negative suction pattern. Selecting the negative suction pattern may comprise selecting a predetermined negative suction pattern. Selecting the negative suction pattern may comprise customizing a negative suction pattern.

In some embodiments, an aspiration system may comprise, or alternatively consist essentially of, a pump and a control system in communication with the pump.

Upon receiving a signal, the control system may operate the pump. Operation of the pump may create negative pressure according to the signal. The negative pressure may comprise a variable suction pattern according to the signal. The variable suction pattern may comprise a first suction level and a second suction level greater than the first suction level. The variable suction pattern may comprise a third suction level greater than the second suction level. The variable suction pattern may comprise a plurality of suction levels. The variable suction pattern may comprise immediate transition between the plurality of suction levels. The variable suction pattern may comprise no suction between the plurality of suction levels. The control system may comprise an antenna configured to receive the signal. The system may further comprise a control device configured to send the signal to the antenna, the variable suction pattern selectable by a user of the control device. The variable suction pattern may be selectable based on a type of procedure. The system of Claim 128, wherein the variable suction pattern may be selectable based on a type of clot. The control device may be configurable to customize the variable suction pattern. The control device may comprise a computer. The control device may comprise a smart phone. The control device may comprise a tablet computer. The control system may comprise a microcontroller in communication with the antenna. The control system may comprise a pump control board in communication with the microcontroller. The signal may comprise a wireless signal.

The system may further comprise a cannula. The cannula may comprise an aspiration lumen. The cannula may comprise a blunt tip. The cannula may comprise a tapered tip. The cannula may be in electrical communication with a switch. The switch may comprise a foot pedal. The system may further comprise a handle coupled to the cannula. The cannula may comprise an aspiration lumen. The handle may comprise a vacuum port in communication with the aspiration lumen and the pump. The vacuum port may be configured to be covered by a hand of a user to complete a fluid circuit. The vacuum port may be configured to be covered by at least one of a spring-loaded mechanical linkage and porous membrane to complete a fluid circuit.

The pump may comprise a rotary vane pump. The pump may comprise an oil-less dry running low-vibration rotary vane pump. The pump may have a maximum flow rate between 0.25 L/min and 283 L/min. The pump may have a high negative vacuum suction pressure between 0 mm Hg and −698.4 mm Hg. The pump may comprise a linear pump. The pump may have a maximum flow rate between 0.9 L/min and 375 L/min. The pump may have a high negative vacuum suction pressure between 0 mm Hg and −338 mm Hg. The pump may comprise a diaphragm pump. The pump may have a maximum flow rate between 0.38 L/min and 91 L/min. The pump may have a high negative vacuum suction pressure between 0 mm Hg and −742 mm Hg. The pump may comprise a peristaltic pump. The pump may have a maximum flow rate between 0.0001 L/min and 3 L/min. The pump may have a high negative vacuum suction pressure between 0 mm Hg and −760 mm Hg. The pump may comprise a piston pump. The pump may have a maximum flow rate between 2.5 L/min and 200 L/min. The pump may have a high negative vacuum suction pressure between 0 mm Hg and −742 mm Hg. The pump may have a maximum flow rate between 0.25 L/min and 300 L/min. The pump may have a high negative vacuum suction pressure between 0 mm Hg and −700 mm Hg. The pump may be reversible.

In some a method of treating an intracerebral hemorrhage using the system comprises inserting an end of the cannula into the skull, receiving the signal, and aspirating blood using the negative pressure through the cannula. The method may further comprise selecting a negative suction pattern. Selecting the negative suction pattern may comprise selecting a predetermined negative suction pattern. Selecting the negative suction pattern may comprise customizing a negative suction pattern.

In some embodiments, a device for treating an aneurysm comprises a first plurality of wires woven to form a first textile structure expandable from a collapsed configuration to an expanded configuration, a second plurality of wires woven to form a second textile structure expandable from a collapsed configuration to an expanded configuration, a first bulb, a second bulb, a third bulb longitudinally between the first bulb and the second bulb, a first neck radially inward of the third bulb and the first bulb, and a second neck radially inward of the third bulb and the second bulb. The second textile structure is in a lumen of the first textile structure. The third bulb is longitudinally spaced from the first bulb by the first neck. The third bulb is longitudinally spaced from the second bulb by the second neck. The third bulb, at least a portion of the first neck, and at least a portion of the second neck comprise the first textile structure and the second textile structure. Porosity of the third bulb is less than porosity of the first bulb and the second bulb.

The first textile structure may comprise a first radiopaque pattern and the second textile structure may comprise a second radiopaque pattern different than the first radiopaque pattern. The first textile structure may comprise a first braid angle and the second textile structure may comprise a second braid angle less than the first braid angle. The first braid angle may be between 145° and 175°. The second braid angle may be between 50° and 110°. The second braid angle may be between 40° and 100° less than the first braid angle. The second braid angle may be between 45% and 75% less than the first braid angle. The bulbs and necks may be configured to inhibit longitudinal migration of the first textile structure relative to the second textile structure.

In some embodiments, a method of treating an aneurysm comprises deploying the device in a body lumen across an aneurysm. After deployment of the device, blood may be inhibited from flowing into the aneurysm. The method may comprise using radiopaque patterns to position the third bulb across a mouth of the aneurysm. The aneurysm may comprise an aneurysm in neurovasculature. The aneurysm may comprise an aneurysm in an iliac artery. The aneurysm may comprise an aneurysm in a visceral renal artery. The aneurysm may comprise an aneurysm in a thoracic aorta. The method may comprise not forming an anastomosis between a left subclavian artery and a left carotid artery. The bulbs and necks may be configured to inhibit longitudinal migration of the device in the body lumen. The method may comprise inhibiting endoleak proximate to a mouth of the aneurysm.

In some embodiments, a method of manufacturing the device comprises inserting the second textile structure into the first textile structure. The second textile structure has a second diameter larger than the first diameter. After inserting the second textile structure into the first textile structure, a first portion of the second textile structure may be radially compressed by the first textile structure and a second portion of the second textile structure may be not radially compressed by the first textile structure. A third portion of the second textile structure may be not radially compressed by the first textile structure. The first portion may be longitudinally between the first portion and the second portion. The method may further comprise shape setting the first textile structure and the second textile structure into a bulbous structure. Shape setting the first textile structure and the second textile structure into the bulbous structure may comprise positioning the first textile structure and the second textile structure around a mandrel. The mandrel may comprise a plurality of pieces. The mandrel may comprise a single piece. The mandrel may comprise a tapered portion. Shape setting the first textile structure and the second textile structure into the bulbous structure may comprise wrapping wire around the first textile structure and the second textile structure. Wrapping wire around the first textile structure and the second textile structure may comprise wrapping a continuous wire around the first textile structure and the second textile structure. Wrapping wire around the first textile structure and the second textile structure may comprise wrapping a plurality of wires around the first textile structure and the second textile structure. At least some of the plurality of wires may not overlap each other. Wrapping wire around the first textile structure and the second textile structure may comprise wrapping stainless steel wire. The method may further comprise shape setting the first textile structure into a tubular structure and shape setting the second textile structure into a tubular structure. The method may further comprise forming the first textile structure. The method may further comprise forming the second textile structure.

In some embodiments, a device for treating an aneurysm comprises, or alternatively consists essentially of, a first textile structure expandable from a collapsed configuration to an expanded configuration, a second textile structure expandable from a collapsed configuration to an expanded configuration, and a bulb comprising the first textile structure and the second textile structure. The second textile structure is radially inward of the first textile structure.

The first textile structure may comprise a first radiopaque pattern and the second textile structure may comprise a second radiopaque pattern different than the first radiopaque pattern. The first textile structure may comprise a first braid angle and the second textile structure may comprise a second braid angle less than the first braid angle. The first braid angle may be between 145° and 175°. The second braid angle may be between 50° and 110°. The second braid angle may be between 40° and 100° less than the first braid angle. The second braid angle may be between 45% and 75% less than the first braid angle. The bulb may be configured to inhibit longitudinal migration of the first textile structure relative to the second textile structure.

In some embodiments, a method of treating an aneurysm comprising deploying the device in a body lumen across an aneurysm. After deployment of the device, blood may be inhibited from flowing into the aneurysm. The method may comprise using radiopaque patterns to position the third bulb across a mouth of the aneurysm. The aneurysm may comprise an aneurysm in neurovasculature. The aneurysm may comprise an aneurysm in an iliac artery. The aneurysm may comprise an aneurysm in a visceral renal artery. The aneurysm may comprise an aneurysm in a thoracic aorta. The method may comprise not forming an anastomosis between a left subclavian artery and a left carotid artery. The bulb may be configured to inhibit longitudinal migration of the device in the body lumen. The method may comprise inhibiting endoleak proximate to a mouth of the aneurysm.

In some embodiments, a method of manufacturing the device comprises inserting the second textile structure into the first textile structure. The second textile structure has a second diameter larger than the first diameter. After inserting the second textile structure into the first textile structure, a first portion of the second textile structure may be radially compressed by the first textile structure and a second portion of the second textile structure may be not radially compressed by the first textile structure. A third portion of the second textile structure may be not radially compressed by the first textile structure. The first portion may be longitudinally between the first portion and the second portion. The method may further comprise shape setting the first textile structure and the second textile structure into a bulbous structure. Shape setting the first textile structure and the second textile structure into the bulbous structure may comprise positioning the first textile structure and the second textile structure around a mandrel. The mandrel may comprise a plurality of pieces. The mandrel may comprise a single piece. The mandrel may comprise a tapered portion. Shape setting the first textile structure and the second textile structure into the bulbous structure may comprise wrapping wire around the first textile structure and the second textile structure. Wrapping wire around the first textile structure and the second textile structure may comprise wrapping a continuous wire around the first textile structure and the second textile structure. Wrapping wire around the first textile structure and the second textile structure may comprise wrapping a plurality of wires around the first textile structure and the second textile structure. At least some of the plurality of wires may not overlap each other. Wrapping wire around the first textile structure and the second textile structure may comprise wrapping stainless steel wire. The method may further comprise shape setting the first textile structure into a tubular structure and shape setting the second textile structure into a tubular structure. The method may further comprise forming the first textile structure. The method may further comprise forming the second textile structure.

In some embodiments, a method of treating an aneurysm comprises, or alternatively consists essentially of, inserting a structure comprising a plurality of bulbs into the aneurysm. At least one bulb of the plurality of bulbs has a different porosity than another bulb of the plurality of bulbs.

The plurality of bulbs may comprise a first bulb and a second bulb. The first bulb may have a lower porosity than the second bulb, the first bulb proximate to a mouth of the aneurysm. The plurality of bulbs may comprise a first bulb, a second bulb, and a third bulb. The first bulb may have a higher porosity than the second bulb. The third bulb may have a higher porosity than the second bulb. The first bulb may be most proximate to a mouth of the aneurysm. The second bulb may be next most proximate to the mouth of the aneurysm. The structure may comprise a proximal neck and an intermediate neck between a first bulb and a second bulb. The proximal neck may be longitudinally offset from the intermediate neck. The structure may comprise a proximal neck and a distal neck. The proximal neck may be longitudinally offset from the distal neck. The aneurysm may comprise an aneurysm in neurovasculature. The aneurysm may comprise an aneurysm in an iliac artery. The aneurysm may comprise an aneurysm in a visceral renal artery.

Certain embodiments described herein disclose devices and methods for removing a thrombus or thrombi. These thrombi include, but are not limited to, blood clots (e.g., attached to the blood vessel) and emboli (e.g., floating blood clots), as well as other debris. Several embodiments provide devices comprising multiple bulbs. Vessels or other tissues in the body can become partially or fully clogged or blocked by a thrombus or thrombi. Although some clot retrievers or thrombectomy devices that employ a laser cut hypotube on a distal end of a wire are commercially available, some embodiments disclosed herein do not use laser cut struts and are gentle on the vessel wall, while effectively and efficiently capturing a thrombus in any location in the body. Some devices can be torsional rasped (e.g., wrung or twisted) to help capture thrombi. Certain embodiments described herein disclose devices and methods for treating aneurysms, vascular malformations, fistulas, and the like. Several embodiments of the devices and methods described herein may be particularly beneficial by achieving one, some, or all of the following advantages:

- adapted for, and gentle on, the fragile blood vessels in contrast to an expansile laser-cut stent-based mechanical thrombectomy device;
- tapered to at least partially mimic the tapering of the human blood vessels, which can allow for the use of a single tapered device to remove blood clots extending across different tapering blood vessel diameters;
- flexible during deployment and retrieval in tortuous human blood vessels, which can allow for longer usable lengths of the device;
- comprises a usable length customizable to the length of a thrombus or clot burden without having to use multiple devices to remove the thrombus piecemeal;
- a textile structure-based mechanical thrombectomy device that can allow for torsional rasping of the textile structure around a thrombus to entrap and retrieve the thrombus;
- patterns of radiopaque filaments or wires that increase visibility under X-ray fluoroscopy;
- allows for longitudinal crowding of filaments that varies pore sizes of certain sections during operation for selective filtering into bifurcated vessels;
- patterns of radiopaque filaments or wires provide measurement estimates under X-ray fluoroscopy;
- provides filtering of distal emboli or debris that may be released;
- employs processes to couple a textile structure to a hypotube by bonding of different metals or alloys;
- has a low overall profile in which the outer diameter of the mechanical thrombectomy device in the collapsed configuration is less than, e.g., about 0.0125 inches (approx. 0.317 mm);
- has a low overall profile in which the mechanical thrombectomy device in the collapsed configuration can be deployed using a microcatheter that has an inner lumen diameter of less than, e.g., about 0.014 inch (approx. 0.355 mm);
- varying slit patterns along the length of a hypotube, which can provide distal flexibility and proximal support;
- varying shape set properties along the length of a hypotube, which can provide distal flexibility and proximal support;
- a hypotube that can support the ability to perform torsional rasping of a thrombus;
- a laser-cut hypotube with multiple transition points incorporated as the core braid for the wall of the microcatheter, which can allow for distal flexibility and proximal support for allowing the safe and effective deployment of the textile structure based mechanical thrombectomy device;
- can be used without a separate embolic protection member (e.g., distal embolic protection member) to capture emboli;
- can be used without reversal of blood flow, or otherwise impeding blood flow, to protect against release of distal emboli; and/or
- can be used without a balloon or other inflation device.

In some embodiments, a device for treating a thrombus in a vessel comprises a first portion, a second portion including a tubular member, and a bonding zone coupling the first portion and the second portion. The first portion comprises a plurality of wires woven to form a textile structure expandable from a collapsed configuration to an expanded configuration. The textile structure comprises, in the expanded configuration, five to twenty self-expanding bulbs and a plurality of necks. Pairs of the five to twenty self-expanding bulbs are spaced along a longitudinal axis of the textile structure by a neck of the plurality of necks. The plurality of wires comprises shape-memory wires.

The five to twenty self-expanding bulbs may comprise a first bulb, a second bulb distal to the first bulb, a third bulb distal to the second bulb, a fourth bulb distal to the third bulb, a fifth bulb distal to the fourth bulb, a sixth bulb distal to the fifth bulb, a seventh bulb distal to the sixth bulb, an eighth bulb distal to the seventh bulb, a ninth bulb distal to the eighth bulb, and a tenth bulb distal to the ninth bulb. The first bulb and the second bulb may have a first diameter. The third bulb and the fourth bulb may have a second diameter smaller than the first diameter. The fifth bulb, the sixth bulb, and the seventh bulb may have a third diameter smaller than the second diameter. The eighth bulb, the ninth bulb, and the tenth bulb may have a fourth diameter smaller than the third diameter. One, some, or all of the first bulb, the second bulb, the third bulb, the fourth bulb, the fifth bulb, the sixth bulb, the seventh bulb, the eighth bulb, the ninth bulb, and the tenth bulb may have a spherical shape. One, some, or all of the first bulb, the second bulb, the third bulb, the fourth bulb, the fifth bulb, the sixth bulb, the seventh bulb, the eighth bulb, the ninth bulb, and the tenth bulb may have an oblong shape. The second portion may comprise a hypotube having a longitudinal axis. The hypotube may comprise a first pattern of longitudinally-spaced rows and a second pattern of longitudinally-spaced rows. Some or each of the rows of the first pattern include two kerfs and two stems. The two stems in some or each of the rows of the first pattern may be circumferentially opposite. The stems of the first pattern may be offset in a first circumferential direction. Some or each of the rows of the second pattern may include two kerfs and two stems. The two stems in some or each of the rows of the second pattern may be circumferentially opposite. The rows of the second pattern may be singly alternatingly interspersed with the rows of the first pattern. The stems of the second pattern may be offset in a second circumferential direction opposite the first circumferential direction. The longitudinally-spaced rows of the first pattern may be at an angle with respect to the longitudinal axis of the hypotube. The longitudinally-spaced rows of the second pattern may be at an angle with respect to the longitudinal axis of the hypotube. The two kerfs in some or each of the rows of the first pattern may have rounded edges. The two kerfs in some or each of the rows of the second pattern may rounded edges. The hypotube may comprise a first section having a first pitch of the longitudinally-spaced rows of the first pattern and the longitudinally-spaced rows of the second pattern, a second section having a second pitch of the longitudinally-spaced rows of the first pattern and the longitudinally-spaced rows of the second pattern, the second section proximal to the first section, the second pitch greater than the first pitch, a third section having a third pitch of the longitudinally-spaced rows of the first pattern and the longitudinally-spaced rows of the second pattern, the third section proximal to the second section, the third pitch greater than the second pitch, and a fourth section having a fourth pitch of the longitudinally-spaced rows of the first pattern and the longitudinally-spaced rows of the second pattern, the fourth section proximal to the third section, the fourth pitch greater than the third pitch. At least two of the five to twenty self-expanding bulbs may have different outer diameters in the radially expanded configuration. At least two of the five to twenty self-expanding bulbs may have different shapes in the radially expanded configuration. At least one of the five to twenty self-expanding bulbs may have a spherical shape in the radially expanded configuration. At least one of the five to twenty self-expanding bulbs may have an oblong shape in the radially expanded configuration. The first portion may be hollow (e.g., completely hollow). The first portion may comprise a free (e.g., not coupled to anything) distal end. A diameter of the first portion in the collapsed configuration may be between 0.25 mm and 0.5 mm. The textile structure may be tapered or stepped from a proximal end to a distal end. The bonding zone may include a proximal end of the first portion within a distal end of the second portion. The bonding zone may comprise a ring or cylinder around the plurality of wires. The plurality of wires may be welded to the ring or cylinder. The bonding zone may include a distal end of the second portion within a proximal end of the first portion. The bonding zone may comprise heat-shrink tubing around the proximal end of the first portion. The bonding zone may include a distal end of the second portion within a distal end of the first portion. The first portion may comprise a free (e.g., not coupled to anything) proximal end.

The bonding zone may comprise silver-based lead-free solder. The plurality of wires may comprise radiopaque wires. The radiopaque wires may be spaced or clustered to increase visibility under x-ray. At least two of the radiopaque wires may form at least two longitudinally offset sine waves visibly distinct from the shape memory wires under x-ray. The at least two longitudinally offset sine waves may facilitate length measurement in the vessel. Crossings of the at least two longitudinally offset sine waves may be spaced at regular intervals. At least one of the at least two longitudinally offset sine waves may comprise a plurality of circumferentially adjacent radiopaque wires that are parallel and longitudinally spaced along the textile structure. A first neck of the plurality of necks may have a different parameter than a second neck of the plurality of necks. The different neck parameter may include at least one of length, diameter, and shape. The first portion may comprise a distal end comprising a distal end of each of the plurality of wires trimmed along a plane transverse to the longitudinal axis of the textile structure. The distal end of each of the plurality of wires may be trimmed at an angle of 90° to the longitudinal axis of the textile structure. The distal end of the first portion may comprise a polymer coating at least the distal end of each of the plurality of wires. The polymer may comprise radiopaque particles. The distal end of the first portion may comprise a lumen maintained by absence of the polymer. The five to twenty bulbs may be phase shifted relative to the longitudinal axis of the textile structure. The textile structure may comprise a first shape at a first temperature, a second shape at a second temperature higher than the first temperature, and a third shape comprising stress-induced martensite. The first shape may comprise a spiral. The second shape may comprise the expanded configuration. The third shape may be different than the first shape and the second shape. The textile structure may be configured to self-expand from the third shape to the second shape upon deployment from a sheath. The textile structure may be configured to transform from the second shape to the first shape upon exposure to the first temperature or lower. The first temperature may be less than 25° C. The second temperature may be between 25° C. and 37° C. The tubular member may comprise a wire and a hypotube. The hypotube may comprise lumen. The hypotube may be distal to the wire. A portion of the wire may be coupled inside the lumen of the hypotube. The tubular member may comprise a plurality of different austenitic finish temperatures along a longitudinal axis of the tubular member. The tubular member may comprise a plurality of different shape sets along a longitudinal axis of the tubular member. The tubular member may comprise a plurality of different materials along a longitudinal axis of the tubular member. The first portion may comprise pores between the plurality of wires. The second portion may comprise a wire and a tubular element. The wire may comprise shape-memory material. The wire may have a distal end comprising a first shape at a first temperature and a second shape at a second temperature different than the first temperature. The second shape may be a straightened form of the first shape. The bonding zone may reversibly couple the first portion and the second portion. The bonding zone may comprise the plurality of wires and the pores of the first portion being engaged with the wire in the first shape and with the tubular element. The wire may comprise a coiling portion proximal to the distal end. The coiling portion may comprise a coil at the first temperature and a straightened form of the coil at the second temperature. The bonding zone may comprise solder between the proximal portion and the distal portion. The bonding zone may have a tensile strength less than 18,600 kPa. A proximal part of the first portion may have a first shape at a first temperature and a second shape at a second temperature different than the first temperature. The second shape may be a straightened form of the first shape. The tubular member may comprise a distal end comprising a socket. The bonding zone may reversibly couple the first portion and the second portion. The bonding zone may comprise the proximal part of the first portion mechanically forced into the socket. The socket may include at least one of a slit, a recess, and a radially outward dimple. The bonding zone may comprise the first portion radially outward of the tubular member. The bonding zone may comprise the tubular member radially outward of the first portion. The first portion may comprise pores between the plurality of wires creating a plurality of grooves. The second portion may comprise a distal end comprising a plurality of ridges. The bonding zone may reversibly couple the first portion and the second portion. The bonding zone may comprise the plurality of ridges mechanically forced into the plurality of grooves. The ridges may comprise threads at an angle to a longitudinal axis of the distal end of the second portion. The ridges may be perpendicular to a longitudinal axis of the distal end of the second portion. The five to twenty self-expanding bulbs may comprise a first bulb, a second bulb distal to the first bulb, a third bulb distal to the second bulb, a fourth bulb distal to the third bulb, a fifth bulb distal to the fourth bulb, and a sixth bulb distal to the fifth bulb. The first bulb and the second bulb may have a first diameter. The third bulb and the fourth bulb may have a second diameter smaller than the first diameter. The fifth bulb and the sixth bulb may have a third diameter smaller than the second diameter. The bonding zone may include a distal end of the second portion within at least part of the first portion. A method of treating a thrombus in a vessel may comprise providing the device, expanding from the collapsed configuration to the expanded configuration at least some of the five to twenty self-expanding bulbs, and entrapping the thrombus in the at least some of the five to twenty self-expanding bulbs. Entrapping the thrombus may include torsionally rasping the thrombectomy device (e.g., enveloping the thrombus by torsionally rasping).

In some embodiments, a method of treating a thrombus comprises expanding from a collapsed configuration to an expanded configuration at least some bulbs out of five to twenty bulbs of a textile structure of a first portion of a thrombectomy device. A plurality of wires are woven to form the textile structure. The plurality of wires comprises shape-memory wires. The textile structure comprises a plurality of necks. Pairs of the five to twenty bulbs are spaced along a longitudinal axis of the textile structure by a neck of the plurality of necks. The thrombectomy device further comprises a second portion including a tubular member and a bonding zone coupling the first portion and the second portion. The method further comprises entrapping the thrombus in the at least some bulbs in the expanded configuration and retracting the thrombectomy device from the vessel.

Expanding the at least some bulbs to the expanded configuration may comprise retracting a microcatheter surrounding the five to twenty bulbs in the collapsed configuration. Retracting the microcatheter may be at least until a distal end of the microcatheter is proximal to the thrombus. Retracting the thrombectomy device from the vessel may comprise retracting the microcatheter at a similar rate. The second portion may include a hypotube including a plurality of longitudinally spaced kerfs. The plurality of longitudinally spaced kerfs may include a plurality of interspersed cut patterns. A pitch of the plurality of longitudinally spaced kerfs may vary longitudinally along the hypotube. At least some of the plurality of longitudinally spaced kerfs may include rounded edges. Retracting the thrombectomy device from the vessel may comprise applying negative suction to the vessel. Expanding the at least some bulbs from the collapsed configuration to the expanded configuration may comprise expanding the vessel by 0% to 30%. Entrapping the thrombus may include torsionally rasping the thrombectomy device (e.g., enveloping the thrombus by torsionally rasping). Torsionally rasping may effect at least one of removing portions of the thrombus attached to an endothelium wall of the vessel, entrapping the thrombus in the distal portion of the thrombectomy device (e.g., enveloping the thrombus), and collecting emboli in the distal portion of the thrombectomy device. Torsionally rasping may comprise rotating the second portion of the thrombectomy device. During torsionally rasping the thrombectomy device, a ratio of rotation of the first portion of the thrombectomy device to rotation of the second portion of the thrombectomy device may be not 1:1 (e.g., greater than 1:1 or less than 1:1). Torsionally rasping the thrombectomy device may comprise rotating the second portion of the thrombectomy device at least 360 degrees, which may result in a rotation of the first portion of the thrombectomy device of less than 360 degrees. The vessel may comprise a blood vessel in a brain or a blood vessel in a leg. The method may further comprise measuring a length of the thrombus in the vessel, measuring a length of the thrombus out of the vessel, and comparing the length of the thrombus in the vessel to the length of the thrombus out of the vessel. Retracting the thrombectomy device from the vessel may comprise removing the thrombus from the vessel in substantially one piece. The method may further comprise, if the length of the thrombus out of the vessel is less than the length of the thrombus in the vessel, removing remaining thrombus from the vessel. Measuring the length of the thrombus out of the vessel may comprise placing the thrombus proximate to a ruler on a package of the thrombectomy device. The method may further comprise measuring a length of the thrombus in the vessel. Expanding the at least some bulbs may include retracting a sheath surrounding the five to twenty bulbs in the collapsed configuration by a customizable retraction length. The customizable retraction length may be based at least partially on the measured length of the thrombus in the vessel. The customizable retraction length may be greater than a length of the at least some bulbs after expanding. The plurality of wires may comprise radiopaque wires. At least two of the radiopaque wires may be configured to form crossing points visible under x-ray. The crossing points may be configured to provide approximate length measurement. The textile structure may comprise a second shape upon exposure to a temperature or lower than the temperature. The second shape may comprise a spiral. The temperature may be 25° C. The temperature may be 18° C. The textile structure may comprise a third shape upon exposure to a second temperature or higher than the second temperature. The second temperature may be 37° C.

In some embodiments, a method of treating a thrombus in a vessel with self-expanding bulbs comprises advancing a guidewire in the vessel proximal to the thrombus, advancing a guide catheter in the vessel and over the guidewire, after advancing the guide catheter, removing the guidewire from the vessel, and advancing a microwire in the vessel and through the guide catheter. Advancing the microwire includes crossing the thrombus (e.g., crossing the distal-most portion of the thrombus by 0.5 mm to 5 mm). The method further comprises advancing a microcatheter in the vessel and over the microwire. Advancing the microcatheter includes crossing the thrombus with a distal end of the microcatheter. The method further comprises, after advancing the microcatheter, removing the microwire from the vessel, and, after removing the microwire, inserting a thrombectomy device from an introducer sheath into the microcatheter. The thrombectomy device includes an elongate support structure and a delivery system coupled to the elongate support structure. The elongate support structure includes a plurality of wires woven to form a textile fabric. The elongate support structure may comprise or consist essentially of at least three (e.g., at least four, at least six, at least ten, five to twenty, four to ten, etc.) self-expanding bulbs, a plurality of necks (e.g., longitudinally between and radially inward of the self-expanding bulbs), and a distal neck (e.g., radially inward of a distal-most bulb of the self-expanding bulbs). The delivery system includes a hypotube including a plurality of longitudinally-spaced kerfs including a plurality of interspersed cut patterns. A pitch of the plurality of longitudinally-spaced kerfs varies longitudinally along the hypotube. Each of the plurality of longitudinally-spaced kerfs includes rounded edges. The method further comprises, after inserting the thrombectomy device from the introducer sheath into the microcatheter, advancing the thrombectomy device in the vessel and through the microcatheter proximate to the distal end of the microcatheter. Advancing the thrombectomy device includes crossing the thrombus (e.g., with the distal-most bulb of the self-expanding bulbs). The method further comprises, after advancing the thrombectomy device, maintaining a location of the delivery system of the thrombectomy device while retracting the microcatheter. Upon being unsheathed from the microcatheter, at least some of the self-expanding bulbs of the elongate support structure of the thrombectomy device self-expand from a radially compressed state to a radially expanded state. The microcatheter, in several embodiments, is retracted at least until the distal end of the microcatheter is proximal to the thrombus. The method further comprises retracting the microcatheter and the delivery system of the thrombectomy device into the guide catheter. During retraction of the microcatheter and the delivery system of the thrombectomy device, the some of the self-expanding bulbs remain in the radially expanded state, while others of the self-expanding bulbs of the elongate support structure of the thrombectomy device in the radially compressed state remain in the radially compressed state. In some embodiments, all the bulbs are partially or fully expanded during retraction. In other embodiments, all the bulbs are partially or fully compressed during retraction.

The method may further comprise, before retracting the microcatheter and the delivery system of the thrombectomy device into the guide catheter, torsionally rasping the thrombectomy device to, for example, remove portions of the thrombus attached to an endothelium wall, entrap the thrombus in the radially expanded elongate support structure of the thrombectomy device, and/or collect emboli in the radially expanded elongate support structure. Retracting the microcatheter and the delivery system may be performed at a similar rate and while optionally applying negative pressure to the vessel. The vessel may comprise a blood vessel in a brain, leg, or other vessel or structure in the body. The method may further comprise torsionally rasping the thrombectomy device including entrapping the thrombus in the portion of the elongate support structure. The elongate support structure may comprise at least two of the, e.g., five to twenty bulbs, having different outer diameters in the radially expanded state. The elongate support structure may be tapered. The thrombectomy device in the radially compressed state may have a thickness less than 0.0125 inches. Torsionally rasping the thrombectomy device may include removing portions of the thrombus attached to an endothelium wall. Torsionally rasping the thrombectomy device may include collecting one or more emboli released from the thrombus in the portion of the elongate support structure. Expanding the portion of the elongate support structure from the radially compressed state to the radially expanded state may comprise expanding the vessel by 0% to 30%. During torsionally rasping the thrombectomy device, a ratio of rotation of the delivery system of the thrombectomy device to rotation of the elongate support structure may be between 1:0.5 and 1:0.25. During torsionally rasping the thrombectomy device, a ratio of rotation of the delivery system of the thrombectomy device to rotation of the elongate support structure may be not 1:1.

In some embodiments, a method of treating a thrombus in a vessel with self-expanding bulbs comprises advancing a thrombectomy device through a microcatheter in the vessel and across the thrombus. The thrombectomy device includes an elongate support structure including more than two (e.g., five to twenty, four to ten) self-expanding bulbs and a delivery system coupled to the elongate support structure. The delivery system includes a hypotube including a plurality of longitudinally-spaced kerfs. The method further comprises retracting the microcatheter and expanding at least a portion of the elongate support structure of the thrombectomy device from a radially compressed state to a radially expanded state, torsionally rasping the thrombectomy device including entrapping the thrombus in the portion of the elongate support structure, and retracting the microcatheter and the delivery system of the thrombectomy device into a guide catheter in the vessel. Although the bulbs are self-expanding in several embodiments, bulbs that expand upon exertion of force (e.g., mechanical force) can be substituted in various embodiments described herein.

The elongate support structure may comprise at least two of the more than two bulbs having different outer diameters in the radially expanded state. The elongate support structure may be tapered. The plurality of longitudinally spaced kerfs of the hypotube may include a plurality of interspersed cut patterns. A pitch of the plurality of longitudinally spaced kerfs of the hypotube may vary longitudinally along the hypotube. The thrombectomy device in the radially compressed state may have a thickness less than 0.0125 inches. Torsionally rasping the thrombectomy device may include removing portions of the thrombus attached to an endothelium wall. Torsionally rasping the thrombectomy device may include collecting one or more emboli released from the thrombus in the portion of the elongate support structure. Expanding the portion of the elongate support structure from the radially compressed state to the radially expanded state may comprise expanding the vessel by 0% to 30%. During torsionally rasping the thrombectomy device, a ratio of rotation of the delivery system of the thrombectomy device to rotation of the elongate support structure of the thrombectomy device may be between 1:0.5 and 1:0.25. During torsionally rasping the thrombectomy device, a ratio of rotation of the delivery system of the thrombectomy device to rotation of the elongate support structure of the thrombectomy device may be not 1:1. Torsionally rasping the thrombectomy device may comprise rotating the delivery system of the thrombectomy device at least 360 degrees, resulting in a rotation of the elongate support structure of the thrombectomy device of less than 360 degrees. The vessel may comprise a blood vessel in a brain, leg, or other vessel or structure in the body.

In some embodiments, a method of treating a thrombus in a vessel with self-expanding bulbs comprises advancing a thrombectomy device through a microcatheter in the vessel. The thrombectomy device includes a plurality of self-expanding bulbs and a hypotube coupled to the self-expanding bulbs. The method further comprises retracting the microcatheter to expand from a radially compressed state to a radially expanded state at least some of the plurality of self-expanding bulbs, entrapping the thrombus in at least some of the plurality of self-expanding bulbs in the radially expanded state, and retracting the microcatheter and the thrombectomy device.

The hypotube may include a plurality of longitudinally-spaced kerfs. The method may further comprise torsionally rasping the thrombectomy device. Torsionally rasping the thrombectomy device may include entrapping the thrombus in the at least some of the plurality of self-expanding bulbs in the radially expanded state. The vessel may comprise a blood vessel in a brain, leg, or other vessel or structure in the body.

In some embodiments, a thrombectomy device comprises, or consists essentially of, an elongate support structure, a delivery system, and a bonding zone where the delivery system is coupled to the elongate support structure. The elongate support structure includes a plurality of shape-memory and radiopaque wires woven to form a textile fabric having a collapsed state and an expanded state. The elongate support structure includes, or consists essentially of, a plurality of self-expanding generally spherical bulbs in the expanded state, necks longitudinally between and radially inward of the self-expanding bulbs, and a distal neck distal to and radially inward of a distal-most bulb of the self-expanding bulbs. In one embodiment, the plurality of bulbs consists essentially of five to fifteen bulbs that have rounded or curved portions. In several embodiments, the plurality of self-expanding generally spherical bulbs includes a first bulb, a second bulb distal to the first bulb, a third bulb distal to the second bulb, a fourth bulb distal to the third bulb, a fifth bulb distal to the fourth bulb, a sixth bulb distal to the fifth bulb, a seventh bulb distal to the sixth bulb, an eighth bulb distal to the seventh bulb, a ninth bulb distal to the eighth bulb, and a tenth bulb distal to the ninth bulb. The first bulb and the second bulb have a first diameter. The third bulb and the fourth bulb have a second diameter smaller than the first diameter. The fifth bulb, the sixth bulb, and the seventh bulb have a third diameter smaller than the second diameter. The eighth bulb, the ninth bulb, and the tenth bulb have a fourth diameter smaller than the third diameter. The distal neck includes a coated distal end in several embodiments. The delivery system may include a hypotube including two longitudinally interspersed and circumferentially staggered cut patterns. The cut patterns may each include a plurality of rows each including two longitudinally-spaced kerfs angled with respect to a longitudinal axis of the hypotube and including rounded edges. A longitudinally-spacing of the kerfs may vary along the hypotube. The bonding zone includes a radiopaque marker band in some embodiments.

An outer diameter of the elongate support structure in the collapsed state may be less than 0.0125 inches. An outer diameter of the elongate support structure in the collapsed state may be in a range of 0.1-0.9 mm (e.g., 0.25 mm to 0.5 mm). The first diameter may be 4.5 mm. The second diameter may be 4 mm. The third diameter may be 3.5 mm. The fourth diameter may be 3 mm. The elongate support structure may be completely hollow.

In some embodiments, a thrombectomy device comprises an elongate support structure and a delivery system. The elongate support structure includes a plurality of wires woven to form a textile fabric having a collapsed state and an expanded state. The elongate support structure includes a plurality of longitudinally-spaced self-expanding bulbs in the expanded state. The delivery system includes a hypotube including a plurality of longitudinally interspersed cut patterns each including a plurality of rows of longitudinally-spaced kerfs.

The plurality of bulbs may comprise or consist essentially of ten or more bulbs. At least two of the plurality of bulbs may have different outer diameters in the expanded state. At least two of the plurality of bulbs may have different shapes in the expanded state. At least one of the plurality of bulbs may have a spherical shape in the expanded state. At least one of the plurality of bulbs may have a oblong shape in the expanded state. Longitudinal spacing between the plurality of bulbs may be constant. The plurality of wires may include shape memory and radiopaque wires. The radiopaque wires may be clustered to enhance visibility under x-ray. An outer diameter of the elongate support structure in the collapsed state may be less than 0.0125 inches. Each of the rows may be angled with respect to a longitudinal axis of the hypotube. The kerfs may include rounded edges. Although ten or more bulbs (e.g., 15, 20, 25, 30, or more bulbs) are provided in some embodiments, fewer than ten bulbs are provided in other embodiments (for example, for shorter targeted segments). The elongate support structure may be completely hollow.

In some embodiments, a device for treating a thrombus in a vessel comprises or consists essentially of an elongate support structure including a plurality of wires woven to form a textile structure including a plurality of bulbs in a radially expanded state, a delivery system including a hypotube including at least two interspersed patterns of longitudinally-spaced rows of kerfs, and a bonding zone where the delivery system may be coupled to the elongate support structure. The bonding zone includes a radiopaque marker band in some embodiments.

The bonding zone may include a proximal end of the elongate support structure within a distal end of the delivery system. The bonding zone may include a proximal end of the elongate support structure over a distal end of the delivery system. The bonding zone may include a distal end of the elongate support structure over a distal end of the delivery system. The elongate support structure may be completely hollow.

In some embodiments, a method of treating a thrombus in a vessel with self-expanding bulbs comprises advancing a microwire in the vessel and through a guide catheter. Advancing the microwire includes crossing the thrombus with a distal end of the microwire. The method further comprises advancing a microcatheter in the vessel and over the microwire. Advancing the microcatheter includes crossing the thrombus with a distal end of the microcatheter. The method further comprises, after advancing the microcatheter, removing the microwire from the vessel, and, after removing the microwire, inserting a thrombectomy device in a radially compressed state into the microcatheter. The thrombectomy device includes a distal portion and a proximal portion bonded to the distal portion. The distal portion includes a plurality of wires woven to form a textile fabric. The distal portion comprises at least three (e.g., at least four, at least six, at least ten, five to twenty, four to ten, etc.)

self-expanding bulbs and necks between and radially inward of the self-expanding bulbs. The proximal portion includes a hypotube including a plurality of longitudinally-spaced kerfs including a plurality of interspersed cut patterns. A pitch of the plurality of longitudinally-spaced kerfs varies longitudinally along the hypotube. The method further comprises, after inserting the thrombectomy device into the microcatheter, advancing the thrombectomy device in the vessel and through the microcatheter proximate to the distal end of the microcatheter. Advancing the thrombectomy device includes crossing the thrombus with the distal-most bulb of the self-expanding bulbs. The method further comprises, after advancing the thrombectomy device, maintaining a location of the proximal portion of the thrombectomy device while proximally retracting the microcatheter. Upon being unsheathed from the microcatheter, at least some of the self-expanding bulbs of the elongate support structure of the thrombectomy device self-expand from a radially compressed state to a radially expanded state. Retracting the microcatheter is at least until the distal end of the microcatheter is proximal to the thrombus. The method further comprises, after retracting the microcatheter, torsionally rasping the thrombectomy device including removing portions of the thrombus attached to an endothelium wall, entrapping the thrombus in the radially expanded distal portion of the thrombectomy device, and collecting emboli in the radially expanded distal portion of the thrombectomy device. The method further comprises, after torsionally rasping the thrombectomy device, retracting at a similar rate the microcatheter and the proximal portion of the thrombectomy device. The vessel may comprise a blood vessel in a brain, leg, or other vessel or structure in the body.

In some embodiments, a method of treating a thrombus in a vessel with self-expanding bulbs comprises expanding from a radially compressed state to a radially expanded state a plurality of self-expanding bulbs of a distal portion of a thrombectomy device, entrapping the thrombus in at least some of the plurality of self-expanding bulbs in the radially expanded state, and retracting the thrombectomy device from the vessel. Retracting a microcatheter surrounding the plurality of self-expanding bulbs in the radially compressed state may cause expansion of the plurality of self-expanding bulbs to the radially expanded state.

The distal portion of the thrombectomy device comprises at least two of the plurality of bulbs may have different outer diameters in the radially expanded state. The distal portion of the thrombectomy device may be tapered. The distal portion of the thrombectomy device may comprise at least two of the plurality of self-expanding bulbs having different shapes in the radially expanded state. The distal portion of the thrombectomy device may comprise at least two of the plurality of self-expanding bulbs separated by a neck. The thrombectomy device may comprise a proximal portion coupled to the distal portion. The proximal portion may include a hypotube including a plurality of longitudinally spaced kerfs. The plurality of longitudinally spaced kerfs may include a plurality of interspersed cut patterns. A pitch of the plurality of longitudinally spaced kerfs may vary longitudinally along the hypotube. At least some of the plurality of longitudinally spaced kerfs may include rounded edges. Expanding the plurality of self-expanding bulbs may include proximally retracting a microcatheter surrounding the plurality of self-expanding bulbs in the radially compressed state. The distal portion may comprise five to twenty, four to ten, or other plural numbers of self-expanding bulbs. Retracting the microcatheter may be at least until a distal end of the microcatheter is proximal to the thrombus. Retracting the thrombectomy device from the vessel comprises retracting the microcatheter may be at a similar rate. Entrapping the thrombus may include torsionally rasping the thrombectomy device (e.g., enveloping the thrombus by torsionally rasping). The vessel may comprise a blood vessel in a brain, leg, or other vessel or structure in the body.

In some embodiments, a method of treating a thrombus in a vessel with self-expanding bulbs comprises torsionally rasping a distal portion of a thrombectomy device. The distal portion includes a plurality of self-expanding bulbs. Torsionally rasping may effect at least one of: removing portions of the thrombus attached to an endothelium wall of the vessel, entrapping the thrombus in the distal portion of the thrombectomy device (e.g., enveloping the thrombus), and collecting emboli in the distal portion of the thrombectomy device. The method may further comprise expanding from a radially compressed state to a radially expanded state the plurality of self-expanding bulbs of the distal portion of the thrombectomy device. Retracting a microcatheter surrounding the plurality of self-expanding bulbs in the radially compressed state may cause expansion of the plurality of self-expanding bulbs to the radially expanded state.

Torsionally rasping the distal portion of the thrombectomy device may comprise rotating a proximal portion of the thrombectomy device coupled to the distal portion of the thrombectomy device. The proximal portion may include a hypotube including a plurality of longitudinally-spaced kerfs. The vessel may comprise a blood vessel in a brain, leg, or other vessel or structure in the body.

In some embodiments, a device for treating a thrombus in a vessel comprises a distal portion and a proximal portion coupled to a proximal end of the distal portion. The distal portion includes a plurality of wires woven to form a textile structure. The plurality of wires includes radiopaque wires and shape-memory wires. The distal portion includes at least ten self-expanding bulbs, at least nine necks longitudinally between the ten self-expanding bulbs and radially inward of the ten self-expanding bulbs, and a distal neck distal to the distal-most of the at least ten self-expanding bulbs. The proximal portion includes a hypotube having a longitudinal axis. The proximal portion comprises a first pattern of longitudinally-spaced rows each including two kerfs and two stems and a second pattern of longitudinally-spaced rows each including two kerfs and two stems. The rows of the first pattern are at an angle with respect to the longitudinal axis of the hypotube. The two kerfs in each of the rows of the first pattern have rounded edges. The two stems in each of the rows of the first pattern are circumferentially opposite (e.g., 180° apart). The stems of the first pattern are offset in a first circumferential direction. A pitch of the longitudinally-spaced rows of the first pattern varies longitudinally along the hypotube. The rows of the second pattern is at an angle with respect to the longitudinal axis of the hypotube. The two kerfs in each of the rows of the second pattern have rounded edges. The two stems in each of the rows of the second pattern are circumferentially opposite (e.g., 180° apart). The rows of the second pattern are singly alternatingly interspersed with the rows of the first pattern. The stems of the second pattern offset in a second circumferential direction opposite the first circumferential direction. A pitch of the longitudinally-spaced kerfs of the second pattern varies longitudinally along the hypotube. The distal portion may be completely hollow.

The at least ten self-expanding bulbs may comprise a first bulb, a second bulb distal to the first bulb, a third bulb distal to the second bulb, a fourth bulb distal to the third bulb, a fifth bulb distal to the fourth bulb, a sixth bulb distal to the fifth bulb, a seventh bulb distal to the sixth bulb, an eighth bulb distal to the seventh bulb, a ninth bulb distal to the eighth bulb, and a tenth bulb distal to the ninth bulb. The first bulb and the second bulb may have a first diameter. The third bulb and the fourth bulb may have a second diameter smaller than the first diameter. The fifth bulb, the sixth bulb, and the seventh bulb may have a third diameter smaller than the second diameter. The eighth bulb, the ninth bulb, and the tenth bulb may have a fourth diameter smaller than the third diameter. The second bulb may have a generally spherical shape. The third bulb may have a generally oblong shape. The fourth bulb may have a generally spherical shape. The fifth bulb may have a generally oblong shape. The sixth bulb may have a generally spherical shape. The seventh bulb may have a generally spherical shape. The eighth bulb may have a generally oblong shape. The ninth bulb may have a generally spherical shape. The tenth bulb may have a generally spherical shape.

In some embodiments, a device for treating a thrombus in a vessel comprises a first portion and a second portion bonded to the first portion. The first portion includes a plurality of wires woven to form a textile structure. The plurality of wires includes radiopaque wires and shape-memory wires, the textile structure includes a plurality of bulbs and a plurality of necks in a radially expanded state. The plurality of bulbs are spaced by the plurality of necks. The second portion includes a hypotube having a longitudinal axis. The hypotube includes at least two interspersed patterns of longitudinally-spaced rows of kerfs. A pitch of the longitudinally-spaced rows of kerfs varies along the longitudinal axis of the hypotube. The first portion may be completely hollow.

The plurality of bulbs may include ten or more bulbs. Fewer bulbs are included in some embodiments. At least two of the plurality of bulbs may have different outer diameters in the radially expanded state. At least two of the plurality of bulbs may have different shapes in the radially expanded state. At least one of the plurality of bulbs may have a spherical shape in the radially expanded state. At least one of the plurality of bulbs may have an oblong shape in the radially expanded state. The radiopaque wires are spaced or clustered to increase visibility under x-ray. Each of the rows may be angled with respect to the longitudinal axis of the hypotube. Each of the rows may include two kerfs and two stems. The stems in each of the rows may be circumferentially opposite (e.g., 180° apart). The at least two interspersed patterns may include a first pattern including the stems circumferentially offset in a first direction and a second pattern including the stems circumferentially offset in a second direction opposite the first direction.

In some embodiments, a device for treating a thrombus in a vessel comprises a first portion including a plurality of wires woven to form a textile structure including a plurality of bulbs in a radially expanded state, a second portion including a hypotube including at least two interspersed patterns of longitudinally-spaced rows of kerfs, and a joint coupling the first portion and the second portion. The first portion may be completely hollow. The textile structure may include a plurality of necks, the plurality of bulbs spaced by the plurality of necks.

The joint may include lead-free solder. The joint may include a proximal end of the first portion within a distal end of the second portion. The joint may include a proximal end of the first portion over a distal end of the second portion. The joint may include a distal end of the first portion over a distal end of the second portion.

In some embodiments, a device for treating a thrombus in a vessel comprises a plurality of wires woven to form a textile fabric. The textile fabric includes ten self-expanding bulbs, nine necks longitudinally between the ten self-expanding bulbs, and a distal neck distal to the distal-most of the ten self-expanding bulbs. The plurality of wires includes a plurality of radiopaque wires and a plurality of shape-memory wires. The textile fabric may be completely hollow.

The ten self-expanding bulbs may comprise a first bulb, a second bulb distal to the first bulb, a third bulb distal to the second bulb, a fourth bulb distal to the third bulb, a fifth bulb distal to the fourth bulb, a sixth bulb distal to the fifth bulb, a seventh bulb distal to the sixth bulb, an eighth bulb distal to the seventh bulb, a ninth bulb distal to the eighth bulb, and a tenth bulb distal to the ninth bulb. The first bulb and the second bulb may have a first diameter. The third bulb and the fourth bulb may have a second diameter smaller than the first diameter. The fifth bulb, the sixth bulb, and the seventh bulb may have a third diameter smaller than the second diameter. The eighth bulb, the ninth bulb, and the tenth bulb may have a fourth diameter smaller than the third diameter. The first bulb may have a generally oblong shape. The second bulb may have a generally spherical shape. The third bulb may have a generally oblong shape. The fourth bulb may have a generally spherical shape. The fifth bulb may have a generally oblong shape. The sixth bulb may have a generally spherical shape. The seventh bulb may have a generally spherical shape. The eighth bulb may have a generally oblong shape. The ninth bulb may have a generally spherical shape. The tenth bulb may have a generally spherical shape. The first bulb and the second bulb may have a first diameter. The third bulb and the fourth bulb may have a second diameter smaller than the first diameter. The fifth bulb, the sixth bulb, and the seventh bulb may have a third diameter smaller than the second diameter. The eighth bulb, the ninth bulb, and the tenth bulb may have a fourth diameter smaller than the third diameter.

In some embodiments, a device for treating a thrombus in a vessel comprises a plurality of wires woven to form a textile fabric including a plurality of bulbs spaced by a plurality of necks in a radially expanded state. The plurality of wires includes shape-memory wires and clustered radiopaque wires. The textile fabric may be completely hollow. The textile structure may include a plurality of necks, the plurality of bulbs spaced by the plurality of necks.

The radiopaque wires may include platinum tungsten. The shape memory wires may include nickel titanium. The plurality of bulbs may include ten bulbs. At least two of the plurality of bulbs may have different outer diameters in the radially expanded state. A diameter of the device in a collapsed state may be no more than 0.0125 inches (approx. 0.317 mm). At least two of the plurality of bulbs may have different shapes in the radially expanded state. At least one of the plurality of bulbs may have a spherical shape in the radially expanded state. At least one of the plurality of bulbs may have an oblong shape in the radially expanded state.

In some embodiments, a device for treating a thrombus in a vessel comprises a plurality of wires woven to form a textile fabric including a radially collapsed state having a diameter between 0.1 mm and 0.9 mm (e.g., between 0.25 mm and 0.5 mm) and a radially expanded state having a diameter between 1 mm and 30 mm (e.g., between 1 mm and 6.5 mm, between 3 mm and 4.5 mm). In some embodiments, the radially contracted state is 10 to 30 times smaller in at least one dimension than the radially expanded state. The textile fabric includes a plurality of bulbs in the radially expanded state. The textile fabric may be completely hollow.

The textile structure may include a plurality of necks, the plurality of bulbs spaced by the plurality of necks.

The plurality of bulbs may include ten bulbs. At least two of the plurality of bulbs may have different outer diameters in the radially expanded state. At least two of the plurality of bulbs may have different shapes in the radially expanded state. At least one of the plurality of bulbs may have a spherical shape in the radially expanded state. At least one of the plurality of bulbs may have an oblong shape in the radially expanded state. The plurality of bulbs may be spaced by necks.

In some embodiments, a device for treating a thrombus in a vessel comprises a hypotube having a longitudinal axis. The hypotube includes a first pattern of longitudinally-spaced rows each including two kerfs and two stems and a second pattern of longitudinally-spaced rows each including two kerfs and two stems. The rows of the first pattern are at an angle with respect to the longitudinal axis of the hypotube. The two kerfs in each of the rows of the first pattern have rounded edges. The two stems in each of the rows of the first pattern are circumferentially opposite (e.g., 180° apart). The stems of the first pattern are offset in a first circumferential direction. The rows of the second pattern are at an angle with respect to the longitudinal axis of the hypotube. The two kerfs in each of the rows of the second pattern have rounded edges. The two stems in each of the rows of the second pattern are circumferentially opposite (e.g., 180° apart). The rows of the second pattern are singly alternatingly interspersed with the rows of the first pattern. The stems of the second pattern are offset in a second circumferential direction opposite the first circumferential direction. A pitch of the longitudinally-spaced kerfs of first pattern and the second pattern varies longitudinally along the hypotube.

The hypotube may include a first section, a second section, a third section, a fourth section, a fifth section, and a sixth section. The first section may have a pitch of 0.005 inches (approx. 0.13 mm). The second section may have a pitch of 0.01 inches (approx. 0.25 mm). The third section may have a pitch of 0.02 inches (approx. 0.51 mm). The fourth section may have a pitch of 0.04 inches (approx. 1 mm). The fifth section may have a pitch of 0.08 inches (approx. 2 mm). The sixth section may have a pitch of 0.016 inches (approx. 4 mm). The first section may be a distal-most section of the hypotube. The first section may be 20% of the hypotube. The second section may be proximal to the first section. The second section may be 15% of the hypotube. The third section may be proximal to the second section. The third section may be 15% of the hypotube. The fourth section may be proximal to the third section. The fourth section may be 15% of the hypotube. The fifth section may be proximal to the fourth section. The fifth section may be 15% of the hypotube. The sixth section may be proximal to the fifth section. The sixth section may be 20% of the hypotube. The first pattern and the second pattern may be laser-cut.

In some embodiments, a device for treating a thrombus in a vessel comprises a hypotube having a longitudinal axis. The hypotube includes a first pattern of longitudinally-spaced rows each including two kerfs and two stems and a second pattern of longitudinally-spaced rows each including two kerfs and two stems. The two stems in each of the rows of the first pattern are circumferentially opposite (e.g., 180° apart). The stems of the first pattern are offset in a first circumferential direction. The two stems in each of the rows of the second pattern are circumferentially opposite (e.g., 180° apart). The rows of the second pattern are interspersed with the rows of the first pattern. The stems of the second pattern are offset in a second circumferential direction opposite the first circumferential direction.

The first pattern may be singly alternatingly dispersed with the second pattern. Each of the rows may be angled with respect to the longitudinal axis of the hypotube. The kerfs in each of the rows of the first pattern and the second pattern may have rounded edges. A pitch of the longitudinally-spaced rows of the first pattern and the second pattern may vary longitudinally along the hypotube. The hypotube may include a first section, a second section, a third section, a fourth section, a fifth section, and a sixth section. The first section may have a pitch of 0.005 inches (approx. 0.13 mm). The second section may have a pitch of 0.01 inches (approx. 0.25 mm). The third section may have a pitch of 0.02 inches (approx. 0.51 mm). The fourth section may have a pitch of 0.04 inches (approx. 1 mm). The fifth section may have a pitch of 0.08 inches (approx. 2 mm). The sixth section may have a pitch of 0.16 inches (approx. 4 mm). The first section may be a distal-most section of the hypotube. The first section may be 20% of the hypotube. The second section may be proximal to the first section. The second section may be 15% of the hypotube. The third section may be proximal to the second section. The third section may be 15% of the hypotube. The fourth section may be proximal to the third section. The fourth section may be 15% of the hypotube. The fifth section may be proximal to the fourth section. The fifth section may be 15% of the hypotube. The sixth section may be proximal to the fifth section. The sixth section may be 20% of the hypotube. The first pattern and the second pattern may be laser-cut.

In some embodiments, a device for treating a thrombus in a vessel comprises a hypotube including a first pattern of longitudinally-spaced rows each including two kerfs and two stems and a second pattern of longitudinally-spaced rows each including two kerfs and two stems. The stems of the first pattern are offset in a first circumferential direction. The rows of the second pattern are interspersed with the rows of the first pattern. The stems of the second pattern are offset in a second circumferential direction opposite the first circumferential direction.

The two stems in each of the rows of the first pattern may be circumferentially opposite (e.g., 180° apart). The two stems in each of the rows of the second pattern may be circumferentially opposite (e.g., 180° apart). The hypotube may have a longitudinal axis. A pitch of the longitudinally-spaced rows of kerfs may vary along the longitudinal axis of the hypotube. The first pattern may be singly alternatingly dispersed with the second pattern. Each of the rows may be angled with respect to the longitudinal axis of the hypotube. The kerfs in each of the rows of the first pattern and the second pattern may have rounded edges. The first pattern and the second pattern may be laser-cut. The hypotube may comprise stainless steel or nitinol.

In some embodiments, a method of manufacturing a thrombus treatment device comprises arranging a plurality of spools on a yarn wheel, braiding the radiopaque wires and the shape memory wires in a one-over-one-under-one pattern around a first mandrel to form a textile structure, shape setting the textile structure in a substantially cylindrical shape, securing the shape-set textile structure on a second mandrel including bulbs and necks, shape setting the shape-set textile structure on the second mandrel, and removing the shape-set textile structure from the second mandrel. At least some of the spools including radiopaque wires and at least some of the spools include shape memory wires.

The method may further comprise providing the second mandrel. The method may further comprise forming the second mandrel. The second mandrel may comprise bulbs threaded along a strand. Securing the shape-set textile structure on the second mandrel may include wrapping wire around the necks of the second mandrel. Securing the shape-set textile structure on the second mandrel may include wrapping bangles and/or c-shaped clamps around the necks of the second mandrel. The radiopaque wires may include platinum tungsten wires. The shape memory wires may include nickel titanium wires. The method may further comprise bonding the shape-set textile structure to a delivery system. Bonding the shape-set textile structure to the delivery system may comprise inlay bonding. The method may further comprise, before bonding the shape-set textile structure to the delivery system, positioning the wires in a pinch ring or a pinch cylinder. Bonding the shape-set textile structure to the delivery system may comprise overlay bonding. Bonding the shape-set textile structure to the delivery system may comprise bonding a proximal end of the shape-set textile structure to a distal end of the delivery system. Bonding the shape-set textile structure to the delivery system may comprise bonding a distal end of the shape-set textile structure to a distal end of the delivery system. Bonding the shape-set textile structure to the delivery system may comprise placing a tubing around a bonding area. Bonding the shape-set textile structure to the delivery system may comprise soldering the shape-set textile structure to the cut hypotube. The delivery system may comprise a cut hypotube. The delivery system may comprise a hypotube including a first pattern and a second pattern. The method may further comprise cutting the first pattern of longitudinally-spaced rows each including two kerfs and two stems into the hypotube and cutting the second pattern of longitudinally-spaced rows each including two kerfs and two stems into the hypotube. The two stems in each of the rows of the first pattern are circumferentially opposite (e.g., 180° apart). The stems of the first pattern are offset in a first circumferential direction. The two stems in each of the rows of the second pattern are circumferentially opposite (e.g., 180° apart). The stems of the second pattern are offset in a second circumferential direction opposite the first circumferential direction. The second pattern is singly alternatingly interspersed with the first pattern. Cutting the first pattern and cutting the second pattern may comprise cutting rounded edges of the kerfs in each of the rows of the first pattern and the second pattern. Cutting the first pattern and cutting the second pattern may comprise cutting each of the rows of the first pattern and the second pattern at an angle with respect to a longitudinal axis of the hypotube. The hypotube may comprise stainless steel. The hypotube may comprise nitinol. A pitch of the longitudinally-spaced rows of the first pattern and the second pattern may vary longitudinally along the hypotube.

In some embodiments, a method of manufacturing a thrombus treatment device comprises cutting a first pattern of longitudinally-spaced rows each including two kerfs and two stems into a hypotube and cutting a second pattern of longitudinally-spaced rows each including two kerfs and two stems into the hypotube. The two stems in each of the rows of the first pattern are circumferentially opposite (e.g., 180° apart). The stems of the first pattern are offset in a first circumferential direction. The two stems in each of the rows of the second pattern are circumferentially opposite (e.g., 180° apart). The stems of the second pattern are offset in a second circumferential direction opposite the first circumferential direction. The second pattern is singly alternatingly interspersed with the first pattern.

Cutting the first pattern and cutting the second pattern may comprise cutting rounded edges of the kerfs in each of the rows of the first pattern and the second pattern. Cutting the first pattern and cutting the second pattern may comprise cutting each of the rows of the first pattern and the second pattern at an angle with respect to a longitudinal axis of the hypotube. Cutting the first pattern and cutting the second pattern may comprise varying a pitch of the longitudinally-spaced rows of the first pattern and the second pattern longitudinally along the hypotube. Cutting the first pattern and cutting the second pattern may comprise cutting the hypotube with a laser. The hypotube may comprise stainless steel. The hypotube may comprise nitinol. The method may further comprise bonding the hypotube to a shape-set textile structure. Bonding the hypotube to a shape-set textile structure may comprise inlay bonding. Bonding the hypotube to a shape-set textile structure may comprise overlay bonding. Bonding the hypotube to a shape-set textile structure may comprise bonding a proximal end of the shape-set textile structure to a distal end of the hypotube. Bonding the hypotube to a shape-set textile structure may comprise bonding a distal end of the shape-set textile structure to a distal end of the hypotube. Bonding the hypotube to a shape-set textile structure may comprise placing a tubing around a bonding area. Bonding the hypotube to a shape-set textile structure may comprise soldering the shape-set textile structure to the hypotube. The shape-set textile structure may include a plurality of bulbs. The method may further comprise forming the shape-set textile structure. Forming the shape-set textile structure may comprise braiding a plurality of wires to form a textile structure and shape setting the textile structure on a mandrel comprising bulbs and necks. The method may further comprise, before shape setting the textile structure on the mandrel comprising bulbs and necks, shape setting the textile structure in a substantially cylindrical shape. Shape setting the textile structure on the mandrel comprising bulbs and necks may comprise wrapping wire around the necks of the mandrel. The plurality of wires may comprise a plurality of radiopaque wires and a plurality of shape memory wires.

In some embodiments, a method of treating a thrombus in a vessel comprises measuring a length of the thrombus in the vessel and advancing a microcatheter in the vessel. Advancing the microcatheter includes crossing the thrombus with a distal end of the microcatheter. The method further comprises inserting a thrombectomy device in a radially compressed state from an introducer sheath into the microcatheter. The thrombectomy device includes a textile structure including a plurality of filaments woven to form a plurality of self-expanding bulbs. At least two of the plurality of filaments comprise radiopaque material and configured to form crossing points visible under x-ray. The crossing points are configured to provide approximate length measurement of an expanded length of the thrombectomy device. The method further comprises, after inserting the thrombectomy device from the introducer sheath into the microcatheter, advancing the thrombectomy device in the vessel and through the microcatheter proximate to the distal end of the microcatheter. Advancing the thrombectomy device includes crossing the thrombus with the distal-most bulb of the plurality of self-expanding bulbs. The method further comprises, after advancing the thrombectomy device, retracting the microcatheter to unsheathe a length of the thrombectomy device. Upon being unsheathed from the microcatheter, at least some of the plurality of self-expanding bulbs of the elongate support structure of the thrombectomy device self-expand from the radially compressed state to a radially expanded state. Retracting the microcatheter is at least until the length of the thrombectomy device is at least as long as the measured length of the thrombus in the vessel. The method further comprises entrapping the thrombus in the unsheathed self-expanding bulbs, after entrapping the thrombus in the unsheathed self-expanding bulbs, removing the thrombus from the vessel in substantially one piece using the thrombectomy device, measuring a length of the thrombus out of the vessel, and comparing the length of the thrombus in the vessel to the length of the thrombus out of the vessel.

The method may further comprise, after retracting the microcatheter, torsionally rasping the thrombectomy device, wherein torsionally rasping the thrombectomy device may include entrapping the thrombus in the unsheathed self-expanding bulbs. The vessel may comprise a blood vessel in a brain, leg, or other vessel or structure in the body.

In some embodiments, a method of treating a thrombus in a vessel comprises measuring a length of the thrombus in the vessel and expanding a length of a thrombectomy device (e.g., at least part of a thrombectomy device) in the vessel proximate to the thrombus. The expanded length of the thrombectomy device (e.g., a customizable retraction length) is based at least partially on the measured length of the thrombus in the vessel.

Measuring the length of the thrombus in the vessel may comprise at least one of computerized axial tomography (CAT) scan digital imaging measurement, CAT scan angiogram, magnetic resonance imaging (MRI) angiogram, and catheter angiogram. Expanding the length of the thrombectomy device or the at least part of the thrombectomy device may include retracting a sheath from around the thrombectomy device (e.g., by a customizable retraction length, which may be based at least partially on the measured length of the thrombus in the vessel). Retracting the sheath may be for a length greater than the expanded length of the thrombectomy device. The thrombectomy device may comprise a plurality of filaments woven into a textile structure. At least two of the plurality of filaments may include radiopaque material configured to form crossing points visible under x-ray. The crossing points may be configured to provide approximate length measurement of the expanded length of the thrombectomy device. The thrombectomy device may include a plurality of self-expanding bulbs. After expanding the length of the thrombectomy device, at least one of the plurality of self-expanding bulbs may be distal to the thrombus. After expanding the length of the thrombectomy device, at least two of plurality of bulbs may have different outer diameters. The method may further comprise removing the thrombus from the vessel in substantially one piece using the thrombectomy device, measuring a length of the thrombus out of the vessel, and comparing the length of the thrombus in the vessel to the length of the thrombus out of the vessel. The method may further comprise, if the length of the thrombus out of the vessel is less than the length of the thrombus in the vessel, removing remaining thrombus from the vessel. Measuring the length of the thrombus out of the vessel may comprise placing the thrombus proximate to a ruler on a package of the thrombectomy device. The vessel may comprise a blood vessel in a brain, leg, or other vessel or structure in the body.

In some embodiments, a method of treating a thrombus in a vessel comprises measuring a length of the thrombus in the vessel, removing the thrombus from the vessel in substantially one piece using a thrombectomy device, measuring a length of the thrombus out of the vessel, and comparing the length of the thrombus in the vessel to the length of the thrombus out of the vessel.

The method may further comprise, if the length of the thrombus out of the vessel is less than the length of the thrombus in the vessel, removing remaining thrombus from the vessel. Measuring the length of the thrombus in the vessel may comprise at least one of computerized axial tomography (CAT) scan digital imaging measurement, CAT scan angiogram, magnetic resonance imaging (MRI) angiogram, and catheter angiogram. Measuring the length of the thrombus out of the vessel may comprise placing the thrombus proximate to a ruler on a package of the thrombectomy device. The vessel may comprise a blood vessel in a brain, leg, or other vessel or structure in the body.

In some embodiments, a method of treating a thrombus in a vessel comprises advancing a microcatheter in the vessel including crossing a distal end of the thrombus with a distal end of the microcatheter, and, after advancing the microcatheter, inserting a thrombectomy device in a radially compressed state into the microcatheter. The thrombectomy device includes a plurality of wires woven to form a textile fabric including a first shape upon advancing out of the microcatheter and a second shape upon exposure to a temperature or lower. The method further comprises, after inserting the thrombectomy device into the microcatheter, advancing the thrombectomy device in the vessel and through the microcatheter proximate to the distal end of the microcatheter, and, after advancing the thrombectomy device, maintaining a location of a proximal portion of the thrombectomy device while proximally retracting the microcatheter. Upon being unsheathed from the microcatheter, the textile fabric changes from the radially compressed shape to the first shape. The method further comprises, after retracting the microcatheter, injecting fluid at the temperature or lower. Upon being contact with the temperature or lower, the textile fabric changes to the second shape. The method further comprises, while the textile structure is in the second shape, torsionally rasping the thrombectomy device, and, after torsionally rasping the thrombectomy device, retracting at a similar rate the microcatheter and the proximal portion of the thrombectomy device.

The first shape may comprise a plurality of bulbs and the second shape may comprise a spiral. The first temperature may be less than 25° C. (e.g., 18° C.). The textile fabric may include a third shape upon exposure to a second temperature or higher. The first shape may comprise an expanded cylinder, the second shape may comprise a spiral, and the third shape may comprise a plurality of bulbs. The second temperature may be greater than 25° C. (e.g., 37° C.). Torsionally rasping the thrombectomy device may include at least one of removing portions of the thrombus attached to an endothelium wall, entrapping the thrombus in the radially expanded distal portion of the thrombectomy device, and collecting emboli in the radially expanded distal portion of the thrombectomy device. The vessel may comprise a blood vessel in a brain, leg, or other vessel or structure in the body.

In some embodiments, a method of treating a thrombus in a vessel comprises advancing a thrombectomy device in a radially compressed state in the vessel and through a microcatheter until the thrombectomy is proximate to a distal end of the microcatheter and a distal end of the thrombus. The thrombectomy device includes a plurality of wires woven to form a textile fabric including a first shape upon advancing out of the microcatheter and a second shape upon exposure to a temperature or higher. The method further comprises, after advancing the thrombectomy device, maintaining a location of a proximal portion of the thrombectomy device while proximally retracting the microcatheter. Upon being unsheathed from the microcatheter, the textile fabric changes from the radially compressed shape to the first shape and wherein upon being exposed to the temperature or higher the textile fabric changes from the first shape to the second shape. The method further comprises entrapping the thrombus in the second state.

The first shape may comprise a cylinder and the second shape may comprise a plurality of bulbs. The second shape may comprise at least two of the plurality of bulbs may have different outer diameters, different shapes, or different outer diameters and different shapes. The second shape may be tapered. The second shape may comprise at least two of the plurality of bulbs separated by a neck. The first shape may comprise a cylinder and the second shape may comprise a spiral. Entrapping the thrombus may include torsionally rasping the thrombectomy device (e.g., enveloping the thrombus by torsionally rasping). The vessel may comprise a blood vessel in a brain, leg, or other vessel or structure in the body.

In some embodiments, a method of treating a thrombus in a vessel comprises advancing a thrombectomy device in a radially compressed state in the vessel and through a microcatheter until the thrombectomy is proximate to a distal end of the microcatheter and a distal end of the thrombus. The thrombectomy device includes a first shape upon advancing out of the microcatheter, a second shape upon exposure to a first temperature or lower, and a third shape upon exposure to a second temperature or higher. The method further comprises, after advancing the thrombectomy device, maintaining a location of a proximal portion of the thrombectomy device while proximally retracting the microcatheter. Upon being unsheathed from the microcatheter, the thrombectomy device changes from the radially compressed shape to the first shape. The method further comprises, after retracting the microcatheter, injecting fluid at the temperature or lower. Upon contact with the first temperature or lower, the thrombectomy device changes to the second shape. The method further comprises, upon exposure to the second temperature or higher, the thrombectomy device changes to the third shape.

The thrombectomy device may comprise a textile structure including the first shape, the second shape, and the third shape. The thrombectomy device may comprise a laser cut structure including the first shape, the second shape, and the third shape. At least one of the first shape and the second shape may be non-cylindrical.

In some embodiments, a method of coupling a woven tubular device to a hypotube comprises inserting a proximal end of the woven tubular device into a distal end of the hypotube. The woven tubular device includes a plurality of self-expanding bulbs. The hypotube includes a plurality of kerfs. The method further comprises inserting a delivery device including a J-shaped tube proximate to the proximal end of the woven tubular device through a distal-most kerf of the plurality of kerfs, delivering solder from the delivery device at a first location and between the woven tubular structure and the hypotube, moving the delivery device to a second location circumferentially spaced 180° from the first location, delivering solder from the delivery device at the second location and between the woven tubular structure and the hypotube, moving the delivery device to a third location circumferentially spaced 90° from the first location and from the second location, delivering solder from the delivery device at the third location and between the woven tubular structure and the hypotube, moving the delivery device to a fourth location circumferentially spaced 90° from the first location and from the second location and 180° from the third location, delivering solder from the delivery device at the fourth location and between the woven tubular structure and the hypotube, and allowing the solder to cool. The solder may comprise silver-based lead-free solder.

In some embodiments, a method of coupling a woven tubular device to a hypotube comprises inserting a proximal end of the woven tubular device into a distal end of the hypotube. The hypotube includes a plurality of kerfs. The method further comprises delivering bonding material from the delivery device between the woven tubular structure and the hypotube in at least one circumferential location. Delivering the bonding material (e.g., solder, epoxy) includes inserting the delivery device including a J-shaped tube proximate to the proximal end of the woven tubular device through a distal-most kerf of the plurality of kerfs.

The bonding material may comprise at least one of solder and epoxy. The solder may comprise silver-based lead-free solder. The solder may comprise gold-based lead-free solder. Delivering the bonding material may include delivering the bonding material fully arcuately. Delivering the bonding material may include delivering the bonding material in a plurality of circumferentially spaced locations. Delivering the bonding material in the plurality of circumferentially spaced locations may include delivering bonding material from the delivery device at a first location and between the woven tubular structure and the hypotube, moving the delivery device to a second location circumferentially spaced 180° from the first location, delivering bonding material from the delivery device at the second location and between the woven tubular structure and the hypotube, moving the delivery device to a third location circumferentially spaced 90° from the first location and from the second location, delivering bonding material from the delivery device at the third location and between the woven tubular structure and the hypotube, moving the delivery device to a fourth location circumferentially spaced 90° from the first location and from the second location and 180° from the third location, and delivering bonding material from the delivery device at the fourth location and between the woven tubular structure and the hypotube. The proximal end of the woven tubular device may include a proximal segment including a sleeve around filaments of the woven tubular device and a distal segment including exposed filaments of the woven tubular device. The circumferential location may include at least parts of the proximal segment and the distal segment. The proximal end of the woven tubular device may include a first segment including a ring around filaments of the woven tubular device, a second segment distal to the first segment including exposed filaments of the woven tubular device, and a third segment proximal to the first segment including exposed filaments of the woven tubular device. The circumferential location may include at least parts of the first segment and at least one of the second segment and the third segment. The rings may be crimped around the filaments. The filaments may be welded to the ring.

In some embodiments, a method of coupling a woven tubular device to a hypotube comprises inserting a distal end of the hypotube into an interior of the woven tubular device at a longitudinal location and delivering bonding material between the woven tubular device and the hypotube at the longitudinal location.

The method may further comprise positioning a sleeve around the woven tubular device at the location. The bonding material may comprise at least one of solder and epoxy. After coupling, the distal end of the hypotube may be proximate to a proximal end of the woven tubular device. After coupling, the distal end of the hypotube may be proximate to a distal end of the woven tubular device. The woven tubular device may include a plurality of bulbs. After coupling, the distal end of the hypotube may be proximal to a distal-most bulb.

In some embodiments, a method of manufacturing a thrombus treatment device comprises arranging a plurality of spools on spindles on a yarn wheel. At least some of the spools include radiopaque wires and at least some of the spools including shape memory wires. The method further comprises attaching an end of each of the wires to a ring over a first mandrel and braiding the radiopaque wires and the shape memory wires in a one-over-one-under-one pattern around the first mandrel to form a textile structure. Braiding includes at least one of rotating the yarn wheel, rotating the spindles, and longitudinally extending (e.g., pulling) the ring along the first mandrel away from the yarn wheel. The method further comprises shape setting the textile structure into a substantially cylindrical shape, securing the shape-set textile structure on a second mandrel including bulbs and necks, shape setting the shape-set textile structure on the second mandrel, and removing the shape-set textile structure from the second mandrel.

The second mandrel may comprise bulbs threaded along a strand. Securing the shape-set textile structure on the second mandrel may include wrapping at least one of wire, bangles, and c-shaped clamps around the necks of the second mandrel. The method may further comprise forming the second mandrel. Forming the mandrel may include stringing bulbs along a strand. Stringing the bulbs along the strand may include selecting shapes of the bulbs, sizes of the bulbs, and spacing between the bulbs. Forming the mandrel may include stringing hypotubes along the strand and between at least some of the bulbs. Arranging the plurality of spools may include positioning at least two of the spools including radiopaque wires adjacent to each other. The method may further comprise bonding the shape-set textile structure to a hypotube. The textile structure may include two sine waves each comprising a radiopaque wire and phase shifted from each other by 180°. The textile structure may include three sine waves each comprising a radiopaque wire and phase shifted from each other by 120°. The textile structure may include a first sine wave comprising a radiopaque wire, a second sine wave comprising a radiopaque wire offset from the first sine wave by 180°, a third sine wave comprising a radiopaque wire and phase shifted from the first sine wave by 7.5°, and a fourth sine wave comprising a radiopaque wire and phase shifted from the third sine wave by 7.5°. Securing the shape-set textile structure on the second mandrel may comprise wrapping bangles around the necks of the second mandrel Securing the shape-set textile structure on the second mandrel may comprise wrapping c-shaped clamps around the necks of the second mandrel.

In some embodiments, a method of manufacturing a thrombus treatment device comprises arranging a plurality of spools of wire on spindles on a yarn wheel, braiding the wires around a mandrel including bulbs and necks to form a textile structure, shape setting the textile structure on the mandrel, and removing the shape-set textile structure from the mandrel.

The second mandrel may comprise bulbs threaded along a strand. Braiding may comprise pulling a ring attached to an end of each of the wires away from the yarn wheel. The method may further comprise securing the textile structure on the mandrel before shape setting. The method may further comprise forming the mandrel. Forming the mandrel may include stringing bulbs along a strand. Stringing the bulbs along the strand may include selecting shapes of the bulbs, sizes of the bulbs, and spacing between the bulbs. Forming the mandrel may include stringing hypotubes along the strand and between at least some of the bulbs. The method may further comprise bonding the shape-set textile structure to a hypotube. Securing the shape-set textile structure on the second mandrel may comprise wrapping a wire around the necks of the second mandrel. Securing the shape-set textile structure on the second mandrel may comprise wrapping bangles around the necks of the second mandrel. Securing the shape-set textile structure on the second mandrel may comprise wrapping c-shaped clamps around the necks of the second mandrel.

In some embodiments, a method of manufacturing a thrombus treatment device comprises arranging a plurality of spools on spindles on a yarn wheel. At least some of the spools include radiopaque wires and at least some of the spools include shape memory wires. Arranging the plurality of spools includes positioning at least two of the spools including radiopaque wires adjacent to each other. The method further comprises braiding the radiopaque wires and the shape memory wires to form a textile structure.

The textile structure may include two sine waves each comprising a radiopaque wire and phase shifted from each other by 180°. The textile structure may include three sine waves each comprising a radiopaque wire and phase shifted from each other by 120°. The textile structure may include a first sine wave comprising a radiopaque wire, a second sine wave comprising a radiopaque wire offset from the first sine wave by 180°, a third sine wave comprising a radiopaque wire and phase shifted from the first sine wave by 7.5°, and a fourth sine wave comprising a radiopaque wire and phase shifted from the third sine wave by 7.5°. The method may further comprise bonding the shape-set textile structure to a hypotube.

In some embodiments, a method of manufacturing a thrombus treatment device comprises holding a hypotube using at least one bushing and at least one collet and cutting a pattern including a plurality of kerfs into the hypotube. Cutting the pattern includes directing a focused laser beam at the hypotube and longitudinally and rotationally moving the hypotube in a design such that the focused laser beam cuts the hypotube to form the plurality of kerfs. The focused laser creates a heat impact puddle. The heat impact puddle is less than a width and a length of each of the plurality of kerfs. The method further comprises, during cutting the pattern, flowing fluid through the hypotube.

Directing the focused laser beam may include creating the heat impact puddle inward of edges of the plurality of kerfs. Cutting the pattern may include cutting away the heat impact puddle. Directing the focused laser beam may include creating the heat impact puddle at edges of the plurality of kerfs. Directing the focused laser beam may include creating the heat impact puddle at corners of the plurality of kerfs. The design may include outlining edges of the plurality of kerfs. The design may include moving the hypotube may include relatively moving the focused laser beam diagonal to the plurality of kerfs. The design may include a spiral. Holding the hypotube may comprise using at least one bushing comprising an aperture may have a diameter at least 0.001 inches greater than an outer diameter of the hypotube. Holding the hypotube may comprise using at least one collet comprising an aperture may have a diameter at least 0.001 inches greater than an outer diameter of the hypotube. Holding the hypotube may comprise adjusting a diameter of an aperture of the collet(s). Flowing the fluid may include adjusting a height of a reservoir containing the fluid. Flowing the fluid may include adjusting a height of a water inlet gate between a reservoir containing the fluid and the hypotube.

In some embodiments, a method of manufacturing a thrombus treatment device comprises cutting a pattern including a plurality of rows of kerfs into the hypotube. Cutting the pattern includes directing a focused laser beam at the hypotube and longitudinally and rotationally moving the hypotube such that the focused laser beam cuts the hypotube to form the plurality of kerfs. The focused laser creates a heat impact puddle. The heat impact puddle is inward of edges of the plurality of kerfs.

The method may further comprise flowing fluid through the hypotube. The method may further comprise holding a hypotube using at least one of a bushing and a collet.

In some embodiments, a method of manufacturing a thrombus treatment device comprises cutting a pattern into a hypotube and, during cutting the pattern, flowing fluid through the hypotube. The pattern includes a first pattern of longitudinally-spaced rows each including two kerfs and two stems and a second pattern of longitudinally-spaced rows each including two kerfs and two stems. The two stems in each of the rows of the first pattern are circumferentially opposite (e.g., 180° apart). The stems of the first pattern are offset in a first circumferential direction. The two stems in each of the rows of the second pattern are circumferentially opposite (e.g., 180° apart). The rows of the second pattern are interspersed with the rows of the first pattern. The stems of the second pattern are offset in a second circumferential direction opposite the first circumferential direction.

Each of the rows may be angled with respect to a longitudinal axis of the hypotube. The kerfs in each of the rows of the first pattern and the second pattern may have rounded edges. A pitch of the longitudinally-spaced rows of the first pattern and the second pattern may varies longitudinally along the hypotube.

In some embodiments, a device for treating a thrombus in a vessel comprises a plurality of wires woven to form a self-expanding textile structure. The plurality of wires includes shape-memory wires and at least two radiopaque wires forming at two offset sine waves.

Crossings of the at least two sine waves ray may be substantially uniformly spaced. At least one of the at least two sine waves may include a plurality of radiopaque wires. Each of the at least two sine waves may include a plurality of radiopaque wires. The at least two sine waves may be offset by 180°. The at least two sine waves may include three sine waves offset by 120°. The textile structure may include a plurality of bulbs.

In some embodiments, a device for facilitating measurement in a vessel comprises a plurality of wires woven to form a self-expanding textile structure. The self-expanding textile structure comprises a plurality of woven bulbs in a non-compressed state. The plurality of wires comprises shape-memory wires and at least two radiopaque wires forming at least two longitudinally offset sine waves visibly distinct from the shape memory wires under x-ray. The at least two longitudinally offset sine waves facilitate length measurement in the vessel.

Measurement in the vessel may comprise measurement of a length of a blood clot, a neck of an aneurysm, and/or a length of a stenosis. Crossings of the at least two longitudinally offset sine waves may be uniformly spaced. At least one of the at least two longitudinally offset sine waves may comprise a plurality of circumferentially adjacent radiopaque wires that are parallel and longitudinally spaced along the textile structure. At least one of the at least two longitudinally offset sine waves may comprise two circumferentially adjacent radiopaque wires that are parallel and longitudinally spaced along the textile structure. At least one of the at least two longitudinally offset sine waves may comprise three circumferentially adjacent radiopaque wires that are parallel and longitudinally spaced along the textile structure. Each of the at least two longitudinally offset sine waves may comprise a plurality of circumferentially adjacent radiopaque wires that are parallel and longitudinally spaced along the textile structure. Each of the at least two longitudinally offset sine waves may comprise two circumferentially adjacent radiopaque wires that are parallel and longitudinally spaced along the textile structure. Each of the at least two longitudinally offset sine waves may comprise three circumferentially adjacent radiopaque wires that are parallel and longitudinally spaced along the textile structure. The at least two longitudinally offset sine waves may be offset by 180°. The at least two longitudinally offset sine waves may comprise at least three radiopaque wires forming at least three longitudinally offset sine waves visible under x-ray. The three longitudinally offset sine waves may be offset by 120°. The textile structure may comprise a first section comprising the bulbs and a second section proximal to the first section. The second section may be radially inward of the plurality of bulbs. Crossings of the at least two sine waves may be spaced a first distance along the first section and may be spaced a second distance along the second section. The first distance may be different than the second distance.

In some embodiments, a device for facilitating measurement in a vessel comprises a plurality of wires woven to form a self-expanding textile structure. The plurality of wires comprises shape-memory wires and at least two radiopaque wires forming at least two longitudinally offset sine waves visibly distinct from the shape memory wires under x-ray. The device comprises a first section comprising the at least two longitudinally offset sine waves uniformly spaced by a first distance and a second section comprising the at least two longitudinally offset sine waves uniformly spaced by a second distance different than the first distance.

At least one of the at least two longitudinally offset sine waves may comprise a plurality of circumferentially adjacent radiopaque wires that are parallel and longitudinally spaced along the textile structure. Each of the at least two longitudinally offset sine waves may comprise a plurality of circumferentially adjacent radiopaque wires that are parallel and longitudinally spaced along the textile structure.

In some embodiments, a device for facilitating measurement in a vessel comprises a plurality of wires woven to form a self-expanding textile structure. The plurality of wires comprises shape-memory wires and at least two radiopaque wires forming at least two longitudinally offset sine waves visibly distinct from the shape memory wires under x-ray. The at least two longitudinally offset sine waves facilitate measurement in the vessel.

Crossings of the at least two longitudinally offset sine waves may be uniformly spaced. At least one of the at least two longitudinally offset sine waves may comprise a plurality of circumferentially adjacent radiopaque wires that are parallel and longitudinally spaced along the textile structure. Each of the at least two longitudinally offset sine waves may comprise a plurality of circumferentially adjacent radiopaque wires that are parallel and longitudinally spaced along the textile structure.

In some embodiments, a device for treating a thrombus in a vessel comprises a plurality of wires woven to form a textile structure including a plurality of bulbs. The textile structure includes a distal end including an end treatment.

The end treatment may comprise a polymer coating. The polymer may comprise radiopaque particles. The end treatment may comprise a radiopaque marker. The distal end may be radially inward of the plurality of bulbs.

In some embodiments, a device for treating a vessel comprises a plurality of wires woven to form a textile structure. The textile structure comprises a proximal end, a distal end, at least three woven bulbs, and a longitudinal axis. The distal end of each of the plurality of wires is trimmed along a plane transverse to the longitudinal axis of the textile structure, thereby generating cut distal ends of the plurality of wires that are configured to provide at least one of flexibility and reduced risk that the vessel will be punctured by the device.

The cut distal ends may be further subject to a treatment. The treatment may comprise welding and/or polishing. The cut distal ends may be subject to no further treatment. The cut distal ends may be not frayed. The device may further comprise a polymer coating at least the cut distal ends. The polymer may comprise radiopaque particles. The device may comprise an inner lumen maintained by absence of the polymer. The device may further comprise a radiopaque marker coupled to at least one of the polymer and the cut distal ends. The device may further comprise a radiopaque marker coupled to the cut distal ends. The distal ends of the plurality of wires may be trimmed at an angle of 90° to the longitudinal axis of the textile structure.

In some embodiments, a device for treating a vessel comprises a plurality of wires woven to form a textile structure. The textile structure comprises a longitudinal axis, a lumen parallel to the longitudinal axis, and a plurality of woven bulbs. The textile structure comprises a proximal end and a distal end. The distal end of the textile structure comprises a distal end of each of the plurality of wires trimmed along a plane transverse to the longitudinal axis of the textile structure. The distal end of the textile structure comprises an end treatment selected from the group consisting of a polymer coating at least the distal ends of the plurality of wires and a radiopaque marker coupled to the distal ends of the plurality of wires. The end treatment maintains the lumen of the textile structure.

The end treatment may comprise the polymer coating at least the distal ends of the plurality of wires. The polymer may comprise radiopaque particles. The end treatment may further comprise a radiopaque marker coupled to the polymer. The end treatment may further comprise a radiopaque marker coupled to the distal ends of the plurality of wires. The end treatment may comprise the radiopaque marker coupled to the distal ends of the plurality of wires. The distal ends of the plurality of wires may be trimmed at an angle of 90° to the longitudinal axis of the textile structure.

In some embodiments, a device for treating a vessel comprises a plurality of wires woven to form a textile structure. The textile structure comprises a distal end comprising a polymer coating. The polymer coating comprises radiopaque particles. The distal end of the textile structure is at least partially defined by distal ends of the plurality of wires trimmed along a plane transverse to a longitudinal axis of the textile structure.

The device may comprise an inner lumen maintained by absence of the polymer coating. The distal ends of the plurality of wires may be trimmed at an angle of 90° to the longitudinal axis of the textile structure.

In some embodiments, a device for treating a thrombus in a vessel comprises a plurality of wires woven to form a textile structure including a plurality of bulbs and necks between the bulbs. The necks are circumferentially offset around textile structure.

Each of the plurality of bulbs may have a generally circular cross-section in a radially expanded state. The necks may be aligned along chords of the bulbs. Each of the plurality of bulbs may have a generally spherical shape in a radially expanded state. The necks may be aligned along chords of the spheres. The necks may alternate 180° between a first longitude and a second longitude. The necks may circumferentially rotate 120° between each of the bulbs. The necks may circumferentially rotate 90° between each of the bulbs. Each of the plurality of bulbs may have a generally polygonal cross-section in a radially expanded state. The necks may be aligned along apices of the bulbs.

In some embodiments, a device for treating a thrombus in a vessel comprises a plurality of wires woven to form a textile structure. The textile structure comprises a first bulb, a second bulb, and a neck between the first bulb and the second bulb. The first bulb comprises a generally circular cross-section in an expanded state and a first chord. The second bulb comprises a generally circular cross-section in an expanded state and a second chord radially spaced from the first chord. The device further comprises a longitudinal axis aligned to the first chord and the second chord. The neck is aligned along the longitudinal axis.

Each of the bulbs may have a generally spherical shape in a radially expanded state. The textile structure may comprise a plurality of bulbs comprising the first bulb and the second bulb. The plurality of bulbs may each comprise a generally circular cross-section in an expanded state and a chord. A plurality of necks may be between the plurality of bulbs. The plurality of necks may alternate 180° between a first longitude and a second longitude. The plurality of necks may circumferentially rotate 120° between each of the plurality of bulbs. The plurality of necks may circumferentially rotate 90° between each of the plurality of bulbs.

In some embodiments, a device for treating a vessel comprises a plurality of wires woven to form a textile structure. The textile structure comprises a plurality of bulbs and necks between the bulbs. The necks are circumferentially offset around the textile structure.

Each of the plurality of bulbs may have a generally hemispherical shape in a radially expanded state. The necks may be aligned along chords of the hemispheres. Each of the plurality of bulbs may have a generally polygonal cross-section in a radially expanded state. The necks may be aligned along apices of the bulbs. The necks may alternate 180° between a first longitude and a second longitude. The necks may circumferentially rotate 120° between the plurality of bulbs. The necks may circumferentially rotate 90° between the plurality of bulbs.

In some embodiments, a device for treating a vessel comprises a plurality of wires woven to form a textile structure. The textile structure comprises a longitudinal axis and a plurality of bulbs. Bulbs of the plurality of bulbs are phase shifted relative to the longitudinal axis of the textile structure.

The bulbs may be phase shifted by a phase shift angle of 180°. The bulbs may be phase shifted by a phase shift angle of 120°. The bulbs may be phase shifted by a phase shift angle of 90°. The bulbs may be phase shifted by a plurality of asymmetric phase shift angles. Each of the plurality of bulbs may have a generally spherical shape in a radially expanded state. Each of the plurality of bulbs may have a generally hemispherical shape in a radially expanded state. Each of the plurality of bulbs may have a generally polygonal cross-section in a radially expanded state. The device may further comprise a neck between at least two bulbs of the plurality of bulbs, proximal to the plurality of bulbs, and/or distal to the plurality of bulbs.

In some embodiments, a device for treating a thrombus in a vessel comprises a plurality of wires woven to form a textile structure. The textile structure comprises a longitudinal axis, a first bulb, a second bulb, and a neck between the first bulb and the second bulb. The first bulb comprises a generally circular cross-section in an expanded state. The first bulb intersects the longitudinal axis at an off-center position. The second bulb comprises a generally circular cross-section in an expanded state. The second bulb intersects the longitudinal axis at an off-center position. The neck is aligned along the longitudinal axis. The first bulb and the second bulb are differently radially offset from the longitudinal axis.

Each of the bulbs may have a generally spherical shape in a radially expanded state. The textile structure may comprise a plurality of bulbs comprising the first bulb and the second bulb. Each of the plurality of bulbs may comprise a generally circular cross-section in an expanded state intersecting the longitudinal axis at an off-center position. The textile structure may further comprise a neck between pairs of bulbs of the plurality of bulbs. A radial offset of the plurality of bulbs from the longitudinal axis may be 180° between pairs of bulbs of the plurality of bulbs. A radial offset of the plurality of bulbs from the longitudinal axis may be 120° between pairs of bulbs of the plurality of bulbs. A radial offset of the plurality of bulbs from the longitudinal axis may be 90° between pairs of bulbs of the plurality of bulbs.

In some embodiments, a device for treating a vessel comprises a plurality of wires woven to form a textile structure. The textile structure comprises a longitudinal axis, a plurality of bulbs, and necks between the bulbs. The necks are differently radially offset from the longitudinal axis.

Each of the plurality of bulbs may have a generally hemispherical shape in a radially expanded state. The necks may be aligned along chords of the hemispheres. Each of the plurality of bulbs may have a generally polygonal cross-section in a radially expanded state. The necks may be aligned along apices of the bulbs. The necks may alternate 180° between a first longitude and a second longitude. The necks may circumferentially rotate 120° between the plurality of bulbs. The necks may circumferentially rotate 90° between the plurality of bulbs.

In some embodiments, a device for treating a vessel comprises a plurality of wires woven to form a textile structure. The textile structure comprises a longitudinal axis, a plurality of bulbs, and a plurality of necks between the bulbs. Bulbs of the plurality of bulbs are phase shifted relative to the longitudinal axis of the textile structure.

The bulbs may be phase shifted by a phase shift angle of 180°. The bulbs may be phase shifted by a phase shift angle of 120°. The bulbs may be phase shifted by a phase shift angle of 90°. The bulbs may be phase shifted by a plurality of asymmetric phase shift angles. Each of the plurality of bulbs may have a generally spherical shape in a radially expanded state. Each of the plurality of bulbs may have a generally hemispherical shape in a radially expanded state. Each of the plurality of bulbs may have a generally polygonal cross-section in a radially expanded state. The textile structure may further comprise a neck proximal to the plurality of bulbs and/or a neck distal to the plurality of bulbs.

In some embodiments, a device for treating a thrombus in a vessel comprises a plurality of wires woven to form a textile structure. The textile structure includes a first shape at a first temperature, a second shape at a second temperature higher than the first temperature, and a third shape including stress-induced martensite.

The third shape may comprise a cylindrical shape. The stress-induced martensite may be induced by inner sidewalls of a sheath. The first shape may comprise a spiral. The second shape may comprise a plurality of bulbs. The first temperature may be less than 25° C. (e.g., 18° C.). The second temperature may be at least 25° C. (e.g., 37° C.).

In some embodiments, a device for treating a vessel comprises a plurality of wires woven to form a textile structure. The textile structure comprises a first shape at a first temperature, a second shape at a second temperature higher than the first temperature, and a third shape comprising stress-induced martensite. The first temperature is less than 25° C. The second shape comprises a plurality of bulbs. The second shape is different than the first shape. The third shape is different than the first shape and the second shape. The textile structure is configured to self-expand from the third shape to the second shape upon deployment from a sheath. The textile structure is configured to transform from the second shape to the first shape upon exposure to the first temperature or lower.

The first shape may comprise a spiral. The third shape may comprise a cylindrical shape. The stress-induced martensite may be induced by inner sidewalls of the sheath. The plurality of bulbs may comprise at least three bulbs. The first temperature may be less than 18° C. The second temperature may be at least 25° C.

In some embodiments, a device for treating a vessel comprises a plurality of wires woven to form a textile structure. The textile structure comprises a first shape at a first temperature, a second shape at a second temperature higher than the first temperature, and a third shape comprising stress-induced martensite. The first temperature is less than 25° C. The second shape comprises a plurality of bulbs. The second shape is different than the first shape. The third shape is different than the first shape and the second shape.

The first shape may comprise a spiral. The third shape may comprise a cylindrical shape. The stress-induced martensite may be induced by inner sidewalls of the sheath. The plurality of bulbs may comprise at least three bulbs. The first temperature may be less than 18° C. The second temperature may be at least 25° C. The textile structure may be configured to self-expand from the third shape to the second shape upon deployment from a sheath. The textile structure may be configured to transform from the second shape to the first shape upon exposure to the first temperature or lower.

In some embodiments, a device for treating a thrombus in a vessel comprises a plurality of wires woven to form a textile structure. The textile structure includes a first shape at a first temperature, a second shape at a second temperature higher than the first temperature, and a third shape at a third temperature higher than the second temperature.

The second shape may comprise a cylindrical shape. The third shape may comprise a plurality of bulbs. The first shape may comprise a spiral. The first temperature may be less than 25° C. (e.g., 18° C.). The second temperature may be between 25° C. and 37° C. The third temperature may be at least 37° C.

In some embodiments, a device for treating a vessel comprises a plurality of wires woven to form a textile structure. The textile structure comprises a first shape at a first temperature, a second shape at a second temperature higher than the first temperature, and a third shape at a third temperature higher than the second temperature. The first shape comprises a spiral. The second shape comprises a cylindrical shape. The second shape is different than the first shape. The third shape comprises a plurality of bulbs. The third shape is different than the first shape and the second shape. The textile structure is configured to transform from the third shape to the second shape upon exposure to the first temperature or lower. The textile structure is configured to transform from the second shape to the third shape upon at least one of exposure to the third temperature or higher and deployment from a sheath.

The first temperature may be less than 25° C. The second temperature may be between 25° C. and 37° C. The third temperature may be at least 37° C. The plurality of bulbs may comprise five to twenty bulbs. The textile structure may be completely hollow. The first shape may comprise a spiral. The third shape may comprise a cylindrical shape.

In some embodiments, a method of forming a device for treating a thrombus in a vessel comprises heat treating a structure to impart a first shape to the structure at a first temperature. The structure includes shape memory material. The method further comprises heat treating the structure to impart a second shape to the structure and heat treating the structure to impart a third shape to the structure.

The method may further comprise weaving a plurality of wires to form the structure, at least some of the plurality of wires including the shape memory material. The method may further comprise selecting temperatures of the heat treating based at least partially on a composition of the shape memory material. Heat treating the structure to impart the first shape may be at a temperature between 400° C. and 450° C. for 2 minutes to 10 minutes. Heat treating the structure to impart the second shape may be at a temperature between 500° C. and 550° C. for 20 minutes to 180 minutes. Heat treating the structure to impart the first shape may be at a temperature between 400° C. and 450° C. for 3 minutes to 10 minutes. Heat treating the structure to impart the first shape may be at a temperature between 500° C. and 550° C. for 5 minutes to 10 minutes. Heat treating the structure to impart the second shape may be at a temperature between 400° C. and 450° C. for 3 minutes to 10 minutes. Heat treating the structure to impart the first shape may be at a temperature between 500° C. and 550° C. for 3 minutes to 10 minutes. The second shape may comprise a plurality of bulbs. The third shape may comprise a spiral.

In some embodiments, a catheter comprises a hypotube including having a longitudinal axis. The hypotube includes a working lumen, a first pattern including a plurality of longitudinally-spaced rows each including two kerfs and two stems offset in a first circumferential direction, and a second pattern including a plurality of longitudinally-spaced rows each including two kerfs and two stems offset in a second circumferential direction opposite the first circumferential direction. The rows of the second pattern are singly alternatingly interspersed with the rows of the first pattern. A pitch of the longitudinally-spaced kerfs of first pattern and the second pattern vary along the longitudinal axis of the hypotube.

The hypotube may include a first section, a second section, a third section, a fourth section, a fifth section, and a sixth section. The first section may have a pitch of 0.005 inches (approx. 0.13 mm). The second section may have a pitch of 0.01 inches (approx. 0.25 mm). The third section may have a pitch of 0.02 inches (approx. 0.51 mm). The fourth section may have a pitch of 0.04 inches (approx. 1 mm). The fifth section may have a pitch of 0.08 inches (approx. 2 mm). The sixth section may have a pitch of 0.016 inches (approx. 4 mm). The first section may be a distal-most section of the hypotube. The first section may be 20% of the hypotube. The second section may be proximal to the first section. The second section may be 15% of the hypotube. The third section may be proximal to the second section. The third section may be 15% of the hypotube. The fourth section may be proximal to the third section. The fourth section may be 15% of the hypotube. The fifth section may be proximal to the fourth section. The fifth section may be 15% of the hypotube. The sixth section may be proximal to the fifth section. The sixth section may be 20% of the hypotube. The first pattern and the second pattern may be laser-cut. The catheter may further comprise a polymer coating on at least a portion of an outside of the hypotube. At least one parameter of the polymer coating may vary along the longitudinal axis of the hypotube. The parameter(s) may be selected from the group consisting of one or more of: material, thickness, and durometer. The variation of parameter(s) of the polymer coating may be aligned (e.g., substantially aligned) with the variation of the pitch of the longitudinally-spaced kerfs. The catheter may further comprise a polymer coating on at least a portion of an inside of the hypotube. The hypotube may comprise stainless steel. The hypotube may comprise a shape memory material. Each of the kerfs may include rounded edges. Each of the rows may be at an angle with respect to the longitudinal axis of the hypotube. The polymer coating may be hydrophobic.

In some embodiments, a catheter comprises a hypotube including having a longitudinal axis, a first polymer coating radially outward of at least a portion of an outside of the hypotube, and a second polymer coating radially inward of at least a portion of an inside of the hypotube. The hypotube includes at least one pattern including a plurality of longitudinally-spaced rows each including two kerfs and two stems offset in a first circumferential direction.

The first polymer coating may be different from the second polymer coating (e.g., comprising a different material). At least one parameter of the first polymer coating may vary along the longitudinal axis of the hypotube. The parameter(s) may be selected from the group consisting of one or more of: material, thickness, and durometer. The pattern may include a first pattern including a plurality of longitudinally-spaced rows and a second pattern including a plurality of longitudinally-spaced rows. Each of the rows of the first pattern may include two kerfs and two stems offset in a first circumferential direction. Each of the rows of the second pattern may include two kerfs and two stems offset in a second circumferential direction opposite the first circumferential direction. The rows of the second pattern may be singly alternatingly interspersed with the rows of the first pattern. A pitch of the longitudinally-spaced kerfs may vary along the longitudinal axis of the hypotube. The variation of parameter(s) of the first polymer coating may be aligned (e.g., substantially aligned) with the variation of the pitch of the longitudinally-spaced kerfs. The first polymer coating may be hydrophobic.

In some embodiments, a catheter comprises a hypotube having a longitudinal axis and a polymer coating over at least a portion of an outside of the hypotube. The hypotube includes at least one pattern including a plurality of longitudinally-spaced rows. A pitch of the longitudinally-spaced rows varies along the longitudinal axis of the hypotube. At least one parameter of the polymer coating varies along the longitudinal axis of the hypotube. The parameter(s) may be selected from the group consisting of at least one of material, thickness, and durometer.

The variation of the parameter(s) of the polymer coating may be aligned (e.g., substantially aligned) with the variation of the pitch of the longitudinally-spaced rows. Each of the longitudinally-spaced rows may include two kerfs and two stems offset in a first circumferential direction. The polymer coating may be hydrophobic. The catheter may further comprise an inner polymer coating at least a portion of an inside of the hypotube. The polymer coating may be different from the inner polymer coating (e.g., comprising a different material).

In some embodiments, a system for heat treating a device comprises a chamber configured to contain bath media, a container within the chamber and configured to hold the device, an air inlet gate fluidly upstream of the chamber and configured to be coupled to a gas source to flow gas into the chamber to fluidize the bath media, a heating element between the air inlet gate and the chamber, and a porous plate between the air inlet gate and the chamber. The chamber includes a detachable flange. The container is mechanically coupled to the detachable flange.

The bath media may include sand. The bath media may include non-flammable particles. The porous plate may be between the heating element and the air inlet gate. The detachable flange may include a conduit configured to allow passage of an arm mechanically coupling the container and the detachable flange. Adjustment of a length of the arm may adjust a height of the container in the chamber. Temperature in the chamber may vary vertically with distance from the heating device. The system may further comprise an air inflow regulator coupled to the air inlet gate. A height of the air inflow regulator may be adjustable to adjust a velocity of the gas into the chamber. The gas source may comprise nitrogen. The gas source may comprise air. The gas source may comprise hydrogen. The gas source may comprise carbon monoxide.

In some embodiments, a system for heat treating a device comprises a chamber configured to contain bath media, a container within the chamber and configured to hold the device, an air inlet gate fluidly upstream of the chamber and configured to be coupled to a gas source to flow gas into the chamber to fluidize the bath media, a heating element between the air inlet gate and the chamber, and a temperature regulator configured to regulate temperature in the chamber by adjusting at least one of the air inlet gate and the heating element. The system may further comprise thermal sensors electrically connected to the temperature regulator.

In some embodiments, a system (e.g., for heat treating a device) comprises a chamber configured to contain bath media, a container within the chamber and configured to hold the device, and an arm mechanically coupling the chamber to the detachable flange. Gas flow into the chamber is configured to fluidize the bath media. The chamber includes a detachable flange including a handle. A height of the container is adjustable in several embodiments.

The arm may comprise at least one of a wire, a plurality of wires, and a hypotube. Adjustment of a length of the arm may adjust the height of the container in the chamber. Detachment of the detachable flange may allow removal of the container from the chamber. The system may further comprise air-sealant rivets on at least one of an inner surface of the detachable flange and an outer surface of the detachable flange.

In some embodiments, a system for cutting a hypotube comprises a laser configured to produce a focused laser beam, a bushing configured to at least partially support a hypotube, a collet configured to at least partially support the hypotube, a fluid flow system, and a conveyor system configured to longitudinally advance the hypotube (e.g., during cutting of the hypotube by the focused laser beam). The collet includes an adjustable diameter aperture. The fluid flow system includes a water inlet device and a water inlet gate configured to be fluidly coupled to an end of the hypotube (e.g., during cutting of the hypotube by the focused laser beam).

The focused laser beam may have a widest dimension less than a narrowest dimension of a pattern to be cut. The focused laser beam may have a widest dimension no more than 120% greater than a narrowest dimension of a pattern to be cut. The bushing may include an aperture may have a diameter at least 0.001 inches (approx. 0.025 mm) greater than an outer diameter of the hypotube. The collet may include an aperture may have a diameter at least 0.001 inches (approx. 0.025 mm) greater than an outer diameter of the hypotube. The water inlet device may have an adjustable height. The water inlet gate may have an adjustable height. The laser may comprise a YAG laser. The laser may have a wavelength of 1060 nm or less.

In some embodiments, a system for cutting a hypotube comprises a fluid flow system, a conveyor system configured to longitudinally advance the hypotube, and at least one of a bushing and a collet configured to at least partially support the hypotube (e.g., during cutting of the hypotube). The fluid flow system includes a water inlet device and a water inlet gate configured to be fluidly coupled to an end of the hypotube.

The collet may include an adjustable diameter aperture. The bushing may include an aperture may have a diameter at least 0.001 inches (approx. 0.025 mm) greater than an outer diameter of the hypotube. The collet may include an aperture may have a diameter at least 0.001 inches (approx. 0.025 mm) greater than an outer diameter of the hypotube. The water inlet device may have an adjustable height. The water inlet gate may have an adjustable height. A plurality of bushings and collets longitudinally may be spaced so that sag of the hypotube may be less than 3% of a height of the hypotube.

In some embodiments, a system for cutting a hypotube comprises a fluid flow system including a water inlet device may have an adjustable height and a water inlet gate may have an adjustable height and configured to be fluidly coupled to an end of a hypotube (e.g., during cutting of the hypotube).

The water inlet device may include a plurality of reservoirs. The plurality of reservoirs may be vertically stacked and fluidly coupled. The water inlet gate may be configured to adjust fluid flow based on a height of the water inlet device.

In some embodiments, a device for treating a vessel comprises a plurality of wires woven to form a textile structure. The textile structure comprises a proximal end, a distal end, a longitudinal axis extending from the proximal end to the distal end, a plurality of bulbs, and a plurality of necks. The textile structure is expandable from a radially-compressed state to a radially-expanded state. The plurality of wires comprises a plurality of shape-memory wires and a plurality of radiopaque wires. Pairs of bulbs of the plurality of bulbs are spaced along the longitudinal axis of the textile structure by a neck of the plurality of necks. A first neck of the plurality of necks has a different neck parameter than a second neck of the plurality of necks at least when the textile structure is in the radially-expanded state. The different neck parameter includes at least one of a neck length along the longitudinal axis and a neck diameter transverse to the longitudinal axis.

Each of the plurality of bulbs may have a generally spherical shape in the radially expanded state. Each of the plurality of necks may be generally cylindrical along the longitudinal axis. Outer diameters of the plurality of bulbs may vary between the proximal end to the distal end. The textile structure may be tapered or stepped from the proximal end to the distal end. The different neck parameter may be the neck length. The different neck parameter may be the neck diameter. The first neck may have a different neck length than a third neck. The plurality of necks may comprise the first neck having a first neck length, the second neck having a second neck length, and a third neck having a third neck length. The first neck length may be shorter than the second neck length. The third neck length may be longer than the second neck length. The first neck and the second neck may be not consecutive along the longitudinal axis. The plurality of bulbs may comprise nine bulbs and the plurality of necks may comprise a first neck between a first bulb and a second bulb, a second neck between the second bulb and a third bulb, a third neck between the third bulb and a fourth bulb, a fourth neck between the fourth bulb and a fifth bulb, a fifth neck between the fifth bulb and a sixth bulb, a sixth neck between the sixth bulb and a seventh bulb, a seventh neck between the seventh bulb and an eighth bulb, and an eighth neck between the eighth bulb and a ninth bulb. The first neck may have a first neck diameter and a first neck length. The second neck may have the first neck diameter and the first neck length. The third neck may have a second neck diameter and the first neck length. The second neck diameter may be larger than the first neck diameter. The fourth neck may have the first neck diameter and a second neck length. The second neck length may be longer than the first neck length. The fifth neck may have the first neck diameter and the first neck length. The sixth neck may have the second neck diameter and the first neck length. The seventh neck may have the first neck diameter and the second neck length. The eighth neck may have a third neck diameter and the first neck length. The third neck diameter may be larger than the second neck diameter.

In some embodiments, a device for treating a vessel comprises a plurality of shape-memory wires and a plurality of radiopaque wires woven to form a textile structure. The textile structure is expandable from a radially-compressed state to a radially-expanded state. The textile structure comprises a plurality of bulbs spaced along a longitudinal axis of the textile structure by a plurality of necks. At least one neck of the plurality of necks has a different neck parameter than another neck of the plurality of necks. The neck parameter including at least one of length, diameter, and shape.

Each of the plurality of bulbs may have a generally spherical shape in the radially-expanded state. Each of the plurality of necks may be generally cylindrical. Outer diameters of the plurality of bulbs may vary from a first end of the textile structure to a second end of the textile structure. The different neck parameter may be length. The different neck parameter may be diameter. The different neck parameter may be shape.

In some embodiments, a device for treating a vessel comprises a plurality of wires woven to form a textile structure. The textile structure is expandable from a radially-compressed state to a radially-expanded state. The textile structure comprises a plurality of bulbs and a plurality of necks. Pairs of bulbs of the plurality of bulbs are spaced along a longitudinal axis of the textile structure by a neck of the plurality of necks. A first neck of the plurality of necks and a second neck of the plurality of necks have at least one of a different neck length, a different neck diameter, and a different neck shape.

The device may be sized for treatment of the vessel in a brain or a leg. At least two necks of the plurality of necks that are consecutive along the longitudinal axis may have the different neck length. At least two necks of the plurality of necks that are consecutive along the longitudinal axis may have the different neck diameter. Each of the at least two necks having the different neck length and/or the different neck diameter may comprise the same necks, may share at least one neck, or comprise different necks. The first neck and the second neck may have a different neck length. The second neck and a third neck may have a different neck diameter.

In some embodiments, a device for treating a vessel comprises a plurality of wires woven to form a textile structure having a longitudinal axis. The textile structure is expandable between a radially compressed state and a radially expanded state. The textile structure comprises, in the radially expanded state, a first bulb, a first neck, a second bulb between the first bulb and the first neck along the longitudinal axis, a second neck between the first bulb and the second bulb along the longitudinal axis, a lateral neck extending from the first bulb at an angle to the longitudinal axis, and a medial neck extending from the first bulb at an angle to the longitudinal axis. The first bulb has a first diameter and a first braid angle. The first neck has a second diameter and a second braid angle. The second diameter is less than the first diameter. The second braid angle is less than the first braid angle. The second bulb has a third diameter. The third diameter is greater than the first diameter. The second neck has a fourth diameter. The fourth diameter is less than the first diameter and less than the third diameter. The lateral neck has a first length. The medial neck has a second length less than the first length.

The first bulb may be generally spherical or ovoid. The second bulb may have a third braid angle greater than the second braid angle. Each of the first bulb and the second bulb may have a porosity configured to decrease flow into an aneurysm. The first bulb may have a porosity configured to decrease flow into an aneurysm. The lateral neck and the medial neck may each be in a different plane. The first diameter may be between 5 mm and 6 mm and the second diameter may be between 3.25 mm and 4 mm. The first diameter may be between 18 mm and 22 mm and the second diameter may be between 18 mm and 22 mm. The lateral neck may have a diameter between 2.75 mm and 3.25 mm and the medial neck may have a diameter between 2.25 mm and 2.75 mm. The lateral neck may have a diameter between 8 mm and 12 mm and the medial neck may have a diameter between 8 mm and 12 mm.

In some embodiments, a device for treating a vessel comprises a plurality of wires forming a textile structure changeable between a radially compressed state and a radially expanded state. The textile structure comprises, in the radially expanded state, an anchor bulb, a first neck extending from the anchor bulb, a second neck extending from the anchor bulb, and a third neck extending from the anchor bulb. The anchor bulb has a first braid angle. The first neck comprises a first generally cylindrical portion proximate to the anchor bulb, a second generally cylindrical portion distant to the anchor bulb, and a second bulb between the first generally cylindrical portion and the second generally cylindrical portion. The second neck has a second braid angle. The second braid angle is less than the first braid angle. The third neck has a third braid angle. The third braid angle is less than the first braid angle.

The second bulb may have a fourth braid angle greater than the second braid angle and the third braid angle. Each of the anchor bulb and the second bulb may have a porosity configured to decrease flow into an aneurysm. The anchor bulb may have a porosity configured to decrease flow into an aneurysm. At least one of the first neck, the second neck, and the third neck may be on a different plane than the others of the first neck, the second neck, and the third neck. The second neck may have a first length and the third neck may have a second length less than the first length.

In some embodiments, a device for treating a vessel comprises a plurality of wires forming a textile structure transformable between a radially compressed state and a radially expanded state. The textile structure comprises, in the radially expanded state, an first bulb having a first braid angle, a first neck extending from the first bulb, a second neck extending from the first bulb, the second neck having a second braid angle less than the first braid angle, and a third neck extending from the first bulb, the second neck having a third braid angle less than the first braid angle.

The first neck may comprise a second bulb. Each of the first bulb and the second bulb may have a porosity configured to decrease flow into an aneurysm. The first bulb may have a porosity configured to decrease flow into an aneurysm. The first neck may have a first length, the second neck may have a second length less than the first length, and the third neck may have a third length less than the second length. At least one of the first neck, the second neck, and the third neck may be on a different plane than the others of the first neck, the second neck, and the third neck.

In some embodiments, a device for treating a vascular cavity comprises a plurality of wires woven to form a textile structure expandable between a radially compressed state and a radially expanded state. The textile structure in the radially expanded state comprises a first bulb, a second bulb, a third bulb, a first neck between the first bulb and the second bulb, a second neck between the second bulb and the third bulb, a third neck extending from the third bulb, and a fourth neck extending from the first bulb. The first bulb has a first braid angle. The first bulb has a first diameter. The first bulb has a porosity configured to decrease flow into and out of the vascular cavity. The second bulb has a second braid angle less than the first braid angle. The second bulb has a second diameter. The second bulb is between the first bulb and the third bulb. The third bulb has a third braid angle less than the first braid angle. The third bulb has a third diameter less than the first diameter. The first neck has a fourth braid angle less than the first braid angle. The first neck has a fourth diameter less than the first diameter and the second diameter. The second neck has a fifth braid angle less than the first braid angle. The second neck has a fifth diameter less than the second diameter and the third diameter.

The textile structure in the radially expanded state may further comprise a fourth bulb between the first bulb and the first neck and a fourth neck between the first bulb and the fourth bulb. The fourth bulb may have a sixth braid angle greater than the second braid angle, the third braid angle, the fourth braid angle, and the fifth braid angle. The fourth bulb may have a sixth diameter. The fourth neck may have a seventh diameter less than the first diameter and the sixth diameter. The sixth diameter may be less than the first diameter and greater than the third diameter. The fourth bulb may have a porosity configured to decrease flow into the vascular cavity. Each of the first bulb, the second bulb, and the third bulb may have a shape of an ellipsoid or oblate spheroid may have a polar axis diameter smaller than an equatorial axis diameter. The first bulb, the second bulb, and the third bulb may be coupled along the polar axes of the first bulb, the second bulb, and the third bulb. The device of Claim 1, wherein the textile structure may be mechanically and/or electrolytically detachable from a proximal portion at a joint. The first braid angle may be between 91° and 180°. The device may further comprise a proximal portion detachably coupled to the textile structure. Each of the first bulb, the second bulb, and the third bulb may have a shape of an ellipsoid or oblate spheroid may have a polar axis diameter smaller than an equatorial axis diameter. The first bulb, the second bulb, and the third bulb may be coupled along the polar axes of the first bulb, the second bulb, and the third bulb. The textile structure in the radially expanded state may further comprise a fourth bulb between the first bulb and the first neck and a fourth neck between the first bulb and the fourth bulb. The fourth bulb may have a sixth braid angle greater than the second braid angle, the third braid angle, the fourth braid angle, and the fifth braid angle. The fourth bulb may have a sixth diameter less than the first diameter and greater than the third diameter. The fourth bulb may have a porosity configured to decrease flow into the vascular cavity. The fourth neck may have a seventh diameter less than the first diameter and the sixth diameter.

In some embodiments, a device for treating a vascular cavity comprises a textile structure changeable between a radially compressed state and a radially expanded state. The textile structure comprises, in the radially expanded state, a plurality of bulbs along a longitudinal axis from a proximal end to a distal end. Each bulb is longitudinally spaced from another bulb by a neck. A proximal-most bulb of the plurality of bulbs has a porosity configured to reduce flow into the vascular cavity. The device further comprises proximal portion coupled to the textile structure at a joint proximal to the proximal-most bulb. The textile structure is detachable from the proximal portion at the joint.

The plurality of bulbs may comprise the proximal-most bulb, a second bulb distal to the proximal-most bulb, and a third bulb distal to the second bulb. The proximal-most bulb may have a first braid angle. The second bulb may have a second braid angle less than the first braid angle. The third bulb may have a third braid angle less than the first braid angle. The plurality of bulbs may comprise the proximal-most bulb, a second bulb distal to the proximal-most bulb, a third bulb distal to the second bulb, and a fourth bulb distal to the third bulb. The proximal-most bulb may have a first braid angle. The second bulb may have a second braid angle. The third bulb may have a third braid angle less than the first braid angle and the second braid angle. The fourth bulb may have a fourth braid angle less than the first braid angle and the second braid angle. Each of the plurality of bulbs may have a shape of an ellipsoid or oblate spheroid having a polar axis diameter smaller than an equatorial axis diameter. The plurality of bulbs may be coupled along the polar axes. The device of Claim 10, wherein the textile structure may be mechanically detachable from the proximal portion at the joint. The device of Claim 10, wherein the textile structure may be electrolytically detachable from the proximal portion at the joint. The plurality of bulbs may comprise the proximal-most bulb, a second bulb distal to the proximal-most bulb, and a third bulb distal to the second bulb. The proximal-most bulb may have a first braid angle. The second bulb may have a second braid angle less than the first braid angle. The third bulb may have a third braid angle less than the first braid angle. Each of the plurality of bulbs may have a shape of an ellipsoid or oblate spheroid having a polar axis diameter smaller than an equatorial axis diameter. The plurality of bulbs may be coupled along the polar axes.

In some embodiments, a device for treating a vascular cavity comprises a structure transformable between a radially compressed state and a radially expanded state. The structure comprises, in the radially expanded state, a plurality of bulbs. Each bulb is longitudinally spaced from another bulb by a neck. The plurality of bulbs comprises a proximal-most bulb having a porosity configured to inhibit flow into the vascular cavity.

The structure may comprise a plurality of wires. The plurality of bulbs may comprise the proximal-most bulb, a second bulb distal to the proximal-most bulb, and a third bulb distal to the second bulb. The proximal-most bulb may have a first braid angle. The second bulb may have a second braid angle less than the first braid angle. The third bulb may have a third braid angle less than the first braid angle. Each of the plurality of bulbs may have a shape of an ellipsoid or oblate spheroid having a polar axis diameter smaller than an equatorial axis diameter. The plurality of bulbs may be coupled along the polar axes.

In some embodiments, a method of treating a vessel comprises positioning a distal portion of a treatment device in the vessel. The distal portion comprises a plurality of filaments and pores between the filaments. The treatment device comprises a proximal portion. The proximal portion comprises a wire. The wire comprises shape-memory material. The wire has a distal end. The distal end of the wire comprises a first shape at a first temperature and a second shape at a second temperature different than the first temperature. The second shape is a straightened form of the first shape. The distal portion is coupled to the proximal portion at least by the pores between the filaments being entangled with the wire in the first shape. The method further comprises decoupling the proximal portion of the treatment device and the distal portion of the treatment device.

Decoupling may comprise changing the wire from the first temperature to the second temperature. The first temperature may be 25° C. and the second temperature may be 37° C. The first temperature may be 25° C. and the second temperature may be 18° C. The first shape may include a ball having an outer diameter greater than an inner diameter of the distal portion where the distal portion is coupled to the proximal portion. The first shape may include radially outward dimples. The second shape may include linear. The wire may comprise a coiling portion proximal to the distal end. The coiling portion may comprise a coil at the first temperature and a straightened form of the coil at the second temperature. During decoupling, a proximal end of the wire may retract proximally. The distal portion may be coupled to the proximal portion at least by the plurality of filaments being welded to the wire by solder at a joint may have a tensile strength less than 2700 psi. Decoupling may comprise exerting a shear strength on the wire greater than 2700 psi. Decoupling may comprise changing the wire from the first temperature to the second temperature. The first temperature may be 25° C. and the second temperature may be 37° C. The first temperature may be 25° C. and the second temperature may be 18° C. The first shape may include a ball having an outer diameter greater than an inner diameter of the distal portion where the distal portion is coupled to the proximal portion. The wire may comprise a coiling portion proximal to the distal end. The coiling portion may comprise a coil at the first temperature and a straightened form of the coil at the second temperature. During decoupling, a proximal end of the wire may retract proximally.

In some embodiments, a method of treating a vessel comprises positioning a distal portion of a treatment device in the vessel. The treatment device comprises a proximal portion and a distal portion. The proximal portion comprises a tubular member. The tubular member comprises a distal end. The distal end of the tubular member comprises a socket. The distal portion comprises a plurality of filaments. At least one filament of the plurality of filaments comprises shape memory material. The at least one filament has a first shape at a first temperature and a second shape at a second temperature different than the first temperature. The first shape comprises a segment coupled to the proximal portion by interaction between the segment and the socket of the distal end of the tubular member. The second shape is a straightened form of the first shape. The method further comprises decoupling the proximal portion of the treatment device and the distal portion of the treatment device. Decoupling comprises changing the at least one filament from the first temperature to the second temperature.

The first temperature may be 25° C. and the second temperature may be 37° C. The first temperature may be 25° C. and the second temperature may be 18° C. The socket may include at least one of a slit, a recess, and a radially outward dimple. Before decoupling, the distal portion may be radially outward of the tubular member. Before decoupling, the tubular member may be radially outward of the distal portion.

In some embodiments, a method of treating a vessel comprises positioning a distal portion of a treatment device in the vessel. The treatment device comprises a proximal portion and a distal portion. The proximal portion comprises a distal end. The distal end comprising a plurality of ridges. The distal portion comprises a plurality of filaments radially outward of the distal end of the proximal portion and pores between the filaments creating a plurality of grooves. The distal portion is coupled to the proximal portion at least by the plurality of grooves being entangled with the plurality of ridges. The method further comprises decoupling the proximal portion of the treatment device and the distal portion of the treatment device. Decoupling comprises disentangling the plurality of ridges and the plurality of grooves. Decoupling the proximal portion and the distal portion may comprise rotating the proximal portion. The ridges may comprise threads at an angle to a longitudinal axis of the distal end of the proximal portion. The ridges may be transverse to a longitudinal axis of the distal end of the proximal portion. The ridges may be perpendicular to a longitudinal axis of the distal end of the proximal portion. The distal end of the proximal portion may comprise a wire. The plurality of ridges may extend radially outward from the wire.

In some embodiments, a method of aspirating thrombi using a varying suction pattern includes inserting a distal end of a microcatheter within vasculature and advancing the distal end of the microcatheter to a location proximal to a thrombus. The method may optionally include inserting a thrombectomy device to at least partially span the thrombus. The thrombectomy device may comprise a first bulb having a first diameter, a second bulb having a second diameter and a third bulb having a third diameter. The second diameter may be greater than the first diameter and a third diameter is greater than the second diameter. The method may comprise applying suction to a proximal end of the microcatheter to aspirate the thrombus. The suction applied may comprises a repetitive pattern of varying suction intensity levels each applied for a particular time duration. In one embodiment, the repetitive pattern is a crescendo pattern.

The repetitive pattern may include three different suction intensity levels and at least one pause for a pause time duration. In some embodiments, the time duration of a first suction intensity level of the repetitive pattern is longer than the time duration of a second suction intensity level of the repetitive pattern. Applying suction to the proximal end of the microcatheter can comprise causing an automated control unit to apply the suction having the repetitive pattern. The repetitive pattern may comprise a first intensity level for a first time duration, a second intensity level for a second time duration, and a third intensity level for a third time duration, wherein the first intensity level is lower than the second intensity level and wherein the second intensity level is lower than the third intensity level. In one embodiment, the repetitive pattern comprises a pause for a fourth time duration between the third time duration and the first time duration. In some embodiments, the repetitive pattern comprises a pause for a fourth time duration between each of the time durations. The first time duration, the second time duration and the third time duration may be uniform or may vary. In some embodiments, the first intensity level is within a range between 100 mm Hg (approx. 13.3 kPa) and 350 mm Hg (approx. 46.7 kPa), the second intensity level is within a range between 351 mm Hg (approx. 46.8 kPa) and 550 mm Hg (approx. 73.3 kPa), and the third intensity level is within a range between 551 mm Hg (approx. 73.5 kPa) and 769 mm Hg (approx. 102.5 kPa).

In accordance with several embodiments, a method of aspirating thrombi using a varying suction pattern includes inserting a distal end of a microcatheter within vasculature to a location proximate a thrombus and causing suction to be applied to the location through the microcatheter in a repetitive suction pattern. In some embodiments, the repetitive suction pattern comprises a first intensity level for a first time duration, a second intensity level for a second time duration, a third intensity level for a third time duration, and a fourth time duration wherein suction is paused. The second intensity level may be greater than the first intensity level and the third intensity level may be greater than the second intensity level. In one embodiment, the first time duration, the second time duration and the third time duration are uniform. The repetitive suction pattern may comprise a pause having the fourth time duration between each of the first, second and third time durations. In one embodiment, the repetitive suction pattern comprises, in order, the first intensity level for the first time duration, a first pause for the fourth time duration, the second intensity level for the second time duration, a second pause for the fourth time duration, the third intensity level for the third time duration, and a third pause for the fourth time duration. In one embodiment, the repetitive suction pattern comprises, in order, the first intensity level for the first time duration, the second intensity level for the second time duration, the third intensity level for the third time duration, and a pause for the fourth time duration. In one embodiment, at least one of the four time durations is different from at least one of the other three time durations.

A method of aspirating thrombi using a varying suction pattern may include providing an aspiration system comprising a microcatheter, a thrombectomy device, suction tubing and a suction control unit. The aspiration system may be configured for causing suction to be applied by the suction control unit to a location proximate the thrombectomy device through the suction tubing coupled to a proximal end of the microcatheter upon user selection of one of a plurality of preconfigured repetitive suction patterns. Each of the repetitive suction pattern may comprise a first intensity level having a first time duration, a second intensity level having a second time duration, a third intensity level having a third time duration, and a fourth time duration wherein suction is paused. In one embodiment, the second intensity level is greater than the first intensity level and the third intensity level is greater than the second intensity level. A diameter of a lumen of the microcatheter may taper from a proximal end of the microcatheter to a distal end of the microcatheter or may be uniform. The thrombectomy device may comprise five to twenty self-expanding bulbs spaced apart by necks.

In some embodiments, a system for aspirating thrombi using a varying suction pattern includes a distal access microcatheter comprising a proximal end, a distal end and a lumen. The distal end may include a balloon configured to provide flow arrest within a vessel. The system can include a second microcatheter sized to fit within the lumen of the distal access microcatheter, the second microcatheter comprising a proximal end, a distal end and a lumen. The system may also include a disposable canister and a peristaltic motor pump comprising power electronics configured to control the peristaltic motor pump to provide suction having one of a plurality of preconfigured suction patterns. A particular suction pattern of the plurality of preconfigured suction patterns may be selected on a user interface of a control panel of the peristaltic motor pump unit. The particular suction pattern may be selected based on a particular clot burden or profile, thereby providing flexibility and customizability. Each of the plurality of preconfigured suction patterns may comprise a repetitive cycle pattern that includes at least two different suction intensity levels and at least one pause duration. The system may further include suction tubing coupled to the disposable canister, the suction tubing configured to extend from the disposable canister to a hub or port at the proximal end of the guide catheter or distal access microcatheter or the second microcatheter. The distal access microcatheter may include a hypotube having interspersed cut patterns, a plurality of filaments, a polymer and/or other features to facilitate suction. The different suction intensity levels and the at least one pause duration of the plurality of preconfigured suction patterns are configured for facilitating increased aspiration of thrombi. In some embodiments, the system includes a thrombectomy device comprising a woven textile structure, the woven textile structure comprising a first bulb having a first diameter, a second bulb having a second diameter and a third bulb having a third diameter, wherein the second diameter is greater than the first diameter and wherein the third diameter is greater than the second diameter.

The repetitive cycle pattern may include three different suction intensity levels. The three different suction intensity levels may comprise a crescendo suction pattern. The repetitive cycle pattern may include at least one pause duration between each change in suction intensity level. In one embodiment, the repetitive cycle pattern comprises the following order: a first intensity level for a first time duration, a second intensity level for a second time duration, a third intensity level for a third time duration, wherein the second intensity level is greater than the first intensity level, and wherein the third intensity level is greater than the second intensity level. In one embodiment, the first intensity level is within a range between 100 mm Hg (approx. 13.3 kPa) and 350 mm Hg (approx. 46.7 kPa), the second intensity level is within a range between 351 mm Hg (approx. 46.8 kPa) and 550 mm Hg (approx. 73.3 kPa), and the third intensity level is within a range between 551 mm Hg (approx. 73.5 kPa) and 769 mm Hg (approx. 102.5 kPa). The suction tubing of the aspiration system may have a length ranging from 15 cm to 150 cm. The suction tubing may include an on/off switch or valve. In one embodiment, the lumen of the distal access microcatheter and the lumen of the second microcatheter are substantially uniform along their lengths. In one embodiment, the lumen of the distal access microcatheter and/or the second microcatheter includes a gradual tapering from the proximal end to the distal end. The time duration of a first suction intensity level of the repetitive cycle pattern may be longer than the duration of a second suction intensity level of the repetitive cycle pattern.

In some embodiments, a system for aspirating thrombi using a varying suction pattern includes a microcatheter comprising a proximal end, a distal end and a lumen. The system may also include an automated motor pump and power electronics configured to provide suction through the lumen of the microcatheter having one of a plurality of preconfigured suction patterns. Each of the plurality of preconfigured suction patterns may comprise a repetitive pattern that includes at least three different suction intensity levels and at least one pause duration. The different intensity levels and the at least one pause duration of the plurality of preconfigured suction patterns are configured for facilitating increased aspiration of thrombi. The system may also include suction tubing configured to extend from the automated motor pump to a hub or port at the proximal end of the microcatheter. The automated motor pump may be a peristaltic motor pump. In one embodiment, the repetitive pattern comprises at least one pause duration between each change in suction intensity level. In one embodiment, the repetitive pattern comprises the following order: a first intensity level for a first time duration, a second intensity level for a second time duration, a third intensity level for a third time duration, wherein the second intensity level is greater than the first intensity level, and wherein the third intensity level is greater than the second intensity level. The durations of the first time duration, the second time duration and the third time duration may each be between 1 second and 30 seconds. In one embodiment, a total suction duration is between 1 minute and 15 minutes.

In some embodiments, a system for aspirating thrombi using a varying suction pattern includes a guide catheter, a distal access microcatheter, or a microcatheter, (each comprising a proximal end, a distal end and a lumen), and an automated suction device configured to provide suction through the lumen of the guide catheter, distal access microcatheter, or microcatheter having one of a plurality of preconfigured suction patterns, and suction tubing configured to extend from the automated suction device to a hub or port at the proximal end of the guide catheter, distal access microcatheter, or microcatheter. Each of the plurality of preconfigured suction patterns may comprise a repetitive pattern that includes at least two different suction intensity levels and at least one pause duration. In some embodiments, the repetitive pattern comprises at least one pause duration between each change in suction intensity level. In one embodiment, the repetitive pattern comprises the following order: a first intensity level for a first time duration, a second intensity level for a second time duration, a third intensity level for a third time duration, wherein the second intensity level is greater than the first intensity level, and wherein the third intensity level is greater than the second intensity level. The time durations may vary or may be uniform. In one embodiment, the suction pattern is a crescendo suction pattern.

In some embodiments, a system for aspirating thrombi using a varying suction pattern includes a mobile pump with an external control panel for generating repetitive suction patterns for aspiration. The system may also include a disposable canister and a peristaltic motor pump comprising power electronics configured to control the peristaltic motor pump to provide suction having one of a plurality of preconfigured suction patterns. In some embodiments, the mobile peristaltic motor pump is connected to an exhaust unit.

In some embodiments, the system may include a peristaltic motor pump that is controlled by power electronics to generate the repetitive suction patterns including crescendo suction patterns, diminuendo suction patterns, a combination of both crescendo and diminuendo suction patterns, or combinations of other repetitive suction patterns, with a desired intensity and/or duration of negative suction pressure. The system may also include power electronics that may comprise a customized integrated circuit board or an integrated chip. The system may also include an external control panel that allows the operator to choose between various preconfigured repetitive suction patterns.

In some embodiments, the system may comprise an external control panel that may be customized by the operator to generate a plurality of new repetitive suction patterns. Each of the plurality of new repetitive suction patterns may comprise of at least two different suction intensity levels and at least one pause duration. The different intensity levels and the at least one pause duration of the plurality of customized new repetitive suction patterns are configured for facilitating increased aspiration of thrombi.

In some embodiments, an implantable device for treating a vascular cavity comprises a plurality of wires woven to form a textile structure expandable from a compressed state to an expanded state. The textile structure comprises, in the expanded state, a first bulb, a second bulb, a first neck, a third bulb, a second neck, and a lumen configured to allow perfusion of blood through the textile structure. The first bulb comprises a first braid angle, a first diameter, and a first shape. The second bulb comprises a second braid angle, a second diameter, and a second shape. The first neck is between the first bulb and the second bulb. The third bulb comprises a third braid angle, a third diameter, and a third shape. The second bulb is between the first bulb and the third bulb. The second neck is between the second bulb and the third bulb. At least one of the first braid angle, the second braid angle, and the third braid angle is different from at least one other of the first braid angle, the second braid angle, and the third braid angle.

The second braid angle may be greater than the first braid angle and the third braid angle. The second diameter may be greater than the first diameter and the third diameter. The second diameter may be greater than the first diameter and the second diameter may be less than the third diameter. The second bulb may be elongate. The second braid angle may be less than the first braid angle and the third braid angle. The first braid angle may be greater than the second braid angle and the third braid angle. The second bulb may comprise a first portion having the second braid angle and a second portion having the first braid angle, and the second portion may be proximate to the first bulb. The second diameter may be greater than the first diameter and the third diameter. At least one of the plurality of wires may comprise a shape-memory alloy and the textile structure may be configured to self-expand from the compressed state to the expanded state. At least one of the first diameter, the second diameter, and the third diameter may be different from at least one other of the first diameter, the second diameter, and the third diameter. The textile structure may be tapered in the expanded state. The textile structure may be non-tapered in the expanded state. The first diameter may be between 2.75 mm and 3.25 mm, the second diameter may be between 5 mm and 6 mm, and the third diameter may be between 3.25 mm and 4 mm. The first diameter may be between 8 mm and 12 mm, the second diameter may be between 6 mm and 10 mm, and the third diameter may be between 6 mm and 10 mm. At least one of the first shape, the second shape, and the third shape may be different from at least one other of the first shape, the second shape, and the third shape. At least one of the first shape, the second shape, and the third shape may be spherical. At least one of the first shape, the second shape, and the third shape may be elongate. The textile structure may further comprise, in the expanded state, a third neck and a fourth neck, the first bulb between the first neck and the third neck and the third bulb between the second neck and the fourth neck. At least one of the first braid angle, the second braid angle, and the third braid angle may be between 91° and 180°. At least one of the first braid angle, the second braid angle, and the third braid angle may be configured to divert blood flow from the vascular cavity. At least one of the first bulb, the second bulb, and the third bulb may comprise a porosity between 60% and 78%. At least one of the first braid angle, the second braid angle, and the third braid angle may be between 0° and 90°. At least part of the textile structure may comprise a polymer coating. At least one of the first braid angle, the second braid angle, and the third braid angle may be configured to allow perfusion of blood to branch or perforating vessels. At least one of the first bulb, the second bulb, and the third bulb may be configured to at least partially expand a vessel proximate to the vascular cavity. A braid angle transition between the at least one of the first braid angle, the second braid angle, and the third braid angle and the at least one other of the first braid angle, the second braid angle, and the third braid angle may be gradual. At least two of the first braid angle, the second braid angle, and the third braid angle may be configured to divert blood flow from a plurality of aneurysms, the plurality of aneurysms including the vascular cavity. At least one of the first bulb, the second bulb, and the third bulb may have a picks per inch between 125 and 175. At least one the first neck and the second neck may have a same braid angle as the at least one of the first braid angle, the second braid angle, and the third braid angle.

An implantable device for treating a vascular cavity comprises a plurality of wires woven to form a textile structure expandable from a compressed state to an expanded state. The textile structure comprises, in the expanded state, a first segment, a second segment, and a lumen configured to allow perfusion of blood through the textile structure. The first segment comprises a first braid angle. The second segment comprises a second braid angle. The second braid angle is greater than the first braid angle. At least one of the first segment and the second segment comprises a bulb.

The first segment may comprise the bulb. The first segment may comprise the bulb and at least a portion of a second bulb. The second segment may comprise the bulb. The second segment may comprise the bulb and at least a portion of a second bulb. The bulb may be generally spherical. The bulb may be generally elongate. The textile structure may further comprise, in the expanded state, a third segment comprising a third braid angle greater than the first braid angle, the first segment between the second segment and the third segment. The textile structure may further comprise, in the expanded state, a third segment comprising a third braid angle, the second braid angle greater than the third braid angle, the second segment between the first segment and the third segment. The first segment may comprise the bulb, the second segment may comprise a second bulb, and the third segment may comprise a third bulb. The first bulb may be spherical and may have a first diameter, the second bulb may be elongate and may have a second diameter less than the first diameter, and the third bulb may be spherical and may have a third diameter less than the second diameter. The first segment may comprise the bulb and the second segment may comprise a second bulb. The first bulb may be elongate and may have a first diameter and the second bulb may be spherical and may have a second diameter greater than the first diameter. The second segment may comprise a first portion on a first circumferential side of the textile structure and a second portion on a second circumferential side of the textile structure opposite the first circumferential side. The second portion may comprise the second braid angle. The first portion may comprise a third braid angle less than the second braid angle. At least one of the plurality of wires may comprise a shape-memory alloy and the textile structure may be configured to self-expand from the compressed state to the expanded state. At least one of the plurality of wires may comprise radiopaque material. The second braid angle may be between 91° and 180°. The second braid angle may be configured to divert blood flow from the vascular cavity. The second segment may comprise a porosity between 60% and 78%. The first braid angle may be between 0° and 90°. The first segment may be configured to allow perfusion of blood to branch or perforating vessels. The bulb may be configured to at least partially expand a vessel proximate to the vascular cavity. A braid angle transition between the first braid angle and the second braid angle may be gradual.

In some embodiments, a vascular treatment device comprises a plurality of wires woven to form a textile structure expandable from a compressed state to an expanded state. The textile structure comprises a bulb in the expanded state, a lumen configured to allow perfusion of blood through the textile structure, a first portion configured to allow perfusion of blood transverse to a longitudinal axis of the textile structure, and a second portion configured to divert blood flow away from a vascular cavity. The second portion is circumferentially offset from at least part of the first portion.

The first portion may comprise a first braid angle and the second portion may comprise a second braid angle greater than the second braid angle. The second braid angle may be between 91° and 180°. The second portion may comprise a porosity between 60% and 78%. The first braid angle may be between 0° and 90°. The second portion may comprise a polymer coating. At least one of the plurality of wires may comprise a shape-memory alloy and the textile structure may be configured to self-expand from the compressed state to the expanded state. The bulb may be spherical. The bulb may be elongate. The bulb may comprise the second portion. The textile structure may comprise a plurality of bulbs, the plurality of bulbs comprising the bulb.

In some embodiments, a method of manufacturing a device for treating a vessel comprises arranging a first mandrel extension on a bulbous mandrel, arranging a second mandrel extension on the bulbous mandrel, arranging a third mandrel extension on the bulbous mandrel, and braiding a plurality of wires over the bulbous mandrel, the first mandrel extension, the second mandrel extension, and the third mandrel extension to form a textile structure comprising a first bulb, a first neck, a second bulb between the first bulb and the first neck, a second neck between the first bulb and the second bulb, a lateral neck, and a medial neck. The first neck, the second bulb, and the second neck extend from the first bulb along a longitudinal axis. The lateral neck extends from the first bulb at a first angle to the longitudinal axis. The medial neck extends from the first bulb at a second angle to the longitudinal axis.

Arranging the first mandrel extension may comprise coupling the first mandrel extension to a first sprocket in a first retainer in the bulbous mandrel. Arranging the second mandrel extension may comprise coupling the second mandrel extension to a second sprocket in a second retainer in the bulbous mandrel. Arranging the third mandrel extension may comprise coupling the third mandrel extension to a third sprocket in a third retainer in the bulbous mandrel. The method may further comprise, after arranging the first mandrel extension, the second mandrel extension, and the third mandrel extension, removing sprockets that are not coupled to the first mandrel extension, the second mandrel extension, or the third mandrel extension from other retainers in the bulbous mandrel. At least one of the first sprocket, the second sprocket, and the third sprocket may be rotatable between 0° and 180° relative to a surface of the bulbous mandrel proximate to the at least one sprocket. Arranging the first mandrel extension may comprise coupling the first mandrel extension in a first retainer in the bulbous mandrel. Arranging the second mandrel extension may comprise coupling the second mandrel extension in a second retainer in the bulbous mandrel. Arranging the third mandrel extension may comprise coupling the third mandrel extension in a third retainer in the bulbous mandrel. The method may further comprise heat treating the textile structure. The first bulb may have a first diameter, the first neck may have a second diameter less than the first diameter, the second bulb may have a third diameter greater than the first diameter, and the second neck may have a fourth diameter less than the second diameter and less than the third diameter. The first bulb may have a first braid angle and the first neck may have a second braid angle less than the first braid angle. The second bulb may have a third braid angle greater than the second braid angle. Each of the first bulb and the second bulb may have a porosity configured to decrease flow into an aneurysm. The first bulb may have a porosity configured to decrease flow into an aneurysm. The lateral neck may have a first length and the medial neck may have a second length less than the first length. The first bulb may have a first diameter and a first braid angle. The first neck may have a second diameter less than the first diameter and a second braid angle less than the first braid angle. The second bulb may have a third diameter greater than the first diameter. The second neck may have a fourth diameter less than the second diameter and less than the third diameter. The lateral neck may have a first length and the medial neck may have a second length less than the first length. At least one of the first mandrel extension, the second mandrel extension, and the third mandrel extension may comprise a bulb. The bulb may be generally spherical. At least one of the first mandrel extension, the second mandrel extension and the second mandrel extension may comprise a cylindrical shape. The lateral neck and the medial neck may each be in a different plane.

In some embodiments, a method of manufacturing a device for treating a vessel comprises arranging a plurality of mandrel extensions on a bulbous mandrel and braiding a plurality of wires around the bulbous mandrel and the plurality of mandrel extensions to form a textile structure. At least two of the plurality of mandrel extensions are at a non-linear angle to each other. The textile structure comprises an anchor bulb, a first neck extending from the anchor bulb, and a second neck extending from the anchor bulb. The second neck is at the non-linear angle to the first neck.

Arranging the plurality of mandrel extensions may comprise coupling each of the plurality of mandrel extensions to a sprocket in a retainer in the bulbous mandrel. Arranging the plurality of mandrel extensions may comprise coupling each of the mandrel extensions in a retainer in the bulbous mandrel. The method may further comprise heat treating the textile structure. At least one of the plurality of mandrel extensions may comprise a bulb. The first neck may comprise a first generally cylindrical portion, a second bulb, and a second generally cylindrical portion. The first generally cylindrical portion may be between the anchor bulb and the second bulb. The second bulb may be between the first generally cylindrical portion and the second generally cylindrical portion. Each of the anchor bulb and the second bulb may have a porosity configured to decrease flow into an aneurysm. The anchor bulb may have a porosity configured to decrease flow into an aneurysm. The anchor bulb may have a first braid angle and the second neck may have a second braid angle less than the first braid angle. The textile structure may further comprise a third neck extending from the anchor bulb. The anchor bulb may have a first braid angle and the third neck may have a third braid angle less than the first braid angle. At least one of the first neck, the second neck, and the third neck may be on a different plane than the others of the first neck, the second neck, and the third neck. The second neck may have a first length and the third neck may have a second length less than the first length.

In some embodiments, a method of manufacturing a device for treating a vessel comprises braiding a plurality of wires around a bulbous mandrel and a plurality of mandrel extensions to form a textile structure. The textile structure comprises a first bulb having a first braid angle, a first neck extending from the first bulb, and a second neck extending from the first bulb. The second neck has a second braid angle less than the first braid angle.

The method may further comprise arranging the plurality of mandrel extensions on the bulbous mandrel. Arranging the plurality of mandrel extensions may comprise coupling each of the plurality of mandrel extensions to a sprocket in a retainer in the bulbous mandrel. Arranging the plurality of mandrel extensions may comprise coupling each of the mandrel extensions in a retainer in the bulbous mandrel. The method may further comprise heat treating the textile structure. The first neck may comprise a second bulb. Each of the first bulb and the second bulb may have a porosity configured to decrease flow into an aneurysm. The first bulb may have a porosity configured to decrease flow into an aneurysm. The textile structure may comprise a third neck extending from the first bulb. The third neck may have a third braid angle less than the first braid angle. The first neck may have a first length. The second neck may have a second length less than the first length. The third neck may have a third length less than the second length. The first neck may comprise a second bulb.

In some embodiments, a mandrel for manufacturing a vascular device for treating a vessel comprises an elongate strand having a longitudinal axis, a first bulb coupled to the elongate strand, a second bulb coupled to the elongate strand distal to the first bulb along the longitudinal axis of the elongate strand, a third bulb coupled to the elongate strand distal to the second bulb along the longitudinal axis of the elongate strand, a fourth bulb coupled to the elongate strand distal to the third bulb along the longitudinal axis of the elongate strand, a fifth bulb coupled to the elongate strand distal to the fourth bulb along the longitudinal axis of the elongate strand, a sixth bulb coupled to the elongate strand distal to the fifth bulb along the longitudinal axis of the elongate strand, a seventh bulb coupled to the elongate strand distal to the sixth bulb along the longitudinal axis of the elongate strand, an eighth bulb coupled to the elongate strand distal to the seventh bulb along the longitudinal axis of the elongate strand, a ninth bulb coupled to the elongate strand distal to the eighth bulb along the longitudinal axis of the elongate strand, and a tenth bulb coupled to the elongate strand distal to the ninth bulb along the longitudinal axis of the elongate strand. The first bulb comprises a first cylindrical hole. The elongate strand extends through the first cylindrical hole. The second bulb comprises a second cylindrical hole. The elongate strand extends through the second cylindrical hole. The first bulb and the second bulb have a first outer diameter. The third bulb comprises a third cylindrical hole. The elongate strand extends through the third cylindrical hole. The fourth bulb comprises a fourth cylindrical hole. The elongate strand extends through the fourth cylindrical hole. The third bulb and the fourth bulb have a second outer diameter smaller than the first outer diameter. The fifth bulb comprises a fifth cylindrical hole. The elongate strand extends through the fifth cylindrical hole. The sixth bulb comprises a sixth cylindrical hole. The elongate strand extends through the sixth cylindrical hole. The seventh bulb comprises a seventh cylindrical hole. The elongate strand extends through the seventh cylindrical hole. The fifth bulb, the sixth bulb, and the seventh bulb have a third outer diameter smaller than the second outer diameter. The eighth bulb comprises an eighth cylindrical hole. The elongate strand extends through the eighth cylindrical hole. The ninth bulb comprises a ninth cylindrical hole. The elongate strand extends through the ninth cylindrical hole. The tenth bulb comprises a tenth cylindrical hole. The elongate strand extends through the tenth cylindrical hole. The eighth bulb, the ninth bulb, and the tenth bulb have a fourth outer diameter smaller than the third outer diameter. At least one of the first bulb, the second bulb, the third bulb, the fourth bulb, the fifth bulb, the sixth bulb, the seventh bulb, the eighth bulb, the ninth bulb, and the tenth bulb has a spherical shape. A vascular device manufactured utilizing the mandrel is configured to treat a vessel.

The first bulb may have an oblong shape, the second bulb may have a spherical shape, the third bulb may have an oblong shape, the fourth bulb may have a spherical shape, the fifth bulb may have an oblong shape, the sixth bulb may have a spherical shape, the seventh bulb may have a spherical shape, the eighth bulb may have an oblong shape, the ninth bulb may have a spherical shape, and the tenth bulb may have a spherical shape. The first bulb may have a spherical shape, the second bulb may have a spherical shape, the third bulb may have a spherical shape, the fourth bulb may have a spherical shape, the fifth bulb may have a spherical shape, the sixth bulb may have a spherical shape, the seventh bulb may have a spherical shape, the eighth bulb may have a spherical shape, the ninth bulb may have a spherical shape, and the tenth bulb may have a spherical shape. At least two of the first bulb, the second bulb, the third bulb, the fourth bulb, the fifth bulb, the sixth bulb, the seventh bulb, the eighth bulb, the ninth bulb, and the tenth bulb may have different shapes. At least one of the first bulb, the second bulb, the third bulb, the fourth bulb, the fifth bulb, the sixth bulb, the seventh bulb, the eighth bulb, the ninth bulb, and the tenth bulb may have an oblong shape.

In some embodiments, a mandrel for manufacturing a vascular device for treating a vessel comprises an elongate stainless steel strand and a plurality of stainless steel bulbs is coupled to the elongate stainless steel strand. The elongate stainless steel strand has an outer diameter between 0.15 mm and 0.75 mm. The elongate stainless steel strand extends through each of the plurality of stainless steel bulbs. At least one stainless steel bulb of the plurality of stainless steel bulbs has an outer diameter between 2.25 mm and 2.75 mm. At least one stainless steel bulb of the plurality of stainless steel bulbs has an outer diameter between 2.75 mm and 3.25 mm. At least one stainless steel bulb of the plurality of stainless steel bulbs has an outer diameter between 3.25 mm and 4 mm A vascular device manufactured utilizing the mandrel is configured to treat a vessel.

The elongate stainless steel strand may have a longitudinal axis and the plurality of stainless steel bulbs may be aligned along the longitudinal axis of the elongate stainless steel strand. At least one stainless steel bulb of the plurality of stainless steel bulbs may have a spherical shape. A first stainless steel bulb of the plurality of stainless steel bulbs may have a different shape than a second stainless steel bulb of the plurality of stainless steel bulbs. At least one stainless steel bulb of the plurality of stainless steel bulbs may have an outer diameter between 1.5 mm and 2.25 mm A first stainless steel bulb of the plurality of stainless steel bulbs may be spaced from a second steel bulb of the plurality of stainless steel bulbs by a length between 0.25 times and 2 times the outer diameter of the first stainless steel bulb. The first stainless steel bulb may be proximal to the second stainless steel bulb. A first stainless steel bulb of the plurality of stainless steel bulbs may be spaced from a second stainless steel bulb of the plurality of stainless steel bulbs by a hypotube having a diameter between 0.15 mm and 0.75 mm. The elongate stainless steel strand may comprise a separable intermediate portion. The plurality of stainless steel bulbs may comprise six stainless steel bulbs. The plurality of stainless steel bulbs may comprise ten stainless steel bulbs.

In some embodiments, a mandrel for manufacturing a vascular device for treating a vessel comprises a first mandrel piece and a second mandrel piece. The first mandrel piece comprises a first elongate strand and a first plurality of bulbs coupled to the first elongate strand. The first elongate strand includes an uncoupled proximal end and a distal end. The first elongate strand extends through each of the first plurality of bulbs. The second mandrel piece comprises a second elongate strand and a second plurality of bulbs coupled to the second elongate strand. The second elongate strand includes a proximal end and an uncoupled distal end. The second elongate strand extends through each of the second plurality of bulbs. The device further comprises an intermediate portion coupling the distal end of the first elongate strand and the proximal end of the second elongate strand. The first mandrel piece is separable from the second mandrel piece in the intermediate portion. A vascular device manufactured utilizing the mandrel is configured to treat a vessel.

Each of the second plurality of bulbs may have an outer diameter greater than an outer diameter of each of the first plurality of bulbs. Each of the first plurality of bulbs and the second plurality of bulbs may have an outer diameter between 1 mm and 6 mm Each of the first plurality of bulbs and the second plurality of bulbs may have an outer diameter between 4 mm and 10 mm. At least one of the first plurality of bulbs may have a spherical shape and at least one of the second plurality of bulbs may have a spherical shape.

In some embodiments, a device for treating a vessel comprises a hypotube and a balloon. The hypotube comprises a proximal end, a distal end, a longitudinal axis, and a lumen. At least a portion of the hypotube comprises a first pattern and a second pattern. The first pattern comprises longitudinally-spaced rows. Each of the rows of the first pattern comprises two kerfs and two stems. The two stems in each of the rows of the first pattern are circumferentially opposite. The stems of the first pattern are offset in a first circumferential direction. The second pattern comprises longitudinally-spaced rows. Each of the rows of the second pattern comprises two kerfs and two stems. The two stems in each of the rows of the second pattern are circumferentially opposite. The stems of the second pattern are offset in a second circumferential direction opposite the first circumferential direction. The rows of the second pattern are singly alternatingly interspersed with the rows of the first pattern. The balloon is radially outward of the hypotube.

The portion of the hypotube may be radially inward of the balloon. The lumen may be in fluid communication with the balloon through at least some of the kerfs of the first pattern and at least some of the kerfs of the second pattern. The hypotube may further comprise an aperture. The lumen may be in fluid communication with the balloon through the aperture. The portion of the hypotube may include part of the hypotube not radially inward of the balloon. The part of the hypotube not radially inward of the balloon may include a portion of the hypotube proximal to the balloon. The part of the hypotube not radially inward of the balloon may include a portion of the hypotube distal to the balloon. The part of the hypotube not radially inward of the balloon may include a portion of the hypotube proximal to the balloon and a portion of the hypotube distal to the balloon. The part of the hypotube not radially inward of the balloon may include an inner coating and/or an outer coating occluding the kerfs of the first pattern and the kerfs of the second pattern in the part of the hypotube not radially inward of the balloon. The part of the hypotube not radially inward of the balloon may include a polymer occluding the kerfs of the first pattern and the kerfs of the second pattern in the part of the hypotube not radially inward of the balloon. The distal end of the hypotube may comprise an occlusion. The device may further comprise an atraumatic tip distal to the hypotube. The atraumatic tip may comprise a tapered inner diameter and a distal opening occludable by a catheter inserted through the lumen. The device may further comprise a strain relief proximal to the hypotube. The device may further comprise a distal radiopaque marker proximate to a distal end of the balloon and a proximal radiopaque marker proximate to a proximal end of the balloon. At least one of the distal radiopaque marker and the proximal radiopaque marker may comprise a kerf of the first pattern or a kerf of the second pattern filled with radiopaque material. The device may further comprise additional radiopaque markers between the distal radiopaque marker and the proximal radiopaque marker. The additional radiopaque markers may be at intervals configured to provide measurement of features of the vessel. The rows of the first pattern and the rows of the second pattern may be at an angle with respect to the longitudinal axis of the hypotube. At least some of the kerfs of the first pattern and at least some of the kerfs of the second pattern may have rounded edges. A pitch between the rows of the first pattern and the rows of the second pattern may vary along the longitudinal axis. The hypotube may comprise stainless steel. The hypotube may comprise nitinol. The hypotube may have a length between 45 cm and 150 cm. The hypotube may have a length between 80 cm and 100 cm. The hypotube may have a length between 80 cm and 150 cm.

In some embodiments, a device for treating a vessel comprises a tubular member. The tubular member comprises a first portion, a second portion distal to the first portion, and a third portion distal to the second portion. The second portion comprises a plurality of patterns each comprising longitudinally-spaced rows. Each of the rows comprises two kerfs and two stems. The stems within each of the plurality of patterns are offset in a circumferential direction. The circumferential direction of at least two patterns of the plurality of patterns is opposite. The second portion further comprises an inflatable element radially outward of the tubular member.

The tubular member may comprise a lumen in fluid communication with the inflatable element through at least some of the kerfs of the plurality of patterns. The third portion may comprise the plurality of patterns. The third portion may comprise an occlusion of the tubular member. The third portion may comprise an atraumatic tip. The atraumatic tip may comprise a tapered inner diameter and a distal opening occludable by a catheter inserted through a lumen of the tubular member. The device may further comprise a strain relief proximal to the first portion. The rows of the plurality of patterns may be at an angle with respect to a longitudinal axis of the tubular member. At least some of the kerfs of the plurality of patterns may have rounded edges. A pitch between the rows of the plurality of patterns may vary along a length of the tubular member. The tubular member may have a length between 45 cm and 150 cm. The tubular member may have a length between 80 cm and 100 cm. The tubular member may have a length between 80 cm and 150 cm.

In some embodiments, a device for treating a vessel comprises a first segment and a second segment distal to the first segment. The first segment comprises a first portion of a tubular member. The second comprises a second portion of the tubular member. The second portion of the tubular member comprises a plurality of patterns of longitudinally-spaced rows and an inflatable element radially outward of the second portion of the tubular member. Each of the rows comprises two kerfs and two stems. The stems within each of the plurality of patterns are offset in a circumferential direction. The circumferential direction of at least two patterns of the plurality of patterns are opposite.

The device may further comprise a third segment distal to the second segment. The third segment may comprise a third portion of the hypotube. The third portion of the tubular member may comprise the plurality of patterns. The third segment may comprise an occlusion of the tubular member. The third segment may comprise an atraumatic tip. The atraumatic tip may comprise a tapered inner diameter and a distal opening occludable by a catheter inserted through a lumen of the tubular member. The device may further comprise a fourth segment proximal to the first segment. The first segment may comprise a strain relief. The tubular member may comprise a lumen in fluid communication with the inflatable element through at least some of the kerfs of the plurality of patterns. The rows of the plurality of patterns may be at an angle with respect to a longitudinal axis of the tubular member. At least some of the kerfs of the plurality of patterns may have rounded edges. A pitch between the rows of the plurality of patterns may vary along a length of the tubular member. The tubular member may have a length between 45 cm and 150 cm. The tubular member may have a length between 80 cm and 100 cm. The tubular member may have a length between 80 cm and 150 cm.

In some embodiments, a method of treating a vessel comprises providing a device for treating the vessel. The device comprises a hypotube and a balloon. The hypotube comprises a lumen, a proximal end, a distal end, and a longitudinal axis. At least a portion of the hypotube comprises a first pattern of longitudinally-spaced rows and a second pattern of longitudinally-spaced rows. Each of the rows of the first pattern comprises two kerfs and two stems. The two stems in each of the rows of the first pattern are circumferentially opposite. The stems of the first pattern are offset in a first circumferential direction. Each of the rows of the second pattern comprises two kerfs and two stems. The two stems in each of the rows of the second pattern are circumferentially opposite. The stems of the second pattern are offset in a second circumferential direction opposite the first circumferential direction. The rows of the second pattern are singly alternatingly interspersed with the rows of the first pattern. The balloon is radially outward of the hypotube. The balloon is inflatable by delivering fluid through the lumen.

The method may further comprise tracking the device in the vessel. The method may further comprise inflating the balloon. Inflating the balloon may comprise performing angioplasty. Inflating the balloon may comprise performing atherectomy. The method may further comprise rotating the device. Inflating the balloon may comprise expanding an endoprosthesis. The endoprosthesis may comprise a stent. The endoprosthesis may comprise a valve. The method may further comprise inserting a catheter into the lumen until the catheter occludes the distal end of the hypotube. The method may further comprise, after inserting the catheter, inflating the balloon. The method may comprise performing thrombectomy. The method may comprise aspirating a thrombus. The method may comprise providing temporary flow arrest. The method may comprise providing distal embolic protection. The balloon may comprise a drug coated balloon. The balloon may comprise a drug eluting balloon. The device may comprise a plurality of radiopaque markers along at regular intervals. The method may further comprise measuring a dimension. The dimension may comprise a diameter of the vessel. The dimension may comprise a length of a clot in the vessel. The dimension may comprise a degree of a stenosis in the vessel. The dimension may comprise a length of a mouth of an aneurysm. The vessel may comprise a peripheral vessel and the hypotube may have a length between 45 cm and 150 cm. The vessel may comprise a coronary vessel and the hypotube may have a length between 80 cm and 100 cm. The vessel may comprise a neuro vessel and the hypotube may have a length between 80 cm and 150 cm.

In some embodiments, a method of modifying a hypotube comprises holding the hypotube at a height using a bushing, a plurality of collets, and a hypotube clamp. The bushing and plurality of collets are arranged to inhibit sag of the hypotube to be less than 3% of the height. The bushing, the plurality of collets, and the hypotube clamp are aligned at the height. The method further comprises focusing a laser beam at the hypotube. Focusing the laser beam at the hypotube comprises cutting a pattern into the hypotube for a duration. The pattern comprises a first plurality of longitudinally-spaced rows and a second plurality of longitudinally-spaced rows. Each of the first plurality of longitudinally-spaced rows comprises two kerfs and two stems. The stems of the first plurality of longitudinally-spaced rows are offset in a first circumferential direction. Each of the second plurality of longitudinally-spaced rows comprises two kerfs and two stems. The longitudinally-spaced rows of the second plurality of longitudinally-spaced rows are interspersed with the longitudinally-spaced rows of the first plurality of longitudinally-spaced. The stems of the second plurality of longitudinally spaced rows are offset in a second circumferential direction opposite the first circumferential direction. The method further comprises, during cutting the pattern into the hypotube, longitudinally advancing the hypotube toward a spiral collector using the hypotube clamp. The method further comprises winding the hypotube including the pattern in the spiral collector and flowing gas into the spiral collector. Flowing the gas into the spiral collector comprises cooling the hypotube. Flowing the gas into the spiral collector is for at least a portion of the duration.

Cooling the hypotube may comprise reducing a heat affected zone. The gas may comprise air and/or inert gas. Flowing the gas into the spiral collector may comprise flowing the gas into the spiral collector at a temperature between 20° C. and 25° C. Flowing the gas into the spiral collector may be for the duration. Holding the hypotube may comprise applying a variable tension at the hypotube clamp. The method may comprise inhibiting forming fissures (e.g., including fractures) in the hypotube.

In some embodiments, a method of modifying a hypotube comprises focusing a laser beam at the hypotube. Focusing the laser beam at the hypotube comprises cutting a pattern into the hypotube for a duration. The method further comprises, during cutting the pattern into the hypotube, longitudinally advancing the hypotube toward a spiral collector. The method further comprises winding the hypotube including the pattern in the spiral collector and flowing gas into the spiral collector. Flowing the gas into the spiral collector comprises cooling the hypotube.

Cooling the hypotube may comprise reducing a heat affected zone. Flowing the gas into the spiral collector may comprise flowing the gas into the spiral collector at a temperature between 20° C. and 25° C. The gas may comprise air and/or inert gas. Flowing the gas into the spiral collector may occur for the duration. Flowing the gas into the spiral collector may be during a portion of the duration. The method may further comprise holding the hypotube at a height using a bushing, a plurality of collets, and a hypotube clamp. The bushing and plurality of collets may be configured to inhibit sag of the hypotube to be less than 3% of the height. The pattern may comprise a first pattern of longitudinally-spaced rows and a second pattern of longitudinally-spaced rows. The rows of the first pattern may include two kerfs and two stems. The rows of the first pattern may be at an angle with respect to the longitudinal axis of the hypotube. The kerfs of the rows of the first pattern may have rounded edges. The two stems in the rows of the first pattern may be circumferentially opposite. The stems in the rows of the first pattern may be offset in a first circumferential direction. A pitch of the rows of the first pattern may vary longitudinally along the hypotube. The rows of the second pattern may include two kerfs and two stems. The rows of the second pattern may be at an angle with respect to the longitudinal axis of the hypotube. The kerfs of the rows of the second pattern may have rounded edges. The two stems in the rows of the second pattern may be circumferentially opposite. The rows of the second pattern may be singly alternatingly interspersed with the rows of the first pattern. The stems of the second pattern may be offset in a second circumferential direction. The second circumferential direction may be opposite the first circumferential direction. A pitch of the rows of the second pattern may vary longitudinally along the hypotube.

In some embodiments, a method of modifying a hypotube comprises cutting the hypotube with a laser cut pattern, winding the hypotube in a spiral collector and flowing gas into the spiral collector. Flowing the gas into the spiral collector comprises cooling the hypotube. The method may comprise inhibiting forming fissures (e.g., including fractures) in the hypotube.

Flowing the gas into the spiral collector may comprise flowing the gas into the spiral collector at a temperature between 20° C. and 25° C. The gas may comprise air and/or inert gas. The method may further comprise holding the hypotube at a height using a bushing, a plurality of collets, and a hypotube clamp. The bushing and plurality of collets may be configured to inhibit sag of the hypotube to be less than 3% of the height. The bushing, the plurality of collets, and the hypotube clamp may be aligned at the height. The pattern may comprise a plurality of patterns each comprising longitudinally-spaced rows. Each of the longitudinally-spaced rows may comprise two kerfs and two stems. The stems within each of the plurality of patterns being may be offset in a circumferential direction. The circumferential direction of at least two patterns of the plurality of patterns may be opposite.

In some embodiments, a method for making a cut hypotube comprises winding a hypotube in a spiral collector and flowing gas into the spiral collector. Flowing the gas into the spiral collector comprises cooling the hypotube. The hypotube may be cut with a pattern.

Flowing the gas into the spiral collector may comprise flowing the gas into the spiral collector at a temperature between 20° C. and 25° C. The gas may comprise air and/or inert gas. The method may further comprise holding the hypotube at a height using a bushing, a plurality of collets, and a hypotube clamp. The bushing and plurality of collets may be configured to inhibit sag of the hypotube to be less than 3% of the height. The bushing, the plurality of collets, and the hypotube clamp may be aligned at the height. The pattern may comprise a plurality of patterns each comprising longitudinally-spaced rows. Each of the longitudinally-spaced rows may comprise two kerfs and two stems. The stems within each of the plurality of patterns being may be offset in a circumferential direction. The circumferential direction of at least two patterns of the plurality of patterns may be opposite. The method may comprise inhibiting forming fissures (e.g., including fractures) in the hypotube.

In some embodiments, a system for removal of slag during laser cutting of a hypotube by a laser cutting system comprises a laser nozzle, a gas cooling system, a water inlet regulator, and a slag collecting device. The laser nozzle is configured to flow gas onto an external surface of a hypotube during the laser cutting. The gas cooling system includes a gas supply, a connection member fluidly coupling the gas supply and the laser nozzle, and a gas inflow valve positioned along the connection member. The gas inflow valve is configured to regulate the gas that flows into the laser nozzle from the gas supply through the connection member. The water inlet regulator includes a source of water, a plurality of water injection tubes coupled to the source of water and configured to be coupled to an end of the hypotube, a pressure valve configured to flow water through the plurality of water injection tubes, and a water inlet gate configured to inject the water into an inner lumen of the hypotube at a velocity configured to facilitate removal of slag generated during the laser cutting of the hypotube. The external water inlet regulator is configured to cool the hypotube during the laser cutting. The slag collecting device is configured to collect the removed slag.

The gas may comprise air (e.g., ambient air). The gas may comprise inert gas. The gas may have a temperature between 20° C. and 25° C. The plurality of water injection tubes may comprise, consists of, or consist essentially of a first water injection tube coupled to the source of water, a second water injection tube, a third water injection tube, and a fourth water injection tube configured to be proximate to the end of the hypotube. The second water injection tube may be between the first water injection tube and the third water injection tube. The third water injection tube may be between the second water injection tube and the fourth water injection tube. The first water injection tube may have a first diameter. The second water injection tube may have a second diameter. The second diameter may be less than the first diameter. The third water injection tube may have a third diameter. The third diameter may be less than the second diameter. The fourth injection tube may have a fourth diameter. The fourth diameter may be less than the third diameter.

In some embodiments, a system for removal of slag during laser cutting of a hypotube by a laser cutting system comprises a laser nozzle, a cooling system, and a fluid inlet regulator. The laser nozzle is configured to flow gas onto an external surface of a hypotube during the laser cutting. The cooling system includes a supply of gas, a connection member fluidly coupling the supply of gas and the laser nozzle, and a gas inflow valve positioned along the connection member. The gas inflow valve is configured to regulate the gas that flows into the laser nozzle from the supply of gas through the connection member. The fluid inlet regulator includes a source of fluid, a fluid injection tube coupled to the source of fluid and configured to be coupled to an end of the hypotube, a pressure valve configured to flow fluid through the fluid injection tube, and an inlet gate configured to inject the fluid into an inner lumen of the hypotube at a velocity configured to facilitate removal of slag generated during laser cutting of the hypotube.

The fluid may comprise ethylene glycol. The fluid may comprise slurry. The fluid may comprise water. The fluid injection tube may comprise a plurality of fluid injection tubes arranged in series with a diameter of each successive injection tube being smaller than the preceding injection tube. The gas may comprise air (e.g., ambient air). The gas may comprise inert gas. The gas may have a temperature between 20° C. and 25° C.

In some embodiments, a system for removal of slag during laser cutting of a hypotube by a laser cutting system comprises a cooling system and a cooling fluid inlet regulator. The cooling system is configured to be coupled to a laser nozzle of a laser cutting system. The cooling system includes a supply of gas and a gas inflow valve configured to regulate the gas that flows into the laser nozzle from the supply of gas in a manner so as to facilitate slag removal. The cooling fluid inlet regulator is configured to inject cooling fluid into an inner lumen of a hypotube during laser cutting by the laser cutting system at a velocity configured to facilitate removal of slag generated during the laser cutting of the hypotube. The cooling fluid inlet regulator is configured to cool the hypotube during the laser cutting.

The gas may comprise air (e.g., ambient air). The gas may comprise inert gas. The gas may have a temperature between 20° C. and 25° C. The cooling fluid inlet regulator may include a plurality of injection tubes arranged in series with a diameter of each successive injection tube being smaller than the preceding injection tube. The cooling fluid may comprise water.

In some embodiments, a vascular device comprises a wire, a hypotube distal to the wire, and a textile structure coupled to the hypotube. The wire has a first austenitic finish temperature and comprises a first shape set. The hypotube comprises a lumen. A portion of the wire is coupled inside the lumen of the hypotube at a joint. The hypotube has a second austenitic finish temperature and comprises a second shape set. The second austenitic finish temperature is different than the first austenitic finish temperature. The textile structure comprises a plurality of bulbs and a plurality of necks. The first shape set may be different than the second shape set.

In some embodiments, a vascular device comprises a wire and a tubular member. The wire has a first austenitic finish temperature and comprises a first shape set. The tubular member comprises a lumen. The tubular member has a second austenitic finish temperature and comprises a second shape set. The second austenitic finish temperature is different than the first austenitic finish temperature. A portion of the wire is coupled inside the lumen of the tubular member at a joint.

The tubular member may comprise a first longitudinal section and a second longitudinal section. The first longitudinal section may have the second austenitic finish temperature. The first longitudinal section may comprise the second shape set. The second longitudinal section may have a third austenitic finish temperature. The second longitudinal section may comprise a third shape set. The third austenitic finish temperature may be different than the second austenitic finish temperature. The tubular member may be distal to the wire. The first shape set may be different than the second shape set. The tubular member may comprise a hypotube. The tubular member may comprise a braided tubular structure. The device may further comprise a textile structure coupled to the tubular member. The textile structure may comprise a plurality of bulbs and a plurality of necks. The tubular member may comprise a cut pattern.

In some embodiments, a vascular device comprises a tubular element. The tubular element comprises a plurality of longitudinal sections. The plurality of longitudinal sections includes a first longitudinal section and a second longitudinal section. The first longitudinal section has a first austenitic finish temperature. The second longitudinal section has a second austenitic finish temperature different than the first austenitic finish temperature.

The plurality of longitudinal sections may further comprise a third longitudinal section and a fourth longitudinal section. The third longitudinal section may have a third austenitic finish temperature different than the first austenitic finish temperature and the second austenitic finish temperature. The fourth longitudinal section may have a fourth austenitic finish temperature different than the first austenitic finish temperature, the second austenitic finish temperature, and the third austenitic finish temperature. The first longitudinal section may comprise a first material and the second longitudinal section may comprise a second material different than the first material. The first longitudinal section may comprise a material and the second longitudinal section may comprise the same material. The first longitudinal section may comprise a first shape set and the second longitudinal section may comprise a second shape set different than the first shape set. The first longitudinal section may comprise a shape set and the second longitudinal section may comprise the same shape set. The second longitudinal section may be distal to the first longitudinal section. The first longitudinal section may be configured to provide torquability and the second longitudinal section may be configured to provide flexibility. At least one of the first longitudinal section and the second longitudinal section may be shape set to a straight configuration. The device may further comprise a textile structure coupled to the tubular element. The textile structure may comprise a plurality of bulbs and a plurality of necks. The tubular element may comprise a cut pattern.

In some embodiments, a method of heat treating a tubular device comprises spooling part of the tubular device around a first reel. A first longitudinal section of the tubular device extends from the first reel into a heat treatment chamber comprising bath media and towards a second reel. The method further comprises heat treating the first longitudinal section of the tubular device in the heat treatment chamber to have a first austenitic finish temperature. Heat treating the first longitudinal section comprises flowing gas through a heating element and a porous plate and into the heat treatment chamber. The gas fluidizes the bath media. The method further comprises spooling the first longitudinal section of the tubular device around the second reel. A second longitudinal section of the tubular device extends from the first reel into the heat treatment chamber and towards the second reel. The method further comprises heat treating the second longitudinal section of the tubular device in the heat treatment chamber to have a second austenitic finish temperature different than the first austenitic finish temperature. Heat treating the second longitudinal section comprises flowing gas through the heating element and the porous plate and into the heat treatment chamber. The gas fluidizes the bath media. The method further comprises spooling the second longitudinal section of the tubular device around the second reel. A third longitudinal section of the tubular device extends from the first reel into the heat treatment chamber and towards the second reel. The method further comprises heat treating the third longitudinal section of the tubular device in the heat treatment chamber to have a third austenitic finish temperature different than the first austenitic finish temperature and the second austenitic finish temperature. Heat treating the third longitudinal section comprises flowing gas through the heating element and the porous plate and into the heat treatment chamber. The gas fluidizes the bath media. The method further comprises spooling the third longitudinal section of the tubular device around the second reel. A fourth longitudinal section of the tubular device extends from the first reel into the heat treatment chamber and towards the second reel. The method further comprises heat treating the fourth longitudinal section of the tubular device in the heat treatment chamber to have a fourth austenitic finish temperature different than the first austenitic finish temperature, the second austenitic finish temperature, and the third austenitic finish temperature. Heat treating the fourth longitudinal section comprises flowing gas through the heating element and the porous plate and into the heat treatment chamber. The gas fluidizes the bath media.

The tubular device may comprise a hypotube and a wire. The hypotube may comprise a lumen. A portion of the wire may be coupled inside the lumen of the hypotube. The tubular device may comprise a hypotube. The tubular device may comprise a woven tubular structure.

In some embodiments, a method of heat treating a tubular device comprises spooling part of the tubular device around a first reel. The tubular device comprises a plurality of longitudinal sections. The tubular device extends from the first reel into a heat treatment chamber comprising bath media and towards a second reel. The method further comprises heat treating the plurality of longitudinal sections in the heat treatment chamber. After heat treating, each of the plurality of longitudinal sections has a different austenitic finish temperature. Heat treating the plurality of longitudinal sections comprises flowing gas into the heat treatment chamber. The gas fluidizes the bath media. The method further comprises, between heat treating each of the longitudinal sections, spooling the tubular device around the second reel and unspooling the tubular device from the first reel.

Heat treating the plurality of longitudinal sections may comprise flowing the gas through a heating element. Heat treating the plurality of longitudinal sections may comprise flowing the gas through a porous plate. The tubular device may comprise a hypotube and a wire. The hypotube may comprise a lumen. A portion of the wire may be coupled inside the lumen of the hypotube. The tubular device may comprise a hypotube. The hypotube may comprise a cut pattern. The tubular device may comprise a woven tubular structure. At least one longitudinal section of the plurality of longitudinal sections may comprise a different material than another longitudinal section of the plurality of longitudinal sections. At least one longitudinal section of the plurality of longitudinal sections may comprise a different shape set than at least another longitudinal section of the plurality of longitudinal sections. At least one longitudinal section of the plurality of longitudinal sections may be shape set to a straight configuration. The plurality of longitudinal sections may comprise between 1 and 15 longitudinal sections.

In some embodiments, a method of heat treating a tubular device comprises heat treating a first longitudinal section of the tubular device to have a first austenitic finish temperature and heat treating a second longitudinal section of the tubular device to have a second austenitic finish temperature different than the first austenitic finish temperature.

Heat treating each of the first longitudinal section and the second longitudinal section may comprise flowing gas into a heat treatment chamber. The gas may fluidize bath media in the heat treatment chamber. The method may further comprise, between heat treating the first longitudinal section and heat treating the second longitudinal section, spooling the tubular device between a first spool and a second spool. The tubular device may comprise a hypotube. The tubular device may comprise a hypotube and a wire. The hypotube may comprise a lumen. A portion of the wire may be coupled inside the lumen of the hypotube.

In some embodiments, a device for treating a lumen comprises a proximal portion, a distal portion, and a joint reversibly coupling the proximal portion and the distal portion. The proximal portion comprises a wire and a tubular element. The wire comprises shape-memory material and has a distal end. The distal end of the wire comprises a first shape at a first temperature and a second shape at a second temperature different than the first temperature. The second shape is a straightened form of the first shape. The distal portion comprises a plurality of filaments and pores between the filaments. The joint comprises the plurality of filaments and the pores between the filaments being engaged with the wire in the first shape and with the tubular element.

The first shape may include a ball having an outer diameter greater than an inner diameter of the distal portion. The first shape may include radially outward dimples. The second shape may comprise a linear shape. The wire may comprise a coiling portion proximal to the distal end. The coiling portion may comprise a coil at the first temperature and a straightened form of the coil at the second temperature. The distal end of the wire may comprise a third shape at a third temperature different from the first temperature and the second temperature. The third shape may be an expanded form of the first shape. The plurality of filaments may be woven into a textile structure comprising a plurality of bulbs and necks distal to the joint. The joint may comprise solder between the proximal portion and the distal portion. The joint may have a tensile strength less than 18,600 kPa.

In some embodiments, a device for treating a lumen comprises a proximal portion, a distal portion, and a joint reversibly coupling the proximal portion and the distal portion. The proximal portion comprises a tubular member having a distal end comprising a socket. The distal portion comprises a plurality of filaments. At least one filament of the plurality of filaments comprises shape memory material. A proximal part of the distal portion includes the at least one filament. The proximal part has a first shape at a first temperature and a second shape at a second temperature different than the first temperature. The second shape is a straightened form of the first shape. The joint comprises the proximal part of the distal portion mechanically forced into the socket.

The socket may include a slit, a recess, and/or a radially outward dimple. The joint may comprise the distal portion radially outward of the tubular member. The joint may comprise the tubular member radially outward of the distal portion. The proximal part may comprise a third shape at a third temperature different from the first temperature and the second temperature. The third shape may be further mechanically forced into the socket. The plurality of filaments may be woven into a textile structure comprising a plurality of bulbs and necks distal to the joint.

In some embodiments, a device for treating a lumen comprises a proximal portion, a distal portion, and a joint reversibly coupling the proximal portion and the distal portion. The proximal portion comprises a distal end comprising a plurality of ridges. The distal portion comprises a plurality of filaments and pores between the plurality of filaments. The pores create a plurality of grooves. The joint comprises the plurality of ridges mechanically forced into the plurality of grooves. The plurality of ridges are configured to disengage from the plurality of grooves upon rotation of the distal end of the proximal portion.

The ridges may comprise threads at an angle to a longitudinal axis of the distal end of the proximal portion. The ridges may be perpendicular to a longitudinal axis of the distal end of the proximal portion. The distal end of the proximal portion may comprise a wire. The plurality of ridges may extend radially outward from the wire. The plurality of grooves may have variable thicknesses. The plurality of filaments may be woven into a textile structure comprising a plurality of bulbs and necks distal to the joint.

In some embodiments, a system for aspirating thrombi using a varying suction pattern includes a guide catheter and a distal access microcatheter, each comprising a proximal end, a distal end and a lumen. The distal end of the distal access microcatheter may include a balloon configured to provide flow arrest within a vessel. The system can include a second microcatheter sized to fit within the lumen of the distal access microcatheter, the second microcatheter comprising a proximal end, a distal end and a lumen. In some embodiments, the system may include a distal access microcatheter sized to fit within the lumen of the guide catheter, the distal access microcatheter comprising a proximal end, a distal end, and a lumen.

In some embodiments, the guide catheter, the distal access microcatheter, and/or the microcatheter may be used like a balloon guide catheter, for example to provide temporary flow arrest and/or as an adjunct device during thrombus aspiration. In some embodiments, the catheter may have a length between 45 cm and 150 cm, between 45 cm and 80 cm (e.g., 75 cm) (e.g., for use in peripheral vasculature), between 80 cm and 100 cm (e.g., 100 cm) (e.g., for use in coronary vasculature), between 80 cm and 150 cm (e.g., 125 cm) (e.g., for use in neurovasculature). The guide catheter, the distal access microcatheter, and/or the microcatheter may have a wall thickness between 0.00075 inches (approx. 0.02 mm) and 0.04 inches (approx. 1 mm), which can allow for incorporating a proximal portion within the walls of the guide catheter, the distal access microcatheter, and/or the second microcatheter. In some embodiments, the guide catheter, the distal access microcatheter, and/or the second microcatheter may have an inner diameter between 4 Fr (approx. 1.33 mm) and 7 Fr (approx. 2.33 mm) for example, 5 Fr (approx. 1.67 mm), and an outer diameter between 5 Fr (approx. 1.67 mm) and 9 Fr (approx. 3 mm) for example, 6 Fr (approx. 2 mm).

In some embodiments, the guide catheter, the distal access microcatheter, and/or the microcatheter may comprise a hypotube (e.g., an uncut hypotube and/or a hypotube cut with a plurality of interspersed offset patterns as described herein) and/or a plurality of filaments (e.g., woven, knitted, spiraled, etc.) as reinforcement, for example in combination with a polymer inward and/or outward thereof.

In some embodiments, the guide catheter, the distal access microcatheter, and/or the microcatheter is reinforced with the proximal portion, for example to inherit the maneuverability advantages of the proximal portion (e.g., to facilitate proximal support and distal flexibility). In some embodiments, the guide catheter, the distal access microcatheter, and/or the microcatheter comprises a parameter (e.g., slot pitch) that varies from proximal to distal. For example, the pitch between slots and/or windings of a spiral may vary, from the distal end to the proximal end, as follows: 0.005 inches (approx. 0.13 mm), 0.01 inches (approx. 0.25 mm), 0.02 inches (approx. 0.51 mm), 0.04 inches (approx. 1 mm), 0.08 inches (approx. 2 mm), and 0.16 inches (approx. 4 mm). For another example, the pitch between slots and/or windings of a spiral may vary, from the distal end to the proximal end, as follows: 0.005 inches (approx. 0.13 mm) for the distal-most 20%, 0.01 inches (approx. 0.25 mm) for the next 15%, 0.02 inches (approx. 0.51 mm) for the next 15%, 0.04 inches (approx. 1 mm) for the next 15%, 0.08 inches (approx. 2 mm) for the next 15%, and 0.16 inches (approx. 4 mm) for the next (or proximal-most) 20%. In some embodiments, the polymer inwards and/or outwards of the hypotube, may comprise of variations in one of the following parameters (e.g., comprising a different material, durometer, and/or thickness etc.), that align with the variations in slot pitch of the hypotube across the entire length of the hypotube or a partial longitudinal section of the hypotube. In some embodiments, the inner coating of the hypotube may be the same or different than the outer coating (e.g., comprising a different material, thickness, durometer, etc.). In some embodiments, a parameter of a coating (e.g., material, thickness, durometer, etc. of the inner coating and/or the outer coating) may be varied to vary flexibility of the catheter. The variation may be instead of or in addition to (e.g., complementary to) variation in the cut pattern in the hypotube. The variation of the parameter of the polymer coating (e.g., material, thickness, durometer, etc.) may be aligned or substantially aligned with the variation of the pitch of the kerfs or the rows.

In one embodiment, the lumen of the guide catheter, the lumen of the distal access microcatheter, and/or the lumen of the second microcatheter are substantially uniform along their lengths. In such an embodiment, if the inner lumen diameter or cross sectional area of the guide catheter, the distal access microcatheter, and/or the second microcatheter is substantially uniform, then a change in suction pressure to achieve desired thrombus aspiration is negatively impacted by the length of the catheter. In one embodiment, the lumen of the guide catheter, the distal access microcatheter and/or the second microcatheter includes a gradual tapering from the proximal end to the distal end. In such embodiments, whenever the inner lumen diameter or cross sectional area is not substantially uniform (e.g., is tapered), then a change in suction pressure can result in a change in the square of the velocity of blood, which can result in desired thrombus aspiration.

In some embodiments, a method of treating a vessel comprises positioning a guide catheter, a distal access microcatheter, and/or a microcatheter by sequentially advancing until a desired point in vasculature. In some embodiments, the guide catheter, distal access microcatheter, and/or the microcatheter are sequentially advanced proximal to the clot or lesion by 0.5 mm to 15 cm. In some embodiments, thrombus aspiration may be performed through the microcatheter, the distal access microcatheter, and/or the guide catheter depending on the extent of the clot burden. In some embodiments, thrombus aspiration may be performed through the catheter or microcatheter that is closest in proximity to the thrombus (e.g., clot). In some embodiments, thrombus aspiration may be performed using flow arrest, wherein a balloon, such as part of a balloon guide catheter or a balloon as part of a distal access microcatheter, is inflated proximal to the thrombus 500 and anterograde forward flow proximal to the thrombus is temporarily stopped while thrombus aspiration is performed. In some embodiments, thrombus aspiration may be performed without any balloon inflation or temporary flow arrest.

In some embodiments, a method of providing embolic protection during treatment of a vessel comprises advancing a microcatheter in the vessel. Advancing the microcatheter includes crossing a thrombus with a distal end of the microcatheter. The method further comprises inserting a textile structure in a collapsed state into the microcatheter. The textile structure comprises a plurality of self-expanding bulbs and a plurality of necks. The plurality of self-expanding bulbs may comprise five to twenty self-expanding bulbs. Each of the plurality of self expanding bulbs may have a spherical shape. Each of the plurality of self expanding bulbs may have an oblong shape. Pairs of the self-expanding bulbs are spaced by a neck of the plurality of necks. The method further comprises advancing the textile structure through the microcatheter proximate to the distal end of the microcatheter, wherein advancing the textile structure includes crossing the thrombus with a distal-most bulb of the plurality of self-expanding bulbs. The method further comprises, after advancing the textile structure, retracting the microcatheter to unsheathe a length of the textile structure. Retracting the microcatheter to unsheathe the length of the textile structure comprises unsheathing at least the distal-most bulb of the plurality of self-expanding bulbs from the microcatheter and self-expanding at least the distal-most bulb of the plurality of self-expanding bulbs from the collapsed state to an expanded state. The method further comprises removing the thrombus from the vessel. In the expanded state, the distal-most bulb apposes sidewalls of the vessel and filters emboli released during the removing the thrombus from the vessel.

Removing the thrombus may comprise further retracting the microcatheter to unsheathe another length of the textile structure comprising other bulbs of the plurality of self-expanding bulbs. Upon being unsheathed from the microcatheter, the other bulbs may self-expand from the collapsed state to an expanded state. The other bulbs may entrap the thrombus. The method may further comprise torsionally rasping the textile structure. The distal-most bulb of the plurality of self-expanding bulbs may provide a distal anchor for the torsionally rasping. Removing the thrombus may comprise deploying a thrombectomy device proximal to the distal-most bulb of the plurality of self-expanding bulbs. The thrombectomy device may be different than the textile structure. Deploying the thrombectomy device may include crossing the thrombus with a distal section of the thrombectomy device. The method may further comprise, after and/or during removing the thrombus from the vessel, further retracting the microcatheter. Further retracting the microcatheter may comprise unsheathing other bulbs of the plurality of self-expanding bulbs and self-expanding the other bulbs of the plurality of self-expanding bulbs from the collapsed state to an expanded state. The other bulbs of the plurality of self-expanding bulbs in the expanded state may entrap residual thrombus. Retracting the microcatheter to unsheathe the length of the textile structure may comprise expanding the vessel.

In some embodiments, a method of providing embolic protection during treatment of a vessel comprises advancing a microcatheter in the vessel and inserting a textile structure in a collapsed state into the microcatheter. The textile structure comprises a plurality of self-expanding bulbs and a plurality of necks. Pairs of the self-expanding bulbs are spaced by a neck of the plurality of necks. The method further comprises advancing the textile structure through the microcatheter proximate to a distal end of the microcatheter and, after advancing the textile structure, retracting the microcatheter to unsheathe a length of the textile structure. Retracting the microcatheter to unsheathe the length of the textile structure comprises unsheathing at least a distal-most bulb of the plurality of self-expanding bulbs from the microcatheter and self-expanding at least the distal-most bulb of the plurality of self-expanding bulbs from the collapsed state to an expanded state. The method further comprises performing a vascular procedure. Performing the vascular procedure comprises using a vascular device different than the textile structure. In the expanded state, the distal-most bulb of the plurality of self-expanding bulbs filters emboli released during performing the vascular procedure.

The method may further comprise, after and/or during performing the vascular procedure, further retracting the microcatheter. Further retracting the microcatheter may comprise unsheathing other bulbs of the plurality of self-expanding bulbs and self-expanding the other bulbs of the plurality of self-expanding bulbs from the collapsed state to an expanded state. The other bulbs of the plurality of self-expanding bulbs in the expanded state may entrap residual emboli. The method may further comprise torsionally rasping the textile structure. The distal-most bulb of the plurality of self-expanding bulbs may provide a distal anchor for the torsionally rasping. The distal-most bulb of the plurality of self-expanding bulbs in the expanded state may comprise a spherical shape. The distal-most bulb of the plurality of self-expanding bulbs in the expanded state may comprise an oblong shape. The vascular procedure may comprise thrombectomy. The vascular procedure may comprise angioplasty. The vascular procedure may comprise atherectomy. The vascular procedure may comprise aspiration. The vascular procedure may comprise stenting. The vascular procedure may comprise embolic coil insertion. The vascular procedure may comprise intra-arterial thrombolysis. The vascular procedure may comprise bypass. Retracting the microcatheter to unsheathe the length of the textile structure may comprise expanding the vessel.

In some embodiments, a method of providing embolic protection during treatment of a vessel comprises advancing a microcatheter in the vessel, inserting a textile structure in a collapsed state into the microcatheter, advancing the textile structure through the microcatheter proximate to a distal end of the microcatheter, after advancing the textile structure, retracting the microcatheter to unsheathe a self-expanding bulb from the microcatheter and self-expanding the self-expanding bulb from the collapsed state to an expanded state, and performing a vascular procedure. In the expanded state, the self-expanding bulb filters emboli released during performing the vascular procedure.

The method may further comprise, after and/or during performing the vascular procedure, further retracting the microcatheter. Further retracting the microcatheter may comprise unsheathing other self-expanding bulbs and self-expanding the other self-expanding bulbs from the collapsed state to an expanded state. The other self-expanding bulbs in the expanded state may entrap residual emboli. The method may further comprise torsionally rasping the textile structure. The self-expanding bulb may provide an anchor for the torsionally rasping. The self-expanding bulb in the expanded state may comprise a spherical shape. The self-expanding bulb in the expanded state may comprise an oblong shape. The vascular procedure may comprise thrombectomy. The vascular procedure may comprise angioplasty. The vascular procedure may comprise atherectomy. The vascular procedure may comprise aspiration. The vascular procedure may comprise stenting. The vascular procedure may comprise embolic coil insertion. The vascular procedure may comprise intra-arterial thrombolysis. The vascular procedure may comprise bypass. Retracting the microcatheter to unsheathe the self-expanding bulb may comprise expanding the vessel.

In some embodiments, a method of disrupting flow through a fistula comprises advancing a microcatheter through a guide catheter. The guide catheter has a distal end at a first point in vasculature. The microcatheter has a distal end. The method further comprises advancing a steerable microwire through the guide catheter. The steerable microwire extends distal to the distal end of the microcatheter. The method further comprises, after advancing the steerable microwire through the guide catheter, further advancing and steering the steerable microwire to a second point in the vasculature. The fistula is proximate to the second point in the vasculature. The method further comprises, after further advancing and steering the steerable microwire, advancing the microcatheter over the steerable microwire to the second point in the vasculature. The method further comprises, after further advancing the microcatheter over the steerable microwire to the second point in the vasculature, removing the steerable microwire. The method further comprises advancing a flow disruptor through the microcatheter to the second point in the vasculature. The flow disruptor comprises, in an expanded state, a first bulb, a second bulb, a first neck between the first bulb and the second bulb, a third bulb, a second neck between the second bulb and the third bulb, a fourth bulb, and a third neck between the third bulb and the fourth bulb. The first bulb has a first braid angle. The fourth bulb has a second braid angle. The second neck has a third braid angle less than the first braid angle and the second braid angle. The method further comprises expanding the first bulb and the second bulb on a first side of the fistula, extending the second neck through the fistula, and expanding the third bulb and the fourth bulb on a second side of the fistula.

The first point in the vasculature may be an internal jugular vein at a base of a skull. Expanding the first bulb and the second bulb on the first side of the fistula may comprise expanding the first bulb and the second bulb in a left cavernous sinus. Expanding the third bulb and the fourth bulb on the second side of the fistula may comprise expanding the third bulb and the fourth bulb in a right cavernous sinus. The fistula may be one of a carotid-cavernous fistula, a coronary fistula, an atrial septal defect, and a ventricular septal defect. The second bulb may have a fourth braid angle and the third bulb may have a fifth braid angle. The third braid angle may be less than the fourth braid angle and the fifth braid angle. The second neck may have an outer diameter oversized between 10% and 25% to a width of the fistula. The second neck may have a length oversized between 10% and 25% to a length of the fistula. The method may further comprise inserting the guide catheter and a dilator into an entry point in the vasculature. The dilator may have a distal end. The method may further comprise inserting a steerable guidewire into the guide catheter and the dilator. The steerable guidewire may extend distal to the distal end of the dilator. The method may further comprise advancing and steering the steerable guidewire. The method may further comprise, after advancing and steering the steerable guidewire, advancing the guide catheter and dilator over the steerable guidewire. The method may further comprise, after advancing the guide catheter and dilator over the steerable guidewire, removing the dilator. The method may further comprise, after removing the dilator, further advancing and steering the steerable guidewire to the first point in the vasculature. The method may further comprise, after further advancing and steering the steerable guidewire, advancing the guide catheter over the steerable guidewire to the first point in the vasculature. The method may further comprise, after advancing the guide catheter over the steerable guidewire to the first point in the vasculature, removing the steerable guidewire.

In some embodiments, a method of disrupting flow through a fistula comprises deploying a flow disruptor across the fistula through a microcatheter at a point in vasculature proximate to the fistula. Deploying the flow disruptor comprises expanding a first plurality of bulbs on a first side of the fistula, expanding a second plurality of bulbs on a second side of the fistula, and extending a neck through the fistula. The second side of the fistula is longitudinally opposite the first side of the fistula. The neck is between the first plurality of bulbs and the second plurality of bulbs.

The first plurality of bulbs may comprise a first bulb having a first braid angle. The second plurality of bulbs may comprise a second bulb having a second braid angle. The neck may have a third braid angle less than the first braid angle and the second braid angle. The first plurality of bulbs may comprise a third bulb having a fourth braid angle. The second plurality of bulbs may comprise a fourth bulb having a fifth braid angle. The third braid angle may be less than the fourth braid angle and the fifth braid angle. The first plurality of bulbs may comprise a proximal-most bulb having a first diameter and a third bulb having a second diameter less than the first diameter. The second plurality of bulbs may comprise a distal-most bulb having a third diameter and a fourth bulb having a fourth diameter less than the third diameter. The flow disruptor may have a longitudinal axis. The flow disruptor may comprise a second neck proximal to the first plurality of bulbs. The flow disruptor may comprise a third neck distal to the second plurality of bulbs. The second neck and the third neck may be radially offset from the longitudinal axis. The second neck and the third neck may be differently radially offset from the longitudinal axis. The neck may have an outer diameter oversized between 10% and 25% to a width of the fistula. The neck may have a length oversized between 10% and 25% to a length of the fistula. The point in the vasculature may be a cavernous sinus.

In some embodiments, a method of disrupting flow through a fistula comprises deploying a flow disruptor across the fistula through a microcatheter at a point in vasculature proximate to the fistula. Deploying the flow disruptor comprises expanding a first bulb on a first side of the fistula and expanding a second bulb on a second side of the fistula. The first bulb has a first braid angle. The second bulb has a second braid angle. The flow disruptor comprises a neck between the first bulb and the second bulb. The neck traverses the fistula. The neck has a third braid angle less than the first braid angle and the second braid angle.

Deploying the flow disruptor may further comprise expanding a third bulb on the first side of the fistula and expanding a fourth bulb on the second side of the fistula. The first bulb may have a first diameter. The second bulb may have a second diameter. The third bulb may have a third diameter less than the first diameter. The fourth bulb may have a fourth diameter less than the third diameter. The flow disruptor may have a longitudinal axis. The flow disruptor may comprise a second neck proximal to the first bulb. The flow disruptor may comprise a third neck distal to the second bulb. The second neck and the third neck may be radially offset from the longitudinal axis. The second neck and the third neck may be differently radially offset from the longitudinal axis. The second neck may have an outer diameter oversized between 10% and 25% to a width of the fistula. The second neck may have a length oversized between 10% and 25% to a length of the fistula.

In some embodiments, a method of manufacturing a device for treating a vessel comprises arranging a plurality of spools on a yarn wheel. Each of the spools comprises wire. The method further comprises braiding the wire from each of the plurality of spools for a first duration to form a first segment of a textile structure. Braiding the wire during the first duration comprises pulling a ring away from the yarn wheel at a first speed. The method further comprises, after forming the first segment, rearranging at least some of the plurality of spools on the yarn wheel. The method further comprises, after rearranging at least some of the plurality of spools, braiding the wire from each of the plurality of spools for a second duration to form a second segment of the textile structure. Braiding the wire during the second duration comprises pulling the ring away from the yarn wheel at a second speed different than the first speed.

The first speed may be greater than the second speed. Porosity of the first segment of the textile structure may be greater than porosity of the second segment of the textile structure. The braid angle of the first segment may be between 0° and 90°. The braid angle of the second segment may be between 91° and 180°. The second speed may be greater than the first speed. Porosity of the first segment of the textile structure may be less than porosity of the second segment of the textile structure. One of arranging the plurality of spools and rearranging at least some of the plurality of spools may comprise symmetrically arranging the plurality of spools and the other of arranging the plurality of spools and rearranging at least some of the plurality of spools may comprise asymmetrically arranging the plurality of spools. One of arranging the plurality of spools and rearranging at least some of the plurality of spools may comprise asymmetrically arranging the plurality of spools and the other of arranging the plurality of spools and rearranging at least some of the plurality of spools may comprise symmetrically arranging the plurality of spools. The yarn wheel may comprise an eastern hemisphere and a western hemisphere. Braiding the wire during at least one of the first duration and the second duration may comprise varying speed of rotation of one of the eastern hemisphere and the western hemisphere with respect to speed of rotation of the other of the eastern hemisphere and the western hemisphere. During varying the speed of rotation, the textile structure may comprise a first portion and a second portion circumferentially opposite the first portion. A braid angle of the first portion may be different than a braid angle of the second portion. At least one spool of the plurality of spools may comprise wire comprising shape-memory material. At least one spool of the plurality of spools may comprise wire comprising radiopaque material. The braid angle of one of the first segment and the second segment may be between 91° and 180° and the braid angle of the other of the first segment and the second segment may be between 0° and 90°. Pulling the ring away from the yarn wheel during at least one of the first duration and the second duration may comprise pulling the ring away from the yarn wheel in a direction perpendicular to the yarn wheel. The ring may comprise a circular ring.

In some embodiments, a method of manufacturing a device for treating a vessel comprises arranging a plurality of spools on a yarn wheel. Each of the spools comprises wire. The method further comprises braiding the wire from each of the plurality of spools for a first duration to form a first segment of a textile structure. The method further comprises, after forming the first segment, rearranging at least some of the plurality of spools on the yarn wheel, and, after rearranging at least some of the plurality of spools, braiding the wire from each of the plurality of spools for a second duration to form a second segment of the textile structure.

Porosity of the first segment of the textile structure may be greater than porosity of the second segment of the textile structure. Porosity of the first segment of the textile structure may be less than porosity of the second segment of the textile structure. The method may further comprise, during at least one of the first duration and the second duration, varying speed of pulling of a puller away from the yarn wheel. The method may comprise, during the first duration, pulling a puller away from the yarn wheel at a first speed, and, during the second duration, pulling the puller away from the yarn wheel at a second speed different than the first speed. One of arranging the plurality of spools and rearranging at least some of the plurality of spools may comprise symmetrically arranging the plurality of spools and the other of arranging the plurality of spools and rearranging at least some of the plurality of spools may comprise asymmetrically arranging the plurality of spools. One of arranging the plurality of spools and rearranging at least some of the plurality of spools may comprise asymmetrically arranging the plurality of spools and the other of arranging the plurality of spools and rearranging at least some of the plurality of spools may comprise symmetrically arranging the plurality of spools. The yarn wheel may comprise an eastern hemisphere and a western hemisphere. Braiding the wire during at least one of the first duration and the second duration may comprise varying speed of rotation of one of the eastern hemisphere and the western hemisphere with respect to speed of rotation of the other of the eastern hemisphere and the western hemisphere. During varying the speed of rotation, the textile structure may comprise a first portion and a second portion circumferentially opposite the first portion. A braid angle of the first portion may be different than a braid angle of the second portion. The braid angle of the first portion may be between 91° and 180°. The braid angle of the second portion may be between 0° and 90°. At least one spool of the plurality of spools may comprise wire comprising shape-memory material. At least one spool of the plurality of spools may comprise wire comprising radiopaque material. The braid angle of one of the first segment and the second segment may be between 91° and 180° and the braid angle of other of the first segment and the second segment may be between 0° and 90°. The puller may comprise a circular ring.

In some embodiments, a method of manufacturing a device for treating a vessel comprises braiding a plurality of wires to form a textile structure. Each of the plurality of wires extends from one of a plurality of spools on a yarn wheel. Braiding the wires comprises braiding the wires for a first duration to form a first segment of the textile structure and braiding the wires for a second duration to form a second segment of the textile structure. Braiding the wires during the first duration comprises pulling a puller away from the yarn wheel at a first speed. The first segment has a braid angle between 91° and 180°. Braiding the wires during the second duration comprises pulling the puller away from the yarn wheel at a second speed greater than the first speed. The second segment has a braid angle between 0° and 90°.

The first duration may be before the second duration. Porosity of the first segment of the textile structure may be greater than porosity of the second segment of the textile structure. The first duration may be after the second duration. Porosity of the first segment of the textile structure may be less than porosity of the second segment of the textile structure. Pulling the puller during at least one of the first duration and the second duration may be in a direction perpendicular to the yarn wheel. The method may further comprise, during braiding the wires during at least one of the first duration and the second duration, rearranging at least some of the plurality of spools. The yarn wheel may comprise an eastern hemisphere and a western hemisphere. Braiding the wires during at least one of the first duration and the second duration may comprise varying speed of rotation one of the eastern hemisphere and the western hemisphere with respect to speed of rotation of the other of the eastern hemisphere and the western hemisphere. During varying the speed of rotation, the textile structure may comprise a first portion and a second portion circumferentially opposite the first portion. A braid angle of the first portion may be different than a braid angle of the second portion. At least one spool of the plurality of spools may comprise wire comprising shape-memory material. At least one spool of the plurality of spools may comprise wire comprising radiopaque material. The puller may comprise a circular ring. The first segment may have a porosity between 60% and 78%.

In some embodiments, a method of manufacturing a device for treating a vascular cavity comprises arranging a plurality of spools on a yarn wheel. Each of the spools comprises wire. The yarn wheel comprises an eastern hemisphere and a western hemisphere. The method further comprises braiding the wire from each of the plurality of spools to form a textile structure. Braiding the wire comprises braiding the wire for a first duration to form a first segment of the textile structure. Braiding the wire during the first duration comprises rotating the eastern hemisphere of the yarn wheel at a first speed, rotating the western hemisphere of the yarn wheel at a second speed, and pulling a puller at a third speed. At least one of the first speed and the second speed is greater than the third speed. Braiding the wires further comprises braiding the wire for a second duration to form a second segment of the textile structure. Braiding the wire during the second duration comprises rotating the eastern hemisphere of the yarn wheel at a fourth speed, rotating the western hemisphere of the yarn wheel at a fifth speed, and pulling the puller at a sixth speed, at least one of the fourth speed and the fifth speed less than the sixth speed. The method further comprises heat treating the textile structure. After the heat treatment the textile structure is expandable from a compressed state to an expanded state. The textile structure comprises a bulb in the expanded state.

The first duration may be before the second duration. The first duration may be after the second duration. The first segment may comprise the bulb. The second segment may comprise the bulb. The textile structure may further comprise a second bulb. The first segment may comprise the bulb and the second segment may comprise the second bulb. A braid angle of the first segment may be between 91° and 180°. The first segment may have a porosity configured to reduce flow into the vascular cavity. A braid angle of the second segment may be between 0° and 90°. The second segment may have a porosity configured to allow perfusion to perforating vessels. Braiding the wire may further comprise braiding the wire for a third duration to form a third segment of the textile structure. Braiding the wire during the third duration may comprise rotating the eastern hemisphere of the yarn wheel at a seventh speed, rotating the western hemisphere of the yarn wheel at an eighth speed, and pulling the horn gear at a ninth speed. At least one of the seventh speed and the eighth speed may be greater than the ninth speed. The textile structure may further comprise a second bulb and a third bulb. The first segment may comprise the bulb, the second segment may comprise the second bulb, and the third segment may comprise a third bulb of the plurality of bulbs. At least one of the seventh speed and the eighth speed may be less than the ninth speed. The method may further comprise, between the first duration and the second duration, rearranging the plurality of spools on the yarn wheel. During the first duration, the first speed may be the same as the second speed. During the first duration, the first speed may be different than the second speed. The first segment may comprise a first portion and a second portion circumferentially opposite the first portion. A braid angle of the first portion may be between 91° and 180°. A braid angle of the second portion may be between 0° and 90°. During the second duration, the fourth speed may be the same as the fifth speed. During the second duration, the fourth speed may be different than the fifth speed. At least one spool of the plurality of spools may comprise wire comprising shape-memory material. At least one spool of the plurality of spools may comprise wire comprising radiopaque material. Braiding the textile structure may be around a first mandrel. The method may further comprise a first heat treatment before the heat treatment. The heat treatment may be on a second mandrel different than the first mandrel. Braiding the textile structure may be around a mandrel. The heat treatment may be on a first mandrel. The method may further comprise coating a portion of the bulb with a polymer. The method may further comprise masking at least part of the textile structure during coating the portion. Masking at least part of the textile structure may comprise coating while the textile structure may be on a mandrel. Coating the portion may comprise spray coating the portion. Coating the portion may comprise dip coating the portion.

In some embodiments, a method of manufacturing a device for treating a vascular cavity comprises braiding a plurality of wires to form a textile structure. Each of the plurality of wires extends from one of a plurality of spools on a yarn wheel. The yarn wheel comprises an eastern hemisphere and a western hemisphere. Braiding the wires comprises braiding the wires for a first duration to form a first segment of the textile structure. Braiding the wires during the first duration comprises rotating the eastern hemisphere of the yarn wheel at a first speed, rotating the western hemisphere of the yarn wheel at a second speed different than the first speed, and pulling a puller at a third speed. The method further comprises heat treating the textile structure to impart an expanded shape comprising a bulb.

At least one of the first speed and the second speed may be greater than the third speed. At least one of the first speed and the second speed may be less than the third speed. Braiding the wires may further comprise braiding the wires for a second duration to form a second segment of the textile structure. Braiding the wires during the second duration may comprise rotating the eastern hemisphere of the yarn wheel at a fourth speed and rotating the western hemisphere of the yarn wheel at a fifth speed. The first duration may be before the second duration. The first duration may be after the second duration. Braiding the wires for the second duration may further comprise pulling the horn gear at a sixth speed. The fourth speed may be the same as the second speed. The fourth speed and the fifth speed may each be less than the sixth speed. The fourth speed and the fifth speed may each be greater than the sixth speed. The first segment may comprise the bulb. The second segment may comprise the bulb. A plurality of bulbs may comprise the bulb. The first segment may comprise a first bulb of the plurality of bulbs and the second segment may comprise a second bulb of the plurality of bulbs. At least one wire of the plurality of wires may comprise shape-memory material. At least one wire of the plurality of wires may comprise radiopaque material. Braiding the textile structure may be around a first mandrel. The method may further comprise a first heat treatment before the heat treatment. The heat treatment may be on a second mandrel different than the first mandrel. Braiding the textile structure may be around a mandrel. The heat treatment may be on a first mandrel. The method may further comprise coating a portion of the bulb with a polymer. The method may further comprise masking at least part of the textile structure during coating the portion. Masking at least part of the textile structure may comprise coating while the textile structure may be on a mandrel.

In some embodiments, a method of manufacturing a device for treating a vascular cavity comprises braiding a plurality of wires to form a textile structure comprising a bulb. Each of the wires is on a spool. The spools are arranged on a yarn wheel. After braiding the plurality of wires, the textile structure comprises a first longitudinal segment. The first longitudinal segment comprises a first portion having a braid angle between 91° and 180° and a second portion having a braid angle between 0° and 90°. The second portion is circumferentially opposite the first portion.

The textile structure may comprise a second longitudinal segment adjacent to the first longitudinal segment. The first longitudinal segment may comprise the bulb. The second longitudinal segment may comprise the bulb. The bulb may comprise a plurality of bulbs. The first longitudinal segment may comprise a first bulb and the second longitudinal segment may comprise a second bulb. The second longitudinal segment may have a braid angle between 0° and 90°. The second longitudinal segment may have a braid angle between 91° and 180°. The spools may be arranged on a yarn wheel comprising an eastern hemisphere and a western hemisphere. Braiding the plurality of wires may comprise rotating the eastern hemisphere of the yarn wheel at a first speed, and rotating the western hemisphere of the yarn wheel at a second speed different than the first speed. At least one wire of the plurality of wires may comprise shape-memory material. At least one wire of the plurality of wires may comprise radiopaque material.

In some embodiments, a method of forming a structure for treating a vessel comprises arranging a plurality of filaments extending from individual carriers of a yarn wheel. At least one of the plurality of filaments is a shape memory filament and at least another of the plurality of filaments is a radiopaque filament. The method further comprises providing a mandrel. The mandrel comprises a strand having a longitudinal axis and a plurality of balls coupled to the strand along the longitudinal axis. Pairs of the plurality of balls are spaced along the longitudinal axis. The method further comprises braiding the plurality of filaments around the mandrel including, during braiding, forming a plurality of bulbs around the plurality of balls and forming necks between pairs of the plurality of balls. The method further comprises, after braiding the plurality of filaments, heat treating the plurality of filaments on the mandrel. The method further comprises, after heat treating the plurality of filaments on the mandrel, removing the plurality of filaments from the mandrel. The structure comprises the heat-treated plurality of filaments includes the plurality of bulbs and the necks.

The method may further comprise, before heat treating the plurality of filaments on the mandrel, securing portions of the braided plurality of filaments to the mandrel. Securing the portions of the braided plurality of filaments to the mandrel may comprise using bangles, wire, and/or adhesive. The method may comprise, during braiding the plurality of filaments around the mandrel, rearranging the plurality of filaments. The method may further comprise attaching an end of each of the filaments to a puller over the mandrel. Braiding the plurality of filaments may comprise rotating the yarn wheel, rotating the individual carriers, and longitudinally extending the puller along the mandrel away from the yarn wheel. Braiding the plurality of filaments may comprise varying a speed of at least one of rotating the yarn wheel, rotating the individual carriers, and longitudinally extending the puller along the mandrel away from the yarn wheel.

In some embodiments, a method of forming a structure for treating a vessel comprises providing a mandrel. The mandrel comprises a strand having a longitudinal axis and a plurality of balls coupled to the strand along the longitudinal axis. Pairs of the plurality of balls are spaced along the longitudinal axis. The method further comprises braiding a plurality of filaments around the mandrel including, during braiding, forming a plurality of bulbs around the plurality of balls and forming necks between pairs of the plurality of balls. The method further comprises, after braiding the plurality of filaments, heat treating the plurality of filaments on the mandrel. The heat-treated plurality of filaments includes the plurality of bulbs and the necks.

The method may comprise, during braiding the plurality of filaments around the mandrel, rearranging the plurality of filaments. Rearranging the plurality of filaments may be from a symmetric pattern to an asymmetric pattern. Rearranging the plurality of filaments may be from an asymmetric pattern to a symmetric pattern. The method may further comprise, before heat treating the plurality of filaments on the mandrel, securing portions of the braided plurality of filaments to the mandrel. Securing the portions of the braided plurality of filaments to the mandrel may comprise using bangles, wire, and/or adhesive.

In some embodiments, a method of forming a structure for treating a vessel comprises knitting a plurality of filaments into a textile, wrapping the textile around a mandrel, and heat treating the textile on the mandrel. The mandrel comprises a strand having a longitudinal axis and a plurality of balls coupled to the strand along the longitudinal axis. Pairs of the plurality of balls are spaced along the longitudinal axis. The heat-treated textile includes a plurality of bulbs around the plurality of balls and necks between pairs of the plurality of balls.

The textile may comprise a sheet. The method may further comprise, before wrapping the textile around the mandrel, heat treating the sheet into a tube. A length of the heat-treated textile may include stray filaments. Knitting the plurality of filaments may comprise weft knitting. The textile may comprise a tube. Knitting the plurality of filaments may comprise forming interlocking loops. The method may further comprise, before heat treating the textile on the mandrel, securing portions of the textile to the mandrel. Securing the portions of the textile to the mandrel may comprise using bangles, wire, and/or adhesive.

In some embodiments, a system for modifying a hypotube comprises a hypotube holding subsystem, a spiral hypotube collector, and a cooling subsystem. The hypotube holding subsystem comprises a bushing, a plurality of collets, and a hypotube clamp configured to longitudinally advance a hypotube. The bushing, the plurality of collets, and the hypotube clamp are aligned at a height. The bushing and plurality of collets are arranged to inhibit sag of a hypotube to be less than 3% of the height. The spiral hypotube collector is configured to wind a hypotube after laser cutting. The cooling subsystem is configured to flow gas at a temperature between 20° C. and 25° C. into the spiral hypotube collector. The cooling subsystem comprises a valve configured to regulate gas flow from the cooling system into the spiral hypotube collector.

The cooling subsystem may be further configured to flow gas into a laser nozzle and toward a hypotube being cut by a focused laser beam. The cooling subsystem may further comprise a second valve configured to regulate gas flow from the cooling subsystem into the laser nozzle. The gas may comprise air (e.g., ambient air) and/or inert gas. The hypotube clamp may be configured to apply variable tension to a held hypotube. The system may be configured to inhibit forming fissures (e.g., including fractures) in the hypotube.

In some embodiments, a system for modifying a hypotube comprises a hypotube holding subsystem, a hypotube collection subsystem, and a cooling subsystem. The hypotube holding subsystem is configured to inhibit sag of a held hypotube. The hypotube collection subsystem is configured to collect a hypotube after laser cutting. The cooling subsystem comprises a valve configured to direct gas into the hypotube collection subsystem.

The cooling subsystem may further comprise a second valve configured to direct gas into a laser nozzle and towards a hypotube being cut by a focused laser beam. The cooling subsystem may comprise an inert gas source. The gas may comprise air (e.g., ambient air). The gas may be at a temperature between 20° C. and 25° C. The hypotube collection subsystem may comprise a spiral hypotube collector configured to wind a hypotube after laser cutting. The hypotube holding subsystem may comprise a bushing, a plurality of collets, and a hypotube clamp configured to longitudinally advance a hypotube. The bushing, the plurality of collets, and the hypotube clamp may be aligned at a height. The bushing and plurality of collets may be arranged to inhibit sag of a hypotube to be less than 3% of the height. The hypotube clamp may be configured to apply variable tension to the hypotube. The hypotube holding subsystem may further comprise a conveyor. The cooling subsystem may be configured to reduce a heat affected zone. The system may be configured to inhibit forming fissures (e.g., including fractures) in the hypotube.

In some embodiments, a system for modifying a hypotube comprises a cooling subsystem. The cooling subsystem comprises a first valve and a second valve. The first valve is configured to direct gas into a spiral hypotube collector. The spiral hypotube collector is configured to wind a hypotube after laser cutting. The second valve is configured to direct gas into a laser nozzle and towards a hypotube being cut by a focused laser beam.

The cooling subsystem may comprise an inert gas source. The gas may comprise air (e.g., ambient air). The gas may be at a temperature between 20° C. and 25° C. The system may further comprise the spiral hypotube collector. The cooling subsystem may be configured to reduce a heat affected zone. The system may be configured to inhibit forming fissures (e.g., including fractures) in the hypotube.

In some embodiments, a method of removing slag during laser cutting a hypotube comprises flowing cooling gas onto an external surface of the hypotube using a gas cooling system. Flowing the cooling gas comprises reducing a heat impact puddle. Flowing the cooling gas comprises reducing a heat impact zone. The cooling gas has a temperature between 20° C. and 25° C. The method further comprises injecting water into an inner lumen of the hypotube at a velocity inhibit a portion of slag from adhering to the inner lumen of the hypotube. Flowing the cooling gas and injecting the water comprises removing the slag from the external surface of the hypotube. The method further comprises collecting the removed slag in a slag collecting device. The method is performed during laser cutting of the hypotube.

The cooling gas may comprise air (e.g., ambient air). The cooling gas may comprise inert gas. The method may further comprise flowing cooling gas onto a cut hypotube collection device. Injecting the water into the inner lumen of the hypotube may include controlling the velocity. Controlling the velocity may include delivering the water from a water supply to the inner lumen of the hypotube through a plurality of water injection tubes arranged in series proximate to the hypotube to distant to the hypotube. Each of the plurality of water injection tubes may have a diameter. The diameter of each of the plurality of water injection tubes more proximate to the hypotube may be smaller than the diameter of each of the plurality of water injection tubes distant to the hypotube. The plurality of injection tubes may comprise, consist essentially of, or consists of four water injection tubes.

In some embodiments, a method of removing slag during laser cutting a hypotube comprises flowing cooling gas onto an external surface of the hypotube using a gas cooling system and injecting cooling fluid into an inner lumen of the hypotube. Flowing the cooling gas and injecting the cooling fluid comprises at least partially removing slag from the external surface of the hypotube. Flowing the cooling gas comprises reducing at least one of a heat impact puddle and a heat impact zone. Injecting the cooling fluid comprises at least partially removing slag from the external surface of the hypotube. The method further comprises collecting the removed slag.

The cooling fluid may comprise ethylene glycol. The cooling fluid may comprise slurry. The cooling fluid may comprise water. The method may be performed continuously during the entire laser cutting process. The method may be only performed during a portion of the laser cutting process. The cooling gas may comprise air (e.g., ambient air) (e.g., between 20° C. and 25° C.). The cooling gas may comprise inert gas. The cooling gas may have an ambient temperature (e.g., between 20° C. and 25° C.).

In some embodiments, a method of removing slag during laser cutting of a hypotube comprises flowing cooling gas into a laser nozzle, directing flow of the cooling gas onto an external surface of the hypotube, and injecting cooling fluid into an inner lumen of the hypotube at a velocity.

The cooling gas may air (e.g., ambient air) and/or inert gas. The cooling gas may have an ambient temperature (e.g., between 20° C. and 25° C.). The method may further comprise controlling the velocity by injecting the cooling fluid through a plurality of injection tubes arranged in a series of sequentially smaller diameters with distance to the hypotube. Injecting the cooling fluid may be performed continuously during the entire laser cutting process.

In some embodiments, a device for disrupting flow through a fistula comprises a woven textile having a compressed state and an expanded state. The woven textile comprises, in the expanded state, a first bulb, a second bulb, a first neck between the first bulb and the second bulb, a third bulb, a second neck between the second bulb and the third bulb, a fourth bulb, and a third neck between the third bulb and the fourth bulb. The first bulb has a first braid angle. The fourth bulb has a second braid angle. The second neck has a third braid angle less than the first braid angle and the second braid angle. The second neck is configured to extend through a fistula. The first bulb and the second bulb are configured to be on a first side of the fistula. The third bulb and the fourth bulb are configured to be on a second side of the fistula.

The second bulb may have a fourth braid angle. The third bulb may have a fifth braid angle. The third braid angle may be less than the fourth braid angle and the fifth braid angle. Each of the second bulb and the third bulb may comprise an oblate spheroid having a diameter of a polar axis that is shorter than a diameter of an equatorial axis. The second bulb and the third bulb may be connected along the polar axes of the second bulb and the third bulb. Each of the first bulb and the fourth bulb may comprise an oblate spheroid having a diameter of a polar axis that is shorter than a diameter of an equatorial axis. The first bulb and the second bulb may be connected along the polar axes of the first bulb and the second bulb. The third bulb and the fourth bulb may be connected along the polar axes of the third bulb and the fourth bulb. The first bulb may have a first diameter. The second bulb may have a second diameter larger than the first diameter. The third bulb may have a third diameter. The fourth bulb may have a fourth diameter smaller than the third diameter. At least one of the first bulb, the second bulb, the third bulb, and the fourth bulb may be longitudinally offset from another of the first bulb, the second bulb, the third bulb, and the fourth bulb.

In some embodiments, a device for disrupting flow through a fistula comprises a woven textile having a longitudinal axis, a compressed state, and an expanded state. The woven textile comprises, in the expanded state, a first bulb, a first neck proximal to the first bulb, a second bulb, a second neck distal to the second bulb, and a third neck between the first bulb and the second bulb. Each of the first neck and the second neck is radially offset from the longitudinal axis. The third neck is configured to extend through a fistula.

Each of the first neck and the second neck may be differently radially offset from the longitudinal axis. The first bulb may have a first braid angle. The second bulb may have a second braid angle. The third neck may have a third braid angle less than the first braid angle and the second braid angle. Each of the first bulb and the second bulb may comprise an oblate spheroid having a diameter of a polar axis that is shorter than a diameter of an equatorial axis. The woven textile structure may further comprise, in the expanded state, a third bulb between the first bulb and the third neck and a fourth bulb between the second bulb and the third neck. The first bulb may have a first diameter. The third bulb may have a second diameter larger than the first diameter. The second bulb may have a third diameter. The fourth bulb may have a fourth diameter larger than the third diameter. The third neck may have a diameter between 2 mm and 16 mm. The third neck may have a length between 2 mm and 26 mm.

In some embodiments, a device for disrupting flow through a fistula comprises a woven textile having a compressed state and an expanded state. The woven textile comprises, in the expanded state, a neck, a first plurality of bulbs coupled to a proximal side of the neck, and a second plurality of bulbs coupled to a distal side of the neck. The neck has a first braid angle. At least a first bulb of the first plurality of bulbs has a second braid angle greater than the first braid angle. At least a second bulb of the second plurality of bulbs has a third braid angle greater than the first braid angle.

The first plurality of bulbs may comprise a proximal-most bulb having a first diameter and a third bulb having a second diameter less than the first diameter. The second plurality of bulbs may comprise a distal-most bulb having a third diameter and a fourth bulb having a fourth diameter less than the third diameter. The third bulb may have a fourth braid angle. The fourth bulb may have a fifth braid angle. The first braid angle may be less than the fourth braid angle and the fifth braid angle. Each of the first plurality of bulbs may comprise an oblate spheroid having a diameter of a polar axis that is shorter than a diameter of an equatorial axis. Each of the second plurality of bulbs may comprise an oblate spheroid having a diameter of a polar axis that is shorter than a diameter of an equatorial axis. The first plurality of bulbs may be connected along the polar axes. The second plurality of bulbs may be connected along the polar axes. The first plurality of bulbs may be connected to the second plurality of bulbs along the polar axes of a distal-most bulb of the first plurality of bulbs and a proximal-most bulb of the second plurality of bulbs. The neck may have a diameter between 2 mm and 16 mm. The neck may have a length between 2 mm and 26 mm.

In some embodiments, an implantable device for treating a vascular cavity or vascular malformation comprises a plurality of wires woven to form a textile structure expandable from a compressed state to an expanded state. The textile structure has a longitudinal axis. The textile structure comprises, in the expanded state, a first bulb, a second bulb, a third bulb, a first neck, and a second neck. The first bulb has a spherical shape. The second bulb has an elongate shape. The second bulb comprises a first circumferential portion and a second circumferential portion. The first circumferential portion comprises a first braid angle. The second circumferential portion comprises a second braid angle greater than the first braid angle. The second circumferential portion is opposite the first circumferential portion. The third bulb has a spherical shape. The second bulb is between the first bulb and the third bulb along the longitudinal axis. The first neck is between the first bulb and the second bulb along the longitudinal axis. The second neck is between the second bulb and the third bulb along the longitudinal axis.

The first bulb may comprise a third braid angle. The third bulb may comprise a fourth braid angle. The third braid angle may be less than the second braid angle. The fourth braid angle may be less than the second braid angle. The textile structure may further comprise, in the expanded state, a third neck and a fourth neck. The first bulb may be between the first neck and the third neck along the longitudinal axis. The third bulb may be between the second neck and the fourth neck along the longitudinal axis. The first braid angle may be between 0° and 90°. The second braid angle may be between 91° and 180°.

In some embodiments, an implantable device for treating a vascular cavity or vascular malformation comprises a plurality of wires woven to form a textile structure expandable from a compressed state to an expanded state. The textile structure has a longitudinal axis. The textile structure comprises, in the expanded state, a first bulb, a second bulb, a third bulb, a first neck, and a second neck. The first bulb has a spherical shape. The second bulb has an elongate shape. The second bulb comprises a first circumferential portion and a second circumferential portion opposite the first circumferential portion. The first circumferential portion comprises a polymer. The third bulb has a spherical shape. The second bulb is between the first bulb and the third bulb along the longitudinal axis. The first neck is between the first bulb and the second bulb along the longitudinal axis. The second neck is between the second bulb and the third bulb along the longitudinal axis.

The polymer may be non-porous. The polymer may comprise radiopaque material. The polymer may be coated onto the first circumferential portion of the third bulb. An inner surface of the first circumferential portion of the second bulb may be free of the polymer. The textile structure may further comprise, in the expanded state, a third neck. The first bulb may be between the first neck and the third neck along the longitudinal axis. Each of the first bulb, the second bulb, and the third bulb may have the same diameter.

In some embodiments, an implantable device for treating a vascular cavity or vascular malformation comprises a plurality of wires woven to form a textile structure expandable from a compressed state to an expanded state. The textile structure comprises, in the expanded state, a first longitudinal segment and a second longitudinal segment. The first longitudinal section comprises a first circumferential portion comprising a first braid angle and a second circumferential portion comprising a second braid angle greater than the first braid angle. The second circumferential portion is opposite the first circumferential portion. At least one of the first longitudinal segment and the second longitudinal segment comprises a bulb. A lumen is configured to allow perfusion of blood through the textile structure parallel to the longitudinal axis.

The first longitudinal segment may comprise the bulb. The second longitudinal segment may comprise the bulb. The first circumferential portion may be configured to allow perfusion of blood through the first circumferential portion at a first rate. The second circumferential portion may be configured to allow perfusion of blood through the second circumferential portion at a second rate less than the first rate. The textile structure may further comprise, in the expanded state, a third longitudinal segment. The first longitudinal segment may be between the second longitudinal segment and the third longitudinal segment. The first longitudinal segment may comprise the bulb, the second longitudinal segment may comprise a second bulb, and the third longitudinal segment may comprise a third bulb. The textile structure may comprise a first neck longitudinally between the bulb and the second bulb and a second neck longitudinally between the bulb and the third bulb. The second bulb may be spherical, the bulb may be elongate, and the third bulb may be spherical. The second bulb may have a first diameter, the bulb may have a second diameter less than the first diameter, and the third bulb may have a third diameter less than the second diameter. The second bulb may be spherical and may have a first diameter, the bulb may be elongate and may have a second diameter less than the first diameter, and the third bulb may be spherical and may have a third diameter less than the second diameter. The second bulb may have a first diameter, the bulb may have a second diameter less than the first diameter, and the third bulb may have a third diameter less than the second diameter.

The methods summarized above and set forth in further detail below describe certain actions taken by a practitioner; however, it should be understood that they can also include the instruction of those actions by another party. Thus, actions such as "advancing a guidewire" include "instructing the advancement of a guidewire."

BRIEF DESCRIPTION OF THE DRAWINGS

FIG. 1A is a schematic side elevational view of an example embodiment of a vascular treatment device.

FIG. 2E-2 is a perspective view of still another embodiment of a distal portion of a vascular treatment device.

FIG. 2H-2 is a schematic diagram illustrating the radial force of an example embodiment of a distal portion of a vascular treatment device.

FIG. 4E is a schematic side elevational view of yet another example embodiment of a distal portion of a vascular treatment device.

FIG. 4I is a schematic side elevational view of still yet another example embodiment of a distal portion of a vascular treatment device.

FIG. 6I is a schematic side elevational view of another example embodiment of a distal portion of a vascular treatment device.

FIG. 6J is a schematic side elevational view of yet another example embodiment of a distal portion of a vascular treatment device.

FIG. 6K-1*ii* is a side elevational view of the vascular treatment device of FIG. 6K-1*i*.

FIGS. 6K-2 to 6K-10 schematically illustrate methods of manufacturing a vascular treatment device.

FIG. 6K-11*i* is a schematic diagram of an example embodiment of a vascular treatment device of FIG. 6K-1*i* deployed across an aneurysm in vasculature.

FIG. 6K-11*ii* is a schematic diagram of an example embodiment of a vascular treatment device of FIG. 6K-1*i* deployed across an aneurysm in vasculature.

FIG. 6K-1*iii* is a schematic diagram of an example embodiment of a vascular treatment device of FIG. 6K-1*i* deployed across an aneurysm in vasculature.

FIG. 6K-11*iv* is a schematic diagram of an example embodiment of a vascular treatment device of FIG. 6K-1*i* deployed across an aneurysm in vasculature.

FIG. 6K-12 is a schematic diagram of an example embodiment of a vascular treatment device deployed across an aneurysm in vasculature.

FIG. 6K-13 is a schematic side elevational view of yet another example embodiment of a vascular treatment device.

FIG. 7B is a schematic side elevational view of still yet another example embodiment of a distal portion of a vascular treatment device.

FIG. 7C-2 is a schematic side elevational view of yet another example embodiment of a distal portion of a vascular treatment device.

FIG. 7E is a schematic side elevational view of still another example embodiment of a distal portion of a vascular treatment device.

FIG. 8I is a schematic diagram illustrating an example setup of a braid carrier mechanism for forming the distal portion of FIG. 8H.

FIG. 8O is a schematic perspective view illustrating a plurality of radiopaque filaments of the distal portion of FIG. 8M on a mandrel.

FIG. 8T-1 is a schematic side elevational view of still yet another example embodiment of a distal portion of a vascular treatment device illustrating an example pattern of radiopaque filaments.

FIG. 8T-2 is a schematic side elevational view of another example embodiment of a distal portion of a vascular treatment device illustrating an example pattern of radiopaque filaments.

FIG. 8T-3 is a schematic diagram illustrating an example setup of a braid carrier mechanism for forming the distal portions of FIGS. 8T-1 and 8T-2.

FIG. 8T-4 is an x-ray photograph illustrating an example of a plurality of radiopaque filaments of the distal portion of FIG. 8T-2.

FIG. 8X is a schematic side elevational view of yet another example embodiment of a distal portion of a vascular treatment device illustrating an example pattern of radiopaque filaments.

FIG. 8Z is a magnified view of the distal portion of FIG. 8X.

FIG. 9E is a schematic diagram illustrating an example embodiment of a mandrel for heat treatment of a distal portion of a vascular treatment device.

FIG. 9F is a schematic diagram illustrating another example embodiment of a mandrel for heat treatment of a distal portion of a vascular treatment device.

FIG. 10I is a schematic side elevational view of another example embodiment of a woven tubular structure having a transition angle.

FIG. 10J is a schematic side elevational view of another example embodiment of a woven tubular structure around a mandrel.

FIG. 11D is a schematic side elevational view of another example embodiment of braiding around of forming a textile structure.

FIG. 12A is a schematic perspective view of an example embodiment of a filament end treatment of a distal portion of a vascular treatment device.

FIG. 12C is a schematic perspective view of another example embodiment of a filament end treatment of a distal portion of a vascular treatment device.

FIG. 12D is a front elevational view of the filament end treatment of FIG. 12C.

FIG. 12E is a schematic perspective view of yet another example embodiment of a filament end treatment of a distal portion of a vascular treatment device.

FIG. 12F is a schematic perspective view of still another example embodiment of a filament end treatment.

FIG. 13A is a schematic perspective view illustrating an example embodiment of a plurality of filaments being knitted into an example biomedical textile structure.

FIG. 13B is a schematic perspective view illustrating an example embodiment of a plurality of filaments knitted woven into another example biomedical textile structure.

FIG. 14A is a schematic perspective view of an example of a segment of an example embodiment of a proximal portion of a vascular treatment device.

FIG. 14B is a schematic perspective view of another example segment of an example embodiment of a proximal portion of a vascular treatment device.

FIG. 14C is a schematic front elevational view of yet another example embodiment of a proximal portion of a vascular treatment device.

FIG. 14D is a schematic side partial cross-sectional view of an example embodiment of a balloon catheter.

FIG. 15A is a schematic diagram illustrating an example embodiment of a cut pattern.

FIG. 15B is a schematic diagram illustrating an example embodiment of a portion of a cut pattern.

Figure 15A:
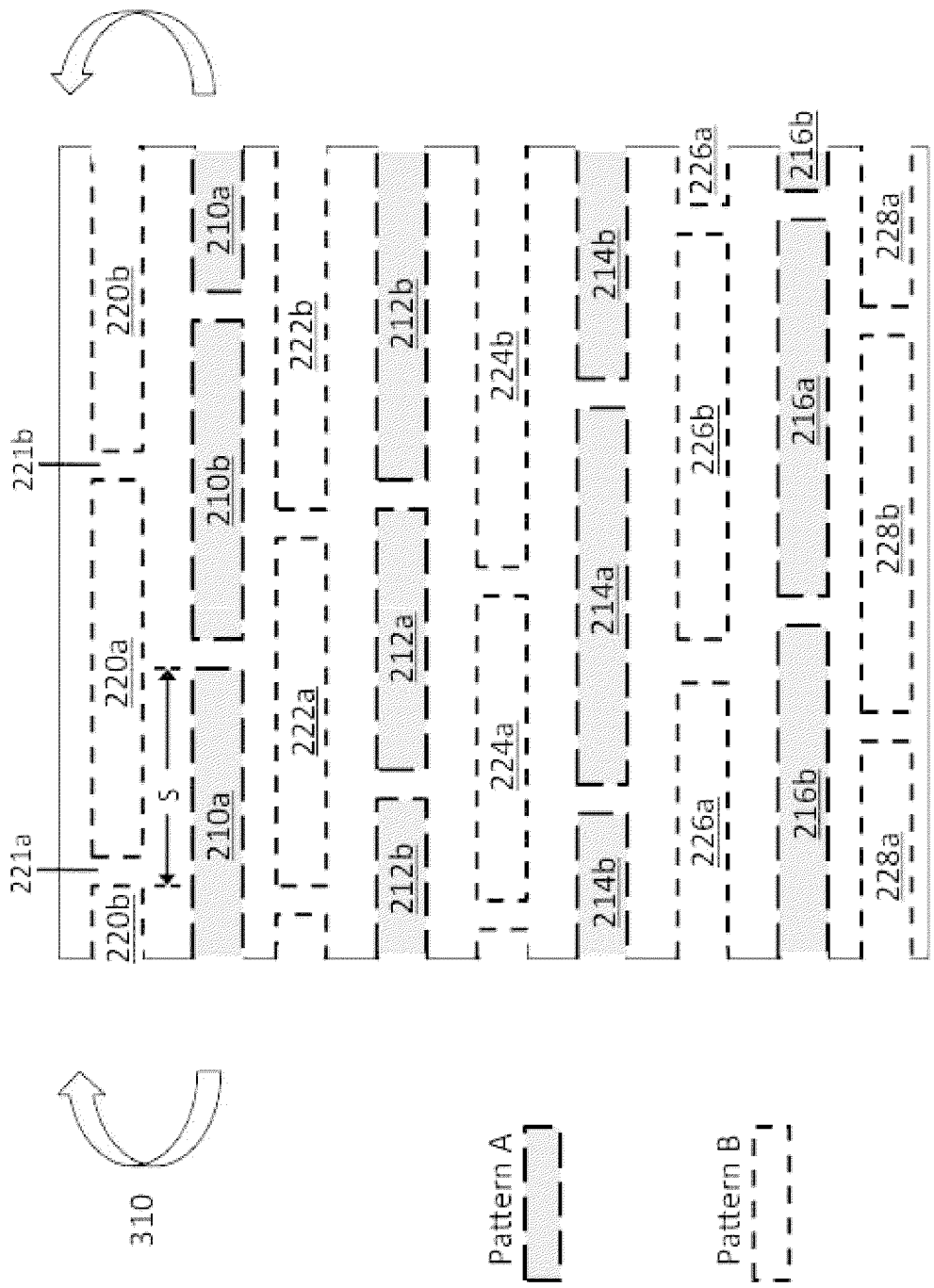
Figure 15B:
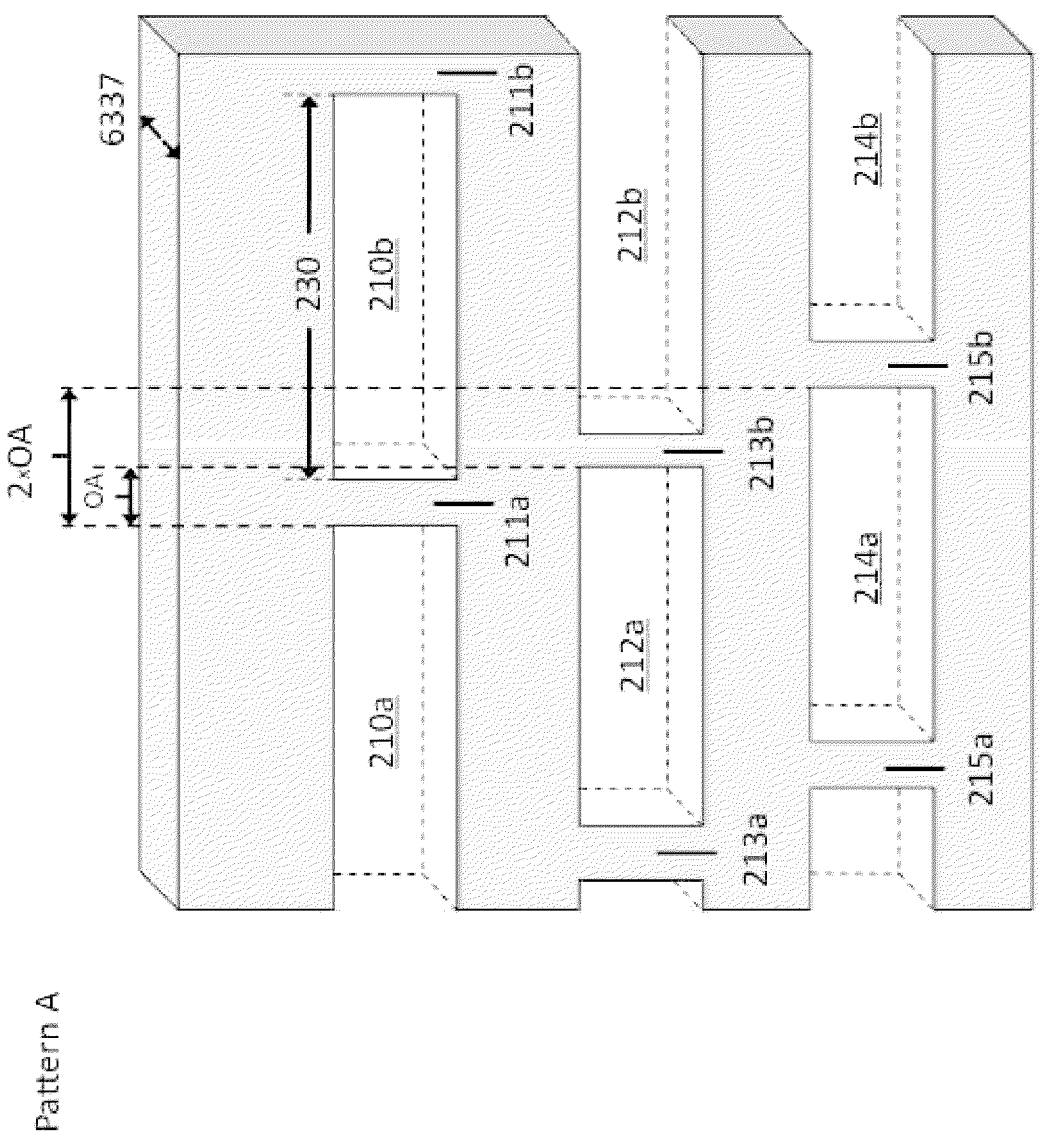
Figure 15C:
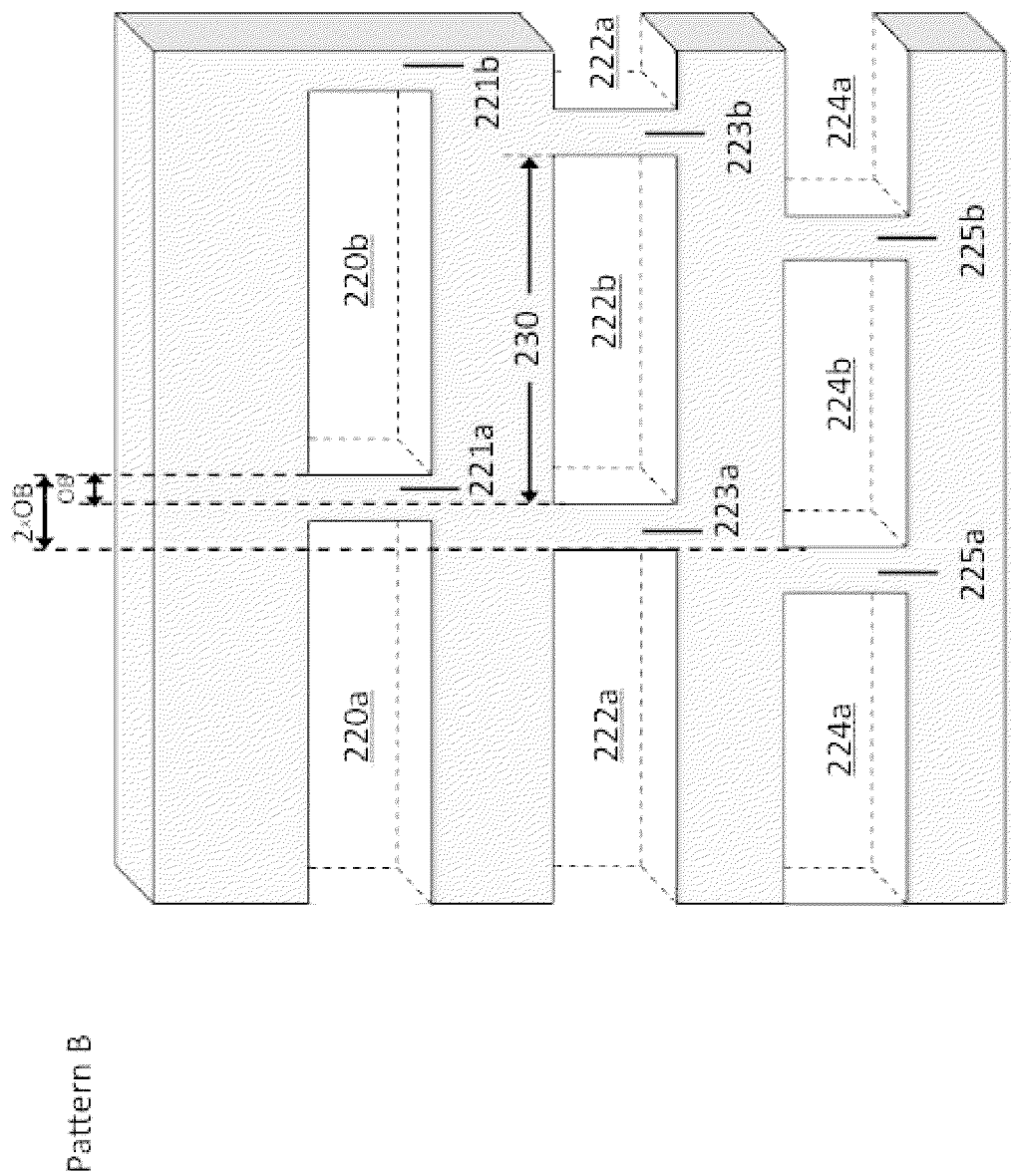

FIG. 15C is a schematic diagram illustrating another example embodiment of a portion of a cut pattern.

Figure 15D:
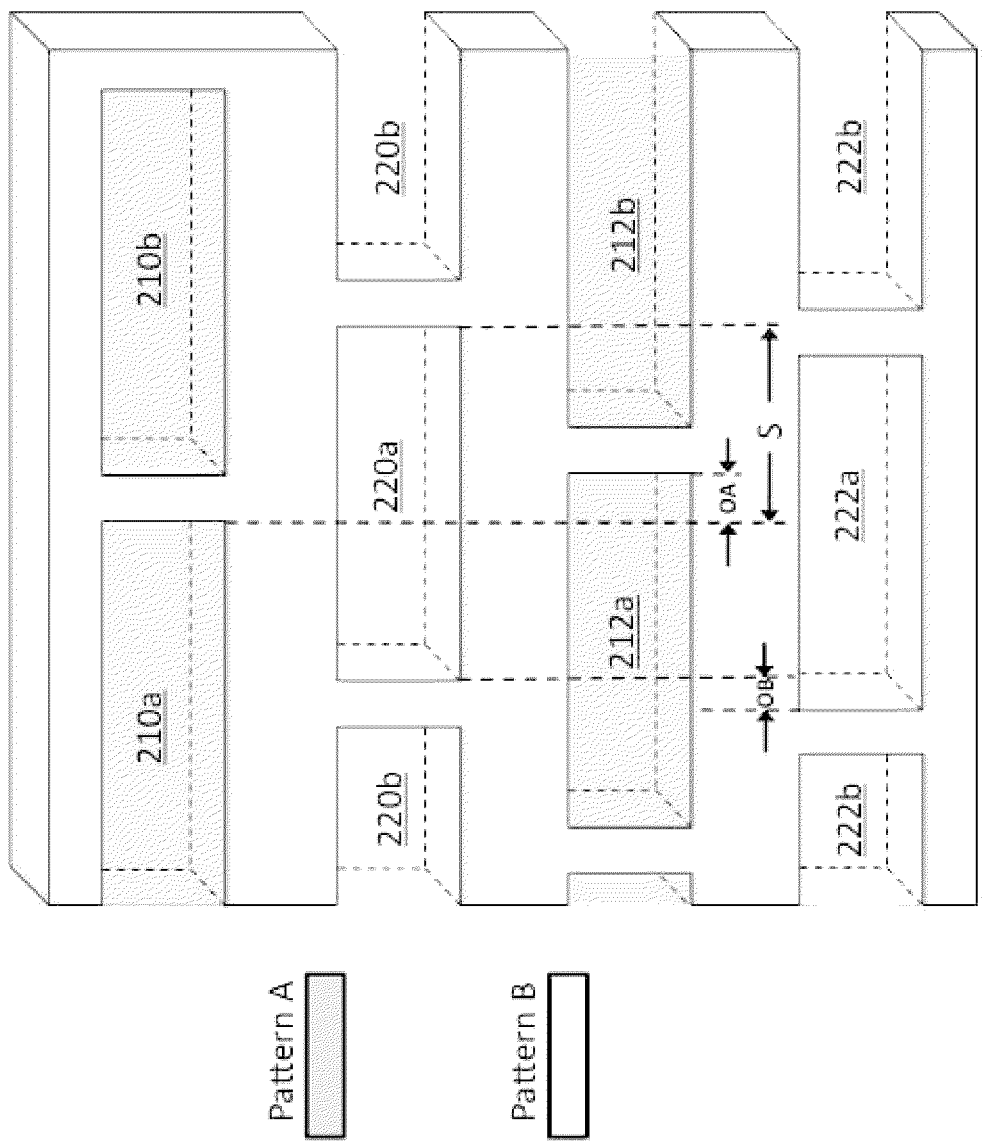

FIG. 15D is a schematic diagram illustrating an example embodiment of staggered interspersed cut patterns.

Figure 15E:
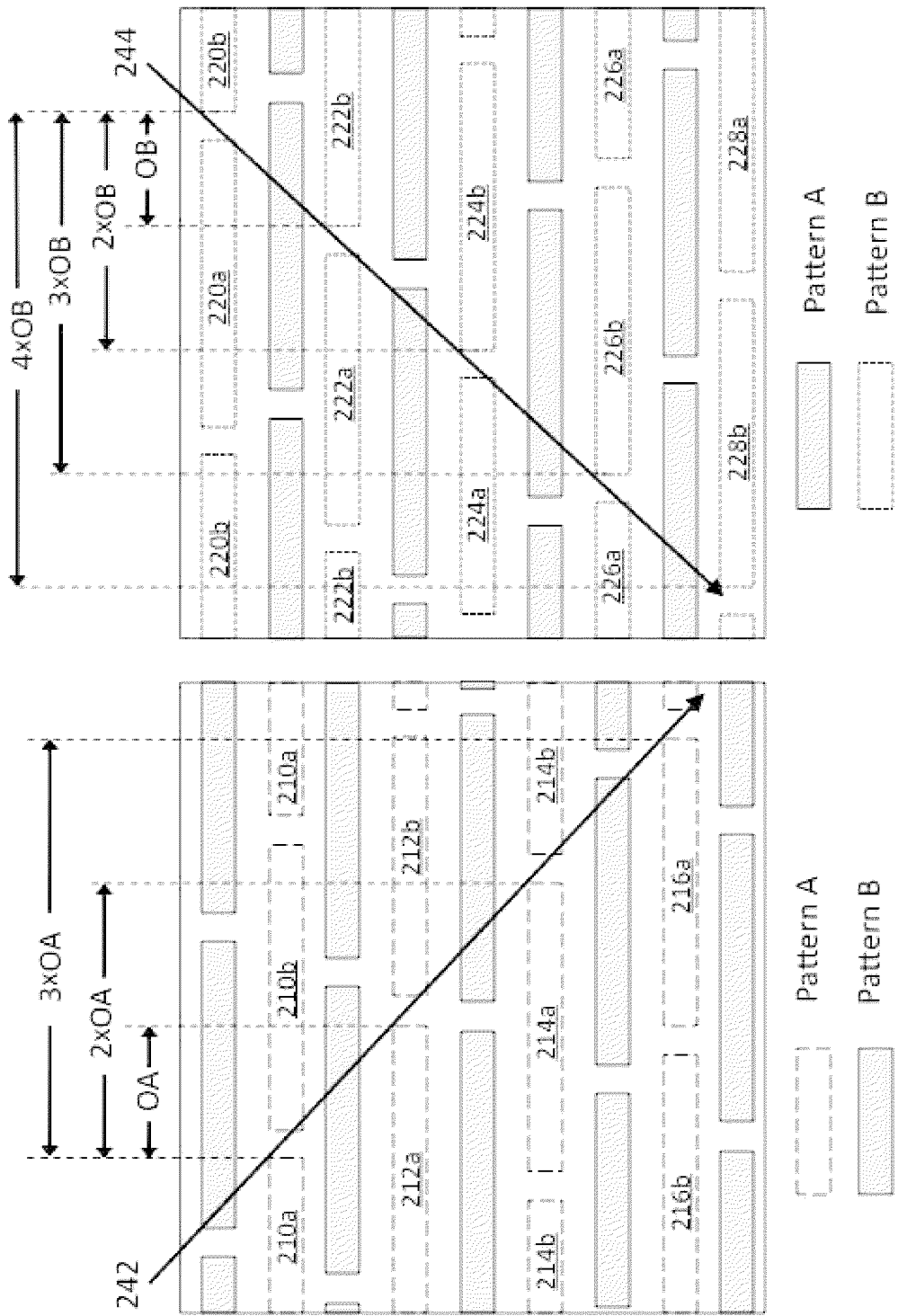

FIG. 15E is a schematic diagram illustrating an example embodiment of staggered interspersed offset cut patterns.

Figure 16A:
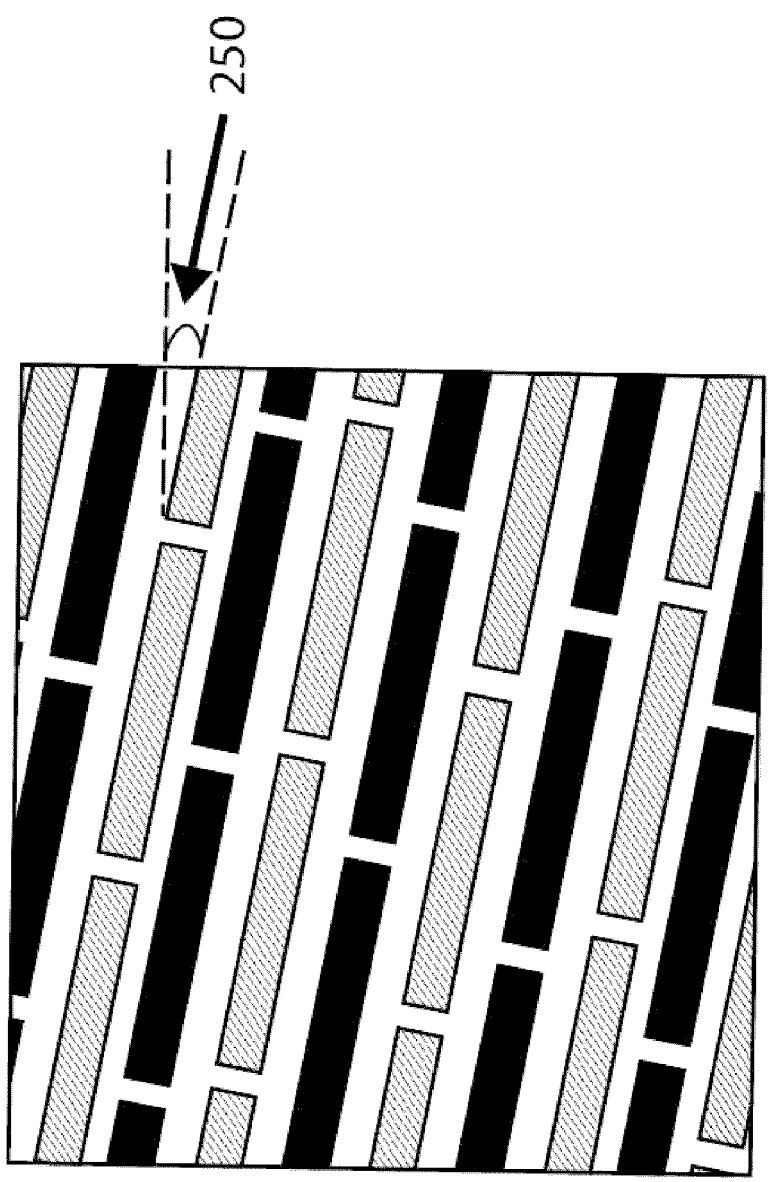

FIG. 16A is a schematic diagram illustrating an example embodiment of an angled pattern including sharp edges.

Figure 16B:
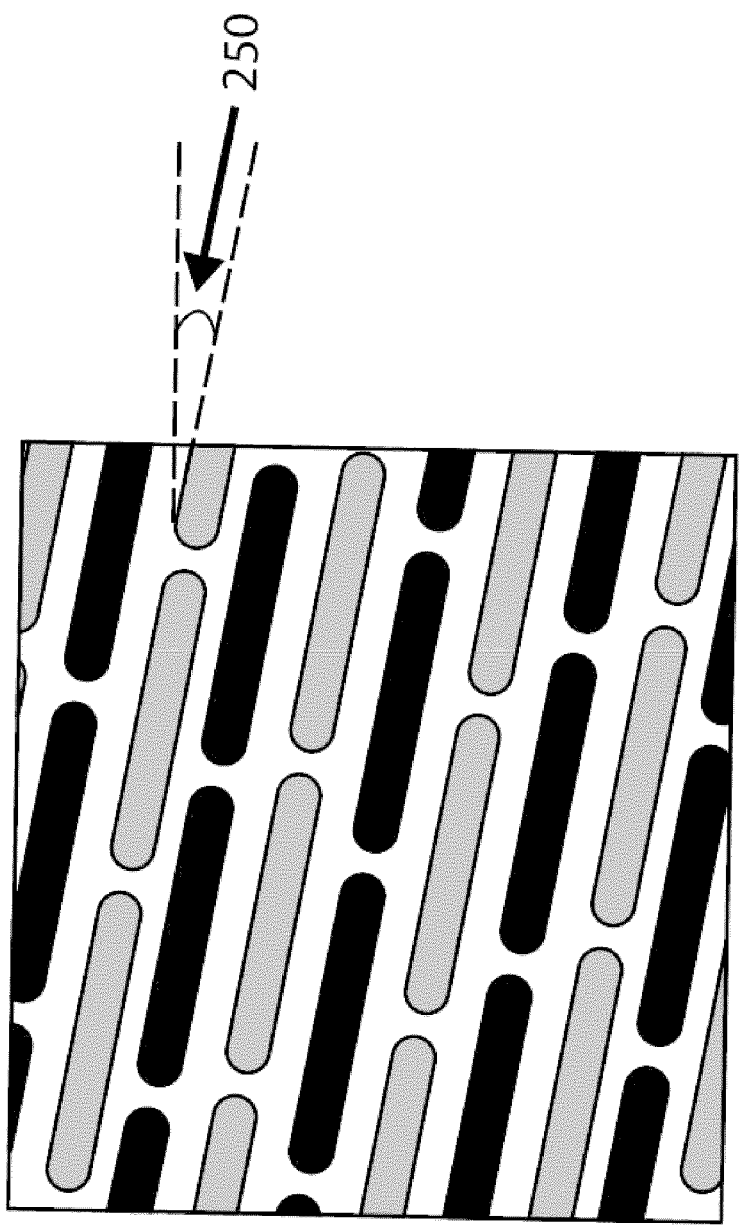

FIG. 16B is a schematic diagram illustrating an example embodiment of an angled pattern including rounded edges.

Figure 16C:
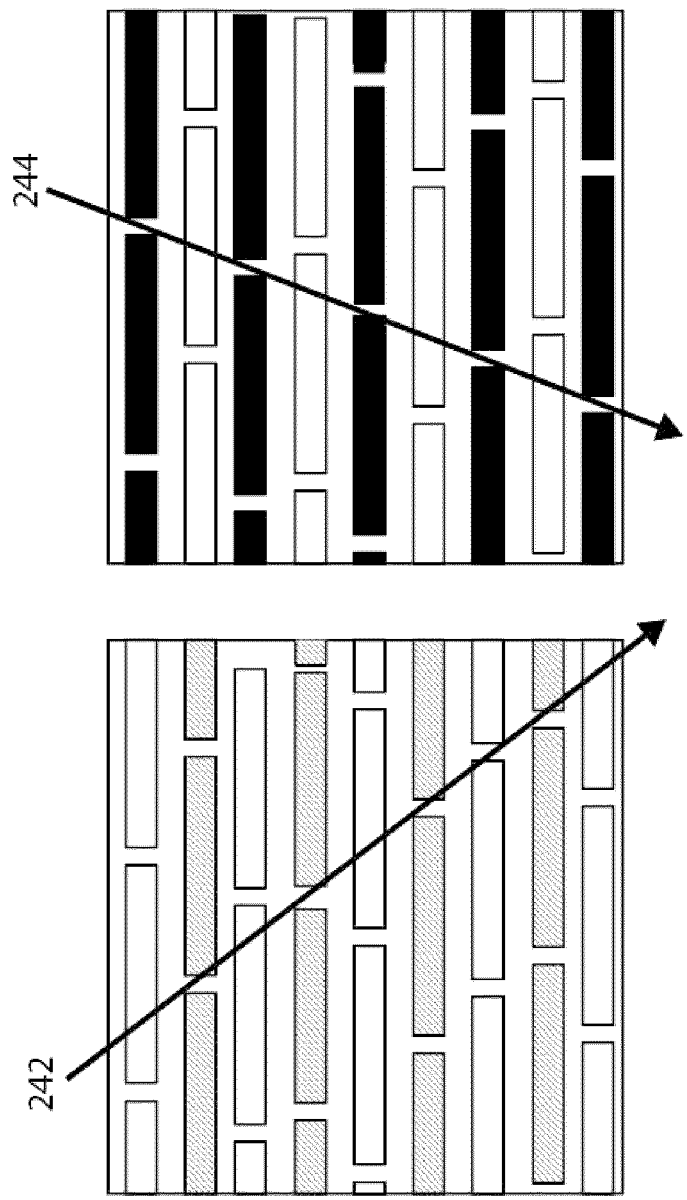

FIG. 16C is a schematic diagram illustrating an example embodiment of interspersed offset horizontal patterns including sharp edges.

FIG. 16D is a schematic diagram illustrating an example embodiment of interspersed offset horizontal patterns including rounded edges.

FIG. 16E is a schematic diagram illustrating an example embodiment of slits and stems along the length of an example embodiment of a proximal portion of a vascular treatment device.

Figure 16F:
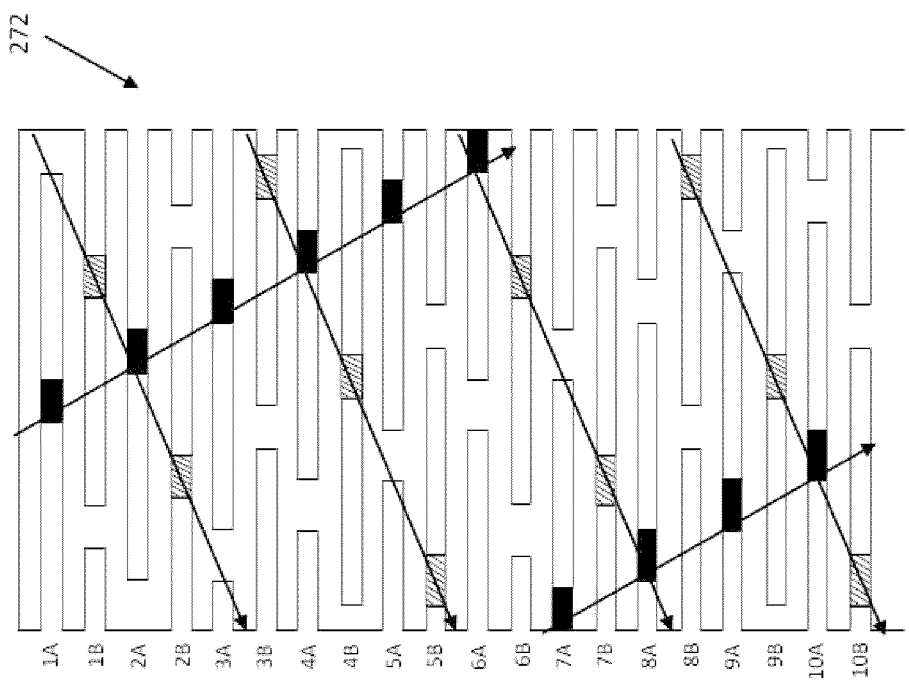

FIG. 16F is a schematic diagram illustrating another example embodiment of slits and stems along the length of an example embodiment of a proximal portion of a vascular treatment device.

Figure 17A:
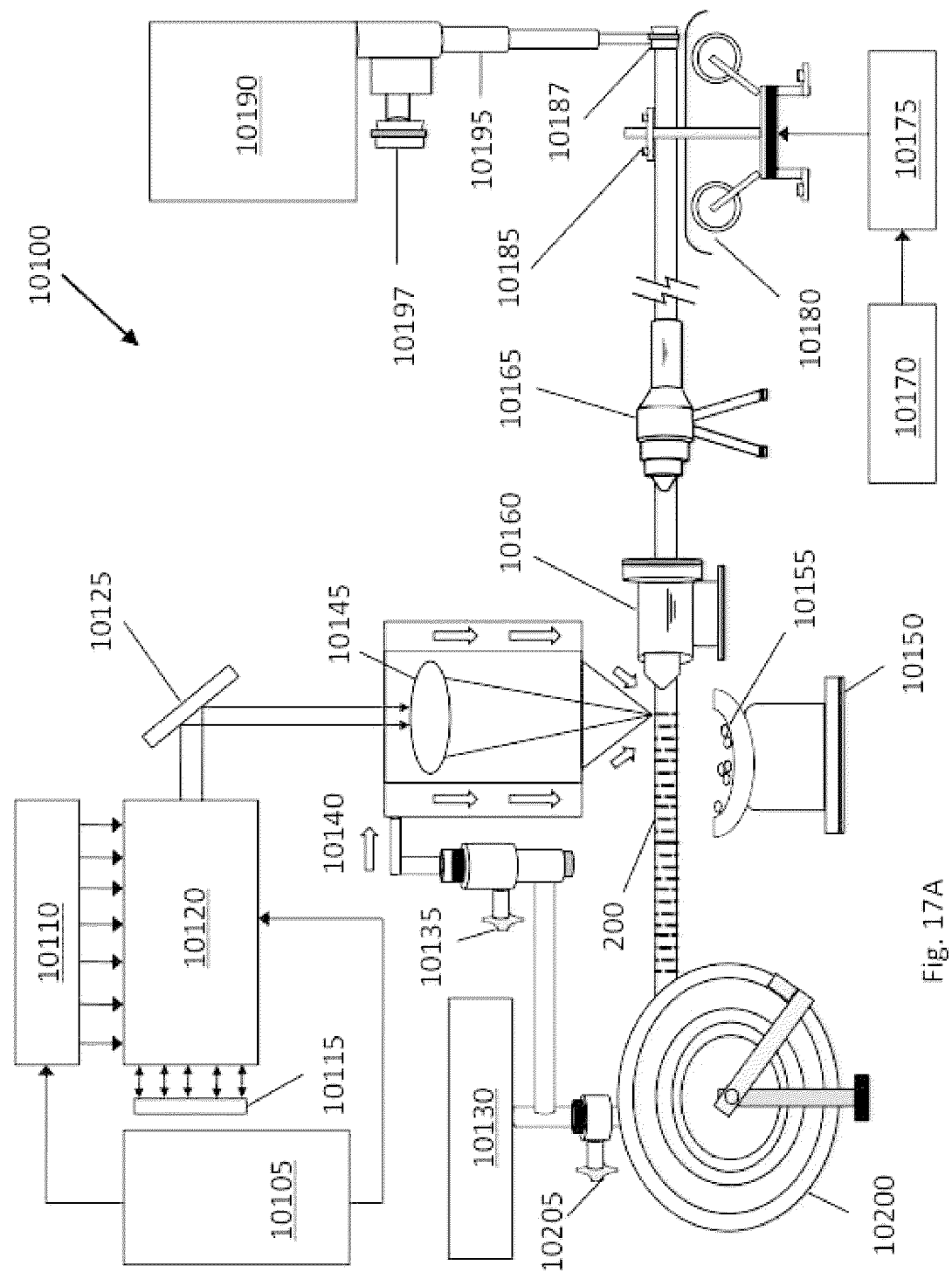

FIG. 17A is a schematic diagram illustrating an example embodiment of a laser cutting system.

Figure 17B:
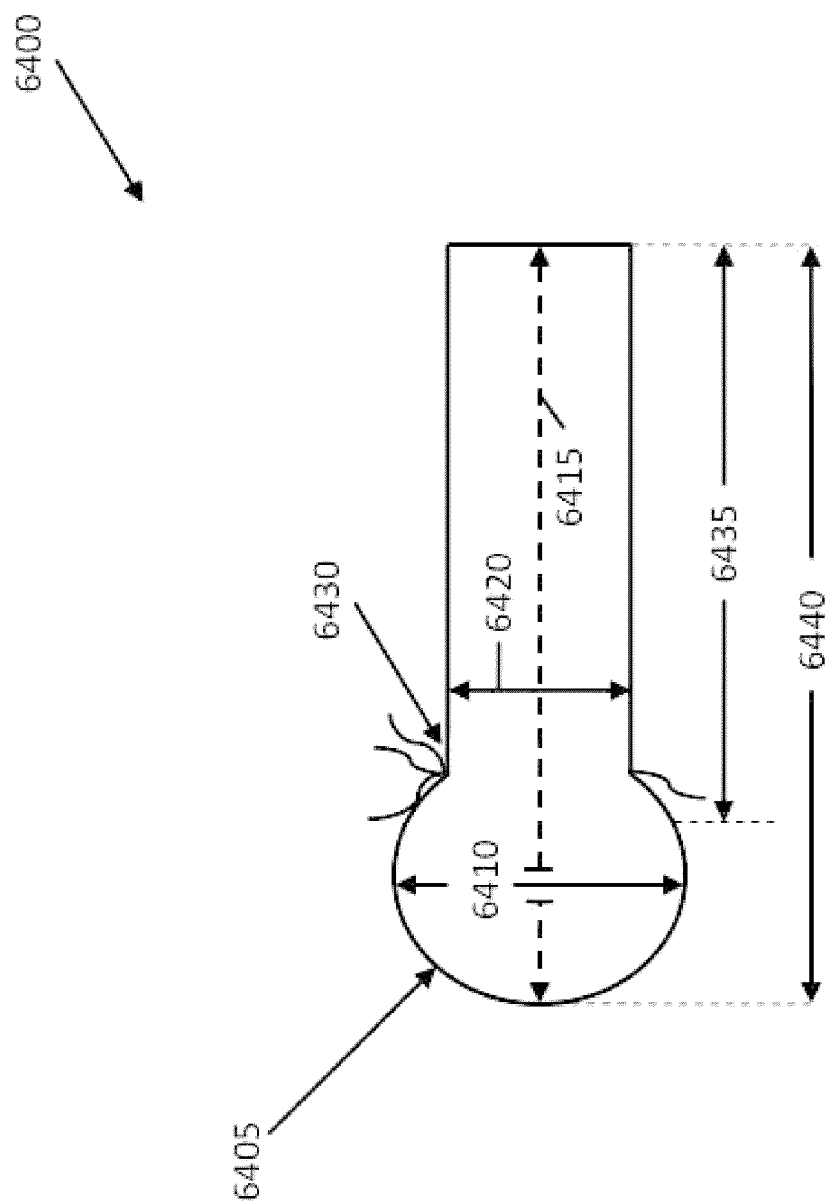

FIG. 17B is a schematic diagram illustrating an example embodiment of cut design of a slit.

FIG. 17C is a schematic diagram illustrating an example embodiment of an interspersed offset horizontal pattern including slits and heat impact puddles.

Figure 17D:
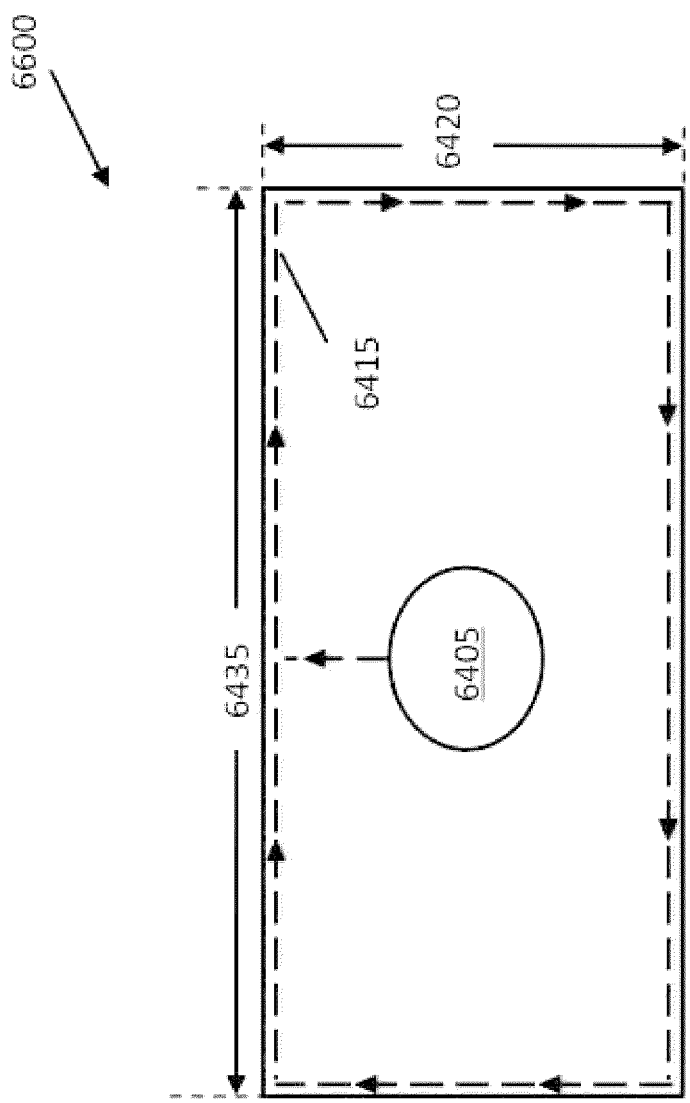

FIG. 17D is a schematic diagram illustrating another example embodiment of a cut design of a slit.

Figure 17E:
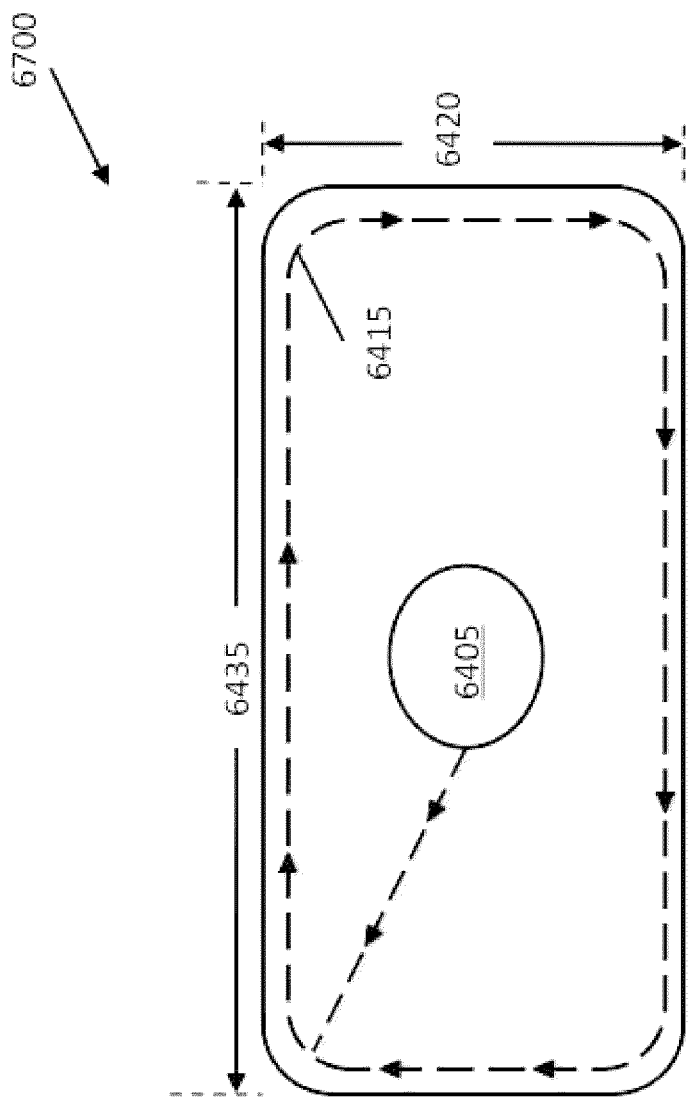

FIG. 17E is a schematic diagram illustrating yet another example embodiment of a cut design of a slit.

Figure 17F:
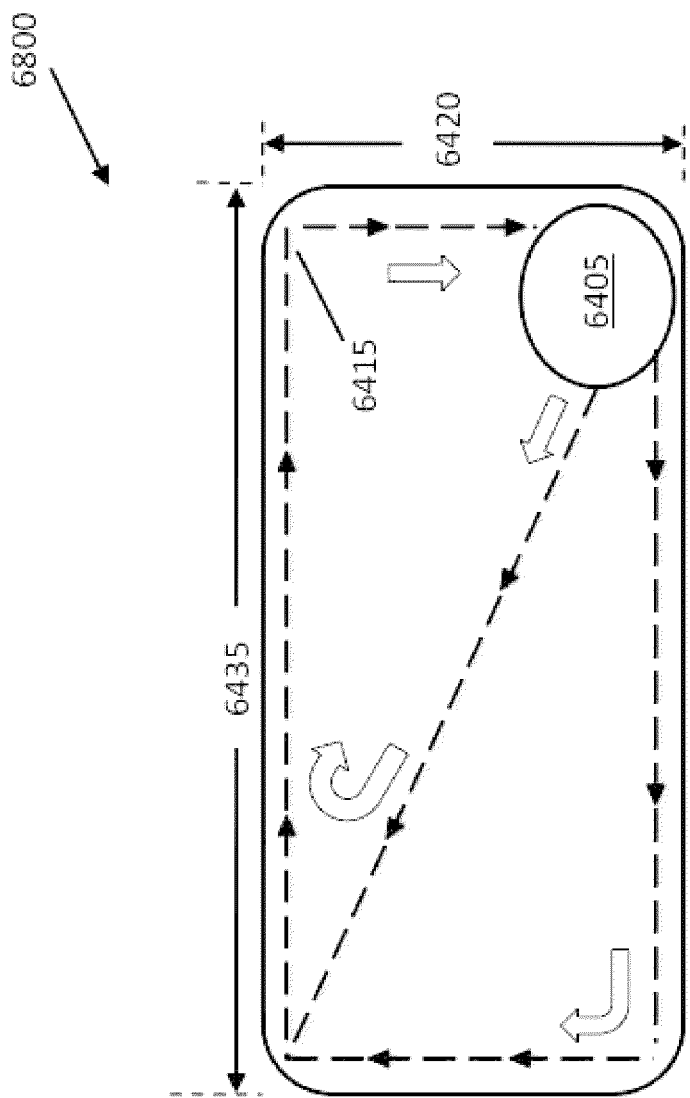

FIG. 17F is a schematic diagram illustrating still another example embodiment of a cut design of a slit.

Figure 17G:
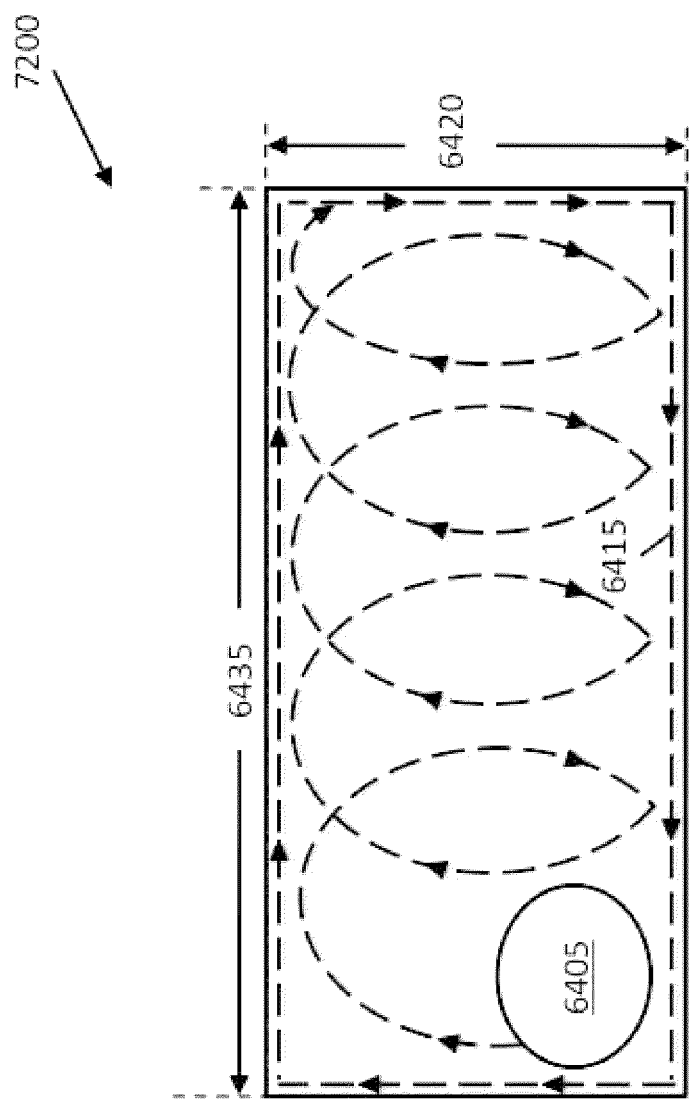

FIG. 17G is a schematic diagram illustrating still yet another example embodiment of a cut design of a slit.

Figure 17H:
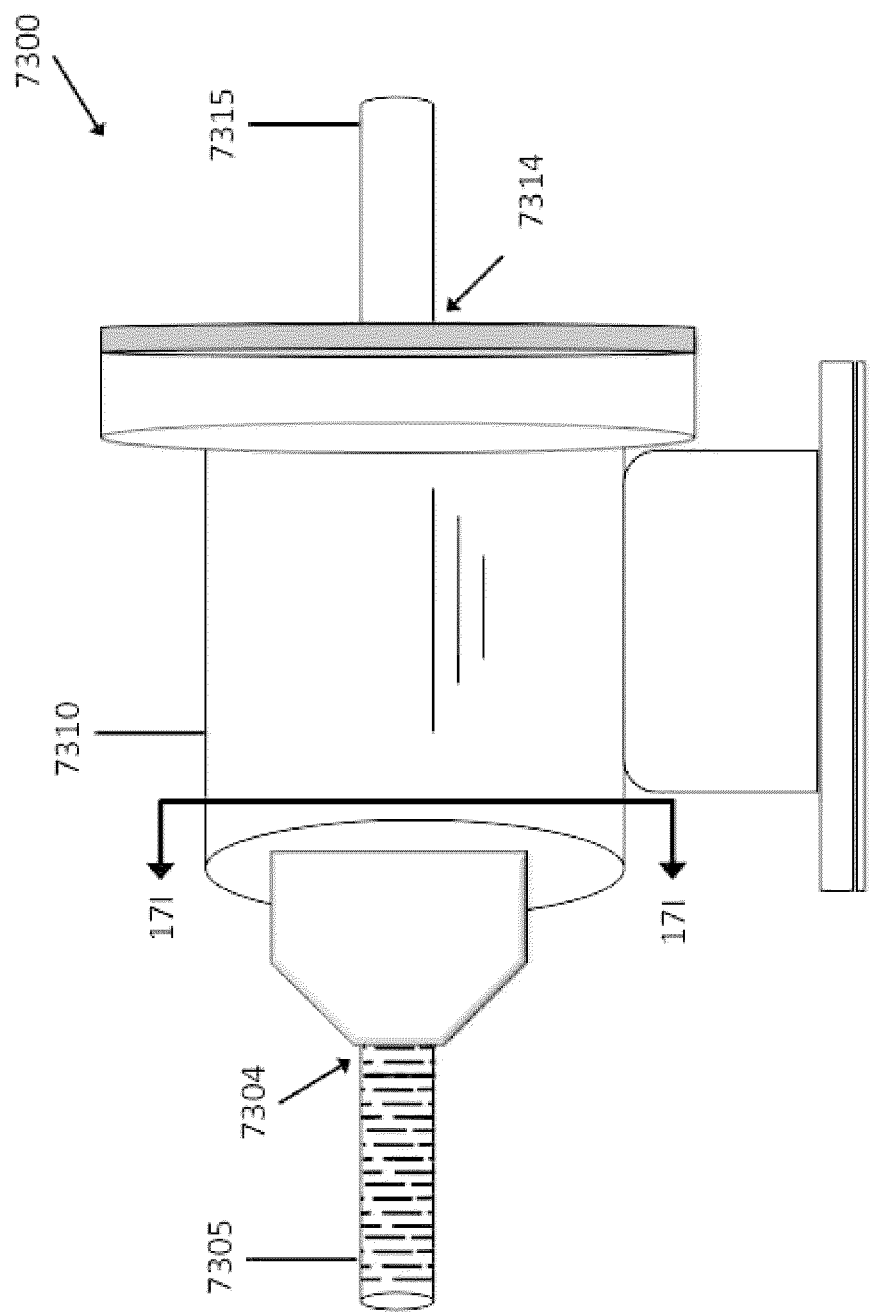
Figure 171:
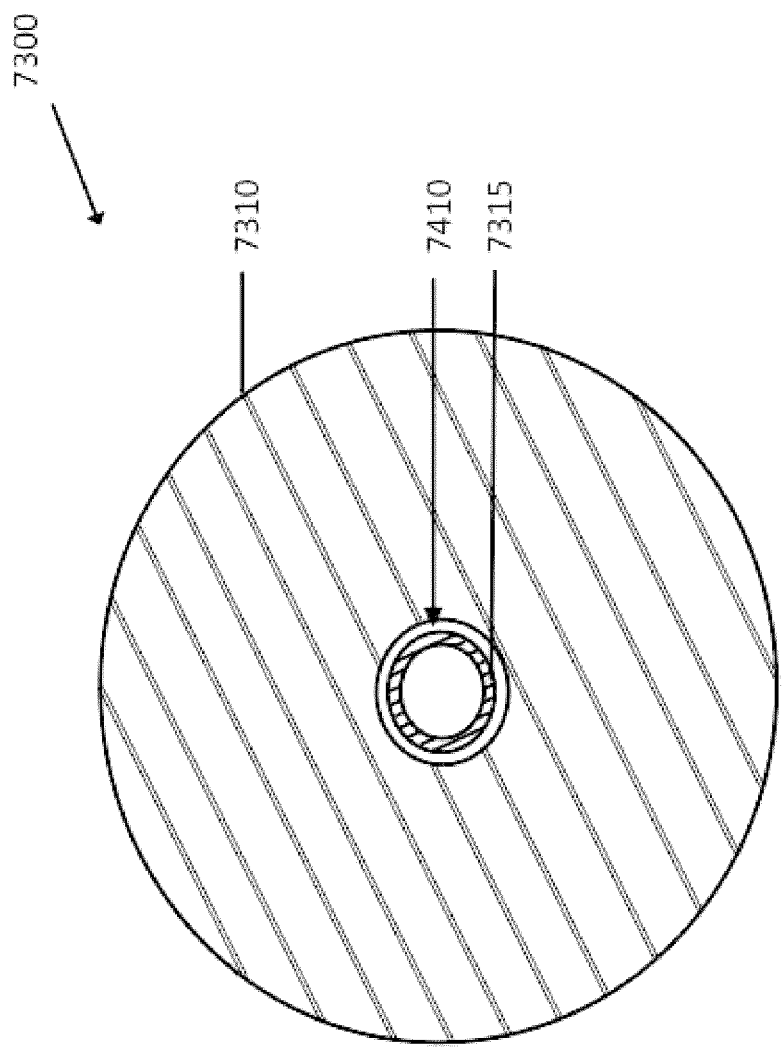

FIG. 17H is a schematic side elevational view of an example embodiment of a bushing.

FIG. 17I is a schematic cross-sectional front elevational view of the bushing of FIG. 17H along the line 17I-17I.

FIG. 17J is a schematic side elevational view of an example embodiment of a collet.

Figure 17K:
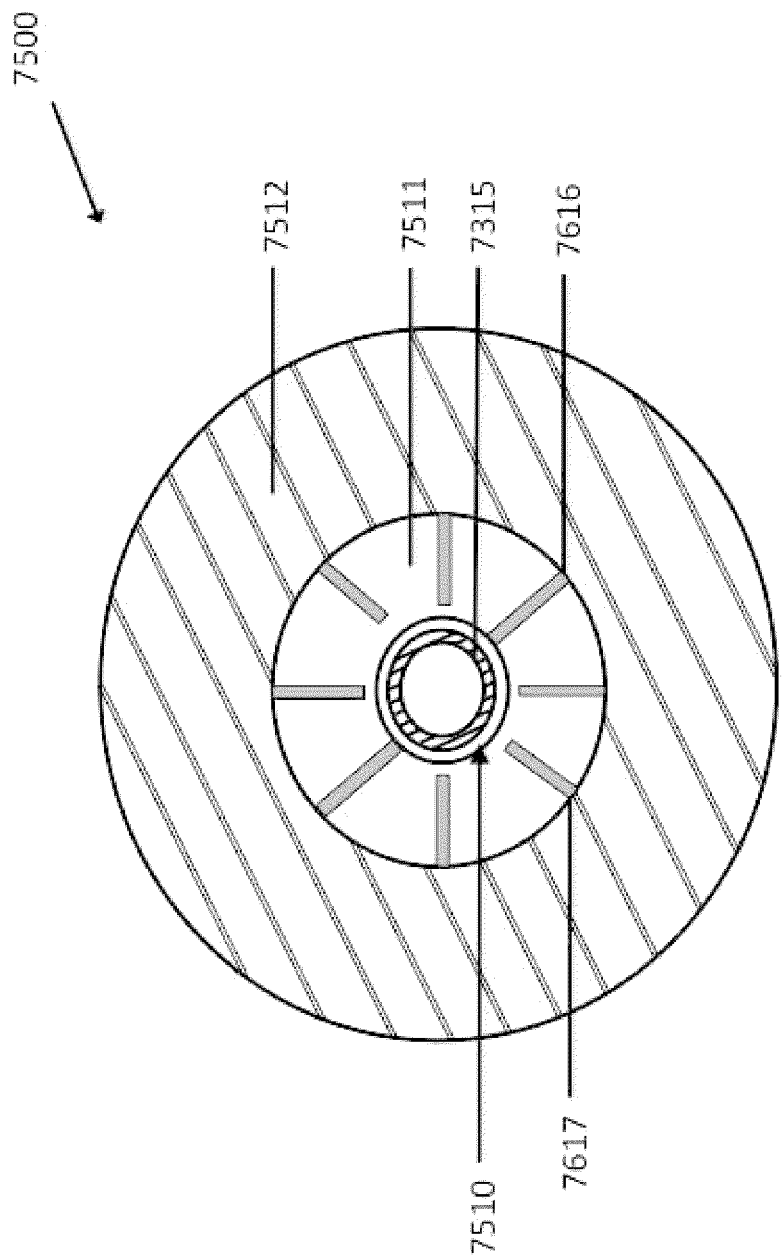

FIG. 17K is a schematic cross-sectional front elevational view of the collet of FIG. 17J along the line 17K-17K.

Figure 17L:
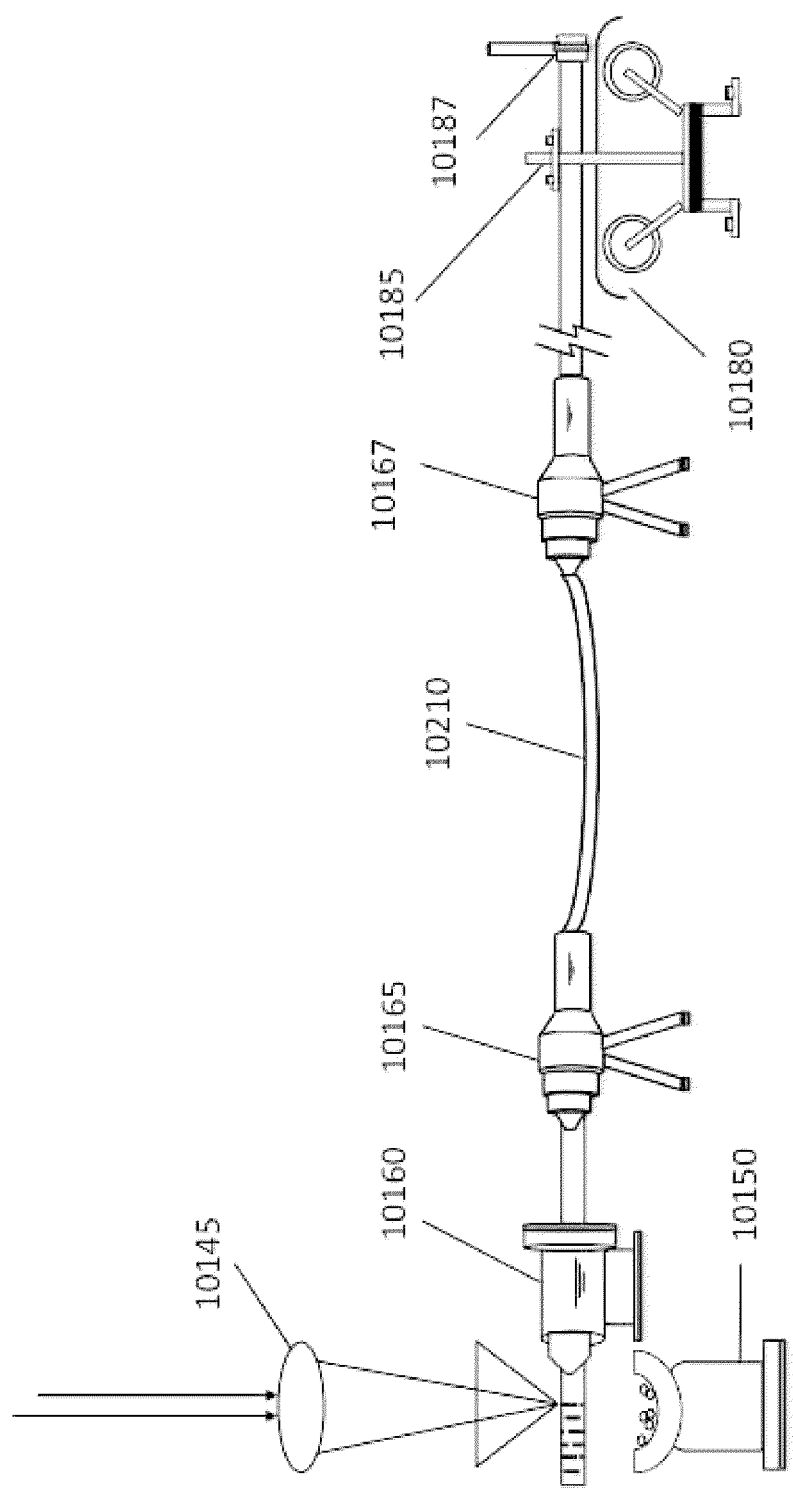

FIG. 17L is a schematic diagram illustrating an example embodiment of an arrangement of bushings and collets.

Figure 17M:
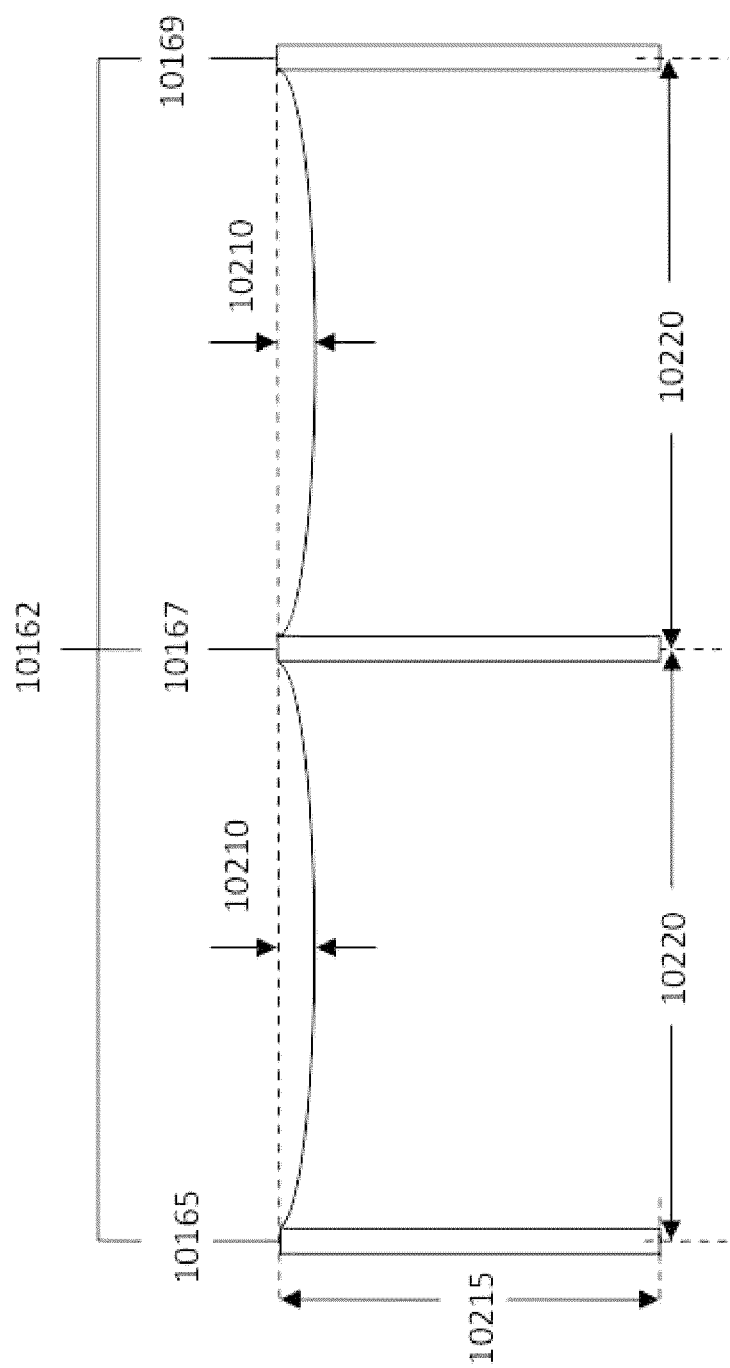

FIG. 17M is a schematic diagram illustrating an example embodiment of the sag of a hypotube in an arrangement of bushings and collets.

Figure 17N:
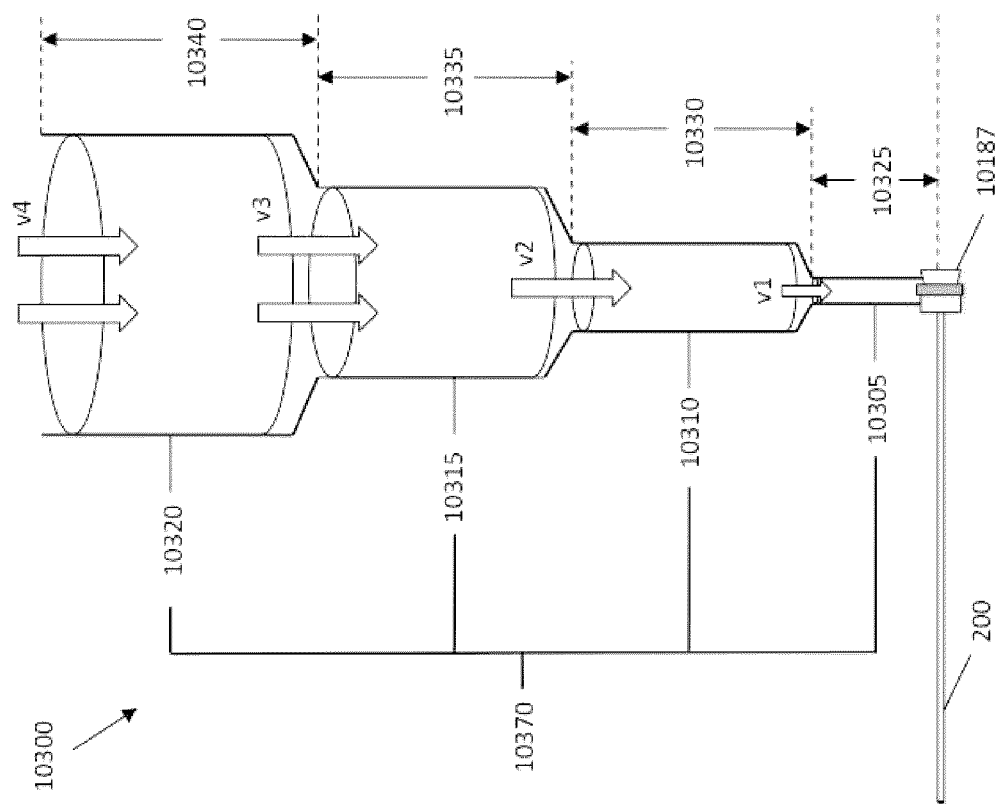

FIG. 17N is a schematic diagram illustrating an example embodiment of a water inlet device.

Figure 18A:
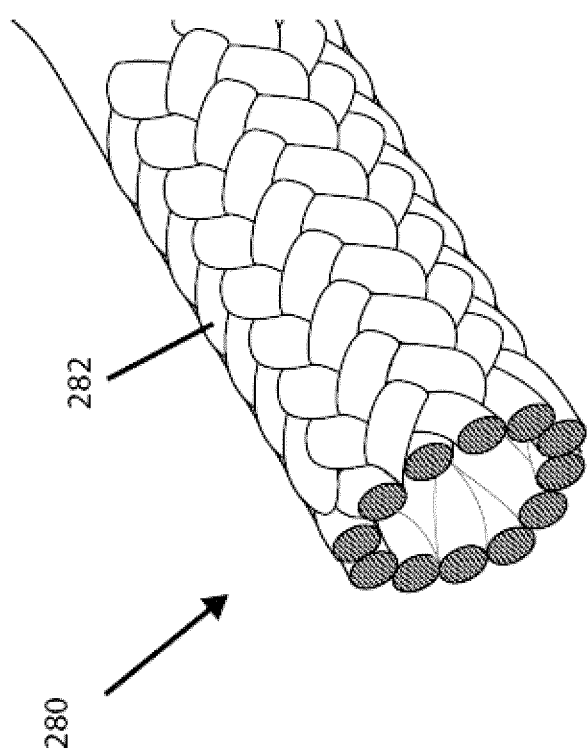

FIG. 18A is a schematic perspective view of an example embodiment of a proximal portion of a vascular treatment device comprising a plurality of filaments.

Figure 18B:
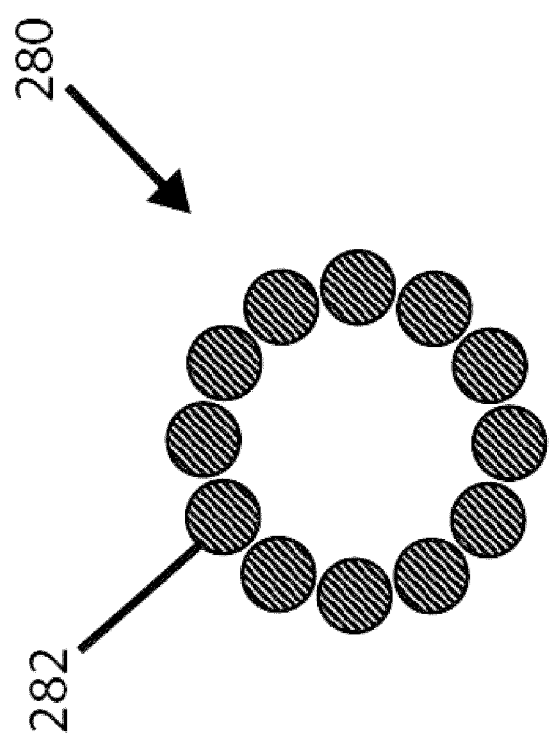

FIG. 18B is a schematic front perspective view of the proximal portion of FIG. 18A.

FIG. 18C is a schematic perspective view of another example embodiment of a proximal portion of a vascular treatment device comprising a plurality of filaments.

Figure 18D:
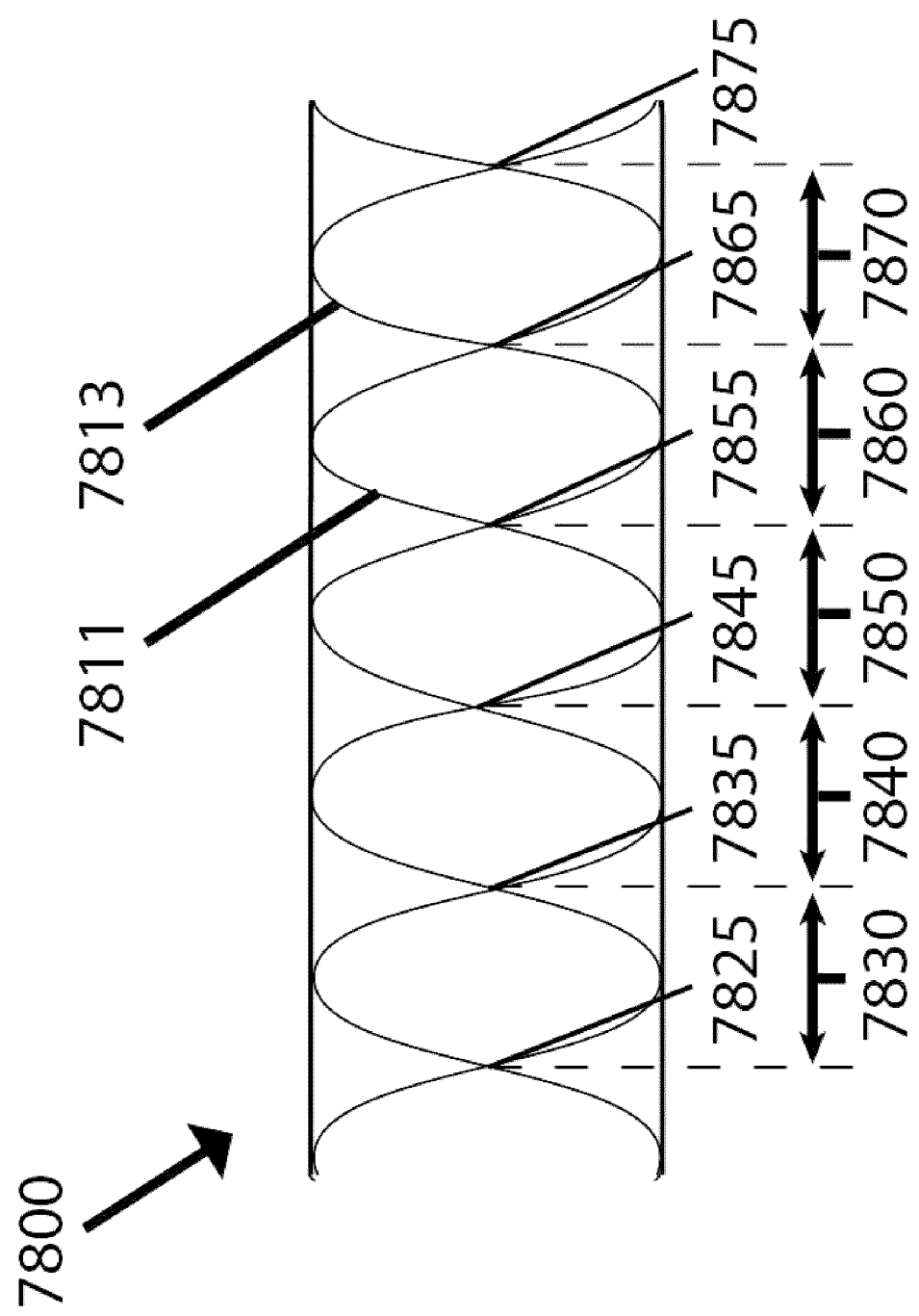

FIG. 18D is a schematic side elevational view of an example embodiment of a proximal portion of a vascular treatment device illustrating an example pattern of radiopaque filaments.

FIG. 18E is a schematic front elevational view of the proximal portion of FIG. 18D.

Figure 18F:
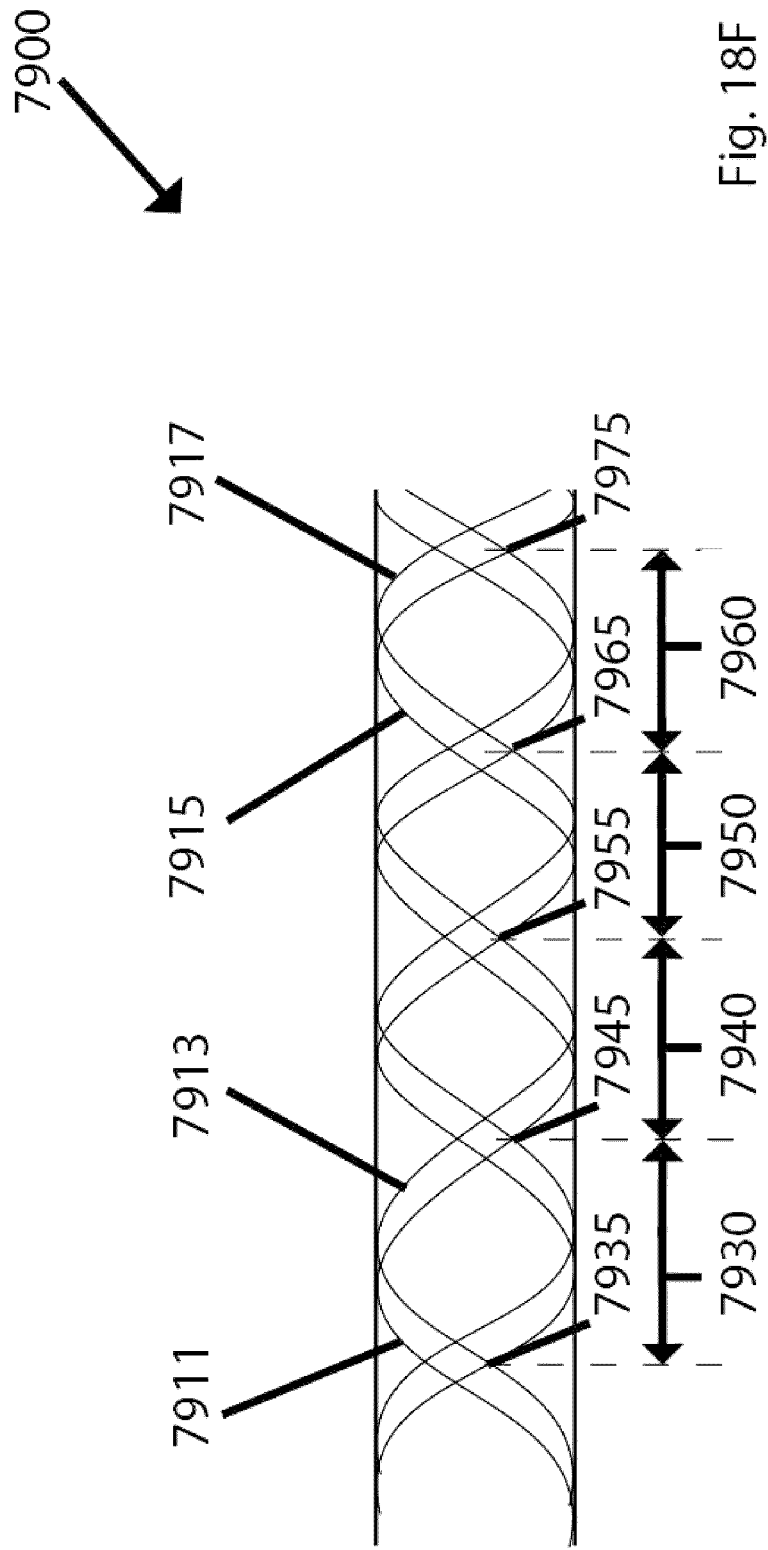

FIG. 18F is a schematic side elevational view of another example embodiment of a proximal portion of a vascular treatment device illustrating an example pattern of radiopaque filaments.

FIG. 18G is a schematic front elevational view of the proximal portion of FIG. 18F.

Figure 18H:
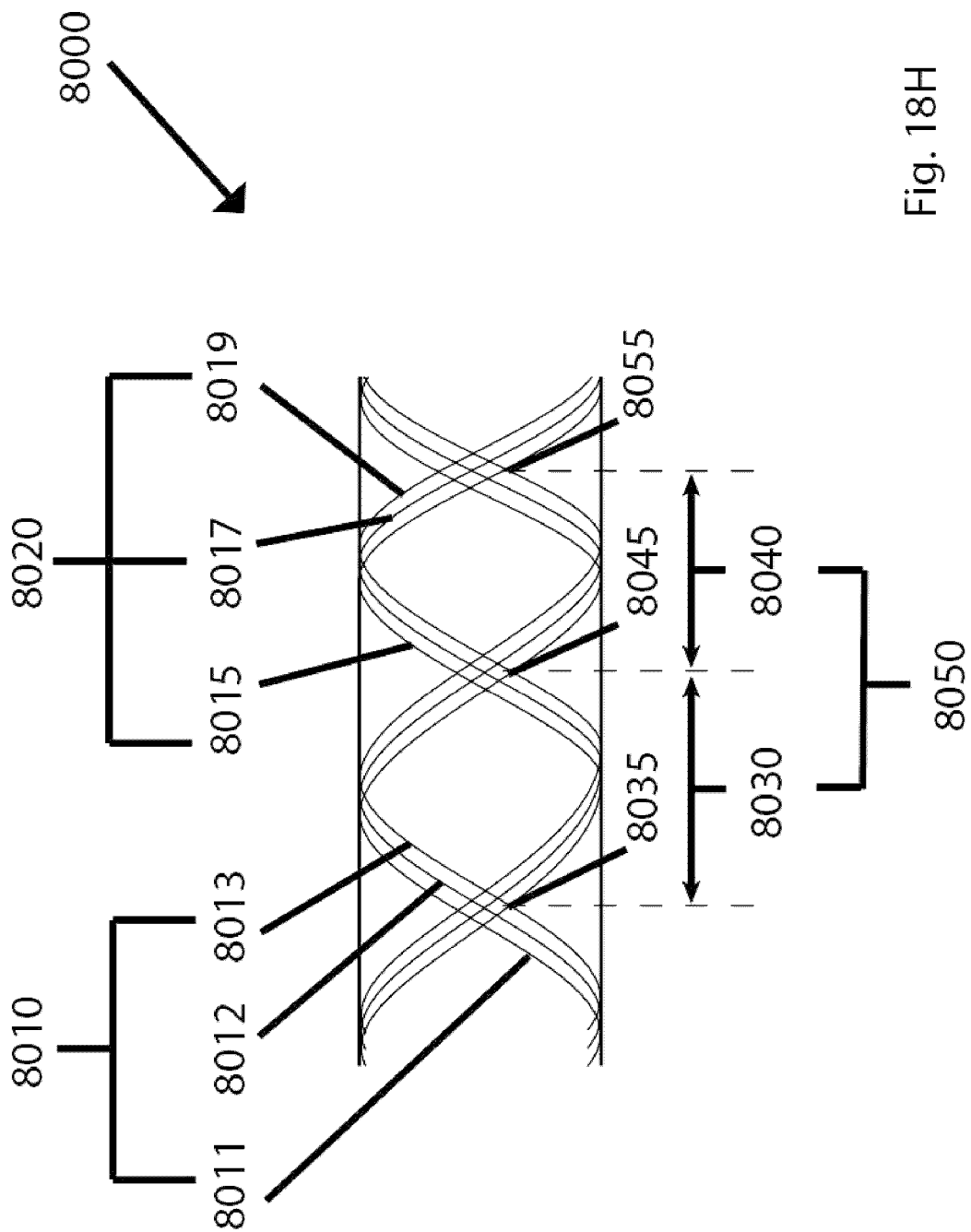

FIG. 18H is a schematic side elevational view of still another example embodiment of a proximal portion of a vascular treatment device illustrating an example pattern of radiopaque filaments.

FIG. 18I is a schematic front elevational view of the proximal portion of FIG. 18H.

Figure 18J:
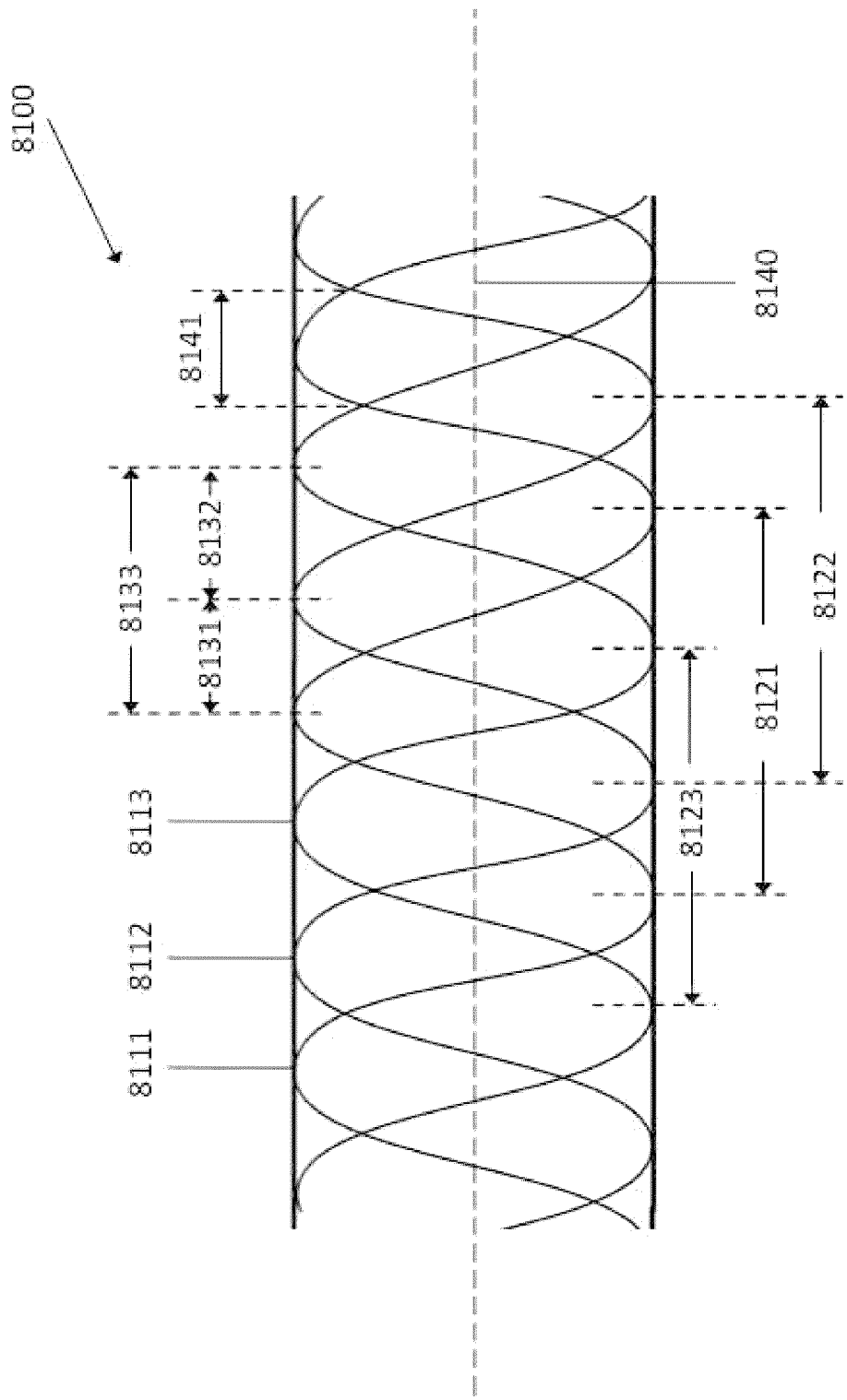

FIG. 18J is a schematic side elevational view of yet another example embodiment of a proximal portion of a vascular treatment device illustrating an example pattern of radiopaque filaments.

Figure 18K:
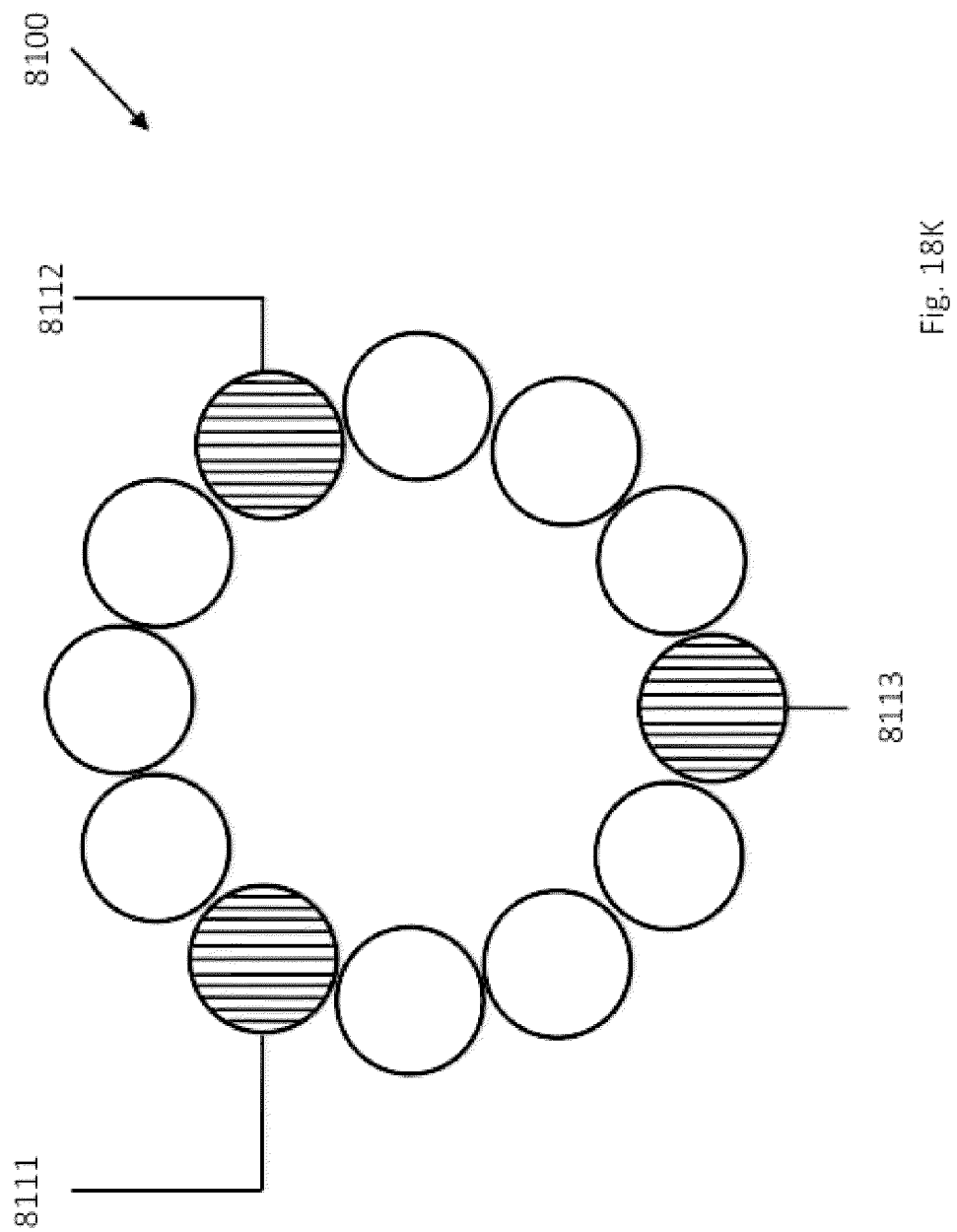

FIG. 18K is a schematic front elevational view of the proximal portion of FIG. 18J.

FIG. 18L is a schematic side elevational view of still yet another example embodiment of a proximal portion of a vascular treatment device illustrating an example pattern of radiopaque filaments.

FIG. 18M is a schematic front elevational view of the proximal portion of FIG. 18L.

Figure 18N:
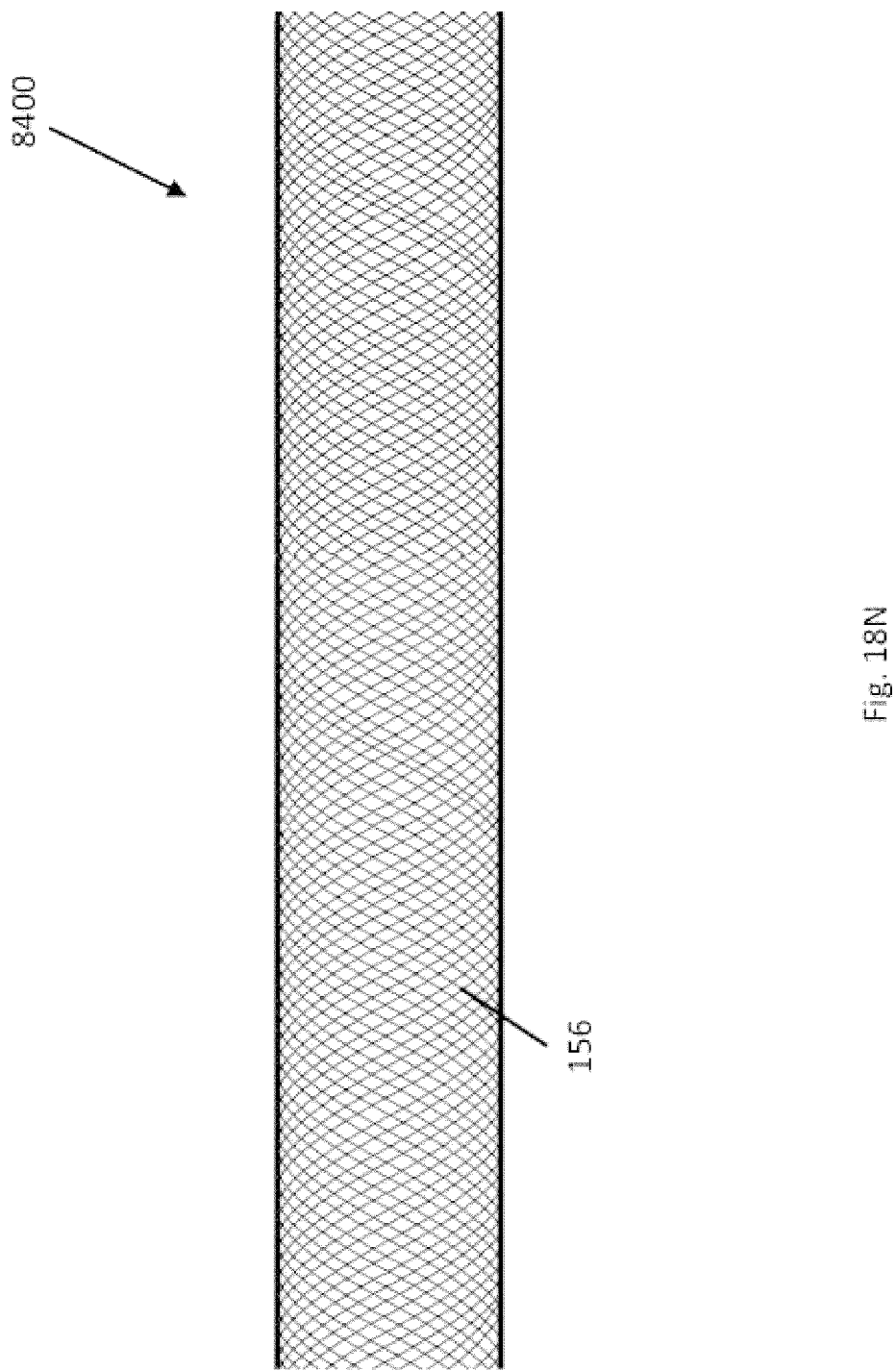

FIG. 18N is a schematic side elevational view of another example embodiment of a proximal portion of a vascular treatment device comprising a plurality of filaments.

Figure 19A:
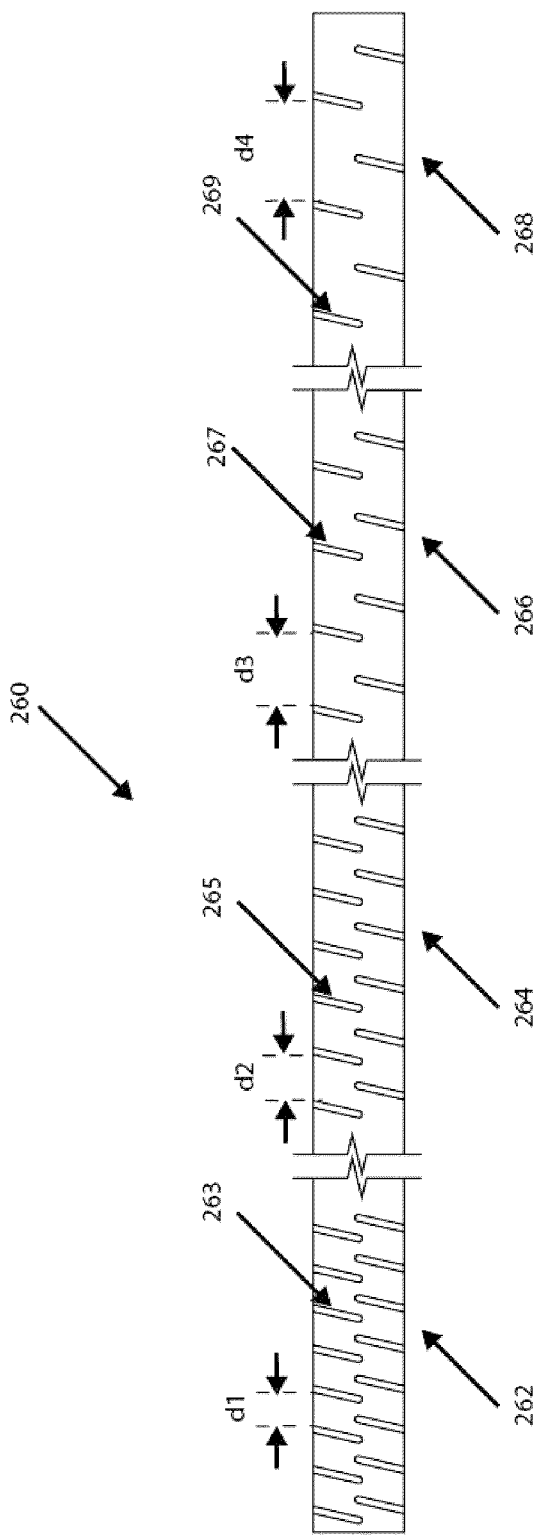

FIG. 19A is a schematic diagram illustrating an example embodiment of variation of slits along the length of an example embodiment of a proximal portion of a vascular treatment device.

Figure 19B:
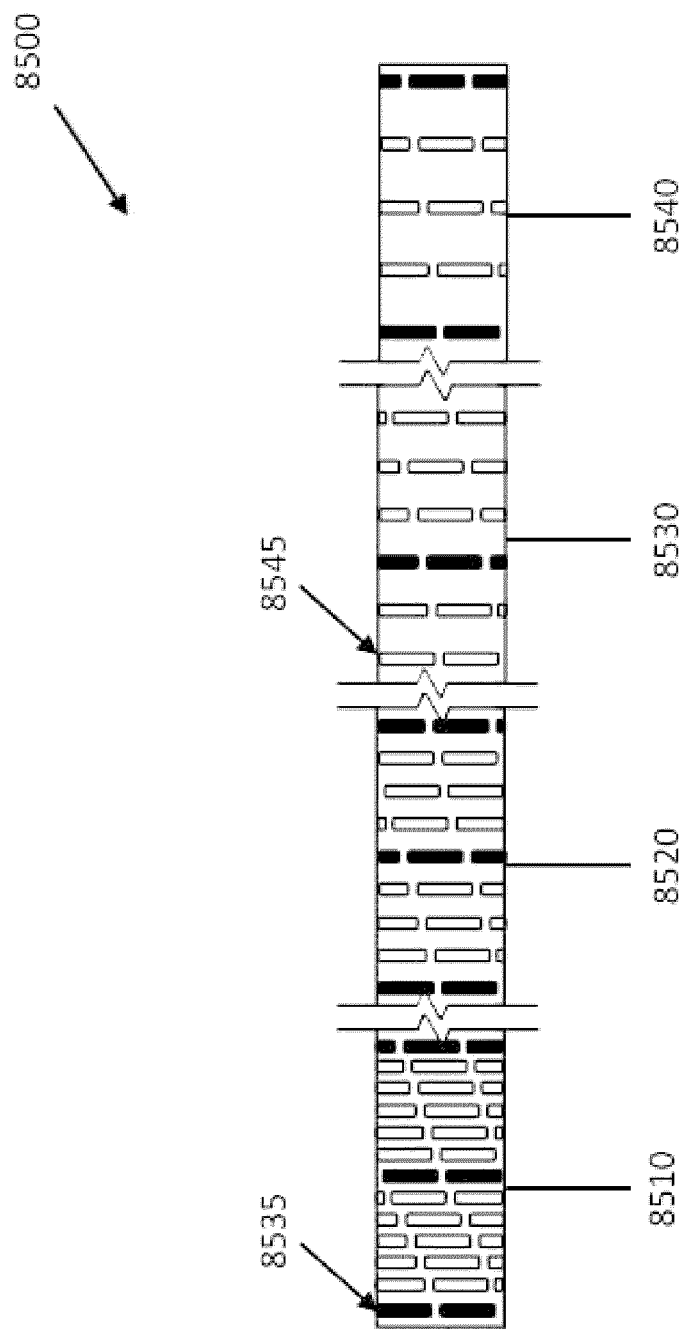

FIG. 19B is a schematic diagram illustrating an example embodiment of variation of slits and radiopaque markers along the length of an example embodiment of a proximal portion of a vascular treatment device.

Figure 19C:
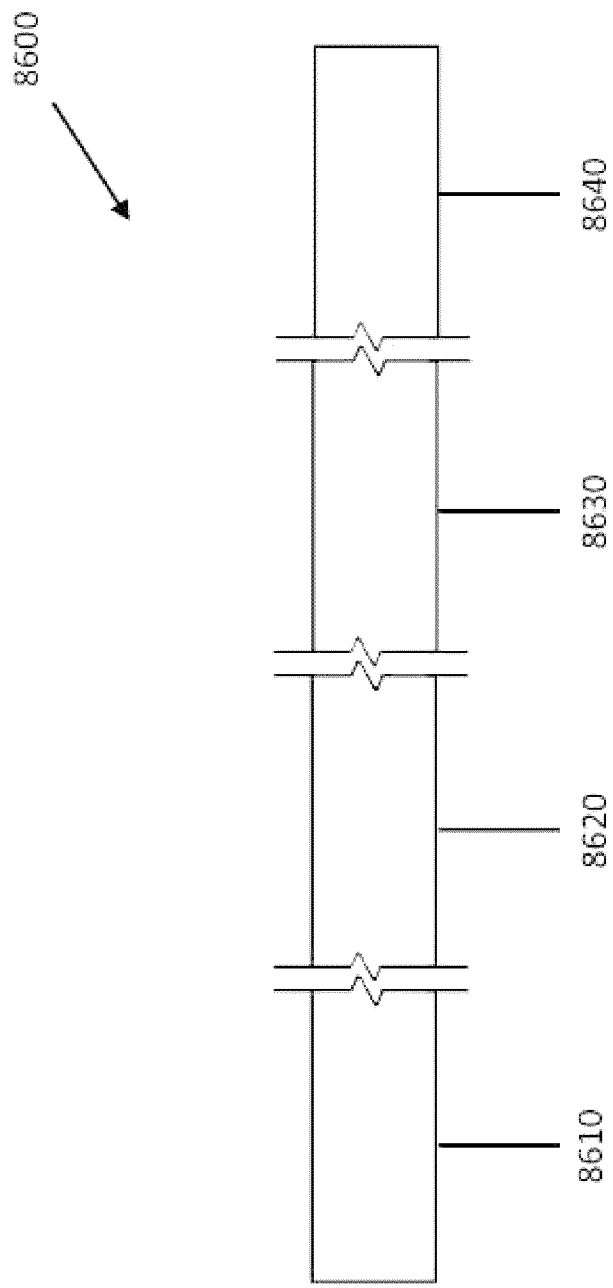

FIG. 19C is a schematic diagram illustrating still another example embodiment of a proximal portion of a vascular treatment device.

Figure 19D:
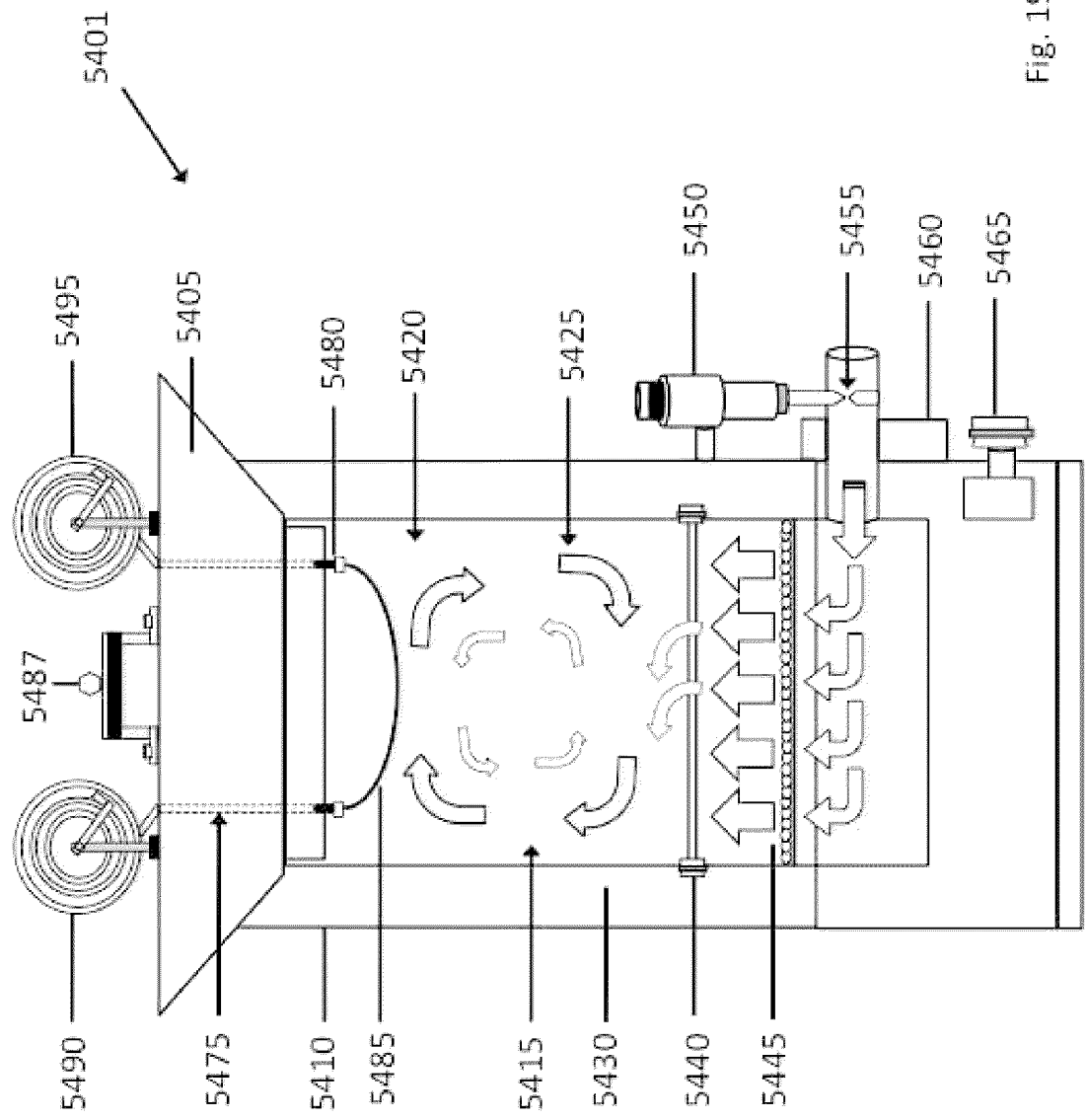

FIG. 19D is a schematic partial cut away side view of another example embodiment of a heat treatment device.

Figure 19E:
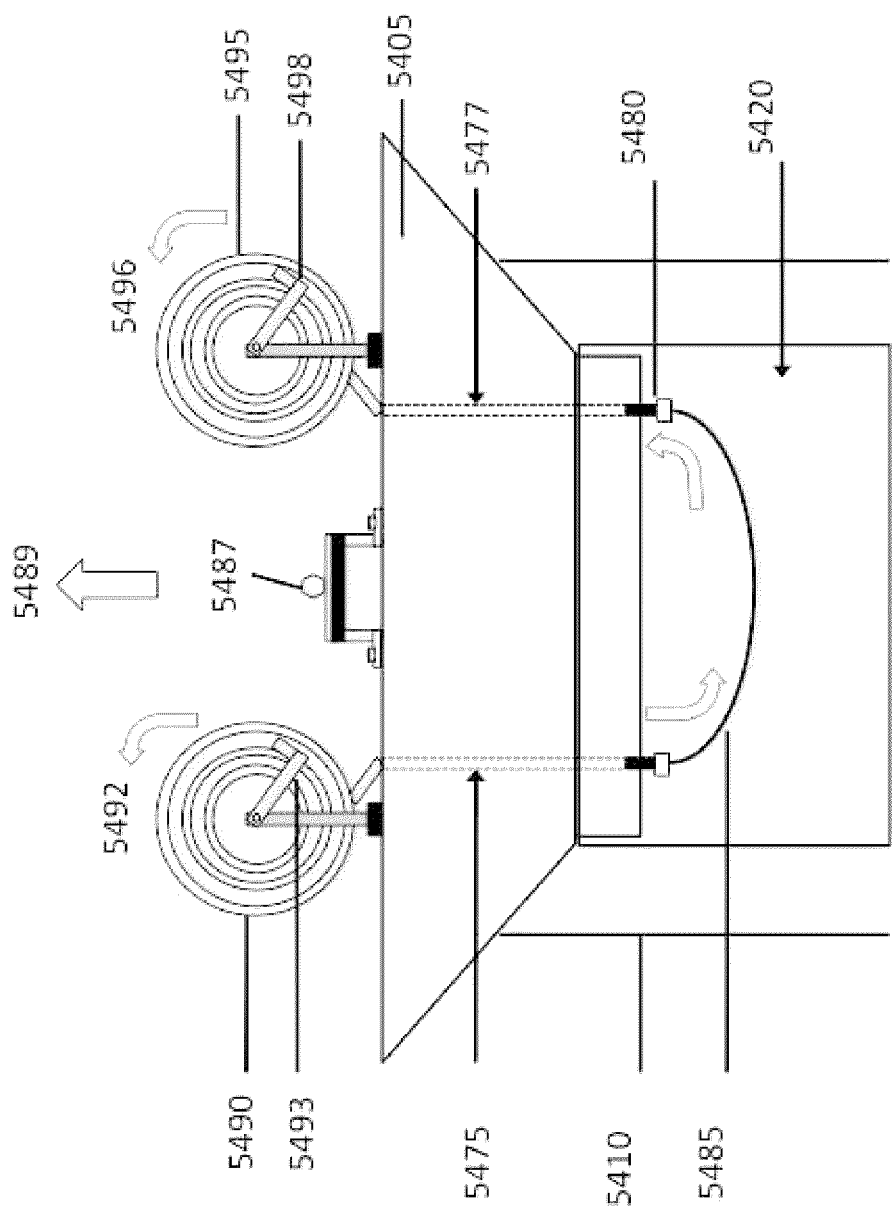

FIG. 19E is a schematic partial cut away side view of a portion of the heat treatment device of FIG. 19D.

Figures 2, 19F:
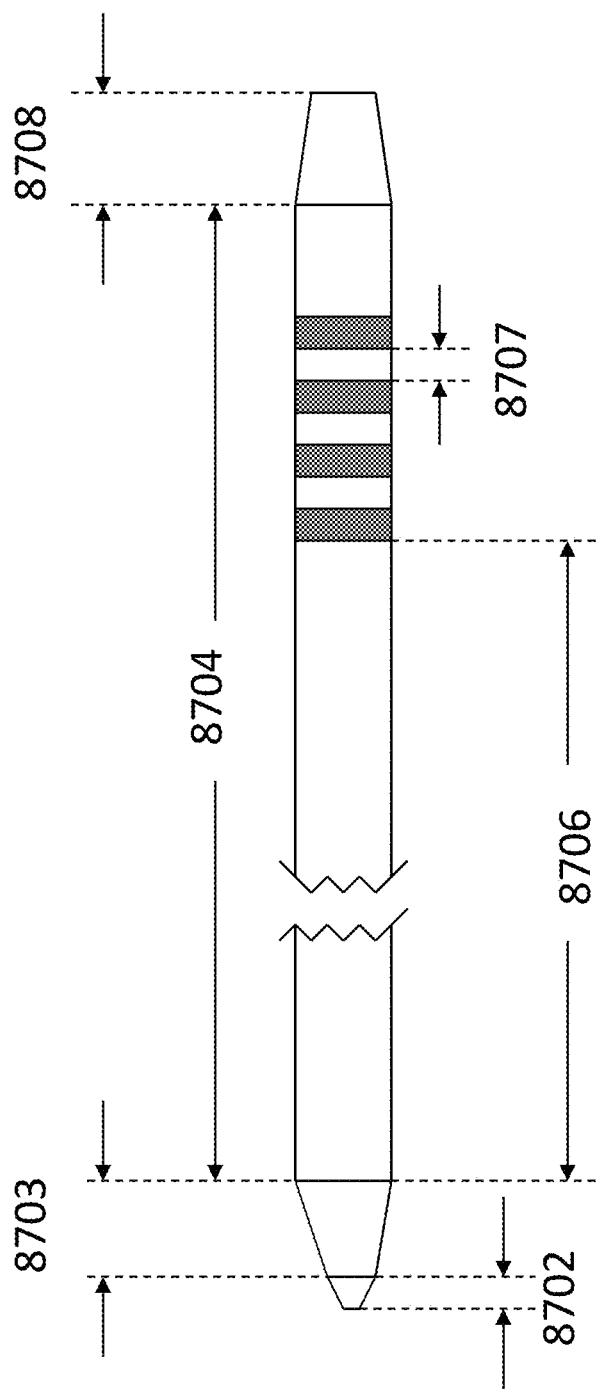

FIG. 19F is a schematic diagram illustrating still yet another example embodiment of a proximal portion of a vascular treatment device.

Figure 2A:
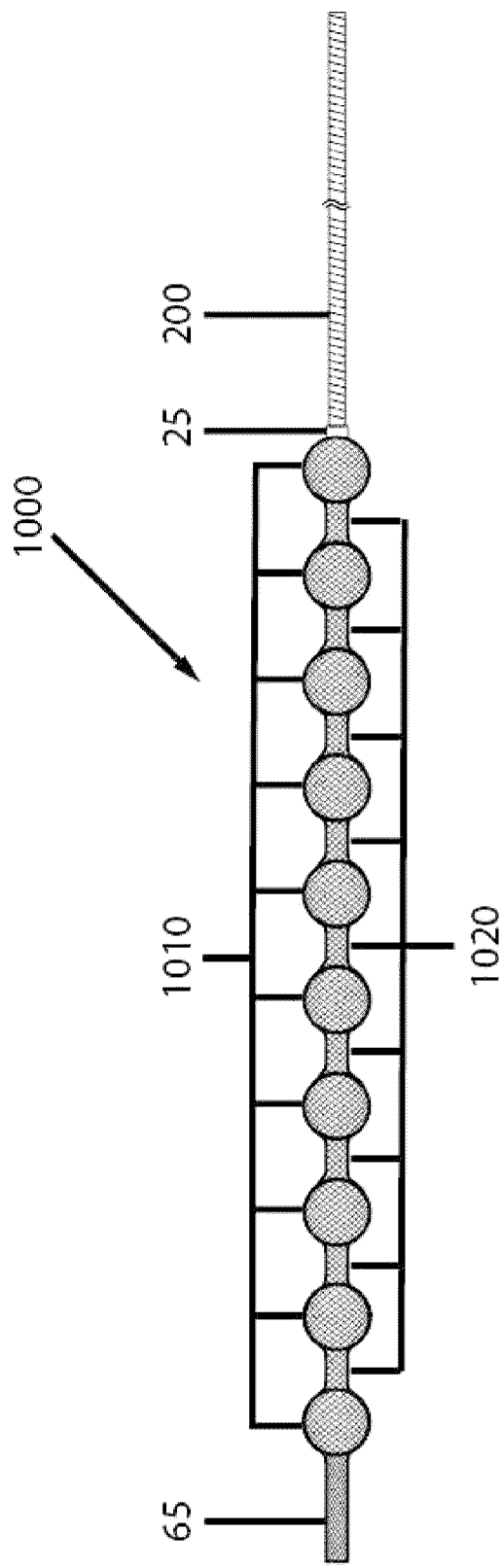
FIG. 2A is a schematic side elevational view of an example embodiment of a distal portion of a vascular treatment device.
Figure 2B:
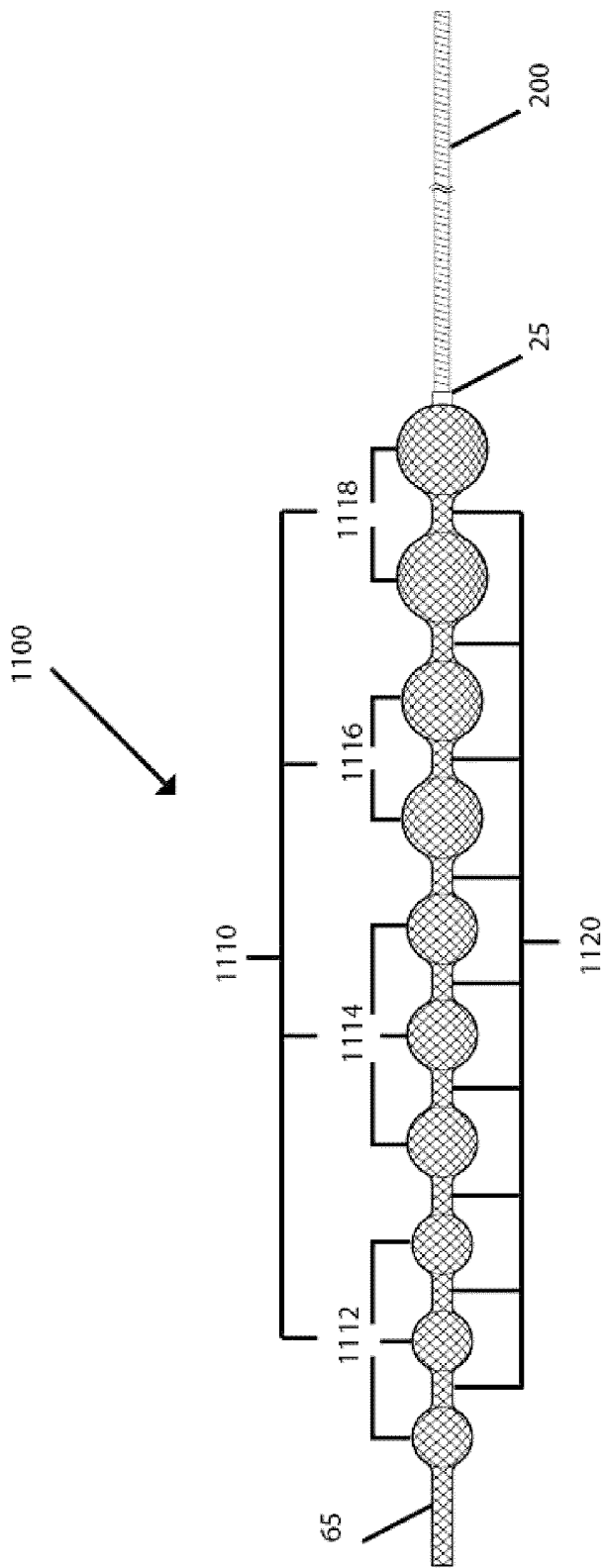
FIG. 2B is a schematic side elevational view of another example embodiment of a distal portion of a vascular treatment device.
Figure 2C:
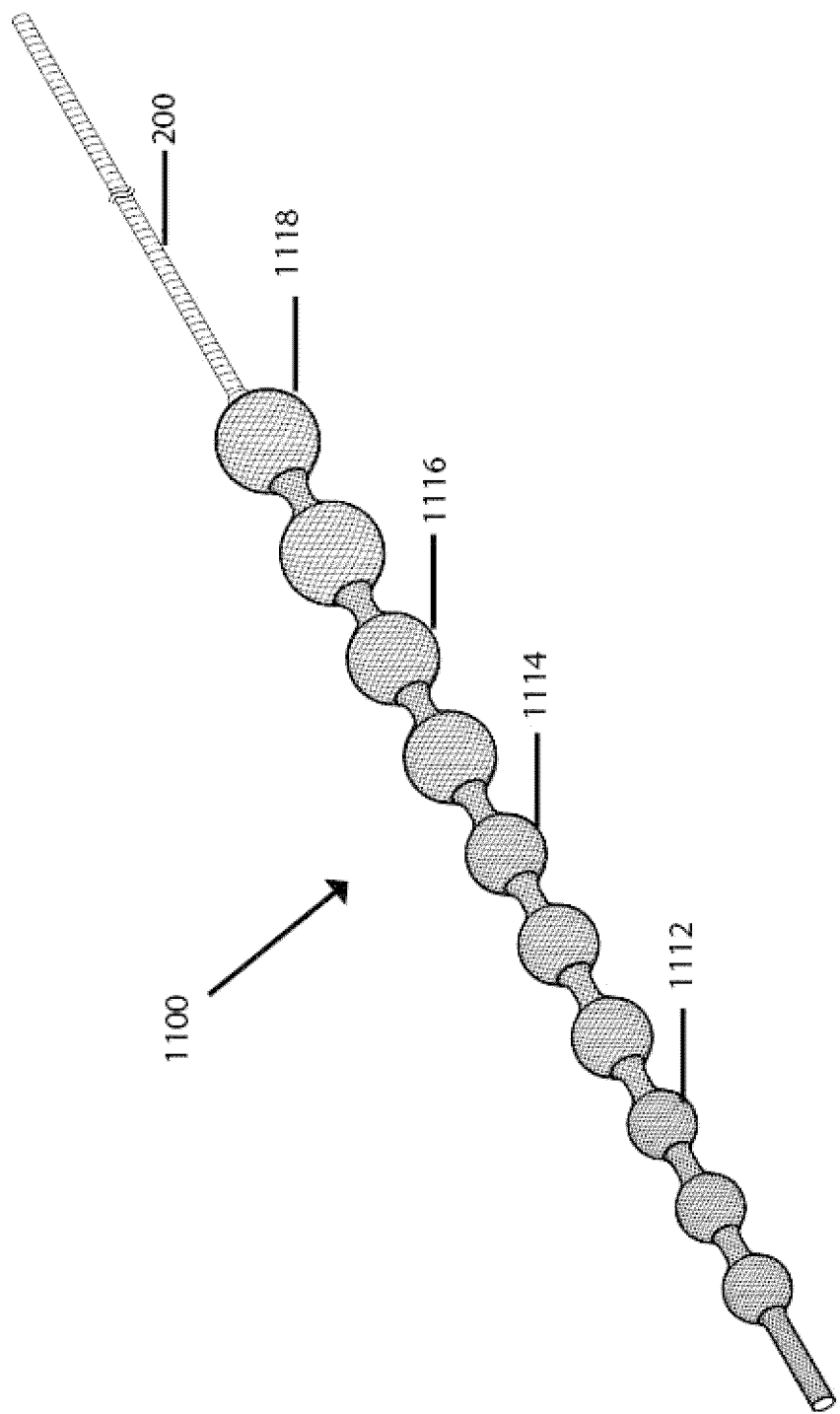
FIG. 2C is a perspective view of the distal portion of FIG. 2B.
Figure 2D:
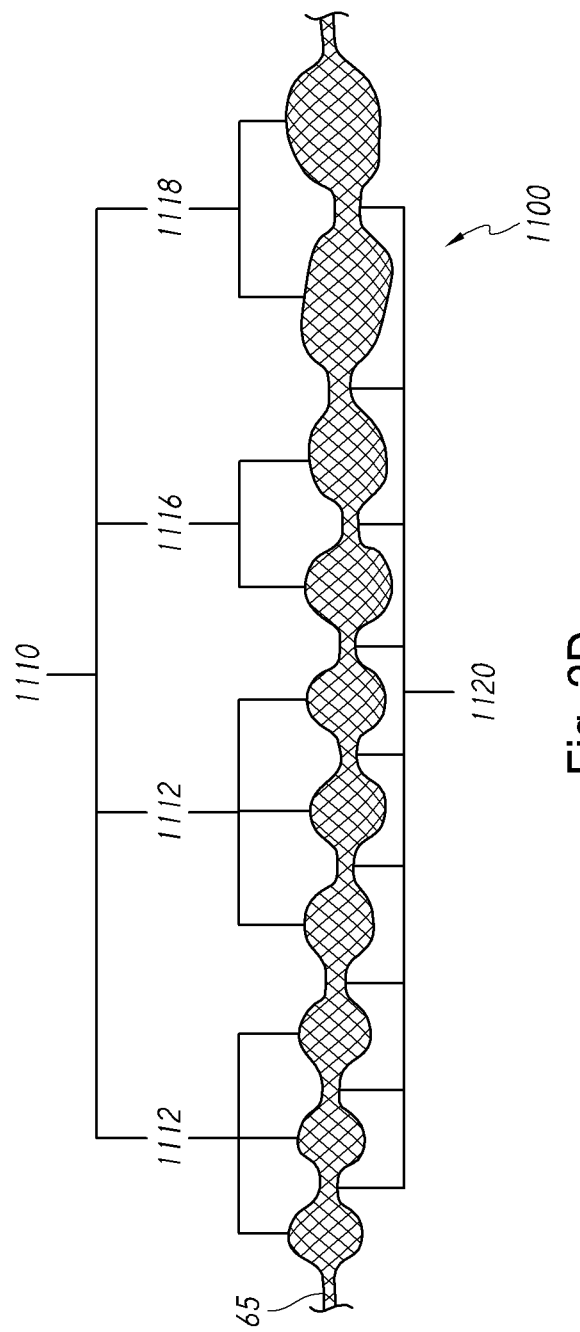
FIG. 2D is another schematic side elevational view of the distal portion of FIG. 2B.
Figure 2E:
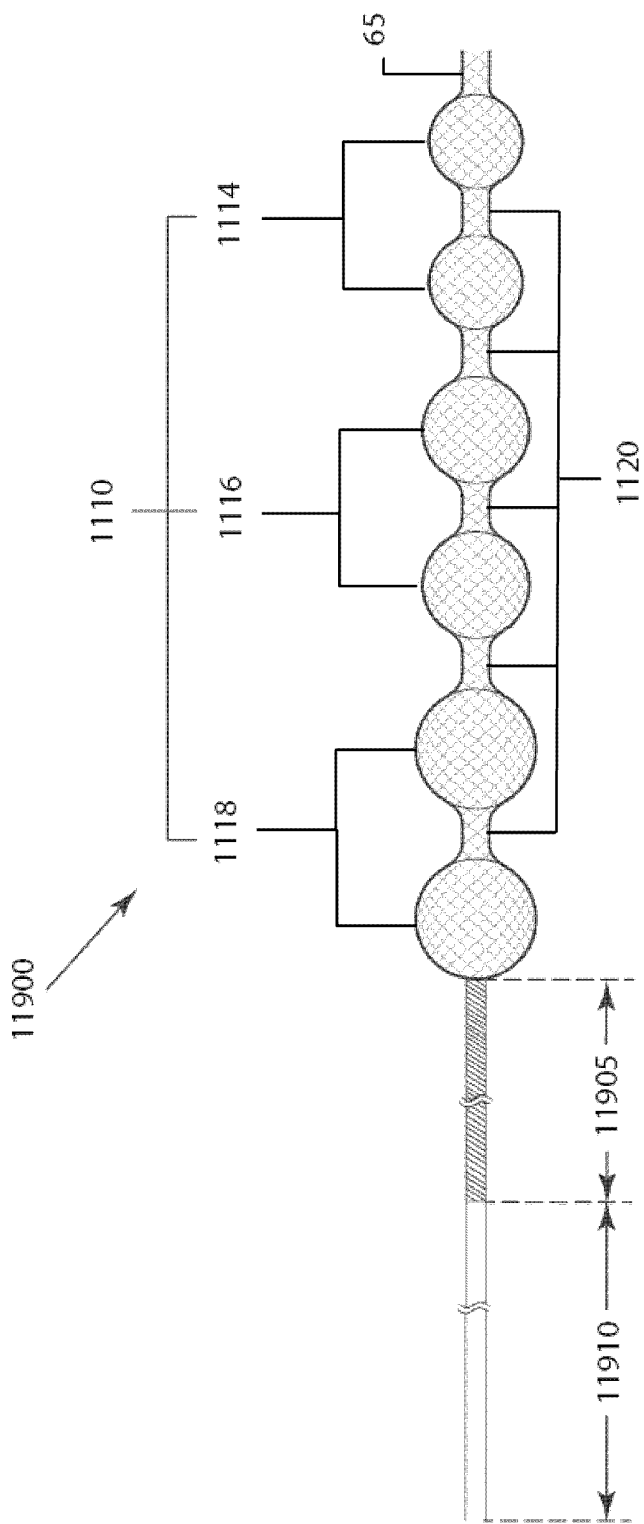
FIG. 2E is a schematic side elevational view of yet another example embodiment of a distal portion of a vascular treatment device.
Figures 2, 2E:
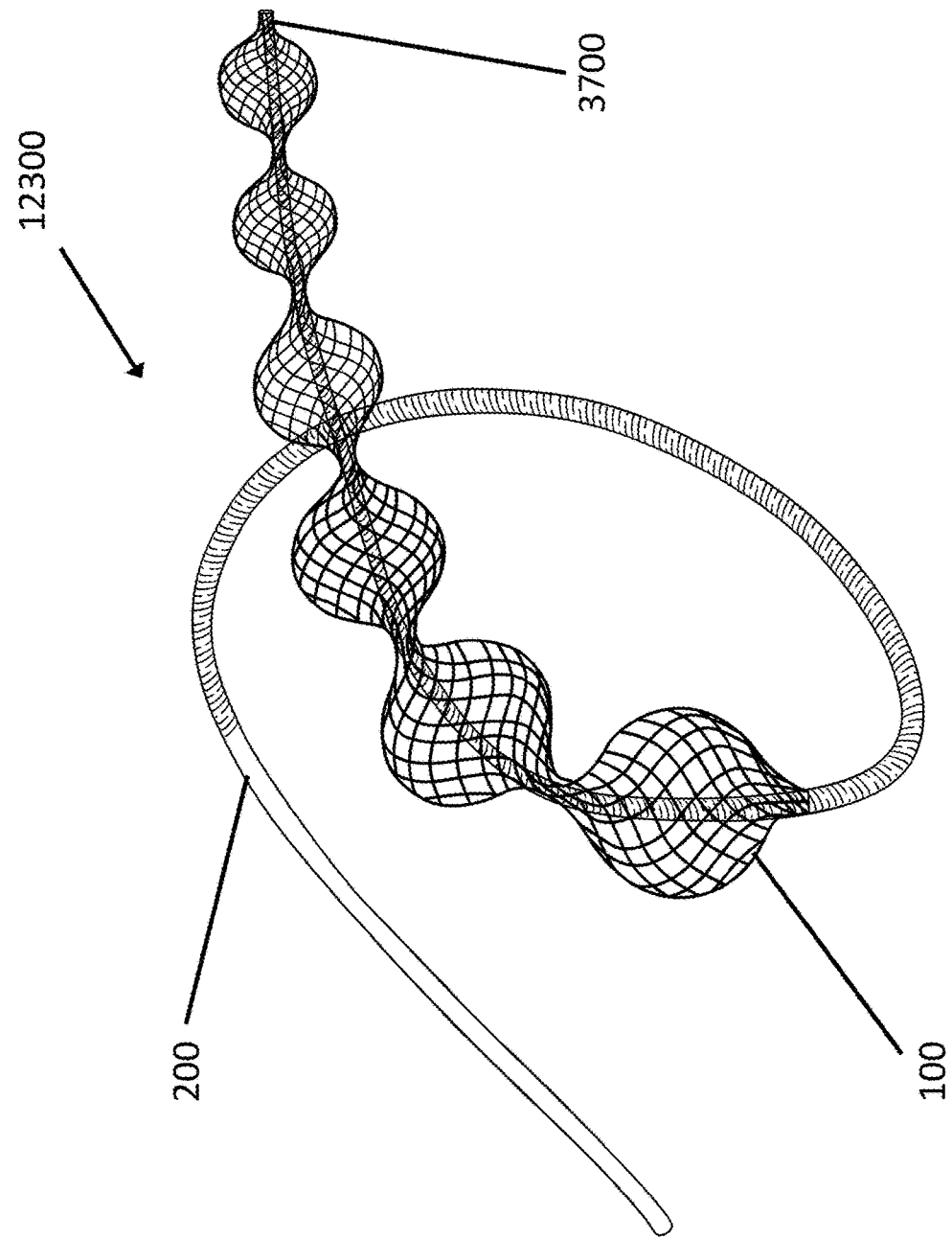

FIG. 19F-2 is a schematic diagram illustrating an example embodiment of a part of proximal portion of a vascular treatment device.

FIG. 20A is a schematic diagram illustrating an example embodiment of a joint between a proximal portion and a distal portion.

FIG. 20B is a schematic cross-section of the joint of FIG. 20A along the line 20B-20B.

Figure 20C:
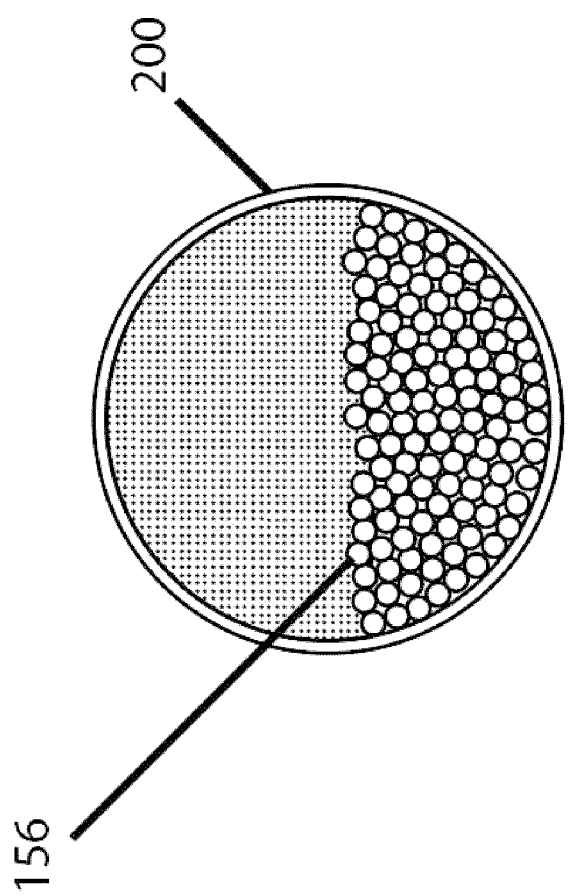

FIG. 20C is a schematic cross-section illustrating and example embodiment of filament area in comparison to tube area.

Figure 20D:
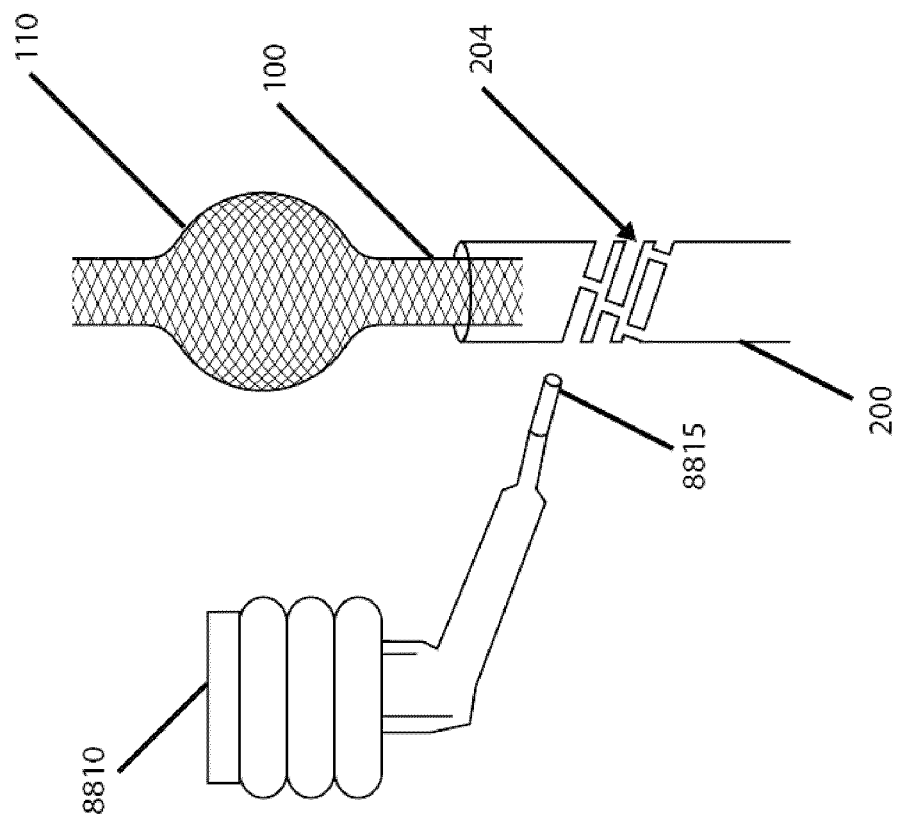
Figure 20E:
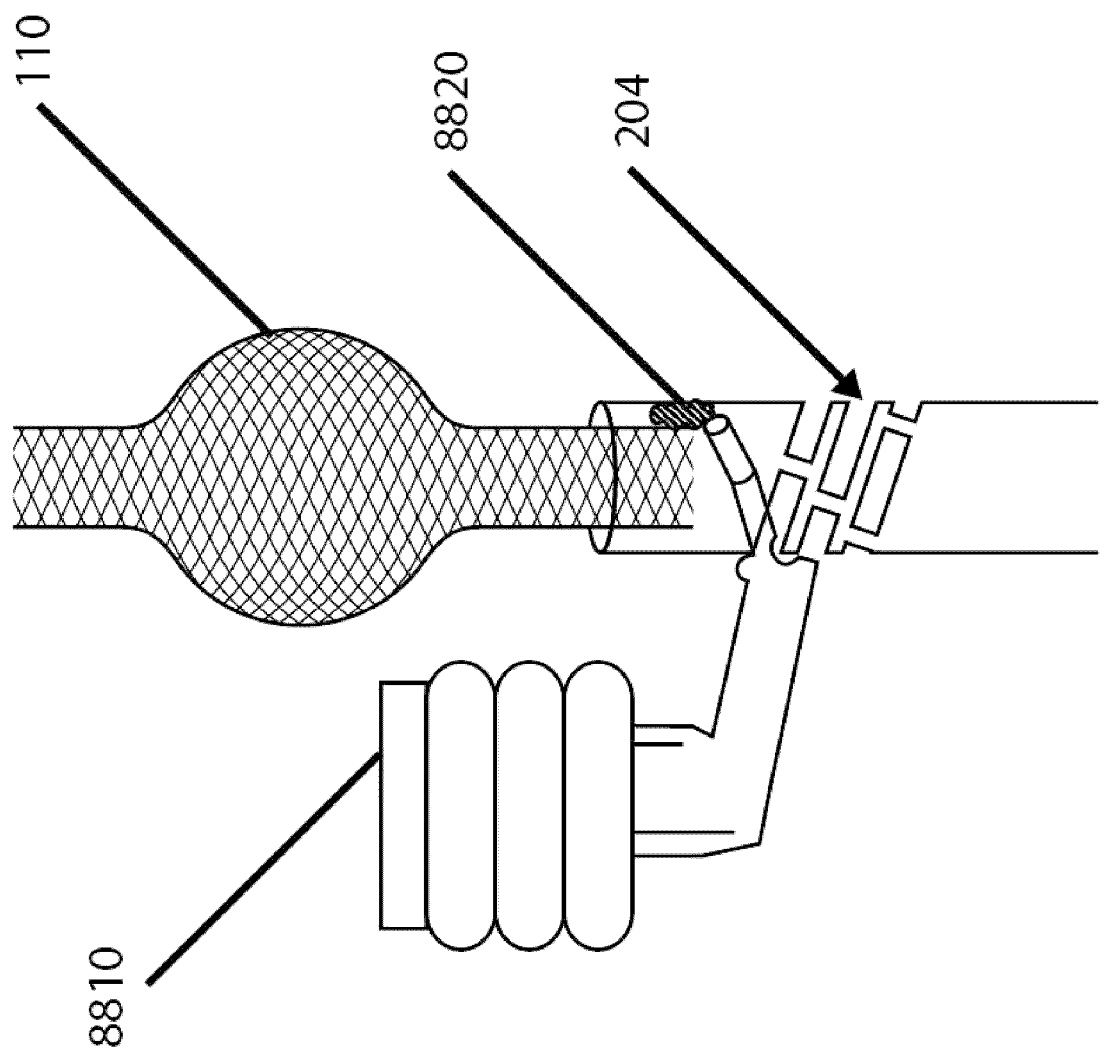
Figure 20F:
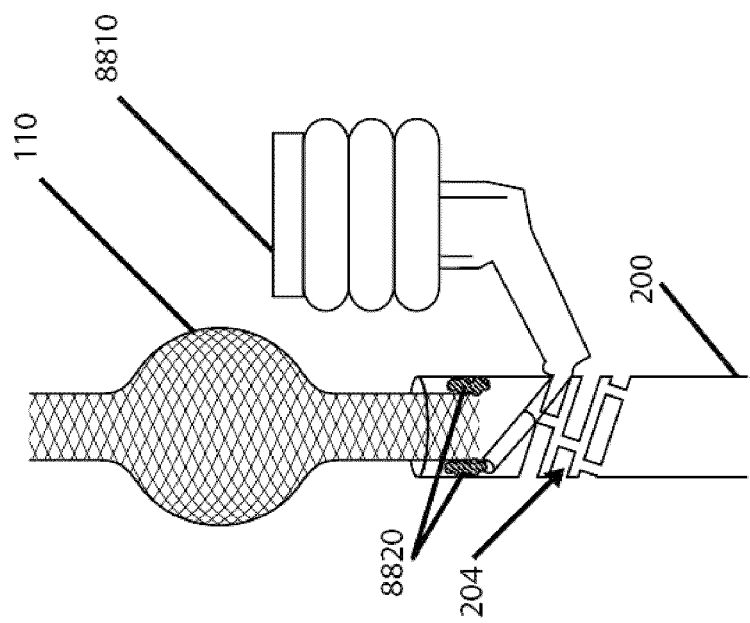

FIGS. 20D-20F schematically illustrate a method of coupling a braided tube to a hypotube.

Figure 21A:
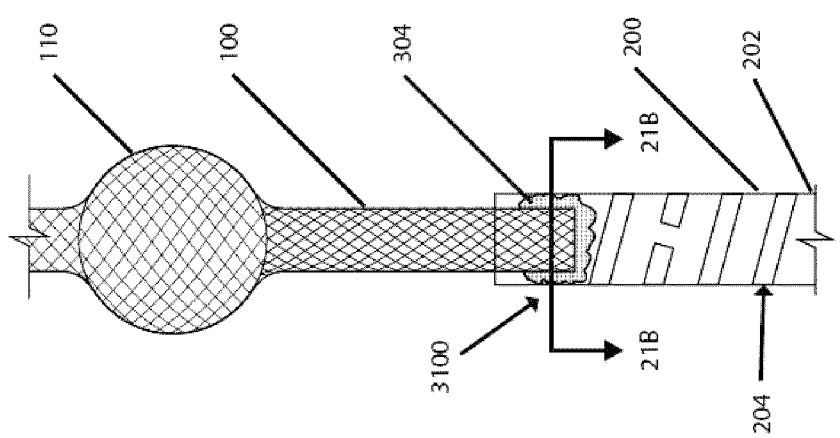

FIG. 21A is a schematic diagram illustrating another example embodiment of a joint between a proximal portion and a distal portion.

Figure 21B:
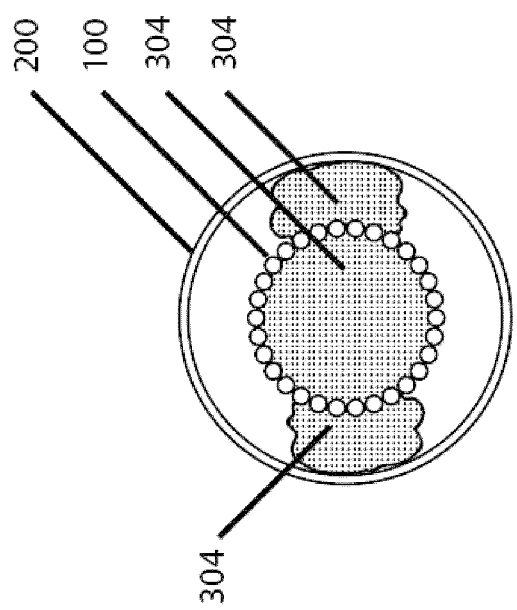

FIG. 21B is a schematic cross-section of the joint of FIG. 21A along the line 21B-21B.

Figure 21C:
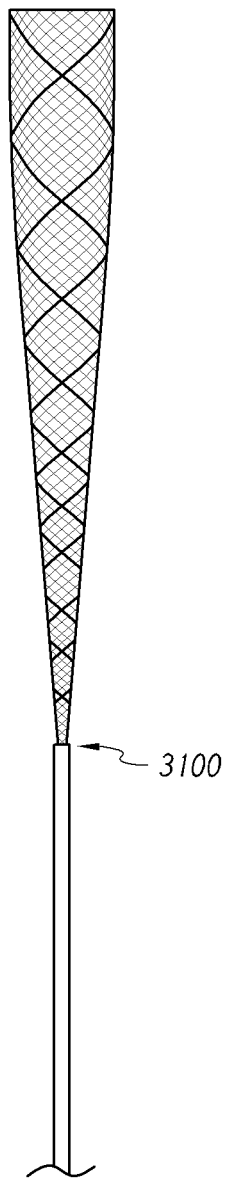

FIG. 21C is a schematic side elevational view illustrating the inlay bonding approach of FIG. 21.

Figure 22A:
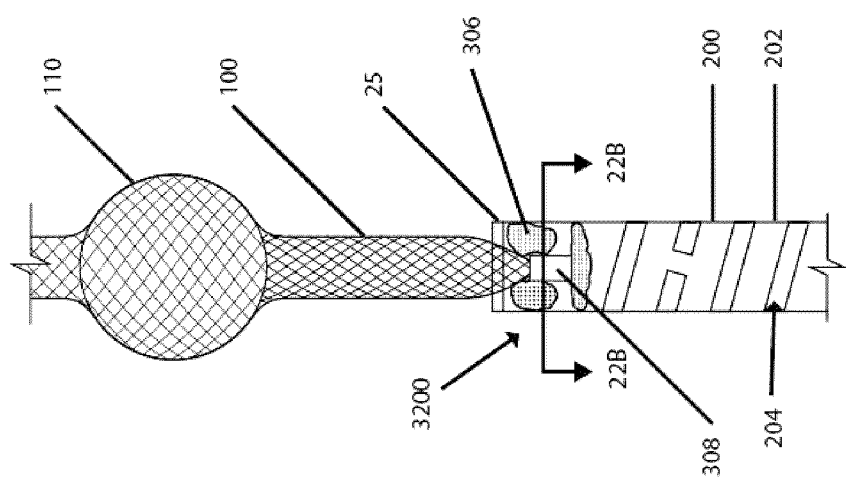

FIG. 22A is a schematic diagram illustrating yet another example embodiment of a joint between a proximal portion and a distal portion.

Figure 22B:
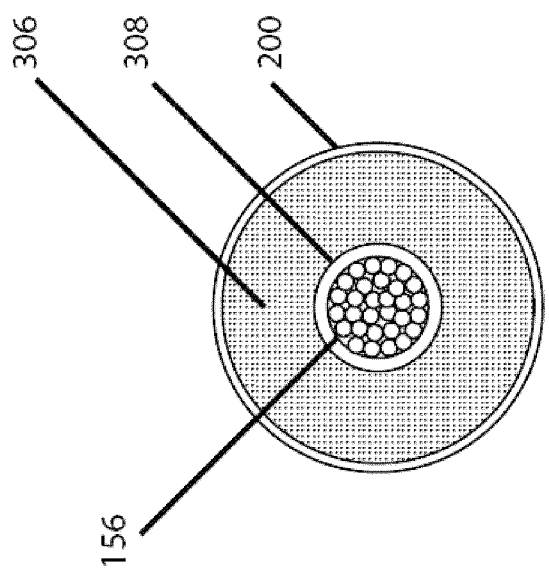

FIG. 22B is a schematic cross-section of the joint of FIG. 22A along the line 22B-22B.

Figure 23A:
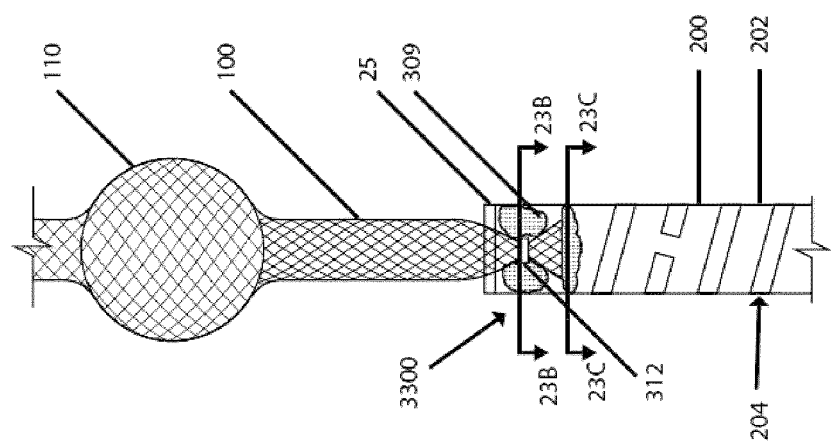

FIG. 23A is a schematic diagram illustrating still another example embodiment of a joint between a proximal portion and a distal portion.

Figure 23B:
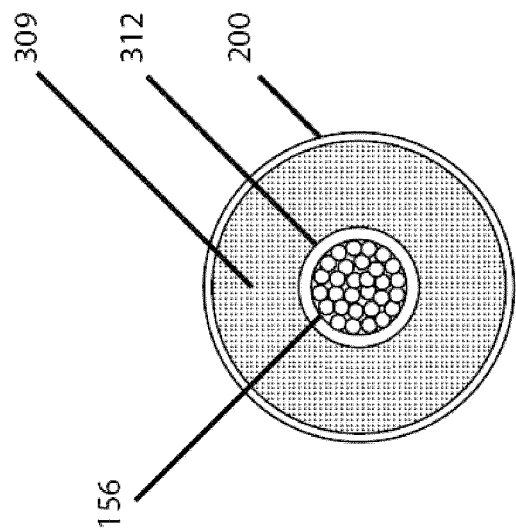

FIG. 23B is a schematic cross-section of the joint of FIG. 23A along the line 23B-23B.

Figure 23C:
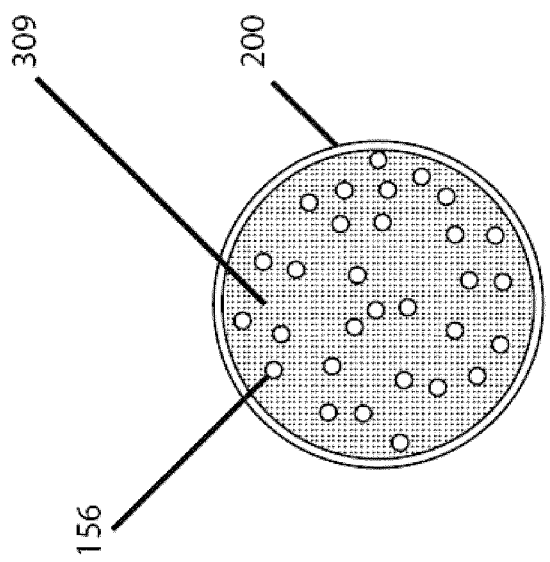

FIG. 23C is a schematic cross-section of the joint 300 of FIG. 23A along the line 23C-23C.

Figure 24A:
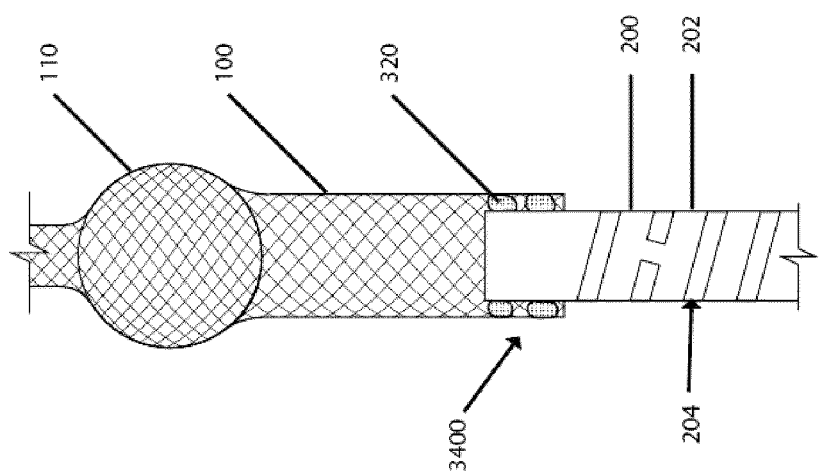

FIG. 24A is a schematic diagram illustrating another example embodiment of a joint between a proximal portion and a distal portion.

Figure 24B:
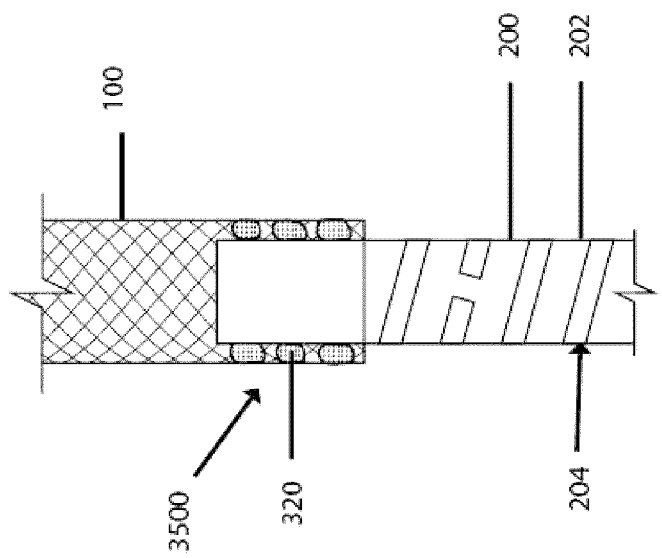

FIG. 24B is a schematic diagram illustrating yet another example embodiment of a joint between a proximal portion and a distal portion.

Figure 24C:
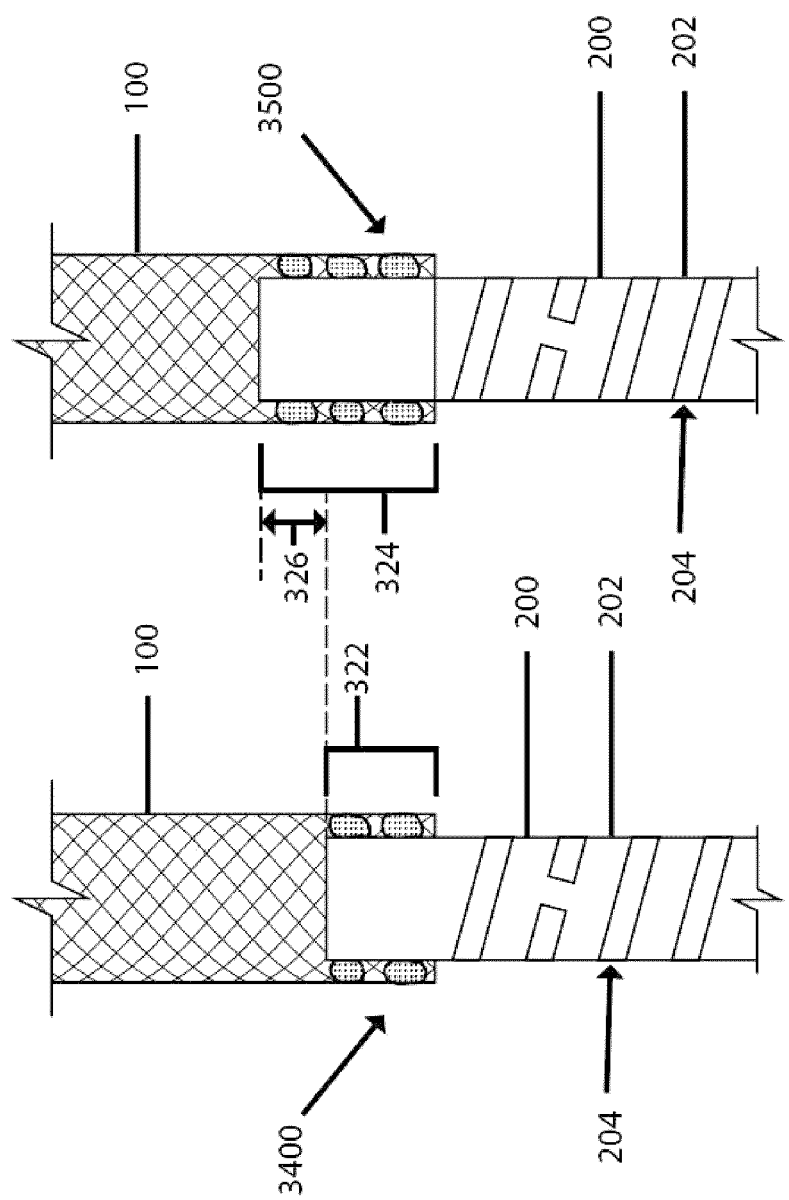

FIG. 24C is a schematic diagram showing the joints of FIGS. 24A and 24B.

Figure 24D:
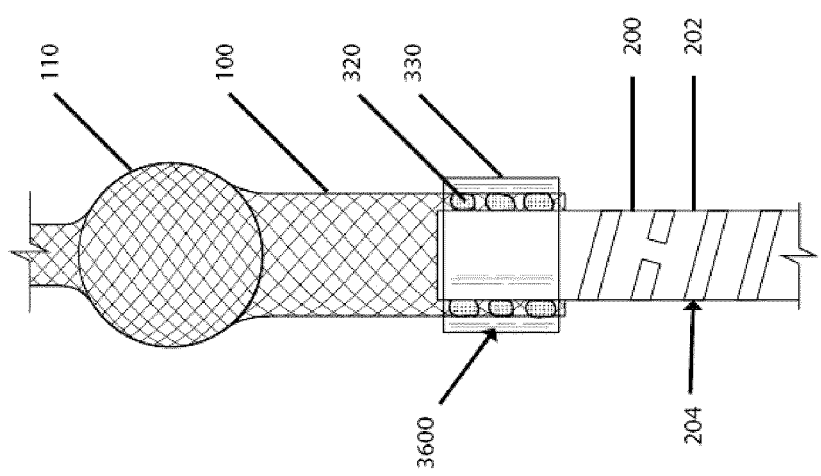

FIG. 24D is a schematic diagram illustrating yet another example embodiment of a joint between a proximal portion and a distal portion.

Figure 2F:
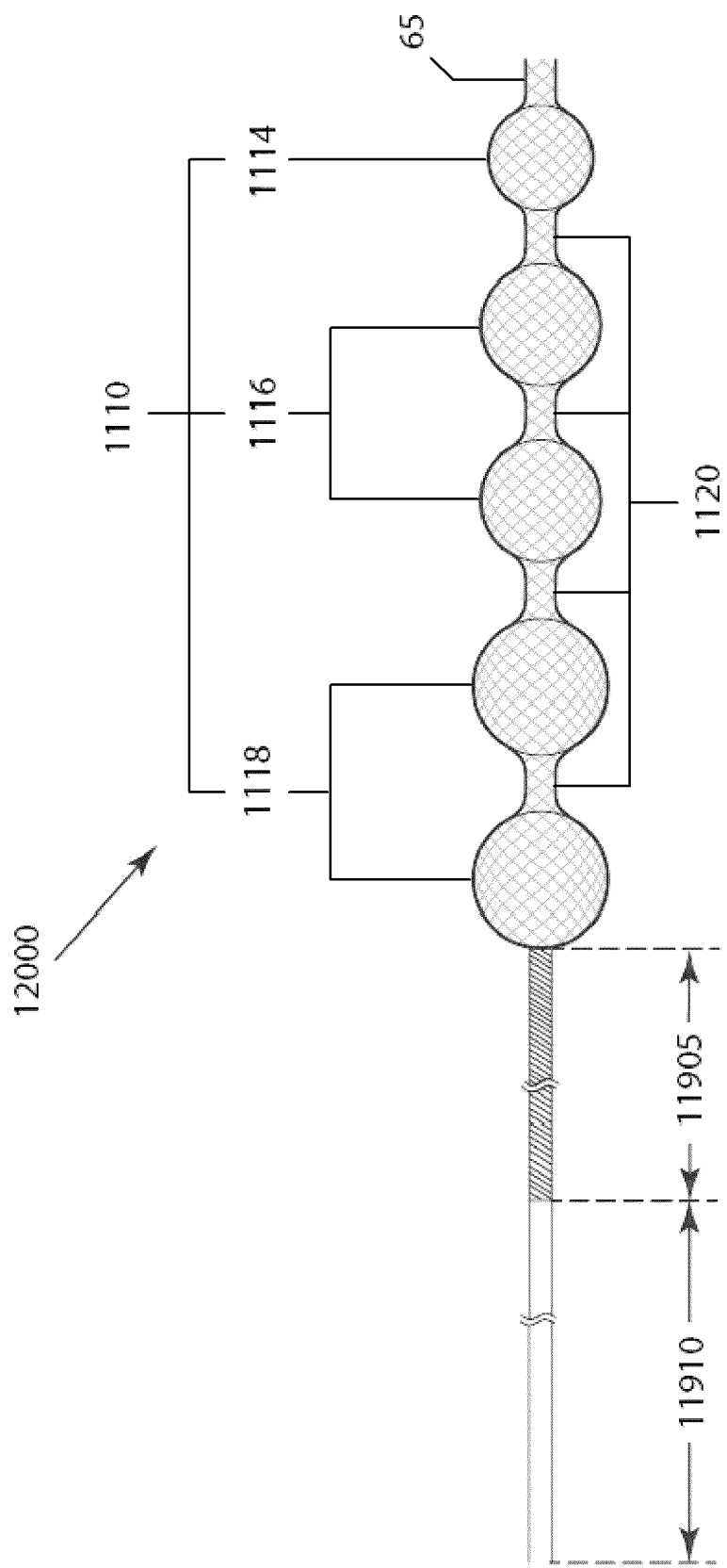
FIG. 2F is a schematic side elevational view of still yet another example embodiment of a distal portion of a vascular treatment device.
Figure 2G:
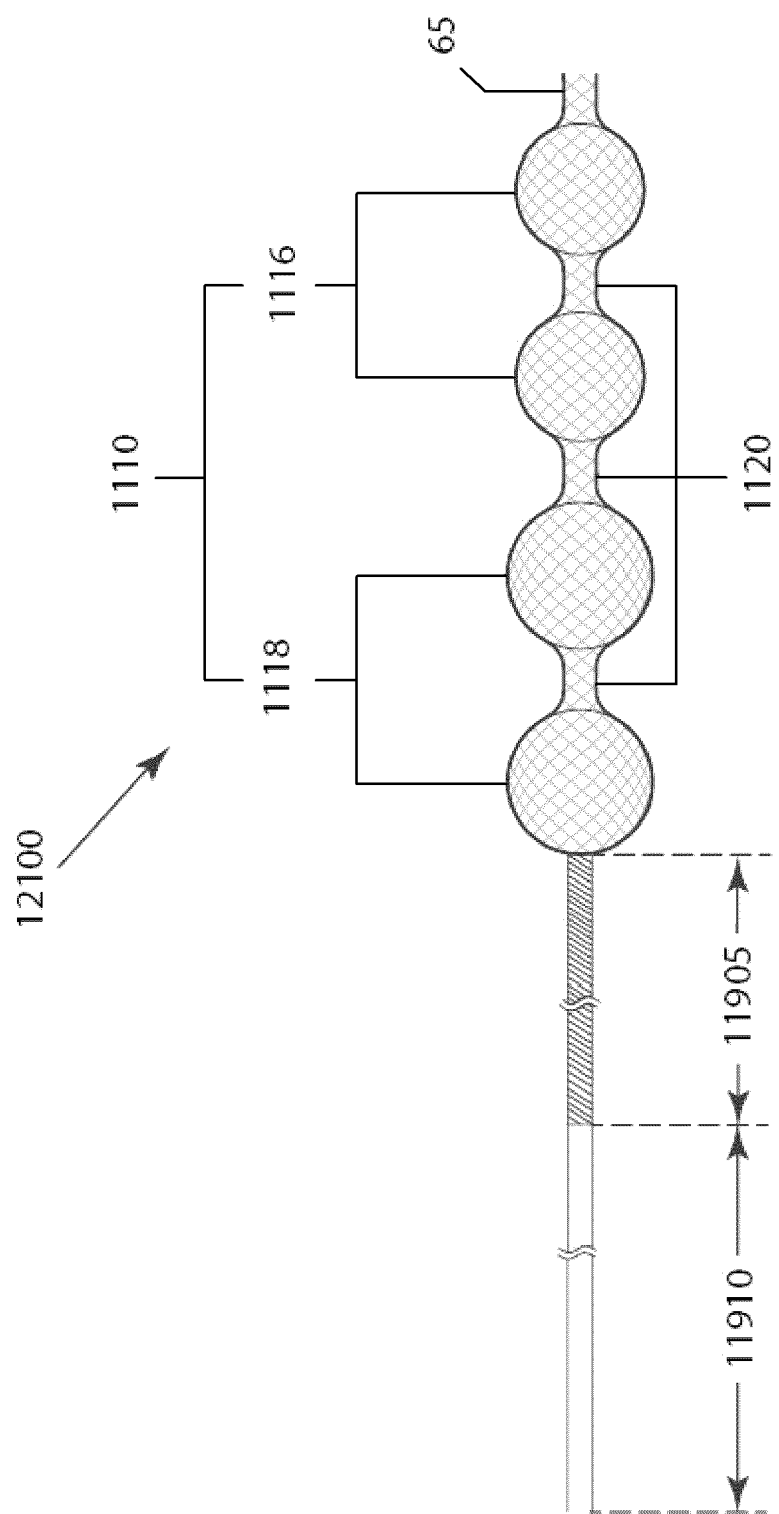
FIG. 2G is a schematic side elevational view of another example embodiment of a distal portion of a vascular treatment device.
Figures 1, 2H:
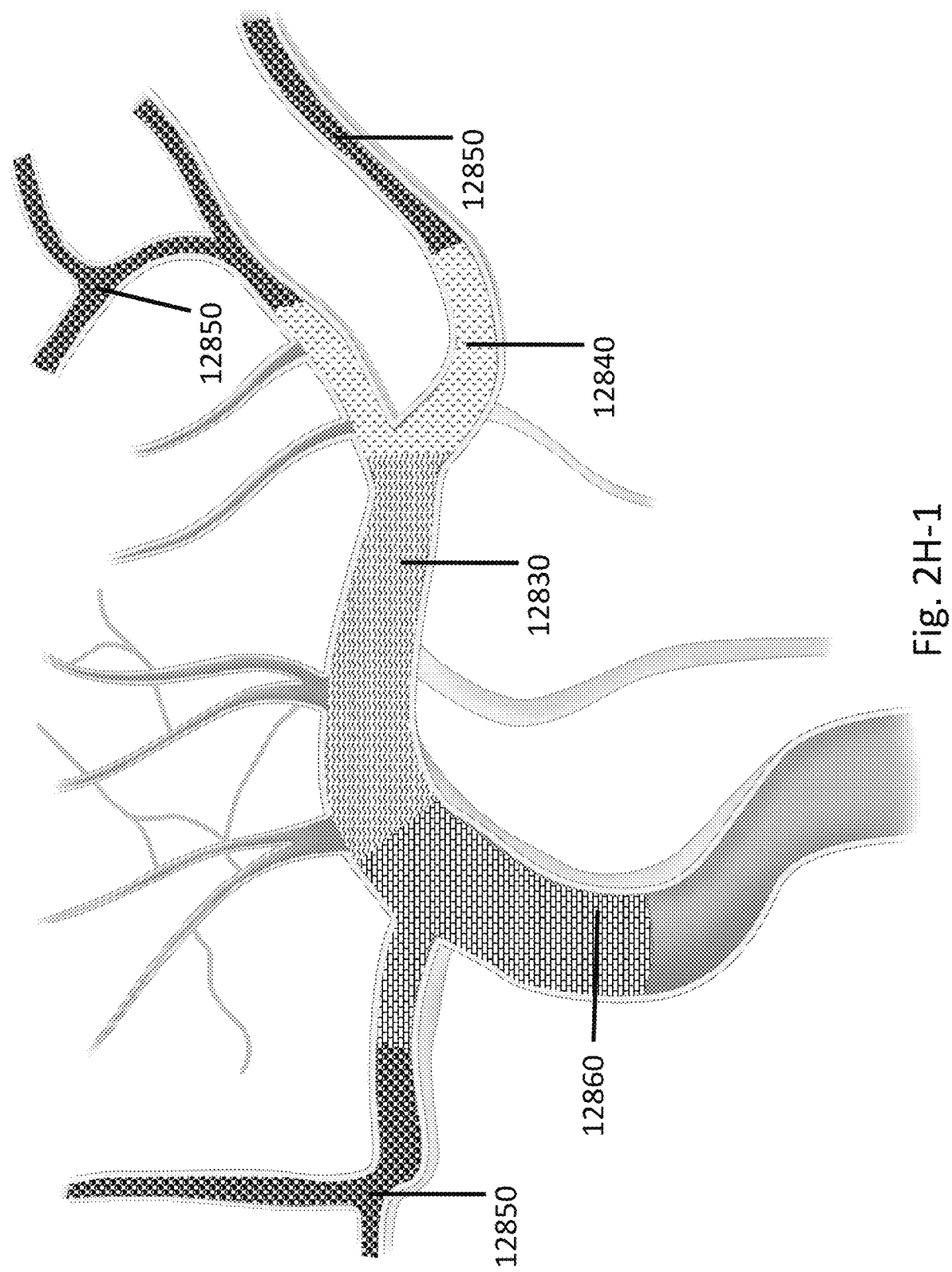
FIG. 2H-1 is a schematic diagram illustrating an example of the proximal and distal segments of the cerebral vasculature.
Figures 2, 2H:
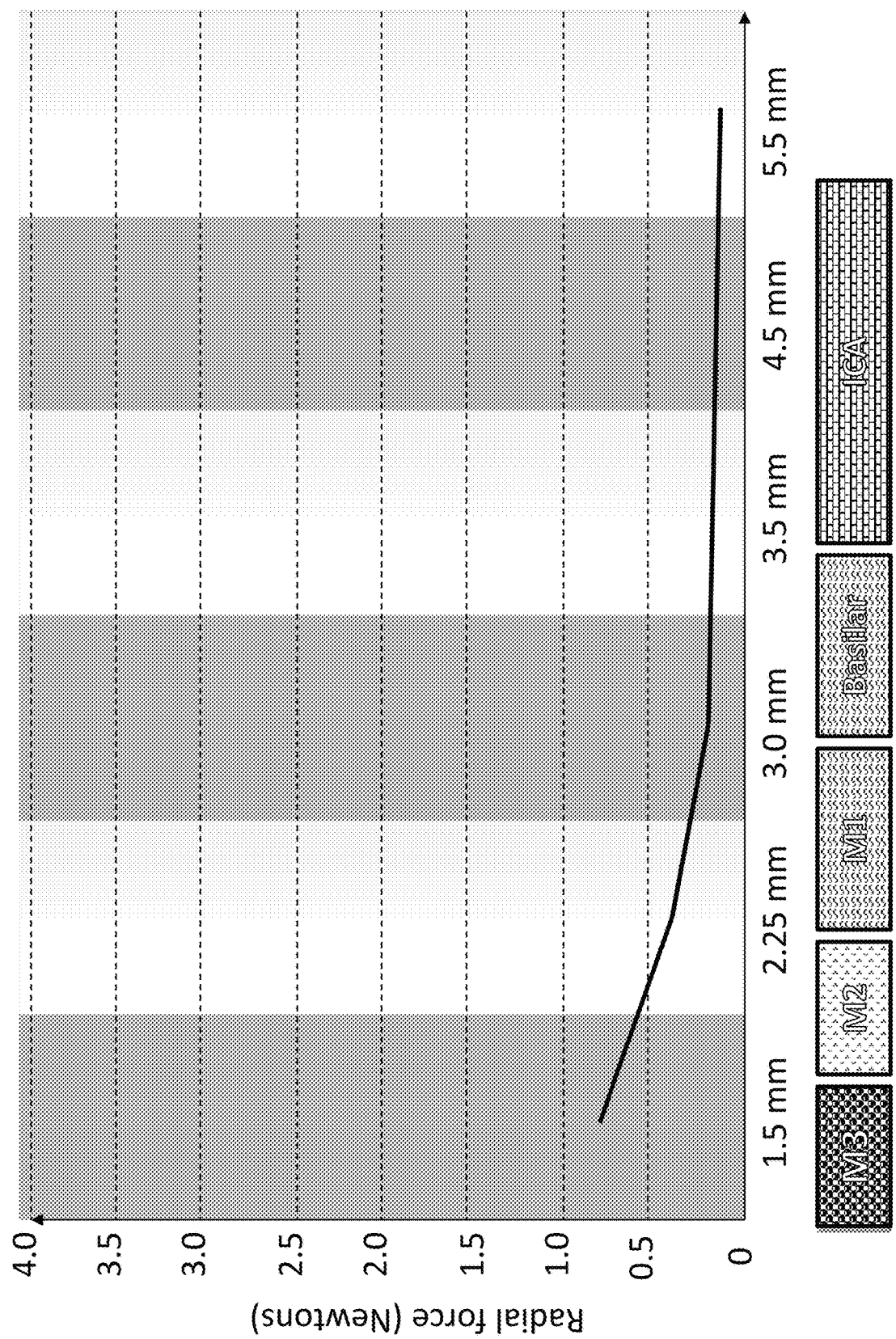
Figures 2, 25A:
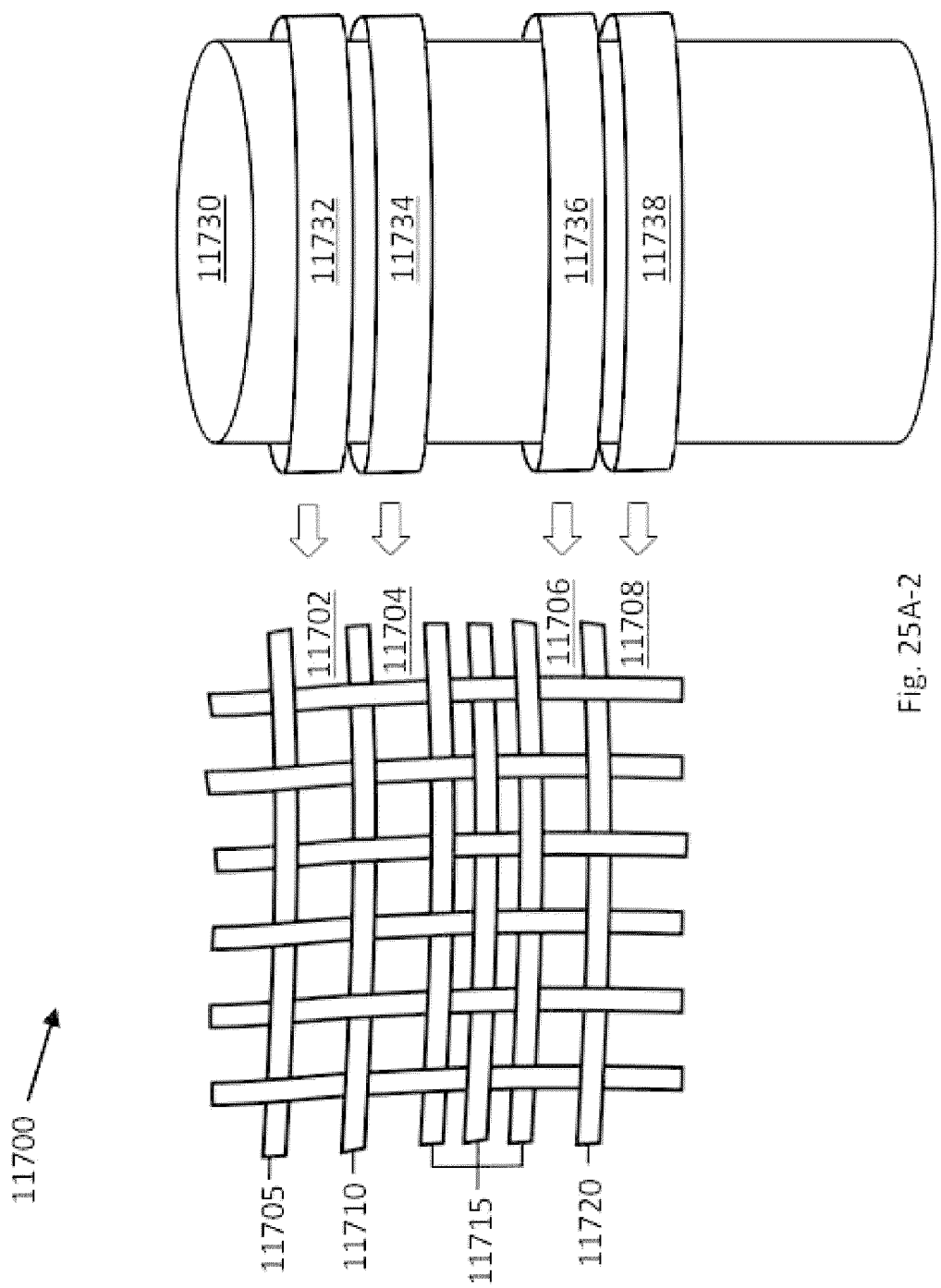

FIG. 25A-1 is a schematic diagram illustrating an example embodiment of a mechanical detachment system.

FIG. 25A-2 is a schematic diagram illustrating an example embodiment of the components of the mechanical detachment system of FIG. 25A-1.

Figure 25B:
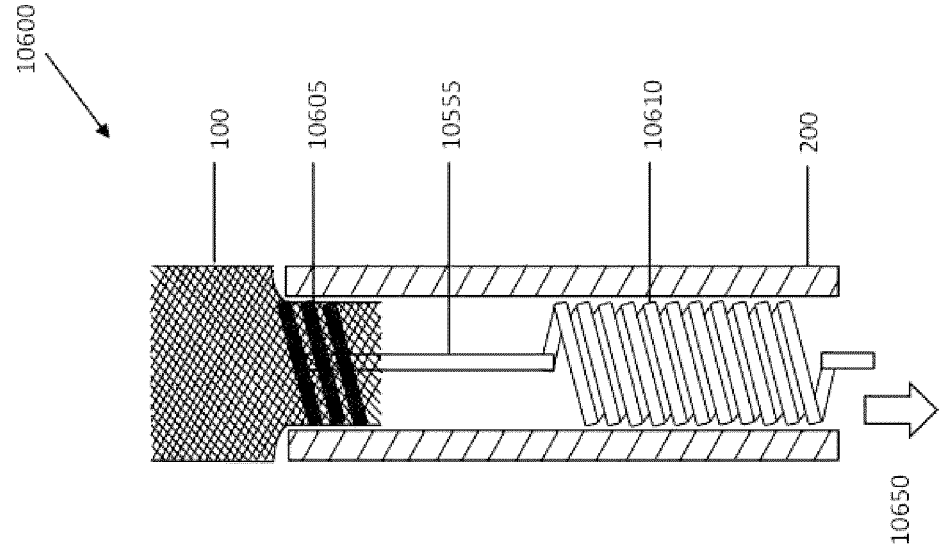

FIG. 25B is a schematic diagram of a partial cross-sectional view of an example embodiment of a mechanical detachment system.

Figure 25C:
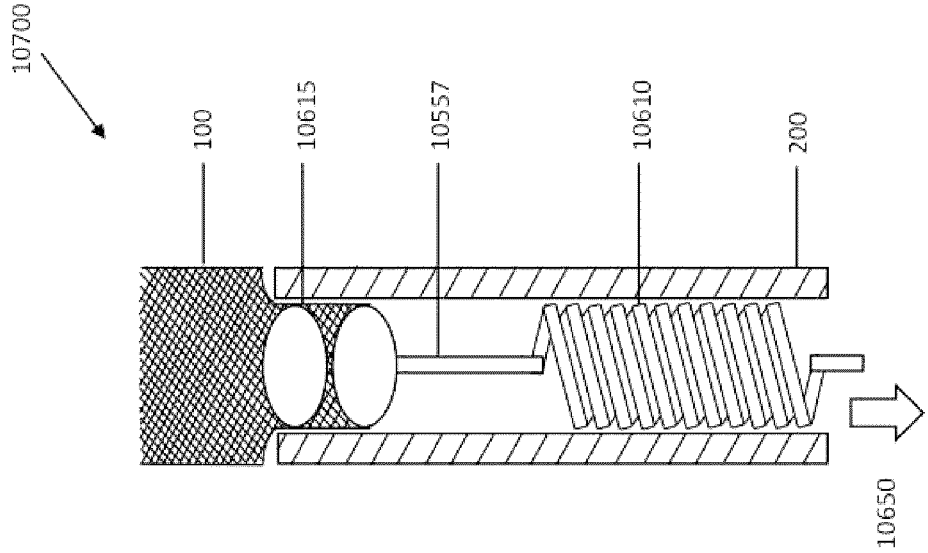

FIG. 25C is a schematic diagram of a partial cross-sectional view of another example embodiment of a mechanical detachment system.

Figure 25D:
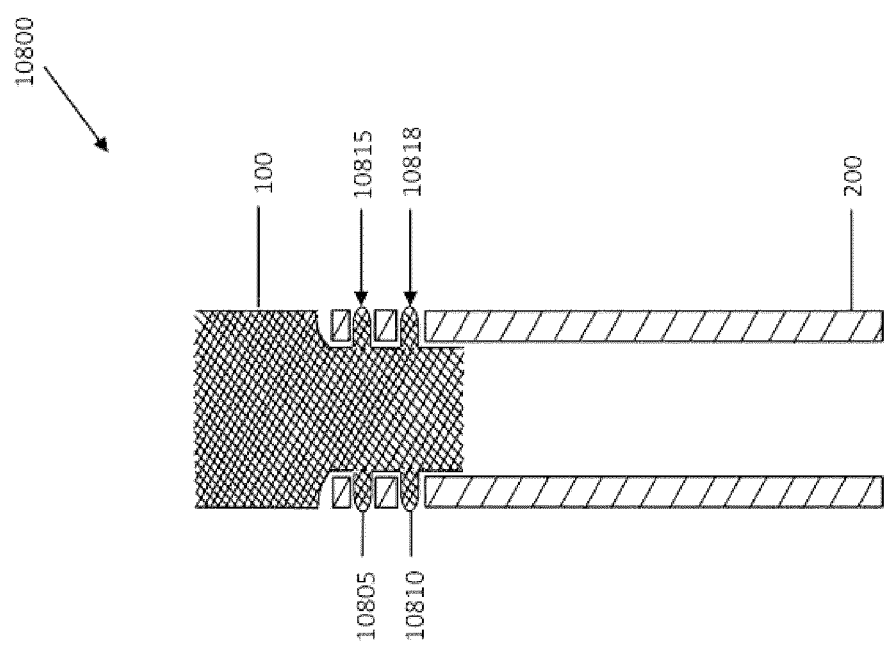

FIG. 25D is a schematic diagram of a partial cross-sectional view of yet another example embodiment of a mechanical detachment system.

Figure 25E:
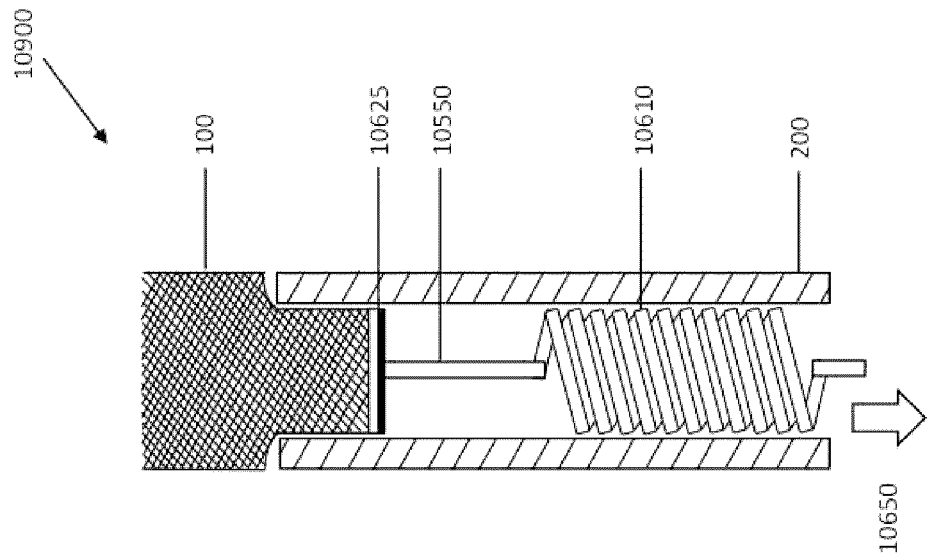

FIG. 25E is a schematic diagram of a partial cross-sectional view of still another example embodiment of a mechanical detachment system.

Figure 26A:
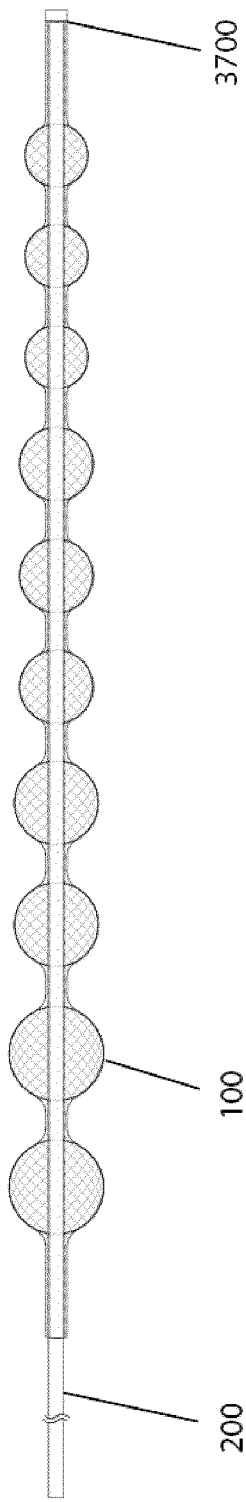

FIG. 26A is a schematic diagram illustrating still another example embodiment of a joint between a proximal portion and a distal portion.

Figure 26B:
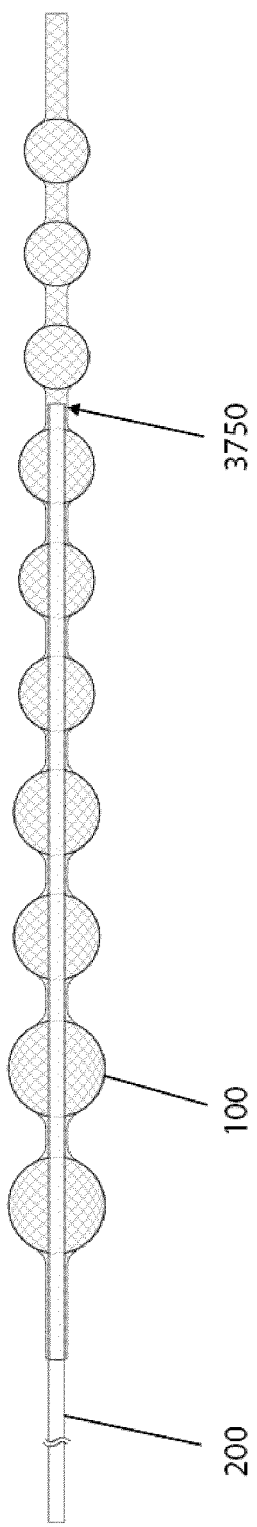

FIG. 26B is a schematic diagram illustrating yet still another example embodiment of a joint between a proximal portion and a distal portion.

Figure 26C:
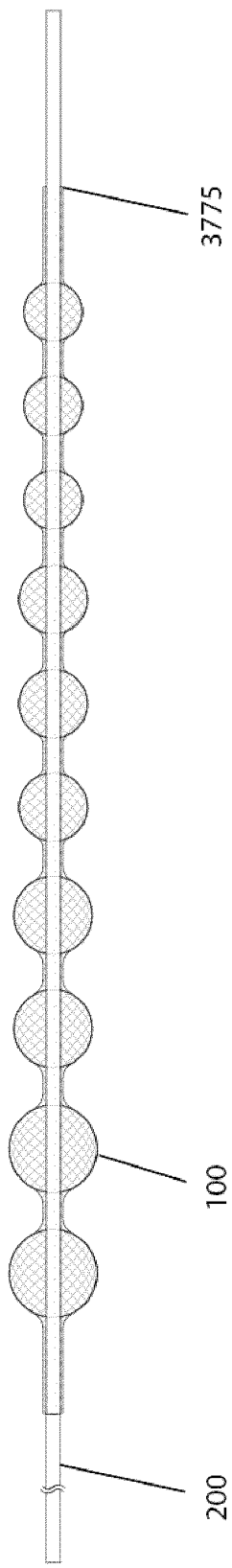

FIG. 26C is a schematic diagram illustrating another example embodiment of a joint between a proximal portion and a distal portion.

Figure 27A:
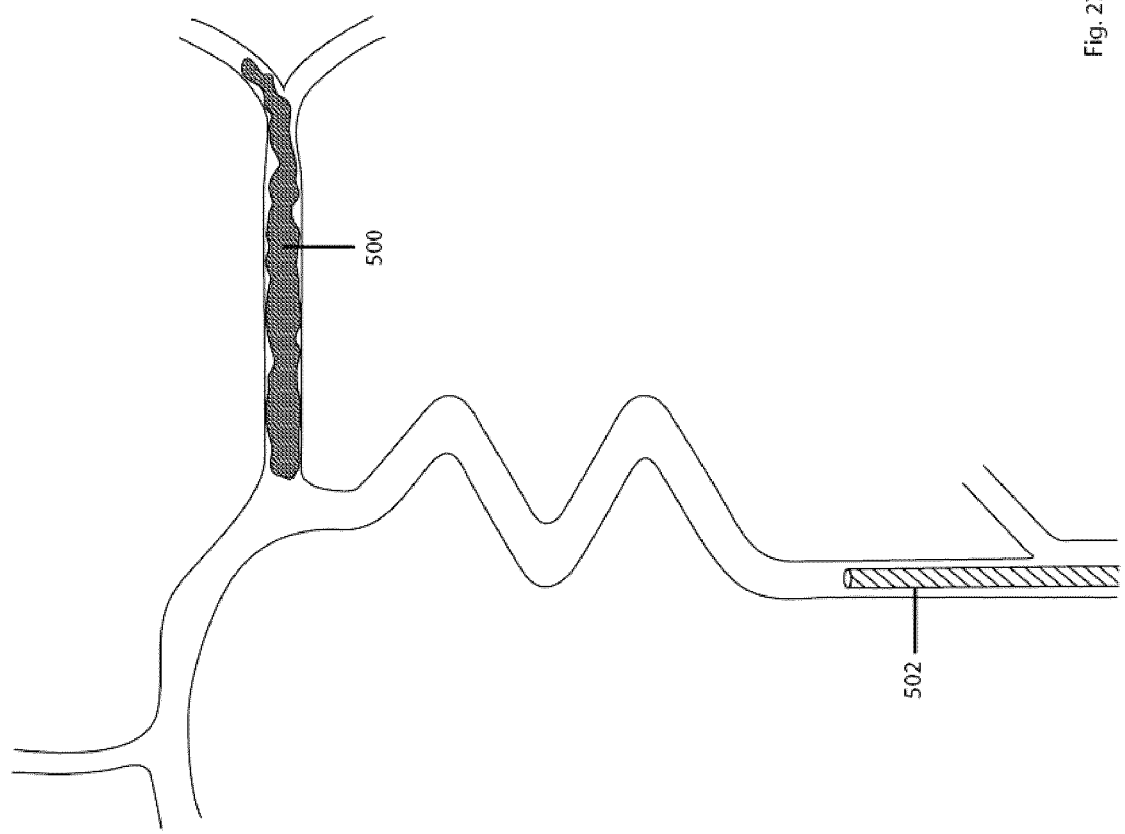

FIG. 27A is a schematic diagram of a guide catheter proximal to a clot in vasculature.

FIG. 27B is a schematic diagram of a microwire distal to a clot in vasculature and a microcatheter over the microwire.

Figure 27C:
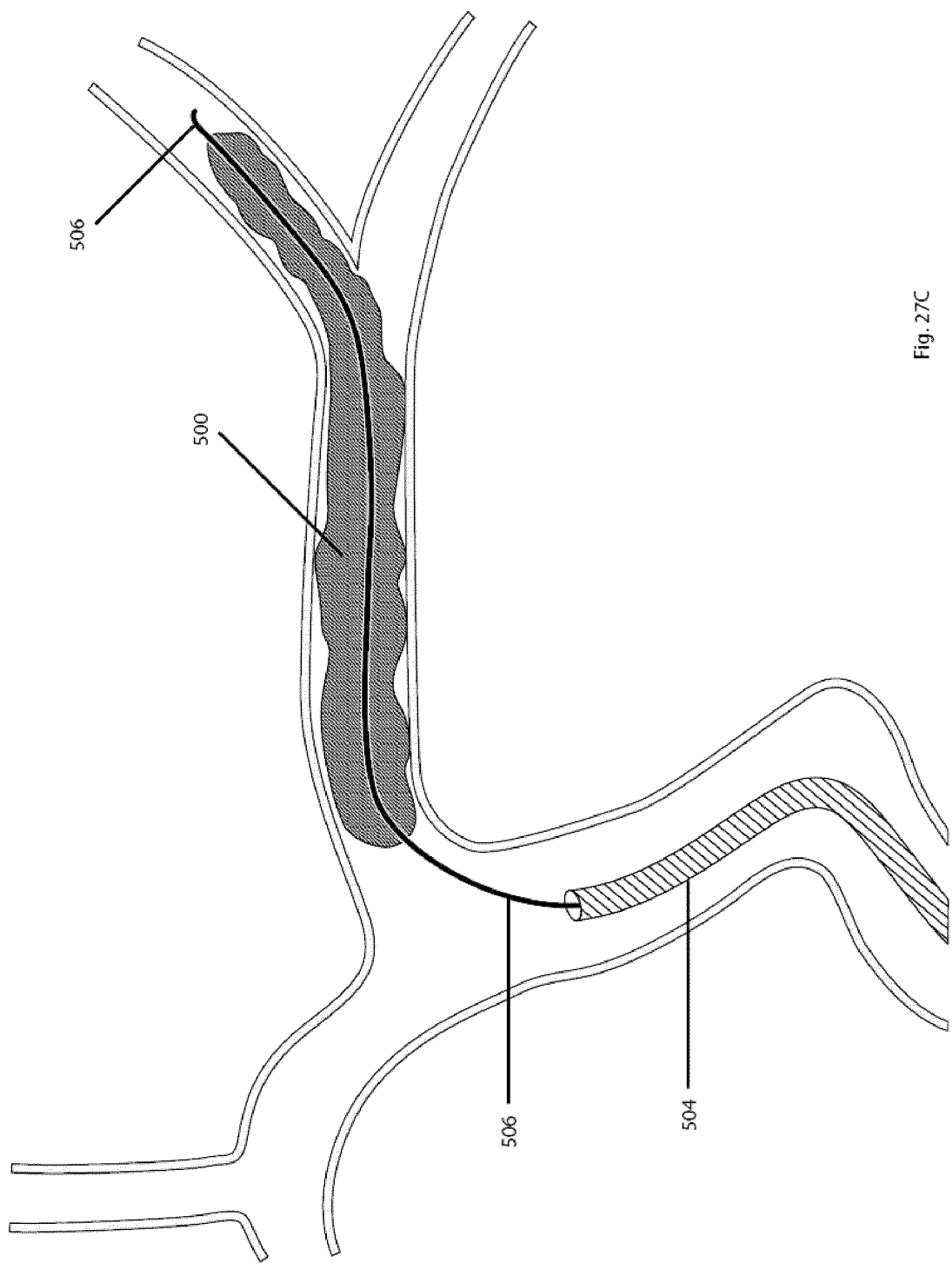

FIG. 27C is an expanded view of FIG. 27B in the area of the clot.

Figure 27D:
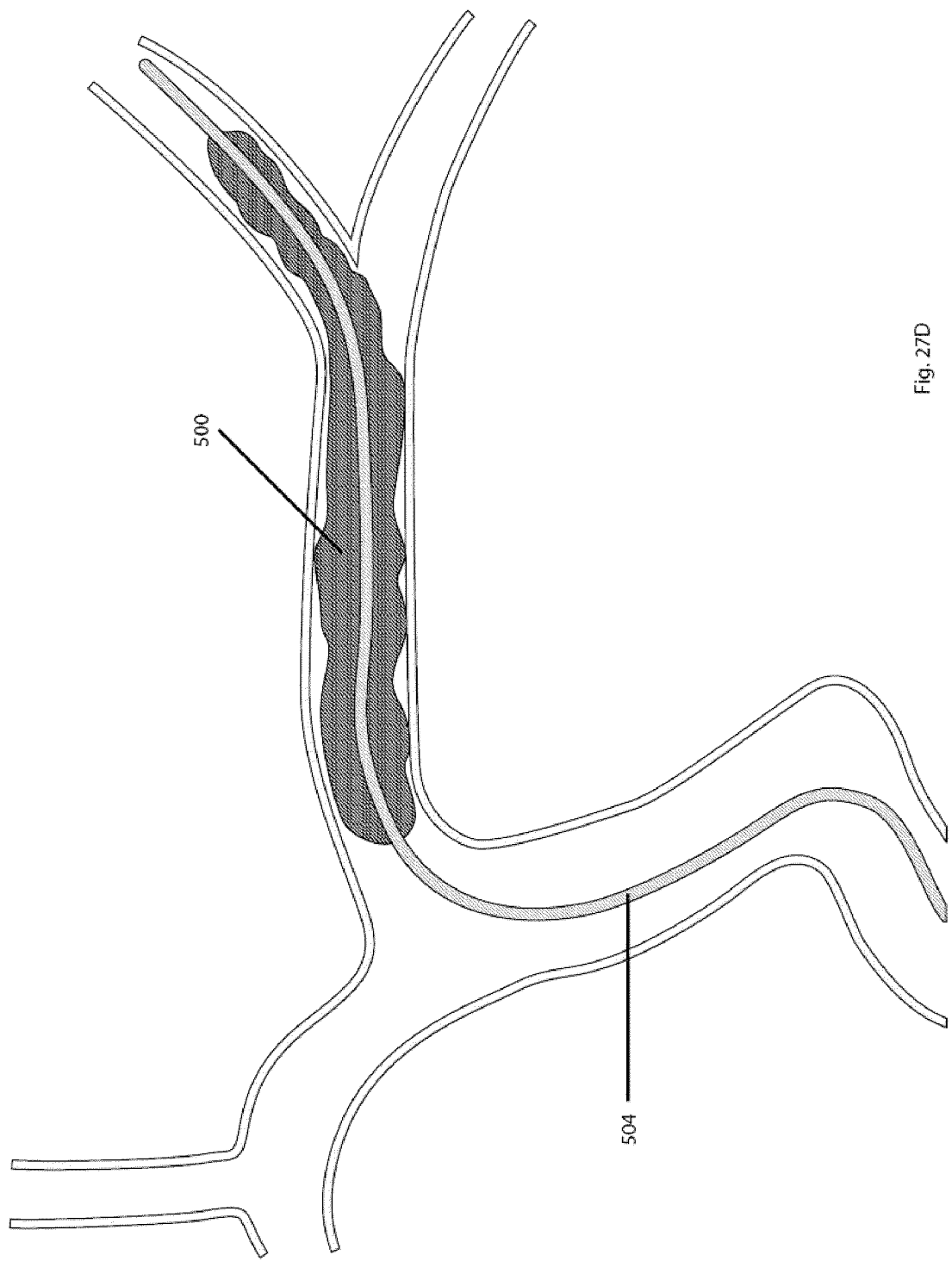

FIG. 27D is a schematic diagram of a microcatheter distal to a clot in vasculature.

Figure 27E:
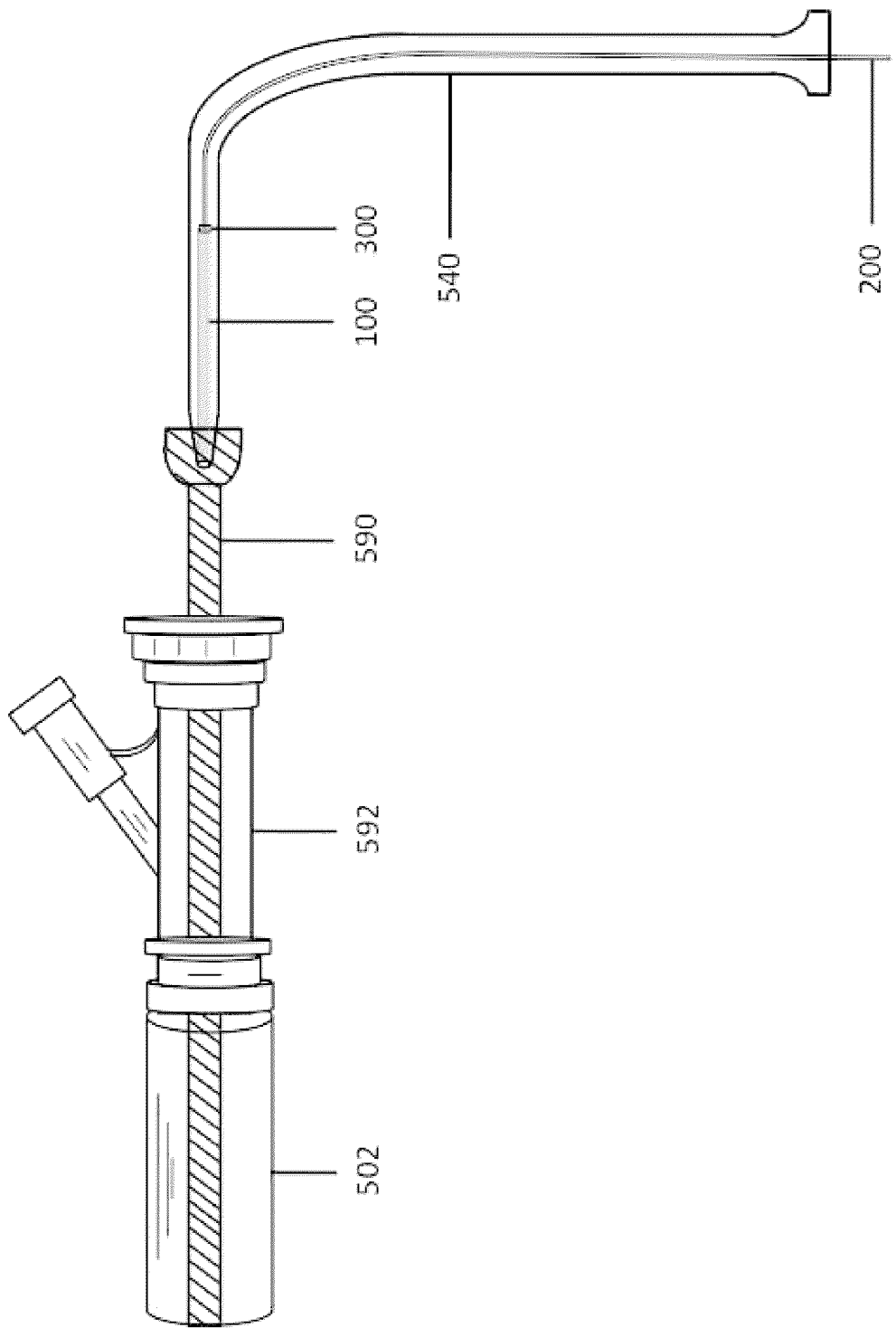

FIG. 27E is a schematic diagram illustrating an example embodiment of the distal portion of a vascular treatment device being introduced into the hub of a microcatheter through an introducer sheath.

FIG. 27F is a schematic partial cross-sectional view of an example embodiment of a distal portion of a vascular treatment device within an introducer sheath.

Figure 27G:
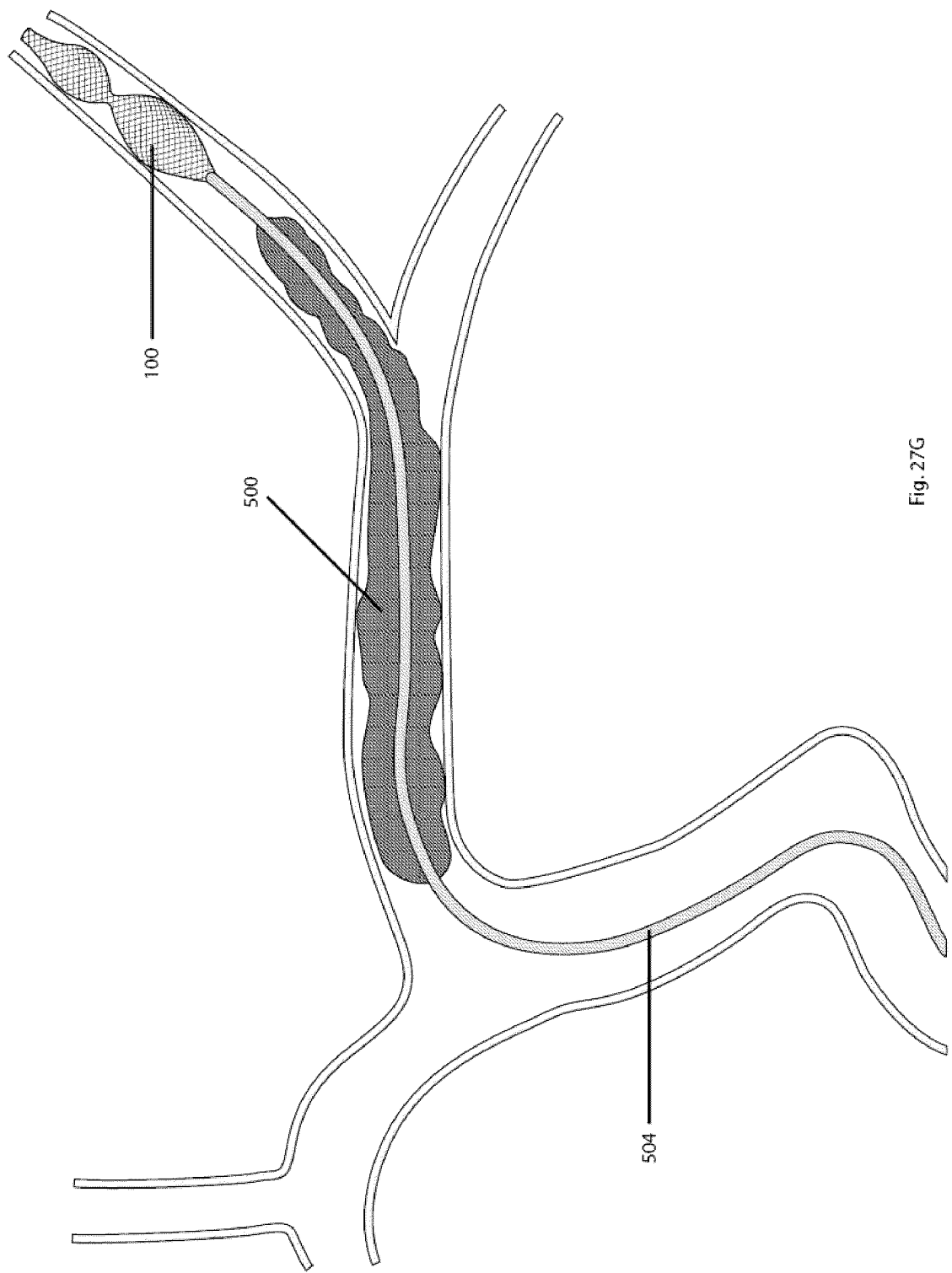

FIG. 27G is a schematic diagram of part of a distal portion of a vascular treatment device being deployed distal to a clot in vasculature.

Figure 27H:
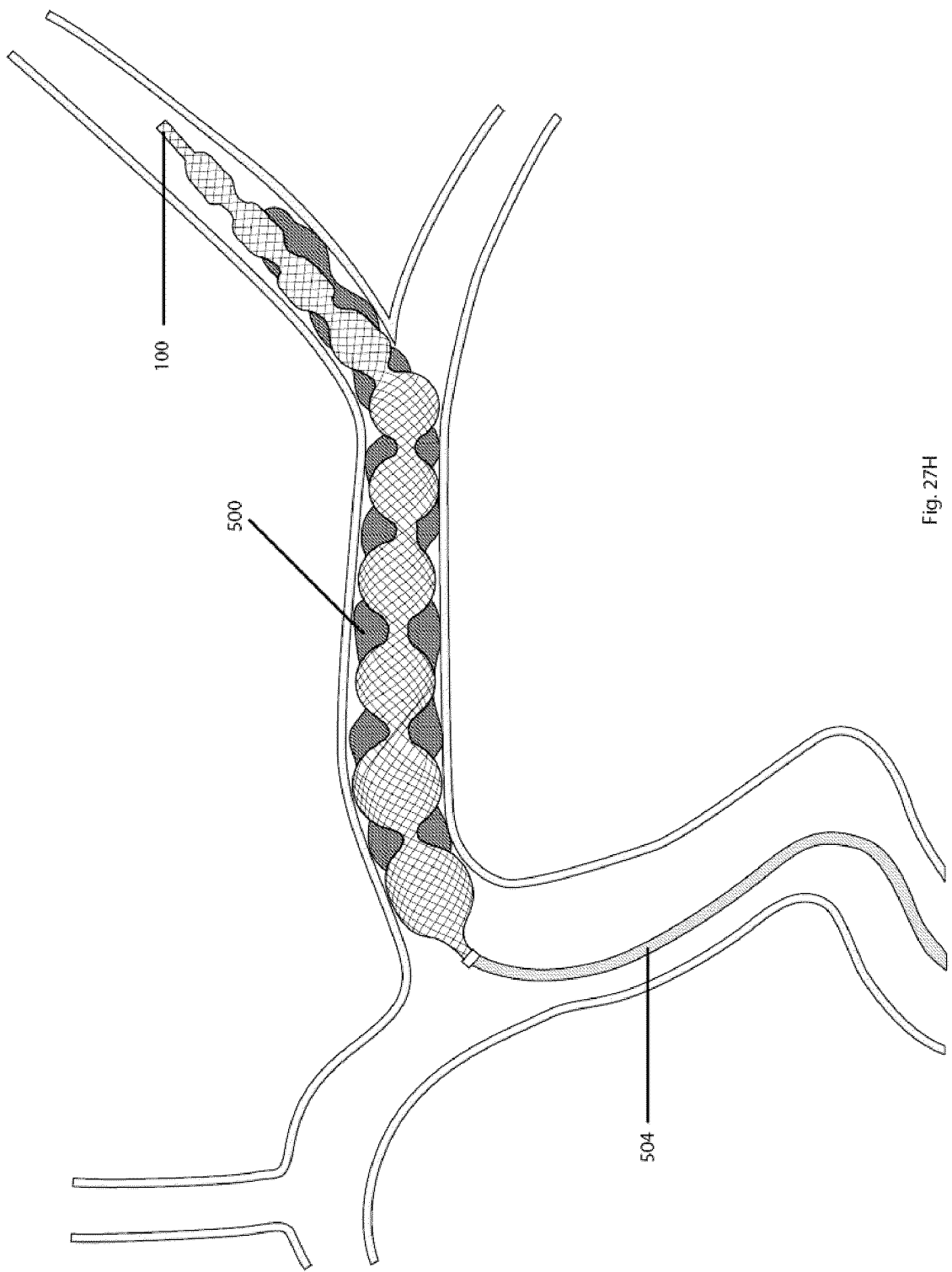

FIG. 27H is a schematic diagram of a distal portion of a vascular treatment device being deployed across a clot in vasculature.

Figures 1, 27I:
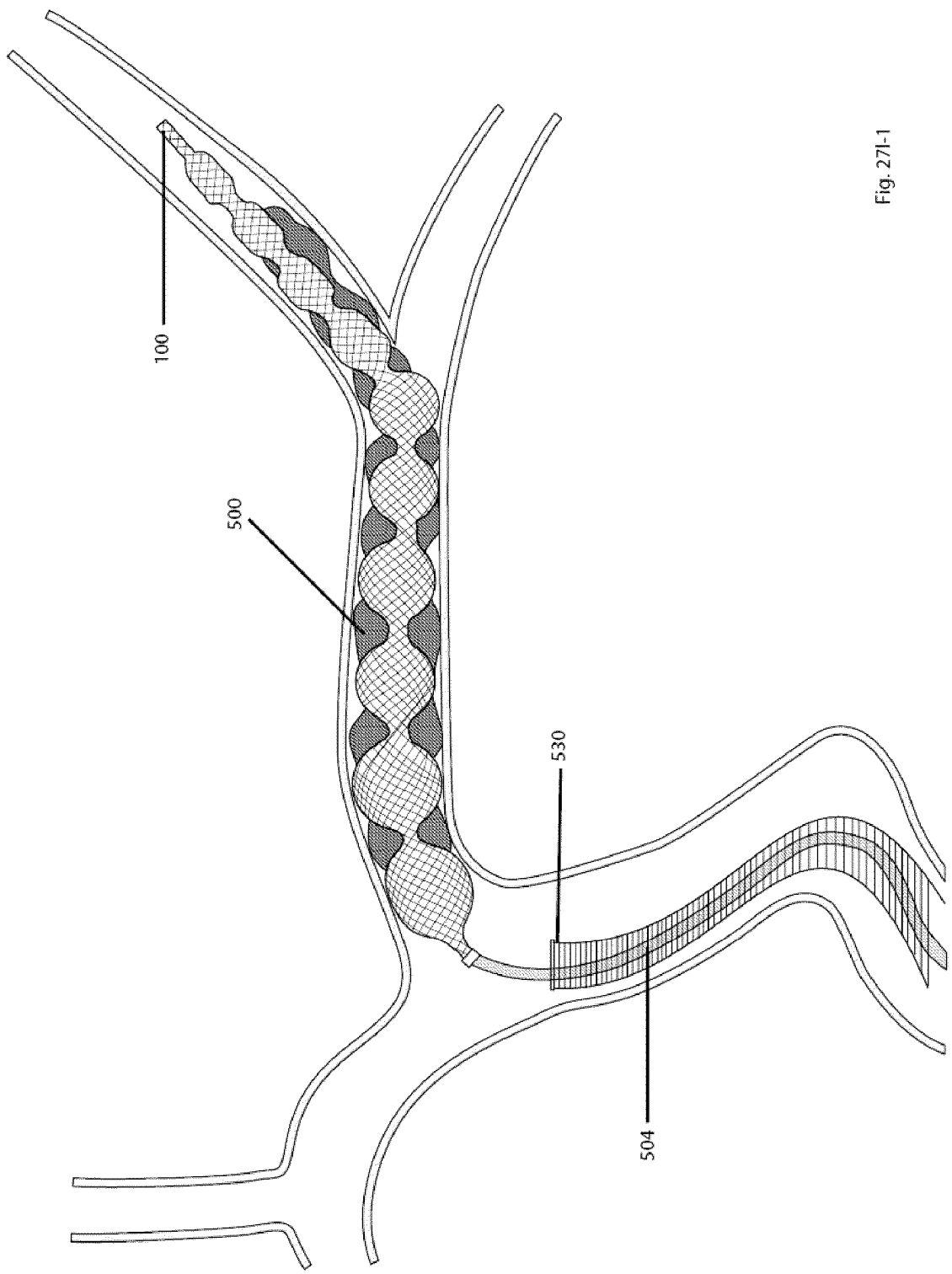
Figures 3, 271:
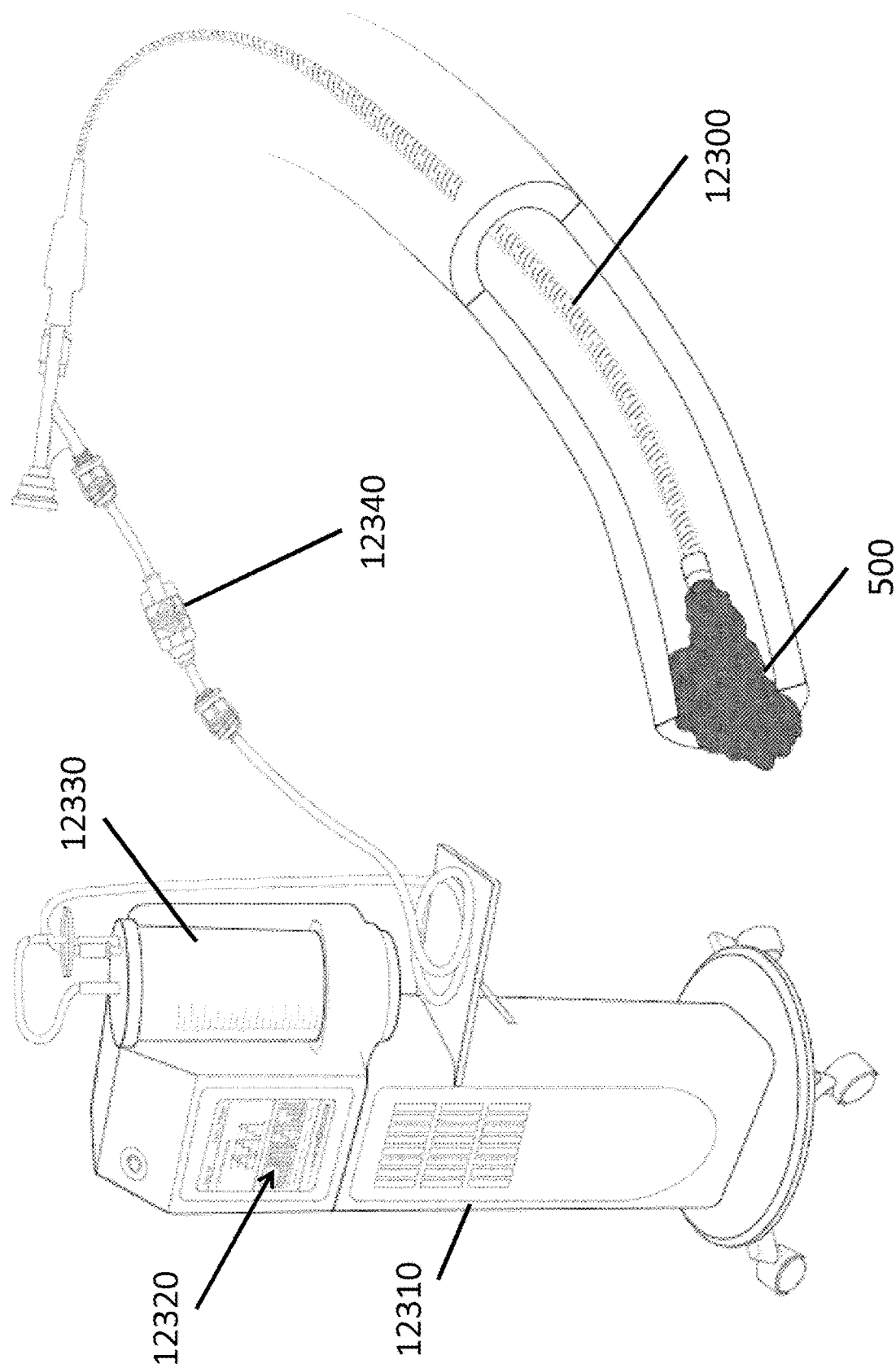
Figures 4, 271:
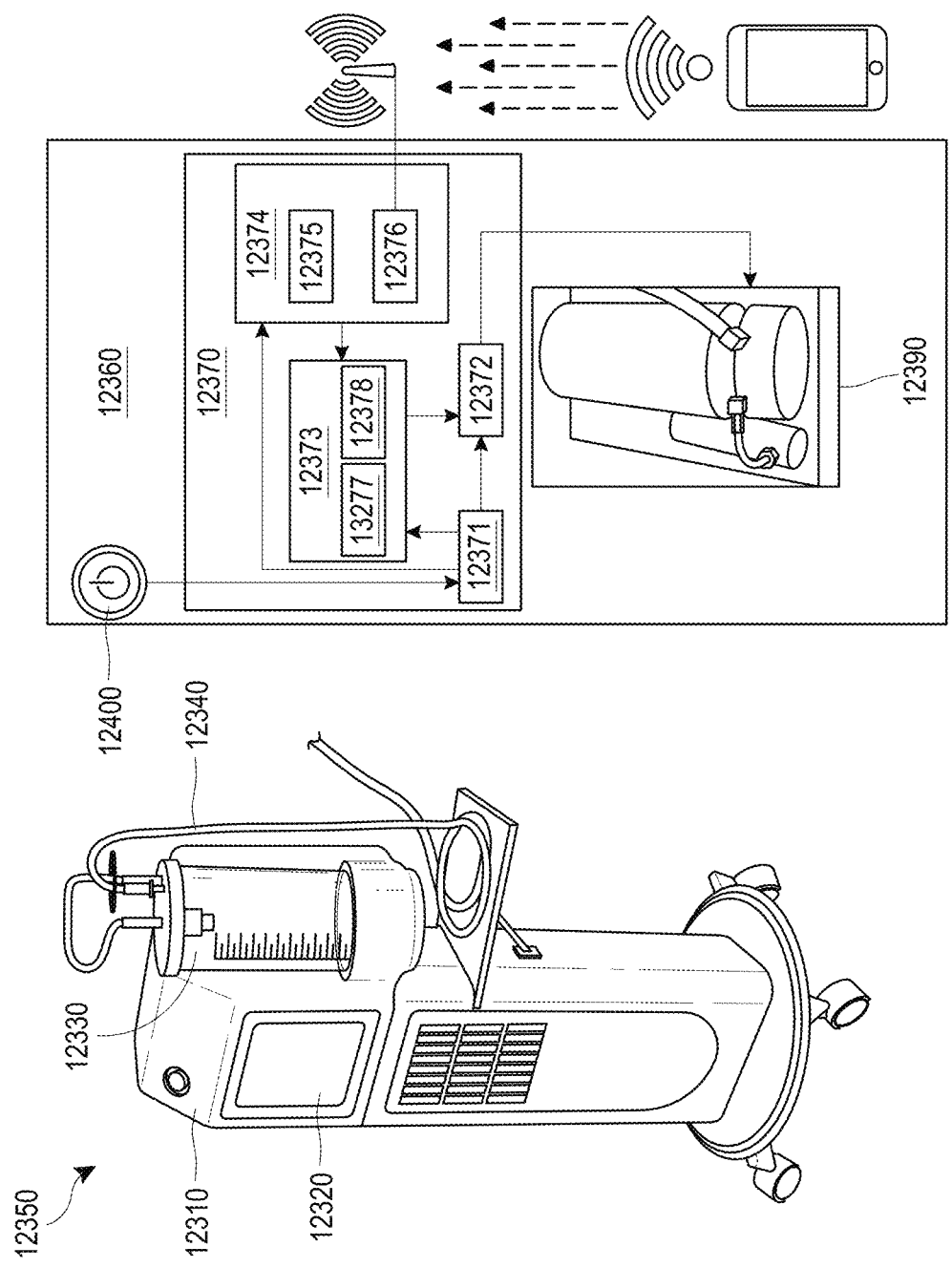
Figures 5, 27I:
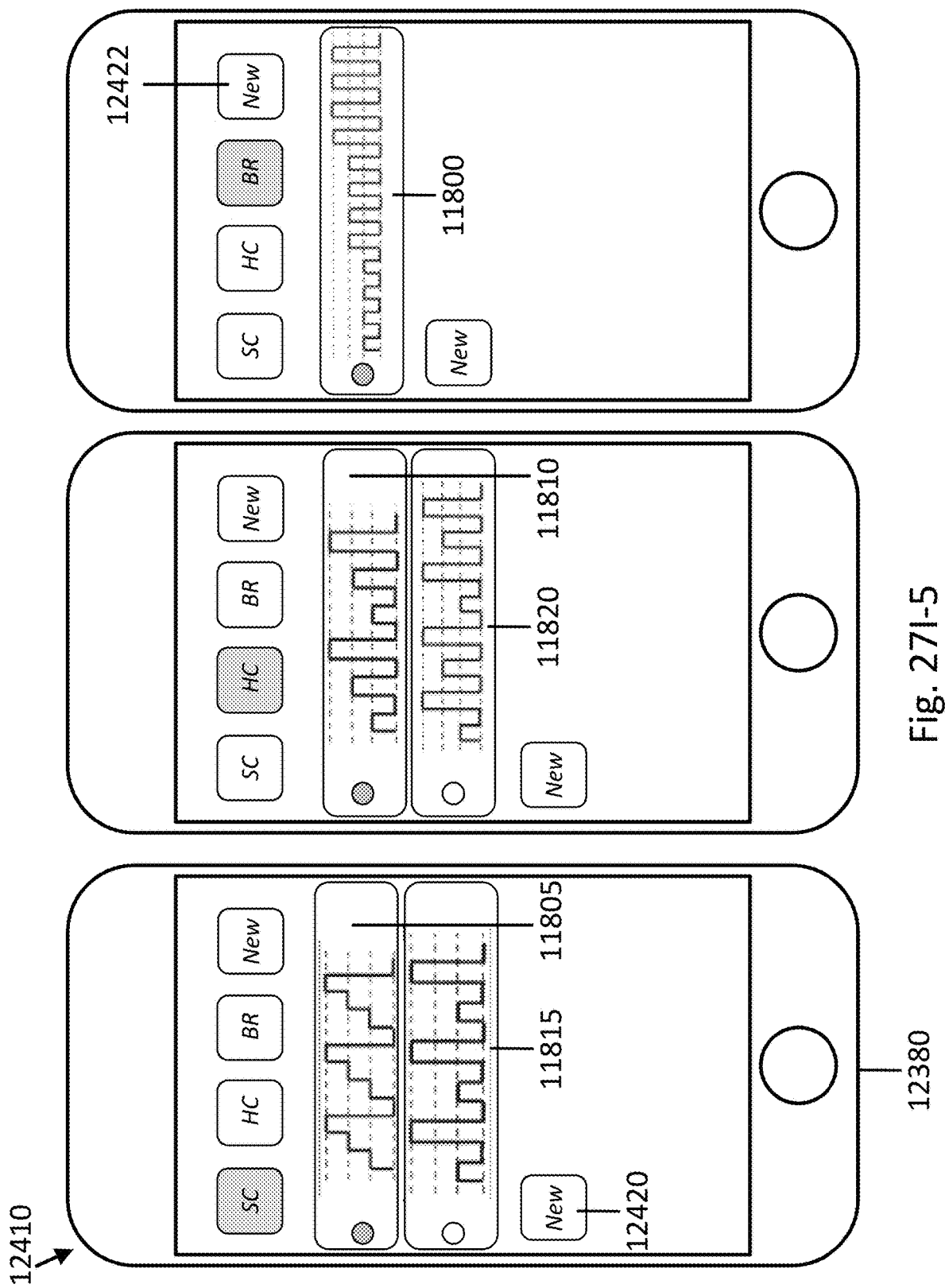
Figures 6, 271:
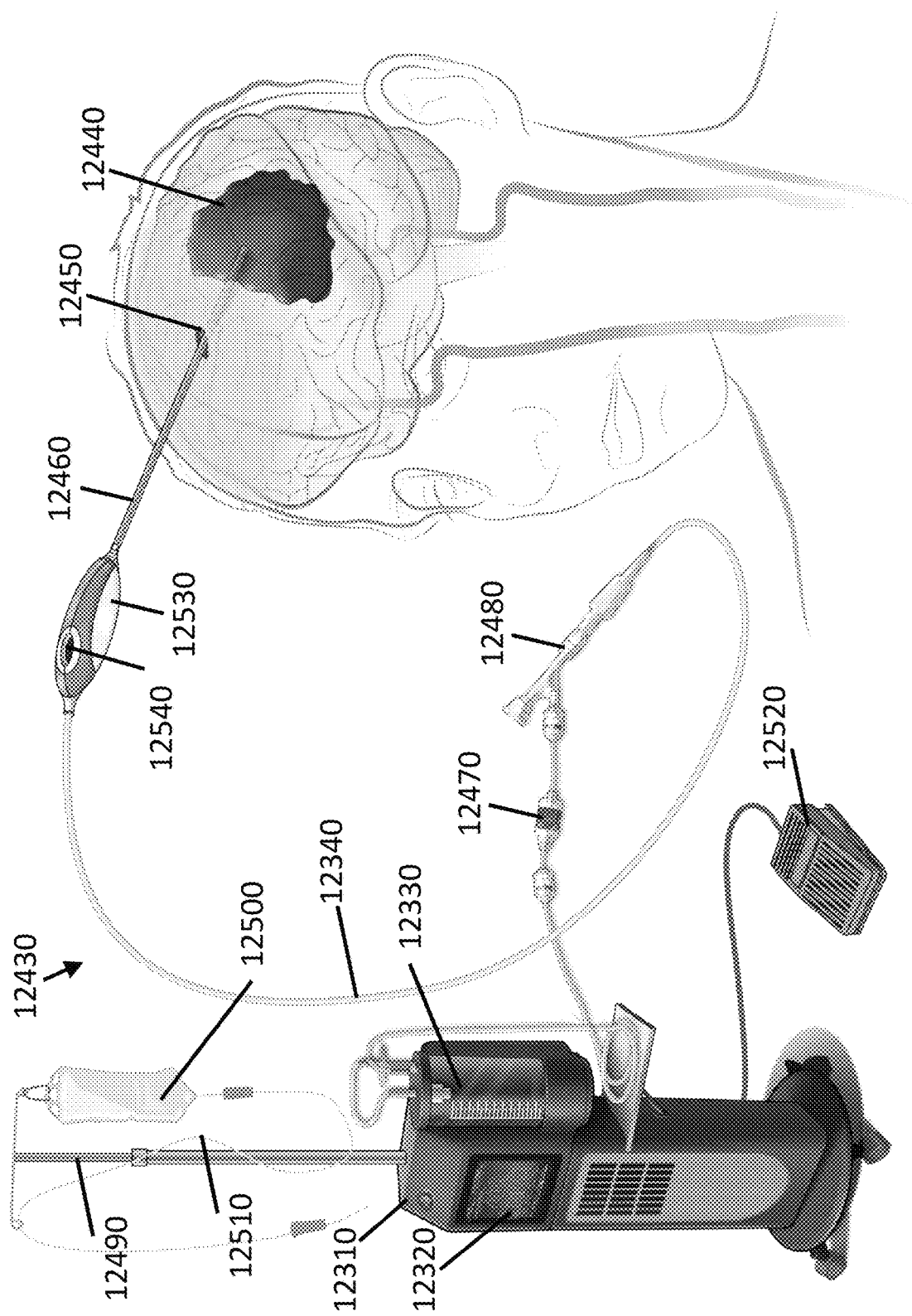

FIG. 27I-1 is a schematic diagram illustrating an example embodiment of the distal portion of a vascular treatment device being used in conjunction with thrombus aspiration.

FIG. 27I-2 is a table schematically illustrating an example embodiment of crescendo suction patterns for aspiration.

Figure 6A:
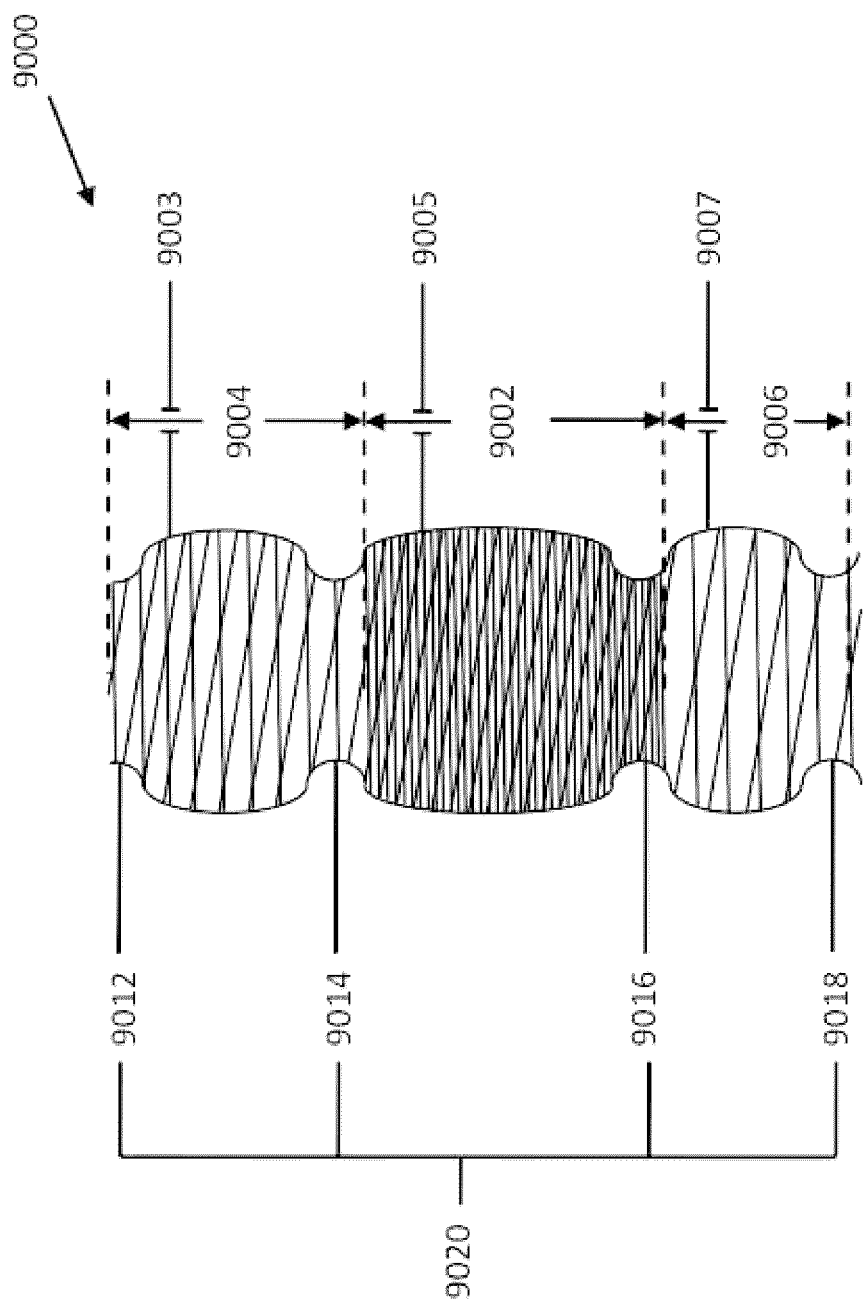
FIG. 6A is a schematic side elevational view of another example embodiment of a distal portion of a vascular treatment device.
Figure 6B:
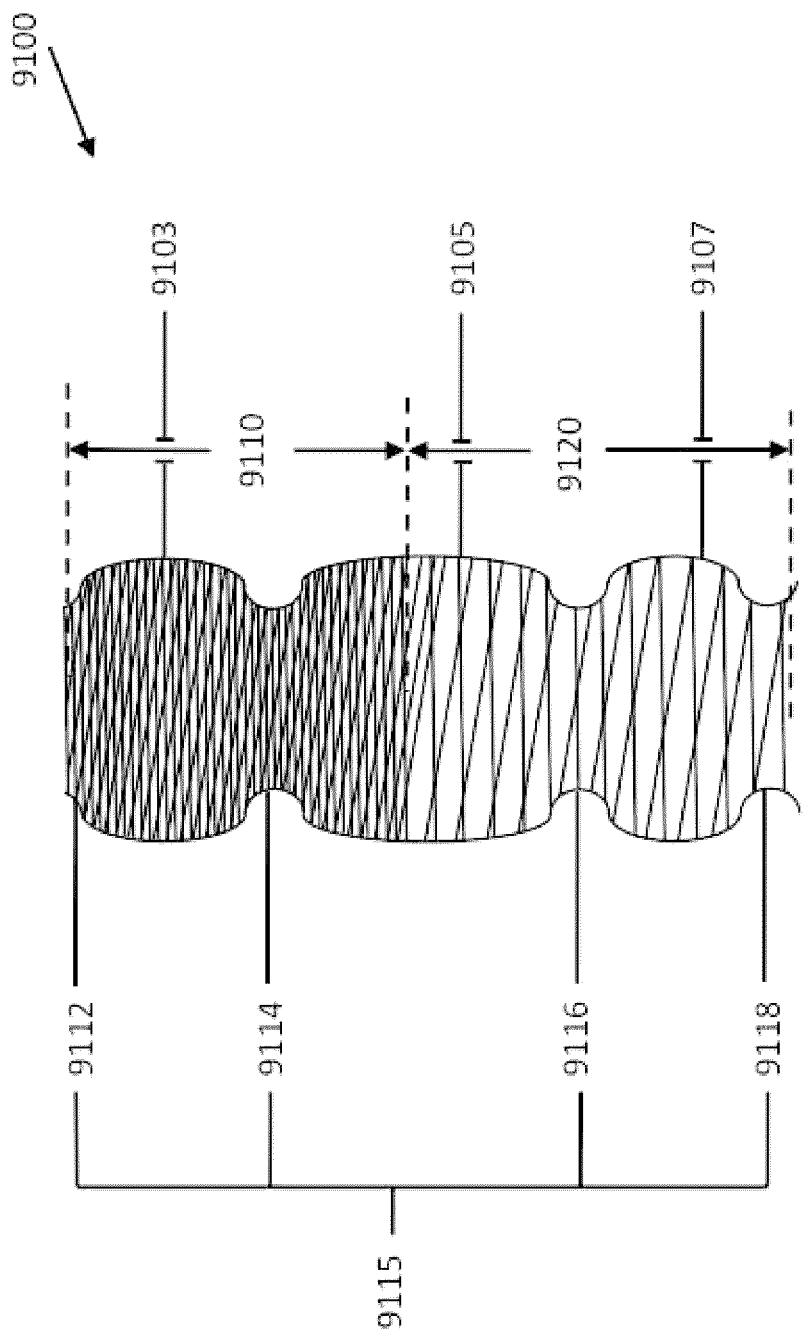
FIG. 6B is a schematic side elevational view of yet another example embodiment of a distal portion of a vascular treatment device.
Figure 6C:
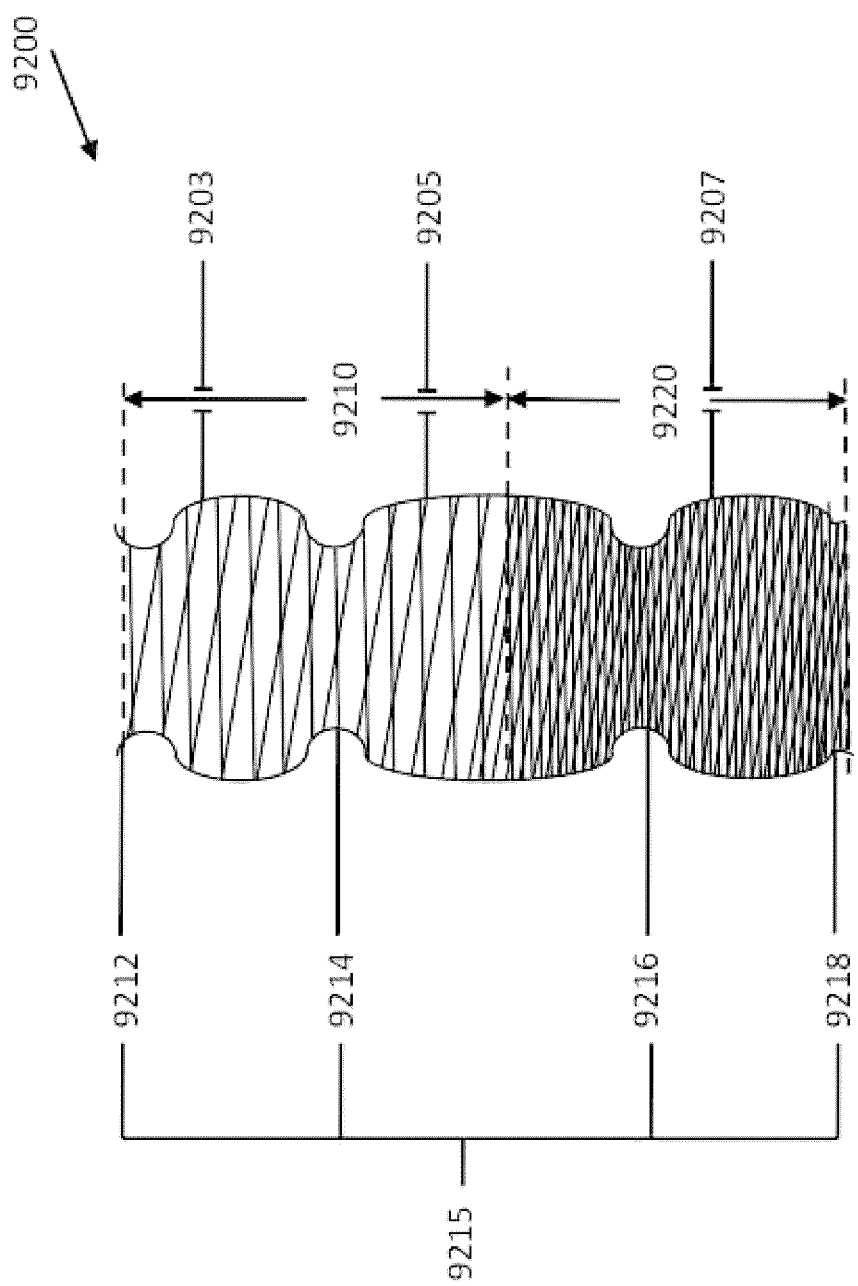
FIG. 6C is a schematic side elevational view of still another example embodiment of a distal portion of a vascular treatment device.
Figure 6D:
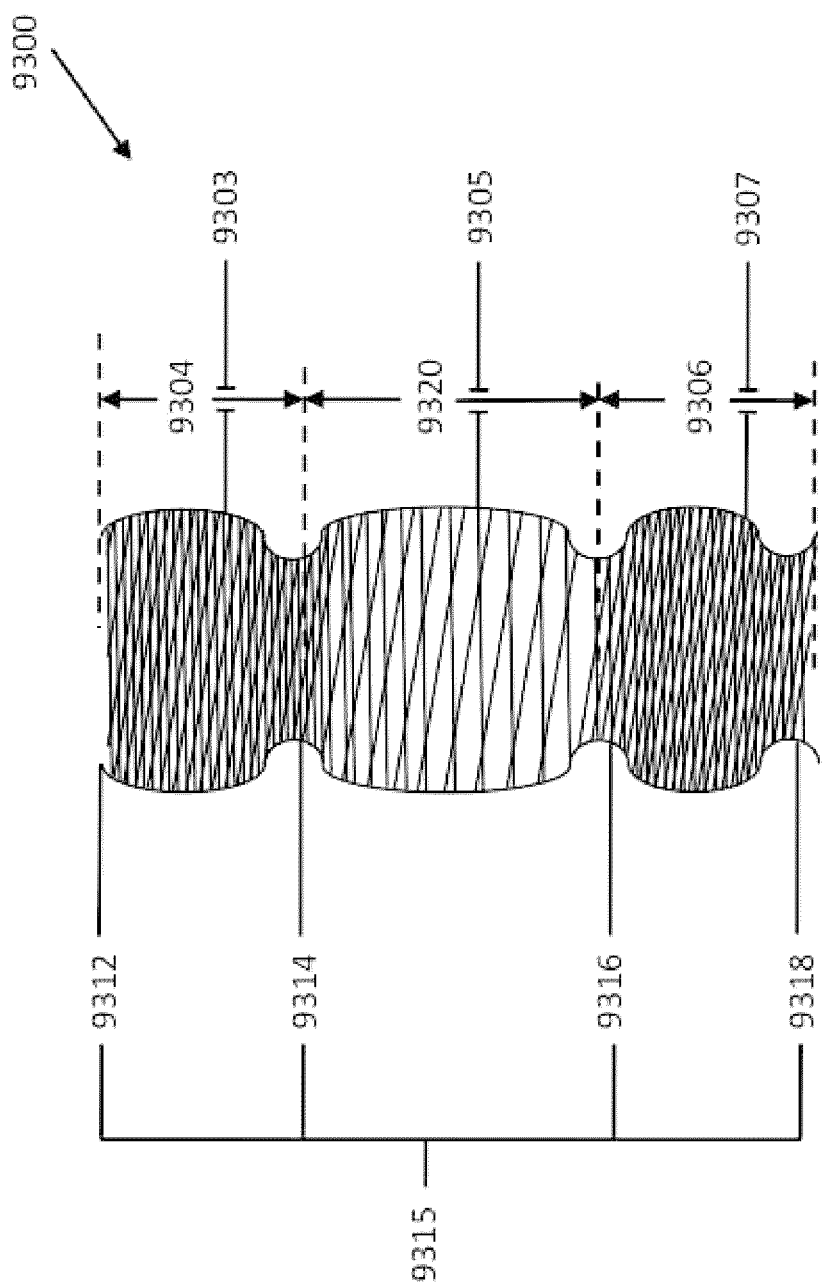
FIG. 6D is a schematic side elevational view of still yet another example embodiment of a distal portion of a vascular treatment device.
Figure 6E:
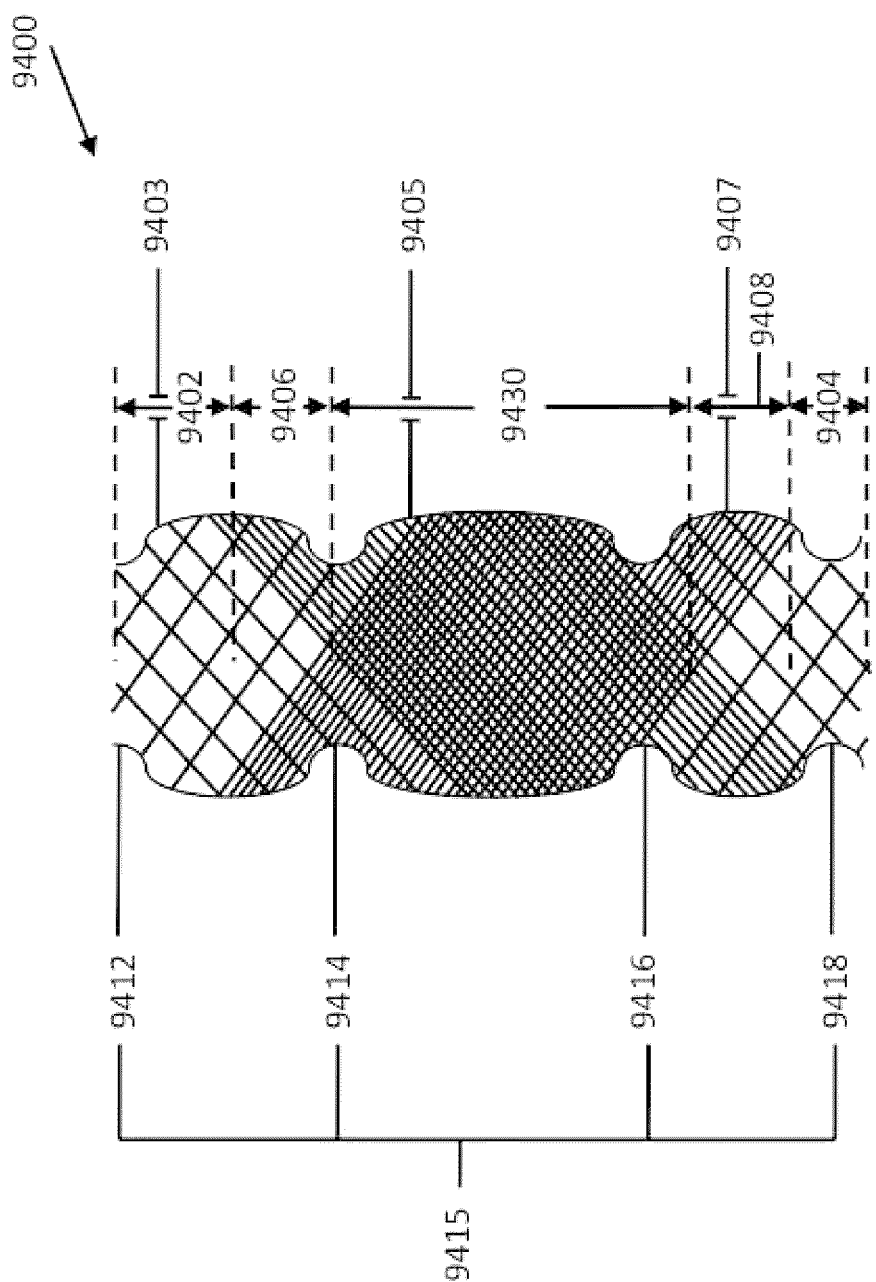
FIG. 6E is a schematic side elevational view of another example embodiment of a distal portion of a vascular treatment device.
Figure 6F:
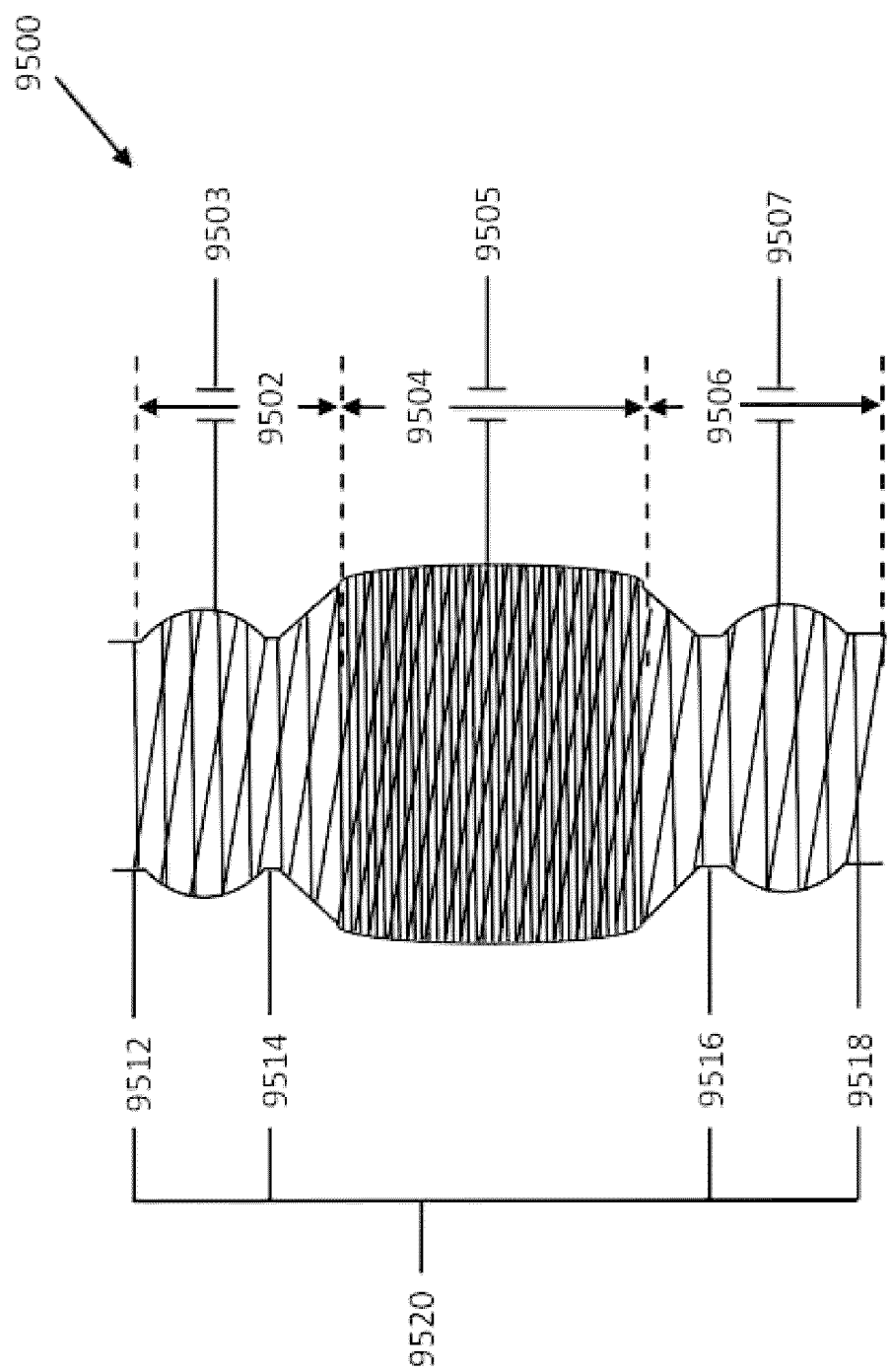
FIG. 6F is a schematic side elevational view of yet another example embodiment of a distal portion of a vascular treatment device.
Figure 6G:
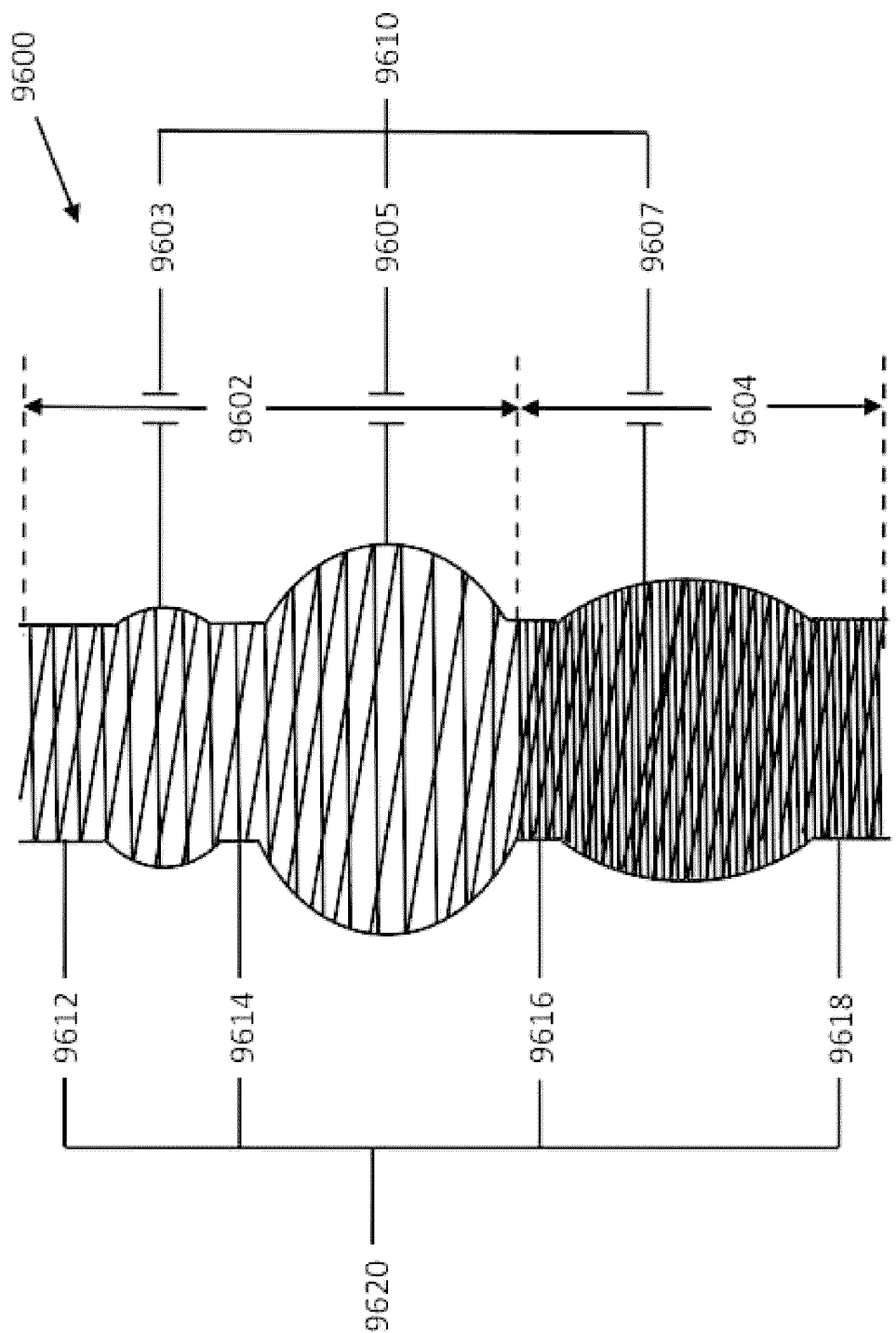
FIG. 6G is a schematic side elevational view of still another example embodiment of a distal portion of a vascular treatment device.
Figure 6H:
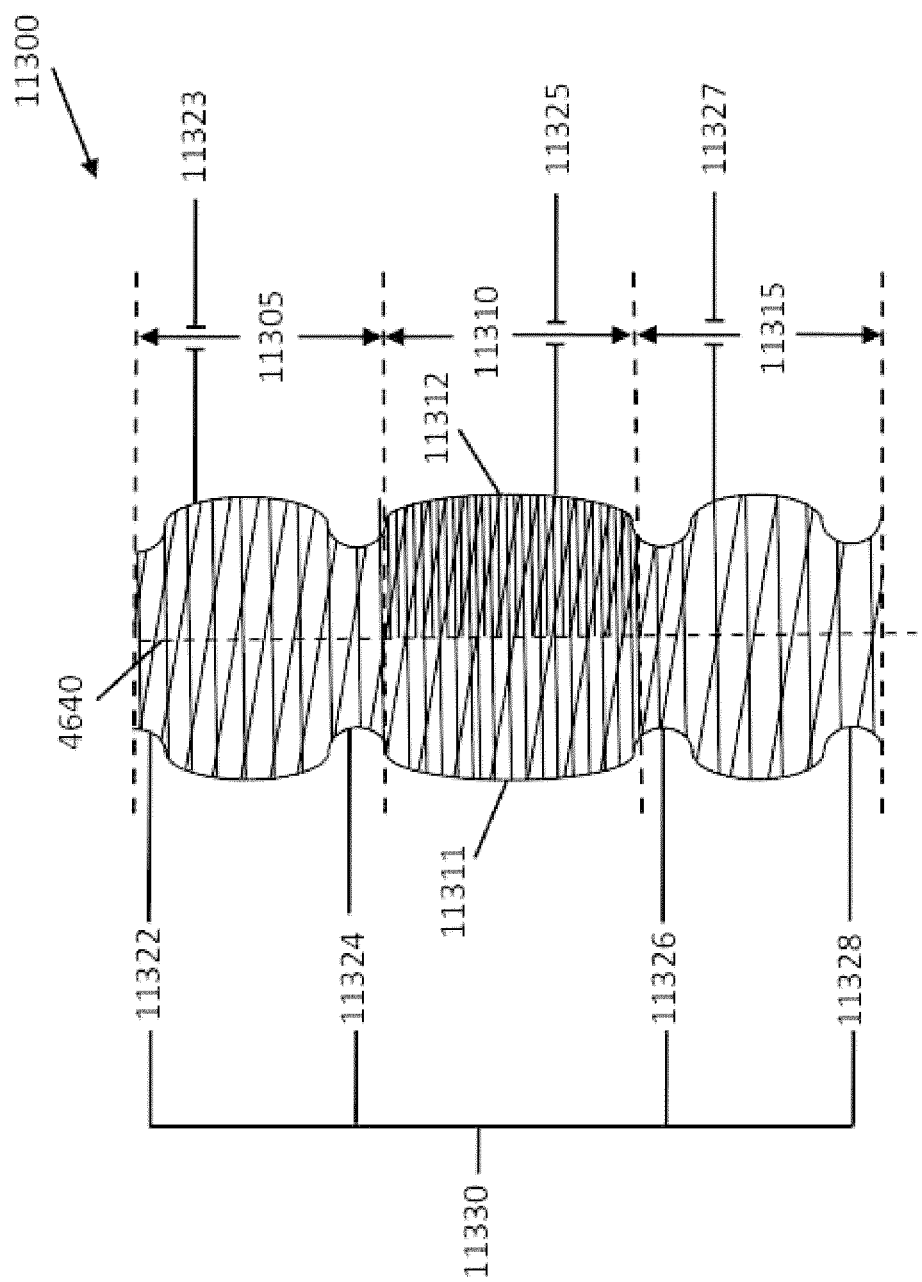
FIG. 6H is a schematic side elevational view of still yet another example embodiment of a distal portion of a vascular treatment device.
Figure 61:
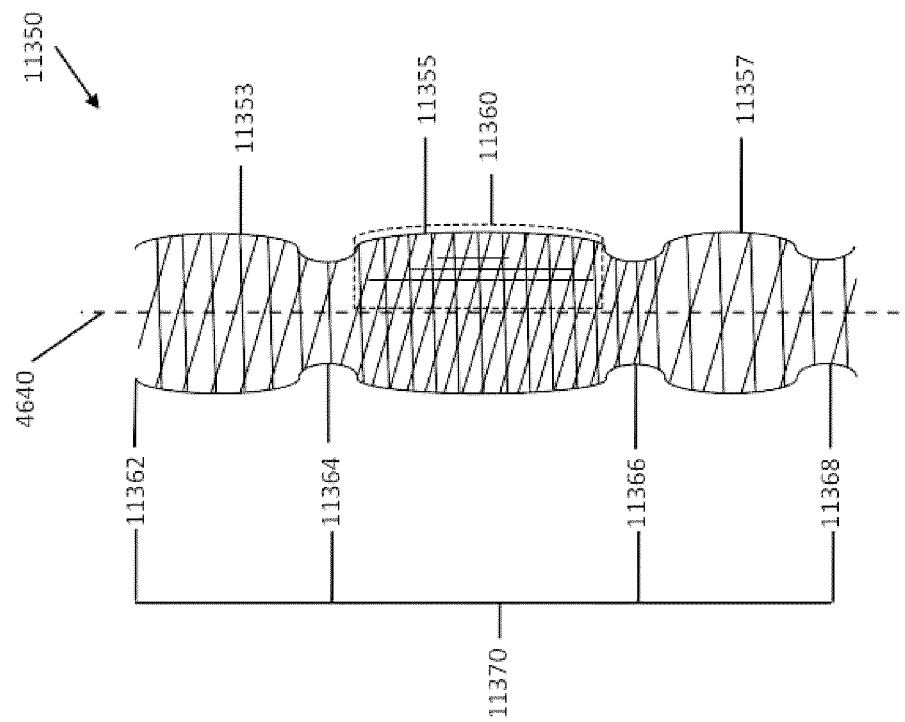
Figures 1I, 6K:
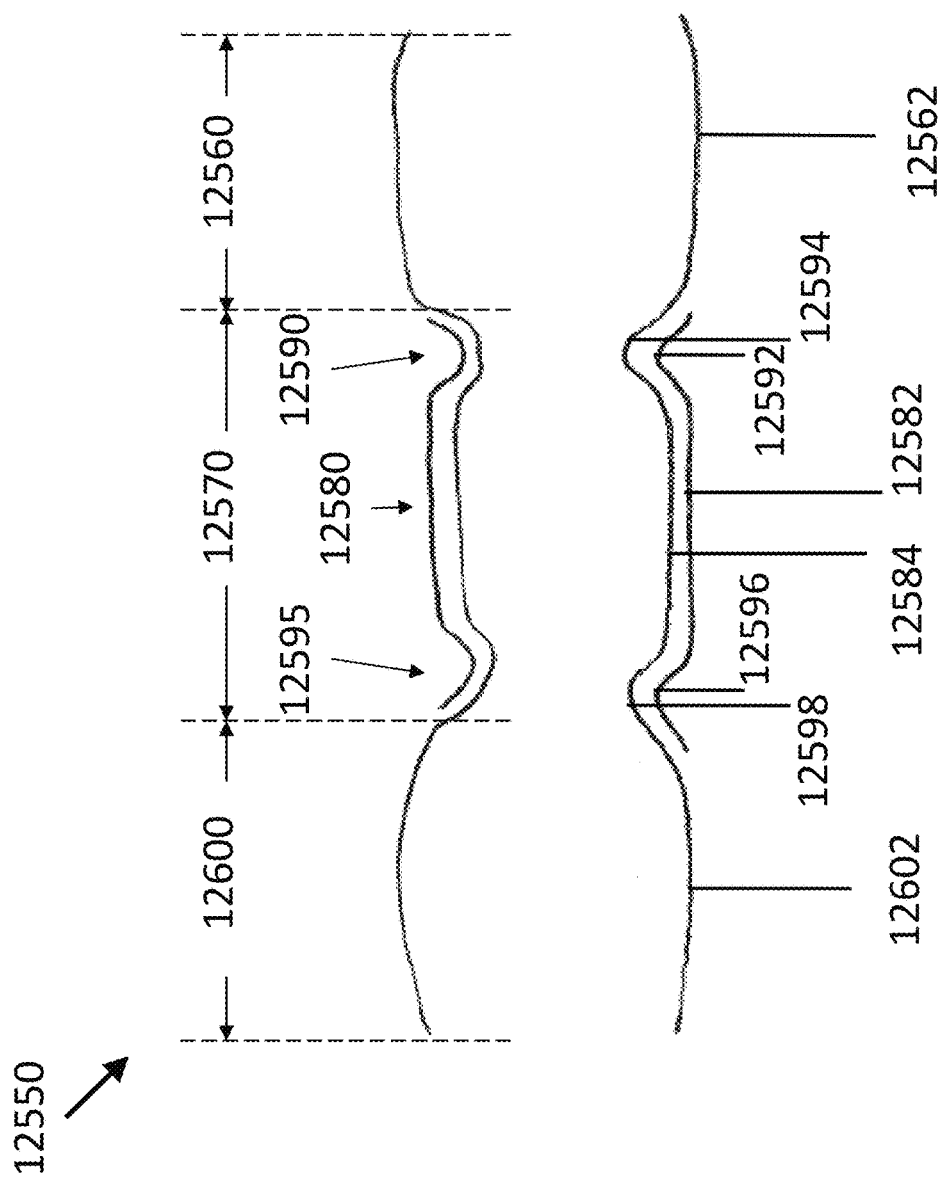
FIG. 6K-1*i* is a schematic cross sectional view of another example embodiment of a vascular treatment device.
Figures 2, 6K:
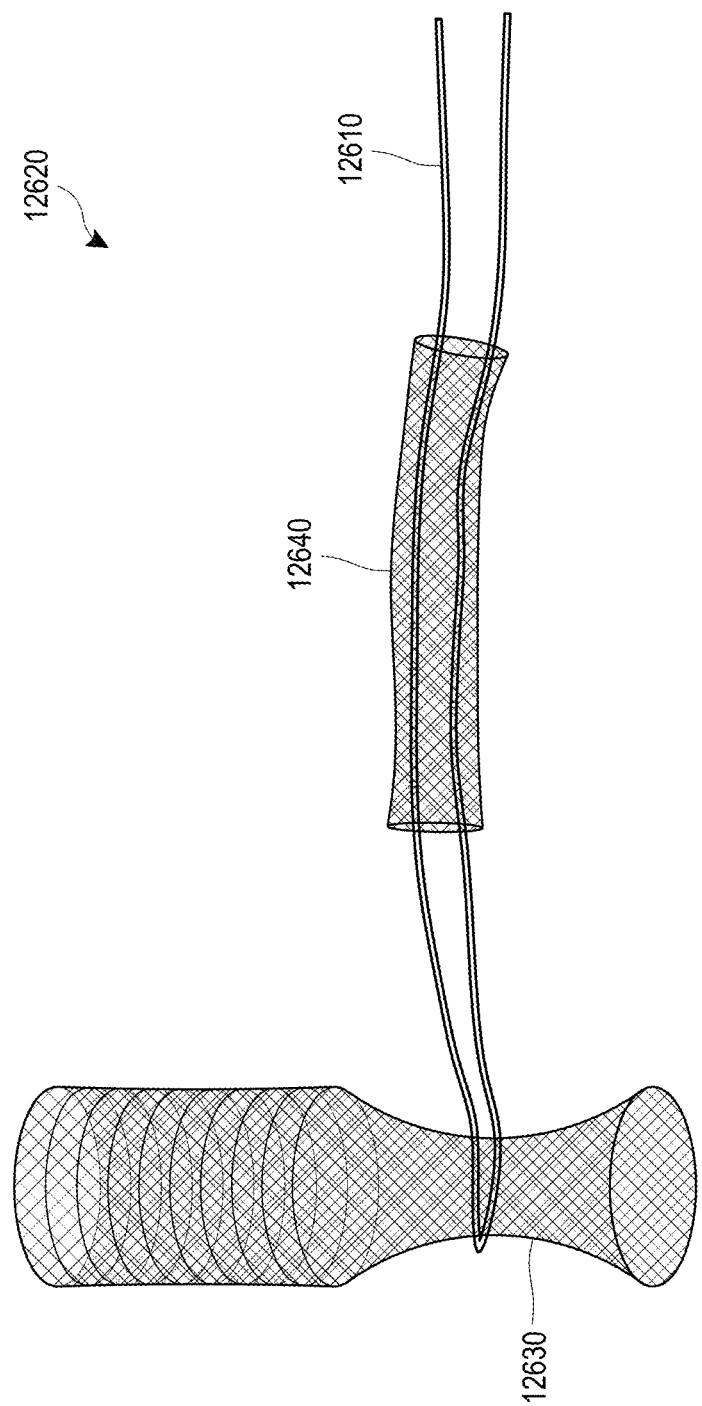
Figures 3, 6K:
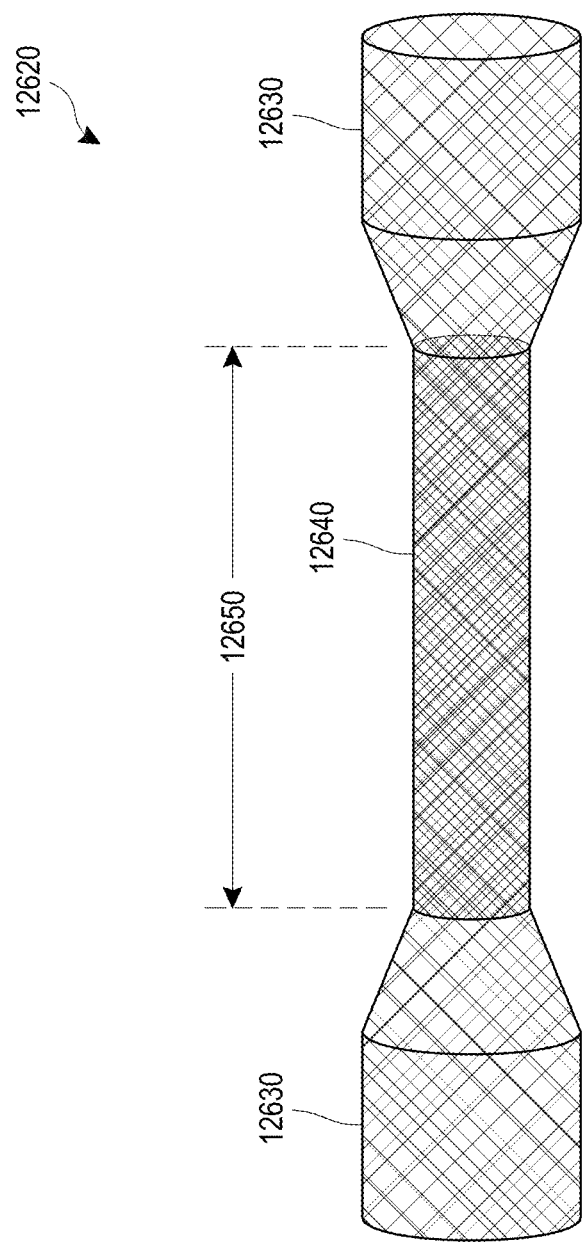

FIG. 27I-3 is a schematic diagram illustrating an example embodiment of a mobile peristaltic motor pump with an external control panel for crescendo suction patterns for aspiration.

Figures 4, 6K:
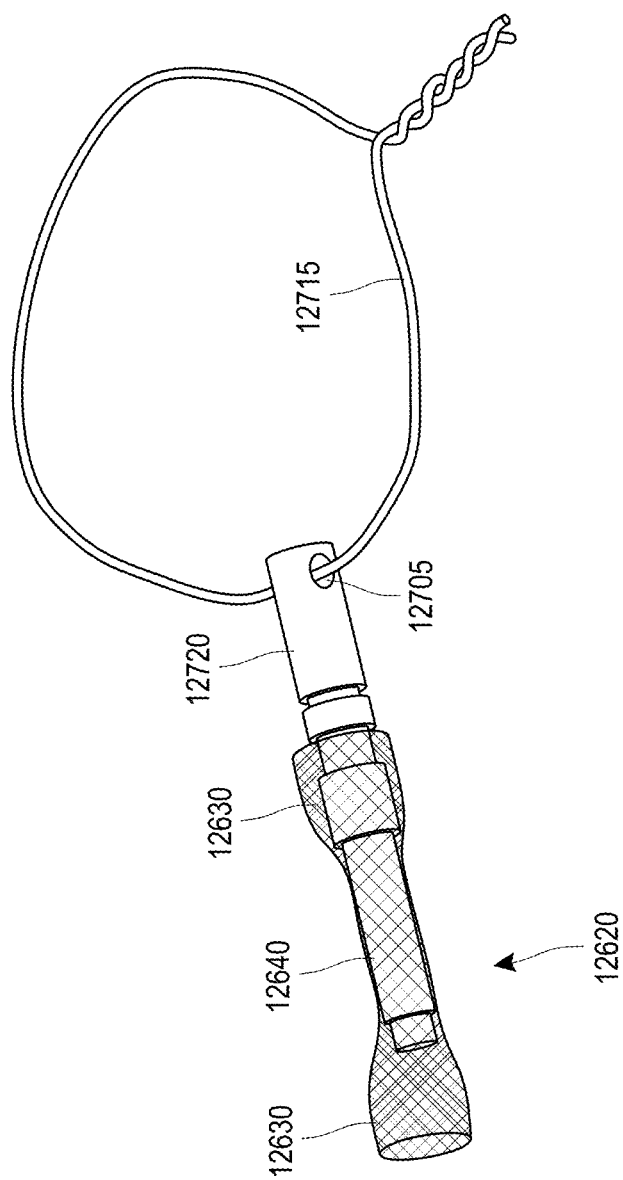

FIG. 27I-4 is a schematic diagram illustrating suction pump devices.

Figures 5, 6K:
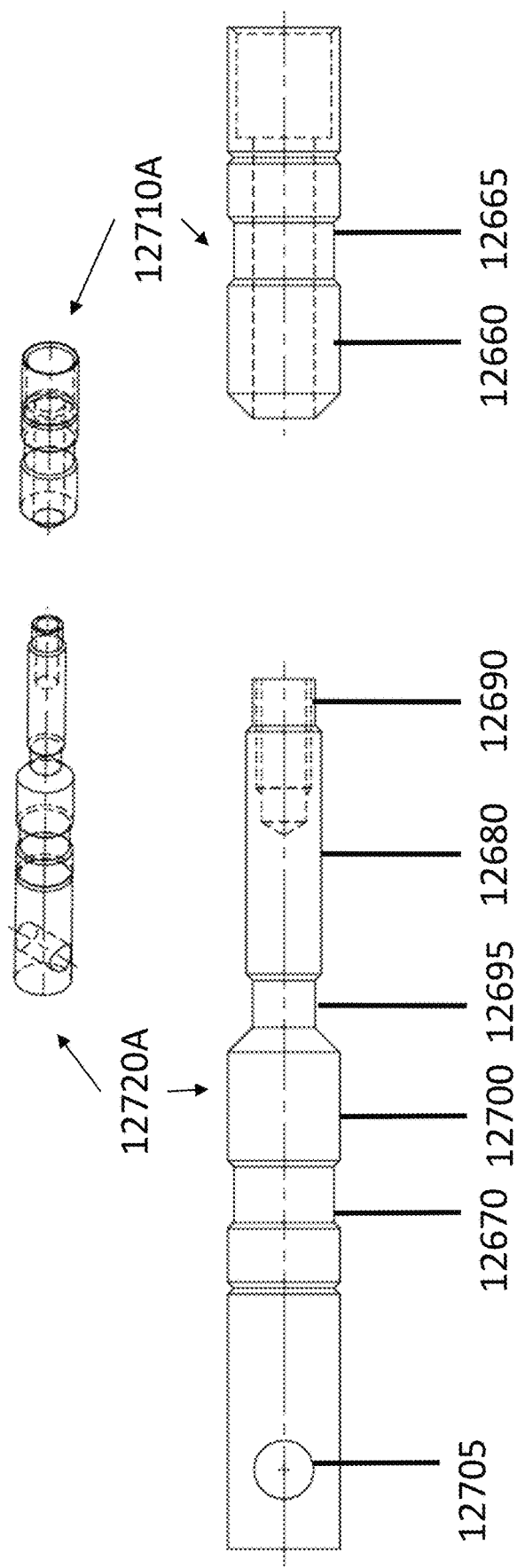

FIG. 27I-5 is a schematic diagram illustrating an example embodiment of the user interface on a smart device.

Figures 6, 6K:
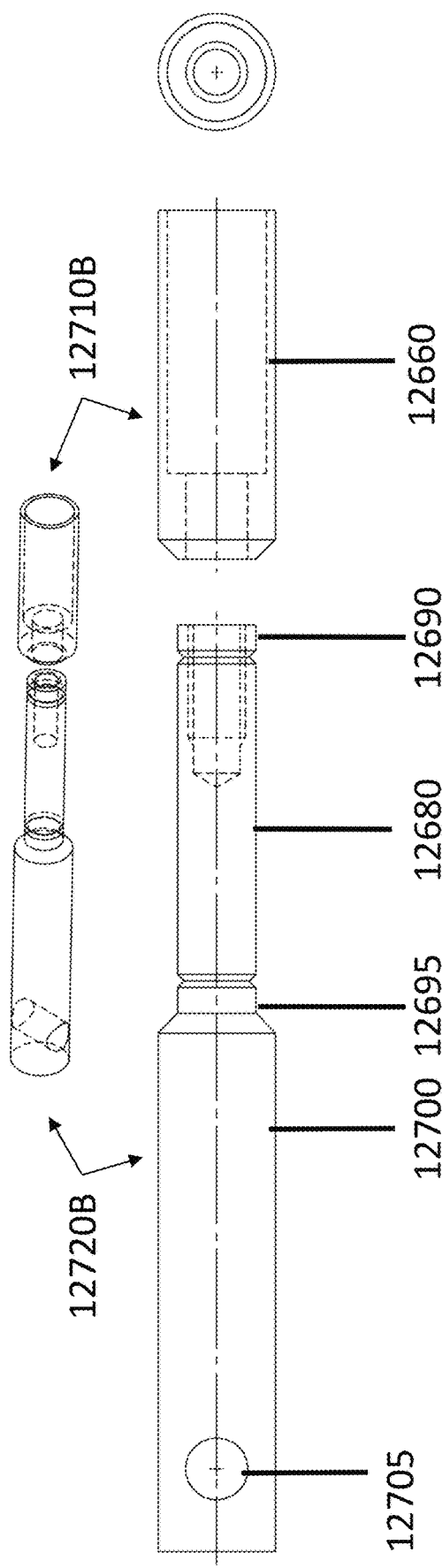

FIG. 27I-6 is a schematic diagram illustrating an example embodiment of a suction pump system for aspiration of brain bleeds.

FIG. 27J is a schematic diagram of a distal portion of a vascular treatment device illustrating longitudinal bunching of filaments during deployment.

Figure 27K:
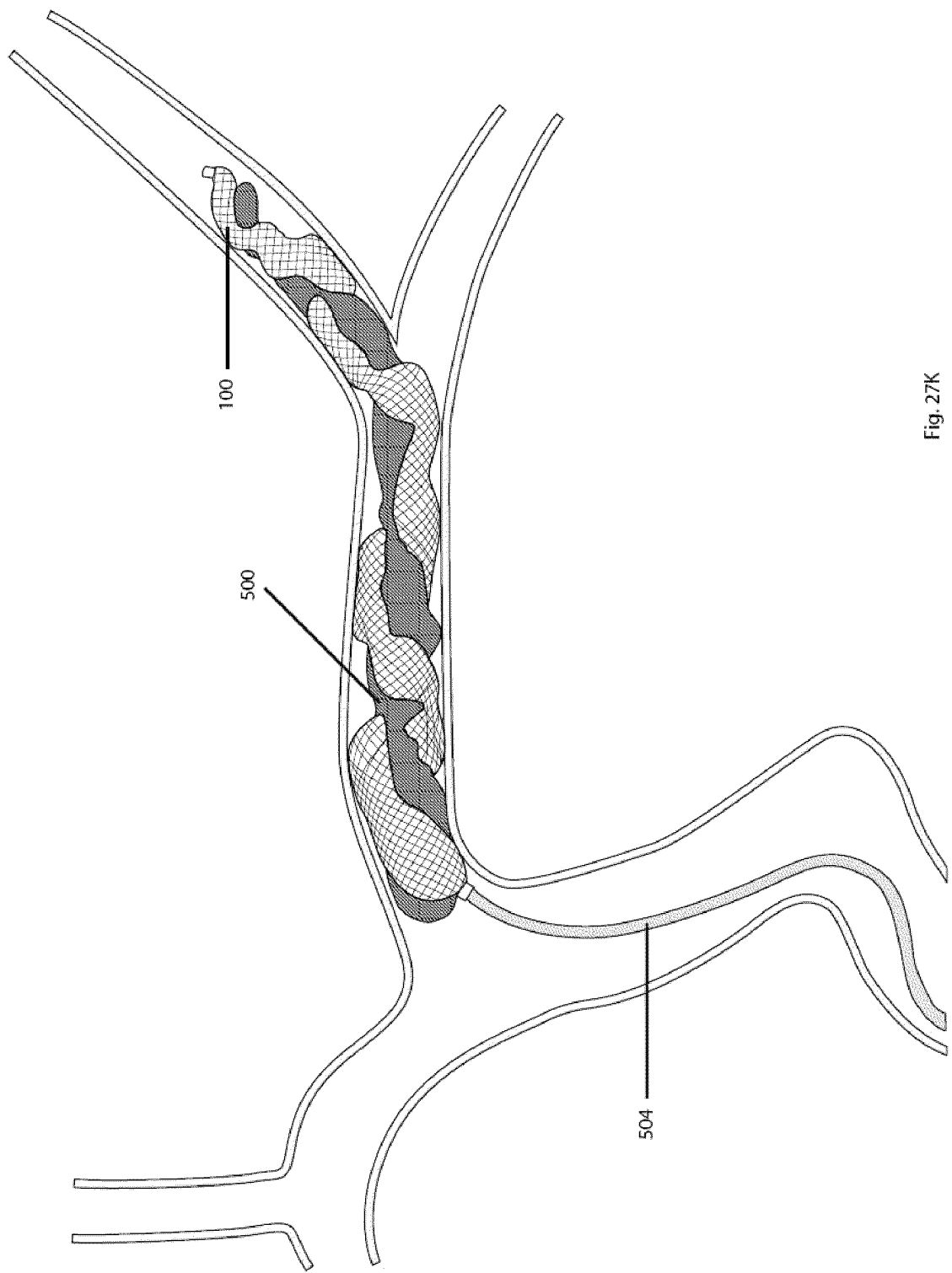

FIG. 27K is a schematic diagram of a distal portion of a vascular treatment device being torsionally rasped.

Figure 27L:
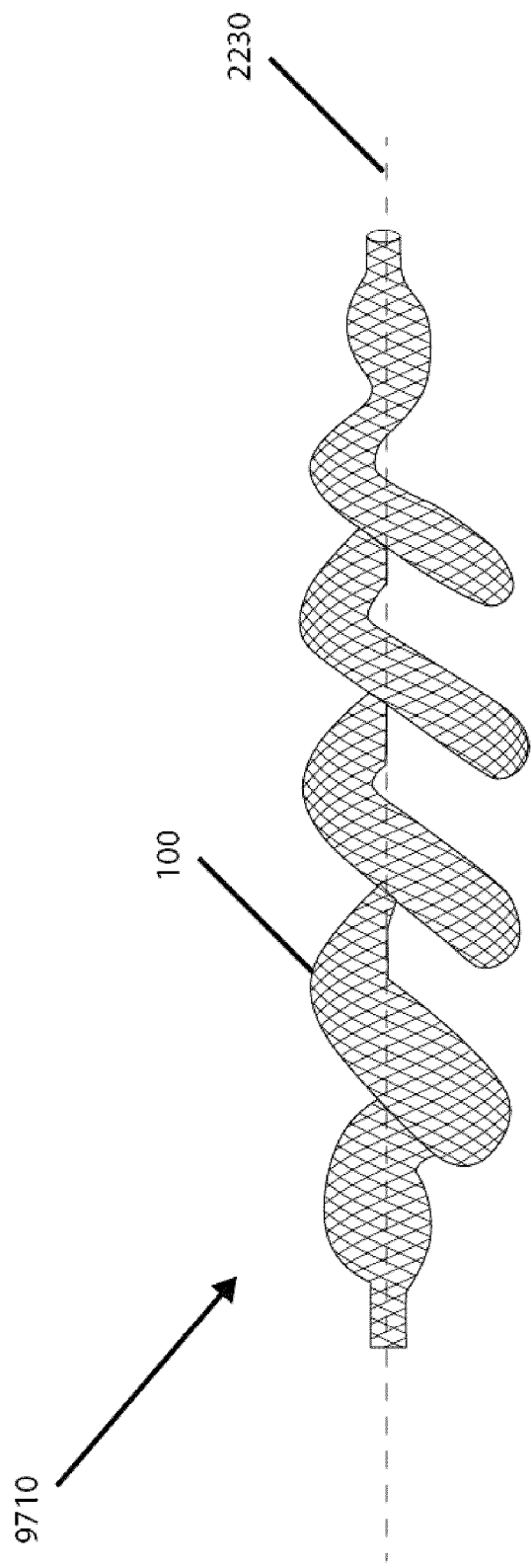

FIG. 27L is a schematic diagram illustrating an example embodiment of a two-way shape memory effect of a distal portion of a vascular treatment device.

FIG. 27M is a schematic diagram illustrating the retraction of a distal portion of a vascular treatment device and a clot.

FIG. 27N illustrates an example embodiment of a comparison of a clot length to a ruler.

Figure 27O:
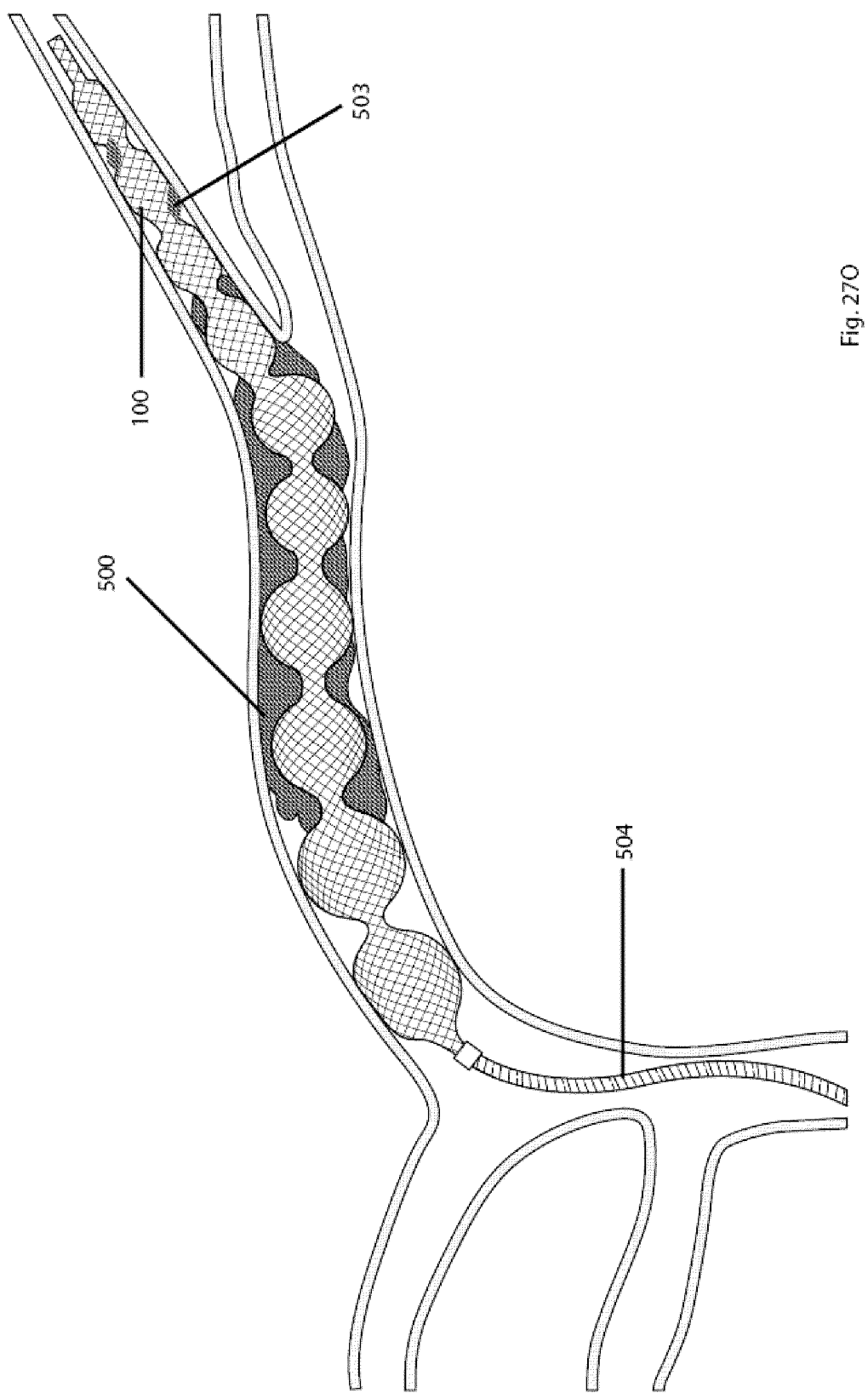

FIG. 27O is a schematic diagram of a distal portion of a thrombectomy device acting as a filter device.

Figure 27P:
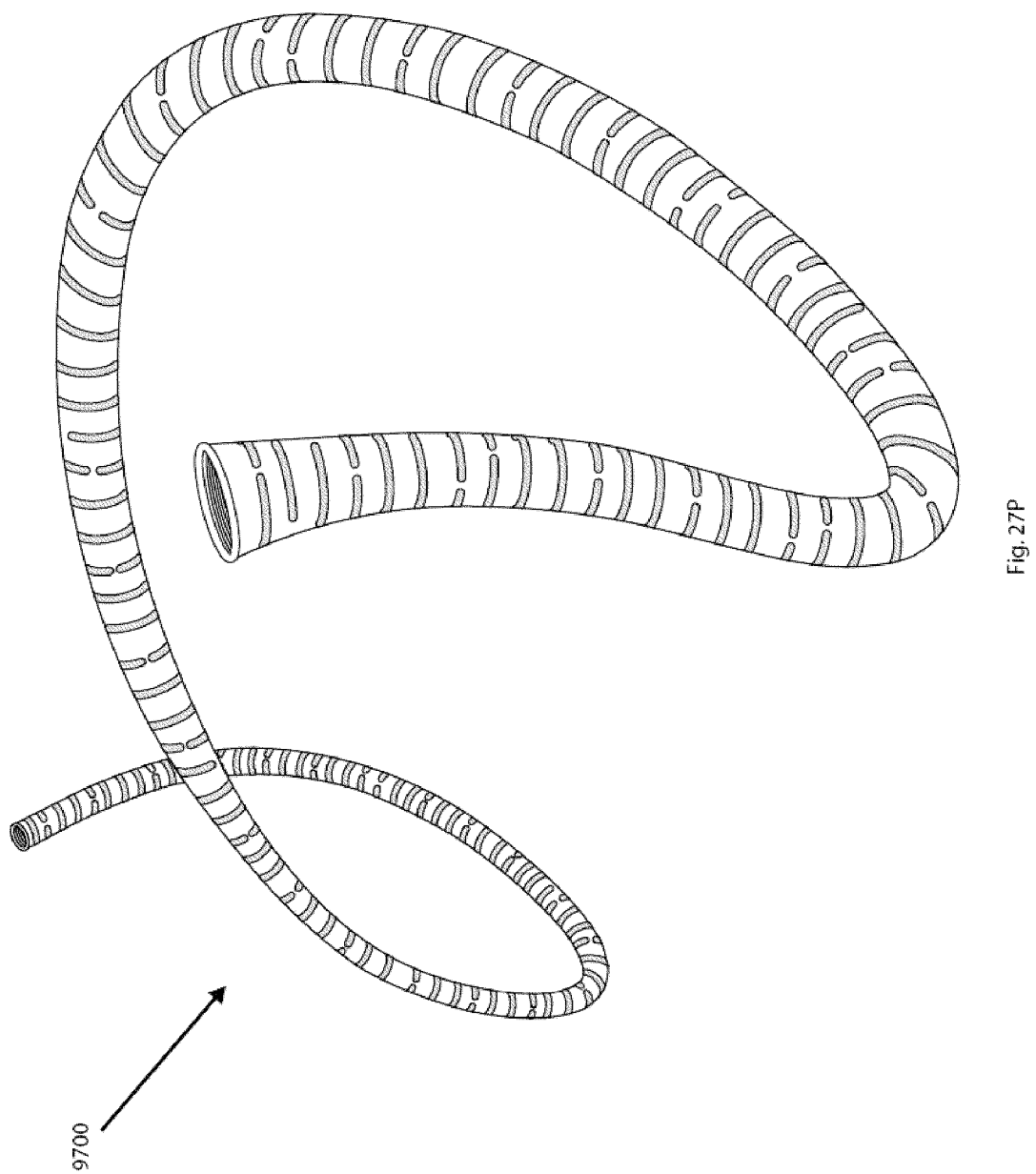

FIG. 27P is a schematic diagram illustrating an example embodiment of a two-way shape memory effect of the proximal portion of a thrombectomy device.

FIG. 28A is a schematic diagram of a guide catheter proximal to an aneurysm in vasculature.

Figure 28C:
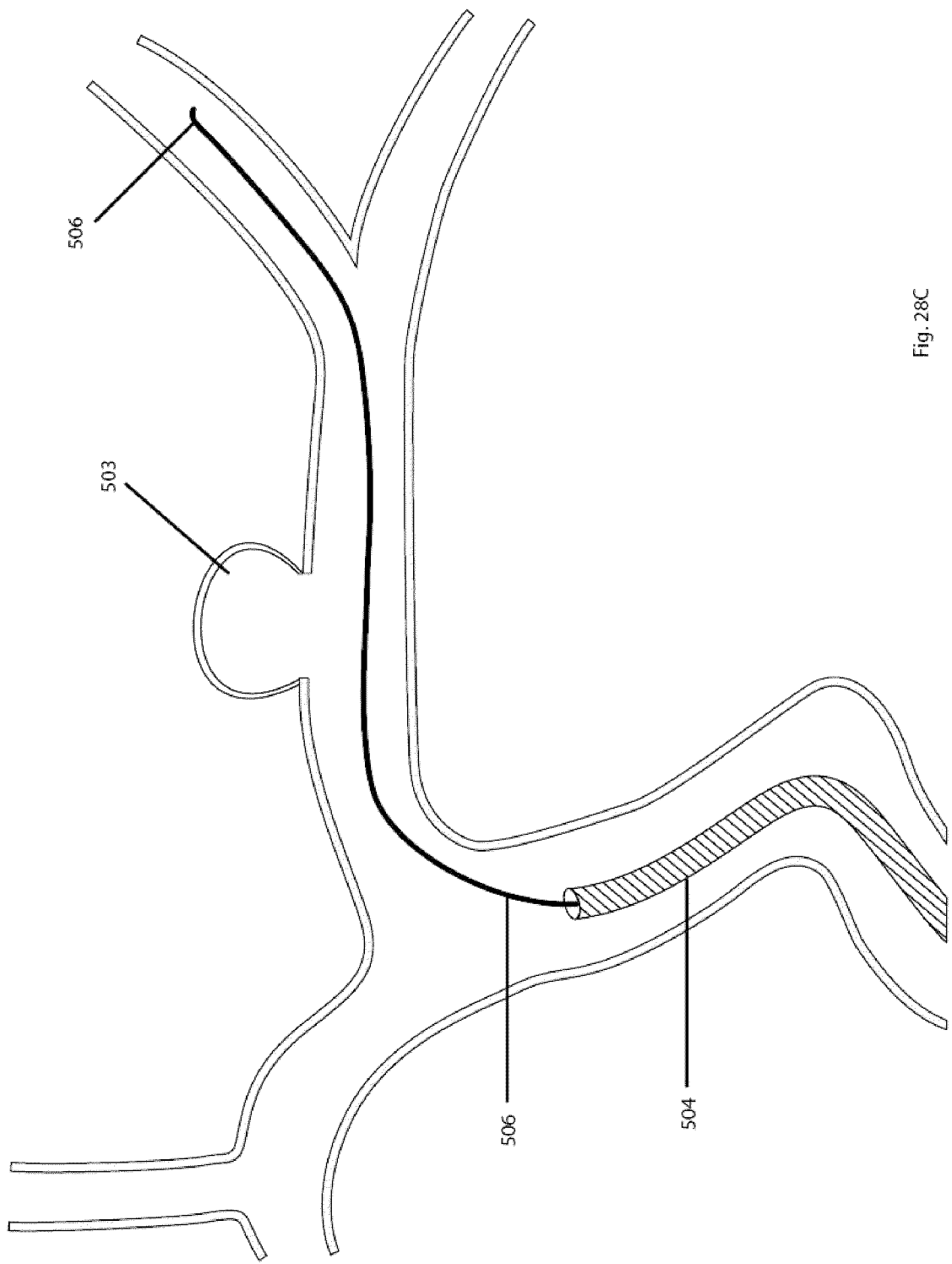

FIGS. 28B and 28C are schematic diagrams of a microwire distal to an aneurysm in vasculature and a microcatheter over the microwire.

FIG. 28D is a schematic diagram of a microcatheter distal to an aneurysm in vasculature.

Figure 28E:
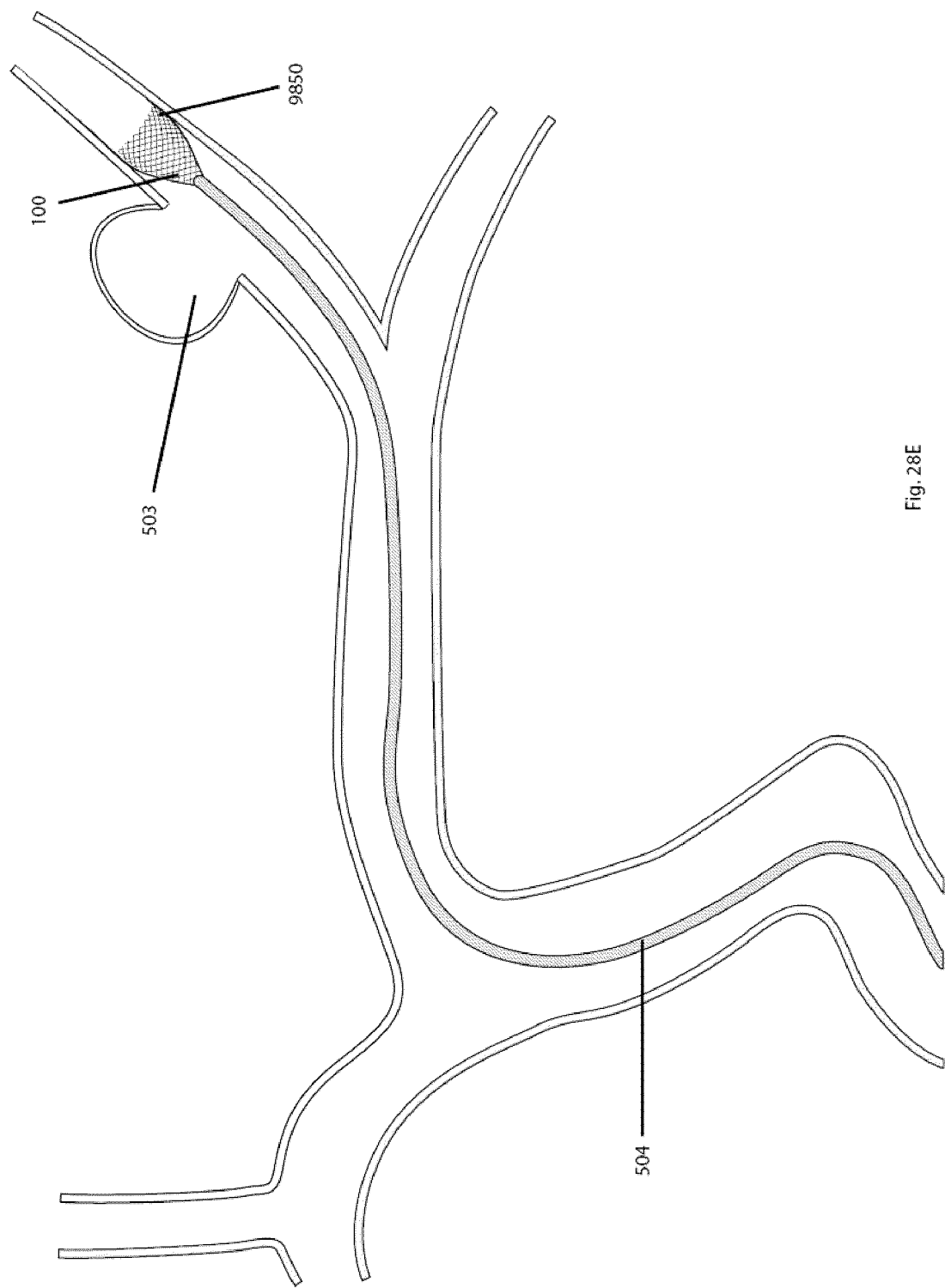

FIG. 28E is a schematic diagram of an example embodiment of the distal portion of a vascular treatment device being deployed distal to an aneurysm in vasculature.

Figure 28F:
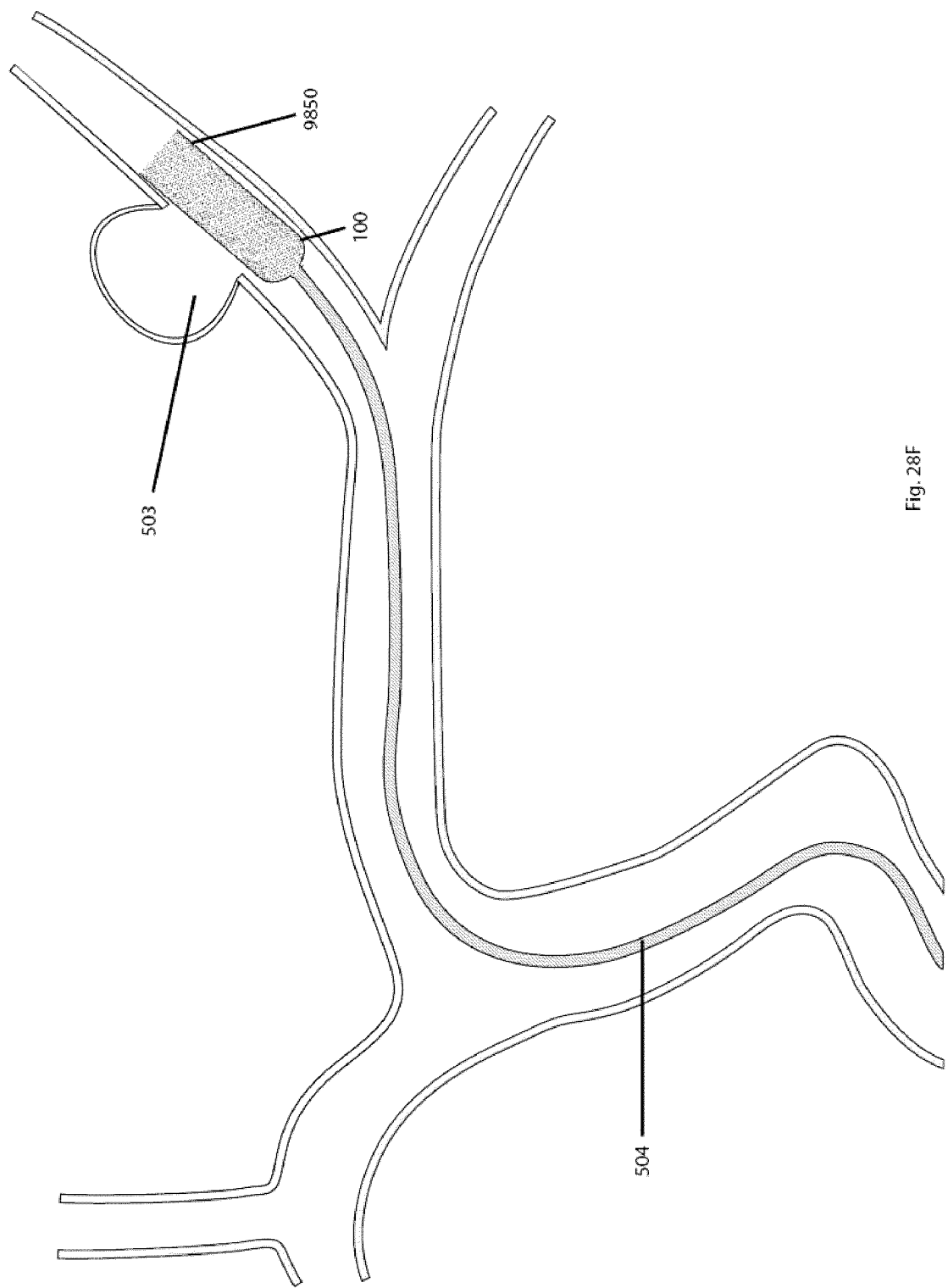

FIG. 28F is a schematic diagram of an example embodiment of the distal portion of a vascular treatment device being deployed across an aneurysm in vasculature.

FIG. 28G is a schematic diagram of an example embodiment of the distal portion of FIG. 6G deployed across an aneurysm in vasculature.

Figure 28H:
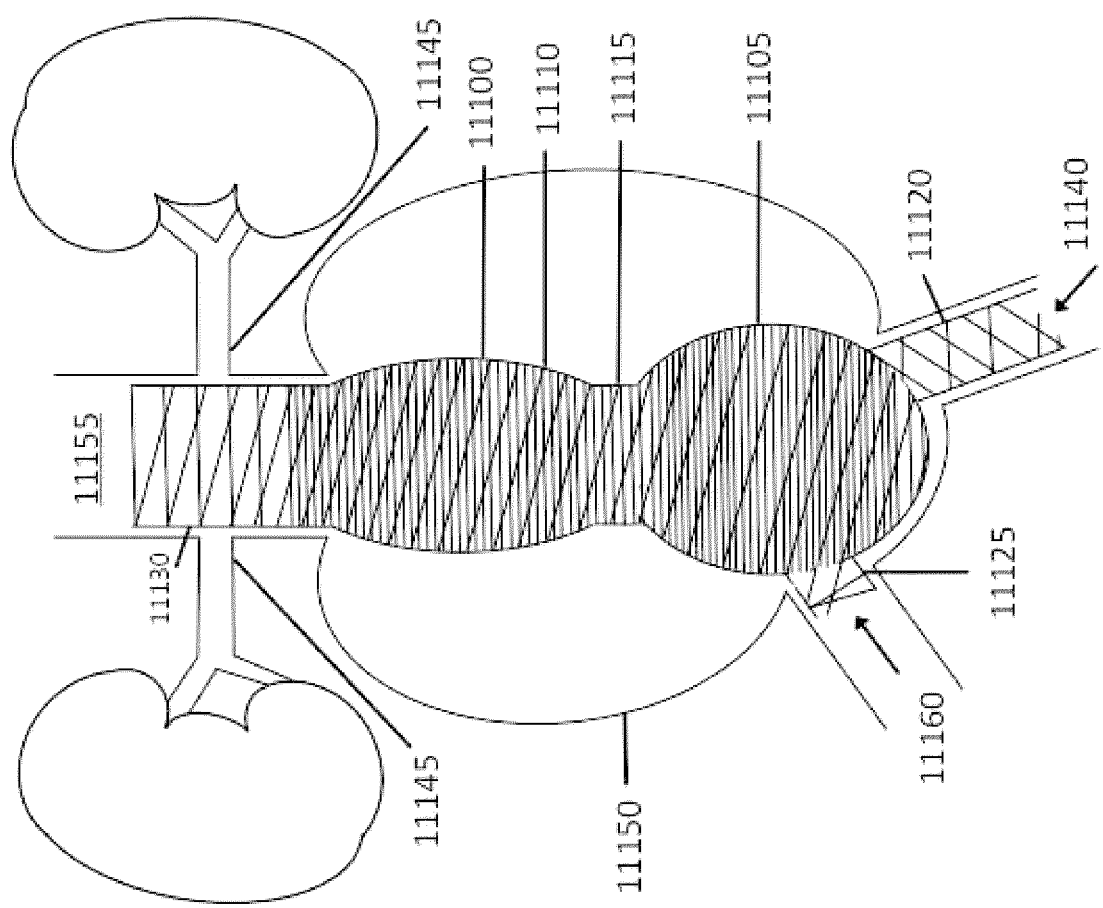

FIG. 28H is a schematic diagram of an example embodiment of the distal portion of FIG. 7B deployed across an aneurysm in vasculature.

Figure 28I:
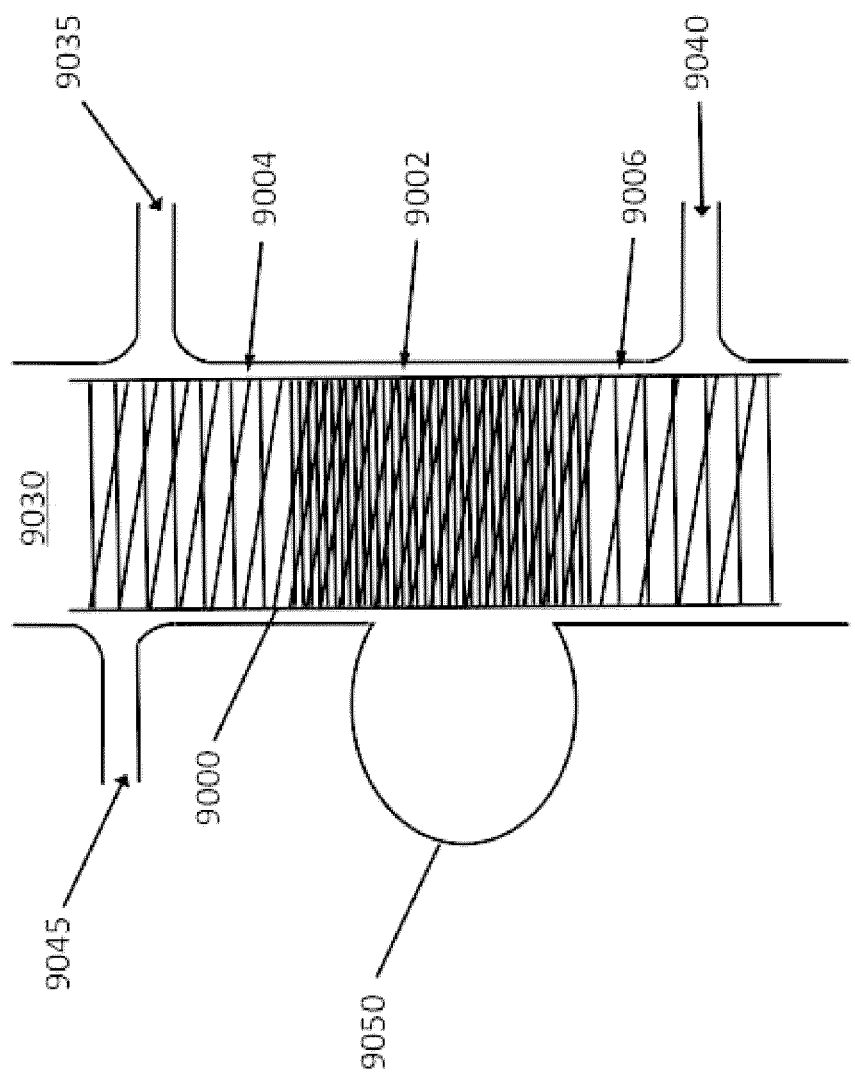

FIG. 28I is a schematic diagram of an example embodiment of the distal portion of FIG. 6A deployed across an aneurysm in vasculature.

Figure 28J:
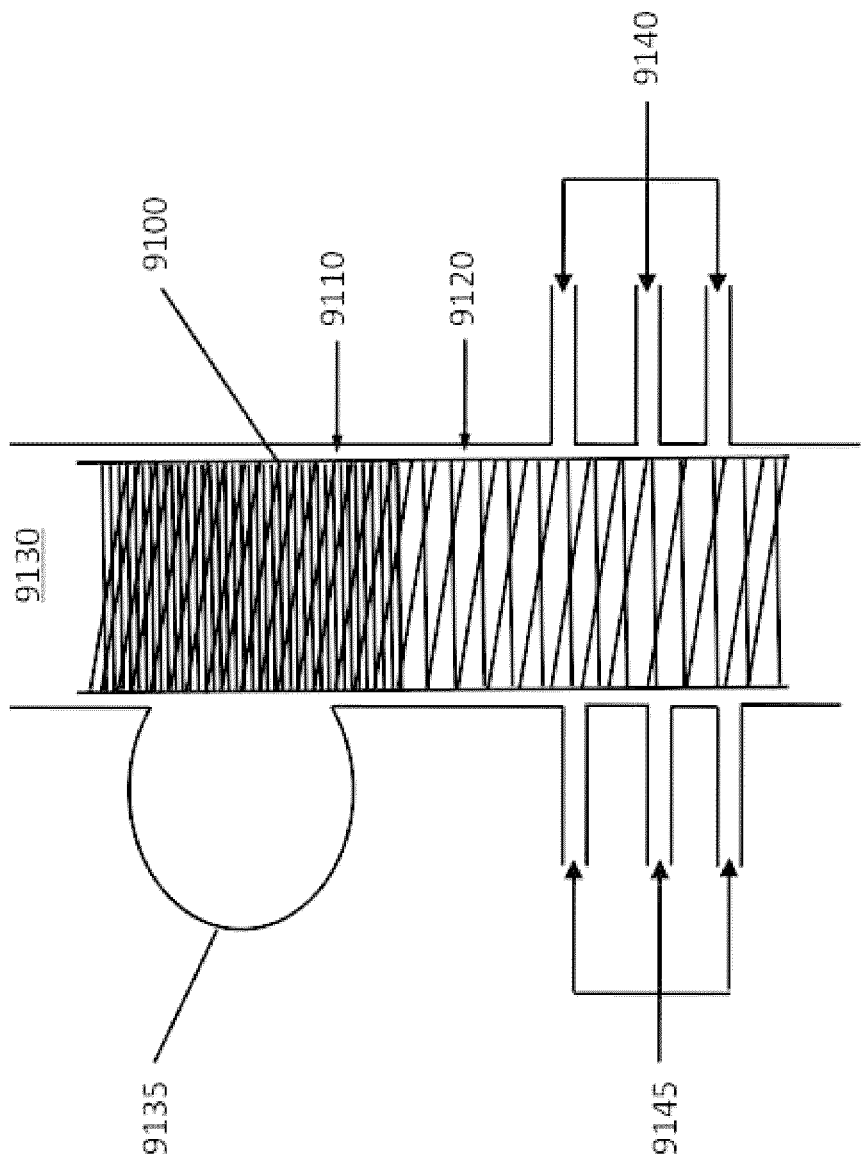

FIG. 28J is a schematic diagram of an example embodiment of the distal portion of FIG. 6B deployed across an aneurysm in vasculature.

Figure 28K:
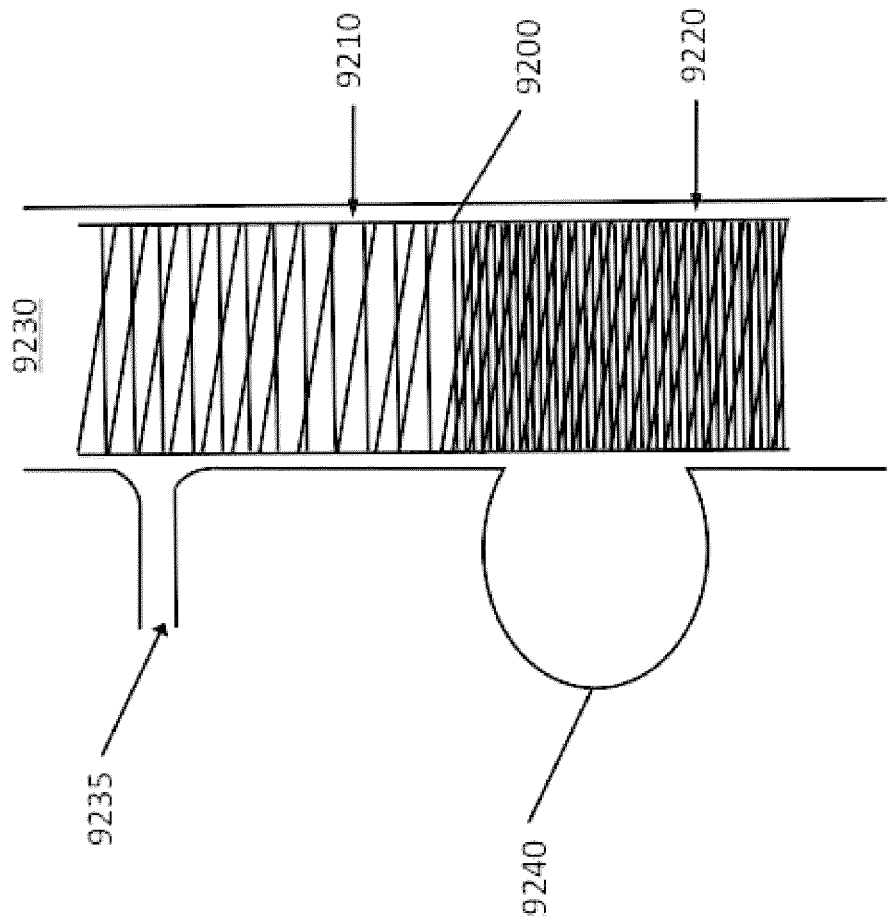

FIG. 28K is a schematic diagram of an example embodiment of the distal portion of FIG. 6C deployed across an aneurysm in vasculature.

Figure 28L:
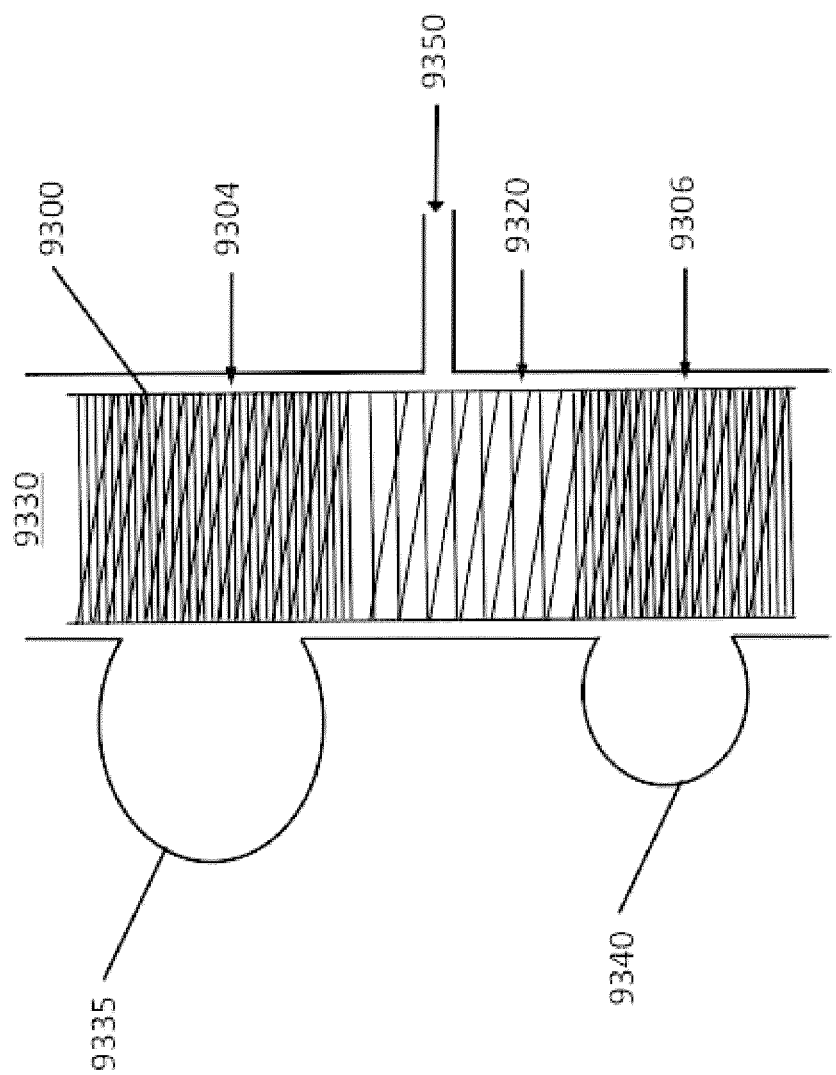

FIG. 28L is a schematic diagram of an example embodiment of the distal portion of FIG. 6D deployed across aneurysms in vasculature.

Figure 28M:
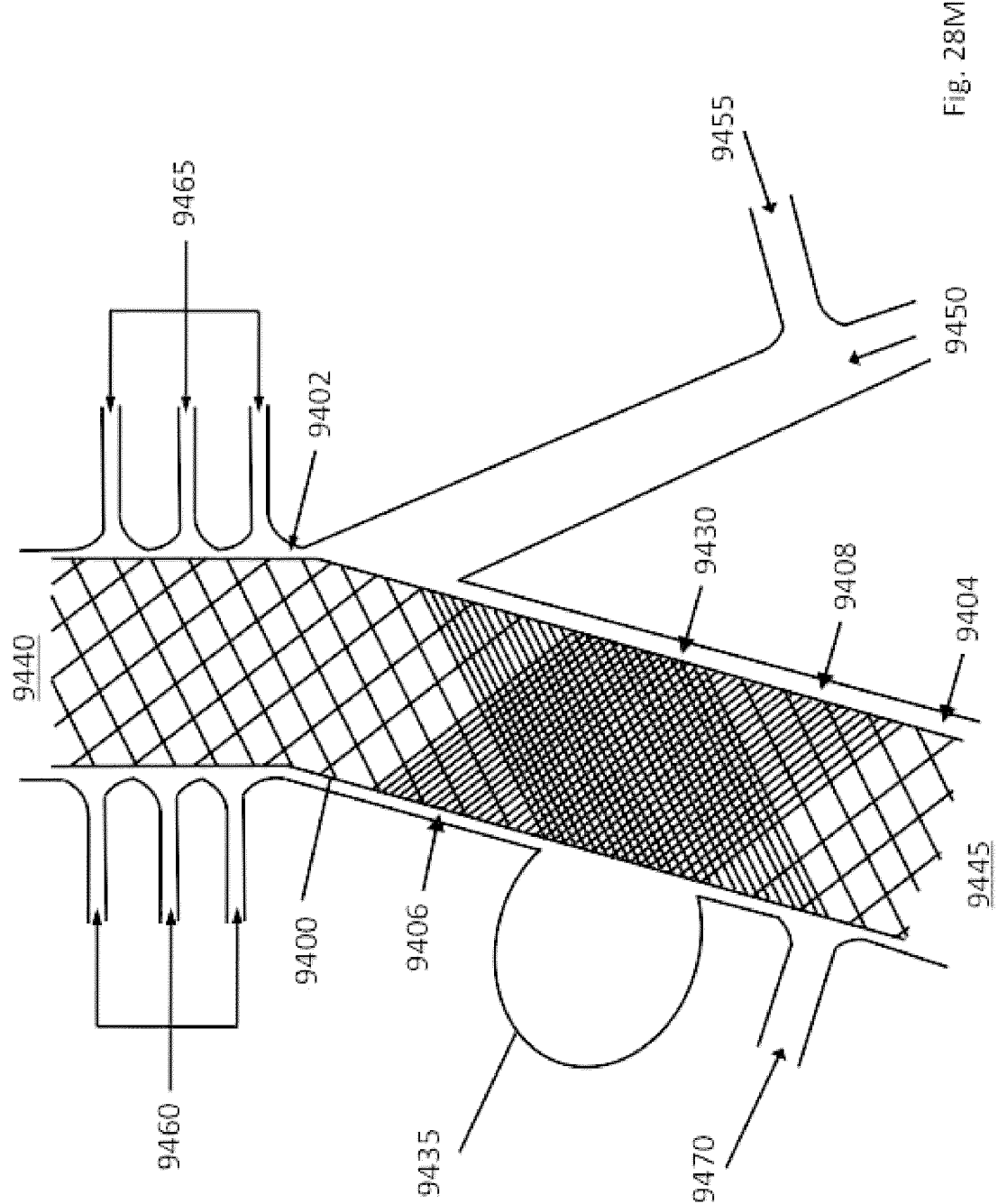

FIG. 28M is a schematic diagram of an example embodiment of the distal portion of FIG. 6E deployed across an aneurysm in vasculature.

Figure 28N:
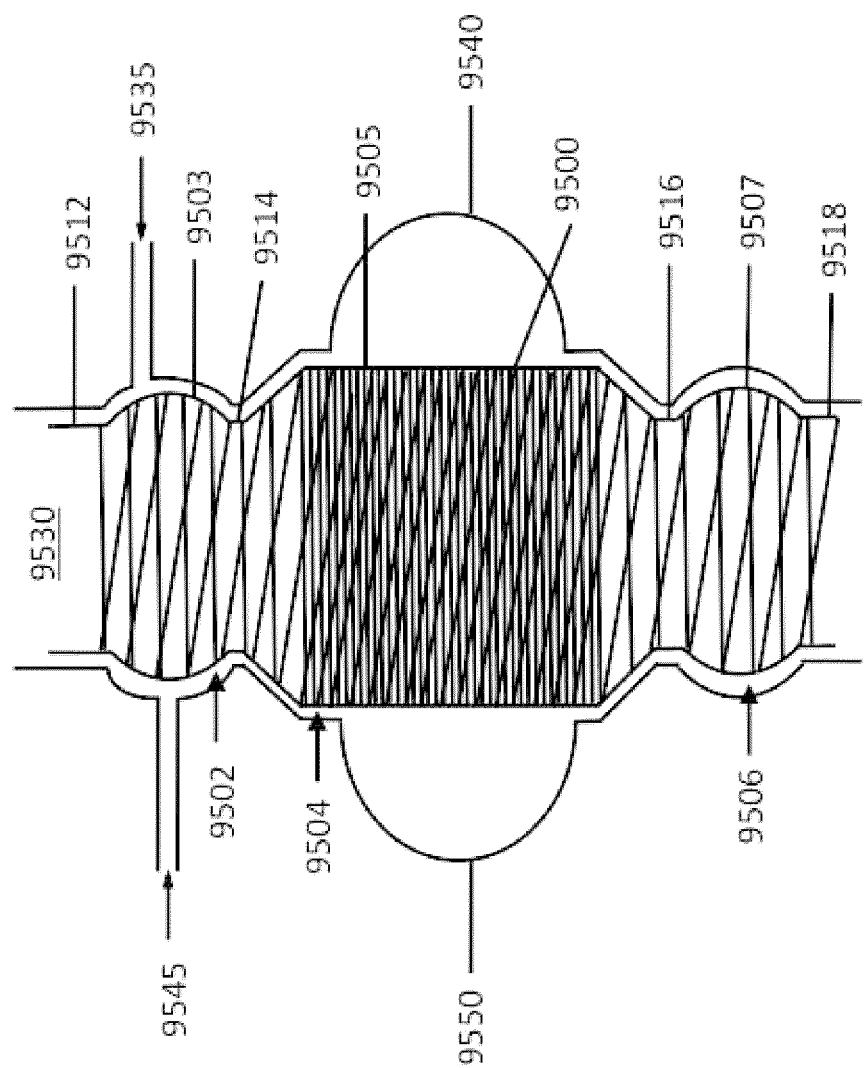

FIG. 28N is a schematic diagram of an example embodiment of the distal portion of FIG. 6F deployed across an aneurysm in vasculature.

Figure 7A:
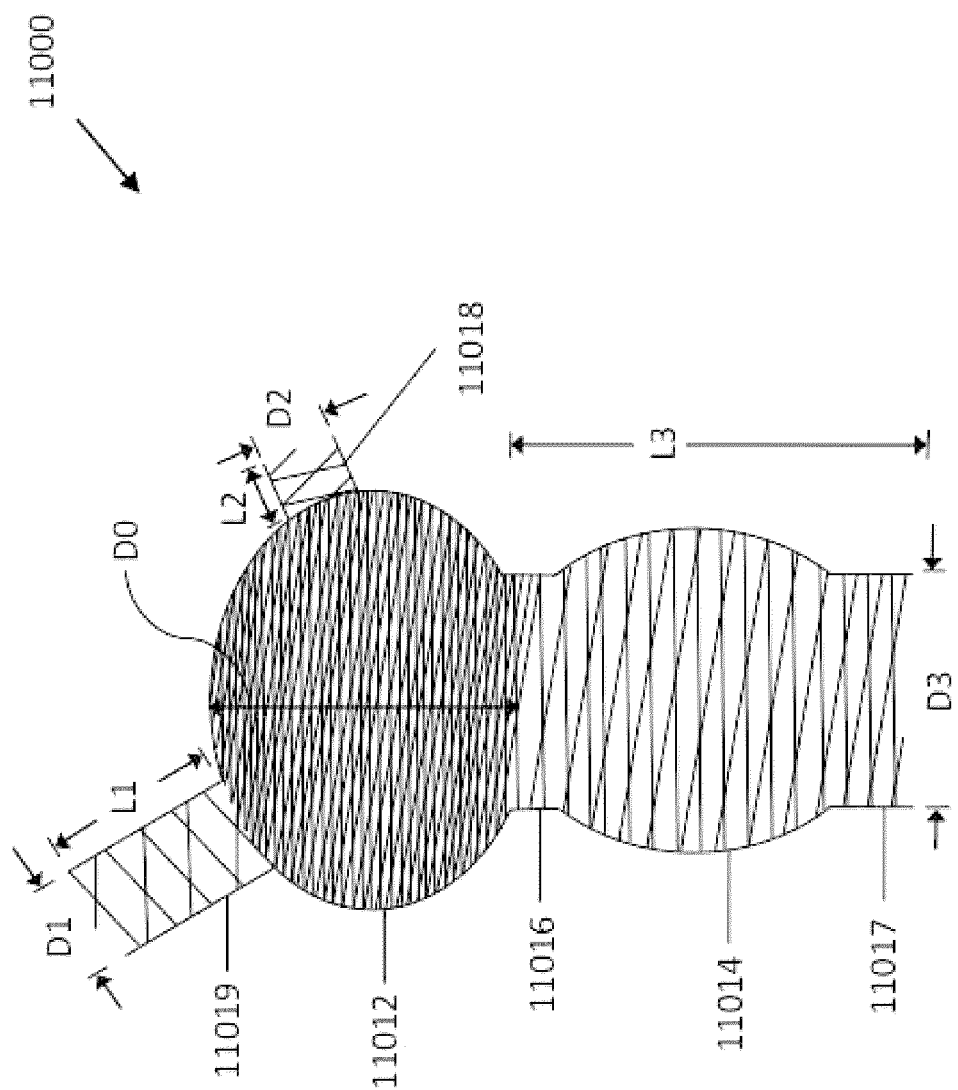
FIG. 7A is a schematic side elevational view of still another example embodiment of a distal portion of a vascular treatment device.
Figure 28O:
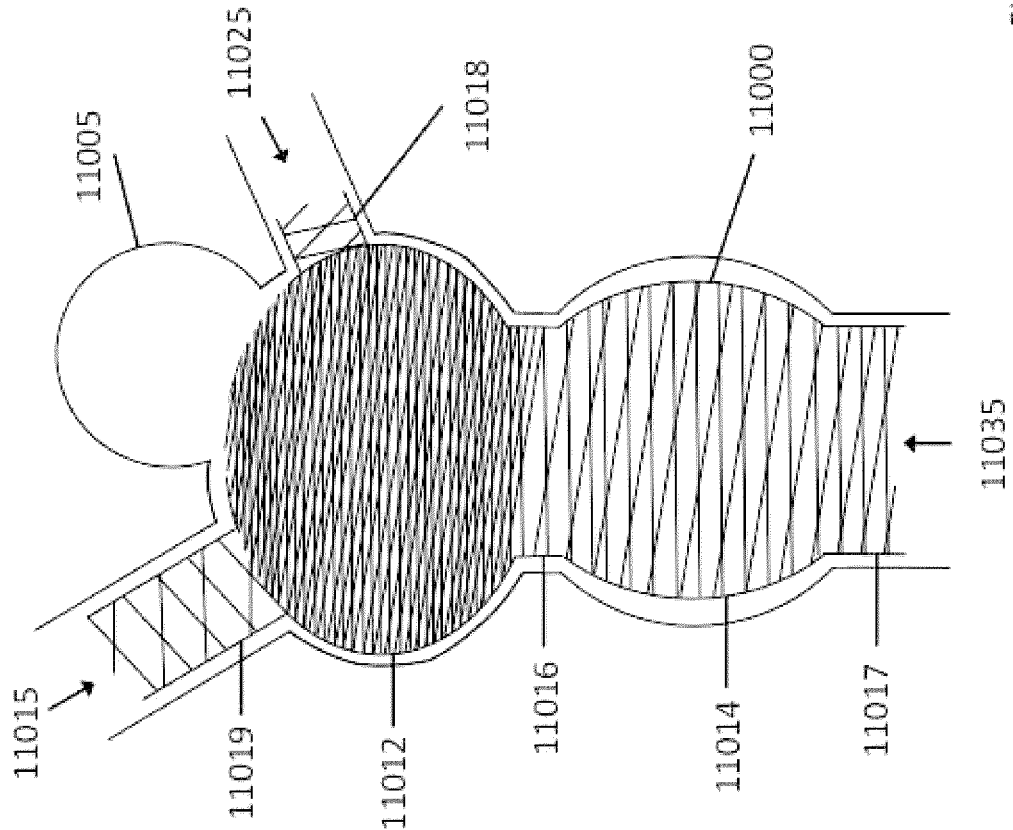

FIG. 28O is a schematic diagram of an example embodiment of the distal portion of FIG. 7A deployed across a bifurcation aneurysm in vasculature.

Figure 28P:
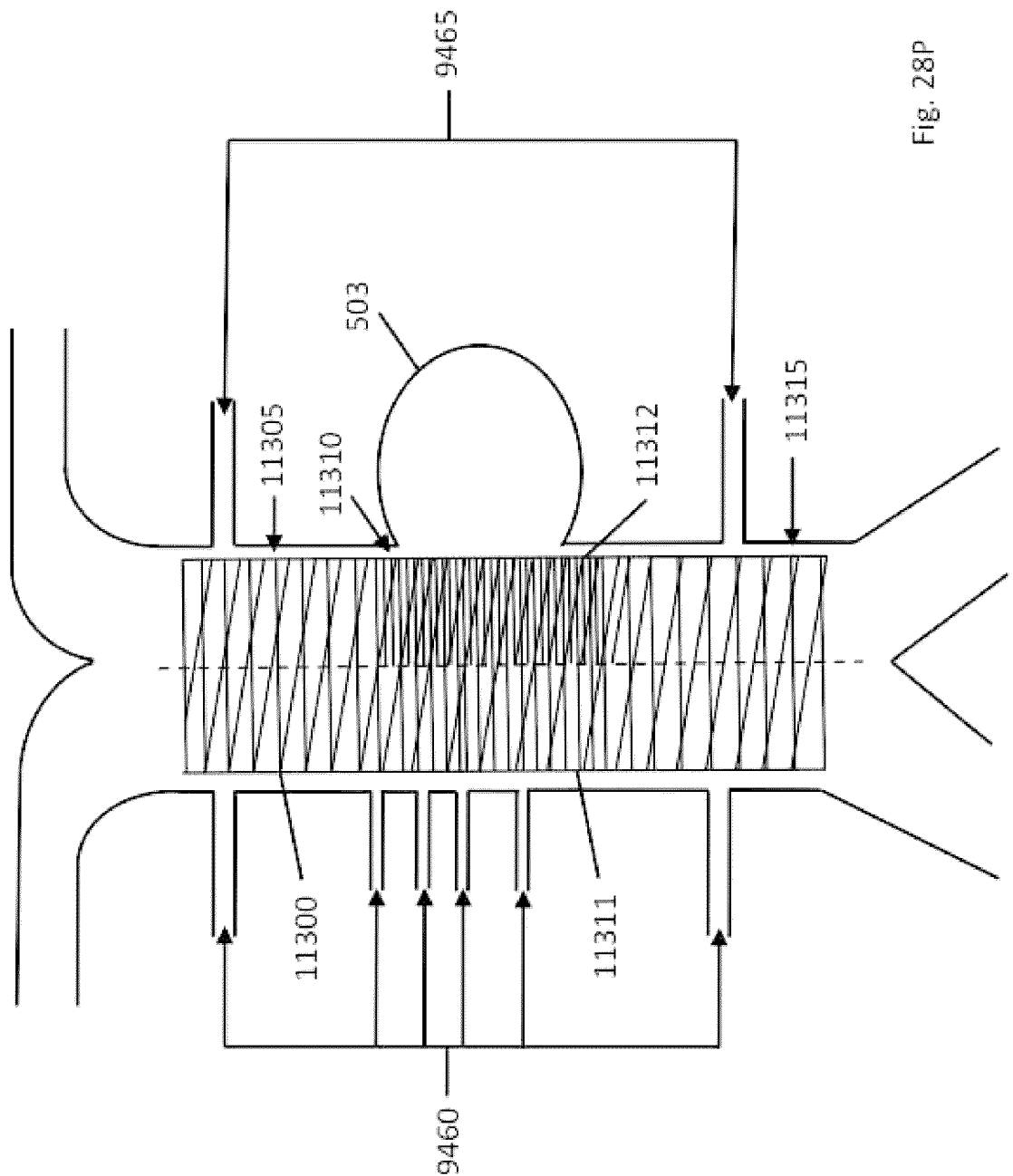

FIG. 28P is a schematic diagram of an example embodiment of the distal portion of FIG. 6H deployed across a side-wall aneurysm in vasculature.

Figure 28Q:
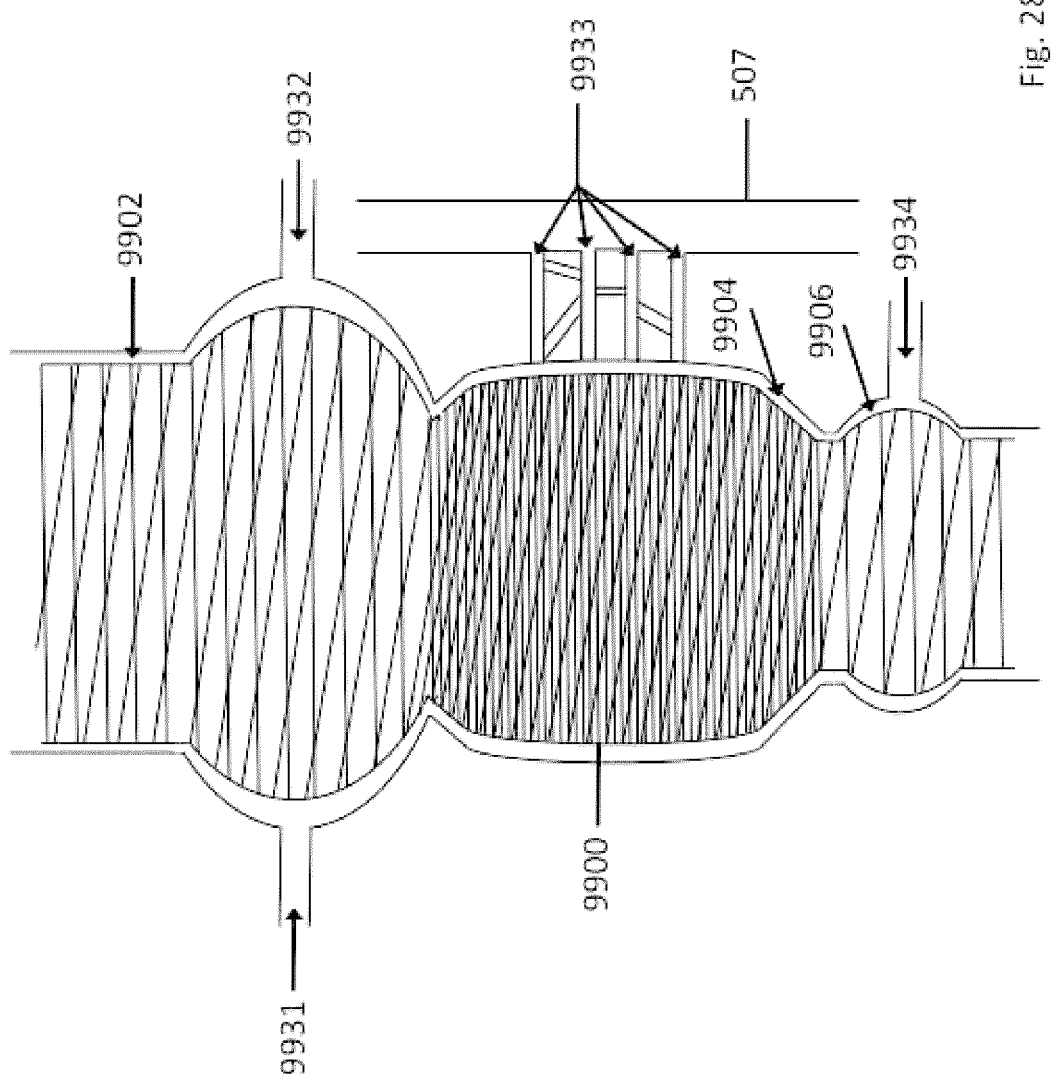

FIG. 28Q is a schematic diagram of an example embodiment of the distal portion of FIG. 6J deployed across a vascular malformation in vasculature.

Figure 7C:
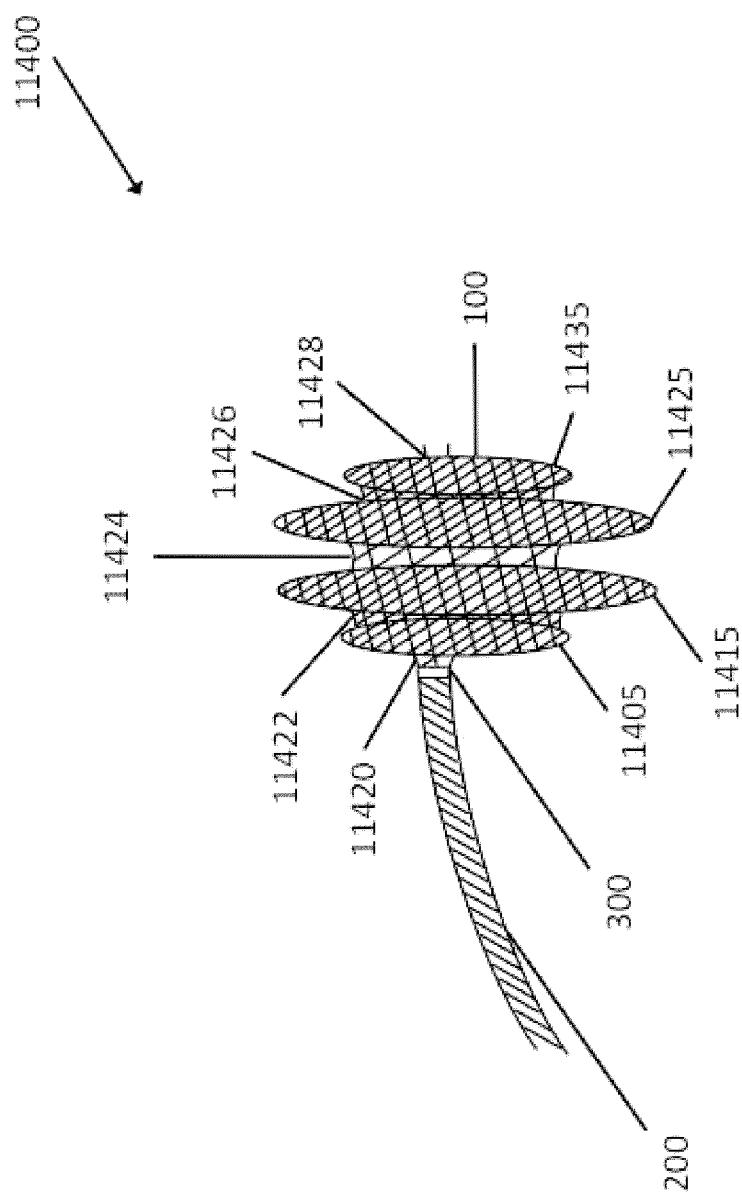
FIG. 7C is a schematic side elevational view of another example embodiment of a distal portion of a vascular treatment device.
Figures 2, 7C:
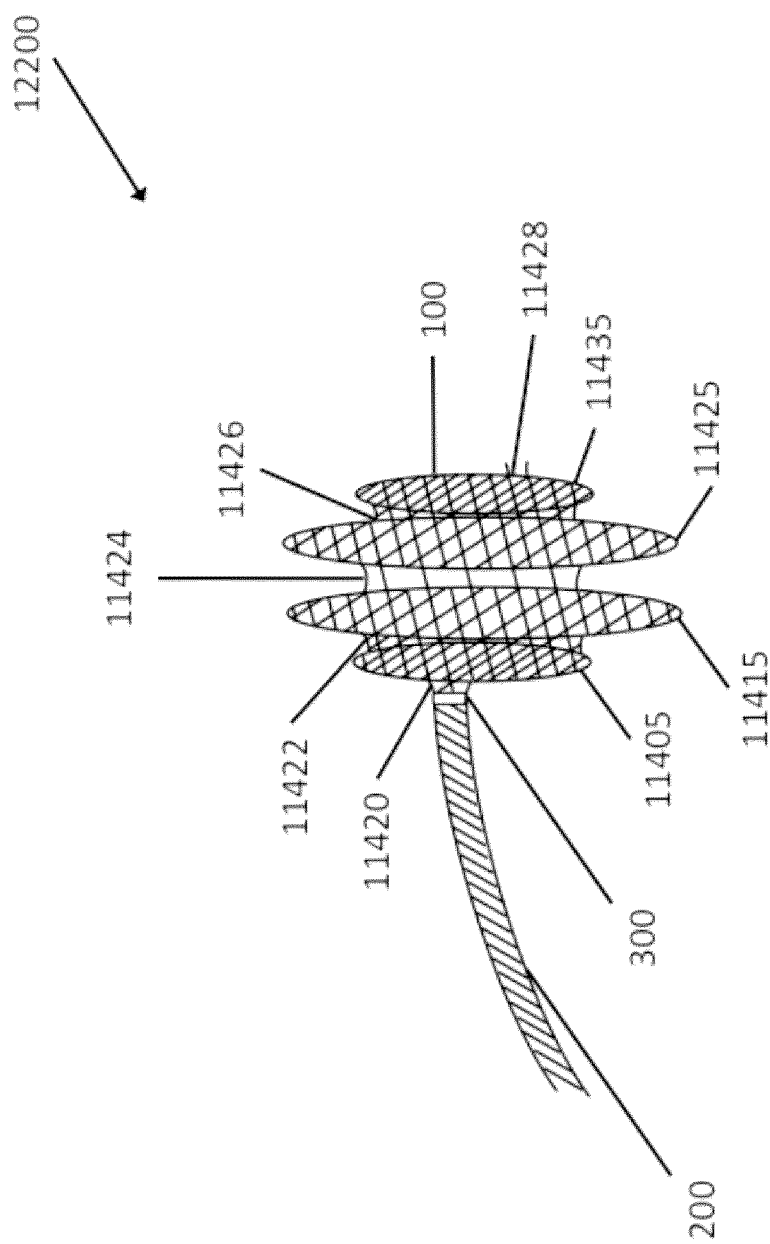
Figure 29A:
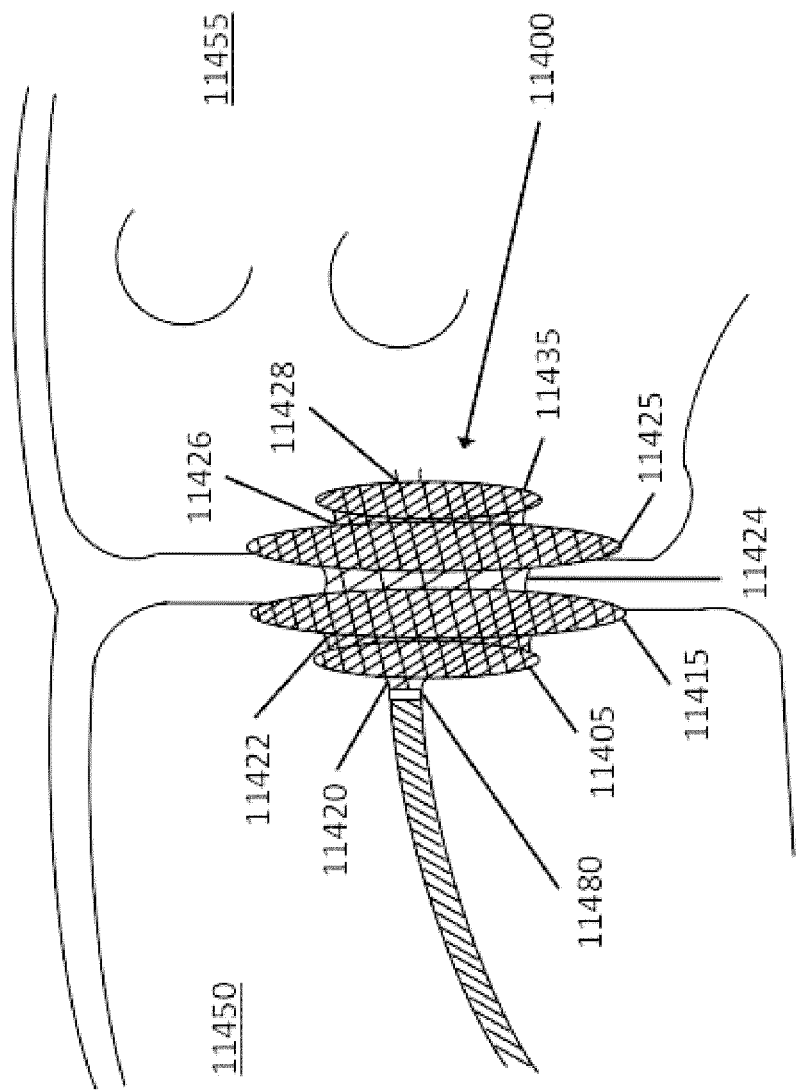

FIG. 29A is a schematic diagram of an example embodiment of the distal portion of FIG. 7C deployed across a fistula.

Figure 7D:
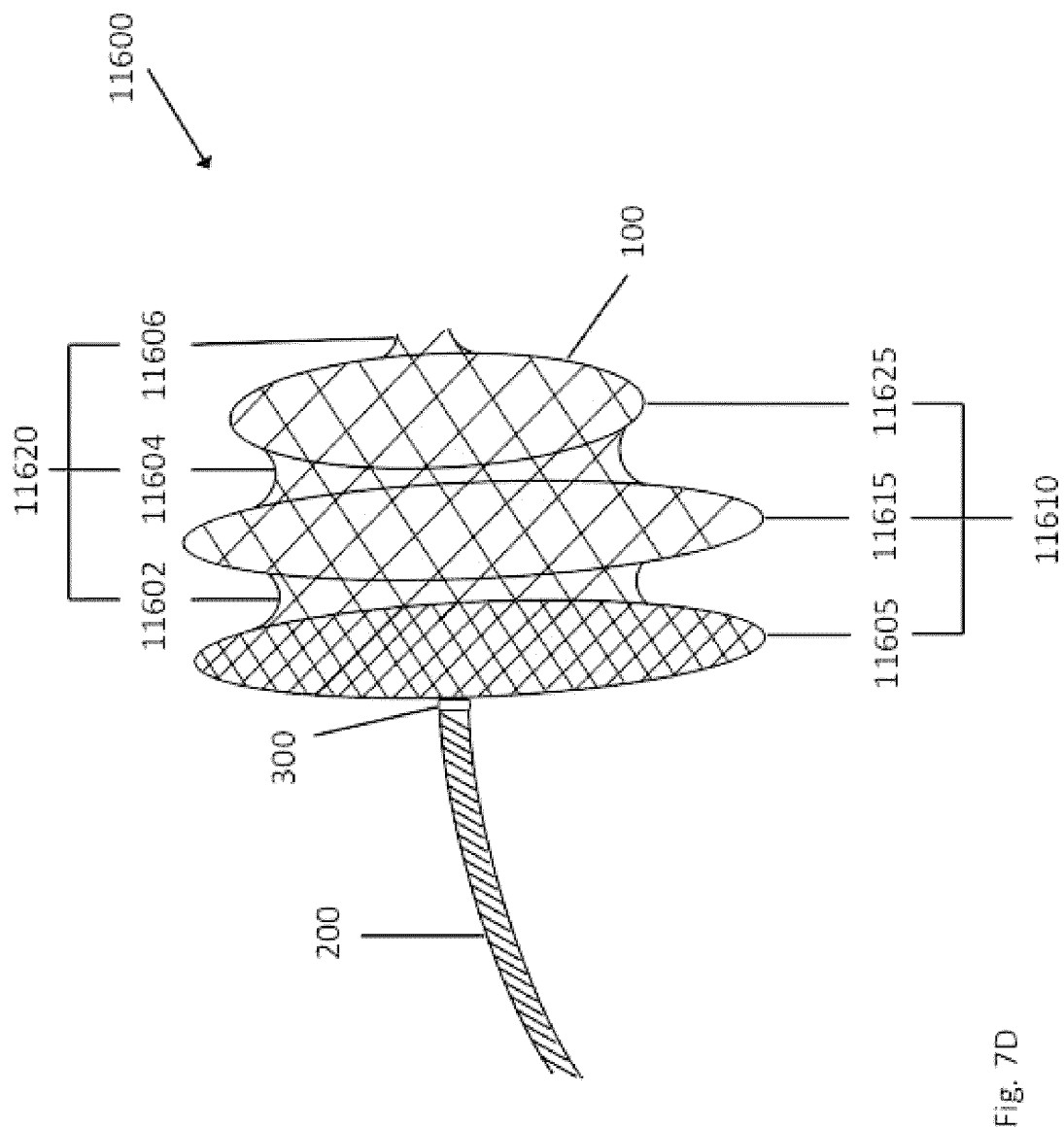
FIG. 7D is a schematic side elevational view of yet another example embodiment of a distal portion of a vascular treatment device.
Figure 29B:
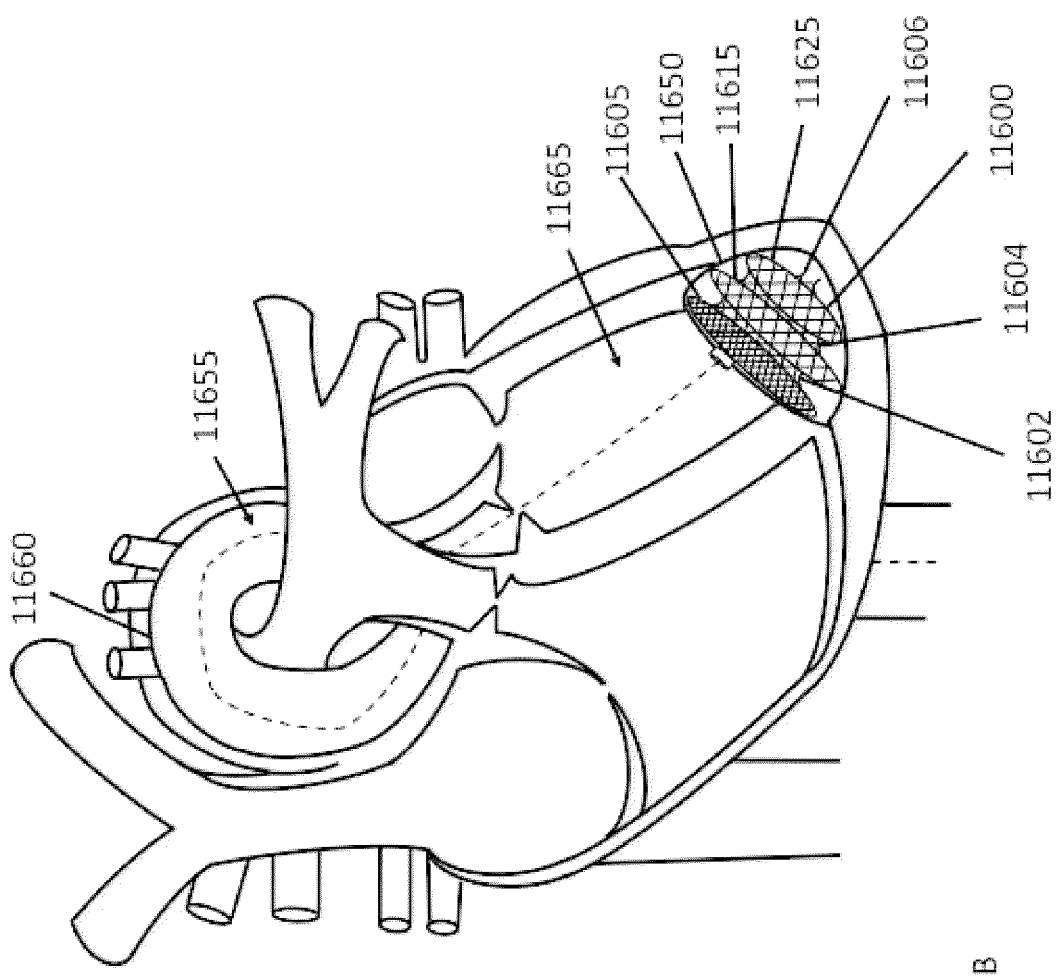

FIG. 29B is a schematic diagram of an example embodiment of the distal portion of FIG. 7D deployed in a cardiac wall aneurysm.

Figure 29C:
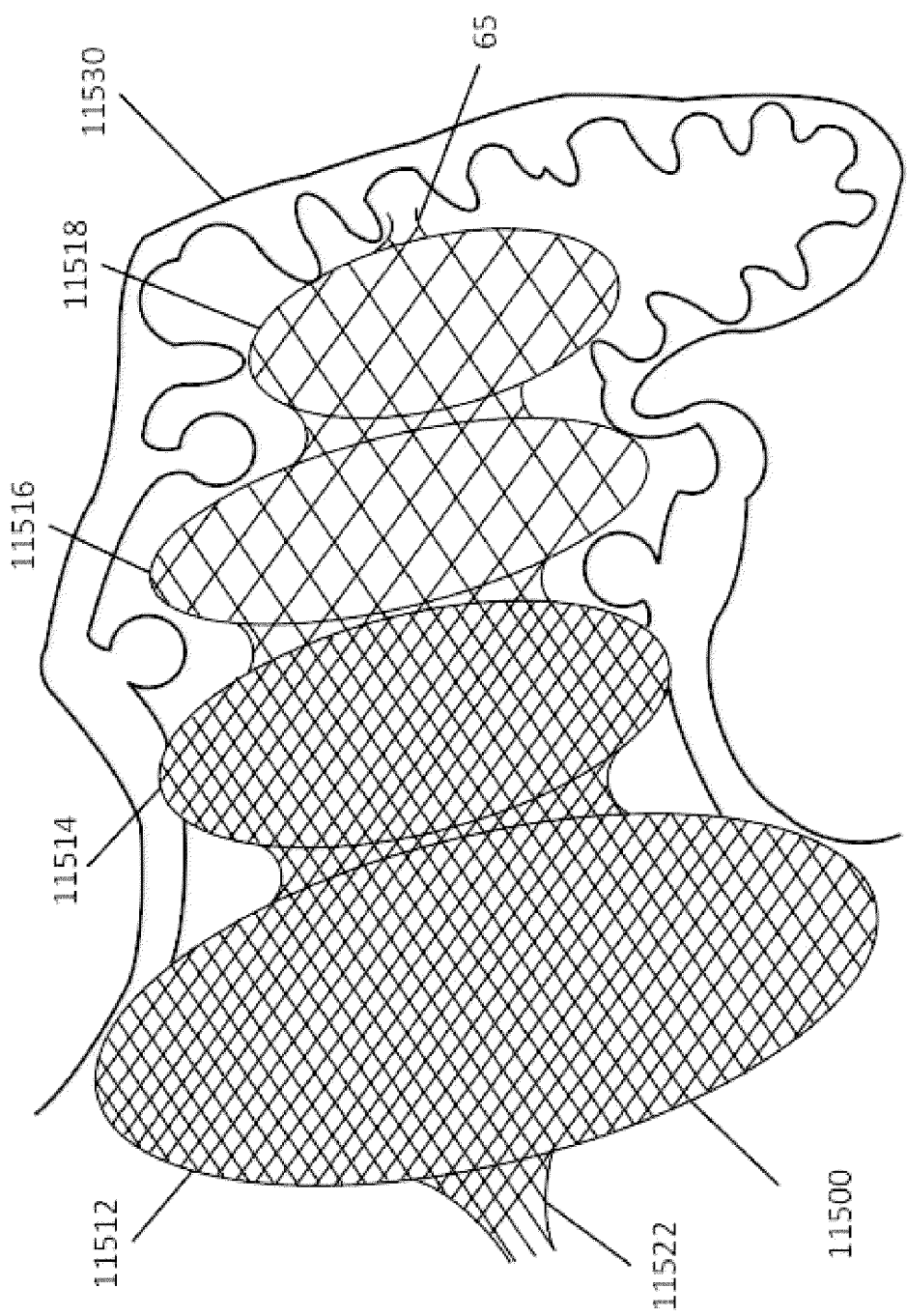

FIG. 29C is a schematic diagram of an example embodiment of the distal portion of FIG. 7E deployed in the left atrial appendage of the heart.

Figure 29D:
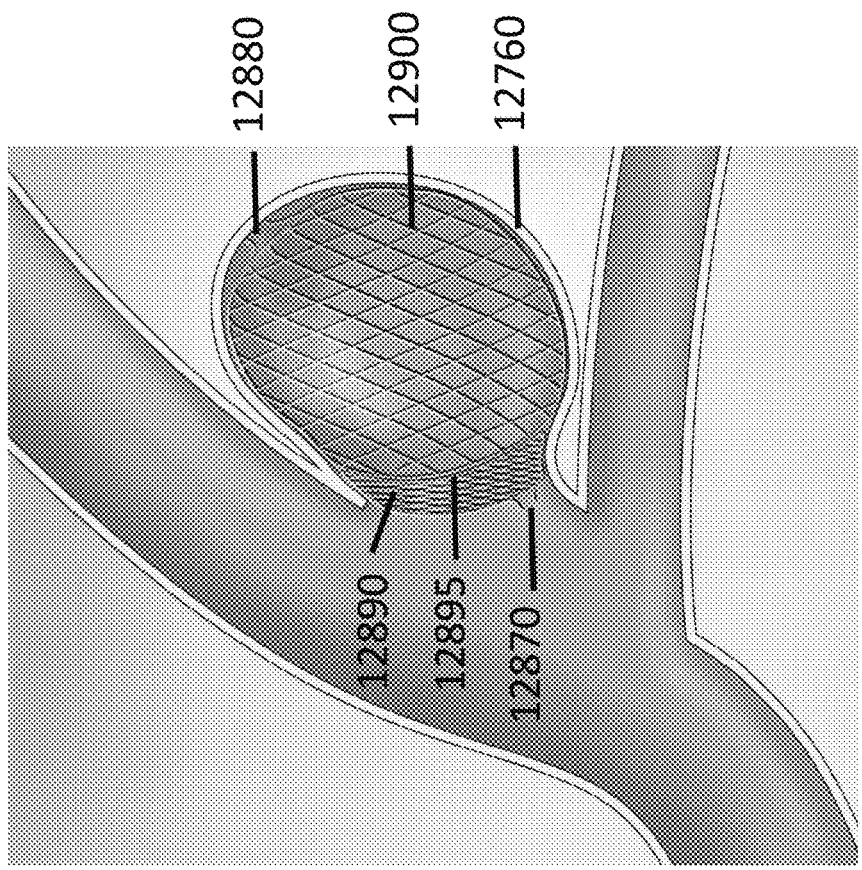

FIG. 29D is a schematic diagram of an example embodiment of a vascular treatment device deployed in an aneurysm.

Figure 29E:
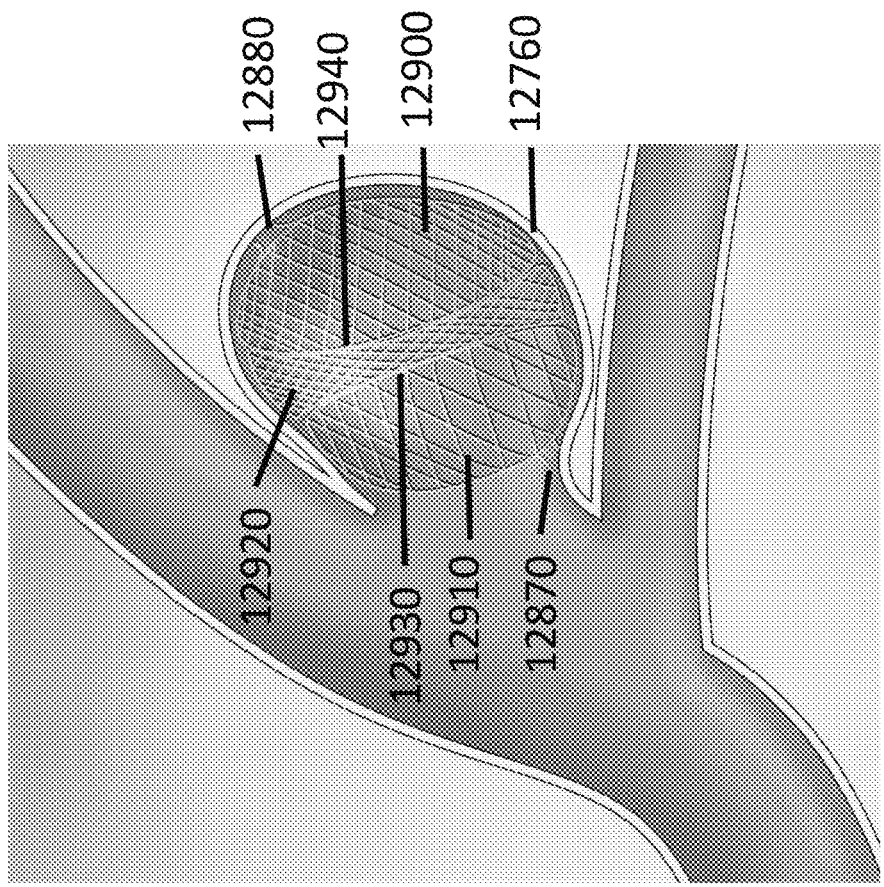

FIG. 29E is a schematic diagram of another example embodiment of a vascular treatment device deployed in an aneurysm.

DETAILED DESCRIPTION

FIG. 1A is a schematic side elevational view of an example embodiment of a vascular treatment device 10. The device 10 includes a distal portion 100, a proximal portion 200, and a joint 300 coupling the distal portion 100 to the proximal portion 200. In the device 10, the joint 300 couples a proximal segment of the distal portion 100 to a distal segment of the proximal portion 200.

Figure 1B:
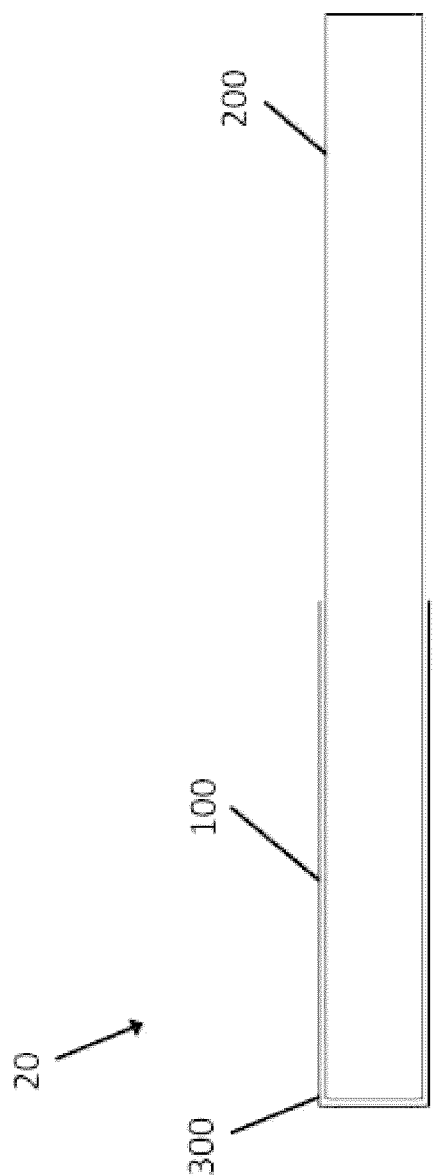
FIG. 1B is a schematic side elevational view of another example embodiment of a vascular treatment device.

FIG. 1B is a schematic side elevational view of another example embodiment of a vascular treatment device 20. The device 20 includes a distal portion 100, a proximal portion 200, and a joint 300 coupling the distal portion 100 to the proximal portion 200. In the device 20, the joint 300 couples a distal segment of the distal portion 100 to a distal segment of the proximal portion 200. The proximal portion 200 extends through the distal portion 100.

Figure 1C:
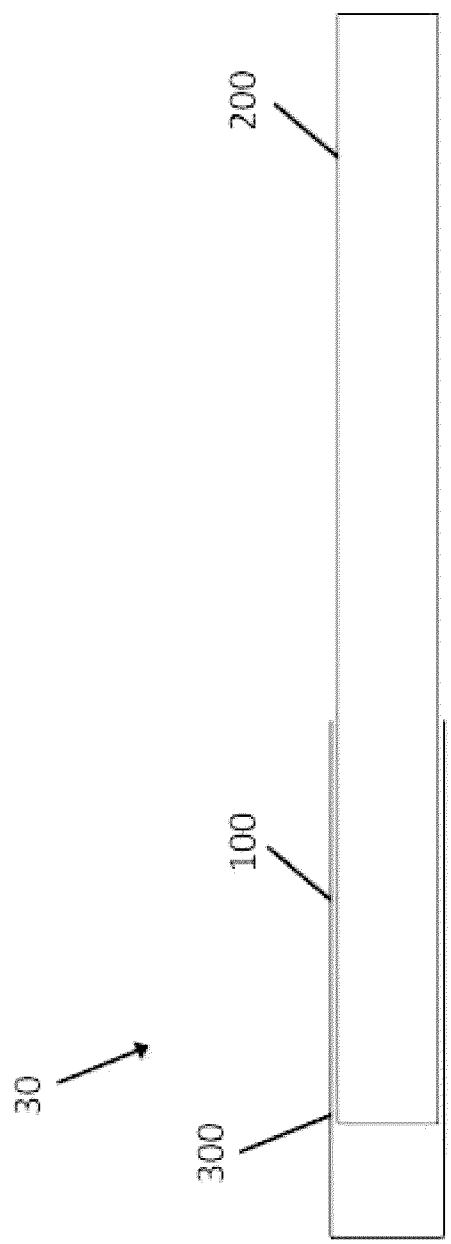
FIG. 1C is a schematic side elevational view of yet another example embodiment of a vascular treatment device.

FIG. 1C is a schematic side elevational view of yet another example embodiment of a vascular treatment device 30. The device 30 includes a distal portion 100, a proximal portion 200, and a joint 300 coupling the distal portion 100 to the proximal portion 200. In the device 30, the joint 300 couples a segment between the proximal end and distal the end of the distal portion 100 to a distal segment of the proximal portion 200. The proximal portion 200 partially extends through the distal portion 100.

Figure 1D:
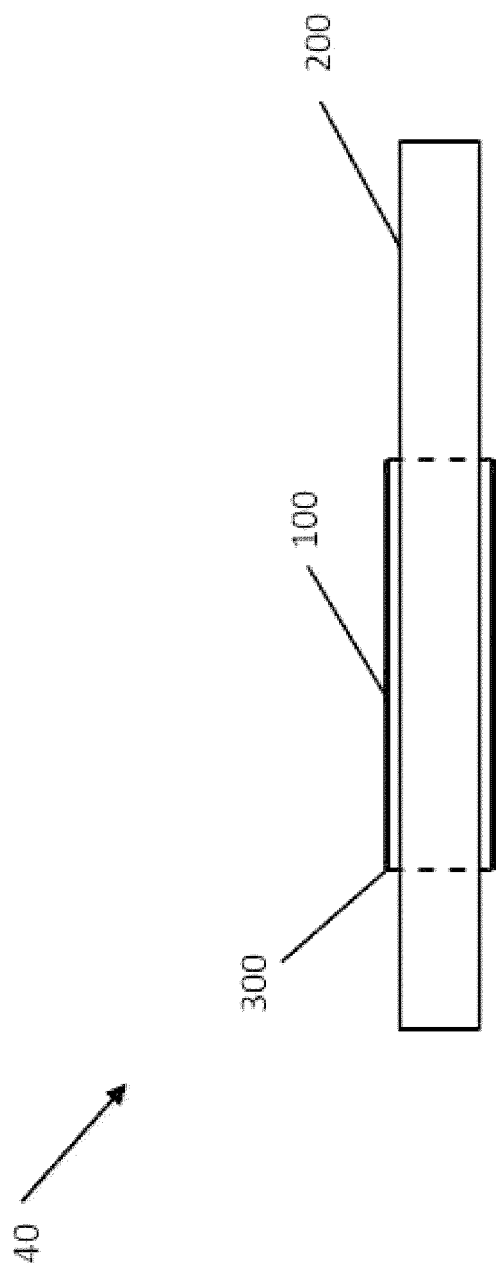
FIG. 1D is a schematic side elevational view of still another example embodiment of a vascular treatment device.

FIG. 1D is a schematic side elevational view of still another example embodiment of a vascular treatment device 40. The device 40 includes a distal portion 100, a proximal portion 200, and a joint 300 coupling the distal portion 100 to the proximal portion 200. In the device 40, the joint 300 couples the distal portion 100 to a segment of the proximal portion 200 that is proximal to the distal end of the proximal portion 200. The distal end of the proximal portion 200 extends beyond the distal end of the distal portion 100.

For each of the devices 10, 20, 30, 40, a wide variety of distal portions 100, proximal portions 200, and joints 300 are possible, including the distal portions 100, proximal portions 200, and joints 300 described herein. In some embodiments, the distal portion 100 includes a plurality of woven bulbs spaced longitudinally apart by woven necks. In some embodiments, the proximal portion 200 includes a cut hypotube having variable longitudinal flexibility. Other varieties of distal portions 100 and proximal portions 200 are also possible. In some embodiments, the distal portion 100 comprises a shape-set textile structure, the proximal portion 200 comprises a delivery system or hypotube, and the joint 300 comprises a bonding zone in a marker band region. In some embodiments, coupling the distal portion 100 and the proximal portion 200 at the joint 300 may be fixed or reversible.

In some embodiments, the distal portion 100 in a radially-collapsed configuration has an outer diameter of about 0.0125 inches (approx. 0.317 mm) or less and in a radially-expanded configuration has varying diameters. In some embodiments, the distal portion 100 in the radially-collapsed configuration has a diameter in the range of about 0.1 mm to about 0.9 mm (e.g., about 0.25 mm to about 0.5 mm). In some embodiments, the distal portion 100 in the radially-expanded configuration has a diameter in the range of about 1 mm to about 6.5 mm (e.g., about 3 mm to about 4.5 mm). In some embodiments, for example embodiments in which the distal portion 100 is configured or intended for use in larger vessels or bodily conduits, the distal portion 100 in the radially-expanded configuration has a diameter in the range of about 5 mm to about 40 mm and a diameter in the radially-collapsed configuration in the range of about 0.5 mm to about 5 mm In some embodiments, the ratio of the diameter of the distal portion 100 in the radially-expanded configuration to the diameter of the distal portion 100 in the radially-collapsed configuration is about 1.2:1 to about 100:1 (e.g., about 1.2:1 to about 20:1, about 9:1 to about 15:1).

FIG. 2A is a schematic side elevational view of an example embodiment of a distal portion 1000 of a vascular treatment device, for example the distal portion 100 of the device 10, 20, 30, or 40. The distal portion 1000 includes a plurality of woven bulbs 1010 and woven necks 1020. The distal portion 1000 includes a woven neck 65 at the distal end. A radiopaque marker band 25 is coupled to the distal end of the proximal portion 200, discussed in further detail herein. The bulbs 1010 are longitudinally spaced from each other by the woven necks 1020. In some embodiments, the bulbs 1010 and the necks 1020 are an integral textile structure in which the filaments that form the bulbs 1010 are the same as and longitudinally continuous with the filaments that form the necks 1020. The bulbs 1010 are generally spherical or spheroid, although the proximal and distal ends of the bulbs 1010 may begin to form the necks 1020. The bulbs 1010 extend radially outward from the longitudinal axis, increasing in diameter from proximal to distal, reaching an intermediate point, and then decreasing in diameter from proximal to distal. The necks 1020 are cylindrical or generally cylindrical along the longitudinal axis, although the ends of the necks 1020 may flare outwardly to begin to form the bulbs 1010. The bulbs 1010 in FIG. 2A have substantially uniform dimensions or diameters (e.g., within about ±5%, about ±10%, about ±15%, or about 20% of each other) such that the distal portion 1000 may be considered non-tapered or cylindrical.

FIG. 2B is a schematic side elevational view of another example embodiment of a distal portion 1100 of a vascular treatment device, for example the distal portion 100 of the device 10, 20, 30, or 40. FIG. 2C is a perspective view of the distal portion 1100 of FIG. 2B. FIG. 2D is another schematic side elevational view of the distal portion 1100 of FIG. 2B, which was derived from a photograph of the distal portion 1100. The distal portion 1100 includes a plurality of woven bulbs 1110 and woven necks 1120. The distal portion 1100 includes a woven neck 65 at the distal end. A radiopaque marker band 25 is coupled to the distal end of the proximal portion 200, discussed in further detail herein. The bulbs 1110 are longitudinally spaced from each other by the woven necks 1120. In some embodiments, the bulbs 1110 and the necks 1120 are an integral textile structure in which the filaments that form the bulbs 1110 are the same as and longitudinally continuous with the filaments that form the necks 1120. The bulbs 1110 are generally spherical or spheroid, although the proximal and distal ends of the bulbs 1110 may begin to form the necks 1120. The bulbs 1110 extend radially outward from the longitudinal axis, increasing in diameter from proximal to distal, reaching an intermediate point, and then decreasing in diameter from proximal to distal. The necks 1120 are cylindrical or generally cylindrical along the longitudinal axis, although the ends of the necks 1120 may flare outwardly to begin to from the bulbs 1110.

The distal portion 1100 includes ten bulbs 1110: three bulbs 1112, three bulbs 1114, two bulbs 1116, and two bulbs 1118. The bulbs 1112 have a smaller diameter than the bulbs 1114, which have a smaller diameter than the bulbs 1116, which have a smaller diameter than the bulbs 1118. The bulbs 1112 have substantially uniform diameters, the bulbs 1114 have substantially uniform diameters, the bulbs 1116 have substantially uniform diameters, and the bulbs 1118 have substantially uniform diameters. Due to the differing diameters of the bulbs 1110, the distal portion 1100 may be considered tapered, for example inwardly tapered from proximal to distal or outwardly tapered from distal to proximal, or the distal portion 1100 may be considered stepped, for example inwardly stepped from proximal to distal or outwardly stepped from distal to proximal. Other and opposite configurations are also possible. For example, the bulbs 1110 may be inwardly tapered or stepped from distal to proximal or outwardly stepped from proximal to distal. For another example, the bulbs 1110 may have random (e.g., non-sequential) diameters along the length of the distal portion 1100, which may include sections that are substantially cylindrical and/or sections that are stepped or tapered distally and/or proximally.

In some embodiments, the outer diameters of the bulbs 1110 in the radially-expanded configuration are as follows: the three distal extra-small spherical bulbs 1112 have an outer diameter configured to be oversized to the extra-small vessel segments such as the M2 segments of the middle cerebral artery (e.g., about 1.5 mm to about 2.25 mm); the proximally-next three small spherical bulbs 1114 have an outer diameter configured to be oversized to the smaller vessel segments such as the distal M1 segment of the middle cerebral artery (e.g., about 2.25 mm to about 2.75 mm); the proximally-next two medium spherical bulbs 1116 have an outer diameter configured to be oversized to the medium vessel segments such as the proximal M1 segment of the middle cerebral artery (e.g., about 2.75 mm to about 3.25 mm); and the proximal two large spherical bulbs 1118 have an outer diameter configured to be oversized to the large vessel segments such as the distal supra-clinoid segment of the internal carotid artery (e.g., about 3.25 mm to about 4 mm). A tapered configuration of the distal portion 1100 can allow for adequate and safe deployment of the distal portion 1100 across blood vessels with multiple and/or varying diameters (e.g., vasculature that progressively reduces in size). Although some example diameters are provided herein, some embodiments of the distal portion 1100 may include diameters of the bulbs 1112, 1114, 1116, 1118 in accordance with the values provided above and/or diameters that are within about ±5%, about ±10%, about ±15%, or about ±20% of any such values.

FIG. 2E is a schematic side elevational view of yet another example embodiment of a distal portion 11900 of a vascular treatment device, for example the distal portion 100 of the device 10, 20, 30, or 40. The distal portion 11900 includes a plurality of woven bulbs 1110 and woven necks 1120. The distal portion 11900 includes a woven neck 65 at the distal end. The bulbs 1110 are longitudinally spaced from each other by the woven necks 1120. In some embodiments, the bulbs 1110 and the necks 1120 are an integral textile structure in which the filaments that form the bulbs 1110 are the same as and longitudinally continuous with the filaments that form the necks 1120. The bulbs 1110 are generally spherical or spheroid, although the proximal and distal ends of the bulbs 1110 may begin to form the necks 1120. The bulbs 1110 extend radially outward from the longitudinal axis, increasing in diameter from proximal to distal, reaching an intermediate point, and then decreasing in diameter from proximal to distal. The necks 1120 are cylindrical or generally cylindrical along the longitudinal axis, although the ends of the necks 1120 may flare outwardly to begin to from the bulbs 1110.

The distal portion 11900 includes six bulbs 1110: two bulbs 1114, two bulbs 1116, and two bulbs 1118. The bulbs 1114 have a smaller diameter than the bulbs 1116, which have a smaller diameter than the bulbs 1118. The bulbs 1114 have substantially uniform diameters, the bulbs 1116 have substantially uniform diameters, and the bulbs 1118 have substantially uniform diameters. Due to the differing diameters of the bulbs 1110, the distal portion 11900 may be considered tapered, for example inwardly tapered from proximal to distal or outwardly tapered from distal to proximal, or the distal portion 11900 may be considered stepped, for example inwardly stepped from proximal to distal or outwardly stepped from distal to proximal. Other and opposite configurations are also possible. For example, the bulbs 1110 may be inwardly tapered or stepped from distal to proximal or outwardly stepped from proximal to distal. For another example, the bulbs 1110 may have random (e.g., non-sequential) diameters along the length of the distal portion 11900, which may include sections that are substantially cylindrical and/or sections that are stepped or tapered distally and/or proximally.

In some embodiments, the outer diameters of the bulbs 1110 in the radially-expanded configuration are as follows: the two distal small spherical bulbs 1114 have an outer diameter configured to be oversized (e.g., about 2.5 mm to about 3.5 mm, about 3 mm) to the small vessel segments such as the M2 segments of the middle cerebral artery (e.g., about 1.5 mm to about 2.25 mm); the proximally-next two medium spherical bulbs 1116 have an outer diameter configured to be oversized (e.g., about 3.5 mm to about 5 mm, about 4 mm) to the medium vessel segments such as the M1 segments of the middle cerebral artery (e.g., about 2.25 mm to about 3.25 mm); and the proximal two large spherical bulbs 1118 have an outer diameter configured to be oversized (e.g., about 4 mm to about 5 mm, about 4.5 mm) to the large vessel segments such as the distal supra-clinoid segment of the internal carotid artery (e.g., about 3.25 mm to about 4 mm). A tapered configuration of the distal portion 11900 can allow for adequate and safe deployment of the distal portion 11900 across blood vessels with multiple and/or varying diameters (e.g., vasculature that progressively reduces in size). Although some example diameters are provided herein, some embodiments of the distal portion 11900 may include diameters of the bulbs 1114, 1116, 1118 in accordance with the values provided above and/or diameters that are within about ±5%, about ±10%, about ±15%, or about ±20% of any such values.

FIG. 2F is a schematic side elevational view of still another example embodiment of a distal portion 12000 of a vascular treatment device, for example the distal portion 100 of the device 10, 20, 30, or 40. The distal portion 12000 includes a plurality of woven bulbs 1110 and woven necks 1120. The distal portion 12000 includes a woven neck 65 at the distal end. The bulbs 1110 are longitudinally spaced from each other by the woven necks 1120. In some embodiments, the bulbs 1110 and the necks 1120 are an integral textile structure in which the filaments that form the bulbs 1110 are the same as and longitudinally continuous with the filaments that form the necks 1120. The bulbs 1110 are generally spherical or spheroid, although the proximal and distal ends of the bulbs 1110 may begin to form the necks 1120. The bulbs 1110 extend radially outward from the longitudinal axis, increasing in diameter from proximal to distal, reaching an intermediate point, and then decreasing in diameter from proximal to distal. The necks 1120 are cylindrical or generally cylindrical along the longitudinal axis, although the ends of the necks 1120 may flare outwardly to begin to from the bulbs 1110.

The distal portion 12000 includes five bulbs 1110: one bulb 1114, two bulbs 1116, and two bulbs 1118. The bulb 1114 has a smaller diameter than the bulbs 1116, which have a smaller diameter than the bulbs 1118. The bulbs 1116 have substantially uniform diameters and the bulbs 1118 have substantially uniform diameters. Due to the differing diameters of the bulbs 1110, the distal portion 12000 may be considered tapered, for example inwardly tapered from proximal to distal or outwardly tapered from distal to proximal, or the distal portion 12000 may be considered stepped, for example inwardly stepped from proximal to distal or outwardly stepped from distal to proximal. Other and opposite configurations are also possible. For example, the bulbs 1110 may be inwardly tapered or stepped from distal to proximal or outwardly stepped from proximal to distal. For another example, the bulbs 1110 may have random (e.g., non-sequential) diameters along the length of the distal portion 12000, which may include sections that are substantially cylindrical and/or sections that are stepped or tapered distally and/or proximally.

In some embodiments, the outer diameters of the bulbs 1110 in the radially-expanded configuration are as follows: the one distal small spherical bulb 1114 has an outer diameter configured to be oversized (e.g., about 2.5 mm to about 3.5 mm, about 3 mm) to the small vessel segments such as the M2 segments of the middle cerebral artery (e.g., about 1.5 mm to about 2.25 mm); the proximally-next two medium spherical bulbs 1116 have an outer diameter configured to be oversized (e.g., about 3.5 mm to about 5 mm, about 4 mm) to the medium vessel segments such as the M1 segments of the middle cerebral artery (e.g., about 2.25 mm to about 3.25 mm); and the proximal two large spherical bulbs 1118 have an outer diameter configured to be oversized (e.g., about 4 mm to about 5 mm, about 4.5 mm) to the large vessel segments such as the distal supra-clinoid segment of the internal carotid artery (e.g., about 3.25 mm to about 4 mm). A tapered configuration of the distal portion 12000 can allow for adequate and safe deployment of the distal portion 12000 across blood vessels with multiple and/or varying diameters (e.g., vasculature that progressively reduces in size). Although some example diameters are provided herein, some embodiments of the distal portion 12000 may include diameters of the bulbs 1114, 1116, 1118 in accordance with the values provided above and/or diameters that are within about ±5%, about ±10%, about ±15%, or about ±20% of any such values.

FIG. 2G is a schematic side elevational view of still yet another example embodiment of a distal portion 12100 of a vascular treatment device, for example the distal portion 100 of the device 10, 20, 30, or 40. The distal portion 12100 includes a plurality of woven bulbs 1110 and woven necks 1120. The distal portion 12100 includes a woven neck 65 at the distal end. The bulbs 1110 are longitudinally spaced from each other by the woven necks 1120. In some embodiments, the bulbs 1110 and the necks 1120 are an integral textile structure in which the filaments that form the bulbs 1110 are the same as and longitudinally continuous with the filaments that form the necks 1120. The bulbs 1110 are generally spherical or spheroid, although the proximal and distal ends of the bulbs 1110 may begin to form the necks 1120. The bulbs 1110 extend radially outward from the longitudinal axis, increasing in diameter from proximal to distal, reaching an intermediate point, and then decreasing in diameter from proximal to distal. The necks 1120 are cylindrical or generally cylindrical along the longitudinal axis, although the ends of the necks 1120 may flare outwardly to begin to from the bulbs 1110.

The distal portion 12100 includes four bulbs 1110: two bulbs 1116 and two bulbs 1118. The bulbs 1116 have a smaller diameter than the bulbs 1118. The bulbs 1116 have substantially uniform diameters and the bulbs 1118 have substantially uniform diameters. Due to the differing diameters of the bulbs 1110, distal portion 12100 may be considered tapered, for example inwardly tapered from proximal to distal or outwardly tapered from distal to proximal, or the distal portion 12100 may be considered stepped, for example inwardly stepped from proximal to distal or outwardly stepped from distal to proximal. Other and opposite configurations are also possible. For example, the bulbs 1110 may be inwardly tapered or stepped from distal to proximal or outwardly stepped from proximal to distal. For another example, the bulbs 1110 may have random (e.g., non-sequential) diameters along the length of the distal portion 12100, which may include sections that are substantially cylindrical and/or sections that are stepped or tapered distally and/or proximally.

In some embodiments, the outer diameters of the bulbs 1110 in the radially-expanded configuration are as follows: the two distal medium spherical bulbs 1116 have an outer diameter configured to be oversized (e.g., about 3.5 mm to about 5 mm, about 4 mm) to the medium vessel segments such as the M1 segments of the middle cerebral artery (e.g., about 2.25 mm to about 3.25 mm); and the proximal two large spherical bulbs 1118 have an outer diameter configured to be oversized (e.g., about 4 mm to about 5 mm, about 4.5 mm) to the large vessel segments such as the distal supraclinoid segment of the internal carotid artery (e.g., about 3.25 mm to about 4 mm). A tapered configuration of the distal portion 12100 can allow for adequate and safe deployment of the distal portion 12100 across blood vessels with multiple and/or varying diameters (e.g., vasculature that progressively reduces in size). Although some example diameters are provided herein, some embodiments of the distal portion 12100 may include diameters of the bulbs 1114, 1116, 1118 in accordance with the values provided above and/or diameters that are within about ±5%, about ±10%, about ±15%, or about ±20% of any such values.

The vascular treatment devices illustrated in FIGS. 2E-2G include a proximal portion 200 coupled to the distal portion 11900, 12000, 12100. The proximal portion 200 comprises a first segment 11905 and a second segment 11910. The distal end of the first segment 11905 is coupled to the proximal end of the distal portion 11900, 12000, 12100 (e.g., as described with respect to FIG. 1A), although other coupling arrangements are also possible (e.g., as described with respect to FIGS. 1B-1D). For example, FIG. 2E-2 shows the distal end of the proximal portion 200 coupled to the distal end of the distal portion 100 at a joint 3700 (e.g., as described herein with respect to FIG. 1B). In some embodiments, the distal end of the first segment 11905 of the proximal portion 200, which may also the distal end of the proximal portion 200, includes a radiopaque marker band. The distal end of the second segment 11910 may be coupled to the proximal end of the first segment 11905. In some embodiments, for example as described with respect to FIG. 19F, the first segment 11905 comprises a hypotube and the second segment 11910 comprises a wire. Other proximal portions 200 for the vascular treatment devices illustrated in FIGS. 2E-2G are also possible (e.g., a patterned tubular structure, a shape-set tubular structure, a braided structure, combinations thereof, and the like). For example, FIG. 2E-2 is a perspective view of yet another embodiment of a distal portion 12300 of a vascular treatment device. The distal portion 12300 may for example be the same as or similar to the distal portion 11900 described with respect to FIG. 2E. The distal end of the distal portion 12300 is coupled to the distal end of the proximal portion 200. The proximal portion 200 comprises a hypotube that is cut along at least a distal portion thereof, and a proximal longitudinal segment of the proximal portion 200 is not cut in any fashion.

FIGS. 2A-2G show example embodiments of a pattern of bulb shapes in which the bulbs 1010 in FIG. 2A and the bulbs 1110 in FIGS. 2B-2G have substantially the same shape. With reference to FIGS. 2B-2G, this substantially same shape pattern persists even when the bulbs 1110 have different sizes. In the embodiments illustrated in FIGS. 2A-2G, the bulbs 1010, 1110 are each spherical, but distal portions 100 including bulbs having other shapes that are substantially the same (e.g., oblong) are also possible.

FIG. 2H-1 is a schematic diagram in the anterio-posterior view illustrating an example of the proximal and distal segments of the brain vasculature. The internal carotid artery supplying blood to the brain is depicted in the FIG. 2H-1 along with locations where blood clots tend to cause large vessel occlusions (LVOs) or blockages in the brain blood vessels causing an ischemic stroke. A first location where LVOs may occur is the carotid T-bifurcation (aka T-occlusion) where the internal carotid artery bifurcates into the M1 segment of the middle cerebral artery as well as the A1 segment 12860 of the anterior cerebral artery (shown as horizontal bricks in FIG. 2H-1). The average diameter of the internal carotid artery in adults can range from 3.5 mm to 5.5 mm, or about 4 mm A second location where LVOs may occur is the M1 segment 12830 of the middle cerebral artery (shown as waves in FIG. 2H-1). The average diameter of the middle cerebral artery in adults can range from 2.25 mm to 3.5 mm, or about 3 mm LVOs in the carotid T-bifurcation or the M1 segment of the middle cerebral artery proximal segments are described as proximal LVOs.

A third location where LVOs may occur is the proximal M2 segment 12840 of the middle cerebral artery (shown as divots in FIG. 2H-1). The average diameter of the proximal M2 segment of the middle cerebral artery can range from 1.5 mm to 2.25 mm, or about 2 mm A fourth location where LVOs may occur is the distal M2 segments 12850 of the middle cerebral artery, the M3 segments of the middle cerebral artery, and A2/A3 segments of the anterior cerebral artery (shown as spheres in FIG. 2H-1). LVOs in the above third and fourth locations are described as distal LVOs. Other locations for proximal and/or distal LVOs are also possible.

FIG. 2H-2 is a schematic diagram illustrating the radial force of a distal portion of a vascular treatment device, for example the distal portion 11900 of a vascular treatment device as shown in FIG. 2E, for example the distal portion 100 of the device 10, 20, 30, or 40. The radial force of the distal portion 11900, where two bulbs 1114 have a diameter of 3.5 mm in the expanded state, two bulbs 1116 have a diameter of 4 mm in the expanded state, and two bulbs 1118 have a diameter of 4.5 mm in the expanded state and 48 filaments each having a diameter of 0.001 inches (approx. 0.025 mm), is graphically represented in FIG. 2H-2, which shows that the radial force (in Newtons (N)) is low and ranges from 0 to 1 Newton across vessel diameters in the brain vasculature from 1.5 mm to 5.5 mm, ranges from 0 to 0.4 N across vessel diameters in the brain vasculature from 2.25 mm to 5.5 mm, and ranges from 0 to 0.2 N across vessel diameters in the brain vasculature from 3 mm to 5.5 mm. The low radial force of the distal portion 11900 enables a safety profile for use in the fragile brain vasculature, including in the distal segments. The low radial force, less than 1 Newton, can also be maintained in larger vessels with larger diameter devices, for example by maintaining or appropriately adjusting the number of filaments, filament diameter, etc. Beneath the x-axis labels, reference vessel diameters corresponding to vessel segments in the brain vasculature are coded in accordance with FIG. 2H-1. Even in distal LVOs, the radial force is less than 1 N and has a safety profile appropriate for distal LVOs. A radial force greater than 3 N has been shown in animal studies to potentially cause vasospasm, endothelial vessel injury, fracture of the internal elastic lamina, and vessel occlusion. Brain vessels are more fragile than coronary vasculature due to less muscle layers (e.g., thin tunica media, no external elastic lamina, less adventitia) such that radial force can be a consideration in whether and how to safely treat brain vessels.

Figure 3A:
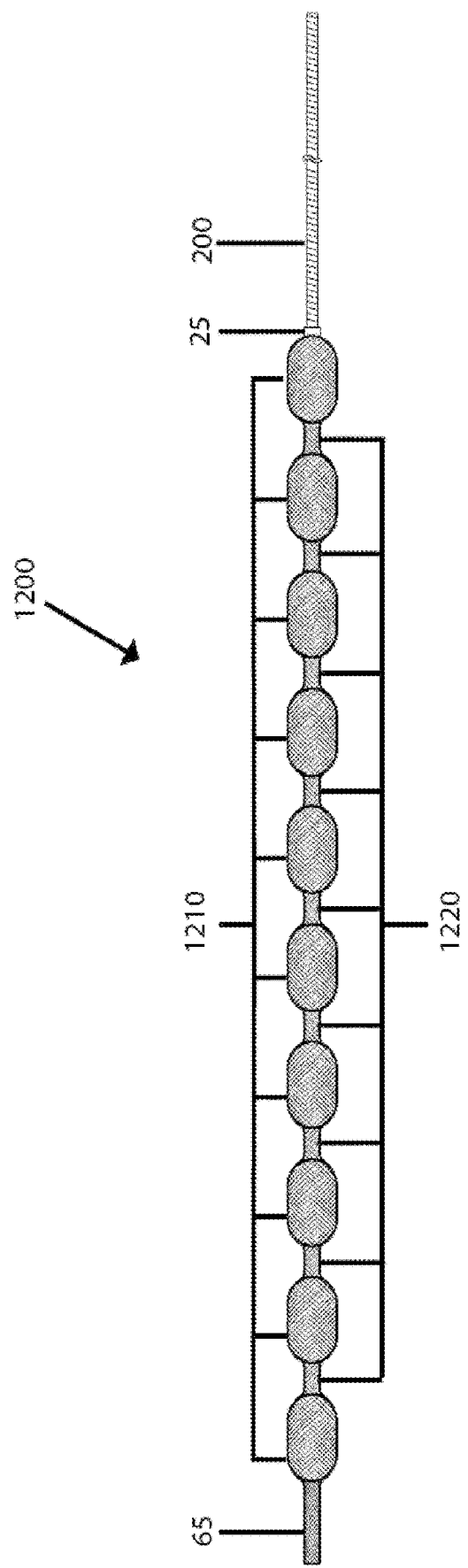
FIG. 3A is a schematic side elevational view of another example embodiment of a distal portion of a vascular treatment device.

FIG. 3A is a schematic side elevational view of another example embodiment of a distal portion 1200 of a vascular treatment device, for example the distal portion 100 of the device 10, 20, 30, or 40. The distal portion 1200 includes a plurality of woven bulbs 1210 and woven necks 1220. The distal portion 1200 includes a woven neck 65 at the distal end. A radiopaque marker band 25 is coupled to the distal end of the proximal portion 200, discussed in further detail herein. The bulbs 1210 are longitudinally spaced from each other by the woven necks 1220. In some embodiments, the bulbs 1210 and the necks 1220 are an integral textile structure in which the filaments that form the bulbs 1210 are the same as and longitudinally continuous with the filaments that form the necks 1220. The bulbs 1210 are generally oblong, although the proximal and distal ends of the bulbs 1210 may begin to form the necks 1220. The bulbs 1210 extend radially outward from the longitudinal axis, increasing in diameter from proximal to distal, reaching an intermediate point, staying at the intermediate diameter for some length, and then decreasing in diameter from proximal to distal. The necks 1220 are cylindrical or generally cylindrical along the longitudinal axis, although the ends of the necks 1220 may flare outwardly to begin to from the bulbs 1210. The bulbs 1210 in FIG. 3A have substantially uniform dimensions or diameters (e.g., within about ±5%, about ±10%, about ±15%, or about 20% of each other) such that the distal portion 1200 may be considered non-tapered or cylindrical.

Figure 3B:
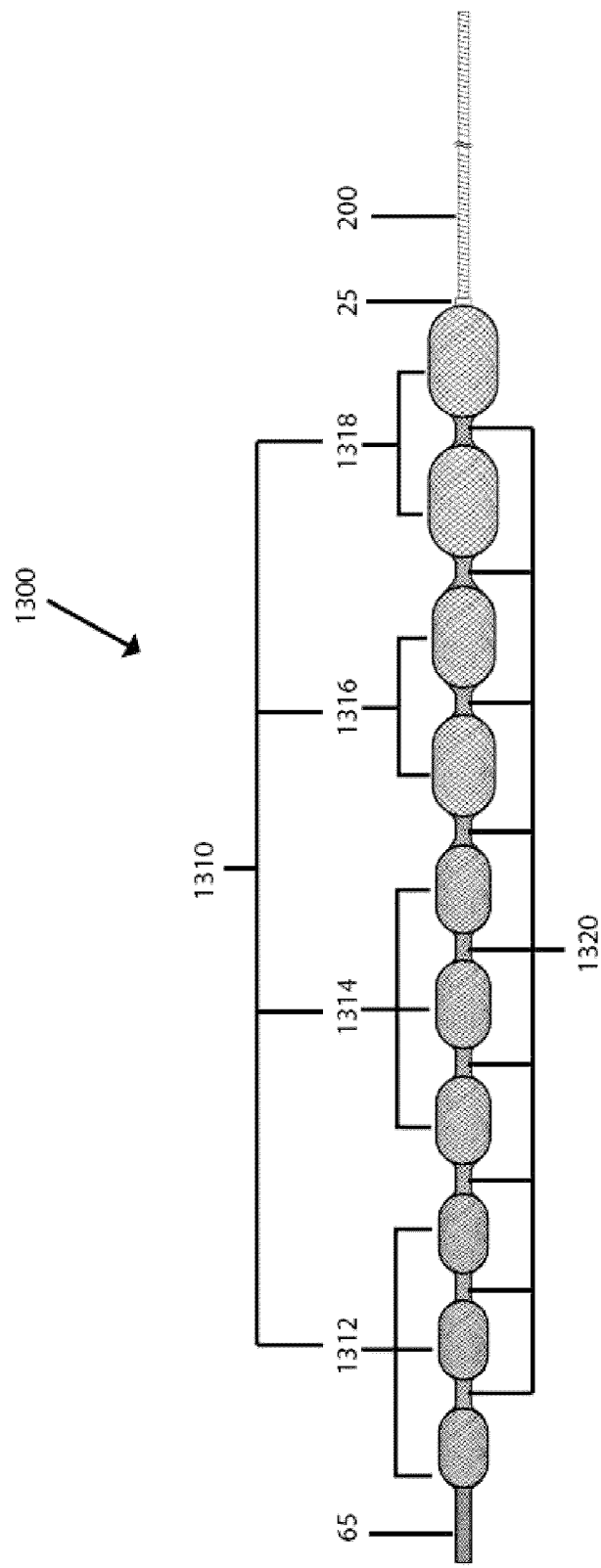
FIG. 3B is a schematic side elevational view of another example embodiment of a distal portion of a vascular treatment device.
Figure 3C:
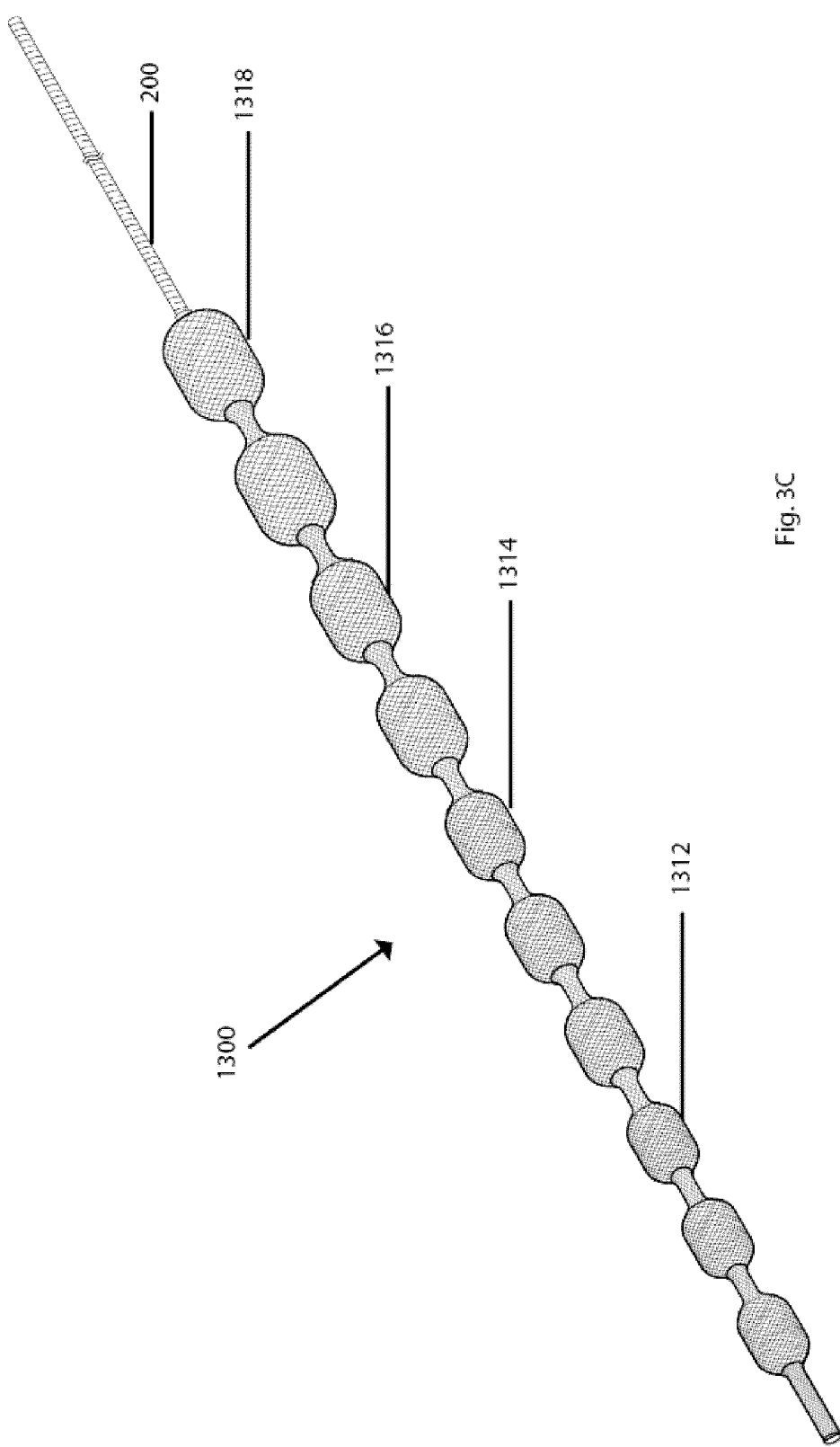
FIG. 3C is a perspective view of the distal portion of FIG. 3B.

FIG. 3B is a schematic side elevational view of another example embodiment of a distal portion 1300 of a vascular treatment device, for example the distal portion 100 of the device 10, 20, 30, or 40. FIG. 3C is a perspective view of the distal portion 1300 of FIG. 3B. The distal portion 1300 includes a plurality of woven bulbs 1310 and woven necks 1320. The distal portion 1300 includes a woven neck 65 at the distal end. A radiopaque marker band 25 is coupled to the distal end of the proximal portion 200, discussed in further detail herein. The bulbs 1310 are longitudinally spaced from each other by the woven necks 1320. In some embodiments, the bulbs 1310 and the necks 1320 are an integral textile structure in which the filaments that form the bulbs 1310 are the same as and longitudinally continuous with the filaments that form the necks 1320. The bulbs 1310 are generally oblong, although the proximal and distal ends of the bulbs 1310 may begin to form the necks 1320. The bulbs 1310 extend radially outward from the longitudinal axis, increasing in diameter from proximal to distal, reaching an intermediate point, staying at the intermediate diameter for some length, and then decreasing in diameter from proximal to distal. The necks 1320 are cylindrical or generally cylindrical along the longitudinal axis, although the ends of the necks 1320 may flare outwardly to begin to from the bulbs 1310.

The distal portion 1300 includes ten bulbs 1310: three bulbs 1312, three bulbs 1314, two bulbs 1316, and two bulbs 1318. The bulbs 1312 have a smaller diameter than the bulbs 1314, which have a smaller diameter than the bulbs 1316, which have a smaller diameter than the bulbs 1318. The bulbs 1312 have substantially uniform diameters, the bulbs 1314 have substantially uniform diameters, the bulbs 1316 have substantially uniform diameters, and the bulbs 1318 have substantially uniform diameters. Due to the differing diameters of the bulbs 1310, the distal portion 1300 may be considered tapered, for example inwardly tapered from proximal to distal or outwardly tapered from distal to proximal, or the distal portion 1300 may be considered stepped, for example inwardly stepped from proximal to distal or outwardly stepped from distal to proximal. Other and opposite configurations are also possible. For example, the bulbs 1310 may be inwardly tapered or stepped from distal to proximal or outwardly stepped from proximal to distal. For another example, the bulbs 1310 may have random (e.g., non-sequential) diameters along the length of the distal portion 1300, which may include sections that are substantially cylindrical and/or sections that are stepped or tapered distally and/or proximally.

In some embodiments, the outer diameters of the bulbs 1310 in the radially-expanded configuration are as follows: the three distal extra-small oblong bulbs 1312 have an outer diameter configured to be oversized to the extra-small vessel segments such as the M2 segments of the middle cerebral artery (e.g., about 1.5 mm to about 2.25 mm); the proximally-next three small oblong bulbs 1314 have an outer diameter configured to be oversized to the smaller vessel segments such as the distal M1 segment of the middle cerebral artery (e.g., about 2.25 mm to about 2.75); the proximally-next two medium oblong bulbs 1316 have an outer diameter configured to be oversized to the medium vessel segments such as the proximal M1 segment of the middle cerebral artery (e.g., about 2.75 mm to about 3.25 mm); and the proximal two large oblong bulbs 1318 have an outer diameter configured to be oversized to the large vessel segments such as the distal supra-clinoid segment of the internal carotid artery (e.g., about 3.25 mm to about 4 mm). A tapered configuration of the distal portion 1300 can allow for adequate and safe deployment of the distal portion 1300 across blood vessels with multiple and/or varying diameters (e.g., vasculature that progressively reduces in size). Although some example diameters are provided herein, some embodiments of the distal portion 1300 may include diameters of the bulbs 1312, 1314, 1316, 1318 in accordance with the values provided above and/or diameters that are without about ±5%, about ±10%, about ±15%, or about ±20% of any such values.

Figure 4A:
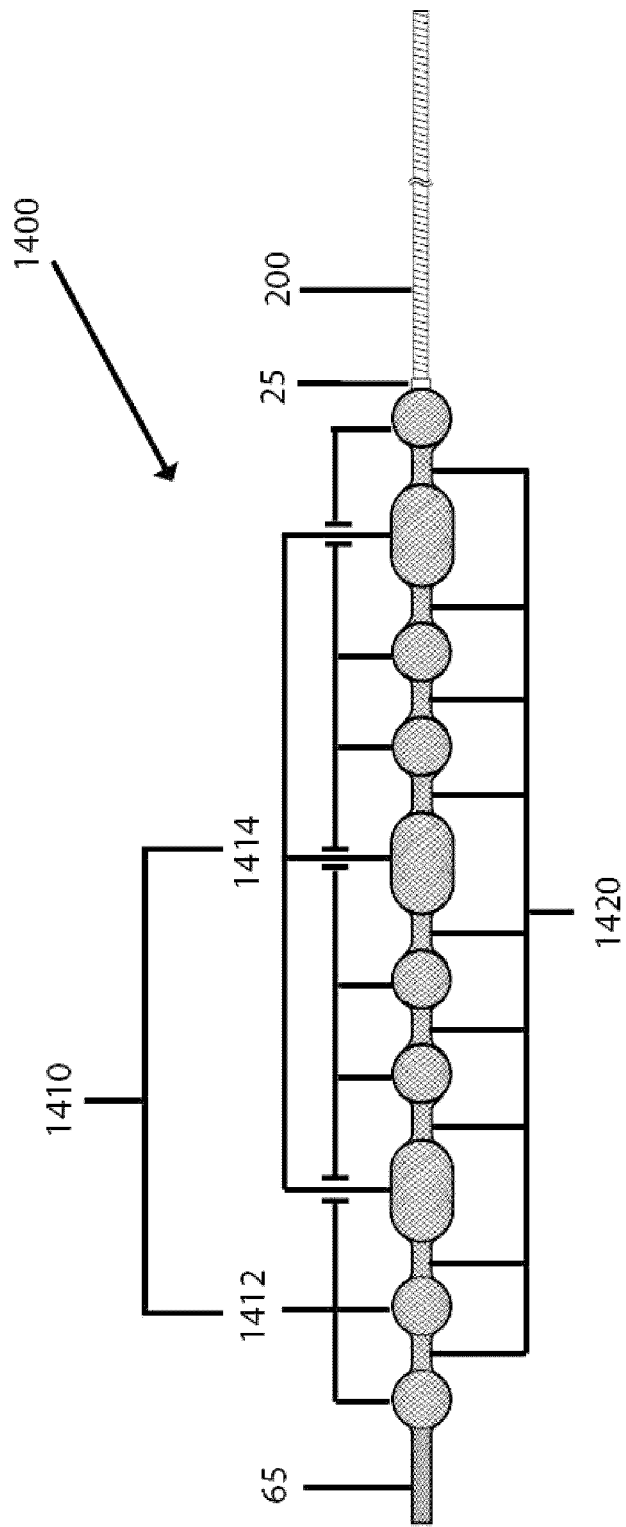
FIG. 4A is a schematic side elevational view of another example embodiment of a distal portion of a vascular treatment device.

FIG. 4A is a schematic side elevational view of another example embodiment of a distal portion 1400 of a vascular treatment device, for example the distal portion 100 of the device 10, 20, 30, or 40. The distal portion 1400 includes a plurality of woven bulbs 1410 and woven necks 1420. The distal portion 1400 includes a woven neck 65 at the distal end. A radiopaque marker band 25 is coupled to the distal end of the proximal portion 200, discussed in further detail herein. The bulbs 1410 are longitudinally spaced from each other by the woven necks 1420. In some embodiments, the bulbs 1410 and the necks 1420 are an integral textile structure in which the filaments that form the bulbs 1410 are the same as and longitudinally continuous with the filaments that form the necks 1420. The necks 1420 are cylindrical or generally cylindrical along the longitudinal axis, although the ends of the necks 1420 may flare outwardly to begin to from the bulbs 1410. The bulbs 1410 in FIG. 4A have substantially uniform diameters such that the distal portion 1400 may be considered non-tapered or cylindrical.

The distal portion 1400 includes ten bulbs 1410: seven generally spherical bulbs 1412 and three generally oblong bulbs 1414, in an interspersed pattern, from distal to proximal, of two bulbs 1412, one bulb 1414, two bulbs 1412, one bulb 1414, two bulbs 1412, one bulb 1414, and one bulb 1412. Other interspersing patterns are also possible. For example, an interspersed pattern may include one bulb 1412, one bulb 1414, one bulb 1412, one bulb 1414, one bulb 1412, one bulb 1414, one bulb 1412, one bulb 1414, one bulb 1412, and one bulb 1414. For another example, interspersed pattern may include one bulb 1412, two bulbs 1414, one bulb 1412, two bulbs 1414, one bulb 1412, two bulbs 1414, and one bulb 1412.

Figure 4B:
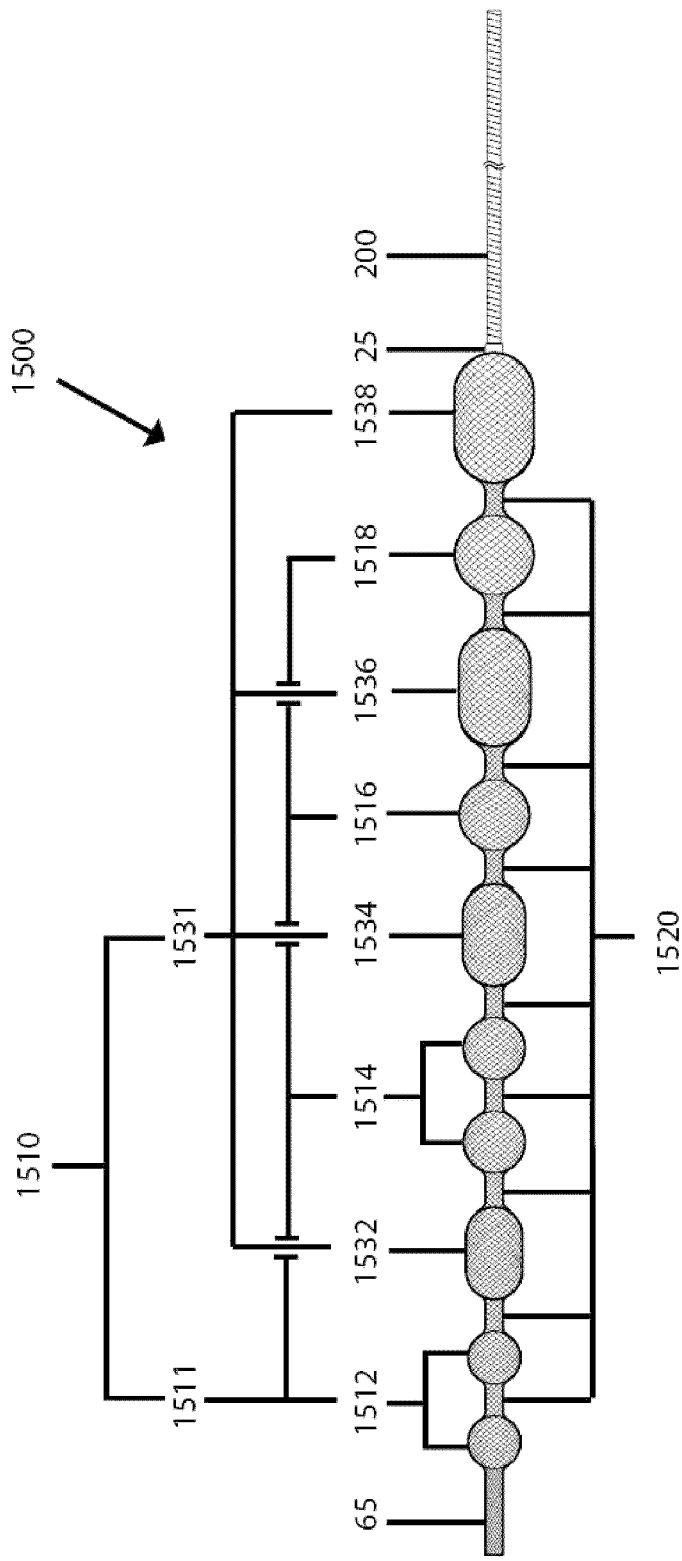
FIG. 4B is a schematic side elevational view of another example embodiment of a distal portion of a vascular treatment device.

FIG. 4B is a schematic side elevational view of another example embodiment of a distal portion 1500 of a vascular treatment device, for example the distal portion 100 of the device 10, 20, 30, or 40. The bulbs 1510 are longitudinally spaced from each other by the woven necks 1520. The distal portion 1500 includes a woven neck 65 at the distal end. A radiopaque marker band 25 is coupled to the distal end of the proximal portion 200, discussed in further detail herein. In some embodiments, the bulbs 1510 and the necks 1520 are an integral textile structure in which the filaments that form the bulbs 1510 are the same as and longitudinally continuous with the filaments that form the necks 1520. The necks 1520 are cylindrical or generally cylindrical along the longitudinal axis, although the ends of the necks 1520 may flare outwardly to begin to from the bulbs 1510.

The distal portion 1500 includes ten bulbs 1510: six generally spherical bulbs 1511 and four generally oblong bulbs 1531. The generally spherical bulbs 1511 include two bulbs 1512, two bulbs 1514, one bulb 1516, and one bulb 1518. The bulbs 1512 have a smaller diameter than the bulbs 1514, which have a smaller diameter than the bulb 1516, which has a smaller diameter than the bulb 1518. The bulbs 1512 have substantially uniform diameters and the bulbs 1514 have substantially uniform diameters. The generally oblong bulbs 1531 include one bulb 1532, one bulb 1534, one bulb 1536, and one bulb 1538. The bulb 1532 has a smaller diameter than the bulb 1534, which has a smaller diameter than the bulb 1536, which has a smaller diameter than the bulb 1538. Due to the differing diameters of the bulbs 1510, the distal portion 1500 may be considered tapered, for example inwardly tapered from proximal to distal or outwardly tapered from distal to proximal, or the distal portion 1500 may be considered stepped, for example inwardly stepped from proximal to distal or outwardly stepped from distal to proximal. Other and opposite configurations are also possible. For example, the bulbs 1510 may be inwardly tapered or stepped from distal to proximal or outwardly stepped from proximal to distal. For another example, the bulbs 1510 may have random (e.g., non-sequential) diameters along the length of the distal portion 1500, which may include sections that are substantially cylindrical and/or sections that are stepped or tapered distally and/or proximally.

In some embodiments, the outer diameters of the bulbs 1510 in the radially-expanded configuration are as follows: the two distal extra-small spherical bulbs 1512 and the distal extra-small oblong bulb 1532 have an outer diameter configured to be oversized to the extra-small vessel segments such as the M2 segments of the middle cerebral artery (e.g., about 1.5 mm to about 2.25 mm); the proximally-next two small spherical bulbs 1514 and the small oblong bulb 1534 have an outer diameter configured to be oversized to the smaller vessel segments such as the distal M1 segment of the middle cerebral artery (e.g., about 2.25 mm to about 2.75 mm); the proximally-next medium spherical bulb 1516 and the medium oblong bulb 1536 have an outer diameter configured to be oversized to the medium vessel segments such as the proximal M1 segment of the middle cerebral artery (e.g., about 2.75 mm to about 3.25 mm); and the proximally-next large spherical bulb 1518 and the large oblong bulb 1538 have an outer diameter configured to be oversized to the large vessel segments such as the distal supra-clinoid segment of the internal carotid artery (e.g., about 3.25 mm to about 4 mm). A tapered configuration of the distal portion 1500 can allow for adequate and safe deployment of the distal portion 1500 across blood vessels with multiple and/or varying diameters (e.g., vasculature that progressively reduces in size). Although some example diameters are provided herein, some embodiments of the distal portion 1500 may include diameters of the bulbs 1512, 1514, 1516, 1518, 1532, 1534, 1536, 1538 in accordance with the values provided above and/or diameters that are within about ±5%, about ±10%, about ±15%, or about ±20% of any such values.

The distal portion 1500 includes ten bulbs 1510: six generally spherical bulbs 1511 and four generally oblong bulbs 1531, in an interspersed pattern. Other interspersing patterns are also possible. For example, an interspersed pattern may include one bulb 1512, one bulb 1532, two bulbs 1514, one bulb 1534, two bulbs 1516, one bulb 1536, one bulb 1518, and one bulb 1538. For another example, interspersed pattern may include one bulb 1512, two bulbs 1532, two bulbs 1514, one bulb 1534, one bulb 1516, one bulb 1536, one bulb 1518, and one bulb 1538.

Figure 4C:
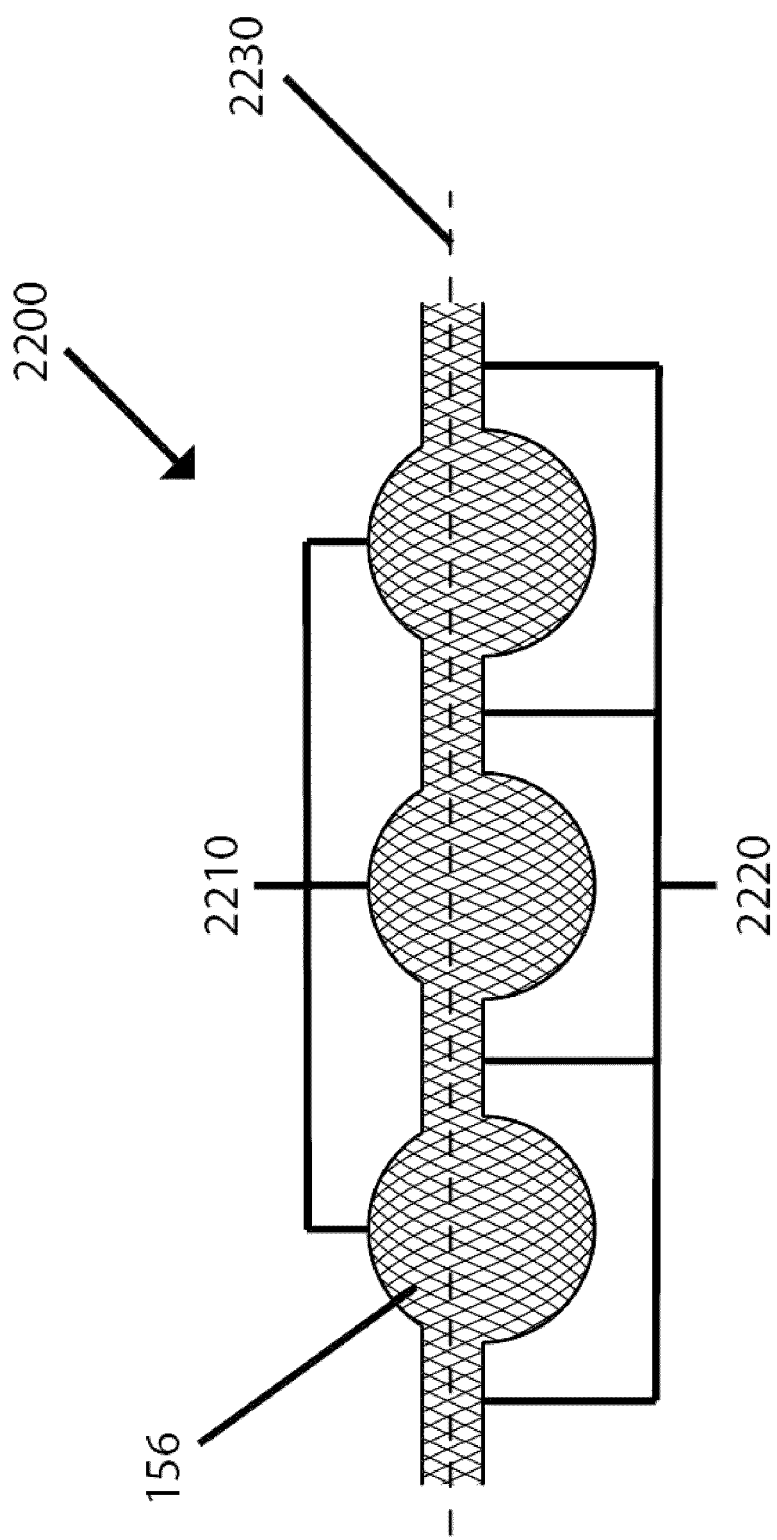
FIG. 4C is a schematic side elevational view of another example embodiment of a distal portion of a vascular treatment device.
Figure 4D:
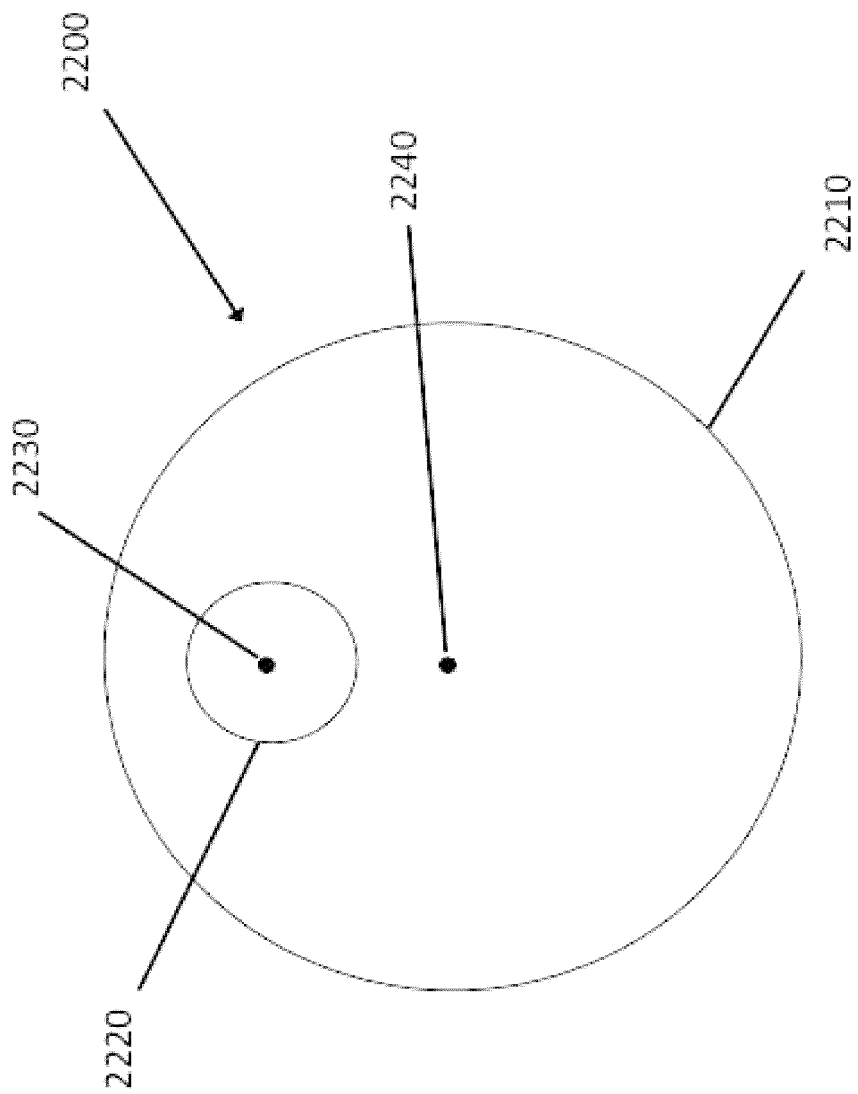
FIG. 4D is a schematic proximal end view of the distal portion of FIG. 4C.

FIG. 4C is a schematic side elevational view of another example embodiment of a distal portion 2200 of a vascular treatment device, for example the distal portion 100 of the device 10, 20, 30, or 40, including any example embodiments thereof described herein. FIG. 4D is a schematic proximal end view of the distal portion 2200 shown in FIG. 4C. The distal portion 2200 includes a plurality of woven bulbs 2210 and woven necks 2220 including filaments 156. The bulbs 2210 are longitudinally spaced from each other by the woven necks 2220. In some embodiments, the bulbs 2210 and the necks 2220 are an integral textile structure in which the filaments that form the bulbs 2210 are the same as and longitudinally continuous with the filaments that form the necks 2220. The bulbs 2210 are generally spherical, although the proximal and distal ends of the bulbs 2210 may begin to form the necks 2220. The necks 2220 are aligned along a longitudinal axis 2230. The bulbs 2210 are aligned along a longitudinal axis 2240. The longitudinal axis 2240 may run through a center of the distal portion 2200. The longitudinal axis 2230 is radially offset from the longitudinal axis 2240. The necks 2220 are aligned with chords of the bulbs 2210. The necks 2220 are cylindrical or generally cylindrical along the central or longitudinal axis, although the ends of the necks 2220 may flare outwardly to begin to from the bulbs 2210. The bulbs 2210 in FIG. 4C have substantially uniform dimensions or diameters (e.g., within about ±5%, about ±10%, about ±15%, or about 20% of each other) such that the distal portion 2200 may be considered non-tapered or cylindrical.

Figure 4F:
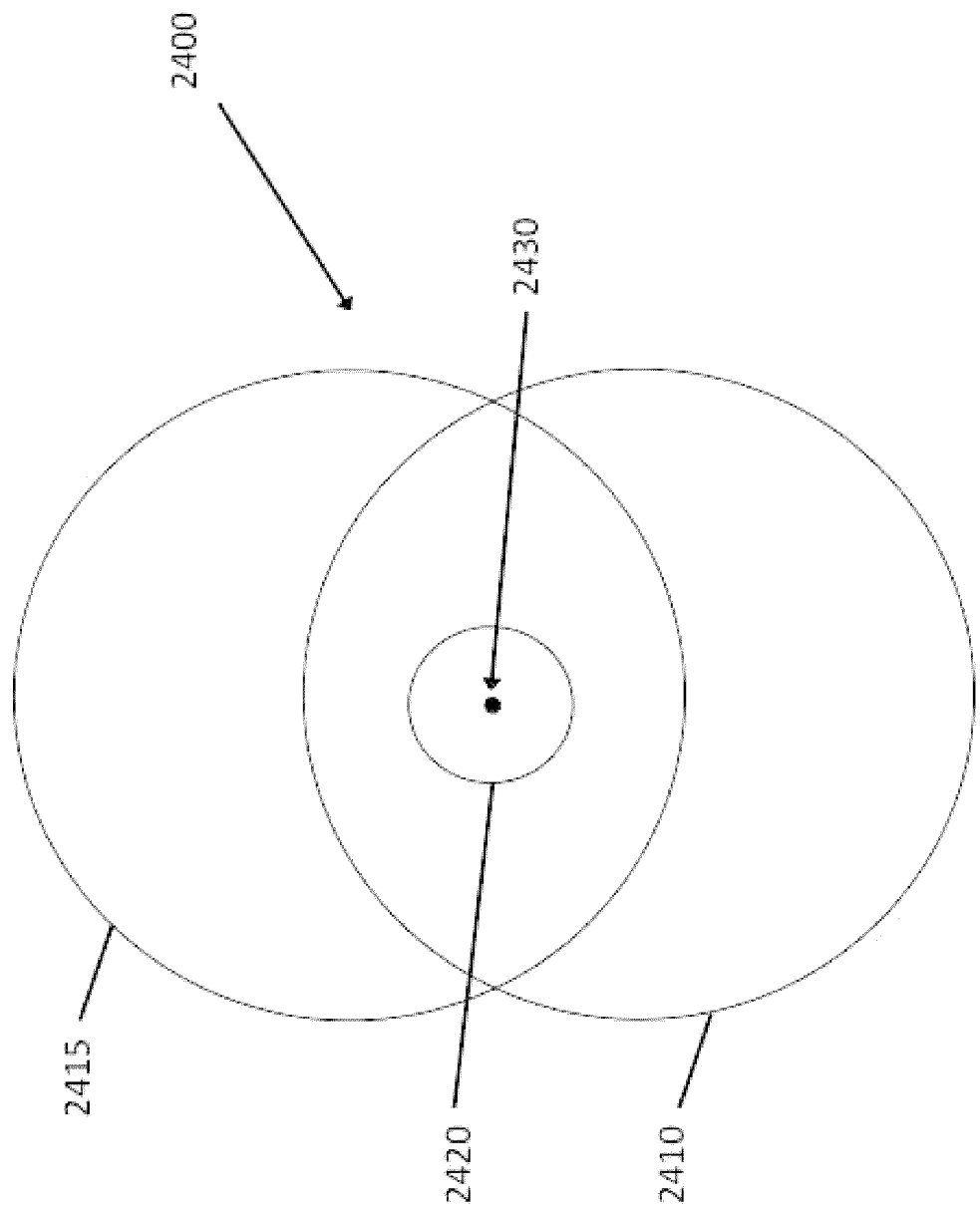
FIG. 4F is a schematic proximal end view of the distal portion of FIG. 4E.

FIG. 4E is a schematic side elevational view of yet another example embodiment of a distal portion 2400 of a vascular treatment device, for example the distal portion 100 of the device 10, 20, 30, or 40, including any example embodiments thereof described herein. FIG. 4F is a schematic proximal end view of the distal portion 2400 of FIG. 4E. The distal portion 2400 includes a plurality of woven bulbs 2410, 2415 and woven necks 2420. The bulbs 2410, 2415 are longitudinally spaced from each other by the woven necks 2420. In some embodiments, the bulbs 2410, 2415 and the necks 2420 are an integral textile structure in which the filaments 156 that form the bulbs 2410, 2415 are the same as and longitudinally continuous with the filaments 156 that form the necks 2420. The bulbs 2410, 2415 are generally spherical, although the proximal and distal ends of the bulbs 2410, 2415 may begin to form the necks 2420. The necks 2220 are aligned along a longitudinal axis 2430. The longitudinal axis 2430 may run through a center of the distal portion 2400. The longitudinal axis 2430 is aligned to the chords of bulbs 2410 and to the chords of the bulbs 2415. The chords through the each of the bulbs 2410 are the same. The chords through each of the bulbs 2415 are the same. The chords through the bulbs 2410 are different from the chords through the bulbs 2415. The longitudinal position of the bulbs 2410, 2415 may alternate. The necks 2420 are between different chords of the bulbs 2410, 2415. The necks 2420 are cylindrical or generally cylindrical along the central or longitudinal axis, although the ends of the necks 2420 may flare outwardly to begin to from the bulbs 2410, 2415. The bulbs 2410 in FIG. 4E have substantially uniform dimensions or diameters (e.g., within about ±5%, about ±10%, about ±15%, or about 20% of each other) such that the distal portion 2400 may be considered non-tapered or cylindrical.

Figure 4G:
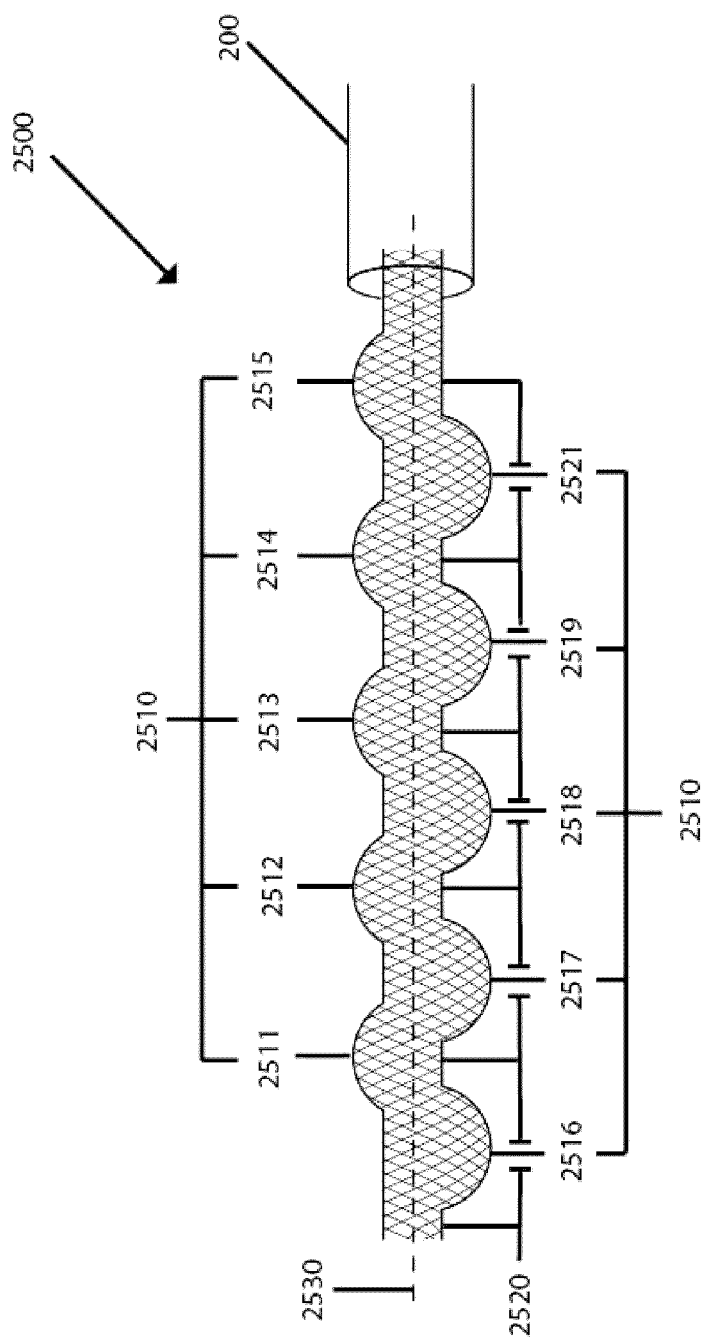
FIG. 4G is a schematic side elevational view of yet another example embodiment of a distal portion of a vascular treatment device.
Figure 4H:
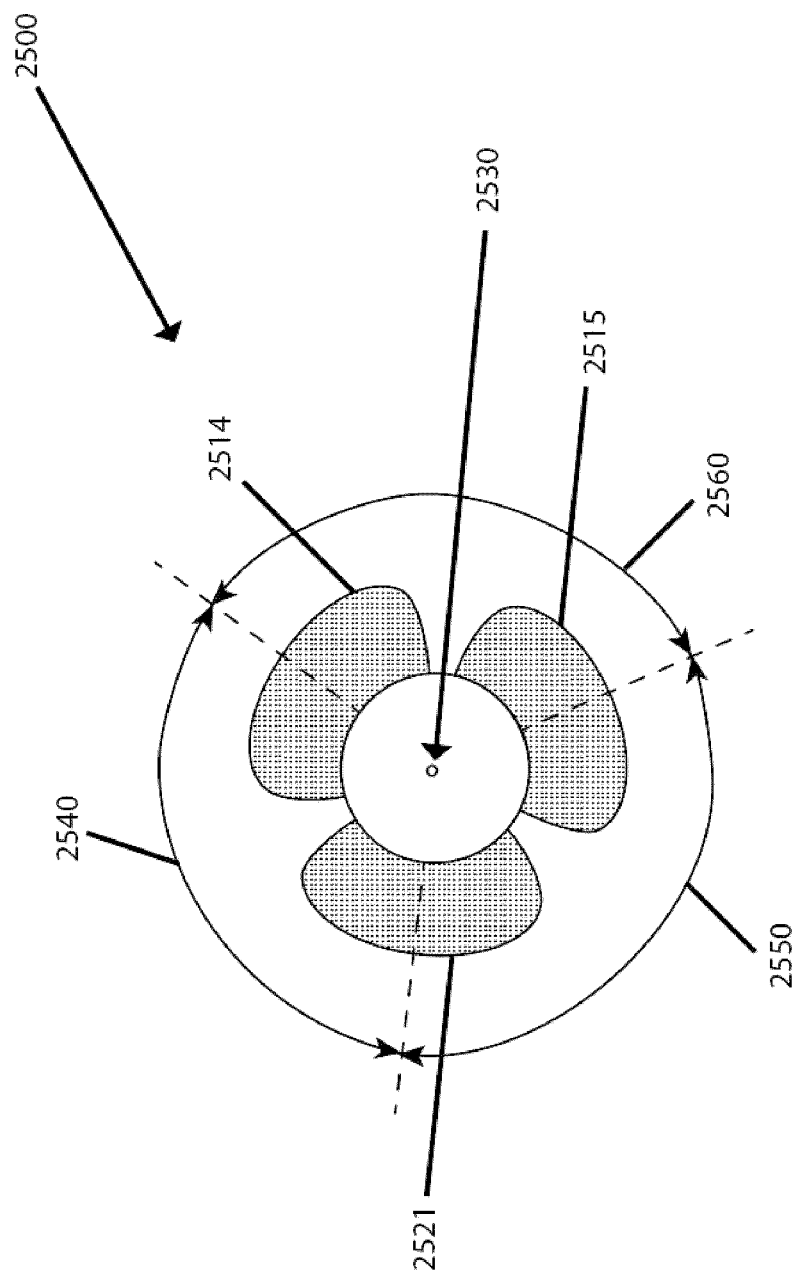
FIG. 4H is a schematic proximal end view of the distal portion of FIG. 4G.
Figure 41:
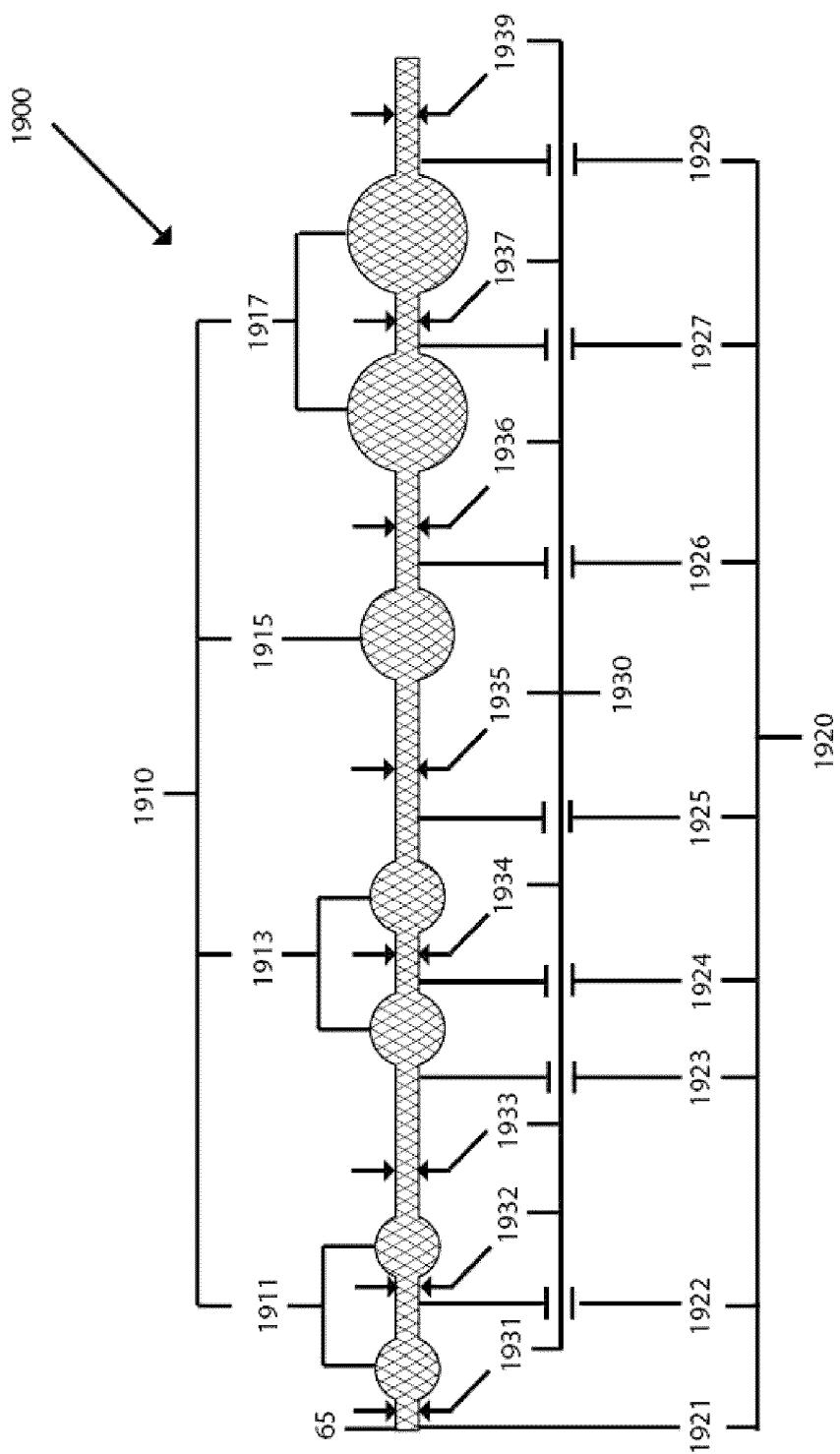

FIG. 4G is a schematic side elevational view of yet another example embodiment of a distal portion 2500 of a vascular treatment device, for example the distal portion 100 of the device 10, 20, 30, or 40. FIG. 4H is a schematic proximal end view of the distal portion 2500 of FIG. 4G. The distal portion 2500 includes a plurality of woven bulbs 2510 along an elongate support structure 2520 (such as a neck, tube, spindle, spine, rod, backbone, etc.). The elongate support structure 2520 is aligned along a longitudinal axis 2530. The longitudinal axis 2530 may run through a center of the distal portion 2500. The bulbs 2510 are hemispherical or generally hemi-spherical along the longitudinal axis 2530, although the elongate support structure 2520 between the bulbs 2510 may flare outwardly to begin to from the bulbs 2510. In some embodiments, the bulbs 2510 are hemispherical or generally hemi-spherical and so they appear as bulges on the sides of a single elongate support structure 2520 rather than as bulbs separated by a plurality of necks. The bulbs 2510 have substantially uniform dimensions or diameters (e.g., within about ±5%, about ±10%, about ±15%, or about 20% of each other) such that the distal portion 2500 may be considered non-tapered.

The distal portion 2500 includes bulbs 2510 that are phase-shifted. The bulbs 2510 are phase-shifted from each other by a phase-shift angle of about 120° relative to the longitudinal axis 2530 (for e.g., the bulbs 2516, 2512, 2519, 2515 are phase-shifted from the bulbs 2511, 2518, 2514 by a phase-shift angle 2560 of about 120°; the bulbs 2511, 2518, 2514 are phase-shifted from the bulbs 2517, 2513, 2521 by a phase-shift angle 2540 of about 120°; and the bulbs 2517, 2513, 2521 are phase-shifted from the bulbs 2516, 2512, 2519, 2515 by a phase-shift angle 2550 of about 120°). A phase-shifted configuration of the bulbs 2510 in the distal portion 2500 can allow for effective torsional rasping and mechanical thrombectomy of hard clots or organized thrombus adherent to the endothelium wall (inner walls of blood vessels). The term thrombus, as used herein, shall be given its ordinary meaning and shall include, but not be limited to, blood clots (e.g., attached to the blood vessel), emboli (e.g., floating blood clots), and other debris that may be removed from vessels. The terms thrombus, clot, and embolus may be used interchangeably depending on context. Although some example phase-shift angles are provided herein, some embodiments of the distal portion 2500 may include symmetric phase-shift angles that are uniform to each other with values that range between about 15° and about 345° (e.g., the phase-shift angles 2540, 2550, 2560 each being about 120°). For another example, some embodiments of the distal portion 2500 may include asymmetric phase-shift angles that are varying to each other with values that range between about 15° and about 345° (e.g., the phase shift-angles 2540, 2550 both being about 80° and the phase-shift angle 2560 being about 200°).

FIG. 4I is a schematic side elevational view of another example embodiment of a distal portion 1900 of a vascular treatment device, for example the distal portion 100 of the device 10, 20, 30, or 40. The distal portion 1900 includes a plurality of woven bulbs 1910 and woven necks 1920. The distal portion 1900 includes a woven neck 65 at the distal end. The necks 1920 are cylindrical or generally cylindrical along the longitudinal axis, although the ends of the necks 1920 may flare outwardly to begin to from the bulbs 1910.

The distal portion 1900 includes seven bulbs 1910: two bulbs 1911, two bulbs 1913, one bulb 1915, and two bulbs 1917. The bulbs 1911 have a smaller diameter than the bulbs 1913, which have a smaller diameter than the bulb 1915, which has a smaller diameter than the bulbs 1917. The bulbs 1911 have substantially uniform diameters, the bulbs 1913 have substantially uniform diameters, and the bulbs 1917 have substantially uniform diameters.

In some embodiments, the outer diameters of the bulbs 1910 in the radially-expanded configuration are as follows: the two distal extra-small spherical bulbs 1911 have an outer diameter configured to be oversized to the extra-small vessel segments such as the M2 segments of the middle cerebral artery (e.g., about 1.5 mm to about 2.25 mm); the proximally-next two small spherical bulbs 1913 have an outer diameter configured to be oversized to the smaller vessel segments such as the distal M1 segment of the middle cerebral artery (e.g., about 2.25 mm to about 2.75 mm); the proximally-next medium spherical bulb 1915 has an outer diameter configured to be oversized to the medium vessel segments such as the proximal M1 segment of the middle cerebral artery (e.g., about 2.75 mm to about 3.25 mm); and the proximally-next large spherical bulbs 1917 have an outer diameter configured to be oversized to the large vessel segments such as the distal supra-clinoid segment of the internal carotid artery (e.g., about 3.25 mm to about 4 mm). Due to the differing diameters of the bulbs 1910, the distal portion 1900 may be considered tapered, for example inwardly tapered from proximal to distal or outwardly tapered from distal to proximal, or the distal portion 1900 may be considered stepped, for example inwardly stepped from proximal to distal or outwardly stepped from distal to proximal. Other and opposite configurations are also possible. For example, the bulbs 1910 may be inwardly tapered or stepped from distal to proximal or outwardly stepped from proximal to distal. For another example, the bulbs 1910 may have random (e.g., non-sequential) diameters along the length of the distal portion 1900, which may include sections that are substantially cylindrical and/or sections that are stepped or tapered distally and/or proximally. A tapered configuration of the distal portion 1900 can provide adequate and safe deployment of the distal portion 1900 across blood vessels with multiple and/or varying diameters (e.g., vasculature that progressively reduces in size). Although some example diameters are provided herein, some embodiments of the distal portion 1900 may include diameters of the bulbs 1911, 1913, 1915, 1917 in accordance with the values provided above and/or diameters that are within about ±5%, about ±10%, about ±15%, or about ±20% of any such values.

The necks 1920 include a first neck 1921 having a first neck diameter 1931 (also the distal neck 65), a second neck 1922 having a second neck diameter 1932, a third neck 1923 having a third neck diameter 1933, a fourth neck 1924 having a fourth neck diameter 1934, a fifth neck 1925 having a fifth neck diameter 1935, a sixth neck 1926 having a sixth neck diameter 1936, a seventh neck 1927 having a seventh neck diameter 1937, and an eighth neck 1929 having an eighth neck diameter 1939 (also the proximal neck). The neck diameters 1930 including 1931, 1932, 1933, 1934, 1935, 1936, 1937, 1939 are uniform or substantially uniform. The distal portion 1900 includes necks 1920 having varying lengths: four necks 1921, 1922, 1924, 1927 having relatively short lengths, two necks 1926, 1929 having relatively medium lengths, and two necks 1923, 1925 having relatively long lengths in an interspersed pattern. Other interspersing patterns are also possible. For example, an interspersed pattern may include four necks 1921, 1922, 1924, 1927 with relatively short lengths, two necks 1926, 1929 with relatively medium lengths, and two necks 1923, 1925 with relatively long lengths.

Necks 1921, 1922, 1923, 1924, 1925, 1926, 1927, 1929 having varying lengths can provide controlled expansion of the bulbs 1910 adjacent to the necks 1920 during torsional rasping, aid in wall apposition of the bulbs 1910, and/or inhibit or prevent distal emboli. Necks 1921, 1922, 1923, 1924, 1925, 1926, 1927, 1929 having varying lengths may be deployed in such a manner that necks 1920 with longer lengths are deployed at the region of maximal clot burden, which can provide effective torsional rasping by entrapping soft clots or non-organized thrombus between the undulations of the bulbs 1910 on the varying lengths of the necks 1920.

Figure 4J:
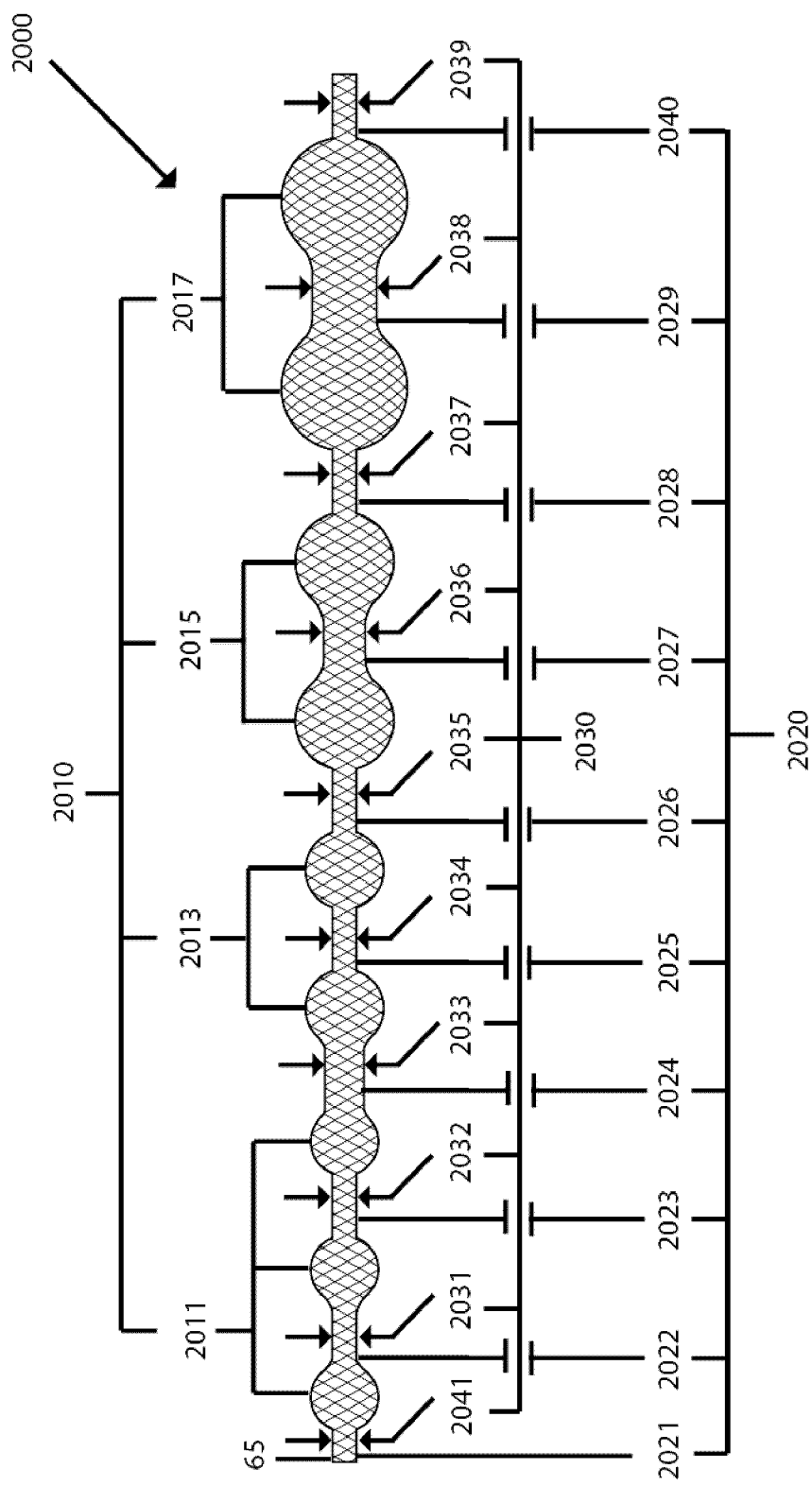
FIG. 4J is a schematic side elevational view of another example embodiment of a distal portion of a vascular treatment device.

FIG. 4J is a schematic side elevational view of another example embodiment of a distal portion 2000 of a vascular treatment device, for example the distal portion 100 of the device 10, 20, 30, or 40. The distal portion 2000 includes a plurality of woven bulbs 2010 and woven necks 2020. The distal portion 2000 includes a woven neck 65 at the distal end. The necks 2020 are cylindrical or generally cylindrical along the longitudinal axis, although the ends of the necks 2020 may flare outwardly to begin to from the bulbs 2010.

The distal portion 2000 includes nine bulbs 2010: three bulbs 2011, two bulbs 2013, two bulbs 2015, and two bulbs 2017. The bulbs 2011 have a smaller diameter than the bulbs 2013, which have a smaller diameter than the bulbs 2015, which have smaller diameters than the bulbs 2017. The bulbs 2011 have substantially uniform diameters, the bulbs 2013 have substantially uniform diameters, the bulbs 2015 have substantially uniform diameters, and the bulbs 2017 have substantially uniform diameters.

In some embodiments, the outer diameters of the bulbs 2010 in the radially-expanded configuration are as follows: the three distal extra-small spherical bulbs 2011 have an outer diameter configured to be oversized to the extra-small vessel segments such as the M2 segments of the middle cerebral artery (e.g., about 1.5 mm to about 2.25 mm); the proximally-next two small spherical bulbs 2013 have an outer diameter configured to be oversized to the smaller vessel segments such as the distal M1 segment of the middle cerebral artery (e.g., about 2.25 mm to about 2.75 mm); the proximally-next two medium spherical bulbs 2015 have an outer diameter configured to be oversized to the medium vessel segments such as the proximal M1 segment of the middle cerebral artery (e.g., about 2.75 mm to about 3.25 mm); and the proximally-next large spherical bulbs 2017 have an outer diameter configured to be oversized to the large vessel segments such as the distal supra-clinoid segment of the internal carotid artery (e.g., about 3.25 mm to about 4 mm). Due to the differing diameters of the bulbs 2010, the distal portion 2000 may be considered tapered, for example inwardly tapered from proximal to distal or outwardly tapered from distal to proximal, or the distal portion 2000 may be considered stepped, for example inwardly stepped from proximal to distal or outwardly stepped from distal to proximal. Other and opposite configurations are also possible. For example, the bulbs 2010 may be inwardly tapered or stepped from distal to proximal or outwardly stepped from proximal to distal. For another example, the bulbs 2010 may have random (e.g., non-sequential) diameters along the length of the distal portion 2000, which may include sections that are substantially cylindrical and/or sections that are stepped or tapered distally and/or proximally. A tapered configuration of the distal portion 2000 can provide adequate and safe deployment of the distal portion 2000 across blood vessels with multiple and/or varying diameters (e.g., vasculature that progressively reduces in size). Although some example diameters are provided herein, some embodiments of the distal portion 2000 may include diameters of the bulbs 2011, 2013, 2015, 2017, 2019 in accordance with the values provided above and/or diameters that are within about ±5%, about ±10%, about ±15%, or about ±20% of any such values.

The necks 2020 include a first neck 2021 having a first neck diameter 2041 (also the distal neck 65), a second neck 2022 having a second neck diameter 2031, a third neck 2023 having a third neck diameter 2032, a fourth neck 2024 having a fourth neck diameter 2033, a fifth neck 2025 having a fifth neck diameter 2034, a sixth neck 2026 having a sixth neck diameter 2035, a seventh neck 2027 having a seventh neck diameter 2036, and an eighth neck 2028 having an eighth neck diameter 2037, a ninth neck 2029 having a ninth neck diameter 2038, a tenth neck 2040 having a tenth neck diameter 2039 (also the proximal neck). The distal portion 2000 includes varying neck diameters 2030: seven necks 2021, 2022, 2023, 2025, 2026, 2028, 2040 having relatively narrow neck diameters 2041, 2031, 2032, 2034, 2035, 2037, 2039, respectively, and three necks 2024, 2027, 2029 having relatively wide neck diameters 2033, 2036, 2038, respectively, in an interspersed pattern. Other interspersing patterns are also possible. For example, an interspersed pattern may include seven necks 2021, 2022, 2023, 2025, 2027, 2029, 2040 having relatively narrow neck diameters 2041, 2031, 2032, 2034, 2036, 2038, 2039, respectively, and three necks 2024, 2026, 2028 having relatively wider neck diameters 2033, 2035, 2037, respectively (e.g., relatively wider neck diameters between changing bulb diameters). For another example, an interspersed pattern may include five necks 2021, 2024, 2026, 2028, 2040 having relatively narrow neck diameters 2041, 2033, 2035, 2037, 2039, respectively, and five necks 2022, 2023, 2025, 2027, 2029 having relatively wider neck diameters 2031, 2032, 2034, 2036, 2038, respectively (e.g., relatively narrow neck diameters between changing bulb diameters).

Varying neck diameters 2031, 2032, 2033, 2034, 2035, 2036, 2037, 2038, 2039, 2041 can allow for the outer diameters of the bulbs 2010 and/or the varying neck diameters 2030 to have adequate wall apposition across blood vessels with multiple and/or varying diameters (e.g., vasculature that progressively reduces in size), which can inhibit or prevent emboli from drifting into side branches of blood vessels during torsional rasping and/or mechanical thrombectomy. Varying neck diameters 2031, 2032, 2033, 2034, 2035, 2036, 2037, 2038, 2039, 2041 can allow the distal portion 2000 to be deployed in such a way that the wider neck diameters are deployed at the region of bifurcations or higher blood vessel branches and/or at regions of blood vessel diameter transitions, which can allow the distal portion 2000 to serve as a filter to inhibit emboli from drifting into the branches of the blood vessels during torsional rasping and/or mechanical thrombectomy.

Figure 4K:
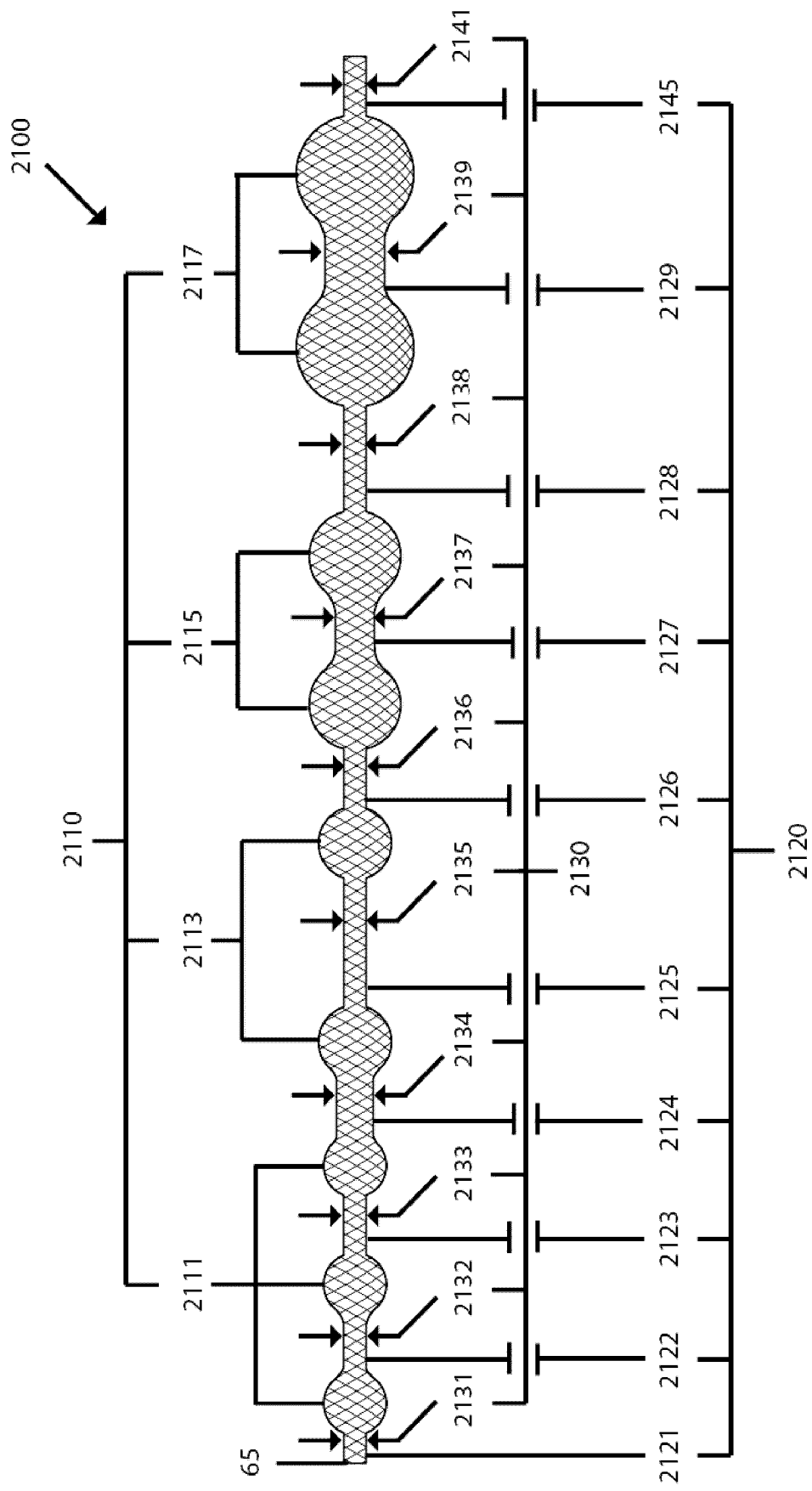
FIG. 4K is a schematic side elevational view of yet another example embodiment of a distal portion of a vascular treatment device.

FIG. 4K is a schematic side elevational view of another example embodiment of a distal portion 2100 of a vascular treatment device, for example the distal portion 100 of the device 10, 20, 30, or 40. The distal portion 2100 includes a plurality of woven bulbs 2110 and woven necks 2120. The distal portion includes a woven neck 65 at the distal end. The necks 2120 are cylindrical or generally cylindrical along the longitudinal axis, although the ends of the necks 2120 may flare outwardly to begin to from the bulbs 2110.

The distal portion 2100 includes nine bulbs 2110: three bulbs 2111, two bulbs 2113, two bulbs 2115, and two bulbs 2117. The bulbs 2111 have a smaller diameter than the bulbs 2113, which have a smaller diameter than the bulbs 2115, which have smaller diameters than the bulbs 2117. The bulbs 2111 have substantially uniform diameters, the bulbs 2113 have substantially uniform diameters, the bulbs 2115 have substantially uniform diameters, and the bulbs 2117 have substantially uniform diameters.

In some embodiments, the outer diameters of the bulbs 2110 in the radially-expanded configuration are as follows: the three distal extra-small spherical bulbs 2111 have an outer diameter configured to be oversized to the extra-small vessel segments such as the M2 segments of the middle cerebral artery (e.g., about 1.5 mm to about 2.25 mm); the proximally-next two small spherical bulbs 2113 have an outer diameter configured to be oversized to the smaller vessel segments such as the distal M1 segment of the middle cerebral artery (e.g., about 2.25 mm to about 2.75 mm); the proximally-next medium spherical bulbs 2115 have an outer diameter configured to be oversized to the medium vessel segments such as the proximal M1 segment of the middle cerebral artery (e.g., about 2.75 mm to about 3.25 mm); and the proximally-next large spherical bulbs 2117 have an outer diameter configured to be oversized to the large vessel segments such as the distal supra-clinoid segment of the internal carotid artery (e.g., about 3.25 mm to about 4 mm). Due to the differing diameters of the bulbs 2110, the distal portion 2100 may be considered tapered, for example inwardly tapered from proximal to distal or outwardly tapered from distal to proximal, or the distal portion 2100 may be considered stepped, for example inwardly stepped from proximal to distal or outwardly stepped from distal to proximal. Other and opposite configurations are also possible. For example, the bulbs 2110 may be inwardly tapered or stepped from distal to proximal or outwardly stepped from proximal to distal. For another example, the bulbs 2110 may have random (e.g., non-sequential) diameters along the length of the distal portion 2100, which may include sections that are substantially cylindrical and/or sections that are stepped or tapered distally and/or proximally. A tapered configuration of the distal portion 2100 can provide adequate and safe deployment of the distal portion 2100 across blood vessels with multiple and/or varying diameters (e.g., vasculature that progressively reduces in size). Although some example diameters are provided herein, some embodiments of the distal portion 2100 may include diameters of the bulbs 2111, 2113, 2115, 2117 in accordance with the values provided above and/or diameters that are within about ±5%, about ±10%, about ±15%, or about ±20% of any such values.

The necks 2120 include a first neck 2121 having a first neck diameter 2131 (also the distal neck 65), a second neck 2122 having a second neck diameter 2132, a third neck 2123 having a third neck diameter 2133, a fourth neck 2124 having a fourth neck diameter 2134, a fifth neck 2125 having a fifth neck diameter 2135, a sixth neck 2126 having a sixth neck diameter 2136, a seventh neck 2127 having a seventh neck diameter 2137, an eighth neck 2128 having an eighth neck diameter 2138, a ninth neck 2129 having a ninth neck diameter 2129, a tenth neck 2145 having a tenth neck diameter 2141 (also the proximal neck). The necks 2120 have varying neck diameters 2130 and varying lengths.

The distal portion 2100 includes varying neck diameters 2130: seven necks 2121, 2122, 2123, 2125, 2126, 2128, 2145 having relatively narrow neck diameters 2131, 2132, 2133, 2135, 2136, 2138, 2141, respectively, and three necks 2124, 2127, 2129 having relatively wide neck diameters 2134, 2137, 2139, respectively, in an interspersed pattern. Other interspersing patterns are also possible. For example, an interspersed pattern may include seven necks 2121, 2122, 2123, 2125, 2127, 2129, 2145 having relatively narrow neck diameters 2131, 2132, 2133, 2135, 2137, 2139, 2141, respectively, and three necks 2124, 2126, 2128 having relatively wider neck diameters 2134, 2136, 2138, respectively (e.g., relatively wider neck diameters between changing bulb diameters). For another example, an interspersed pattern may include five necks 2121, 2124, 2126, 2128, 2145 having relatively narrow neck diameters 2131, 2134, 2136, 2138, 2141, respectively, and five necks 2122, 2123, 2125, 2127, 2129 having relatively wider neck diameters 2132, 2133, 2135, 2137, 2139, respectively (e.g., relatively narrow neck diameters between changing bulb diameters).

The distal portion 2100 includes necks 2120 having varying lengths: eight necks 2121, 2122, 2123, 2124, 2126, 2127, 2129, 2145 having relatively short lengths, one neck 2128 having a relatively medium length, and one neck 2125 having a relatively long length in an interspersed pattern. Other interspersing patterns are also possible. For example, an interspersed pattern may include four necks 2121, 2122, 2123, 2124 having relatively short lengths, four necks 2126, 2127, 2129, 2145 having relatively medium lengths, and two necks 2125, 2128 having relatively large lengths.

Varying neck diameters 2131, 2132, 2133, 2134, 2135, 2136, 2137, 2138, 2139, 2141 can allow for the outer diameters of the bulbs 2110 and/or the varying neck diameters 2130 to have adequate wall apposition across blood vessels with multiple and/or varying diameters (e.g., vasculature that progressively reduces in size), which can inhibit or prevent emboli from drifting into side branches of blood vessels during torsional rasping and/or mechanical thrombectomy. Varying neck diameters 2130 including 2131, 2132, 2133, 2134, 2135, 2136, 2137, 2138, 2139, 2141 can allow the distal portion 2100 to be deployed in such a way that the wider neck diameters are deployed at the region of bifurcations or higher blood vessel branches and/or at regions of blood vessel diameter transitions, which can allow the distal portion 2100 to serve as a filter to inhibit emboli from drifting into the branches of the blood vessels during torsional rasping and/or mechanical thrombectomy. Necks 2121, 2122, 2123, 2124, 2125, 2126, 2127, 2128, 2129, 2145 having varying lengths can provide controlled expansion of the bulbs 2110 adjacent to the necks 2120 during torsional rasping, aid in wall apposition of the bulbs 2110, and/or inhibit or prevent distal emboli. Necks 2121, 2122, 2123, 2124, 2125, 2126, 2127, 2128, 2129, 2145 having varying lengths may be deployed in such a manner that necks 2120 with longer lengths are deployed at the region of maximal clot burden, which can provide effective torsional rasping by entrapping soft clots or non-organized thrombus between the undulations of the bulbs 2110 on the varying lengths of the necks 2120. Necks 2121, 2122, 2123, 2124, 2125, 2126, 2127, 2128, 2129, 2145 with varying lengths and/or diameters 2131, 2132, 2133, 2134, 2135, 2136, 2137, 2138, 2139, 2141 may provide for combinations of some or all of these advantages.

As illustrated, for example in FIGS. 2A-4K, and described herein, the distal portion 100 of the device 10, 20, 30, or 40 may include a wide variety of different bulb parameters such as bulb quantity, shape, size, spacing, phase-shifting with regards to the longitudinal axis or to a chord of the axis, filament parameters (e.g., material, material ratio, thickness, shape, etc.), different neck parameters (e.g., neck diameter, neck length, etc.), braid parameters (e.g., pattern, angle, density, pore size, etc.), alignment to the longitudinal axis or to a chord of the axis, combinations thereof, and the like.

Each of the distal portions 1000, 1100 illustrated in FIGS. 2A and 2B includes ten bulbs 1010, 1110. Other numbers of bulbs 1010, 1110 are also possible. For example, in some embodiments, the distal portion includes between one and nine bulbs, between five and twenty bulbs, between four and ten bulbs, between three and fifteen bulbs, between 11 and 30 bulbs, or more than 30 bulbs. In some embodiments, the distal portion includes 2 (e.g., as illustrated in FIG. 5E), 3 (e.g., as illustrated in FIGS. 4C, 5B, 5F, and 5G), 4 (e.g., as illustrated in FIGS. 2G and 4E), 5 (e.g., as illustrated in FIG. 2F), 6 (e.g., as illustrated in FIGS. 2E and 2E-2), 7 (e.g., as illustrated in FIG. 4I), 8, 9 (e.g., as illustrated in FIGS. 4J and 4K), 10 (e.g., as illustrated in FIGS. 2A-4B), 11, 12, 13, 14, 15, 16, 17, 18, 19, or 20 bulbs. In some implementations, for example in which the device is configured to be used in peripheral vessels (e.g., in the leg), where clots can be up to 20 cm or even 40 cm, 11 to 30 or more, or 40 to 60, bulbs may be used. In some embodiments, 1 bulb is used for about every 0.2 cm to 5 cm (e.g., about every 0.5 cm to 2 cm). A larger quantity of bulbs along a longer length distal portion 100 may provide more flexibility in treating a range of clot lengths including longer clots than a smaller quantity of bulbs along a shorter length distal portion 100. A smaller quantity of bulbs along a shorter length distal portion 100 may provide better pushability of the distal portion 100 through a microcatheter and/or higher torque in a vessel (e.g., because the torque is spread across the shorter length and/or the fewer quantity of bulbs).

The term bulb, as used herein, shall be given its ordinary meaning and shall include, but not be limited to, protruding or bulging portions that may be rounded (e.g., rounded balls, spheres, cylinders, or beads) or non-rounded, which are typically, but not necessarily, provided along (e.g., separately or integrated with) a support structure. A bulb may have a consistent cross-section or may have two or more different cross-sections. A bulb may have one, two, or more than two open ends or lumens therethrough. Bulb shapes may include, for example, e.g., with respect to a top view, side view, and/or cross-section, at least one of sphere, oblong, egg, oval, ellipse, cylinder, spiral, twisted, helical, triangle, rectangle, parallelogram, rhombus, square, diamond, pentagon, hexagon, heptagon, octagon, nonagon, decagon, quatrefoil, trapezoid, trapezium, other polygons, oblate spheroids (e.g., flattened spheroids), prolate spheroids (e.g., elongated spheroids), curvilinear or bulged versions of these and other shapes, combinations thereof (e.g., a distal section of bulb having a different shape than a proximal section of a bulb), and the like. Different shapes of bulbs may be used in a distal portion 100. For example, as illustrated in FIGS. 4A and 4B, spherical bulbs and oblong bulbs may be used in the same distal portion 100. In some embodiments, different shapes of bulbs are alternated. In some embodiments, the distal portion 100 includes a series of various shapes of bulbs (e.g., including two or more bulbs each having different shapes), and each series is repeated two, three, four, five, six, seven, or more times. In some embodiments, the distal portion 100 includes bulbs having a first shape at the ends and bulbs having a second different shape between the end bulbs. In some embodiments, the distal portion 100 includes bulbs having a first shape in a distal section and bulbs having a second different shape in a proximal section.

In some embodiments in which a bulb comprises an egg, oval or elliptical shape, a tapered portion of the bulb facing the distal end of the distal portion 100 can aid navigation to increasingly small vessels, for example at the transition point to a smaller vessel. For example, the tapered end of can help the distal portion 100 from internal carotid artery (ICA) to M1 or from M1 to M2 segments of the brain.

In some embodiments, at least some of the bulbs have a size (with respect to the outer diameter in an expanded configuration) of about 1 mm to about 80 mm (e.g., about 2 mm to about 12 mm). Bulbs in range of about 1 mm to about 6 mm, about 3 mm to about 4.5 mm, about 0.5 mm to about 3 mm (e.g., about 3 mm), 0.75 mm to about 3 mm (e.g., about 3 mm), about 3.1 mm to about 3.9 mm (e.g., about 3.5 mm), about 4 mm to about 4.4 mm (e.g., 4 mm), and about 4.5 mm to about 7.5 mm (e.g., about 4.5 mm) may be particular beneficial for smaller clots and/or vessels (e.g., in the brain). Bulbs in range of about 4 mm to about 10 mm and about 5 mm to about 40 mm may be particular beneficial for larger clots and/or vessels (e.g., in the leg). In some embodiments, all of the bulbs have a size (with respect to the outer diameter in an expanded configuration) greater than about 0.75 mm, greater than about 1 mm, greater than about 1.5 mm, greater than about 2 mm, greater than about 2.5 mm, or greater than about 2.75 mm Large sizes may be particularly beneficial in some embodiments because they effectively engage or appose vessel walls, are simpler to manufacture, etc.

The bulb sizes described herein may be reduced by about 1.3 times to about 10 times (e.g., about 1.3 to about 2.5 times, about 2.5 to about 4 times, about 4 to about 7 times, about 7 to about 10 times, and overlapping ranges therein) in the collapsed configuration. In some embodiments, the collapsed configuration of the bulbs is about 50% to about 80% of the inner diameter of the delivery catheter (e.g., microcatheter). For example, in embodiments in which a microcatheter has an inner diameter of about 0.0125 inches (approx. 0.32 mm), the bulbs in the collapsed state can have a diameter between about 0.006 inches (approx. 0.16 mm) and about 0.01 inches (approx. 0.25 mm). In some embodiments, for example for use in small vessels, the bulbs may have a size in the collapsed state of about 0.1 mm and about 0.9 mm (e.g., about 0.25 mm to about 0.5 mm). In some embodiments, for example for use in small vessels, the bulbs may have a size in the collapsed state of about 0.5 mm and about 5 mm.

In some embodiments, the dimensions of the bulbs vary based on the shape of the bulb. For example, the diameter may vary if the shape is a sphere. For another example, the diameter and/or length may vary if the shape is oblong. For yet another example, the length of a side and/or the angle of a vertex of a may vary if the shape of is a polygon (e.g., triangle).

The diameter or width of the distal portion 100 varies along the length of the distal portion 100. Examples of diameters or widths of bulbs are described above. In some embodiments, the diameter or width of the necks between, proximal to, and/or distal to bulbs is in the range of about 0.15 mm to about 4.5 mm (e.g., about 0.15 mm, about 0.35 mm, about 0.38 mm, about 0.65 mm, about 0.4 mm, about 0.45 mm, about 0.75 mm, about 1 mm, about 1.25 mm, about 1.5 mm, about 1.75 mm, about 2 mm, about 2.25 mm, about 2.5 mm, about 2.75 mm, about 3 mm, about 3.25 mm, about 3.5 mm, about 3.75 mm, about 4 mm, about 4.25 mm, about 4.5 mm, ranges between such values, etc.) in an expanded configuration and in the range of about 0.1 mm to about 0.5 mm, about 0.1 mm to about 0.34 mm, about 0.27 mm to about 0.37 mm, or about 0.25 mm to about 0.33 mm (e.g., about 0.32 mm) in the collapsed configuration. The diameter of a neck in the expanded configuration is less than the diameter of a bulb proximal or distal to and adjoining that neck. For example, for large proximal bulbs having a diameter of 4.5 mm, a neck between two 4.5 mm bulbs could be 4.25 mm, even though such neck may be larger than the diameter of a more distal 4 mm bulb. In some embodiments, the diameter or width of the distal portion 100 is in the range of about 0.1 mm to about 0.34 mm (e.g., about 0.25 mm to about 0.33 mm) in the collapsed configuration, for example small enough to fit in the smallest currently commercially available microcatheter, which has an inner diameter of 0.017 inches (approx. 0.43 mm). In some implementations, for example in which the device is configured to be used in larger vessels, the diameter or width of the distal portion 100 is in the range of about 1 mm to about 40 mm (e.g., about 5 mm to about 20 mm) in the expanded configuration and the in the range of about 0.5 mm to about 10 mm (e.g., about 1 mm to about 2 mm) in the collapsed configuration.

The diameter or dimension of the necks may be the same or different. For example, the diameters of the necks may vary across the longitudinal length of the distal portion 100. In some embodiments, the diameter of the neck at least partially depends on the size of one or both adjacent bulbs. For example, referring again to FIG. 2B, the diameter of the necks 1120 between the bulbs 1118 may be larger than the diameter of the necks 1120 between the bulbs 1116, which may be larger than the diameter of the necks 1120 between the bulbs 1114, which may be larger than the diameter of the necks 1120 between the bulbs 1112. In some embodiments, varying the diameter or dimension of the necks with variance in the diameter or dimension of the bulbs can help to vary or maintain an undulation pattern, which can help to trap thrombus and/or inhibit or prevent distal emboli with enhanced wall apposition by the bulbs 1110 and the necks 1120.

In some embodiments, starting at the distal end of the distal portion 100, each consecutively proximal bulb is larger than the other. In some embodiments, two or more bulb sizes may be in an alternating pattern. As an example, a series of three bulb sizes may be alternated seven times for a total of twenty-one bulbs. In some embodiments, three or more bulb sizes are in a series, and each series is repeated two, three, four, five, six, seven, or more times. In some embodiments, larger bulbs may be at the ends of the distal portion 100, while smaller bulbs are in the middle of the distal portion 100. In some embodiments, smaller bulbs may be at the ends of the distal portion 100, while larger bulbs are in the middle of the distal portion 100. In some embodiments, the distal portion 100 comprises bulbs of varying dimensions without specificity to a longitudinal position.

The positioning or spacing of the bulbs may be beneficial for certain vessel sizes and/or clot locations, material, and/or sizes. Bulbs may be touching (e.g., contiguous) or non-touching. The distal portion 100 may include bulbs that are both touching and non-touching. In some embodiments, the distal portion 100 includes bulbs that are all non-touching and/or are spaced apart by one or more necks. These necks may be of the same or different material than the bulbs. The necks may also be shaped differently than the bulbs. The necks may comprise, be embedded with, or coated by markers or other visualization aids (such as radiopaque portions).

The bulbs may be separated by distances or neck lengths of about 0.1 mm to about 50 mm, including, but not limited to, about 0.5 mm to about 1 mm, about 1 mm to about 2 mm, about 2 mm to about 3 mm, about 3 mm to about 4 mm, about 4 mm to about 5 mm, about 5 mm to about 8 mm, about 8 mm to about 10 mm, about 10 mm to about 12 mm, about 12 mm to about 15 mm, about 15 mm to about 25 mm, about 25 mm to about 35 mm, and about 35 mm to about 50 mm apart, including overlapping ranges thereof. The spaces between the bulbs in the distal portion 100 may be constant, or spacing between two or more (or all) of the bulbs may be different. In some embodiments, some bulbs are spaced the same distance from one another, while other bulbs have different spacing. In some embodiments, the length of the necks can at least partially depend on the length of at least one adjacent bulb. For example, the length of a neck may be between about 0.25 to about 2 times the length of a bulb proximal thereto, a bulb distal thereto, or an average length of the bulbs proximal and distal thereto. The necks can be more than an inert link between two bulbs. For example, when a distal portion 100 is torsionally rasped, longer necks may be squeezed tighter as they are rotated, allowing the bulbs ahead and behind to bulge even further. When the necks are the same length and a distal portion 100 is torsionally rasped, each of the necks will be squeezed moderately, resulting in moderate radial force out of the preceding and following bulbs.

In some embodiments, lengths of the necks may be at least partially based on the size and quantity of the bulbs the desired length of the distal portion 100, and/or the desired length of a distal neck 65, described further herein. For example, if the desired length of the distal portion 100 is about 60.5 cm, if three spherical bulbs having a diameter of about 3 mm, three spherical bulbs having a diameter of about 3.5 mm, two spherical bulbs having a diameter of about 4 mm, and two spherical bulbs having a diameter of about 4.5 mm are desired, and approximately equal spacing with a distal neck 65 having a length of about 4 mm, the necks may have a length of about 2 mm including a neck proximal to the proximal-most bulb.

Neck shapes may include, for example, e.g., with respect to a cross-section, at least one of a circle, oblong, egg, oval, ellipse, triangle, rectangle, parallelogram, rhombus, square, diamond, pentagon, hexagon, heptagon, octagon, nonagon, decagon, quatrefoil, trapezoid, trapezium, other polygons, curvilinear or bulged versions of these and other shapes, combinations thereof (e.g., a distal section of neck having a different shape than a proximal section of a neck), and the like. Different shapes of necks may be used in a distal portion 100. In some embodiments, the distal shape of the neck at least partially depends on the shape of at least one adjacent bulb.

The distal portion 100 may be braided, knitted, or woven with two or more strands (e.g., about 6 strands to about 144 strands, about 12 strands to about 120 strands, about 12 strands to about 96 strands, about 12 strands to about 72 strands, about 48 strands) in some embodiments. Strands may include filaments, wires, ribbons, etc. having a circular cross-section, an arcuate non-circular cross-section (e.g., oval, ellipsoid, etc.), a rectangular cross-section (e.g., square), a trapezoidal cross-section, combinations thereof, and the like. In some embodiments, the number of strands of a distal portion 100 is at least partially based on the desired expanded configuration diameter of the distal portion 100. For example, in some embodiments, 32 strands are used for a distal portion 100 expanded configuration diameter ranging from 2.5 mm and smaller, 48 strands are used for a distal portion 100 expanded configuration diameter ranging from about 2.5 mm to about 4.5 mm, 64 strands are used for a distal portion 100 expanded configuration diameter ranging from about 4.5 mm to about 6.0 mm, 72 strands are used for a distal portion 100 expanded configuration diameter ranging from 6.0 mm and greater, etc. In some embodiments, the strands have a diameter between about 0.0005 inches (approx. 0.013 mm) and about 0.04 inches (approx. 1 mm) (e.g., between about 0.0005 inches (approx. 0.013 mm) and about 0.0015 inches (approx. 0.038 mm), between about 0.0008 inches (approx. 0.02 mm) and about 0.012 inches (approx. 0.3 mm), between about 0.0008 inches (approx. 0.02 mm) and about 0.002 inches (approx. 0.05 mm), e.g., about 0.001 inches (approx. 0.025 mm), about 0.00125 inches (approx. 0.032 mm)). As the diameter of the vessel(s) to be treated increases, the diameter of the distal portion 100 increases, and at least one of the number of filaments, filament density, filament diameter, etc. may also increase, for example to provide the same density, picks (or pixels) per inch (PPI), etc. of the distal portion 100 or a portion thereof. In some embodiments, the necks have a uniform PPI.

The thickness or diameter of filaments comprising shape memory material may influence mechanical properties such as hoop strength, for example thicker filaments imparting more hoop strength. The thickness or diameter of filaments comprising radiopaque material may influence the visibility under x-ray and/or fluoroscopy, for example thicker filaments being easier to visualize. In some embodiments, the distal portion 100 comprises a shape memory filament having a first diameter or thickness and a radiopaque filament having a second diameter or thickness different than the first diameter or thickness. Different thicknesses or diameters can, for example allow adjustment to filament size based at least partially on the intended use of that filament. For example, if large hoop strength is not desired but high visibility is desired, relatively lower diameter shape memory filaments and relatively larger radiopaque filaments may be used. Other combinations are also possible. For example, in some embodiments, the distal portion 100 comprises a first shape memory filament having a first diameter or thickness and a second shape memory filament having a second diameter or thickness different than the first diameter or thickness. For another example, in some embodiments, the distal portion 100 comprises a first radiopaque filament having a first diameter or thickness and a second radiopaque filament having a second diameter or thickness different than the first diameter or thickness.

In some embodiments, the distal portion 100 is configured to allow the user of a device 10, 20, 30, 40 to crowd, compress, or bunch parts of the distal portion 100 such that some parts of the distal portion 100 have a higher density in some sections than in other sections, which may be useful, for example, for removing stubborn clots inhibiting or preventing inadvertent emboli, and/or decreasing flow into an aneurysm or an arterio-venous fistula to aid thrombosis.

The distal portion 100 may have a length in the range of about 0.5 cm to about 20 cm (e.g., about 1 cm to about 20 cm, about 5 cm to about 10 cm, about 4 cm to about 8 cm, etc.). In some implementations, for example in which the device is configured to be used in larger vessels (e.g., outside the brain), the distal portion 100 may have a length greater than about 20 cm (e.g., about 20 cm to about 50 cm). The length of the distal portion 100 may be characterized by the length of the distal portion 100 configured to appose the sidewalls of a vessel. For example, the length of the distal portion 100 may be characterized by approximately the center of the proximal-most bulb to the center of the distal-most bulb. In some embodiments, the usable length of the distal portion is between about 5 mm and about 60 mm (e.g., about 55.25 mm, which would be slightly oversized for treatment of any clot up to about 55 mm in length). As described further herein, the entire length of the distal portion 100 need not be used in every procedure.

The distal portion 100 may have a wall thickness, in some embodiments, ranging from about 0.01 mm to about 4 mm, about 0.02 mm to about 1 mm, or about 0.02 mm to about 0.05 mm (e.g., about 0.025 mm). The wall thickness may be between the thickness or diameter of one strand and the thickness or diameter of two strands (e.g., at a strand crossing point), in accordance with strand dimensions described herein. In some embodiments, the distal neck 65 or the distal end of the distal portion 100 may have the same or a different wall thickness than sections of the distal portion 100 proximal thereto. For example, the distal neck 65 or the distal end of the distal portion 100 may have a wall thickness between about 0.01 mm and about 4 mm, between about 0.02 mm and about 1 mm, or between about 0.02 mm and about 0.05 mm (e.g., about 0.025 mm). In some embodiments, the distal neck 65 or the distal end of the distal portion 100 may have the same or a different number of filaments than sections of the distal portion 100 proximal thereto. For example, the distal neck 65 or the distal end of the distal portion 100 may have a number of filaments between about 6 and about 144, between about 12 and about 120, between about 12 and about 96, or between about 12 and about 72 (e.g., about 48). In some embodiments, the distal neck 65 or the distal end of the distal portion 100 may have the same or a different ratio between diameter or dimension in an expanded state to diameter or dimension in a collapsed state. For example, the distal neck 65 or the distal end of the distal portion 100 may have a ratio between about 1:1 (e.g., collapsed state and expanded state are the same) and about 10:1 (e.g., about 1.2:1).

At least some of the strands of the distal portion 100 may comprise a shape memory alloy (e.g., nickel titanium or cobalt chromium). In some embodiments, about 50% to about 95% (e.g., about 75%) of the strands of the distal portion 100 comprise a shape memory alloy (e.g., nickel titanium, cobalt chromium, etc.) and about 5 to about 50% (e.g., 25%) of the strands of the distal portion 100 comprise a radiopaque material (e.g., platinum iridium, platinum tungsten, etc.). In some embodiments, the distal portion 100 comprises between about 1 strand and about 144 strands, between about 1 strand and about 120 strands, between about 1 strand and about 60 strands, between about 2 strands and about 48 strands (e.g., about 36 strands), etc. comprising a shape memory alloy (e.g., nickel titanium, cobalt chromium, etc.). In some embodiments, the distal portion 100 comprises between about 1 strand and about 60 strands, between about 1 strand and about 48 strands, between about 2 strands and about 24 strands (e.g., about 12 strands), etc. comprising a radiopaque material (e.g., platinum iridium, platinum tungsten, etc.). The shape memory filaments may help with heat treating to an expanded distal portion 100 shape, and the radiopaque filaments may aid in visualizing the device under x-ray and/or fluoroscopy during a procedure using the distal portion 100. The radiopaque strands can be spaced or clustered to increase visibility under x-ray and/or fluoroscopy. For example, a thick-band pattern may be used, which can include a plurality of radiopaque strands (e.g., 2 to 12 radiopaque strands) that are circumferentially adjacent.

In some embodiments, the distal portion 100 (e.g., the elongate support structure and/or the bulbs) comprises filaments including materials that are biocompatible or surface-treated to produce biocompatibility. Suitable materials may include, for example, platinum, titanium, nickel, chromium, cobalt, tantalum, tungsten, iron, manganese, molybdenum, and alloys thereof including nickel titanium (e.g., nitinol), nickel titanium niobium, chromium cobalt, copper aluminum nickel, iron manganese silicon, silver cadmium, gold cadmium, copper tin, copper zinc, copper zinc silicon, copper zinc aluminum, copper zinc tin, iron platinum, manganese copper, platinum alloys, cobalt nickel aluminum, cobalt nickel gallium, nickel iron gallium, titanium palladium, nickel manganese gallium, stainless steel, shape memory alloys, etc. Suitable materials may also include polymers such as polylactic acid (PLA), polyglycolic acid (PGA), poly lactic co-glycolic acid (PLGA), polycaprolactone (PCL), polyorthoesters, polyanhydrides, and copolymers thereof. Suitable materials may also include alloys (e.g., nitinol, chromium cobalt, platinum tungsten, etc.) and combinations of materials (e.g., filaments with a radiopaque core or cladding in combination with a cladding or core, respectively, of a different material, a plurality of filaments including different materials, etc.). In some embodiments, the distal portion 100 comprises nitinol and platinum tungsten.

In some embodiments, prior to braiding, the shape memory filaments are cold worked (e.g., without heat treatment). In some embodiments, prior to braiding, the shape memory filaments are straight annealed (e.g., undergone heat treatment and straightened as a wire).

In some embodiments, the braid pattern of the distal portion 100 is one-over-one-under-one, one-over-one-under-two, one-over-two-under-two, two-over-one-under-one, two-over-one-under-two, three-over-one-under-one, three-over-one-under-two, three-over-one-under-three, three-over-two-under-one, three-over-two-under-two, three-over-three-under-one, three-over-three-under-two, three-over-three-under-three, two-over-two-under-one, two-over-two-under-two, etc. In some embodiments, a braid pattern of one-over-one-under-one can results in the highest radial force and smallest pore size. Other patterns may result in a relatively higher pore size and/or relatively lower radial force. The braid pattern may be constant along the entire length of the distal portion 100, or may vary, for example along the longitudinal axis of the distal portion 100. For example, the braid pattern may vary between the necks and bulbs, from proximal to distal, etc. The braid pattern or filament crossover pattern, which is generally due to rotation and spinning of the braiding device or carrier braider during braiding, is different than a radiopaque banding pattern, which is generally due to the arrangement of the filaments on the spools or carriers prior to braiding and/or the rotation and spinning of the braiding device or carrier braider.

Figure 4L:
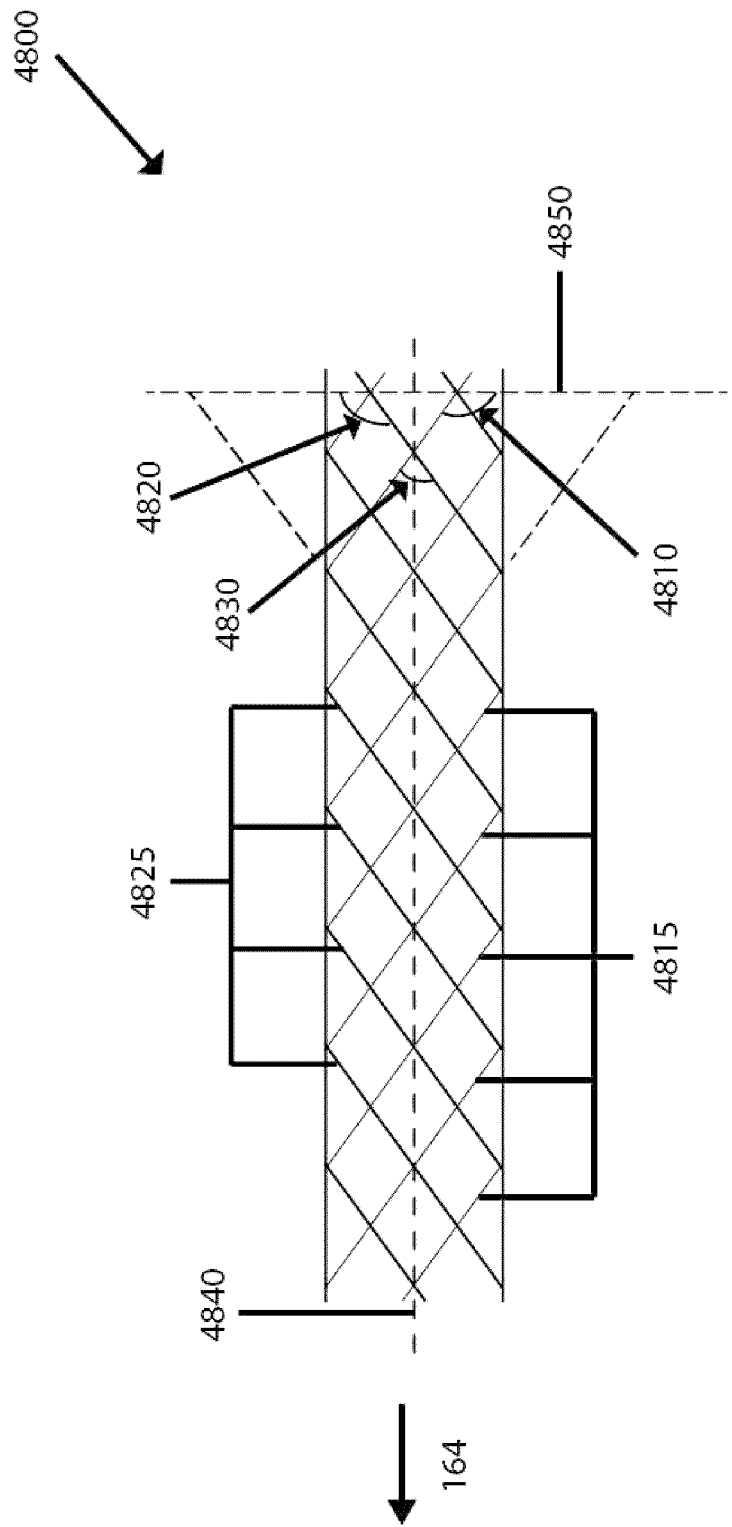
FIG. 4L is a schematic side elevational view of still another example embodiment of a distal portion of a vascular treatment device.
Figure 4M:
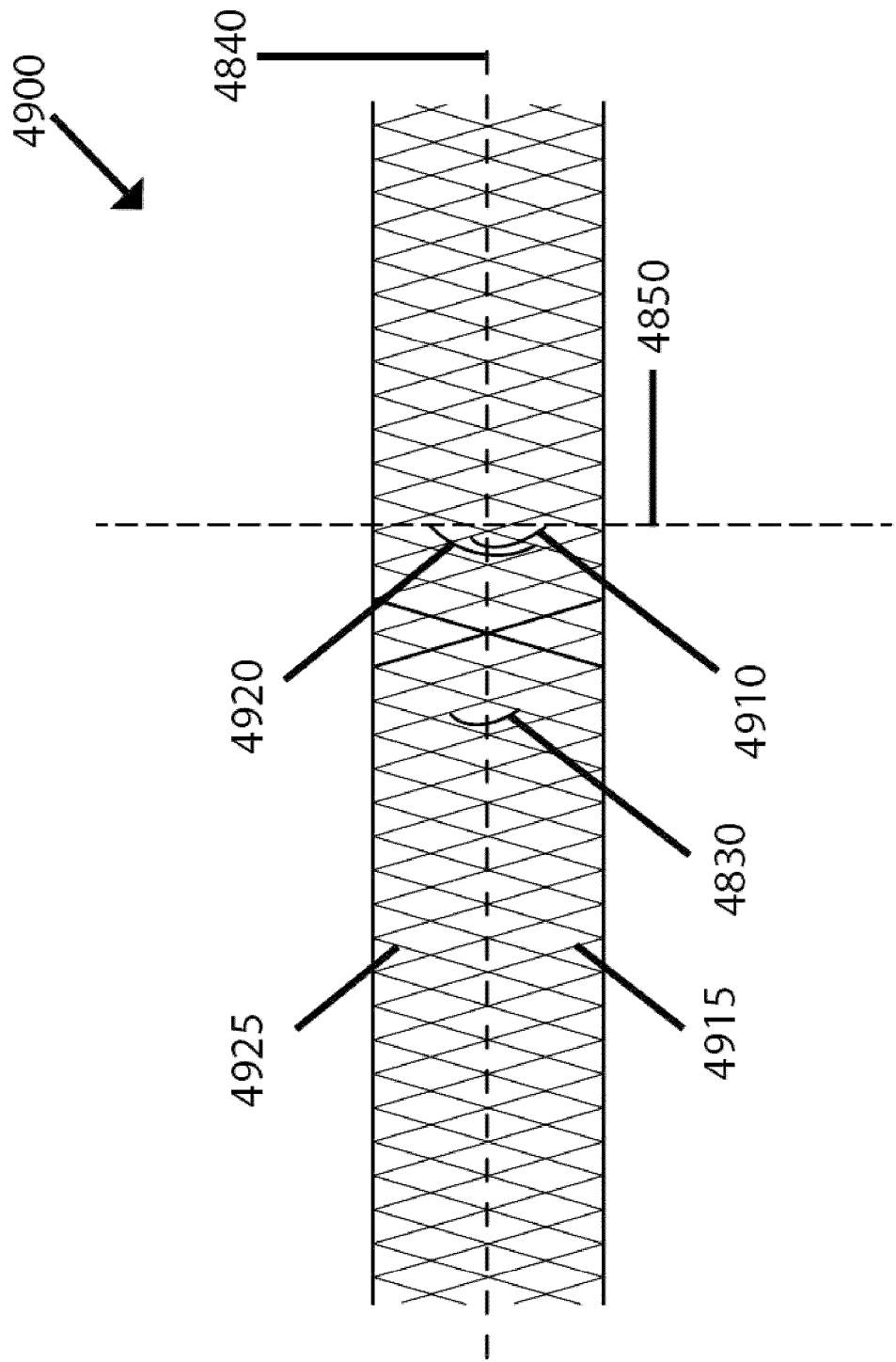
FIG. 4M is a schematic side elevational view of still yet another example embodiment of a distal portion of a vascular treatment device.

The braid angle is the angle between the filaments and an axis perpendicular to the longitudinal or production axis of the distal portion 100, which can range from about 0° to about 180°. FIG. 4L is a schematic side elevational view of still another example embodiment of a distal portion 4800 of a vascular treatment device, for example the distal portion 100 of the device 10, 20, 30 or 40. The distal portion 4800 comprises a plurality of filaments including left-leaning filaments 4815 and right-leaning filaments 4825 that are woven over a longitudinal or production axis 4840. FIG. 4M is a schematic side elevational view of still another example embodiment of a distal portion 4900 of a vascular treatment device, for example the distal portion 100 of the device 10, 20, 30 or 40. The distal portion 4900 comprises a plurality of filaments including left-leaning filaments 4915 and right-leaning filaments 4925 that are woven over a longitudinal or production axis 4840. In each of FIGS. 4L and 4M, an axis that is perpendicular to the longitudinal or production axis 4840 is the braid axis 4850. The relative speed of rotation of the horn gear in the horizontal plane, which is part of the braider device or carrier braider as described herein, and the motion of the puller in the vertical direction 164 can at least partially determine the braid angle. The left-leaning filaments 4815, 4915 have a braid angle ($BA_L$) 4810, 4910 and the right-leaning filaments 4825, 4925 have a braid angle ($BA_R$) 4820, 4920. The braid angle 4810, 4910 of the left-leaning filaments 4815, 4925 is the obtuse angle 4810, 4910 formed by each left-leaning filament 4815, 4915 and the braid axis 4850. The braid angle 4820, 4920 of the right-leaning filaments 4825, 4925 is the obtuse angle 4820, 4920 formed by each right-leaning filament 4825, 4925 and the braid axis 4850. In the embodiment illustrated in FIG. 4L, the braid angle 4810 is about 120° and the braid angle 4820 is about 120°. In the embodiment illustrated in FIG. 4M, the braid angle 4910 is about 155° and the braid angle 4920 is about 155°.

In some embodiments in which the filaments 4815, 4825, 4915, 4925 extend from spools mounted on the spindles of a braider device or carrier braider that are symmetrically arranged, the $BA_L = BA_R$, which can result in symmetric pore sizes for the distal portion 100. In some embodiments in which the filaments 4815, 4825, 4915, 4925 extend from spools mounted on the spindles of a braider device or carrier braider that are asymmetrically arranged, the $BA_L$ and $BA_R$ can be different, which can result in asymmetric pore sizes for the distal portion 100.

The interlacing angle is the angle between the right-leaning filaments 4825, 4925 and the left-leaning filaments 4815, 4915 of the distal portion 100, which can range from about 0° to about 180° (e.g., about 0° to about 90°). In the embodiment illustrated in FIG. 4L, the interlacing angle 4830 is about 60°. In the embodiment illustrated in FIG. 4M, the interlacing angle 4930 is about 130°.

In some embodiments, braid angle may be influenced by a ratio between the speed of rotation $S_h$ of the circular horn gear or yarn wheel and the speed of motion $S_y$ in the vertical direction of the puller ($S_h/S_y$). For example, if the speed of rotation $S_h$ is slower than the speed of motion $S_y$ (e.g., when the horn gear ratio $S_h/S_y$ is less than 1.0), a relatively low braid angle can be obtained, for example as illustrated in FIG. 4M. For another example, if the speed of rotation $S_h$ is faster than the speed of motion $S_y$ (e.g., when the horn gear ratio $S_h/S_y$ is greater than 1.0), a relatively high braid angle can be obtained, for example as illustrated in FIG. 4L. The braid angle may influence, for example, the overall radial force of the distal portion 100 as exerted on the walls of the vessel. In some embodiments, the braid angle is in the range of about 45° to about 179°, about 130° to about 160° (e.g., about 151°), about 95° to about 125° (e.g., about 111°, about 112°), etc. Braid angles below about 50° may lack radial strength and/or be too porous. In some embodiments, the average radial resistive force (RRF), which is a measure of the radial outward force that the distal portion 100 exerts as it resists compression, the hoop strength, which is a measure of the ability of a distal portion 100 to withstand radial compressive forces, and/or the chronic outward force (COF), which is a measure of the force that the distal portion 100 exerts as it expands to its expanded state, along the distal portion 100 is between about 2 mm Hg (approx. 0.27 kilopascals (kPa)) and about 50 mm Hg (approx. 6.7 kPa). In some embodiments, the differential force (e.g., COF minus RRF) is sufficient to expand a target vessel between about 0% and about 30% (e.g., between about 0% and about 10%, between about 10% and about 20%, between about 20% and about 30%, and overlapping ranges thereof). In some embodiments, the force of the device (e.g., one or more bulbs) is sufficient to entangle the clot without perforating the vessel.

Figure 4N:
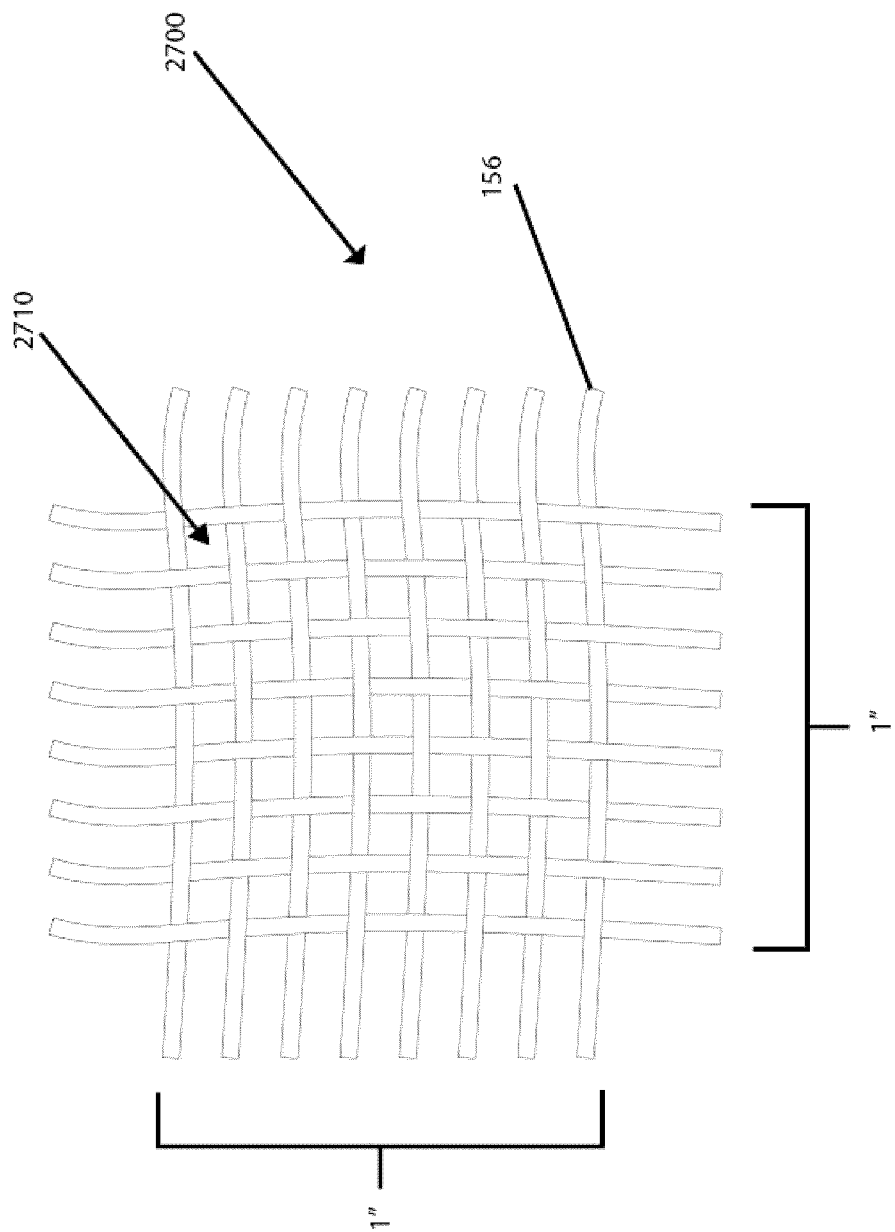
FIG. 4N is a schematic side elevational view of an example square inch of an example embodiment of a distal portion of a vascular treatment device.

PPI is an example parameter reflecting how much filament material exists in a square inch (approx. 6.5 cm²) of the distal portion 100. FIG. 4N is a schematic side elevational view of an example square inch (approx. 6.5 cm$^2$) of an example embodiment of a distal portion 2700 of a vascular treatment device, for example the distal portion 100 of the device 10, 20, 30, or 40. FIG. 4N illustrates a one-over-one-under-one braid pattern with pores 2710 being created by the intersection of a plurality of crossing filaments 156, which may comprise shape memory material and/or radiopaque material. The PPI may range from about 30 PPI to about 300 PPI, about 30 PPI to about 75 PPI (e.g., about 32 PPI, about 57 PPI), about 150 PPI to about 190 PPI (e.g., about 171 PPI), about 75 PPI to about 125 PPI (e.g., about 104 PPI), about 143 PPI to about 171 PPI (e.g., about 157 PPI), about 125 PPI to about 175 PPI (e.g., about 143 PPI), etc. Higher PPI can result in smaller pore size, which can inhibit or prevent debris and small thrombi from being uncaptured, dislodged during capture, and/or released into downstream vasculature (e.g., in the brain). Higher PPI can result in a smaller pore size, which can decrease flow into an aneurysm or a vascular malformation such as an arterio-venous fistula, which can aid in thrombosis of the aneurysm or vascular malformation. Lower PPI can result in a larger pore size, which can allow adequate flow into perforating vessels or small blood vessels, which can maintain flow in these small but important blood vessels. Porosity between about 60% and about 78% may decrease flow into aneurysms or vascular malformations including arterio-venous fistulae and/or permit perfusion to branch vessels.

Pore size is another example parameter reflecting the amount of filament material, and is the size of a hole or aperture or pore created by the intersection of a plurality crossing filaments. Pore dimensions are a corollary to PPI, but they are different in that PPI is a measure of the amount of metal or filaments you would find in a square inch. In embodiments in which the braid pattern is one-over-one-under-one, for example, referring again to FIG. 4N, four crossing filaments may create a quadrilateral-shaped (e.g., rectangle, square, parallelogram, rhombus, diamond, trapezoid) pore. Pores may be large enough to permit perfusion of blood (e.g., at least about 5 microns or micrometers (μm)) to at least about 7 μm should permit red blood cells to pass therethrough), but small enough to trap stroke-causing debris, which generally has a size greater than about 200 μm. In some embodiments, the distal portion 100 comprises pores having a diameter or dimension (e.g., length of a side) between about 0.02 mm$^2$ and about 1 mm$^2$, between about 0.02 mm$^2$ and about 0.05 mm$^2$, or between about 0.02 mm$^2$ and about 0.025 mm$^2$.

In some embodiments, the pore size is substantially uniform across the entire distal portion 100. In some embodiments, the pore size varies across the length of the distal portion 100. For example, the pore size may be substantially uniform along necks and vary along bulbs. For another example, variable pore size may take into account bulbs extending radially outward from necks, and reducing the pore size in the largest dimension areas of the bulbs can help to inhibit debris from being released (e.g., into the brain).

A ratio of the diameter of a filament in the distal portion 100 (e.g., in mm) to the area of the pore between the filaments in the distal portion (e.g., in mm$^2$) may be about 1:1 (e.g., in 1/mm), for example on average along the length of the distal portion 100. In some embodiments, the ratio may be about 1:0.5, about 1:0.6, about 1:0.7, about 1:0.8, about 1:0.9, about 1:1, about 1:1.2, about 1:1.3, about 1:1.4, or about 1:1.5. Larger and smaller ratios are also possible.

In some embodiments, increased outward expansile force and/or compression resistance can be provided by a higher braid angle and/or higher PPI. In some embodiments, the force/resistance (e.g., radial force) is in a range sufficient to expand target vessel(s) in the range of about 0% to about 30%. In some embodiments, the total diameter of the distal portion 100 in the expanded state is about 0.5 mm to about 1.5 mm greater than the diameter of the target vessel(s). In some embodiments, the total diameter or size of the distal portion 100 in the expanded state is oversized by about 10% to about 50% with respect to the diameter of the target vessel(s), which can provide radial force sufficient to appose the sidewalls of the vessel and/or slightly expand the vessel and to inhibit debris from flowing between the vessel walls and bulbs of the distal portion 100.

In some embodiments, forming the distal portion 100 includes cutting (e.g., sheared, clipping, trimming, severing, or the like) the distal ends of the filaments of the distal portion 100. In some embodiments, the cut distal ends of the filaments of the distal portion 100 are left loose, with no further treatment. In certain such embodiments, the size of the filaments allows them to be flexible enough to not puncture tissue. In some embodiments, after cutting, the distal ends of the filaments of the distal portion 100 may be treated in a variety of ways. For example, the distal ends of the filaments of the distal portion 100 may be bent back, welded (e.g., ball welded), polished (e.g., to a dull end), coupled in sleeves, dip coated (e.g., in polymer such as polyurethane), coupled (e.g., adhered, welded, etc.), for example to an arcuate member (e.g., a radiopaque marker band, for example as illustrated in FIG. 5D), combinations thereof, and the like.

In some embodiments, forming the distal portion 100 includes cutting (e.g., sheared, clipping, trimming, severing, laser cut, combinations thereof, and the like) the proximal ends of the filaments of the distal portion 100. In some embodiments, the lengths of the distal neck 65, bulbs, and necks between bulbs have a predetermined length, and the length of an optional neck proximal to the proximal-most bulb can be used to control the total length of the distal portion 100. The proximal ends of the filaments of the distal portion may be coupled to the proximal portion 200, as described further herein. The length of the proximal neck may take into account the length of the joint 300.

In some embodiments, the bulbs are integral with the necks in the distal portion 100. For example, the plurality of woven filaments may make up the bulbs and the necks between, proximal to, and/or distal to the bulbs. In some embodiments, the filaments may extend continuously longitudinally from a proximal end of the distal portion to a distal end of the distal portion 100. In some embodiments, the filaments may extend continuously longitudinally for a portion of the distal portion 100 (e.g., including one bulb and one neck, including a plurality of bulbs and a plurality of necks, including a plurality of bulbs and one neck, including one bulb and a plurality of necks, etc.).

In some embodiments, the bulbs are coupled (fixably or reversibly coupled) on or along an elongate support structure (such as a neck, tube, spindle, spine, rod, backbone, etc.). For example, the bulbs may be welded, glued, soldered, dip-coated, spray-coated, combinations thereof, and the like to the elongate support structure. The elongate support structure may be hollow (e.g., completely hollow), filled, or partially hollow. The elongate support structure may comprise a wire, a woven tubular member, a hypotube, combinations thereof, and the like. In certain such embodiments, the distal portion 100 may comprise a single elongate support structure or a plurality of elongate support structures (e.g., a series of tubular members between bulbs).

FIGS. 2A, 2B, 2E, 2E-2, 2F, 2G, 3A, 3B, 4A, 4B, and 4I-4K illustrate an optional distal neck 65, which extends distally from the distal-most bulb. The distal neck 65 may be cylindrical or substantially cylindrical, although the proximal end of the distal neck 65 may flare outwardly to begin the distal-most bulb. In some embodiments, in an expanded configuration, the distal neck 65 has an outer diameter of less than about 0.017 inches (approx. 0.43 mm) and, in a collapsed configuration, has an outer diameter of less than about 0.0125 inches (approx. 0.32 mm). In some embodiments, the distal neck 65 has a diameter in the expanded configuration in the range of about 0.35 mm to about 0.65 mm (e.g., about 0.40 mm to about 0.45 mm). In some embodiments, the distal neck 65 has a diameter in the collapsed configuration in the range of about 0.1 mm to about 0.34 mm (e.g., about 0.25 mm to about 0.33 mm). In some embodiments, for example in which the device is configured to be used in larger vessels (e.g., the leg, outside the brain), the distal neck in the expanded configuration has a diameter in the range of about 1 mm to about 40 mm and in the collapsed configuration has a diameter in the range of about 0.5 mm to about 10 mm In some embodiments, a ratio of the diameter of the distal neck 65 in the expanded configuration to the diameter of the distal neck 65 in the collapsed configuration is about 1.2:1 to about 10:1. Smaller ratios may be useful, for example, in smaller vessels, and larger ratios may be useful, for example, in larger vessels. In some embodiments, the distal neck 65 is narrow and has similar outer diameter in the expanded and collapsed configuration. The distal neck 65 may have a length that ranges from about 1 mm to about 5 mm. The length of the distal neck 65 may at least partially depend on the desired usable length of the distal portion 100, parameters of the bulbs, and/or parameters of the neck. For example, a length of the distal neck 65 may be a multiple of an average length of necks between bulbs (e.g., about 1.5 times to about 2.5 times, e.g., about 2 times). In some embodiments, the distal neck 65 may have a pigtail or other shape that can make the distal neck 65 more atraumatic.

Proximal to the proximal-most bulb, FIGS. 2A, 2B, 3A, 3B, 4A, 4B, and 4I-4K illustrate a proximal portion 200 and a marker band 25, for example as further discussed herein. Although illustrated in FIGS. 2A, 2B, 3A, 3B, 4A, 4B, and 4I-4K as being coupled to the distal portion 1000, 1100, 1200, 1300, 1400, 1500, 1900, 2000, 2100 proximal to the proximal-most bulb as schematically illustrated in FIG. 1A, the proximal portion 200 may be coupled to the distal portion 1000, 1100, 1200, 1300, 1400, 1500, 1900, 2000, 2100 distal to the distal-most bulb, for example as schematically illustrated in FIG. 1B, the proximal portion 200 may be coupled to the distal portion 1000, 1100, 1200, 1300, 1400, 1500, 1900, 2000, 2100 distal to the distal-most bulb and proximal to the distal end of the proximal portion 200, for example as schematically illustrated in FIG. 1C, or the proximal portion 200 may be coupled to the distal portion 1000, 1100, 1200, 1300, 1400, 1500, 1900, 2000, 2100 proximal to the distal-most bulb, for example as schematically illustrated in FIG. 1D.

FIGS. 2A, 2B, 2E, 2E-2, 2F, 2G, 3A, 3B, 4A, 4B, 4I, 4J, and 4K illustrate example embodiments of distal portions 1000, 1100, 11900, 12000, 12100, 1200, 1300, 1400, 1500, 1900, 2000, 2100 in which each of the longitudinal axes of the necks 1020, 1120, 1220, 1320, 1420, 1520, 1920, 2020, 2150 is substantially aligned with or substantially the same as the longitudinal axis of the distal portion 1000, 1100, 11900, 12000, 12100, 1200, 1300, 1400, 1500, 1900, 2000, 2100, which in some embodiments can allow the distal portions 1000, 1100, 11900, 12000, 12100, 1200, 1300, 1400, 1500, 1900, 2000, 2100 to exert substantially even radial forces on the sidewalls of a vessel being treated. In some embodiments, referring again to FIGS. 4C and 4E, the longitudinal axes 2230, 2430 of the necks 2220, 2420 may be non-aligned with longitudinal axes of the distal portion 2200, 2400. For example, in embodiments in which the distal portion 2200, 2400, comprises spherical bulbs, the longitudinal axes 2230, 2430 of the necks 2220, 2420 may be aligned along chords of the spheres, which in some embodiments can allow the distal portions 2200, 2400 to exert substantially uneven radial forces on the sidewalls of a vessel being treated, which may be useful, for example, to dislodge clots adherent to the endothelium. Each of the following embodiments is possible: coaxially aligned necks with substantially uniform diameter and substantially uniform lengths; coaxially aligned necks with substantially uniform diameter and varying lengths; coaxially aligned necks with varying diameters and substantially uniform lengths; and coaxially aligned necks with varying diameters and varying lengths.

In some embodiments, referring again to FIG. 4E, in which the distal portion 2400 comprises spherical bulbs 2410, 2415, the longitudinal axes of the necks may be aligned along different chords of the spheres, for example connecting different parts of the circumferences of the bulbs. For example, the necks may alternate about 180° between an upper longitude and a lower longitude. For another example, the necks may circumferentially rotate about 90°, about 120°, etc. between each bulb. In some embodiments in which the distal portion 2500 comprises triangular bulbs, the longitudinal axes of the necks may be aligned along different axes of the triangles, referring again to FIG. 4G, for example shifting vertices between each bulb 2510. Phase shifting of the neck positions, or viewed alternatively as phase-shifting of the bulb shapes, along the longitudinal axis of the distal portion 2500 can help to capture stubborn or aged clots. In certain implantable devices described herein, necks that are radially offset and/or that are not longitudinally aligned can help to create a tortuous path, which can promote thrombus formation.

Figure 5A:
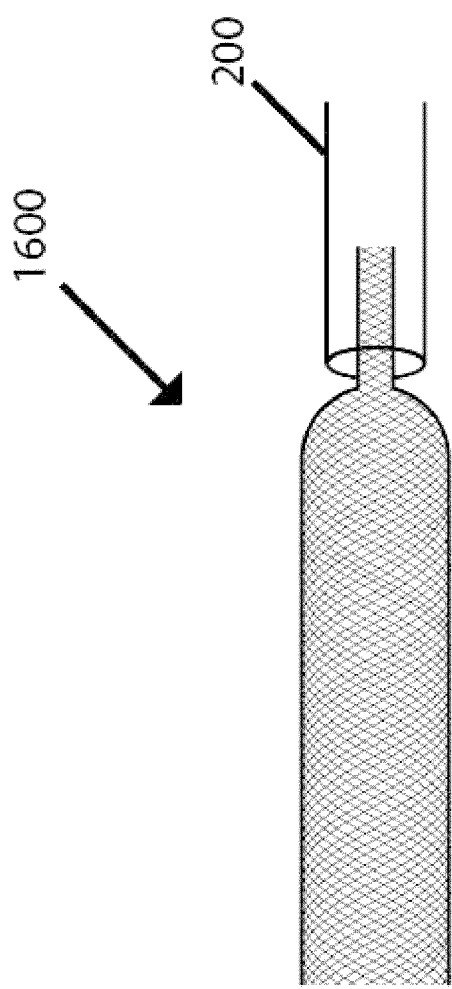
FIG. 5A is a schematic side elevational view of another example embodiment of a distal portion of a vascular treatment device.
Figure 5B:
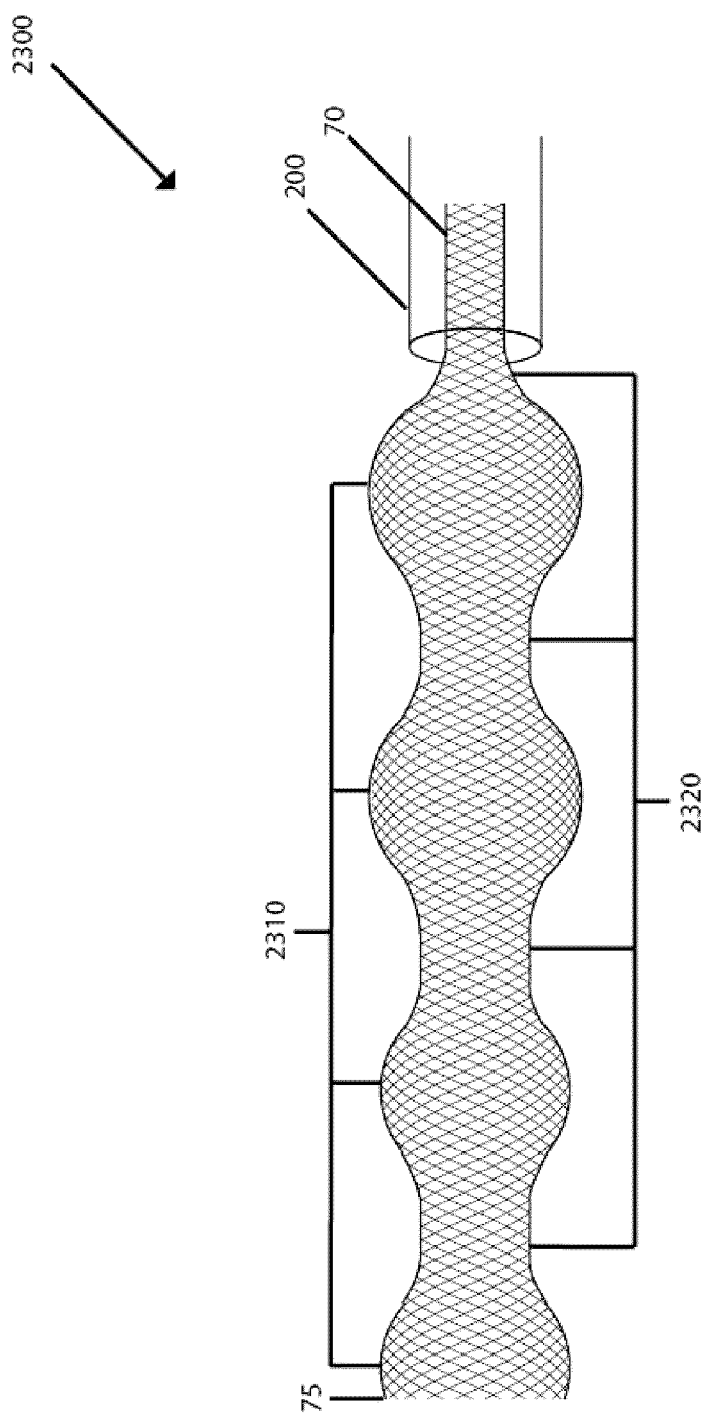
FIG. 5B is a schematic side elevational view of yet another example embodiment of a distal portion of a vascular treatment device.

FIG. 5A is a schematic side elevational view of another example embodiment of a distal portion 1600 of a vascular treatment device, for example the distal portion 100 of the device 10, 20, 30, or 40. The distal portion 1600 includes, in an expanded state, a cylindrical wide-mouthed textile structure that expands radially outwardly from proximal to distal, and then stays at the larger diameter until the distal end. FIG. 5B is a schematic side elevational view of yet another example of a distal portion 2300 of a vascular treatment device, for example the distal portion 100 of the device 10, 20, 30, or 40. The distal portion 2300 includes, in an expanded state, a proximal neck 70 and a wave-shaped wide-mouthed textile structure that alternatingly expands radially outwardly to a peak or hill 2310 and radially inward to a valley 2320 from proximal to distal and then stays at the larger diameter until the distal end 75. The expanding section may be generally hemispherical (e.g., as illustrated in FIG. 5A), wave-shaped (e.g., as illustrated in FIG. 5B), tapered, stepped, combinations thereof, and the like. The distal-most bulb of distal portions described herein may be adapted to extend radially outward from the longitudinal axis, increasing in diameter from proximal to distal, reaching an intermediate point, and then staying at the intermediate diameter (e.g., without a distal neck 65). The distal portions 1600, 2300 may be useful, for example, for apposing sidewalls of a vessel along substantially an entire length of a clot and/or for apposing sidewalls of a vessel having an aneurysm or a vascular malformation such as an arterio-venous fistula, which can decrease flow into the aneurysm or the vascular malformation such as an arterio-venous fistula and aiding thrombosis.

Figure 5C:
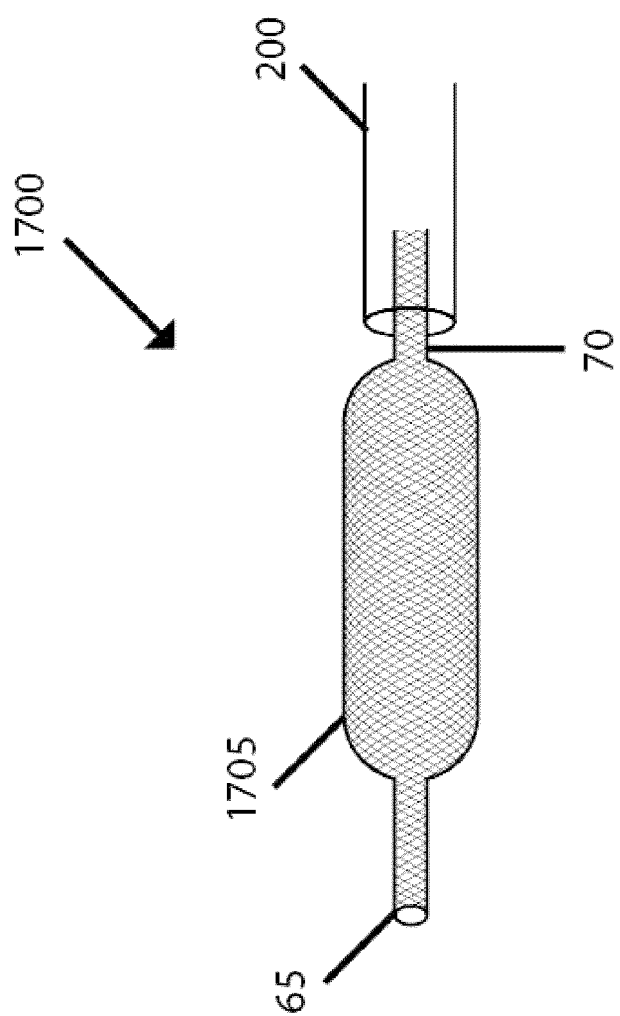
FIG. 5C is a schematic side elevational view of still another example embodiment of a distal portion of a vascular treatment device.
Figure 5D:
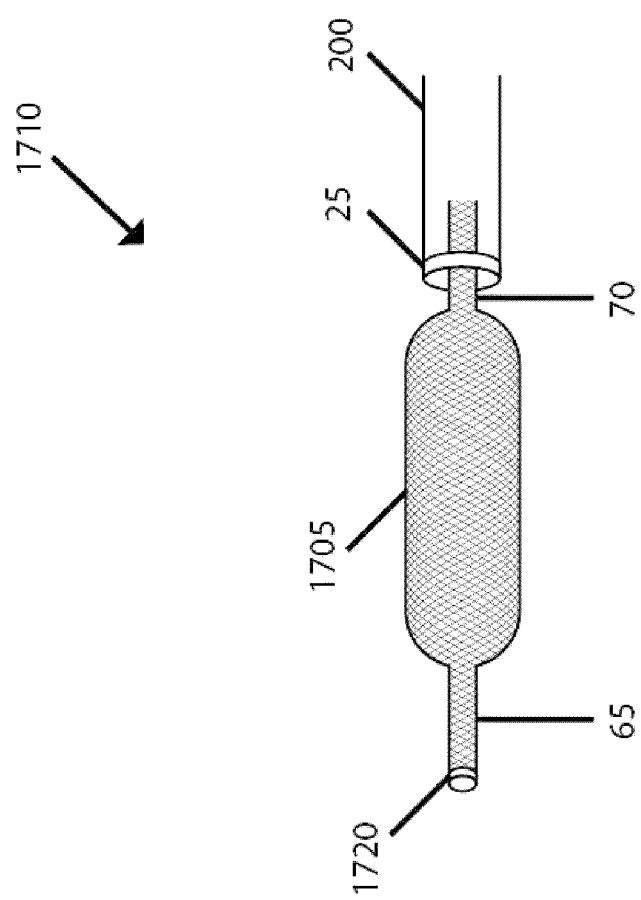
FIG. 5D is a schematic side elevational view of still yet another example embodiment of a distal portion of a vascular treatment device.
Figure 5E:
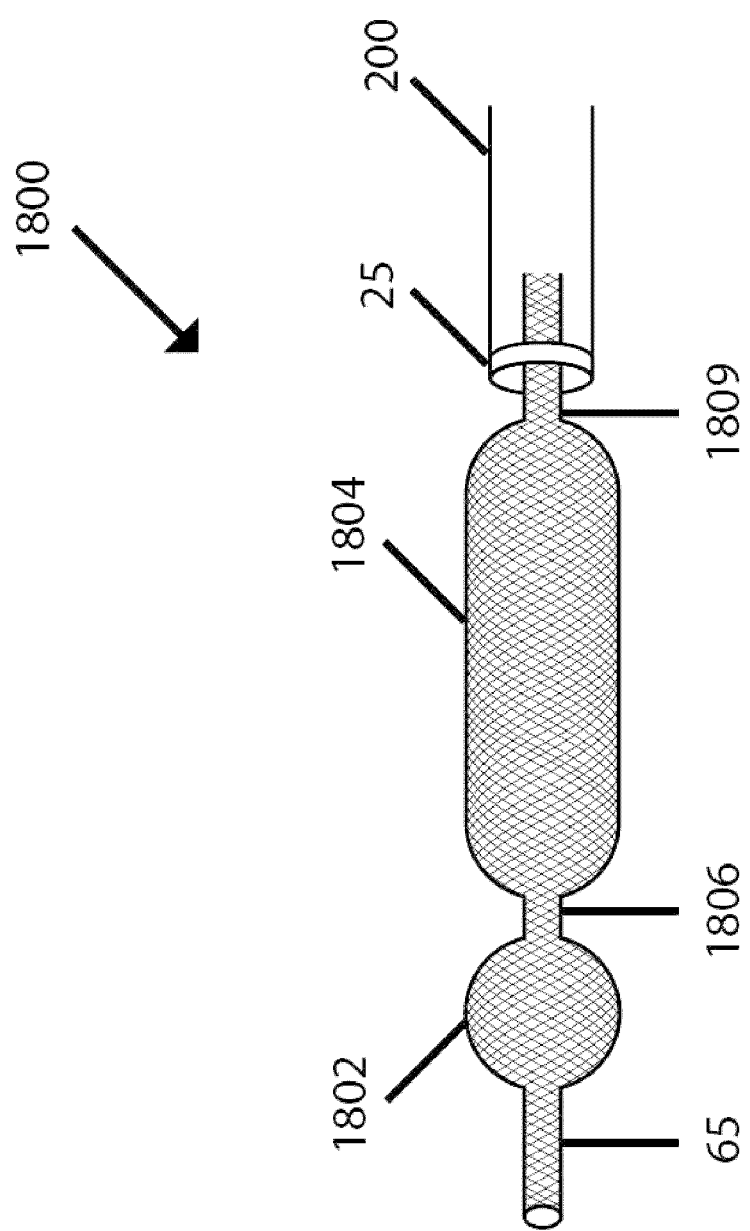
FIG. 5E is a schematic side elevational view of another example embodiment of a distal portion of a vascular treatment device.

FIG. 5C is a schematic side elevational view of still another example embodiment of a distal portion 1700 of a vascular treatment device, for example the distal portion 100 of the device 10 20, 30, or 40. The distal portion 1700 includes, in an expanded state, one elongate bulb 1705, a proximal neck 70, and a distal neck 65. FIG. 5D is a schematic side elevational view of still yet another example embodiment of a distal portion 1710 of a vascular treatment device, for example the distal portion 100 of the device 10, 20, 30, or 40. The distal portion 1710 illustrated in FIG. 5D, like the distal portion 1700 illustrated in FIG. 5C, includes one elongate bulb 1705, a proximal neck 70, and a distal neck 65. The distal portion 1710 also includes a radiopaque marker band 1720 coupled to the distal end of the distal neck 65, which may be used to determine the position of the bulb 1705 within a vessel. FIG. 5D also illustrates a radiopaque marker band 25 coupled to the distal end of the proximal portion 200, discussed in further detail herein. The distal portions 1700, 1710 may be useful, for example, for apposing sidewalls of a vessel along substantially an entire length of a clot, and radially inwardly displacing filament ends (e.g., to further reduce the risk of puncturing tissue).

The mouths, or open end, at the proximal end of the distal portion 100 and at the distal end of the distal portion 100 may be wide (e.g., as illustrated by the distal end of the distal portion 1600 in FIG. 5A, the distal portion 2300 in FIG. 5B) or narrow (e.g., as illustrated by the distal end of the distal portion 1700 in FIG. 5C and the distal end of the distal portion 1710 in FIG. 5D). Each of the following embodiments is possible: a distal portion 100 including a wide mouth at the distal end and a wide mouth at the proximal end; a distal portion 100 including a wide mouth at the distal end and a narrow mouth at the proximal end; a distal portion 100 including a narrow mouth at the distal end and a wide mouth at the proximal end; and a distal portion 100 including a narrow mouth at the distal end and a narrow mouth at the proximal end. A narrow mouth at the distal end of the distal portion 100 can help navigation to increasingly smaller vessels and/or may serve as an atraumatic distal tip. A narrow mouth at the proximal end of the distal portion 100 can help insertion into the distal end of a proximal portion 200 (e.g., as described with respect to FIGS. 20A-23C). A wide mouth at the distal end and the proximal end of the distal portion 100 can help with wall apposition (e.g., the distal end at least partially acting as an embolic filter and/or when the distal portion 100 is used to treat aneurysms or vascular malformations such as arterio-venous fistula).

FIG. 5E is a schematic side elevational view of another example embodiment of a distal portion 1800 of a vascular treatment device, for example the distal portion 100 of the device 10, 20, 30, or 40. The distal portion 1800 includes, in an expanded state, one generally spherical distal bulb 1802, one generally proximal elongate bulb 1804, a neck 1806 between the bulb 1802 and the bulb 1804, a proximal neck 1809, and a distal neck 65. The neck 1806 has a shorter length than the proximal neck 1809 and the distal neck 1808. FIG. 5E also illustrates a radiopaque marker band 25 coupled to the distal end of the proximal portion 200, discussed in further detail herein. The distal portion 1800 may be useful, for example, for apposing sidewalls of a vessel along substantially an entire length of a clot, providing a distal bulb 1802 that can act as a distal embolic protection device, and radially inwardly displacing filament ends (e.g., to further reduce the risk of puncturing tissue).

Figure 5F:
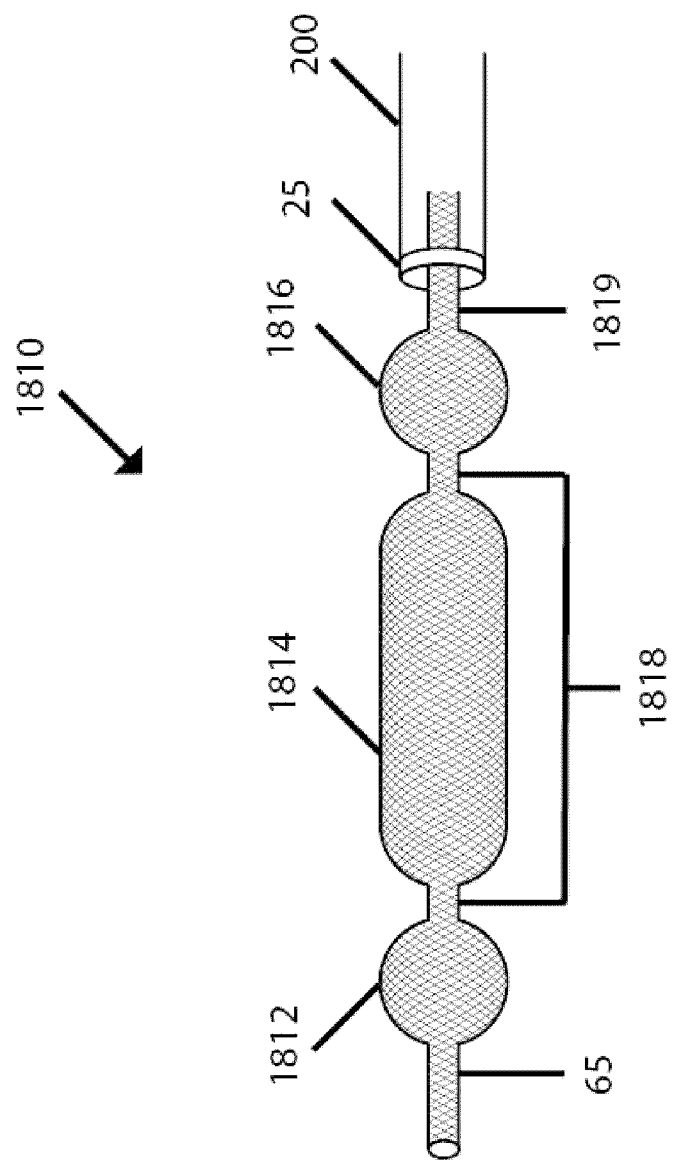
FIG. 5F is a schematic side elevational view of yet another example embodiment of a distal portion of a vascular treatment device.

FIG. 5F is a schematic side elevational view of yet another example embodiment of a distal portion 1810 of a vascular treatment device, for example the distal portion 100 of the device 10, 20, 30, or 40. The distal portion 1810 includes, in an expanded state, one generally spherical distal bulb 1812, one generally spherical proximal bulb 1816, one generally elongate bulb 1814 between the bulb 1812 and the bulb 1816, necks 1818 between the bulbs 1812, 1814 and between the bulbs 1814, 1816, a proximal neck 1819, and a distal neck 65. FIG. 5F also illustrates a radiopaque marker band 25 coupled to the distal end of the proximal portion 200, discussed in further detail herein. The distal portion 1810 may be useful, for example, for apposing sidewalls of a vessel along substantially an entire length of a clot, providing a distal bulb 1812 that can act as a distal embolic protection device, providing a proximal spherical bulb 1816 that can be optionally deployed if a clot is longer than expected, and radially inwardly displacing filament ends (e.g., to further reduce the risk of puncturing tissue).

FIGS. 4A, 4B, 5E, and 5F show example embodiments of a pattern of bulb shapes in which at least one of the bulbs 1412 in FIG. 4A, at least one of the bulbs 1511 in FIG. 4B, at least one of the bulbs 1802 in FIG. 5E, and at least one of the bulbs 1812 in FIG. 5F has a shape different than at least one of the other bulbs 1414 in FIG. 4A, at least one of the other bulbs 1531 in FIG. 4B, at least one of the other bulbs 1804 in FIG. 5E, and at least one of the other bulbs 1814 in FIG. 5F, respectively. With reference to FIG. 4B, this different or combination shape pattern persists even when the bulbs have different sizes. In the embodiments illustrated in FIGS. 4A, 4B, 5E, and 5F, some of the bulbs 1412, 1511, 1802, 1812 are spherical and some of the bulbs 1414, 1531, 1804, 1814 are oblong, but distal portions 100 including bulbs having other combinations of shapes are also possible.

Figure 5G:
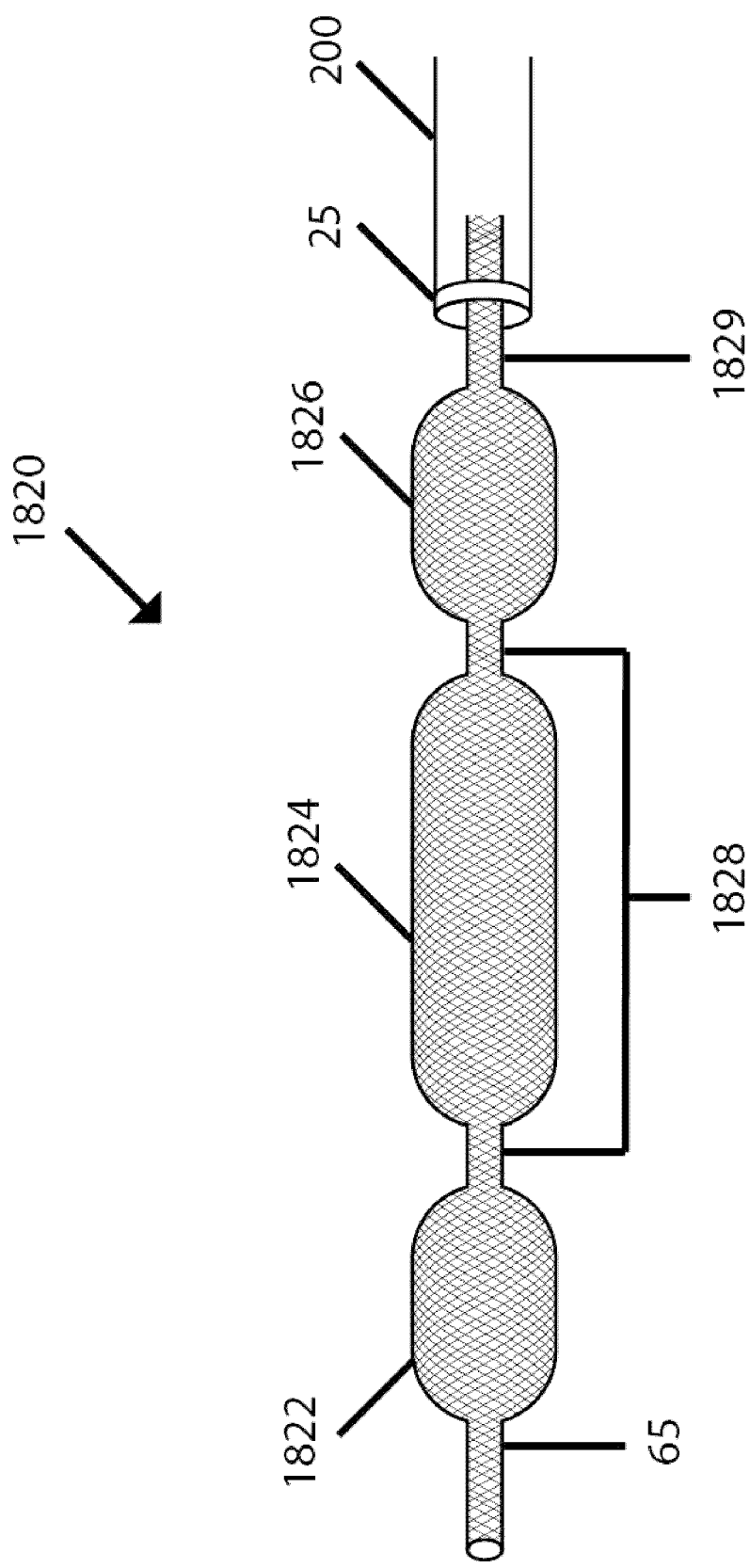
FIG. 5G is a schematic side elevational view of still another example embodiment of a distal portion of a vascular treatment device.

FIG. 5G is a schematic side elevational view of still another example embodiment of a distal portion 1820 of a vascular treatment device, for example the distal portion 100 of the device 10, 20, 30, or 40. The distal portion 1820 includes, in an expanded state, one generally elongate distal bulb 1822, one generally elongate proximal bulb 1826, one generally elongate bulb 1824 between the bulb 1822 and the bulb 1826, necks 1828 between the bulbs 1822, 1824 and between the bulbs 1824, 1826, a proximal neck 1829, and a distal neck 65. FIG. 5G also illustrates a radiopaque marker band 25 coupled to the distal end of the proximal portion 200, discussed in further detail herein. The bulb 1824 is longer than the bulbs 1822, 1824. The distal portion 1820 may be useful, for example, for apposing sidewalls of a vessel along substantially an entire length of a clot, providing a distal bulb 1822 that can act as a distal embolic protection device, providing a proximal bulb 1826 that can be optionally deployed if a clot is longer than expected, and radially inwardly displacing filament ends (e.g., to further reduce the risk of puncturing tissue).

FIG. 6A is a schematic side elevational view of another example embodiment of a distal portion 9000 of a vascular treatment device, for example the distal portion 100 of the device 10, 20, 30, or 40. The distal portion 9000 includes, in an expanded state, a plurality of woven bulbs 9003, 9005, 9007 and necks 9020 with braid angles that vary along the length of the distal portion 9000. The distal portion 9000 includes, in an expanded state, one generally spherical distal bulb 9003, one generally spherical proximal bulb 9007, one generally elongate bulb 9005 between the bulb 9003 and the bulb 9007, a neck 9014 between the bulbs 9003, 9005, a neck 9016 between the bulbs 9005, 9007, a wide-mouth proximal neck 9018, and a wide-mouth distal neck 9012. In some embodiments, the distal portion 9000 includes a plurality of segments, at least one of which has a different braid angle. The distal portion 9000 illustrated in FIG. 6A includes a proximal segment 9006 having a relatively low braid angle, a middle segment 9002 having a relatively high braid angle, and a distal segment 9004 having a relatively low braid angle 9004. In some embodiments, segments 9004, 9006 may have braid angles ranging from about 0° to about 90° (e.g., about 17°, about 22°, about 45°, etc.). Lower braid angle segments generally have lower PPI and tend to be more porous. Lower PPI can result in a larger pore size, which can allow adequate flow into perforating vessels or small blood vessels adjoining an aneurysm or a vascular malformation such as an arterio-venous fistula, which can maintain flow in these small but important blood vessels. In some embodiments, the segment 9002 may have braid angles ranging from about 91° to about 180° (e.g., about 111°, about 112°, about 151°, etc.). Higher braid angle segments generally have a higher PPI and tend to be less porous. Higher PPI can result in a smaller pore size, which can decrease flow into an aneurysm or a vascular malformation such as an arterio-venous fistula, which can aid in thrombosis of the aneurysm or vascular malformation. The bulbs have substantially uniform dimensions or diameters (e.g., within about ±5%, about ±10%, about ±15%, or about 20% of each other) such that the distal portion 9000 may be considered non-tapered.

FIG. 6B is a schematic side elevational view of yet another example embodiment of a distal portion 9100 of a vascular treatment device, for example the distal portion 100 of the device 10, 20, 30, or 40. The distal portion 9100 includes, in an expanded state, a plurality of woven bulbs 9103, 9105, 9107 and necks 9115 having braid angles that vary along the length of the distal portion 9100. In some embodiments, the distal portion 9100 includes, in an expanded state, one generally spherical distal bulb 9103, one generally spherical proximal bulb 9107, one generally elongate bulb 9105 between the bulb 9103 and the bulb 9107, a neck 9114 between the bulbs 9103, 9105, a neck 9116 between the bulbs 9105, 9107, a wide-mouth proximal neck 9118, and a wide-mouth distal neck 9112. The distal portion 9100 illustrated in FIG. 6B includes a proximal segment 9120 having a relatively low braid angle and a distal segment 9110 having a relatively high braid angle. In some embodiments, the segment 9120 may have braid angles ranging from about 0° to about 90° (e.g., about 17°, about 22°, about 45°, etc.). Lower braid angle segments generally have lower PPI and tend to be more porous. Lower PPI can result in a larger pore size, which can allow adequate flow into perforating vessels or small blood vessels adjoining an aneurysm or a vascular malformation such as an arterio-venous fistula, which can maintain flow in these small but important blood vessels. In some embodiments, the segment 9110 may have braid angles ranging from about 91° to about 180° (e.g., about 111°, about 112°, about 151°, etc.). Higher braid angle segments generally have a higher PPI and tend to be less porous. Higher PPI can result in a smaller pore size, which can decrease flow into an aneurysm or a vascular malformation such as an arterio-venous fistula, which can aid in thrombosis of the aneurysm or vascular malformation. The bulbs have substantially uniform dimensions or diameters (e.g., within about ±5%, about ±10%, about ±15%, or about 20% of each other) such that the distal portion 9100 may be considered non-tapered.

FIG. 6C is a schematic side elevational view of still another example embodiment of a distal portion 9200 of a vascular treatment device, for example the distal portion 100 of the device 10, 20, 30, or 40. The distal portion 9200 includes, in an expanded state, a plurality of woven bulbs 9203, 9205, 9207 and necks 9215 having braid angles that vary along the length of the distal portion 9200. The distal portion 9200 includes, in an expanded state, one generally spherical distal bulb 9203, one generally spherical proximal bulb 9207, one generally elongate bulb 9205 between the bulb 9203 and the bulb 9207, a neck 9214 between the bulbs 9203, 9205, a neck 9216 between the bulbs 9205, 9207, a wide-mouth proximal neck 9218, and a wide-mouth distal neck 9212. In some embodiments, the distal portion 9200 includes a plurality of segments, at least one of which has a different braid angle. The distal portion 9200 illustrated in FIG. 6C includes a distal segment 9210 having a relatively low braid angle and a proximal segment 9220 having a relatively high braid angle. In some embodiments, the segment 9210 may have braid angles ranging from about 0° to about 90° (e.g., about 17°, about 22°, about 45°, etc.). Lower braid angle segments generally have lower PPI and tend to be more porous. Lower PPI can result in a larger pore size, which can allow adequate flow into perforating vessels or small blood vessels adjoining an aneurysm or a vascular malformation such as an arterio-venous fistula, which can maintain flow in these small but important blood vessels. In some embodiments, the segment 9220 may have braid angles ranging from about 91° to about 180° (e.g., about 111°, about 112°, about 151°, etc.). Higher braid angle segments generally have a higher PPI and tend to be less porous. Higher PPI can result in a smaller pore size, which can decrease flow into an aneurysm or a vascular malformation such as an arterio-venous fistula, which can aid in thrombosis of the aneurysm or vascular malformation. The bulbs have substantially uniform dimensions or diameters (e.g., within about ±5%, about ±10%, about ±15%, or about 20% of each other) such that the distal portion 9200 may be considered non-tapered.

FIG. 6D is a schematic side elevational view of still yet another example embodiment of a distal portion 9300 of a vascular treatment device, for example the distal portion 100 of the device 10, 20, 30, or 40. The distal portion 9300 includes, in an expanded state, a plurality of woven bulbs 9303, 9305, 9307 and necks 9315 having braid angles that vary along the length of the distal portion 9300. The distal portion 9300 includes, in an expanded state, one generally spherical distal bulb 9303, one generally spherical proximal bulb 9307, one generally elongate bulb 9305 between the bulb 9303 and the bulb 9307, a neck 9314 between the bulbs 9303, 9305, a neck 9316 between the bulbs 9305, 9307, a wide-mouth proximal neck 9318, and a wide-mouth distal neck 9312. In some embodiments, the distal portion 9300 includes a plurality of segments, at least one of which has a different braid angle. The distal portion 9300 illustrated in FIG. 6D includes a proximal segment 9306 having a relatively high braid angle, a middle segment 9320 having a relatively low braid angle, and a distal segment 9304 having a relatively high braid angle. In some embodiments, the segment 9320 may have braid angles ranging from about 0° to about 90° (e.g., about 17°, about 22°, about 45°, etc.). Lower braid angle segments generally have lower PPI and tend to be more porous. Lower PPI can result in a larger pore size, which can allow adequate flow into perforating vessels or small blood vessels adjoining an aneurysm or a vascular malformation such as an arterio-venous fistula, which can maintain flow in these small but important blood vessels. In some embodiments, the segments 9304, 9306 may have braid angles ranging from about 91° to about 180° (e.g., about 111°, about 112°, about 151°, etc.). Higher braid angle segments generally have a higher PPI and tend to be less porous. Higher PPI can result in a smaller pore size, which can decrease flow into an aneurysm or a vascular malformation such as an arterio-venous fistula, which can aid in thrombosis of the aneurysm or vascular malformation. The bulbs have substantially uniform dimensions or diameters (e.g., within about ±5%, about ±10%, about ±15%, or about 20% of each other) such that the distal portion 9300 may be considered non-tapered.

FIG. 6E is a schematic side elevational view of another example embodiment of a distal portion 9400 of a vascular treatment device, for example the distal portion 100 of the device 10, 20, 30, or 40. The distal portion 9400 includes, in an expanded state, a plurality of woven bulbs 9403, 9405, 9407 and necks 9415 having braid angles that vary along the length of the distal portion 9400. The distal portion 9400 includes, in an expanded state, one generally spherical distal bulb 9403, one generally spherical proximal bulb 9407, one generally elongate bulb 9405 between the bulb 9403 and the bulb 9407, a neck 9414 between the bulbs 9403, 9405, a neck 9416 between the bulbs 9405, 9407, a wide-mouth proximal neck 9418, and a wide-mouth distal neck 9412. In some embodiments, the distal portion 9400 includes a plurality of segments, at least one of which has a different braid angle. The distal portion 9400 illustrated in FIG. 6E includes a proximal segment 9404 having a relatively low braid angle, a segment 9408 having a medium braid angle, a middle segment 9430 having a relatively high braid angle, a segment 9406 having a medium braid angle, and a distal segment 9402 having a relatively low braid angle. In some embodiments, the lower braid angle segments 9402, 9404 may have braid angles ranging from about 0° to about 80° (e.g., about 17°, about 22°, about 45°, etc.). Lower braid angle segments generally have lower PPI and tend to be more porous. Lower PPI can result in a larger pore size, which can allow adequate flow into perforating vessels or small blood vessels adjoining an aneurysm or a vascular malformation such as an arterio-venous fistula, which can maintain flow in these small but important blood vessels. In some embodiments, the higher braid angle segment 9430 may have braid angles ranging from about 111° to about 180° (e.g., about 111°, about 112°, about 151°, etc.). Higher braid angle segments generally have a higher PPI and tend to be less porous. Higher PPI can result in a smaller pore size, which can decrease flow into an aneurysm or a vascular malformation such as an arterio-venous fistula, which can aid in thrombosis of the aneurysm or vascular malformation. In some embodiments, the medium braid angle segments 9406, 9408 may have braid angles ranging from about 81° to about 110° (e.g., about 90°, about 105°, etc.). Medium braid angle segments generally have moderate pore size and avoid for abrupt transitions in pore size, which can allow for operator error in adequate placement of the flow diverters across aneurysms and blood vessels. The bulbs have substantially uniform dimensions or diameters (e.g., within about ±5%, about ±10%, about ±15%, or about 20% of each other) such that the distal portion 9400 may be considered non-tapered.

The variable porosities described for example with respect to FIGS. 6A-6E can be combined with bulbs and necks as described herein, for example, the plurality of woven bulbs and necks illustrated in FIGS. 6F and 6G as described herein.

FIG. 6F is a schematic side elevational view of yet another example embodiment of a distal portion 9500 of a vascular treatment device, for example the distal portion 100 of the device 10, 20, 30, or 40. The distal portion 9500 includes a plurality of woven bulbs 9503, 9505, 9507 and woven necks 9520. The distal portion 9500 includes, in an expanded state, one generally spherical distal bulb 9503, one generally spherical proximal bulb 9507, one generally elongate bulb 9505 between the bulb 9503 and the bulb 9507, a neck 9514 between the bulbs 9503, 9505, a neck 9516 between the bulbs 9505, 9507, a wide-mouth proximal neck 9518, and a wide-mouth distal neck 9512. In some embodiments, the distal portion 9500 includes a plurality of segments, at least one of which has a different braid angle. The distal portion 9500 illustrated in FIG. 6F includes a proximal segment 9506 having a relatively low braid angle, a middle segment 9504 having a relatively high braid angle, and a distal segment 9502 having a relatively low braid angle. In some embodiments, the lower braid angle segments 9502, 9506 may have braid angles ranging from about 0° to about 90° (e.g., about 17°, about 22°, about 45°, etc.). Lower braid angle segments generally have lower PPI and tend to be more porous. Lower PPI can result in a larger pore size, which can allow adequate flow into perforating vessels or small blood vessels adjoining an aneurysm or a vascular malformation such as an arterio-venous fistula, which can maintain flow in these small but important blood vessels. In some embodiments, the higher braid angle segment 9504 may have braid angles ranging from about 91° to about 180° (e.g., about 111°, about 112°, about 151°, etc.). Higher braid angle segments generally have a higher PPI and tend to be less porous. Higher PPI can result in a smaller pore size, which can decrease flow into an aneurysm or a vascular malformation such as an arterio-venous fistula, which can aid in thrombosis of the aneurysm or vascular malformation. The bulbs 9510 have substantially uniform dimensions or diameters (e.g., within about ±5%, about ±10%, about ±15%, or about 20% of each other) such that the distal portion 9500 may be considered non-tapered.

FIG. 6G is a schematic side elevational view of still another example embodiment of a distal portion 9600 of a vascular treatment device, for example the distal portion 100 of the device 10, 20, 30, or 40. The distal portion 9600 includes a plurality of woven bulbs 9610 and woven necks 9620. The distal portion 9600 includes, in an expanded state, one generally spherical distal bulb 9603, one generally elongate proximal bulb 9607, one generally spherical bulb 9605 between the bulb 9603 and the bulb 9607, a neck 9614 between the bulbs 9603, 9605, a neck 9616 between the bulbs 9605, 9607, a proximal neck 9618, and a distal neck 9612. In some embodiments, the distal portion 9600 includes a plurality of segments, at least one of which has a different braid angle. The distal portion 9600 illustrated in FIG. 6G includes a proximal segment 9604 having a relatively high braid angle and a distal segment 9602 having a relatively low braid angle. In some embodiments, the lower braid angle segment 9602 may have braid angles ranging from about 0° to about 90° (e.g., about 17°, about 22°, about 45°, etc.). Lower braid angle segments generally have lower PPI and tend to be more porous. Lower PPI can result in a larger pore size, which can allow adequate flow into perforating vessels or small blood vessels adjoining an aneurysm or a vascular malformation such as an arterio-venous fistula, which can maintain flow in these small but important blood vessels. In some embodiments, the higher braid angle segment 9604 may have braid angles ranging from about 91° to about 180° (e.g., about 111°, about 112°, about 151°, etc.). Higher braid angle segments generally have a higher PPI and tend to be less porous. Higher PPI can result in a smaller pore size, which can decrease flow into an aneurysm or a vascular malformation such as an arterio-venous fistula, which can aid in thrombosis of the aneurysm or vascular malformation.

In some embodiments, the outer diameters of the bulbs 9610 in the radially-expanded configuration are as follows: the distal medium spherical bulb 9603 has an outer diameter configured to be oversized to the medium vessel segments such as the proximal M1 segment of the middle cerebral artery (e.g., about 2.75 mm to about 3.25 mm); the middle extra-large spherical bulb 9605 has on outer diameter configured to be oversized by about 25% to about 50% of the largest diameter of one of the bifurcation of vessels such as the internal carotid artery bifurcation (e.g., about 5 mm to about 6 mm); and the proximally-next large elongate bulb 9607 has an outer diameter configured to be oversized to the large vessel segments such as the distal supra-clinoid segment of the internal carotid artery (e.g., about 3.25 mm to about 4 mm). Although some example diameters are provided herein, some embodiments of the distal portion 9600 may include diameters of the bulbs 9603, 9605, 9607 in accordance with the values provided above and/or diameters that are within about ±5%, about ±10%, about ±15%, or about ±20% of any such values.

FIG. 6H is a schematic side elevational view of still yet another example embodiment of a distal portion 11300 of a vascular treatment device, for example the distal portion 100 of the device 10, 20, 30, or 40. The distal portion 11300 includes, in an expanded state, a plurality of woven bulbs 11323, 11325, 11327 and necks 11330 including a plurality of segments having variable pore size along the length of the distal portion 11300. The distal portion 11300 includes, in an expanded state, one generally spherical distal bulb 11323, one generally spherical proximal bulb 11327, one generally elongate bulb 11325 between the bulb 11323 and the bulb 11327, a neck 11324 between the bulbs 11323, 11325, a neck 11326 between the bulbs 11325, 11327, a wide-mouth proximal neck 11328, and a wide-mouth distal neck 11322. In some embodiments, the distal portion 11300 includes a proximal segment 11315 having a relatively low braid angle and relatively higher porosity and a distal segment 11305 having a relatively low braid angle and relatively higher porosity. The middle segment 11310 includes a first portion 11311 on one side of the longitudinal axis 4640 having a relatively low braid angle and that is relatively more porous and a second portion 11312 another side of the longitudinal axis 4640 having a relatively high braid angle and that is relatively less porous, which may be achieved, for example, by varying speed of rotation of the two hemispheres of the circular horn gear or yarn wheel used for braiding the textile structure 11300.

In some embodiments, the speed of rotation of the circular horn gear or yarn wheel for 180° rotation of the yarn wheel, for example the speed of rotation of the western hemisphere $(S_{h-w})$ of spindles on the yarn wheel, is different compared to the remaining 180° rotation of the yarn wheel, for example the eastern hemisphere (She) of spindles of the yarn wheel. In certain such embodiments, the pore size can be varied in the vertical plane on either side of the longitudinal axis 4640. In some embodiments, for example if the speed of rotation in the horizontal direction of the western hemisphere $(S_{h-w})$ of the circular horn gear is faster than the speed of motion in the vertical direction $(S_v)$ of the puller (e.g., when the horn gear ratio $(S_{h-w}/S_v)$ is greater than 1.0), a high braid angle can be obtained. For example, the higher braid angle portion 11312 of the middle segment 11310 may have braid angles ranging from about 91° to about 180° (e.g., about 111°, about 112°, about 151°, etc.). Higher braid angle segments generally have a higher PPI and tend to be less porous. Higher PPI can result in a smaller pore size, which can decrease flow into an aneurysm or a vascular malformation such as an arterio-venous fistula, which can aid in thrombosis of the aneurysm or vascular malformation. In some embodiments, for example if the speed of rotation in the horizontal direction of the eastern hemisphere $(S_{h-e})$ of the circular horn gear is slower than the speed of motion in the vertical direction $(S_v)$ of the puller (e.g., when the horn gear ratio $(S_{h-e}/S_v)$ is less than 1.0), a low braid angle can be obtained. For example, the first portion 11311 of the middle segment 11310 and the low braid angle segments 11305, 11315 may have braid angles ranging from about 0° to about 90° (e.g., about 17°, about 22°, about 45°, etc.).

In some embodiments, for example if the speed of rotation in the horizontal direction of the circular horn gear $(S_h)$ is slower than the speed of motion in the vertical direction $(S_v)$ of the puller wherein the speed of rotation of both hemispheres of the circular horn gear are the same $(S_{h-w}=S_{h-e})$ (e.g., when the horn gear ratio $(S_h/S_v)$ is less than 1.0), a low braid angle can be obtained. Lower braid angle segments generally have lower PPI and tend to be more porous. Lower PPI can result in a larger pore size, which can allow adequate flow into perforating vessels or small blood vessels adjoining an aneurysm or a vascular malformation such as an arterio-venous fistula, which can maintain flow in these small but important blood vessels. Although some example embodiments are provided herein, some embodiments of the distal portion 11300 may include one or more segments with variable pore size, combinations thereof, and the like. The bulbs have substantially uniform dimensions or diameters (e.g., within about ±5%, about ±10%, about ±15%, or about 20% of each other) such that the distal portion 11300 may be considered non-tapered.

In some embodiments of distal portions described herein (e.g., the distal portions 9000, 9100, 9200, 9300, 9400, 9500, 9600, 11300, 11350, 9900), the force/resistance (e.g., radial force) of the bulbs and/or necks is in a range sufficient to slightly expand the target vessel(s) in the range of about 0% to about 30% (e.g., anchoring the distal portion to the vessel, which can inhibit or prevent distal drift of the distal portion), and the shapes of the bulbs and necks are at least partially preserved. In some embodiments of distal portions described herein (e.g., the distal portions 9000, 9100, 9200, 9300, 9400, 9500, 9600, 11300, 11350, 9900), the radial force of the bulbs and/or necks is in a range sufficient to appose the sidewalls of the vessel (e.g., anchoring the distal portion to the vessel, which can inhibit or prevent distal drift of the distal portion), which can inhibit or prevent an endo-leak, but not sufficient to expand the vessel, and the shapes of the bulbs and necks are no longer preserved such that the shape of the distal portion 11300 is substantially tubular, whether tapered or non-tapered, for example based on the shape of the target vessel.

FIG. 6I is a schematic side elevational view of another example embodiment of a distal portion 11350 of a vascular treatment device, for example the distal portion 100 of the device 10, 20, 30, or 40. The distal portion 11350 includes, in an expanded state, a plurality of woven bulbs 11353, 11355, 11357 and necks 11370. The distal portion 11350 includes, in an expanded state, one generally spherical distal bulb 11353, one generally spherical proximal bulb 11357, one generally elongate bulb 11355 between the bulb 11353 and the bulb 11357, a neck 11364 between the bulbs 11353, 11355, a neck 11366 between the bulbs 11355, 11357, a wide-mouth proximal neck 11368, and a wide-mouth distal neck 11362. The distal portion 11350 is aligned along a longitudinal axis 4640. The longitudinal axis 4640 may run through a center of the distal portion 11350. The bulb 11355 may be hemi-spherical or generally hemi-spherical along the longitudinal axis 4640. In some embodiments, the bulb 11355 is hemispherical, trapezoidal, generally hemi-spherical, or generally trapezoidal so that the bulb 11355 appears as a bulge on one side of the distal portion 11350.

In some embodiments, the woven bulb 11355 or a portion thereof (e.g., one side) that bulges on the side of the distal portion 11350 may be dip-coated or spray coated with a polymer 11360 (e.g., silicone, polyurethane (e.g., Polyslix, available from Duke Extrusion of Santa Cruz, Calif.), polyethylene (e.g., Rexell®, available from Huntsman) including low density polyethylene (LDPE), linear low density polyethylene (LLDPE), medium density polyethylene (MDPE), and high density polyethylene (HDPE), fluoropolymers such as fluorinated ethylene propylene, PFA, MFA, PVDF, THV, ETFE, PCTFE, ECTFE (e.g., Teflon® 1-BP, available from DuPont), polypropylene, polyesters including polyethylene terephthalate (PET), PBT, PETG (e.g., Hytrel®, available from DuPont), PTFE, combination polymer compounds such as thermoplastic polyurethanes and polyether block amides (e.g., Propell™ available from Foster Corporation of Putnam, Conn.), polyether block amides (e.g. Pebax® available from Arkema of Colombes, France, PebaSlix, available from Duke Extrusion of Santa Cruz, Calif.), polyether soft blocks coupled with polyester hard blocks vinyls such as PVC, PVDC, polyimides (e.g., polyimides available from MicroLumen of Oldsmar, Fla.), polyamides (e.g., Durethan, available from Bayer, Nylon 12, available from Duke Extrusion of Santa Cruz, Calif.), polycarbonate (e.g., Corethane™, available from Corvita Corp. of Miami, Fla.), styrenics such as PS, SAN, ABS, and HIPS, acetals such as copolymers or homopolymers, PLA, PGA, PLGA, PCL, polyorthoesters, polyanhydrides, and copolymers thereof, high temperature performance polymers such as PEEK, PES, PPS, PSU, LCP, combinations thereof, and the like). In some embodiments, the polymer may include a radiopaque material (e.g., particles of radiopaque material dispersed in the polymer). In some embodiments, masking a portion of the bulb section of the distal portion 11350 during dip coating or spray coating can inhibit polymer from depositing in the area of masking. For example, if the distal portion 11350 is dip coated or spray coated while still on a mandrel, the polymer may be inhibited from being deposited on the inside of the distal portion 11350, which can maintain an inner diameter of the distal portion 11350.

In some embodiments, the distal portion 11350 includes plurality of woven filaments having a relatively low braid angle, for example ranging from about 0° to about 90° (for e.g., about 17°, about 22°, about 45°, etc.). Lower braid angle segments generally have lower PPI and tend to be more porous. Lower PPI can result in a larger pore size, which can allow adequate flow into perforating vessels or small blood vessels adjoining an aneurysm or a vascular malformation such as an arterio-venous fistula, which can maintain flow in these small but important blood vessels. In some embodiments, the bulb 11355 that is dip coated or spray coated with a polymer 11360 may be non-porous, which can decrease flow into an aneurysm or a vascular malformation such as an arterio-venous fistula, which can aid in thrombosis of the aneurysm or vascular malformation. The distal portion 11350 may be useful, for example, for deployment of the non-porous polymer coated bulb 11355 across a side-wall basilar arterial brain aneurysm, which can aid in thrombosis of the aneurysm. The deployment of the rest of the distal portion 11350 having a relatively high pore size, across arteries on either side of the aneurysm can allow blood flow into these arteries, for example the anterior-inferior cerebellar arteries proximally, the basilar perforators on the other side of the aneurysm, and/or the superior cerebellar arteries distally, and which can inhibit or prevent occlusion of the basilar perforators and the other branches and/or resulting dysfunction, which could otherwise cause a brainstem stroke, paralysis of the arms, and/or paralysis of the legs. The bulbs have substantially uniform dimensions or diameters (e.g., within about ±5%, about ±10%, about ±15%, or about 20% of each other) such that the distal portion 11350 may be considered non-tapered.

FIG. 6J is a schematic side elevational view of still yet another example embodiment of a distal portion 9900 of a vascular treatment device, for example the distal portion 100 of the device 10, 20, 30, or 40. The distal portion 9900 includes a plurality of woven bulbs 9910 and woven necks 9920. The distal portion 9900 includes, in an expanded state, one generally spherical distal bulb 9903, one generally spherical proximal bulb 9907, one generally elongate bulb 9905 between the bulb 9903 and the bulb 9907, a neck 9914 between the bulbs 9903, 9905, a neck 9916 between the bulbs 9905, 9907, a wide-mouth proximal neck 9918 with a diameter 9930, and a wide-mouth distal neck 9912 with a diameter 9925. In some embodiments, the distal portion 9900 includes a plurality of segments, at least one of which has a different braid angle. The distal portion 9900 illustrated in FIG. 6J includes a proximal segment 9906 having a relatively low braid angle, a middle segment 9904 having a relatively high braid angle, and a distal segment 9902 having a relatively low braid angle. In some embodiments, the lower braid angle segments 9902, 9906 may have braid angles ranging from about 0° to about 90° (e.g., about 17°, about 22°, about 45°, etc.). Lower braid angle segments generally have lower PPI and tend to be more porous. Lower PPI can result in a larger pore size, which can allow adequate flow into perforating vessels or small blood vessels adjoining an aneurysm or a vascular malformation such as an arterio-venous fistula, which can maintain flow in these small but important blood vessels. In some embodiments, the higher braid angle segment 9904 may have braid angles ranging from about 91° to about 180° (e.g., about 111°, about 112°, about 151°, etc.). Higher braid angle segments generally have a higher PPI and tend to be less porous. Higher PPI can result in a smaller pore size, which can decrease flow into an aneurysm or a vascular malformation such as an arterio-venous fistula, which can aid in thrombosis of the aneurysm or vascular malformation.

In some embodiments, the outer diameters of the bulbs 9910 in the radially-expanded configuration are as follows: the distal extra-large spherical bulb 9603 has an outer diameter configured to be oversized by about 25% to about 50% to the diameter of the transverse-sigmoid cerebral venous sinus (e.g., about 8 mm to about 12 mm, about 10 mm); the middle elongate bulb 9905 has on outer diameter configured to be oversized by about 25% to about 50% to the diameter of the sigmoid cerebral venous sinus (e.g., about 6 mm to about 10 mm, about 9 mm); and the proximally-next spherical bulb 9907 has an outer diameter configured to be oversized to the junction of the sigmoid venous sinus and the internal jugular vein at the base of skull (e.g., about 6 to about 10 mm, about 8 mm). Although some example diameters are provided herein, some embodiments of the distal portion 9900 may include diameters of the bulbs 9903, 9905, 9907 in accordance with the values provided above and/or diameters that are within about ±5%, about ±10%, about ±15%, or about ±20% of any such values, such that the distal portion 9900 may be considered to be tapered.

FIG. 6K-1*i* is a schematic cross sectional view of an example embodiment of a vascular treatment device 12550. FIG. 6K-1*ii* is a side elevational view of the device 12550 of FIG. 6K-1*i*. The device 12550 includes a plurality of woven bulbs and woven necks. The device 12550 includes, in an expanded state, one generally elongate distal bulb 12602, one generally elongate proximal bulb 12562, one generally elongate middle bulb 12580 between the proximal bulb 12562 and the distal bulb 12602, a proximal neck 12590 between the proximal 12562 and middle bulb 12580, a distal neck 12595 between the middle 12580 and distal bulb 12602. In some embodiments, the device includes a plurality of segments, at least one of which has a different porosity. The device 12550 illustrated in FIG. 6K-1*i* includes a proximal segment 12560 comprising the proximal bulb 12562 having a relatively high porosity, an intermediate segment 12570 comprising the middle bulb 12580 along with the proximal neck 12590 and distal necks 12595, having a relatively low porosity, and a distal segment 12600 comprising the distal bulb 12602 having a relatively high porosity. The proximal bulb 12562 and distal bulb 12602 with high porosity can enable flow into branch vessels proximate to the mouth of the aneurysm, which can preserve vital structures supplied by these branch vessels. The intermediate segment 12570 with low porosity can reduce flow into the mouth of the aneurysm, which can increase thrombosis within the aneurysm sac. In some embodiments, the device comprises three bulbs 12562, 12580, 12602 and two necks 12590, 12595. In certain such embodiments, the outer layer comprises at least one bulb 12582 and two necks 12592, 12596 and the inner layer comprises three bulbs 12562, 12584, 12602 and two necks 12594, 12598, even if the layers were separated from each other. In some embodiments, the device comprises a single layer, for example as shown in FIGS. 6A-6J.

In some embodiments, the intermediate segment 12570 comprises more than two layers, for example between about 2 and about 10 (e.g., about 2, about 3, about 5, about 7, about 9, about 10, ranges between these values, etc.). The layers may be discrete or not braided together. Multiple layers in a segment can reduce porosity of that segment. Smaller porosity can decrease flow into an aneurysm or a vascular malformation, such as an arterio-venous fistula, which can aid in thrombosis of the aneurysm or vascular malformation. In some embodiments in which the device comprises more than two layers, adjustments can be made to accommodate the additional layer(s) (e.g., lower diameter or deeper necks, fewer filaments, etc.). In some embodiments, the proximal segment 12560 and distal segment 12600 comprise a single layer. The single layer of the proximal segment 12560 and distal segment 12600 can make the proximal segment 12560 and distal segment 12600 more porous than the intermediate segment 12570. Higher pore size can allow adequate flow into perforating vessels or small blood vessels proximate to an aneurysm or a vascular malformation, such as an arterio-venous fistula, which can maintain flow in these small but important blood vessels. In some embodiments in which the device 12550 comprises two layers, for example as shown in FIGS. 6K-1*i* and 6K-1*ii*, the porosity of the inner layer can vary depending on the number of filaments and can range between about 50 microns and 500 microns (e.g., about 50 microns, about 100 microns, about 150 microns, about 200 microns, about 250 microns, about 300 microns, about 350 microns, about 400 microns, about 450 microns, about 500 microns, ranges between these values, etc.), and the porosity of the outer layer can vary depending on the number of filaments and can range between about 50 microns and 500 microns (e.g., about 50 microns, about 100 microns, about 150 microns, about 200 microns, about 250 microns, about 300 microns, about 350 microns, about 400 microns, about 450 microns, about 500 microns, ranges between these values, etc.). In the table below, for each pore, "x" represents the length of the pore transverse to the longitudinal axis of the braid, and "y" represents the length of the pore parallel to the longitudinal axis of the braid.

| Number of filaments | Primary braid diameter (mm) | PPI | Estimated braid angle | Estimated "X" (mm) | Estimated "Y" (mm) |
|---|---|---|---|---|---|
| 48 (inner layer) | 6 | 165 | 158 | 0.473 | 0.093 |
| 48 (outer layer) | 4 | 50 | 92 | 0.487 | 0.473 |
| 72 (outer layer) | 4 | 73 | 90 | 0.139 | 0.312 |
| 96 (outer layer) | 4 | 97 | 90 | 0.226 | 0.226 |
| 144 (outer layer) | 4 | 145 | 90 | 0.139 | 0.139 |
| 192 (outer layer) | 4 | 180 | 90 | 0.095 | 0.094 |

In some embodiments, the braid angles of the inner and outer layers may be different. The inner layer may have a greater braid angle than the outer layer. The inner layer may have a braid angle ranging between about 145° and about 175° (e.g., about 145°, about 155°, about 158°, about 160°, about 165°, about 175°, ranges between these values, etc.). Greater braid angle segments generally are more amenable to secondary shape setting into smaller diameter bulbs and necks than lower braid angle segments. In some embodiments, the outer layer has a lower braid angle than the inner layer, for example ranging between about 50° and about 120° (e.g., about 50°, about 70°, about 90°, about 92°, about 100°, about 111°, about 120°, ranges between these values, etc.). In some embodiments, the outer layer has a lower braid angle than the inner layer by between about 50° and about 110° (e.g., about 50°, about 70°, about 90°, about 110°, ranges between these values, etc.). In some embodiments, the outer layer has a lower braid angle than the inner layer by between about 45% and about 75% (e.g., about 45%, about 50%, about 55%, about 60%, about 65%, about 70%, about 75%, ranges between these values, etc.). Lower braid angle segments generally are more amenable to secondary shape setting into bulbs and necks when the outer diameter of the primary braid is equal to or marginally higher (e.g., both outer diameters equal to each other or within 25% of each other) than the outer diameter of the secondary shape set bulbs and necks. Although some example outer diameters, pore diameters, PPI, or braid angles are provided herein, some embodiments of the vascular treatment device may include values in accordance with the values provided above and/or values that are within about ±5%, about ±10%, about ±15%, or about ±20% of any such values.

FIGS. 6K-2 to 6K-10 schematically illustrate methods of manufacturing vascular treatment devices using customized mandrels. FIG. 6K-2 illustrates a hairpin-like tool 12610 (e.g., 304 stainless steel wire, nickel-titanium wire, etc.) that is advanced through a lumen of an outer layer 12640 of a vascular treatment device 12620 (e.g., having a relatively smaller outer diameter) and the hairpin loop clasps the proximal end of the inner layer 12630 of the vascular treatment device 12640 (e.g., with a greater outer diameter than the outer layer 12640). The hairpin-like tool 12610 is then pulled into the lumen of the outer layer 12640 the vascular treatment device 12620 until the inner layer 12630 extends through the outer layer 12640. FIG. 6K-3 illustrates the inner layer 12630 within the outer layer 12640. In areas where the inner layer 12630 is constrained by the outer layer 12640 (e.g., overlap areas), the inner layer 12630 has a smaller diameter than in areas where the inner layer 12630 is not constrained by the outer layer 12640. The outer layer 12640 may taper from the constrained smaller diameter to the greater diameter (e.g., as shown in FIG. 6K-3). The overlap areas 12650 may be in an intermediate length of the device with proximal and distal greater diameter areas (e.g., as shown in FIG. 6K-3), or the overlap areas may be generally proximate to one side. In some embodiments, a plurality of discontinuous overlap areas is possible. In such embodiments, the outer layers can be the same or different from each other (e.g., comprising the same or different diameter, braid angle, material, etc.).

FIG. 6K-4 illustrates positioning the vascular treatment device 12620 of FIG. 6K-3 over a partial mandrel 12720 (e.g., one piece of a 2-piece mandrel). The partial mandrel 12720 includes a ring or loop formed of a wire 12715 that extends through a groove or aperture 12705 in the partial mandrel 12720. The wire 12715 can be used to suspend the mandrel 12720 and the vascular treatment device 12620 for secondary shape setting, for example in a fluidized sand bath. The wire 12715 can be shaped as a hook, a spiral, or other shapes.

Figures 6, 6K, 7:
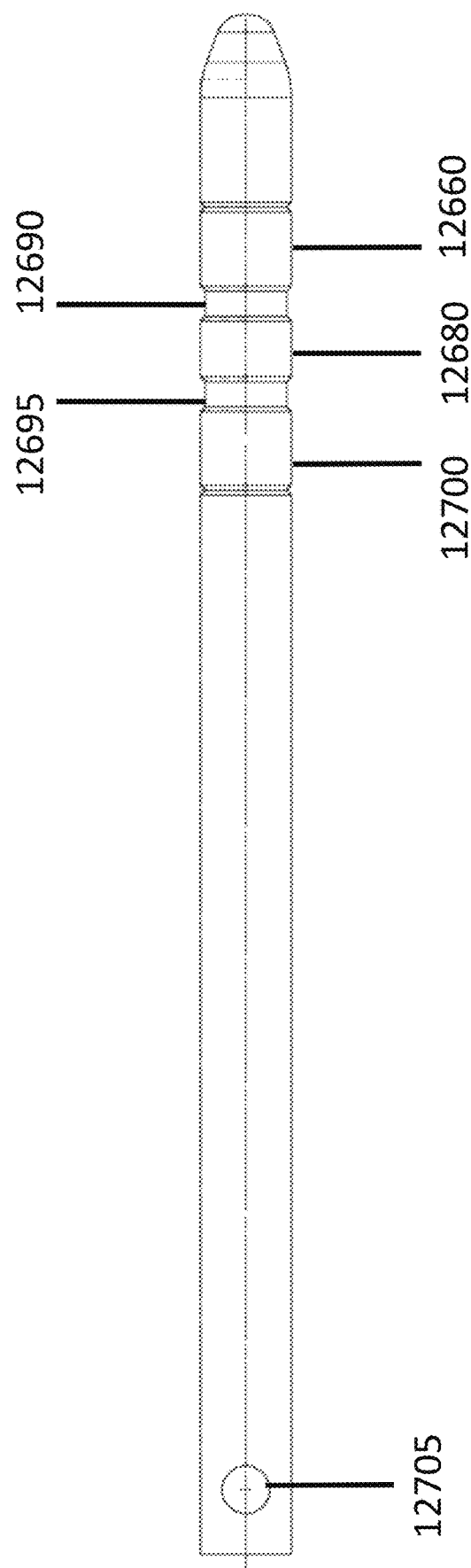
Figures 6, 6K, 7, 8:
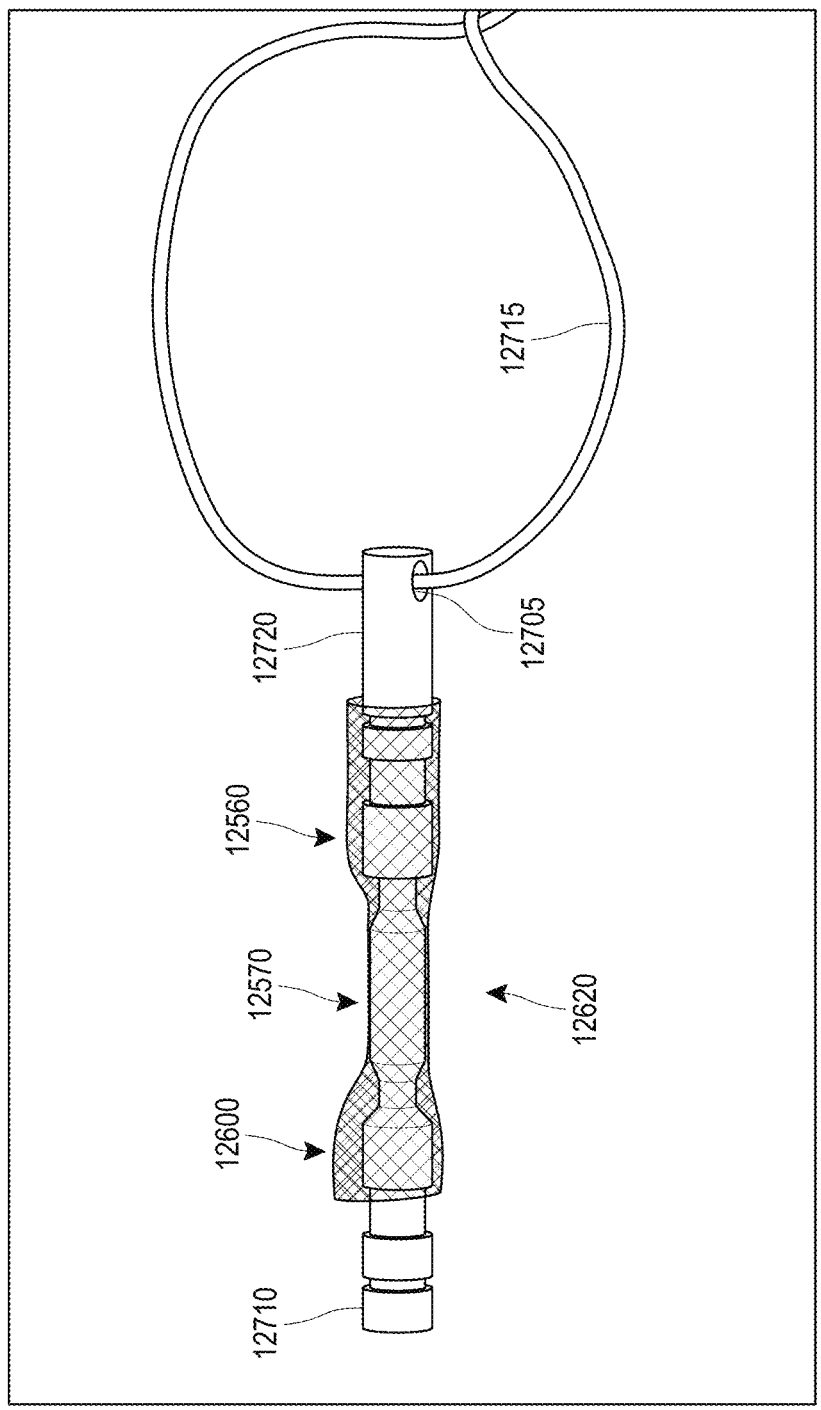
Figures 6, 6K, 7, 8, 9, 9I:
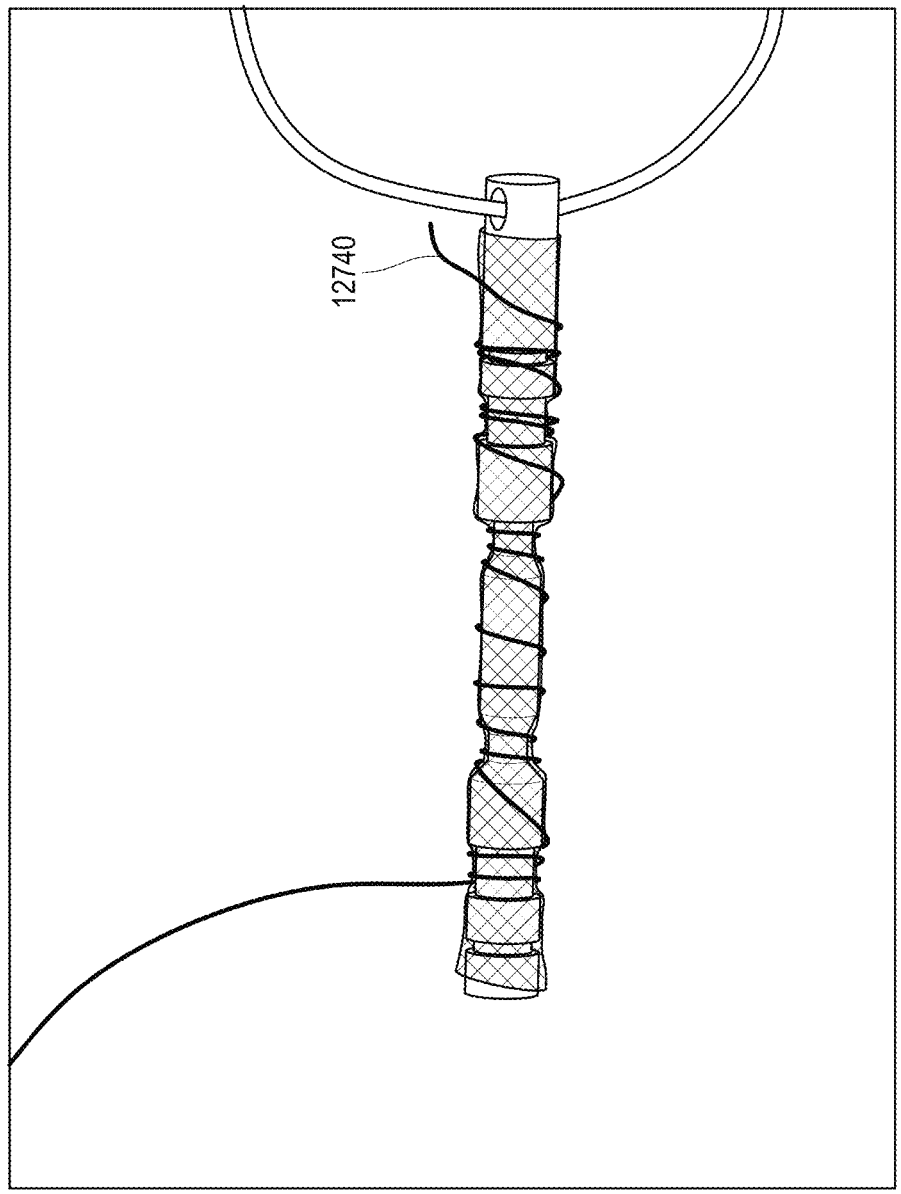
Figures 6, 6K, 7, 8, 9, 9I:
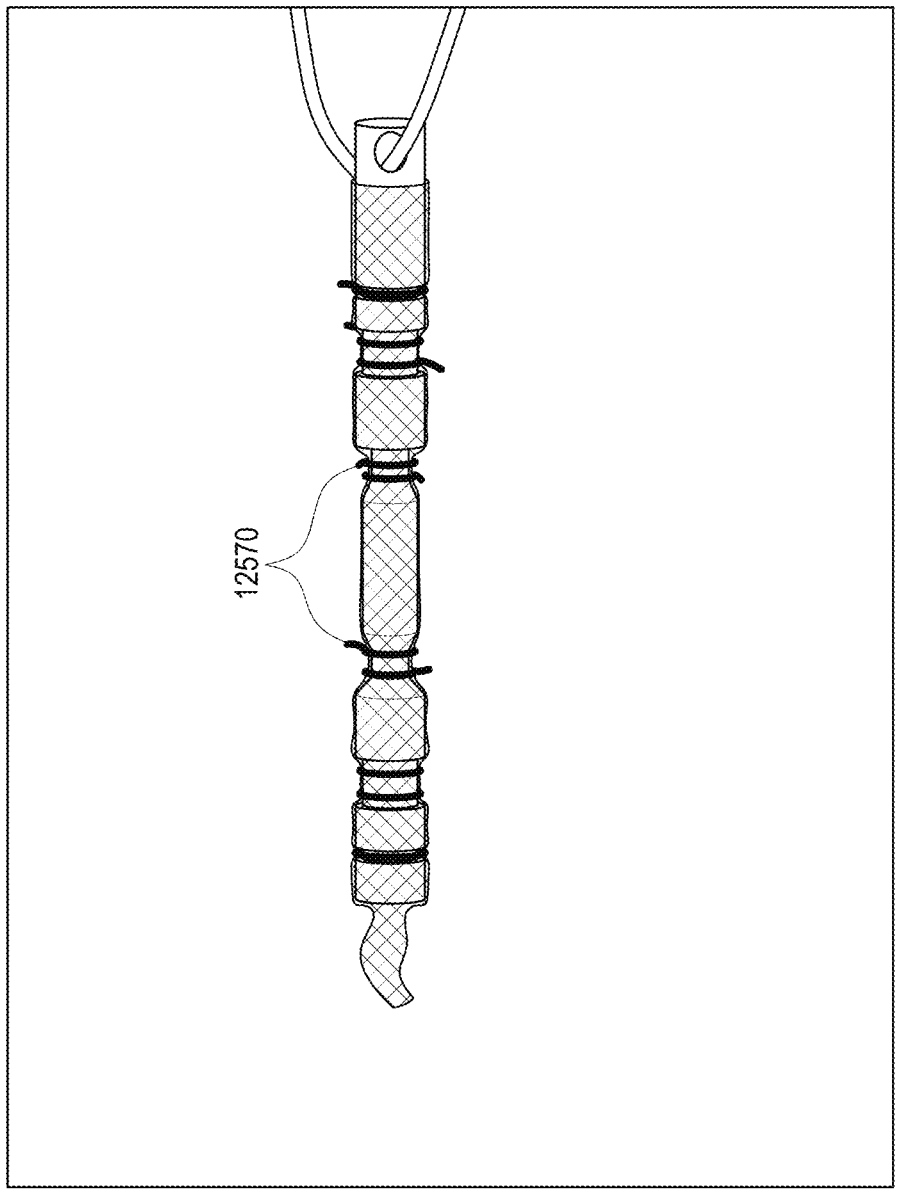
Figures 6, 6K, 7, 8, 9, 10:
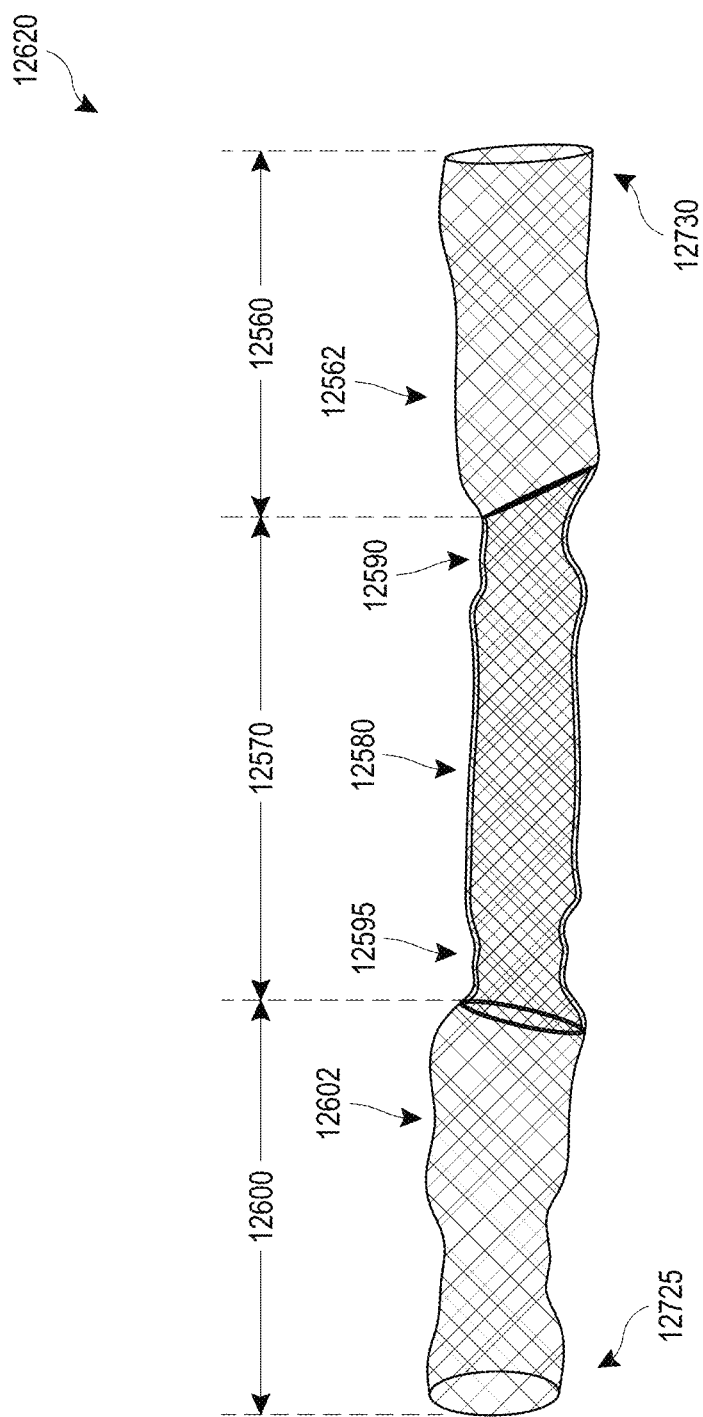
Figures 6, 6K, 7, 8, 9, 10, 11, 11I:
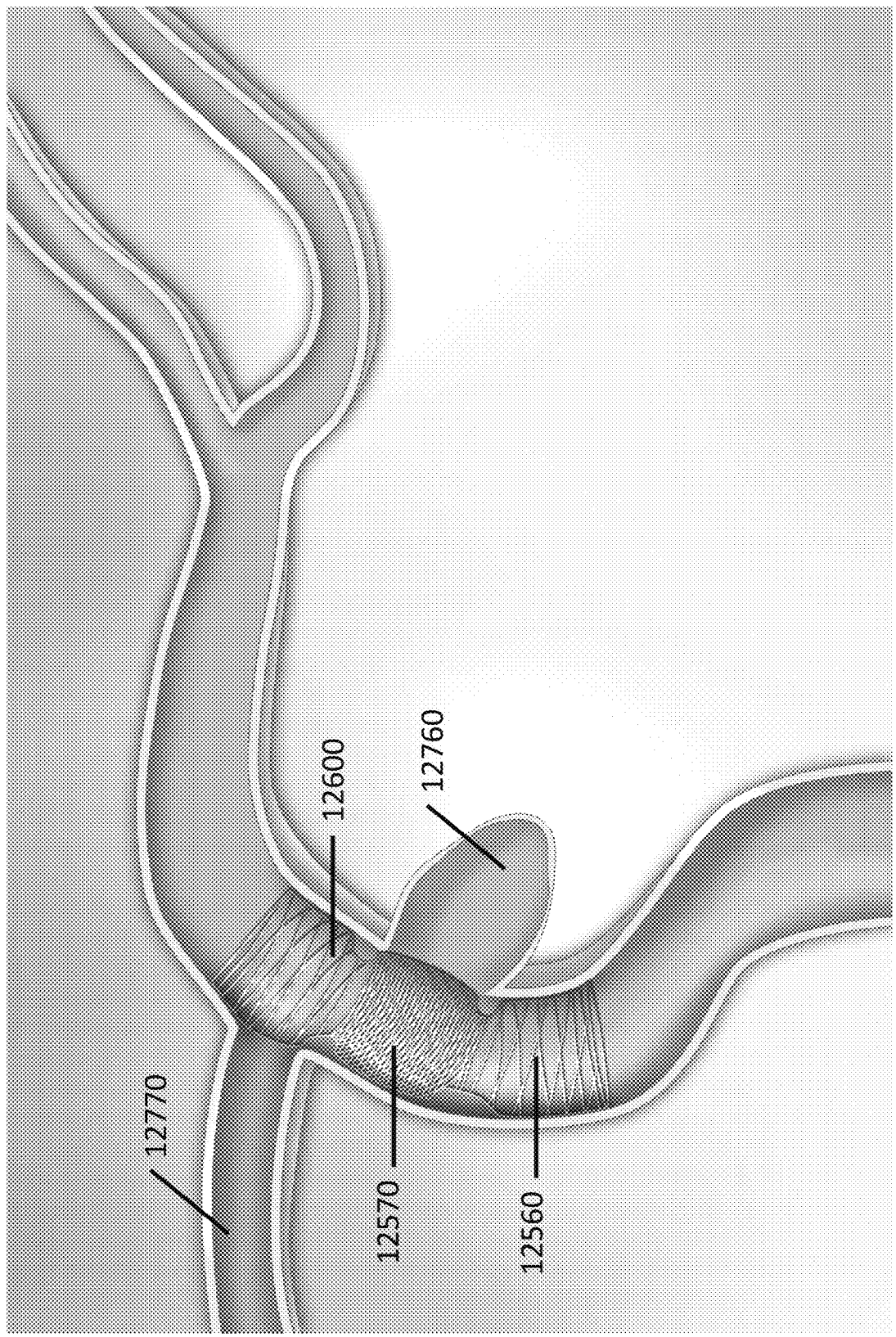
Figures 6, 6K, 7, 8, 9, 10, 11, 11I:
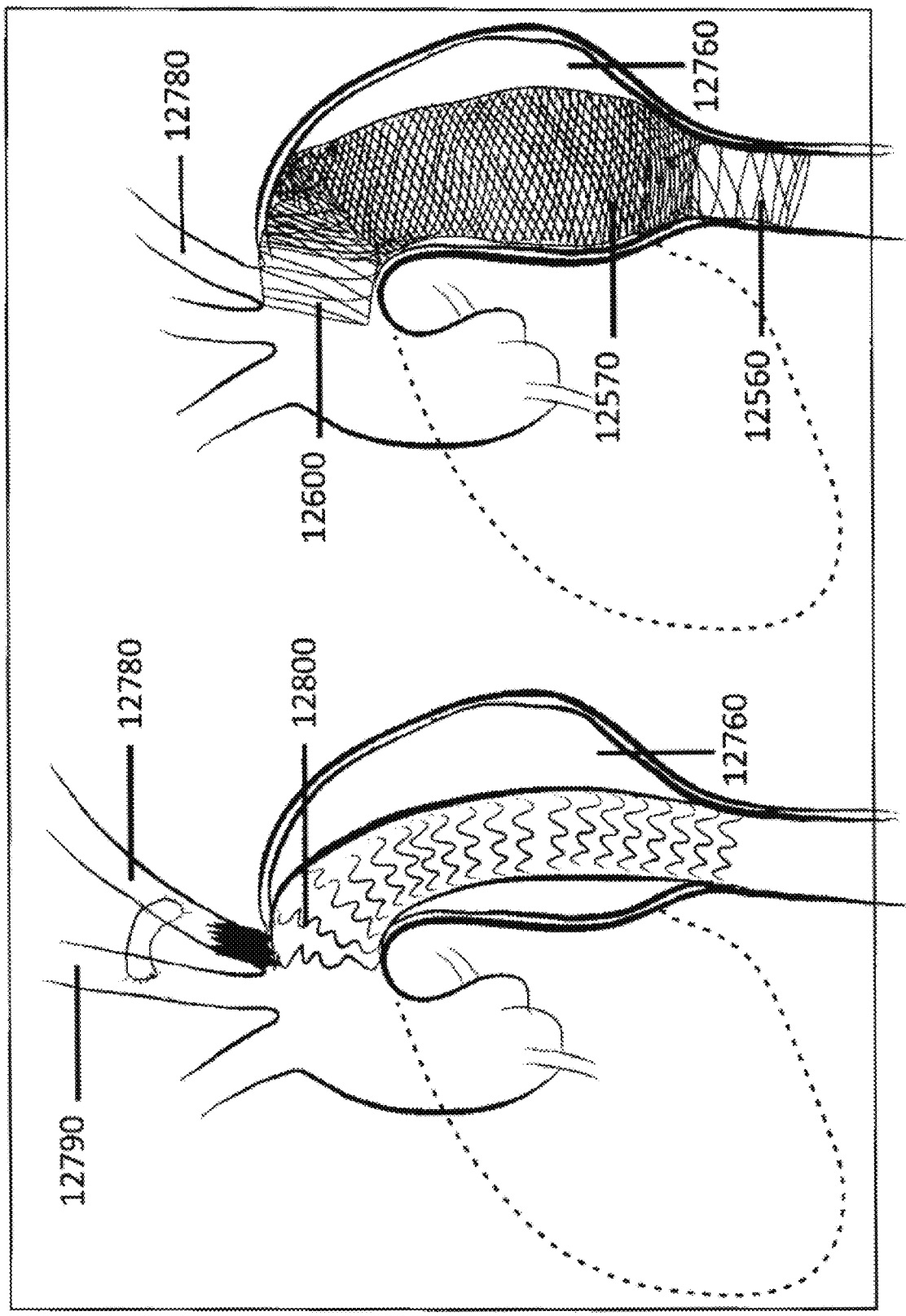
Figures 6, 6K, 7, 8, 9, 10, 11, 12:
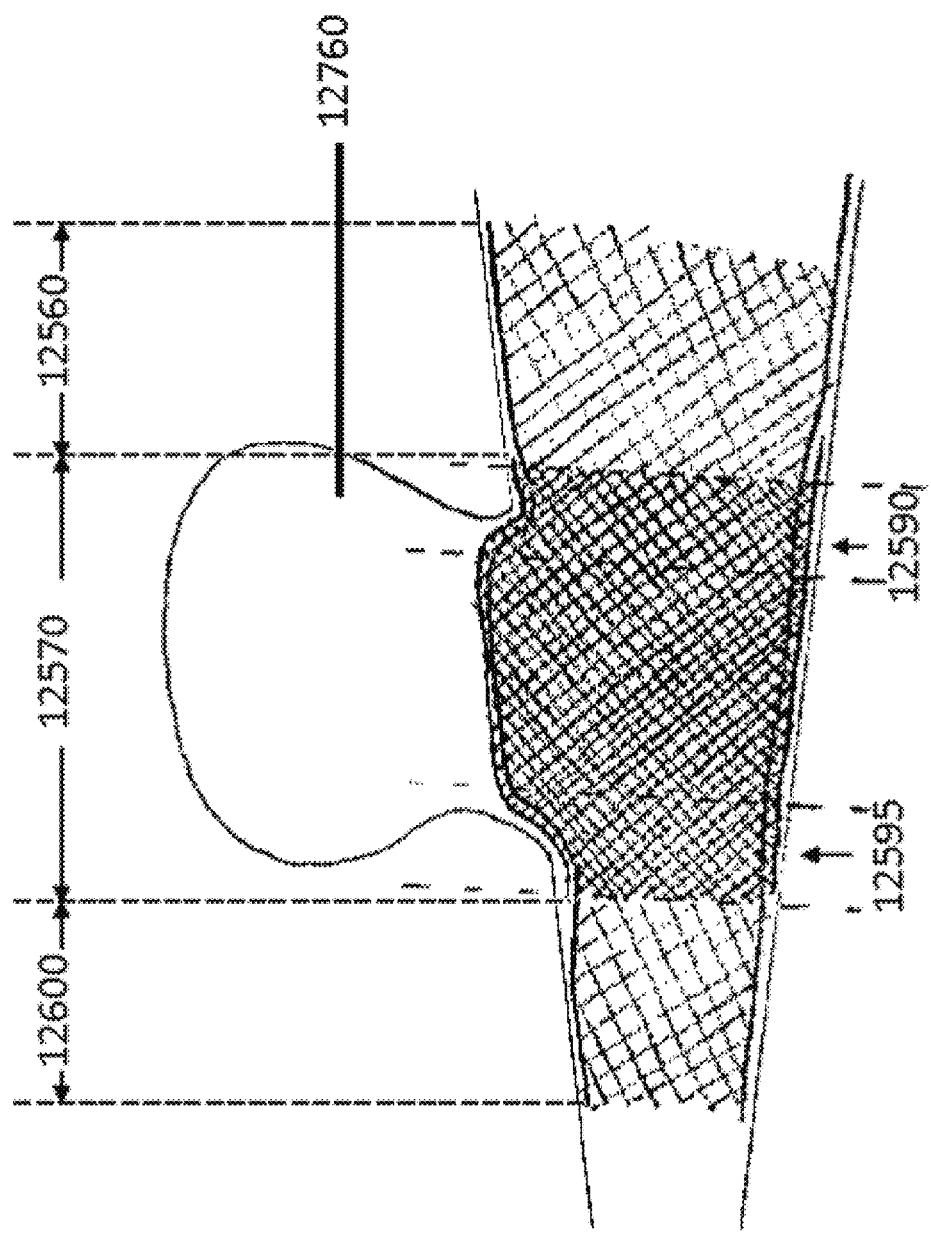
Figures 6, 6K, 7, 8, 9, 10, 11, 12, 13:
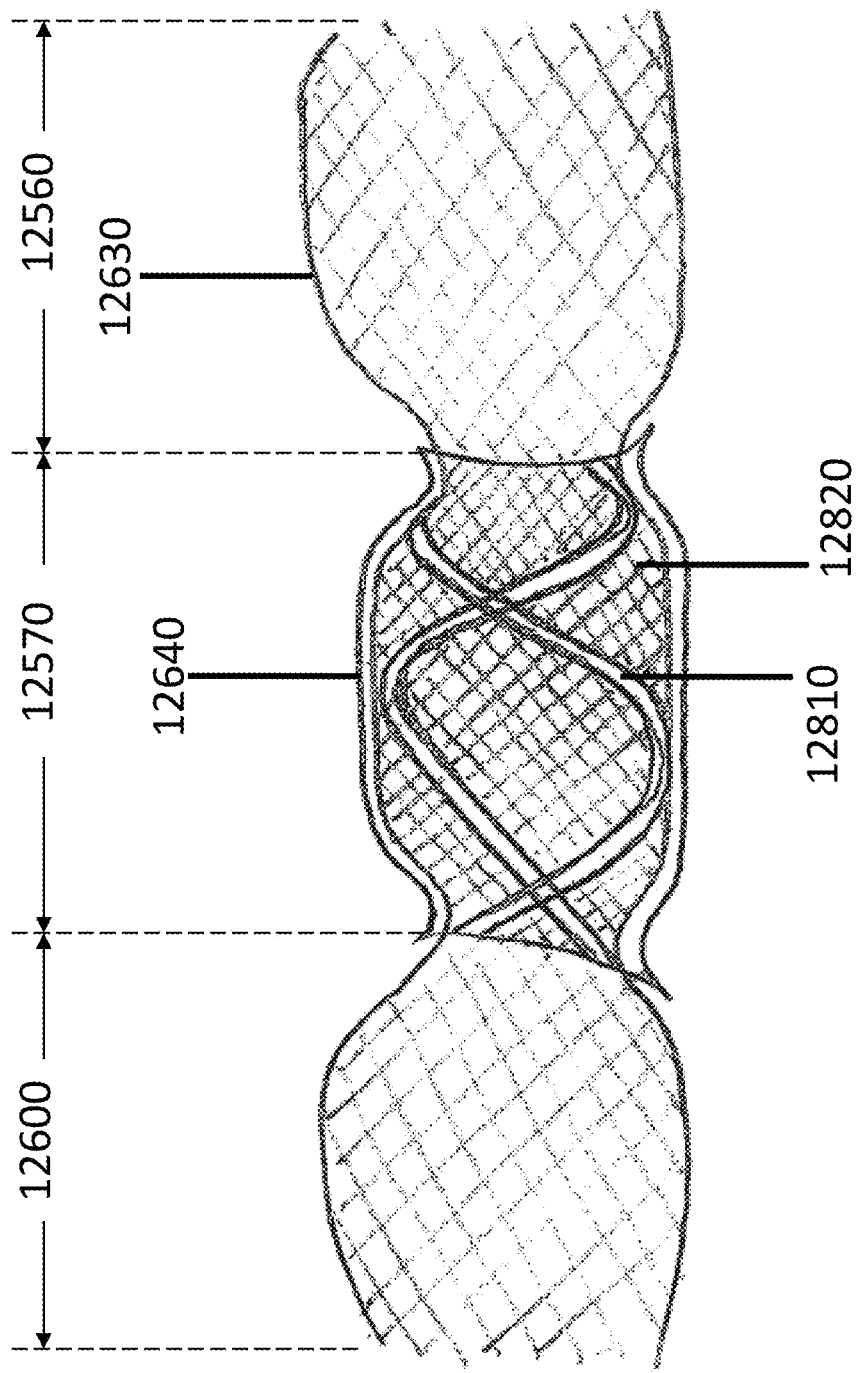
Figure 6L:
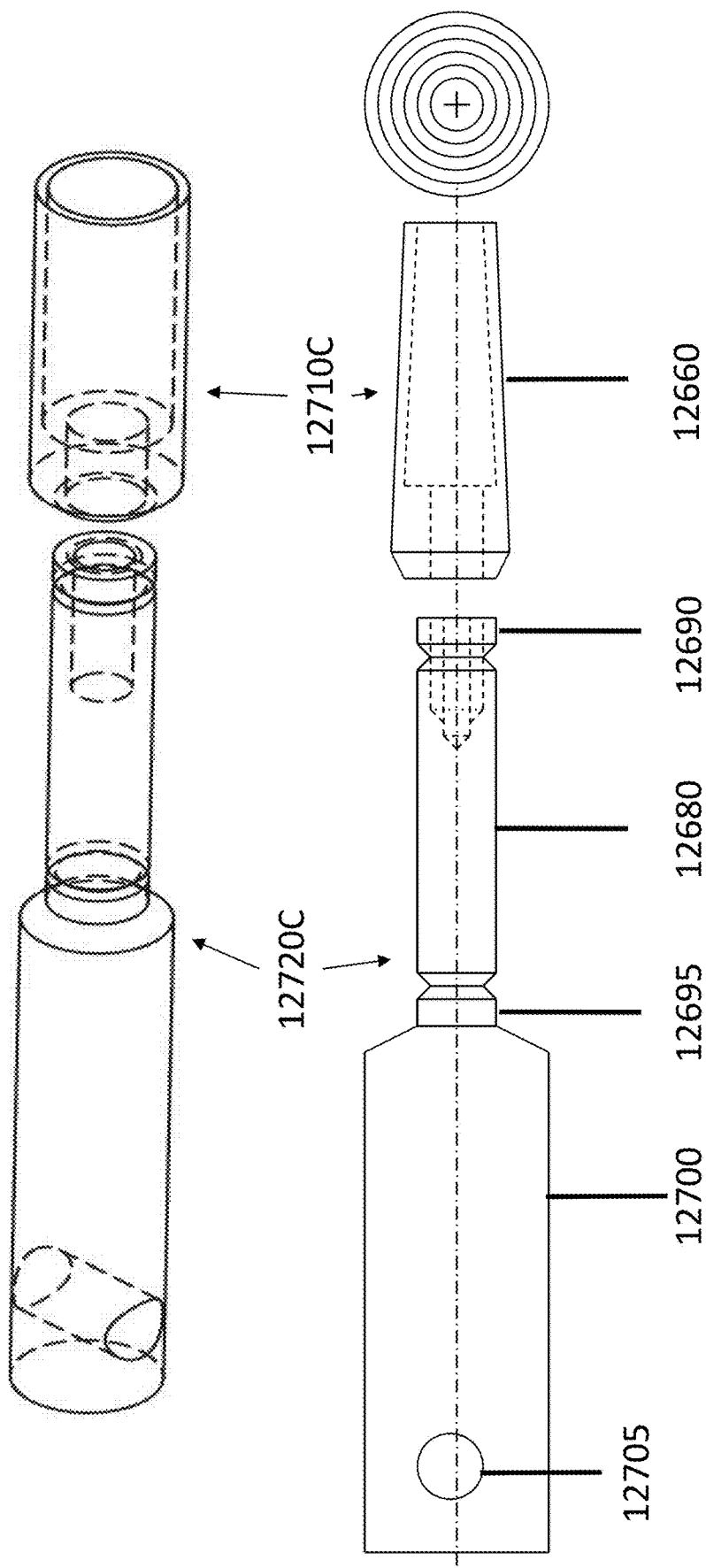
FIG. 6L is schematic views of an example embodiment of a mandrel.

FIGS. 6K-5, 6K-6, and 6L illustrate example embodiments of 2-piece mandrels for secondary shape setting a vascular treatment device. Each of FIGS. 6K-5, 6K-6, and 6L include an exploded side-end perspective view and an exploded side elevational view. FIGS. 6K-6 and 6L additionally include an end elevational view. In some embodiments, for example as shown in FIGS. 6K-5, 6K-6, and 6L, the two-piece mandrel comprises a first piece 12720 and a second piece 12710. More pieces and a single piece mandrel are also possible.

In FIG. 6K-5, the first piece 12720A comprises a bulb 12700, a middle bulb 12680, and necks 12670, 12695, 12690 configured to shape a first (e.g., distal) segment of the vascular treatment device and an intermediate segment of the vascular treatment device. The second piece 12710A includes a bulb 12660 and a neck 12665 configured to shape a second (e.g., proximal) segment of the vascular treatment device. The mandrel of FIG. 6K-5 includes more necks than the mandrels of FIGS. 6K-6 and 6L.

In FIG. 6K-6, the first piece 12720B comprises a bulb 12700, a middle bulb 12680, and necks 12695, 12690 configured to shape a first (e.g., distal) segment of the vascular treatment device and an intermediate segment of the vascular treatment device. The second piece 12710B includes a bulb 12660 configured to shape a second (e.g., proximal) segment of the vascular treatment device.

In FIG. 6L, the first piece 12720C comprises a bulb 12700, a middle bulb 12680, and necks 12695, 12690 configured to shape a first (e.g., distal) segment of the vascular treatment device and an intermediate segment of the vascular treatment device. The second piece 12710B includes a bulb 12660 configured to shape a second (e.g., proximal) segment of the vascular treatment device. The second piece 12710C of the mandrel of FIG. 6L includes a tapered segment. In some embodiments, a tapered configuration of a vascular treatment device can be achieved using a tapered mandrel, for example as shown in FIG. 6L.

At least one of the first piece 12720 of the mandrel and the second piece 12710 of the mandrel comprises a connection mechanism (e.g., a luer lock, screw, snap fit, friction fit, ball and socket, etc.) to connect to the other piece of the mandrel. In some embodiments in which the middle bulb 12680 in the intermediate segment of the device has an outer diameter less than that of the bulbs in the proximal segment 12660 and distal segment 12700, using a two-piece mandrel as shown in FIGS. 6K-5, 6K-6, and 6L for a secondary shape setting of the vascular treatment device can aid in removal of the mandrel after shape setting.

In some embodiments in which the middle bulb 12680 in the intermediate segment of the device has an outer diameter greater than or equal to that of the proximal and distal segments, using a one-piece mandrel as shown in FIG. 6K-7 for a secondary shape setting of the vascular treatment device can provide simpler handling. The one-piece mandrel of FIG. 6K-7 comprises bulbs 12660, 12680, 12700 and necks 12690, 12695. In some embodiments, the mandrel can have tapered configurations with varying outer diameters in various combinations thereof (e.g., along some or all of one piece and/or two pieces).

FIG. 6K-8 illustrates the second piece 12710 of a two-piece mandrel connected to the first piece 12720 of the mandrel and introduced within the proximal segment 12600, intermediate segment 12570, and distal segment 12560 of the vascular treatment device 12620.

FIG. 6K-9i illustrates a method of continuous winding a wire 12740 (e.g., 304 stainless steel wire, nickel-titanium wire, etc.) over a two-piece mandrel such that the wire 12740 winds around the bulbs as well as the necks, which may provide consistent bulb shapes and/or be easier for an operator.

FIG. 6K-9ii illustrates a method of intermittent winding pieces of wire 12750 (e.g., 304 stainless steel wire, nickel-titanium wire, etc.) over a two-piece mandrel such that the pieces of wire 12750 wind around the necks, which may avoid damage to the bulbs. Maintaining tension between positioning of intermittent wires can provide consistent bulb shapes. Other mechanisms to tighten the braided structure to the mandrel are also possible, for example as described herein (e.g., c-shaped clamps, bangles, etc.).

FIG. 6K-10 illustrates the vascular treatment device 12620 after heat setting over a two-piece mandrel. The device 12620 includes a proximal segment 12560 having relatively high porosity, and intermediate segment 12570 having relatively low porosity, and a distal segment 12600 having relatively high porosity. The proximal segment 12560 includes a proximal bulb 12562. The intermediate segment 12570 includes a proximal neck 12590, a middle bulb 12580, and a distal neck 12595. The distal segment 12600 includes a distal bulb 12602. In some embodiments, the distal ends of the secondary shape set vascular treatment device are post-processed to trim the edges 12725, 12730 for the appropriate total length of the vascular treatment device.

FIG. 6K-11i is a schematic diagram of an example embodiment of the vascular treatment device 12550 of FIG. 6K-1i deployed across an aneurysm 12760 in vasculature. A trans-femoral trans-arterial route may be used for the procedure using a tri-axial approach (e.g., a standard microcatheter within a distal access microcatheter within a guide catheter). A standard microcatheter may be advanced distal to the aneurysm 12760 over a microwire. The microwire may be removed, and the vascular treatment device 12550 may be advanced around a thin segment of a variable thickness microwire through the microcatheter such that the tip of the vascular treatment device 12550 is at the tip of the microcatheter. The microcatheter is then proximally withdrawn while the microwire position is maintained to deploy the distal segment of the vascular treatment device 12550 distal to the aneurysm 12760. The distal end of the distal segment 12600 of device 12550 expands and apposes sidewalls of the vasculature. A low resistive force can be gentle on vascular sidewalls during proximal retraction of the distal end of the distal segment 12600 of the device 12550. The microcatheter along with the variable thickness delivery wire are together proximally retracted, which proximally retracts the distal end of the distal segment 12600 of the vascular treatment device 12550 until it is proximate, but still distal to, (e.g., adjacent to) the distal end of the mouth of the aneurysm 12760. The microcatheter is then withdrawn while the microwire position is maintained such that the intermediate segment 12570 of the vascular treatment device 12550 covers the mouth of the aneurysm 12760. Deployment of the distal segment 12600 and intermediate segment 12570 of the vascular treatment device 12550 may be performed under single plane or biplane angiography equipment. Low risk deployment can also be performed using visible marker bands on the proximal end of the delivery wire, for example as described in FIG. 19F-2. At this juncture, if the intermediate segment 12570 of the device 12550 is not appropriately deployed across the mouth of the aneurysm 12760 (e.g., based on a pattern such as described with respect to FIGS. 6K-13, 8F-9, etc.), the device 12550 can be retrieved into the microcatheter by advancing the microcatheter over the vascular treatment device 12550 while the microwire position is maintained, also recapturing the microwire in the microcatheter. If the device 12550 deployment is felt to be adequate, for example based on radiopaque patterns of the intermediate segment 12570 being different from the distal segment 12600, the operator can further withdraw the microcatheter while the microwire position is maintained and deploy the entire device 12550. The variable thickness delivery microwire can then be safely removed. The proximal segment 12560 and distal segment 12600 of the vascular treatment device 12550 have high porosity and allow flow into branch vessels 12770 proximate to the mouth of the aneurysm 12760, while the intermediate segment 12570 of the vascular treatment device 12550 has low porosity and covers the mouth of the aneurysm 12760 and aids in the thrombosis of the aneurysm sac, for example by inhibiting blood from flowing into the aneurysm 12760.

FIG. 6K-11*ii* is a schematic diagram of an example embodiment of the vascular treatment device 12550 of FIG. 6K-1*i* deployed across an aneurysm 12760 in vasculature. In some embodiments, the vascular treatment device 12550 of 6K-1*i* is deployed across a peripheral artery aneurysm 12760 (e.g., iliac aneurysm, femoral aneurysm, popliteal aneurysm, etc.). A trans-femoral trans-arterial route may be used for the procedure using a bi-axial approach (e.g., a standard microcatheter within a guide catheter) from the contralateral common femoral artery. The proximal segment 12560 and distal segment 12600 of the vascular treatment device 12550 have high porosity and allow flow into branch vessels 12770 proximate to the mouth of the aneurysm 12760, while the intermediate segment 12570 of the vascular treatment device 12550 covers the mouth of the aneurysm 12760 and aids in the thrombosis of the aneurysm sac, for example by inhibiting blood from flowing into the aneurysm 12760.

FIG. 6K-11*iii* is a schematic diagram of an example embodiment of the vascular treatment device 12550 of FIG. 6K-1*i* deployed across an aneurysm 12760 in vasculature. In some embodiments, the vascular treatment device 12550 of 6K-1*i* is deployed across a visceral artery aneurysm 12760 (e.g., renal aneurysm, splenic aneurysm, gastric aneurysm, hepato-biliary aneurysm etc.). A trans-femoral trans-arterial route may be used for the procedure using a bi-axial approach (e.g., a standard microcatheter within a guide catheter) from the contralateral common femoral artery. The proximal segment 12560 and distal segment 12600 segment of the vascular treatment device 12550 have high porosity and allow flow into branch vessels 12770 proximate to the mouth of the aneurysm 12760, while the intermediate segment 12570 of the vascular treatment device 12550 covers the mouth of the aneurysm 12760 and aids in the thrombosis of the aneurysm sac, for example by inhibiting blood from flowing into the aneurysm 12760.

FIG. 6K-11*iv* is a schematic diagram of an example embodiment of the vascular treatment device of FIG. 6K-1*i* deployed across an aneurysm 12760 in vasculature. The left panel of FIG. 6K-11*iv* illustrates a commercially available stent graft 12800 deployed in the descending thoracic aorta to treat a thoracic aortic aneurysm (TAA) extending from the left subclavian artery 12780 superiorly to the mid-thorax inferiorly. The left panel of FIG. 6K-11*iv* illustrates the distal end of the commercially available stent graft 12800 occluding the origin of the left subclavian artery 12780, which generally requires a bypass surgical procedure between the left common carotid artery 12790 and the left subclavian artery 12780. The right panel of FIG. 6K-11*iv* illustrates a vascular treatment device 12550 of FIG. 6K-1*i* deployed across the TAA 12760 with the distal segment 12600 across the origin of the left subclavian artery 12780 and preserving the origin of the left subclavian artery 12780 due to the high porosity of the distal segment 12600 of the vascular treatment device 12550 of FIG. 6K-1*i*. The intermediate segment 12570 of the vascular treatment device 12550 is shown across the mouth of the fusiform TAA 12760. A trans-femoral trans-arterial route or surgical route may be used for the procedure using a uni-axial or bi-axial approach (e.g., a standard microcatheter within a guide catheter, or through a guide catheter). The proximal segment 12560 and distal segment 12600 of the vascular treatment device 12550 have high porosity and allow flow into branch vessels 12780 proximate to the mouth of the aneurysm 12760, while the intermediate segment 12570 of the vascular treatment device 12550 has low porosity and covers the mouth of the aneurysm 12760 and aids in the thrombosis of the aneurysm sac, for example by inhibiting blood from flowing into the aneurysm 12760.

FIG. 6K-12 is a schematic diagram of an example embodiment of the vascular treatment device 12550 of FIG. 6K-1*i* deployed across an aneurysm 12760 in vasculature. In some embodiments, the proximal neck 12590 and distal neck 12595 in the intermediate segment 12570 can assist with inhibiting or preventing intra-device migration (the outer and inner layers sliding relative to each other) and/or intra-vessel migration of the device 12550 (the device 12550 sliding within the vasculature). The proximal neck 12590 and distal neck 12595 proximate to the edges of the mouth of the aneurysm 12760 can assist with inhibiting or preventing intra-vessel migration (e.g., by locking the device 12550 into place using the mouth of the aneurysm 12760). The proximal segment 12560 and distal segment 12600 proximate to the walls of the tapered vessels can inhibit or prevent intra-vessel migration of the vascular treatment device 12550, for example due outward radial force on the vascular walls. The proximal neck 12590 and distal neck 12595 proximate to the edges of the mouth of the aneurysm 12760 can assist with inhibiting or preventing intra-device migration (e.g., because the inner layer pushes against the outer layer in the mouth of the aneurysm 12760 and at the necks 12590, 12595). The low porosity of the necks 12590, 12595 proximate to the mouth of the aneurysm 12760 can inhibit or prevent endoleak at transitional zones.

FIG. 6K-13 is a schematic side elevational view of yet another example embodiment of a vascular treatment device. The outer layer 12640 of the vascular treatment device in the intermediate segment 12570 has a different radiopaque pattern than the inner layer 12630, allowing the operator to differentiate the lower porosity intermediate segment 12570 from the higher porosity proximal segment 12560 and distal segment 12600. In some embodiments, the outer layer 12640 and the inner layer 12630 have different numbers of radiopaque wires, different helical winding, different circumferential bunching, different diameter of radiopaque wires 12810 with larger diameter radiopaque wires 12810 with or without shape memory relative to the rest of the radiopaque wires 12810 and/or shape memory wires 12820, etc. Radiopaque patterns of various combinations may be used for the different layers, for example as shown in FIGS. 8F to 9D. The radiopaque pattern of the overlap areas 12570 may be used, for example, to help a user to position the overlap areas of the device across the mouth of an aneurysm.

FIG. 7A is a schematic side elevational view of still another example embodiment of a distal portion 11000 of a vascular treatment device, for example the distal portion 100 of the device 10, 20, 30, or 40. The distal portion 11000 includes a plurality of woven bulbs and woven necks. The distal portion 11000 includes, in an expanded state, one generally spherical distal bulb or central anchor bulb 11012, one generally spherical proximal bulb 11014, a neck 11016 between the bulbs 11012, 11014, a proximal neck 11017, a distal medial neck 11018, and a distal lateral neck 11019. The bulb 11012 has a diameter $D_0$. In some embodiments, the neck 11016 between the two bulbs 11012, 11014, the elongate proximal bulb 11014, and the proximal neck 11017 form a proximal segment having a length $L_3$. The neck 11017 has a wide mouth and a diameter $D_3$. The distal medial neck 11018 is relatively short, having a length $L_2$, and has a diameter $D_2$. The distal lateral neck 11019 has a length $L_1$ and has a diameter $D_1$.

In some embodiments, the distal spherical bulb 11012 has a relatively high braid angle and the rest of the distal portion 11000 has a relatively low braid angle. Lower braid angle segments generally have lower PPI and tend to have relatively high porosity. Lower PPI can result in a larger pore size, which can allow adequate flow into perforating vessels or small blood vessels adjoining an aneurysm or a vascular malformation such as an arterio-venous fistula, which can maintain flow in these small but important blood vessels. In some embodiments, the proximal segment has a relatively low braid angle. Higher braid angle segments generally have a higher PPI and tend to have relatively low porosity. Higher PPI can result in a smaller pore size, which can decrease flow into an aneurysm or a vascular malformation such as an arterio-venous fistula, which can aid in thrombosis of the aneurysm or vascular malformation.

In some embodiments, the outer diameters of the bulbs and necks in the radially-expanded configuration are as follows: $D_1$ is configured to be oversized to the medium vessel segments such as the proximal M1 segment of the middle cerebral artery (e.g., about 2.75 mm to about 3.25 mm); $D_2$ is configured to be oversized to the medium vessel segments such as the proximal A1 segment of the anterior cerebral artery (e.g., about 2.25 mm to about 2.75 mm); $D_0$ is configured to be oversized by about 25% to about 50% of the largest diameter of one of the bifurcation of vessels such as the internal carotid artery bifurcation (e.g., about 5 mm to about 6 mm); and $D_3$ is configured to be oversized to the large vessel segments such as the distal supra-clinoid segment of the internal carotid artery (e.g., about 3.25 mm to about 4 mm). Although some example diameters are provided herein, some embodiments of the distal portion 11000 may include diameters of the bulbs 11012, 11014 and necks 11016, 11017, 11018, 11019 in accordance with the values provided above and/or diameters that are within about ±5%, about ±10%, about ±15%, or about ±20% of any such values.

Although the necks 11017, 11018, 11019 are illustrated in FIG. 7A as being in the same plane (e.g., the plane of the page or the screen), the necks 11017, 11018, 11019 may be in different planes, for example based on certain vasculature. In contrast to pure balls deployed at bifurcations, necks 11017, 11018, 11019 can preserve anatomy for later procedures. For example, a thrombectomy device could be inserted through the neck 11017 and then into the vessel in which the neck 11018 resides and/or in which the neck 11019 resides. Certain distal portions described herein can be described as an endoprosthesis, a stent, etc. A proximal portion can be attached to endoprosthesis through detachable joint (e.g., Guglielmi electrolytic detachment, mechanical detachment, etc.).

FIG. 7B is a schematic side elevational view of still yet another example embodiment of a distal portion 11100 of a vascular treatment device, for example the distal portion 100 of the device 10, 20, 30, or 40. The distal portion 11100 includes a plurality of woven bulbs and woven necks. The distal portion 11100 includes, in an expanded state, one generally spherical or ovoid proximal bulb 11105 having a diameter $D_0$, one generally elongate distal bulb 11110, a neck 11115 between the bulbs 11105, 11110, a wide-mouth distal neck 11130 having a diameter $D_3$, a proximal medial neck 11125, and a proximal lateral neck 11120. In some embodiments, the neck 11115, the elongate distal bulb 11110, and the distal neck 11130 form a distal segment having a length $L_3$. The proximal medial neck 11125 is short, having a length $L_2$, and has a narrow mouth having a diameter $D_2$. The proximal lateral neck 11120 is short, having a length $L_1$, and has a narrow mouth having a diameter $D_1$.

In some embodiments, the distal portion 11100 includes a proximal spherical or ovoid bulb 11105, the elongate distal bulb 11110, and the neck 11115 between the bulbs 11105, 11110 each having a relatively high braid angle, and segments including the rest of the woven necks have a relatively low braid angle. For example, the lower braid angle segments may have braid angles ranging from about 0° to about 90° (e.g., about 17°, about 22°, about 45°, etc.). Lower braid angle segments generally have lower PPI and tend to have relatively high porosity. Lower PPI can result in a larger pore size, which can allow adequate flow into perforating vessels or small blood vessels adjoining an aneurysm or a vascular malformation such as an arterio-venous fistula, which can maintain flow in these small but important blood vessels. For example, the higher braid angle segment may have braid angles ranging from about 91° to about 180° (e.g., about 111°, about 112°, about 151°, etc.). Higher braid angle segments generally have a higher PPI and tend to have relatively low porosity. Higher PPI can result in a smaller pore size, which can decrease flow into an aneurysm or a vascular malformation such as an arterio-venous fistula, which can aid in thrombosis of the aneurysm or vascular malformation.

In some embodiments, the outer diameters of the bulbs and necks in the radially-expanded configuration are as follows: the proximal lateral neck 11120 has an outer diameter $D_1$ configured to be oversized to the large vessel segments such as the common iliac artery (e.g., about 8 mm to about 12 mm); the proximal medial neck 11125 has an outer diameter $D_2$ configured to be oversized to the large vessel segments such as the common iliac artery (e.g., about 8 mm to about 12 mm); the proximal spherical bulb 11105 has on outer diameter $D_0$ configured to be oversized by about 20% to about 50% of the largest diameter of abdominal aorta (e.g., about 10 mm to about 40 mm, about 18 mm to about 22 mm); and the distal segment $D_3$ has an outer diameter configured to be oversized by about 20% to about 50% to the large vessel segments such as the supra-renal or infra-renal abdominal aorta (e.g., about 10 mm to about 40 mm, about 18 mm to about 22 mm). The bulbs 11105, 11110 the necks 11115, 11120, 11125, and the distal neck 11130 can provide good wall apposition, which can inhibit or prevent the risk of an endo-leak into the aneurysm. The bulbs 11105, 11110 have substantially uniform dimensions or diameters (e.g., within about ±5%, about ±10%, about ±15%, or about 20% of each other) such that the distal portion 11100 may be considered non-tapered. Although some example diameters are provided herein, some embodiments of the distal portion 11100 may include diameters of the bulbs 11105, 11110 and necks 11115, 11120, 11125, 11130 in accordance with the values provided above and/or diameters that are within about ±5%, about ±10%, about ±15%, or about ±20% of any such values.

Although the necks 11120, 11125, 11130 are illustrated in FIG. 7B as being in the same plane (e.g., the plane of the page or the screen), the necks 11120, 11125, 11130 may be in different planes, for example based on certain vasculature. In contrast to endovascular or surgical endoprostheses that require deployment through both common femoral arteries or both common iliac arteries, the example embodiment illustrated in FIG. 7B can be deployed through one artery such as a common femoral artery. Certain distal portions described herein can be described as an endoprosthesis, a stent, etc. A proximal portion can be attached to endoprosthesis through detachable joint (e.g., Guglielmi electrolytic detachment, mechanical detachment, etc.).

FIG. 7C is a schematic side elevational view of another example embodiment of a distal portion 11400 of a vascular treatment device, for example the distal portion 100 of the device 10, 20, 30, or 40. FIG. 7C-2 is a schematic side elevational view of yet another example embodiment of a distal portion 12200 of a vascular treatment device, for example the distal portion 100 of the device 10, 20, 30, or 40. The distal portion 11400, 12200 includes a plurality of woven bulbs 11405, 11415, 11425, 11435, a woven neck 11422 between the bulbs 11405, 11415, a woven neck 11424 between the bulbs 11415, 11425, a woven neck 11426 between the bulbs 11425, 11435, a woven proximal neck 11420, and a woven distal neck 11428. In some embodiments, the distal portion 11400, 12200 includes, in an expanded state, two ovoid or ellipsoid or oblate spheroid outer bulbs 11405, 11435 and two ovoid or ellipsoid or oblate spheroid inner bulbs 11415, 11425, wide-mouthed necks 11422, 11424, 11426 between the bulbs 11405, 11415, a proximal narrow-mouthed neck 11420 attached to the proximal portion 200 at a joint 300, and a distal narrow-mouthed neck 11428. In some embodiments, the bulbs 11405, 11415, 11425, 11435 comprise ellipsoids or oblate spheroids in which the diameter of the polar axis is shorter than the diameter of the equatorial axis (e.g., flattened discs stacked proximate to each other). The necks 11422, 11424, 11426 between the bulbs 11405, 11415, 11425, 11435 may be connected at the polar axis rather than being connected at the equatorial axis.

In some embodiments, the distal portion 11400, 12200 includes a distal neck 11428 that is radially offset from the longitudinal polar axis and/or that is not longitudinally aligned to the proximal neck 11420 (e.g., as shown in FIG. 7C-2). Distal portions 100 comprising necks that are radially offset and/or that are not longitudinally aligned are described in further detail herein.

In some embodiments, the distal portion 11400, 12200 may comprise more or fewer bulbs. For example, one side may include only one bulb (e.g., if the jet effect through the fistula is primarily in a single direction). For another example, at least one side may include more than two bulbs (e.g., to provide a more tortuous path for blood flow, which can inhibit or prevent the jet effect, and/or to promote thrombus formation and/or capture).

In some embodiments, the distal portion 11400, 12200 includes a plurality of segments, at least one of which has a different braid angle. The distal portion 11400 illustrated in FIG. 7C includes a middle segment comprising the wide-mouthed woven neck 11424 between the two inner bulbs 11415, 11425. The middle segment, comprising the neck 11424, has a relatively low braid angle, and the woven necks 11420, 11422, 11426, 11428 and the woven bulbs 11405, 11415, 11425, 11435 have a relatively high braid angle. The distal portion 12200 illustrated in FIG. 7C-2 includes a middle segment comprising the wide-mouthed woven neck 11424 and the two inner bulbs 11415, 11425. The middle segment, comprising the neck 11424 and the two inner bulbs 11415, 11425, has a relatively low braid angle, and the woven necks 11420, 11422, 11426, 11428 and the woven bulbs 11405, 11435 have a relatively high braid angle. In some embodiments, the lower braid angle segment may have braid angles ranging from about 0° to about 90° (e.g., about 17°, about 22°, about 45°, etc.). Lower braid angle segments generally have lower PPI and tend to have relatively high porosity. Lower PPI can result in lower chronic outward force (COF), which can cause flow disruption within a fistula or an abnormal communication between two hollow cavities by forming a soft scaffold within the fistula or abnormal communication between two hollow cavities, which can aid in thrombosis of the fistula or abnormal communication between two hollow cavities. Lower PPI can result in better conformability of the inner bulbs 11415, 11425 to, and integration with, the walls surrounding a cavernous fistula. In some embodiments, the higher braid angle segment(s) (e.g., proximal and distal to the lower braid angle segment as illustrated in FIGS. 7C and 7C-2) may have braid angles ranging from about 91° to about 180° (e.g., about 111°, about 112°, about 151°, etc.). Higher braid angle segments generally have a higher PPI and tend to have relatively low porosity. Higher PPI can result in a smaller pore size, which can decrease flow into a fistula or abnormal communication between two hollow cavities, which can aid in thrombosis of the fistula or abnormal communication between two hollow cavities. A relatively low pore size can serve as a filter to inhibit or prevent a thrombus formed within the fistula or abnormal communication between two hollow cavities from forming emboli or small debris that could otherwise break off and enter the normal vasculature. Referring again to FIGS. 4I-4K, the neck 11424 having a high pore size may have a variable length and/or a variable diameter, which can allow the neck 11424 to conform to the dimensions of a fistula or abnormal communication between two hollow cavities, which can provide good wall apposition and/or aid in thrombosis of the fistula or abnormal communication between two hollow cavities. Although some examples of fistulas are provided herein, the distal portion 11400 illustrated in FIG. 7C and FIG. 7C-2 and the like may be useful in any fistula or abnormal communication between two hollow cavities in the body.

In some embodiments, the outer diameters of the woven bulbs in the radially-expanded configuration are as follows: the two inner ellipsoid or oblate spheroid bulbs 11415 and 11425 have an outer diameter configured to be oversized between about 50% and about 75% to the width of the orifice of the fistula or abnormal communication between two hollow cavities (e.g., between about 2 mm and about 16 mm, about 8 mm); the two outer ellipsoid or oblate spheroid bulbs 11405 and 11435 have an outer diameter configured to be oversized between about 25% and about 50% to the width of the orifice of the fistula or abnormal communication between two hollow cavities (e.g., between about 2 mm and about 16 mm, about 8 mm); the middle segment neck 11424 has an outer diameter configured to be oversized between about 10% and about 25% to the width of the orifice of the fistula or abnormal communication between two hollow cavities (e.g., between about 2 mm and about 16 mm, about 8 mm); and the middle segment neck 11424 has a length configured to be oversized between about 10% and about 25% to the length of the orifice of the fistula or abnormal communication between two hollow cavities (e.g., between about 2 mm and about 26 mm, between about 4 mm and about 8 mm, about 6 mm). Although some example diameters are provided herein, some embodiments of the distal portion 11400, 12200 may include diameters of the woven necks 11420, 11422, 11424, 11426, 11428, diameters of the woven bulbs 11405, 11415, 11425, 11435, and/or length of the woven neck 11424 in accordance with the values provided above and/or diameters that are ±5%, ±10%, ±15%, or ±20% of any such values.

FIG. 7D is a schematic side elevational view of yet another example embodiment of a distal portion 11600 of a vascular treatment device, for example the distal portion 100 of the device 10, 20, 30, or 40. The distal portion 11600 includes a plurality of woven bulbs 11610 and woven necks 11620. In some embodiments, the distal portion 11600 includes, in an expanded state, three ovoid or ellipsoid or spheroid woven bulbs 11610 including a distal bulb 11625, a middle bulb 11615, and a proximal bulb 11605, a wide-mouthed neck 11604 between the bulbs 11625, 11615, a wide-mouthed neck 11602 between the bulbs 11615, 11605, a proximal narrow-mouthed neck that is attached to the proximal portion at joint 300, and a distal narrow-mouthed neck 11606. In some embodiments, the bulbs 11610 are ellipsoids or oblate spheroids having a polar axis diameter that is smaller than an equatorial axis diameter (e.g., flattened discs stacked proximate to each other). The necks 11602, 11604 between the bulbs 11610 may be connected at the polar axis rather than the equatorial axis. In some embodiments, the distal portion 11600 includes a distal neck 11606 that is radially offset from the longitudinal axis and/or that is not longitudinally aligned to the proximal neck. In some embodiments, the distal portion 11600 includes a plurality of segments, at least one of which has a different braid angle. The distal portion 11600 illustrated in FIG. 7D includes a proximal segment, comprising the proximal bulb 11605, which is attached to the proximal portion 200 at the joint 300, that has a relatively high braid angle and a distal segment, comprising the middle bulb 11615, the distal bulb 11625 and the necks 11602, 11604, 11606, that has a relatively low braid angle. In some embodiments, the lower braid angle segment may have braid angles ranging from about 0° to about 90° (e.g., about 17°, about 22°, about 45°, etc.). Lower braid angle segments generally have lower PPI and tend to have relatively high porosity. Lower PPI can result in a larger pore size, which can cause flow disruption within an aneurysm by forming a soft scaffold within the aneurysm and aid in the thrombosis of the aneurysm. In some embodiments, the higher braid angle segment may have braid angles ranging from about 91° to about 180° (e.g., about 111°, about 112°, about 151°, etc.). Higher braid angle segments generally have a higher PPI and tend to have relatively low porosity. Higher PPI can result in a smaller pore size, which can decrease flow into an aneurysm, which can aid in thrombosis of the aneurysm. A relatively low pore size can serve as a filter to inhibit or prevent a thrombus formed within the aneurysm from breaking off (e.g., as emboli or small debris) and entering the normal vasculature.

In some embodiments, the outer diameters of the bulbs 11610 in the radially-expanded configuration are as follows: the distal oval or ellipsoid bulb 11625 has an outer diameter configured to be undersized between about 25% to about 50% of the largest diameter of the ventricular wall aneurysm within the heart (e.g., about 5 mm to about 7.5 mm for a ventricular wall aneurysm with the largest diameter about 10 mm); the middle oval or ellipsoid bulb 11615 and the proximal oval or ellipsoid bulb 11605 have an outer diameter configured to be oversized between about 50% to about 75% of the diameter of the neck of the ventricular wall aneurysm such that the proximal bulb 11605 is anchored within the aneurysm with limited risk of the bulb 11605 falling out of the aneurysm into the ventricle of the heart. The proximal oval or ellipsoid bulb 11605 and the middle oval or ellipsoid bulb 11615 may have an outer diameter that is no greater than the largest diameter of the ventricular aneurysm such that there is no or limited significant outward force on the aneurysm wall that could otherwise cause a rupture (e.g., about 7.5 mm to about 8.75 mm for a ventricular wall aneurysm with the largest diameter about 10 mm having a neck with a diameter of about 5 mm). Although some example diameters are provided herein, some embodiments of the distal portion 11600 may include diameters of the bulbs 11625, 11615, 11605 in accordance with the values provided above and/or diameters that are within about ±5%, about ±10%, about ±15%, or about ±20% of any such values, such that the distal portion 11600 may be considered to be tapered.

FIG. 7E is a schematic side elevational view of still another example embodiment of a distal portion 11500 of a vascular treatment device, for example the distal portion 100 of the device 10, 20, 30, or 40. The distal portion 11500 includes a plurality of woven bulbs 11510 and woven necks 11520. In some embodiments, the distal portion 11500 includes, in an expanded state, four ovoid or ellipsoid or spheroid woven bulbs 11510 including a distal bulb 11518, a second bulb 11516, a third bulb 11514, and a proximal bulb 11512, wide-mouthed necks 11520 between the bulbs 11510, a proximal narrow-mouthed neck 11522 that is attached to the proximal portion 200 at joint 300, and a distal narrow-mouthed neck 65. In some embodiments, the bulbs 11510 comprise ellipsoids or oblate spheroids having a polar axis diameter that is shorter than an equatorial axis diameter (e.g., flattened discs stacked proximate to each other). In some embodiments, the distal portion 11500 includes a distal neck 65 that is radially offset from the longitudinal axis and/or that is not longitudinally aligned to the proximal neck 11522. The necks 11520 between the bulbs 11510 may be connected at the polar axis rather than the equatorial axis. In some embodiments, the distal portion 11500 includes a plurality of segments, at least one of which has a different braid angle. The distal portion 11500 illustrated in FIG. 7E includes a proximal segment, comprising the proximal two bulbs 11512, 11514 and the proximal neck 11522, that has a relatively high braid angle and a distal segment, comprising segments including the rest of the distal portion 11500 including the distal two bulbs 11516, 11518 and the distal neck 65, that has a relatively low braid angle. In some embodiments, the lower braid angle segment may have braid angles ranging from about 0° to about 90° (e.g., about 17°, about 22°, about 45°, etc.). Lower braid angle segments generally have lower PPI and tend to have relatively high porosity. Lower PPI can result in a larger pore size, which can cause flow disruption within an aneurysm by forming a soft scaffold within the aneurysm or hollow cavity and can aid in the thrombosis of the aneurysm or hollow cavity. In some embodiments, the higher braid angle segment may have braid angles ranging from about 91° to about 180° (e.g., about 111°, about 112°, about 151°, etc.). Higher braid angle segments generally have a higher PPI and tend to have relatively low porosity. Higher PPI can result in a smaller pore size, which can decrease flow into an aneurysm or hollow cavity, which can aid in thrombosis of the aneurysm or the hollow cavity. A relatively low pore size can serve as a filter to inhibit or prevent a thrombus formed within the aneurysm from breaking off (e.g., as emboli or small debris) and entering the normal vasculature.

In some embodiments, the outer diameters of the bulbs 11510 in the radially-expanded configuration are as follows: the distal ellipsoid or oblate spheroid bulb 11518 has an outer diameter configured to be undersized between about 25% to about 50% to the width of the left atrial appendage within the heart (e.g., between 8 mm to about 35 mm, about 17 mm); the second ellipsoid or oblate spheroid bulb 11516 and the third ellipsoid or oblate spheroid bulb 11514 have an outer diameter configured to be oversized between about 25% to about 50% to the width of the left atrial appendage within the heart (e.g., between 8 mm to about 35 mm, about 17 mm). The proximal ellipsoid or oblate spheroid bulb 11512 has an outer diameter configured to be oversized between about 50% to about 75% to the width of the orifice of the left atrial appendage within the heart (e.g., between 5 mm to about 20 mm, about 10 mm). The length of the distal portion 11500 along the longitudinal axis, illustrated in FIG. 7E with a dashed line, is between 13 mm and about 45 mm (e.g., about 26 mm). Although some example diameters are provided herein, some embodiments of the distal portion 11600 may include diameters of the bulbs 11518, 11516, 11514, 11512 in accordance with the values provided above and/or diameters that are within about ±5%, about ±10%, about ±15%, or about ±20% of any such values, such that the distal portion 11500 may be considered to be tapered.

Figure 8A:
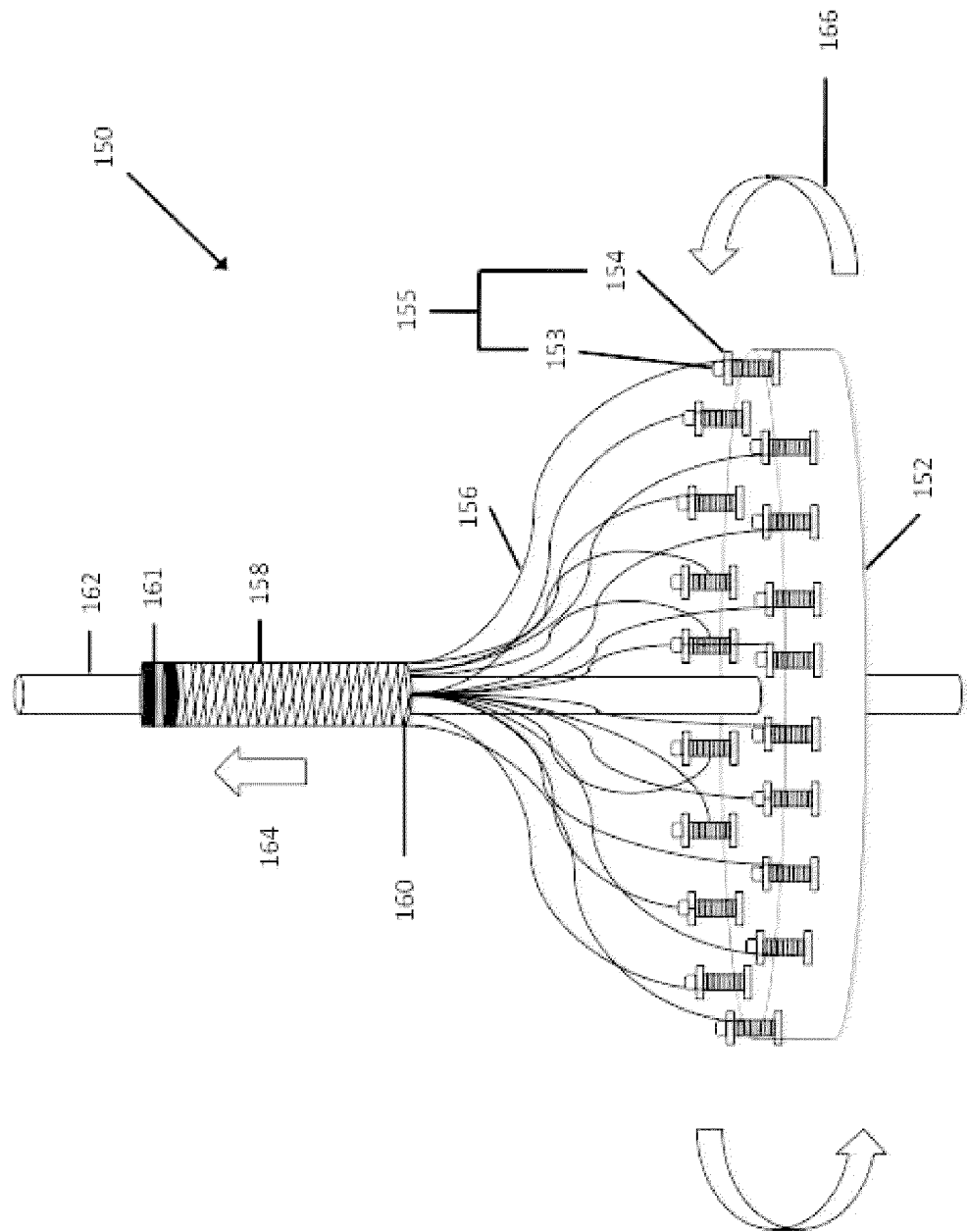
FIG. 8A is a schematic side perspective view of an example embodiment of a braiding device.

FIG. 8A is a schematic side perspective view of an example embodiment of a braiding device or carrier braider 150. The braiding device 150 includes a yarn wheel or braid carrier mechanism or circular horn gear 152 and a plurality of spindles 153 and individual carriers 155. A spindle 153 is a stick on the circular horn gear 152. A spool 154 is a hollow device that fits onto a spindle 153 and includes filaments 156 wound around it. An individual carrier 155 includes a spindle 153 and a spool 154 on the spindle 153. The terms spindle, spool, and individual carrier may be used interchangeably depending on context. The individual carriers 155 include spools 154 including filaments 156 that are woven together to form the textile structure 158 of the distal portion 100. The filaments 156 each extend from an individual carrier 155 to a ring or vertical puller 161 over a mandrel 162 and are braided around the mandrel 162 by spinning the circular horn gear 152, spinning the spindles 153, and pulling the ring 161 away from the circular horn gear 152. Although some examples of the carrier braider 150 with 18 spindles 153 or individual carriers 155 are provided herein, some embodiments of the carrier braider 150 may include 6 to 144 spindles 153 or individual carriers 155 in accordance with the values provided above and/or carrier braiders 150 that have 6, 12, 24, 36, 48, 60, 72, 84, 96, 120, 144, etc. spindles 153 or individual carriers 155. As the textile structure 158 is woven at preform point 160, the textile structure 158 advances in the direction of the arrow 164. The circular horn gear 152 spins in the direction of the arrows 166, and the spindles 153, which are part of the individual carriers 154, rotate within the circular horn gear 154 to create the desired braiding pattern.

In some embodiments, the mandrel 162 comprises a rod or tube (e.g., comprising stainless steel) having a uniform outer diameter. In some embodiments, the outer diameter of the mandrel 162 is between about 4 mm and about 9 mm (e.g., about 6 mm, about 6.5 mm). In some embodiments, the outer diameter of the mandrel 162 is between about 33% and about 200% larger than the largest bulb that the distal portion 100 will include. In some embodiments, the smaller the diameters or widths of the filaments, the more oversizing the mandrel 162 may reduce defects at later stages of fabrication.

Figure 8B:
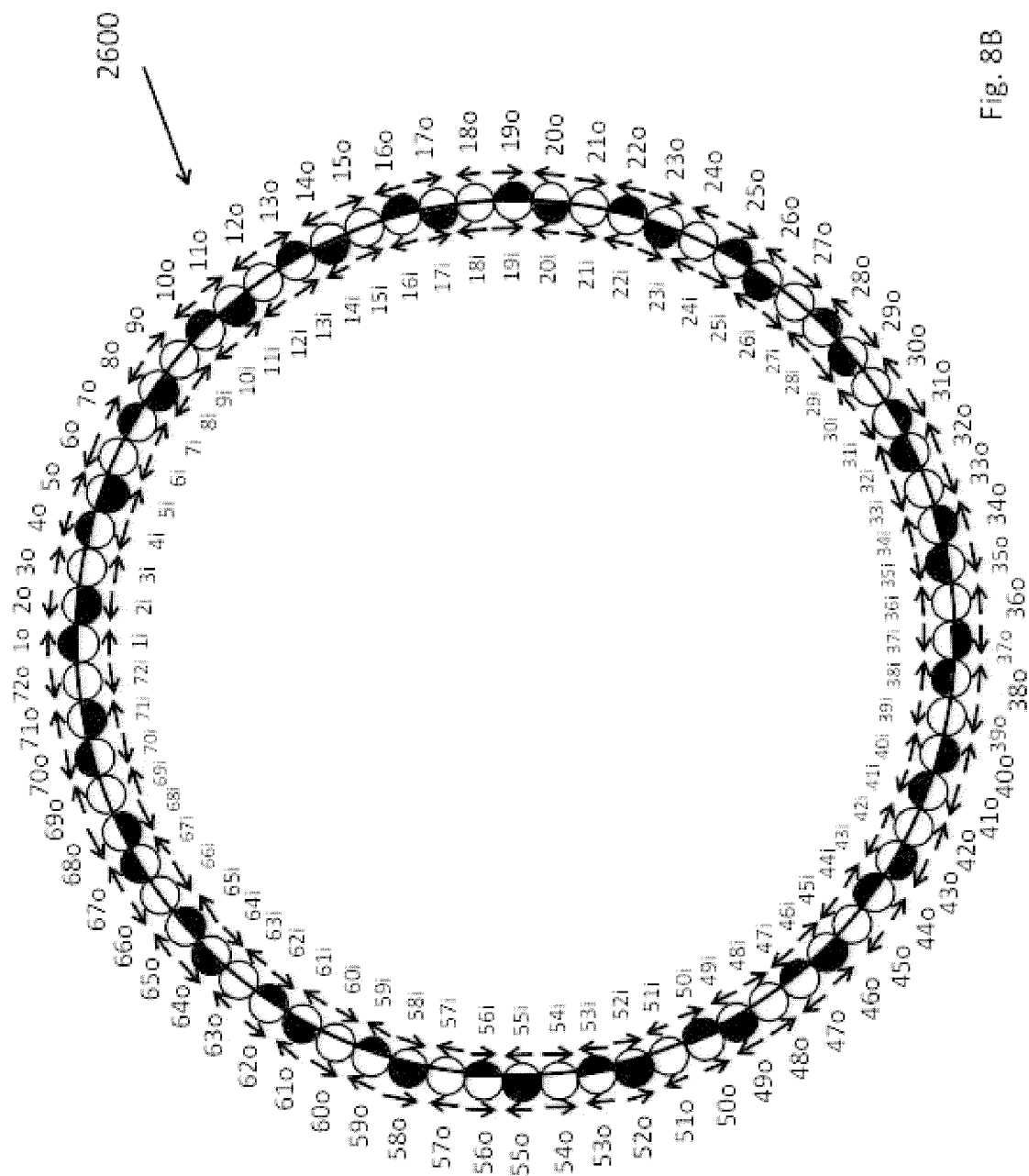
FIG. 8B is a schematic diagram illustrating an example setup of a braid carrier mechanism.

FIG. 8B is a schematic diagram illustrating an example setup of a braid carrier mechanism 2600. The yarn wheel 2600 includes spindles 153 without spools 155 or without forming individual carriers 154 and spindles 153 with spools 155 including filaments 156 together forming individual carriers 154. In FIG. 8B, the half circles with dark shading indicate individual carriers 155 including spools 154 including shape memory filaments, the half circles with hatched shading indicate individual carriers 155 including spools 154 including radiopaque filaments, and the half circles with no shading indicate spindles without spools 154 or filaments 156. The yarn wheel 2600 illustrated in FIG. 8B includes 144 spindles 153 or individual carriers 154 with 72 outer spindles labeled 1*o* through 72*o* and 72 inner spindles labeled 1*i* through 72*i*. One outer spindle and one inner spindle form a "double spindle pair." The spindles 154 spin in the direction indicated by the arrow proximate to the shading. In the arrangement illustrated in FIG. 8B, spindles 1*o*, 2*i*, 4*o*, 5*i*, 7*o*, 8*i*, 10*o*, 11*i*, 13*o*, 14*i*, 16*o*, 17*i*, 19*o*, 20*i*, 22*o*, 23*i*, 25*o*, 26*i*, 28*o*, 29*i*, 31*o*, 32*i*, 34*o*, 35*i*, 37*o*, 38*i*, 40*o*, 41*i*, 43*o*, 44*i*, 46*o*, 47*i*, 49*o*, 50*i*, 52*o*, 53*i*, 55*o*, 56*i*, 58*o*, 59*i*, 61*o*, 62*i*, 64*o*, 65*i*, 67*o*, 68*i*, 70*o*, and 71*i* include spools including shape-memory material (e.g., 48 of the filaments 156 comprise shape-memory material) and the remaining spindles are empty. None of the spindles includes radiopaque material.

Certain patterns can be discerned based on spindle arrangement and spin direction. For example, in the braid carrier mechanism 2600 of FIG. 8B, spindles 1*o* and 2*i* spin in opposite directions such that during weaving, filaments extending from the spools 154 on the spindles 1*o* and 2*i* will cross over each other, spindles 2*i* and 4*o* spin in the same direction such that during weaving, filaments extending from the spools 154 on the spindles 2*i* and 4*o* cross under each other, and spindles 4*o* and 5*i* spin in opposite directions such that during weaving, filaments extending from the spools 154 on the spindles 4o and 5i cross over each other, such that a one-over-one-under-one braiding pattern for the shape memory filaments can be discerned by analysis of the braid carrier mechanism 2600 of FIG. 8B.

Figure 8C:
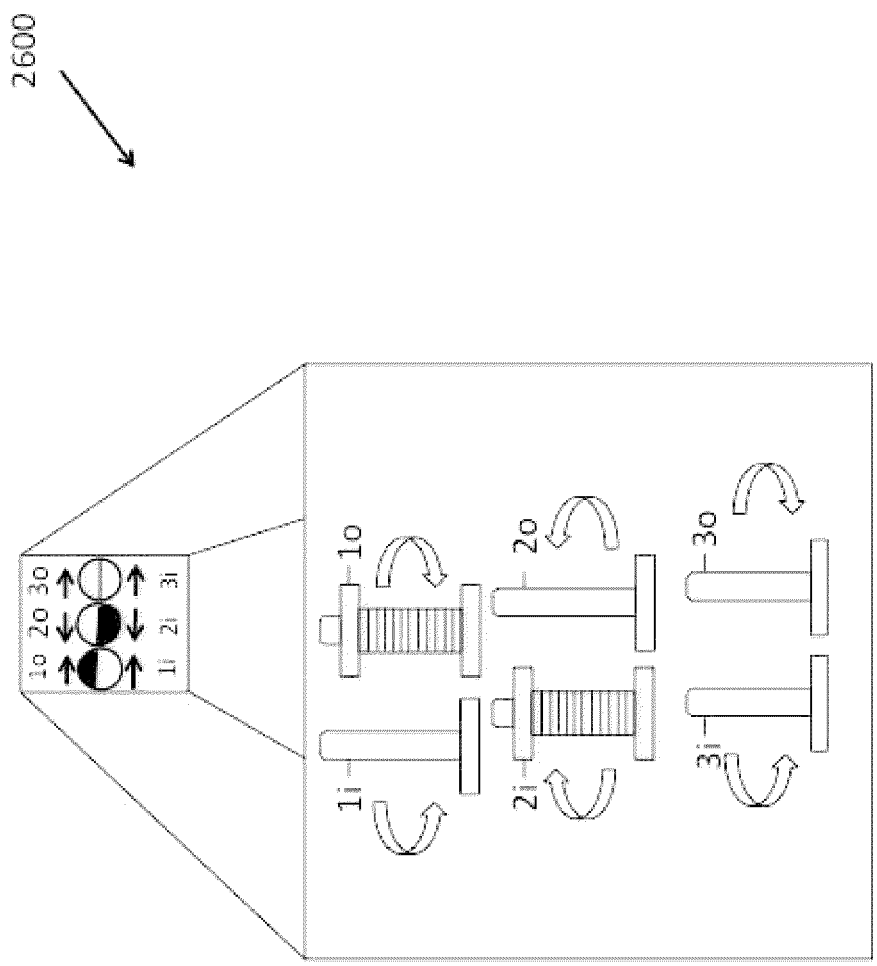
FIG. 8C is a schematic diagram illustrating a magnified view of three pairs of spindles in the example setup of the braid carrier mechanism of FIG. 8B.

FIG. 8C is a schematic diagram illustrating a magnified view of three pairs of spindles 1o, 1i, 2o, 2i, 3o, 3i in the example setup of the braid carrier mechanism 2600 of FIG. 8B. In FIGS. 8B and 8C, the pattern of the filaments 156 is symmetrical because there is a spool 154 including a shape memory filament in the outer spindle 1o paired with an empty inner spindle 1i, followed by an empty outer spindle 2o paired with a spool 154 including a shape memory filament in the inner spindle 2i, and then followed by an empty double spindle pair 3o, 3i, and then the pattern repeats itself in the pairs of spindles 4o, 4i, 5o, 5i, 6o, 6i and so on. Symmetrical patterns of filaments 156 may be associated with a uniform pore size. Filament adjacency may be defined as the angular circumference of the yarn wheel 152, which is 360°, divided by the number of filament spools. For example, if the yarn wheel 152 includes 48 filament spools, the filament adjacency would be 360°/48=7.5°. Filament adjacency may be used, for example, to help control symmetry of patterns. In some embodiments, the pattern of spools including the filaments 156 on spindles 153 can be asymmetrical, which can lead to varying pore size along the braid axis.

Figure 8D:
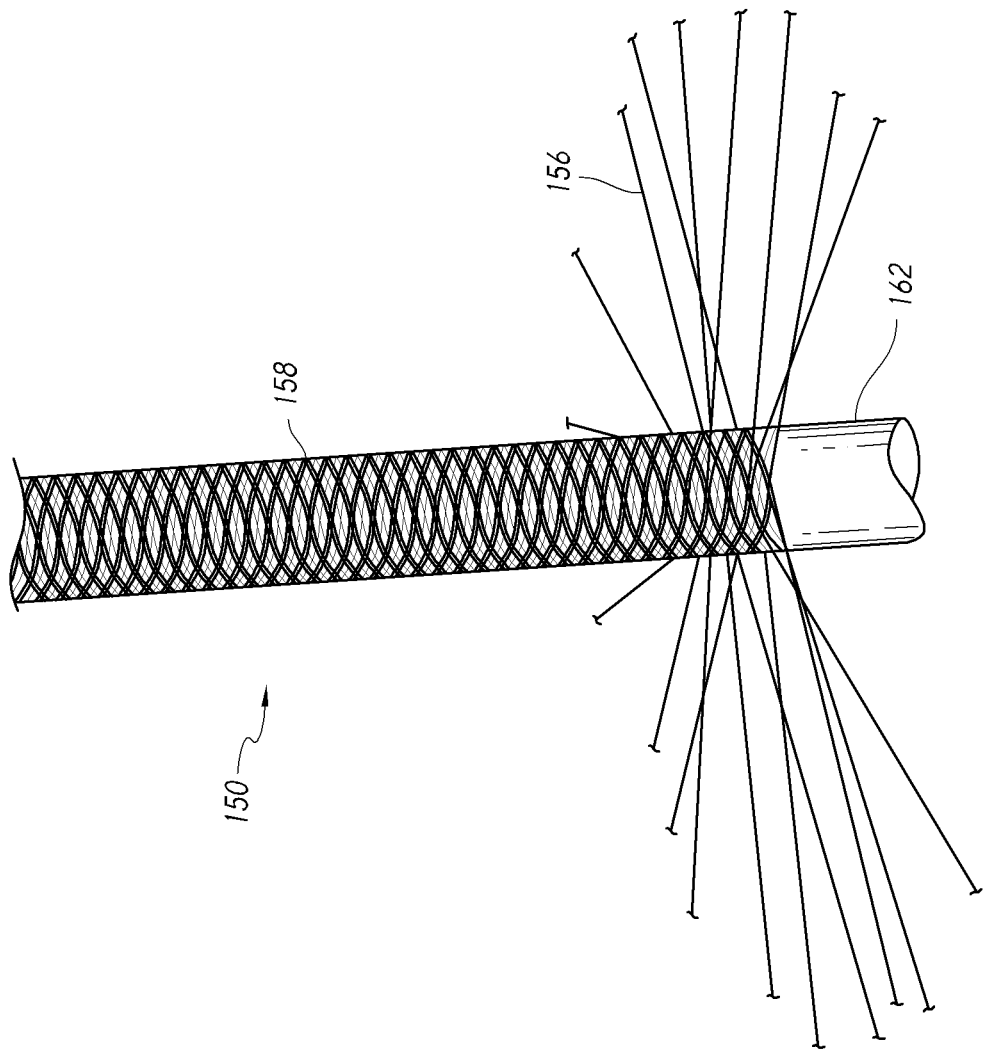
FIG. 8D is a schematic perspective view illustrating a plurality of filaments being braided on a mandrel.

In some embodiments, placement of spools 154 or lack of placement of spools 154 including filaments 156 on spindles 153 adjacent to each other can affect properties of the textile structure 158 such as pore size. Spindle adjacency may be defined as the angular circumference of the yarn wheel 152, which is 360°, divided by the number of double spindle pairs. For example, if the yarn wheel 152 includes 144 spindles 153 or 72 double spindle pairs, the spindle adjacency would be 360°/72=5°. In some embodiments, each double spindle pair that is empty creates a pore. Increasing the number of empty spindles 154 adjacent to each other (e.g., one, two, or more spindle pairs adjacent to each other) may increase the size of the pore. FIG. 8D is a schematic perspective view illustrating a plurality of filaments 156 being braided on a mandrel 162 using a braiding device or carrier braider 150. In FIG. 8D, the reflectivity of the radiopaque filaments 156 contrast with the reflectivity of the shape-memory filaments 156, creating a crisscross appearance of the tubular textile structure 158. In some embodiments, the placement of spools 154 including filaments 156 of a particular type of material on spindles 153 adjacent to each other can affect properties such as visibility under x-ray. Filament material adjacency may be defined as the angular circumference of the yarn wheel 152, which is 360°, divided by the number of filament spools of a particular type of material. For example, if the yarn wheel 152 includes 12 filament spools including radiopaque filaments evenly spaced from each other, the filament material adjacency would be 360°/12=30°. Filament material adjacency may be used to help control helical crossing points that are visible under x-ray. The arrangement of the filaments 156 illustrated in FIG. 8B, in which some radiopaque filaments 156 are circumferentially adjacent or proximate to each other, groups some radiopaque filaments to form an intertwining band of radiopaque material. A band of radiopaque material, for example as opposed to evenly distributed radiopaque material, may be easier to identify during fluoroscopy, particularly if the filaments are small.

In some embodiments, the radiopaque material includes metals or alloys including, but not limited to, iridium, platinum, tantalum, gold, palladium, tungsten, tin, silver, titanium, nickel, zirconium, rhenium, bismuth, molybdenum, combinations thereof, and the like, which can increase visibility of the distal portion 100 under fluoroscopy during interventional procedures. The radiopaque material may be part of an alloy (e.g., 92% platinum and 8% tungsten alloy), part of a core or cladding around a core (e.g., nitinol with a tungsten core), combinations thereof, and the like.

Figure 8E:
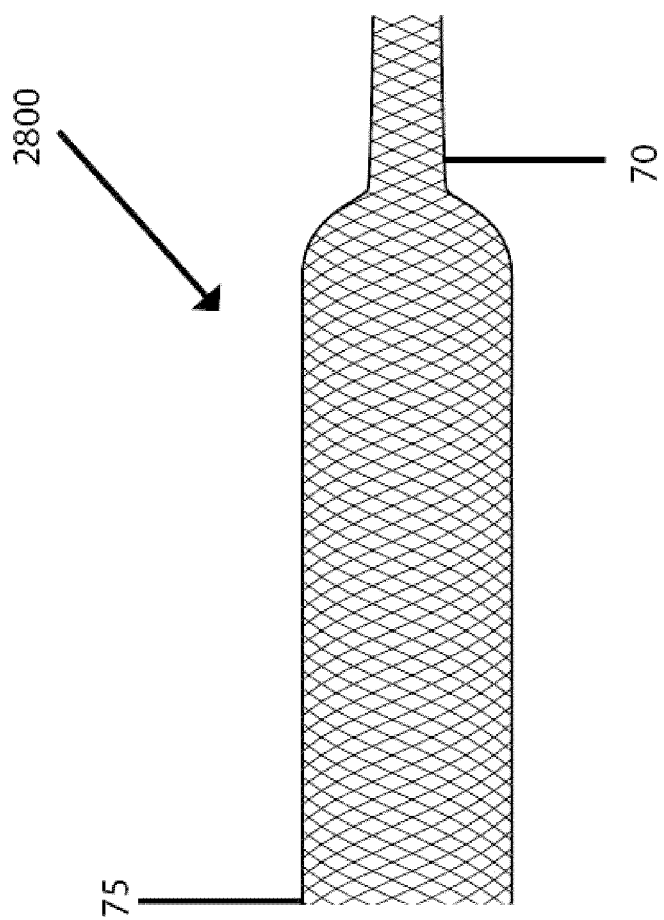
FIG. 8E is a schematic side elevational view of another example embodiment of a distal portion of a vascular treatment device.
Figure 8F:
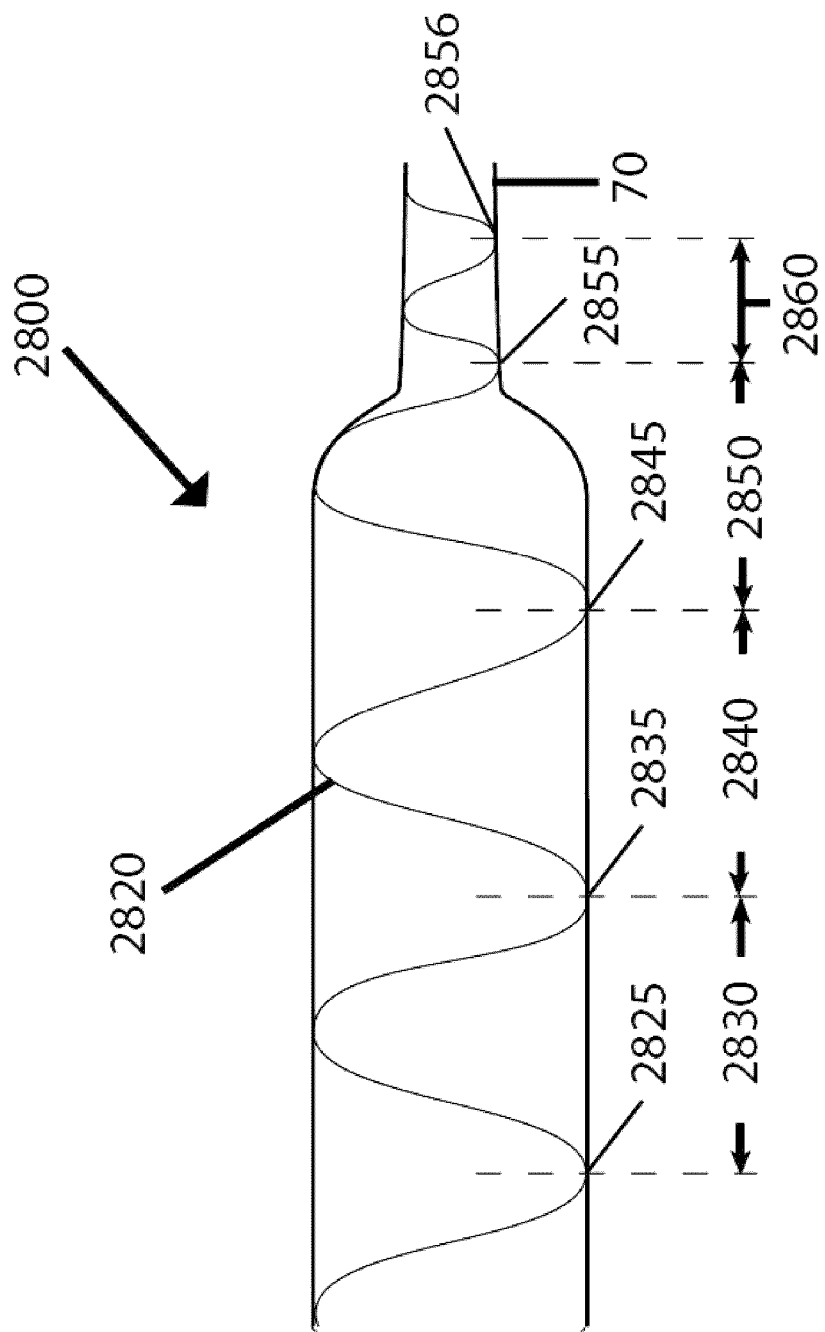
FIG. 8F is a schematic side elevational view of the distal portion of FIG. 8E illustrating an example pattern of radiopaque filaments.

FIG. 8E is a schematic side elevational view of still another example embodiment of a distal portion 2800 of a vascular treatment device, for example the distal portion 100 of the device 10, 20, 30, or 40. The distal portion 2800 includes, in an expanded state, a proximal neck 70 and a cylindrical wide-mouthed textile structure 75 including shape-memory filaments and radiopaque filaments. The textile structure 75 expands radially outwardly from proximal to distal, and then stays at the larger diameter until the distal end. FIG. 8F is a schematic side elevational view of the distal portion 2800 of FIG. 8E, illustrating an example pattern of radiopaque filaments, for example under x-ray. The distal portion 2800 includes, in an expanded state, a single radiopaque filament 2820 that is interlaced in the form a single sine wave that appears like a "simple helix" at least under x-ray. The pattern of radiopacity can allow an operator of a device comprising the distal portion 2800 to visualize and identify the distal portion 2800 at least under x-ray. In some embodiments, the single simple helix includes troughs and peaks, for example at the sides of the distal portion 2800 that the simple helix at least partially creates. In FIG. 8F, the helical intersection points 2825, 2835, 2845, 2855 are substantially uniformly spaced by distances 2830, 2840, 2850, which can allow the distal portion 2800 to serve as an angiographic measurement ruler. For example, the distances 2830, 2840, 2850 can help an operator to measure the length of blood clots, the neck of an aneurysm, the length of a stenosis, etc. In some embodiments, a distance 2860 between points 2855, 2856 at least partially along the proximal neck 70 has different dimensions than the simple helix in the rest of the larger diameter part of the distal portion 2800, which may serve as an identifier of the proximal neck 70 beyond which the distal portion 2800 should not be deployed.

Figure 8G:
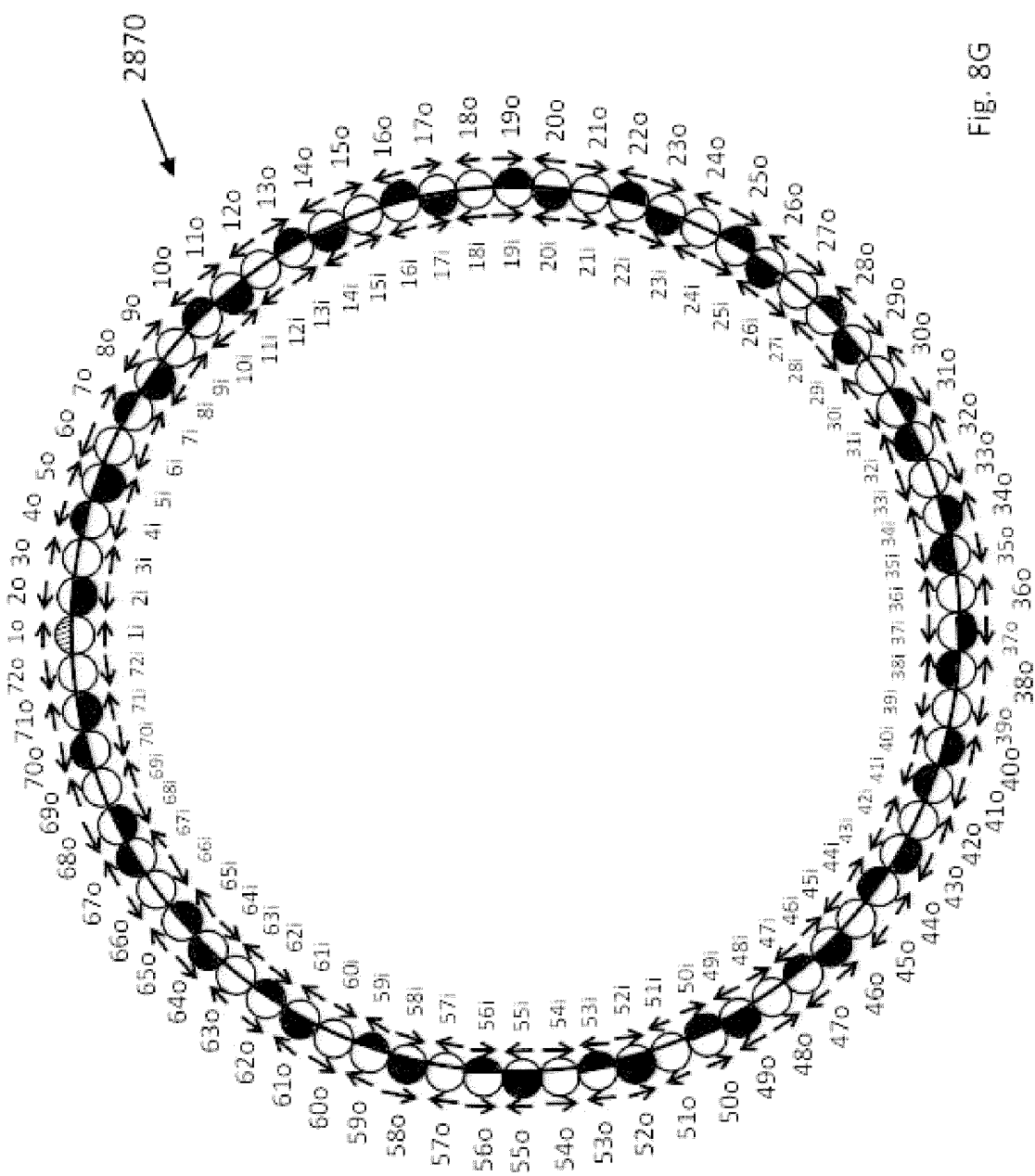
FIG. 8G is a schematic diagram illustrating an example setup of a braid carrier mechanism for forming the distal portion of FIG. 8E.

FIG. 8G is a schematic diagram illustrating an example setup of a braid carrier mechanism 2870 for forming the distal portion 2800 of FIG. 8E. In FIG. 8G, the half circles with dark shading indicate individual carriers 155 including spools 154 including shape memory filaments 156, the half circles with hatched shading indicate individual carriers 155 including spools 154 including radiopaque filaments 156, and the half circles with no shading indicate spindles without spools 154 or filaments 156. In the arrangement illustrated in FIG. 8G, spindles 2i, 4o, 5i, 7o, 8i, 10o, 11i, 13o, 14i, 16o, 17i, 19o, 20i, 22o, 23i, 25o, 26i, 28o, 29i, 31o, 32i, 34o, 35i, 37o, 38i, 40o, 41i, 43o, 44i, 46o, 47i, 49o, 50i, 52o, 53i, 55o, 56i, 58o, 59i, 61o, 62i, 64o, 65i, 67o, 68i, 70o, 71i include spools 154 including shape-memory material (e.g., 47 of the filaments 156 comprise shape-memory material), the spindle 1o includes a spool including radiopaque material (e.g., 1 of the 48 filaments 156 comprises radiopaque material), and the remaining spindles 153 are empty. The braid carrier mechanism 2870 setup illustrated in FIG. 8G can generate a pattern of radiopacity described with respect to FIG. 8F, for example a single sine wave or simple helix pattern. The radiopaque filament 156 forms a sine wave having a spindle adjacency of about 5° (360°/72), a filament adjacency of about 7.5° (360°/48), and a radiopaque filament material adjacency of about 360° (360°/1). Although some examples of the carrier braider 150 with 48 spindles 153 or individual carriers 155 are provided herein, some embodiments of the carrier braider 150 may include 6 to 144 spindles 153 or individual carriers 155 in accordance with the values provided above and/or carrier braiders 150 that have 6, 12, 24, 36, 48, 60, 72, 84, 96, 120, 144, etc. spindles 153 or individual carriers 155, and the number and positioning of radiopaque filaments 156 can remain as provided in the example braid carrier mechanism 2870 setup.

Figure 8H:
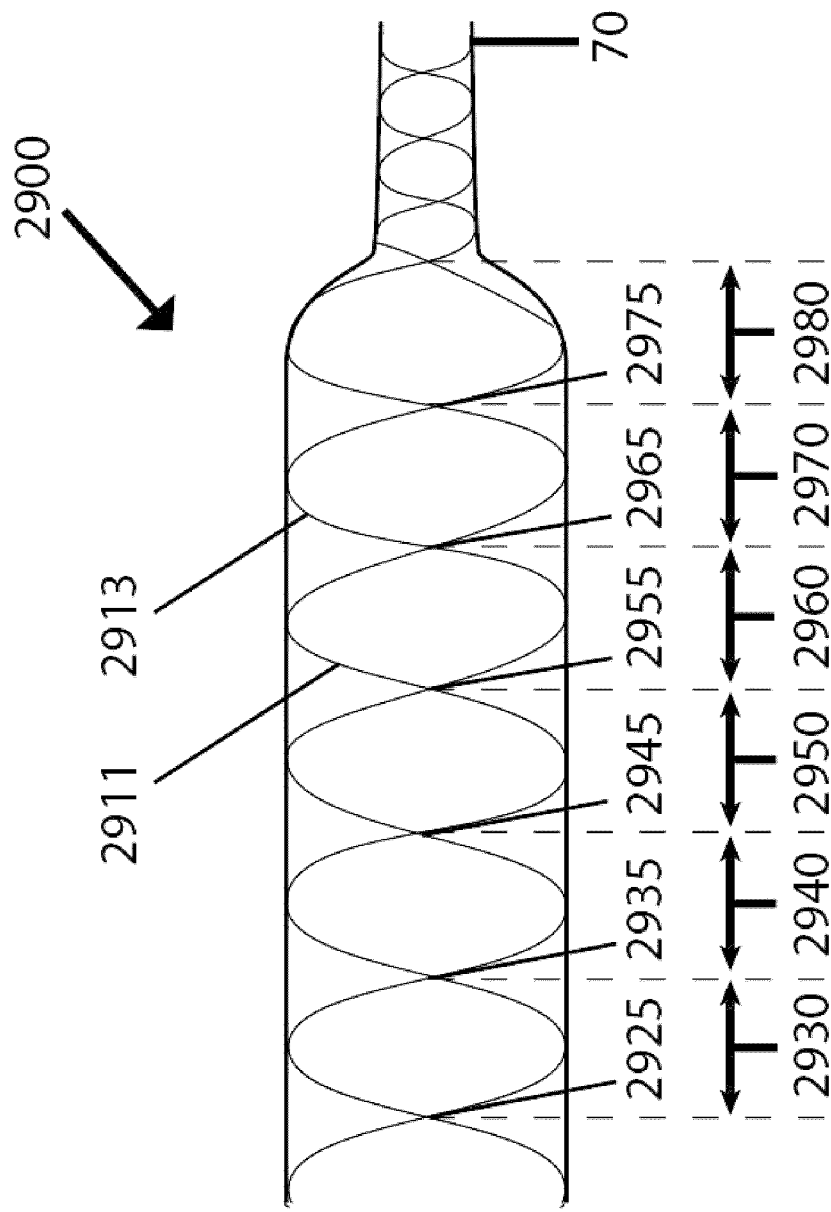
FIG. 8H is a schematic side elevational view of another example embodiment of a distal portion of a vascular treatment device illustrating an example pattern of radiopaque filaments.
Figure 81:
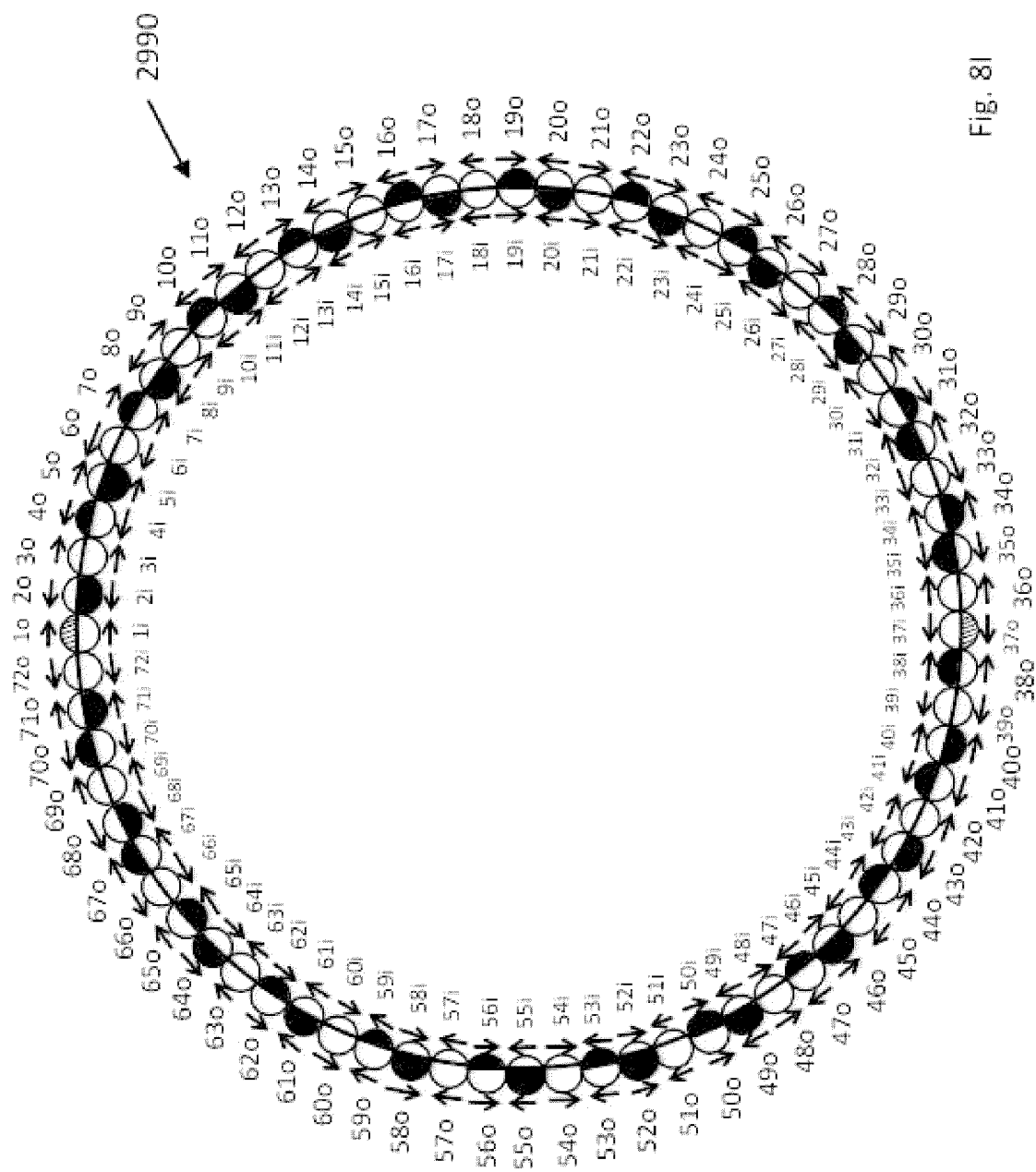

FIG. 8H is a schematic side elevational view of another example embodiment of a distal portion 2900 of a vascular treatment device illustrating an example pattern of radiopaque filaments, for example under x-ray. The distal portion 2900 may be the distal portion 100 of the device 10, 20, 30, or 40. The distal portion 2900 includes, in an expanded state, a proximal neck 70 and a cylindrical wide-mouthed textile structure 75 including shape-memory filaments and radiopaque filaments. The textile structure 75 expands radially outwardly from proximal to distal, and then stays at the larger diameter until the distal end. The distal portion 2900 includes, in an expanded state, two radiopaque filaments 2911, 2913 that are interlaced in the form a double sine wave like a "double helix" at least under x-ray. The pattern of radiopacity can allow an operator of a device comprising the distal portion 2900 to visualize and identify the distal portion 2900 at least under x-ray. In some embodiments, the double helix includes troughs and peaks, for example at the sides of the distal portion 2900 that the double helix at least partially create. In FIG. 8H, the helical intersection points 2925, 2935, 2945, 2955, 2965, 2975 are substantially uniformly spaced by distances 2930, 2940, 2950, 2960, 2970, 2980, which can allow the distal portion 2900 to serve as an angiographic measurement ruler. For example, the distances 2930, 2940, 2950, 2960, 2970, 2980 can help an operator to measure the length of blood clots, the neck of an aneurysm, the length of a stenosis, etc. In some embodiments, distances between helical intersection points in the proximal neck 70 has different dimensions than the double helix in the rest of the large diameter part of the distal portion 2900, which may serve as an identifier of the proximal neck 70 beyond which the distal portion 2900 should not be deployed.

FIG. 8I is a schematic diagram illustrating an example setup of a braid carrier mechanism 2990 for forming the distal portion 2800 of FIG. 8H. In FIG. 8I, the half circles with dark shading indicate individual carriers 155 including spools 154 including shape memory filaments 156, the half circles with hatched shading indicate individual carriers 155 including spools 154 including radiopaque filaments 156, and the half circles with no shading indicate spindles without spools 154 or filaments 156. In the arrangement illustrated in FIG. 8I, spindles 2i, 4o, 5i, 7o, 8i, 10o, 11i, 13o, 14i, 16o, 17i, 19o, 20i, 22o, 23i, 25o, 26i, 28o, 29i, 31o, 32i, 34o, 35i, 38i, 40o, 41i, 43o, 44i, 46o, 47i, 49o, 50i, 52o, 53i, 55o, 56i, 58o, 59i, 61o, 62i, 64o, 65i, 67o, 68i, 70o, 71i include spools 154 including shape-memory material (e.g., 46 of the 48 filaments 156 comprise shape-memory material), the spindles 1o and 37o include spools 154 including radiopaque material (e.g., 2 of the 48 filaments 156 comprise radiopaque material), and the remaining spindles are empty. The braid carrier mechanism 2990 setup illustrated in FIG. 8I can generate a pattern of radiopacity described with respect to FIG. 8H, for example a double sine wave or double helix pattern. The radiopaque filaments 156 form two sine waves having a spindle adjacency of about 5° (360°/72), a filament adjacency of about 7.5° (360°/48), and a radiopaque filament material adjacency of about 180° (360°/2). Although some examples of the carrier braider 150 with 48 spindles 153 or individual carriers 155 are provided herein, some embodiments of the carrier braider 150 may include 6 to 144 spindles 153 or individual carriers 155 in accordance with the values provided above and/or carrier braiders 150 that have 6, 12, 24, 36, 48, 60, 72, 84, 96, 120, 144, etc. spindles 153 or individual carriers 155, and the number and positioning of radiopaque filaments 156 can remain as provided in the example braid carrier mechanism 2990 setup.

Figure 8J:
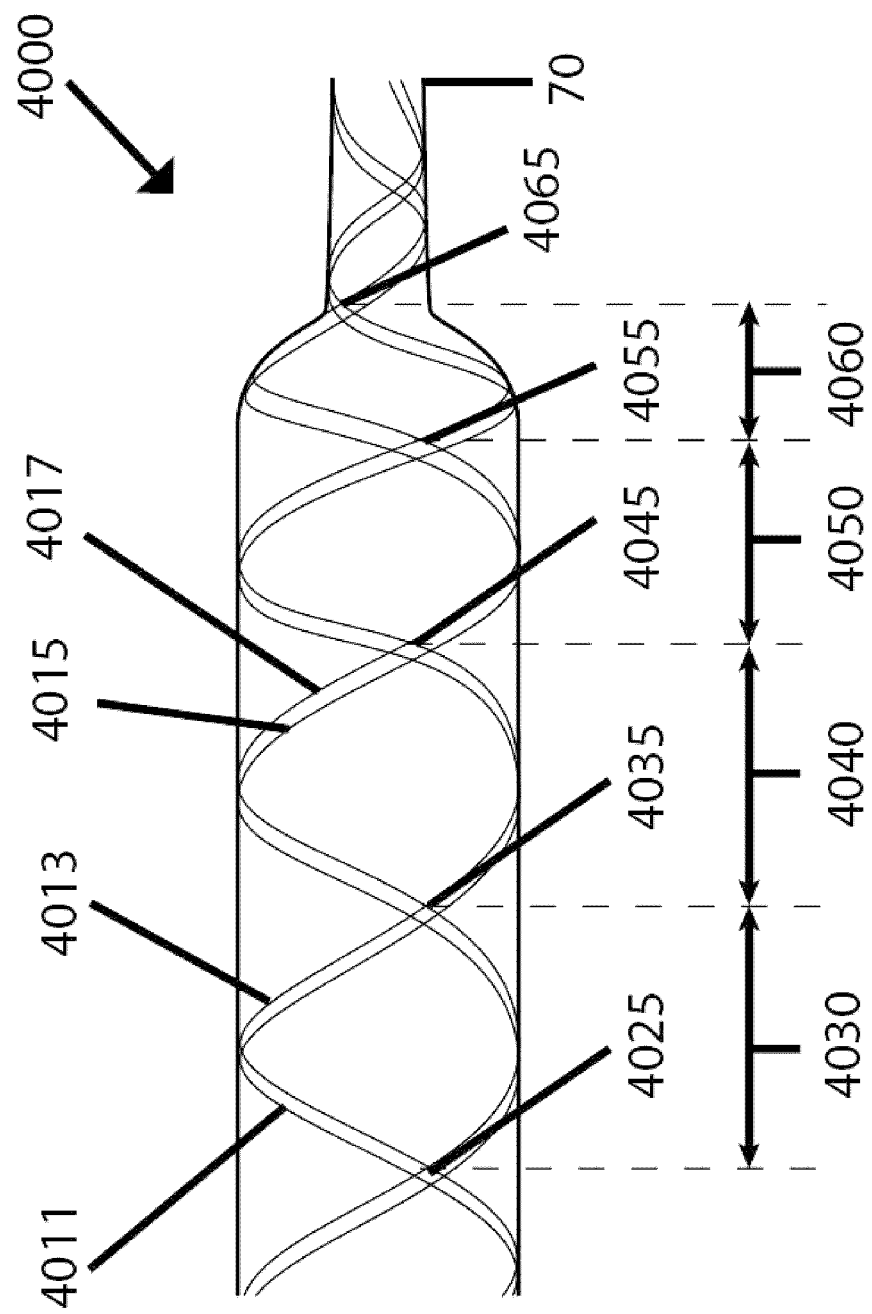
FIG. 8J is a schematic side elevational view of yet another example embodiment of a distal portion of a vascular treatment device illustrating an example pattern of radiopaque filaments.

FIG. 8J is a schematic side elevational view of yet another example embodiment of a distal portion 4000 of a vascular treatment device illustrating an example pattern of radiopaque filaments, for example under x-ray. The distal portion 4000 may be the distal portion 100 of the device 10, 20, 30, or 40. The distal portion 4000 includes, in an expanded state, a proximal neck 70 and a cylindrical wide-mouthed textile structure 75 including shape-memory filaments and radiopaque filaments. The textile structure 75 expands radially outwardly from proximal to distal, and then stays at the larger diameter until the distal end. The distal portion 4000 includes, in an expanded state, two pairs of radiopaque filaments 4011, 4013 and 4015, 1017 that are interlaced in the form a paired double sine wave like a "dual double helix" at least under x-ray. The pattern of radiopacity can allow an operator of a device comprising the distal portion 4000 to visualize and identify the distal portion 4000 at least under x-ray. In some embodiments, the dual double helix includes troughs and peaks, for example at the sides of the distal portion 4000 that the dual double helix at least partially create. In FIG. 8J, the helical intersection points 4025, 4035, 4045, 4055 are substantially uniformly spaced by distances 4030, 4040, 4050, which can allow the distal portion 4000 to serve as an angiographic measurement ruler. For example, the distances 4030, 4040, 4050 can help an operator to measure the length of blood clots, the neck of an aneurysm, the length of a stenosis, etc. In some embodiments, a distance 4060 between points 4055, 4065 at least partially along the proximal neck 70 has different dimensions than the dual double helix in the rest of the large diameter part of the distal portion 4000, which may serve as an identifier of the proximal neck 70 beyond which the distal portion 4000 should not be deployed.

Figure 8K:
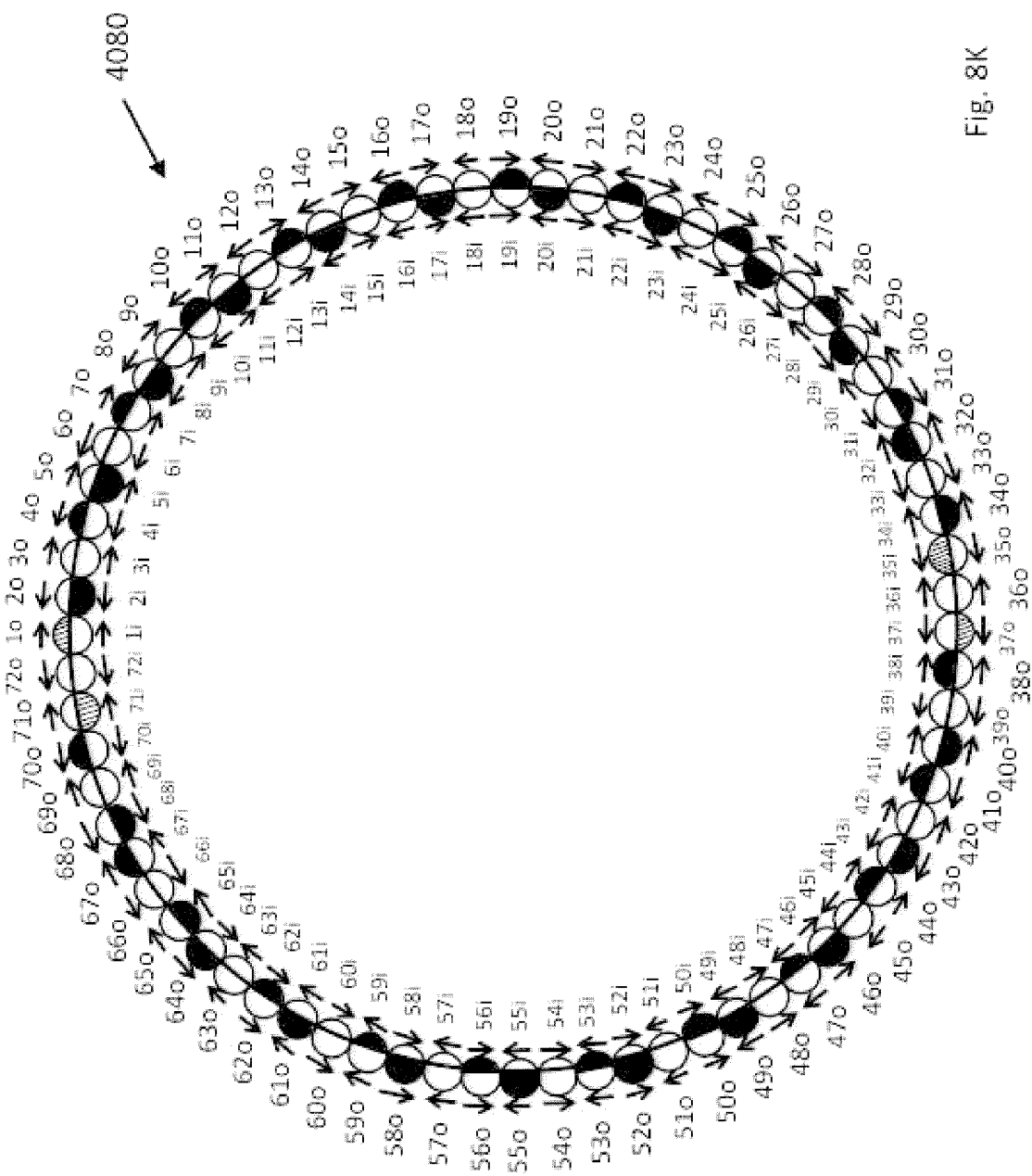
FIG. 8K is a schematic diagram illustrating an example setup of a braid carrier mechanism for forming the distal portion of FIG. 8J.

FIG. 8K is a schematic diagram illustrating an example setup of a braid carrier mechanism 4080 for forming the distal portion 4000 of FIG. 8J. In FIG. 8K, the half circles with dark shading indicate individual carriers 155 including spools 154 including shape memory filaments 156, the half circles with hatched shading indicate individual carriers 155 including spools 154 including radiopaque filaments 156, and the half circles with no shading indicate spindles without spools 154 or filaments 156. In the arrangement illustrated in FIG. 8K, spindles 2i, 4o, 5i, 7o, 8i, 10o, 11i, 13o, 14i, 16o, 17i, 19o, 20i, 22o, 23i, 25o, 26i, 28o, 29i, 31o, 32i, 34o, 38i, 40o, 41i, 43o, 44i, 46o, 47i, 49o, 50i, 52o, 53i, 55o, 56i, 58o, 59i, 61o, 62i, 64o, 65i, 67o, 68i, 70o include spools 154 including shape-memory material (e.g., 44 of the 48 filaments 156 comprise shape-memory material), the spindles 1o, 35i, 37o, 71i include spools 154 including radiopaque material (e.g., 4 of the 48 filaments 156 comprise radiopaque material), and the remaining spindles are empty. The braid carrier mechanism 4080 setup illustrated in FIG. 8K can generate a pattern of radiopacity described with respect to FIG. 8J, for example pairs of double sine waves or a dual double helix pattern. Although some examples of the carrier braider 150 with 48 spindles 153 or individual carriers 155 are provided herein, some embodiments of the carrier braider 150 may include 6 to 144 spindles 153 or individual carriers 155 in accordance with the values provided above and/or carrier braiders 150 that have 6, 12, 24, 36, 48, 60, 72, 84, 96, 120, 144, etc. spindles 153 or individual carriers 155, and the number and positioning of radiopaque filaments can remain as provided in the example braid carrier mechanism 4080 setup.

Figure 8L:
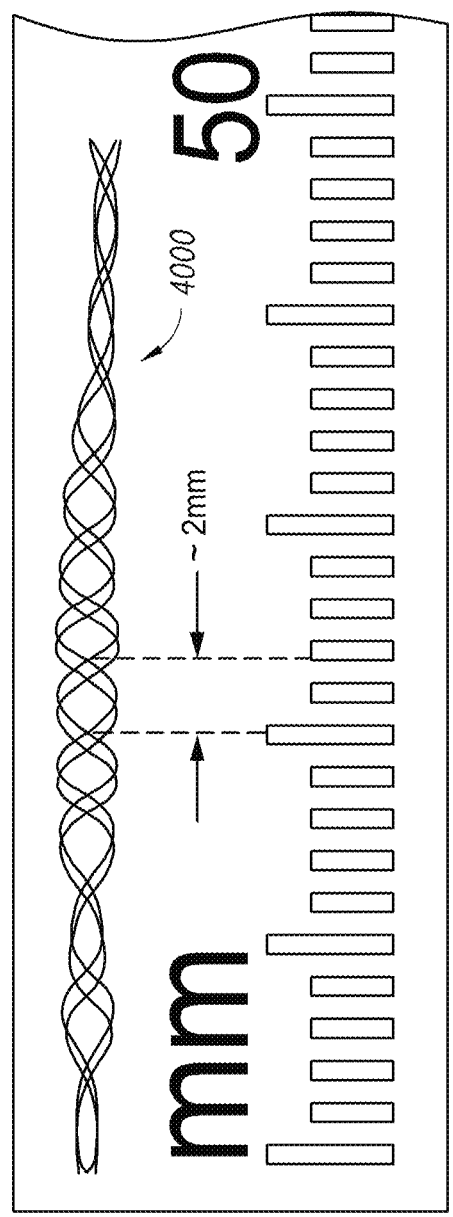
FIG. 8L is an x-ray photograph illustrating an example of a plurality of radiopaque filaments of the distal portion of FIG. 8J.

FIG. 8L is an x-ray photograph illustrating an example of a plurality of radiopaque filaments of the distal portion 4000 of FIG. 8J, in which the radiopaque filaments 4011, 4013, 4015, 4017 form a dual double helix or four sine waves, pairs of which are offset by about 180° and the sine waves in each pair being offset from each other by about 7.5°. In some embodiments, crossings of the radiopaque filaments 4011, 4013, 4015, 4017 of the distal portion 4000 can be used as a rough measurement guide. For example, in FIG. 8L, the spacing between helical intersections points is about 2 mm, which can help serve as an angiographic measurement ruler. For example, the distal portion 4000 can help measure the length of blood clots, the neck of an aneurysm, the length of a stenosis, etc.

Figure 8M:
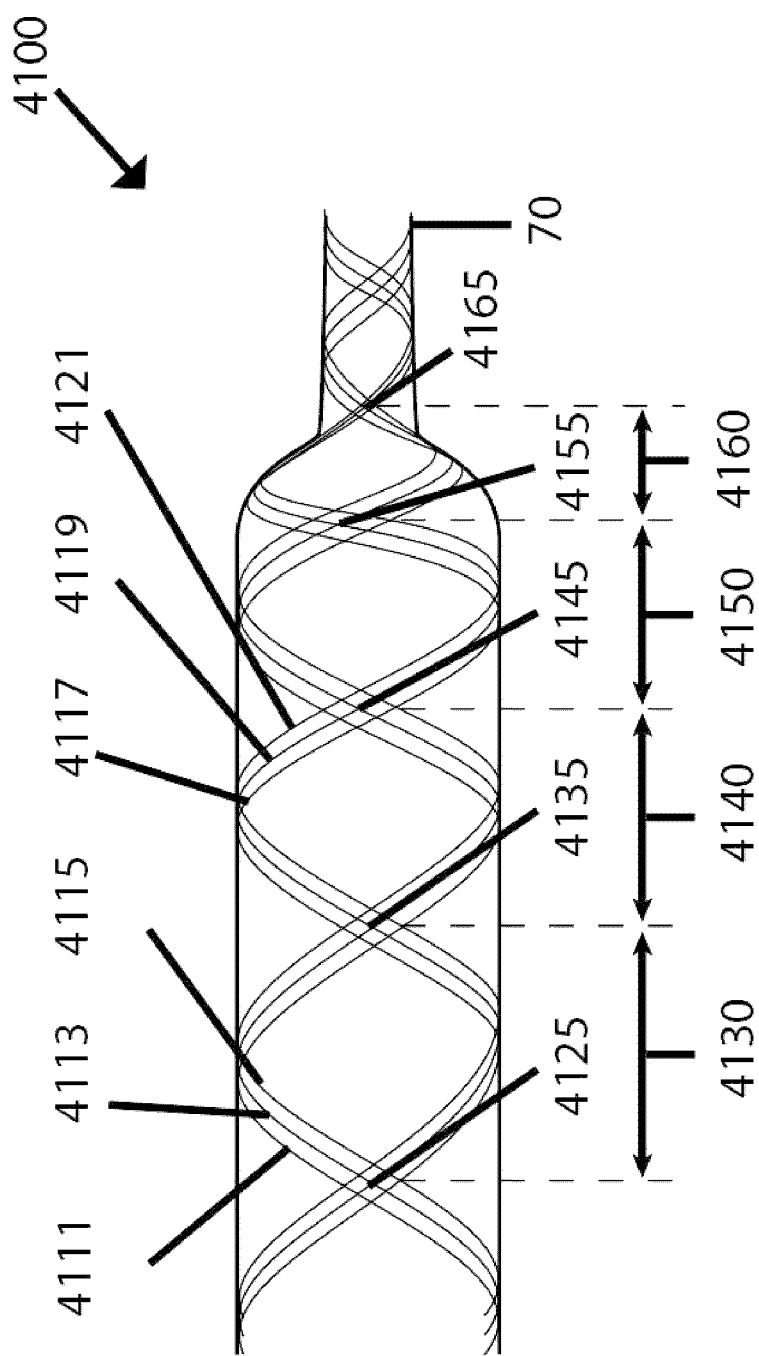
FIG. 8M is a schematic side elevational view of still another example embodiment of a distal portion of a vascular treatment device illustrating an example pattern of radiopaque filaments.

FIG. 8M is a schematic side elevational view of still another example embodiment of a distal portion 4100 of a vascular treatment device illustrating an example pattern of radiopaque filaments, for example under x-ray. The distal portion 4100 may be the distal portion 100 of the device 10, 20, 30, or 40. The distal portion 4100 includes, in an expanded state, a proximal neck 70 and a cylindrical wide-mouthed textile structure 75 including shape-memory filaments and radiopaque filaments. The textile structure 75 expands radially outwardly from proximal to distal, and then stays at the larger diameter until the distal end. The distal portion 4100 includes, in an expanded state, two trios of radiopaque filaments 4111, 4113, 4115 and 4117, 4119, 4121 that are interlaced in the form a paired triple sine wave like a "reinforced double helix" at least under x-ray. The pattern of radiopacity can allow an operator of a device comprising the distal portion 4100 to visualize and identify the distal portion 4100 at least under x-ray. In some embodiments, the reinforced double helix includes troughs and peaks, for example at the sides of the distal portion 4100 that the reinforced double helix at least partially creates. In FIG. 8M, the intersection points 4125, 4135, 4145 along the reinforced double helix are substantially uniformly spaced by distances 4130, 4140, 4150, which can allow the distal portion 4100 to serve as an angiographic measurement ruler. For example, the distances 4130, 4140, 4150 can help an operator to measure the length of blood clots, the neck of an aneurysm, the length of a stenosis, etc. In some embodiments, a distance 4160 between points 4155, 4165 at least partially along the proximal neck 70 has different dimensions than the reinforced double helix in the rest of the large diameter part of the distal portion 4100, which may serve as an identifier of the proximal neck 70 beyond which the distal portion 4100 should not be deployed.

Figure 8N:
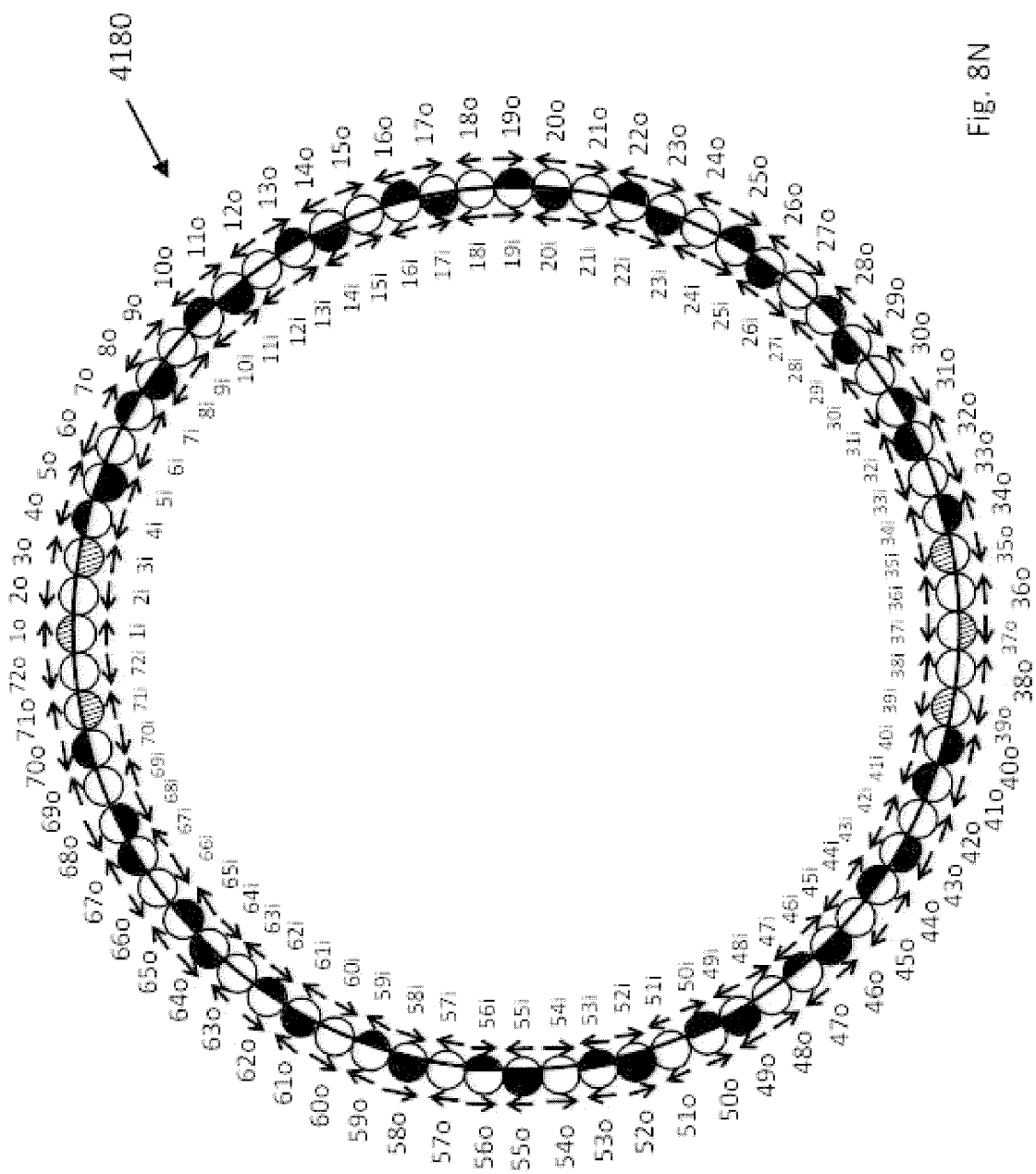
FIG. 8N is a schematic diagram illustrating an example setup of a braid carrier mechanism for forming the distal portion of FIG. 8M.
Figure 80:
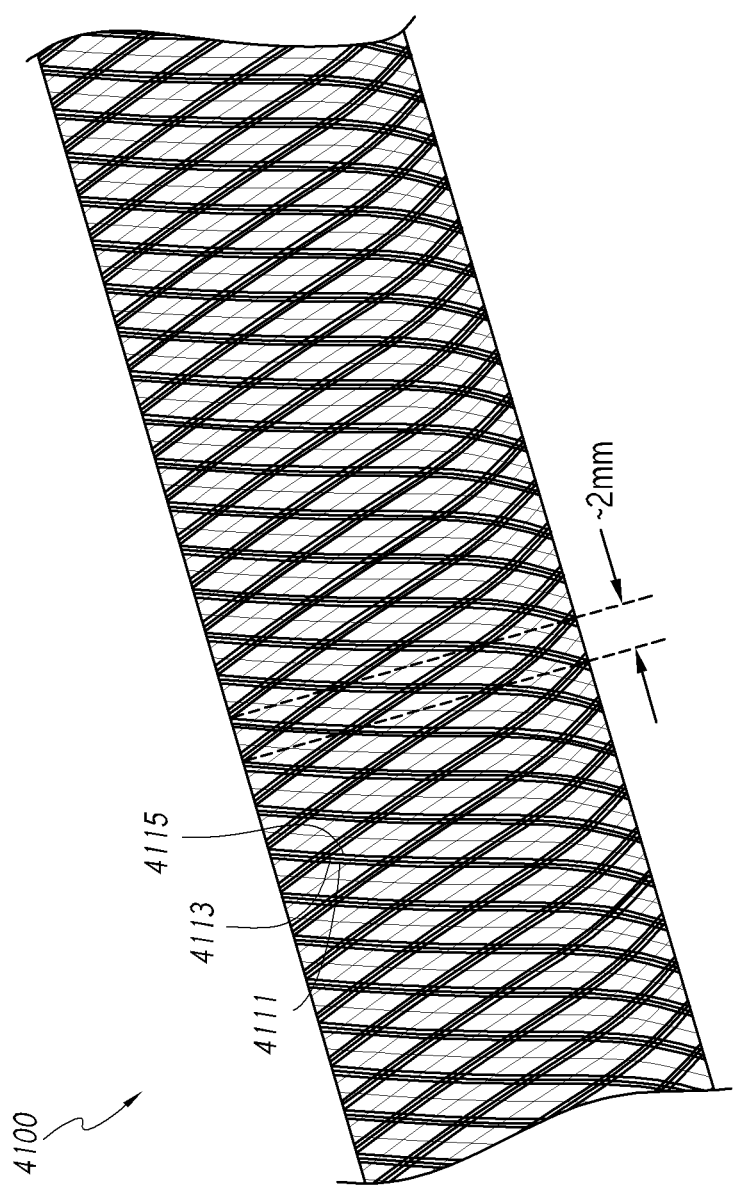

FIG. 8N is a schematic diagram illustrating an example setup of a braid carrier mechanism 4180 for forming the distal portion 4100 of FIG. 8M. In FIG. 8N, the half circles with dark shading indicate individual carriers 155 including spools 154 including shape memory filaments 156, the half circles with hatched shading indicate individual carriers 155 including spools 154 including radiopaque filaments 156, and the half circles with no shading indicate spindles without spools 154 or filaments 156. In the arrangement illustrated in FIG. 8N, spindles 4o, 5i, 7o, 8i, 10o, 11i, 13o, 14i, 16o, 17i, 19o, 20i, 22o, 23i, 25o, 26i, 28o, 29i, 31o, 32i, 34o, 40o, 41i, 43o, 44i, 46o, 47i, 49o, 50i, 52o, 53i, 55o, 56i, 58o, 59i, 61o, 62i, 64o, 65i, 67o, 68i, 70o include spools 154 including shape-memory material (e.g., 42 of the 48 filaments 156 comprise shape-memory material), the spindles 1o, 3i, 35i, 37o, 39i, 71i include spools 154 including radiopaque material (e.g., 6 of the 48 filaments 156 comprise radiopaque material), and the remaining spindles are empty. The braid carrier mechanism 4180 setup illustrated in FIG. 8N can generate a pattern of radiopacity described with respect to FIG. 8M, for example pairs of triple sine waves or a reinforced double helix pattern. Although some examples of the carrier braider 150 with 48 spindles 153 or individual carriers 155 are provided herein, some embodiments of the carrier braider 150 may include 6 to 144 spindles 153 or individual carriers 155 in accordance with the values provided above and/or carrier braiders 150 that have 6, 12, 24, 36, 48, 60, 72, 84, 96, 120, 144, etc. spindles 153 or individual carriers 155, and the number and positioning of the radiopaque filaments can remain as provided in the example braid carrier mechanism 4180 setup.

FIG. 8O is a schematic perspective view illustrating a plurality of radiopaque filaments of the distal portion 4100 of FIG. 8M. The distal portion 4100 includes a plurality of shape-memory filaments and a plurality of radiopaque filaments over a mandrel, in which the radiopaque filaments form a reinforced double helix or in which the radiopaque filaments form pairs of sine waves trios, one of which includes the radiopaque filaments 4111, 4113, 4115. The trios are offset by about 180° and the sine waves in each trio are offset from each other by about 7.5°. In some embodiments, crossings of the radiopaque filaments of the distal portion 4100 can be used as a rough measurement guide. For example, in FIG. 8O, the spacing between the crossings of the helical intersections points is about 2 mm, which can help serve as an angiographic measurement ruler. For example, the distal portion 4100 can help measure the length of blood clots, the neck of an aneurysm, the length of a stenosis, etc.

Figure 8P:
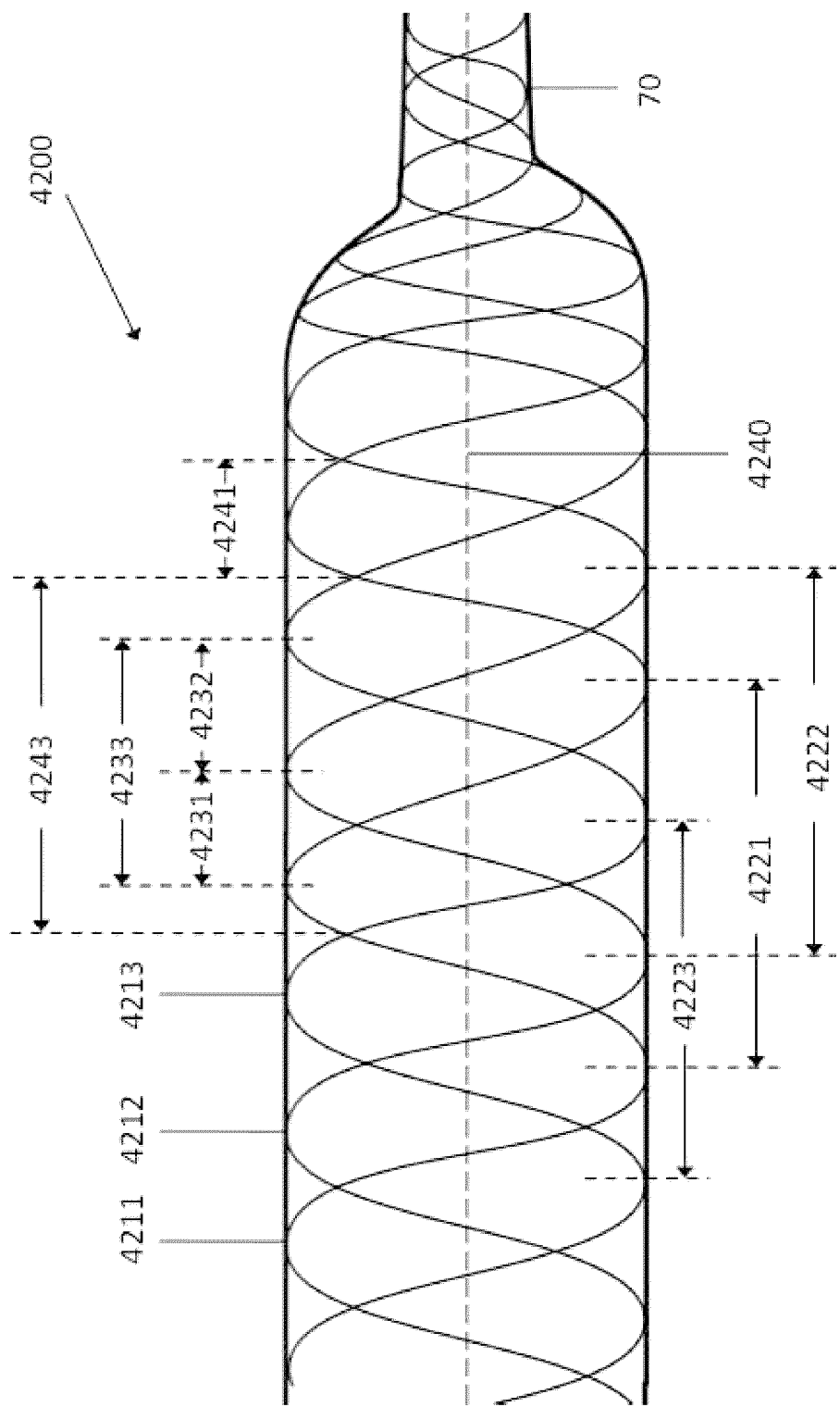
FIG. 8P is a schematic side elevational view of yet another example embodiment of a distal portion of a vascular treatment device illustrating an example pattern of radiopaque filaments.
Figure 8Q:
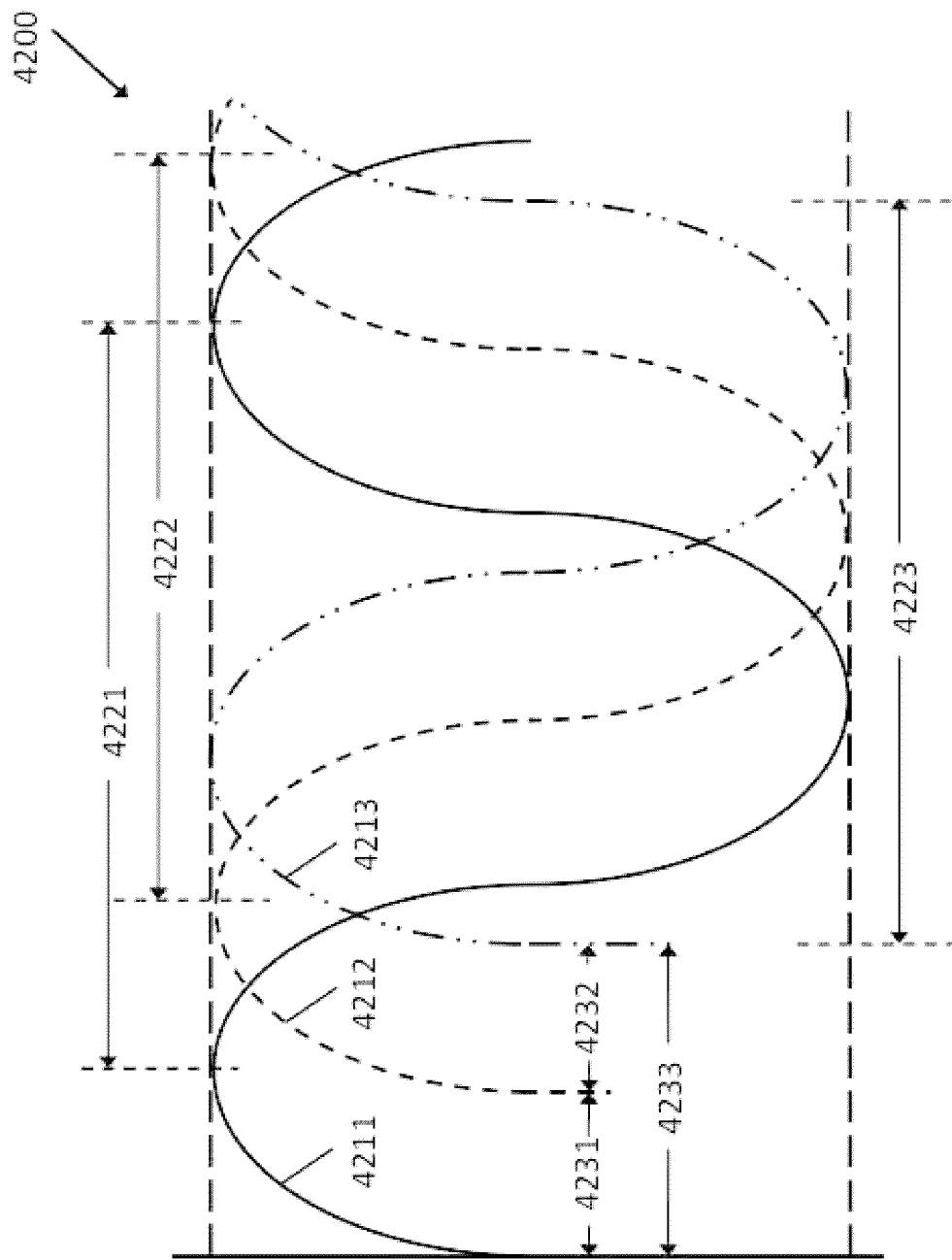
FIG. 8Q is a magnified view of the radiopaque filaments of the distal portion of FIG. 8P.

FIG. 8P is a schematic side elevational view of yet still another example embodiment of a distal portion 4200 of a vascular treatment device, for example of the distal portion 100 of the device 10, 20, 30, or 40. The distal portion 4200 includes, in an expanded state, a proximal neck 70 and a cylindrical wide-mouthed textile structure 75 including shape-memory filaments and radiopaque filaments. The textile structure 75 expands radially outwardly from proximal to distal, and then stays at the larger diameter until the distal end. The distal portion 4200 includes three radiopaque filaments 4211, 4212, 4213 that form a three sine waves like a "three phase helix" at least under x-ray. FIG. 8Q is a magnified view of the radiopaque filaments 4211, 4212, 4213 of the distal portion 4200 of FIG. 8P, for example under x-ray. FIG. 8Q illustrates the filament 4211 as a solid line, the filament 4212 as a dashed line, and the filament 4213 as a dash-dot-dot line for easier differentiation between the filaments 4211, 4212, 4213. In some embodiments, the first radiopaque filament 4211 forms a sine wave having a phase A, the second radiopaque filament 4212 forms a sine wave having a phase B, and the third radiopaque filament 4213 forms a sine wave having a phase C. In some embodiments, the three phase helix includes troughs and peaks, for example at the sides of the distal portion 4200 that the three sine waves at least partially create.

The distance between two similarly situated points on a sine wave (e.g., a first intersection of a sine wave and the central longitudinal axis of the distal portion and the next intersection of the sine wave with the central longitudinal axis after forming a peak and a trough, the distance between a first peak of a sine wave and the next peak of the sine wave, the distance between a first trough of the sine wave and the next trough of the sine wave, etc.) is called the pitch or period or wavelength or cycle of the sine wave. Embodiments comprising a three phase sine wave include three pitches: the sine wave formed by the radiopaque filament 4211 has a pitch 4221, the sine wave formed by the radiopaque filament 4212 has a pitch 4222, and the sine wave formed by the radiopaque filament 4213 has a pitch 4223. FIG. 8P shows the pitches 4221, 4222, 4223 as the distances between the lower peaks of the respective sine waves, and FIG. 8Q shows the pitches 4221, 4222 as the distances between the upper peaks of the respective sine waves. In the embodiments illustrated in FIGS. 8P and 8Q, the pitches of the sine waves formed by the radiopaque filaments 4211, 4212, 4213 have substantially uniform dimensions (e.g., pitches), except near the proximal neck 70, although the sine waves may have differing dimensions (e.g., pitches).

In some embodiments, the distance between each trough or peak of a radiopaque filament 4211, 4212, 4213 with another trough or peak of an adjacent radiopaque filament of the three phase helix is called a phase shift. In FIG. 8P, phase A is offset from phase B by about 7.5° (shown by the distance 4231), phase B is offset from phase C by about 7.5° (shown by the distance 4232), and phase A is offset from phase C by about 15° (shown by the distance 4233). FIG. 8P shows the phase shifts 4231, 4232, 4233 as the distances between the upper peaks of the respective sine waves, and FIG. 8Q shows the phase shifts 4231, 4232, 4233 as the distances between the centers following upper peaks of the respective sine waves. The pattern of radiopacity can allow an operator of a device comprising the distal portion 4200 to visualize and identify the distal portion 4200 at least under x-ray. In FIGS. 8P and 8Q, the intersection points along the three phase helix are substantially uniformly spaced by distances 4241 or multiples thereof (e.g., the distance 4243 is the distance between three intersection points, the distance 4242 in FIG. 8S is the distance between two intersection points, etc.), which can allow the distal portion 4200 to serve as an angiographic measurement ruler. For example, the distances 4241, 4242, 4243 can help an operator to measure the length of blood clots, the neck of an aneurysm, the length of a stenosis, etc. In some embodiments, distances between intersection points at least partially along the three phase helix near the proximal neck 70 have different dimensions than the three phase helix in the rest of the large diameter portion of the distal portion 4200, which may serve as an identifier of the proximal neck 70 beyond which the distal portion 4200 should not be deployed.

Figure 8R:
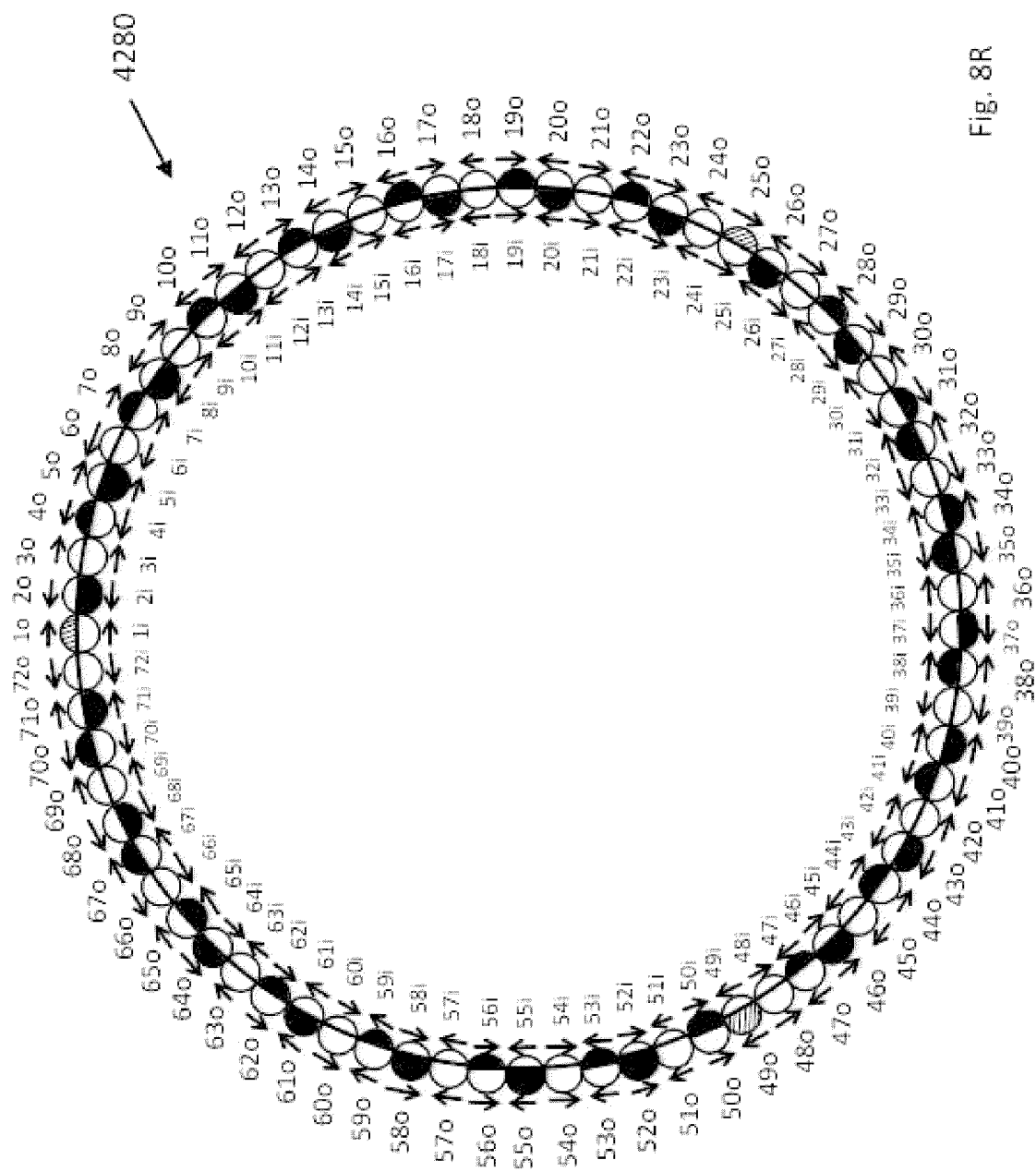
FIG. 8R is a schematic diagram illustrating an example setup of a braid carrier mechanism for forming the distal portion of FIG. 8P.
Figure 8S:
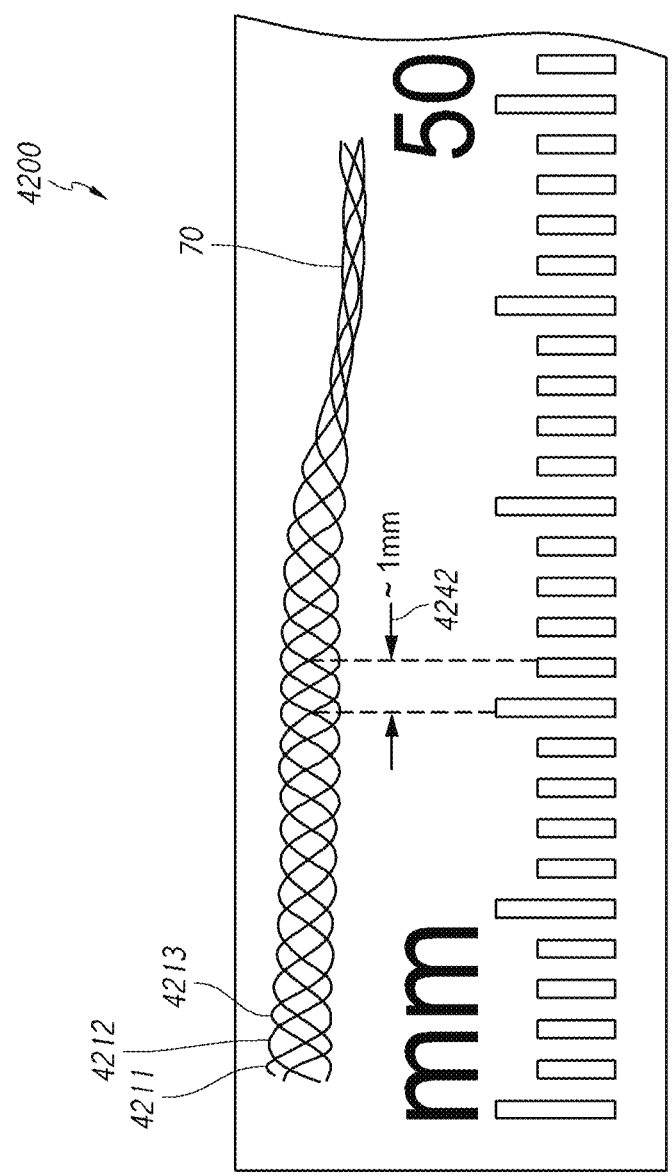
FIG. 8S is an x-ray photograph illustrating an example of a plurality of radiopaque filaments of the distal portion of FIG. 8P.

FIG. 8R is a schematic diagram illustrating an example setup of a braid carrier mechanism 4280 for the distal portion 4200 of FIG. 8P. In FIG. 8R, the half circles with dark shading indicate individual carriers 155 including spools 154 including shape memory filaments 156, the half circles with hatched shading indicate individual carriers 155 including spools 154 including radiopaque filaments 156, and the half circles with no shading indicate spindles without spools 154 or filaments 156. In the arrangement illustrated in FIG. 8R, spindles 2i, 4o, 5i, 7o, 8i, 10o, 11i, 13o, 14i, 16o, 17i, 19o, 20i, 22o, 23i, 26i, 28o, 29i, 31o, 32i, 34o, 35i, 37o, 40o, 41i, 43o, 44i, 46o, 47i, 50i, 52o, 53i, 55o, 56i, 58o, 59i, 61o, 62i, 64o, 65i, 67o, 68i, 70o, 71i include spools 154 including shape-memory material (e.g., 45 of the 48 filaments 156 comprise shape-memory material), the spindles 1o, 25o, 490 include spools 154 including radiopaque material (e.g., 3 of the 48 filaments 156 comprise radiopaque material), and the remaining spindles are empty. The braid carrier mechanism 4280 setup illustrated in FIG. 8Q can generate a pattern of radiopacity described with respect to FIG. 8P, for example a three phase-shifted sine waves or a three phase helix pattern. Although some examples of the carrier braider 150 with 48 spindles 153 or individual carriers 155 are provided herein, some embodiments of the carrier braider 150 may include 6 to 144 spindles 153 or individual carriers 155 in accordance with the values provided above and/or carrier braiders 150 that have 6, 12, 24, 36, 48, 60, 72, 84, 96, 120, 144, etc. spindles 153 or individual carriers 155, and the number and positioning of the radiopaque filaments can remain as provided in the example braid carrier mechanism 4280 setup.

FIG. 8S is an x-ray photograph illustrating an example of a plurality of radiopaque filaments 4211, 4212, 4213 of the distal portion 4200 of FIG. 8P, in which the radiopaque filaments 4211, 4212, 4213 form a three phase helix, or in which the radiopaque filaments form three sine waves offset by about 120°. In some embodiments, crossings or intersection points of the radiopaque filaments 4211, 4212, 4213 of the distal portion 4200 can be used as a rough measurement guide. For example, in FIG. 8S, the distance 4242 between the three intersections points is about 1 mm, which can allow the distal portion 4200 to serve as an angiographic measurement ruler. For example, the distance 4242 can an operator to measure the length of blood clots, the neck of an aneurysm, the length of a stenosis, etc. Use of other distances are also possible (e.g., a distance 4241 between two intersection points (e.g., as shown in FIG. 8P), a distance 4243 between four intersection points (e.g., as shown in FIG. 8P), distances between similar portions of one or more sine waves (e.g., peaks, troughs, etc.), etc.).

Figures 1, 8T:
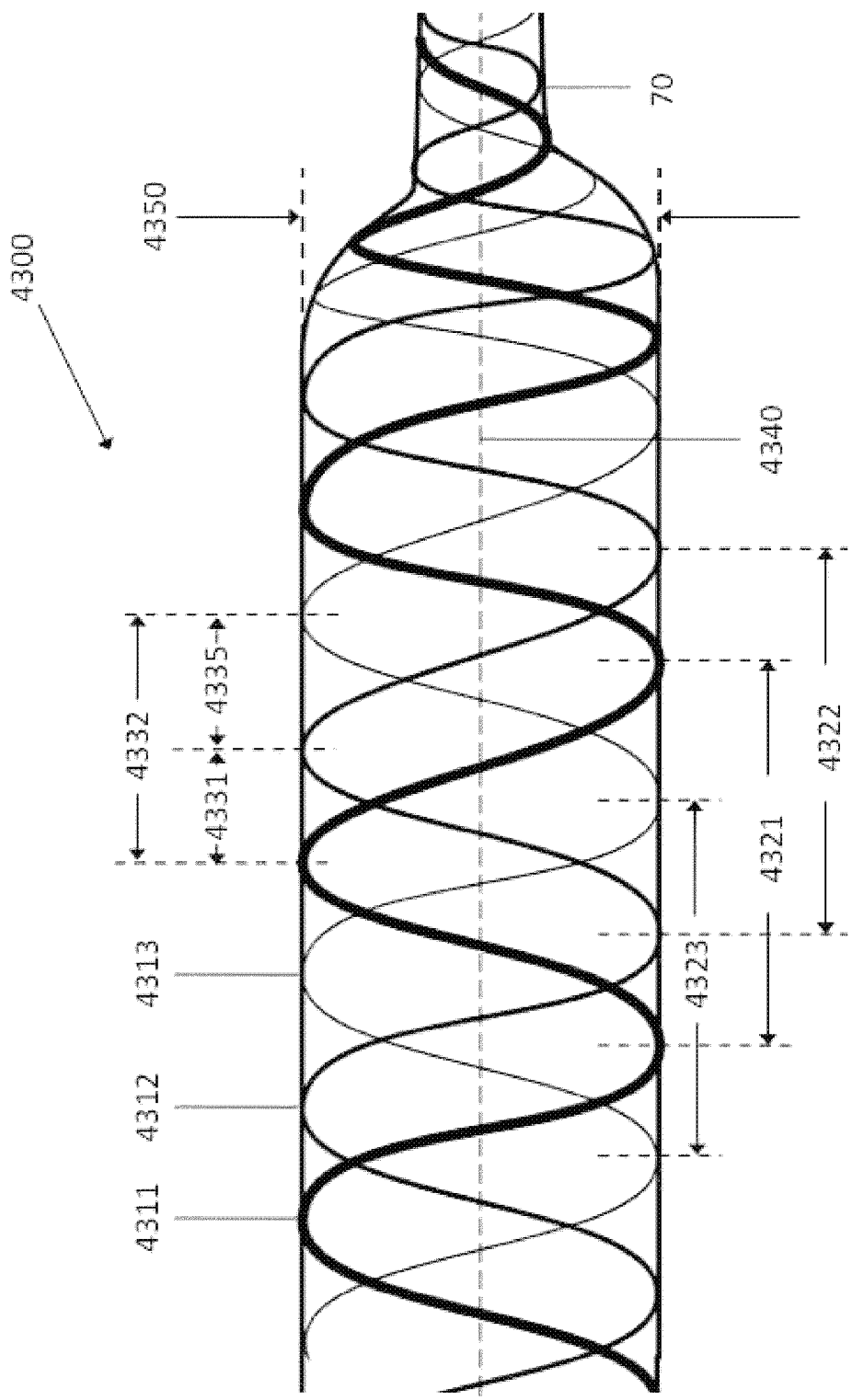
Figures 2, 8T:
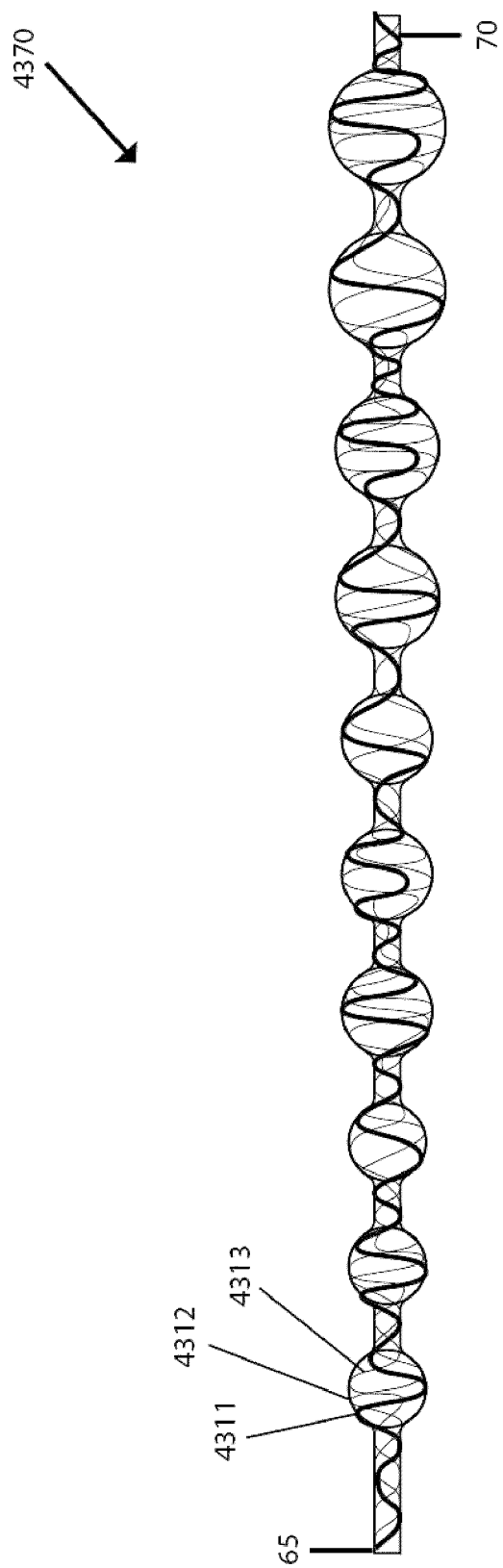
Figures 3, 8T:
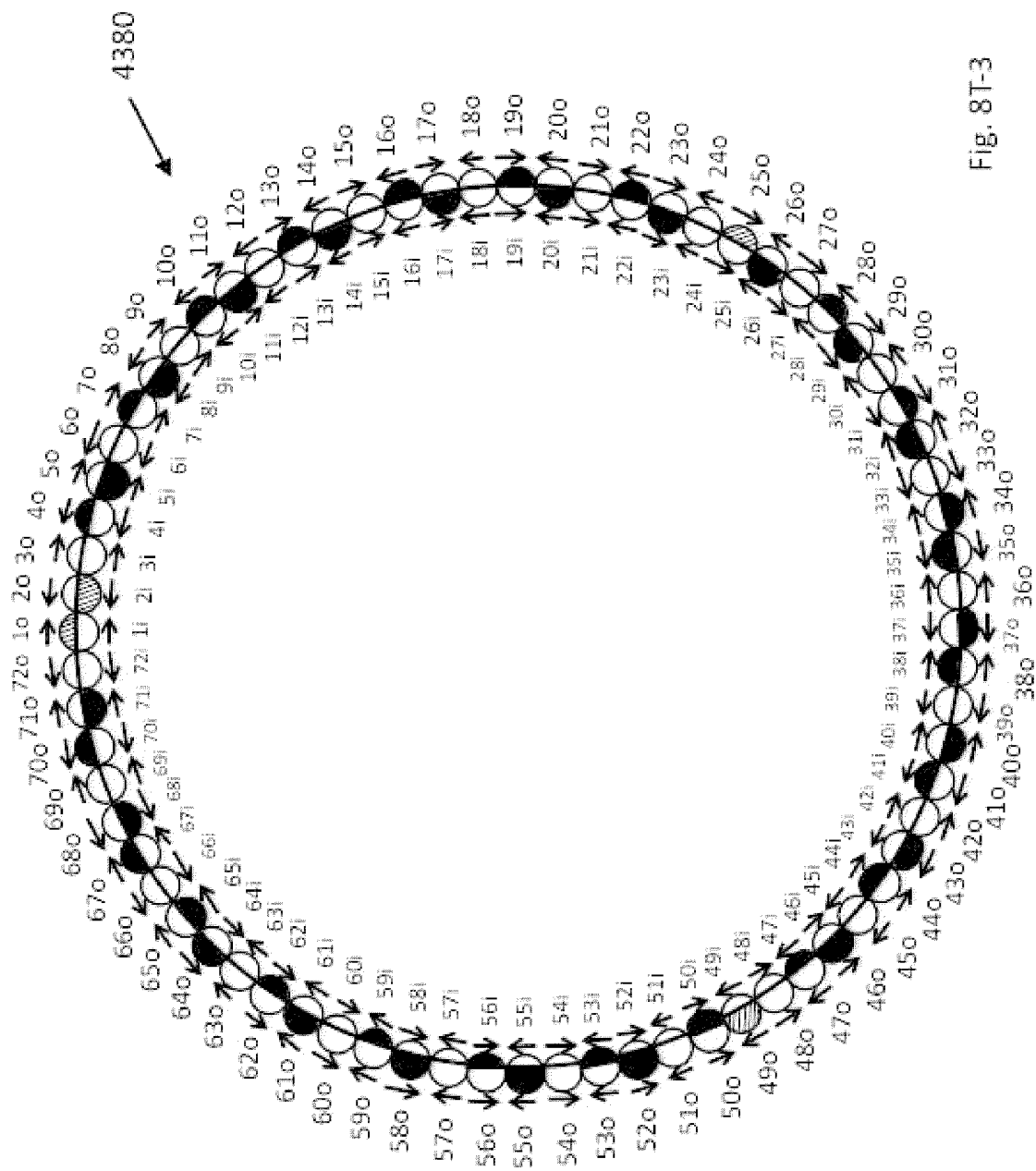
Figures 4, 8T:
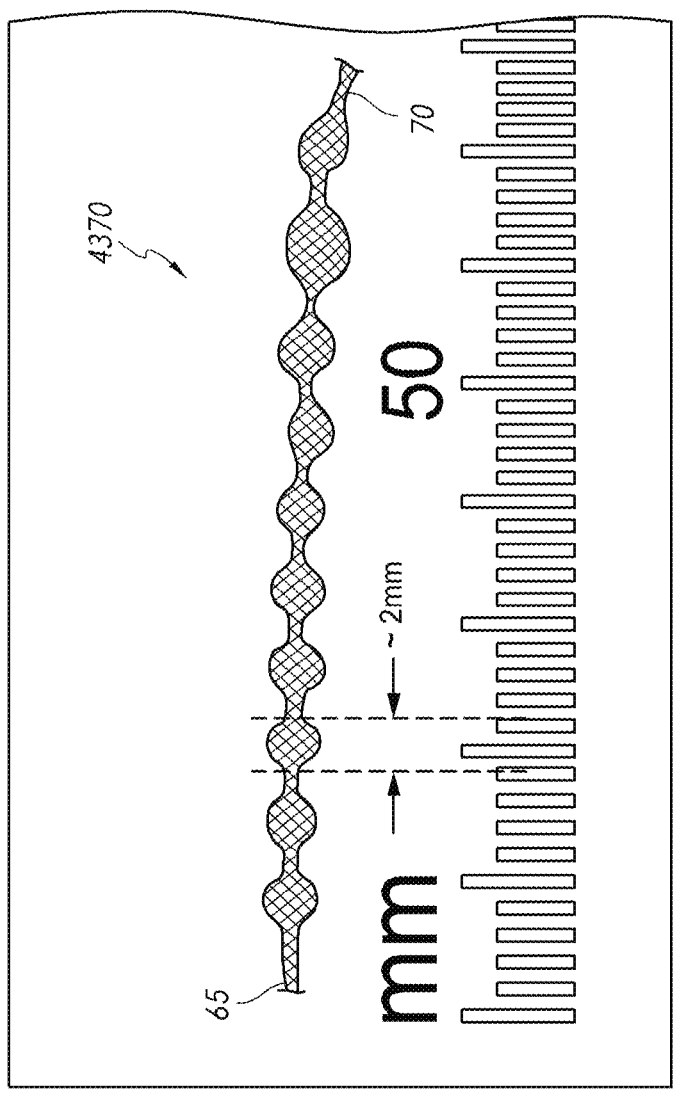

FIG. 8T-1 is a schematic side elevational view of still yet another example embodiment of a distal portion 4300 of a vascular treatment device illustrating an example pattern of radiopaque filaments, for example under x-ray. The distal portion 4300 may be the distal portion 100 of the device 10, 20, 30, or 40. The distal portion 4300 includes, in an expanded state, a proximal neck 70 and a cylindrical widemouthed textile structure including shape-memory filaments and radiopaque filaments. The textile structure 75 expands radially outwardly from proximal to distal, and then stays at the larger diameter until the distal end. FIG. 8T-1 also illustrates an example dimension 4350 (e.g., diameter) of the cylindrical wide-mouthed textile structure, which also corresponds to an amplitude of the sine waves created by the radiopaque filaments (e.g., being twice the amplitude, or a radius being equal to the amplitude (e.g., as measured from the longitudinal axis 4340)).

FIG. 8T-2 is a schematic side elevational view of another example embodiment of the distal portion 4370 of a vascular treatment device illustrating an example pattern of radiopaque filaments 4311, 4312, 4313, for example under x-ray. The distal portion 4370 may be the distal portion 100 of the device 10, 20, 30, or 40. In FIG. 8T-2, the distal portion 4370 comprises a plurality of woven bulbs, woven necks, a proximal neck 70, and a distal neck tip 65, for example similar to the distal portion 1100 of FIG. 2B.

The distal portions 4300, 4370 include, in an expanded state, radiopaque filaments 4311, 4312, 4313 that are interlaced in the form a three phase helix at least under x-ray. One or more of the filaments 4311, 4312, 4313 may be reinforced (e.g., the filament 4311) with a second radiopaque filament and the distal portions 4300, 4370 may include additional radiopaque filaments that are non-reinforced (e.g., the filaments 4312, 4313), for example as described herein with respect to FIG. 8T-3. The pattern of radiopacity can allow an operator of a device comprising the distal portion 4300, 4370 to visualize identify the distal portion 4300, 4370 at least under x-ray. In some embodiments, the three phase helix includes troughs and peaks, for example at the sides of the distal portion 4300, 4370 that the paired three phase helix at least partially create. In FIG. 8T-1, the spacing or phase difference between the apices of the sine waves along the triple helix are substantially uniformly spaced, which can allow the distal portion 4300 to serve as an angiographic measurement ruler. For example, the distances 4331, 4332, 4335 between apices of different sine waves and/or the distances 4321, 4322, 4323 between apices of the same sine wave (e.g., the pitch of the sine wave) can help an operator to measure the length of blood clots, the neck of an aneurysm, the length of a stenosis, etc. In FIGS. 8T-1 and 8T-2, the intersection points along the triple helix are substantially uniformly spaced, which can allow the distal portion 4300, 4370 to serve as an angiographic measurement ruler. For example, the distances between intersections can help an operator to measure the length of blood clots, the neck of an aneurysm, the length of a stenosis, etc. In some embodiments, a distance at least partially along the proximal neck 70, along the distal neck 65, and/or along the bulbs has different dimensions than paired triple helix in the rest of the distal portion 4300, which may serve as an identifier of the proximal neck 70, the distal neck 65, and/or the bulbs, for example beyond which the distal portion 4300, 4370 should not be deployed.

FIG. 8T-3 is a schematic diagram illustrating an example setup of a braid carrier mechanism 4380 for the distal portions 4300, 4370 of FIGS. 8T-1 and 8T-2. In FIG. 8T-3, the half circles with dark shading indicate individual carriers 155 including spools 154 including shape memory filaments 156, the half circles with hatched shading indicate individual carriers 155 including spools 154 including radiopaque filaments 156, and the half circles with no shading indicate spindles without spools 154 or filaments 156. In the arrangement illustrated in FIG. 8T-3, spindles 4o, 5i, 7o, 8i, 10o, 11i, 14i, 16o, 17i, 19o, 20i, 22o, 23i, 28o, 29i, 31o, 32i, 34o, 35i, 40o, 41i, 43o, 44i, 46o, 47i, 52o, 53i, 55o, 56i, 58o, 59i, 62i, 64o, 65i, 67o, 68i, 70o, 71i include spools 154 including shape-memory material (e.g., 39 of the 48 filaments 156 comprise shape-memory material), the spindles 1o, 2i, 13o, 25o, 26, 37o, 49o, 50i 61o include spools 154 including radiopaque material (e.g., 9 of the 48 filaments 156 comprise radiopaque material), and the remaining spindles are empty. The braid carrier mechanism 4380 setup illustrated in FIG. 8T-3 can generate a pattern of radiopacity described with respect to FIGS. 8T-1 and 8T-2, for example a reinforced three phase helix (including a sine wave formed by each radiopaque filament pairs 1o/2i, 25o/26i, 49o/50i) and a non-reinforced three phase helix (including a sine wave formed by each single radiopaque filament 13o, 37o, 61o) or a reinforced three phase helix. Although some examples of the carrier braider 150 with 48 spindles 153 or individual carriers 155 are provided herein, some embodiments of the carrier braider 150 may include 6 to 144 spindles 153 or individual carriers 155 in accordance with the values provided above and/or carrier braiders 150 that have 6, 12, 24, 36, 48, 60, 72, 84, 96, 120, 144, etc. spindles 153 or individual carriers 155 and the number and positioning of the radiopaque filaments can remain as provided in the example braid carrier mechanism 4380 setup. Different weights are also possible. For example, a reinforced three phase helix may include three or more radiopaque filaments per phase. For another example, a non-reinforced three phase helix may include more than one radiopaque filament per phase, for example as long as the reinforced three phase helix in that paired three phase helix includes more filaments per wave such that the latter is relatively reinforced.

FIG. 8T-4 is an x-ray photograph illustrating an example of a plurality of radiopaque filaments of the distal portion 4370 of FIG. 8T-2. The distal portion 4370 includes a proximal neck 70 and a distal neck 65, and includes a plurality of radiopaque filaments in which the radiopaque filaments form a reinforced three phase helix. In some embodiments, crossings of the radiopaque filaments 4311, 4312, 4313, 4314, 4315 of the distal portion 43700 can serve as an angiographic measurement ruler. For example, the distances between the crossings can help an operator of a device comprising the distal portion 4370 to measure the length of blood clots, the neck of an aneurysm, the length of a stenosis, etc. Other features can also be used. For example, in FIG. 8T-4, the width of a bulb measurable due to the paired triple helix is about 2 mm.

Figure 8U:
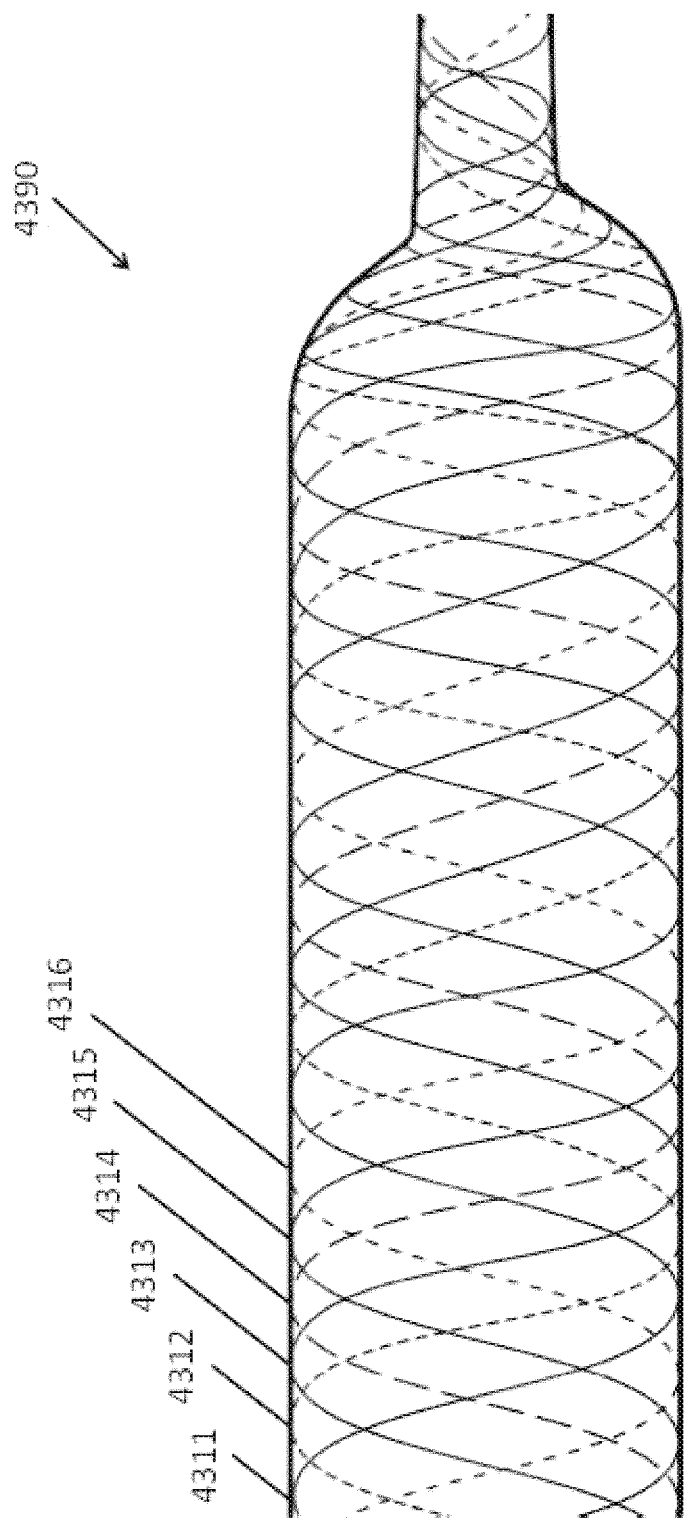
FIG. 8U is a schematic side elevational view of another example embodiment of a distal portion of a vascular treatment device illustrating an example pattern of radiopaque filaments.

FIG. 8U is a schematic side elevational view of another example embodiment of a distal portion 4390 of a vascular treatment device illustrating an example pattern of radiopaque filaments, for example under x-ray. The distal portion 4390 may be the distal portion 100 of the device 10, 20, 30, or 40. The distal portion 4390 includes, in an expanded state, a proximal neck 70 and a cylindrical wide-mouthed textile structure including shape-memory filaments and radiopaque filaments. The textile structure 75 expands radially outwardly from proximal to distal, and then stays at the larger diameter until the distal end.

The distal portion 4390 includes, in an expanded state, radiopaque filaments 4311, 4312, 4313 that are interlaced in the form a paired three phase helix at least under x-ray. The filaments 4311, 4312, 4313 may be reinforced with a second radiopaque filament and additional the distal portions 4390 may include additional radiopaque filaments that are non-reinforced. The pattern of radiopacity can allow an operator of a device comprising the distal portion 4390 to visualize identify the distal portion 4390 at least under x-ray. In some embodiments, the paired three phase helix includes troughs and peaks, for example at the sides of the distal portion 4390 that the paired three phase helix at least partially creates. A paired three phase helix includes a pitch for each reinforced filament (e.g., a pitch 4321 for the sine wave created by the filaments 4311, a pitch 4322 for the sine wave created by the filaments 4312, and a pitch 4323 for the sine wave crated by the filaments 4313) and a pitch for each non-reinforced filament (e.g., a pitch 4341 for the sine wave created by the filament 4314, a pitch 4342 for the sine wave created by the filament 4315, a pitch 4343 for the sine wave created by the filament 4316). In FIG. 8U, the intersection points along the paired triple helix are substantially uniformly spaced, which can allow the distal portion 4390 to serve as an angiographic measurement ruler. For example, the distances between intersections can help an operator to measure the length of blood clots, the neck of an aneurysm, the length of a stenosis, etc. In some embodiments, a distance at least partially along the proximal neck 70, along the distal neck 65, and/or along the bulbs has different dimensions than paired triple helix in the rest of the distal portion 4380, which may serve as an identifier of the proximal neck 70, the distal neck 65, and/or the bulbs, for example beyond which the distal portion 4390 should not be deployed.

Figure 8V:
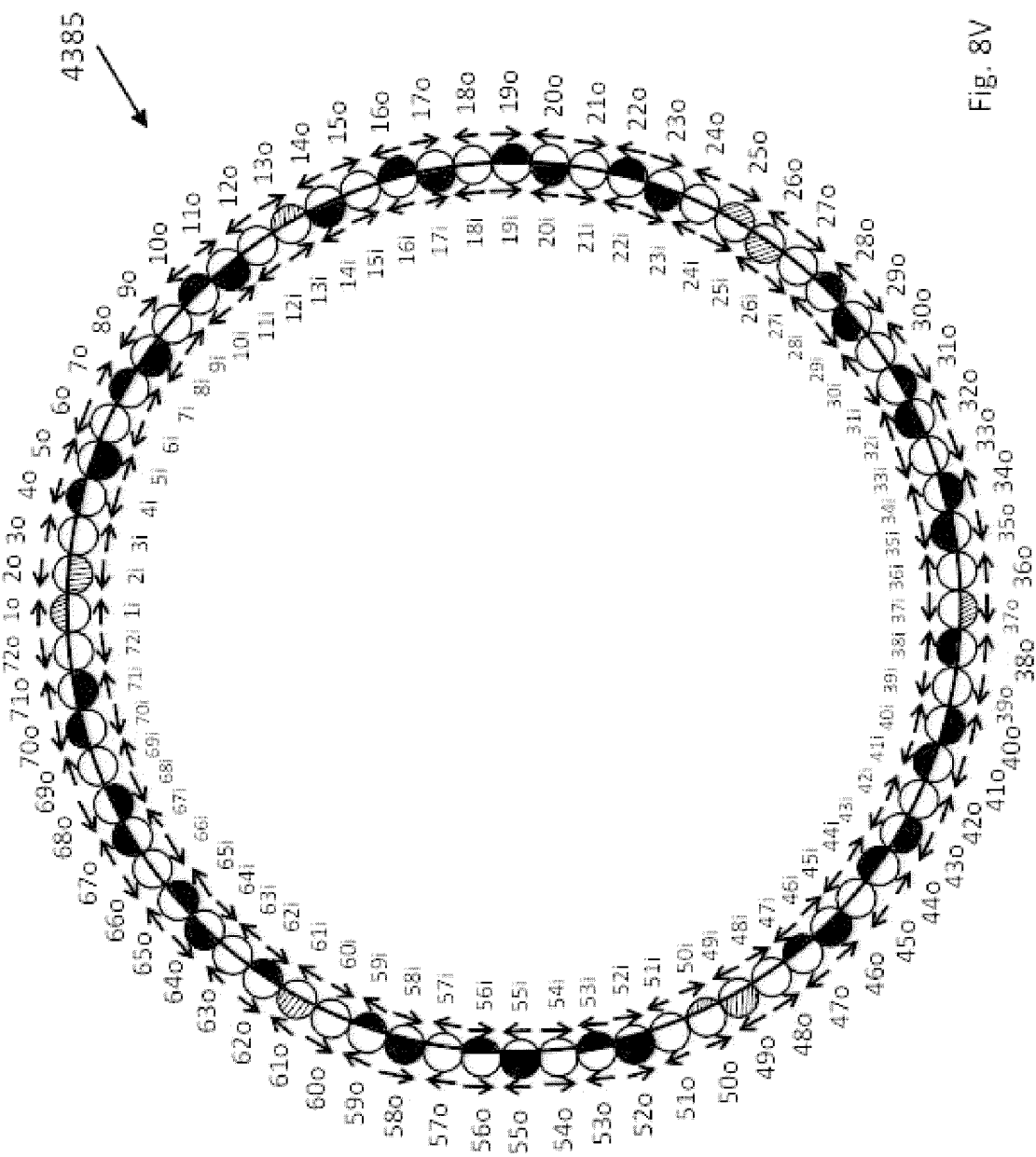
FIG. 8V is a schematic diagram illustrating an example setup of a braid carrier mechanism for forming the distal portion of FIG. 8U.

FIG. 8V is a schematic diagram illustrating an example setup of a braid carrier mechanism 4385 for the distal portion 4390 of FIG. 8U. In FIG. 8U, the half circles with dark shading indicate individual carriers 155 including spools 154 including shape memory filaments 156, the half circles with hatched shading indicate individual carriers 155 including spools 154 including radiopaque filaments 156, and the half circles with no shading indicate spindles without spools 154 or filaments 156. In the arrangement illustrated in FIG. 8U, spindles 4o, 5i, 7o, 8i, 10o, 11i, 14i, 16o, 17i, 19o, 20i, 22o, 23i, 28o, 29i, 31o, 32i, 34o, 35i, 40o, 41i, 43o, 44i, 46o, 47i, 52o, 53i, 55o, 56i, 58o, 59i, 62i, 64o, 65i, 67o, 68i, 70o, 71i include spools 154 including shape-memory material (e.g., 39 of the 48 filaments 156 comprise shape-memory material), the spindles 1o, 2i, 13o, 25o, 26, 37o, 49o, 50i 61o include spools 154 including radiopaque material (e.g., 9 of the 48 filaments 156 comprise radiopaque material), and the remaining spindles are empty. The braid carrier mechanism 4385 setup illustrated in FIG. 8V can generate a pattern of radiopacity described with respect to FIG. 8U, for example a reinforced three phase helix (including a sine wave formed by each radiopaque filament pairs 1o/2i, 25o/26i, 49o/50i) and a non-reinforced three phase helix (including a sine wave formed by each single radiopaque filament 13o, 37o, 61o) or a reinforced three phase helix. Although some examples of the carrier braider 150 with 48 spindles 153 or individual carriers 155 are provided herein, some embodiments of the carrier braider 150 may include 6 to 144 spindles 153 or individual carriers 155 in accordance with the values provided above and/or carrier braiders 150 that have 6, 12, 24, 36, 48, 60, 72, 84, 96, 120, 144, etc. spindles 153 or individual carriers 155 and the number and positioning of the radiopaque filaments can remain as provided in the example braid carrier mechanism 4380 setup. Different weights are also possible. For example, a reinforced three phase helix may include three or more radiopaque filaments per phase. For another example, a non-reinforced three phase helix may include more than one radiopaque filament per phase, for example as long as the reinforced three phase helix in that paired three phase helix includes more filaments per wave such that the latter is relatively reinforced.

Figure 8W:
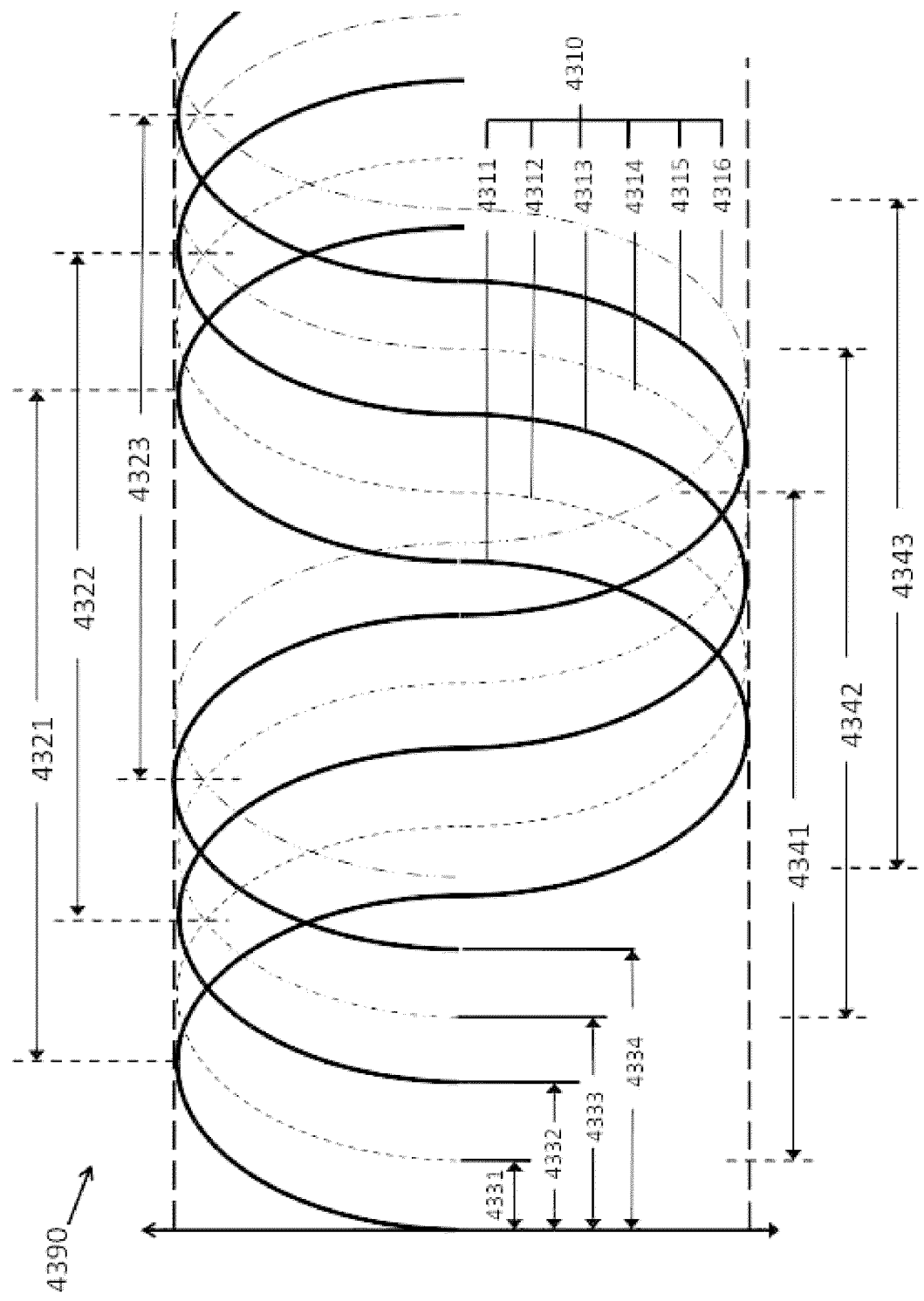
FIG. 8W is a magnified view of the distal portion of FIG. 8U.

FIG. 8W illustrates a paired three phase helix including a reinforced triple helix and a non-reinforced triple helix. The reinforced triple helix includes a first sine wave formed by the two radiopaque filaments 4311, a second sine wave formed by the two radiopaque filaments 4312, and a third sine wave formed by the two radiopaque filaments 4313. The non-reinforced three phase helix includes a first sine wave formed by the radiopaque filament 4314, a second sine wave formed by the radiopaque filament 4315, and a third sine wave formed by the radiopaque filament 4316. In some embodiments, each sine wave within the reinforced three phase helix is offset from the adjacent sine wave within the reinforced three phase helix by about 120° and each sine wave within the non-reinforced three phase helix is offset from the adjacent sine wave within the non-reinforced three phase helix by about 120°.

FIG. 8X is a schematic side elevational view of yet another example embodiment of the distal portion 4600 of a vascular treatment device illustrating an example pattern of radiopaque filaments, for example under x-ray. The distal portion 4600 may be the distal portion 100 of the device 10, 20, 30, or 40. The distal portion 4600 includes a plurality of woven spherical bulbs 4617, 4619, a woven neck 4631, a proximal neck 70, and a distal neck 65 along a longitudinal axis 4640. The distal portion 4600 includes relatively low braid angle segments 4611, 4615. In some embodiments, the segments 4611, 4615 have braid angles ranging from about 0° to about 90° (e.g., about 17°, about 22°, about 45°, etc.). Lower braid angle segments generally have lower PPI and tend to have relatively high porosity. Lower PPI can result in a larger pore size, which can allow adequate flow into perforating vessels or small blood vessels adjoining blood clot, an aneurysm, or a vascular malformation such as an arterio-venous fistula, which can maintain flow in these small but important blood vessels. The distal portion 4600 further includes a relatively high braid angle segment 4613. In some embodiments, the segment 4613 has braid angles ranging from about 91° to about 180° (e.g., about 111°, about 112°, about 151°, etc.). Higher braid angle segments generally have a higher PPI and tend to have relatively low porosity. Higher PPI can result in a smaller pore size, which can decrease flow into an aneurysm or a vascular malformation such as an arterio-venous fistula, which can aid in thrombosis of the aneurysm or vascular malformation.

Referring back to FIG. 8A, at least two variables can be modified to impact porosity: (1) ability to vary the speed of rotation of the circular horn gear 152 for an entire rotation of the horn gear 152 in the horizontal direction 166 relative to the speed of motion of the vertical ring or puller 161 in the vertical direction 164 along the mandrel 162; and (2) ability to start or stop movement of the vertical puller 161, and, once stopped, ability to rearrange the spools 154 with filaments from one spindle 153 to another ("Start-Stop"). Changes in one or both of these variables can directly affect, for example, braid angle and porosity. In some embodiments in which the speed of rotation $S_h$ in the horizontal direction of the circular horn gear 152 is faster than the speed of motion $S_v$ in the vertical direction of the puller 161 such that the horn gear ratio ($S_h/S_v$) is greater than 1.0, a high braid angle and relative low porosity can be obtained. In some embodiments in which the speed of rotation $S_h$ in the horizontal direction of the circular horn gear 152 is slower than the speed of motion $S_v$ in the vertical direction of the puller 161 such that the horn gear ratio ($S_h/S_v$) is less than 1.0, a lower braid angle and a relative high porosity can be obtained.

In some embodiments, crossings of the radiopaque filaments of the distal portion 4600 can be used as a guide for deployment of the distal portion 4600. For example, the "circumferential asymmetric" radiopaque pattern may serve as a visual guide to understand the deployment of woven bulbs by observation of an asymmetric pattern including low braid angles and the deployment of necks by observation of a symmetric pattern including high braid angles.

Figure 8Y:
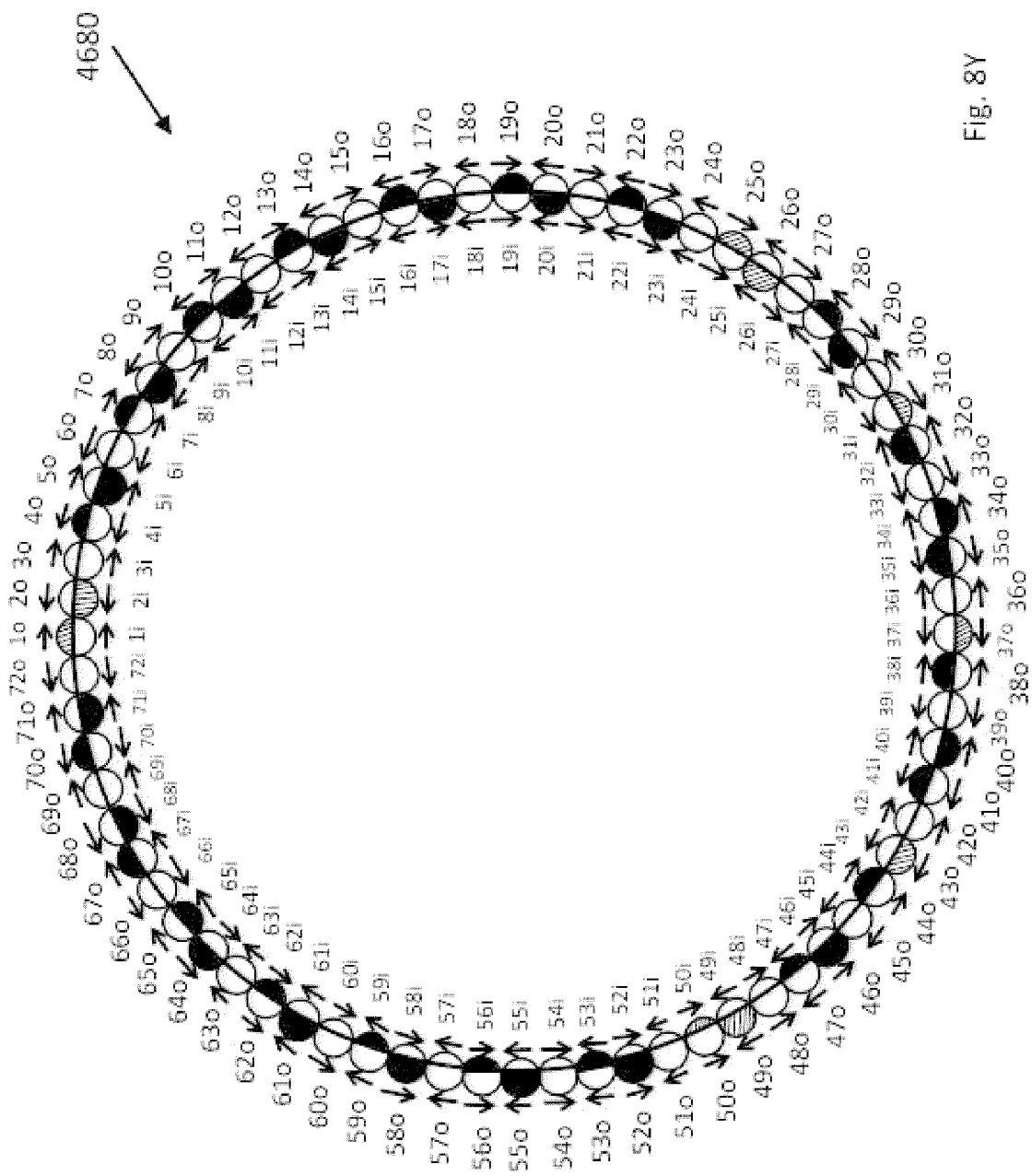
FIG. 8Y is a schematic diagram illustrating an example setup of a braid carrier mechanism for forming the distal portion of FIG. 8X.
Figure 82:
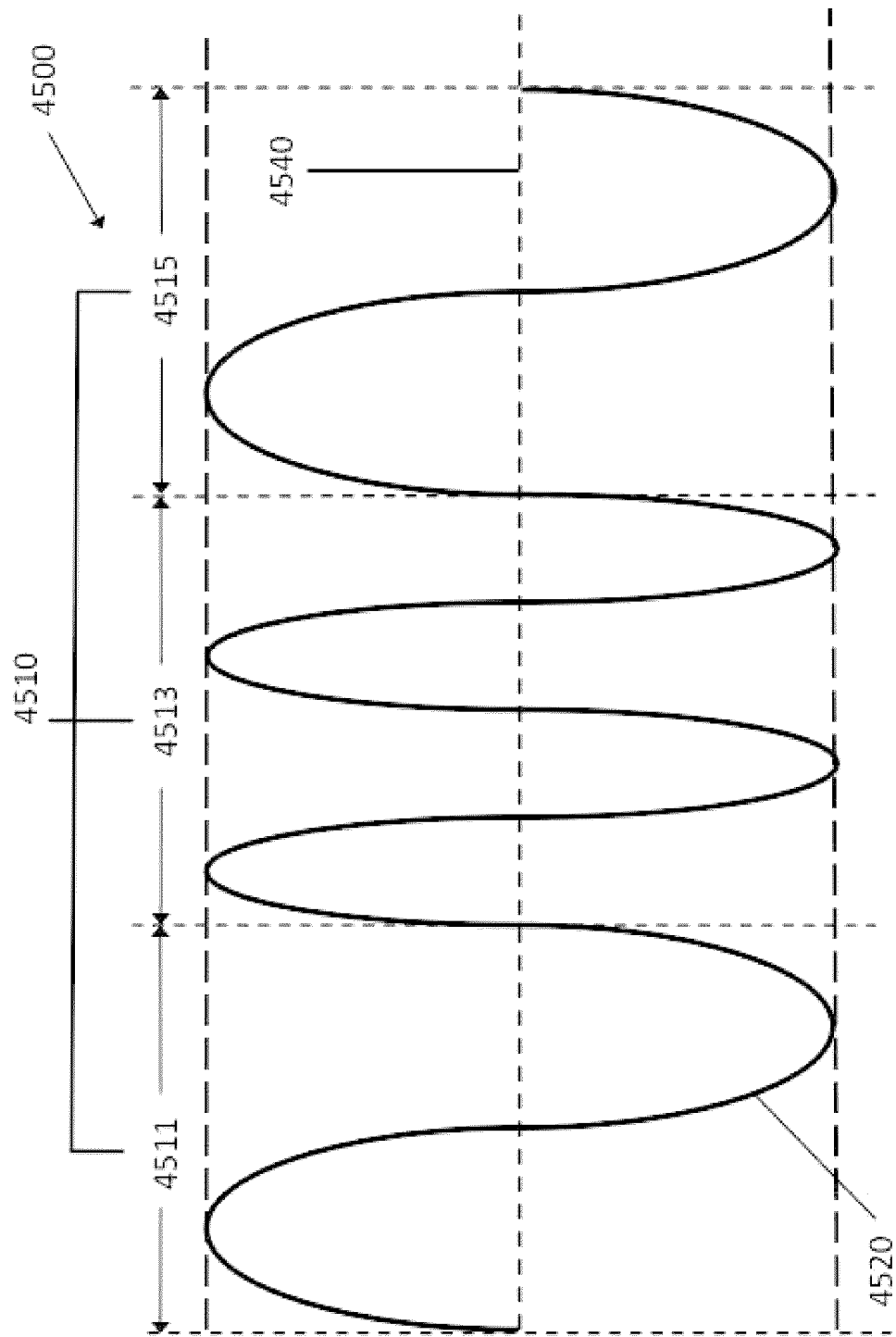

FIG. 8Y is a schematic diagram illustrating an example setup of a braid carrier mechanism 4680 for the distal portion 4600 of FIG. 8X illustrating a pattern of a "circumferential asymmetric helix." In FIG. 8Y, the half circles with dark shading indicate individual carriers 155 including spools 154 including shape memory filaments 156, the half circles with hatched shading indicate individual carriers 155 including spools 154 including radiopaque filaments 156, and the half circles with no shading indicate spindles without spools 154 or filaments 156. In the arrangement illustrated in FIG. 8Y, spindles 4o, 5i, 7o, 8i, 10o, 11i, 13o, 14i, 16o, 17i, 19o, 20i, 22o, 23i, 28o, 29i, 31o, 32i, 34o, 35i, 40o, 41i, 43o, 44i, 46o, 47i, 52o, 53i, 55o, 56i, 58o, 59i, 61o, 62i, 64o, 65i, 67o, 68i, 70o, 71i include spools 154 including shape-memory material (e.g., 39 of the 48 filaments 156 comprise shape-memory material) spindles 1o, 2i, 25o, 26i, 49o, 50i, 31o, 37o, 43o include spools 154 including radiopaque material (e.g., 9 of the 48 filaments 156 comprise radiopaque material), and the remaining spindles are empty. The braid carrier mechanism setup 4680 illustrated in FIG. 8Y can generate a pattern of radiopacity described with respect to FIG. 8X, for example a reinforced three phase helix and a non-reinforced asymmetric three phase helix to form a "circumferential asymmetric" radiopacity pattern. Although some examples of the carrier braider 150 with 48 spindles 153 or individual carriers 155 are provided herein, some embodiments of the carrier braider 150 may include 6 to 144 spindles 153 or individual carriers 155 in accordance with the values provided above and/or carrier braiders 150 that have 6, 12, 24, 36, 48, 60, 72, 84, 96, 120, 144, etc. spindles 153 or individual carriers 155.

In some embodiments, each sine wave within the reinforced three phase helix is offset from the adjacent sine wave within the three phase helix by about 120° and each sine wave within the non-reinforced three phase helix is offset from the adjacent sine wave by about 37.5°. The reinforced three phase helix is asymmetrically offset from the non-reinforced three phase helix.

FIGS. 8L, 8S, and 8T-4 each include a scale to provide a rough, non-limiting, sizing of an example of a distal portion 100 and spacing between radiopaque filaments. In some embodiments, crossings of the radiopaque filaments of the distal portion 100 can be used as a rough measurement guide. For example, in FIG. 8S, every two crossings or the distance between two helical intersection points is about 1 mm. For another example, in FIG. 8L, every one crossing is about 2 mm In a radially expanded state in a vessel, the distal portion 100 may not achieve full radial expansion (e.g., limited by the sidewalls of the vessel), so the guides are not precise, but can provide approximation for, e.g., deployment length, clot length, neck of the aneurysm, stenosis length, etc.

If the distance between helical intersection points is substantially uniform (e.g., about 5 mm), then the user can determine that unsheathing up to 4 intersection points unsheathes about 20 mm (4×5 mm) of the distal portion 100. If the distance between helical intersection points is variable (e.g., about 5 mm proximate to the distal end of the distal portion 100 and about 10 mm proximate to the proximal end of the distal portion 100, with stepped or intermediate distances therebetween), then the user can determine that visualization of wider distances are approaching unsheathing of the proximal end of the distal portion 100, which can be useful, for example, when treating long clots (e.g., long clots in neuro and/or peripheral vessels, treatment of critical limb ischemia, etc.) and/or which can serve as a visual guide for when to stop unsheathing the distal portion 100 during device deployment.

Certain arrangements of radiopaque filaments, for example a double helix or a three phase helix, may be easier to see and/or use for length approximation. In some embodiments, a double helix may include between about 1 radiopaque strand and about 12 radiopaque strands concentrated around part of a circumference of a distal portion 100 (e.g., adjacent to each other, spaced by less than about 5 non-radiopaque filaments, less than about 3 non-radiopaque filaments, less than about 2 non-radiopaque filaments, etc.). In some embodiments, the double helix may comprise a simple double helix which may include about 2 radiopaque strands (e.g., one strand for each helix), a dual double helix which may include about 4 radiopaque strands (e.g., two strands for each helix), and/or a reinforced double helix which may include about 6 radiopaque strands (e.g., three strands for reinforcing each helix), about 8 radiopaque strands (e.g., four strands for reinforcing each helix), about 60 radiopaque strands (e.g., 30 strands for reinforcing each helix), etc. A double helix may be created, for example, by placing at least two spools 154 including radiopaque filaments 156 adjacent to each other around a circumference of the distal portion 100. Circumferential adjacentness may by produced, for example, by placing spools 154 including radiopaque filaments 156 on adjacent spindles 153 or spindles 153 without a non-radiopaque filament therebetween on the yarn wheel 152.

In some embodiments, the three phase helix may comprise a simple three phase helix, which may include about 3 radiopaque strands, a reinforced three phase helix, which may include about 4 radiopaque strands (e.g., two strands for reinforcing one of the phases and one strand for each of the other two phases), and/or a circumferential helix with a reinforced three phase helix, which may include between about 9 radiopaque strands (e.g., six strands for reinforcing the three phase helix and three strands for the non-reinforced three phase helix), about 12 radiopaque strands (e.g., nine strands for reinforcing the three phase helix, and three strands for the non-reinforced three phase helix), about 15 radiopaque strands (e.g., twelve strands for reinforcing the three phase helix, and three strands for the non-reinforced three phase helix), about 60 radiopaque strands (e.g., 54 strands for reinforcing each helix reinforcing the three phase helix, and six strands for the non-reinforced three phase helix), etc. In some embodiments, referring to FIG. 8U, a ratio of the number of radiopaque filaments in the reinforced three phase helix to the number of radiopaque filaments in the non-reinforced three phase helix may include ratios of about 2:1, about 3:1, about 4:1, about 9:1, etc.

FIG. 8Z is a schematic magnified side elevational view of still another example embodiment of a distal portion 4500 of a vascular treatment device illustrating an example pattern of radiopaque filaments 4520. The distal portion 4500 may be the distal portion 100 of the device 10, 20, 30, or 40. The distal portion 4500 includes, in an expanded state, a textile structure including shape-memory filaments (not shown) and radiopaque filaments 4520. The distal portion 4500 includes a plurality of zones 4510 along the longitudinal axis 4540. The plurality of zones 4510 includes a first zone 4511, a second zone 4513, and a third zone 4515. The first zone 4511 includes different braid angles than the second zone 4513. The second zone 4513 includes different braid angles than the third zone 4515. In the embodiment illustrated in FIG. 8Z, the first zone 4511 includes the same braid angles than the third zone 4515, although the first zone 4511 may includes different braid angles than the third zone 4515. In some embodiments, the radiopaque filaments 4520 form a "circumferential asymmetric helix" 4510.

Referring again to FIG. 8A, the braiding parameters may be varied to produce the desired properties of the textile structure 158, including, for example braid angle, PPI, pore size, porosity, etc. There are at least two variables that can be modified to directly affect the braid angle: (1) speed of rotation of the horn gear 152 for an entire rotation of the horn gear 152 in the horizontal direction 166; and (2) speed of motion of the puller or ring 161 in the vertical direction 164 along the mandrel 162. Changes in one or both of these variables can directly affect, for example, braid angle. In some embodiments in which the speed of rotation in the horizontal direction ($S_h$) of the circular horn gear 152 is faster than the speed of motion in the vertical direction ($S_v$) of the puller 161 such that the horn gear ratio ($S_h/S_v$) is greater than 1.0, a high braid angle can obtained. In some embodiments in which the speed of rotation in the horizontal direction of the circular horn gear 152 is slower than the speed of motion in the vertical direction of the puller 161 such that the horn gear ratio ($S_h/S_v$) is less than 1.0, a lower braid angle can be obtained. Referring again to FIG. 8Z, the first zone 4511 of the distal portion 4500 has a relatively low braid angle, implying that the horn gear ratio is less than 1.0, the second zone 4513 of the distal portion 4500 has a relatively high braid angle, implying that the horn gear ratio is greater than 1.0, and the third zone 4515 of the distal portion 4500 has a relatively low braid angle, implying that the horn gear ratio is less than 1.0.

Although shown with respect to a single radiopaque filament 4520 of a radiopaque pattern that may be formed, for example, by the braid carrier mechanism 2870 shown in FIG. 8G, variation of the horn gear ratio can be used to vary braid angles of a plurality of shape-memory and radiopaque filaments in any braid carrier mechanism setup (e.g., the braid carrier mechanisms setups shown in FIGS. 8B, 8I, 8K, 8N, 8R, 8T-3, 8V, etc.). In braid carrier mechanism setups including radiopaque filaments, the braid angle may be varied along the longitudinal length of the device being braided.

Figure 9A:
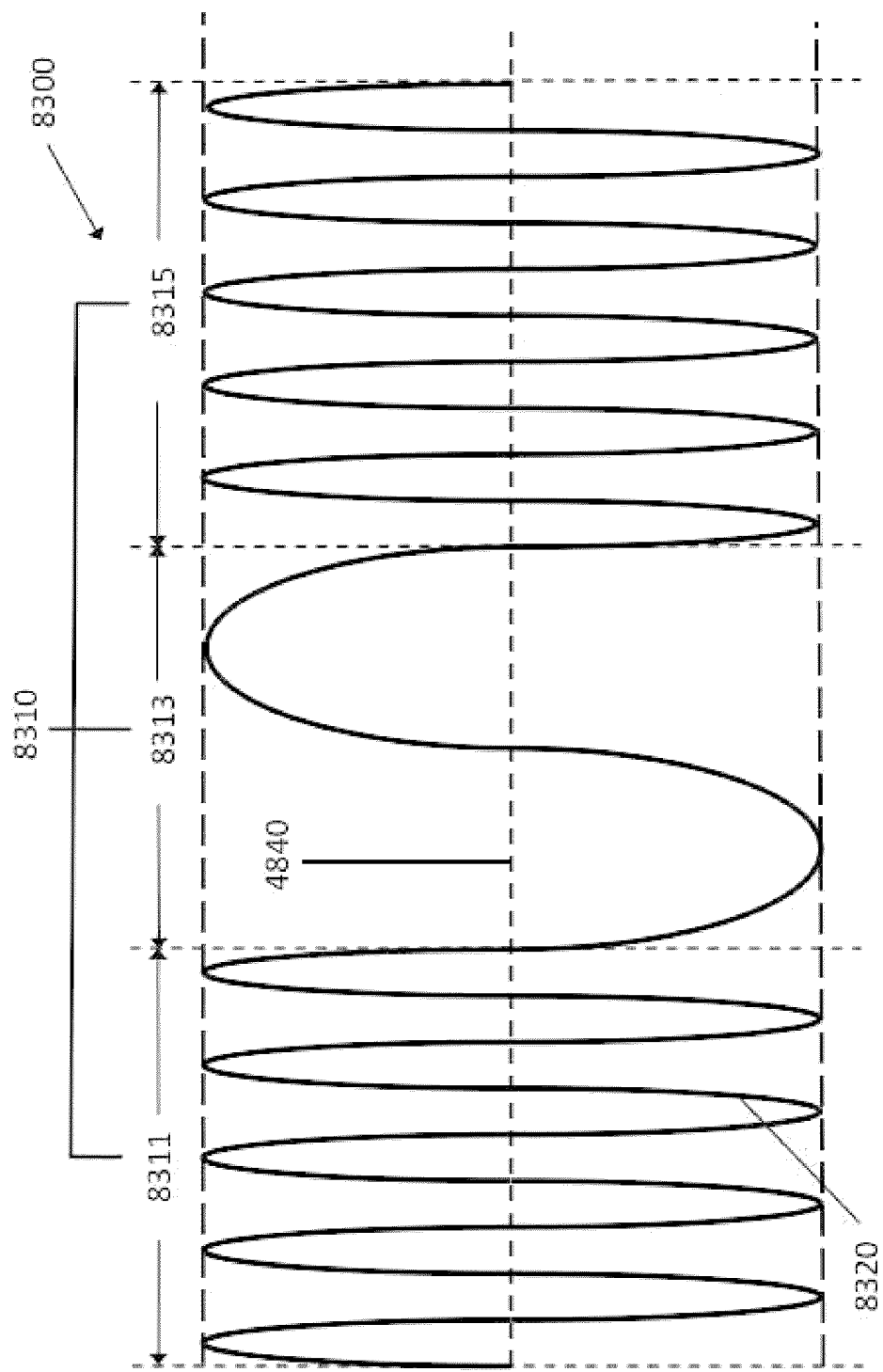
FIG. 9A is a schematic magnified side elevational view of a portion of another example embodiment of a distal portion of a vascular treatment device illustrating an example pattern of one or more filaments.

FIG. 9A is a schematic magnified side elevational view of a portion of another example embodiment of a distal portion 8300 of a vascular treatment device illustrating an example pattern of one or more filaments 8320. The distal portion 8300 may be the distal portion 100 of the device 10, 20, 30, or 40. The distal portion 8300 includes, in an expanded state, a textile structure including shape-memory and/or radiopaque filaments and a plurality of zones 8310. The filament(s) 8320 may be part of a woven textile structure, for example as described herein. In some embodiments, at least one of the plurality of zones 8310 has a different porosity and/or pore size than at least one of the other of the plurality of zones 8310. Referring back to FIG. 8A, at least two variables can be modified to directly affect braiding parameters such as porosity or pore size: (1) ability to start or stop movement of the vertical puller 161, and, once stopped, ability to rearrange the spools 154 from one spindle 153 to another spindle 153 ("Start-Stop"); and (2) ability to vary speed of rotation of portions of the circular horn gear 152. In some embodiments, movement of the vertical puller 161 is temporarily stopped, and the spools 154 including filaments 156 are rearranged from one spindle 153 to another spindle 153 on the braid carrier mechanism 152 to create a different pattern (e.g., from symmetric as shown in FIG. 8V to asymmetric as shown in FIG. 8Y). Adjusting the arrangement of the braid carrier mechanism can vary the pore size in the horizontal plane on either side of the braid axis. In some other embodiments, the speed of rotation of the circular horn gear 152 for a portion of rotation of the yarn wheel 152 (e.g., 180°, or for the western hemisphere of the yarn wheel 152) is different compared to the remaining portion of rotation of the yarn wheel 152 (e.g., 180°, or for the eastern hemisphere of the yarn wheel 152), which can vary pore size and/or porosity in the vertical plane on either side of the longitudinal axis.

In FIG. 9A, the distal portion 8300 includes a first zone 8311, a second zone 8312, and a third zone 8315. The second zone 8313 has a higher porosity and/or larger pore size than the first zone 8311 and the third zone 8315. In some embodiments, the porosity and/or pore size of the second zone may be varied by adjusting at least one of Start-Stop and rotation of a portion of the yarn wheel 152 during the braiding process. In some embodiments, the filaments 8320 form a helix including troughs and peaks, for example at the sides the distal portion 8300 that the helix at least partially creates. In FIG. 9C, the first zone 8311 and the third zone 8315 have a relatively high PPI and are less porous than the second zone 8313. Higher PPI can result in a smaller pore size, which can decrease flow into an aneurysm or a vascular malformation such as an arterio-venous fistula, which can aid in thrombosis of the aneurysm or vascular malformation. The second zone 8313 has a relatively low PPI and is more porous than the first zone 8311 and the third zone 8315. Lower PPI can result in a larger pore size, which can allow adequate flow into perforating vessels or small blood vessels adjoining blood clot, an aneurysm, or a vascular malformation such as an arterio-venous fistula, which can maintain flow in these small but important blood vessels.

Figure 9B:
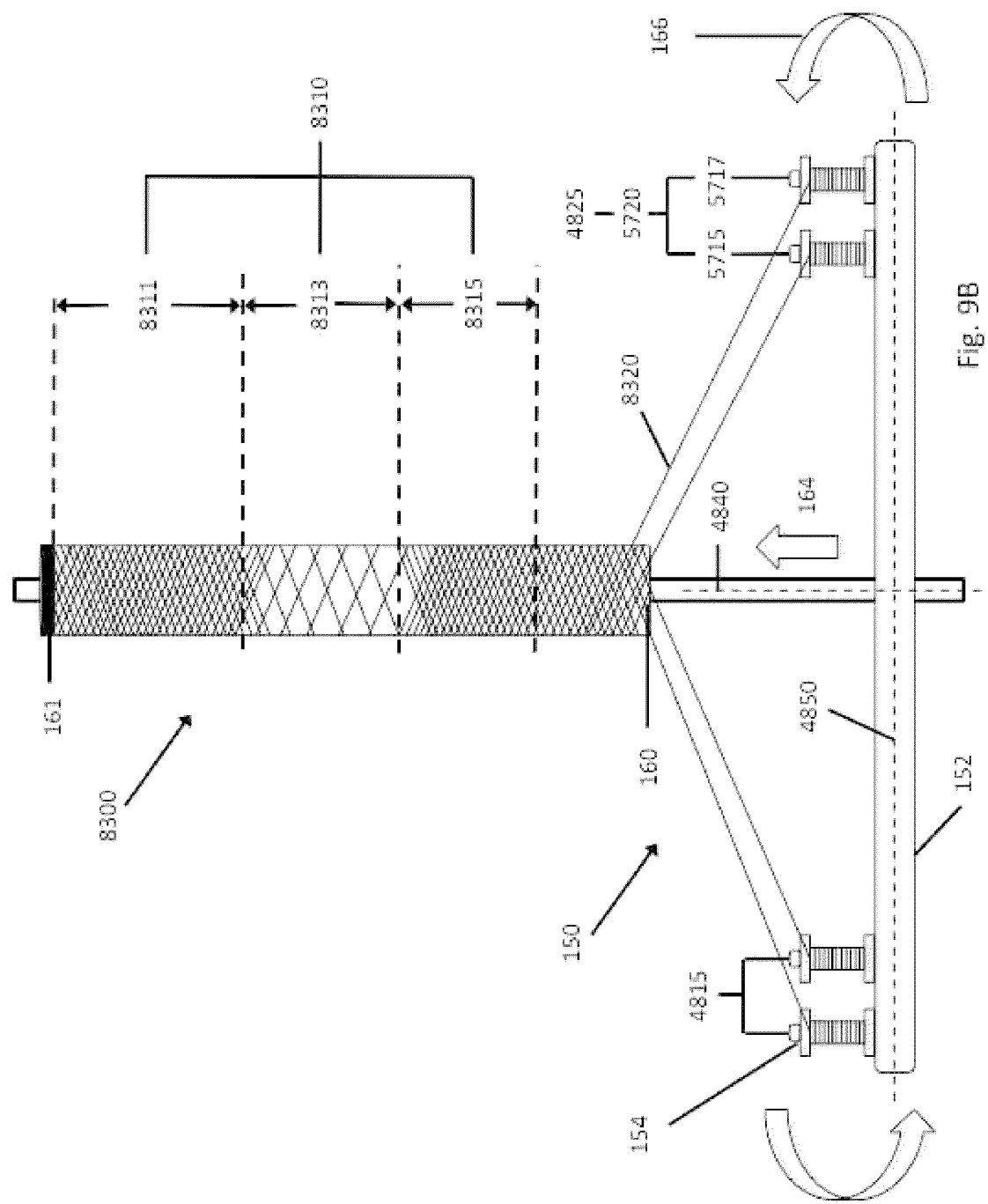
FIG. 9B is a schematic side elevational view of an example embodiment of forming the distal portion of FIG. 9A.
Figure 9C:
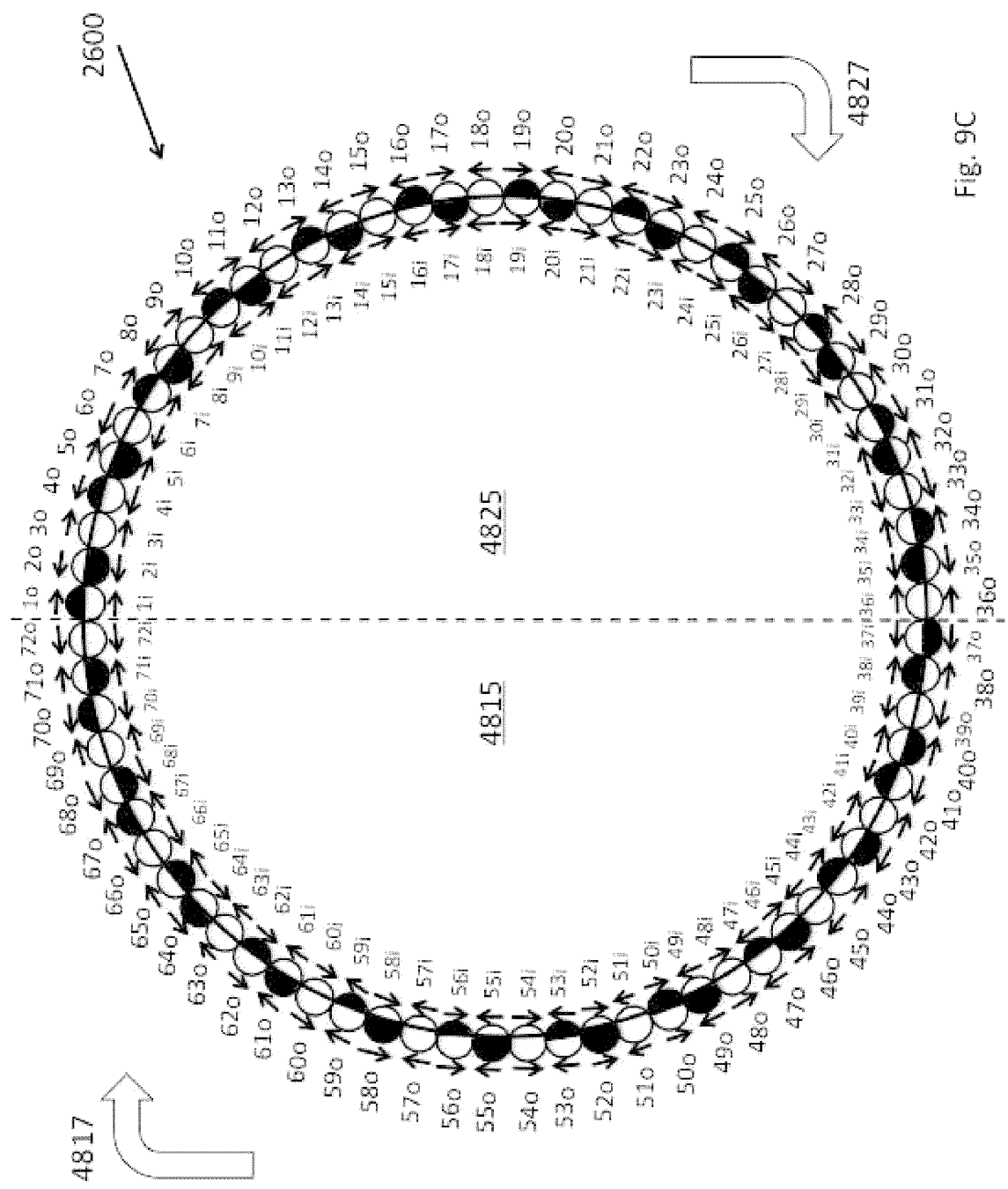
FIG. 9C is a schematic diagram illustrating still another example setup of a braid carrier mechanism for forming the distal portion of FIG. 9B.

FIG. 9B is a schematic side elevational view of an example embodiment of forming the distal portion 8300 of FIG. 9A. FIG. 9B shows a braiding device or carrier braider 150 braiding a pattern in the distal portion 8300 including variable pore size. For example as described with respect to FIG. 8A, the braiding device 150 includes a yarn wheel or braid carrier mechanism or circular horn gear 152 and a plurality of spindles 153 and individual carriers 155. A spindle 153 is a stick on the circular horn gear 152. A spool 154 is a hollow device that fits onto a spindle 153 and includes filaments 156 wound around it. An individual carrier 155 includes a spindle 153 and a spool 154 on the spindle 153. The terms spindle, spool, and individual carrier may be used interchangeably depending on context. The individual carriers 155 include spools 154 including filaments 156 that are woven together to form the textile structure of the distal portion 8300. Each spindle pair includes an outer spindle 5717 and an inner spindle 5715. The filaments 156 each extend from an individual carrier 155 to a ring or vertical puller 161 over a mandrel along the central longitudinal axis 4840, and are braided around the mandrel 160 along the central longitudinal axis 4840 by spinning the circular horn gear 152, spinning the spindles 153, and pulling the ring 161 away from the circular horn gear 152 in a vertical direction 164. The distal portion 8300 includes filaments that are left leaning, for example the filaments 8320 that are shown to the left of the longitudinal axis 4840, and right leaning, for example the filaments 8320 that are shown to the right of the longitudinal axis 4840. In some embodiments, the left leaning filaments correlate with the individual carriers 4815 in the western hemisphere of the circular braid mechanism or circular horn gear 152 and the right leaning filaments correlate with the individual carriers 4825 in the eastern hemisphere of the circular braid mechanism or circular horn gear 152. Although some examples of the carrier braider 150 with 4 spindles 153 or individual carriers 155 are provided herein, some embodiments of the carrier braider 150 may include 6 to 144 spindles 153 or individual carriers 155 in accordance with the values provided above and/or carrier braiders 150 that have 6, 12, 24, 36, 48, 60, 72, 84, 96, 120, 144, etc. spindles 153 or individual carriers 155. As the textile structure 8300 is woven at preform point 160, the textile structure advances in the direction of the arrow 164. The circular horn gear 152 spins in the direction of the arrows 166 in a horizontal plane around the longitudinal axis 4840, and the spindles 153 rotate within the circular horn gear 152 to create the desired braiding pattern.

FIG. 9C is a schematic diagram illustrating an example setup of a braid carrier mechanism 2600 for forming the distal portion 8300 of FIG. 9A, illustrating an example pattern for creating variable pore size. In FIG. 9C, the half circles with dark shading indicate individual carriers 155 including spools 154 including shape memory filaments 154, the half circles with hatched shading indicate individual carriers 155 including spools 154 including radiopaque filaments 156, and the half circles with no shading indicate spindles without o spools 154 or filaments 156. Although some examples of the spindles 153 or individual carriers 155 are provided herein, the spindles 153 may include spools 154 including shape memory material, spools 154 including radiopaque material, be empty, be arranged in symmetric or asymmetric patterns, combinations thereof, and the like. In the arrangement illustrated in FIG. 9C, spindles 1o, 2i, 4o, 5i, 7o, 8i, 10o, 11i, 13o, 14i, 16o, 17i, 19o, 20i, 22o, 23i, 25o, 26i, 28o, 29i, 31o, 32i, 34o, 35i, 37o, 38i, 40o, 41i, 43o, 44i, 46o, 47i, 49o, 50i, 52o, 53i, 55o, 56i, 58o, 59i, 61o, 62i, 64o, 65i, 67o, 68i, 70o, 71i include spools 154 including shape-memory material (e.g., 48 of the 48 filaments 156 comprise shape-memory material) and the remaining spindles are empty. Although some examples of the carrier braider 150 with 48 spindles 153 or individual carriers 155 are provided herein, some embodiments of the carrier braider 150 may include 6 to 144 spindles 153 or individual carriers 155 in accordance with the values provided above and/or carrier braiders 152 that have 6, 12, 24, 36, 48, 60, 72, 84, 96, 120, 144, etc. spindles 153 or individual carriers 155.

Figure 9D:
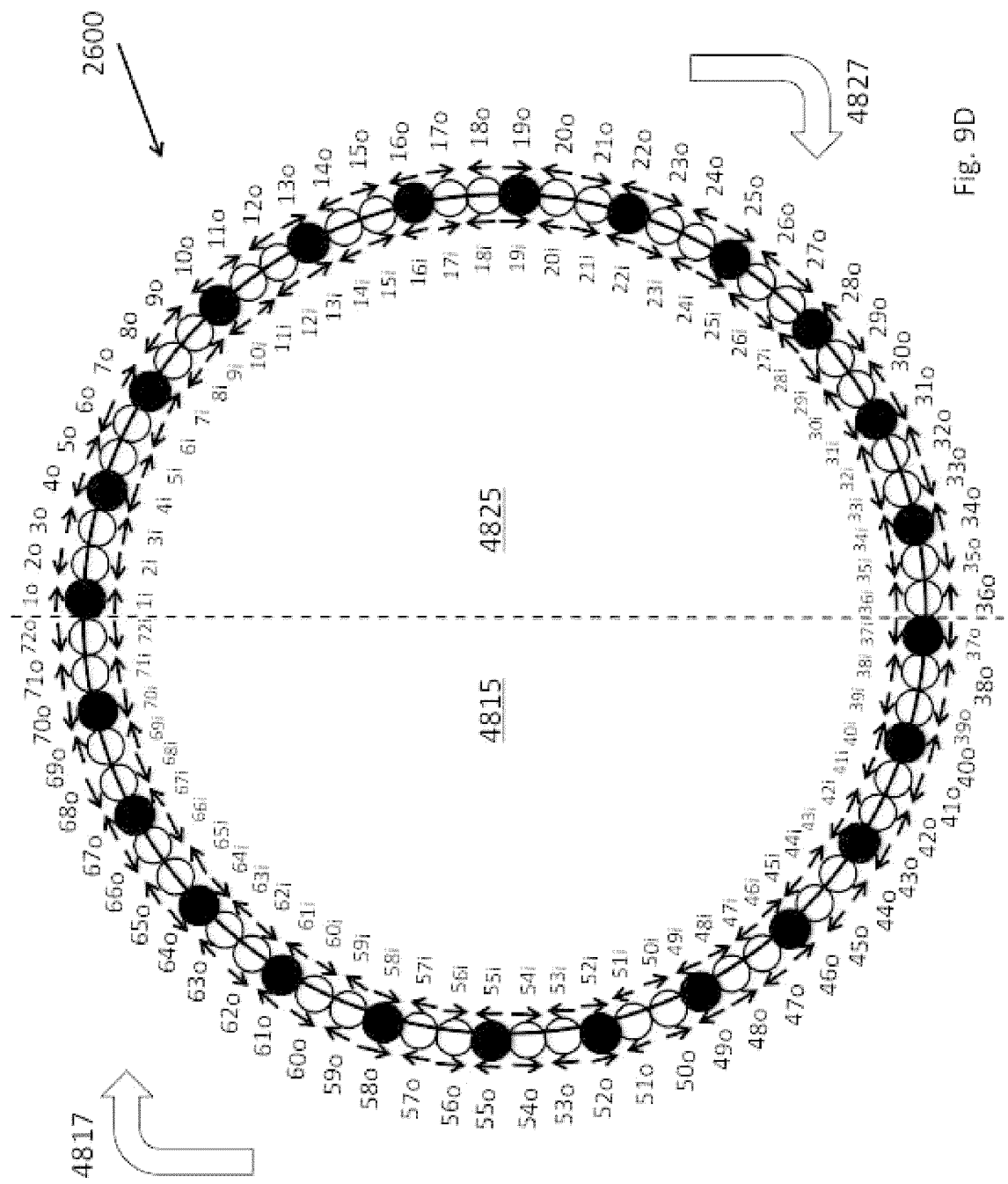
FIG. 9D is a schematic diagram illustrating yet another example setup of a braid carrier mechanism for forming the distal portion of FIG. 9B.

FIG. 9D is a schematic diagram illustrating another example setup of a braid carrier mechanism 2600 for forming the distal portion 8300 of FIG. 9A, illustrating another example pattern for creating variable pore size after rearranging the individual carriers 155 such that all of the spindles 153 with spools 154 including filaments 156 form spindle pairs, which can increase the number of empty spindle pairs and pore size. In the arrangement illustrated in FIG. 9D, the spindles 1o, 1i, 4o, 4i, 7o, 7i, 10o, 10i, 13o, 13i, 16o, 6i, 19o, 19i, 22o, 22i, 25o, 25i, 28o, 28i, 31o, 31i, 34o, 34i, 37o, 37i, 40o, 40i, 43o, 43i, 46o, 46i, 49o, 49i, 52o, 52i, 55o, 55i, 58o, 58i, 61o, 61i, 64o, 64i, 67o, 67i, 70o, 70i include spools 154 including shape-memory material (e.g., 48 of the 48 filaments 156 comprise shape-memory material) and the remaining spindles are empty. Compared to the arrangement illustrated in FIG. 9E, the spool 154 on spindle 2i was moved to the spindle 1i, the spool 154 on spindle 5i was moved to the spindle 4i, the spool 154 on spindle 8i was moved to the spindle 7i, the spool 154 on spindle 11i was moved to the spindle 10i, the spool 154 on spindle 14i was moved to the spindle 13i, the spool 154 on spindle 17i was moved to the spindle 16i, the spool 154 on spindle 20i was moved to the spindle 19i, the spool 154 on spindle 23i was moved to the spindle 22i, the spool 154 on spindle 26i was moved to the spindle 25i, the spool 154 on spindle 29i was moved to the spindle 28i, the spool 154 on spindle 32i was moved to the spindle 31i, the spool 154 on spindle 35i was moved to the spindle 34i, the spool 154 on spindle 38i was moved to the spindle 37i, the spool 154 on spindle 41i was moved to the spindle 40i, the spool 154 on spindle 44i was moved to the spindle 43i, the spool 154 on spindle 47i was moved to the spindle 46i, the spool 154 on spindle 50i was moved to the spindle 49i, the spool 154 on spindle 53i was moved to the spindle 52i, the spool 154 on spindle 56i was moved to the spindle 55i, the spool 154 on spindle 59i was moved to the spindle 58i, the spool 154 on spindle 62i was moved to the spindle 61i, the spool 154 on spindle 65i was moved to the spindle 64i, the spool 154 on spindle 68i was moved to the spindle 67i, and the spool 154 on spindle 71i was moved to the spindle 70i. Although some examples of the carrier braider 150 with 48 spindles 153 or individual carriers 154 are provided herein, some embodiments of the carrier braider 150 may include 6 to 144 spindles 153 or individual carriers 155 in accordance with the values provided above and/or carrier braiders that have 6, 12, 24, 36, 48, 60, 72, 84, 96, 120, 144, etc. spindles 153 or individual carriers 155 and the number and positioning of the spools 154 including filaments 156 can remain as provided in the example braid carrier mechanism 2600 setup of FIG. 9D.

In some embodiments, for example the arrangement illustrated in FIG. 9C, can result in a braiding pattern of the distal portion 8300, as noted in FIG. 9B, having a relatively high PPI and relatively low porosity, for example the distal segment 8311 of the distal portion 8300. If the "Start-Stop" capability is activated after the braiding of the distal segment 8311 of the distal portion 8300, and once the vertical puller or ring 161 is stopped to be able to rearrange the spools 154 including filaments 156 between spindles 153 in the arrangement illustrated in FIG. 9D, further braiding can result in a braiding pattern having a relatively low PPI and relatively high porosity, for example the middle segment 8313 of the distal portion 8300. If the "Start-Stop" capability is again activated after the braiding of the middle segment 8313 of the distal portion 8300, and once the vertical puller or ring 161 is stopped to be able to rearrange the spools 154 including filaments 156 between spindles 153 in the arrangement illustrated in FIG. 9C, further braiding can result in a braiding pattern having a relatively high PPI and relatively low porosity, for example the proximal segment 8315 of the distal portion 8300.

In some embodiments, referring back to FIGS. 9B and 9C, the speed of rotation of the circular horn gear 152 for 180 degrees rotation of the yarn wheel, for example the speed of rotation $S_{h-w}$ of the western hemisphere of individual carriers 4815 on the yarn wheel in the horizontal direction 4817, is different compared to the remaining 180 degrees rotation of the yarn wheel, for example the speed of rotation $S_{h-e}$ of the eastern hemisphere of individual carriers 4825 of the yarn wheel in the horizontal direction 4827, which can vary the pore size in the vertical plane on either side of the longitudinal axis 4840.

In the arrangement illustrated in FIGS. 9C and 9D, for example, if the speed of rotation $S_{h-w}$ in the horizontal direction 4817 of the western hemisphere of the circular horn gear 152 is faster than the speed of motion $S_y$ in the vertical direction of the puller 161, the horn gear ratio ($S_{h-w}/S_w$) is greater than 1.0, and a high braid angle can be obtained. For example, the higher braid angle segments may have braid angles ranging from about 91° to about 180° (e.g., about 111°, about 112°, about 151°, etc.). Higher braid angle segments generally have a higher PPI and tend to have relatively low porosity. Higher PPI can result in a smaller pore size, which can decrease flow into an aneurysm or a vascular malformation such as an arterio-venous fistula, which can aid in thrombosis of the aneurysm or vascular malformation.

In the arrangement illustrated in FIGS. 9C and 9D, for example, if the speed of rotation $S_{h-e}$ in the horizontal direction 4827 of the eastern hemisphere of the circular horn gear 152 is slower than the speed of motion $S_y$ in the vertical direction of the puller 161, the horn gear ratio ($S_{h-e}/S_v$) is less than 1.0, and a lower braid angle can be obtained. For example, the lower braid angle segments may have braid angles ranging from about 0° to about 90° (e.g., about 17°, about 22°, about 45°, etc.). Lower braid angle segments generally have lower PPI and tend to have relatively high porosity. Lower PPI can result in a larger pore size, which can allow flow into perforating vessels or small blood vessels adjoining blood clot, an aneurysm, or a vascular malformation such as an arterio-venous fistula, which can maintain flow in these small but important blood vessels.

FIG. 9E is a schematic diagram illustrating an example embodiment of a mandrel for forming a distal portion of a vascular treatment device, for example the distal portion 11000 of FIG. 7A and/or the distal portion 11100 of FIG. 7B. FIG. 9F is a schematic diagram illustrating another example embodiment of a mandrel for forming a distal portion of a vascular treatment device, for example the distal portion 11000 of FIG. 7A and/or the distal portion 11100 of FIG. 7B. In the embodiments illustrated in FIGS. 9E and 9F, the bulbous mandrel can be customized for any Y-shaped configuration of the distal portion 100 of a vascular treatment device.

In FIG. 9E, the bulbous mandrel includes a spherical bulb or central anchor bulb 11205 and a plurality of retainer cavities including sprockets. In some embodiments, the retainer cavity and sprockets are interspersed on substantially the entire outer circumference of the central anchor bulb 11205, and have the ability to rotate between about 0° and about 180°. Depending on the distal portion 100 to be manufactured, a first mandrel extension 11210 is coupled to a first sprocket 11212, a second mandrel extension 11220 is coupled to a second sprocket 11222, and a third mandrel extension 11230 is coupled to a third sprocket 11232. The remaining sprockets can then be removed. In FIG. 9F, the bulbous mandrel includes a spherical bulb or central anchor bulb 11205 and a plurality of retainer cavities. Depending on the distal portion 100 to be manufactured, a first mandrel extension 11210 is coupled to a first sprocket 11262, a second mandrel extension 11220 is coupled to a second sprocket 11242, and a third mandrel extension 11230 is coupled to a third sprocket 11252.

Although FIGS. 9E and 9F are shown and described with respect to three mandrel extensions 11210, 11220, 11230, more or fewer mandrel extensions are also possible. The first mandrel extension 11210 comprises a generally spherical bulb and a generally cylindrical neck on each side of the generally spherical bulb, which can allow a neck formed over the first mandrel extension 11210 to include a generally spherical bulb and a generally cylindrical neck on each side of the generally spherical bulb. The second mandrel extension 11220 and the third mandrel extension 11230 are each generally cylindrical, which can allow a neck formed over the second mandrel extension 11220 and the third mandrel extension 11230 to be generally cylindrical. Mandrel extensions with any size and shape can be coupled to the central anchor bulb 11205 depending on the desired size and shape of the neck to be formed thereover. In some embodiments, mandrel extensions can be selected to form a distal portion 100 customized for a pathology such as a location of an aneurysm, and even sized for a particular patient.

Referring again to FIG. 7A, the lengths $L_1$, $L_2$, $L_3$, and diameters $D_1$, $D_2$, $D_3$), the diameter of the central anchor bulb $D_0$, and the angulation of the mandrel extensions 11210, 11220, 11230 from the central anchor bulb 11205 can be customized to vasculature, a pathology such as location of the aneurysm at a vessel bifurcation, and/or aneurysm dimensions and blood vessel diameters and angulations in a patient in non-emergent situations. Referring again to FIG. 9B, a bulbous mandrel can be mounted on a carrier braider or braiding device for primary braiding over the customized bulbous mandrel. In some embodiments, the customized bulbous mandrel may include metals or alloys (e.g., comprising stainless steel or alloy of nickel and titanium). Suitable materials may include, for example, platinum, titanium, nickel, chromium, cobalt, tantalum, tungsten, iron, manganese, molybdenum, and alloys thereof including nickel titanium (e.g., nitinol), nickel titanium niobium, chromium cobalt, copper aluminum nickel, iron manganese silicon, silver cadmium, gold cadmium, copper tin, copper zinc, copper zinc silicon, copper zinc aluminum, copper zinc tin, iron platinum, manganese copper, platinum alloys, cobalt nickel aluminum, cobalt nickel gallium, nickel iron gallium, titanium palladium, nickel manganese gallium, stainless steel, shape memory alloys, etc.

Referring again to FIG. 7A, a textile structure formed over the central anchor bulb 11205 can form the distal generally spherical bulb 11012, a textile structure formed over the mandrel extension 11210 can form the proximal segment including the bulb 11012 and the necks 11016, 11017, a textile structure formed over the mandrel extension 11220 can form the lateral distal neck 11019, and a textile structure formed over the mandrel extension 11230 can form the distal neck 11018. Referring again to FIG. 7B, a textile structure formed over the central anchor bulb 11205 can form the proximal generally spherical bulb 11105, a textile structure formed over the mandrel extension 11210 can form the distal segment including the bulb 11110 and the necks 11115, 11130, a textile structure formed over the mandrel extension 11220 can form the lateral proximal neck 11120, and a textile structure formed over the mandrel extension 11230 can form the proximal medial neck 11125. Porosity of any section or portion thereof can be varied, for example as described herein (e.g., varying speed of a horn gear and/or puller, rearranging braid carrier mechanism setups).

Figure 10A:
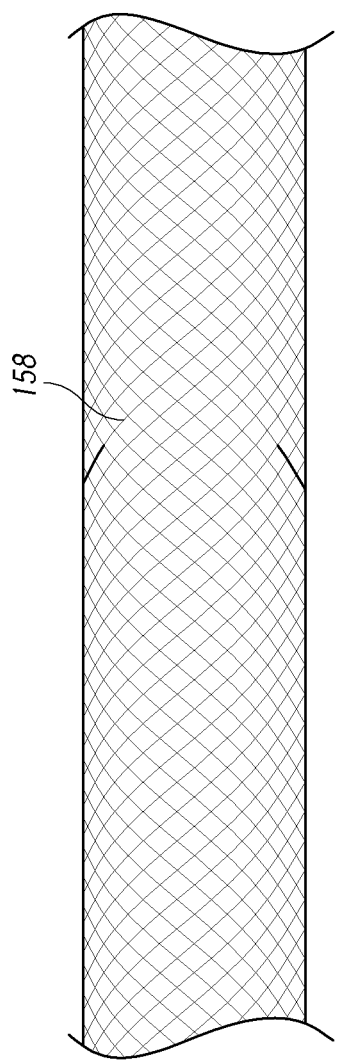
FIG. 10A is a schematic side elevational view illustrating an example woven tubular structure after being removed from a mandrel.

After a tubular textile structure 158 is formed, the filaments 156 may be severed (e.g., close to the mandrel 162), and the textile structure 158 may be removed from the mandrel 162. FIG. 10A is a schematic side elevational view illustrating an example woven tubular structure 158 after being removed from a mandrel 162. The textile structure 158 is then slid onto a second mandrel having the same or a substantially similar outer diameter as the mandrel 162. The textile structure 158 and the second mandrel are heat treated to impart shape memory to at least some of the filaments 156 (e.g., at least the filaments 156 comprising shape-memory material).

The temperature at which a material transforms from martensite to austenite depends at least partially on heat treatment of that material, which can influence the super-elastic or shape memory properties of a shape memory material. For example, upon a change in temperature of an alloy of nickel and titanium, super-elastic or shape memory properties may be achieved.

In some embodiments, the heat treatment of shape memory allow (e.g., comprising between about 55.8 wt % and about 57 wt % nickel) is performed in a fluidized sand bath at an annealing temperature between about 500° C. and about 550° C. (e.g., about 520° C.) for between about 5 minutes and about 10 minutes (e.g., about 7 minutes) in an atmosphere (e.g., ambient air). Between at least about room temperature and about body temperature, the textile structure 158 maintains the tubular shape absent stress-induced martensite. Heat treatment at annealing temperatures that are relatively high (e.g., between about 550° C. and about 600° C.) for between about 20 minutes and about 180 minutes can result in increasing the temperature range at which the textile structure 158 displays shape memory effect (e.g., greater than about body temperature). Heat treatment at annealing temperatures that are relatively low (e.g., between about 400° C. and about 450° C.) for between about 2 minutes and about 10 minutes can also result in increasing the temperature range at which the textile structure 158 displays shape memory effect (e.g., greater than about body temperature). In some embodiments, heat treatment of shape memory alloys, for example binary alloys of nickel and titanium with lower nickel content (e.g., between about 54.5 wt % and 55.3 wt % nickel) or ternary alloys of nickel, titanium, and cobalt, may be performed at annealing temperatures that are relatively low (e.g., between about 400° C.

and about 450° C.) for between about 2 minutes and about 10 minutes may also result in the textile structure 158 that can maintain the tubular shape between at least about room temperature and about body temperature absent stress-induced martensite. The heat treatment temperature can be adjusted based on the particular shape-memory alloy. For example, a ternary alloy comprising cobalt may exhibit properties similar to a relatively low nickel shape-memory alloy.

In some embodiments, the heat treatment is performed in a fluidized sand bath in inert atmosphere (e.g., nitrogen, a mixture of hydrogen and nitrogen, a mixture of carbon monoxide, hydrogen, and nitrogen, etc.), which can inhibit surface oxidation (e.g., formation of nickel oxides in alloys of nickel and titanium) of the shape memory materials. In some embodiments, after heat treatment, the distal portion is then placed in a water bath (e.g., between about 20° C. and about 25° C.) for between about 15 minutes and 45 minutes (e.g., about 30 minutes). Rapid heating and/or cooling can help to retain the shape (e.g., to achieve the austenite finish temperature $A_f$). In some systems, the mandrel 162 may be removed and the textile structure 158 may be heat treated on the mandrel 162 (e.g., without transfer to a second mandrel). After this initial heat treatment, the textile structure 158 may be referred to as a primary heat set or shape set structure.

Figure 10B:
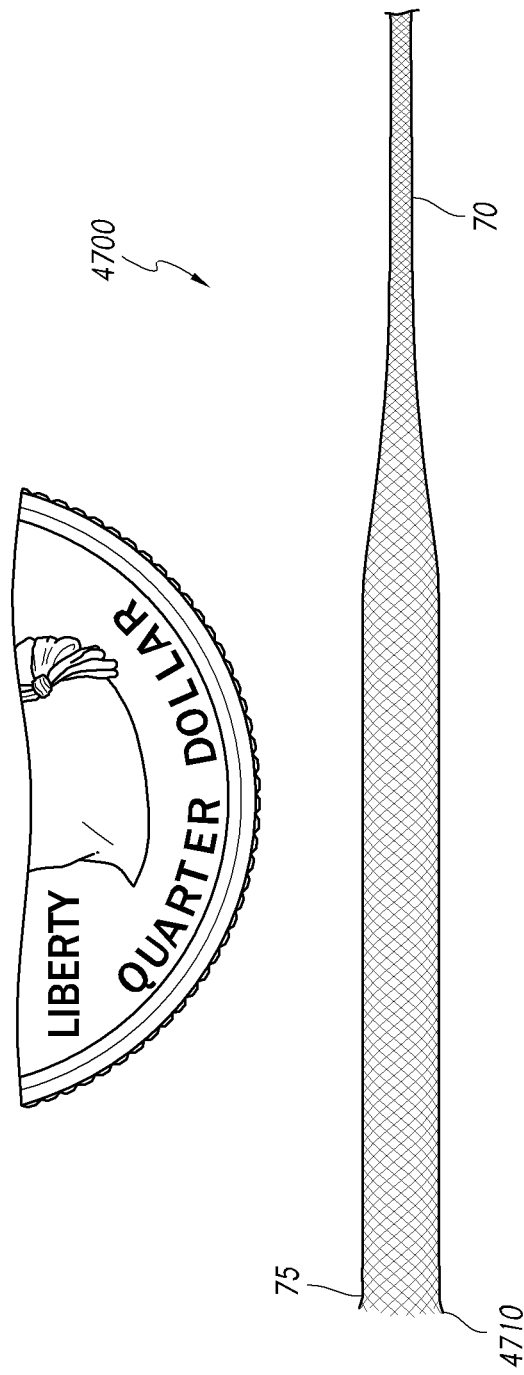
FIG. 10B is a schematic top plan view illustrating an example woven tubular structure after being removed from a mandrel.

FIG. 10B is a schematic top plan view illustrating an example woven tubular structure 4700 after being removed from a mandrel 162, or from a secondary mandrel. The stray filaments ends 4710 on the left side show that the ends 4710 of the filaments may benefit from further processing. For example, at least some of the ends of the filaments may be bent back, welded (e.g., ball welded), polished (e.g., to a dull end), coupled in sleeves, dip coated (e.g., in polymer such as polyurethane), coupled (e.g., adhered, welded, etc.), for example to an arcuate member (e.g., a radiopaque marker band 1720, for example as illustrated in FIG. 5D), combinations thereof, and the like. Lack of filament end treatment (e.g., no radiopaque marker band 1720, polymer, etc.) can allow the distal portion 100 to have a lower profile when collapsed, for example because compression is only limited to the area of the filaments and spacing therebetween. In embodiments including a radiopaque marker band 1720, the radiopaque marker band 1720 may include metals or alloys including, but not limited to, iridium, platinum, tantalum, gold, palladium, tungsten, tin, silver, titanium, nickel, zirconium, rhenium, bismuth, molybdenum, combinations, thereof, and the like. In some of the embodiments, a radiopaque marker band 1720 can be sandwich welded to the free end of the textile structure 158 (e.g., which is being fabricated into a distal portion 100 including bulbs). A radiopaque marker band 1720 may increase visibility of the distal end of the distal portion 100 during interventional procedures. In some embodiments, the ends of the filaments are not further processed. FIG. 10B, which was derived from a photograph, also includes a United States quarter (0.25 or 25¢) to provide a rough, non-limiting, sizing of an example distal portion 100 and its filaments. In some embodiments, laser cutting can inhibit fraying of the filaments (e.g., by reducing mechanical shear forces during the cutting process).

Figure 10C:
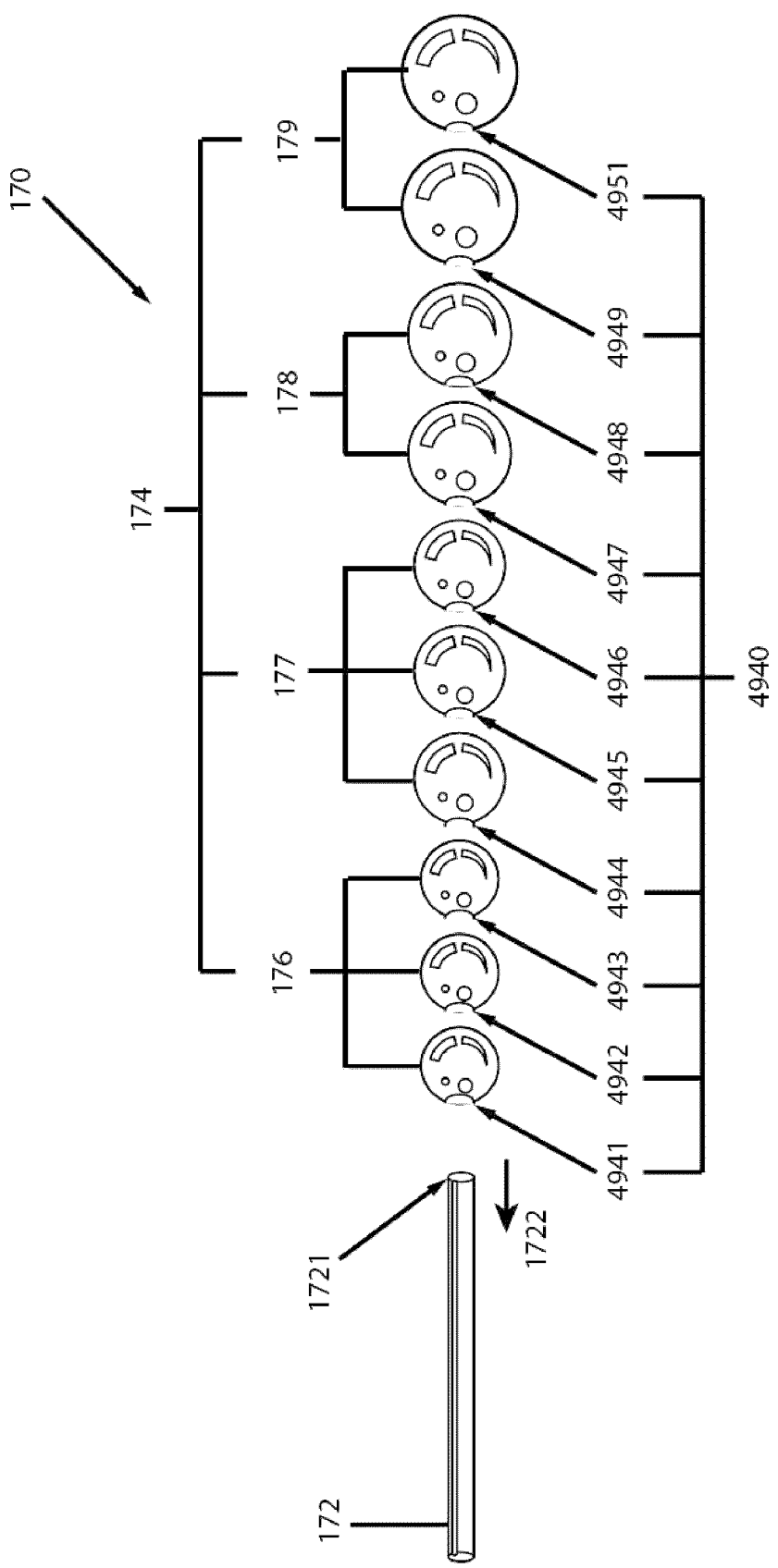
FIG. 10C is schematic exploded side elevational view of an example embodiment of a mandrel.

FIG. 10C is a schematic exploded side elevational view of an example embodiment of a mandrel 170, for example for heat treatment of distal portion 100 of a vascular treatment device. In some embodiments, the mandrel 170 includes a strand 172 and ten spherical bulbs 174: three distal extra-small spherical bulbs 176 having an outer diameter configured to be oversized to extra-small vessel segments such as the M2 segments of the middle cerebral artery (e.g., about 1.5 mm to about 2.25 mm); the proximally-next three small spherical bulbs 177 having an outer diameter configured to be oversized to smaller vessel segments such as the distal M1 segment of the middle cerebral artery (e.g., about 2.25 mm to about 2.75 mm); the proximally-next two medium spherical bulbs 178 having an outer diameter configured to be oversized to medium vessel segments such as the proximal M1 segment of the middle cerebral artery (e.g., about 2.75 mm to about 3.25 mm); and the proximal two large spherical bulbs 179 having an outer diameter configured to be oversized to large vessel segments such as the distal supra-clinoid segment of the internal carotid artery (e.g., about 3.25 mm to about 4 mm). In some embodiments, at least some of the bulbs of the mandrel 170 have a size of about 1 mm to about 80 mm (e.g., about 2 mm to about 12 mm). Bulbs in range of about 1 mm to about 6 mm, about 3 mm to about 4.5 mm, about 0.5 mm to about 3 mm (e.g., about 3 mm), 0.75 mm to about 3 mm (e.g., about 3 mm), about 3.1 mm to about 3.9 mm (e.g., about 3.5 mm), about 4 mm to about 4.4 mm (e.g., 4 mm), and about 4.5 mm to about 7.5 mm (e.g., about 4.5 mm) may be particular beneficial for smaller clots and/or vessels (e.g., in the brain). Bulbs of the mandrel 170, in range of about 4 mm to about 10 mm and about 5 mm to about 40 mm, may be particular beneficial for larger clots and/or vessels (e.g., in the leg). Although some example diameters are provided herein, some embodiments of the mandrel 170 may include diameters of the bulbs 176, 177, 178, 179 in accordance with the values provided above and/or diameters that are within about ±5%, about ±10%, about ±15%, or about ±20% of any such values.

In some embodiments, the spherical bulbs 176 include a cylindrical hole, proximally to distally, 4941, 4942, 4943, the spherical bulbs 177 include a cylindrical hole, proximally to distally, 4944, 4945, 4946, the spherical bulbs 178 include a cylindrical hole, proximally to distally, 4947, 4948, and the spherical bulbs 179 include a cylindrical hole, proximally to distally, 4949, 4951. The holes 4940 may, for example, be drilled through the centers of the spherical bulbs 174. The outer diameters of the cylindrical holes 4940 may be oversized to the outer diameter of the strand 172 to allow the spherical bulbs 174 to be threaded in a direction 1722 over the end 1721 of the strand 172. The bulbs 174 may be threaded one or more at a time. In some embodiments, the diameter or width of the strand 172 of the mandrel 170 for the distal portions 100 configured to be deployed in smaller blood vessels is in the range of about 0.15 mm to about 0.75 mm, about 0.35 mm to about 0.65 mm (e.g., about 0.38 mm), or about 0.4 mm to about 0.45 mm In some embodiments, the diameter or width of the strand 172 of the mandrel 170 for distal portions 100 configured to be deployed in larger blood vessels in the range of about 1 mm to about 40 mm (e.g., about 5 mm to about 20 mm). A tapered configuration of the mandrel 170 can allow for adequate and safe deployment of the distal portion 100 across blood vessels with multiple and/or varying diameters (e.g., vasculature that progressively reduces in size). In some embodiments, the mandrel 170 may include a wide variety of different bulb parameters such as bulb quantity, shape, size, spacing, phase-shifting with regards to the longitudinal axis or to a chord of the axis, material parameters, different neck parameters (e.g., neck diameter, neck length, etc.), alignment to the longitudinal axis or to a chord of the axis, combinations thereof, and the like.

Figure 10D:
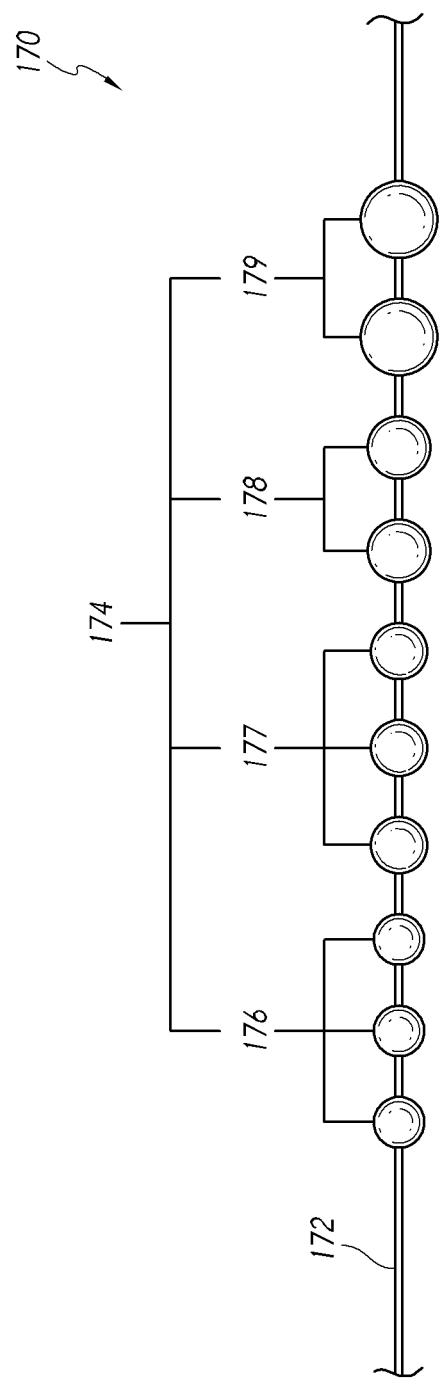
FIG. 10D is a schematic side elevational view of an example embodiment of a mandrel.

FIG. 10D is a schematic side elevational view of an example embodiment of a mandrel 170. In some embodiments, the mandrel 170 is the third mandrel used in fabricating a distal portion 100, after the mandrel 162 and the second mandrel used for heat treating. In some embodiments, the mandrel 170 is the second mandrel used in fabricating a distal portion 100, after the mandrel 162 if the mandrel 162 is used for heat treating. The mandrel 170 includes a strand 172 and a plurality of bulbs 174, for example after assembly of the pieces illustrated in FIG. 10C. In some embodiments, the strand 172 may comprise a wire (e.g., comprising stainless steel or alloy of nickel and titanium), a hypotube, etc. In some embodiments, the bulbs 174 may comprise a ball (e.g., comprising stainless steel or alloy of nickel and titanium). In some embodiments, the strand 172 has an outer diameter of between about 0.001 inches (approx. 0.025 mm) to about 0.0018 inches (approx. 0.045 mm). The bulbs 174 may comprise solid or hollow structures with a bore therethrough to allow the bulbs 174 to be positioned along the strand 172. The bulbs 174 may be coupled to the strand by adhesion (e.g., epoxy), welding, soldering, combinations thereof, and the like. In some embodiments, the bulbs 174 have an outer diameter that is slightly smaller (e.g., about a wall thickness smaller or 1 to 2 strand thicknesses smaller) than a desired outer diameter of a bulb of the distal portion. The bulbs 174 illustrated in FIG. 10D include three generally spherical extra-small bulbs 176, three generally spherical small bulbs 177, two generally spherical medium bulbs 178, and two generally spherical large bulbs 179, which can help form the distal portion 1100 described above. Other selection and arrangement of bulbs 174 is also possible, for example to form other distal portions described herein or other types of distal portions (e.g., the bulbs 176 and the left bulb 177 may be omitted to form the distal portion 11900, 12300, the bulbs 176 and the left and middle bulbs 177 may be omitted to form the distal portion 12000, the bulbs 176 and the bulbs 177 may be omitted to form the distal portion 12100, etc.). In some embodiments, for example to vary the diameter of the necks, the mandrel 170 includes hypotubes between the bulbs 174 having outer diameters corresponding to the desired inner diameter of the neck at that position. The selection and arrangement of the bulbs 174 along the strand 172 and optional neck hypotubes allows the formation of a distal portion 100 having bulbs of nearly any quantity, shape, size, spacing, etc.

Figure 10E:
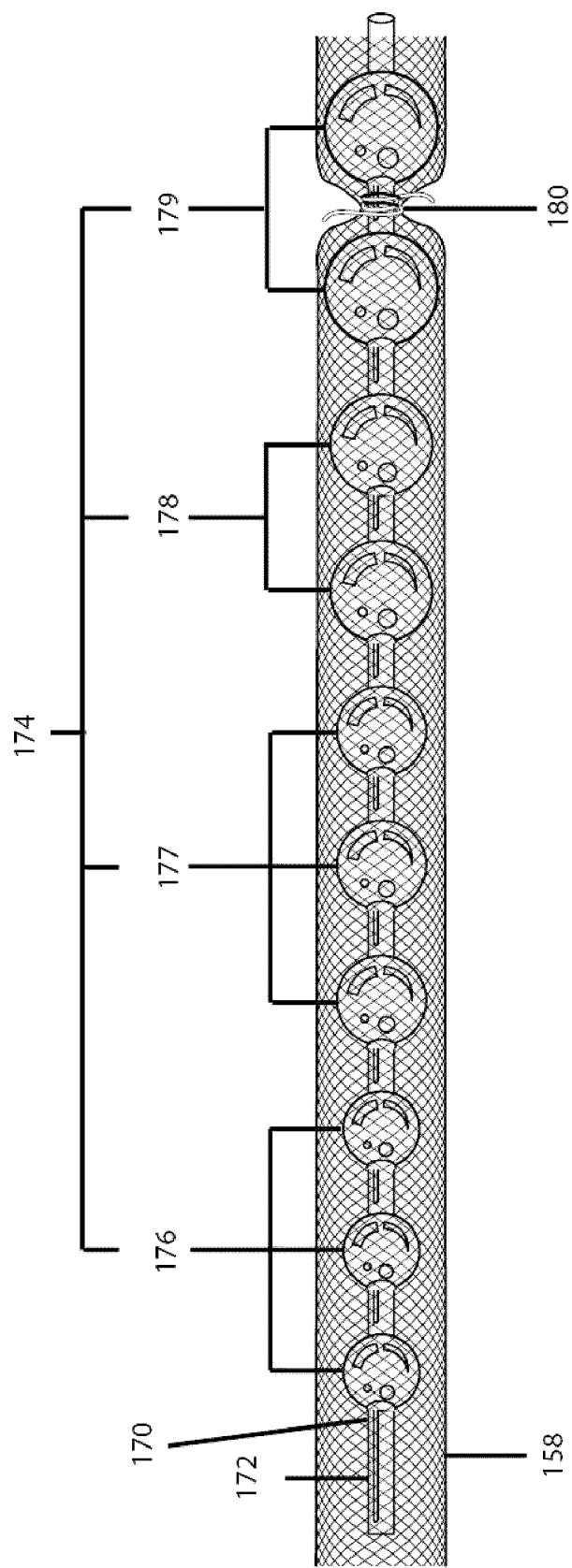
FIG. 10E is a schematic side elevational view illustrating an example embodiment of a woven tubular structure around a mandrel.

FIG. 10E is a schematic diagram illustrating an example embodiment of a woven tubular structure 158 around a mandrel 170. FIG. 10E illustrates the textile structure 158 being tightened around the mandrel 170 using wire 180 (e.g., comprising stainless steel) between the two proximal large bulbs 179. The textile structure 158 can also be tightened around the mandrel 170 using wire 180 or other means between other bulbs 174.

Figure 10F:
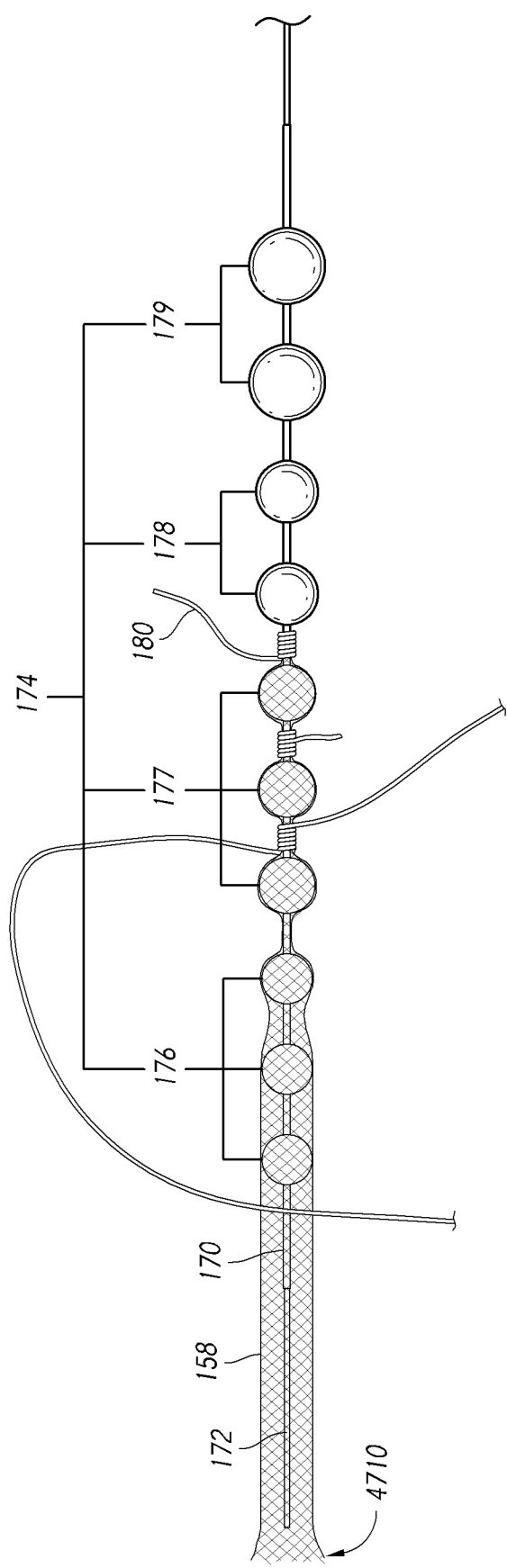
FIG. 10F is a schematic side elevational view illustrating an example embodiment of a woven tubular structure around a mandrel.
Figure 10G:
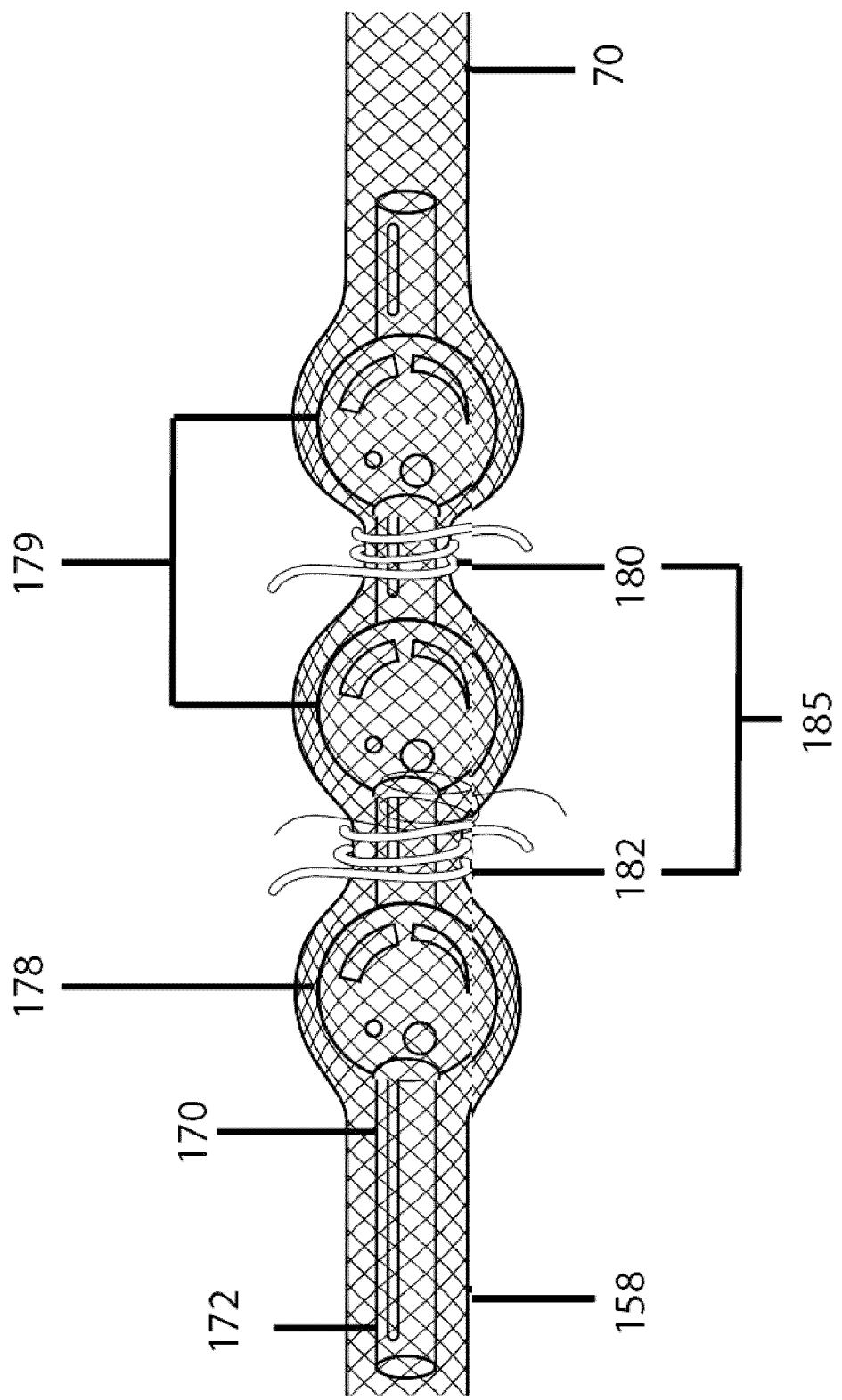
FIG. 10G is a schematic side elevational view of another example embodiment of a woven tubular structure around a mandrel.

FIG. 10F is a schematic side elevational view illustrating an example embodiment a woven tubular structure 158 around a mandrel 170. FIG. 10F illustrates the textile structure 158 being tightened around the mandrel 170 using wire 180 (e.g., comprising stainless steel or alloy of nickel and titanium) between the left bulb 178 and the right bulb 177, between the right bulb 177 and the middle bulb 177, and between the middle bulb 177 and the left bulb 177. The frayed ends 4710 of the distal tip of the textile structure 158 are near the distal end of the strand 172. Although the mandrel 170 illustrated in FIGS. 10C-10F can be used to form the distal portion 1100 of FIG. 2B, the mandrel 170 can also be used to form other distal portions 100, for example not including medium or large bulbs (e.g., a distal portion including three bulbs 178, 179 as illustrated in FIG. 10G, or any desired shape). The wire 180 is wrapped around the textile structure 158 between the bulbs 174, and the textile structure 158 tightens around the bulbs 174. In some embodiments, the wire 180 is wrapped tightly the entire spacing between the bulbs 174 (e.g., to form discrete necks and bulbs). In some embodiments, the wire 180 is wrapped mainly at an intermediate point between the bulbs 174 to create a more undulating pattern without discrete bulbs and necks. Discrete necks and bulbs, or pronounced undulation, may be more effective at treating hard clots than gentle undulations.

FIG. 10G is a schematic side elevational view of another example embodiment of a woven tubular structure 158 around a mandrel 170. FIG. 10G illustrates the textile structure 158 being tightened around the mandrel 170 using wire 180 between the two large spherical bulbs 179 near the proximal end of the woven tubular structure 158 and using wire 182 between the medium spherical bulb 178 and the distal large spherical bulb 179. In some embodiments, wire 185 is wrapped tightly around the textile structure 158 including the strand 172 to form discrete valleys in the region of the wires 180 and 182, and to form discrete hills in the region of the bulbs 178 and 179.

Figure 10H:
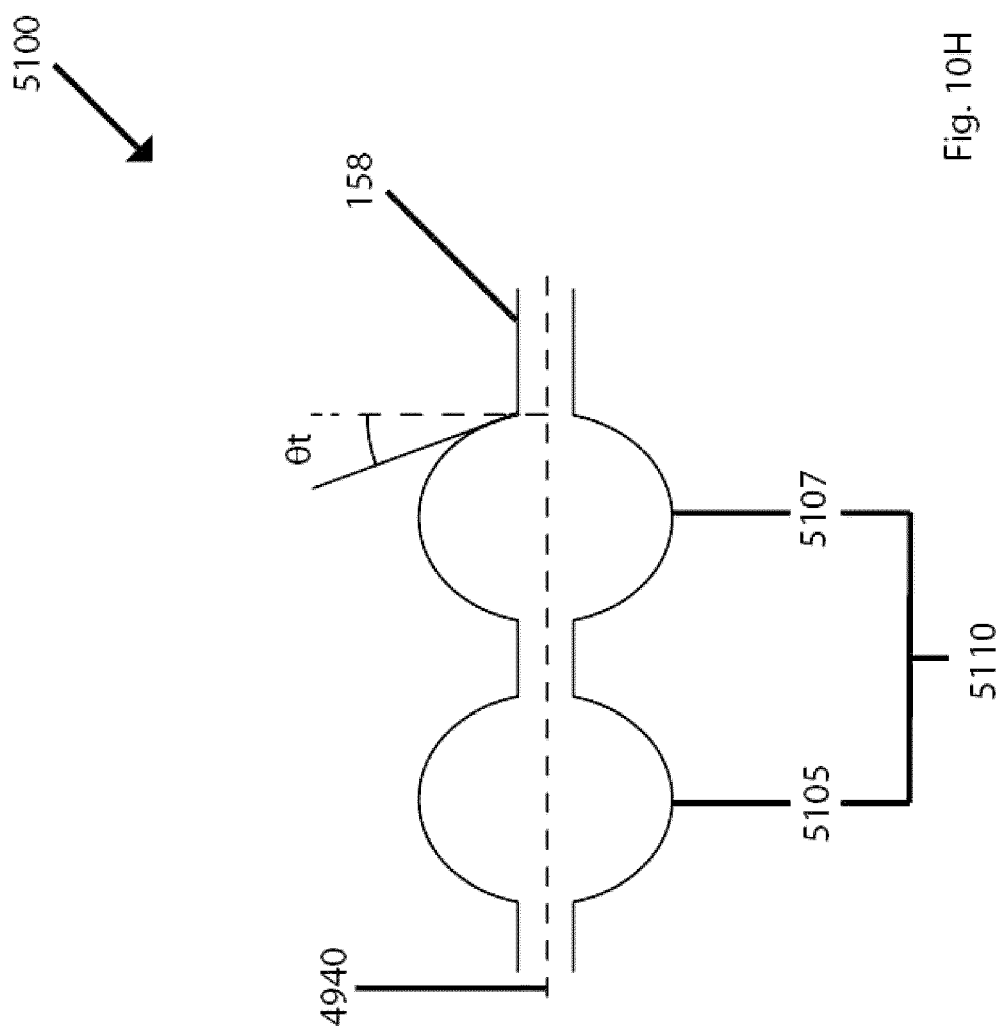
FIG. 10H is a schematic side elevational view of an example embodiment of a woven tubular structure having a transition angle.

FIG. 10H is a schematic side elevational view of another example embodiment of a distal portion 5100 of a vascular treatment device illustrating a high transition angle $\theta_t$. The distal portion 5100 includes, in an expanded state, a plurality of woven bulbs 5110 and a neck between the bulbs 5105, 5107. The distal portion 5100 may be formed, for example, by tightly wrapping wire, bangles, etc. around the textile structure 158 during a second heat treatment to form distinct bulbs 5105, 5107. FIG. 10I is a schematic side elevational view of another example embodiment of a distal portion 5200 of a vascular treatment device illustrating a low transition angle $\theta_t$. The distal portion 5200 includes, in an expanded state, a plurality of woven bulbs 5210 and a depression between the bulbs 5205, 5207. The distal portion 5200 may be formed, for example, by tightly wrapping wire, bangles, etc. around the center of a neck of the textile structure 158 during a second heat treatment to form less distinct bulbs 5205, 5207. The distal portions 5100, 5200 may be the distal portion 100 of the device 10, 20, 30, or 40. A hill-to-valley transition angle $\theta_t$ is indicative of the amount of bulging of the bulbs relative to the necks, and is defined as the angle formed between the slope of the hill towards the valley and the plane perpendicular to the central longitudinal axis 4940. In some embodiments, the angle $\theta_t$ is between about 0° and about 90°. At higher transition angles $\theta_t$, the amount of bulging is higher, and, at lower transition angles $\theta_t$, the amount of bulging is lower. A higher transition angle $\theta_t$ may enhance torsional rasping of hard clots adherent to the vessel endothelium. A lower transition angle $\theta_t$ may enhance wall apposition of flow diverters or flow disruptors in the treatment of aneurysms or vascular malformations. Referring again to FIGS. 10H and 10I, a schematic representation of the measurement of transition angle $\theta_t$ is shown. In the embodiment illustrated in FIG. 10H, the transition angle $\theta_t$ is about 20°. In the embodiment illustrated in FIG. 10I, the transition angle $\theta_t$ is about 75°.

FIG. 10J is a schematic side elevational view of another example embodiment of a woven tubular structure 158 around a mandrel 175. In some embodiments, bangles or c-shaped clamps 190 may be used to tighten the textile structure 158 around the mandrel 175 instead of or in addition to the wire 180, 182. FIG. 10J illustrates the textile structure 158 being tightened around the mandrel 175 using bangles or c-shaped clamps 187, instead of wire, between the two large spherical bulbs 179 near one end of the woven tubular structure 158 and using bangles or c-shaped clamps 189 between the medium spherical bulb 178 and the left large spherical bulb 179, instead of wire, near the other end of the woven tubular structure 158. The bangles 190 may include a slit 191 that allows the bangle 190 to be pried open and wrapped around the textile structure 158 and the mandrel 175 but small enough that filaments of the textile structure 158 generally cannot protrude out of the slit 191.

Figure 10K:
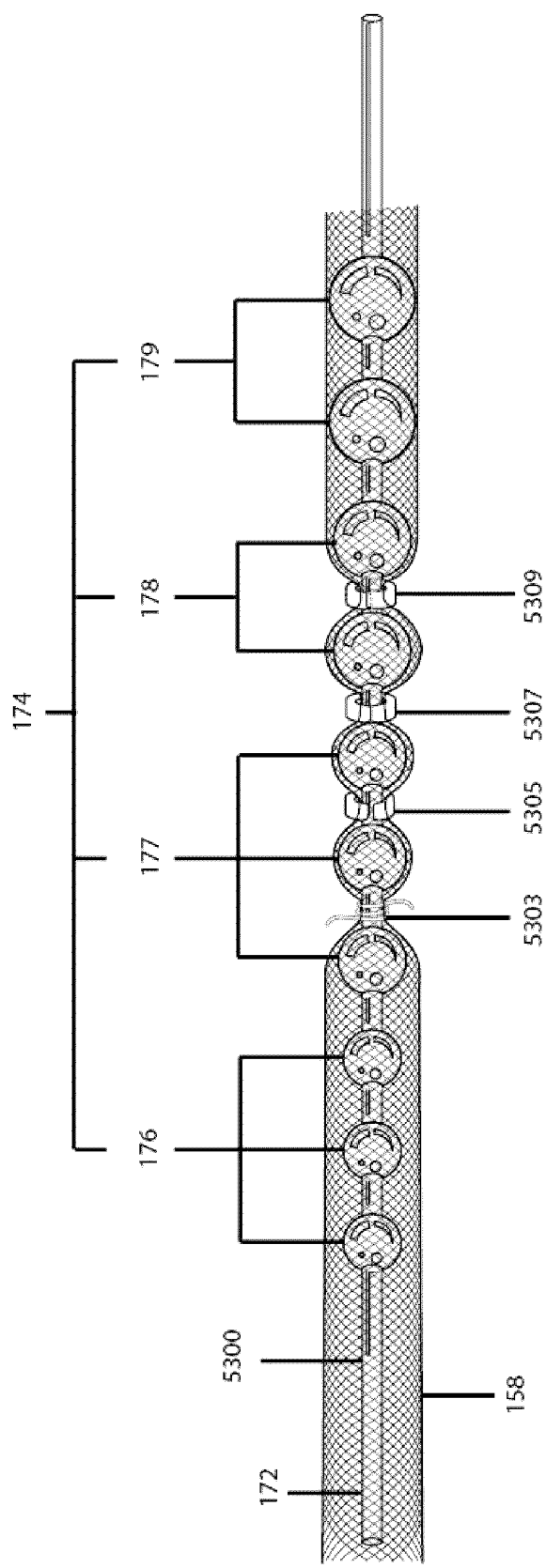
FIG. 10K is a schematic side elevational view of yet another example embodiment of a woven tubular structure around a mandrel.

FIG. 10K is a schematic side elevational view of yet another example embodiment of a woven tubular structure 158 around a mandrel 5300. FIG. 10K illustrates the textile structure 158 being tightened around the mandrel 5300 including the strand 172 using three different types of bangles or c-shaped clamps 5305, 5307, 5309 and wire 5303 to form discrete valleys and discrete hills in the region of the bulbs 177 and 178. In some embodiments, the bangle has a length close to that of the neck. In some embodiments, the bangle is thin enough that a plurality of bangles may be placed between the bulbs 174. In some embodiments as illustrated in FIG. 10K, circumferential ends of the bangles or c-shaped clamps may be circumferentially spaced by a slit 191 as shown by the bangle 5305, abut as shown by the bangle 5307, longitudinally overlap or circumferentially overlap as shown by the bangle 5309, etc. In some embodiments, temporary high-temperature adhesive may be used instead of or in addition to mechanical fasteners such as wire and/or bangles.

The textile structure 158 to the left of the left bulb 176 or the distal-most bulb may also be secured to the strand 172 to form the distal neck 65. The portions of the strand 172 beyond the bulbs 174 may include markers to help determine the length of any proximal and distal necks. In some embodiments, the distal neck 65 may be curled, for example into a pigtail (e.g., by curling the strand 172 to the left of the left bulb 176).

In some embodiments, the strand 172 may be substantially omitted. For example, the bulbs 174 can be placed inside the textile structure 158 and then the textile structure 158 tightened around each side of the bulbs 174. An external template, for example, may be used to ensure proper spacing. Such a method may increase adaptability for forming different types of distal portions 100 using the same bulbs 174. In some embodiments, the strand 172 may be removed from the bulbs 174 after securing the textile structure 158 around the bulbs 174.

The textile structure 158 and the bulbs 174, and optionally the strand 172, are heat treated to impart shape memory to at least some of the filaments (e.g., at least the filaments 156 comprising shape memory material). In some embodiments, the secondary heat treatment of shape memory (e.g., comprising between about 55.8 wt % and about 57 wt % nickel) is at a temperature between about 500° C. and about 550° C. (e.g., about 525° C.) for between about 3 minutes and about 10 minutes (e.g., about 5 minutes) in an atmosphere (e.g., a sand bath fluidized with ambient air). As described herein, certain such heat treatment processes can maintain the shape of the distal portion 100 (e.g., including the bulbs and necks) between at least about room temperature and about body temperature absent stress-induced martensite, for example because the austenitic finish temperature $A_f$ is between about 10° C. and about 18° C. (e.g., the distal portion 100 is super-elastic at temperatures greater than about 18° C.).

In some embodiments, the secondary heat treatment of shape memory (e.g., comprising between about 54.5 wt % and about 55.3 wt % nickel) is at a temperature between about 400° C. and about 450° C. (e.g., about 425° C.) for between about 3 minutes and about 10 minutes (e.g., about 5 minutes) in an atmosphere (e.g., a sand bath fluidized with ambient air). As described herein, certain such heat treatment processes can maintain the shape of the distal portion 100 (e.g., including the bulbs and necks) between at least about room temperature and about body temperature absent stress-induced martensite, for example because the austenitic finish temperature $A_f$ is between about 10° C. and about 18° C. (e.g., the distal portion 100 is super-elastic at temperatures greater than about 18° C.).

In some embodiments, the secondary heat treatment of shape memory (e.g., comprising between about 55.8 wt % and about 57 wt % nickel) is at a temperature between about 400° C. and about 450° C. (e.g., about 425° C.) for between about 3 minutes and about 10 minutes (e.g., about 5 minutes) in an atmosphere (e.g., a sand bath fluidized with ambient air). Certain such heat treatment processes can maintain the tubular shape of the distal portion 100 (e.g., without the bulbs and necks) between at least about room temperature and about body temperature absent stress-induced martensite, for example because the austenitic finish temperature $A_f$ is increased from between about 10° C. and about 18° C. to between about 25° C. and about 37° C. (e.g., the distal portion 100 slowly transitions to the bulb and neck shape at temperatures between about 25° C. and 37° C.). This dual heat treatment and slow shape transformation at room and/or body temperature can be referred to as one-way shape memory effect.

In some embodiments, the secondary heat treatment of shape memory (e.g., comprising between about 54.5 wt % and about 55.3 wt % nickel) is at a temperature between about 500° C. and about 550° C. (e.g., about 525° C.) for between about 20 minutes and about 180 minutes (e.g., about 25 minutes) in an atmosphere (e.g., a sand bath fluidized with ambient air). Certain such heat treatment processes can maintain the tubular shape of the distal portion 100 (e.g., without the bulbs and necks) between at least about room temperature and about body temperature absent stress-induced martensite, for example because the austenitic finish temperature $A_f$ is increased from between about 10° C. and about 18° C. to between about 25° C. and about 37° C. (e.g., the distal portion 100 slowly transitions to the bulb and neck shape at temperatures between about 25° C. and 37° C.).

In some embodiments, the secondary heat treatment of shape memory (e.g., comprising between about 55.8 wt % and about 57 wt % nickel) is at a temperature between about 400° C. and about 450° C. (e.g., about 425° C.) for between about 3 minutes and about 10 minutes (e.g., about 5 minutes) in an atmosphere (e.g., a sand bath fluidized with ambient air), which can have the effect described above. In some embodiments, a tertiary heat treatment may be performed, for example to impart the shape of the distal portion 100 shown in FIG. 27L at certain temperatures. In certain such embodiments, the tertiary heat treatment of shape memory (e.g., comprising between about 55.8 wt % and about 57 wt % nickel) is at a temperature between about 500° C. and about 550° C. (e.g., about 525° C.) for between about 3 minutes and about 10 minutes (e.g., about 5 minutes) in an atmosphere (e.g., a sand bath fluidized with ambient air). Certain such heat treatment processes can maintain the spiral or twisted or helical shape of the distal portion 100 between about 10° C. and about 18° C. absent stress-induced martensite, which can be achieved in a body, for example, by injecting cold saline (e.g., between about 5° C. and about 18° C.) for a localized temperature change or cooling effect. This triple heat treatment can be referred to as two-way shape memory effect.

In some embodiments, the secondary heat treatment of shape memory (e.g., comprising between about 54.5 wt % and about 55.3 wt % nickel) is at a temperature between about 500° C. and about 550° C. (e.g., about 525° C.) for between about 20 minutes and about 180 minutes (e.g., about 25 minutes) in an atmosphere (e.g., a sand bath fluidized with ambient air), which can have the effect described above. In some embodiments, a tertiary heat treatment may be performed, for example to impart the shape of the distal portion 100 shown in FIG. 27L at certain temperatures. In certain such embodiments, the tertiary heat treatment of shape memory (e.g., comprising between about 54.5 wt % and about 55.3 wt % nickel) is at a temperature between about 400° C. and about 450° C. (e.g., about 425° C.) for between about 3 minutes and about 10 minutes (e.g., about 5 minutes) in an atmosphere (e.g., a sand bath fluidized with ambient air). Certain such heat treatment processes can maintain the spiral or twisted or helical shape of the distal portion 100 between about 10° C. and about 18° C. absent stress-induced martensite, which can be achieved in a body, for example, by injecting cold saline (e.g., between about 5° C. and about 18° C.) for a localized temperature change or cooling effect.

The secondary and/or tertiary heat treatment temperature can be adjusted based on the particular shape-memory alloy. For example, a ternary alloy comprising cobalt may exhibit properties similar to a relatively low nickel shape-memory alloy.

In some embodiments, after heat treating, the distal portion is then placed in a water bath (e.g., between about 20° C. and about 25° C.) for between about 15 minutes and 45 minutes (e.g., about 30 minutes). Rapid heating and/or cooling can help to retain the shape (e.g., to achieve the austenite finish temperature $A_f$). After this second heat treatment, the textile structure 158 may be referred to as a secondary heat set or shape set structure.

Figure 10L:
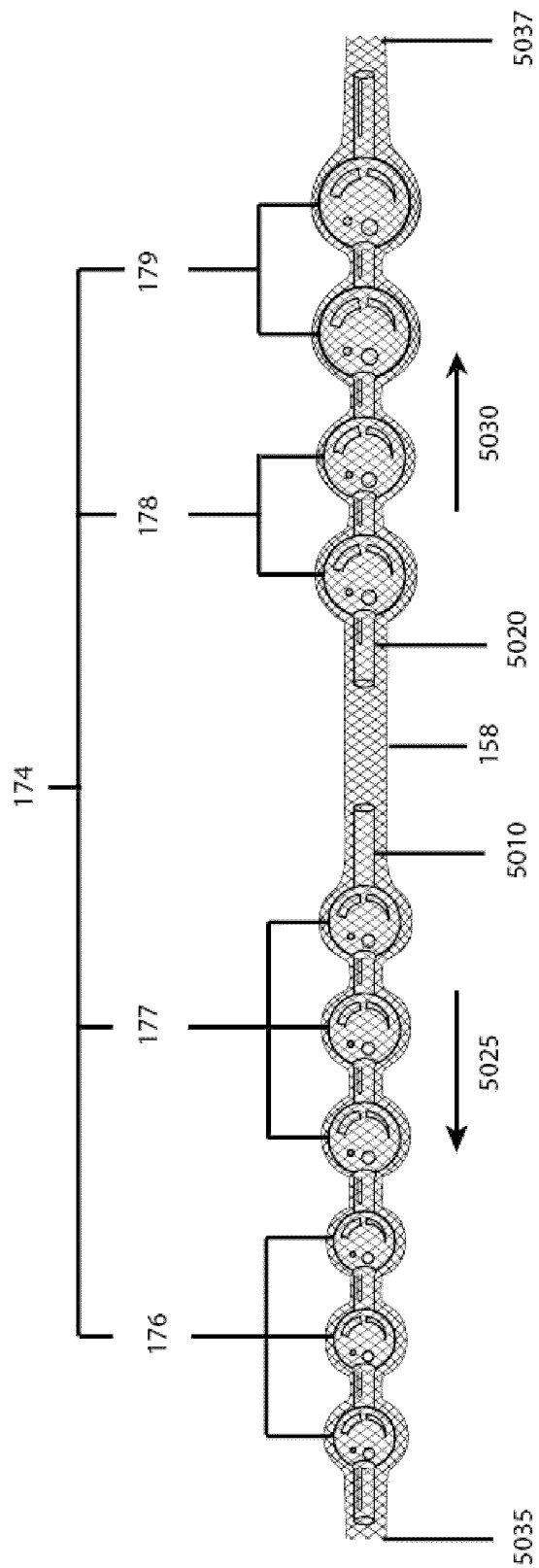
FIG. 10L is a schematic side elevational view of an example embodiment of removal of a mandrel from within a woven tubular structure.

FIG. 10L is a schematic side elevational view of an example embodiment of removal of a mandrel from a woven tubular structure 158. The wire, bangles, adhesive, etc. has been removed after heat treating to impart the shape of the mandrel to the textile structure. The mandrel includes a first mandrel piece 5010 and a second mandrel piece 5020. The first mandrel piece 5010 is shown being removed from one side (proximal or distal), as indicated by the arrow 5025, and the second mandrel piece 5020 is shown being removed from the other side, as indicated by the arrow 5030 (e.g., by being separable in an intermediate portion between the first mandrel piece 5010 and the second mandrel piece 5020). In some embodiments, after heat treatment, removing the mandrel piece 5020 including the proximal four spherical bulbs in the proximal direction and removing the mandrel piece 5010 including the distal six spherical bulbs 5010 in the distal direction may inhibit damage to the integrity of the woven tubular structure 158. A one piece mandrel or a multiple piece mandrel may also be removed from one side. Although some examples of mandrels are provided herein, some embodiments of mandrels may include a wide variety of different bulb parameters such as bulb quantity, shape, size, spacing, phase-shifting with regards to the longitudinal axis or to a chord of the axis, material parameters, different neck parameters (e.g., neck diameter, neck length, etc.), alignment to the longitudinal axis or to a chord of the axis, number of mandrels, combinations thereof, and the like.

The primary heat treatment in the cylindrical shape can allow the bulbs to radially expand to at least the diameter of the mandrel 162 without being damaged, and the secondary heat treatment can provide shape setting. In some embodiments, the first heat treatment process may be omitted (e.g., the textile structure 158 slid off the mandrel 162 and then onto the mandrel 170 (e.g., secured with wires, bangles, adhesive, etc.) with no primary heat treatment).

Figure 10M:
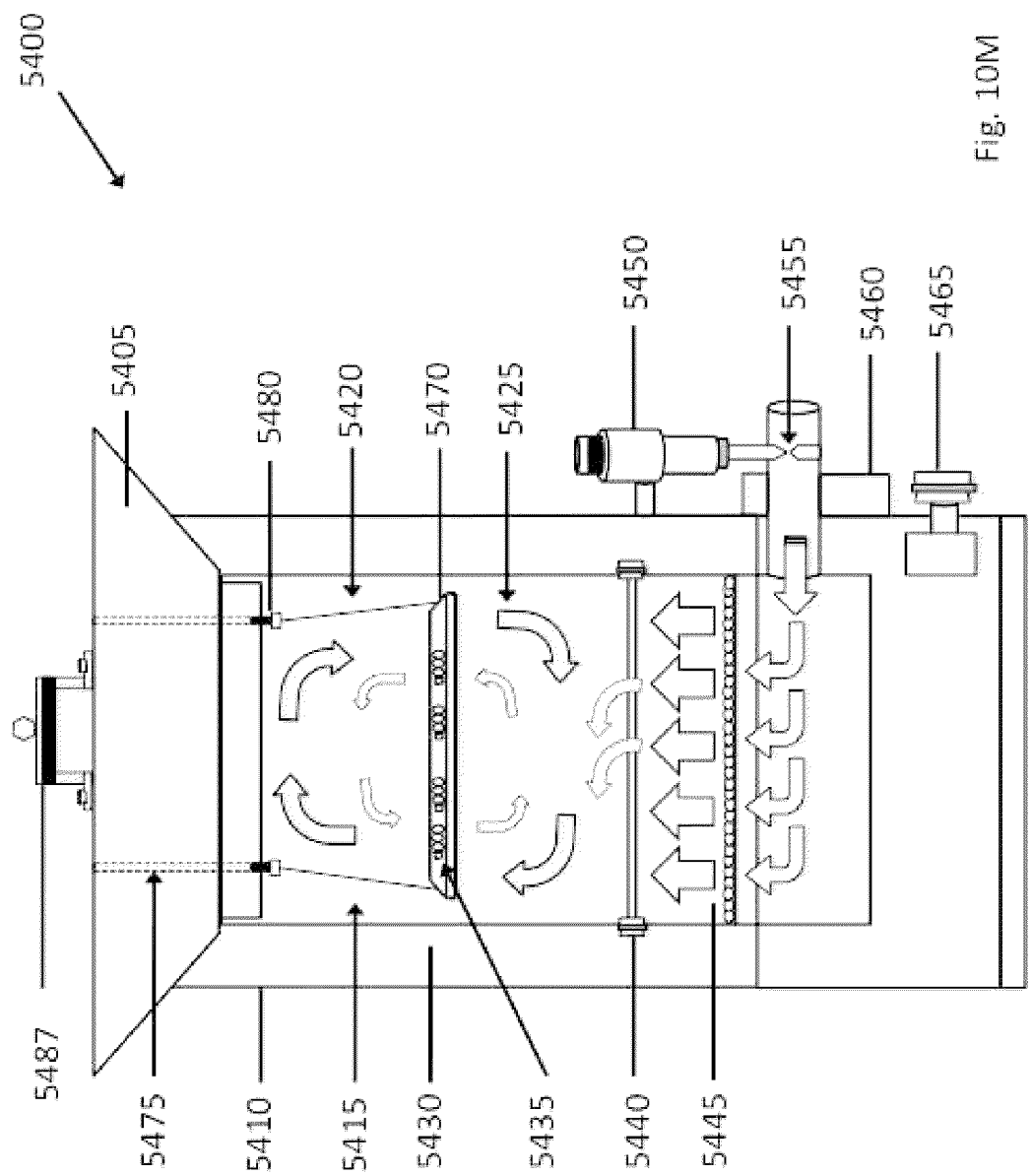
FIG. 10M is a schematic partial cut away side view of an example embodiment of a heat treatment device.

FIG. 10M is a schematic partial cut away side view of an example embodiment of heat treatment device. In some embodiments, the heat treatment device comprises a fluidized sand bath 5400. The fluidized sand bath 5400 includes an outer wall 5410 and an inner thermal insulation layer 5430. The fluidized sand bath 5400 includes a constrictive air inlet gate 5455 that allows the inflow of ambient air for heat treatment at atmosphere, or inflow of select gases (e.g., nitrogen, a mixture of hydrogen and nitrogen, a mixture of carbon monoxide, hydrogen, and nitrogen, combinations thereof, and the like) for heat treatment in an inert atmosphere. In some embodiments, the heat treatment is performed in a fluidized sand bath 5400 in inert atmosphere to inhibit oxidation of the surface of shape memory material, for example to inhibit formation of nickel oxides in alloys of nickel and titanium, during heat treatment.

In some embodiments, the heat treatment device 5400 includes an external air inflow regulator 5450 having an adjustable height $h_1$, which can regulate the velocity of the air inflow into the inner chamber 5415 of the sand bath 5400 through the constrictive air inlet gate 5455, to create an adequate fluidized state in the sand bath 5400. The external air inflow regulator 5450 is at a height $h_1$ above the ground, which can be adjusted by increasing or decreasing the height $h_1$, has a pressure $P_1$, and a velocity of gas $v_1$. The gas 5425 entering the inner chamber 5415 of the sand bath 5400 through the constrictive air inlet gate 5455 is at a height $h_2$ above the ground, has a pressure $P_2$, and a velocity of gas $v_2$. As the sum of the kinetic energy per unit volume ($\frac{1}{2}\rho v^2$), the potential energy per unit volume ($\rho gh$), and the pressure energy (P) remain the same, the density of the gas $\rho$ and the acceleration due to gravity g (980 cm/second$^2$) remain constant, the velocity of the gas $v_2$ entering the inner chamber 5415 of the sand bath 5400 can be calculated using Equation 1:

$$\tfrac{1}{2}\rho v_1^2 + \rho g h_1 + P_1 = \tfrac{1}{2}\rho v_2^2 + \rho g h_2 + P_2$$

or, rearranged, $v_2 = \sqrt{[v_1^2 + 1960(h_1 - h_2) + 2(P_1 - P_2)/\rho]}$.   (Eq. 1)

In some embodiments, if the pressures $P_1$ and $P_2$ are equal to atmospheric pressure ($P_1 = P_2 = P_{atm}$) the height $h_2$ of the constrictive air inlet gate 5455 is at ground level ($h_2 = 0$), and the gas velocity at the level of the external air inflow regulator 5450 is initially at rest ($v_1 = 0$), then the velocity $v_2$ of the gas entering the inner chamber 5415 of the sand bath 5400 is directly proportional to the height $h_1$ of the external air inflow regulator 5450. By increasing the height $h_1$ of the external air inflow regulator 5450, the velocity $v_2$ of the gas can be increased, and $v_2$ can be calculated in cm$^3$/s using Equation 2:

$$v_2 = \sqrt{(1960 \times h_1)}$$   (Eq. 2)

In some embodiments, the sand bath 5400 includes a fail safe temperature regulator 5460 and an electric energy regulator 5465. The fail safe temperature regulator 5460 can help regulate the temperature within the fluidized sand bath 5400. For example, during the heat treatment of an alloy of nickel and titanium, if the temperature is above 550° C., the fail safe temperature regulator 5460 may turn off the air inlet gate 5455 or, through the electric energy regulator 5465, turn off the power to a heating element 5440, as elevated annealing temperatures may adversely impact the $A_f$ temperature as discussed herein. In some embodiments, the electric energy regulator 5465 can help regulate the voltage (AC or DC voltages) to inhibit electrical surges that may increase or decrease the temperature of the fluidized sand bath 5400 through the heating element 5440. For example, if an electrical surge during the heat treatment of an alloy of nickel and titanium impacted the heating element 5440 and increased the temperature above 550° C., the electric energy regulator 5465 may turn off the power to the heating element 5440, as elevated annealing temperatures may adversely impact the $A_f$ temperature as discussed herein. In some embodiments, the fail safe temperature regulator 5460 and the electric energy regulator 5465 may be controlled and regulated by sensors, for example thermal sensors, pressure sensors, electrical sensors, combinations thereof, and the like.

In the example embodiment illustrated in FIG. 10M, the gas 5425 that enters through the air inlet gate 5455 passes through a porous plate 5445 and a heating element 5440 prior to entering the inner chamber 5415 of the sand bath 5400. The heating element 5440 may be electrically controlled and regulated via the fail safe temperature regulator 5460 and/or the electric energy regulator 5465. The inner chamber 5415 of the sand bath 5400 includes sand bath media 5420, for example dry inert non-flammable particles such as alumina (aluminum oxide), metallic beads such as stainless steel, combinations thereof, and the like. Fluidized sand bath media or particles 5420 may have a melting point and/or boiling point well above the heat treatment temperature such that solidification, which could otherwise occur upon on cooling (e.g., as in salt baths) and fumes (e.g., as in hot oil baths) are inhibited.

In the embodiment illustrated in FIG. 10M, when the gas 5425 is passed through the sand bath media or particles (e.g., aluminum oxide particles) 5420 via the porous plate 5445 and the heating element 5440, the sand bath media 5420 are separated and suspended in the gas flow 5425 and take on the appearance of a boiling liquid with excellent heat transfer characteristics. When the fluidized sand bath media 5420 are heated, heat is distributed quickly and evenly throughout the sand bath 5400 and transferred rapidly to any devices or components 5435 in the sand bath 5400.

In some embodiments, the fluidized sand bath 5400 comprises a detachable flange 5405 that covers the roof of the sand bath 5400. The detachable flange 5405 of FIG. 10M includes a handle 5487 and one or more hollow conduits 5475 to allow passage of the arms of the container or basket 5470 carrying the devices or components 5435 being heat treated. The container 5470 may take a variety of shapes, for example, sphere, oblong, egg, oval, ellipse, helical, triangle, rectangle, parallelogram, rhombus, square, diamond, pentagon, hexagon, heptagon, octagon, nonagon, decagon, trapezoid, trapezium, other polygons, or bulged versions of these and other shapes, combinations thereof, and the like, based on the devices or components 5435 being heat treated. The arms of the container 5470 may include single filament wires, multi-filament wires, hypotubes, combinations thereof, and the like. In some embodiments, the arms of the container 5470 are reversibly attached to the flange 5405 via detachable air-sealant rivets 5480 on the outside of the flange 5405, in which case the arms of the container 5470 pass through the hollow conduits 5475, on the inside of the flange 5405, in which case the arms of the container 5470 do not pass through the hollow conduits 5475, or on both the inside and the outside of the flange 5405. The reversible attachment points of the arms of the container 5470 to the air-sealant rivets 5480 may include a luer lock mechanism, a ball and socket mechanism, a wire and hook mechanism, a c-shaped clasp and hook mechanism, combinations thereof, and the like. The detachable flange 5405 can allow placement of the container 5470 with the devices or components 5435 being heat treated in the fluidized sand bath 5400 and/or removal of the container 5470 and the devices or components 5435 from the fluidized sand bath 5400 for placement in the cooling bath after heat treatment.

Figure 11A:
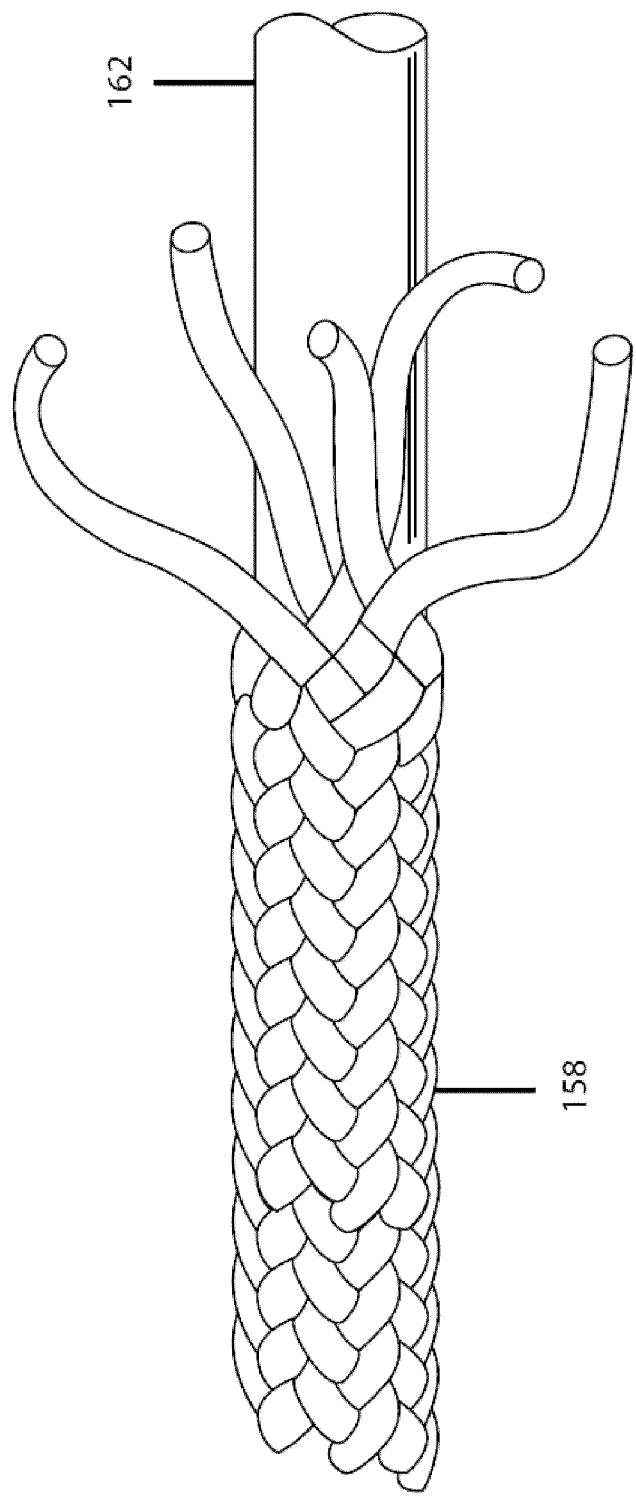
FIG. 11A is a schematic side elevational view of an example embodiment of braiding around a mandrel.

FIG. 11A is a schematic side elevational view of an example embodiment of braiding around a mandrel 162. For example, FIG. 11A schematically shows what is occurring in FIGS. 8A and 8D. The mandrel 162 may be used in a heat treatment process to impart a cylindrical shape, or the textile structure may be slid off of the mandrel 162 for heat treatment on another mandrel.

Figure 11B:
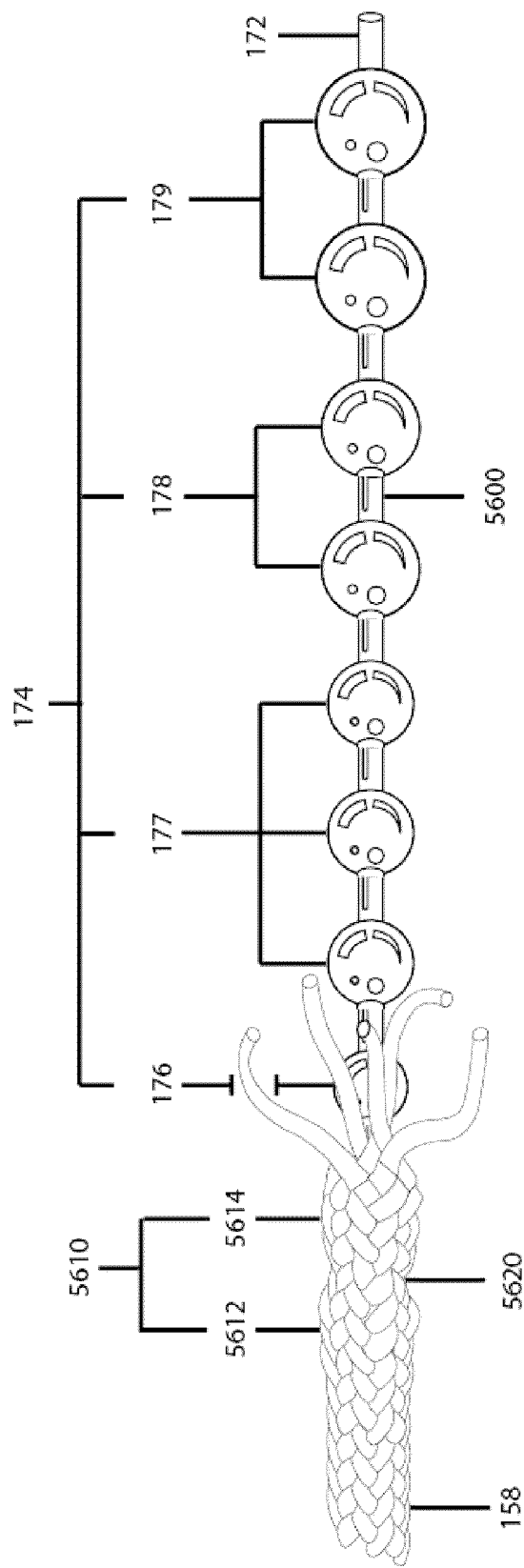
FIG. 11B is a schematic side elevational view of another example embodiment of braiding around a mandrel.

FIG. 11B is a schematic side elevational view of another example embodiment of braiding around a mandrel 5600. The mandrel 5600 includes bulbs 174 and strand 172, for example as describe with respect to FIGS. 10C and 10D. The textile structure 158 may be braided around the mandrel 5600 so that woven bulbs 5610 are formed during the braiding process, for example the woven bulbs 5612, 5614 with a woven neck 5620 between the woven bulbs 5612, 5614. The textile structure 158 may be heat treated on the mandrel 5600 to impart the bulb shapes, reducing manufacturing steps compared to a two-step heat treatment. During or after the braiding process, bangles, wire, adhesive, etc. may be used to secure portions of the textile structure more tightly to the mandrel 5600, for example as described with respect to FIGS. 10G, 10J, and 10K. In some embodiments, a single heat treatment after braiding around a bulbous mandrel 5600 as illustrated in FIG. 11B may include the same parameters as the second heat treatment around the mandrel 170 as described above.

Figure 11C:
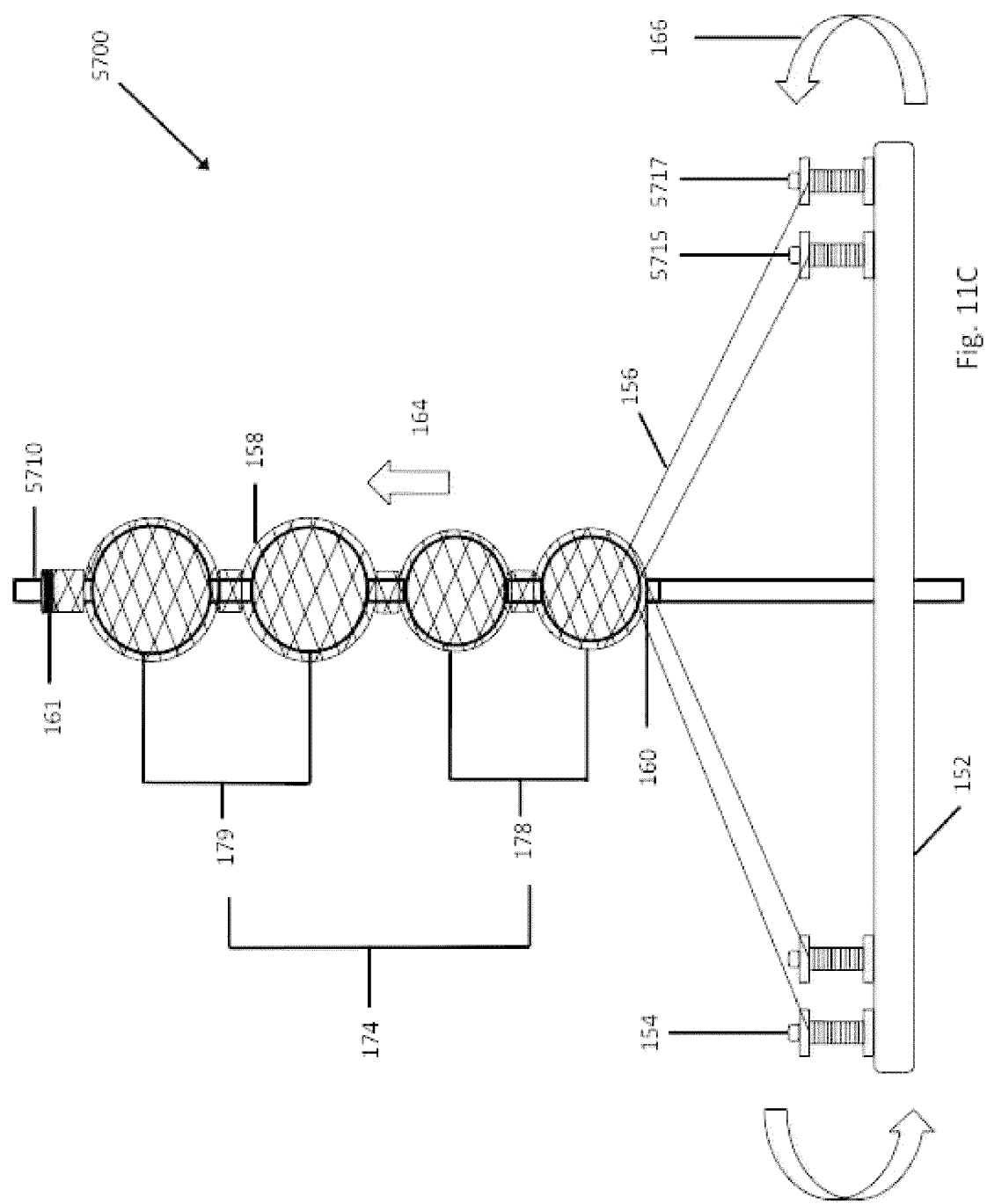
FIG. 11C is a schematic side elevational view of an example embodiment of an example embodiment of forming a textile structure.

FIG. 11C is a schematic side elevational view of an example embodiment of forming a textile structure. The textile structure 158 may form a distal portion of a vascular treatment device, for example of the distal portion 100 of the device 10, 20, 30, or 40. For example as described with respect to FIG. 8A and/or FIG. 9B, the braiding device 5700 includes a yarn wheel or braid carrier mechanism or circular horn gear 152 and a plurality of spindles 153 and individual carriers 155. A spindle 153 is a stick on the circular horn gear 152. A spool 154 is a hollow device that fits onto a spindle 153 and includes filaments 156 wound around it. An individual carrier 155 includes a spindle 153 and a spool 154 on the spindle 153. The terms spindle, spool, and individual carrier may be used interchangeably depending on context. The individual carriers 155 include spools 154 including filaments 156 that are woven together to form the textile structure 158 of the distal portion 100. The filaments 156 each extend from a individual carrier 155 to a ring or vertical puller 161 over a bulbous mandrel 5710 comprising spherical bulbs (e.g., the mandrel 5600 of FIG. 11B), and are braided around the bulbous mandrel 5710 by spinning the circular horn gear 152, spinning the spindles 153, and pulling the ring 161 away from the circular horn gear 152 (e.g., in a vertical direction 164). In some embodiments, the ring 161 may be pulled away from the horn gear 152 by moving the entire mandrel 5710 away from the horn gear 152. In some embodiments, the ring 161 may be pulled away from the horn gear 152 over the bulbs 174 of the mandrel 5710 (e.g., by being elastic and/or by being larger than the bulbs 174). As the textile structure 158 is woven at preform point 160, the textile structure 158 advances in the direction of the arrow 164. The circular horn gear 152 spins in the direction of the arrows 166 in a horizontal plane, and the spools 154 including filaments 156 on the spindles 153 rotate within the circular horn gear 152 to create the desired braiding pattern including plurality of woven bulbs 174, which includes in this example two large spherical bulbs 179 and two medium spherical bulbs 178, and necks between the bulbs 174. Although some examples of the carrier braider 150 with 4 spindles 153 or individual carriers 155 are provided herein, some embodiments of the carrier braider 150 may include 6 to 144 spindles 153 or individual carriers 155 in accordance with the values provided above and/or carrier braiders 150 that have 6, 12, 24, 36, 48, 60, 72, 84, 96, 120, 144, etc. spindles 153 or individual carriers 155. The textile structure 158 may be heat treated on the mandrel 5710 to impart the bulb shapes, reducing manufacturing steps compared to a two-step heat treatment. In some embodiments, a single heat treatment after braiding around a bulbous mandrel 5710 as illustrated in FIG. 11C may include the same parameters as the second heat treatment around the mandrel 170 as described above.

FIG. 11D is a schematic side elevational view of another example embodiment of forming a textile structure 158. The textile structure 158 may form a distal portion of a vascular treatment device, for example of the distal portion 100 of the device 10, 20, 30, or 40. For example as described with respect to FIG. 8A, FIG. 9B, and/or FIG. 11C, the braiding device 5800 includes a yarn wheel or braid carrier mechanism or circular horn gear 152 and a plurality of spindles 153 and individual carriers 155. A spindle 153 is a stick on the circular horn gear 152. A spool 154 is a hollow device that fits onto a spindle 153 and includes filaments 156 wound around it. An individual carrier 155 includes a spindle 153 and a spool 154 on the spindle 153. The terms spindle, spool, and individual carrier may be used interchangeably depending on context. The individual carriers 155 include spools 154 including filaments 156 that are woven together to form the textile structure 158 of the distal portion 100. Each spindle pair 5720 includes an outer spindle or individual carrier 5717 and an inner spindle or individual carrier 5715. The filaments 156 each extend from an individual carrier 155 to a ring or vertical puller 161 over a bulbous mandrel 5710 comprising spherical bulbs (e.g., the mandrel 5600 of FIG. 11B), and are braided around the bulbous mandrel 5710 by spinning the circular horn gear 152, spinning the spindles 153, and pulling the ring 161 away from the circular horn gear 152 (e.g., in a vertical direction 164), for example as described with respect to FIG. 11C. As the textile structure 158 is woven at preform point 160, the textile structure 158 advances in the direction of the arrow 164. The circular horn gear 152 spins in the direction of the arrows 166 in a horizontal plane, and the spools 154 including filaments 156 on the spindles 153 rotate within the circular horn gear 152 to create the desired braiding pattern including a plurality of woven bulbs 174, which in this example includes two large spherical bulbs 179 and two medium spherical bulbs 178, and necks between the bulbs 174. The textile structure 158 may include a plurality of segments, at least one of the segments having a different pore size than at least one other segment. For example, in the textile structure 158 illustrated in FIG. 11D, the distal segment 5810 has relatively high PPI and has relatively low porosity, the middle segment 5820 has relatively low PPI and has relatively high porosity, and the proximal segment 5830 has relatively high PPI and has relatively low porosity. Although some examples of the carrier braider 150 with 4 spindles 153 or individual carriers 155 are provided herein, some embodiments of the carrier braider 150 may include 6 to 144 spindles 153 or individual carriers 155 in accordance with the values provided above and/or carrier braiders 150 that have 6, 12, 24, 36, 48, 60, 72, 84, 96, 120, 144, etc. spindles 153 or individual carriers 155. The textile structure 158 may be heat treated on the mandrel 5710 to impart the bulb shapes, reducing manufacturing steps compared to a two-step heat treatment. In some embodiments, a single heat treatment after braiding around a bulbous mandrel 5710 as illustrated in FIG. 11D may include the same parameters as the second heat treatment around the mandrel 170 as described above.

Figure 11E:
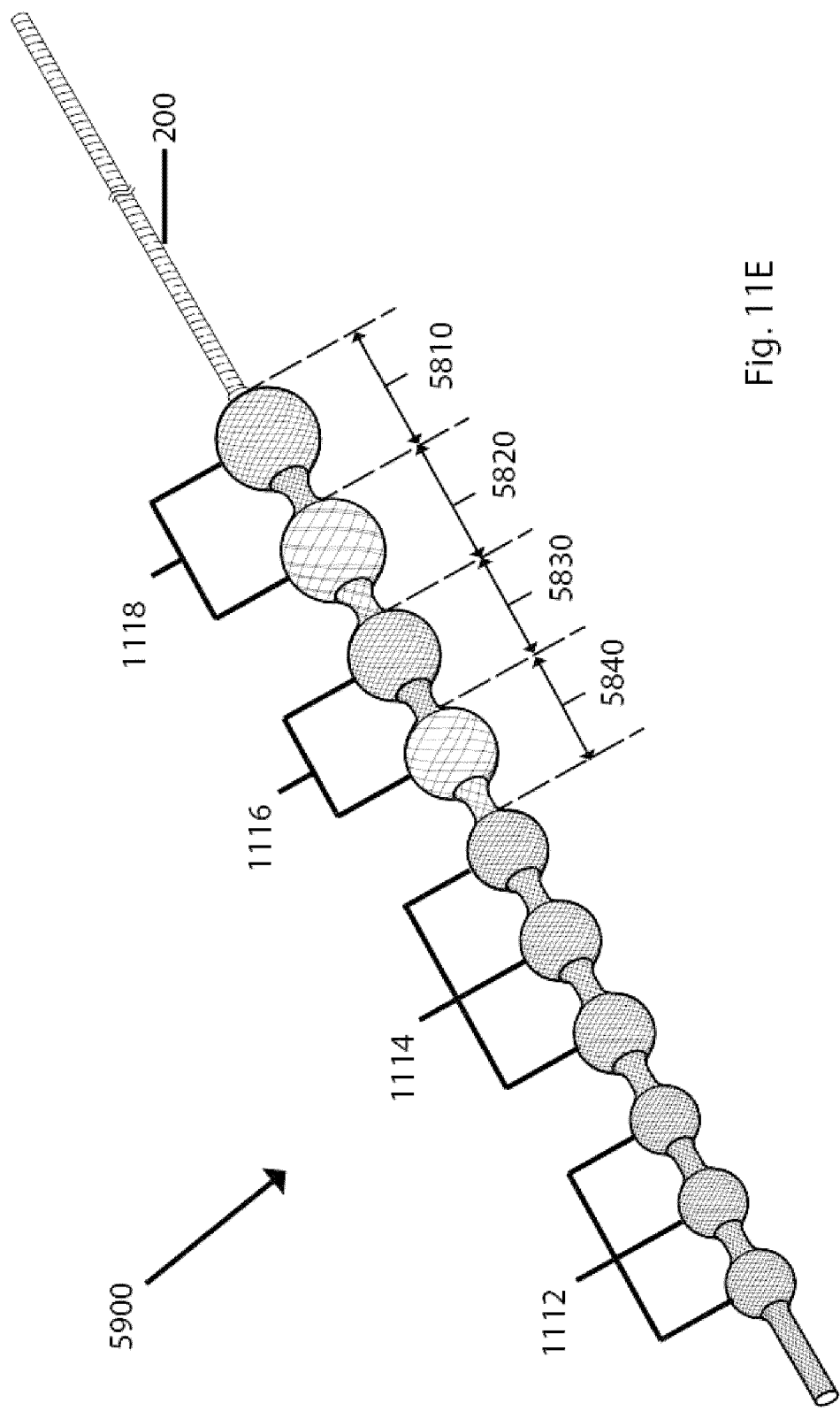
FIG. 11E is perspective view of an example embodiment of a distal portion of a vascular treatment device.

FIG. 11E is a perspective view of an example embodiment of a distal portion 5900 of a vascular treatment device, for example the result of the braiding process illustrated in FIG. 11D. Referring again to FIGS. 2B and 2C, the distal portion 5900 in FIG. 11E comprises a plurality of woven bulbs (1112, 1114, 1116, and 1118) and woven necks similar to the distal portion 1100 in FIGS. 2B and 2C, with a modification being segments 5810, 5820, 5830, 5840 having variable pore size. In some embodiments, the braid carrier mechanism 2600 setup illustrated in FIG. 9C can form a braiding pattern of the distal portion 158 as shown in FIG. 11E, in which the distal segment 5810, for example, has a relatively high PPI and has relatively low porosity. If the "Start-Stop" capability is activated after the braiding the distal segment 5810, and once the vertical puller or ring 161 is stopped to allow the spools 154 including filaments 156 to be rearranged between one spindle 153 and another spindle 153 in a symmetric pattern or an asymmetric pattern by increasing the number of empty spindle pairs, for example the braid carrier mechanism 2650 setup illustrated in FIG. 9D, the middle segment 5820 can have a relatively low PPI and can have relatively high porosity.

In some embodiments, if the "Start-Stop" capability is activated again after braiding the middle segment 5820, and once the vertical puller or ring 161 is stopped to allow the spools 154 including filaments 156 to be rearranged between one spindle 153 and another spindle 153 in another pattern, for example back to the braid carrier mechanism 2600 setup illustrated in FIG. 9C, the proximal segment 5830 can have a relatively high PPI and can have relatively low porosity. Higher PPI can result in a smaller pore size, which can decrease flow into an aneurysm or a vascular malformation such as an arterio-venous fistula, which can aid in thrombosis of the aneurysm or vascular malformation or serve to filter any debris or emboli that may be released during thrombectomy. In some embodiments, by alternating between the arrangements of the braid carrier mechanism illustrated in FIGS. 9C and 9D, low porosity and/or high porosity segments of the distal portion can be achieved.

Referring again to FIG. 10L, for example, after the textile structure 158 has been removed from the mandrel 170 after the second heat treatment, the proximal and distal ends may be trimmed to a desired size. For example, precise or approximate proximal and distal necks may be formed by laser cutting, or mechanically cutting a certain distance from a proximal-most or distal-most bulb. In some embodiments, the distal portion 100 has a total length greater than about 60 mm In some embodiments, the filaments are sheared using a device similar to a pole pruner. The ends may be trimmed transverse (e.g., perpendicular) to the longitudinal axis or at an angle. The filaments may be trimmed individually, or two or more filaments (including all or substantially all of the filaments) may be trimmed at substantially the same time (e.g., with a single cutting stroke or motion). The cross-section of the ends of the filaments may depend at least partially on the trim angle and the angle of the braiding pattern at the trim point. The trimmed ends may be further treated or left as is.

Figure 12B:
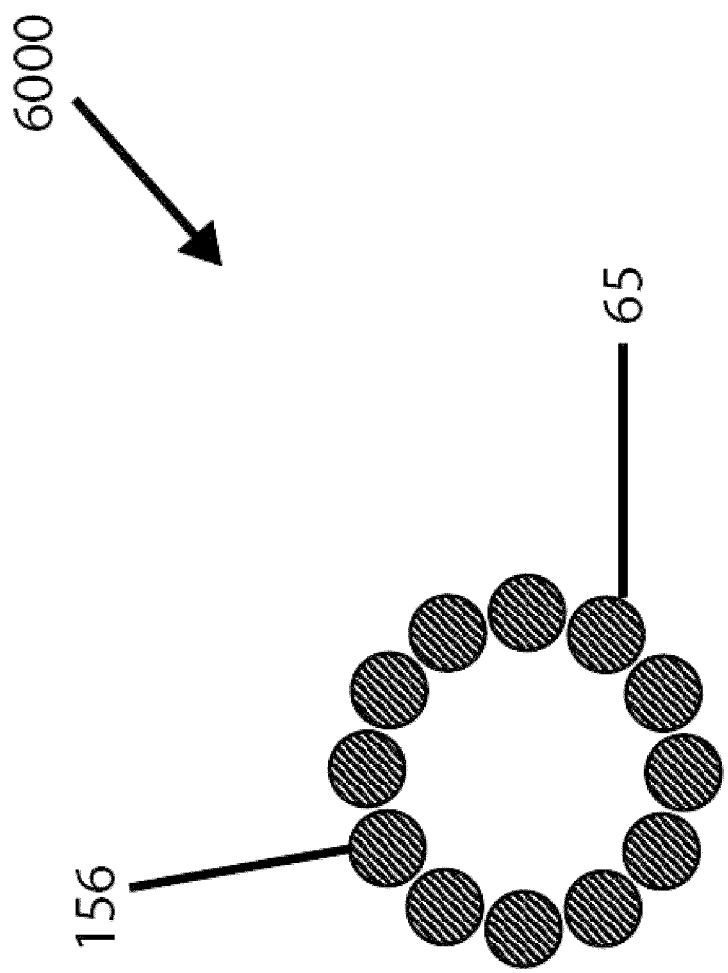
FIG. 12B is a front elevational view of the filament end treatment of FIG. 12A.

FIG. 12A is a schematic perspective view of an example embodiment of a filament end treatment of a distal portion 6000 of a vascular treatment device. The distal portion 6000 may be the distal portion 100 of the device 10, 20, 30, or 40. The part of the distal portion 6000 shown in FIG. 12A is the distal neck 65, but could also or alternatively be a wide mouth distal section, a proximal neck, a wide mouth proximal section, etc. For illustration purposes, the distal portion 6000 includes 12 woven filaments 156, although end treatments described herein may be suitable for higher or lower quantities of filaments 156. FIG. 12B is a front elevational view of the filament end treatment of FIG. 12A. The filament end treatment illustrated in FIGS. 12A and 12B includes leaving the ends of the filaments 156 as is or untreated after they have been trimmed.

Figure 12C:
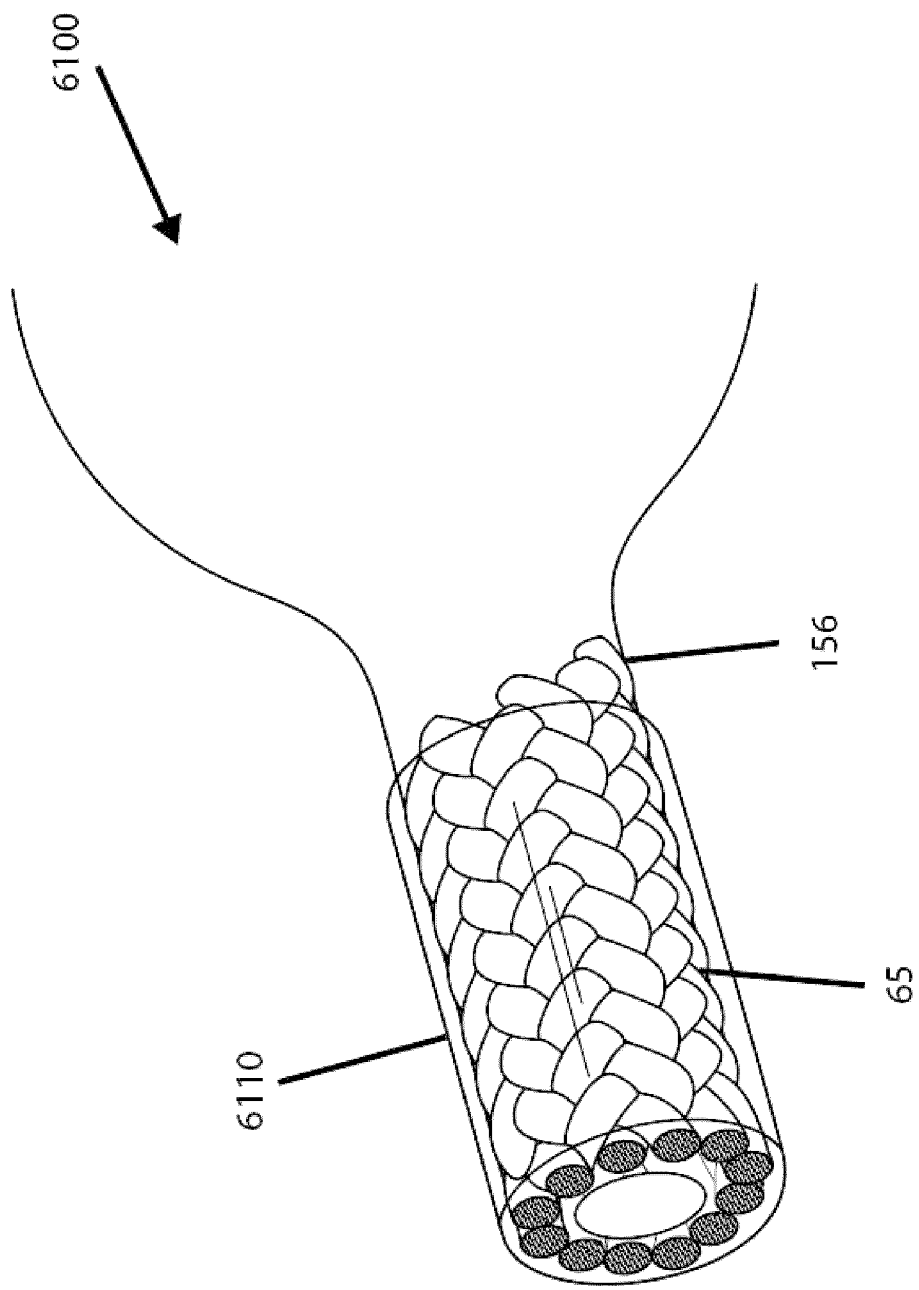
Figure 12D:
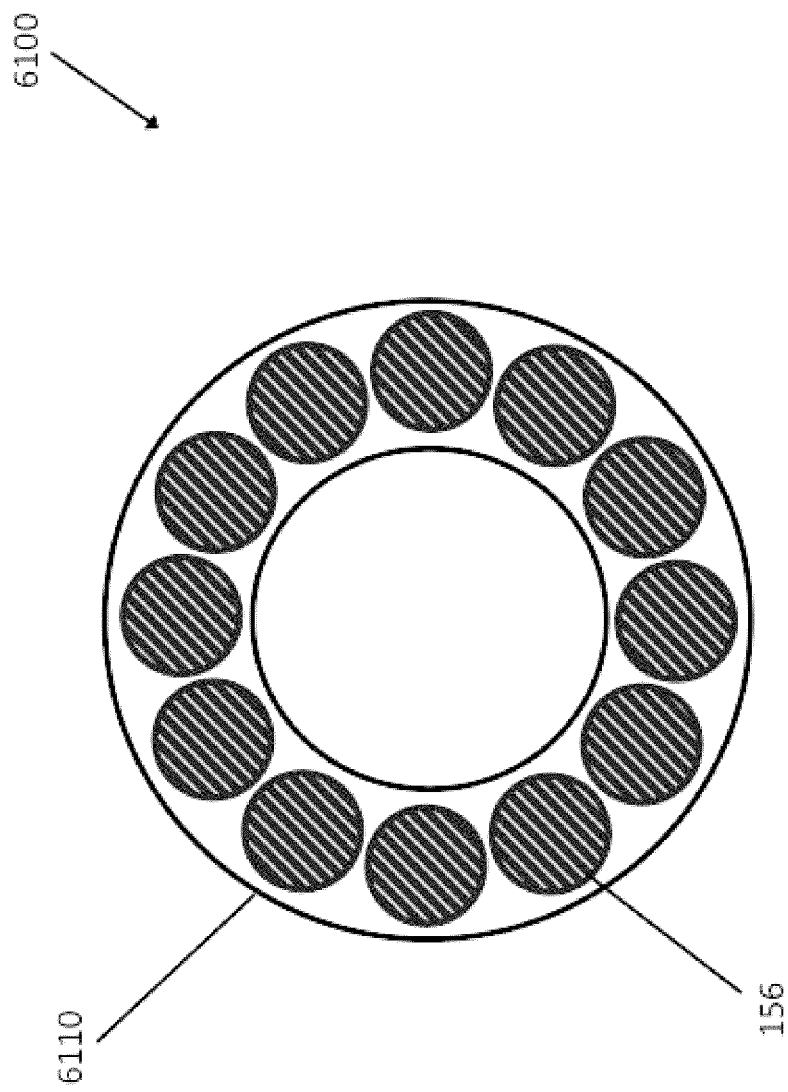

FIG. 12C is a schematic perspective view of another example embodiment of a filament end treatment of a distal portion 6100 of a vascular treatment device. The distal portion 6100 may be the distal portion 100 of the device 10, 20, 30, or 40. The part of the distal portion 6100 shown in FIG. 12C is the distal neck 65, but could also or alternatively be a wide mouth distal section, a proximal neck, a wide mouth proximal section, etc. For illustration purposes, the distal portion 6100 includes 12 woven filaments 156, although end treatments described herein may be suitable for higher or lower quantities of filaments 156. FIG. 12D is a front elevational view of the filament end treatment of FIG. 12C. The filament end treatment illustrated in FIGS. 12C and 12D includes dip-coating or spray coating the distal neck 65 with a polymer. The polymer may comprise a biomedical polymer, for example silicone, polyurethane (e.g., Polyslix, available from Duke Extrusion of Santa Cruz, Calif.), polyethylene (e.g., Rexell®, available from Huntsman) including low density polyethylene (LDPE), linear low density polyethylene (LLDPE), medium density polyethylene (MDPE), and high density polyethylene (HDPE), fluoropolymers such as fluorinated ethylene propylene, PFA, MFA, PVDF, THV, ETFE, PCTFE, ECTFE, (e.g., Teflon® FEP, available from DuPont), polypropylene, polyesters including polyethylene terephthalate (PET), PBT, PETG (e.g., Hytrel®, available from DuPont), PTFE, combination polymer compounds such as thermoplastic polyurethanes and polyether block amides (e.g., Propell™ available from Foster Corporation of Putnam, Conn.), polyether block amides (e.g. Pebax® available from Arkema of Colombes, France, PebaSlix, available from Duke Extrusion of Santa Cruz, Calif.), polyether soft blocks coupled with polyester hard blocks vinyls such as PVC, PVDC, polyimides (e.g., polyimides available from MicroLumen of Oldsmar, Fla.), polyamides (e.g., Durethan, available from Bayer, Nylon 12, available from Duke Extrusion of Santa Cruz, Calif.), polycarbonate (e.g., Corethane™, available from Corvita Corp. of Miami, Fla.), styrenics such as PS, SAN, ABS, and HIPS, acetals such as copolymers or homopolymers, PLA, PGA, PLGA, PCL, polyorthoesters, polyanhydrides, and copolymers thereof, high temperature performance polymers such as PEEK, PES, PPS, PSU, LCP, combinations thereof, and the like. In some embodiments, the polymer may include a radiopaque material (e.g., particles of radiopaque material dispersed in the polymer). In some embodiments, masking a portion of the end section of the distal portion 6100 during dip coating or spray coating can inhibit polymer from depositing in the area of masking. For example, if the distal portion 6100 is dip coated or spray coated while still on the mandrel 170, the polymer may be inhibited from being deposited on the inside of the distal portion 6100, which can preserve the inner lumen and maintain an inner diameter of the distal portion 6100. In some embodiments, dip coating or spray coating prior to trimming the ends of the filaments 156 is also possible. In certain such embodiments, the polymer may maintain the position of the filaments 156 so that they are not frayed. The coated end section may then be trimmed and left as is or further coated. For example, the end section may be spray coated on the mandrel 170, trimmed, and then dip coated.

In some embodiments, coating may include coating radiopaque material (e.g., particles of iridium, platinum, tantalum, gold, palladium, tungsten, tin, silver, titanium, nickel, zirconium, rhenium, bismuth, molybdenum, combinations thereof, and the like, and/or other radiopaque agents such as barium sulfate, tungsten powder, bismuth subcarbonate, bismuth oxychloride, iodine containing agents such as iohexol (e.g., Omnipaque™, available from Amersham Health, a division of GE Healthcare), etc.) The radiopaque material may be coated after the polymer, along with the polymer, and/or interspersed with the coating of the polymer. The filaments 156 may be cut in a manner that reduces fraying (e.g., laser cut) since a coating a frayed filament 156 may result in a coated but still frayed filament 156.

Referring again to FIGS. 12C and 12D, at least the distal end of the distal neck 65 is coated with polymer 6110. In some embodiments, the polymer 6110 covers about 10% to about 75% (e.g., about 25% to about 50%) of the length of the distal neck 65. In some embodiments, the polymer 6110 covers about 0.5 mm to about 3 mm (e.g., about 1 mm to about 2 mm) of the length of the distal neck 65. More or less polymer 6110 can be used depending on the size of the distal portion 6100 and/or the distal neck 65.

Figure 12E:
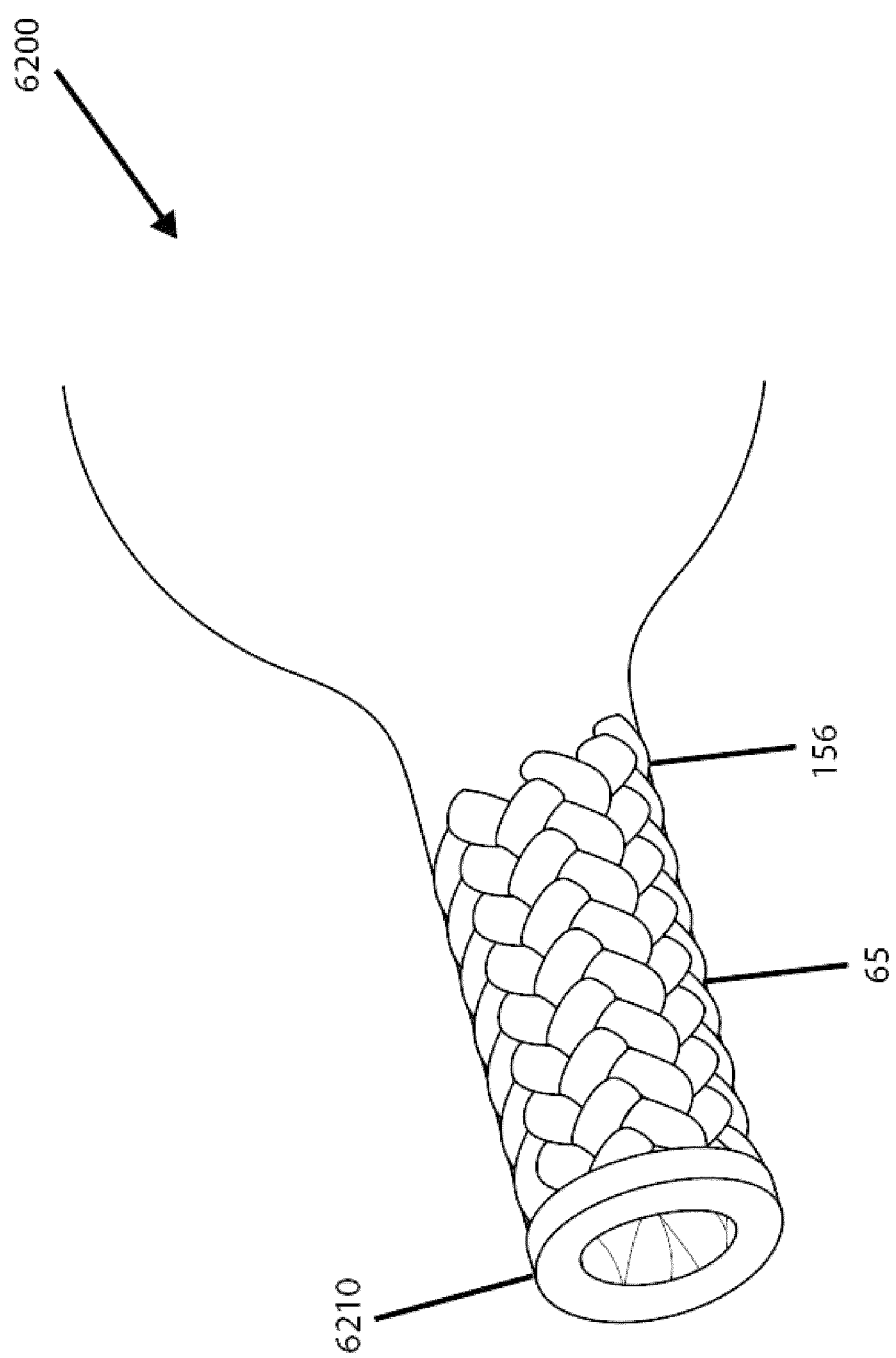

FIG. 12E is a schematic perspective view of yet another example embodiment of a filament end treatment of a distal portion 6200 of a vascular treatment device. The distal portion 6200 may be the distal portion 100 of the device 10, 20, 30, or 40. The part of the distal portion 6200 shown in FIG. 12E is the distal neck 65, but could also or alternatively be a wide mouth distal section, a proximal neck, a wide mouth proximal section, etc. The filament end treatment illustrated in FIG. 12E includes coupling a radiopaque marker band 6210 to the distal end of the distal neck 65. In some embodiments, the material of the radiopaque marker band may include metals or alloys, including but not limited to iridium, platinum, tantalum, gold, palladium, tungsten, tin, silver, titanium, nickel, zirconium, rhenium, bismuth, molybdenum, combinations thereof, and the like.

Figure 12F:
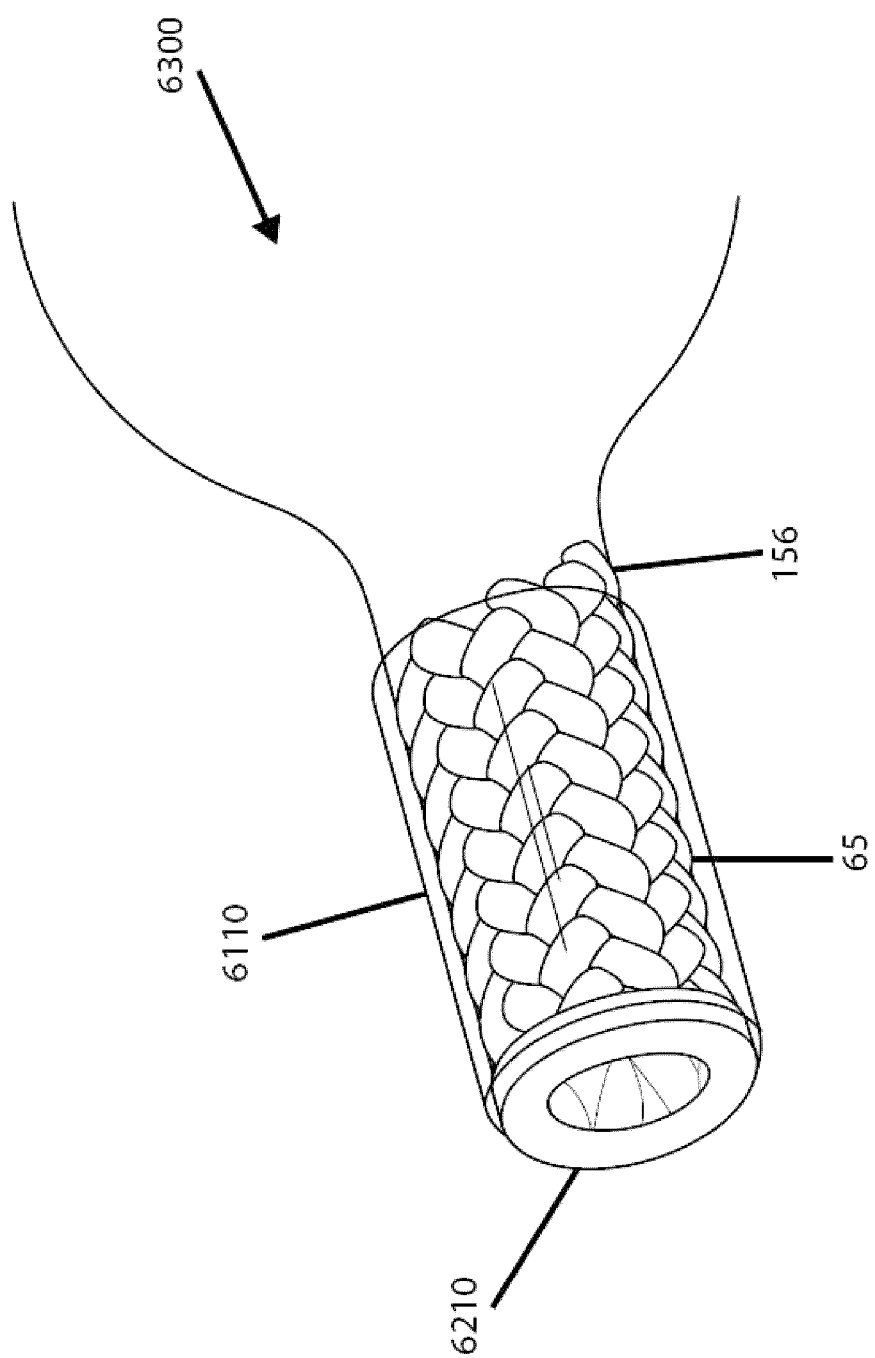

FIG. 12F is a schematic perspective view of still another example embodiment of a filament end treatment of a distal portion 6300 of a vascular treatment device. The distal portion 6300 may be the distal portion 100 of the device 10, 20, 30, or 40. The part of the distal portion 6300 shown in FIG. 12F is the distal neck 65, but could also or alternatively be a wide mouth distal section, a proximal neck, a wide mouth proximal section, etc. The filament end treatment illustrated in FIG. 12F includes dip coating or spray coating with a polymer 6110 at least the distal end of the distal neck 65 (e.g., as described with respect to FIGS. 12C and 12D) and coupling a radiopaque marker band 6210 to the distal end of the distal neck 65 (e.g., as described with respect to FIG. 12E).

Coating the ends of the distal portion 100 can inhibit the end from fraying and/or inhibit frayed ends from puncturing body tissue. The ends of the distal portion can be left loose, for example in embodiments in which the small size of the filaments allows them to be flexible enough to be unlikely to puncture tissue. Omission of a polymer tip (e.g., with no further processing or, for example, by coupling a radiopaque marker band without polymer) can allow the distal portion 100 to be sterilized using gamma radiation, which could damage polymers such as polyurethane and which is generally less expensive than chemical sterilization techniques such as ethylene oxide sterilization.

In some embodiments, the distal portion 100 includes a braided structure (e.g., produced by intertwining or interlacing two or more filaments diagonal or at an angle to the longitudinal or production axis of the distal portion 100). Woven structures are not limited to those in which the filaments are oriented at about 90° angles to each other.

Figure 13A:
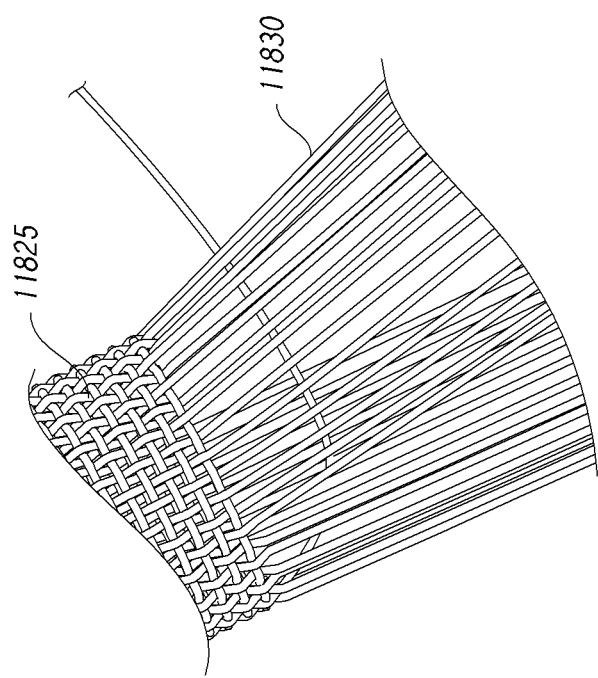

In some embodiments, the distal portion 100 includes a knitted structure (e.g., produced by interlocking a series of loops of the filaments to create the distal portion 100). FIG. 13A is a schematic perspective view illustrating an example embodiment of a plurality of filaments 11830 being knitted into an example biomedical textile structure 11825. In contrast to some textile structures 158 described herein, the structure 11825 illustrated in FIG. 13A includes one or more filaments 11830 being transverse (e.g., perpendicular) to the longitudinal axis, which can result in poor radial force, poor wall apposition, and poor clot capture, along with having poor filtering ability (e.g., due to low porosity), but can allow longitudinal crowding to permit varying pore size during deployment. The size of pores of the textile structure 11825 may be substantially uniform over a large area. In some embodiments, at least a segment of the distal portion 100 includes knitting.

Figure 13B:
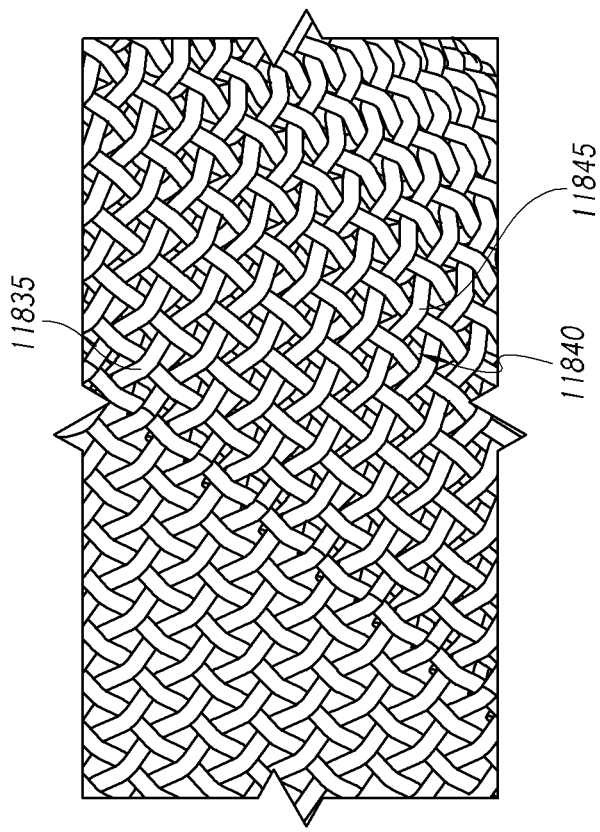

FIG. 13B is a schematic perspective view illustrating an example embodiment of a plurality of filaments 11845 being knitted into another example biomedical textile structure 11835. In contrast to some other textile structures 158 described herein, the structure 11835 illustrated in FIG. 13B is not formed as a cylinder, but is knitted as a sheet, here characterized by interlocking loops. The sheet 11835 may then be rolled into a cylinder and heat treated, mechanically fixed, etc. to impart the cylindrical structure, and the cylinder may then be wrapped around a bulbous mandrel, for example as described with respect to FIG. 10D. The sheet may be wrapped directly around a bulbous mandrel (e.g., without first being shape set into a cylinder), reducing manufacturing steps. A rolled sheet may include stray filaments along an entire length of the distal portion 100, which may be advantageous for scraping some plaques or other such usages. The size of pores 11840 of the textile structure 11835 may be substantially uniform over a large area. Knitting into tubular shapes is also possible (e.g., weft knitting).

In some embodiments, after removal from a bulbous mandrel, the distal portion 100 does not include a crimping element around the necks or between the bulbs. In some embodiments, after removal from a bulbous mandrel, the distal portion 100 does not include a central wire or any other inner member such as an actuation member, other than the filaments used to form the shape-set textile structure (e.g., the bulbs and necks are hollow (e.g., completely hollow)). In some embodiments, the distal portion 100 does not include radiopaque markers (e.g., marker bands), which can reduce a collapsed profile of the distal portion 100. In some embodiments, at least one bulb of the distal portion 100 (e.g., the distal-most bulb) is larger than an aneurysm and/or a mouth of an aneurysm (e.g., in contrast to balls woven for the sole purpose of insertion into an aneurysm). In some embodiments, the distal portion is configured to capture a thrombus between undulations (e.g., between hills and valleys created by bulbs and necks and/or between crossing filaments) such that an interior volume of the distal portion 100 (e.g., radially inward of the necks and bulbs) is not configured to receive a thrombus.

Distal portions 100 are generally described herein as integral structures in which the same filaments form all of the bulbs and necks. In some embodiments, the distal portion 100 may include a plurality of woven textile structures coupled to each other. For example, each textile structure may include one bulb, a plurality of bulbs having the same size or different sizes, a plurality of bulbs having the same shape or different shapes, etc. Certain such embodiments can enable manufacturing of a plurality of woven textile structures at one time, and at a later time assembling distal portions 100 from selected woven textile structures.

Distal portions 100 are described in certain portions herein as being textile structures formed by braiding filaments. In some embodiments, the distal portion 100 may include a structure formed from a cut hypotube or sheet. For example, a hypotube may be cut (e.g., to form a mesh pattern, a cell pattern including open cell, closed cell, combinations thereof, and the like, struts, spaced scaffolds, undulations, etc.) and then shape set to have bulbs and necks using a bulbous mandrel (e.g., the mandrel 170). For another example, a sheet may be cut (e.g., to form a mesh pattern, a cell pattern including open cell, closed cell, combinations thereof, and the like, struts, spaced scaffolds, undulations, etc.) and then shape set to have bulbs and necks using a bulbous mandrel (e.g., the mandrel 170). In some embodiments, the distal portion 100 may include a polymer tubular structure. For example, a polymer tube may be extruded to have bulbs and necks. For another example, a polymer tube may be compressed around a bulbous mandrel (e.g., the mandrel 170). For yet another example, a polymer tube may be blow outwardly to form bulbs (e.g., using a mold or die having a shape opposite the mandrel 170). For still another example, a polymer sheet may be compressed around a bulbous mandrel (e.g., the mandrel 170) or into a mold or die (e.g., having a shape opposite the mandrel 170). For another example, a polymer dip-coating of a bulbous mandrel (e.g., the mandrel 170) may form bulbs and necks made from the polymer. The polymer optionally may be cut before and/or after shape setting. Forming distal portions 100 may comprise some or all of the techniques described herein. As one non-limiting example, forming a distal portion can comprise forming a textile structure and coupling the textile structure to a cut hypotube mesh, one or both of which comprises a bulb.

The distal portions described above may also constitute an entire vascular or other body lumen treatment device. For example, the distal portions may be a deployable endoprosthesis or stent, part of a vascular treatment device such as an intermediate or proximal portion, etc. The endoprosthesis may be coupled to a proximal portion 200 or other device by a detachable joint (e.g., Guglielmi electrolytic detachment, mechanical detachment (e.g., as described herein), etc.).

The distal portion 100 can be coupled to a proximal portion 200 at a joint 300, as described in further detail herein. In some embodiments, only the distal end of the distal portion 100 is coupled to the proximal portion at the joint 300. In some embodiments, the proximal end of the distal portion 100 is not coupled, joined, affixed, adhered, bonded, etc. to the proximal portion 200.

Figure 14A:
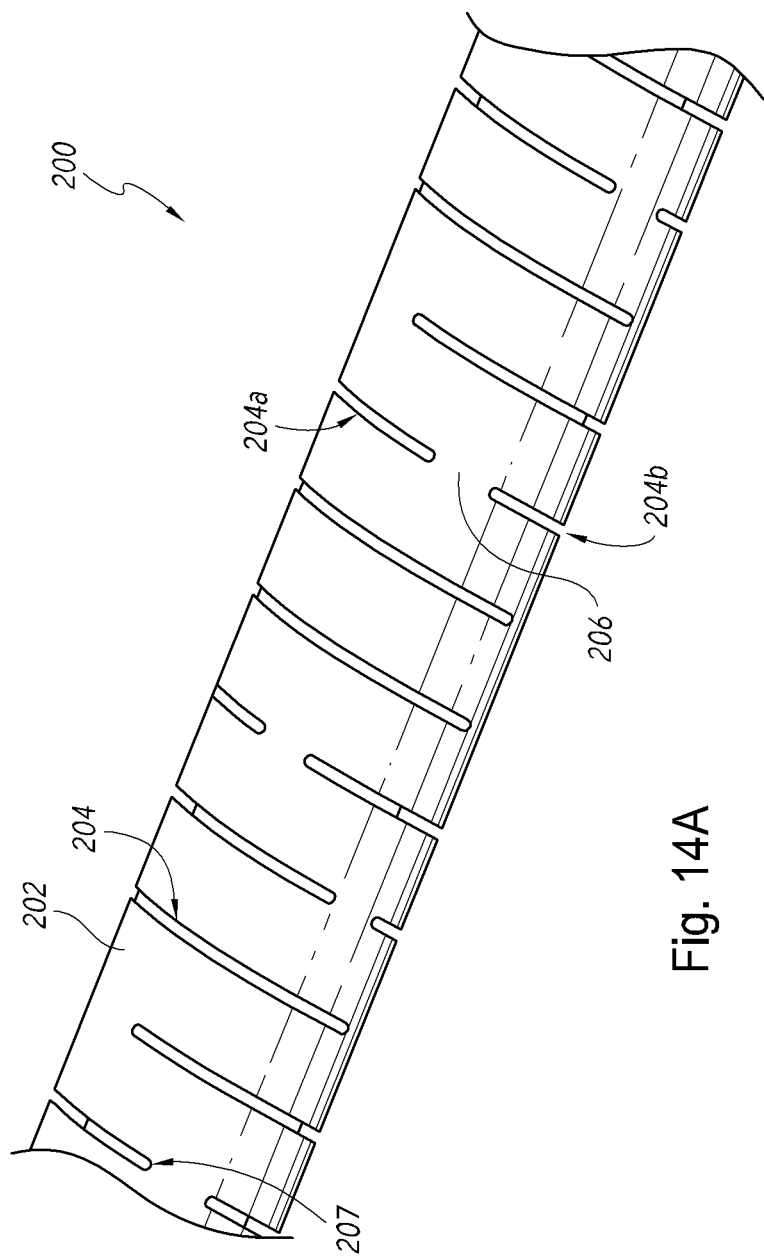
Figure 14B:
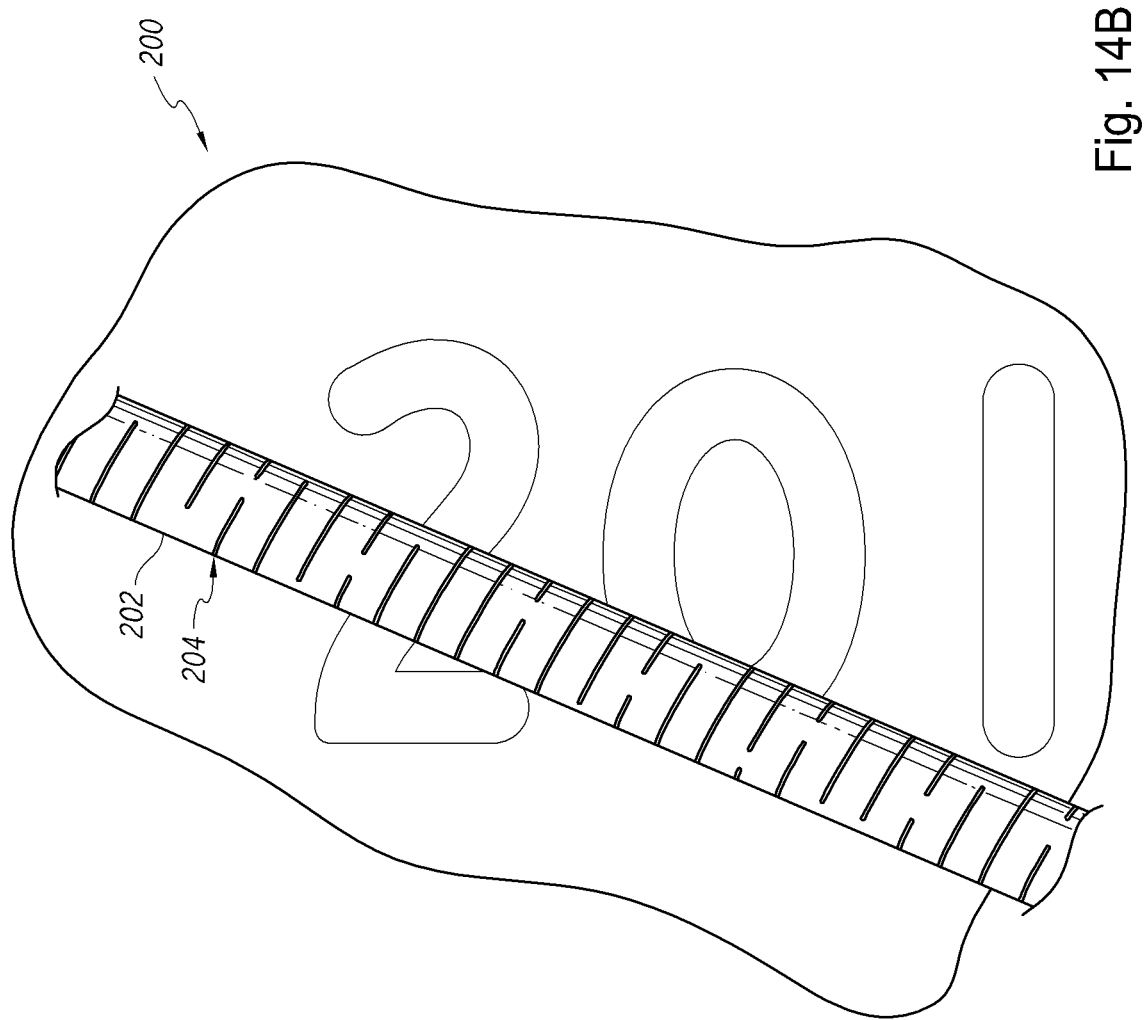

FIG. 14A is a schematic perspective view of an example of an example embodiment of a segment of an example embodiment of a proximal portion 200 of a vascular treatment device. FIG. 14B is a schematic perspective view of another example segment of an example embodiment of a proximal portion 200 of a vascular treatment device. FIG. 14B, which was derived from a photograph, also includes in the background a portion the date on a United States penny ($0.01 or 10) to provide a rough, non-limiting, sizing of an example distal portion 200 and its kerfs 204. The proximal portion 200 comprises a tubular structure 202 and a plurality of openings (slits, kerfs, cuts, incisions, etc.) 204. FIG. 14A also shows a heat impact puddle 207, for example as described herein with respect to FIG. 17B. As used herein, the term kerf shall be given its ordinary meaning and shall include slits, slots, and other openings that typically extend completely through a wall (e.g., sidewall), but may also partially extend into a wall (e.g., notches, grooves, etc.). In some embodiments, the tubular structure 202 comprises a hypotube (e.g., comprising stainless steel). In some embodiments, the proximal portion 200 comprises for example, platinum, titanium, nickel, chromium, cobalt, tantalum, tungsten, iron, manganese, molybdenum, and alloys thereof including nickel titanium (e.g., nitinol), nickel titanium niobium, chromium cobalt, copper aluminum nickel, iron manganese silicon, silver cadmium, gold cadmium, copper tin, copper zinc, copper zinc silicon, copper zinc aluminum, copper zinc tin, iron platinum, manganese copper, platinum alloys, cobalt nickel aluminum, cobalt nickel gallium, nickel iron gallium, titanium palladium, nickel manganese gallium, stainless steel, shape memory alloys, etc., polymers such as, for example, silicone, polyurethane (e.g., Polyslix, available from Duke Extrusion of Santa Cruz, Calif.), polyethylene (e.g., Rexell®, available from Huntsman) including low density polyethylene (LDPE), linear low density polyethylene (LLDPE), medium density polyethylene (MDPE), and high density polyethylene (HDPE), fluoropolymers such as fluorinated ethylene propylene, PFA, MFA, PVDF, THV, ETFE, PCTFE, ECTFE (e.g., Teflon® FEP, available from DuPont), polypropylene, polyesters including polyethylene terephthalate (PET), PBT, PETG (e.g., Hytrel®, available from DuPont), PTFE, combination polymer compounds such as thermoplastic polyurethanes and polyether block amides (e.g., Propell™ available from Foster Corporation of Putnam, Conn.), polyether block amides (e.g. Pebax® available from Arkema of Colombes, France, PebaSlix, available from Duke Extrusion of Santa Cruz, Calif.), polyether soft blocks coupled with polyester hard blocks vinyls such as PVC, PVDC, polyimides (e.g., polyimides available from MicroLumen of Oldsmar, Fla.), polyamides (e.g., Durethan, available from Bayer, Nylon 12, available from Duke Extrusion of Santa Cruz, Calif.), polycarbonate (e.g., Corethane™ available from Corvita Corp. of Miami, Fla.), styrenics such as PS, SAN, ABS, and HIPS, acetals such as copolymers or homopolymers, PLA, PGA, PLGA, PCL, polyorthoesters, polyanhydrides, and copolymers thereof, high temperature performance polymers such as PEEK, PES, PPS, PSU, LCP, combinations thereof, and the like.

In some embodiments, the tubular structure 202 has an outer diameter between about 0.35 mm and about 0.65 mm (e.g., between about 0.4 mm and about 0.45 mm), between about 0.1 mm and about 0.5 mm (e.g., between about 0.25 mm and about 0.33 mm (e.g., about 0.0125 inches (approx. 0.318 mm))). In some embodiments, for example for use with peripheral vasculature, the tubular structure 202 has an outer diameter between about 0.5 mm and about 10 mm In some embodiments, the tubular structure 202 has an inner diameter between about 0.2 mm and about 0.4 mm (e.g., about 0.25 mm). In some embodiments, the tubular structure 202 has a wall thickness $t_w$, or difference between the outer diameter (OD) and the inner diameter (ID) (OD−ID=$t_w$) between about 0.001 inches (approx. 0.025 mm) and about 0.02 inches (approx. 0.5 mm).

In some embodiments, the tubular structure 202 has a length between about 2 feet (approx. 61 cm) and about 10 feet (approx. 305 cm) (e.g., about 7 feet (approx. 213 cm)). In some embodiments, the tubular structure 202 has a length between about 80 cm and about 210 cm, between about 80 cm and about 120 cm, between about 120 cm and about 150 cm, between about 150 cm and about 210 cm (e.g., about 180 cm). The length of the proximal portion 200 may at least partially depend on a length desired to reach somewhat proximate to a treatment site (e.g., proximal to the treatment site at least by the length of the distal portion 100). For example, a length between about 80 cm and about 120 cm may be useful for treating peripheral vasculature, a length between about 120 cm and about 150 cm may be useful for treating coronary vasculature, and a length between about 180 cm and about 210 cm (e.g., about 180 cm) may be useful for treating neurovasculature. In some embodiments, the tubular structure 202 has a length greater than about 6 feet (approx. 183 cm).

At least some of the slits 204 include a first slit portion 204*a* and a second slit portion 204*b* with struts or stems or anchor points 206 between the first slit portion 204*a* and the second slit portion 204*b*. The struts 206 illustrated in FIGS. 14A and 14B are circumferentially between about 175° and about 185° (e.g., about 180°) apart and act as pivot points or anchor points for the tubular structure 202. Other circumferential spacing is also possible, for example to provide more flexibility in one of the two degrees of freedom provided by that slit.

The slits 204 illustrated in FIGS. 14A and 14B are at an angle with respect to the longitudinal axis of the tubular structure 202. In some embodiments, the angle is between about 85° and about 115°, between about 95° and about 115°, or between about 65° and about 85° (e.g., the slits 204 are transverse (e.g., perpendicular or substantially perpendicular) to the longitudinal axis). In some embodiments, the angle is about 90° (e.g., the slits are transverse (e.g., perpendicular or substantially perpendicular) to the longitudinal axis).

In some embodiments, forming the slits 204 includes laser cutting the tubular structure 202. In certain such embodiments, the laser is programmed to cut all the way through a wall of the tubular structure 202. The slit 204 may be thin enough that the laser can cut the entire slit 204 in one pass, or the slit 204 may be thick enough that the laser creates an outline of the slit 204, which can remove the material between the outline. Other methods of forming the slits 204 are also possible (e.g., mechanical cutting, lithographic patterning, etc.).

Figure 14C:
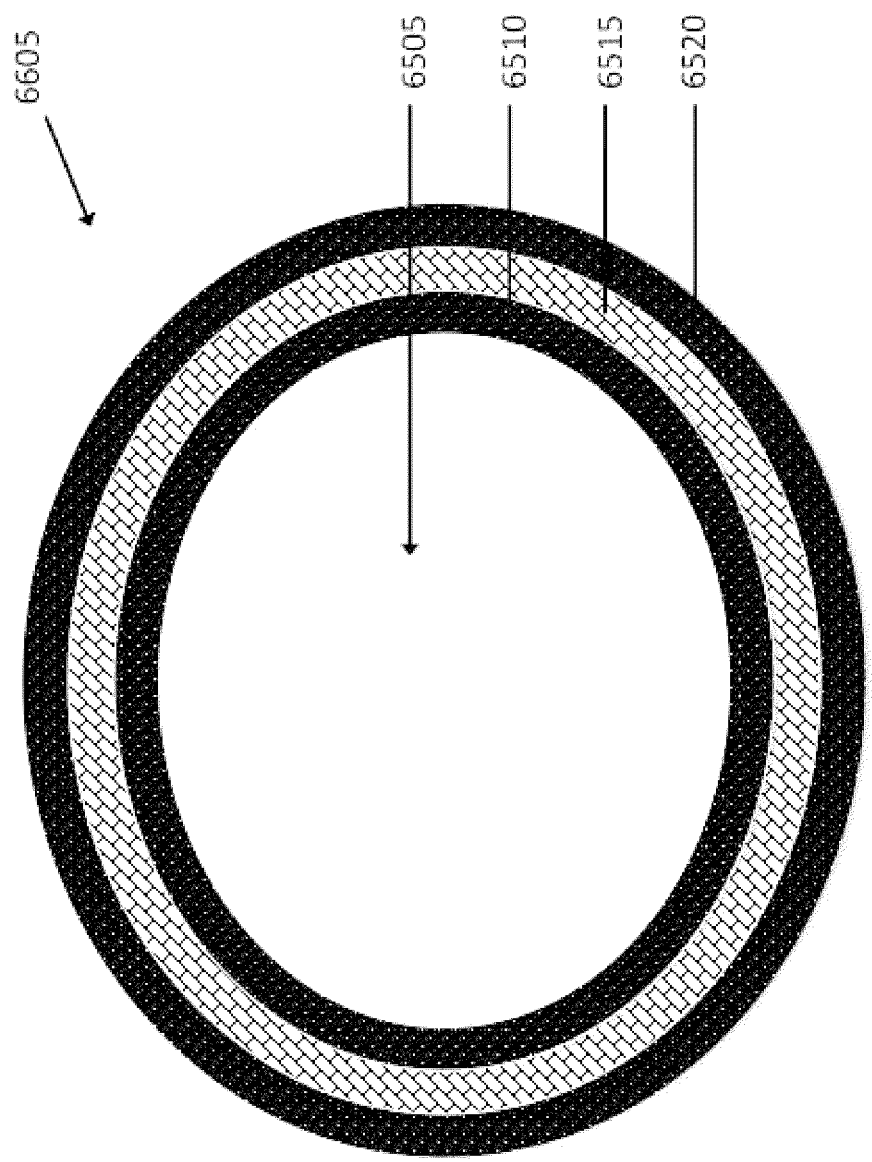

FIG. 14C is a schematic front elevational view of an example embodiment of a proximal portion 6605 of a vascular treatment device. As described herein, certain features of a cut pattern can inhibit or avoid pinch points such that in some implementations the outer surface of the hypotube 6515 can remain uncovered. In some embodiments, the hypotube 6515 can include an outer coating 6520 due to being coated (e.g., dip-coated, spray coated, polymer extruded) with a polymer (e.g., to a thickness between about 0.0001 inches and about 0.0002 inches (approx. between about 0.0025 mm and about 0.0051 mm)). In some embodiments, the inner walls of the hypotube 6515 can include a coating 6310 (e.g., a hydrophilic coating or a hydrophobic coating) due to being coated (e.g., dip-coated, spray coated, polymer extruded) with a polymer (e.g., to a thickness between about 0.0001 inches and about 0.0002 inches (approx. between about 0.0025 mm and about 0.0051 mm)). The inner coating 6510 may be the same or different than the outer coating 6520 (e.g., comprising a different material, thickness, durometer, etc.). In some embodiments, a parameter of a coating (e.g., material, thickness, durometer, etc. of the inner coating and/or the outer coating) may be varied to vary flexibility of the catheter. The variation may be instead of or in addition to (e.g., complementary to) variation in the cut pattern in the hypotube 6515. The variation of the parameter of the polymer coating (e.g., material, thickness, durometer, etc.) may be aligned (e.g., substantially aligned) with the variation of the pitch of the kerfs or the rows. The catheter may include a working lumen 6505.

In some embodiments, a hypotube 6515 with a cut pattern as described herein may be used as a catheter (e.g., a microcatheter, a distal access microcatheter, a guide catheter) including an inner lumen 6505. In some embodiments, a hypotube 6515 with a cut pattern as described herein, with or without other layers such as an inner coating and/or an outer coating, may be used for a portion of a catheter or any other tubular device that might benefit from an advantage provided thereby. For example, the hypotube 6515 may be used as a pusher wire for a stent deployment system. For another example, the hypotube 6515 may be used as an outer sheath for vascular treatment system. For further examples, the hypotube 6515 may be used as a tracheostomy tube, an endoscopy tube, a colonoscope, a laparoscope, a transesophageal echo (TEE) probe, a ventriculostomy catheter, a chest tube, a central venous catheter, a cooling catheter, etc.

Figure 14D:
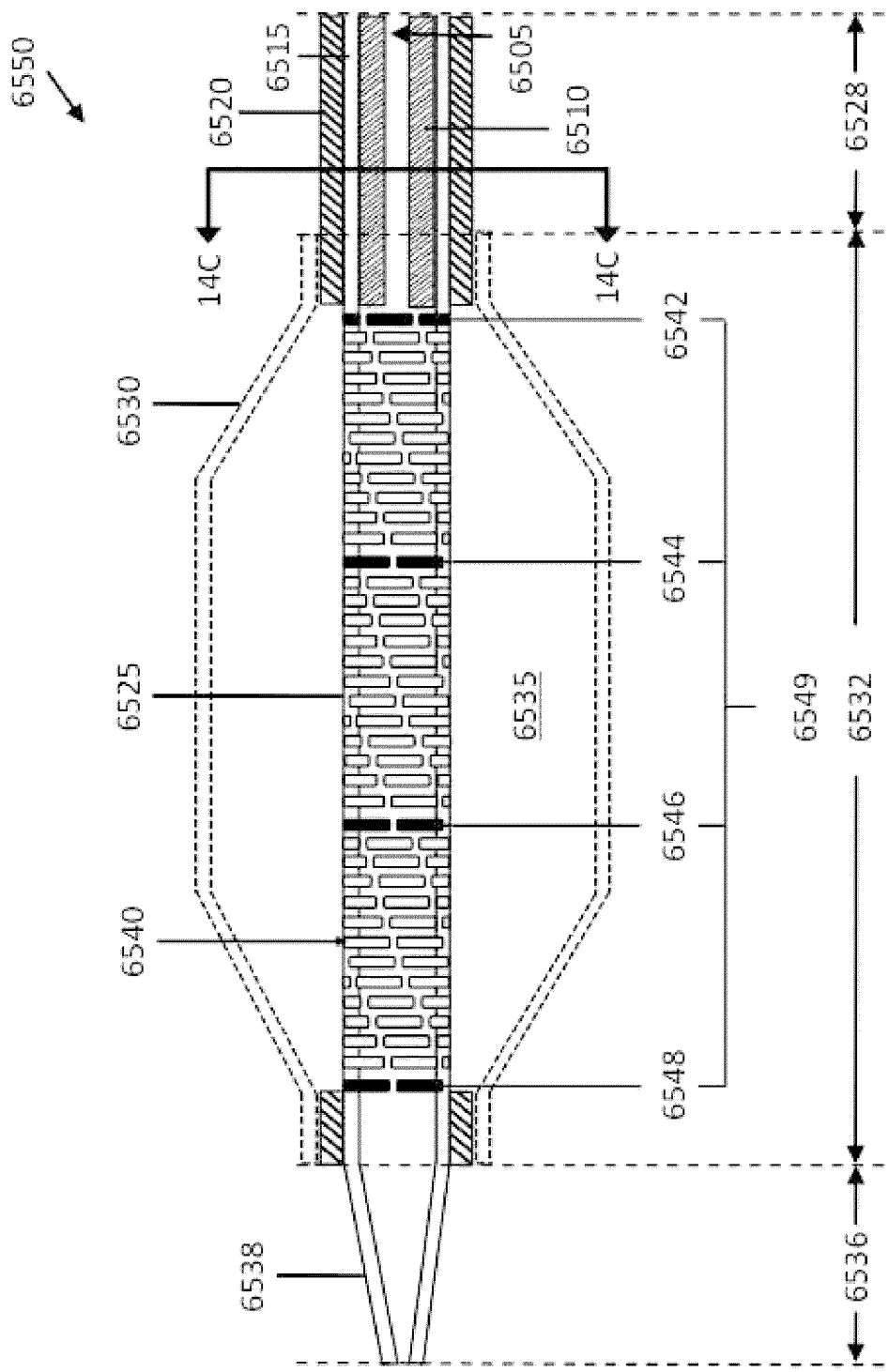

FIG. 14D is a schematic side partial cross-sectional view of an example embodiment of a balloon catheter 6550. The balloon catheter 6550 may be, for example, a balloon guide catheter or a distal access microcatheter including a balloon. The balloon catheter 6550 can be used, for example, for angioplasty (e.g., plain old balloon angioplasty (POBA), drug-coated balloon (DCB, DEB) angioplasty), atherectomy (e.g., if the balloon 6530 comprises a cutting balloon, expansion of a endoprosthesis (e.g., stent, valve), temporary flow arrest during mechanical thrombectomy, thrombus aspiration, proximal embolic protection device, other devices, etc.

The balloon catheter 6550 comprises a hypotube 6515 and a balloon 6530. The hypotube 6515 includes a lumen 6505 configured to inflate and/or deflate the balloon 6530. At least part of the length of the hypotube 6515 includes a cut pattern 6525, for example the staggered and offset interspersed cut pattern as described herein, which can provide at least one of flexibility, torquability, etc. as described herein to the balloon catheter 6530. The cut pattern may be angled or non-angled (e.g., as shown in FIG. 14D). Other variations of the cut patterns described herein are also possible. In the embodiment illustrated in FIG. 14D, the part of the hypotube 6515 radially inward of the balloon 6532 includes the cut pattern, and, for clarity in illustration, the parts of the hypotube 6515 proximal and distal to the balloon 6530 are illustrated without a cut pattern. Fluid (e.g., air, water, saline, etc.) used to inflate the balloon 6530 can traverse between the lumen 6505 and the interior volume of the balloon 6535 through the kerfs 6540 of the cut pattern. In some embodiments, the part of the hypotube 6515 radially inward of the balloon 6532 includes a different cut pattern (e.g., configured to deliver fluid).

In the embodiment illustrated in FIG. 14D, the parts of the hypotube 6515 proximal and/or distal to the balloon 6530 include the cut pattern (not shown), an outer coating 6520, and an inner coating 6510. For example, parts proximal to the balloon 6528 may include the cut pattern and parts distal to the balloon 6536 may not include the cut pattern. The inner coating 6510 and/or the outer coating 6520 occlude the kerfs 6540, which can allow the fluid to flow through the lumen 6505 to the part including the balloon 6530. FIG. 14C may be a cross-section of the balloon catheter 6550 across the line 14C-14C in FIG. 14D, which is at a point along the hypotube 6515 that does not include kerfs. In some embodiments, the hypotube 6515 includes only one of the inner coating 6510 and the outer coating 6520. In some embodiments, different parts of the hypotube 6515 proximal and distal to the balloon 6530 comprise one or both of the inner coating 6510 and the outer coating 6520. In some embodiments, parts of the hypotube 6515 do not include the inner coating 6510 or the outer coating 6520, but the kerfs 6540 are occluded by a polymer. For example, the polymer may be flush with the inner and/or outer surfaces of the hypotube 6515. In embodiments in which the balloon 6530 is at the distal end of the hypotube 6515, the parts of the hypotube 6515 distal to the balloon 6536 are short, do not exist, and/or do not include the cut pattern. In certain such embodiments, parts of the hypotube 6515 distal to the balloon 6536 do not include the cut pattern, the outer coating 6520, and/or the inner coating 6510. In some embodiments, parts of the hypotube 6515 without the cut pattern do not include the inner coating 6510 or the outer coating 6520, for example because those parts do not include kerfs 6540. The distal end of the hypotube 6515 may be occluded, for example by a polymer, solder, crimping, a plug, combinations thereof, and the like. In some embodiments, the distal end of the balloon catheter 6536 comprises an atraumatic polymer tip 6538 including a tapered inner diameter. In certain such embodiments, a second catheter (e.g., a distal access catheter or a microcatheter) and/or a third catheter (e.g., a distal access catheter or a microcatheter) may be inserted through a working lumen created by the hypotube 6515. The outer diameter (e.g., 6 Fr) of the second catheter and/or the third catheter is substantially similar to or at least as large as the inner diameter (e.g., 6 Fr) of the polymer tip, which can create an arcuate seal of the working lumen, which can allow inflation of the balloon 6530 without permanent occlusion. A proximal segment of the hypotube 6515 where torque applied by an operator of the balloon catheter 6550 is the greatest may be configured to reduce kinking, for example comprising a strain relief (e.g., polymer sheath that may be the same as or different to the outer coating 6520), a braided structure, combinations thereof, and the like.

The hypotube 6515 can comprise hypotube materials, dimensions, etc. described herein. Portions of the balloon catheter 6550 (e.g., the balloon 6530, the inner coating 6510, the outer coating 6520) may comprise a biomedical polymer, for example, silicone, polyurethane (e.g., Polyslix, available from Duke Extrusion of Santa Cruz, Calif.), polyethylene (e.g., Rexell®, available from Huntsman) including low density polyethylene (LDPE), linear low density polyethylene (LLDPE), medium density polyethylene (MDPE), and high density polyethylene (HDPE), fluoropolymers such as fluorinated ethylene propylene, PFA, MFA, PVDF, THV, ETFE, PCTFE, ECTFE (e.g., Teflon® FEP, available from DuPont), polypropylene, polyesters including polyethylene terephthalate (PET), PBT, PETG (e.g., Hytrel®, available from DuPont), PTFE, combination polymer compounds such as thermoplastic polyurethanes and polyether block amides (e.g., Propell™ available from Foster Corporation of Putnam, Conn.), polyether block amides (e.g. Pebax® available from Arkema of Colombes, France, PebaSlix, available from Duke Extrusion of Santa Cruz, Calif.), polyether soft blocks coupled with polyester hard blocks vinyls such as PVC, PVDC, polyimides (e.g., polyimides available from MicroLumen of Oldsmar, Fla.), polyamides (e.g., Durethan, available from Bayer, Nylon 12, available from Duke Extrusion of Santa Cruz, Calif.), polycarbonate (e.g., Corethane™, available from Corvita Corp. of Miami, Fla.), styrenics such as PS, SAN, ABS, and HIPS, acetals such as copolymers or homopolymers, PLA, PGA, PLGA, PCL, polyorthoesters, polyanhydrides, and copolymers thereof, high temperature performance polymers such as PEEK, PES, PPS, PSU, LCP, combinations thereof, and the like. In some embodiments, the balloon catheter 6550 comprises radiopaque markers 6542, 6548, proximate to the proximal and distal ends of the balloon 6530. For example, as illustrated in FIG. 14D, the radiopaque markers 6542, 6544, 6546, 6548, comprise filled in kerfs (e.g., as described in further detail with respect to FIG. 19B). In the embodiment illustrated in FIG. 14D, the balloon catheter 6530 comprises a plurality of radiopaque markers 6549 at regular intervals, which may help to measure clot length, degree or length of a stenosis in a vessel, diameter of a vessel, dimensions of an aneurysm arising from a vessel (e.g., the mouth of the aneurysm), etc. for intra-operative decision making on device selection.

FIG. 15A is a schematic diagram illustrating an example embodiment of a cut pattern. The pattern includes two interspersed patterns: Pattern A, indicated by the shaded blocks, and Pattern B, indicated by the unshaded blocks. FIG. 15B is a schematic diagram illustrating an example embodiment of a portion of a cut pattern, Pattern A illustrated in FIG. 15A without Pattern B. FIG. 15C is a schematic diagram illustrating another example embodiment of a portion of a cut pattern, Pattern B illustrated in FIG. 15A without Pattern A.

Pattern A includes a series of arcuate slits 210 (including the slit halves 210a, 210b), 212 (including the slit halves 212a, 212b), 214 (including the slit halves 214a, 214b), 216 (including the slit halves 216a, 216b), etc. Pattern B includes a series of arcuate slits 220 (including the slit halves 220a, 220b), 222 (including the slit halves 222a, 222b), 224 (including the slit halves 224a, 224b), 226 (including the slit halves 226a, 226b), 228 (including the slit halves 228a, 228b), etc. The slits 210, 220, et al. are not fully arcuate (360°), which would cut the tubular structure 202 in two pieces, but are interrupted by two stems or struts or anchor points (e.g., the stems 221a, 221b between the slit halves 220a, 220b, the stems 211a, 211b between the slit halves 210a, 210b) circumferentially spaced about 180° apart by the two halves of an arcuate slit. When the slits 210 are perpendicular to the longitudinal axis, a row is defined by slit halves 210a, 210b around that circumference. When the slits 210 are angled other than perpendicular to the longitudinal axis, a row is defined by slit halves 210a, 210b and stems 211a, 211b therebetween that have traversed a full circumference of the tubular structure 202.

The arrows 310 indicate that the view is exploded outward, or that if this is a laser cut sheet that is rolled into a tube by bending the left and right sides into the page such that the pattern shown is for an outer circumference. The inside of the tubular structure 202 has a circumference $c_i = \pi d_h$, where $d_h$ is the inner diameter of the tubular structure 202. The outside of the tubular structure 202 has a circumference $c_o = \pi d_o$, where $d_o$ is the outer diameter of the tubular structure 202. A ratio of the circumferential length of a slit 204 to the circumference $c_o$ can be calculated. Parameters of the slits 204 can be represented as absolute values (e.g., in inches or mm) or as a percentage of $c_i$ or $c_o$. Once the ratio between $c_i$ and $c_o$ is known, values related to the proximal portion 200 that are known for $c_o$ (e.g., as may be provided to a manufacturer) may be calculated and/or derived therefrom with reference to $c_i$, and vice versa.

In some embodiments, the slit 210, for example, includes one slit and one stem. In some embodiments, the slit 210 includes two slit portions 210a, 210b (e.g., for example as described in detail herein). In some embodiments, the slit 210 includes four slit portions (e.g., with stems spaced about 90° apart). Other numbers of slit portions and stems are also possible.

Anchor points that are substantially diametrically opposed along a circumference of the tubular structure 202 (e.g., two anchor points 211a, 211b spaced about 180° apart) can allow a freedom of flexibility about the anchor points. Anchor points that are not substantially diametrically opposed are also possible, which can create uneven freedom of movement about the anchor points to create a higher degree of freedom of flexibility in one direction and a lower degree of freedom of flexibility in the opposite direction. The anchor points can inhibit or prevent compression of the proximal portion 200 in the direction in which they extend, but can support freedom of movement in a direction 90° away from the location of the anchor points, the direction of freedom.

In some embodiments, longitudinally adjacent stems are generally not longitudinally aligned (parallel along the longitudinal axis of the tubular structure 202), which could result in pinching at any point along the proximal portion 200, similar to the pinching that may be caused by a continuous coil or spiral cut. Rather, stems in adjacent rows of Pattern A are offset by a circumferential distance $O_A$ (FIG. 15B) and stems in adjacent rows of Pattern B are offset in the opposite direction by a circumferential distance $O_B$ (FIG. 15C). Stems in adjacent rows of the overall cut pattern are staggered by a circumferential distance S. Staggering and/or offsetting the circumferential positioning of the stems can increase the number of degrees of motion and/or increase safety by reducing or eliminating the possibility of pinching. In embodiments comprising two patterns (e.g., Patterns A and B), both patterns can be offset in a clockwise direction, both patterns can be offset in a counterclockwise direction, or one pattern can be offset in a clockwise direction and the other pattern can progress in a counterclockwise direction (e.g., as illustrated in FIG. 15A).

In some embodiments, the value of the offset $O_A$ (and $O_B$) is proportional to the circumferential length 230 of the slit half between the stems, also called the kerf length. The ratio of the offset to the circumferential length of the slit half may determine how quickly the stems are aligned longitudinally or, colloquially, how quickly a particular slit or row repeats itself along the tubular structure 202. For example, if the ratio is ⅛, then the first, ninth, seventeenth, etc. slits would be the same, the second, tenth, eighteenth, etc. slits would be the same, and so on. In some embodiments, a row of a pattern may repeat between about every 2 rows and about every 20 rows. Higher repetition may be desired, but may be limited by geometry, manufacturing tolerances, etc.

Referring again to FIG. 15A, the stems 211a, 211b in Pattern A and the stems 221a, 221b in Pattern B do not start out aligned and are staggered by a value S. In some embodiments, the stems 211a, 211b in Pattern A and the stems 221a, 221b in Pattern B are never aligned along the length of the tubular structure 202. In some embodiments, the stagger S between the stems 211a, 211b in the first row of Pattern A and the stems 221a, 221b in the first row of Pattern B can help inhibit alignment of the stems of Patterns A and B if related to the length 230 of the slit halves. For example, an initial stagger S that is about 40% of the length of the slit halves can reduce or minimize the incidence of longitudinally adjacent stems of Patterns A and B being longitudinally aligned.

FIG. 15D is a schematic diagram illustrating an example embodiment of staggered interspersed cut patterns. Patterns A and B are interspersed. The right end of the slit 210a of Pattern A is staggered from the right end of the slit 220a of Pattern B by a value S. The right end of the slit 210a of Pattern A is also offset from the right end of the slit 212a of Pattern A by a value $O_A$. The left end of the slit 220a of Pattern B is offset from the left end of the slit 222a of Pattern B by a value $O_B$. In some embodiments, the number of cut patterns that are interspersed is between 1 (e.g., the same cut pattern without any interspersing) and 5 (e.g., 2 as described in detail herein). A proximal portion 200 including two interspersed patterns can increase the number of degrees of freedom of rotation or movement, which can help with navigation through narrow vessels. The interspersing can be the entire length of the proximal portion 200 or sections thereof. In some embodiments, two cut patterns are interspersed for a first length of the proximal portion 200 and two cut patterns (one or both of which may be different than the two cut patterns along the first length) for a second length of the proximal portion 200, etc.

FIG. 15E is a schematic diagram illustrating an example embodiment of staggered interspersed offset cut patterns. The left and right sides of FIG. 15E show the same cuts, but shaded differently to highlight the various cut patterns. On the left side, Pattern A is shown in dashed outline without shading and Pattern B is shown in solid outline and with shading. The right end of the slit 210a is offset from the right end of the slit 212a by a value of $O_A$. The right end of the slit 212a is offset from the right end of the slit 214a by a value of $O_A$. The right end of the slit 214a is offset from the right end of the slit 216a by a value of $O_A$. The right end of the slit 210a is offset from the right end of the slit 214a by a value of $2 \times O_A$. The right end of the slit 210a is offset from the right end of the slit 216a by a value of $3 \times O_A$. The offset $O_A$ is to the right, as indicated by the arrow 242.

On the right side, Pattern B is shown in dashed outline without shading and Pattern A is shown in solid outline and with shading. The left end of the slit 220a is offset from the left end of the slit 222a by a value of $O_B$. The left end of the slit 222a is offset from the left end of the slit 224a by a value of $O_B$. The left end of the slit 224a is offset from the left end of the slit 226a by a value of $O_B$. The left end of the slit 226a is offset from the left end of the slit 228a by a value of $O_B$. The left end of the slit 220a is offset from the left end of the slit 224a by a value of $2 \times O_B$. The left end of the slit 220a is offset from the left end of the slit 226a by a value of $3 \times O_B$. The left end of the slit 220a is offset from the left end of the slit 228a by a value of $4 \times O_B$. The offset $O_B$ is to the left, as indicated by the arrow 244. The offset $O_B$ may be considered negative in comparison to the offset $O_A$ because it is in the opposite direction.

The offset $O_A$ is different than the offset $O_B$, which may be easily seen by the different slopes of the lines 242, 244, or the intra-pattern anchor point stagger angle. Referring also again to FIG. 15D, the offset $O_A$, offset $O_B$, and stagger S may at least partially influence the repetition a single row or frequency of rows having longitudinally aligned stems.

Although some patterns illustrated herein are interspersed by having alternating slits of a first pattern and a second pattern (e.g., Pattern A slit, Pattern B slit, Pattern A slit, Pattern B slit, etc.), slit patterns may be interspersed in other ways. For example, two slits from each of two patterns may alternate (e.g., Pattern A slit, Pattern A slit, Pattern B slit, Pattern B slit, Pattern A slit, Pattern A slit, Pattern B slit, Pattern B slit, etc.). For another example, one slit of a first pattern may alternate with two slits of a second pattern (e.g., Pattern A slit, Pattern B slit, Pattern B slit, Pattern A slit, Pattern B slit, Pattern B slit, etc.). For yet another example, slits from three or more patterns may be interspersed (e.g., Pattern A slit, Pattern B slit, Pattern C slit, Pattern A slit, etc.).

In some embodiments, the proximal portion 200 includes a plurality of longitudinally-spaced slits 204 including a first slit 220, a second slit 210, a third slit 222, and a fourth slit 212. The slit 220 includes a first slit half 220a and a second slit half 220b. A first stem 221a is between the first slit half 220a and the second slit half 220b, and a second stem 221b is between the first slit half 220a and the second slit half 220b and circumferentially about 180° from the first stem 221b. The slit 210 includes a first slit half 210a and a second slit half 210b. A first stem 211a is between the first slit half 210a and the second slit half 210b, and a second stem 211b is between the first slit half 210a and the second slit half 210b and circumferentially about 180° from the first stem 211b. The slit 222 includes a first slit half 222a and a second slit half 222b. A first stem 223a is between the first slit half 222a and the second slit half 222b, and a second stem 223b is between the first slit half 222a and the second slit half 222b and circumferentially about 180° from the first stem 223b. The slit 212 includes a first slit half 212a and a second slit half 212b. A first stem 213a is between the first slit half 212a and the second slit half 212b, and a second stem 213b is between the first slit half 212a and the second slit half 212b and circumferentially about 180° from the first stem 221b. The stems 221a, 221b are each circumferentially offset from the stems 211a, 211b, the stems 223a, 223b, and the stems 213a, 213b. The stems 211a, 211b are each circumferentially offset from the stems 221a, 221b, the stems 223a, 223b, and the stems 213a, 213b. The stems 223a, 223b are each circumferentially offset from the stems 221a, 221b, the stems 211a, 211b, and the stems 213a, 213b. The stems 213a, 213b are each circumferentially offset from the stems 221a, 221bm the stems 211a, 211b, and the stems 223a, 223b. Within a three ring window or a four ring window, none of the stems are circumferentially aligned. Other larger windows without circumferential stem alignment are also possible (e.g., between about 3 rings and about 100 rings, between about 3 rings and about 50 rings, between about 3 rings and about 25 rings), for example depending on offset and stagger values.

FIG. 16A is a schematic diagram illustrating an example embodiment of an angled pattern including sharp edges. The pattern is angled from the orthogonal, indicated by the dashed line, by the angle 250. The angle 250 may be between about 5° and about 25°. The angle 250 may be between about −5° and about −25° (e.g., angled in the opposite direction). The pattern(s) include slits having sharp edges, for example ends with 90° corners. Other sharp ends are also possible (e.g., trapezoidal slits with corners more or less than 90°). Sharp edges may provide greater slit end robustness, but may produce cilia, or minute hair-like follicles of material, that can result from rerouting a cutter (e.g., a laser cutter) at sharp corners. Cilia can be removed by a process like electropolishing, but that can increase cost and risk unremoved cilia, which could be fatal if herniated into vasculature.

FIG. 16B is a schematic diagram illustrating an example embodiment of an angled pattern including rounded edges.

The pattern is angled from the orthogonal, indicated by the dashed line, by the angle 250. The angle 250 may be between about 5° and about 25°. The angle 250 may be between about −5° and about −25° (e.g., angled in the opposite direction). The pattern(s) include slits having rounded edges, for example arcuate or rounded (e.g., semi-circular, rounded corners) ends. Rounded slits may reduce or eliminate the incidence of cilia. Reduced or eliminated cilia can eliminate cilia-removal processes, reducing manufacturing costs. Reduced or eliminated cilia can increase safety of the device by reducing or eliminating the chances of a cilium herniating into vasculature. Rounded slits may reduce or minimize fracture points.

FIG. 16C is a schematic diagram illustrating an example embodiment of interspersed offset horizontal patterns including sharp edges. The left and right sides of FIG. 16C show the same cuts, but shaded differently to highlight the various cut patterns. Similar to FIG. 15E, described in detail above, the left side of FIG. 16C shows an arrow 242 connecting the right sides of a first pattern including a first offset and the right side of FIG. 16C shows an arrow 244 connecting the left sides of a second pattern including a second offset, the first pattern and the second pattern interspersed with and staggered from each other. The patterns in FIG. 16C are shown horizontal, but could be angled, for example as illustrated in FIG. 16A.

FIG. 16D is a schematic diagram illustrating an example embodiment of interspersed offset horizontal patterns including rounded edges. The left and right sides of FIG. 16D show the same cuts, but shaded differently to highlight the various cut patterns. Similar to FIG. 15E, described in detail above, the left side of FIG. 16D shows an arrow 242 connecting the right sides of a first pattern including a first offset and the right side of FIG. 16D shows an arrow 244 connecting the left sides of a second pattern including a second offset, the first pattern and the second pattern interspersed with and staggered from each other. The patterns in FIG. 16D are shown horizontal, but could be angled, for example as illustrated in FIG. 16C.

FIG. 16E is a schematic diagram illustrating an example embodiment of slits and stems along the length of an example embodiment of a proximal portion 270. Above the dashed line, one of two stems of a first pattern in a numbered slit row is shaded for easier visualization of the repetition of the row. The shaded stem or anchor point in row 1 is the same as the shaded stem or anchor point in row 11, showing that the stems repeat every 10th row. As described above, the ratio of the offset to the circumferential length of the slit half may determine how quickly the stems are aligned longitudinally or, colloquially, how quickly a particular slit repeats itself along the tubular member. For example, in the example illustrated in the top half of FIG. 16E, such a ratio may be $\frac{1}{10}$ so that the first, eleventh, etc. slits and stems would be the same, the second, twelfth, etc. slits and stems would be the same, and so on. The pattern for which the stems are shaded is interspersed with a second pattern so that the actual repetition rate is about half of the ratio. For example, nine rows of the second pattern are between the first and eleventh row of the first pattern, so there are actually nineteen rows of slits and stems before the repetition of a row.

Below the dashed line in FIG. 16E, one of two stems of a second pattern in a numbered slit row is shaded for easier visualization of the repetition of the row. The shaded stem in row 1 is the same as the shaded stem in row 11, showing that the stems repeat every 10th row. As described above, the ratio of the offset to the circumferential length of the slit half may determine how quickly the stems are aligned longitudinally or, colloquially, how quickly a particular slit repeats itself along the tubular member. For example, in the example illustrated in the bottom half of FIG. 16E, such a ratio may be $\frac{1}{10}$ so that the first, eleventh, etc. slits and stems would be the same, the second, twelfth, etc. slits and stems would be the same, and so on. The pattern for which the stems are shaded is interspersed with the first pattern so that the actual repetition rate is about half of the ratio. For example, nine rows of the first pattern are between the first and eleventh row of the second pattern, so there are actually nineteen rows of slits and stems before the repetition of a row.

FIG. 16F is a schematic diagram illustrating another example embodiment of slits and stems along the length of an example embodiment of a proximal portion 272. One of two stems of each of two interspersed and staggered offset patterns is shaded for easier visualization of the pattern. Arrows are also provided connecting similar points of the patterns for easier visualization of the pattern. In the section of the proximal portion 272 illustrated in FIG. 16F, neither of the patterns repeats, and the patterns do not have any rows that match. The section of the proximal portion 272, which has twenty rows, has twenty degrees of freedom of movement, one at each row. In contrast, slotted hypotubes in which stems are offset by 90° every row such that every other row matches have only two degrees of freedom along the entire length of the hypotube. Fewer degrees of freedom generally causes less flexibility and/or maneuverability.

The flexibility of the proximal portion 200 can vary along at least a section of the length of the proximal portion 200, for example by varying one or more parameter (e.g., angle of cut relative to longitudinal axis, slit width, pitch or spacing between slits, ratio of slit width to pitch, stem offset, ratio of stem offset to slit half length, pattern stagger, etc.). The variation can be in discrete longitudinal segments, gradual, or combinations thereof. Gradual transition between parameters, for example pitch, can inhibit or avoid kink points.

FIG. 17A is a schematic diagram illustrating an example embodiment of a laser cutting system 10100. The laser cutting system 10100 may include customized components that can be used to laser cut the interspersed patterns of rows of kerfs in thin-walled tubes over relatively long lengths to form the proximal portions 200 of device 10, 20, 30 or 40, for example compared to stents are only few inches long at most. The laser cutting system 10100 comprises a cooling system 10105 configured to cool the laser excitation source 10110 and/or the laser media or laser generating medium 10120.

In some embodiments, the laser cutting system 10100 includes a yttrium aluminum garnet ($Y_3Al_5O_{12}$, YAG) laser excitation source 10110, for example instead of a carbon dioxide ($CO_2$) laser source for laser cutting a proximal portion 200. The YAG laser utilizes infrared wavelength in the 1.064 µm wavelength for laser cutting compared to a $CO_2$ laser that utilizes infrared wavelength in the 10.64 µm wavelength for laser cutting. Compared to a $CO_2$ laser, the beam from the YAG laser has a wavelength that is ten times smaller for laser cutting complex interspersed smaller patterns and can create smaller heat impact puddles and heat affected zones, which can reduce the risk of fissures or fractures in the stems of the laser cut hypotubes. The heat impact puddle is the initial point of contact of the laser beam on the hypotube during the laser cutting process. The heat affected zone is the area of the base material of the hypotube surrounding the initial point of contact of the laser beam, which can have its microstructure and properties altered because of heat intensive laser cutting operations of the laser beam.

In some embodiments, a relatively smaller heat impact puddle and heat impact zone can be achieved by utilizing an infrared wavelength between about 1.060 µm and about 1.070 µm, which can generate a smaller laser beam, which can reduce the risk of fissures or fractures during laser cutting small patterns on the proximal portion 200. In some embodiments, a ytterbium ($Yb^{3+}$) doped YAG laser or a neodymium ($Nd^{3+}$) doped YAG laser can help generate infrared wavelengths between about 1.060 µm and about 1.070 µm, for example compared to an erbium ($Er^{3+}$) doped YAG laser.

The laser cutting system 10100 illustrated in FIG. 17A comprises a laser excitation source 10110 that can help excite the ions in the laser medium or crystal in the laser medium or laser generating medium 10120. Excitation of the $Yb^{3+}$ or $Nd^{3+}$ ions by the laser excitation source 10110 can result in specific energy level transitions for the $Yb^{3+}$ or $Nd^{3+}$ ions, and the resulting energy level transitions from a higher or upper energy level to a lower energy level can create specific infrared wavelengths between about 1.060 µm and about 1.070 µm, which can generate a relatively smaller laser beam with relatively smaller heat impact puddles and heat affected zones.

In some embodiments in which the laser cutting system 10100 includes a laser medium 10120 that is ytterbium-doped yttrium aluminum garnet ($Yb:Y_3Al_5O_{12}$), the laser excitation source 10110 can excite the $Yb^{3+}$ ions, which can result in ytterbium ion energy level transitions from the upper energy level or the upper Stark level manifold $^2F_{5/2}$ to the lower energy level or lower Stark level manifold $^2F_{7/2}$, which can generate a wavelength of about 1.060 µm in the infrared wavelength range, which can generate relatively smaller heat impact puddles and heat affected zones.

In some embodiments in which the laser cutting system 10100 includes a laser medium 10120 that is neodymium-doped yttrium aluminum garnet ($Nd:Y_3Al_5O_{12}$), the laser excitation source 10110 can excite the $Nd^{3+}$ ions, which can result in neodymium ion energy level transitions from the upper energy level or the upper Stark level manifold $^4F_{3/2}$ to the lower energy level or lower Stark level manifold $^4I_{11/2}$, which can generate a wavelength of about 1.060 µm in the infrared wavelength range, which can generate relatively smaller heat impact puddles and heat affected zones.

Referring again to FIG. 17A, the infrared wavelength laser beam that is generated by exciting the ions of the laser medium 10120 may be reflected across a plurality of mirrors and lenses, for example a rear mirror 10115 and a front mirror 10125. In some embodiments, the concentrated laser beam can be focused onto the hypotube of the proximal portion 200 via a lens 10145.

Heat may be generated during the process of the laser beam impacting the hypotube of the proximal portion 200. In some embodiments, an external gas (e.g., air) based cooling system 10130 for the laser beam can reduce the heat impact puddle and the heat affected zone, and may help remove external slag 10155 generated during the laser cutting process, which may be collected in an external slag collecting device 10150. The external gas cooling system 10130 includes a supply of gas that can flow into a laser nozzle in the direction indicated by the 10140. An external gas inflow valve 10135 can regulate the gas that circulates into the laser nozzle to reduce the heat impact puddle and/or to reduce the heat impact zone.

In some embodiments, the hypotube of the proximal portion 200 that is being laser cut may be carefully handled to reduce the chance of kinking or fracturing the hypotube 200. The laser cutting system 10100 includes a hypotube collector device 10200 including a spiral collector configured to wind the hypotube of the proximal portion 200 after laser cutting, which can inhibit kinking or otherwise damaging the laser-cut hypotube 200. The external gas cooling system 10130 can provide cooling to the hypotube collector device 10200. The external gas cooling system 10130 includes a supply of gas that can flow into the hypotube collector device 10200. An external gas inflow valve 10205 can regulate the gas that circulates into the hypotube collector device 10200, which can cool the laser-cut hypotube 200, which can reduce the heat affected zone. The gas used for the external cooling system 10130 can include, for example, ambient air and/or inert gas. In some embodiments, the temperature of the gas is at about ambient temperature (e.g., between about 20° C. and about 25° C.) and the external gas cooling is continued for all or a portion of the duration of the laser cutting process.

In the laser cutting system 10100 illustrated in FIG. 17A, the hypotube of the proximal portion 200 is held in position by a bushing 10160 configured to inhibit motion of the hypotube 200 prior to the laser beam impacting the hypotube 200, one or more collets 10165 configured to reduce sag of the relatively long hypotube 200 and/or to maintain adequate tension $F_t$ on the hypotube 200 as the hypotube 200 is being advanced towards the laser beam, and a hypotube clamp that is part of a motor 10175 and hypotube dispenser 10180 that hold the hypotube 200 and help advance the hypotube 200 forward towards the laser beam.

In some embodiments, the system 10100 includes an external water inlet regulator device 10190 including a pressure valve 10197 configured to pump water through a series of water injection tubes 10195 and a constrictive water inlet gate 10187 configured to inject water into the inner lumen of the hypotube 200. The external water inlet regulator device 10190 injects water into the hypotube 200 at a certain velocity, which can assist with removal of the slag 10155 that is generated during the laser cutting process by removing the slag 10155 before the slag 10155 has time to sediment and adhere to the inner lumen of the hypotube 200. The external water inlet regulator device 10190 can assist with cooling the hypotube 200 during the laser cutting process and reduce the size of the heat impact puddle and/or the size of the heat affected zone. The laser cutting system 10100 may include a laser controller box 10170 configured to control one, some, or all the processes within laser cutting system 10100 (e.g., shown in communication with the water inlet regulator device 10190.

In some embodiments, a proximal portion 200 comprises a hypotube including the Patterns A and B described herein with a variable pitch between slits, which increases flexibility from proximal to distal. The Patterns A and B may be formed, for example, by laser cutting using, for example, the system 10100. Each slit has a width along the longitudinal axis (which may take into account an angle of the kerf) of about 0.001 inches (approx. 0.025 mm). The longitudinal slit widths may have a tolerance of ±0.0002 inches (approx. 0.005 mm). Longitudinally thicker and thinner slits are also possible. For example, a thicker slit may provide flexibility for thicker hypotubes. For another example, a thinner slit may provide strength for thinner hypotubes. The kerf width may be greater than the width of a laser beam used to cut the kerf, which can inhibit formation of a heat impact puddle on an edge of the kerf because the initial heat impact puddle can be in a middle of the kerf and removed upon finishing cutting the kerf. The hypotube may have an outer diameter of about 0.0125 inches (approx. 0.318 mm) and an inner diameter between about 0.001 inches (approx. 0.025 mm) and about 0.0011 inches (approx. 0.028 mm).

In some embodiments, a ratio of a width of a kerf along a longitudinal axis and a circumferential width of a strut at least partially defined by the kerf is between about 1:1 and about 2:1. For example, the kerf width may be about 0.003 inches (approx. 0.076 mm) and the strut width may be about 0.003 inches (approx. 0.076 mm) such that the ratio is 1:1.

FIG. 17B is a schematic diagram illustrating an example embodiment of a cut design of a slit 6400. A heat impact puddle 6405 is the initial point of contact of the laser beam on the hypotube during the process of cutting the kerf 6400 with the laser. The path of the laser beam is a straight line 6415 and the heat impact puddle 6405 is formed at the edge of the kerf 6400. The heat affected zone is the area in which the microstructure and/or properties of the base material of the hypotube is altered by the laser beam. The diameter 6410 of the heat impact puddle 6405 is larger than the width 6420 of the kerf 6400 such that the heat affected zone around the heat impact puddle 6405 remains part of the cut pattern, which can make the struts between the kerfs more prone to fractures or fissures 6430. The circumferential length 6440 of the kerf 6400 is larger than the intended circumferential length of the kerf 6400 due to the heat impact puddle 6405 being on the edge of the kerf 6400.

In some embodiments, the diameter 6410 of the heat impact puddle 6405 can be larger than a width 6420 of the kerf 6400 without damaging the structural integrity of the struts proximate to the heat impact puddle 6405. Certain patterns described herein include struts and slits that are close to each other along with the complexity of the interspersed laser cut patterns in a thin-walled hypotube over the relatively long length of the proximal portion 200 compared to, for example, laser-cut stents, and fractures and fissures may be inhibited or prevented if the laser intensity and the laser beam angle are set such that the diameter of the heat impact puddle 6405 does not exceed about 120% of the width 6420 of the kerf 6400. FIG. 17C is a schematic diagram illustrating an example embodiment of an interspersed offset horizontal pattern 6500 including slits 6400 and heat impact puddles 6405. FIG. 17C shows the possible proximity of the kerfs 6400 with heat impact puddles 6405 and fractures 6430.

FIG. 17D is a schematic diagram illustrating another example embodiment of a cut design of a slit 6600. In some embodiments, the width 6420 and length 6435 of the kerf 6600 may be greater than the width of a laser beam used to cut the kerf 6600, which can inhibit formation of a heat impact puddle on an edge of the kerf 6600. In the embodiment illustrated in FIG. 17D, the path 6415 of the laser beam starts with the heat impact puddle 6405 in a central or intermediate or middle of the kerf 6600 and travels up to an edge of the kerf 6600 and then along the edges of the kerf 6600, surrounding the heat impact puddle 6405, such that the heat impact puddle and the heat affected zone can be removed or substantially removed by the cutting process. In certain such embodiments, the removal of the heat impact puddle 6405 and the heat affected zone can maintain the structural integrity of the struts and/or inhibit or prevent formation of fractures or fissures.

FIG. 17E is a schematic diagram illustrating yet another example embodiment of a cut design of a slit 6700. In some embodiments, the width 6420 and length 6435 of the kerf 6700 may be greater than the width of a laser beam used to cut the kerf 6700, which can allow the heat impact puddle 3405 to be within the edges of the slit 6700. In the embodiment illustrated in FIG. 17E, the path 6415 of the laser beam starts with the heat impact puddle 6405 in a central or intermediate or middle of the kerf 6700 and travels diagonally to the upper left corner of the kerf 6700 and then along the edges of the kerf 6700, surrounding the heat impact puddle 6405, such that the heat impact puddle and the heat affected zone can be removed or substantially removed by the cutting process. In certain such embodiments, the removal of the heat impact puddle 6405 and the heat affected zone can maintains the structural integrity of the struts and/or inhibit or prevent the formation of fractures or fissures.

FIG. 17F is a schematic diagram illustrating still another example embodiment of a cut design of a slit 6800. In some embodiments, the width 6420 and length 6435 of the kerf 6800 may be greater than the width of a laser beam used to cut the kerf 6800, which can allow the heat impact puddle 6405 to be within the edges of the slit 6800. In the embodiment illustrated in FIG. 17F, the path 6415 of the laser beam starts with the heat impact puddle 6405 near the bottom right corner of the kerf 6800 but also within the edges of the slit 6800 and travels diagonally to the upper left corner of the kerf 6800 and then along the edges of the kerf 6800, surrounding the heat impact puddle 6405, such that the heat impact puddle and the heat affected zone can be removed or substantially removed by the cutting process. In certain such embodiments, the removal of the heat impact puddle 6405 and the heat affected zone can maintains the structural integrity of the struts and/or inhibit or prevent the formation of fractures or fissures.

FIG. 17G is a schematic diagram illustrating still yet another example embodiment of a cut design of a slit 7200. In some embodiments, the width 6420 and length 6435 of the kerf 7200 may be greater than the width of a laser beam used to cut the kerf 7200, which can allow the heat impact puddle 6405 to be within the edges of the slit 7200. In the embodiment illustrated in FIG. 17F, the path 6415 of the laser beam starts with the heat impact puddle 6405 near the bottom left corner of the kerf 7200 but also within the edges of the slit 7200 and travels in an overlapping spiral pattern within the edges of the kerf 7200 and then along the edges of the kerf 7200, surrounding the heat impact puddle 6405, such that the heat impact puddle and the heat affected zone can be removed or substantially removed by the cutting process. In certain such embodiments, the removal of the heat impact puddle 6405 and the heat affected zone can maintains the structural integrity of the struts and/or inhibit or prevent the formation of fractures or fissures.

FIG. 17H is a schematic side elevational view of an example embodiment of a bushing 7300. FIG. 17I is a schematic cross-sectional front elevational view of the bushing 7300 of FIG. 17H along the line 17I-171. The bushing 7300 can the used to assist fixation of a hypotube 7315 to inhibit movement of the hypotube 7315 during a laser cutting process. The hypotube 7315 may be cut to be, for example, the proximal portion 200 of the device 10, 20, 30, or 40. In some embodiments, the bushing 7300 includes a proximal end 7314 through which an uncut hypotube 7315 may be inserted, a middle segment 7310 within which the hypotube 7315 is stabilized, and a distal end 7304 through which the hypotube 7315 emerges to be cut by the laser (e.g., as shown by the slits 7305 in the hypotube 7315 distal to the distal end 7304). As illustrated in FIG. 17I, the bushing 7300 includes a cylindrical hole or aperture 7410 within the middle segment of the bushing 7310 through which the hypotube 7315 traverses. In some embodiments, the aperture 7410 has an inner diameter of at least about 0.001 inches (approx. 0.025 mm) greater than the outer diameter of the hypotube 7315, which can provide stabilization and inhibit friction. The bushing 7300 may comprise metals including, for example, platinum, titanium, nickel, chromium, cobalt, tantalum, tungsten, iron, manganese, molybdenum, alloys thereof including nickel titanium (e.g., nitinol), nickel titanium niobium, chromium cobalt, copper aluminum nickel, iron manganese silicon, silver cadmium, gold cadmium, copper tin, copper zinc, copper zinc silicon, copper zinc aluminum, copper zinc tin, iron platinum, manganese copper, platinum alloys, cobalt nickel aluminum, cobalt nickel gallium, nickel iron gallium, titanium palladium, nickel manganese gallium, stainless steel, shape memory alloys, etc.

FIG. 17J is a schematic side elevational view of an example embodiment of a collet 7500. FIG. 17K is a schematic cross-sectional front elevational view of the collet 7500 of FIG. 17J along the line 17K-17K. The collet 7500 is a holding device comprising a cylindrical inner surface including kerfs that forms an inner collar 7511 around a hypotube 7315 to be held and the cylindrical hole or aperture 7510 within the inner collar 7511 exerts a clamping force or tension $F_t$, measurable in Newtons or pound-feet, on the hypotube 7315 when tightened, for example by an outer collar 7512. In some embodiments, the amount of the clamping force or tension $F_t$ can be measured in real time using a tension gauge 7513. The collet 7500 may be used to assist with holding a proximal portion 200 of a vascular treatment device, for example the device 10, 20, 30, or 40, and releasing the proximal portion 200 to be advanced forward during a laser cutting process. The amount of clamping force or tension $F_t$ can be increased or decreased by tightening or releasing the outer collar 7512, either by a manual or automated approach.

In some embodiments, the collet 7500 includes a proximal end 7514 through which an uncut hypotube 7315 is inserted, a long segment 7515 within which the hypotube is held with tension $F_t$ and stabilized to reduce sag (e.g., between two collets 7300, between a collet 7300 and the bushing 7500, between the bushing 7500 and another bushing 7500), and a distal end 7504 through which the hypotube 7315 passes to be advanced into another collet 7500 or a bushing 7300. The collet 7500 includes a cylindrical hole or aperture 7510 within the inner collar 7511 through which a hypotube 7315 can traverse and be stabilized from motion during a laser cutting process. In some embodiments, the cylindrical hole 7510 has an inner diameter of at least about 0.001 inches (approx. 0.025 mm) greater than the outer diameter of the hypotube 7315. In some embodiments, the collet 7500 may be split into two halves, and each half includes a number of nooks ranging from about 1 nook to about 24 nooks (e.g., between about 1 nook and about 3 nooks, between about 5 nooks and about 7 nooks, between about 9 nooks and about 11 nooks, about 3 nooks). In some embodiments, the nooks may have full thickness 7616, wherein the nook extends fully between the outer surface of the inner collar 7511 to the cylindrical hole or aperture 7510 within the inner collar 7511, or the nooks may have partial thickness 7617, wherein the nook extends partially from outer surface of the inner collar 7511 towards the cylindrical hole or aperture 7510 but does not reach the cylindrical hole or aperture 7510. The nooks 7616 and 7617 within the inner collar 7511 can allow the outer collar 7512 to reduce the diameter of the aperture 7510 within the inner collar 7511 to adequately hold hypotubes 7315 of varying diameters without using different collets 7500. The cylindrical hole or aperture 7510 within the inner collar 7511 can be tightened around the hypotube 7315 to increase or decrease the tension, and the nooks 7616 and 7617 help adjust the tension on the hypotube 7315.

In some embodiments, the collet 7500 comprises metals such as platinum, titanium, nickel, chromium, cobalt, tantalum, tungsten, iron, manganese, molybdenum, alloys thereof including nickel titanium (e.g., nitinol), nickel titanium niobium, chromium cobalt, copper aluminum nickel, iron manganese silicon, silver cadmium, gold cadmium, copper tin, copper zinc, copper zinc silicon, copper zinc aluminum, copper zinc tin, iron platinum, manganese copper, platinum alloys, cobalt nickel aluminum, cobalt nickel gallium, nickel iron gallium, titanium palladium, nickel manganese gallium, stainless steel, shape memory alloys, etc.

FIG. 17L is a schematic diagram illustrating an example embodiment of an arrangement of bushings 10160 and collets 10165. The arrangement is configured to hold a hypotube of a proximal portion 200 during a laser cutting process. During the laser cutting process, the hypotube 10210 is advanced forward and held firmly in place substantially without lateral motion and/or substantially without horizontal motion (e.g., undesired or unintended motion) when the laser beam is cutting the hypotube 10210, for example in interspersed patterns of rows of kerfs. In some embodiments, the concentrated laser beam is focused onto the hypotube 10210 of the proximal portion 200 via a lens 10145. Any untoward motion of the hypotube 10210 can cause slits or other patterns being cut to have incorrect shapes or to be in incorrect locations. In the example illustrated in FIG. 17L, the hypotube 10210 is held in position by a bushing 10160, which is configured to inhibit motion of the hypotube 10210 prior to the laser beam impact, and two collets 10165, 10167 configured to reduce parabolic sag of the relatively long hypotube 10210 and/or can maintain adequate tension $F_t$ on the hypotube 10210 as the hypotube 10210 is being advanced towards the laser beam. More or fewer collets 10165, 10167 can be used, for example depending on the length, stiffness, material, etc. of the hypotube 10210. The arrangement further includes a hypotube clamp 10185 that is part of a hypotube dispenser 10180. The hypotube clamp 10185 is configured to hold the hypotube 10210 in position and advance the hypotube 10210 towards the laser beam.

FIG. 17M is a schematic diagram illustrating an example embodiment of the sage of a hypotube between in an arrangement of bushings and collets 10162. For example, the bushings and collets 10162 can include three bushings 10165, 10167, 10169, three collets 10165, 10167, 10169, or combinations of bushings and collets. Referring again to in FIGS. 17A and 17L, the handling (e.g., manipulating, controlling, managing, treating, modifying) of a thin-walled relatively long hypotube (e.g., about 7 feet, about 210 cm) can be very different from handling of hypotubes for stents (e.g., about 1 inch, about 2.5 cm). In the example illustrated in FIG. 17M, the hypotube does not lay between the bushings and collets 10162 in a perfectly straight line, but with parabolic sag 10220. The arrangement of bushings and collets 10162 can reduce the parabolic sag 10220 to reduce cutting errors due to sag.

The parabolic sag 10220 can be reduce by at least one of the following four procedures: (1) ensure that all of the collets, bushings, and the hypotube clamp are at the exact or substantially the same height 10215 and placing all of the collets, bushings, and the hypotube clamp in or on the same a horizontal plane (e.g., a flat table that may be part of the laser cutting system 10100); (2) optimizing the distance 10215 between the collets, bushings and hypotube clamp; (3) applying variable tension $F_t$ at the level of the hypotube clamp 10185; and/or (4) ensuring that the sag 10220 is no more than between about 2% and about 3% of the height 10215. If the distance 10215 is too high, then the parabolic sag 10220 increases. If the distance 10215 is too short, the cost of the system 10100 can be excessively high and tends to clutter the workspace area around the laser cutting device. The parabolic sag s can be calculated using Equation 3:

$$s = w d_2 / 8 F_t \quad \text{(Eq. 3)}$$

where s is the sag 10220 of the hypotube, w is the weight of the hypotube per inch, d is the distance 10215 between collets, and $F_t$ is the tension applied to the hypotube by the hypotube clamp 10185.

FIG. 17N is a schematic diagram illustrating an example embodiment of a water inlet device 10300. The water inlet device 10300 can regulate the velocity of the water inflow into a hypotube 7315 through a constrictive water inlet gate 10187. The flow of water can cool the hypotube 7315 during laser cutting and help remove slag created from the laser cutting process. Fluids other than water may also be used, for example including ethylene glycol (e.g., to increase heat transfer), slurry (e.g., to increase slag removal), etc.

The water inlet device 10300 includes a series of water inlet tubes or reservoirs 10370 through which the fluid flows before entering the lumen of the proximal portion 200. In some embodiments, the water inlet device 10300 includes four water inlet tubes 10370: the highest water inlet tubing 10320 has a fluid velocity $v_4$ and flows through a height $h_4$ that is the sum of the distances 10340, 10335, 10330, 10325; the next highest water inlet tube 10315 has a fluid velocity $v_3$ and flows through a height $h_3$ that is the sum of the distances 10335, 10330, 10325; the next highest water inlet tube 10310 has a fluid velocity $v_2$ and flows through a height $h_2$ that is the sum of the distances 10330, 10325; the lowest water inlet tube 10305 has a fluid velocity $v_1$ and flows through a height $h_1$ that is the distance 10325.

At a height $h_4$ above the ground, the water inlet device 10300 has a pressure $P_4$ and a fluid velocity $v_4$. The fluid entering the hypotube 7315 through the constrictive water inlet gate 10187, which is at a height $h_1$ above the ground, has a pressure $P_1$, and a fluid velocity $v_1$. As the sum of the kinetic energy per unit volume ($\frac{1}{2}\rho v^2$), the potential energy per unit volume ($\rho g h$), and the pressure energy (P) remain the same, the density of the fluid p and the acceleration due to gravity g (980 cm/second$^2$) remain constant, the fluid velocity $v_1$ entering the hypotube 7315 through the constrictive water inlet gate 10187 can be calculated using Equation 4:

$$\tfrac{1}{2}\rho v_1^2 + \rho g h_1 + P_1 = \tfrac{1}{2}\rho v_4^2 + \rho g h_4 + P_4$$

$$\text{or, rearranged, } v_1 = \sqrt{[v_4^2 + 1960(h_4 - h_1) + 2(P_4 - P_1)/\rho]}. \quad \text{(Eq. 4)}$$

In some embodiments, if the pressures $P_1$ and $P_4$ are equal to atmospheric pressure ($P_1 = P_4 = P_{atm}$), the height $h_1$ of the constrictive water inlet gate 10187 is at ground level ($h_1 = 0$), and the fluid velocity $v_4$ is initially at rest ($v_4 = 0$), then the fluid velocity $v_1$ entering the hypotube 7315 through the constrictive water inlet gate 10187 is directly proportional to the height $h_4$ of the external water inlet regulator device 10300. By increasing the height $h_4$ of the external water inlet regulator device 10300, the fluid velocity $v_1$ can be increased, and $v_1$ can be calculated in cm$^3$/s using Equation 5:

$$v_1 = \sqrt{(1960 \times h_4)} \quad \text{(Eq. 5)}$$

At a height $h_3$ above the ground, the water inlet device 10300 has a pressure $P_3$ and a fluid velocity $v_3$. At a height $h_2$ above the ground, the water inlet device 10300 has a pressure $P_2$ and a fluid velocity $v_2$. Adaptations of Equations 4 and 5 can be used to calculate the fluid velocity $v_1$ when the fluid is in the tubes 10315, 10305, 10305.

The proximal portion 200 may have between 1 longitudinal section (e.g., the same cut pattern) and about 100 longitudinal sections, between 1 longitudinal section and about 50 longitudinal sections, or between about 1 longitudinal section and about 20 longitudinal sections (e.g., about 15 longitudinal sections), for example depending on the intended use. For example, a distal section of the proximal portion 200 may be sturdy and torquable and a distal section of the proximal portion 200 may be soft and flexible, with one or more sections therebetween. One or more longitudinal transitional sections can be between longitudinal sections having a certain pattern, which can inhibit kinking that could result from a direct transition. The transitional sections can be include a linear or nonlinear change to the cut pattern, and, on average, can be the same as the average of the sections proximal and distal thereto.

The proximal portion 200 comprises, in some embodiments, in longitudinal order from distal to proximal, a first section, a second section, a third section, a fourth section, a fifth section, a sixth section, a seventh section, an eighth section, a ninth section, a tenth section, an eleventh section, a twelfth section, and a thirteenth section. The first section is about 16 inches (approx. 41 cm) long and includes a pitch between slits of about 0.005 inches (approx. 0.13 mm). The third section is about 10 inches (approx. 25 cm) long and includes a pitch between slits of about 0.01 inches (approx. 0.25 mm). The second section is about 2 inches (approx. 5 cm) long and includes a pitch gradually changing from about 0.005 inches (approx. 0.13 mm) to about 0.01 inches (approx. 0.25 mm), with an average pitch of about 0.0075 inches (approx. 0.19 mm). The fifth section is about 10 inches (approx. 25 cm) long and includes a pitch between slits of about 0.02 inches (approx. 0.51 mm). The fourth section is about 2 inches (approx. 5 cm) long and includes a pitch gradually changing from about 0.01 inches (approx. 0.25 mm) to about 0.02 inches (approx. 0.51 mm), with an average pitch of about 0.015 inches (approx. 0.38 mm). The seventh section is about 10 inches (approx. 25 cm) long and includes a pitch between slits of about 0.04 inches (approx. 1 mm). The sixth section is about 2 inches (approx. 5 cm) long and includes a pitch gradually changing from about 0.02 inches (approx. 0.51 mm) to about 0.04 inches (approx. 1 mm), with an average pitch of about 0.03 inches (approx. 0.76 mm). The ninth section is about 10 inches (approx. 25 cm) long and includes a pitch between slits of about 0.08 inches (approx. 2 mm). The eighth section is about 2 inches (approx. 5 cm) long and includes a pitch gradually changing from about 0.04 inches (approx. 1 mm) to about 0.08 inches (approx. 2 mm), with an average pitch of about 0.06 inches (approx. 1.5 mm). The eleventh section is about 10 inches (approx. 25 cm) long and includes a pitch between slits of about 0.16 inches (approx. 4.1 mm). The tenth section is about 2 inches (approx. 5 cm) long and includes a pitch gradually changing from about 0.08 inches (approx. 2 mm) to about 0.16 inches (approx. 4.1 mm), with an average pitch of about 0.12 inches (approx. 3 mm). The thirteenth section is about 6 inches (approx. 15 cm) long and includes no slits. The twelfth section is about 2 inches (approx. 5 cm) long and includes a pitch gradually changing from about 0.16 inches (approx. 4.1 mm) to no slits, with an average pitch of about 0.24 inches (approx. 6.1 mm). The pitches may have a tolerance of ±0.0005 inches (approx. 0.013 mm). The lengths of the sections may have a tolerance of ±0.25 inches (approx. 6.4 mm). The proximal portion 200 may have a length of about 84 inches (approx. 210 cm). A distal-most section distal to the first section of the proximal portion 200 (e.g., about 2 mm to about 4 mm) may remain uncut for coupling to the distal portion 100 at the joint 300.

Although the patterns are illustrated in certain figures herein as being generally horizontal or perpendicular to the longitudinal axis of the tubular structure 202, the slits 204 may be angled, for example between about 95° and about 115° from the longitudinal axis of the tubular structure 202. In some embodiments, an angle greater than 90° (up to about) 180° can help to translate torque applied to a proximal segment of the proximal portion 200 during rasping by spreading force across stems and uncut portions of the tubular structure 202. In some embodiments, an angle greater than 90° can reduce the duration of cutting the slits 204 in the tubular structure 202.

In some embodiments, the proximal portion 200 is formed by laser cutting a hypotube. For example, at least the proximal end of a hypotube may be clamped for treatment in a laser cutting device that has been programmed with a desired pattern (e.g., interspersed staggered offset patterns as described herein). The distal end may also be clamped in some embodiments. A laser is directed at material to be removed. In some embodiments, the distal end of the proximal portion 200 is not cut to form a bonding zone for coupling the proximal portion 200 to a distal portion 100. The bonding zone may have a length between about 1 mm and about 4 mm (e.g., about 2 mm). The section of the proximal portion 200 proximal to the proximal end of the cut pattern may be trimmed (e.g., to provide the proximal portion 200 with a specific length, to fit into packaging, etc.), or may remain uncut, for example to reduce manufacturing steps, since that section of the proximal portion 200 is intended to be outside of a body during a procedure. The proximal end of the proximal portion 200 may be coupled to a handle, coated, etc. for increased manipulability by a user.

Interrupted spiral cut hypotubes may suffer from similar issues as 90 degree alternating slotted hypotubes. Certain strut patterns and interspersed patterns (e.g., the struts in Patterns A and B, which include staggered and offset struts) described herein may be adapted for use by interrupting a spiral cut in a hypotube. In certain such embodiments, the hypotube does not include discrete rows including two kerfs, but include kerfs of varying circumferential widths depending on the desired pattern of struts.

Although certain embodiments described herein are with respect to cutting a tubular structure 202, a flat sheet may also be cut and then rolled into a tubular member, and optionally heat set to retain the tubular shape. For example, FIGS. 16E and 16F can represent either an example of a cut pattern on a sheet or the cut pattern of a flattened tube.

In some embodiments, the proximal portion 200 may comprise something other than or in addition to a tubular member. For example, the proximal portion 200 may comprise a braided structure or a hybrid of a braided structure and a tubular member. Certain such structures may have the same or similar, or different, characteristics (e.g., dimensions, variable flexibility, etc.) as the tubular member described in detail herein and/or the textile structure (e.g., filament material, weave pattern, etc.) 158 described in detail with respect to the distal portion 100 herein.

In embodiments in which the proximal portion 200 is homogenous (e.g., being a single hypotube or braided structure), the proximal portion includes zero attachment points. For example, the proximal portion may comprise a single integral hypotube with a plurality of cut patterns and/or shape setting along a longitudinal length. For another example, the proximal portion may comprise a single integral textile structure with a plurality of weave parameters and/or shape setting along a longitudinal length. Homogenous proximal portions 200 can also include one attachment point or a plurality of attachment points. For example, a plurality of sections of hypotube each having different pattern spacing may be coupled. For another example, a plurality of sections of hypotube each having different shape setting (e.g., with or without a cut pattern) may be coupled. Can have no pitch (straight wires) or pitch (length to complete a circumference). Pitch can be different for each longitudinal section, which can help with heat setting during manufacturing. Pitch can also help with x-ray length measurement. Lengths of longitudinal sections can vary.

FIG. 18A is a schematic perspective view of a proximal portion 280 of a vascular treatment device comprising a plurality of filaments 282. The filaments 282 are braided together, for example as described herein with respect to embodiments of distal portions 100. FIG. 18B is a front perspective view of the proximal portion 280. In some embodiments, for example for use in the neurovasculature, the filaments may have a diameter between about 0.35 mm and about 0.65 mm (e.g., between about 0.4 mm and about 0.45 mm), between about 0.1 mm and about 0.34 mm (e.g., between about 0.25 mm and about 0.33 mm), about 0.00125 inches (approx. 0.317 mm). In some embodiments, for example for use in the peripheral vasculature, the filaments may have a diameter between about 0.5 mm and about 10 mm Filament materials, shape memory characteristics, braid patterns, oxidation state, etc. may be the same or similar to those described herein with respect to the distal portion 100, or may be adapted for the proximal portion 200. For example, the filaments may cross at a smaller angle (e.g., between about 1° and about 45° (e.g., about 17°). For other examples, the porosity may be smaller, the density may be larger (e.g., between about 5 PPI and about 50 PPI (e.g., about 32 PPI)), the number of filaments may be more or fewer, the filaments may be thicker or thinner, the radiopacity may be different, the shape memory characteristics may be different, etc.

FIG. 18C is a perspective view of another example embodiment of a proximal portion 7700 of a vascular treatment device comprising a plurality of filaments 282. The filaments 282 are not braided. For example, the filaments 282 may be spiraled or helically wound in one direction (e.g., allowing torsional rasping in a first direction), in an opposite direction (e.g., allowing torsional rasping in a second direction), not at all (e.g., filaments 282 parallel to the longitudinal axis, as shown in FIG. 18C), and combinations thereof (e.g., coaxial helically wound filaments 282). In some embodiments, the plurality of filaments 282 includes shape memory filaments and radiopaque filaments, combinations thereof, and the like. The embodiment illustrated in FIG. 18C includes 12 filaments 282 that are parallel to the longitudinal axis. Although some examples of the proximal portion 7700 with 12 filaments 282 are provided herein, some embodiments of the proximal portion 200 may include between about 6 filaments and about 120 filaments in accordance with the values provided above and/or proximal portion may include about 6 filaments to about 96 filaments, about 6 filaments to about 72 filaments, about 6 filaments to about 12 filaments, and about 48 filaments.

FIG. 18D is a schematic side elevational view of an example embodiment of a proximal portion 7800 of a vascular treatment device illustrating an example pattern of radiopaque filaments, for example under x-ray. The proximal portion 7800 may be the proximal portion 200 of the device 10, 20, 30, or 40. The proximal portion 7800 includes, in an expanded state, a plurality of filaments that are spirally or helically wound in one direction. The plurality of filaments includes shape-memory filaments and radiopaque filaments. In some embodiments, the proximal portion 7800 includes, in an expanded state, two radiopaque filaments 7811, 7813 that are interlaced in the form a double sine wave like a "double helix" at least under x-ray. The pattern of radiopacity can allow an operator of a device comprising the proximal portion 7800 to visualize identify the proximal portion 7800 under x-ray. In some embodiments, the double helix includes troughs and peaks, for example at the sides of the proximal portion 7800 that the double helix at least partially creates. In FIG. 18D, distances 7830, 7840, 7850, 7860, 7870 between helical intersection points 7825, 7835, 7845, 7855, 7865, 7875 have substantially uniform dimensions, which can allow the proximal portion 7800 to serve as an angiographic measurement ruler. For example, the distances 7820 can help measure the length of blood clots, the neck of an aneurysm, the length of a stenosis, etc.

FIG. 18E is a schematic front elevational view of the proximal portion 7800 of FIG. 18D. In FIG. 18E, the material of the filaments is indicated by shading: filaments with no shading include shape-memory material and filaments 7811, 7813 with hatched shading include radiopaque material. The example set up of radiopaque filaments 7811, 7813 illustrated with respect to FIG. 18E can generate a pattern of radiopacity described in FIG. 18D, for example a double sine wave or double helix pattern. The radiopaque filaments 7811, 7813 form two sine waves, which are offset by about 180°, and the sine waves in each pair are offset from the other filaments by about 30°. Although some examples of the proximal portion 7800 including 12 filaments are provided herein, some embodiments of the proximal portion 200 may include between about 6 filaments and about 120 filaments in accordance with the values provided above and/or the proximal portion 200 may include about 6 filaments to about 96 filaments, about 6 filaments to about 72 filaments, about 6 filaments to about 12 filaments, and about 48 filaments, and the number and/or percentage of radiopaque filaments can remain as described above.

FIG. 18F is a schematic side elevational view of another example embodiment of a proximal portion 7900 of a vascular treatment device illustrating an example pattern of radiopaque filaments, for example under x-ray. The proximal portion 7900 may be the proximal portion 200 of the device 10, 20, 30, or 40. The proximal portion 7900 includes, in an expanded state, a plurality of filaments that are spirally or helically wound in one direction. The plurality of filaments includes shape-memory filaments and radiopaque filaments. In some embodiments, the proximal portion 7900 includes, in an expanded state, two pairs 7910, 7920 of radiopaque filaments 7911, 7913 and 7915, 7917, respectively. The first pair 7910 of radiopaque filaments 7911, 7913 and second pair 7920 of radiopaque filaments 7915, 7917 are interlaced in the form a paired double sine wave like a "dual double helix" at least under x-ray. The pattern of radiopacity can allow an operator of a device comprising the proximal portion 7900 to visualize identify the proximal portion 7900 under x-ray. In some embodiments, the dual double helix includes troughs and peaks, for example at the sides of the proximal portion 7900 that the dual double helix at least partially creates. In FIG. 18F, distances 7930, 7940, 7950, 7960 between intersection points 7935, 7945, 7955, 7965, 7975 have substantially uniform dimensions, which can allow the proximal portion 7900 to serve as an angiographic measurement ruler. For example, the distances 7970 can help measure the length of blood clots, the neck of an aneurysm, the length of a stenosis, etc.

FIG. 18G is a schematic front elevational view of the proximal portion 7900 of FIG. 18F. In FIG. 18G, the material of the filaments is indicated by shading: filaments with no shading include shape-memory material and filaments 7911, 7913, 7915, 7917 with hatched shading include radiopaque material. The example set up of radiopaque filaments 7911, 7913, 7915, 7917 illustrated in FIG. 18G can generate a pattern of radiopacity described with respect to FIG. 18F, for example a paired double sine wave or dual double helix pattern. The radiopaque filaments 7911, 7913, 7915, 7917 form four sine waves, pairs 7910, 7920 of which are offset by about 180°, and the sine waves in each pair 7910, 7920 are offset from each other by about 30°. Although some examples of the proximal portion 7900 including 12 filaments are provided herein, some embodiments of the proximal portion 200 may include between about 6 filaments and about 120 filaments in accordance with the values provided above and/or the proximal portion 200 may include about 6 filaments to about 96 filaments, about 6 filaments to about 72 filaments, about 6 filaments to about 12 filaments, and about 48 filaments, and the number and/or percentage of radiopaque filaments can remain as described above.

FIG. 18H is a schematic side elevational view of still another example embodiment of a proximal portion 8000 of a vascular treatment device illustrating an example pattern of radiopaque filaments, for example under x-ray. The proximal portion 8000 may be the proximal portion 200 of the device 10, 20, 30, or 40. The proximal portion 8000 includes, in an expanded state, a plurality of filaments that are spirally or helically wound in one direction. The plurality of filaments includes shape-memory filaments and radiopaque filaments. In some embodiments, the proximal portion 8000 includes, in an expanded state, two pairs 8010, 8020 of radiopaque filaments 8011, 8012, 8013 and 8015, 8017, 8019, respectively. The first pair 8010 of radiopaque filaments 8011, 8012, 8013 and the second pair 8020 of radiopaque filaments 8015, 8017, 8019 are interlaced in the form a paired triple sine wave like a "reinforced double helix" at least under x-ray. The pattern of radiopacity can allow an operator of a device comprising the proximal portion 8000 to visualize identify the proximal portion 8000 under x-ray. In some embodiments, the reinforced double helix includes troughs and peaks, for example at the sides of the proximal portion 8000 that the reinforced double helix at least partially creates. In FIG. 18H, distances 8030, 8040 between intersection points 8035, 8045, 8055 have substantially uniform dimensions, which can allow the proximal portion 8000 to serve as an angiographic measurement ruler. For example, the distances 8050 can help measure the length of blood clots, the neck of an aneurysm, the length of a stenosis, etc.

FIG. 18I is a schematic diagram illustrating a front elevational view of the proximal portion 8000 of FIG. 18H. In FIG. 18I, the material of the filaments is indicated by shading: filaments with no shading include shape-memory material and filaments 8011, 8012, 8013, 8015, 8017, 8019 with hatched shading include radiopaque material. The example set up of radiopaque filaments 8011, 8012, 8013, 8015, 8017, 8019 illustrated in FIG. 18I can generate a pattern of radiopacity described in FIG. 18H, for example a paired triple sine wave or reinforced double helix pattern. The radiopaque filaments 8011, 8012, 8013, 8015, 8017, 8019 form pairs 8010, 8020 of three sine waves that are offset by about 180°, and the sine waves in each pair 8010, 8020 are offset from each other by about 30°. Although some examples of the proximal portion 8000 including 12 filaments are provided herein, some embodiments of the proximal portion 200 may include between about 6 filaments and about 120 filaments in accordance with the values provided above and/or the proximal portion 200 may include about 6 filaments to about 96 filaments, about 6 filaments to about 72 filaments, about 6 filaments to about 12 filaments, and about 48 filaments, and the number and/or percentage of radiopaque filaments can remain as described above.

FIG. 18J is a schematic side elevational view of yet another example embodiment of a proximal portion 8100 of a vascular treatment device illustrating an example pattern of radiopaque filaments, for example under x-ray. The proximal portion 8100 may be the proximal portion 200 of the device 10, 20, 30, or 40. The proximal portion 8100 includes, in an expanded state, a plurality of filaments that are spirally or helically wound in one direction along the central longitudinal axis 8140 at a diameter 8150. The plurality of filaments includes shape-memory filaments and radiopaque filaments. In some embodiments, the proximal portion 8100 includes, in an expanded state, three radiopaque filaments 8111, 8112, 8113 that are interlaced in the form a three phase sine wave like a "three phase helix" at least under x-ray. The pattern of radiopacity can allow an operator of a device comprising the proximal portion 8100 to visualize and identify the proximal portion 8100 under x-ray. In some embodiments, the three phase helix includes troughs and peaks, for example at the sides of the proximal portion 8100 that the three phase helix at least partially creates.

In some embodiments, the first radiopaque filament 8111 forms a sine wave having a phase A, the second radiopaque filament 8112 forms a sine wave having a phase B, and the third radiopaque filament 8113 forms a sine wave having a phase C. In some embodiments, the three phase helix includes troughs and peaks, for example at the sides of the distal portion 8100 that the three sine waves at least partially create. Embodiments comprising a three phase sine wave include three pitches: the sine wave formed by the radiopaque filament 8111 has a pitch 8121, the sine wave formed by the radiopaque filament 8112 has a pitch 8122, and the sine wave formed by the radiopaque filament 8113 has a pitch 8123. FIG. 18J shows the pitches 8121, 8122, 8123 as the distances between the lower peaks of the respective sine waves. In the embodiment illustrated in FIG. 18J, the pitches of the sine waves formed by the radiopaque filaments 8111, 8112, 8113 have substantially uniform dimensions (e.g., pitches), although the sine waves may have differing dimensions (e.g., pitches).

In some embodiments, the distance between each trough or peak of a radiopaque filament 8111, 8112, 8113 with another trough or peak of an adjacent radiopaque filament of the three phase helix is called a phase shift. In FIG. 18J, phase A is offset from phase B by about 7.5° (shown by the distance 8131), phase B is offset from phase C by about 7.5° (shown by the distance 8132), and phase A is offset from phase C by about 15° (shown by the distance 8133). FIG. 18J shows the phase shifts 8131, 8132, 8133 as the distances between the upper peaks of the respective sine waves. The pattern of radiopacity can allow an operator of a device comprising the proximal portion 8100 to visualize and identify the proximal portion 8100 at least under x-ray. In FIG. 18J, the intersection points along the three phase double helix are substantially uniformly spaced by distances 8141 or multiples thereof, which can allow the proximal portion 8100 to serve as an angiographic measurement ruler. For example, the distance 8141 can help an operator to measure the length of blood clots, the neck of an aneurysm, the length of a stenosis, etc.

FIG. 18K is a schematic front elevational view of the proximal portion 8100 of FIG. 18J. In FIG. 18K, the material of the filaments is indicated by shading: filaments with no shading include shape-memory material and filaments 8111, 8112, 8113 with hatched shading include radiopaque material. The example set up of radiopaque filaments 8111, 8112, 8113 illustrated in FIG. 18K can generate a pattern of radiopacity described in FIG. 18J, for example a three phase helix pattern, or a pattern in which the radiopaque filaments 8111, 8112, 8113 form three sine waves offset by about 120°.

FIG. 18L is a schematic side elevational view of still yet another example embodiment of a proximal portion 8200 of a vascular treatment device illustrating an example pattern of radiopaque filaments, for example under x-ray. The proximal portion 8200 may be the proximal portion 200 of the device 10, 20, 30, or 40. The proximal portion 8200 includes a textile structure including shape-memory filaments and radiopaque filaments. The proximal portion 8200 includes, in an expanded state, radiopaque filaments 8211, 8212, 8213 that are interlaced in the form a paired three phase helix at least under x-ray. The filament 8211 is reinforced with a second radiopaque filament and the proximal portion 8200 may include additional radiopaque filaments that are non-reinforced. The pattern of radiopacity can allow an operator of a device comprising the proximal portion 8200 to visualize identify the proximal portion 8200 at least under x-ray. In some embodiments, the paired three phase helix includes troughs and peaks, for example at the sides of the proximal portion 8200 that the paired three phase helix at least partially create. A paired three phase helix includes a pitch for each reinforced filament (e.g., a pitch 8221 for the sine wave created by the filaments 8211) and a pitch for each non-reinforced filament (e.g., a pitch 8222 for the sine wave created by the filament 8212, a pitch 8223 for the sine wave created by the filament 8213). In FIG. 18L, the intersection points along the paired triple helix are substantially uniformly spaced, which can allow the proximal portion 8200 to serve as an angiographic measurement ruler. For example, the distances between intersections can help an operator to measure the length of blood clots, the neck of an aneurysm, the length of a stenosis, etc.

FIG. 18M is a schematic front elevational view of the proximal portion 8200 of FIG. 18L. In FIG. 18M, the material of the filaments is indicated by shading: filaments with no shading include shape-memory material and filaments 8211, 8212, 8213 with hatched shading include radiopaque material. The example set up of radiopaque filaments 8211, 8212, 8213 illustrated in FIG. 18M, will generate a pattern of radiopacity described in FIG. 18L, for example a reinforced three phase helix, or a pattern in which the radiopaque filaments offset by about 120°, and the radiopaque filaments 8211 within the reinforced sine wave are offset by about 30°.

FIG. 18N is a schematic side elevational view of another example embodiment of a proximal portion 8400 of a vascular treatment device comprising a plurality of filaments 156 braided together with uniform braid angle and pore size. In some embodiments, the braid angle, the PPI, and the pore size may be uniform or variable across the length of the proximal portion 8400.

In some embodiments in which the proximal portion 200 comprises a plurality of filaments, radiopaque markers as described above with respect to a distal end of the distal portion 100 (e.g., dip-coated polymer with radiopaque particles) may be used instead of or in addition to a radiopaque marker band 25.

As discussed above, a knitted structure (e.g., comprising transverse wires) may be more rigid than a woven structure and more suitable for a proximal portion 200. In certain such embodiments, a woven or knitted proximal portion 200 and a woven distal portion 100 may comprise at least some of the same filaments, with at least one parameter (e.g., existence of transverse filaments, weave pattern, etc.) changing between the proximal portion 200 and the distal portion 100 and/or along the length of the proximal portion 200 (e.g., to longitudinally vary flexibility).

In some embodiments, the proximal portion 200 comprises a hybrid of a braided structure and a patterned hypotube. In certain such embodiments, the number of attachment points between different sections of the proximal portion is at least 1. In some embodiments, the length of a hypotube section of the proximal portion 200 is between about 0.1 cm and about 60 cm (e.g., between about 30 cm and about 60 cm) and the length of a braided section of the proximal portion 200 is between about 20 cm and about 209.9 cm (e.g., between about 150 cm and about 180 cm). In embodiments in which length of the hypotube section is between about 1 mm and about 10 mm, the hypotube section can act as a bridge between the distal portion 100 and the proximal portion 200. In certain such embodiments, the hypotube may be uncut, for example because the short length may provide adequate flexibility at that section.

In some embodiments, the proximal portion 200 comprises a cut tube as described herein, and the distal portion 100 comprises a device such as a vascular treatment device homogenously or integrally cut (e.g., from the same tube or sheet) or cut separately and then attached to the proximal portion 200.

FIG. 19A is a schematic diagram illustrating an example embodiment of variation of slits along the length of an example embodiment of a proximal portion 260. The schematic nature of FIG. 19A is apparent, for example, by the illustration of the slits as being incomplete (showing only one slit half) and having stems that are substantially aligned. The proximal portion 260 includes a first longitudinal section 262 including slits 263, a second longitudinal section 264 including slits 265, a third longitudinal section 266 including slits 267, and a fourth longitudinal section 268 including slits 269. In the first longitudinal section 262, the slits 263 are spaced apart by a distance $d_1$. In the second longitudinal section 264, the slits 265 are spaced apart by a distance $d_2$. In the third longitudinal section 266, the slits 267 are spaced apart by a distance $d_3$. In the fourth longitudinal section 268, the slits 269 are spaced apart by a distance $d_4$. The distance $d_4$ is greater than the distance $d_3$, which is greater than the distance $d_2$, which is greater than the distance $d_1$. The variation in the distances $d_1$, $d_2$, $d_3$, $d_4$ can affect the flexibility of the proximal portion 260, in which a shorter distance provides more flexibility and a longer distance provides less flexibility. The first longitudinal section 262 is more flexible than the second longitudinal section 264, which is more flexible than the third longitudinal section 266, which is more flexible than the fourth longitudinal section 266. Although some examples of the proximal portion 200 with 4 longitudinal sections are provided herein, some embodiments of the proximal portion 200 may include between about 1 longitudinal section and about 15 longitudinal sections, in accordance with the values provided above and/or proximal portion may include about 2 longitudinal sections to about 4 longitudinal sections, about 6 longitudinal sections to about 8 longitudinal sections, about 10 longitudinal sections to about 12 longitudinal sections, and about 13 longitudinal sections.

Referring again to FIGS. 2A, 2B, 3A, 3B, 4A, 4B, and 5D-5G, in some embodiments, a radiopaque marker band 25 is welded (e.g., butt welded, laser welded), bonded, and/or soldered to the distal end of the proximal portion 200. The marker band 25 can help distinguish the distal end of the proximal portion 200 and the proximal end of the distal portion 100 and/or to identify the joint 300. In some embodiments, a ring (e.g., comprising platinum and/or other radiopaque material) is welded (e.g., laser-welded) to the distal end of the proximal portion 200 using a plurality of rivets. For example, the ring may be welded using two rivets circumferentially spaced about 180° apart.

FIG. 19B is a schematic diagram illustrating an example embodiment of variation of slits and radiopaque markers along the length of an example embodiment of a proximal portion 8500 of a vascular treatment device. The proximal portion 8500 may be the proximal portion 200 of the device 10, 20, 30, or 40. In some embodiments, a radiopaque marker band is welded (e.g., butt welded, laser welded), bonded, and/or soldered to the proximal portion 200 at regular intervals, which may help to measure clot length (e.g., because the length of the distal portion 100 is known). In some embodiments, as illustrated in FIG. 19B, radiopaque material is attached (e.g., laser welded) like "rivets" into the slits 8535 of the proximal portion 8500 at regular intervals and interspersed with slits 8545 that are not filled with radiopaque material or rivets, which may help to measure clot length (e.g., because the length of the distal portion 100 is known) or to measure the degree or length of a stenosis in a vessel, or to measure the diameter of a vessel or to measure the dimensions of an aneurysm arising from a vessel for example, measuring the neck of the aneurysm for intra-operative decision making on device selection. Referring again to FIG. 19A, the distance between slits $d_4$ in the fourth longitudinal section 8540 of the proximal portion 8500 is greater than the distance $d_3$ in the third longitudinal section 8530 of the proximal portion 8500, which is greater than the distance $d_2$ in the second longitudinal section 8520 of the proximal portion 8500, which is greater than the distance $d_1$ in the first longitudinal section 8510 of the proximal portion 8500. Whether the regularly-spaced radiopaque material is a band or attached material, the radiopaque markers may be separated by distances of about 0.1 mm to about 50 mm, including, but not limited to, about 0.5 mm to about 1 mm, about 1 mm to about 2 mm, about 2 mm to about 3 mm, about 3 mm to about 4 mm, about 4 mm to about 5 mm, about 5 mm to about 8 mm, about 8 mm to about 10 mm, about 10 mm to about 12 mm, about 12 mm to about 15 mm, about 15 mm to about 25 mm, about 25 mm to about 35 mm, and about 35 mm to about 50 mm, including overlapping ranges thereof. In some embodiments, indicia (e.g., numbers, radiopaque material of different dimensions, etc.) may be used to provide further information about all or some of the markers. Although some examples of the proximal portion 8500 with 4 longitudinal sections are provided herein, some embodiments of the proximal portion 200 may include between about 1 longitudinal section and about 15 longitudinal sections, in accordance with the values provided above and/or proximal portion 200 may include about 2 longitudinal sections to about 4 longitudinal sections, about 6 longitudinal sections to about 8 longitudinal sections, about 10 longitudinal sections to about 12 longitudinal sections, and about 13 longitudinal sections.

In some embodiments, the tubular structure 202 is cold worked or has not been subjected to heat treatment. In some embodiments, the tubular structure 202 is straight annealed or undergoes heat treatment in a straight orientation, for example before or after patterning. Heat treating certain materials can impart shape memory such that the proximal portion 200 has a certain shape (e.g., straight, including curved sections, etc.) absent outside forces.

In some embodiments, the proximal portion 200 includes at least some super-elastic material that can, for example, return to a certain shape after bending due to stress-induced Martensite (SIM) without any particular change in temperature. Super-elastic materials can unbend (or, if the shape is curved, return to that curve) substantially instantaneously when forces causing the bend are removed (e.g., by advancement to different vasculature). In some embodiments, unbending of the proximal portion 200 is at least partially because the proximal portion 200 includes at least some shape memory material that can, for example, return to a certain shape after bending due to heat-activated austenitic transformation (e.g., upon a particular change in temperature such as greater than room temperature (about 25° C.), about body temperature (approx. 37° C.), etc.). Shape-memory materials can unbend slowly upon contact with warm fluid (e.g., blood at body temperature, warm saline).

In some embodiments, the shape memory effect can be one-way (e.g., a stress-induced change in shape returns to a baseline shape upon heating, while there is no further change upon cooling). The material remembers one shape with the one-way shape memory effect, the shape at high temperature. In some embodiments, the shape memory effect can be two-way (e.g., a stress-induced change in shape returns close to baseline shape upon heating, while a second shape can be achieved upon cooling). The material remembers two shapes with the two-way shape memory effect, a first shape at high temperature and a second shape at low temperature.

FIG. 19C is a schematic diagram illustrating still another example embodiment of a proximal portion 8600 of a vascular treatment device. The proximal portion 8600 may be the proximal portion 200 of the device 10, 20, 30, or 40. In some embodiments, different longitudinal sections of the proximal portion 8600 can include different materials and/or shape setting with different austenitic temperatures. For example, a distal section coupled to the proximal portion 8600 may be shape set to a straight configuration such that the distal section returns to a straight shape when not acted upon by vascular forces. For another example, each of the longitudinal sections 8610, 8620, 8630, 8640 can have a different shape set. In some embodiments, the distal-most sections 8610, 8620 of the proximal portion 8600 may be significantly martensitic, which can allow distal flexibility, and sections 8630, 8640 proximal thereto can be significantly austenitic namely, which can provide sturdiness and/or torquability. In some embodiments, at least about 25%, at least about 50%, or at least about 75% of the length of the proximal portion 8600 is martensitic. Although some examples of the proximal portion 8600 including 4 longitudinal sections are provided herein, some embodiments of the proximal portion 200 may include between about 1 longitudinal section and about 15 longitudinal sections, in accordance with the values provided above and/or proximal portion may include about 2 longitudinal sections to about 4 longitudinal sections, about 6 longitudinal sections to about 8 longitudinal sections, about 10 longitudinal sections to about 12 longitudinal sections, and about 13 longitudinal sections.

FIG. 19D is a schematic cut away side view of another example embodiment of heat treatment device 5401. In some embodiments, the heat treatment device 5401 may be similar to the heat treatment device 5400 described with respect to FIG. 10M. For example, the heat treatment device 5401 comprises a fluidized sand bath including a detachable flange 5405 as described herein. The device 5485 to be heat treated may comprise, for example, a proximal portion 200 of device 10, 20, 30 or 40. The heat treatment device 5401 comprises portion a reel-to-reel device or spiral dispenser 5490, 5495 configured to deploy the device 5485 into the fluidized sand bath 5401 to selectively heat treat each longitudinal section of the device 5485, for example in contrast to the devices 5435 in the basket 5470. Proximal portions 200 may also be heat treated in a basket 5470 and distal portions 100 may also be heat treated by being fed through the reel-to-reel device 5490, 5495.

FIG. 19E is a schematic partial cut away side view of a portion of the heat treatment device 5401 of FIG. 19D. In some embodiments, the material of the proximal portion 5485 (e.g., hypotube, textile structure, wire) is loaded into the reel-to-reel device 5490 and the free end of the proximal portion 5485 is passed through the hollow conduit 5475, exposes a longitudinal section loop inside the fluidized sand bath 5401, passes through the hollow conduit 5477, and is loaded into the reel-to-reel device 5495. In some embodiments, the reel-to-reel device 5490, 5495 can be rotated using a manual or automated approach such that the direction of motion of the reel-to-reel device 5490 is in the direction 5492 and the direction of motion of the reel-to-reel device 5495 is in the direction 5496. The reel-to-reel device 5490 includes a rotating handle or gear 5493 for rotating the reel-to-reel device 5490 in the direction 5492 either using a manual or automated approach. The reel-to-reel device 5495 includes a rotating handle or gear 5498 for rotating the reel-to-reel device 5495 in the direction 5498 either using a manual or automated approach.

In some embodiments, the detachable flange 5405 includes detachable air-sealant rivets 5480 on the outer surface of the flange 5405, on the inner surface of the flange 5405, or on the outside surface and the inside surface of the flange 5405. The reversible attachment points of the air-sealant rivets 5480 to the hollow conduits 5475, 5477 may include a luer lock mechanism, a ball and socket mechanism, a wire and hook mechanism, a c-shaped clasp and hook mechanism, combinations thereof, and the like. The detachable flange 5405 and the air-sealant rivets 5480 can mete longitudinal sections the device 5485 for heat treatment in the fluidized sand bath 5401 and can permit the safe removal of the device 5485 from the fluidized sand bath 5401, for example for placement in a cooling bath after heat treatment.

In some embodiments, the reel-to-reel device 5490, 5495 allows different longitudinal sections of the device 5485 to be shape set with different austenitic temperatures. For example, in some embodiments, the distal-most sections of a proximal portion 200 may be significantly martensitic, which can allow distal flexibility, and sections proximal thereto can be significantly austenitic, which can provide sturdiness and/or torquability. For another example, some sections of a proximal portion can be shape set to take a certain shape upon cooling (e.g., a straight shape in a water bath below room temperature).

FIG. 19F is a schematic diagram illustrating still yet another example embodiment of a proximal portion 8700 of a vascular treatment device, for example the proximal portion 200 of the device 10, 20, 30, or 40. The proximal portion 8700 comprises a wire 8715 and a hypotube 8705 that are fixably coupled at a joint 8710, for example as described with respect to the joints 300 herein. In some embodiments, the joint 8710 may be formed using processes such as laser welding the distal end of the microwire 8715 to the proximal end of the hypotube 8705, coupling the distal end of the microwire 8715 to the proximal end of the hypotube 8705 using a plurality of rivets, butt welding the distal end of the microwire 8715 to the proximal end of the hypotube 8705, centerless grinding of the distal end of the microwire 8715 such that the microwire 8715 can be inlayed into the inner lumen of the proximal end of the hypotube 8705 and then welded, etc. In some embodiments, the hypotube 8705 includes the distal end of the proximal portion 200 and the wire 8715 includes the proximal end of the proximal portion 200. In some embodiments, the length of the proximal portion 8700 may range from about 80 cm to about 210 cm, including the length of the hypotube 8705 ranging from about 0.1 cm to about 60 cm (e.g., about 30 cm, about 60 cm) and the length of the wire ranging from about 20 cm to about 209.9 cm (e.g., about 150 cm, about 180 cm). In some embodiments, the hypotube 8705 and the wire 8715 have an outer diameter between about 0.35 mm and about 0.65 mm (e.g., between about 0.4 mm and about 0.45 mm), between about 0.1 mm and about 0.5 mm (e.g., between about 0.25 mm and about 0.33 mm (e.g., about 0.0125 inches (approx. 0.318 mm))). In some embodiments, for example for use with peripheral vasculature, the hypotube 8705 and the wire 8715 have an outer diameter between about 0.5 mm and about 10 mm Substantially the entire length, portions, or none of the hypotube 8705 may be laser cut, for example with the interspersed kerf patterns described herein. A braided tubular structure may be substituted for some or all of the hypotube 8705.

FIG. 19F-2 is a schematic diagram illustrating another example embodiment of a proximal portion 8700 of a vascular treatment device as shown in FIG. 19F, for example the proximal portion 200 of the device 10, 20, 30, or 40. The proximal portion comprises a centerless ground microwire that has four segments from proximal to distal: Segment A 8708, Segment B 8704, Segment C 8703, and Segment D 8702. For example as described with respect to FIG. 19F, the proximal portion further comprises a hypotube (not shown) over and coupled to Segment D 8702 (e.g., Segment D 8702 being at least partially in the lumen of the hypotube). If the microwire fully extends through the hypotube, the proximal portion has a length that is the same as the length of the microwire. The distal portion 100 of the device may be coupled to the hypotube.

Segment A 8708 is tapered from a proximal outer diameter ranging between about 0.15 mm and about 0.3 mm (e.g., about 0.006" (approx. 0.15 mm), about 0.008" (approx. 0.2 mm), about 0.01" (approx. 0.25 mm), about 0.012" (approx. 0.3 mm), ranges between such values, etc.) to a distal outer diameter ranging between about 0.4 mm and about 0.5 mm (e.g., about 0.016" (approx. 0.41 mm), about 0.017" (approx. 0.43 mm), about 0.018" (approx. 0.46 mm), 0.019" (approx. 0.48 mm), ranges between such values, etc.). The tapering of Segment A 8708 may help the operator with ease of re-loading the introducer sheath over the microwire after a deployment and retrieval attempt. The length of Segment A 8708 ranges between about 20 mm and about 30 mm (e.g., about 0.8" (approx. 20 mm), about 0.85" (approx. 22 mm), about 1" (approx. 25 mm), about 1.15" (approx. 29 mm), about 1.2" (approx. 30 mm), ranges between such values, etc.).

Segment B 8704 is non-tapered or substantially cylindrical and has an outer diameter ranging between about 0.4 mm and about 0.5 mm (e.g., about 0.016" (approx. 0.41 mm), about 0.017" (approx. 0.43 mm), about 0.018" (approx. 0.46 mm), 0.019" (approx. 0.48 mm), ranges between such values, etc.). The length of Segment B 8704 ranges between about 1 m and about 1.1 m (e.g., about 1 m, about 1.01 m, about 1.02 m, about 1.03 m, about 1.04 m, about 1.05 m, about 1.06 m, about 1.08 m, about 1.1 m, ranges between such values, etc.). The non-tapered Segment B can provide proximal support during deployment and retrieval of the proximal portion. Segment B 8704 comprises a plurality of marker bands comprising a first plurality of oxide-free marker band segments 8707 interspersed between a second plurality of oxide coated marker band segments. Each segment 8707 and each oxide coated marker band segment has a length of about 1 cm for a total marker area length of about 7 cm (e.g., if three oxide-free marker band segments 8707 interspersed between four oxide coated maker band segments, which in some embodiments correlates to approximately the length of the distal portion of the vascular treatment device in the collapsed configuration, such that each marker band corresponds to one bulb of the distal portion of the vascular treatment device. The length of the centerless ground microwire from the distal end of the marker bands to the distal tip of the microwire (and thus the distal tip of the proximal portion) can be about 143 cm and along with the total length of the marker bands can be about 150 cm, which is the length of a standard microcatheter. Matching the length from the distal tip of the proximal portion to the length of a standard microwire can allow the operator to advance the proximal portion of the vascular treatment device through a standard microcatheter until the marker bands are proximate to the hub of the microcatheter without deploying the distal portion of the vascular treatment device. At that point, the distal end of the distal portion of the vascular treatment device would be generally proximate to the distal end of the microcatheter. As the standard microcatheter is then withdrawn in about 1 cm increments (about one marker band), approximately one bulb of the distal portion may be deployed out of the distal end of the microcatheter. If the standard microcatheter is withdrawn about 3 cm (about three marker bands, two oxide coated marker band segments and one oxide free marker band segment 8707), approximately three bulbs of the distal portion may be deployed out of the distal end of the microcatheter. In cases where x-ray image quality may be low, where the distal portion is not radiopaque or has limited radiopacity, where reduced x-ray may be desired (e.g., for health reasons, user preference), etc., this method can provide a low-risk deployment and retrieval system without fluoroscopy or with limited fluoroscopy (e.g., between guidewire retraction from the microcatheter and advancement of the treatment device proximate to the distal end of the microcatheter, it is possible to use no fluoroscopy). Such method still allows a customized length with selective deployment of bulbs based on clot length.

Segment C 8703 is tapered from a proximal outer diameter ranging between about 0.4 mm and about 0.5 mm (e.g., about 0.016" (approx. 0.41 mm), about 0.017" (approx. 0.43 mm), about 0.018" (approx. 0.46 mm), 0.019" (approx. 0.48 mm), ranges between such values, etc.) to a distal outer diameter ranging between about 0.15 mm and about 0.3 mm (e.g., about 0.006" (approx. 0.15 mm), about 0.008" (approx. 0.2 mm), about 0.01" (approx. 0.25 mm), about 0.012" (approx. 0.3 mm), ranges between such values, etc.). The tapering of Segment C 8703 may provide flexibility of the proximal portion during deployment and retrieval, for example because a smaller diameter of the same material is generally more flexible than a larger diameter. The length of Segment C 8703 ranges from between about 400 mm and about 500 mm (e.g., about 400 mm, about 425 mm, about 450 mm, about 460 mm, about 475 mm, about 500 mm, ranges between such values, etc.).

Segment D 8702 is tapered from a proximal outer diameter ranging between about 0.15 mm and about 0.3 mm (e.g., about 0.006" (approx. 0.15 mm), about 0.008" (approx. 0.2 mm), about 0.01" (approx. 0.25 mm), about 0.012" (approx. 0.3 mm), ranges between such values, etc.) to a distal outer diameter ranging between about 0.1 mm and about 0.15 mm (e.g., about 0.004" (approx. 0.1 mm), about 0.0045" (approx. 0.11 mm), about 0.005" (approx. 0.13 mm), about 0.006" (approx. 0.15 mm), ranges between such values, etc.). The tapering of Segment D 8702 allows Segment D to be inlayed into the inner lumen of the proximal end and/or substantially entire length of the hypotube, and then soldered, welded, etc. to the hypotube. The length of Segment D ranges between about 250 mm and 350 mm (e.g., about 250 mm, about 275 mm, about 300 mm, about 315 mm, about 325 mm, about 350 mm, ranges between such values, etc.). In embodiments in which the microwire is partially inlayed into the inner lumen of the hypotube, the length of the hypotube may be accounted for in the positioning of the marker bands so that the bulb deployment system described above can still be used.

In some embodiments, the hypotube 8705 and/or the wire 8715 may comprise shape memory material that is shape set differently (e.g., different austenitic temperature, different shape, etc.) over different longitudinal sections. In some embodiments, the hypotube 8705 and/or the wire may be uniformly super-elastic. In some embodiments, the hypotube 8705 and/or the wire may comprise non-shape memory material. In some embodiments, the hypotube 8705 and the wire 8715 may comprise the same material or different materials. Suitable materials for the hypotube 8705 and the wire 8715 may include, for example, platinum, titanium, nickel, chromium, cobalt, tantalum, tungsten, iron, manganese, molybdenum, and alloys thereof including nickel titanium (e.g., nitinol), nickel titanium niobium, chromium cobalt, copper aluminum nickel, iron manganese silicon, silver cadmium, gold cadmium, copper tin, copper zinc, copper zinc silicon, copper zinc aluminum, copper zinc tin, iron platinum, manganese copper, platinum alloys, cobalt nickel aluminum, cobalt nickel gallium, nickel iron gallium, titanium palladium, nickel manganese gallium, stainless steel, shape memory alloys, etc. Suitable materials for the hypotube 8705 and the wire 8715 may also include, for example, polymers such as polylactic acid (PLA), polyglycolic acid (PGA), poly lactic co-glycolic acid (PLGA), polycaprolactone (PCL), polyorthoesters, polyanhydrides, and copolymers thereof. Suitable materials may also include alloys (e.g., nitinol, chromium cobalt, platinum tungsten, etc.) and combinations of materials (e.g., filaments with a radiopaque core or cladding in combination with a cladding or core, respectively, of a different material, a plurality of filaments including different materials, etc.).

The proximal portion 200 can be coupled to a distal portion 200 at a joint 300, as described in further detail herein.

The distal portion 100 and the proximal portion 200 may be coupled at a joint 300. In some embodiments, the joint includes bonding material such as solder or epoxy. Solder may be easier to control during manufacturing processes than epoxy, for example because its flow properties are very temperature dependent. Use of solder rather than epoxy can allow a device comprising the joint 300 to be sterilized using gamma radiation, which could damage polymers such as epoxy and which is generally less expensive than chemical sterilization techniques such as ethylene oxide sterilization.

The proximal end of the distal portion 100 may be coupled within the distal end of the proximal portion 200 (e.g., filaments coupled to the inside of a hypotube) using inlay bonding. In some embodiments, inlay bonding does not increase the diameter or thickness beyond the diameter or thickness of the distal portion 100 or the proximal portion 200. In some embodiments, inlay bonding does not reduce the flexibility below the flexibility of the distal portion 100 or the distal section of the proximal portion 200. The proximal end of the distal portion 100 may be coupled outside the distal end of the proximal portion 200 (e.g., filaments coupled to the outside of a hypotube) using overlay bonding. A combination of inlay bonding and overlay bonding is also possible (e.g., some filaments coupled to the inside of a hypotube and some filaments coupled to the outside of the hypotube, or at least some filaments coupled to both the inside and outside of a hypotube). Inlay bonding may inhibit coupling material such as solder or epoxy from flaking off. In some embodiments comprising overlay bonding, a heat-shrink tube (e.g., comprising a heat shrink polymer such as PTFE or PVC) may reduce the risk of material flaking and may make the outer surface more uniform (e.g., compared to round filaments on a round hypotube), but could increase the outer diameter of the device and/or reduce the availability of gamma radiation sterilization.

FIG. 20A is a schematic diagram illustrating an example embodiment of a joint 3000 between a proximal portion 200 and a distal portion 100. The distal portion 100 includes a plurality of woven filaments and a proximal bulb 110 and the proximal portion 200 includes a tubular structure 202, a plurality of slits 204, and a radiopaque marker band 25, although other distal portions 100 and/or proximal portions 200 (e.g., as described herein) are also possible. FIG. 20B is a schematic cross-section of the joint of FIG. 20A along the line 20B-20B. FIG. 20A illustrates an example embodiment of an inlay bond including solder 302 at the joint 3000 between the distal portion 100 and the proximal portion 200. FIGS. 20D-20F schematically illustrate a method of coupling a braided tube to a hypotube.

In some embodiments using inlay bonding, a distal end (e.g., a flared distal end) of the proximal portion 200 may be mechanically crimped around the inlayed proximal end of the distal portion 100.

In some embodiments, the solder comprises a silver-based lead-free solder including about 96.5% tin and about 2.5% silver. The solder may comprise a eutectic solder having a solidus temperature $T_S$ that is substantially the same as the liquidus temperature $T_L$ at which the solder completely melts into a liquid ($T_S=T_L$), for example about 221° C. (approx. 430° F.) (e.g., Indalloy #121, available from Indium Corporation of Clinton, N.Y.). The eutectic silver-based lead-free solder is slowly melted at a rate of between about 1° C. and about 2° C. per second (e.g., for a duration of about 50 seconds) from about 171° C. up to the liquidus temperature $T_L$. Once the liquidus temperature $T_L$ has been reached, the rate of melting increases to between about 2.5° C. and about 3° C. per second (e.g., for a duration of about 20 seconds) from about 221° C. up to the peak melting temperature $T_m$, for example between about 246° C. and about 271° C. The duration of melting of the silver-based lead-free solder from the liquidus temperature $T_L$ to the peak melting temperature $T_m$ may be less than about 45 seconds. The liquid solder may be injected using a precision injector syringe, for example as described with respect to FIGS. 20A-20F. The molten solder is then rapidly cooled at a rate of less than about 4° C. per second (e.g., about 2° C. per second for a duration of about 50 seconds) from the peak melting temperature $T_m$ to the cooling temperature $T_c$, which may be about 171° C., resulting in a strong solder joint because of formation of a fine grain structure. A strong solder joint may be useful for procedures that can place strain on the solder joint, for example torsional rasping. Further cooling below the cooling temperature $T_c$ may be performed at a extremely rapid rate of greater than about 4° C. per second (e.g., about 5° C. per second for a duration of about 35 seconds). The rapid cooling may be performed using a water bath (e.g., at a temperature between about 20° C. and about 25° C.) for a duration of between about 30 seconds and about 120 seconds. The water bath may remove flux that was used in the soldering process. The tensile strength of a joint achievable with using silver-based lead-free solder is relatively high at about 5,800 psi (approx. 40,000 kPa). If the eutectic silver-based lead-free solder is rapidly melted at a rate of greater than about 2° C. per second (e.g., for a duration of less than 25 seconds) from about 171° C. up to the liquidus temperature $T_L$, then the solder joint strength may be compromised, for example due to formation of solder balls or beads. In some embodiments, if the soldering is attempted at a temperature below or above the peak melting temperature $T_m$ and/or if the duration of the melting of the silver-based lead-free solder from the liquidus temperature $T_L$ to the peak melting temperature $T_m$ is greater than about 45 seconds, then the solder joint strength may be compromised, for example due to formation of intermetallics.

In some embodiments, if the eutectic silver-based lead-free solder is extremely rapidly cooled at a rate of greater than about 4° C. per second (e.g., about 5° C. per second for a duration of about 20 seconds) from the peak melting temperature $T_m$ to the cooling temperature $T_c$, then the solder joint strength may be compromised, for example forming a joint having a tensile strength of less than about 2700 psi (approx. 18,600 kPa), for example due to formation of a coarse grain structure. Mechanical detachment can achieve shear strengths greater than 2700 psi (approx. 18,600 kPa), and may be useful in vascular treatment devices in which the distal portion 100 is desirably detachable from the proximal portion 200 at the region of joint 300, for example in flow diverters or flow disruptors as described herein.

In some embodiments, the solder comprises a gold-based lead-free solder including about 80% gold and about 20% tin. The solder may comprise a eutectic solder having a solidus temperature $T_S$ that is substantially the same as the liquidus temperature $T_L$ at which the solder completely melts into a liquid ($T_S=T_L$), for example about 280° C. (approx. 535° F.) (e.g., Indalloy #182, available from Indium Corporation of Clinton, N.Y.). The eutectic gold-based lead-free solder is slowly melted at a rate of between about 1° C. and about 2° C. per second (e.g., for a duration of about 50 seconds) from about 230° C. up to the liquidus temperature $T_L$. Once the liquidus temperature $T_L$ has been reached, the rate of melting increases to between about 2.5° C. and about 3° C. per second (e.g., for a duration of about 20 seconds) from about 280° C. up to the peak melting temperature $T_m$, for example between about 305° C. and about 330° C. The duration of melting of the gold-based lead-free solder from the liquidus temperature $T_L$ to the peak melting temperature $T_m$ may be less than about 45 seconds. The liquid solder may be injected using a precision injector syringe, for example as described with respect to FIGS. 20A-20F. The molten solder is then rapidly cooled at a rate of less than about 4° C. per second (e.g., about 2° C. per second for a duration of about 50 seconds) from the peak melting temperature $T_m$ to the cooling temperature $T_c$, which may be about 230° C., resulting in a strong solder joint because of formation of a fine grain structure. A strong solder joint may be useful for procedures that can place strain on the solder joint, for example torsional rasping. Further cooling below the cooling temperature $T_c$ may be performed at a extremely rapid rate of greater than about 4° C. per second (e.g., about 5° C. per second for a duration of about 35 seconds). The rapid cooling may be performed using a water bath (e.g., at a temperature between about 20° C. and about 25° C.) for a duration of between about 30 seconds and about 120 seconds. The water bath may remove flux that was used in the soldering process. The tensile strength of a joint achievable with using silver-based lead-free solder is relatively extremely high at about 40,000 psi (approx. 276,000 kPa). If the eutectic gold-based lead-free solder is rapidly melted at a rate of greater than about 2° C. per second (e.g., for a duration of less than 25 seconds) from about 230° C. up to the liquidus temperature $T_L$, then the solder joint strength may be compromised, for example due to formation of solder balls or beads. In some embodiments, if the soldering is attempted at a temperature below or above the peak melting temperature $T_m$ and/or if the duration of the melting of the gold-based lead-free solder from the liquidus temperature $T_L$ to the peak melting temperature $T_m$ is greater than about 45 seconds, then the solder joint strength may be compromised, for example due to formation of intermetallics.

In some embodiments, prior to coupling, the proximal end of the distal portion 100 and/or the distal end of the proximal portion 200 are treated to at least partially or completely remove oxide. For example, the distal end of the proximal portion 200 may be substantially burr-free and/or substantially oxide-free, and the proximal end of the distal portion 100 is etched (e.g., dipped in acid) to be substantially oxide-free.

In some embodiments, prior to soldering an alloy of nickel and titanium (e.g., nitinol) to nitinol or to a different material (e.g., stainless steel), flux (e.g., Indalloy Flux #3 or Indalloy Flux #2, both available from Indium Corporation of Clinton, N.Y.) can be used to reduce nickel and titanium surface oxides. Flux #3 has an activation temperature of between about 96° C. and about 343° C. and contains chlorides. Flux #2 has an activation temperature of between about 100° C. and about 371° C. and does not contain zinc or heavy metal chlorides. The appropriate flux can be applied using a brush, a swab, a spray, combinations thereof, and the like. After the soldering process, the flux residual can be removed by cooling and washing the solder joint in a water bath as described herein, by adding citric acid to the water bath, by a water sonication process, by mechanical scrubbing, combinations thereof, and the like.

In some embodiments in which the surface oxides of nickel and titanium cannot be adequately removed from the distal portion 100 using flux, soldering at the joint 300 can still be performed between the distal portion 100 and a proximal portion 200 comprising a different material (e.g., stainless steel) by soldering the radiopaque filaments within the distal portion 100 (e.g., comprising platinum tungsten, etc.) to the proximal portion 200 (e.g., comprising stainless steel). Increasing the number of radiopaque filaments in the distal portion 100 (e.g., to between about 25% and about 50% of the total number of filaments) can result in a strong solder joint, whereas decreasing the number of radiopaque filaments in the distal portion (e.g., to between about 5% and about 25% of the total number filaments) can result in a weak solder joint that may be useful in devices wherein the distal portion 100 of a vascular treatment device is desirably detachable from the proximal portion 200 at the region of joint 300, for example in flow diverters or flow disruptors as described herein.

In some embodiments in which filaments of the distal portion 100 and/or the proximal portion 200 comprises nickel (e.g., including nitinol strands), nickel oxide may be formed when the strands are heat treated in gas including oxygen such as ambient air. Nickel oxide can inhibit soldering of the distal portion 100 to the proximal portion 200, for example when the distal portion 100 and the proximal portion 200 comprise dissimilar materials. For example after soldering, a process for joining a distal portion 100 including oxidized nitinol filaments to a proximal portion 200 comprising a different material may include post-processing, polishing, and/or sandblasting, which could weaken the filaments. Non-oxidized filaments (e.g., by performing the heat treatment in an inert atmosphere such as argon or nitrogen) can generally be joined to dissimilar materials without such post-processing, polishing, and/or sandblasting. Filaments including other oxides (e.g., titanium oxide) may also be joined to dissimilar materials without such post-processing, polishing, and/or sandblasting.

Referring again to FIGS. 20A and 20D-20F, the proximal end of the distal portion 100 is inserted into the distal end of the proximal portion 200. In some embodiments, solder 302 and optionally flux are delivered from a delivery device 8810 (e.g., comprising a J-shaped tube 8815 that can be inserted through the distal-most slit 204 of the proximal portion 200) in the gap between the filaments of the distal portion 100 and the tubular structure 202 of the proximal portion 200 in a first position (e.g., as illustrated by the solder 8820 in FIG. 20E and the solder 302b in FIG. 20B), then the delivery device is rotated about 90°, then solder 302 and optionally flux are delivered in a second position (e.g., as illustrated by the solder 302c in FIG. 20B), then the delivery device is rotated about 90°, then solder 302 and optionally flux are delivered in a third position (e.g., as illustrated by the solder 8820 in FIG. 20F and the solder 302d in FIG. 20B), then the delivery device is rotated about 90°, then solder 302 and flux are delivered in a fourth position (e.g., as illustrated by the solder 302a in FIG. 20B), and then the delivery device 8810 is removed and the solder 302 allowed to cool. In some embodiments, solder 302 and optionally flux are delivered from a delivery device 8810 (e.g., comprising a J-shaped tube 8815 that can be inserted through the distal-most slit 204 of the proximal portion 200, for example to serve as a precision injector syringe) in the gap between the filaments of the distal portion 100 and the tubular structure 202 of the proximal portion 200 in a first position (e.g., as illustrated by the solder 8820 in FIG. 20E and the solder 302b in FIG. 20B), then the delivery device is rotated about 180°, then solder 302 and optionally flux are delivered in a second position (e.g., as illustrated by the solder 8820 in FIG. 20F and the solder 302d in FIG. 20B), then the delivery device is rotated about 90°, then solder 302 and optionally flux are delivered in a third position (e.g., as illustrated by the solder 302a in FIG. 20B), then the delivery device is rotated about 180°, then solder 302 and flux are delivered in a fourth position (e.g., as illustrated by the solder 302c in FIG. 20B), and then the delivery device 8810 is removed and the solder 302 allowed to cool. FIG. 20B shows solder 302a, 302b, 302c, 302d between the distal portion 100 and the proximal portion 200 and spaced about 90° apart, which may be formed for example by the methods described herein. The device may be tilted during soldering to inhibit the solder 302 from occluding the distal-most slit 204, which could reduce flexibility in an area where flexibility is generally desired.

Other solder amounts and positions are also possible. For example, the solder can be fully arcuate or in more or fewer positions (e.g., three positions about 120° apart, five positions about 72° apart, etc.), but embodiments such as illustrated in FIG. 20B may reduce manufacturing complexity (e.g., because about ¼ circumference or about 90° spacing can be an intuitive measurement). Substantially equal spacing can inhibit the formation of uneven strengths and stresses, which could, for example, break the joint 300 during use. Increasing the number of positions can reduce defects due to spacing error (e.g., the more positions, the less effect of any one inaccurate position), but increase the manufacturing complexity (e.g., using smaller angles, less solder per delivery, more precise spacing, etc.). The amount and placement of solder may affect strength (e.g., more solder generally increases strength, which may be beneficial to uses such as torsional rasping) and/or flexibility (e.g., more solder generally reduces flexibility, which may be disadvantageous for maneuverability). Embodiments including localized bonding agent 302 (e.g., as illustrated in FIGS. 20A and 20B) have been found to have good flexibility without compromising strength.

FIG. 20C is a schematic cross-section illustrating and example embodiment of filament 156 area in comparison to tubular structure 202 area. The filaments 156 of the distal portion 100 each have an area $\pi d_f^2/4$, where $d_f$ is the diameter of the filament 156. The inside of the proximal portion 200 has an area $\pi d_h^2/4$, where $d_h$ is the inner diameter of the tubular structure 202. The area of the inside of the tubular structure 202 not occupied by a filament 156 is approximately $\pi(d_h^2 - nd_f^2)/4$, where n is the number of filaments 156. For example, if the distal portion 100 comprises 48 filaments 156 each having a diameter of 0.001 inches (approx. 0.025 mm) and the proximal portion 200 comprises a tubular structure 202 having an inner diameter of 0.01 inches (approx. 0.25 mm), the area not occupied by a filament 156 is $\pi(0.25^2 - 48 \times 0.025^2)/4 = 0.026$ mm². The ratio of the area occupied by filaments 156 to the inner area of the tubular structure 202 is $nd_f^2/d_h^2$. For example, if the distal portion 100 comprises 48 filaments 156 each having a diameter of 0.001 inches (approx. 0.025 mm) and the proximal portion 200 comprises a tubular structure 202 having an inner diameter of 0.01 inches (approx. 0.25 mm), the ratio is $48 \times 0.025^2/0.25^2 = 0.48$ or 48%.

Using the length of the joint 3000 and the area available for filaments 156, a volume of bonding agent (e.g., the solder 302) may be determined. If bonding agent is only to be between the outside of the filaments 156 and the inside of the tubular structure 202, even less area is available, with the area of the proximal neck of the distal portion 100 subtracted. In some embodiments, between about 45% and about 60% (e.g., between about 51% and about 55%) of the cross-sectional area between the distal portion 100 and the proximal portion 200 is bonding agent. If the filaments 156 have different shapes and/or dimensions, the formulae can be appropriately adjusted.

FIG. 21A is a schematic diagram illustrating another example embodiment of a joint 3100 between a proximal portion 200 and a distal portion 100. The distal portion 100 includes a plurality of woven filaments 156 and a proximal bulb 110 and the proximal portion 200 includes a tubular structure 202 and a plurality of slits 204, although other distal portions 100 and/or proximal portions 200 (e.g., as described herein) are also possible. FIG. 21B is a schematic cross-section of the joint 3100 of FIG. 21A along the line 21B-21B. FIG. 21A illustrates an example embodiment of an inlay bond including epoxy 304 at the joint 3100 between the distal portion 100 and the proximal portion 200.

The proximal end of the distal portion 100 is inserted into the distal end of the proximal portion 200. In some embodiments, epoxy is delivered from a delivery device (e.g., a J-shaped tube inserted through the distal-most slit 204 of the proximal portion 200) in the gap between the filaments of the distal portion 100 and the tubular structure 202 of the proximal portion 200 in a first position, then the delivery device is rotated about 180°, then epoxy 304 is delivered in a second position, and then the delivery device is removed and the epoxy 304 allowed to dry. FIG. 21B shows epoxy 304a, 304b between the distal portion 100 and the proximal portion 200 and spaced about 180° apart and epoxy 304c between the filaments, as epoxy tends to flow. FIG. 21A also shows the epoxy 304 having flowed down around the proximal end of the distal portion 100. Excess epoxy 304 may optionally be removed using a bore or the like. FIG. 21C is a schematic side elevational view illustrating the inlay bonding approach of FIG. 21A.

FIG. 22A is a schematic diagram illustrating yet another example embodiment of a joint 3200 between a proximal portion 200 and a distal portion 100. The distal portion 100 includes a plurality of woven filaments and a proximal bulb 110 and the proximal portion 200 includes a tubular structure 202, a plurality of slits 204, and a radiopaque marker band 25, although other distal portions 100 and/or proximal portions 200 (e.g., as described herein) are also possible. FIG. 22B is a schematic cross-section of the joint 3200 of FIG. 22A along the line 22B-22B. FIG. 22A illustrates an example embodiment of an inlay bond including bonding material (e.g., solder (and optionally flux) or epoxy) 306 at the joint 3200 between the distal portion 100 and the proximal portion 200.

The filaments 156 at the proximal end of the distal portion 100 are inserted onto a sleeve or tube or pinch cylinder 308. The sleeve 308 may comprise metal (e.g., a portion of a hypotube (e.g., comprising stainless steel), platinum, titanium, nickel, chromium, cobalt, tantalum, tungsten, iron, manganese, molybdenum, alloys thereof (e.g., nitinol, chromium cobalt, stainless steel, etc.), and combinations thereof (e.g., cladding, banding, etc.)), polymer (e.g., a heat shrink tube), combinations thereof, and the like. In some embodiments, the sleeve 308 has a length between about 1 mm and about 5 mm In some embodiments, the sleeve 308 has a wall thickness or a difference between outer diameter and inner diameter between about 0.001 inches (approx. 0.025 mm) and about 0.002 inches (approx. 0.51 mm). In some embodiments, a metal sleeve 308 does not inhibit the use of gamma radiation sterilization. The filaments 156 may be pressure fit into the sleeve 308 or loosely inserted into the sleeve 308.

In some embodiments, the sleeve 308 is clamped after insertion of the filaments 156. In some of the embodiments, at least some of the filaments 156 may be welded (e.g., laser welded, laser butt welded, laser rivet welded, etc.) to the sleeve 308.

The proximal end of the distal portion 100, including the sleeve 308, is inserted into the distal end of the proximal portion 200. In some embodiments, bonding material 306 is delivered from a delivery device (e.g., a J-shaped tube inserted through the distal-most slit 204 of the proximal portion 200) in the gap between the sleeve 308 and the tubular structure 202 of the proximal portion 200 while rotating the delivery device, and then the delivery device is removed and the bonding material 306 is allowed to set. FIG. 22B shows bonding material 306 between the sleeve 308 and the tubular structure 202. The bonding material 306 is shown as being arcuate, but can be in generally discrete spots, for example as discussed above. The embodiment illustrated in FIGS. 22A and 22B has been found to have a strong bond, but somewhat limited flexibility.

Referring again to FIG. 22A, in some embodiments, the bonding material 306 is between the sleeve 308 and the tubular structure 202, and being between the filaments 156 and the sleeve 308 and/or between the filaments 156 and the tubular structure 202. Bonding material 306 at the distal end of the sleeve 308 can help secure the filaments 156 to the sleeve 308 and/or to each other.

In some embodiments in which the bonding material 306 comprises epoxy, some bonding material may be below the sleeve 308, as epoxy tends to flow. FIG. 22A also shows an example of some bonding material 306 having flowed down around the proximal end of the distal portion 100. Excess bonding material 306 may optionally be removed using a bore or the like. In some embodiments in which the bonding material 306 comprises solder, the device may be tilted during soldering to inhibit the solder 306 from occluding the distal-most slit 204, which could reduce flexibility in an area where flexibility is generally desired.

FIG. 23A is a schematic diagram illustrating still another example embodiment of a joint 3300 between a proximal portion 200 and a distal portion 100. The distal portion 100 includes a plurality of woven filaments 156 and a proximal bulb 110 and the proximal portion 200 includes a tubular structure 202, a plurality of slits 204, and a radiopaque marker band 25, although other distal portions 100 and/or proximal portions 200 (e.g., as described herein) are also possible. FIG. 23B is a schematic cross-section of the joint 3300 of FIG. 23A along the line 23B-23B. FIG. 23C is a schematic cross-section of the joint 3300 of FIG. 23A along the line 23C-23C. FIG. 23A illustrates an example embodiment of an inlay bond including bonding material (e.g., solder (and optionally flux) or epoxy) 310 at the joint 3300 between the distal portion 100 and the proximal portion 200.

The filaments 156 at the proximal end of the distal portion 100 are inserted onto a ring or pinch ring 312. The ring 312 may comprise metal (e.g., a portion of a hypotube (e.g., comprising stainless steel)), polymer (e.g., a heat shrink tube), combinations thereof, and the like. In some embodiments, a metal ring 312 does not inhibit the use of gamma radiation sterilization. The filaments 156 may be pressure fit into the ring 312 or loosely inserted into the ring 312. In some embodiments, the ring 312 is clamped after insertion of the filaments 156. In some of the embodiments, at least some of the filaments 156 may be welded (e.g., laser welded, laser butt welded, laser rivet welded, etc.) to the ring 312. The filaments 156 are radially outwardly frayed proximal to the proximal end of the ring 312, which can help to secure the filaments 156 in the ring 312.

The proximal end of the distal portion 100, including the ring 312 and the frayed proximal ends of the filaments 156, is inserted into the distal end of the proximal portion 200. In some embodiments, bonding material 310 is delivered from a delivery device (e.g., a J-shaped tube inserted through the distal-most slit 204 of the proximal portion 200) in the gap between the ring 312 and the tubular structure 202 of the proximal portion 200 while rotating the delivery device, and then the delivery device is removed and the bonding material 310 is allowed to set. FIG. 23B shows bonding material 310 between the ring 312 and the tubular structure 202. The bonding material 310 is shown as being arcuate, but can be in generally discrete spots, for example as discussed above. The embodiment illustrated in FIGS. 23A-23C has been found to be more flexible than the embodiment illustrated in FIGS. 22A and 22B, and the bond is nearly as strong, for example because the bond in the cross-sections illustrated in FIGS. 22B and 23B are substantially similar or identical.

Referring again to FIG. 23A, in some embodiments, the bonding material 310 is between the ring 312 and the tubular structure 202, and being between the filaments 156 and the ring 312 and/or between the filaments 156 and the tubular structure 202. Bonding material 310 at the proximal end and/or the distal end of the ring 312 can help secure the filaments 156 to the ring 312 and/or to each other.

In some embodiments in which the bonding material 310 comprises epoxy, some bonding material may be below the ring 312, as epoxy tends to flow. FIGS. 23A and 23C also shows an example of some bonding material 310 having flowed down around the proximal end of the distal portion 100. In FIG. 23C, the frayed ends of the filaments 156 are dispersed in the bonding material 310. Excess bonding material 310 may optionally be removed using a bore or the like. In some embodiments in which the bonding material 310 comprises solder, the device may be tilted during soldering to inhibit the solder 310 from occluding the distal-most slit 204, which could reduce flexibility in an area where flexibility is generally desired.

FIG. 24A is a schematic diagram illustrating another example embodiment of a joint 3400 between a proximal portion 200 and a distal portion 100. The distal portion 100 includes a plurality of woven filaments and a proximal bulb 110 and the proximal portion 200 includes a tubular structure 202 and a plurality of slits 204, although other distal portions 100 and/or proximal portions 200 (e.g., as described herein) are also possible. FIG. 24A illustrates an example embodiment of an overlay bond including bonding material 320 at the joint 3400 between the distal portion 100 and the proximal portion 200. The distal end of the proximal portion 200 is inserted into the proximal end of the distal portion 100. In some embodiments, the proximal neck of the distal portion 100 is wide enough to accept the distal end of the proximal portion 200, for example being tubular with a large enough diameter, including an outward proximal flare, etc. Adjusting the diameter of necks of the distal portion 100 can include, for example, using hypotube during a shape-setting process as described above. The distal end of the proximal portion 200 to which the distal portion 100 is bonded may be devoid of slots 204.

FIG. 24B is a schematic diagram illustrating yet another example embodiment of a joint 3500 between a proximal portion 200 and a distal portion 100. The distal portion 100 includes a plurality of woven filaments and the proximal portion 200 includes a tubular structure 202 and a plurality of slits 204, although other distal portions 100 and/or proximal portions 200 (e.g., as described herein) are also possible. FIG. 24B illustrates another example embodiment of an overlay bond including bonding material 320 at the joint 3400 between the distal portion 100 and the proximal portion 200. The distal end of the proximal portion 200 is inserted into the proximal end of the distal portion 100. In some embodiments, the proximal neck of the distal portion 100 is wide enough to accept the distal end of the proximal portion 200, for example being tubular with a large enough diameter, including an outward proximal flare, etc. Adjusting the diameter of necks of the distal portion 100 can include, for example, using hypotube during a shape-setting process as described above. The distal end of the proximal portion 200 to which the distal portion 100 is bonded may be devoid of slots 204.

In some embodiments, for example the embodiment illustrated in FIG. 24A and/or the embodiment illustrated in FIG. 24B, bonding material (e.g., solder and optionally flux, and/or epoxy) 320 is delivered from a delivery device in the gap between the filaments of the distal portion 100 and the tubular structure 202 of the proximal portion 200. The bonding material 320 can be fully arcuate, in one position, or in a plurality of positions. Overlay bonding can be at least partially through the filaments of the distal portion 100, so the control over the bonding material 320 may be greater than inlay bonding approaches. The amount and placement of bonding material 320 may affect strength (e.g., more bonding material 320 generally increases strength, which may be beneficial to uses such as torsional rasping) and/or flexibility (e.g., more bonding material 320 generally reduces flexibility, which may be disadvantageous for maneuverability).

FIG. 24C is a schematic diagram showing the joints 3400, 3500 of FIGS. 24A and 24B. The length of the joint 3400 is 322, the length of the joint 3500 is 324, and the difference between the length of the joint 3400 and the joint 3500 is 326. The length of a joint 300 may be at least partially based on the bonding material used. For example, solder may be stronger than epoxy such that less solder, and less length, is used. In some embodiments, the joint 3400 comprises solder and the joint 3500 comprises epoxy, and FIG. 24C provides a schematic comparison of the longer length used based on the weaker bond of epoxy. In some embodiments, the length of a joint 300 comprising solder is about 25% to about 50% less than the length of a joint 300 comprising epoxy (e.g., the length 322 is about 25% to about 50% less than the length 324 and/or the length 326 is about 25% to about 50% of the length 324). A shorter length of the joint 300 may increase flexibility, for example by reducing the areas of the device without flexibility-imparting slots 204 and/or flexible filaments.

FIG. 24D is a schematic diagram illustrating yet another example embodiment of a joint 3600 between a proximal portion 200 and a distal portion 100. The distal portion 100 includes a plurality of woven filaments and the proximal portion 200 includes a tubular structure 202 and a plurality of slits 204, although other distal portions 100 and/or proximal portions 200 (e.g., as described herein) are also possible. FIG. 24D illustrates yet another example embodiment of an overlay bond including bonding material 320 at the joint 3600 between the distal portion 100 and the proximal portion 200. The distal end of the proximal portion 200 is inserted into the proximal end of the distal portion 100. In some embodiments, the proximal neck of the distal portion 100 is wide enough to accept the distal end of the proximal portion 200, for example being tubular with a large enough diameter, including an outward proximal flare, etc.

Adjusting the diameter of necks of the distal portion 100 can include, for example, using hypotube during a shape-setting process as described above. The distal end of the proximal portion 200 to which the distal portion 100 is bonded may be devoid of slots 204.

In some embodiments, for example the embodiment illustrated in FIG. 24D, bonding material (e.g., solder and optionally flux, and/or epoxy) 320 is delivered from a delivery device in the gap between the filaments of the distal portion 100 and the tubular structure 202 of the proximal portion 200. The bonding material 320 can be fully arcuate, in one position, or in a plurality of positions. Overlay bonding can be at least partially through the filaments of the distal portion 100, so the control over the bonding material 320 may be greater than inlay bonding approaches. The amount and placement of bonding material 320 may affect strength (e.g., more bonding material 320 generally increases strength, which may be beneficial to uses such as torsional rasping) and/or flexibility (e.g., more bonding material 320 generally reduces flexibility, which may be disadvantageous for maneuverability).

The joint 3600 further comprises a sleeve 330. The sleeve 330 may comprise metal (e.g., a portion of a hypotube (e.g., comprising stainless steel)), polymer (e.g., a heat shrink tube (e.g., comprising PET, fluoropolymer (e.g., PTFE, Viton, polyvinylidene fluoride (PVDF), fluorinated ethylene propylene (FEP), etc.), silicone rubber, polyolefin (e.g., Iridium™, available from Cobalt Polymers of Cloverdale, Calif.), PVC, Pebax® (e.g., Palladium, available from Cobalt Polymers of Cloverdale, Calif.)), combinations thereof, and the like. In some embodiments, the sleeve 330 has a length between about 1 mm and about 5 mm In some embodiments, the sleeve 330 has a wall thickness or difference between inner diameter and outer diameter between about 0.00025 inches (approx. 0.006 mm) and about 0.00125 inches (approx. 0.03 mm) (e.g., about 0.0005 inches (approx. 0.013 mm), about 0.001 inches (approx. 0.025 mm)). In some embodiments, a metal sleeve 330 does not inhibit the use of gamma radiation sterilization. In some embodiments, the sleeve 330 is clamped after being placed around the proximal end of the distal portion 100. The sleeve 330 may inhibit bonding material 320 from flaking off and/or may make the outer diameter of the joint 3600 more uniform, but may increase the diameter of the device. In some embodiments, the sleeve 330 may be used without the bonding material 320.

FIG. 25A-1 is a schematic diagram illustrating an example embodiment of a mechanical detachment system 10550. FIG. 25A-2 is a schematic diagram illustrating an example embodiment of the components of the mechanical detachment system 10550 of FIG. 25A-1. The mechanical detachment system 10550 can be used, for example, to releasably couple a distal portion 100 (e.g., comprising a woven textile structure 158, which may include woven bulbs 110) to a proximal portion 200 (e.g., comprising a tubular member 202, which may include slits 204 and a radiopaque marker band 25). The detachment system 10550 comprises a wire 11730 comprising a plurality of ridges 11732, 11734, 11736, 11738, which may be in a horizontal or angled pattern, in an staggered interspersed pattern, combinations thereof, and the like (e.g., like the threads of a screw or the threads of a luer lock). The ridges 11732, 11734, 11736, 11738 may be laser cut (e.g., by removing material proximal and distal thereto). In some embodiments, the proximal end of the distal portion 100 comprising a woven textile structure having various braiding patterns, for example including one-over-one-under-one, one-over-one-under-two, one-over-two-under-two, two-over-one-under-one, two-over-one-under-two, three-over-one-under-one, three-over-one-under-two, three-over-one-under-three, three-over-two-under-one, three-over-two-under-two, three-over-three-under-one, three-over-three-under-two, three-over-three-under-three, two-over-two-under-one, two-over-two-under-two, etc. In the embodiment illustrated in FIG. 25A-2, the distal portion 100 has a one-over-one-under-one braiding pattern and variable pore sizes. The pores between the filaments 11705, 11710 create a groove 11702 into which the ridge 11732 can be mechanically forced, the pores between the filament 11710 and the upper filament 11715 create a groove 11704 into which the ridge 11734 can be mechanically forced, the pores between the lower filament 11715 and the filament 11720 create a groove 11706 into which the ridge 11736 can be mechanically forced, and the pores under the filament 11720 create a groove 11708 into which the ridge 11738 can be mechanically forced. During desired attachment, an operator rotates the wire 11730 (e.g., counterclockwise). As the wire 11730 unravels (e.g., unscrews from a luer lock), the ridges 11732, 11734, 11736, 11738 disengage or untangle from the grooves 11702, 11704, 11706, 11708, which can allow the distal portion 100 to exit the proximal portion 200.

In some embodiments, suitable materials for the wire 11730 may include, for example, platinum, titanium, nickel, chromium, cobalt, tantalum, tungsten, iron, manganese, molybdenum, and alloys thereof including nickel titanium (e.g., nitinol), nickel titanium niobium, chromium cobalt, copper aluminum nickel, iron manganese silicon, silver cadmium, gold cadmium, copper tin, copper zinc, copper zinc silicon, copper zinc aluminum, copper zinc tin, iron platinum, manganese copper, platinum alloys, cobalt nickel aluminum, cobalt nickel gallium, nickel iron gallium, titanium palladium, nickel manganese gallium, stainless steel, shape memory alloys, etc. Suitable materials may also include polymers such as polylactic acid (PLA), polyglycolic acid (PGA), poly lactic co-glycolic acid (PLGA), polycaprolactone (PCL), polyorthoesters, polyanhydrides, and copolymers thereof. Suitable materials may also include alloys (e.g., nitinol, chromium cobalt, platinum tungsten, etc.) and combinations of materials (e.g., filaments with a radiopaque core or cladding in combination with a cladding or core, respectively, of a different material, a plurality of filaments including different materials, etc.).

FIG. 25B is a schematic diagram of a partial cross-sectional view of an example embodiment of a mechanical detachment system 10600. The mechanical detachment system 10600 can be used, for example, to releasably couple a distal portion 100 (e.g., comprising a woven textile structure 158) to a proximal portion 200 (e.g., comprising a tubular member 202). The detachment system 10600 comprises a shape-memory wire 10555 formed into one or more shapes 10605 and optionally a coil 10610. The shape 10605 may include one or more of sphere, oblong, egg, oval, ellipse, spiral, twisted, figure-8, helical, triangle, rectangle, parallelogram, rhombus, square, diamond, pentagon, hexagon, heptagon, octagon, nonagon, decagon, quatrefoil, trapezoid, trapezium, other polygons, curvilinear or bulged versions of these and other shapes, combinations thereof, and the like. The wire 10555 is held by an operator or mechanically anchored to a structure proximal to the distal portion 100. When the detachment system 10700 is at a first temperature (e.g., about 25° C.), the shape 10605 engages or entangles intersections of the filaments of the distal portion 100 such that the proximal end of the distal portion is substantially stationarily positioned in the distal end of the proximal portion 200. When the detachment system 10600 is at a second temperature (e.g., about 37° C.), the shape 10605 begins to straighten due to the shape memory properties of the wire 10555, which has been heat treated to assume a non-shape (e.g., substantially linear) shape upon reaching $A_f$. As the shape 10605 transforms, the wire 10555 disengages or untangles from the intersections of the filaments of the distal portion 100, which can allow the distal portion 100 to exit the proximal portion 200. When the detachment system 10600 is at a first temperature (e.g., about 25° C.), the optional coil 10610 is in a coiled state (e.g., as shown in FIG. 25B). When the detachment system 10600 is at a second temperature (e.g., about 37° C.), the coil 10610 begins to straighten due to the shape memory properties of the wire 10555, which has been heat treated to assume a non-coiled (e.g., substantially linear) shape upon reaching $A_f$. As the coil 10610 straightens, the wire 10555 moves in the direction 10650, which can, for example, indicate to a user that the one-way shape memory properties are taking effect.

In some embodiments, the detachment system 10600 comprises a shape-memory wire 10555 formed into one or more shapes 10605 and optionally a coil 10610. The wire 10555 is held by an operator or mechanically anchored to a structure proximal to the distal portion 100. When the detachment system 10600 is at a first temperature (e.g., about 25° C.), the shape 10605 engages or entangles intersections of the filaments of the distal portion 100 such that the proximal end of the distal portion is stationarily positioned in the distal end of the proximal portion 200. When the detachment system 10600 is at a second temperature achieved upon contact with blood at body temperature (e.g., about 37° C.), the distal portion 100 further expands to an expanded configuration and the shape 10605 further expands and engages or entangles intersections of the filaments of the distal portion 100 such that the proximal end of the distal portion is substantially stationarily positioned in the distal end of the proximal portion 200. When the detachment system 10600 is at a third temperature achieved by hand injecting cold saline through the microcatheter or guide catheter (e.g., at about 18° C.), the shape 10605 begins to straighten due to the two-way shape memory properties of the wire 10555, which has been heat treated to assume a non-shape (e.g., substantially linear) shape upon reaching $A_f$ (e.g., between about 10° C. and about 18° C.). As the shape 10605 unravels, the wire 10555 disengages or untangles from the intersections of the filaments of the distal portion 100, which can allow the distal portion 100 to exit the proximal portion 200. When the detachment system 10600 is at a first temperature (e.g., about 25° C.), the optional coil 10610 is in a coiled state (e.g., as shown in FIG. 25C). When the detachment system 10600 is at a second temperature (e.g., about 37° C.), the optional coil 10610 is in a expanded coiled state (e.g., as shown in FIG. 25C). When the detachment system 10600 is at a third temperature (e.g., about 18° C.), the coil 10610 begins to straighten due to the shape memory properties of the wire 10555, which has been heat treated to assume a non-coiled (e.g., substantially linear) shape upon reaching $A_f$ (e.g., between about 10° C. and about 18° C.). As the coil 10610 straightens, the wire 10555 moves in the direction 10650, which can, for example, indicate to a user that the two-way shape memory properties are taking effect.

FIG. 25C is a schematic diagram of a partial cross-sectional view of another example embodiment of a mechanical detachment system 10700. The mechanical detachment system 10700 can be used, for example, to releasably couple a distal portion 100 (e.g., comprising a woven textile structure 158) to a proximal portion 200 (e.g., comprising a tubular member 202). The detachment system 10700 comprises a shape-memory wire 10557 formed into one or more balls 10615 and optionally a coil 10610. The wire 10557 is held by an operator or mechanically anchored to a structure proximal to the distal portion 100. When the detachment system 10700 is at a first temperature (e.g., about 25° C.), the ball 10615 engages or entangles intersections of the filaments of the distal portion 100 such that the proximal end of the distal portion is substantially stationarily positioned in the distal end of the proximal portion 200. When the detachment system 10700 is at a second temperature (e.g., about 37° C.), the ball 10615 begins to straighten due to the shape memory properties of the wire 10557, which has been heat treated to assume a non-ball (e.g., substantially linear) shape upon reaching $A_f$. As the ball 10615 unravels, the wire 10557 disengages or untangles from the intersections of the filaments of the distal portion 100, which can allow the distal portion 100 to exit the proximal portion 200. When the detachment system 10700 is at a first temperature (e.g., about 25° C.), the optional coil 10610 is in a coiled state (e.g., as shown in FIG. 25C). When the detachment system 10700 is at a second temperature (e.g., about 37° C.), the coil 10610 begins to straighten due to the shape memory properties of the wire 10557, which has been heat treated to assume a non-coiled (e.g., substantially linear) shape upon reaching $A_f$. As the coil 10610 straightens, the wire 10557 moves in the direction 10650, which can, for example, indicate to a user that the one-way shape memory properties are taking effect.

In some embodiments, the detachment system 10700 comprises a shape-memory wire 10557 formed into one or more shapes 10605 and optionally a coil 10610. The wire 10557 is held by an operator or mechanically anchored to a structure proximal to the distal portion 100. When the detachment system 10700 is at a first temperature (e.g., about 25° C.), the ball 10615 engages or entangles intersections of the filaments of the distal portion 100 such that the proximal end of the distal portion is stationarily positioned in the distal end of the proximal portion 200. When the detachment system 10700 is at a second temperature achieved upon contact with blood at body temperature (e.g., about 37° C.), the distal portion 100 further expands to an expanded configuration and the ball 10615 further expands and engages or entangles intersections of the filaments of the distal portion 100 such that the proximal end of the distal portion is substantially stationarily positioned in the distal end of the proximal portion 200. When the detachment system 10700 is at a third temperature achieved by hand injecting cold saline through the microcatheter or guide catheter (e.g., at about 18° C.), the ball 10615 begins to straighten due to the two-way shape memory properties of the wire 10557, which has been heat treated to assume a non-shape (e.g., substantially linear) shape upon reaching $A_f$ (e.g., between about 10° C. and about 18° C.). As the ball 10615 unravels, the wire 10557 disengages or untangles from the intersections of the filaments of the distal portion 100, which can allow the distal portion 100 to exit the proximal portion 200. When the detachment system 10700 is at a first temperature (e.g., about 25° C.), the optional coil 10610 is in a coiled state (e.g., as shown in FIG. 25C). When the detachment system 10700 is at a second temperature (e.g., about 37° C.), the optional coil 10610 is in a expanded coiled state (e.g., as shown in FIG. 25C). When the detachment system 10700 is at a third temperature (e.g., about 18° C.), the coil 10610 begins to straighten due to the shape memory properties of the wire 10557, which has been heat treated to assume a non-coiled (e.g., substantially linear) shape upon reaching $A_f$ (e.g., between about 10° C. and about 18° C.). As the coil 10610 straightens, the wire 10557 moves in the direction 10650, which can, for example, indicate to a user that the two-way shape memory properties are taking effect.

FIG. 25D is a schematic diagram of a partial cross-sectional view of yet another example embodiment of a mechanical detachment system 10800. The mechanical detachment system 10800 can be used, for example, to releasably couple a distal portion 100 (e.g., comprising a woven textile structure 158) to a proximal portion 200 (e.g., comprising a tubular member 202). The detachment system 10800 comprises parts of the distal portion 100 and the proximal portion 200. The distal end of the proximal portion 200 comprises slits 10815, 10818, recesses, radially outward dimples, combinations thereof, and the like. Parts 10805, 10810 of the proximal end of the distal portion 100 are mechanically forced into the slits 10815, 10818 of the proximal portion 200. As described above, the distal portion 100 may include shape-memory filaments configured to assume a shape upon reaching a certain temperature. When the detachment system 10800 is at a first temperature (e.g., about 25° C.), the parts 10805, 10810 of the distal portion 100 remain in the slits 10815, 10818 of the proximal portion 200. When the detachment system 10800 is at a second temperature (e.g., about 37° C.), the sections of the distal portion 100 comprising the parts 10805, 10810 begin to straighten due to the one-way shape memory properties of the distal portion 100, which has been heat treated to assume a non-mechanically forced (e.g., substantially cylindrical) shape upon reaching $A_f$. As the section of the distal portion 100 straightens, the parts 10805, 10810 move out of the slits 10815, 10818, which can allow the distal portion 100 to exit the proximal portion 200. Although some examples of the distal portion 100 are provided herein, some embodiments of the ends of the distal portion 100 may be mechanically forced into slits from inside-out or outside-in based on whether the embodiment refers to the distal portion 100 of device 10, 20, 30 or 40.

In some embodiments, the detachment system 10800 comprises parts of the distal portion 100 and the proximal portion 200 of a device 10, 20, 30 or 40 as described herein. The distal end of the proximal portion 200 comprises slits 10815, 10818, and may include recesses, radially outward dimples, combinations thereof, and the like. Parts 10805, 10810 of the proximal end of the distal portion 100 are mechanically forced into the slits 10815, 10818 of the proximal portion 200. As described above, the distal portion 100 may include shape-memory filaments configured to assume a shape upon reaching a certain temperature. When the detachment system 10800 is at a first temperature (e.g., about 25° C.), the parts 10805, 10810 of the distal portion 100 remain in the slits 10815, 10818 of the proximal portion 200. When the detachment system 10800 is at a second temperature achieved on contact with blood at body temperature (e.g., about 37° C.), the parts 10805, 10810 of the distal portion 100 further expand into the slits 10815, 10818 of the proximal portion 200. When the detachment system 10800 is at a third temperature achieved by hand injecting cold saline through a microcatheter or guide catheter (e.g., at about 18° C.), the sections of the distal portion 100 comprising the parts 10805, 10810 begin to straighten due to the two-way shape memory properties of the distal portion 100, which has been heat treated to assume a non-mechanically forced (e.g., substantially cylindrical) shape upon reaching $A_f$ (e.g., between about 10° C. and about 18° C.). As the section of the distal portion 100 straightens, the parts 10805, 10810 move out of the slits 10815, 10818, which can allow the distal portion 100 to exit the proximal portion 200.

Although some examples of the distal portion 100 are provided herein, some embodiments of the ends of the distal portion 100 may be mechanically forced into slits from inside-out or outside-in based on whether the embodiment refers to the distal portion 100 of device 10, 20, 30 or 40. Although some examples of the proximal portion 200 are provided herein, some embodiments of the ends of the proximal portion 200 of device 10, 20, 30 or 40 may include slits or recesses in horizontal or angled laser cut patterns, staggered interspersed patterns, laser cut patterns of different shapes including one of sphere, oblong, egg, oval, ellipse, spiral, twisted, figure-8, helical, triangle, rectangle, parallelogram, rhombus, square, diamond, pentagon, hexagon, heptagon, octagon, nonagon, decagon, quatrefoil, trapezoid, trapezium, other polygons, curvilinear or bulged versions of these and other shapes, combinations thereof, and the like.

FIG. 25E is a schematic diagram of a partial cross-sectional view of an example embodiment of a mechanical detachment system 10900. The mechanical detachment system 10900 can be used, for example, to releasably couple a distal portion 100 (e.g., comprising a woven textile structure 158) to a proximal portion 200 (e.g., comprising a tubular member 202). The detachment system 10900 comprises a shape-memory wire 10550 formed into a substantially linear shape or formed into one or more shapes 10625 and optionally a coil 10610. The shapes 10625 may include one of linear, sphere, oblong, egg, oval, ellipse, spiral, twisted, figure of 8 shape, helical, triangle, rectangle, parallelogram, rhombus, square, diamond, pentagon, hexagon, heptagon, octagon, nonagon, decagon, quatrefoil, trapezoid, trapezium, other polygons, curvilinear or bulged versions of these and other shapes, combinations thereof, and the like. The proximal end of the distal portion 100 is anchored to the wire 10550 by solder (for example, a eutectic silver-based lead-free solder). In some embodiments, if the eutectic silver-based lead-free solder is rapidly cooled at a rate of greater than about 4° C. per second (e.g., about 5° C. per second for a duration of about 20 seconds) from the peak melting temperature $T_m$, which is between about 246° C. and about 271° C., to the cooling temperature $T_c$, which is about 171° C., the joint strength is relatively weak, having a tensile strength of less than about 2700 psi (approx. 18,600 kPa), for example due to formation of a coarse grain structure. The wire 10550 is held by an operator or mechanically anchored to a structure proximal to the distal portion 100. At the time of detachment, the operator exerts a sheer strength on the wire 10550 greater than the tensile strength of the joint (e.g., greater than about 2700 psi (approx. 18,600 kPa)) to detach the distal portion 100 from the proximal portion 200. Such detachment may be useful, for example, in devices in which the distal portion 100 of a vascular treatment device is desirably detached from the proximal portion 200 at the region of joint 300, for example, in flow diverters or flow disruptors as described herein.

In some embodiments, suitable materials for the wire 10550 may include, for example, platinum, titanium, nickel, chromium, cobalt, tantalum, tungsten, iron, manganese, molybdenum, and alloys thereof including nickel titanium (e.g., nitinol), nickel titanium niobium, chromium cobalt, copper aluminum nickel, iron manganese silicon, silver cadmium, gold cadmium, copper tin, copper zinc, copper zinc silicon, copper zinc aluminum, copper zinc tin, iron platinum, manganese copper, platinum alloys, cobalt nickel aluminum, cobalt nickel gallium, nickel iron gallium, titanium palladium, nickel manganese gallium, stainless steel, shape memory alloys, etc. Suitable materials may also include polymers such as polylactic acid (PLA), polyglycolic acid (PGA), poly lactic co-glycolic acid (PLGA), polycaprolactone (PCL), polyorthoesters, polyanhydrides, and copolymers thereof. Suitable materials may also include alloys (e.g., nitinol, chromium cobalt, platinum tungsten, etc.) and combinations of materials (e.g., filaments with a radiopaque core or cladding in combination with a cladding or core, respectively, of a different material, a plurality of filaments including different materials, etc.).

FIG. 26A is a schematic diagram illustrating still another example embodiment of a joint 3700 between a proximal portion 200 and a distal portion 100. Such bonding can produce, for example, the device 20 schematically illustrated in FIG. 1B. In contrast to FIGS. 24A, 24B, and 24D, in which the joints 3400, 3500, 3600 include the proximal end of the distal portion 100 and the distal end of the proximal portion 200 (e.g., to produce the device 10 schematically illustrated in FIG. 1A), the joint 3700 includes the distal end of the distal portion 100 and the distal end of the proximal portion 200. The proximal portion 200 extends through the hollow area created by the woven filaments of the distal portion 100. The proximal portion 200 may still be characterized as proximal because the proximal portion continues to extend proximal to the distal portion 100. The joint 3700 may comprise the features of the joints 3400, 3500, 3600 (e.g., bonding material 320 and/or the sleeve 330).

In some embodiments, the distal ends of the filaments of the distal portion 100 may be configured to be positioned in the distal end of the proximal portion 100 (e.g., by curling radially inward). In certain such embodiments, the joint 3700 may comprise the features of the joints 3000, 3100, 3200, 3300 (e.g., bonding material, a compression sleeve, a compression ring, etc.).

In some embodiments, the proximal end of the distal portion 100 is not coupled to the proximal portion 200 (e.g., the proximal end of the distal portion 100 is free to move longitudinally along the proximal portion 200). In some embodiments, the proximal neck of the distal portion 100 is long (e.g., greater than about 5 mm) to inhibit unsheathing of the entire distal portion 100 during a procedure. In some embodiments, the proximal end of the distal portion 100 comprises a radiopaque marker band 1720, for example as described herein, which can warn against and/or help inhibit unsheathing of the entire distal portion 100 during a procedure.

In some embodiments, the proximal portion 200 of a device 20 is the same other the proximal portions 200 described herein. In some embodiments, the proximal portion 200 of a device 20 includes a longer distal-most segment to account for the length of the distal portion 100 (e.g., a 41 mm distal-most cut section of the proximal portion 200 may be about 101 mm).

The device 20 may be useful for hard clots, aged clots, and/or clots including embedded plaque, for example because the entire longitudinal length of the distal portion 100 is reinforced with the strength of the proximal portion 200 and/or because proximal portion 200 can provide more direct torsional rasping to the entire length of the distal portion 100 rather than the torque being diluted along the length of the distal portion 100 with distance from the proximal portion 200 in a device 10. The device 10 may be useful for acute clots and/or clots that are relatively new.

FIG. 26B is a schematic diagram illustrating yet still another example embodiment of a joint 3750 between a proximal portion 100 and a distal portion 200. Such bonding can produce, for example, the device 30 schematically illustrated in FIG. 1C. In contrast to FIGS. 24A, 24B, and 24D, in which the joints 3400, 3500, 3600 include the proximal end of the distal portion 100 and the distal end of the proximal portion 200 (e.g., to produce the device 10 schematically illustrated in FIG. 1A), the joint 3750 includes an intermediate part of the distal portion 100 and the distal end of the proximal portion 200. The proximal portion 200 extends through the hollow area created by the woven filaments of the distal portion 100 proximal to the joint 3750. The proximal portion 200 may still be characterized as proximal because the proximal portion continues to extend proximal to the distal portion 100. The distal portion 100 that is distal to the joint 3750 may be characterized as hollow (e.g., completely hollow). The joint 3750 may comprise the features of the joints 3400, 3500, 3600 (e.g., bonding material 320 and/or the sleeve 330) and other joints described herein.

In some embodiments, the proximal end of the distal portion 100 is not coupled to the proximal portion 200 (e.g., the proximal end of the distal portion 100 is free to move longitudinally along the proximal portion 200). In some embodiments, the proximal neck of the distal portion 100 is long (e.g., greater than about 5 mm) to inhibit unsheathing of the entire distal portion 100 during a procedure. In some embodiments, the proximal end of the distal portion 100 comprises a radiopaque marker band 1720, for example as described herein, which can warn against and/or help inhibit unsheathing of the entire distal portion 100 during a procedure. In some embodiments, the proximal portion 200 includes a longer distal-most segment to account for the length of the distal portion 100 through which the proximal portion 100 extends (e.g., a 41 mm distal-most cut section of the proximal portion 200 may be about 81 mm).

FIG. 26C is a schematic diagram illustrating another example embodiment of a joint 3775 between a proximal portion 100 and a distal portion 200. Such bonding can produce, for example, the device 40 schematically illustrated in FIG. 1D. In contrast to FIGS. 24A, 24B, and 24D, in which the joints 3400, 3500, 3600 include the proximal end of the distal portion 100 and the distal end of the proximal portion 200 (e.g., to produce the device 10 schematically illustrated in FIG. 1A), the joint 3750 includes the distal end of the distal portion 100 and an intermediate part of the proximal portion 200. The proximal portion 200 extends through the hollow area created by the woven filaments of the distal portion 100 and distal to the distal end of the distal portion 100. The proximal portion 200 may still be characterized as proximal because the proximal portion continues to extend proximal to the distal portion 100. The joint 3775 may comprise the features of the joints 3400, 3500, 3600 (e.g., bonding material 320 and/or the sleeve 330) and other joints described herein.

In some embodiments, the proximal end of the distal portion 100 is not coupled to the proximal portion 200 (e.g., the proximal end of the distal portion 100 is free to move longitudinally along the proximal portion 200). In some embodiments, the proximal neck of the distal portion 100 is long (e.g., greater than about 5 mm) to inhibit unsheathing of the entire distal portion 100 during a procedure. In some embodiments, the proximal end of the distal portion 100 comprises a radiopaque marker band 1720, for example as described herein, which can warn against and/or help inhibit unsheathing of the entire distal portion 100 during a procedure. In some embodiments, the proximal portion 200 includes a longer distal-most segment to account for the length of the distal portion 100 and the extension of the proximal portion 100 beyond the distal portion 200 (e.g., a 41 mm distal-most cut section of the proximal portion 200 may be about 141 mm).

In some embodiments, the distal portion 100 may be joined to the proximal portion 200 between the proximal end of the distal portion 100 and the distal end of the distal portion 100. For example, the joint 300 may be along the neck between the distal-most bulb and the next most distal bulb. Certain such embodiments can provide the benefits of the device 20 and a distal bulb that can provide embolic protection without a separate distal embolic protection device. For another example, the joint 300 may be in an intermediate portion of the distal portion 100, which can provide a smaller diameter in a distal section of the distal portion 100 (e.g., useful for traversing to smaller vessels), which can provide embolic filtering, and/or which can provide structural reinforcement in a proximal section of the distal portion 100.

After joining the distal portion 100 and the proximal portion 200, the entire distal portion 100 and about 50% of the proximal portion 100 may be placed within an introducer sheath. The introducer sheath maintains the distal portion 100 in the contracted or constrained position, and can inhibit the distal section of the proximal portion 200 that it surrounds from kinking. In some embodiments, the introducer sheath comprises a biomedical polymer, for example silicone, polyurethane (e.g., Polyslix, available from Duke Extrusion of Santa Cruz, Calif.), polyethylene (e.g., Rexell®, available from Huntsman) including low density polyethylene (LDPE), linear low density polyethylene (LLDPE), medium density polyethylene (MDPE), and high density polyethylene (HDPE), fluoropolymers such as fluorinated ethylene propylene, PFA, MFA, PVDF, THV, ETFE, PCTFE, ECTFE (e.g., Teflon® FEP, available from DuPont), polypropylene, polyesters including polyethylene terephthalate (PET), PBT, PETG (e.g., Hytrel®, available from DuPont), PTFE, combination polymer compounds such as thermoplastic polyurethanes and polyether block amides (e.g., Propell™ available from Foster Corporation of Putnam, Conn.), polyether block amides (e.g. Pebax®, available from Arkema of Colombes, France, PebaSlix, available from Duke Extrusion of Santa Cruz, Calif.), polyether soft blocks coupled with polyester hard blocks vinyls such as PVC, PVDC, polyimides (e.g., polyimides available from MicroLumen of Oldsmar, Fla.), polyamides (e.g., Durethan, available from Bayer, Nylon 12, available from Duke Extrusion of Santa Cruz, Calif.), polycarbonate (e.g., Corethane™, available from Corvita Corp. of Miami, Fla.), styrenics such as PS, SAN, ABS, and HIPS, acetals such as copolymers or homopolymers, high temperature performance polymers such as PEEK, PES, PPS, PSU, LCP, combinations thereof, and the like. The introducer sheath may have a tapered tip or a straight tip.

In some embodiments, a kit comprises a vascular treatment device at least partially within an introducer sheath. The vascular treatment device includes a distal portion 100 and a proximal portion 200. The distal portion 100 may be in a radially compressed state within the introducer sheath. The distal portion 100 and the proximal portion 200 are coupled at a joint 300. The joint may be reversible or non-reversible. The kit may further comprise tubing in a spiral pattern configured to contain the introducer sheath and/or a thrombus measurement guide (e.g., as illustrated in FIG. 27N). The thrombus measurement guide may be on a backing configured to hold the tubing in the spiral pattern in a plane. Multiple planes are possible for longer vascular treatment devices and/or dimensionally smaller kits.

In some embodiments, the introducer sheath has a length that is between about 10% and about 50% of the length of the proximal portion 200. In some embodiments, the introducer sheath has a length between about 30 cm and about 120 cm (e.g., about 30 cm, about 50 cm, about 75 cm, about 85 cm, about 95 cm, about 105 cm about 120 cm, ranges between such values, etc.). In some embodiments, the introducer sheath has an inner diameter between about 0.4 mm and about 0.5 mm (e.g., about 0.0165 inches (approx. 0.42 mm)). In some embodiments, the introducer sheath has an inner diameter between about 0.5 mm and about 0.6 mm (e.g., about 0.023 inches (approx. 0.58 mm)). In some embodiments, the introducer sheath has an outer diameter between about 0.5 mm and about 0.75 mm (e.g., about 0.024 inches (approx. 0.61 mm)). In some embodiments, the introducer sheath has an outer diameter between about 0.75 mm and about 1 mm (e.g., about 0.035 inches (approx. 0.89 mm)). In some embodiments, the introducer sheath has an inner diameter that is at least about 0.002 inches (approx. 0.05 mm) greater than the outer diameter of the proximal portion 200 and/or the distal portion 100 in the collapsed configuration, which can inhibit or prevent premature deployment of the distal portion 100 and/or allow easier advancing of the distal portion 100. In some embodiments, the introducer sheath has an inner diameter that is at least about 0.002 inches (approx. 0.05 mm) greater than the outer diameter of the proximal portion 200 and/or the distal portion 100 in the collapsed configuration, which can inhibit or prevent premature deployment of the distal portion 100 and/or allow easier advancing of the distal portion 100 in the collapsed configuration. In some embodiments, the introducer sheath has an inner diameter that is no greater about 0.002 inches (approx. 0.05 mm) greater than the inner diameter of the delivery catheter or microcatheter, which can allow smooth advancing of the distal portion 100 in the collapsed configuration from the introducer sheath to the microcatheter. In some embodiments, the introducer sheath has a wall thickness between about 0.002 inches (approx. 0.05 mm) and about 0.006 inches (approx. 0.15 mm), which can inhibit or prevent kinking of the introducer sheath and/or protect the distal portion 100.

The device (the distal portion 100 and the proximal portion 200) and the introducer sheath may be placed in a protective spiral loop to inhibit any portion of the device from kinking, and then sealed in a pouch (e.g., comprising high density polyethylene). The pouch and its contents may be sterilized by gamma radiation and/or chemical treatment (e.g., ethylene oxide gas), and then placed in a box for shipping.

In some embodiments, the box includes a length scale. After a procedure, a user can lay a clot next to the scale to measure the length of clot. Such a measurement can help verify that the length of the removed clot is at least as long as the length of the clot as measured prior to the removal procedure. If the length of the measure clot is less than expected, the user might check the aspiration syringe for additional clot. Certain process, such as torsional rasping described herein, can substantially maintain the length of the clot for accurate measurement, whereas other processes, for example in which a clot is macerated, eliminate the possibility of such measurement or cause the user to try to stack the various pieces of the removed clot, which can be inaccurate.

The devices 10, 20, 30, 40 described herein may be used for thrombectomy, for example according to the procedures described below, but can also be used as an embolic filter, for example during an angioplasty, aspiration, stenting, or other vascular procedure such as flow diversion or flow disruption (e.g., as described herein).

Prior to performing a thrombectomy procedure, a subject having a clot is identified. Subjects showing at least one of ten symptoms of stroke receive a computerized axial tomography (CAT) scan. The CAT scan shows if there is bleeding or no bleeding. If there is bleeding, then the area outside vasculature shows up as hyperdense or bright. If there is no bleeding, then the clot or blockage shows up as hyperdense or bright.

If there is a clot, the length of the clot can be measured, for example, by at least one of: (1) CAT scan print and scale or digital imaging measurement (PACS); (2) CAT scan angiogram where about 50 cm$^3$ to about 100 cm$^3$ of dye comprising iodine (e.g., iohexol, iodixanol, etc.) are injected into a forearm vein IV and pictures of neuro blood vessels are taken; (3) magnetic resonance imaging (MRI) angiogram where 20 cm$^3$ to about 40 cm$^3$ of gadolinium are injected into a forearm vein IV and picture are taken of neuro blood vessels, which can also provide images of the health of brain tissue; and (4) catheter angiogram, in which a guide catheter (e.g., having a length of about 80 cm to about 95 cm and an outer diameter of about 5 Fr to about 9 Fr (about 1.67 mm to about 3 mm)) is routed from a femoral artery to a carotid or vertebral artery, then dye comprising iodine (e.g., iohexol, iodixanol, etc.) is injected for direct imaging of the clot site, which is generally considered the most accurate of these four methods. Other measurement methods are also possible.

When using catheter angiogram for peripheral (e.g., leg) blockages, the guide catheter may be routed from the non-affected leg into the affected leg (e.g., contrafemoral access), which allows the puncture to be in the direction of the head so that blood flow can heal any dissection of the vessel. In some embodiments, the guide catheter of the catheter angiogram can be used for a treatment procedure, providing a general continuity between diagnosis and treatment.

Clots in neurovasculature are generally between about 5 mm and about 55 mm, although other clot lengths are also possible. Clots in peripheral (e.g., leg) vessels are generally between about 25 mm and about 90 mm, although other clot lengths are also possible.

After measurement, certain criteria can be used to determine whether a clot is a candidate for removal, such as the last time the patient was seen acting normal (e.g., removal candidate if less than 12 hours ago), the National Institutes of Health (NIH) stroke scale (e.g., removal candidate if greater than 10), imaging shows that a large vessel is blocked (e.g., removal candidate if large vessel blocked, which could affect many branch vessels), and/or imaging shows a small area of loss of tissue and/or a large area of tissue that can be salvaged. A clot that is a candidate for removal can then be removed.

The femoral artery can act as a percutaneous entry point. As described above with respect to the catheter angiogram, for removal of a neurovascular clot, either leg can be used because both point towards the head, and, for removal of a peripheral clot, the non-affected leg can be used. A guide catheter is partially inserted into the entry point. In some embodiments, the guide catheter may have a length between about 80 cm and about 95 cm, an inner diameter between about 5 Fr and about 9 Fr (between about 1.67 mm and about 3 mm), and an outer diameter between about 6 Fr and about 10 Fr (between about 2 mm and about 3.3 mm). A tapered dilator may extend about 1 inch to about 1.5 inches (approx. 2.5 cm to about 3.8 cm) out of the distal end of the guide catheter for easier navigation.

A first steerable guidewire (e.g., having a length between about 150 cm and about 180 cm) is inserted into the guide catheter and the dilator, extending some distance (e.g., about 2 inches (approx. 5 cm) out of the distal end of the dilator. The steerable guidewire can be advanced and steered for some distance, followed by advancement of the guide catheter and dilator over the guidewire. The guidewire and the guide catheter can be sequentially advanced until the desired point in the vasculature (e.g., the descending aorta). The dilator and guidewire are removed, but the guide catheter is left in place. The desired point of the vasculature where advancement ceases may be the point where further advancement of the dilator could perforate the vasculature.

A diagnostic catheter (e.g., having a length between about 100 cm and about 125 cm (e.g., about 10 cm to about 20 cm longer than the guide catheter)) having an outer diameter smaller than the inner diameter of the guide catheter (e.g., about 5 Fr (about 1.67 mm) when the guide catheter has an inner diameter of about 5 Fr and about 9 Fr (between about 1.67 mm and about 3 mm)) and an inner diameter that can accept a steerable guidewire (e.g., a guidewire having a diameter of about 0.035 inches (approx. 0.9 mm)) (e.g., between about 3 Fr (about 1 mm) and about 4 Fr (about 1.33 mm)) is then inserted into the guide catheter.

A second steerable guidewire (e.g., having a length between about 150 cm and about 180 cm), which may be the same as the first steerable guidewire or a different steerable guidewire, is inserted into the diagnostic catheter, extending some distance (e.g., about 2 inches (approx. 5 cm) out of the distal end of the diagnostic catheter. The steerable guidewire can be advanced and steered for some distance, followed by advancement of the diagnostic catheter over the guidewire. The guidewire and the diagnostic catheter can be sequentially advanced until the desired point in the vasculature (e.g., a carotid artery, a vertebral artery), which may be about three inches (e.g., about 7.6 cm) distal to the distal end of the guide catheter. The dilator and guidewire are removed, but the guide catheter is left in place. The guide catheter is then advanced over the diagnostic catheter to a desired position (e.g., slightly proximal to the distal end of the diagnostic catheter). The diagnostic catheter and guidewire are removed, but the guide catheter is again left in place. The guide catheter may remain in this location for substantially the remainder of the procedure.

FIG. 27A is a schematic diagram of a guide catheter 502 proximal to a thrombus (e.g., clot) 500 in vasculature (e.g., the thrombus 500 in the right middle cerebral artery and the guide catheter 502 in the right internal carotid artery), for example having been routed to that position as described above. The thrombus 500 may have been noted during angiography with the guide catheter 502 or another catheter (e.g., a shuttle or a balloon guide catheter), for example in the right internal carotid artery. A catheter angiogram may be performed using the guide catheter 502 after positioning the guide catheter 502.

In some embodiments, the guide catheter 502 may have a length between about 45 cm and about 125 cm, between about 45 cm and about 80 cm (e.g., about 55 cm) (e.g., for use in peripheral vasculature), between about 80 cm and about 100 cm (e.g., about 100 cm) (e.g., for use in coronary vasculature), between about 80 cm and about 125 cm (e.g., about 95 cm) (e.g., for use in neurovasculature). The guide catheter 502 may have a wall thickness between about 0.002 inches (approx. 0.05 mm) and about 0.04 inches (approx. 1 mm), which can allow for incorporating the proximal portion 200 within the walls of the guide catheter 502. The guide catheter 502 may comprise a biomedical polymer, for example silicone, polyurethane (e.g., Polyslix, available from Duke Extrusion of Santa Cruz, Calif.), polyethylene (e.g., Rexell®, available from Huntsman) including low density polyethylene (LDPE), linear low density polyethylene (LLDPE), medium density polyethylene (MDPE), and high density polyethylene (HDPE), fluoropolymers such as fluorinated ethylene propylene, PFA, MFA, PVDF, THV, ETFE, PCTFE, ECTFE (e.g., Teflon® FEP, available from DuPont), polypropylene, polyesters including polyethylene terephthalate (PET), PBT, PETG (e.g., Hytrel®, available from DuPont), PTFE, combination polymer compounds such as thermoplastic polyurethanes and polyether block amides (e.g., Propell™, available from Foster Corporation of Putnam, Conn.), polyether block amides (e.g. Pebax®, available from Arkema of Colombes, France, PebaSlix, available from Duke Extrusion of Santa Cruz, Calif.), polyether soft blocks coupled with polyester hard blocks vinyls such as PVC, PVDC, polyimides (e.g., polyimides available from MicroLumen of Oldsmar, Fla.), polyamides (e.g., Durethan, available from Bayer, Nylon 12, available from Duke Extrusion of Santa Cruz, Calif.), polycarbonate (e.g., Corethane™ available from Corvita Corp. of Miami, Fla.), styrenics such as PS, SAN, ABS, and HIPS, acetals such as copolymers or homopolymers, high temperature performance polymers such as PEEK, PES, PPS, PSU, LCP, combinations thereof, and the like.

The guide catheter 502 may comprise a hypotube (e.g., an uncut hypotube and/or a hypotube cut with a plurality of interspersed offset patterns as described herein) and/or a plurality of filaments (e.g., woven, knitted, spiraled, etc.) as reinforcement, for example in combination with a polymer inward and/or outward thereof. As described herein, certain cut patterns may inhibit pinching to such a degree that polymer may be omitted. In some embodiments, the guide catheter 502 may include a long sheath, a shuttle, and/or a balloon guide catheter.

In some embodiments, the guide catheter 502 comprises a hypotube including a cut patter, for example as described herein with respect to the proximal portion 200 and catheters comprising the proximal portion 200, for example to inherit the maneuverability advantages that may be provided by the proximal portion 200 (e.g., to facilitate proximal support and distal flexibility). In some embodiments, the guide catheter 502 comprises a parameter (e.g., slot pitch) that varies from proximal to distal. For example, the pitch between slots and/or windings of a spiral may vary, from the distal end to the proximal end, as follows: about 0.005 inches (approx. 0.13 mm), about 0.01 inches (approx. 0.25 mm), about 0.02 inches (approx. 0.51 mm), about 0.04 inches (approx. 1 mm), about 0.08 inches (approx. 2 mm), and about 0.16 inches (approx. 4 mm). For another example, the pitch between slots and/or windings of a spiral may vary, from the distal end to the proximal end, as follows: about 0.005 inches (approx. 0.13 mm) for the distal-most about 20%, about 0.01 inches (approx. 0.25 mm) for the next about 15%, about 0.02 inches (approx. 0.51 mm) for the next about 15%, about 0.04 inches (approx. 1 mm) for the next about 15%, about 0.08 inches (approx. 2 mm) for the next about 15%, and about 0.16 inches (approx. 4 mm) for the next (or proximal-most) about 20%.

The guide catheter 502 may comprise a radiopaque marker (e.g., a radiopaque marker band as described herein) at a distal end and/or at regular intervals (e.g., between about 0.1 mm and about 50 mm, between about 0.5 mm and about 1 mm, between about 1 mm and about 2 mm, between about 2 mm and about 3 mm, between about 3 mm and about 4 mm, between about 4 mm and about 5 mm, between about 5 mm and about 8 mm, between about 8 mm and about 10 mm, between about 10 mm and about 12 mm, between about 12 mm and about 15 mm, between about 15 mm and about 25 mm, between about 25 mm and about 35 mm, between about 35 mm and about 50 mm apart, including overlapping ranges thereof), which can help to visualize the guide catheter 502 and assist in measuring clot length or vessel diameter, or lesion length or by serving as a surrogate marker for a measurement tool.

FIG. 27B is a schematic diagram of a microwire 506 distal to a thrombus (e.g., clot) 500 in vasculature and a microcatheter 504 over the microwire 506. FIG. 27C is an expanded view of FIG. 27B in the area of the thrombus 500. A microcatheter 504 having an outer diameter smaller than the inner diameter of the guide catheter 502 and an inner diameter that can accept a steerable microwire 506 (e.g., a guidewire having a diameter of about 0.014 inches (approx. 0.36 mm)) (e.g., between about 0.0165 inches (approx. 0.42 mm) and about 0.017 inches (approx. 0.43 mm)) is then inserted into the guide catheter 502. Microcatheters used for other thrombectomy devices generally have in internal diameter of 0.021 inches (approx. 0.53 mm), although other inner diameters are also possible (e.g., about 0.014 inches (approx. 0.36 mm) about 0.017 inches (approx. 0.43 mm), about 0.027 inches (approx. 0.69 mm)). The microcatheter 504 may have a wall thickness between about 0.00075 inches (approx. 0.02 mm) and about 0.04 inches (approx. 1 mm), which can allow for incorporating the proximal portion 200 within the walls of the microcatheter 504. A smaller diameter microcatheter 504 can be easier and/or faster to route over a microwire 506, which can reduce procedure time. The microcatheter 504 may have a length between about 80 cm and about 210 cm, between about 80 cm and about 120 cm (e.g., for use in peripheral vasculature), between about 120 cm and about 150 cm (e.g., for use in coronary vasculature), between about 150 cm and about 210 cm (e.g., about 180 cm) (e.g., for use in neurovasculature).

The microcatheter 504 may comprise a biomedical polymer, for example silicone, polyurethane (e.g., Polyslix, available from Duke Extrusion of Santa Cruz, Calif.), polyethylene (e.g., Rexell®, available from Huntsman) including low density polyethylene (LDPE), linear low density polyethylene (LLDPE), medium density polyethylene (MDPE), and high density polyethylene (HDPE), fluoropolymers such as fluorinated ethylene propylene, PFA, MFA, PVDF, THV, ETFE, PCTFE, ECTFE (e.g., Teflon® FEP, available from DuPont), polypropylene, polyesters including polyethylene terephthalate (PET), PBT, PETG (e.g., Hytrel®, available from DuPont), PTI-B, combination polymer compounds such as thermoplastic polyurethanes and polyether block amides (e.g., Propell™, available from Foster Corporation of Putnam, Conn.), polyether block amides (e.g. Pebax®, available from Arkema of Colombes, France, PebaSlix, available from Duke Extrusion of Santa Cruz, Calif.), polyether soft blocks coupled with polyester hard blocks vinyls such as PVC, PVDC, polyimides (e.g., polyimides available from MicroLumen of Oldsmar, Fla.), polyamides (e.g., Durethan, available from Bayer, Nylon 12, available from Duke Extrusion of Santa Cruz, Calif.), polycarbonate (e.g., Corethane™, available from Corvita Corp. of Miami, Fla.), styrenics such as PS, SAN, ABS, and HIPS, acetals such as copolymers or homopolymers, high temperature performance polymers such as PEEK, PES, PPS, PSU, LCP, combinations thereof, and the like.

The microcatheter 504 may comprise a hypotube (e.g., an uncut hypotube and/or a hypotube cut with a plurality of interspersed offset patterns as described herein) and/or a plurality of filaments (e.g., woven, knitted, spiraled, etc.) as reinforcement, for example in combination with a polymer inward and/or outward thereof. As described herein, certain cut patterns may inhibit pinching to such a degree that polymer may be omitted.

The microcatheter 504 may comprise a radiopaque marker (e.g., a radiopaque marker band as described herein) at a distal end and/or at regular intervals (e.g., between about 0.1 mm and about 50 mm, between about 0.5 mm and about 1 mm, between about 1 mm and about 2 mm, between about 2 mm and about 3 mm, between about 3 mm and about 4 mm, between about 4 mm and about 5 mm, between about 5 mm and about 8 mm, between about 8 mm and about 10 mm, between about 10 mm and about 12 mm, between about 12 mm and about 15 mm, between about 15 mm and about 25 mm, between about 25 mm and about 35 mm, between about 35 mm and about 50 mm apart, including overlapping ranges thereof), which can help to visualize the microcatheter 504 and assist in measuring clot length by serving as a surrogate marker for a measurement tool.

A steerable microwire 506 (e.g., having an outer diameter of about 0.014 inches (approx. 0.36 mm) is inserted into the microcatheter 504, extending some distance (e.g., about 2 cm to about 4 cm) out of the distal end of the microcatheter 504. The microwire 506 can be advanced and steered for some distance, followed by advancement of the microcatheter 504 over the microwire 506. The microwire 506 and the microcatheter 504 can be sequentially advanced until the desired point in the vasculature (e.g., distal to the clot by about 0.5 mm to about 5 mm). FIG. 27D is a schematic diagram of a microcatheter 504 distal to a thrombus (e.g., clot) 500 in vasculature (e.g., the thrombus 500 in the right middle cerebral artery).

In some embodiments, the microwire 506 can cross the clot, for example by slicing through a middle part of the clot. If the clot is hard or is difficult for the microwire 506 to traverse, the microwire 506 may be used as a launching pad to guide advance the microcatheter 504 past the clot and the microwire 506. In certain such embodiments, the microcatheter 504 does not traverse the clot. In some embodiments, the microcatheter 504 may have a distal end configured to traverse hard clots (e.g., a generally rigid cylinder). In some embodiments, for example in which the lesion is calcified (e.g., heavily calcified), a thrombolytic and/or crossing device may aid the microwire 506 and/or microcatheter 504 across the clot.

FIG. 27D is a schematic diagram of a microcatheter 504 distal to a thrombus (e.g., clot) 500 in vasculature. Once the microcatheter 504 is distal to the thrombus 500, the microwire 506 is removed or retracted, and the microcatheter 504 is left in place, with the distal end of the microcatheter 504 distal to the distal end of the thrombus 500.

A dye comprising iodine (e.g., iohexol, iodixanol, etc.) can be injected into the microcatheter 504 and/or between the guide catheter and the microcatheter 504, for example to help to define the proximal and distal ends of the thrombus 500. The length and diameter of the thrombus 500 can be measured, from which the volume of the thrombus 500, or the clot burden, can be calculated.

In some systems using a microcatheter (e.g., a microcatheter having in internal diameter of 0.021 inches (approx. 0.53 mm)), a thrombectomy device, for example being laser cut for that purpose or an adapted laser-cut stent, having a set length is advanced to remove the clot piecemeal. For example, if the length of the thrombectomy device is 5 mm and the length of the clot is 15 mm, at least three removal procedures are needed. The thrombectomy device generally must be fully removed from the body to clear the captured clot piece, and removal of each clot piece can take up to about forty minutes. For clots in neurovasculature, about 1,900,000 brain cells die per minute. Thus, for a three-part removal process where each removal takes forty minutes, about 228,000,000 brain cells could die. If the diameter of the vasculature varies, or if one thrombectomy device is otherwise not suitable for removing each piece of the clot, multiple thrombectomy devices may be used, which can greatly increase the cost of the procedure. Users may sometimes opt to remove less than the full clot to reduce procedure time and/or the number of thrombectomy devices used, or in some cases may choose to not retrieve a clot at all due to knowledge that multiple removal iterations and/or thrombectomy devices will be needed. Such practices can produce unacceptable results for patients, doctors, and hospitals.

FIG. 27E is a schematic diagram illustrating an example embodiment of the distal portion 100 of a vascular treatment device being introduced into the hub 590 of a microcatheter 504 through an introducer sheath 540. Referring again to the devices 10, 20, 30, 40 described herein, the introducer sheath 540 is placed into a funnel-shaped proximal end 590 of the microcatheter 504, which is in the guide catheter 502. In some embodiments, the proximal end 590 of the microcatheter 504 is placed into the proximal end of a Y-connector 592 including a valve (e.g., a rotating hemostatic valve) to allow flushing (e.g., with saline) before, during, and/or after advancing the device 10, 20, 30, 40. The distal end of the Y-connector 592 may be attached to the proximal end of the guide catheter 502. The proximal portion 200 is pushed to advance the device 10, 20, 30, 40 through the microcatheter 504, with the distal portion 100 in the constrained state. The introducer sheath 540 can inhibit kinking of the proximal portion 200 during this insertion. The introducer sheath 540 can be retracted relative to the proximal portion 200 to unsheathe the proximal portion 200. In some embodiments, a radiopaque marker (e.g., the radiopaque marker bands 25, 1720 described herein) can be used to track the progress of the advancement of the device 10, 20, 30, 40 and/or portions thereof. For example, in some embodiments, the microcatheter 504 may include a radiopaque marker (e.g., marker band) at a distal tip, and the location of the radiopaque marker of the device 10, 20, 30, 40 can be compared thereto.

In some embodiments, the microcatheter 504 is reinforced with the proximal portion 200, for example to inherit the maneuverability advantages of the proximal portion 200 (e.g., to facilitate proximal support and distal flexibility). In some embodiments, the microcatheter 504 comprises a parameter (e.g., slot pitch) that varies from proximal to distal. For example, the pitch between slots and/or windings of a spiral may vary, from the distal end to the proximal end, as follows: about 0.005 inches (approx. 0.13 mm), about 0.01 inches (approx. 0.25 mm), about 0.02 inches (approx. 0.51 mm), about 0.04 inches (approx. 1 mm), about 0.08 inches (approx. 2 mm), and about 0.16 inches (approx. 4 mm). For another example, the pitch between slots and/or windings of a spiral may vary, from the distal end to the proximal end, as follows: about 0.005 inches (approx. 0.13 mm) for the distal-most 20%, about 0.01 inches (approx. 0.25 mm) for the next 15%, about 0.02 inches (approx. 0.51 mm) for the next 15%, about 0.04 inches (approx. 1 mm) for the next 15%, about 0.08 inches (approx. 2 mm) for the next 15%, and about 0.16 inches (approx. 4 mm) for the next (or proximal-most) 20%.

FIG. 27F is a schematic partial cross-sectional view of an example embodiment of a distal portion 100 of a vascular treatment device within an introducer sheath 540. The introducer sheath includes a tapered distal end 545 configured to mate with the funnel-shaped portion of the proximal end 590 of a microcatheter 504. When the distal portion 100 is within the introducer sheath 540, and when the distal portion 100 is within the microcatheter 504, the distal portion 100 is in a collapsed state (e.g., a tubular state without bulbs).

The device 10, 20, 30, 40 is advanced until the distal end of the distal portion 100 is proximate to the distal end of the microcatheter 504, which is distal to the distal end of the thrombus 500. The microcatheter 504 is then retracted (e.g., unsleeved, unsheathed) while holding the proximal portion 200 still so that the longitudinal position of the device 10, 20, 30, 40 is maintained. FIG. 27G is a schematic diagram of part of a distal portion 100 of a vascular treatment device 10, 20, 30, 40 being deployed distal to a thrombus (e.g., clot) 500 in vasculature. The retraction of the microcatheter 504 exposes the distal portion 100, from the distal end back, which allows the exposed sections of the distal portion 100 to self-expand. For example, the distal neck 65 and the distal-most bulb can expand.

In some embodiments, self-expansion of the exposed sections of the distal portion 100 at least partially because the distal portion 100 includes at least some super-elastic filaments that can, for example, self-expand due to stress-induced martensite (SIM) without any particular change in temperature. Super-elastic materials can expand substantially instantaneously from a collapsed configuration to an expanded configuration when the unsheathed. In some embodiments, self-expansion of the exposed sections of the distal portion 100 is at least partially because the distal portion 100 includes at least some shape memory filaments that can, for example, self-expand due to heat-activated austenitic transformation (e.g., upon a particular change in temperature such as greater than room temperature (about 25° C.), about body temperature (approx. 37° C.), etc.). Shape-memory materials can expand slowly from a collapsed configuration to an expanded configuration when unsheathed upon contact with warm fluid (e.g., blood at body temperature, warm saline).

In some embodiments, the shape memory effect of the shape memory filaments can be one-way (e.g., a stress-induced change in shape returns to a baseline shape upon heating, while there is no further change upon cooling). The material remembers one shape with the one-way shape memory effect, the shape at high temperature. In some embodiments, the shape memory effect of the shape memory filaments can be two-way (e.g., a stress-induced change in shape returns close to baseline shape upon heating, while a second shape can be achieved upon cooling). The material remembers two shapes with the two-way shape memory effect, a first shape at high temperature and a second shape at low temperature.

In some embodiments, the length of the retraction of the microcatheter 504, and the amount of the distal portion 100 exposed, can be related to the length of the thrombus 500, for example as measured as described above. For example, the microcatheter 504 can be retracted until a bulb is proximal to the proximal end of the thrombus 500.

The length of the distal portion 100 and/or number of bulbs that can be unsheathed to treat a thrombus (e.g., clot) 500 is customizable for each thrombus 500. For example, if using the distal portion 1100 described above to treat a 10 mm thrombus 500, the distal-most bulb 1112 could be deployed distal to the thrombus 500, then the next two bulbs 1112, then the distal bulb 1114 could be deployed proximal to the thrombus 500, while the other two bulbs 1114 and the bulbs 1116, 1118 remain in the microcatheter 504. For another example, if using the distal portion 1100 described above to treat a 40 mm thrombus 500, the distal-most bulb 1112 could be deployed distal to the thrombus 500, then the next five bulbs 1112, 1114, 1116, then the distal bulb 1118 could be deployed proximal to the thrombus 500, while the proximal-most bulb 1118 remains in the microcatheter 504. Such customizability can advantageously improve at least one of the drawbacks to treating clots 500 with other thrombectomy devices described above (e.g., treatment time, multiplied costs, user reluctance, etc.).

In some embodiments, if one bulb cannot fully entrap the thrombus (e.g., clot) 500, another bulb (whether the same or different in size and/or shape) and/or a plurality of bulbs can entrap the thrombus 500. In some embodiments, the undulations (e.g., the hills and valleys created by the bulbs and/or at the micro level by the braiding pattern) facilitate thrombus 500 entrapment. Undulating and/or dual undulation may enhance scraping of sidewalls and thrombus 500 entrapment. The thrombus 500, once entrapped or captured by the bulbs, can be removed as the thrombectomy device 10, 20, 30, 40 is removed from the subject. Particles that break off from the clot (e.g., emboli) can be captured by at least one bulb (including, but not limited to, the distal-most bulb(s)).

The procedures described herein are not limited to deploying parts of the distal portion 100 based on an initial thrombus (e.g., clot) size measurement. In some embodiments, the length of the thrombus 500 is not measured. In some embodiments, the number of bulbs deployed can help measure the length of the thrombus 500 as the procedure is occurring (e.g., using radiopaque markers, using radiopaque strand helix crossings, etc.).

As the distal portion 100 expands radially outwardly, some parts of the thrombus (e.g., clot) 500 are pushed towards the vessel sidewalls and some parts of the thrombus 500 are trapped between bulbs of the distal portion 100. Some parts of the thrombus 500 may also be trapped between filament crossings of the distal portion 100. FIG. 27H is a schematic diagram of a distal portion 100 of a vascular treatment device being deployed across a thrombus 500 in vasculature.

FIG. 27I-1 is a schematic diagram illustrating an example embodiment of the distal portion 100 of a vascular treatment device being used in conjunction with thrombus aspiration. In some embodiments, referring again to FIG. 27A, a distal access microcatheter 530 and a microcatheter 504 inserted inside the distal access microcatheter 530 may be advanced over a steerable microwire 506 and through a guide catheter 502 positioned proximal to the thrombus 500. A steerable microwire 506 (e.g., having an outer diameter of about 0.014 inches (approx. 0.36 mm) is inserted into the microcatheter 504, extending some distance (e.g., about 2 cm to about 4 cm) out of the distal end of the microcatheter 504. The microwire 506 can be advanced and steered for some distance, followed by advancement of the microcatheter 504 over the microwire 506, followed by advancement of the distal access microcatheter 530 over the microcatheter 504. The microwire 506, the microcatheter 504, and the distal access microcatheter 530 can be sequentially advanced until the desired point in the vasculature (e.g., distal to the clot or lesion by about 0.5 mm to about 5 mm for the microcatheter 504, and proximal to the clot or lesion by about 0.5 mm to about 15 cm for the distal access microcatheter 530). FIG. 27I-1 schematically shows the distal access microcatheter 530 proximal to a thrombus (e.g., clot) 500 in vasculature (e.g., in the right middle cerebral artery). The microcatheter 504 is also proximal to the thrombus 500 and the distal portion 100 of the device 10, 20, 30 or 40 has been deployed across the entire length of the thrombus 500.

The distal access microcatheter 530 may provide proximal support to the microcatheter 504 and/or for aspiration. In some embodiments, the distal end of the distal access microcatheter 530 includes a balloon, and the distal access microcatheter 530 may be used like a balloon guide catheter, for example to provide temporary flow arrest and/or as an adjunct device during thrombus aspiration. In some embodiments, the distal access microcatheter 530 may have a length between about 45 cm and about 150 cm, between about 45 cm and about 80 cm (e.g., about 75 cm) (e.g., for use in peripheral vasculature), between about 80 cm and about 100 cm (e.g., about 100 cm) (e.g., for use in coronary vasculature), between about 80 cm and about 150 cm (e.g., about 125 cm) (e.g., for use in neurovasculature). The distal access microcatheter 530 may have a wall thickness between about 0.00075 inches (approx. 0.02 mm) and about 0.04 inches (approx. 1 mm), which can allow for incorporating the proximal portion 200 within the walls of the distal access microcatheter 530. In some embodiments, the distal access microcatheter 530 may have an inner diameter between about 4 Fr (about 1.33 mm) and about 7 Fr (about 2.33 mm) for example, about 5 Fr (about 1.67 mm), and an outer diameter between about 5 Fr (about 1.67 mm) and about 9 Fr (about 3 mm) for example, about 6 Fr (about 2 mm).

The distal access microcatheter 530 may comprise a biomedical polymer, for example silicone, polyurethane (e.g., Polyslix, available from Duke Extrusion of Santa Cruz, Calif.), polyethylene (e.g., Rexell®, available from Huntsman) including low density polyethylene (LDPE), linear low density polyethylene (LLDPE), medium density polyethylene (MDPE), and high density polyethylene (HDPE), fluoropolymers such as fluorinated ethylene propylene, PFA, MFA, PVDF, THV, ETFE, PCTFE, ECTFE (e.g., Teflon® FEP, available from DuPont), polypropylene, polyesters including polyethylene terephthalate (PET), PBT, PETG (e.g., Hytrel®, available from DuPont), PTFE, combination polymer compounds such as thermoplastic polyurethanes and polyether block amides (e.g., Propell™, available from Foster Corporation of Putnam, Conn.), polyether block amides (e.g. Pebax®, available from Arkema of Colombes, France, PebaSlix, available from Duke Extrusion of Santa Cruz, Calif.), polyether soft blocks coupled with polyester hard blocks vinyls such as PVC, PVDC, polyimides (e.g., polyimides available from MicroLumen of Oldsmar, Fla.), polyamides (e.g., Durethan, available from Bayer, Nylon 12, available from Duke Extrusion of Santa Cruz, Calif.), polycarbonate (e.g., Corethane™, available from Corvita Corp. of Miami, Fla.), styrenics such as PS, SAN, ABS, and HIPS, acetals such as copolymers or homopolymers, high temperature performance polymers such as PEEK, PES, PPS, PSU, LCP, combinations thereof, and the like.

The distal access microcatheter 530 may comprise a hypotube (e.g., an uncut hypotube and/or a hypotube cut with a plurality of interspersed offset patterns as described herein) and/or a plurality of filaments (e.g., woven, knitted, spiraled, etc.) as reinforcement, for example in combination with a polymer inward and/or outward thereof. As described herein, certain cut patterns may inhibit pinching to such a degree that polymer may be omitted. In some embodiments, the distal access microcatheter 530 may provide an access device for proximal support and/or a thrombus aspiration device.

In some embodiments, the distal access microcatheter 530 is reinforced with the proximal portion 200, for example to inherit the maneuverability advantages of the proximal portion 200 (e.g., to facilitate proximal support and distal flexibility). In some embodiments, the distal access microcatheter 530 comprises a parameter (e.g., slot pitch) that varies from proximal to distal. For example, the pitch between slots and/or windings of a spiral may vary, from the distal end to the proximal end, as follows: about 0.005 inches (approx. 0.13 mm), about 0.01 inches (approx. 0.25 mm), about 0.02 inches (approx. 0.51 mm), about 0.04 inches (approx. 1 mm), about 0.08 inches (approx. 2 mm), and about 0.16 inches (approx. 4 mm). For another example, the pitch between slots and/or windings of a spiral may vary, from the distal end to the proximal end, as follows: about 0.005 inches (approx. 0.13 mm) for the distal-most about 20%, about 0.01 inches (approx. 0.25 mm) for the next about 15%, about 0.02 inches (approx. 0.51 mm) for the next about 15%, about 0.04 inches (approx. 1 mm) for the next about 15%, about 0.08 inches (approx. 2 mm) for the next about 15%, and about 0.16 inches (approx. 4 mm) for the next (or proximal-most) about 20%.

The distal access microcatheter 530 may comprise a radiopaque marker (e.g., a radiopaque marker band as described herein) at a distal end and/or at regular intervals (e.g., between about 0.1 mm and about 50 mm, between about 0.5 mm and about 1 mm, between about 1 mm and about 2 mm, between about 2 mm and about 3 mm, between about 3 mm and about 4 mm, between about 4 mm and about 5 mm, between about 5 mm and about 8 mm, between about 8 mm and about 10 mm, between about 10 mm and about 12 mm, between about 12 mm and about 15 mm, between about 15 mm and about 25 mm, between about 25 mm and about 35 mm, between about 35 mm and about 50 mm apart, including overlapping ranges thereof), which can help an operator of the distal access microcatheter 530 visualize the distal access microcatheter 530, which can assist in measuring clot length, vessel diameter, and/or lesion length, and/or which can serve as a surrogate marker for a measurement tool.

In some embodiments, thrombus aspiration may be performed through the microcatheter 504, the distal access microcatheter 530, and/or the guide catheter 502 depending on the extent of the clot burden. In some embodiments, thrombus aspiration may be performed through the catheter or microcatheter that is closest in proximity to the thrombus (e.g., clot) 500. In some embodiments, thrombus aspiration may be performed using flow arrest, wherein a balloon, such as part of a balloon guide catheter 502 or a balloon as part of a distal access microcatheter 530, is inflated proximal to the thrombus 500 and anterograde forward flow proximal to the thrombus 500 is temporarily stopped while thrombus aspiration is performed. In some embodiments, thrombus aspiration may be performed without any balloon inflation or temporary flow arrest.

In some embodiments, thrombus aspiration may be performed using manual negative intermittent suction (e.g., provided by a syringe) or using an automated negative suction device (e.g., provided by a vacuum pump). The suction device may be connected through suction tubing with a luer lock to the hub 590 of the microcatheter 504, the distal access microcatheter 530, and/or the guide catheter 502, or through a stop cock attached to the side port of a Y-connector 592 connected to the hub 590 of the microcatheter 504, the distal access microcatheter 530, the guide catheter 502, and/or a balloon guide catheter 502. The suction tubing may have a length that ranges from about 15 cm to about 150 cm (e.g., about 90 cm). The suction tubing may comprise a biomedical polymer, for example those described herein.

If the inner lumen of the microcatheter 504 or guide catheter 502 is substantially uniform, then the cross sectional area of the microcatheter 504 or guide catheter 502 can be considered a cylinder having a substantially uniform cross-sectional area $k=\pi r^2$ and a volume $V=\pi r^2 L$. The volume of dead space within the lumen of the microcatheter 504 or the guide catheter 502 prior to starting suction may be considered to be a cylinder ($V_0=\pi r^2 L_0$) with an initial suction pressure $P_0$. The volume of the dead space within the lumen of the microcatheter 504 or the guide catheter 502 after suction may also be considered to be a cylinder ($V_1=\pi r^2 L_1$) with a suction pressure $P_1$. If the suction process is considered an isothermal process, then the suction pressure can be calculated using Equations 6-8:

$$P_0 V_0 = P_1 V_1 \quad (\text{Eq. 6})$$

$$P_0 k_0 L_0 = P_1 k_1 L_1 \quad (\text{Eq. 7})$$

$$P_0 r_0^2 L_0 = P_1 r_1^2 L_1 \quad (\text{Eq. 8})$$

If the inner lumen of the microcatheter 504 or the guide catheter 502 is substantially uniform, then the amount of negative suction pressure is directly proportional to the length of the negative suction column within the microcatheter 504 or the guide catheter 502. The change in suction pressure ($\Delta P$) can be calculated using Equation 9:

$$\Delta P \alpha \Delta L \quad (\text{Eq. 9})$$

If the inner lumen diameter or cross sectional area of a catheter is substantially uniform, then an increase in catheter length increases pressure to achieve desired suction. Higher suction pressures for thrombus aspiration in substantially uniform catheters can have clinical implications, such as: (1) higher suction pressures can result in collapse of blood vessel walls; (2) higher suction pressures can result in collapse or kinking of polymeric microcatheters or catheters; and/or (3) higher suction pressures can have safety implications on the endothelial inner wall of the blood vessels and increase the risk of vessel injury, partial or complete vessel tears, and/or vessel rupture.

The cross sectional area of the distal access microcatheter 530, the microcatheter 504, or the guide catheter 502 may not substantially uniform across the inner lumen (e.g., having a tapered configuration schematically similar to the inlet device 10300 illustrated in FIG. 17N). Referring again to FIG. 17N, in some embodiments, the microcatheter 504, the distal access microcatheter 530, or the guide catheter 502 may include a gradual tapering of the inner lumen diameters or cross sectional areas from proximal to distal, for example as described with respect to the tubes 10305, 10310, 10315, 10320, in which the smaller diameter tubing 10305 would be at the distal end proximate to the thrombus (e.g., clot) 500, and the larger diameter tubing 10320 would be at the proximal end connected to the suction device. The direction of flow of blood during thrombus aspiration would be in the direction opposite to the arrows illustrated in FIG. 17N such that the thrombus 500 is aspirated from the distal end towards the proximal end of the distal access microcatheter 530, the distal end of the microcatheter 504, or the guide catheter 502.

Still with reference to FIG. 17N, a proximal segment 10320 of the microcatheter 504, the distal access microcatheter 530, or the guide catheter 502 may be at an adjustable height $h_4$, has a pressure $P_4$, and has a fluid velocity $v_4$. Blood entering the proximal portion 200 at a distal segment 10305 of the microcatheter 504, the distal access microcatheter 530, or the guide catheter 502 is at a height $h_1$, has a pressure $P_1$, and has a fluid velocity $v_1$. As the sum of the kinetic energy per unit volume ($\frac{1}{2}\rho_b v^2$), the potential energy per unit volume ($\rho_b gh$), and the pressure energy (P) remain the same, the density of the blood $\rho_b$ and the acceleration due to gravity g (9.8 m/second$^2$) remain constant, the fluid velocity $v_4$ entering the proximal portion 200 at the distal end of the microcatheter 504, the distal access microcatheter 530, or the guide catheter 502 can be calculated using Equation 10:

$$\tfrac{1}{2}\rho v_1^2 + \rho b g h_1 + P_1 = \tfrac{1}{2}\rho b v_4^2 + \rho b g h_4 + P_4$$

$$\text{or, rearranged, } v_4 = \sqrt{[v_1^2 + 1960(h_1-h_4) + 2(P_1-P_4)/\rho b]}. \quad (\text{Eq. 10})$$

Since there is no fluid velocity at the distal end of the microcatheter 504, the distal access microcatheter 530, or the guide catheter 502 prior to suction being initiated ($v_1=0$) and the height of the proximal and distal ends of the microcatheter 504, the distal access microcatheter 530, or the guide catheter 502 ($h_1=h_4$), Equation 10 may be reduced to Equation 11, or simplified by the relationship of Equation 12:

$$(P_1-P_4) = \tfrac{1}{2}\rho b v_4^2 \quad (\text{Eq. 11})$$

$$\text{or, rearranged, } v_4 = \sqrt{[2(P_1-P_4)/\rho b]}$$

$$\Delta P \alpha v_4^2 \quad (\text{Eq. 12})$$

In some embodiments, whenever the inner lumen diameter or cross sectional area is not substantially uniform (e.g., is tapered), then a change in suction pressure can result in a change in the square of the velocity of blood, which can result in desired thrombus aspiration. Limited suction pressures for thrombus aspiration in microcatheters or catheters with tapered inner lumens or cross sectional areas can have clinical implications: such as: (1) limited suction pressures can inhibit collapse of blood vessel walls; (2) limited suction pressures and/or presence of a laser cut hypotube for reinforcement can inhibit collapse or kinking of polymeric microcatheters or catheters; and/or (3) limited suction pressures may have a gentle effect on the endothelial inner wall of the blood vessels and reduce the risk of vessel injury.

In some embodiments, suction during thrombus aspiration through a syringe may not be substantially uniform, but can have a "crescendo suction" pattern. FIG. 27I-2 is a table schematically illustrating example embodiments of crescendo suction patterns 11800, 11805, 11810, 11815, 11820 for aspiration (e.g., thrombus aspiration). Cycles of crescendo suction patterns 11800, 11805, 11810, 11815, 11820 may comprise variable intensities of negative suction in a crescendo pattern such as a small intensity negative suction pressure (S), a medium intensity negative suction pressure (M), large intensity negative suction pressure (L), and pauses or temporary stops to the negative suction pressure, which are represented by a dot or period (.) in FIG. 27I-2. The crescendo suction pattern 11800 comprises a small intensity negative suction pressure (S) followed by a pause (.), which is repeated three more times (S.S.S.S.), then the pattern 11800 comprises a medium intensity negative suction pressure (M) followed by a pause (.), which is repeated three more times (M.M.M.M.), then the pattern 11800 comprises a large intensity negative suction pressure (L)

followed by a pause (.), which is repeated three more times (L.L.L.L.). In some embodiments of thrombus aspiration, the crescendo suction pattern may include the following components, combinations thereof, and the like: the crescendo suction pattern 11805 (SML.SML.SML.); the crescendo suction pattern 11810 (S.M.L.S.M.L); the crescendo suction pattern 11815 (S.L.S.L.S.L.); and/or the crescendo suction pattern 11820 (S.L.M.L.S.L.M.L.). The third column graphically illustrates the patterns 11800, 11805, 11810, 11815, 11820 with the x-axis being time and the y-axis being intensity of negative suction pressure. The crescendo suction patterns 11800, 11805, 11810, 11815, 11820 may be useful in different clinical scenarios. For example, the crescendo suction pattern 11810, which includes several pauses or temporary stops, may be useful in thrombus aspiration of hard clots, for example because the gradual increase in intensity of negative suction pressure with frequent pauses can assist agitation of the clot and/or facilitate thrombus aspiration. For another example, the crescendo suction pattern 11805, which includes few pauses or temporary stops, may be useful in thrombus aspiration of soft clots, for example because the gradual increase in intensity of negative suction pressure with few pauses can assist with suction of the soft clot and/or facilitate thrombus aspiration.

In some embodiments, the duration of the components of a crescendo suction pattern 11800, 11805, 11810, 11815, 11820 during thrombus aspiration may vary as follows: the duration of the small intensity negative suction (S) ranges between about 1 second to about 30 seconds (e.g., about 5 seconds); the duration of the medium intensity negative suction (M) ranges between about 1 second to about 30 seconds (e.g., about 5 seconds); the duration of the large intensity negative suction (L) ranges between about 1 second to about 30 seconds (e.g., about 5 seconds); and the pauses or temporary stops ranges between the duration of the small intensity negative suction (S) ranges between about 1 second to about 15 seconds (e.g., about 5 seconds). The total duration of crescendo suction pattern including multiple repetitive cycles of patterns may range from between about 1 minute to about 15 minutes (e.g., about 5 minutes). Although some example durations are provided herein, some embodiments of the crescendo suction patterns 11800, 11805, 11810, 11815, 11820 may include durations of the patterns in accordance with the values provided above and/or durations that are about ±5%, about ±10%, about ±15%, or about ±20% of any such values and combinations thereof, and the like. The crescendo suction patterns 11800, 11805, 11810, 11815, 11820 may be considered to be uniform if the durations of each of the components of the crescendo suction pattern are substantially similar, or may be considered variable if the durations of at least one (e.g., some or all) of the components of the crescendo suction pattern are different.

In some embodiments, the intensity of the components of the crescendo suction pattern 11800, 11805, 11810, 11815, 11820 during thrombus aspiration may vary as follows: (1) the intensity of negative suction pressure for the small intensity negative suction (S) ranges between about 100 mm Hg (approx. 13 kPa) to about 350 mm Hg (approx. 47 kPa) (e.g., about 250 mm Hg (approx. 33 kPa)); (2) the intensity of the medium intensity negative suction (M) ranges between about 351 mm Hg (approx. 47 kPa) to about 550 mm Hg (approx. 73 kPa) (e.g., about 500 mm Hg (approx. 67 kPa); and (3) the intensity of the large intensity negative suction (L) ranges between about 551 mm Hg (approx. 73 kPa) to about 760 mm Hg (approx. 1 atm; approx. 101 kPa) (e.g., about 750 mm Hg (approx. 100 kPa). Although some example intensities are provided herein, some embodiments of the crescendo suction patterns 11800, 11805, 11810, 11815, 11820 may include intensities of the negative suction pressures in accordance with the values provided above and/or durations that are about ±5%, about ±10%, about ±15%, or about ±20% of any such values and combinations thereof, and the like. The crescendo suction patterns 11800, 11805, 11810, 11815, 11820 may be considered to be uniform if the intensities of the negative suction pressure of each of the components of the crescendo suction pattern are substantially similar, or may be considered variable if the intensities of at least one (e.g., some or all) of the components of the crescendo suction pattern are different.

FIG. 27I-3 is a schematic diagram illustrating an example embodiment of a mobile pump with an external control panel for generating crescendo suction patterns for aspiration. In some embodiments, suction tubing 12340 is connected to a disposable canister 12330 and a peristaltic motor pump 12310 and exhaust unit. The suction tubing 12340 may include an on/off switch or valve. In some embodiments, the suction tubing 12340 may be configured to extend from the disposable canister 12330 to a hub or port at the proximal end of a guide catheter, a distal access microcatheter, or the second microcatheter 12300. In some embodiments, the peristaltic motor pump 12310 is controlled by power electronics to generate the crescendo suction patterns 11800, 11805, 11810, 11815, 11820 with a desired intensity and/or duration of negative suction pressure. The power electronics may comprise an customized integrated circuit board or an integrated chip, and the crescendo suction patterns 11800, 11805, 11810, 11815, 11820 can be stored in the power electronics. The peristaltic motor pump 12310 includes a switch or external control panel 12320 for the operator configured to allow the operator to choose from any of the crescendo suction patterns 11800, 11805, 11810, 11815, 11820 during a thrombus aspiration procedure, thereby providing customizability based on clot burden.

FIG. 27I-4 is a schematic diagram illustrating a suction pump with a customized motor controller for customizable suction patterns for aspiration that can be activated using a smart device either wired or wirelessly. The left side of FIG. 27I-4 shows an example housing structure 12350 comprising the pump 12310, controller, and smart device 12320, along with accessories such as the vacuum suction canister 12330 for collecting blood, fluids, tissue, debris, or other aspirate, and vacuum suction 12340 tubing with or without connectors and on/off switches, although other configurations are also possible (e.g., the smart device 12320 being separate or separable from the pump 12310 and/or controller). The right side of FIG. 27I-4 shows an example in which a smart device 12320 wirelessly communicates with a device enclosure 12360 comprising a pump 12390 and a motor controller 12370.

The electrical power supply (e.g., 110 V, 220 V, or 230 V-240 V), for example alternating current (AC), is connected to an on/off switch 12400, which is connected to a BIAS or power supply. If elements of the motor controller cannot function at the rating of the electrical power supply directly from the outlet, the BIAS can convert the high voltage power supply into lower voltages and/or converts to direct current (DC). The BIAS may convert some of the incoming power to be compatible with components such as the Bluetooth Low Energy (BLE) unit and/or microcontroller, and convert other of incoming power to be compatible with the Triode for Alternating Current (TRIAC) and/or motor.

The Triode for Alternating Current (TRIAC) allows electric current to flow in both directions and is compatible to drive an AC motor or a reversible DC motor which forms the underlying basis for the suction pump. A TRIAC is a phase controlled power device that gates an AC power line waveform to limit the power to an end device, which allows the TRIAC to turn the motor ON/OFF. The TRIAC may be retained, omitted, and/or replaced by other compatible electronic switches (e.g., Metal Oxide Semiconductor Field Effect Transistor (MOSFET) or Insulated Gate Bipolar Transistor (IGBT)) in embodiments in which the motor is a DC motor that forms the underlying basis for the suction pump (e.g., 6V, 12 V or 24 V brushless motor, stepper motor, low cost DC motor, etc.).

In some embodiments, the suction motor pump 12390 may comprise an oil-less dry running low-vibration rotary vane pump with a maximum flow rate (e.g., flow rate at open flow) between about 0.25 liters per minute (L/min) and about 300 L/min (e.g., about 0.25 L/min, about 0.3 L/min, about 1.4 L/min, 2.3 L/min, about 3 L/min, 4 L/min, about 20 L/min, about 26 L/min, about 29 L/min, about 30 L/min, about 34 L/min, about 40 L/min, about 110 L/min, about 175 L/min, about 250 L/min, about 283 L/min, about 300 L/min, ranges between such values, etc.) and high negative vacuum suction pressure between about 0 mm Hg and about −700 mm Hg (e.g., about 0 mm Hg, about −18.4 mm Hg, about −25 mm Hg, about −30 mm Hg about −36.8 mm Hg, about −80 mm Hg, about −90 mm Hg, about −120 mm Hg, about −250 mm Hg, about −400 mm Hg, about −550 mm Hg, about −559 mm Hg, about −635 mm Hg, about −698 mm Hg, about −700 mm Hg, ranges between such values, etc.). In some embodiments, the rotary vane pump 12390 may be replaced by other compatible pumps (e.g., linear pumps, diaphragm pumps, peristaltic pumps, or piston pumps, etc.) based on various parameters including flow rate, negative vacuum suction, power supply, among others as shown in the table below, such that the suction motor pump is compatible for a particular medical indication or pathology for example, neurovascular procedures such as for treating arterial and/or venous clots including ischemic strokes and cerebral venous sinus thrombosis, neurosurgical procedures such as for treating brain abscesses, brain tumors (e.g., soft tumors, fibrous tumors, and hard tumors), brain bleeds (e.g., intracerebral hemorrhage, intra-ventricular hemorrhage, subdural hematomas, epidural hematomas, other hemorrhages) and removing fluids, peripheral vascular procedures such as for treating arterial and/or venous clots, interventional radiologic procedures such as for treating clots in dialysis AV grafts or fistulas, laparoscopic procedures, arthroscopic procedures, hysteroscopic procedures, endoscopic procedures (e.g., neuroendoscopy, ENT, GI endoscopy, bronchoscopy), dental and other surgical procedures, etc.

| Parameter | Linear Suction Pump | Rotary Vane Suction Pump | Diaphragm Suction Pump | Peristaltic Suction Pump | Piston Suction Pump |
|---|---|---|---|---|---|
| Operating principle | Direct electrical actuation of pumping method | Pressure increase by volume reduction | Dynamic compression by flexible membrane | Liquid pumping by alternating constriction and relaxation | Dynamic compression by a fixed piston inside cylinder |
| Maximum flowrate | between about 0.9 L/min and about 375 L/min | between about 0.25 L/min and about 283 L/min | between about 0.38 L/min and about 91 L/min | between about 0.0001 L/min and about 3 L/min | between about 2.5 L/min and about 200 L/min |
| Maximum vacuum suction pressure | between about 0 mm Hg and about −338 mm Hg | between about 0 mm Hg and about −698.4 mm Hg | between about 0 mm Hg and about −742 mm Hg | between about 0 mm Hg and about −760 mm Hg | between about 0 mm Hg and about −742 mm Hg |
| Power supply | AC | AC or DC (reversible) | AC or DC | AC or DC (reversible) | AC or DC |
| Vibration | High | Low | Low | Low | Low |

In some embodiments, the custom motor controller printed circuit board (PCB) 12370 comprises a BIAS 12371, a TRIAC 12372, an integrated circuit or microcontroller 12373, and a Bluetooth low energy (BLE) unit 12374 configured to communicate with a smart device 12320 wirelessly through an antenna 12376. The antenna 12376 is configured to receive signals from the smart device 12320. In some embodiments, the BLE unit 12374 (e.g., Bluetooth Smart) is based on Bluetooth 4.2 core specifications and comprises a Bluetooth chip 12375 and an antenna 12376 within the motor controller PCB 12370, although other configurations are also possible (e.g., the antenna 12376 being separate from the motor controller PCB 12370 and externally located for receiving the signals from the smart device 12320, for example depending on antenna strength and/or casing materials). In some embodiments, the BLE unit 12374 has a wireless range between about 0.1 m and about 150 m (e.g., about 0.1 m, about 1 m, about 2 m, about 4 m, about 5 m, about 8 m, about 10 m, about 25 m, about 50 m, about 100 m, about 150 m, ranges between such values, etc.).

In some embodiments, the custom motor controller PCB 12370 comprises a simplified integrated circuit (IC) or a microcontroller 12373 (e.g., an advanced integrated circuit with random access memory (RAM) 12377 and a central processing unit (CPU) 12378) that receives the inputs from the BLE unit 12374, performs actions based on the instructions, and sends the outputs to the suction motor pump 12390 (e.g., via the TRIAC). In some embodiments, the custom motor controller PCB 12370 layout is designed using a software application (e.g., OrCAD etc.) and the results of the physical layout of components on the motor controller PCB 12370 are displayed (e.g., Gerber files in Gerber format).

In some embodiments, the smart device or Human Machine Interface (HMI) 12320, may comprise a computer, a smart phone, tablet, smart watch, or other smart devices that the operator may use during a procedure. In some embodiments, the smart device 12320 includes a software application comprising of the Graphic User Interface (GUI), and other elements of the User Experience (UX), an example of which is provided with respect to FIG. 27I-5. In some embodiments, the smart device or HMI 12320 can communicate with the custom motor controller PCB 12370 wirelessly using wireless protocols (e.g., ZigBee, Wifi, Dash 7, Bluetooth classic, Bluetooth low energy, etc.) and/or through wired connectivity using protocols (e.g., USB, RS232, RS485, CAN-bus technologies, etc.).

The various illustrative logical blocks, modules, processes, methods, and algorithms described in connection with the embodiments disclosed herein can be implemented as electronic hardware, computer software, or combinations of both. To clearly illustrate this interchangeability of hardware and software, various illustrative components, blocks, modules, operations, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The blocks, operations, or steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, an optical disc (e.g., CD-ROM or DVD), or any other form of volatile or non-volatile computer-readable storage medium known in the art. A storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

FIG. 27I-5 is a schematic diagram illustrating an example embodiment of the GUI 12410 on a smart device 12320 configured to activate customizable suction patterns for aspiration. With reference to FIG. 27I-2, patterns 11805, 11815 can assist with aspirating standard or soft clots (SC), patterns 11810, 11820 can assist with aspirating hard or stubborn clots (HC), and pattern 11800 can assist with aspirating soft tumors, abscesses, or brain bleeds through a neurosurgical approach (BR). New customized patterns can also be created using the user interface virtual button 12420 on a smart device 12320, for example to create new patterns for SC, HC, and/or BR, and/or for assisting with indications other than SC, HC, and BR suing the user interface virtual button 12422 on a smart device 12320. Although neurological endoscopic examples are shown in FIG. 27I-5, more or fewer indications and pathologies can be preprogrammed and/or programmable, for example, neurovascular procedures such as for treating arterial and/or venous clots including ischemic strokes and cerebral venous sinus thrombosis, neurosurgical procedures such as for treating brain abscesses, brain tumors (e.g., soft tumors, fibrous tumors, and hard tumors), brain bleeds (e.g., intracerebral hemorrhage, intra-ventricular hemorrhage, subdural hematomas, epidural hematomas, other hemorrhages) and removing fluids, peripheral vascular procedures such as for treating arterial and/or venous clots, interventional radiologic procedures such as for treating clots in dialysis AV grafts or fistulas, laparoscopic procedures, arthroscopic procedures, hysteroscopic procedures, endoscopic procedures (e.g., neuroendoscopy, ENT, GI endoscopy, bronchoscopy), dental and other surgical procedures, etc. In some embodiments, a continuous suction pattern (e.g., a straight line, optionally at one of a plurality of pressures) can be provided as an option.

FIG. 27I-6 is a schematic diagram illustrating an example embodiment 12430 of a suction pump 12310 with a motor controller and control panel or Human Machine Interface (HMI) 12320 for customizable suction patterns for aspiration of brain bleeds using a suction cannula, although other configurations are also possible (e.g., the smart device or HMI 12320 being separate from the pump 12310 and/or controller). The suction pump 12310, along with optional accessories such as the vacuum suction canister 12330 for collecting blood, fluids, tissue, debris, or other aspirate, a fluid infusion pole 12490 for hanging infusion bags 12500 containing saline, medications, or other fluids that are infused through the infusion tubing 12510 into the suction cannula 12460 or into the infusion lumen of a 3-port or 4-port neuro-endoscope during neurosurgical procedures, and the vacuum suction tubing 12340 may have connectors 12480 and on/off switches 12470 as shown in FIG. 27I-6 or the vacuum suction or aspiration tubing 12340 can directly connect the suction cannula 12460 to the canister 12330. In some embodiments, the HMI 12320 may comprise a computer, a smart phone, tablet, smart watch, or other smart devices that the operator may use during a procedure. Aspiration of lesions 12440 in the brain such as brain bleeds, brain abscesses, brain tumors, or other pathologies through a neurosurgical burr-hole 12450 approach can be performed using a customized single lumen aspiration suction cannula 12460 as shown in FIG. 27I-6, or the vacuum suction or aspiration tubing 12340 can be connected to a standard suction cannula, for example for use through a 3-port or 4-port neuro-endoscopes (e.g., comprising a suction lumen, an infusion lumen, an overflow lumen, a working lumen, a light port, etc.). The cannula 12460 can have a blunt tip or a sharp or tapered tip. The cannula 12460 can be in communication with an operator-controlled switch 12520 (e.g., a foot petal, a button on the handle or elsewhere, etc.) that may be wired or wireless. In some embodiments, a handle 12530 coupled to the tip comprises a vacuum port 12540 in fluid communication with the aspiration lumen and the pump 12310. If the user's hand covers the vacuum port 12540, the vacuum circuit is completed, and the negative suction continues to the cannula 12460 and the lesion 12440 in the brain. If the user's hand does not cover the vacuum port 12540, the vacuum circuit is open and the negative pressure can escape through the vacuum port 12540 such that the negative pressure does not reach the cannula 12460 or the lesion 12440 in the brain. In some embodiments, the user's glove may directly cover the vacuum port 12540 such that blood may flow past the glove toward the vacuum canister 12330. In some embodiments, a spring-loaded mechanical linkage and/or porous membrane may be used so that the blood does not contact the user. Suction can also be performed using extra-ventricular drains for intra-ventricular hemorrhage or intracerebral hemorrhages associated with intra-ventricular hemorrhages.

In some embodiments, as the distal portion 100 expands radially outwardly, parts of the vessel wall may slightly expand, the amount of expansion depending on, e.g., braid parameters, filament material, filament size, etc. Vessel expansion can create a channel to the sides of the thrombus (e.g., clot) 500 to at least partially restore blood flow even before removal of the thrombus 500. As described above, about 1,900,000 brain cells die every minute without blood supply, so the brain cells kept alive by this restoration could be significant. To the extent that current thrombectomy devices may also create a channel upon expansion, such channel may only be along a portion of the thrombus 500 such that the tissue distal thereto is still devoid of blood flow. Some current thrombectomy (e.g., laser-cut) devices may also cause stress to vessel sidewalls because they are not size-sensitive, so such vessel expansion could even lead to rupturing and/or causing distal debris. By contrast, some embodiments of the distal portions 100 described herein can create a channel that is proportional to size of vessel, which is gentler and safer than size-blind expansion, and a distal bulb can trap distal debris.

In some embodiments, after unsheathing part of the distal portion 100 (e.g., enough so that a bulb is proximal to the proximal end of the thrombus 500), the device 10, 20, 30, 40 may optionally be torsionally rasped in a rotational direction. Part of the proximal portion 200 outside the subject is rotated by the user. The distal portion 100, coupled to the proximal portion 200, also rotates. In some embodiments, part of the distal portion 100 apposes the sidewalls of the vessel and resists rotation. The rotational forces are generally exerted from proximal to distal along the length of the distal portion 100, so the distal-most part apposing the sidewalls of the vessel are most likely to rotate last. In some embodiments, a distal-most bulb of the distal portion 100 apposes the sidewalls of the vessel distal to the thrombus 500. In certain such embodiments, the distal-most bulb of the distal portion 100 substantially maintains a rotational position until expanded parts of the distal portion 100 proximal to the distal-most bulb are at least partially rotated. Rotation of the distal portion 100 entraps the clot and collects any debris. The distal portion 100 can rotationally scrape the sidewalls of the vessel to remove portions of the clot attached to the endothelium wall, which can remove more than free-floating debris. The non-laser cut braided nature of the bulbs can facilitate gentle entrapment of the clot without perforating the vessel.

As used herein, torsional rasping shall be given its ordinary meaning and shall include wringing and twisting. An incomplete analogy for torsional rasping is wringing out a towel, where a person grabs one end of the towel with one hand and the opposite end of the towel with the other hand, and, while holding the first end still, rotates the second end. The towel twists, generally shrinking in diameter, until physical forces inhibit further rotation. Rather than ends of a towel, ends of the distal portion 100 are grasped, the distal end by apposing sidewalls and the proximal end by the proximal portion. FIG. 27J is a schematic diagram of a distal portion 100 of a vascular treatment device being torsionally rasped. In FIG. 27J, the initial rotation of the proximal-most expanded bulbs of the distal portion 100 are shown. The analogy is incomplete because the towel does not inform clot entrapment. As described herein, the braided nature of the distal portion 100 can trap the clot between undulations between the bulbs and/or undulations of the woven wires. FIG. 27K is a schematic diagram of a distal portion 100 of a vascular treatment device being torsionally rasped. The expanded bulbs of the distal portion are shown wrapped around a thrombus (e.g., clot) 500.

The tension may be applied throughout the torsional rasping by continually rotating the proximal portion 200 or at least not allowing the proximal portion 200 to rotate in the opposite direction. Referring again to the towel analogy, releasing the tension may allow the distal portion 100 to at least partially unfurl, which may, for example, allow trapped clot and/or emboli to escape, although such escaped thrombi may be captured by other parts of the distal portion 100.

In some embodiments, one of the bulbs (e.g., a distal-most bulb of the distal portion 100 apposing the sidewalls of the vessel) can act as an embolic filter during a clot retrieval procedure (e.g., trapping emboli, such as emboli created during expansion of the distal portion 100 and/or torsional rasping of the distal portion 100) such that no other, separate, or additional embolic filter is used. The thrombectomy procedures described herein are different than embolic filters. For example, the devices 10, 20, 30, 40 can actively retrieve a clot, for example according to the procedures described herein, rather than passively collecting emboli.

In some procedures, the devices 10, 20, 30, 40 described herein may be used as an embolic filter in combination with another type of catheter-based or wire-based system (e.g., during performance of another vascular procedure such as angioplasty, atherectomy, aspiration, stenting, embolic coil insertion, intra-arterial thrombolysis, bypass, etc.), or even an additional thrombectomy device (e.g., a device 10 and a device 20). For example, a distal-most bulb of a distal portion 100 may be deployed distal to the site of the procedure. In some embodiments, additional parts of the distal portion 100 may be deployed during and/or after performance of a procedure. In certain such embodiments, the distal portion 100 may be torsionally rasped (e.g., to rotationally scrape sidewalls of a vessel after plaque may have been loosened by angioplasty or atherectomy, to rotationally scrape the inside of a stent, to capture debris proximal to the distal-most bulb of the distal portion 100, etc.). In certain such embodiments, the microcatheter 504 may be advanced slightly more distally to allow the other system to also be at least partially distal to the clot. The lumen of the proximal portion 200 and optionally the distal portion 100 may be used as a working channel for other devices.

The rotational direction may be clockwise or counterclockwise. For example, the handedness (left handed or right handed) of the user may make a particular rotational direction more comfortable (e.g., turning the proximal portion 200 towards the user's body). In some embodiments, a direction of rotation may be based at least partially on the design of the proximal portion 200. For example, referring again to FIGS. 16A and 16B, if the proximal portion 200 includes slits with a positive angle 250, then counterclockwise rotation may better transfer rotational forces and if the proximal portion 200 includes slits with a negative angle 250, then clockwise rotation may better transfer rotational forces.

In some embodiments, the rotation of the distal portion 100 is less than the rotation of the proximal portion 200. For example, in some embodiments, a 360° rotation of the proximal portion 200 results in less than 360° rotation of the distal portion 100 (e.g., rotation of the distal portion between about 90° and about 359°, between about 90° and about 270°, between about 90° and about 180°, etc.). In some embodiments, a ratio of rotational forces at the proximal portion 100 and the distal portion 200 are not 1:1. For example, the ratio may be less than 1:1 (e.g., 1:0.75, 1:0.5, or 1:0.25, etc.). In some embodiments, a non-1:1 ratio may provide a gentle rotation that can reduce the risk that the blood vessel is rotated, displaced, disrupted, or perforated. Resistance of a distal-most bulb or other bulbs of the distal portion 100 apposing the sidewalls of the vessel may contribute to reduced rotation of the distal portion 100.

In some embodiments, a wire torque device, handle, or the like may be used to assist rotation of the proximal portion 200. In some embodiments, the proximal portion is rotated between about 90° and about 3,000°, between about 360° and about 2,500°, or between about 720° and about 1,440°. In some embodiments, the proximal portion is rotated at least three full rotations (e.g., greater than about 1,080°. In some embodiments, the proximal portion is rotated at least six full rotations (e.g., greater than about 2,160°. The upper limit of the amount of rotation may vary by device and by clot. In some embodiments, physical forces may inhibit further rotation (e.g., the wires of the distal portion 100 and/or the clot can no longer be radially compressed). In some embodiments, the diameter of the distal portion 100 may reduce enough that further rotation rotates the distal portion 100 does not effect further torsional rasping.

In some embodiments in which torsional rasping is performed on soft clots, the distal portion 100 of the device 10, 20, 30, 40 comprises bulbs configured to expand from the collapsed state to the expanded state substantially instantaneously (e.g., comprising super-elastic material), and the clot may be entwined around the bulbs in the hills and valleys.

In some embodiments in which torsional rasping is performed on hard clots, the distal portion 100 of the device 10, 20, 30, 40 comprises bulbs configured to expand from the collapsed state to the expanded state with a time-delayed expansion (e.g., comprising shape-memory material), the torsional rasping may be performed while the distal portion 100 is in a secondary shape such as a twisted or spiral shape (e.g., occurring due to contact with blood at body temperature and/or warm saline), and the clot may be entwined by that secondary shape.

FIG. 27L is a schematic diagram illustrating an example embodiment of a two-way shape memory effect of a distal portion 100 of a vascular treatment device, for example the distal portion 100 of device 10, 20, 30, or 40. When the distal portion 100 is at a first temperature such as ambient room temperature (e.g., about 25° C.), the distal portion 100 is in the collapsed configuration as illustrated in FIG. 27F. When the distal portion 100 is at a second temperature (e.g., about 37° C.), which can be achieved on contact with blood at body temperature, the distal portion 100 further expands to the expanded configuration as illustrated in FIGS. 27G and 27H, depending on the length of retraction of the microcatheter 504. When the distal portion 100 is at a third temperature (e.g., about 18° C.), which can be achieved by injecting cold saline through the microcatheter 504, a distal access microcatheter 530, or the guide catheter 502, the distal portion 100 foreshortens to grasp the thrombus (e.g., clot) 500 better in a twisted spiral configuration as illustrated in FIGS. 27K and 27L. In some embodiments, this twisting grabbing can occur without rotation of the proximal portion 200.

If the thrombus (e.g., clot) 500 is not adequately grasped, for example as evidenced during angiography, after stopping the injection of cold saline through the microcatheter 504, a distal access microcatheter 530, or the guide catheter 502, the distal portion 100 returns back to the second temperature (e.g., about 37° C.) on continued contact with blood at body temperature, and the distal portion 100 expands once again to the expanded configuration as illustrated in FIGS. 27G and 27H. When the distal portion 100 is once again exposed to a third temperature (e.g., about 37° C.), which can again be achieved by injecting cold saline through the microcatheter 504, a distal access microcatheter 530, or the guide catheter 502, the distal portion 100 foreshortens again to grasp the thrombus 500 in a twisted spiral configuration as illustrated in FIGS. 27K and 27L. In some embodiments, this twisting grabbing can occur without rotation of the proximal portion 200. In some embodiments, the second twisting may better capture the thrombus 500 than the first twisting.

FIG. 27M is a schematic diagram illustrating the retraction of a distal portion 100 of a vascular treatment device and a thrombus 500. In some embodiments, the device 10, 20, 30, 40 may be proximally retracted (e.g., after torsional rasping or without torsional rasping), for example by retracting (e.g., substantially simultaneously and/or at a similar rate) the proximal portion 200 and the microcatheter 504 until both the proximal portion 200 and the microcatheter 504 are through the guide catheter and out of the body of the subject being treated. During this retraction, the parts of the distal portion 100 that were expanded remain expanded and the parts of the distal portion 100 that were not expanded remain in the contracted state. The proximal portion 200 and the microcatheter 504 may continue to be retracted until the distal portion 100 and the clot are out of the guide catheter.

Negative suction pressure may be applied (e.g., using a crescendo suction pattern (e.g., as described with respect to FIG. 27I-2)) through the guide catheter 502 during proximal retraction. If no blood comes out after stopping aspirating, then the user may know that something, such as the clot, is blocking the guide catheter 502. A user may perform thrombus aspiration until that blockage comes out, as described herein. When blood comes out, the user may, for example flush with fluid (e.g., heparinized saline), perform post-thrombectomy angiogram, etc.

In some embodiments, the removed thrombus (e.g., clot) 500 may be placed next to a ruler 520 on a package containing the device 10, 20, 30, 40 or another ruler. The user may compare the measured length of the removed thrombus (e.g., clot) 501 to the estimated (e.g., before the procedure) and/or known (e.g., measured during the procedure using radiopaque crossings) length. FIG. 27N illustrates an example embodiment of a comparison of a thrombus 501 length to a ruler 520. The thrombus 501 measures about 2 inches (approx. 5.1 cm). If the length of the removed thrombus 501 is substantially less than the estimated and/or known length, the user may deduce that the entire thrombus 500 was not removed. The user may check the aspiration syringe or other equipment for any additional lengths of clot. Knowledge that some of the thrombus 500 may have not been removed allows the user to figure out a further treatment strategy. As described above, such comparison and removal validation is generally not possible with devices that remove a portion of the thrombus 500 at a time (e.g., due to a fixed and limited working length).

FIG. 27O is a schematic diagram of a distal portion 100 of a thrombectomy device acting as a filter device. In some embodiments, upon expansion, the distal-most bulb or bulbs can appose the sidewalls of the vessel distal to the thrombus (e.g., clot) 500, and the distal-most bulb(s) can act as a distal filter or entrapment mechanism that can catch or collect pieces of thrombus (e.g., emboli) 500 that may become separated during thrombectomy, an angioplasty, aspiration, stenting, or other vascular procedures.

FIG. 27P is a schematic diagram illustrating an example embodiment of a two-way shape memory effect of the proximal portion 9700 of a thrombectomy device, for example the proximal portion 200 of device 10, 20, 30, or 40. When the proximal portion 9700 is at a first temperature such as ambient room temperature (e.g., about 25° C.), the proximal portion 9700 is in a substantially linear configuration. When the proximal portion 9700 is at a second temperature (e.g., about 37° C.), which can be achieved on contact with blood at body temperature, some or all the proximal portion 9700 takes shape such as a gentle S-shape, which can mimic curves of the vessel anatomy, which can alleviate stress on the vessels. When the proximal portion 9700 is removed from the body after a vascular procedure, for example a thrombectomy procedure, the parts of or all of the proximal portion 9700 may retain the shape.

If the thrombus (e.g., clot) 500 is not adequately removed after a first thrombectomy attempt, for example as evidenced during angiography, reintroduction of the proximal portion 9700 through the hub 590 of the microcatheter 504 may be difficult. The proximal portion 9700 may be exposed to a third temperature (e.g., about 18° C.) (e.g., by placement in a sterile bowl containing cold saline). Upon reaching the third temperature, the proximal portion 9700 returns to the substantially linear configuration. This two-way shape memory effect of the proximal portion 9700 may be useful, for example, in vascular procedures that may utilize multiple attempts.

In some embodiments, a proximal portion 200 having super-elasticity and that has a substantially linear configuration shape set will attempt to return to that substantially linear configuration as the proximal portion bends in a tortuous blood vessel, which can straighten the tortuous blood vessel, which may lead to rupture of any perforator vessels arising from the tortuous blood vessel. In some embodiments, a proximal portion 200 having a two-way shape memory effect may be gentler on blood vessels than a proximal portion 200 having super-elasticity.

Once the microcatheter 504, and, if used, a distal access microcatheter 530, and the device 10, 20, 30, 40 are out of the subject and no further treatment is to be performed, the guide catheter 502 may be removed and the subject sealed (e.g., stitching the entry point or using a bandage or dressing such as a Tegaderm®, available from 3M). The methods described above need not all be performed or performed in the order recited. Other steps can also be performed. For example, steps such as vessel access, drug treatment, and the like are generally omitted for clarity.

In some embodiments, the devices 10, 20, 30, 40 described herein can be used in the brain. In some embodiments, vasculature in the periphery can be treated using the devices 10, 20, 30, 40 described herein. In some embodiments, coronary vessels may be treated the devices 10, 20, 30, 40 described herein. In some embodiments, the abdominal aorta and branches may be treated using the devices 10, 20, 30, 40 described herein.

FIG. 28A is a schematic diagram of a guide catheter 502 proximal to an aneurysm 503 in vasculature. The aneurysm 503 illustrated in FIG. 28A is in the right middle cerebral artery, although other aneurysms 503 may also be treated, including sidewall aneurysms and bifurcation aneurysms. The guide catheter 502 is in the right internal carotid artery, for example having been routed to that position as described above. The aneurysm 503 may have been noted during CT scan angiography or MRI angiography or angiography with the guide catheter 502 or another catheter (e.g., a shuttle or a balloon guide catheter), for example in the right internal carotid artery. A catheter angiogram may be performed using the guide catheter 502 after positioning the guide catheter 502.

FIGS. 28B and 28C are schematic diagrams of a microwire 506 distal to an aneurysm 503 in vasculature and a microcatheter 504 over the microwire 506. In some embodiments, referring again to FIG. 27I-1, a distal access microcatheter 530 with a microcatheter 504 inserted inside the distal access microcatheter 530 may be through the guide catheter 502, which is positioned in the right internal carotid artery proximal to the aneurysm 503, and over a steerable microwire 506. A steerable microwire 506 (e.g., having an outer diameter of about 0.014 inches (approx. 0.36 mm) is inserted into the microcatheter 504, extending some distance (e.g., about 2 cm to about 4 cm) out of the distal end of the microcatheter 504. In some embodiments, a distal access microcatheter 530 is not used and the microcatheter 504 is advanced over the microwire 506. The microwire 506 can be advanced and steered for some distance into the petrous and cavernous segments of the right internal carotid artery, followed by advancement of the microcatheter 504 over the microwire 506. The microwire 506 and the microcatheter 504 can be sequentially advanced into the supraclinoid segment of the right internal carotid artery and then into the right middle cerebral artery until the desired point in the vasculature distal to the aneurysm 503 or lesion, for example by about 0.5 mm to about 5 mm (e.g., into the superior M2 segment or inferior M2 segment of the middle cerebral artery). Other locations of aneurysms 503 include, but are not limited to, the supraclinoid segment of the right internal carotid artery and the anterior communicating artery at the junction of the right A1 segment and A2 segments of the anterior cerebral arteries.

FIG. 28D is a schematic diagram of a microcatheter 504 distal to an aneurysm 503 in vasculature. The microwire 506 has been removed from the microcatheter 504, leaving the microcatheter 504 distal to the aneurysm 503. The distal end of the microcatheter 504 may range from about 5 mm to 45 mm (e.g., about 15 mm) distal to the aneurysm 503 or a lesion (e.g., in the superior segment of the right middle cerebral artery or the inferior segment of the right middle cerebral artery). In some embodiments in which a distal access microcatheter 530 is used, the distal end of the distal access microcatheter 530 may range from about 5 mm to 50 mm (e.g., about 25 mm) proximal to the aneurysm 503 or a lesion in the vasculature (e.g., in the proximal middle cerebral artery, the supraclinoid right internal carotid artery, or the cavernous segment of the right internal carotid artery for an aneurysm 503 in the right middle cerebral artery).

Referring again to FIG. 27E, the distal portion 100 of vascular treatment device (e.g., flow diverter) can be introduced into the hub 590 of the microcatheter 504 through an introducer sheath 540 with the distal portion 100 in the constrained state. The proximal portion 200 of the vascular treatment device is pushed to advance the device through the microcatheter 504. The device is advanced until the distal end of the distal portion 100 is proximate to the distal end of the microcatheter 504, which is distal to the distal end of the aneurysm 503. The microcatheter 504 is then retracted (e.g., unsleeved, unsheathed) while holding the proximal portion 200 still so that the longitudinal position of the device is maintained.

FIG. 28E is a schematic diagram of an example embodiment of the distal portion 100 of a vascular treatment device being deployed distal to an aneurysm 503 in vasculature. The retraction of the microcatheter 504 exposes the distal portion 100, from the distal end back, which can allow the exposed sections of the distal portion 100 to self-expand. For example, the distal portion 100 may include a wide-mouth distal neck and/or a distal-most bulb 9850 that can expand to appose the sidewalls of the vasculature distal to the aneurysm 503.

In some embodiments, exposed sections of the distal portion 100 can self-expand because the distal portion 100 includes at least some super-elastic filaments configured to self-expand, for example, due to stress-induced martensite (SIM) without any particular change in temperature. Superelastic materials can expand substantially instantaneously from a collapsed configuration to an expanded configuration when the unsheathed. In some embodiments, exposed sections of the distal portion 100 can self-expand because the distal portion 100 includes at least some shape memory filaments that configured to self-expand, for example, due to temperature-activated austenitic transformation (e.g., upon a change in temperature such as greater than room temperature (about 25° C.) (e.g., to about body temperature (approx. 37° C.), less than room temperature (e.g., to about 18° C.), etc.). Shape-memory materials can expand slowly from a collapsed configuration to an expanded configuration when unsheathed upon contact with warm fluid (e.g., blood at body temperature, warm saline) and/or cold fluid (e.g., cold saline).

In some embodiments, the shape memory effect of the shape memory filaments can be one-way (e.g., a stress-induced change in shape returns to a baseline shape upon heating, with no change upon cooling). With the one-way shape memory effect, the material remembers one shape above a certain temperature. In some embodiments, the shape memory effect of the shape memory filaments can be two-way (e.g., a stress-induced change in shape returns close to baseline shape upon heating, and a second shape can be achieved upon cooling). With the two-way shape memory effect, the material remembers a first shape above a first temperature and a second shape below a second temperature.

FIG. 28F is a schematic diagram of an example embodiment of the distal 100 portion of a vascular treatment device being deployed across an aneurysm 503 in vasculature. In contrast to a tubular device, for example, the deployment of a distal portion 100 comprising bulbs and wide-mouthed necks 9850 across the mouth of an aneurysm can allow for better wall apposition and/or reduce the risk of an endo-leak.

FIG. 28G is a schematic diagram of an example embodiment of the distal portion 9600 of FIG. 6G deployed across an aneurysm 9645 in vasculature. Referring again to FIG. 6G, the distal portion 9600 may be useful, for example, in aneurysms 9645 proximal to a vessel bifurcation, for example, for deployment of the high pore size distal bulb 9603 in the proximal M1 segment of the middle cerebral artery 9640 and the high pore size middle bulb 9605 at the internal carotid artery bifurcation near the origin of the middle cerebral artery 9640 and the anterior cerebral artery 9630, which can allow blood flow into the arteries 9630, 9640 and their perforators distal to the aneurysm 9645, which can inhibit or prevent occlusion of blood flow to the arteries 9630, 9640, which could otherwise lead to life-threatening stroke. In some embodiments, deployment of the small pore size proximal segment 9604 across an aneurysm 9645 located in the supraclinoid internal carotid artery 9635, in the illustrated example not involving the internal carotid artery bifurcation, can aid in thrombosis of the aneurysm 9645. The bulbs 9603, 9605, 9607, the wide-mouthed necks in between the bulbs 9614 and 9616, the wide mouthed proximal neck 9618, and the distal neck 9612 can allow provide good wall apposition including the site of vessel bifurcation, which can inhibit or prevent the risk of an endo-leak into the aneurysm 9645. In some embodiments, the force/resistance (e.g., radial force) of the bulbs and/or necks is in a range sufficient to slightly expand the target vessel(s) in the range of about 0% to about 30%, and the shapes of the bulbs and necks are at least partially preserved. In some embodiments, the radial force of the bulbs and/or necks is in a range sufficient to appose the sidewalls of the vessel to inhibit or prevent an endo-leak, but not sufficient to expand the vessel, and the shapes of the bulbs and necks are no longer preserved such that the shape of the distal portion 9600 is substantially tubular, whether tapered or non-tapered, for example based on the shape of the target vessel.

FIG. 28H is a schematic diagram of an example embodiment of the distal portion 11100 of FIG. 7B deployed across an aneurysm 11150 in vasculature. The distal portion 11100 may be useful, for example, for deployment in fusiform aneurysms at a vessel bifurcation such as an abdominal aortic aneurysm (AAA) 11150 illustrated in FIG. 28H. In some embodiments, a procedure may be performed percutaneously and entirely through one arterial access, for example the left common femoral artery and the left common iliac artery 11140. For example, deployment of the large pore sized proximal lateral neck 11120 in the left common iliac artery 11140 and the large pore sized proximal medial neck 11125 in the right common iliac artery 11160 can allow blood flow into these arteries, which can inhibit or prevent occlusion of these arteries, which could otherwise lead to renal failure or life-threatening limb ischemia. In some embodiments, deployment of the large pore sized distal neck 11130 in the supra-renal or infra-renal abdominal aorta can allow blood flow into the renal arteries 11145 and their branches, which can inhibit or prevent occlusion of blood flow to the renal arteries 11145, which could otherwise lead to kidney failure. In some embodiments, deployment of the small pore sized spherical proximal bulb 11105, the elongate distal bulb 11110, and the neck 11115 between the bulbs 11105, 11110 across the abdominal aortic aneurysm 11150 in the infra-renal abdominal aorta can aid in thrombosis of the aneurysm 11150. The large pore sized proximal lateral neck 11120 may be deployed in the left common iliac artery 11140. Given the relatively short length and large pore size of the proximal medical neck 11125, the neck 11125 can be deployed into the origin of the right common iliac artery 11160 while the proximal lateral neck 11120 is deployed in the left common iliac artery 11140, which can allow blood flow into these arteries, which can inhibit or prevent occlusion of blood flow to these arteries, which could otherwise lead to renal failure or life-threatening limb ischemia. In some embodiments, the force/resistance (e.g., radial force) of the bulbs and/or necks is in a range sufficient to slightly expand the target vessel(s) in the range of about 0% to about 30%, and the shapes of the bulbs and necks are at least partially preserved. In some embodiments, the radial force of the bulbs and/or necks is in a range sufficient to appose the sidewalls of the vessel to inhibit or prevent an endo-leak, but not sufficient to expand the vessel, and the shapes of the bulbs and necks are no longer preserved such that the shape of the distal portion 11100 is substantially tubular, whether tapered or non-tapered, for example based on the shape of the target vessel.

FIG. 28I is a schematic diagram of an example embodiment of the distal portion 9000 FIG. 6A deployed across an aneurysm 9050 in vasculature. The distal portion 9000 may be useful, for example, for deployment of the small pore size middle segment 9002 across a wide-mouthed posterior-communicating artery brain arterial aneurysm 9050, which is located in the supraclinoid segment of the internal carotid artery 9030, which can aid in thrombosis of the aneurysm 9050. Deployment of the high pore size proximal segment 9006 and the high pore size distal segment 9004 on either side of the aneurysm 9050 can allow blood flow into arteries proximal and distal to the aneurysm 9050, for example to the proximal ophthalmic artery 9040 and the distal anterior choroidal artery 9045 and superior hypophyseal artery distally 9035, which can inhibit or prevent occlusion of the arteries 9035, 9040, 9045 and/or resulting dysfunction (e.g., occlusion of the ophthalmic artery 9040 can cause blindness, occlusion of the anterior choroidal artery 9045 can cause paralysis of the arms and legs). The bulbs and wide-mouthed necks of the distal portion 9000 can provide good wall apposition, including at the site of vessel bifurcation, which can inhibit or prevent the risk of an endo-leak into the aneurysm 9050. In some embodiments, the force/resistance (e.g., radial force) of the bulbs and/or necks is in a range sufficient to slightly expand the target vessel(s) in the range of about 0% to about 30%, and the shapes of the bulbs and necks are at least partially preserved. In some embodiments, the radial force of the bulbs and/or necks is in a range sufficient to appose the sidewalls of the vessel to inhibit or prevent an endo-leak, but not sufficient to expand the vessel, and the shapes of the bulbs and necks are no longer preserved such that the shape of the distal portion 9000 is substantially tubular, whether tapered or non-tapered, for example based on the shape of the target vessel.

FIG. 28J is a schematic diagram of an example embodiment of the distal portion 9100 of FIG. 6B deployed across an aneurysm 9135 in vasculature. The distal portion 9100 may be useful, for example, for deployment of the small pore size distal segment 9110 across a proximal middle cerebral artery M2 segment brain arterial aneurysm 9135, which is located near the distal M1 segment of the middle cerebral artery 9130, which can aid in the thrombosis of the aneurysm 9135. Deployment of the high pore size proximal segment 9120 across the distal M1 segment of the middle cerebral artery 9130 can allow blood flow into the perforators arising from the distal M1 segment of the middle cerebral artery 9130, for example the proximal lateral lenticulo-striate perforating arteries 9140, 9145, which can inhibit or prevent occlusion of such perforators 9140, 9145 and/or resulting dysfunction (e.g., occlusion of the lenticulo-striate perforators 9140, 9145 can cause paralysis of the arms and legs). The bulbs and wide-mouthed necks of the distal portion 9100 can provide good wall apposition, including at the site of vessel bifurcation, which can inhibit or prevent the risk of an endo-leak into the aneurysm 9135. In some embodiments, the force/resistance (e.g., radial force) of the bulbs and/or necks is in a range sufficient to slightly expand the target vessel(s) in the range of about 0% to about 30%, and the shapes of the bulbs and necks are at least partially preserved. In some embodiments, the radial force of the bulbs and/or necks is in a range sufficient to appose the sidewalls of the vessel to inhibit or prevent an endo-leak, but not sufficient to expand the vessel, and the shapes of the bulbs and necks are no longer preserved such that the shape of the distal portion 9100 is substantially tubular, whether tapered or non-tapered, for example based on the shape of the target vessel.

FIG. 28K is a schematic diagram of an example embodiment of the distal portion 9200 of FIG. 6C deployed across an aneurysm 9240 in vasculature. The distal portion 9200 may be useful, for example, for the deployment of the high pore size distal segment 9210 in internal carotid artery 9230 distal to the cavernous aneurysm 9240, which can allow blood flow into the distal artery 9235, for example the ophthalmic artery, which can inhibit or prevent occlusion of the artery 9235 and/or resulting dysfunction (e.g., occlusion of the ophthalmic artery 9235 can cause blindness). Deployment of the small pore size proximal segment 9220 across a brain aneurysm 9240 located in the distal cavernous segment of the internal carotid artery 9230 can aid in the thrombosis of the aneurysm 9240. The bulbs and wide-mouthed necks of the distal portion 9200 can provide good wall apposition, including at the site of vessel bifurcation, which can inhibit or prevent the risk of an endo-leak into the aneurysm 9240. In some embodiments, the force/resistance (e.g., radial force) of the bulbs and/or necks is in a range sufficient to slightly expand the target vessel(s) in the range of about 0% to about 30%, and the shapes of the bulbs and necks are at least partially preserved. In some embodiments, the radial force of the bulbs and/or necks is in a range sufficient to appose the sidewalls of the vessel to inhibit or prevent an endo-leak, but not sufficient to expand the vessel, and the shapes of the bulbs and necks are no longer preserved such that the shape of the distal portion 9200 is substantially tubular, whether tapered or non-tapered, for example based on the shape of the target vessel.

FIG. 28L is a schematic diagram of an example embodiment of the distal portion 9300 of FIG. 6D deployed across aneurysms 9335, 9340 in vasculature. The distal portion 9300 may be useful, for example, when two aneurysms 9335, 9340 along a vessel 9330 are separated by a segment including a branch vessel 9350. For example, deployment of the small pore size distal segment 9304 across a posterior communicating artery (P-comm) brain aneurysm 9335 in the supraclinoid segment of the internal carotid artery 9330 and deployment of the small pore size proximal segment 9306 across a distal cavernous internal carotid artery aneurysm 9340 in the internal carotid artery 9330 can aid in the thrombosis of the aneurysms 9335, 9340, and deployment of the high pore size middle segment 9320 between the P-comm aneurysm 9335 and the distal cavernous internal carotid artery aneurysm 9340 can allow blood flow into the ophthalmic artery 9350, which can inhibit or prevent occlusion of the ophthalmic artery 9350, which could otherwise cause blindness. The bulbs and wide-mouthed necks of the distal portion 9200 can provide good wall apposition, including at the site of vessel bifurcation, which can inhibit or prevent the risk of an endo-leak into the aneurysms 9335, 9340. In some embodiments, the force/resistance (e.g., radial force) of the bulbs and/or necks is in a range sufficient to slightly expand the target vessel(s) in the range of about 0% to about 30%, and the shapes of the bulbs and necks are at least partially preserved. In some embodiments, the radial force of the bulbs and/or necks is in a range sufficient to appose the sidewalls of the vessel to inhibit or prevent an endo-leak, but not sufficient to expand the vessel, and the shapes of the bulbs and necks are no longer preserved such that the shape of the distal portion 9300 is substantially tubular, whether tapered or non-tapered, for example based on the shape of the target vessel.

FIG. 28M is a schematic diagram of an example embodiment of the distal portion 9400 of FIG. 6E deployed across an aneurysm 9435 in vasculature. The distal portion 9400 may be useful, for example, when an aneurysm 9435 is between several arteries and/or perforators. For example, deployment of the small pore size middle segment 9430 across a dissecting pseudo-aneurysm 9435 in the V4 segment of the vertebral artery 9445 can aid in thrombosis of the aneurysm 9435, and deployment of the high pore size proximal segment 9404 and the high pore size distal segment 9402 across the arteries proximal and distal to the aneurysm 9435 can allow blood flow into these arteries, for example the proximal posterior inferior cerebellar artery (PICA) 9470 and the distal basilar artery 9440 and its perforators 9460, 9465, which can inhibit or prevent occlusion of these arteries and/or resulting dysfunction (e.g., occlusion of the PICA 9470 can cause balance problems while walking, occlusion of the basilar artery 9440 or its perforators can cause life threatening strokes, etc.). The medium braid angle segments 9406, 9408 have medium pore sizes, which can allow for variability and error while deploying the distal portion 9400, which can inhibit or prevent occlusion of these arteries or their perforators. The contralateral V4 segment of the vertebral artery 9450 can supply the contralateral PICA 9455 and the basilar artery 9440 through the woven neck and bulb of the high pore size distal segment 9402. The bulbs and wide-mouthed necks of the distal portion 9400 can provide good wall apposition, including at the site of vessel bifurcation, which can inhibit or prevent the risk of an endo-leak into the aneurysm 9435. In some embodiments, the force/resistance (e.g., radial force) of the bulbs and/or necks is in a range sufficient to slightly expand the target vessel(s) in the range of about 0% to about 30%, and the shapes of the bulbs and necks are at least partially preserved. In some embodiments, the radial force of the bulbs and/or necks is in a range sufficient to appose the sidewalls of the vessel to inhibit or prevent an endo-leak, but not sufficient to expand the vessel, and the shapes of the bulbs and necks are no longer preserved such that the shape of the distal portion 9400 is substantially tubular, whether tapered or non-tapered, for example based on the shape of the target vessel.

FIG. 28N is a schematic diagram of an example embodiment of the distal portion 9500 of FIG. 6F deployed across an aneurysm 9540, 9550 in vasculature. The distal portion 9500 may be useful, for example, for deployment of the small pore size middle segment 9504 across a fusiform aortic aneurysm 9540, 9550 located in the infra-renal abdominal aorta 9530, and not involving the aorto-iliac bifurcation, which can aid in thrombosis of the aneurysm 9540, 9950. Deployment of the high pore size proximal segment 9506 and the high pore size distal segment 9502 across arteries proximal and distal to the aneurysm 9540, 9550 can allow blood flow into these arteries, for example the distal bilateral renal arteries 9535, 9545 and the proximal intercostal and lumbar arteries, which can inhibit or prevent occlusion and/or resulting dysfunction (e.g., lack of blood flow to the kidneys can lead to renal failure, occlusion of the intercostal and lumbar arteries could lead to bowel and bladder dysfunction, etc.). The bulbs 9503, 9505, 9507, the wide-mouthed neck 9514 between the bulbs 9503, 9505, the wide-mouthed neck 9516 between the bulbs 9505, 9507, the wide-mouthed proximal neck 9518, and the wide-mouth distal neck 9512 of the distal portion 9500 can provide good wall apposition, which can inhibit or prevent the risk of an endo-leak into the aneurysm 9540, 9550. In some embodiments, the force/resistance (e.g., radial force) of the bulbs and/or necks is in a range sufficient to slightly expand the target vessel(s) in the range of about 0% to about 30%, and the shapes of the bulbs and necks are at least partially preserved. In some embodiments, the radial force of the bulbs and/or necks is in a range sufficient to appose the sidewalls of the vessel to inhibit or prevent an endo-leak, but not sufficient to expand the vessel, and the shapes of the bulbs and necks are no longer preserved such that the shape of the distal portion 9500 is substantially tubular, whether tapered or non-tapered, for example based on the shape of the target vessel.

FIG. 28O is a schematic diagram of an example embodiment of the distal portion 11000 of FIG. 7A deployed across a bifurcation aneurysm 11005 in vasculature. The distal portion 11000 may be useful in aneurysms at a vessel bifurcation, for example, for deployment of the large pore sized distal lateral neck 11019 in the proximal M1 segment of the middle cerebral artery 11015 and the large pore sized distal medial neck 11018 in the A1 segment of the anterior cerebral artery 11025, which can allow blood flow into these arteries, which can inhibit or prevent occlusion of blood flow to these arteries, which could otherwise lead to life-threatening stroke. In some embodiments, deployment of the small pore sized spherical distal bulb 11012 across the aneurysm 11005 in the distal internal carotid artery 11035 bifurcation can aid in thrombosis of the aneurysm 11005. In some embodiments, deployment of the large pore sized proximal segment of the distal portion 11000, including the wide-mouthed neck 11016, the proximal elongate bulb 11014, and the proximal neck 11017, in the distal supra-clinoid internal carotid artery 11035 can allow blood flow into the branches arising from the distal supra-clinoid arteries, which can inhibit or prevent occlusion of blood flow to these arteries, which could otherwise lead to life-threatening stroke. In some embodiments, the force/resistance (e.g., radial force) of the bulbs and/or necks is in a range sufficient to slightly expand the target vessel(s) in the range of about 0% to about 30%, and the shapes of the bulbs and necks are at least partially preserved. In some embodiments, the radial force of the bulbs and/or necks is in a range sufficient to appose the sidewalls of the vessel to inhibit or prevent an endo-leak, but not sufficient to expand the vessel, and the shapes of the bulbs and necks are no longer preserved such that the shape of the distal portion 11000 is substantially tubular, whether tapered or non-tapered, for example based on the shape of the target vessel.

FIG. 28P is a schematic diagram of an example embodiment of the distal portion 11300 of FIG. 6H deployed across a side-wall aneurysm 503 in vasculature. The distal portion 11300 may be useful, for example, for deployment of the small pore size second portion 11312 of the middle segment 11310 across a side-wall basilar arterial brain aneurysm 503, which can aid in thrombosis of the aneurysm 503. Deployment of the high pore size proximal segment 11315, the high pore size distal segment 11305, and the high pore size first portion 11311 of the middle segment 11310 across arteries 9460, 9465 proximal and distal to the aneurysm 503 can allow blood flow into these arteries, for example the proximal anterior-inferior cerebellar arteries, the distal basilar perforators, and/or the distal superior cerebellar arteries, which can inhibit or prevent occlusion of the basilar perforators and the other branches 9460, 9465 and/or resulting dysfunction, which could otherwise cause a brainstem stroke with paralysis of the arms and legs. In some embodiments, the force/resistance (e.g., radial force) of the bulbs and/or necks is in a range sufficient to slightly expand the target vessel(s) in the range of about 0% to about 30%, and the shapes of the bulbs and necks are at least partially preserved. In some embodiments, the radial force of the bulbs and/or necks is in a range sufficient to appose the sidewalls of the vessel to inhibit or prevent an endo-leak, but not sufficient to expand the vessel, and the shapes of the bulbs and necks are no longer preserved such that the shape of the distal portion 11300 is substantially tubular, whether tapered or non-tapered, for example based on the shape of the target vessel.

FIG. 28Q is a schematic diagram of an example embodiment of the distal portion 9900 of FIG. 6J deployed across a vascular malformation 507 in vasculature. The distal portion 9900 may be useful, for example, in vascular malformations such as an arterio-venous fistula 507. For example, deployment of the high pore size segment 9902 in the transverse cerebral venous sinus and the high pore size proximal segment 9906 at the internal jugular vein near the base of skull can allow for normal venous drainage into these veins, which can inhibit or prevent occlusion of venous drainage from these venous sinuses (e.g., the vein of Labbe 9931, the superior petrosal sinus 9932, the inferior petrosal sinus 9934, etc.), inadvertent occlusion of which could otherwise lead to life-threatening stroke. Deployment of the small pore size middle segment 9904 across the site 9933 of the arterio-venous fistula drainage into the sigmoid cerebral venous sinus can aid in thrombosis of the arterio-venous fistula 507. The bulbs and wide-mouthed proximal and distal necks of the distal portion 9900 can provide good wall apposition in the cerebral venous sinuses and veins. In some embodiments, the force/resistance (e.g., radial force) of the bulbs and/or necks is in a range sufficient to slightly expand the target vessel(s) in the range of about 0% to about 30%, and the shapes of the bulbs and necks are at least partially preserved. In some embodiments, the radial force of the bulbs and/or necks is in a range sufficient to appose the sidewalls of the vessel to inhibit or prevent an endo-leak, but not sufficient to expand the vessel, and the shapes of the bulbs and necks are no longer preserved such that the shape of the distal portion 9900 is substantially tubular, whether tapered or non-tapered, for example based on the shape of the target vessel.

FIG. 29A is a schematic diagram of an example embodiment of the distal portion 11400 of FIG. 7C deployed across a fistula. The distal portion 12200 of FIG. 7C-2 may be similarly deployed across a fistula. Without treatment, blood may flow from one cavernous sinus 11450, through the fistula, and into a second cavernous sinus 11455, and/or vice versa. The flow through the fistula may be characterized by a jet effect in which blood at a higher pressure is able to traverse the fistula into the cavernous sinus at a lower pressure. This jet effect may maintain or enlarge the size of the fistula because the pressure can inhibit or prevent thrombus from forming or remaining in place to allow occlusion or healing of the fistula.

Deployment of the distal portion 11400, 12200 may be as provided herein. A guide catheter and a dilator are partially inserted into the entry point. A trans-femoral, trans-venous approach may be used to treating an arterio-venous fistula such as a carotid cavernous fistula. The femoral vein can act as a percutaneous entry point. As described above with respect to the catheter angiogram, either leg can be used because both point towards the head, and, for peripheral lesions in one leg, the non-affected leg can be used. A steerable guidewire (e.g., having a length between about 150 cm and about 180 cm) is inserted into the guide catheter and the dilator, extending some distance (e.g., about 2 inches (approx. 5 cm)) out of the distal end of the dilator. The steerable guidewire can be advanced and steered for some distance, followed by advancement of the guide catheter and dilator over the steerable guidewire. The dilator is then removed. The steerable guidewire and the guide catheter can be sequentially advanced into the inferior vena cava, through the right atrium of the heart, into the brachiocephalic vein, until the desired point in the vasculature (e.g., internal jugular vein at the base of skull). The steerable guidewire is then removed, and the guide catheter is left in place. The desired point of the vasculature where advancement ceases may be the point where further advancement of the dilator could perforate the vasculature.

In some embodiments, referring again to FIG. 27A, a microcatheter 504 may be advanced over a steerable microwire 506 and through a guide catheter 502 positioned in the internal jugular vein at the base of skull proximal to the arterio-venous fistula. A steerable microwire 506 (e.g., having an outer diameter of about 0.014 inches (approx. 0.36 mm) is inserted into the microcatheter 504, extending some distance (e.g., about 2 cm to about 4 cm) out of the distal end of the microcatheter 504. In some embodiments, a distal access microcatheter 530 is be used and the microcatheter 504 is advanced over the microwire 506. The microwire 506 can be advanced and steered for some distance into the sigmoid and transverse cerebral venous sinuses, followed by advancement of the microcatheter 504 over the microwire 506. The microwire 506 and the microcatheter 504 can be sequentially advanced until the desired point in the vasculature (e.g., into the cavernous sinus). The microwire 506 is then removed or retracted while the microcatheter 504 is in position.

The distal portion 11400 may be useful, for example, as a flow disrupter in fistulas, which are abnormal communications between two hollow cavities. For example, if the distal portion 11400 is deployed in the cavernous venous sinus such that the low pore size bulbs 11435, 11425 are in the left cavernous venous sinus 11455, the low pore size bulbs are 11405, 11415 in the right cavernous venous sinus 11450, and the high pore size neck 11424 is between the two cavernous venous sinuses 11450, 11455, the low pore size segments can cause flow disruption by decreasing flow into the other cavernous venous sinus, which can aid in thrombosis of the carotid-cavernous fistula. For another example, if the distal portion 12200 is deployed in the cavernous venous sinus such that the bulbs 11435, 11425 are in the left cavernous venous sinus 11455, the bulbs are 11405, 11415 in the right cavernous venous sinus 11450, and the high pore size neck 11424 is between the two cavernous venous sinuses 11450, 11455, the low pore size segments (e.g., the bulbs 11405, 11435) can cause flow disruption by decreasing flow into the other cavernous venous sinus, which can aid in thrombosis of the carotid-cavernous fistula. Deployment of the high pore size wide-mouthed neck 11424 between the two cavernous sinuses 11450, 11455 can serve as a soft scaffold between the two cavernous venous sinuses 11450, 11455, which can aid in thrombosis of the carotid-cavernous fistula.

As described herein, FIG. 7C-2 illustrates a distal portion 12200 in which the distal neck 11428 is radially offset from the longitudinal polar axis and/or is not longitudinally aligned to the proximal neck 11420. Fluid may flow from the left cavernous venous sinus 11455 into the distal portion 12200 through the distal neck 11428. The jet effect is disrupted because the proximal neck 11420 is radially offset from the longitudinal polar axis and/or is not longitudinally aligned to the distal neck 11428. Fluid may flow from the right cavernous venous sinus 11450 into the distal portion 12200 through the proximal neck 11420. The jet effect can be disrupted because the distal neck 11428 is radially offset from the longitudinal polar axis and/or is not longitudinally aligned to the proximal neck 11420. The jet effect is may also or alternatively be disrupted by the two outer bulbs 11405, 11435, in which the relatively high braid angle and/or low porosity can reduce the amount of blood that flows longitudinally through the distal portion 11400, 12200. Disruption of the jet effect can promote thrombus formation, which can promote occlusion of the fistula. The thrombus can be captured by the two inner bulbs 11415, 11425. Permitting some perfusion through the fistula and capturing the thrombi in the two inner bulbs 11415, 11425 as is possible with the distal portion 11400 and the distal portion 12200 can promote healing better than total occlusion of the fistula, for example which may prevent thrombus formation and fistula occlusion. In some embodiments described herein, cells can grow over at least the two inner bulbs 11415, 11425 and in the fistula, which can occlude the fistula.

As described herein, FIG. 7C illustrates a distal portion 11400 in which the two inner bulbs 11415, 11425 have a relatively high braid angle. The high braid angle may allow the two inner bulbs 11415, 11425 to aid in disrupting the jet effect, for example of blood perfusing through the two outer bulbs 11405, 11435. As described herein, FIG. 7C-2 illustrates a distal portion 12200 in which the middle segment, including the two inner bulbs 11415, 11425, has a relatively low braid angle. The low braid angle may allow the two inner bulbs 11415, 11425 to tightly conform to the wall between the cavernous sinuses 11450, 11455.

FIG. 29B is a schematic diagram of an example embodiment of the distal portion 11600 of FIG. 7D deployed in a cardiac wall aneurysm 11650. A trans-femoral, trans-arterial approach may be used to treat a cardiac wall aneurysm 11650 such as a ventricular wall aneurysm. The femoral artery can act as a percutaneous entry point. As described above with respect to the catheter angiogram, either leg can be used because both point towards the heart.

Deployment of the distal portion 11600 may be as provided herein. A guide catheter and a dilator are partially inserted into the entry point. A steerable guidewire (e.g., having a length between about 150 cm and about 180 cm) is inserted into the guide catheter and the dilator, extending some distance (e.g., about 2 inches (approx. 5 cm)) out of the distal end of the dilator. The steerable guidewire can be advanced and steered for some distance, followed by advancement of the guide catheter and dilator over the steerable guidewire. The dilator is then removed. The steerable guidewire and the guide catheter can be sequentially advanced into the descending abdominal aorta 11655, through the aortic arch 11660, until the desired point in the vasculature (e.g., the left ventricle 11665 of the heart). The steerable guidewire is then removed, and the guide catheter is left in place. The desired point of the vasculature where advancement ceases may be the point where further advancement of the dilator could perforate the vasculature. A ventriculogram of the heart may be performed using a 4 Fr (e.g., about 1.33 mm) or a 5 Fr (e.g., about 1.67 mm) pig-tail shaped diagnostic catheter advanced through the guide catheter, which is in stable position within the left ventricle 11665. Dye comprising iodine (e.g., iohexol, iodixanol, etc.) is injected through the pig-tail shaped diagnostic catheter for direct imaging of the ventricular wall aneurysm 11160. The pig-tail catheter is then removed with the guide catheter in stable position within the left ventricle 11665.

In some embodiments, referring again to FIG. 27A, a microcatheter 504 may be advanced over a steerable microwire 506 and through a guide catheter 502 positioned in the left ventricle 11665 proximal to the ventricular wall aneurysm 11160. A steerable microwire 506 (e.g., having an outer diameter of about 0.014 inches (approx. 0.36 mm)) is inserted into the microcatheter 504, extending some distance (e.g., about 2 cm to about 4 cm) out of the distal end of the microcatheter 504. In some embodiments, a distal access microcatheter 530 may be used, and the microcatheter 504 is advanced over the microwire 506 and through the distal access microcatheter 530. The microwire 506 can be advanced and steered for some distance into the ventricular wall aneurysm 11650, followed by advancement of the microcatheter 504 over the microwire 506. The microwire 506 and the microcatheter 504 can be sequentially advanced into the dome of the ventricular wall aneurysm 11650. The microwire 506 is then removed or retracted while the microcatheter 504 is in position.

The distal portion 11600 may be useful, for example, in ventricular wall aneurysms 11650. For example, deployment of the small pore size proximal bulb 11605 across the mouth of the ventricular wall aneurysm 11650 can cause flow disruption by decreasing flow into the ventricular wall aneurysm 11650, which can aid in thrombosis of the ventricular wall aneurysm 11650. Deployment of the high pore size middle bulb 11615 and high pore size distal bulb 11625 in the dome of the ventricular wall aneurysm 11650 can cause flow disruption within the aneurysm 11650 by forming a soft scaffold within the aneurysm 11650, which can aid in thrombosis of the aneurysm 11650. The distal neck 11606 is short and has a low braid angle, which can provide soft deployment of the distal portion 11600 within the dome of the aneurysm 11650. The bulbs 11605, 11615, 11625, the necks 11602, 11604, and the distal neck 11606 of the distal portion 11600 can provide good wall apposition within the ventricular wall aneurysm 11650.

In embodiments in which the distal neck 11606 is radially offset from the longitudinal polar axis and/or is not longitudinally aligned to the proximal neck or opening, fluid may flow into the distal portion 11600 through the proximal neck or opening. The fluid flow can be disrupted because the proximal neck or opening and the distal neck 11606 inhibit or prevent direct flow of blood at high pressure, which can promote thrombus formation and closure of the aneurysm 11650. The thrombus can be captured by the bulbs 11615, 11625. Permitting some perfusion into the aneurysm 11650 and capturing the thrombi in the bulbs 11615, 11625 as is possible with the distal portion 11600 can promote healing better than total occlusion of the aneurysm 11650.

FIG. 29C is a schematic diagram of an example embodiment of the distal portion 11500 of FIG. 7E deployed in the left atrial appendage 11530 of the heart. A trans-femoral, trans-venous approach may be used for occluding the left atrial appendage 11530. The femoral vein can act as a percutaneous entry point. As described above with respect to the catheter angiogram, either leg can be used because both point towards the heart.

FIG. 29D is a schematic diagram of an example embodiment of a vascular treatment device deployed in an aneurysm 12760 within the vasculature. The device comprises a proximal bulb 12890, a distal bulb 12900, a proximal neck 12870 proximal to the proximal bulb 12890, a distal neck 12880 distal to the distal bulb 12900, and an intermediate neck 12895 between the proximal bulb 12890 and the distal bulb 12895. A trans-femoral, trans-arterial approach may be used for occluding the aneurysm 12760. Since this device can act as an intra-saccular flow disruptor, it may be used in patients with ruptured aneurysms including brain aneurysms, peripheral aneurysms, visceral aneurysms, and aneurysms in other locations in the body. The proximal bulb 12890 near the inflow zone at the mouth of the aneurysm 12760 has a lower porosity than the distal bulb 12900, which can inhibit or prevent clots generated within the aneurysm 12760 (e.g., due to the flow disruption, etc.) from entering the parent vessel. The distal bulb 12900 has a higher porosity and lower radial force than the proximal bulb 12890, which can be gentle on the walls of the aneurysm 12760. In some embodiments, the proximal neck 12870 and at least one of the intermediate neck 12895 and distal neck 12880 are offset, which can avoid a jet effect of flow from the parent vessel into the aneurysm 12760, which can decrease the risk of aneurysm rupture. In some embodiments, the proximal bulb 12890 and the distal bulb 12900 may have the same porosity (e.g., with or without offset necks).

FIG. 29E is a schematic diagram of another example embodiment of a vascular treatment device deployed in an aneurysm 12760 within the vasculature. The device comprises a proximal bulb 12910, a distal bulb 12900, an intermediate bulb 12920 between the proximal bulb 12910 and the distal bulb 12900, a proximal neck 12870 proximal to the proximal bulb 12910, a distal neck 12880 distal to the distal bulb 12900, a first intermediate neck 12930 between the proximal bulb 12910 and the intermediate bulb 12920, and a second intermediate neck 12940 between the intermediate bulb 12920 and the distal bulb 12900. Since this device can act as an intra-saccular flow disruptor, it may be used in patients with ruptured aneurysms including brain aneurysms, peripheral aneurysms, visceral aneurysms, and aneurysms in other locations in the body. Variable porosity between the bulbs 12900, 12910, 12920 can create scaffolds for thrombosing the aneurysm 12760 and generating a clot. Variable porosity between the bulbs 12900, 12910, 12920 may serve to compartmentalize the clots within the aneurysm 12760, which can inhibit or prevent dislodgement or embolization of clots. The proximal bulb 12910 near the inflow zone at the mouth of the aneurysm may have a lower porosity than the distal bulb 12900, which can inhibit or prevent clots generated within the aneurysm 12760 (e.g., due to the flow disruption, etc.) from entering the parent vessel. The intermediate bulb 12920 may have a lower porosity than the distal bulb 12900, which can inhibit or prevent clots generated within the aneurysm 12760 (e.g., due to the flow disruption, etc.) from entering the parent vessel. In some embodiments, the distal bulb 12900 has a higher porosity with lower radial force than at least one of the proximal bulb 12910 and intermediate bulb 12920, which can be gentle on the walls of the aneurysm 12760. In some embodiments, the proximal neck 12870 may be offset from at least one of the first intermediate neck 12930, the second intermediate neck 12940, the distal neck 12880, which can avoid a jet effect of flow from the parent vessel into the aneurysm 12760, which can decrease the risk of aneurysm rupture. In some embodiments, the proximal bulb 12910, the intermediate bulb 12920, and the distal bulb 12900 may have the same porosity (e.g., with or without offset necks).

Deployment of the distal portion 11500 may be as provided herein. A guide catheter and a dilator are partially inserted into the entry point. A steerable guidewire (e.g., having a length between about 150 cm and about 180 cm) is inserted into the guide catheter and the dilator, extending some distance (e.g., about 2 inches (approx. 5 cm)) out of the distal end of the dilator. The steerable guidewire can be advanced and steered for some distance, followed by advancement of the guide catheter and dilator over the steerable guidewire. The dilator is then removed from the distal inferior vena cava. The steerable guidewire and the guide catheter can be sequentially advanced into the inferior vena cava, through the right atrium of the heart, and, if the foramen ovale is patent, then the guide catheter is advanced over the steerable guidewire from the right atrium into the left atrium until the desired point in the vasculature (e.g., the left atrium of the heart proximal to the left atrial appendage 11530). The steerable guidewire is then removed, and the guide catheter is left in place. If a pre-existing foramen ovale is not patent, then a percutaneous entry into the superior vena cava can be performed. Using a needle and stylet, an iatrogenic hole or perforation is created near the fossa ovalis in the septal wall of the atrium.

In some embodiments, referring again to FIG. 27A, a microcatheter 504 may be advanced over a steerable microwire 506 and through a guide catheter 502 positioned in the left atrium proximal to the orifice of the left atrial appendage 11530. A steerable microwire 506 (e.g., having an outer diameter of about 0.014 inches (approx. 0.36 mm)) is inserted into the microcatheter 504, extending some distance (e.g., about 2 cm to about 4 cm) out of the distal end of the microcatheter 504. In some embodiments, a distal access microcatheter 530 may be used, and the microcatheter 504 is advanced over the microwire 506 and through the distal access microcatheter 530. The microwire 506 can be advanced and steered for some distance into the mouth of the left atrial appendage 11530. The microwire 506, and the microcatheter 504, can be sequentially advanced dome of the left atrial appendage 11530. The microwire 506 is then removed or retracted while the microcatheter 504 is in position.

The distal portion 11500 may be useful, for example, as a flow disrupter in the left atrial appendage 11530 within the heart. For example, deployment of the small pore size proximal bulbs 11512, 11514 across the mouth of the left atrial appendage 11530 can cause flow disruption by decreasing flow into the left atrial appendage 11530, which can aid in thrombosis of the left atrial appendage 11530, which can decrease the risk of stroke in patients with atrial fibrillation and/or reduce or eliminate the need for long term anti-coagulation. Deployment of the high pore size distal bulbs 11516, 11518 inside the dome of the left atrial appendage 11530 can cause flow disruption within the left atrial appendage 11530 by forming a soft scaffold within the left atrial appendage 11530, which can aid in thrombosis of the left atrial appendage 11530. The distal neck 65 is short and has a low braid angle, which can provide soft deployment of the distal portion 11500 within the dome of the left atrial appendage 11530. The proximal neck 11522 is short and has a high braid angle, which can inhibit or prevent any blood flow into the dome of the left atrial appendage 11530. The bulbs and the wide mouthed necks between the bulbs of the distal portion 11500 can provide good wall apposition within the left atrial appendage 11530.

In embodiments in which the distal neck 65 is radially offset from the longitudinal polar axis and/or is not longitudinally aligned to the proximal neck 11522, fluid may flow into the distal portion 11500 through the proximal neck 11522. The fluid flow can be disrupted because the proximal neck 11522 and the distal neck 65 inhibit or prevent direct flow of blood at high pressure, which can promote thrombus formation and closure of the aneurysm left atrial appendage 11530. The thrombus can be captured by at least the bulbs 11516, 11518. Permitting some perfusion into the left atrial appendage 11530 and capturing the thrombi in at least the bulbs 11516, 11518 as is possible with the distal portion 11500 can promote healing better than total occlusion of the left atrial appendage 11530.

The distal portions 100 described herein that are deployed in vasculature may be releasably or non-releasably coupled to a proximal portion 200. For example, after positioning at the site of the vasculature, the distal portion 100 may be mechanically, electrolytically, chemically, etc. released to act as an endoprosthesis. For another example, after positioning at the site of the vasculature, the distal portion 100 may remain only for so long as the treatment takes place, whereupon it may be removed. In certain such embodiments, for example, the distal portion 100 may act as a scaffolding during insertion or packing of coils or other embolic material (e.g., fluid such as Onyx®, available from Covidien) into an aneurysm.

The devices 10, 20, 30, 40 described herein may be gentle and safe on the fragile human blood vessels, customizable by a user to the length of the clot or clot burden, visible under X-ray fluoroscopy, reach the smallest of human blood vessels, compatible with torsional rasping of the clot, have bonding zones or attachment points that are strong even between dissimilar metals or alloys to avoid the risk of any fracture points, and/or include proximal portions 200 that provide good proximal support and good distal flexibility. Some embodiments can provide one or more, or all, of the advantages described herein.

Although described herein in detail with respect to blood vessels, the devices and methods described herein can be used in any appropriate part of the body, for example having a lumen (e.g., blood vessels (e.g., cardiac, peripheral, neuro), biliary ducts, digestive or gastrointestinal tracts, pulmonary tracts, etc.).

In some embodiments, the devices and methods described herein can be used in conjunction with drug therapy. For example, a drug or agent (e.g., r-tpa, heparin, taxol, etc.) can be injected through the microcatheter, through the lumen of the proximal portion 200 and/or a lumen created by the textile structure 158 of the distal portion 100, or separately before, during, or after deployment of at least a segment of the distal portion 100.

The following references are herein incorporated by reference in their entirety: (1) SARTI et al., Int'l trends in mortality from stroke, 1968 to 1994, *Stroke*, 2000; vol. 31, pp. 1588-1601; (2) WOLF et al., Epidemiology of Stroke, In: BARNETT et al., eds., Stroke: Pathophysiology, Diagnosis, and Management, 3rd Ed., New York, N.Y.: Churchill Livingstone, 1998, pp. 6-7; (3) ADAMS et al., Guidelines for the early management of patients with ischemic stroke: A scientific statement from the Stroke Council of the American Stroke Association, Stroke, 2003, vol. 34, pp. 1056-1083; (4) RYMER et al., Organizing regional networks to increase acute stroke intervention, *Neurol. Res.*, 2005, vol. 27, pp. 9-16; and (5) FURLAN et al., Intra-arterial prourokinase for acute ischemic stroke; The PROACT II study: A randomized controlled trial, Prolyse in Acute Cerebral Thromboembolism, *JAMA*, 1999, vol. 282, pp. 2003-2011.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "torsionally rasping a distal portion of a thrombectomy device" include "instructing the torsionally rasping of a distal portion of a thrombectomy device." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 3 mm" includes "3 mm"

What is claimed is:

1. A system for aspirating thrombus using suction patterns during a vascular procedure, the system comprising:
    an automated negative suction device comprising a pump and power electronics configured to control the automated negative suction device, the power electronics storing a plurality of stored suction patterns each including a pattern that includes three different suction intensity levels, at least some of the stored suction patterns designed for a particular clot burden, the power electronics configured to operate the automated negative suction device to create negative pressure according to a chosen one of the stored suction patterns; and
    a control panel allowing a user to choose one of the plurality of stored suction patterns,
    wherein the plurality of stored suction patterns includes a first stored suction pattern configured to aspirate a soft clot and a second stored suction pattern configured to aspirate a hard clot.

2. The system of claim 1, wherein the plurality of stored suction patterns includes a crescendo suction pattern, a diminuendo suction pattern, or a combination of both crescendo and diminuendo suction patterns.

3. The system of claim 1, wherein the three different suction intensity levels comprise:
    a first intensity level within a range between 100 mm Hg and 350 mm Hg;
    a second intensity level greater than the first intensity level, the second intensity level within a range between 351 mm Hg and 550 mm Hg; and
    a third intensity level greater than the second intensity level, the third intensity level within a range between 551 mm Hg and 769 mm Hg.

4. The system of claim 1, wherein the pump is a motor pump.

5. A system for aspirating thrombus using suction patterns during a vascular procedure, the system comprising:
    an automated negative suction device comprising power electronics configured to control the automated negative suction device, the power electronics storing a plurality of stored suction patterns each including a pattern that includes at least two different suction intensity levels, the power electronics configured to operate the automated negative suction device to create negative pressure according to a selected suction pattern of the plurality of stored suction patterns; and
    a control panel allowing a user to preselect one of the plurality of stored suction patterns, the control panel further allowing the user to create a custom suction pattern, wherein the plurality of stored suction patterns includes a first stored suction pattern configured to aspirate a soft clot and a second stored suction pattern configured to aspirate a hard clot.

6. The system of claim 5, wherein at least one of the plurality of stored suction patterns includes a pattern that includes three different suction intensity levels.

7. The system of claim 6, wherein the three different suction intensity levels comprise:
   a first intensity level within a range between 100 mm Hg and 350 mm Hg;
   a second intensity level greater than the first intensity level, the second intensity level within a range between 351 mm Hg and 550 mm Hg; and
   a third intensity level greater than the second intensity level, the third intensity level within a range between 551 mm Hg and 769 mm Hg.

8. The system of claim 5, wherein the plurality of stored suction patterns includes a crescendo suction pattern, a diminuendo suction pattern, or a combination of both crescendo and diminuendo suction patterns.

9. The system of claim 5, wherein the automated negative suction device comprises a motor pump.

10. The system of claim 5, wherein the plurality of stored suction patterns includes a crescendo suction pattern, a diminuendo suction pattern, or a combination of both crescendo and diminuendo suction patterns, wherein at least one of the plurality of stored suction patterns includes a pattern that includes three different suction intensity levels, and wherein the three different suction intensity levels comprise:
   a first intensity level within a range between 100 mm Hg and 350 mm Hg;
   a second intensity level greater than the first intensity level, the second intensity level within a range between 351 mm Hg and 550 mm Hg; and
   a third intensity level greater than the second intensity level, the third intensity level within a range between 551 mm Hg and 769 mm Hg.

11. A system for aspirating thrombus using suction patterns during a vascular procedure, the system comprising:
   an automated negative suction device comprising power electronics configured to control the automated negative suction device, the power electronics storing a plurality of stored suction patterns each including a pattern that includes at least two different suction intensity levels, the power electronics configured to operate the automated negative suction device to create negative pressure according to a selected suction pattern of the plurality of stored suction patterns; and
   a control panel allowing a user to preselect one of the plurality of stored suction patterns, the control panel further allowing the user to create a custom suction pattern,
   wherein the plurality of stored suction patterns includes a first stored suction pattern configured to aspirate a soft clot and a second stored suction pattern configured to aspirate a hard clot.

12. The system of claim 11, wherein at least one of the plurality of stored suction patterns includes a pattern that includes three different suction intensity levels.

13. The system of claim 12, wherein the three different suction intensity levels comprise:
   a first intensity level within a range between 100 mm Hg and 350 mm Hg;
   a second intensity level greater than the first intensity level, the second intensity level within a range between 351 mm Hg and 550 mm Hg; and
   a third intensity level greater than the second intensity level, the third intensity level within a range between 551 mm Hg and 769 mm Hg.

14. The system of claim 11, wherein the plurality of stored suction patterns includes a crescendo suction pattern, a diminuendo suction pattern, or a combination of both crescendo and diminuendo suction patterns.

15. The system of claim 11, wherein the control panel comprises a user interface.

16. The system of claim 11, wherein the automated negative suction device comprises a motor pump.

17. The system of claim 11, wherein the plurality of stored suction patterns includes a crescendo suction pattern, a diminuendo suction pattern, or a combination of both crescendo and diminuendo suction patterns, wherein at least one of the plurality of stored suction patterns includes a pattern that includes three different suction intensity levels, and wherein the three different suction intensity levels comprise:
   a first intensity level within a range between 100 mm Hg and 350 mm Hg;
   a second intensity level greater than the first intensity level, the second intensity level within a range between 351 mm Hg and 550 mm Hg; and
   a third intensity level greater than the second intensity level, the third intensity level within a range between 551 mm Hg and 769 mm Hg.

* * * * *